United States Patent
Almstead et al.

(10) Patent No.: US 9,351,964 B2
(45) Date of Patent: *May 31, 2016

(54) METHODS FOR TREATING CANCER AND NON-NEOPLASTIC CONDITIONS

(75) Inventors: Neil Almstead, Princeton, NJ (US); Tamil Arasu, Edison, NJ (US); Soongyu Choi, Skillman, NJ (US); Liangxian Cao, Parlin, NJ (US); Jeffrey Allen Campbell, Hilton Head Island, SC (US); Donald Corson, Erie, CO (US); Thomas W. Davis, South Orange, NJ (US); Jason D. Graci, Scranton, PA (US); Zhengxian Gu, Princeton, NJ (US); Peter Seongwoo Hwang, Edison, NJ (US); William Lennox, Bedminster, NJ (US); Harry H. Miao, Wellsley, MA (US); Langdon Miller, Seattle, WA (US); Young-Choon Moon, Belle Mead, NJ (US); Hongyan Qi, Plainsboro, NJ (US); Christopher Trotta, Somerset, NJ (US); Marla L. Weetall, Morristown, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,257

(22) PCT Filed: May 27, 2010

(86) PCT No.: PCT/US2010/036467
§ 371 (c)(1),
(2), (4) Date: Apr. 25, 2012

(87) PCT Pub. No.: WO2010/138758
PCT Pub. Date: Dec. 2, 2010

(65) Prior Publication Data
US 2012/0202763 A1    Aug. 9, 2012

Related U.S. Application Data

(60) Provisional application No. 61/181,653, filed on May 27, 2009.

(51) Int. Cl.
| | | |
|---|---|---|
| *A01N 43/04* | (2006.01) | |
| *A61K 31/44* | (2006.01) | |
| *A61K 45/06* | (2006.01) | |
| *A61K 31/4745* | (2006.01) | |
| *A61K 31/437* | (2006.01) | |
| *C07D 471/04* | (2006.01) | |

(52) U.S. Cl.
CPC .............. *A61K 31/44* (2013.01); *A61K 31/437* (2013.01); *A61K 31/4745* (2013.01); *A61K 45/06* (2013.01); *C07D 471/04* (2013.01)

(58) Field of Classification Search
CPC ............................ C07H 471/04; A61K 31/44
USPC .......................................... 546/117; 514/292
See application file for complete search history.

(56) References Cited

U.S. PATENT DOCUMENTS

| | | |
|---|---|---|
| 3,328,412 A | 6/1967 | Atkinson et al. |
| 5,206,377 A | 4/1993 | McAfee |
| 5,314,908 A | 5/1994 | McAfee |
| 5,500,431 A | 3/1996 | Audia et al. |
| 5,760,051 A | 6/1998 | Audia et al. |

(Continued)

FOREIGN PATENT DOCUMENTS

| | | |
|---|---|---|
| EP | 0357122 A2 | 3/1990 |
| EP | 0549916 A2 | 7/1993 |

(Continued)

OTHER PUBLICATIONS

U.S. Appl. No. 13/274,412, filed Oct. 17, 2011, Cao et al.

(Continued)

*Primary Examiner* — Patrick Lewis
(74) *Attorney, Agent, or Firm* — Jones Day

(57) ABSTRACT

Compounds, such as compounds of Formula (I), that selectively inhibit pathological production of human vascular endothelial growth factor (VEGF) and compositions comprising such Compounds are described. Compounds that inhibit viral replication or the production of viral RNA or DNA or viral protein and compositions comprising such Compounds are described. Also described are methods of reducing VEGF using such Compounds and methods for treating cancer and non-neoplastic conditions involving the administration of such Compounds. Further described are methods of inhibiting viral replication or the production of viral RNA or DNA or viral protein using such Compounds and methods for treating viral infections involving the administration of such Compounds. The Compounds may be administered as a single agent therapy or in combination with one or more additional therapies to a human in need of such treatments.

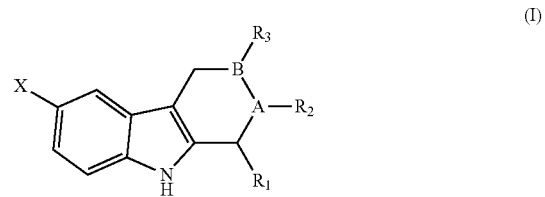

(I)

6 Claims, 25 Drawing Sheets

(56) References Cited

U.S. PATENT DOCUMENTS

| | | | |
|---|---|---|---|
| 5,866,587 | A | 2/1999 | de Nanteuil et al. |
| 6,090,945 | A | 7/2000 | Audia et al. |
| 6,093,723 | A | 7/2000 | Miao et al. |
| 6,720,331 | B2 | 4/2004 | Yeh et al. |
| 7,208,582 | B2 * | 4/2007 | Rosen et al. ............... 530/387.1 |
| 7,341,749 | B2 | 3/2008 | Hall et al. |
| 7,601,840 | B2 | 10/2009 | Moon et al. |
| 7,767,689 | B2 | 8/2010 | Moon et al. |
| 7,872,133 | B2 | 1/2011 | Ohmoto et al. |
| 8,076,352 | B2 | 12/2011 | Cao et al. |
| 8,076,353 | B2 | 12/2011 | Cao et al. |
| 8,367,694 | B2 | 2/2013 | Moon et al. |
| 8,372,860 | B2 | 2/2013 | Moon et al. |
| 8,697,662 | B2 | 4/2014 | Cao et al. |
| 8,703,726 | B2 | 4/2014 | Cao et al. |
| 2003/0040527 | A1 | 2/2003 | Yeh et al. |
| 2003/0130293 | A1 | 7/2003 | Bamdad |
| 2004/0102438 | A1 | 5/2004 | Brueckner et al. |
| 2004/0116458 | A1 | 6/2004 | Sawyer et al. |
| 2005/0143371 | A1 | 6/2005 | Meyers et al. |
| 2005/0282849 | A1 | 12/2005 | Moon et al. |
| 2006/0241084 | A1 | 10/2006 | Roifman et al. |
| 2007/0254878 | A1 | 11/2007 | Cao et al. |
| 2008/0103164 | A1 | 5/2008 | Gudmundsson et al. |
| 2008/0103213 | A1 | 5/2008 | Kurzrock et al. |
| 2008/0293766 | A1 | 11/2008 | Diamond et al. |
| 2009/0017021 | A1 | 1/2009 | Davis et al. |
| 2010/0125065 | A1 | 5/2010 | Moon et al. |
| 2010/0158858 | A1 | 6/2010 | Cao et al. |
| 2010/0179132 | A1 | 7/2010 | Moon et al. |
| 2011/0160190 | A1 | 6/2011 | Moon et al. |
| 2012/0157400 | A1 | 6/2012 | Cao et al. |
| 2012/0157401 | A1 | 6/2012 | Cao et al. |
| 2012/0157402 | A1 | 6/2012 | Cao et al. |
| 2012/0178707 | A1 | 7/2012 | Cao et al. |
| 2012/0202801 | A1 | 8/2012 | Cao et al. |
| 2013/0171103 | A1 | 7/2013 | Davis et al. |

FOREIGN PATENT DOCUMENTS

| | | |
|---|---|---|
| FR | 2662940 A1 | 12/1991 |
| JP | 3-287586 | 12/1991 |
| JP | 4275221 | 9/2002 |
| WO | WO 91/18604 | 12/1991 |
| WO | WO 94/10175 | 5/1994 |
| WO | WO 95/26723 | 10/1995 |
| WO | WO 97/37658 | 10/1997 |
| WO | WO 02/062339 A1 | 8/2002 |
| WO | WO 02/064590 A2 | 8/2002 |
| WO | WO 02/064591 A2 | 8/2002 |
| WO | WO 03/020279 A2 | 3/2003 |
| WO | WO 03/033496 A1 | 4/2003 |
| WO | WO 03/099821 A1 | 12/2003 |
| WO | WO 2004/113336 A1 | 12/2004 |
| WO | WO 2005/007672 A2 | 1/2005 |
| WO | WO 2005/009370 A2 | 2/2005 |
| WO | WO 2005/070930 A2 | 8/2005 |
| WO | WO 2005/089764 A1 | 9/2005 |
| WO | WO 2005/115470 A2 | 12/2005 |
| WO | WO 2006/015035 A1 | 2/2006 |
| WO | WO 2006/058088 A2 | 6/2006 |
| WO | WO 2006/113703 A2 | 10/2006 |
| WO | WO 2007/002051 A1 | 1/2007 |
| WO | WO 2008/127714 A1 | 10/2008 |
| WO | WO 2011/150162 A1 | 12/2011 |

OTHER PUBLICATIONS

Begum et al., 1996, "Chemistry and biological activity of a tryptamine and beta-carboline series of bases", Drug Research; 12(46):1163-1168.

Berrougui et al., 2005, "Cytotoxic activity of methanolic extract and two alkaloids extracted from seeds of Peganum harmala L", Journal of Natural Remedies; 5(1):41-45.

Boyer et al., 2002, "Small molecule inhibitors of KDR (VEGFR-2) kinase: an overview of structure activity relationships", Current Topics in Medicinal Chemistry; 2(9):973-1000.

Cao et al., 2005, "Synthesis and in vitro cytotoxic evaluation of 1,3-disubstituted and 1,3,9-trisubstituted beta-carboline derivatives", European Journal of Medicinal Chemistry; 40(3):249-257.

Database WPI Accession No. 1992-376264, Abstract of JP 4275221, 1992, Taisho Pharm. Co., Ltd.

Fuhrmann-Benzakein et al., 2000, "Elevated levels of angiogenic cytokines in the plasma of cancer patients", International Journal of Cancer; 85(1):40-45.

Hirawat et al., 2006, "51 Poster Phase 1 single-dose safety, PK, and food-effect study of PTC299, a novel VEGF expression inhibitor for treatment of solid tumors", European Journal of Cancer, Suppl; 4(12):19-20.

Hirawat et al., 2007, "Phase 1 studies assessing the safety, PK, and VEGF-modulating effects of PTC299, a novel VEGF expression inhibitor", Journal of Clinical Oncology ASCO Annual Meeting Proceedings Part 1; 25(18s):Abstract 3562.

International Search Report of International application PCT/US2010/036467, mailed Jul. 28, 2010.

Ishida et al., 1999, "Antitumor Agents 201. Cytotoxicity of harmine and beta-carboline analogs", Bioorganic & Medicinal Chemistry Letters; 9(23):3319-3324.

Nicolaus et al., 1983, "Symbiotic approach to drug design", Decision Making in Drug Research; pp. 173-186.

Venkov et al., 1999, "Synthesis of 2-acyltetrahydro-β-carbolines by an intramolecular α-amidoalkylation reaction", Synthetic Communications; 29(3):487-494.

Written Opinion of International application PCT/US2010/036467, mailed Jul. 28, 2010.

Ardill et al., 1990, "X=Y-ZH compounds as potential 1,3-dipoles. Part 29. The iminium ion route to azomethine ylides. Reaction of cyclic secondary amines with mono- and bi-functional aldehydes," Tetrahedron 46(18):6449-6466.

Audia et al., 1996, "Potent, Selective Tetrahydro-beta-carboline Antagonists of the Serotonin 2B ($5HT_{2B}$) Contractile Receptor in the Rat Stomach Fundus," J. Med. Chem. 39:2773-2780.

Belzil, 2006, "Therapeutic Potential for Inhibition of HIV Activation", Lethbridge Undergrad. Res. J. 1(2):1-12.

Cleaveland et al., "Identification of a Novel Inhibitor (NSC 665564) of Dihydroorotate Dehydrogenase with a Potency Equivalent to Brequinar," Biochemical and Biophysical Research Communications 223(3):654-659 (1996).

Corrected Notice of Allowability mailed Nov. 18, 2013 for U.S. Appl. No. 13/321,233.

Database Accession No. 84862, 570837, 578504, 585452, 690268 (XRN) accompanied by Aghbalian et al., 1972, "Synthesis Based on Harmine and Tetrahydroharmine," Armyanskii Khimicheskii Zhurnal 25:689-692; Partial European Search Report for EP11178488 dated May 9, 2012, p. 4.

Database REAXYS [Online], Elsevier Information Systems GmbH, Frankfurt/Main; XP002675485, Database Accession No. 84862, 230057, 306267 (XRN), accompanied by Fischer, 1897, "Über Harmin und Harmalin," Ber. Dtsch. Chem. Ges. 30(3):2481-2489; Fischer, 1901, "Chemische Studien der Alkaloide der Steppenraute (Peganum Harmala)," Chem. Zentralbl. 72(1):957-959; Partial European Search Report for EP11178488 dated May 9, 2012, p. 2.

Database REAXYS [Online], Elsevier Information Systems GmbH, Frankfurt/Main; XP002675486, Database Accession No. 207280, 3918373 (XRN), accompanied by Fischer, 1914, "Über Harmin und Harmalin," Ber. Dtsch. Chem. Ges. 47:99-107 ; Partial European Search Report for EP11178488 dated May 9, 2012, p. 3.

Formagio et al., 2009, "Synthesis and antiviral activity of β-carboline derivatives bearing a substituted carbohydrazide at C-3 against poliovirus and herpes simplex virus (HSV-1)," Eur. J. Med. Chem. 44:4695-4701.

Hino et al., 1990, "2-Hydroxy-1-substituted-1,2,3,4-tetrahydro-β-carbolines. The Pictet-Spengler Reaction of N-Hydroxytryptamine with Aldehydes," Chem. Pharm. Bull. 38(1):59-64.

Iakhontov et al., 1958, "Reduction of Derivatives of Harmine with Sodium Borohydride to Derivatives of Py-Tetrahydroharmine" Zhurnal Obshchei Khimii 28(11):3139-3141.

(56) References Cited

OTHER PUBLICATIONS

International Search Report mailed Aug. 26, 2011 for International Application No. PCT/US11/38067, filed May 26, 2011.
Jiang et al., 2003, "Potassium Superoxide as an Alternative Reagent for Winterfeldt Oxidation of β-Carbolines," Organic Letters 5(1):43-46.
Kawashima et al., 1995, "Synthesis and Pharmacological Evaluation of 1,2,3,4-Tetrahydro-β-Carboline Derivatives," Chem. Pharm. Bull. 43(5):783-787.
Kawate et al., 1999, "Chiral Auxiliary Approach to the Asymmetric Pictet-Spengler Reaction of Tryptamines," Heterocycles 50(2):1033-1039.
Lehmann et al., 1987, "Lactamisation of 4.9-Dihydropyrano [3.4-b] indol-1(3H)-ones.—A New Synthetic Route to the beta-Carboline Ring System," Archiv der Pharmazie 320(1):30-36.
Lehnert et al., 1994, "DNA topoisomerase II inhibition by substituted 1,2,3,4-tetrahydro-β-carboline derivatives," Bioorganic & Medicinal Chemistry Letters 4(20):2411-2416.
McNulty et al., 1991, "Diastereoselective Pictet-Spengler reaction of L-(Boc) prolinal: a biomimetic synthesis of eudistomins H and I, and woodinine," Tetrahedron Letters 32(37):4875-4878.
Miller et al., 2010, "Substituted tetrahydro-β-carbolines as potential agents for the treatment of human papillomavirus infection," Bioorg. Med. Chem. Lett. 20:256-259.
Notice of Allowance mailed Dec. 6, 2013 for U.S. Appl. No. 13/321,213.
Notice of Allowance mailed Nov. 7, 2013 for U.S. Appl. No. 13/321,233.
Office Action mailed Apr. 25, 2013 for U.S. Appl. No. 13/321,233, filed Mar. 9, 2012.
Office Action mailed May 9, 2013 for U.S. Appl. No. 13/321,213, filed Mar. 23, 2012.
Office Action mailed Oct. 8, 2013 for U.S. Appl. No. 13/321,271, filed Mar. 23, 2012.
Rubtsov et al., 1959, "Synthesis of Py-N-Alkyltetrahydroharmines" Zhurnal Obshchei Khimii 29.3232-3235.
Saaristo et al., 2000, "Mechanisms of angiogenesis and their use in the inhibition of tumor growth and metastasis," Oncogene 19:6122-6129.
Saiga et al., 1987, "Synthesis of 1,2,3,4-tetrahydro-beta-carboline derivatives as hepatoprotective agents. III. Introduction of substituents onto methyl 1,2,3,4-tetrahydro-beta-carboline-2-carbodithioate," Chem. Pharm. Bull. 35(8), 3284-3291.
Schoenenberger et al., 1986, "Fragmentation of Optically Active (1-Phenylethyl)- and (1-Naphthylethyl) ureas in Refluxing Alcohols: Easy Preparation of Optically Active Amines of High Optical Purity," Helvetica Chimica Acta 69(6):1486-1497.
Siddiqui et al., 1992, "Preparation of Tetrahydroharmine Analogues—Their Antibacterial, Bronchodilator and Cytotoxic Activity and Effect on Central Nervous System," Proc. Pakistan Acad. Sci. 29(4):285-298.
Soe et al., 1995,"Asymmetric Pictet-Spengler Reaction with a Chiral N-(β-3-indolyl)-ethyl-1-methylbenzylamine," Tetrahedron Letters 36(11):1857-1860.
Solomina et al., 1990, "Synthesis and Pharmacological Properties of 1-R-2-[3'-R'-Amino-2-Hydroxypropyl]-1,2,3,4-Tetrahydro-β-Carbolines," Pharmaceutical Chemistry Journal. 24(4):272-275.
Tsuji et al., 2002, "Pictet-Spengler Reaction of Nitrones and Imines Catalyzed by Yb(OTf)$_3$-TMSC1," Chem. Lett. 4: 428-429.
Written Opinion of the International Searching Authority mailed Aug. 26, 2011 for International Application No. PCT/US11/38067, filed May 26, 2011.
Wu et al., 2002, "A Versatile Linkage Strategy for Solid-Phase Synthesis of N,N-Dimethyltryptamines and β-Carbolines," Organic Letters 4(23):4033-4036.
Yamada et al., 1998, "Chiral Lewis Acid-Mediated Enantioselective Pictet-Spengler Reaction of $N_b$-Hydroxytryptamine with Aldehydes," J. Org. Chem. 63(18):6348-6354.
Office Action mailed Jul. 11, 2014 for U.S. Appl. No. 13/321,242, filed Mar. 9, 2012.

Office Action mailed Jul. 16, 2014 for U.S. Appl. No. 13/321,252, filed Mar. 9, 2012.
Plate et al., 1993, "Up-regulation of vascular endothelial growth factor and its cognate receptors in a rat glioma model of tumor angiogenesis," Cancer Res. 53(23):5822-5827.
Takamiya et al., 1993, "Inhibition of angiogenesis and growth of human nerve-sheath tumors by AGM-1470," J. Neurosurg. 78(3):470-476.
Achen et al., 1998, "The vascular endothelial growth factor family; proteins which guide the development of the vasculature," Int. J. Exp. Pathol., 79:255-265.
Acne Rosacea, http://www.webmd.com/skin-problems-and-treatments/acne/acne-rosacea (last visited Sep. 14, 2014).
Adan et al., 2007, "Intravitreal bevacizumab as initial treatment for choroidal neovascularization associated with presumed ocular histoplasmosis syndrome," Graefes Arch. Clin. Exp. Ophthalmol., 245:1873-1875.
Bello-Reuss et al., 2001, "Angiogenesis in autosomal-dominant polycyctic kidney disease," Kidney Int., 60:37-45.
Benevento et al., 2008, "Toxoplasmosis assiciated neovascular lesions treated successfully with ranibizumab and anti-parasitic therapy," Arch. Ophthalmol., 126(8):1152-1156.
Bhatnagar et al., 2007, "Intravitreal bevacizumab for the management of choroidal neovascularization in pseudoxanthoma elasticum," Retina, 27:897-902.
Brown et al., 1995, "Increased expression of vascular permeability factor (vascular endothelial growth factor) in bullous pemphigoid, dermatitis herpetiformis, and erythema multiforme," J. Invest. Dermatol. 104:744-749.
çekmen et al., 2003, "Vascular endothelial growth factor levels are increased and associated with disease activity in patients with Behcet's syndrome," Int. J. Dermatol., 42:870-875.
Chan et al., 2008, "Changes in aqueous vascular endothelial growth factor and pigment epithelial-derived factor levels following intravitreal bevacizumab injections for choroidal neovascularization secondary to age-related macular degeneration or pathologic myopia," Retina 28:1308-1313.
Goitre (pathology)—Britannica Online Encyclopedia, http://www.britannica.com/EBchecked/topic/237190/goitre (last visited Sep. 13, 2014).
Grisanti et al., 2006, "Intracameral bevacizumab for iris rubeosis," Am. J. Ophthalmol., 142:158-160.
Hamada et al., 2005, "Marked pleural and pericardial effusion with elevated vascular endothelial growth factor production: an uncommon complication of Kawasaki disease," Pediatr. Int., 47:112-114.
Hyperplasia: MedlinePlus Medical Encyclopedia, http://www.nlm.nih.gov/medlineplus/ency/article/003441.htm. (last visited Sep. 13, 2014)
Iitaka et al., 1998, "Increased serum vascular endothelial growth factor levels and intratyroidal vascular area in patients with Graves' Disease and Hashimoto's Thyroiditis," J. Clin. Endocrinol. Metab., 83:3908-3912.
Inoue et al., 1998, "Vascular endothelial growth factor (VEGF) expression in human coronary atherosclerotic lesions: Possible pathophysiological significance of VEGF in progression of atherosclerosis," Circulation 98:2108-2116.
Jackson et al., 1997, "Vascular endothelial growth factor (VEGF) expression in prostate cancer and benign prostatic hyperplasia," J. Urology, 157:2323-2328.
Kikuchi et al., 2005, "Angiogenic cytokines in serum and cutaneous lesions of patients with polyarteritis nodosa," J. Am. Aacd. Dermatol., 53:57-61.
Kuperminc et al., 1997, "Vascular endothelial growth factor is increased in patients with preeclampsia," Am. J. Reprod. Immunol., 38(4):302-306.
Kuryliszyn-Maskal et al., 2007, "Vascular endothelial growth factor in systemic lupus erythematosus: relationship to disease activity, systemic organ manifestation, and nailfold capillaroscopic abnormalities," Arch. Immunol. Ther. Exp., 55:179-185.
Lashkari et al., 2000, "Vascular Endothelial Growth Factor and Hepatocyte Growth Factor Levels Are Differentially Elevated in Patients With Advanced Retinopathy of Prematurity,"Am. J. Pathol., 156:1337-1344.

(56) References Cited

OTHER PUBLICATIONS

Lee et al., 2004, "Vascular Endothelial Growth Factor (VEDF) induces remodeling and enhances TH2-mediated sensitization and imflammation in the lung," Nat. Med, 10:1095-1103.
Leu et al., 2007, "Choroidal neovascularisation secondary to Best's disease in a 13-year-old boy treated by intravitreal bevacizumab," Graefe's Arch. Clin. Exp. Ophthalmol., 245:1723-1725.
Lopez et al., 1991, "Immunohistochemistry of Terrien's and Mooren's Corneal Degeneration," Arch. Ophthalmol., 109:988-992.
Macaron et al., 2003, "Cutaneous lesions of secondary syphilis are highly angiogenic," J. Am. Acad. Dermatol., 48:878-881.
Mastyugin et al., 2001, "Corneal epithelial VEGF and cytochrome P450 4B1 expression in a rabbit model of closed eye contact lens wear," Curr. Eye Res., 23:1-10.
Matsuda et al., 2004, "Sarcoidosis with high serum levels of vascular endothelial growth factor (VEGF), showing RS3PE-like symptoms in extremities," Clin. Rheumatol., 23:246-248.
McColley et al., 2000, "Serum Vascular Endothelial Growth Factor Is Elevated in Cystic Fibrosis and Decreases with Treatment of Acute Pulmonary Exacerbation," Am. J. Respir. Crit. Care Med., 161:1877-1880.
Nishigaki et al., 2006, "Increased serum level of vascular endothelial growth factor in *Mycobacterim aviumcomplex* infection," Respirology 11:407-413.
Paroli et al., 2007, "Increased vascular endothelial growth factor levels in aqueous humor and serum of patients with quiescent uveitis," Eur. J. Ophthalmol., 17:938-942.
Pe'er et al., 1998, "Vascular Endothelial Growth Factor Upregulation in Human Central Retinal Vein Occlusion," Ophthalmology, 105:412-416.
Perentes et al., 2002, "Massive vascular endothelium growth factor (VEGF) expression in Eales' disease," Klin. Monatsbl. Augenheilkd., 219:311-314.
Philipp et al., 2002, "Expression of Vascular Endothelial Growth Factors, Vegf-B, Vegf-C, Vegf-D, and of VegfC Receptors, Flt-4 (VEGFR-3) in Inflamed and Vascularized Human Corneas," AVRO Meeting Abstracts, 43:1755.
Polyarteritis Nodosa (PAN): Vasculitis: Merck Manual Professional, http://www.merckmanuals.com/professional/musculoskeletal_and_connective_tissue_disorders/vasculitis/polyarteritis_nodosa_pan.html (last visited Sep. 14, 2014).
Qian et al., 2008, "Combined Use of Superficial Keratectomy and Subconjunctival Bevacizumab Injection for Corneal Neovascularization," Cornea, 27:1090-1092.
Querques et al., 2008, "Intravitreal ranibizumab (Lucentis) for choroidal neovascularization associated with Stargardt's disease," Graefes Arch. Clin. Exp. Ophthalmol., 246:319-321.
Ray et al., 2004, "Association of the VEGF Gene With Proliferative Diabetic Retinopathy But Not Proteinuria in Diabetes," Diabetes 53:861-864.
Sachanonta et al., 2008, "Host Vascular Endothelial Growth Factor Is Trophic for Plasmodium Falciparum-Infected Red Blood Cells," Asian Pac. J. Allergy 26:37-45.
Schreiber et al., 2003, "Combined Topical Fluconazole and Corticosteroid Treatment for Experimental Candida Albicans Keratomycosis, Invest. Ophthal. Vis. Sci.," 44:2634-2643.
Shah et al., 2007, "Intravitreal bevacizumab (Avastin) for post laser anterior segment ischemia in aggressive posterior retinopathy of prematurity," Indian J. Ophthalmol., 55:75-76.
Silha et al., 2005, "Angiogenic factors are elevated in overweight and obese individuals," Int. J. Obes. 29:1308-1314.
Smith et al., 2007, "Expression of vascular endothelial growth factor and its receptors in rosacea," Br. J. Ophthalmol. 91:226-229.
Solovey et al., 1999, "Sickle Cell Anemia as a Possible State of Enhanced Anti-Apoptotic Tone: Survival Effect of Vascular Endothelial Growth Factor on Circulating and Unanchored Endothelial Cells," Blood 93:3824-3830.
Stompor et al., 2002, "Selected growth factors in peritoneal dialysis: their relationship to markers of inflammation, dialysis adequacy, residual renal function, and peritoneal membrane transport," Perit. Dial. Int. 22: 670-676.
Taichman et al., 1997, "Human neutrophils secrete vascular endothelial growth factor," J. Leukoc. Biol. 62:397-400.
Tasman et al., 2006, "Retinopathy of Prematurity: The Life of a Lifetime Disease," Am. J. Ophthalmol. 141:167-174.
The Eyetech Study Group, 2002, "Preclinical and phase 1a clinical evaluation of an anti-VEGF pegylated aptamer (eye001) for the treatment of exudative age related macular degeneration," Retina 22(2):143-152.
Thickett et al., 1999, "Vascular endothelial growth factor (VEGF) in inflammatory and malignant pleural effusions," Thorax, 54:707-710.
Ueda et al., 2001, "Vascular Endothelial Growth Factor and Its Receptors Expression in the Rat Eye," Acta Histochem. Cytochem. 34(5):329-335.
Uy et al., 2008, "Topical Bevacizumab and Ocular Surface Neovascularization in Patients With Stevens-Johnson Syndrome," Cornea, 27:70-73.
Verheul et al., 2000, "Targeting Vascular Endothelial Growth Factor Blockade: Ascites and Pleural Effusion Formation," Oncologist, 5:45-50.
Wang et al., 1998, "Presence and possible role of vascular endothelial growth factor in thyroid cell growth and function," J. Endocrinol., 157:5-12.
Wasilewska et al., 2006, "Glucocorticoid receptor and vascular endothelial growth factor in nephrotic syndrome," Acta Paediatrica, 95:587-593.
Zheng et al., 2001, "Contribution of Vascular Endothelial Growth Factor in the Neovascularization Process during the Pathogenesis of Herpetic Stromal Keratitis," J. Virol. 75(20):9828-9835.
Fava et al., 1994, "Vascular Permeability Factor/Endothelial Growth Factor (VPF/VEGF): Accumulation and Expression in Human Synovial Fluids and Rheumatoid Synovial Tissue," *J. Exp. Med.* 180(1): 341-346.
Gareth, 2007, "Medicinal Chemistry: An Introduction," Second Edition, John Wiley & Sons Ltd., pp. 75-80.
Kvanta et al., 1996, "Subfoveal Fibrovascular Membranes in Age-Related Macular Degeneration Express Vascular Endothelial Growth Factor," *Invest. Ophthalmol. Vis. Sci.* 37(9):1929-1934.
Lip et al., 2000, "Plasma VEGF and Soluble VEGF Receptor FLT-1 in Proliferative Retinopathy: Relationship to Endothelial Dysfunction and Laser Treatment," *Invest. Ophthalmol. Vis. Sci.* 41(8):2115-2119.
Office Action mailed Mar. 20, 2015 for U.S. Appl. No. 13/321,252, filed Mar. 9, 2012.
Office Action mailed Mar. 24, 2015 for U.S. Appl. No. 13/321,242, filed Mar. 9, 2012.
Office Action mailed Nov. 21, 2014 for U.S. Appl. No. 13/321,271, filed Mar. 23, 2012.
Xia et al., 2003, "Transgenic delivery of VEGF to mouse skin leads to an inflammatory condition resembling human psoriasis," *Blood* 102(1):161-168.

\* cited by examiner

METHODS FOR TREATING CANCER AND NON-NEOPLASTIC CONDITIONS

REFERENCE TO RELATED APPLICATIONS

This application is a national stage application of International Application No. PCT/US2010/036467, filed May 27, 2010, which claims the benefit of priority to U.S. Provisional Patent Application No. 61/181,653, filed May 27, 2009, each of which is incorporated herein by reference in its entirety and for all purposes.

STATEMENT REGARDING FEDERALLY SPONSORED RESEARCH OR DEVELOPMENT

Certain aspects of this invention may have been made with government support under Federal Award ID 1R43CA108330-01 awarded by the National Institutes of Health. The government may have certain rights in the invention.

1. INTRODUCTION

Compounds that selectively inhibit pathological production of human vascular endothelial growth factor (VEGF) and compositions comprising such Compounds are described. Compounds that inhibit viral replication or the production of viral RNA or DNA or viral protein and compositions comprising such Compounds are described. Also described are methods of reducing VEGF using such Compounds and methods for treating cancer and non-neoplastic conditions involving the administration of such Compounds. Further described are methods of inhibiting viral replication or the production of viral RNA or DNA or viral protein using such Compounds and methods for treating viral infections involving the administration of such Compounds. The Compounds may be administered as a single agent therapy or in combination with one or more additional therapies to a human in need of such treatments.

2. BACKGROUND

2.1 Cancer

Cancer is one of the most significant health conditions. In the United States, cancer is second only to heart disease in mortality accounting for one of four deaths. The incidence of cancer is widely expected to increase as the US population ages, further augmenting the impact of this condition.

The current treatment regimens for cancer established in the 1970s and 1980s, have not changed dramatically. These treatments, which include chemotherapy, radiation and other modalities including newer targeted therapies, have shown limited overall survival benefit when utilized in most advanced stage common cancers since, among other things, these therapies primarily target tumor bulk.

Standard oncology regimens have often been largely designed to administer the highest dose of irradiation or a chemotherapeutic agent without undue toxicity, i.e., often referred to as the "maximum tolerated dose" (MTD) or "no observed adverse effect level" (NOAEL). Many conventional cancer chemotherapies and conventional irradiation therapies exert their toxic effects on cancer cells largely by interfering with cellular mechanisms involved in cell growth and DNA replication. Chemotherapy protocols also often involve administration of a combination of chemotherapeutic agents in an attempt to increase the efficacy of treatment. Despite the availability of a large variety of chemotherapeutic agents, these therapies have many drawbacks. For example, chemotherapeutic agents are notoriously toxic due to non-specific side effects on fast-growing cells whether normal or malignant; e.g. chemotherapeutic agents cause significant, and often dangerous, side effects, including bone marrow depression, immunosuppression, and gastrointestinal distress, etc.

Other types of traditional cancer therapies include surgery, hormonal therapy, immunotherapy, anti-angiogenesis therapy, targeted therapy, and radiation treatment to eradicate neoplastic cells in a patient. All of these approaches can pose significant drawbacks for the patient including a lack of efficacy and toxicity. Accordingly, new therapies for improving the long-term prospect of cancer patients are needed.

2.2 Non-Neoplastic Conditions

Angiogenesis is implicated in the pathogenesis of a variety of non-neoplastic conditions, e.g., intraocular neovascular syndromes such as proliferative retinopathies or age-related macular degeneration (AMD), rheumatoid arthritis, and psoriasis.

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (Siemeister et al. (1998) Cancer Metastasis Rev., 17(2):241-248). However, these agents all have drawbacks in that they can cause toxic side effects in the patient and often are not curative of the non-neoplastic condition. Accordingly, new therapies for treating patients with non-neoplastic conditions that are associated with angiogenesis, particularly VEGF production, are needed.

2.3 Viral Conditions

As obligate intracellular parasites, viruses are intimately dependent upon the biological functions of their hosts. Small molecules that affect the host cell biological processes involved in viral replication or the production of viral RNA or DNA or viral protein may therefore inhibit a wide variety of viruses requiring these functions for essential events in the viral life cycle and therefore can be used for treatment of virus infection. Notably, molecules directly affecting host functions that are essential for viral replication or the production of viral RNA or DNA or viral protein should provide a high barrier to the emergence of resistant strains relative to classical antivirals that directly target viral enzymes.

An estimated 170 million people worldwide are reported to be infected with hepatitis C virus, of which at least 6 known genotypes are the causative agent of hepatitis C infection. Up to 80 percent of HCV infections lead to chronic liver infection, which in turn may result in severe liver diseases, including liver fibrosis, cirrhosis, and hepatocellular carcinoma (see Saito I, et al., Hepatitis C virus infection is associated with the development of hepatocellular carcinoma, *Proc Natl Acad Sci USA*, 1990, 87:6547-6549). References have described small molecule β-carboline compounds with antiviral activity against viruses such as human papillomavirus (HPV) (J F Miller et al, Bioorganic & Medicinal Chemistry Letters, 2010, 20(1):256-259), poliovirus (PV) and herpes simplex virus (ASN Formagio et al, European Journal of Medicinal Chemistry, 2009, 44(11):4695-4701). International Patent publications WO2006/015035 and WO2007/002051 describe β-carboline compounds with antiviral activity against human papillomavirus infection (HPV) and a flavivirus infections, including dengue virus, yellow fever virus, West Nile virus and hepatitis C virus (HCV) infection.

Accordingly, new small molecule therapies for treating patients with viral conditions, particularly dengue virus and HCV, are needed.

3. SUMMARY

Encompassed herein are compounds having the formula set forth in Section 5.1 ("Compound") and compositions comprising such Compounds. The Compounds can demonstrate one or more of the following activities: (a) selective inhibition of the pathological production of human VEGF; (b) inhibition of tumor angiogenesis, tumor-related inflammation, tumor-related edema and/or tumor growth; (c) prolongation of the G1/S phase of the cell cycle; (d) inhibition of angiogenesis and/or inflammation associated with a non-neoplastic condition; and/or (e) inhibition of a viral infection.

Methods for treating cancer as well as non-neoplastic conditions and viral infections are described, involving the administration of a Compound to a human subject in need of such treatment. Preferably, the Compound used in the therapeutic method demonstrates one or more of the following activities as determined in cell culture and/or animal model systems, such as those described herein: (a) selective inhibition of the pathological production of human VEGF; (b) inhibition of tumor angiogenesis, tumor-related inflammation, tumor-related edema and/or tumor growth; (c) prolongation of the G1/S phase of the cell cycle; (d) inhibition of angiogenesis and/or inflammation associated with a non-neoplastic condition; and/or (e) inhibition of viral infection. The Compound can be administered as a single agent therapy to a human in need of such treatment. Alternatively, the Compound can be administered in combination with one or more additional therapies to a human in need of such treatment. Such therapies may include the use of anti-cancer agents (e.g., cytotoxic agents, anti-angiogenesis agents, tyrosine kinase inhibitors or other enzyme inhibitors).

Despite differences in the bases for cancer, non-neoplastic conditions and viral infection, the therapies described herein should be effective because they are aimed at interfering with basic mechanisms required for manifestation of each disease (i.e., the pathological production of human VEGF, uncontrolled growth of tumors or inflammation or edema associated with tumors, the pathological angiogenesis or inflammation associated with a non-neoplastic condition, the pathological angiogenesis associated with cancer, or the biological processes involved in viral replication or the production of viral RNA or DNA or viral protein). While not bound by any theory, the therapies described are based, in part, on the pharmacodynamic activities of the Compounds as measured in cell culture and in animal models; in particular, these include: (a) selective inhibition of the pathological production of human VEGF; (b) inhibition of tumor angiogenesis, tumor-related inflammation, tumor-related edema, and/or tumor growth; (c) prolongation of the G1/S phase of the cell cycle of aberrantly proliferating cells and/or (d) inhibition of viral replication or the production of viral RNA or DNA or viral protein.

These pharmacologic activities contribute to limiting solid tumor growth or tumor-related inflammation, tumor-related edema and/or pathological angiogenesis, in several ways. For example, inhibition of pathological production of human VEGF by the tumor will inhibit tumor angiogenesis, thereby limiting vascularization and further growth of solid tumors. An additional benefit is achieved for tumors that respond to VEGF as a growth factor—in such cases, the Compound can limit proliferation of such tumor cells independent of their angiogenic status, that is angiogenesis and vascularization need not be present for the Compound to limit proliferation of the tumor cells. Because the process of tumorigenesis can result in inflammation and edema, a Compound may limit such inflammation or edema. Additionally, prolongation of the cell cycle may contribute to the induction of apoptotic death of the tumor cells, and/or allow for increased efficacy when the Compound is used in combination with a therapy or therapies (e.g., chemotherapeutic agents or radiation) that interfere with nucleic acid synthesis during the cell cycle (e.g., the G1/S phase). Because viral replication is directly dependent on host cells, a Compound that interferes with cellular molecular processes that participate in viral replication may inhibit one or more events of the viral life cycle and thus be used for treatment of a viral infection. Finally, a Compound that interferes with viral replication or the production of viral RNA or DNA or viral protein may inhibit relapse of one or more symptoms associated with recurrence of a viral infection.

Thus, in specific embodiments, the methods for treating cancer can result in inhibition or reduction of the pathological production of human VEGF (including intratumoral VEGF production), thus reducing VEGF concentrations in biological specimens of an afflicted subject; inhibition of tumor angiogenesis, tumor-related inflammation, tumor-related edema, and/or tumor growth in the subject; stabilization or reduction of tumor volume or tumor burden in the subject; stabilization or reduction of peritumoral inflammation or edema in the subject; reduction of the concentrations of angiogenic or inflammatory mediators in biological specimens (e.g., plasma, serum, cerebral spinal fluid, urine, or any other biofluids); and/or a delayed or prolonged late G1/S phase of the cell cycle (i.e., the period between the late resting or pre-DNA synthesis phase, and the early DNA synthesis phase) in tumor cells of the subject. In other specific embodiments, the methods of treating non-neoplastic conditions can result in the inhibition or reduction of pathological angiogenesis; the inhibition or reduction of plasma human VEGF concentrations in an afflicted subject; the inhibition or reduction in inflammation; and/or stabilization or reduction of the one or more symptoms of the non-neoplastic condition in the subject. In another specific embodiment, without being bound by any particular theory, the methods of treating a viral infection can result in interference with viral replication in infected cells in an afflicted subject and prevent or reduce the ability of the virus to appropriate the host apparatus and molecular processes in the subject.

Existing antiangiogenic therapies that have been developed for other diseases (e.g., certain cancers and retinopathies including macular degeneration and the like) are directed at globally neutralizing VEGF activity (e.g., using anti-VEGF antibodies), or inhibiting downstream effects of VEGF signaling (e.g., using tyrosine kinase inhibitors to block the signaling activity of the VEGF receptor). As a result, these existing antiangiogenic therapies neutralize or inhibit physiological or homeostatic VEGF, as well as pathologically produced human VEGF, activity resulting in side effects that, while tolerated for the treatment of life-threatening cancers or to prevent or slow the development of hearing loss or blindness, may not be acceptable for the treatment of certain cancers and non-neoplastic conditions. Since the Compounds used in the therapeutic methods described herein selectively inhibit pathologic production of human VEGF, and do not disturb the production of human VEGF under physiological conditions, side effects that are unacceptable for the treatment of cancer or non-neoplastic conditions may be reduced. Existing antiviral therapies are a combination of interferon and ribavirin, leading to variable outcomes among the six major HCV genotypes. However, only about one-half of all treated patients respond to this combination therapy. Since the Compounds used in the therapeutic methods described herein are small molecules that selectively inhibit viral replication or the production of viral RNA or DNA or viral protein, side effects that are unacceptable for standard antiviral treatment may be reduced.

The efficacy of the therapeutic intervention is supported by the data presented herein, demonstrating that the Compounds inhibit the pathological production of human VEGF (see Section 8.1 et. seq., infra); the Compounds inhibit tumor growth (see Section 8.2 et. seq., infra); the Compounds delay the cell cycle by prolonging the G1/S phase (see Section 8.3 et. seq., infra); and the Compounds inhibit viral replication or the production of viral RNA or DNA or viral protein by interfering with biological processes involved in viral replication or the production of viral RNA or DNA or viral protein (see Section 8.4 et. seq., infra).

3.1 Definitions

As used herein, the term "effective amount" in the context of administering a Compound to a subject with cancer refers to the amount of a Compound that results in a beneficial or therapeutic effect. In specific embodiments, an "effective amount" of a Compound refers to an amount of a Compound which is sufficient to achieve at least one, two, three, four or more of the following effects: (i) the reduction or amelioration of the severity of one or more symptoms associated with cancer; (ii) the reduction in the duration of one or more symptoms associated with cancer; (iii) the prevention in the recurrence of a tumor or one or more symptoms associated with cancer; (iv) the regression of cancer and/or one or more symptoms associated therewith; (v) the reduction in hospitalization of a subject; (vi) the reduction in hospitalization length; (vii) an increase in the survival of a subject; (viii) the inhibition of the progression of cancer and/or one or more symptoms associated therewith; (ix) the enhancement of or improvement of the therapeutic effect of another therapy; (x) a reduction in tumor vascularization before surgery; (xi) a reduction in the growth of a tumor or neoplasm; (xii) a decrease in tumor size (e.g., in volume or diameter); (xiii) a reduction in the formation of a newly formed tumor; (xiv) eradication, removal, or control of primary, regional and/or metastatic cancer; (xv) a decrease in the number or size of metastases; (xvi) a reduction in mortality; (xvii) an increase in tumor-free survival rate of patients; (xviii) an increase in relapse free survival; (xix) an increase in the number of patients in remission; (xx) a decrease in hospitalization rate; (xxi) the size of the tumor is maintained and does not increase or increases by less of the tumor after administration of a standard therapy as measured by conventional methods available to one of skill in the art, such as magnetic resonance imaging (MRI), dynamic contrast-enhanced MRI (DCE-MRI), X-ray, computed tomography (CT) scan, or a positron emission tomography scan; (xxii) the prevention of the development or onset of one or more symptoms associated with cancer; (xxiii) an increase in the length of remission in patients; (xxiv) the reduction in the number of one or more symptoms associated with cancer; (xxv) an increase in symptom-free survival of cancer patients; (xxvi) a decrease in the concentration of circulating VEGF in the plasma of a subject with cancer; (xxvii) a decrease in circulating tumor cells (CTCs) in the blood of a subject with cancer; (xxviii) a decrease in the concentration of VEGF-C, VEGF-D, P1GF, VEGFR-1, VEGFR-2, IL-6 and/or IL-8 in a biological specimen (e.g., the plasma, serum, urine or cerebrospinal fluid (CSF)) of a subject with cancer; (xxix) the inhibition or reduction in tumor vascularization following surgery; (xxx) improvement in neural function, e.g., hearing, balance, tinnitus, or vision; (xxxi) the inhibition or reduction in pathological production of human VEGF; (xxxii) the stabilization or reduction of peritumoral inflammation or edema in a subject; (xxxiii) the reduction of the concentration of VEGF or other angiogenic or inflammatory mediators (e.g., cytokines or interleukins) in biological specimens (e.g., plasma, serum, cerebral spinal fluid, urine, or any other biofluids); (xxxiv) the inhibition or decrease in tumor metabolism or perfusion; (xxxv) the inhibition or reduction in pathological angiogenesis or vascularization; (xxxvi) the improvement in quality of life as assessed by methods well known in the art, e.g., questionnaires; (xxxvii) ease in removal of tumors by reducing vascularization prior to surgery; and/or (xxxviii) an alteration (e.g., a decrease) in a marker for cancer (e.g., a decrease of prostate-specific antigen (PSA) in prostate cancer subjects). In specific embodiments, an "effective amount" of a Compound refers to an amount of a Compound specified in Section 5.6 below.

As used herein, the term "effective amount" in the context of administering a Compound to a subject with a non-neoplastic condition refers to the amount of a Compound that results in a beneficial or therapeutic effect. In specific embodiments, an "effective amount" of a Compound refers to an amount of a Compound which is sufficient to achieve at least one, two, three, four or more of the following effects: (i) the reduction or amelioration of the severity of a non-neoplastic condition and/or one or more symptoms associated therewith; (ii) the reduction in the duration of one or more symptoms associated with a non-neoplastic condition; (iii) the prevention in the recurrence of a one or more symptoms associated with a non-neoplastic condition; (iv) the regression of the non-neoplastic condition and/or one or more symptoms associated therewith; (v) the inhibition of the progression of a non-neoplastic condition and/or one or more symptoms associated therewith; (vi) the enhancement or improvement the therapeutic effect of another therapy; (vii) the prevention of the development or onset of one or more symptoms associated with a non-neoplastic condition; (viii) the reduction in the number of one or more symptoms associated with a non-neoplastic condition; (ix) a decrease in the concentration of circulating VEGF in the plasma of a subject with the non-neoplastic condition; (x) a decrease in the concentration of VEGF-C, VEGF-D, P1GF, VEGFR-1, VEGFR-2, IL-6 and/or IL-8 in a biological specimen (e.g., the plasma, serum, urine or CSF) of a subject with a non-neoplastic condition; (xi) the reduction in hospitalization of a subject; (xii) the reduction in hospitalization length; (xiii) an increase in the survival of a subject; (xiv) the enhancement or improvement of the therapeutic effect of another therapy; (xv) a decrease in hospitalization rate; (xvi) a decrease in pathological production of human VEGF; (xvii) the inhibition or reduction in pathological angiogenesis or vascularization; (xviii) the improvement in the quality of life as assessed, e.g., by questionnaires; (xix) a decrease in mortality; (xx) an increase in duration of survival; and/or (xv) an increase in survival rate. In specific embodiments, an "effective amount" of a Compound refers to an amount of a Compound specified in Section 5.6 below.

As used herein, the term "effective amount" in the context of administering a Compound to a subject with a viral infection refers to the amount of a Compound that results in a beneficial or therapeutic effect. In specific embodiments, an "effective amount" of a Compound refers to an amount of a Compound which is sufficient to achieve at least one, two, three, four or more of the following effects: (i) the reduction or amelioration of the severity of one or more symptoms associated with viral infection; (ii) the reduction in the duration of one or more symptoms associated with viral infection; (iii) the prevention in the recurrence of a viral infection or one or more symptoms associated with viral infection; (iv) the regression of viral infection and/or one or more symptoms associated therewith; (v) the inhibition of the progression of viral infection and/or one or more symptoms associated therewith; (vi) the enhancement of and/or improvement of the therapeutic effect of another antiviral therapy; (vii) a reduction in a viral titer; (viii) a reduction in the progression of viral infection; (ix) a reduction in viral sequestration and/or latency; (x) a decrease in viral proteins in the cells of a subject having a viral infection; (xi) an increase in relapse free infection; (xii) an increase in the number of patients in remission of viral infection; (xiii) a decrease in hospitalization rate associated with viral infection; (xiv) a decrease in organ transplant rate associated with viral infection; (xv) the prevention of the development or onset of one or more symptoms associated with viral infection; (xvi) an increase in the length of remission of viral infection in patients; (xvii) the reduction in the number of one or more symptoms associated with viral infection; (xviii) an increase in symptom-free survival of patients having a viral infection; (xix) a decrease in the concentration of circulating viral RNA or DNA or viral protein in the plasma of a subject having a viral infection; (xx) a decrease in viral replication in the cells of a subject having a viral infection; (xxi) a decrease in the concentration of viral RNA or DNA or viral protein in a biological specimen (e.g., the plasma, serum, urine or tissue of a subject having a viral infection; (xxii) the inhibition or reduction in viral re-infection following organ transplant; (xxiii) the inhibition or reduction in the occurrence of viral infection following a period of latency; (xxiv) improvement in organ function, e.g., liver cirrhosis; (xxv) a decrease in organ function pathology, e.g., liver failure; (xxvi) the inhibition or reduction in production of viral RNA or DNA or viral protein; (xxvii) the stabilization or reduction of viral replication in the cells of a subject; (xxviii) the reduction of the concentration of viral RNA or DNA or viral protein or other viral mediators (e.g., chemokines, cytokines or interleukins) in biological specimens (e.g., plasma, serum, urine, or any other biofluids or tissue specimens); (xxix) the decrease in production of viral proteins; (xxx) the inhibition or reduction in viral protein translation; (xxxi) the inhibition or reduction in viral RNA or DNA or viral protein synthesis; (xxxii) inhibition or prevention of the formation of a viral replication complex in a cell; (xxxiii) inhibition or prevention of the assembly of a viral replication complex in the endoplasmic reticulum (ER); (xxxiv) inhibition or prevention of the assembly and/or release of viral particles from cells; (xxxv) the improvement in quality of life after a viral infection as assessed by methods well known in the art, e.g., questionnaires; (xxxvi) ease in treating, preventing or amelioratiAng viral infection by oral delivery of a Compound; and/or (xxxvii) an alteration (e.g., a decrease) in a viral marker (e.g., a decrease of viral RNA or DNA or viral protein in a subject having a viral infection). In specific embodiments, an "effective amount" of a Compound refers to an amount of a Compound specified in Section 5.6 below.

As used herein, the term "elderly human" refers to a human 65 years or older.

As used herein, the term "human adult" refers to a human that is 18 years or older.

As used herein, the term "middle-aged human" refers to a human between the ages of 30 and 64.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

As used herein, the terms "subject" and "patient" are used interchangeably to refer to an individual being treated for cancer, a non-neoplastic condition or a viral infection. In a specific embodiment, the individual is a human. See Section 5.4 and 5.5 for more information concerning patients treated for cancer or a non-neoplastic condition in accordance with the methods provided herein.

As used herein, the terms "therapies" and "therapy" can refer to any protocol(s), method(s), compositions, formulations, and/or agent(s) that can be used in the prevention, treatment, management, or amelioration of a condition or disorder or one or more symptoms thereof (e.g., cancer or one or more symptoms or one or more conditions associated therewith; a non-neoplastic condition or one or more symptoms or one or more conditions associated therewith; or, a viral infection or one or more symptoms or one or more conditions associated therewith). In certain embodiments, the terms "therapies" and "therapy" refer to drug therapy such as chemotherapy, adjuvant therapy, radiation, surgery, biological therapy, supportive therapy, antiviral therapy and/or other therapies useful in treatment, management, prevention, or amelioration of a condition or disorder or one or more symptoms thereof (e.g., cancer or one or more symptoms or one or more conditions associated therewith; a non-neoplastic condition or one or more symptoms or one or more conditions associated therewith; or, a viral infection or one or more symptoms or one or more conditions associated therewith). In certain embodiments, the term "therapy" refers to a therapy other than a Compound or pharmaceutical composition thereof. In specific embodiments, an "additional therapy" and "additional therapies" refer to a therapy other than a treatment using a Compound or pharmaceutical composition thereof. In a specific embodiment, a therapy includes the use of a Compound as an adjuvant therapy. For example, using a Compound in conjunction with a drug therapy such as chemotherapy, biological therapy, surgery, supportive therapy, antiviral therapy and/or other therapies useful in treatment, management, prevention, or amelioration of a condition or disorder or one or more symptoms thereof (e.g., cancer or one or more symptoms or one or more conditions associated therewith; a non-neoplastic condition or one or more symptoms or one or more conditions associated therewith; or, a viral infection or one or more symptoms or one or more conditions associated therewith).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid.

Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein, the terms "Compound" or "Compound provided herein" generally refer to a compound described in Section 5.1, Section 6.24, and Table 1, and pharmaceutically acceptable salts, racemates and stereoisomers thereof. In one embodiment, the terms refer to a compound of Formula I, II, III or IV. In another embodiment, the terms refer to a compound of Formula Ia, IIa, IIIa or IVa. In a specific embodiment, the terms refer to a compound depicted in Table 1. In one embodiment, the terms refer to a Compound disclosed in WO2005/089764, e.g., Compounds in the table on pages 26-98; WO2006/113703, e.g., Compounds in the table on pages 29-102; WO2008/127715, e.g., Compounds in the table on pages 52-126; WO2008/127714, e.g., Compounds in the table on pages 48-123; and U.S. Provisional Patent Application 61/181,653, entitled: METHODS FOR TREATING CANCER AND NON-NEOPLASTIC CONDITIONS, filed May 27, 2009, all of which are herewith incorporated by reference in their entirety. In certain embodiments, the terms "Compound" or "Compound provided herein" refer to a stereoisomer of a compound described in Section 5.1. The "Compound" or "Compound provided herein" may comprise one or more asymmetric carbon atoms, i.e. n asymmetric carbon atoms, having either R or S configuration as determined by a person skilled in the art. In one embodiment, the terms refer to a particular enantiomer, such as an R or S enantiomer of a "Compound" or "Compound provided herein". In one embodiment, the terms refer to an R or S enantiomer of a compound of Formula I, II, III or IV. In another embodiment, the terms refer to an R or S enantiomer of a compound of Formula Ia, IIa, IIIa or IVa. In a specific embodiment, the terms refer to an R or S enantiomer of a compound depicted in Table 1. It is understood that the terms "Compound" or "Compound provided herein" encompass all possible stereoisomers that may be generated based on all asymmetric carbon atoms. For example, if a Compound has two (n=2) assymetric carbon atoms, the terms "Compound" or "Compound provided herein" encompass all four, i.e. $2^n=2^2=4$, stereoisomers (R,S; R,R; S,S; S;R). The "Compound" or "Compound provided herein" may be a substantially pure (e.g., about 90%, about 95%, about 98%, about 99%, or about 99.9% pure) single stereoisomer or a mixture of two or more stereoisomers.

As used herein, the terms "pathologic," "pathological" or "pathologically-induced," in the context of the production of VEGF described herein, refer to the stress-induced expression of VEGF protein. In one embodiment, oncongenic transformation-induced expression of VEGF protein by tumor cells or other cells in the tumor environment is encompassed by the terms. In another embodiment, hypoxia-induced expression of VEGF protein in a chronic or traumatic inflammatory condition is encompassed by the terms. In another embodiment, in response to environmental stimuli, cells that disregulate or overproduce VEGF protein is also encompassed by the terms. As applicable, expression of VEGF protein supports inflammation, angiogenesis and tumor growth. The inhibition or reduction in pathological production of VEGF protein by a Compound can be assessed in cell culture and/or animal models as described herein.

As used herein, the term "about" means a range around a given value wherein the resulting value is substantially the same as the expressly recited value. In one embodiment, "about" means within 25% of a given value or range. For example, the phrase "about 70% by weight" comprises at least all values from 52% to 88% by weight. In another embodiment, the term "about" means within 10% of a given value or range. For example, the phrase "about 70% by weight" comprises at least all values from 63% to 77% by weight. In another embodiment, the term "about" means within 7% of a given value or range. For example, the phrase "about 70% by weight" comprises at least all values from 65% to 75% by weight.

Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

As used herein, the term "viral infection" refers to one or more RNA viruses belonging to families Bunyaviridae, Coronaviridae, Filoviridae, Flaviviridae, Paramyxoviridae, Picornaviridae, Orthomyxoviridae or Rhabdoviridae. Other embodiments include one or more viruses belonging to families Hepadnaviridae, Reoviridae or Retroviridae. Another embodiment includes one or more DNA viruses belonging to families Adenoviridae, Herpesviridae, Papillomaviridae or Papovaviridae.

As used herein, the term "viral replication," in the context of viral infection, refers to production of viral RNA or DNA or production of one or more viral proteins from viruses using double-stranded (ds) DNA or RNA and/or single-stranded (ss) RNA and/or partial-double-stranded (ps) DNA or RNA and/or positive (+) strand RNA and/or negative (−) strand RNA. In one embodiment, the term includes viral DNA replication or viral RNA replication or viral RNA transcription and translation, resulting in the expression of one or more viral proteins by infected cells in tissues of a subject. In another embodiment, the term includes viral expression and/or sequestration and/or latency of viral proteins in chronic viral infection. In another embodiment, the term includes the effect of viruses on cellular biological processes to produce viral RNA or DNA or one or more viral proteins. As applicable, expression of one or more viral proteins may result in viral sequestration and/or latency, inflammation, organ failure and/or tumor growth. The inhibition or reduction in production of viral RNA or DNA or one or more viral proteins by a Compound can be assessed in cell culture and/or animal models as described herein.

As used herein, the term "viral replication complex," in the context of viral infection, refers to a membrane-associated complex composed of viral proteins, replicating RNA and altered cellular membranes where viral RNA is replicated.

4. DESCRIPTION OF THE DRAWINGS

FIG. 1. Dose Response of Compound 1205 and Compound #10: Inhibition of the Production of Hypoxia-Induced VEGF in HeLa Cells.

FIG. 2A-B. Effect of Compound 1205 on Intra-Tumor Human VEGF Levels.

FIG. 2A. Effect of treatment with vehicle and Compound 1205 on intra-tumor VEGF levels for Study #21 (target tumor size: 1200 mm³) and Study #23 (target tumor size: 1500 mm³). FIG. 2B. Intra-tumor VEGF levels normalized to tumor size.

FIG. 3. Effect of Compound 1205 on Levels of Homeostatic Plasma Human VEGF for Study #21 and Study #23.

FIG. 4. Inhibition of HT1080 Tumor Growth by Compound #10, 1205 and 1330. The symbol "++" represents a p value of p=0.051, signifying the difference in tumor size in Compound #10 treated mice from tumor size in vehicle-treated mice (Student's t-test) on Day 11. The symbol "*" represents a p value of p<0.05, signifying that the differences in tumor size in Compound 1205 (S,S diastereoisomer) treated mice were significantly different from tumor size in vehicle-treated mice and that the differences in tumor size in Compound 1205 (S,S diastereoisomer) treated mice were significantly different from tumor size in Compound 1330 (R,S diastereoisomer)-treated mice (ANOVA, multiple comparisons).

FIG. 5A-B. Cell Cycle Delay After Overnight Exposure to Compound 1205. Histograms depicting relative DNA content in HT1080 cells under normoxic conditions after treatment with Compound 1205 compared to vehicle. FIG. 5A. Histogram showing the effect of treatment with Compound 1205 at 10 nm. FIG. 5B. Histogram showing the effect of treatment with vehicle.

FIG. 6. Effect of Compound 1205 on Mouse Kidney VEGF Levels. Differences in VEGF levels are not statistically significant (p=0.38, ANOVA).

FIG. 7A-B. Effect of Compound #10 as monotherapy and in combination with a PI3-K inhibitor in a 786-0 Renal Cancer Cell Line. FIG. 7A. The effect of Compound #10 as monotherapy (test concentrations of 1 μM and 10 μM) and in combination with a PI3-K inhibitor (test concentrations of 1 μM and 10 μM) on protein expression in a series of Western blot analyses of lysates of various cell lines. FIG. 7B. The effect of Compound #10 as monotherapy and in combination with a PI3-K inhibitor on VEGF expression in a 786-0 Renal Cancer Cell.

FIG. 8A-B-C. Effect of Compound #10 as monotherapy on Protein Expression in Various Renal Cancer Cell Lines. FIG. 8A. The effect of Compound #10 as monotherapy on protein expression in a series of Western blot analyses of lysates of various cell lines from a 786-0 Renal Cancer Cell line. FIG. 8B. The effect of Compound #10 as monotherapy on protein expression in a series of Western blot analyses of lysates of various cell lines from a 769-P Renal Cancer Cell line. FIG. 8C. The effect of Compound #10 as monotherapy on protein expression in a series of Western blot analyses of lysates of various cell lines from a A498 Renal Cancer Cell line.

FIG. 9. Effect of Compound #10 monotherapy and combination therapy with Sunitinib on Tumor Volume in a VHL-Negative Tumor. Symbols for each agent represent the mean±SD for each treatment group (10 mice per group); where the symbol "*" represents a p value of p<0.05, signifying that the differences in tumor size in treated mice were significantly different from tumor size in vehicle-treated mice (ANOVA, multiple comparisons vs vehicle) from Day 7 through Day 57, at which time vehicle-treated mice were taken off study; where the symbol "#" represents a p value of p<0.05, signifying that the differences in tumor size in treated mice were significantly different from tumor size in Compound #10-treated mice (ANOVA, multiple comparisons vs Compound #10) from Day 33 through Day 88, at which time Compound #10-treated mice were taken off study; and, where the symbol "@" represents a p value of p<0.05, signifying that the differences in tumor size in sunitinib-treated or rapamycin-treated mice were significantly different from tumor size in their respective combination-treated mice (ANOVA, multiple comparisons) from Day 63 through Day 119, at which time combination-treated mice were taken off study. The Abbreviations are defined as follows: PO=oral dosing, QD=once per day, SE=standard error.

FIG. 10. Effect of Compound #10 monotherapy and combination therapy with Sunitinib on Body Weight in a VHL-Negative Tumor. Symbols for each agent represent the mean±SD for each treatment group (10 mice per group); where the symbol "*" represents a p value of p<0.05, signifying that the differences in tumor size in treated mice were significantly different from tumor size in vehicle-treated mice (ANOVA, multiple comparisons vs vehicle) from Day 7 through Day 57, at which time vehicle-treated mice were taken off study; where the symbol "#" represents a p value of p<0.05, signifying that the differences in tumor size in treated mice were significantly different from tumor size in Compound #10-treated mice (ANOVA, multiple comparisons vs Compound #10) from Day 33 through Day 88, at which time Compound #10-treated mice were taken off study; and, where the symbol "@" represents a p value of p<0.05, signifying that the differences in tumor size in sunitinib-treated or rapamycin-treated mice were significantly different from tumor size in their respective combination-treated mice (ANOVA, multiple comparisons) from Day 63 through Day 119, at which time combination-treated mice were taken off study. The Abbreviations are defined as follows: PO=oral dosing, QD=once per day, SE=standard error.

FIG. 11. Effect of Compound #10 monotherapy and combination therapy with Rapamycin on Tumor Volume in a VHL-Negative Tumor. Symbols for each agent represent the mean±SD for each treatment group (10 mice per group). The Abbreviations are defined as follows: PO=oral dosing, QD=once per day, SE=standard error.

FIG. 12. Effect of Compound #10 monotherapy and combination therapy with Rapamycin on Body Weight in a VHL-Negative Tumor. Symbols for each agent represent the mean±SD for each treatment group (10 mice per group); where the symbol "*" represents a p value of p<0.05, signifying that the differences in tumor size in treated mice were significantly different from tumor size in vehicle-treated mice (ANOVA, multiple comparisons vs vehicle) from Day 7 through Day 57, at which time vehicle-treated mice were taken off study; where the symbol "#" represents a p value of p<0.05, signifying that the differences in tumor size in treated mice were significantly different from tumor size in Compound #10-treated mice (ANOVA, multiple comparisons vs Compound #10) from Day 33 through Day 88, at which time Compound #10-treated mice were taken off study; and, where the symbol "@" represents a p value of p<0.05, signifying that the differences in tumor size in sunitinib-treated or rapamycin-treated mice were significantly different from tumor size in their respective combination-treated mice (ANOVA, multiple comparisons) from Day 63 through Day 119, at which time combination-treated mice were taken off study. The Abbreviations are defined as follows: PO=oral dosing, QD=once per day, SE=standard error.

FIG. 13. Effect of Compound #10 monotherapy and combination therapy with Sunitinib on Tumor Volume in a VHL-Positive Tumor. Symbols for each agent represent the mean±SD for each treatment group (10 mice per group). The Abbreviations are defined as follows: PO=oral dosing, QD=once per day, SE=standard error.

FIG. 14. Effect of Compound #10 monotherapy and combination therapy with Sunitinib on Body Weight in a VHL-Positive Tumor. Symbols for each agent represent the mean±SD for each treatment group (10 mice per group). The Abbreviations are defined as follows: PO=oral dosing, QD=once per day, SE=standard error.

FIG. 15. Effect of Compound #10 monotherapy and combination therapy with Rapamycin on Tumor Volume in a VHL-Positive Tumor. Symbols for each agent represent the mean±SD for each treatment group (10 mice per group). The Abbreviations are defined as follows: PO=oral dosing, QD=once per day, SE=standard error.

FIG. 16. Effect of Compound #10 monotherapy and combination therapy with Rapamycin on Body Weight in a VHL-Positive Tumor. Symbols for each agent represent the mean±SD for each treatment group (10 mice per group); where the symbol "*" represents a p value of p<0.05, signifying that the differences in tumor size in treated mice were significantly different from tumor size in vehicle-treated mice (ANOVA, multiple comparisons vs vehicle) from Day 11 through Day 25, at which time vehicle-treated mice were taken off study; where the symbol "#" represents a p value of p<0.05, signifying that the differences in tumor size in treated mice were significantly different from tumor size in Compound #10-treated mice (ANOVA, multiple comparisons vs Compound #10); and, where the symbol "α" represents a p value of p<0.05, signifying that the differences in tumor size in sunitinib-treated or rapamycin-treated mice were significantly different from tumor size in their respective combination-treated mice (ANOVA, multiple comparisons). The Abbreviations are defined as follows: PO=oral dosing, QD=once per day, SE=standard error.

FIG. 17. Effect of Compound #10 monotherapy on target plasma concentrations. Target plasma trough levels between 550 and 1010 ng/mL have been achieved in patients having a variety of cancers.

FIG. 18. Effect of Compound #10 monotherapy and combination therapy with docetaxel on target plasma concentrations. Target plasma trough levels between 550 and 1010 ng/mL have been achieved in patients having a variety of cancers. The "*" symbol represents that the docetaxel PK profile is consistent with historical data (see, Bruno, et al., 1994, JCO, 16:187)

FIG. 19. Effect of Compound #10 monotherapy in a patient having thyroid cancer. In a patient having thyroid cancer, after three previous therapeutic modalities, the result of monotherapy treatment with Compound #10 has led to stabilization and reduction in a number of clinical parameters and tumor markers.

FIG. 20. Effect of Compound #10 monotherapy in a patient having melanoma. In a patient having melanoma, after two previous therapeutic modalities, the result of monotherapy treatment with Compound #10 has led to stabilization and reduction in a number of clinical parameters and tumor markers.

FIG. 21. Effect of Compound #10 monotherapy in a patient having chondrosarcoma. In a patient having chondrosarcoma, after one previous therapeutic modalities, the result of monotherapy treatment with Compound #10 has led to stabilization and reduction in a number of clinical parameters and tumor markers.

FIG. 22. Effect of Compound #10 monotherapy in a patient having cholangiocarcinoma. In a patient having cholangiocarcinoma, after four previous therapeutic modalities, the result of monotherapy treatment with Compound #10 has led to stabilization for a tumor marker.

FIG. 23. Effect of Compound #10 monotherapy and combination therapy with docetaxel in a patient having head and neck cancer. In a patient having head and neck cancer with metastasis to the lung, after previous radiotherapy and no prior chemotherapy, the result of treatment with a combination of Compound #10 and docetaxel led to stabilization and reduction in a number of clinical parameters and tumor markers. The arrow symbol represents the timepoint at which docetaxel was reduced to 60 mg/m².

FIG. 24. Effect of Compound #10 monotherapy in a patient jejunal adenocarcinoma. In a patient having cholangiocarcinoma with metastasis to the lung, after five previous therapeutic modalities for the metastasis, the result of monotherapy treatment with Compound #10 is presented.

FIG. 25. Use of Compound #10 monotherapy at various concentrations for treatment of various cancers. The scope of cancers being treated using Compound #10 monotherapy, where the data represented by the arrow symbol indicate individual patients continuing in therapy.

5. DETAILED DESCRIPTION

Encompassed herein are Compounds capable of inhibiting the pathological production of human VEGF. Also encompassed herein are methods of treating cancer and non-neoplastic conditions using the Compounds as well as methods of using the Compounds to reduce pathological human VEGF production. Further encompassed herein are methods of treating viral infections using the Compounds as well as methods of using the Compounds to inhibit or reduce viral replication and/or production of viral RNA or DNA or viral protein.

5.1 Compounds

In one embodiment, provided herein are Compounds having Formula (I):

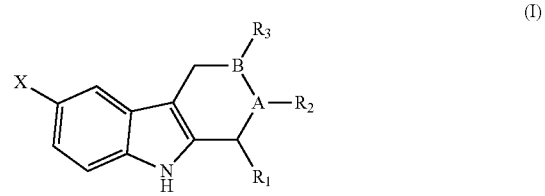

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_5$ alkoxy optionally substituted with aryl;

A is CH or N;

B is CH or N, with the proviso that at least one of A or B is N, and that when A is N, B is CH;

$R_1$ is hydroxyl; $C_1$ to $C_8$ alkyl optionally substituted with alkylthio, 5 to 10 membered heteroaryl, or aryl optionally substituted with one or more independently selected $R_o$ substituents; $C_2$ to $C_8$ alkynyl; $C_2$ to $C_8$ alkynyl; 3 to 12 membered heterocycle optionally substituted with one or more substituents independently selected from halogen, oxo, amino, alkylamino, acetamino, thio, or alkylthio; 5 to 12 membered heteroaryl optionally substituted with one or more substituents independently selected from halogen, oxo, amino, alkylamino, acetamino, thio, or alkylthio; or aryl, optionally substituted with one or more independently selected $R_o$ substituents;

$R_o$ is a halogen; cyano; nitro; sulfonyl optionally substituted with $C_1$ to $C_6$ alkyl or 3 to 10 membered heterocycle; amino optionally substituted with $C_1$ to $C_6$ alkyl, —C(O)—$R_b$, —C(O)O—$R_b$, sulfonyl, alkylsulfonyl, 3 to 10 membered heterocycle optionally substituted with —C(O)O—$R_n$; —C(O)—NH—$R_b$; 5 to 6 membered heterocycle; 5 to 6 membered heteroaryl; $C_1$ to $C_6$ alkyl optionally substituted with one or more substituents independently selected from hydroxyl, halogen, amino, or 3 to 12 membered heterocycle wherein amino and 3 to 12 membered heterocycle are optionally substituted with one or more $C_1$ to $C_4$ alkyl substituents optionally substituted with one or more substituents independently selected from $C_1$ to $C_4$ alkoxy, amino, alkylamino, or 5 to 10 membered heterocycle; —C(O)—$R_n$; or —O$R_a$;

$R_a$ is hydrogen; $C_2$ to $C_8$ alkylene; —C(O)—$R_n$; —C(O)O—$R_b$; —C(O)—NH—$R_b$; $C_3$-$C_{14}$cycloalkyl; aryl; heteroaryl; heterocyclyl; $C_1$ to $C_8$ alkyl optionally substituted with one or more substituents independently selected from hydroxyl, halogen, $C_1$ to $C_4$ alkoxy, amino, alkylamino, acetamide, —C(O)—$R_b$, —C(O)O—$R_b$, aryl, 3 to 12 membered heterocycle, or 5 to 12 membered heteroaryl, further wherein the alkylamino is optionally substituted with hydroxyl, $C_1$ to $C_4$ alkoxy, or 5 to 12 membered heteroaryl optionally substituted with $C_1$ to $C_4$ alkyl, further wherein the acetamide is optionally substituted with $C_1$ to $C_4$ alkoxy, sulfonyl, or alkylsulfonyl, further wherein the 3 to 12 membered heterocycle is optionally substituted with $C_1$ to $C_4$ alkyl optionally substituted with hydroxyl, —C(O)—$R_n$, —C(O)O—$R_a$, or oxo, further wherein the amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

$R_b$ is hydroxyl; amino; alkylamino optionally substituted with hydroxyl, amino, alkylamino, $C_1$ to $C_4$ alkoxy, 3 to 12 membered heterocycle optionally substituted with one or more independently selected $C_1$ to $C_6$ alkyl, oxo, —C(O)O—$R_n$, or 5 to 12 membered heteroaryl optionally substituted with $C_1$ to $C_4$ alkyl; $C_1$ to $C_4$ alkoxy; $C_2$ to $C_8$ alkenyl; $C_2$ to $C_8$ alkynyl; aryl, wherein the aryl is optionally substituted with one or more substituents independently selected from halogen or $C_1$ to $C_4$ alkoxy; 5 to 12 membered heteroaryl; 3 to 12 membered heterocycle optionally substituted with one or more substituents independently selected from acetamide, —C(O)O—$R_n$, 5 to 6 membered heterocycle, or $C_1$ to $C_6$ alkyl optionally substituted with hydroxyl, $C_1$ to $C_4$ alkoxy, amino, or alkylamino; or $C_1$ to $C_8$ alkyl optionally substituted with one or more substituents independently selected from $C_1$ to $C_4$ alkoxy, aryl, amino, or 3 to 12 membered heterocycle, wherein the amino and 3 to 12 membered heterocycle are optionally substituted with one or more substituents independently selected from $C_1$ to $C_6$ alkyl, oxo, or —C(O)O—$R_n$;

$R_2$ is hydrogen; hydroxyl; 5 to 10 membered heteroaryl; $C_1$ to $C_8$ alkyl optionally substituted with hydroxyl, $C_1$ to $C_4$ alkoxy, 3 to 10 membered heterocycle, 5 to 10 membered heteroaryl, or aryl; —C(O)—$R_c$; —C(O)O—$R_d$; —C(O)—N($R_d R_d$); —C(S)—N($R_d R_d$); —C(S)—O—$R_e$; —S($O_2$)—$R_e$; —C(N$R_e$)—S—$R_e$; or —C(S)—S—$R_f$;

$R_c$ is hydrogen; amino optionally substituted with one or more substituents independently selected from $C_1$ to $C_6$ alkyl or aryl; aryl optionally substituted with one or more substituents independently selected from halogen, haloalkyl, hydroxyl, $C_1$ to $C_4$ alkoxy, or $C_1$ to $C_6$ alkyl; —C(O)—$R_n$; 5 to 6 membered heterocycle optionally substituted with —C(O)—$R_n$; 5 to 6 membered heteroaryl; thiazoleamino; $C_1$ to $C_8$ alkyl optionally substituted with one or more substituents independently selected from halogen, $C_1$ to $C_4$ alkoxy, phenyloxy, aryl, —C(O)—$R_n$, —O—C(O)—$R_n$, hydroxyl, or amino optionally substituted with —C(O)O—$R_n$;

$R_d$ is independently hydrogen; $C_2$ to $C_8$ alkenyl; $C_2$ to $C_8$ alkynyl; aryl optionally substituted with one or more substituents independently selected from halogen, nitro, $C_1$ to $C_6$ alkyl, —C(O)O—$R_e$, or —O$R_e$; or $C_1$ to $C_8$ alkyl optionally substituted with one or more substituents independently selected from halogen, $C_1$ to $C_4$ alkyl, $C_1$ to $C_4$ alkoxy, phenyloxy, aryl, 5 to 6 membered heteroaryl, —C(O)—$R_n$, —C(O)O—$R_n$, or hydroxyl, wherein the aryl is optionally substituted with one or more substituents independently selected from halogen or haloalkyl;

$R_e$ is hydrogen; $C_1$ to $C_6$ alkyl optionally substituted with one or more substituents independently selected from halogen or alkoxy; or aryl optionally substituted with one or more substituents independently selected from halogen or alkoxy;

$R_f$ is $C_1$ to $C_6$ alkyl optionally substituted with one or more substituents independently selected from halogen, hydroxyl, $C_1$ to $C_4$ alkoxy, cyano, aryl, or —C(O)—$R_n$, wherein the alkoxy is optionally substituted with one or more $C_1$ to $C_4$ alkoxy substituents and the aryl is optionally substituted with one or more substituents independently selected from halogen, hydroxyl, $C_1$ to $C_4$ alkoxy, cyano, or $C_1$ to $C_6$ alkyl;

$R_n$ is hydroxyl, $C_1$ to $C_4$ alkoxy, amino, or $C_1$ to $C_6$ alkyl;

$R_3$ is hydrogen or —C(O)—$R_g$; and $R_g$ is hydroxyl; amino optionally substituted with cycloalkyl or 5 to 10 membered heteroaryl; or 5 to 10 membered heterocycle, wherein the 5 to 10 membered heterocycle is optionally substituted with —C(O)—$R_n$, with the proviso that the compound of Formula (I) is other than:

(R)-1-(benzo[d][1,3]dioxol-5-yl)-2,3,4,9-tetrahydro-1H-pyrido[3,4-b]indole, 1-(benzo[d][1,3]dioxol-5-yl)-N-benzyl-3,4-dihydro-1H-pyrido[3,4-b]indole-2(9H)-carbothioamide, (R)-1-(benzo[d][1,3]dioxol-5-yl)-N-benzyl-3,4-dihydro-1H-pyrido[3,4-b]indole-2(9H)-carbothioamide, 1-phenyl-2,3,4,9-tetrahydro-1H-pyrido[3,4-b]indole, (R)-1-(benzo[d][1,3]dioxol-5-yl)-N-benzyl-3,4-dihydro-1H-pyrido[3,4-b]indole-2(9H)-carboxamide, N-benzyl-1-phenyl-3,4-dihydro-1H-pyrido[3,4-b]indole-2(9H)-carboxamide, N,1-diphenyl-3,4-dihydro-1H-pyrido[3,4-b]indole-2(9H)-carboxamide, N-(naphthalen-1-yl)-1-phenyl-3,4-dihydro-1H-pyrido[3,4-b]indole-2(9H)-carboxamide, 1-(benzo[d][1,3]dioxol-5-yl)-N-cyclohexyl-3,4-dihydro-1H-pyrido[3,4-b]indole-2(9H)-carboxamide, 1-(benzo[d][1,3]dioxol-5-yl)-N-phenyl-3,4-dihydro-1H-pyrido[3,4-b]indole-2(9H)-carboxamide, 1-(3-chloro-4-methoxyphenyl)-N-phenyl-3,4-dihydro-1H-pyrido[3,4-b]indole-2(9H)-carboxamide, (R)-1-(benzo[d][1,3]dioxol-5-yl)-N—((R)-1-phenylethyl)-3,4-dihydro-1H-pyrido[3,4-b]indole-2(9H)-carboxamide, (R)-1-(benzo[d][1,3]dioxol-5-yl)-N—((S)-1-phenylethyl)-3,4-dihydro-1H-pyrido[3,4-b]indole-2(9H)-carboxamide, (R)-1-(benzo[d][1,3]dioxol-5-yl)-N-benzoyl-3,4-dihydro-1H-pyrido[3,4-b]indole-2(9H)-carboxamide, (R)—N-(1-(benzo[d][1,3]dioxol-5-yl)-2,3,4,9-tetrahydro-1H-pyrido[3,4-b]indole-2-carbonothioyl)benzamide, benzyl 1-(benzo[d][1,3]dioxol-5-yl)-3,4-dihydro-1H-pyrido[3,4-b]indole-2(9H)-carboxylate, (R)-benzyl 1-(benzo[d][1,3]dioxol-5-yl)-3,4-dihydro-1H-pyrido[3,4-b]indole-2(9H)-carboxylate,
methyl 1-phenyl-3,4-dihydro-1H-pyrido[3,4-b]indole-2(9H)-carboxylate,
methyl 5-oxo-5-(1-phenyl-3,4-dihydro-1H-pyrido[3,4-b]indol-2(9H)-yl)pentanoate,
5-(1-(3-chloro-4-methoxyphenyl)-3,4-dihydro-1H-pyrido[3,4-b]indol-2(9H)-yl)-5-oxopentanoic acid,
5-(1-(benzo[d][1,3]dioxol-5-yl)-3,4-dihydro-1H-pyrido[3,4-b]indol-2(9H)-yl)-5-oxopentanoic acid,
3-(2-aminophenyl)-1-(1-(benzo[d][1,3]dioxol-5-yl)-3,4-dihydro-1H-pyrido[3,4-b]indol-2(9H)-yl)propan-1-one,
(R)-1-(benzo[d][1,3]dioxol-5-yl)-N-(2-chlorobenzyl)-3,4-dihydro-1H-pyrido[3,4-b]indole-2(9H)-carbothioamide,
(R)-1-(benzo[d][1,3]dioxol-5-yl)-N-(2,4-dichlorobenzyl)-3,4-dihydro-1H-pyrido[3,4-b]indole-2(9H)-carbothioamide,
(R)-1-(benzo[d][1,3]dioxol-5-yl)-N-(2-fluorobenzyl)-3,4-dihydro-1H-pyrido[3,4-b]indole-2(9H)-carbothioamide,
(R)-1-(benzo[d][1,3]dioxol-5-yl)-N—((S)-1-phenylethyl)-3,4-dihydro-1H-pyrido[3,4-b]indole-2(9H)-carbothioamide,
(R)-4-((1-(benzo[d][1,3]dioxol-5-yl)-2,3,4,9-tetrahydro-1H-pyrido[3,4-b]indole-2-carbothioamido)methyl)benzoic acid,
(R)-methyl 4-((1-(benzo[d][1,3]dioxol-5-yl)-2,3,4,9-tetrahydro-1H-pyrido[3,4-b]indole-2-carbothioamido)methyl)benzoate,
(R)-3-((1-(benzo[d][1,3]dioxol-5-yl)-2,3,4,9-tetrahydro-1H-pyrido[3,4-b]indole-2-carbothioamido)methyl)benzoic acid,
(R)-methyl 3-((1-(benzo[d][1,3]dioxol-5-yl)-2,3,4,9-tetrahydro-1H-pyrido[3,4-b]indole-2-carbothioamido)methyl)benzoate,
(R)-1-(benzo[d][1,3]dioxol-5-yl)-N-(4-chloro-3-(trifluoromethyl)phenyl)-3,4-dihydro-1H-pyrido[3,4-b]indole-2(9H)-carbothioamide,
(R)-1-(benzo[d][1,3]dioxol-5-yl)-N-(2-(trifluoromethyl)phenyl)-3,4-dihydro-1H-pyrido[3,4-b]indole-2(9H)-carbothioamide,
(R)-1-(benzo[d][1,3]dioxol-5-yl)-N-(3-fluorobenzyl)-3,4-dihydro-1H-pyrido[3,4-b]indole-2(9H)-carbothioamide,
(R)-1-(benzo[d][1,3]dioxol-5-yl)-N-(4-chlorobenzyl)-3,4-dihydro-1H-pyrido[3,4-b]indole-2(9H)-carbothioamide,
(R)-1-(benzo[d][1,3]dioxol-5-yl)-N-(3,4-dichlorobenzyl)-3,4-dihydro-1H-pyrido[3,4-b]indole-2(9H)-carbothioamide,
(R)-1-(benzo[d][1,3]dioxol-5-yl)-N-(4-fluorobenzyl)-3,4-dihydro-1H-pyrido[3,4-b]indole-2(9H)-carbothioamide,
(R)-1-(benzo[d][1,3]dioxol-5-yl)-N-(3,4-dimethylbenzyl)-3,4-dihydro-1H-pyrido[3,4-b]indole-2(9H)-carbothioamide,
(R)-1-(benzo[d][1,3]dioxol-5-yl)-N-(3-chlorobenzyl)-3,4-dihydro-1H-pyrido[3,4-b]indole-2(9H)-carbothioamide,
(R)-1-(benzo[d][1,3]dioxol-5-yl)-N-(naphthalen-1-ylmethyl)-3,4-dihydro-1H-pyrido[3,4-b]indole-2(9H)-carbothioamide,
(3,4-difluorophenyl)-(1-phenyl-1,3,4,9-tetrahydro-(3-carbolin-2-yl)-methanone,
6-methoxy-1,2,3,4-tetrahydronorharmane,
1,2,3,4-tetrahydronorharman-3-carboxylic acid,
6-methoxy-1,2,3,4-tetrahydronorharman-1-carboxylic acid,
1-(4-methoxyphenyl)-1,2,3,4-tetrahydronorharman-3-carboxylic acid,
1-methyl-1,2,3,4-tetrahydronorharman-3-carboxylic acid,
1-methyl-1,2,3,4-tetrahydronorharman-1,3-dicarboxylic acid,
1-(diethylmethyl)-1,2,3,4-tetrahydronorharman-3-carboxylic acid,
(6-bromo-1,2,3,4-tetrahydronorharman-1-yl)-3-propionic acid,
1-isobutyl-1,2,3,4-tetrahydronorharman-3-carboxylic acid,
1-phenyl-1,2,3,4-tetrahydronorharman-3-carboxylic acid,
1-propyl-1,2,3,4-tetrahydronorharman-3-carboxylic acid,
1-methyl-1-methoxycarbonyl-6-benzyloxy-1,2,3,4-tetrahydronorharmane,
1-methyl-1-methoxycarbonyl-6-methoxy-1,2,3,4-tetrahydronorharmane,
1-methyl-1-methoxycarbonyl-6-hydroxy-1,2,3,4-tetrahydronorharmane,
1-methyl-1-methoxycarbonyl-6-chloro-1,2,3,4-tetrahydronorharmane,
1-methyl-1-methoxycarbonyl-6-bromo-1,2,3,4-tetrahydronorharmane,
1-methyl-2-N-acetyl-6-methoxy-1,2,3,4-tetrahydro-β-carboline,
2-N-acetyl-1,2,3,4-tetrahydro-β-carboline,
1-methyl-2-N-acetyl-6-methoxy-1,2,3,4-tetrahydro-β-carboline,
4-chlorobenzyl(1S,3R)-1-(2,4-dichlorophenyl)-1,2,3,4-tetrahydro-β-carboline-3-carboxamide,
(3R)-1-(1-benzylindol-3-yl)-2-tert-butoxycarbonyl-1,2,3,4-tetrahydro-β-carboline-3-carboxylic acid,
(3R)-1-(1-butylindol-3-yl)-2-tert-butoxycarbonyl-1,2,3,4-tetrahydro-β-carboline-3-carboxylic acid,
(1S,3R)-1-(indol-3-yl)-2-tert-butoxycarbonyl-1,2,3,4-tetrahydro-β-carboline-3-carboxylic acid,
(1S,3R)-1-(1-methylindol-3-yl)-2-tert-butoxycarbonyl-1,2,3,4-tetrahydro-β-carboline-3-carboxylic acid,
benzothiazol-2-yl(1S,3R)-1-cyclohexyl-2-tert-butoxycarbonyl-1,2,3,4-tetrahydro-β-carboline-3-carboxylic acid,
benzothiazol-2-yl(1S,3R)-1-cyclohexyl-1,2,3,4-tetrahydro-β-carboline-3-carboxylic acid,
1-(4-chlorophenyl)-1,2,3,4-tetrahydro-β-carboline,
1-(4-bromophenyl)-1,2,3,4-tetrahydro-β-carboline,
1-(4-nitrophenyl)-1,2,3,4-tetrahydro-β-carboline,
1-(4-dimethylaminophenyl)-1,2,3,4-tetrahydro-β-carboline,
1-(4-diethylaminophenyl)-1,2,3,4-tetrahydro-β-carboline,
1-(2,4-dimethoxyphenyl)-1,2,3,4-tetrahydro-β-carboline,
1-(3,4-dimethoxyphenyl)-1,2,3,4-tetrahydro-β-carboline,
1-(2,5-dimethoxyphenyl)-1,2,3,4-tetrahydro-β-carboline,
1-(3,5-dimethoxyphenyl)-1,2,3,4-tetrahydro-β-carboline,
1-(3,4,5-trimethoxyphenyl)-1,2,3,4-tetrahydro-β-carboline,
1-(4-nitrobenzo[d][1,3]dioxol-5-yl)-1,2,3,4-tetrahydro-β-carboline,
1-(2-fluorenyl)-1,2,3,4-tetrahydro-β-carboline,
1-(9-ethyl-9H-carbazol-3-yl)-1,2,3,4-tetrahydro-β-carboline,
6-chloro-1-(4-methylphenyl)-2,3,4,9-tetrahydro-1H-β-carboline,
methyl 6-chloro-1-(4-methylphenyl)-1,3,4,9-tetrahydro-2H-β-carboline-2-carboxylate,
6-chloro-1-(4-methylphenyl)-2-(3-phenylpropanoyl)-2,3,4,9-tetrahydro-1H-β-carboline,
phenylmethyl 6-chloro-1-(4-methylphenyl)-1,3,4,9-tetrahydro-2H-β-carboline-2-carboxylate,
6-fluoro-1-(4-methylphenyl)-2,3,4,9-tetrahydro-1H-β-carboline, methyl 6-fluoro-1-(4-methylphenyl)-1,3,4,9-tetrahydro-2H-β-carboline-2-carboxylate,
6-fluoro-1-(4-methylphenyl)-2-(3-phenylpropanoyl)-2,3,4,9-tetrahydro-1H-β-carboline,
phenylmethyl 6-fluoro-1-(4-methylphenyl)-1,3,4,9-tetrahydro-2H-β-carboline-2-carboxylate, 6-bromo-1-(4-methylphenyl)-2,3,4,9-tetrahydro-1H-β-carboline,
methyl 6-bromo-1-(4-methylphenyl)-1,3,4,9-tetrahydro-2H-β-carboline-2-carboxylate,
6-bromo-1-(4-methylphenyl)-2-(3-phenylpropanoyl)-2,3,4,9-tetrahydro-1H-β-carboline,
phenylmethyl 6-bromo-1-(4-methylphenyl)-1,3,4,9-tetrahydro-2H-β-carboline-2-carboxylate,
(1R)-6-chloro-1-(4-methylphenyl)-2-(3-phenylpropanoyl)-2,3,4,9-tetrahydro-1H-β-carboline,
(1S)-6-chloro-1-(4-methylphenyl)-2-(3-phenylpropanoyl)-2,3,4,9-tetrahydro-1H-β-carboline,
1-(4-methylphenyl)-2-(methylsulfonyl)-2,3,4,9-tetrahydro-1H-β-carboline,
2-acetyl-1-(4-methylphenyl)-2,3,4,9-tetrahydro-1H-β-carboline,
1-(4-methylphenyl)-2-(3-phenylpropanoyl)-2,3,4,9-tetrahydro-1H-β-carboline,
6-(methyloxy)-1-(4-methylphenyl)-2-(3-phenylpropanoyl)-2,3,4,9-tetrahydro-1H-β-carboline,
6-methyl-1-(4-methylphenyl)-2-(3-phenylpropanoyl)-2,3,4,9-tetrahydro-1H-β-carboline,
(1R/1S)-1-(2,3-dihydro-1-benzofuran-5-yl)-2,3,4,9-tetrahydro-1H-β-carboline, or
1-(1,3-benzodioxol-5-yl)-2-(2-pyrimidinyl)-2,3,4,9-tetrahydro-1H-β-carboline.

As will be evident to one of skill in the art, Compounds provided herein comprise at least one stereocenter, and may exist as a racemic mixture or as an enantiomerically pure composition. In one embodiment, a Compound provided herein is the (S) isomer, in an enantiomerically pure composition. In certain embodiments, the enantiomeric excess (e.e.) is about 90%, about 95%, about 99% or about 99.9% or greater.

In another embodiment, provided herein are Compounds having Formula (II):

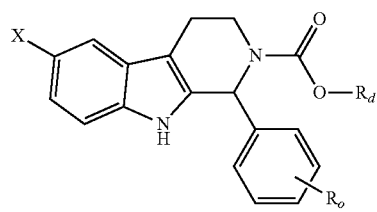

(II)

or a pharmaceutically acceptable salt, racemate or stereoisomer thereof, wherein,
X is hydrogen; $C_1$ to $C_6$ alkyl optionally substituted with one or more halogen substituents; hydroxyl; halogen; or $C_1$ to $C_5$ alkoxy optionally substituted with phenyl;
$R_o$ is halogen; cyano; nitro; sulfonyl substituted with $C_1$ to $C_6$ alkyl or morpholinyl; amino optionally substituted with $C_1$ to $C_6$ alkyl, C(O)$R_b$, —C(O)O—$R_b$, alkylsulfonyl, morpholinyl or tetrahydropyranyl; $C_1$ to $C_6$ alkyl optionally substituted with one or more substituents independently selected from hydroxyl, halogen or amino; C(O)—$R_n$; or —O$R_a$;
$R_a$ is hydrogen; $C_2$ to $C_8$ alkenyl; —C(O)—$R_n$; —C(O)O—$R_b$; —C(O)—NH—$R_b$; $C_1$ to $C_8$ alkyl optionally substituted with one or more substituents independently selected from hydroxyl, halogen, $C_1$ to $C_4$ alkoxy, $C_1$ to $C_4$ alkoxy $C_1$ to $C_4$ alkoxy, amino, alkylamino, dialkylamino, acetamide, —C(O)—$R_b$, —C(O)O—$R_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene or tetrazole;
wherein amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;
wherein alkylamino and dialkylamino are each optionally substituted on alkyl with hydroxyl, $C_1$ to $C_4$ alkoxy, imidazole, pyrazole, pyrrole or tetrazole; and,
wherein morpholinyl, thiomorpholinyl, pyrrolidinyl, piperidinyl, piperazinyl and oxiranyl are each optionally substituted with —C(O)—$R_n$, —C(O)O—$R_n$ or $C_1$ to $C_4$ alkyl, wherein $C_1$ to $C_4$ alkyl is optionally substituted with hydroxyl;
$R_b$ is hydroxyl; amino; alkylamino, optionally substituted on alkyl with hydroxyl, amino, alkylamino or $C_1$ to $C_4$ alkoxy; $C_1$ to $C_4$ alkoxy; $C_2$ to $C_8$ alkenyl; $C_2$ to $C_8$ alkynyl; aryl optionally substituted with one or more substituents independently selected from halogen and $C_1$ to $C_4$ alkoxy; furan; or $C_1$ to $C_8$ alkyl optionally substituted with one or more substituents independently selected from $C_1$ to $C_4$ alkoxy, aryl, amino, morpholinyl, piperidinyl or piperazinyl;
$R_d$ is aryl optionally substituted with one or more substituents independently selected from halogen, nitro, $C_1$ to $C_6$ alkyl, —C(O)O—$R_e$, and —O$R_e$;
$R_e$ is hydrogen; $C_1$ to $C_6$ alkyl optionally substituted with one or more substituents independently selected from halogen and alkoxy; or phenyl, wherein phenyl is optionally substituted with one or more substituents independently selected from halogen and alkoxy; and
$R_n$ is hydroxyl, $C_1$ to $C_4$ alkoxy, amino or $C_1$ to $C_6$ alkyl.

In another embodiment, provided herein are Compounds having Formula (II):

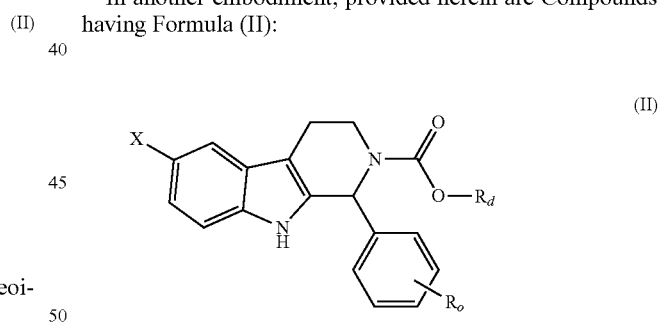

(II)

or a pharmaceutically acceptable salt, racemate or stereoisomer thereof, wherein,
X is halogen;
$R_o$ is halogen, substituted or unsubstituted $C_1$ to $C_8$ alkyl or O$R_a$;
$R_a$ is H, $C_1$ to $C_8$ alkyl optionally substituted with one or more substituents independently selected from hydroxyl and halogen; and
$R_d$ is phenyl optionally substituted with one or more alkoxy or halogen substituents.

In one embodiment, X is chloro or bromo.
In one embodiment, $R_d$ is chloro or bromo.
In one embodiment, $R_o$ is O$R_a$.
In one embodiment, $R_a$ is methyl, ethyl, propyl, isopropyl, butyl, or pentyl, each optionally substituted with one or more hydroxyl substituents.

In another embodiment, provided herein are Compounds having Formula (II):

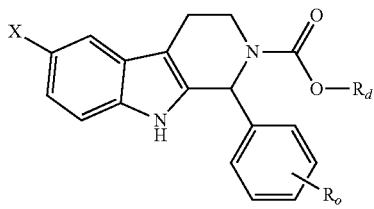
(II)

or a pharmaceutically acceptable salt, racemate or stereoisomer thereof, wherein,
X is halogen;
$R_o$ is halogen, substituted or unsubstituted $C_1$ to $C_8$ alkyl or $OR_a$;
$R_a$ is H, or $C_1$ to $C_8$ alkyl optionally substituted with one or more substituents independently selected from hydroxyl and halogen; and
$R_d$ is phenyl optionally substituted with one or more halogen substituents.

In another embodiment, provided herein are Compounds having Formula (III):

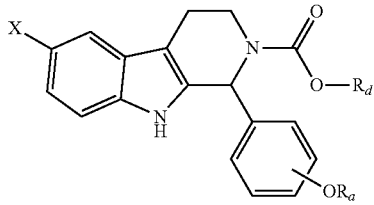
(III)

or a pharmaceutically acceptable salt, racemate or stereoisomer thereof, wherein,
X is halogen;
$R_a$ is H, $C_1$ to $C_8$ alkyl optionally substituted with one or more substituents independently selected from hydroxyl and halogen; and
$R_d$ is phenyl substituted with one or more halogen substituents.

In another embodiment, provided herein are Compounds having Formula (IV):

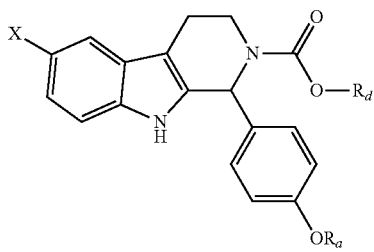
(IV)

or a pharmaceutically acceptable salt, racemate or stereoisomer thereof, wherein,
X is halogen;
$R_a$ is H, $C_1$ to $C_8$ alkyl optionally substituted with one or more substituents independently selected from hydroxyl and halogen; and $R_d$ is phenyl substituted with one or more halogen substituents.

In another embodiment, provided herein are Compounds having Formula (IV):

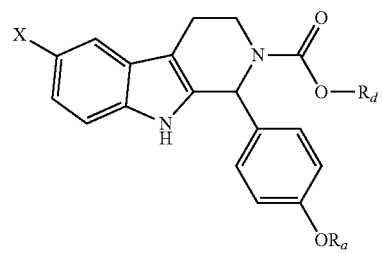
(IV)

or a pharmaceutically acceptable salt, racemate or stereoisomer thereof, wherein,
X is halogen;
$R_a$ is H, $C_1$ to $C_8$ alkyl optionally substituted with one or more substituents independently selected from hydroxyl and halogen; and
$R_d$ is phenyl substituted on a para position with a halogen substituent.

In another embodiment, the Compounds set forth above having a formula selected from Formula (Ia), Formula (IIa), Formula (IIIa) and Formula (IVa):

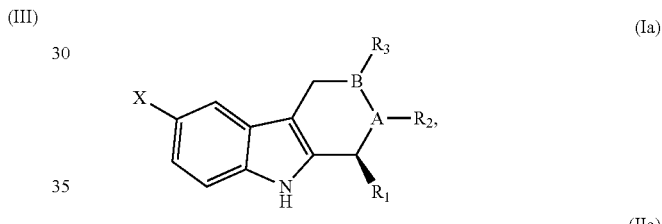
(Ia)

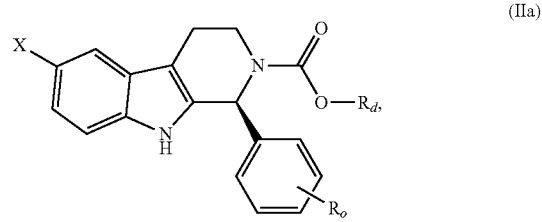
(IIa)

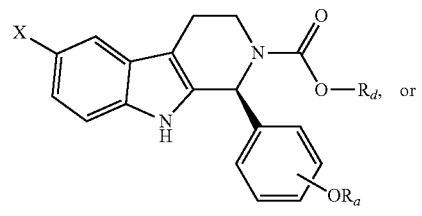
(IIIa)

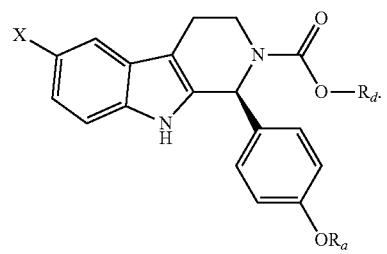
(IVa)

Illustrative examples of Compounds or a pharmaceutically acceptable salt, racemate or stereoisomer thereof provided herein include:

TABLE 1
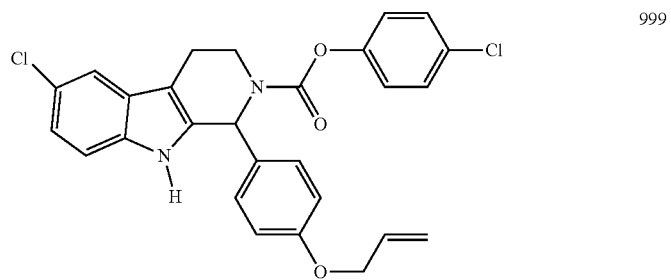
999
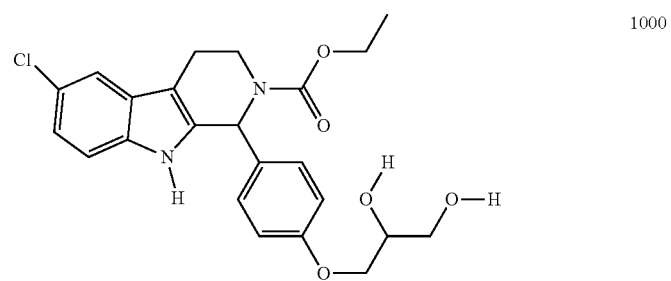
1000
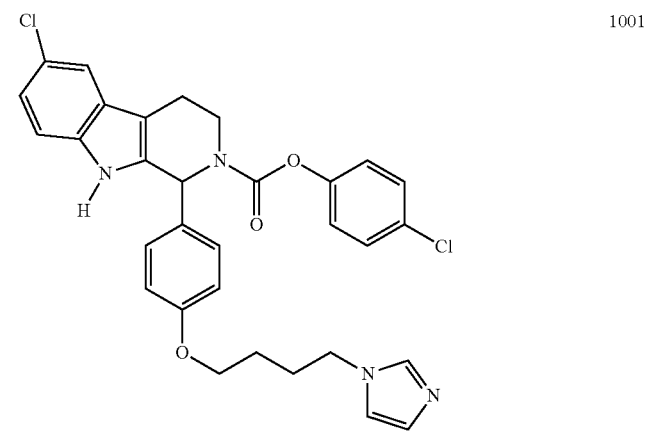
1001
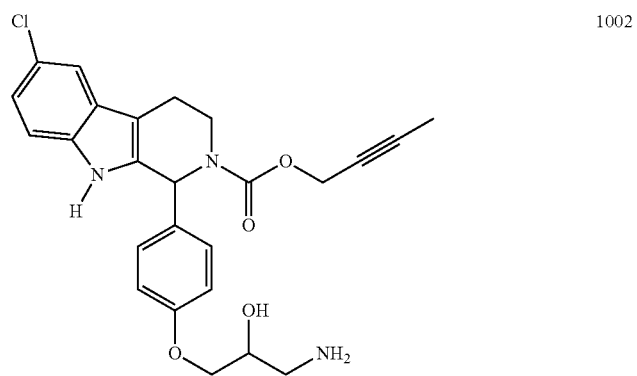
1002

TABLE 1-continued
| | |
|---|---|
| 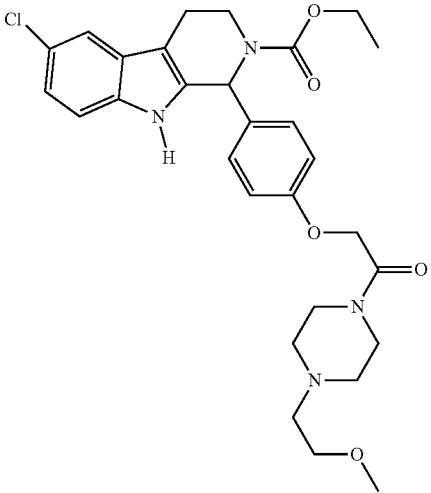 [SMILES: CCOC(=O)N1CCc2c([nH]c3ccc(Cl)cc23)C1c1ccc(OCC(=O)N2CCN(CCOC)CC2)cc1] | 1003 |
| 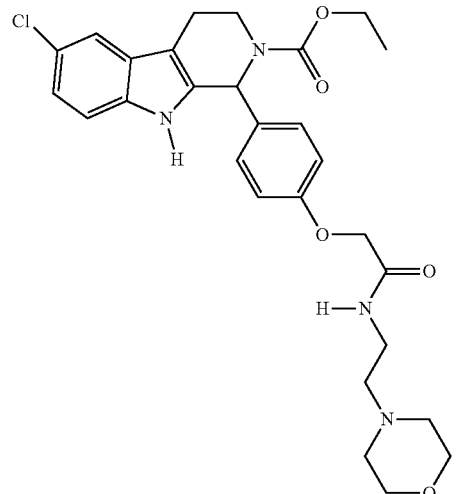 | 1004 |
| 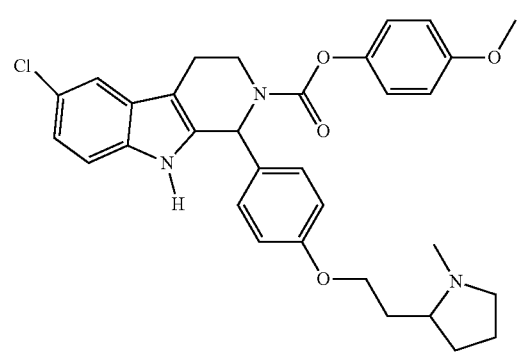 [SMILES: COc1ccc(OC(=O)N2CCc3c([nH]c4ccc(Cl)cc34)C2c2ccc(OCCC3CCCN3C)cc2)cc1] | 1005 |
| 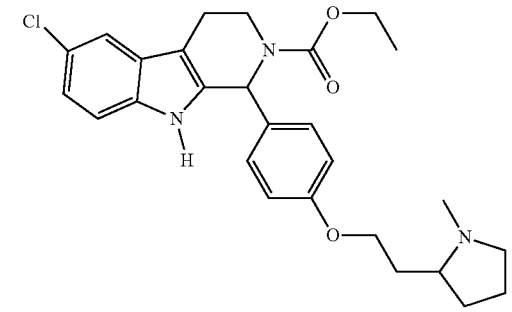 [SMILES: CCOC(=O)N1CCc2c([nH]c3ccc(Cl)cc23)C1c1ccc(OCCC2CCCN2C)cc1] | 1006 |

TABLE 1-continued
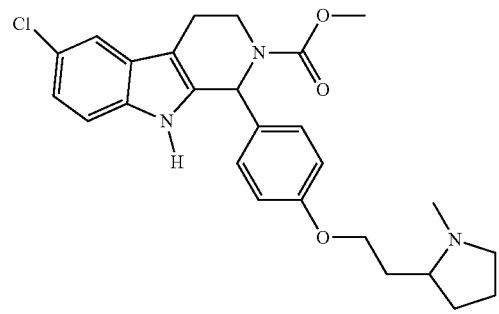 [SMILES: COC(=O)N1CCc2c([nH]c3ccc(Cl)cc23)C1c1ccc(OCCC2CCCN2C)cc1]
1007
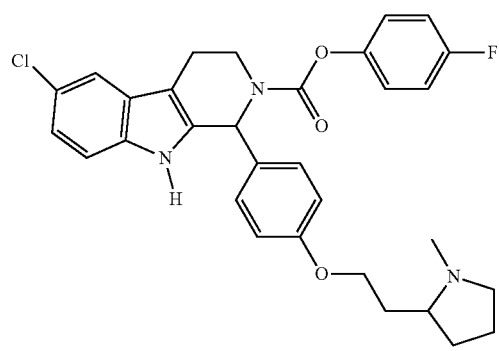 [SMILES: CN1CCCC1CCOc1ccc(C2c3[nH]c4ccc(Cl)cc4c3CCN2C(=O)Oc2ccc(F)cc2)cc1]
1008
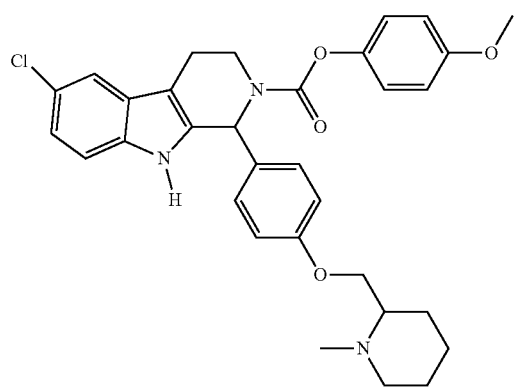 [SMILES: COc1ccc(OC(=O)N2CCc3c([nH]c4ccc(Cl)cc34)C2c2ccc(OCC3CCCCN3C)cc2)cc1]
1009
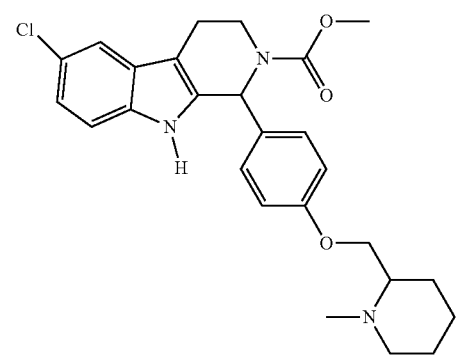 [SMILES: COC(=O)N1CCc2c([nH]c3ccc(Cl)cc23)C1c1ccc(OCC2CCCCN2C)cc1]
1010

TABLE 1-continued
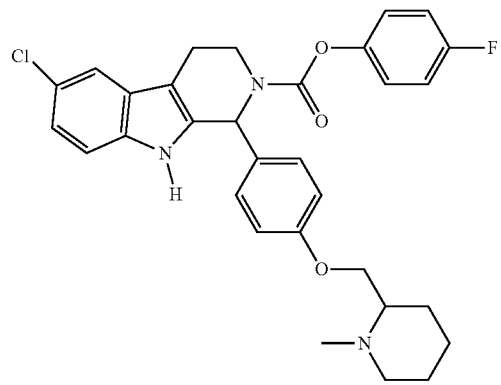 [SMILES: CN1CCCCC1COc1ccc(C2c3[nH]c4ccc(Cl)cc4c3CCN2C(=O)Oc2ccc(F)cc2)cc1]
1011
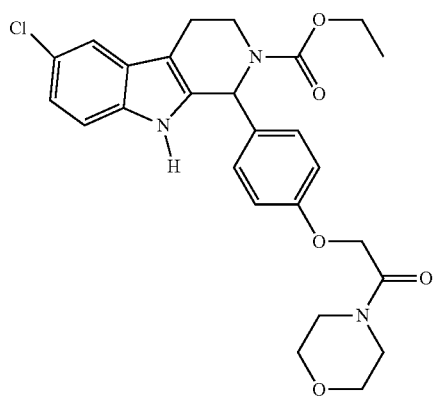 [SMILES: CCOC(=O)N1CCc2c([nH]c3ccc(Cl)cc23)C1c1ccc(OCC(=O)N2CCOCC2)cc1]
1012
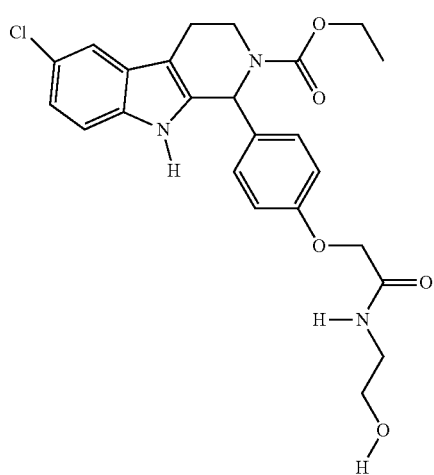 [SMILES: CCOC(=O)N1CCc2c([nH]c3ccc(Cl)cc23)C1c1ccc(OCC(=O)NCCO)cc1]
1013

TABLE 1-continued
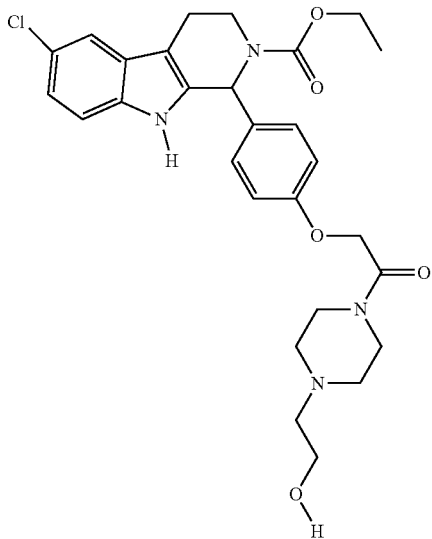 [SMILES: CCOC(=O)N1CCc2c([nH]c3ccc(Cl)cc23)C1c1ccc(OCC(=O)N2CCN(CCO)CC2)cc1]
1014
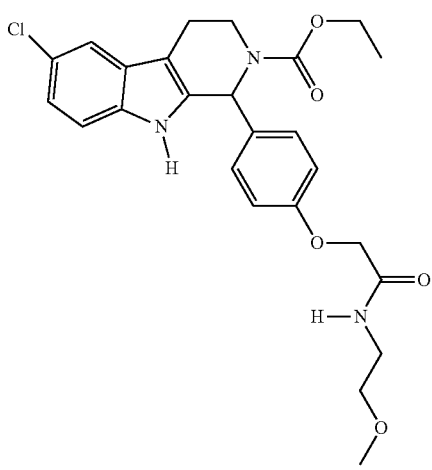 [SMILES: CCOC(=O)N1CCc2c([nH]c3ccc(Cl)cc23)C1c1ccc(OCC(=O)NCCOC)cc1]
1015
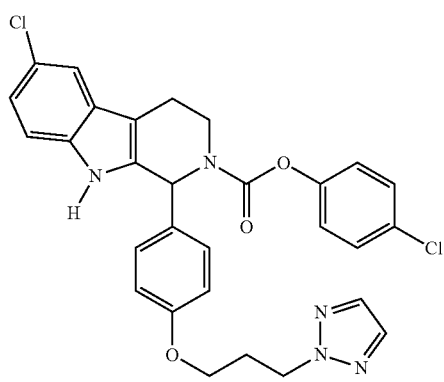 [SMILES: O=C(Oc1ccc(Cl)cc1)N1CCc2c([nH]c3ccc(Cl)cc23)C1c1ccc(OCCCn2nccn2)cc1]
1016

TABLE 1-continued
| | |
|---|---|
| 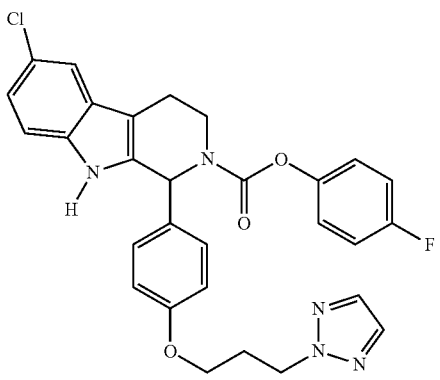 [SMILES: O=C(Oc1ccc(F)cc1)N1CCc2c([nH]c3ccc(Cl)cc23)C1c1ccc(OCCCn2nccn2)cc1] | 1017 |
| 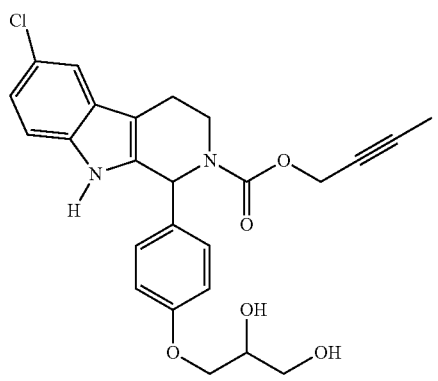 [SMILES: CC#CCOC(=O)N1CCc2c([nH]c3ccc(Cl)cc23)C1c1ccc(OCC(O)CO)cc1] | 1018 |
| 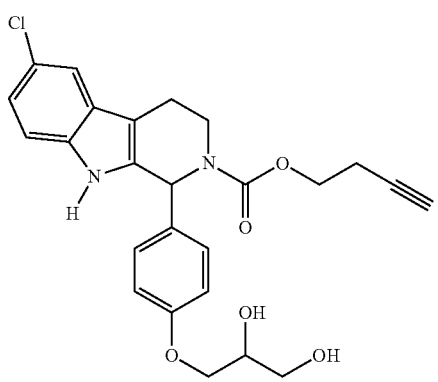 [SMILES: C#CCCOC(=O)N1CCc2c([nH]c3ccc(Cl)cc23)C1c1ccc(OCC(O)CO)cc1] | 1019 |
| 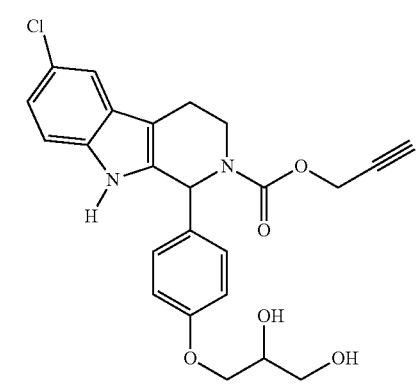 [SMILES: C#CCOC(=O)N1CCc2c([nH]c3ccc(Cl)cc23)C1c1ccc(OCC(O)CO)cc1] | 1020 |

TABLE 1-continued
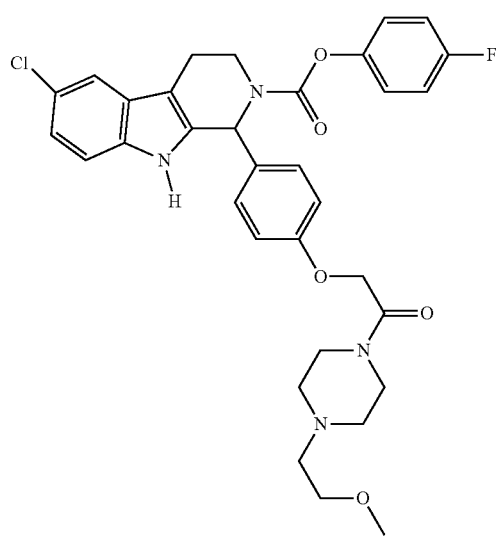 [SMILES: COCCN1CCN(C(=O)COc2ccc(C3c4[nH]c5ccc(Cl)cc5c4CCN3C(=O)Oc3ccc(F)cc3)cc2)CC1]
1021
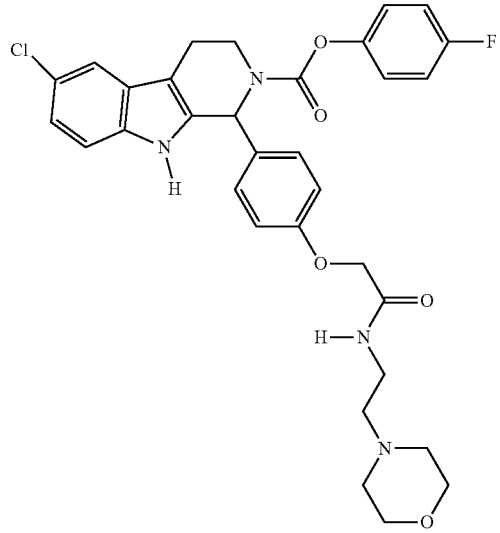 [SMILES: O=C(COc1ccc(C2c3[nH]c4ccc(Cl)cc4c3CCN2C(=O)Oc2ccc(F)cc2)cc1)NCCN1CCOCC1]
1022
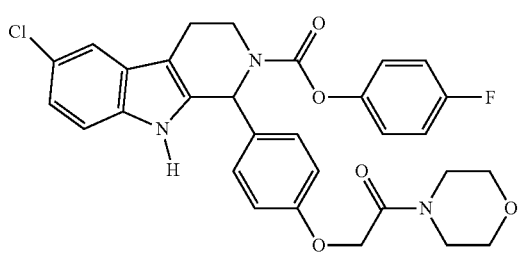 [SMILES: O=C(COc1ccc(C2c3[nH]c4ccc(Cl)cc4c3CCN2C(=O)Oc2ccc(F)cc2)cc1)N1CCOCC1]
1023
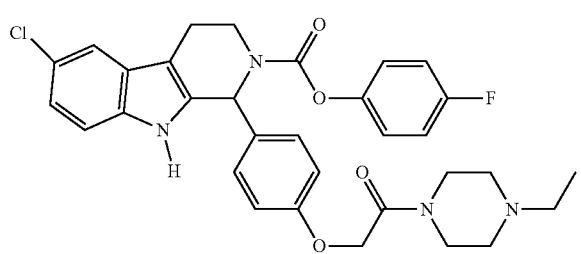 [SMILES: CCN1CCN(C(=O)COc2ccc(C3c4[nH]c5ccc(Cl)cc5c4CCN3C(=O)Oc3ccc(F)cc3)cc2)CC1]
1024

TABLE 1-continued
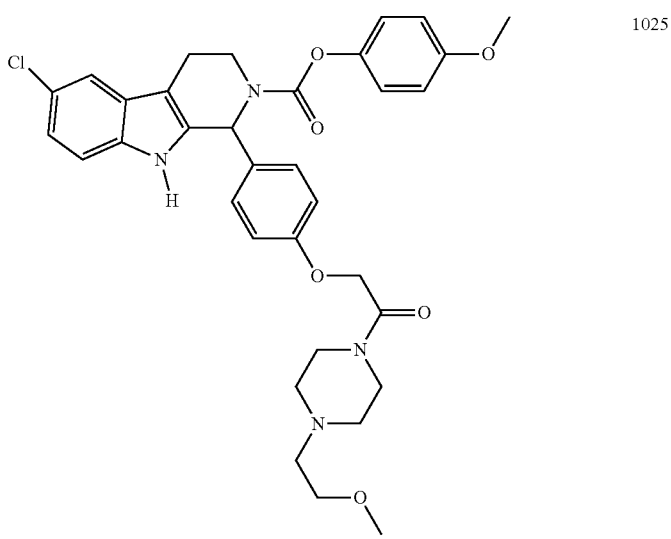
1025
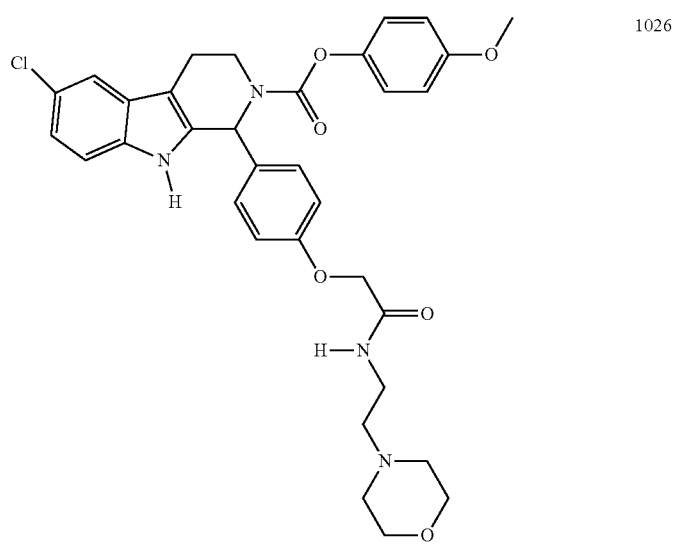
1026
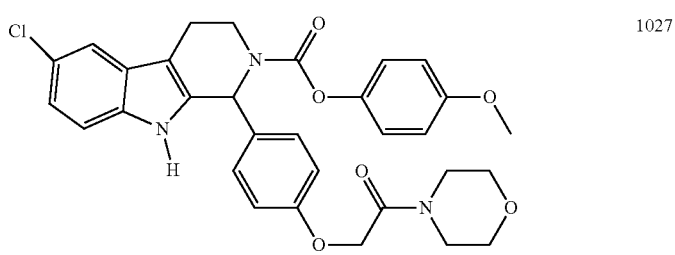
1027
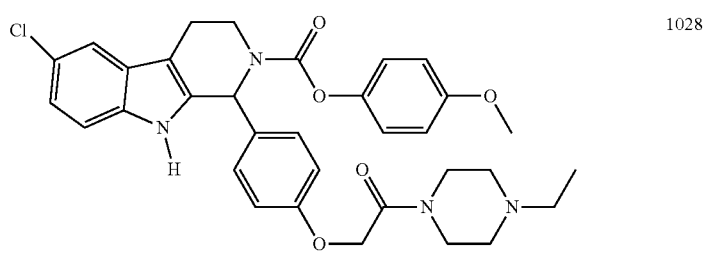
1028

TABLE 1-continued
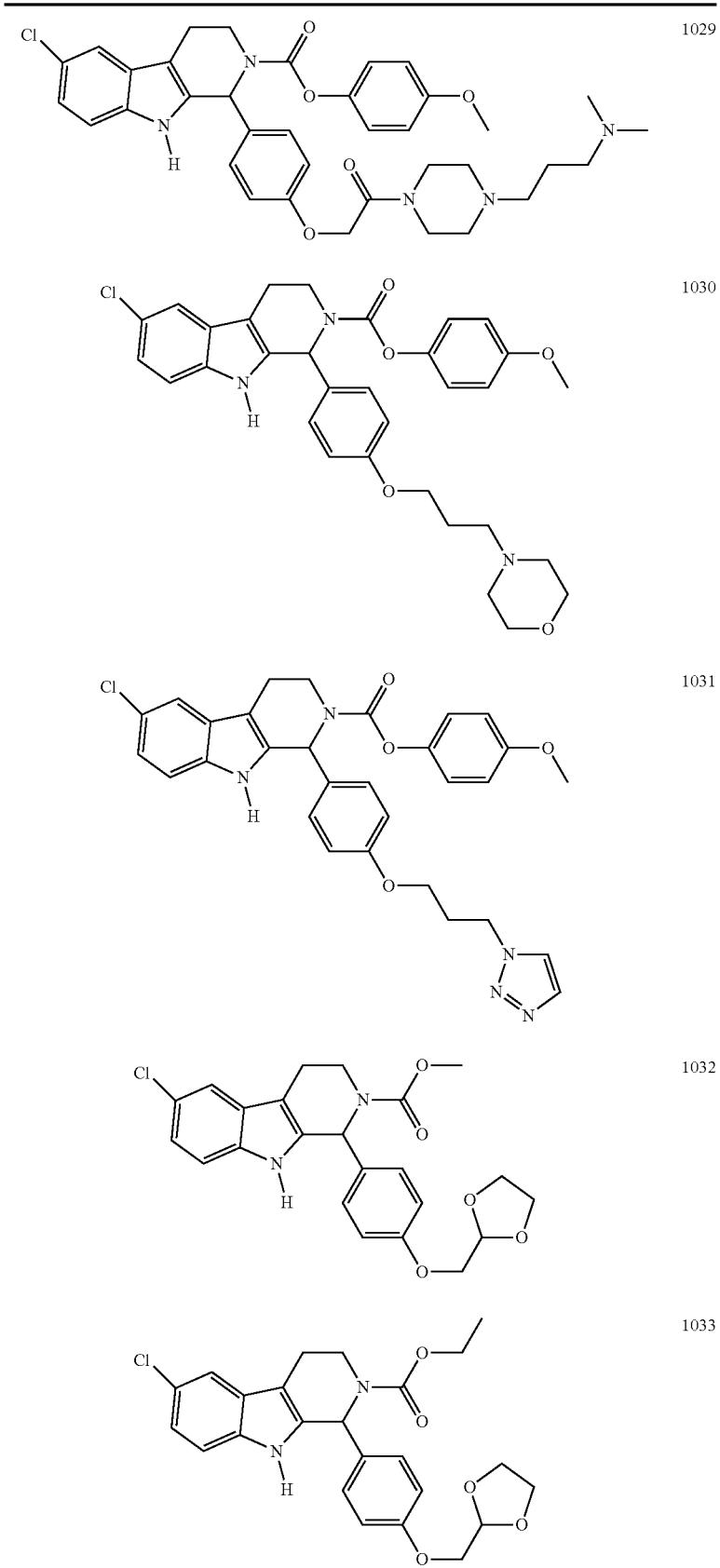

TABLE 1-continued
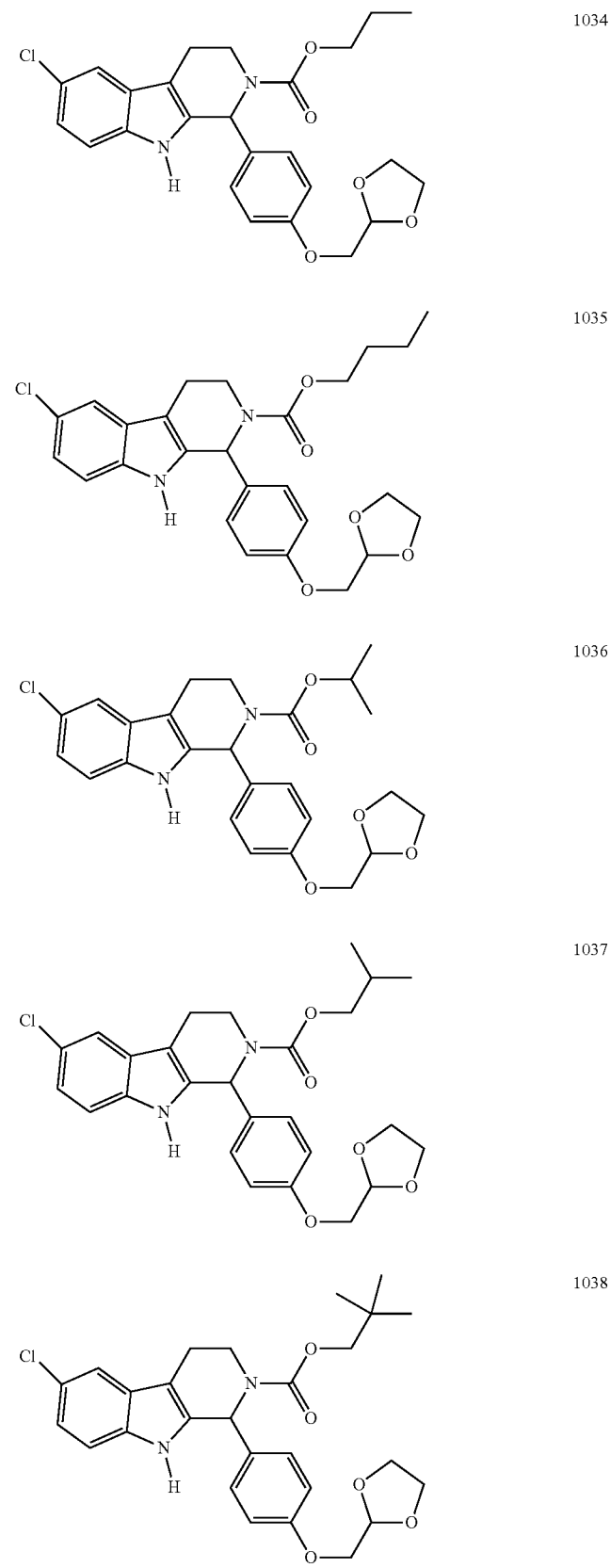

TABLE 1-continued
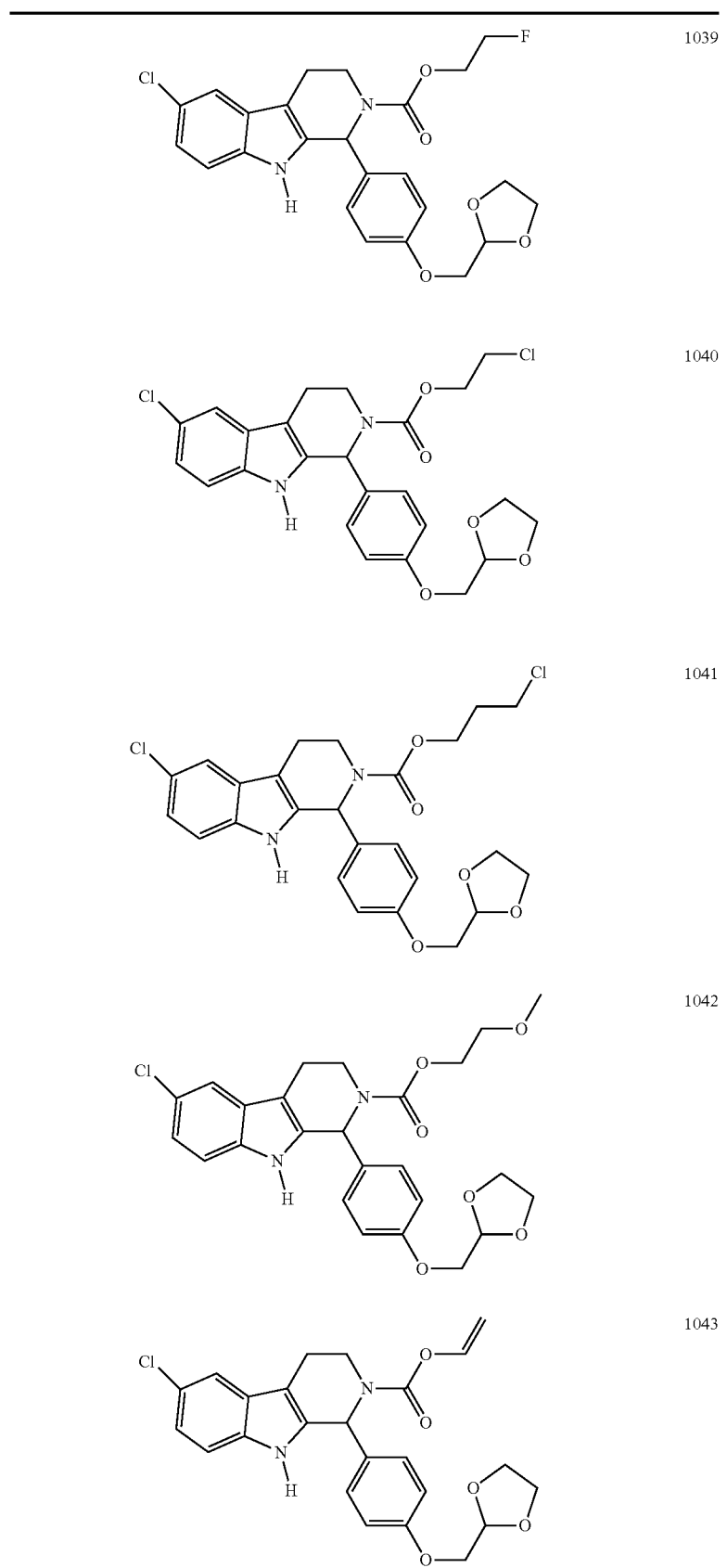

TABLE 1-continued
| | |
|---|---|
| 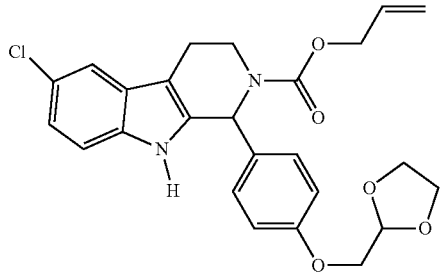 [SMILES: C=CCOC(=O)N1CCc2c([nH]c3ccc(Cl)cc23)C1c1ccc(OCC2OCCO2)cc1] | 1044 |
| 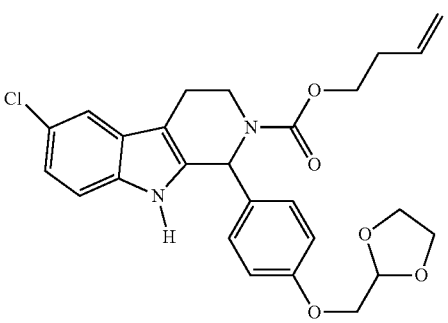 [SMILES: C=CCCOC(=O)N1CCc2c([nH]c3ccc(Cl)cc23)C1c1ccc(OCC2OCCO2)cc1] | 1045 |
| 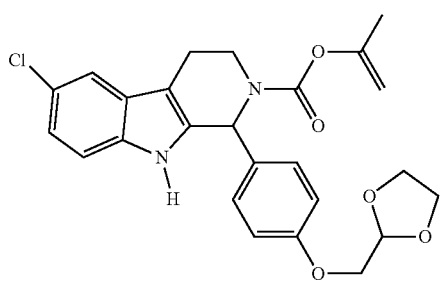 [SMILES: C=C(C)OC(=O)N1CCc2c([nH]c3ccc(Cl)cc23)C1c1ccc(OCC2OCCO2)cc1] | 1046 |
| 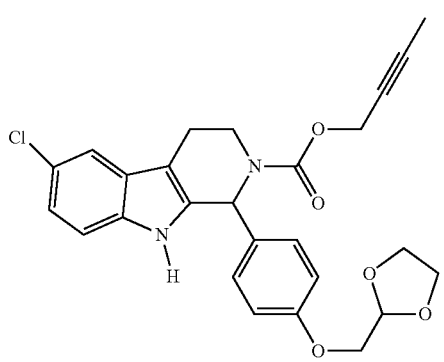 [SMILES: CC#CCOC(=O)N1CCc2c([nH]c3ccc(Cl)cc23)C1c1ccc(OCC2OCCO2)cc1] | 1047 |
| 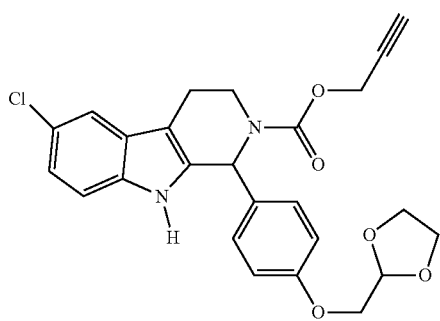 [SMILES: C#CCOC(=O)N1CCc2c([nH]c3ccc(Cl)cc23)C1c1ccc(OCC2OCCO2)cc1] | 1048 |

TABLE 1-continued
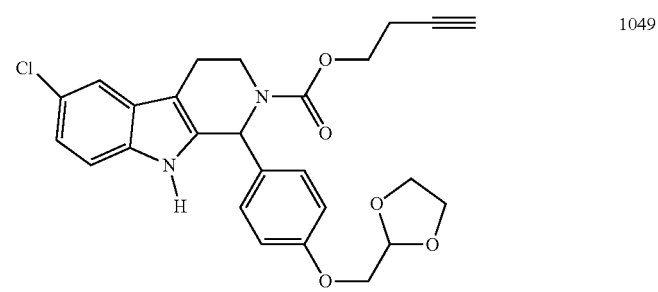
1049
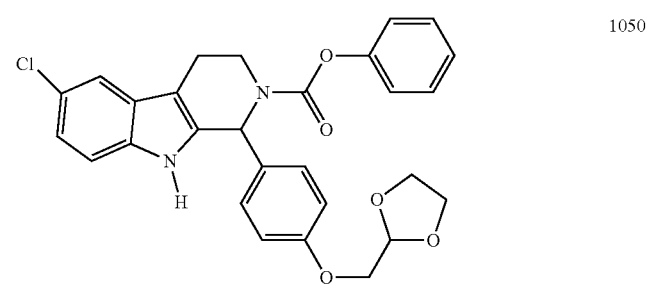
1050
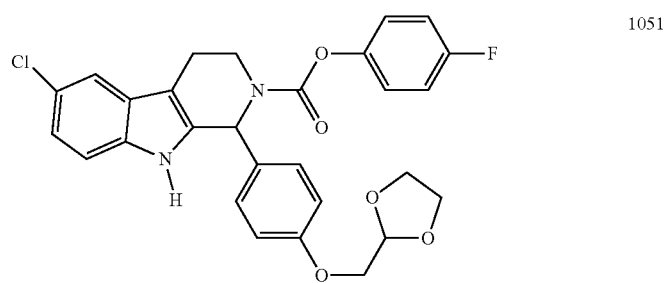
1051
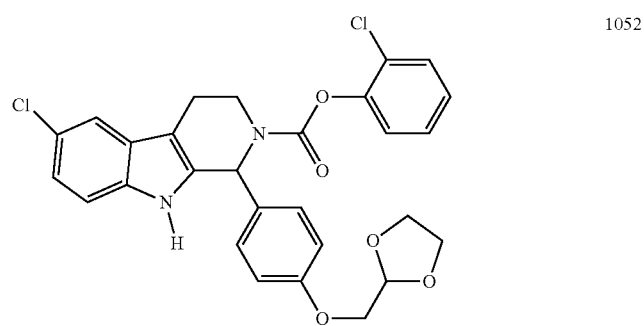
1052
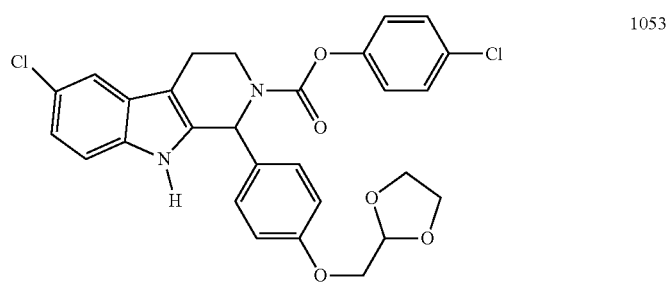
1053

TABLE 1-continued
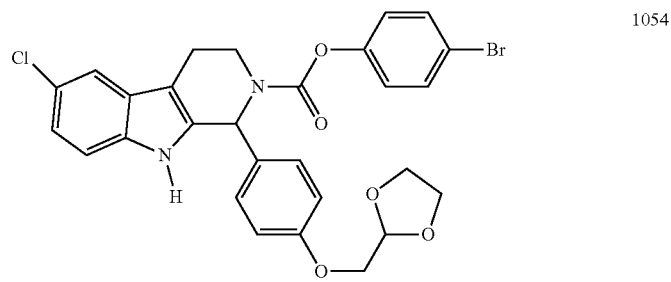
1054
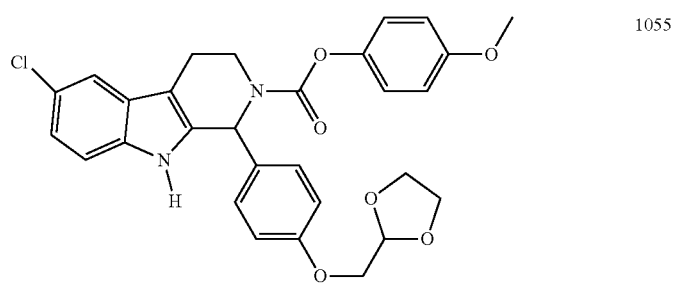
1055
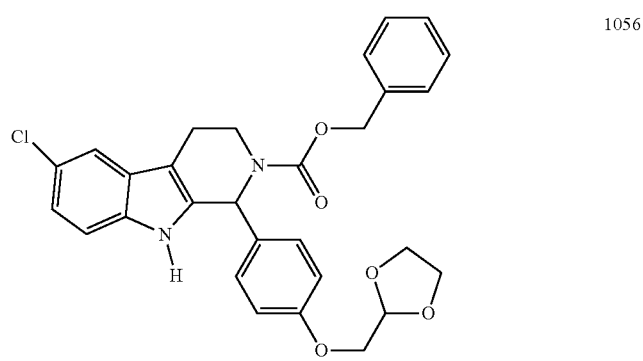
1056
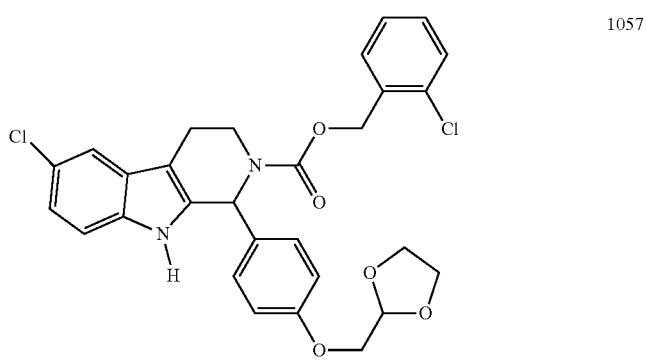
1057
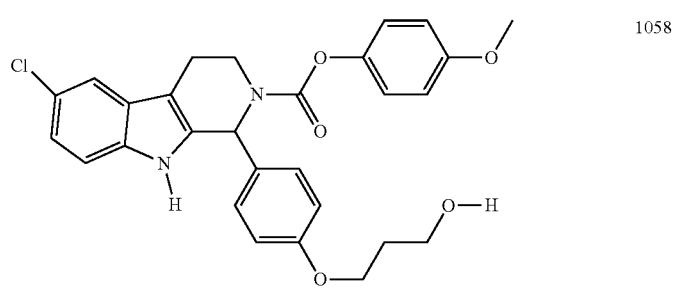
1058

TABLE 1-continued
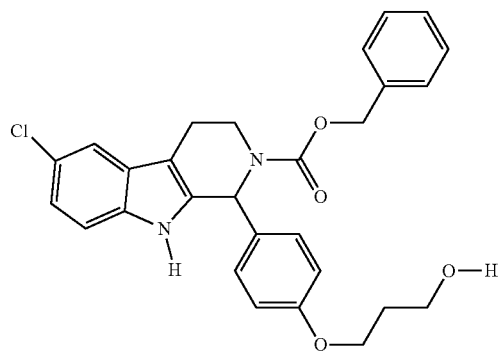 [SMILES: O=C(OCc1ccccc1)N1CCc2c([nH]c3ccc(Cl)cc23)C1c1ccc(OCCCO)cc1]
1059
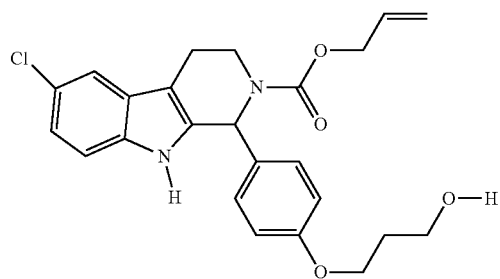 [SMILES: C=CCOC(=O)N1CCc2c([nH]c3ccc(Cl)cc23)C1c1ccc(OCCCO)cc1]
1060
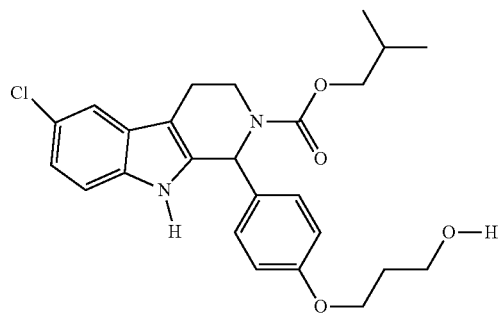 [SMILES: CC(C)COC(=O)N1CCc2c([nH]c3ccc(Cl)cc23)C1c1ccc(OCCCO)cc1]
1061
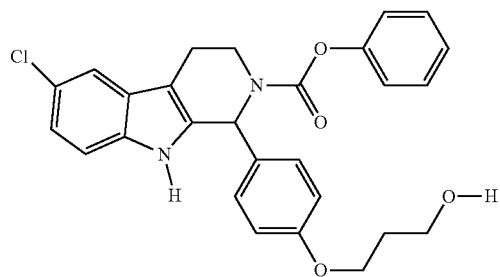 [SMILES: O=C(Oc1ccccc1)N1CCc2c([nH]c3ccc(Cl)cc23)C1c1ccc(OCCCO)cc1]
1062

TABLE 1-continued
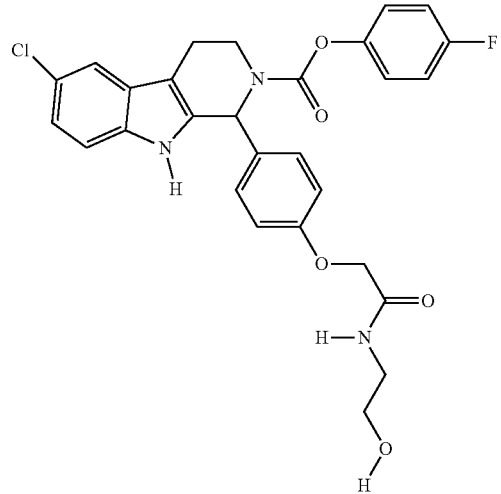 [SMILES: O=C(COc1ccc(C2c3[nH]c4ccc(Cl)cc4c3CCN2C(=O)Oc2ccc(F)cc2)cc1)NCCO]
1063
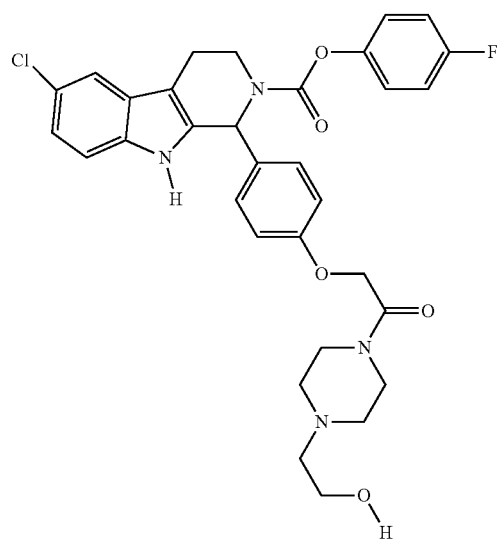 [SMILES: O=C(COc1ccc(C2c3[nH]c4ccc(Cl)cc4c3CCN2C(=O)Oc2ccc(F)cc2)cc1)N1CCN(CCO)CC1]
1064
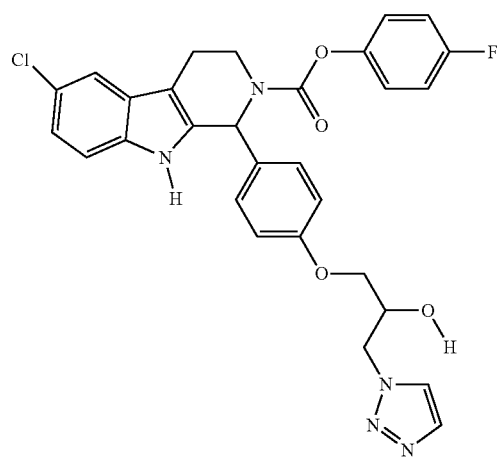 [SMILES: O=C(Oc1ccc(F)cc1)N1CCc2c([nH]c3ccc(Cl)cc23)C1c1ccc(OCC(O)Cn2ccnn2)cc1]
1066

TABLE 1-continued
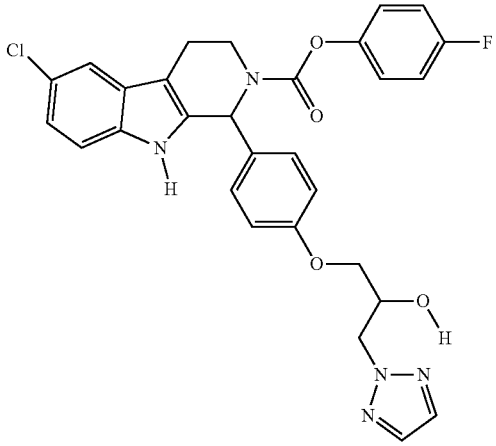 [SMILES: O=C(Oc1ccc(F)cc1)N1CCc2c([nH]c3ccc(Cl)cc23)C1c1ccc(OCC(O)Cn2nccn2)cc1]
1067
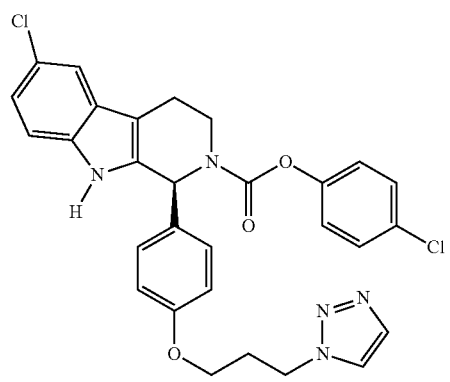 [SMILES: O=C(Oc1ccc(Cl)cc1)N1CCc2c([nH]c3ccc(Cl)cc23)[C@@H]1c1ccc(OCCCn2ccnn2)cc1]
1068
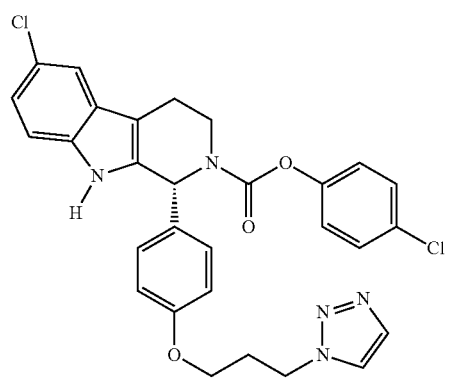 [SMILES: O=C(Oc1ccc(Cl)cc1)N1CCc2c([nH]c3ccc(Cl)cc23)[C@H]1c1ccc(OCCCn2ccnn2)cc1]
1069
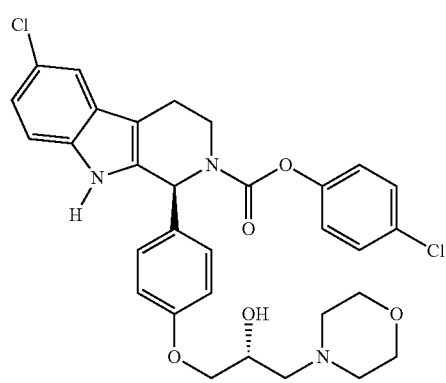 [SMILES: O=C(Oc1ccc(Cl)cc1)N1CCc2c([nH]c3ccc(Cl)cc23)[C@@H]1c1ccc(OC[C@H](O)CN2CCOCC2)cc1]
1070

TABLE 1-continued
| | |
|---|---|
| 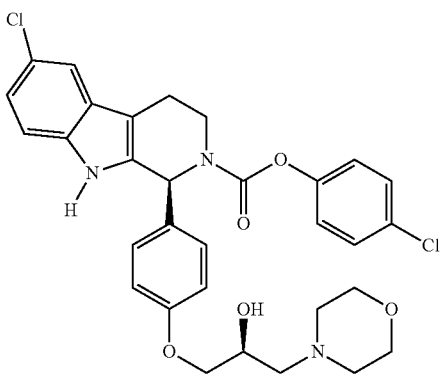 [SMILES: O=C(Oc1ccc(Cl)cc1)N1CCc2c([nH]c3ccc(Cl)cc23)[C@@H]1c1ccc(OC[C@@H](O)CN2CCOCC2)cc1] | 1071 |
| 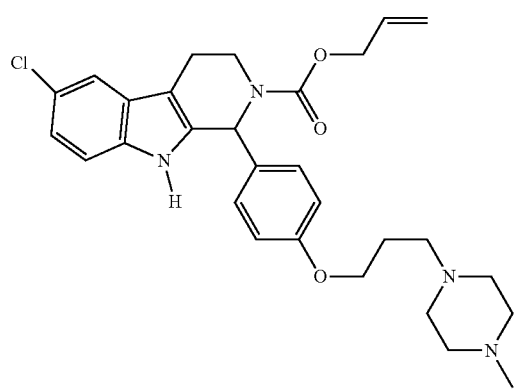 [SMILES: C=CCOC(=O)N1CCc2c([nH]c3ccc(Cl)cc23)C1c1ccc(OCCCN2CCN(C)CC2)cc1] | 1072 |
| 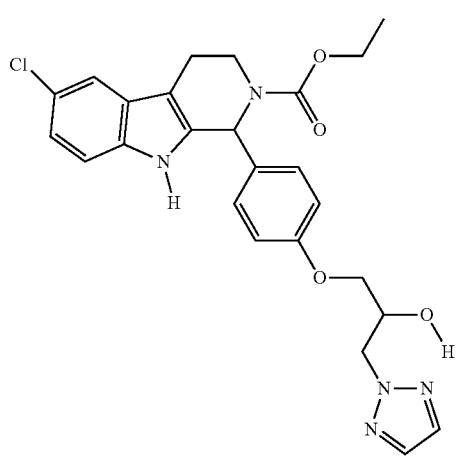 [SMILES: CCOC(=O)N1CCc2c([nH]c3ccc(Cl)cc23)C1c1ccc(OCC(O)Cn2nccn2)cc1] | 1073 |
| 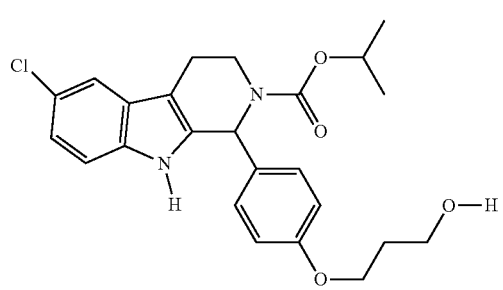 [SMILES: CC(C)OC(=O)N1CCc2c([nH]c3ccc(Cl)cc23)C1c1ccc(OCCCO)cc1] | 1074 |

TABLE 1-continued
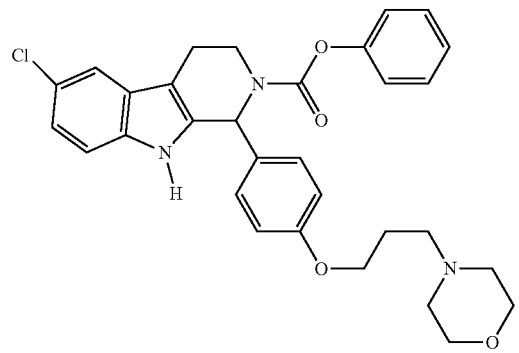 [SMILES: O=C(Oc1ccccc1)N1CCc2c([nH]c3ccc(Cl)cc23)C1c1ccc(OCCCN2CCOCC2)cc1]
1075
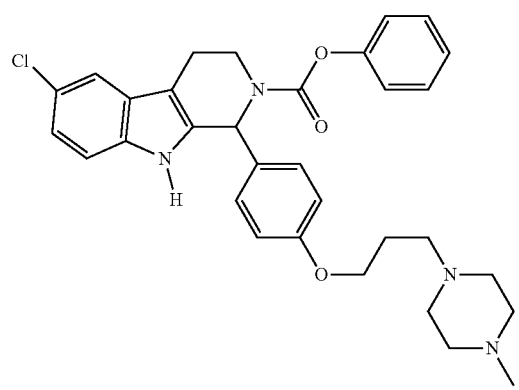 [SMILES: CN1CCN(CCCOc2ccc(C3c4[nH]c5ccc(Cl)cc5c4CCN3C(=O)Oc3ccccc3)cc2)CC1]
1076
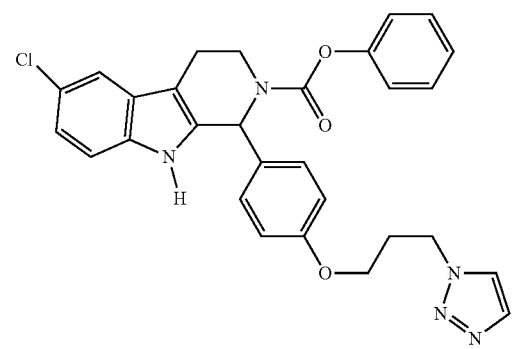 [SMILES: O=C(Oc1ccccc1)N1CCc2c([nH]c3ccc(Cl)cc23)C1c1ccc(OCCCn2ccnn2)cc1]
1077
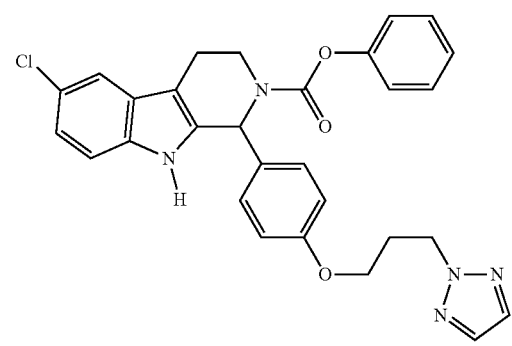 [SMILES: O=C(Oc1ccccc1)N1CCc2c([nH]c3ccc(Cl)cc23)C1c1ccc(OCCCn2nccn2)cc1]
1078

TABLE 1-continued
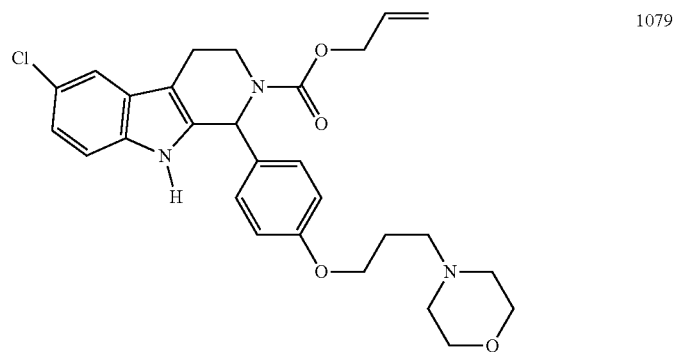
1079
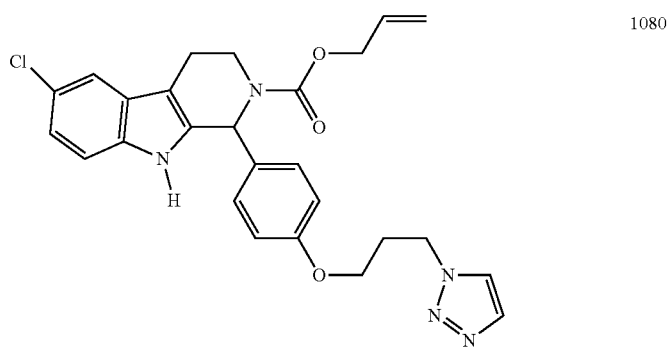
1080
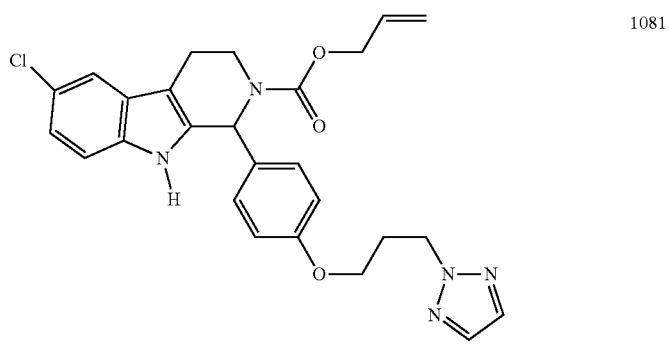
1081
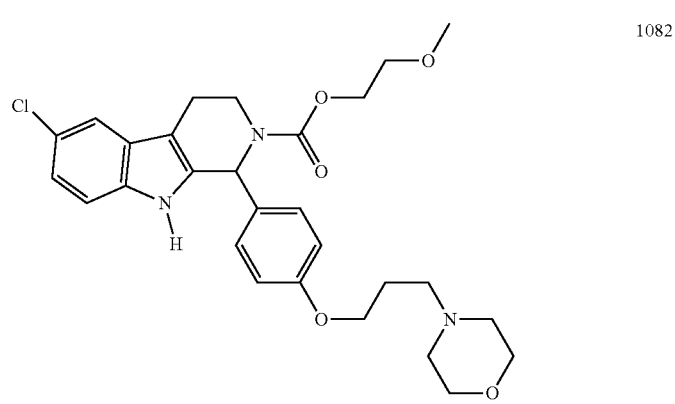
1082

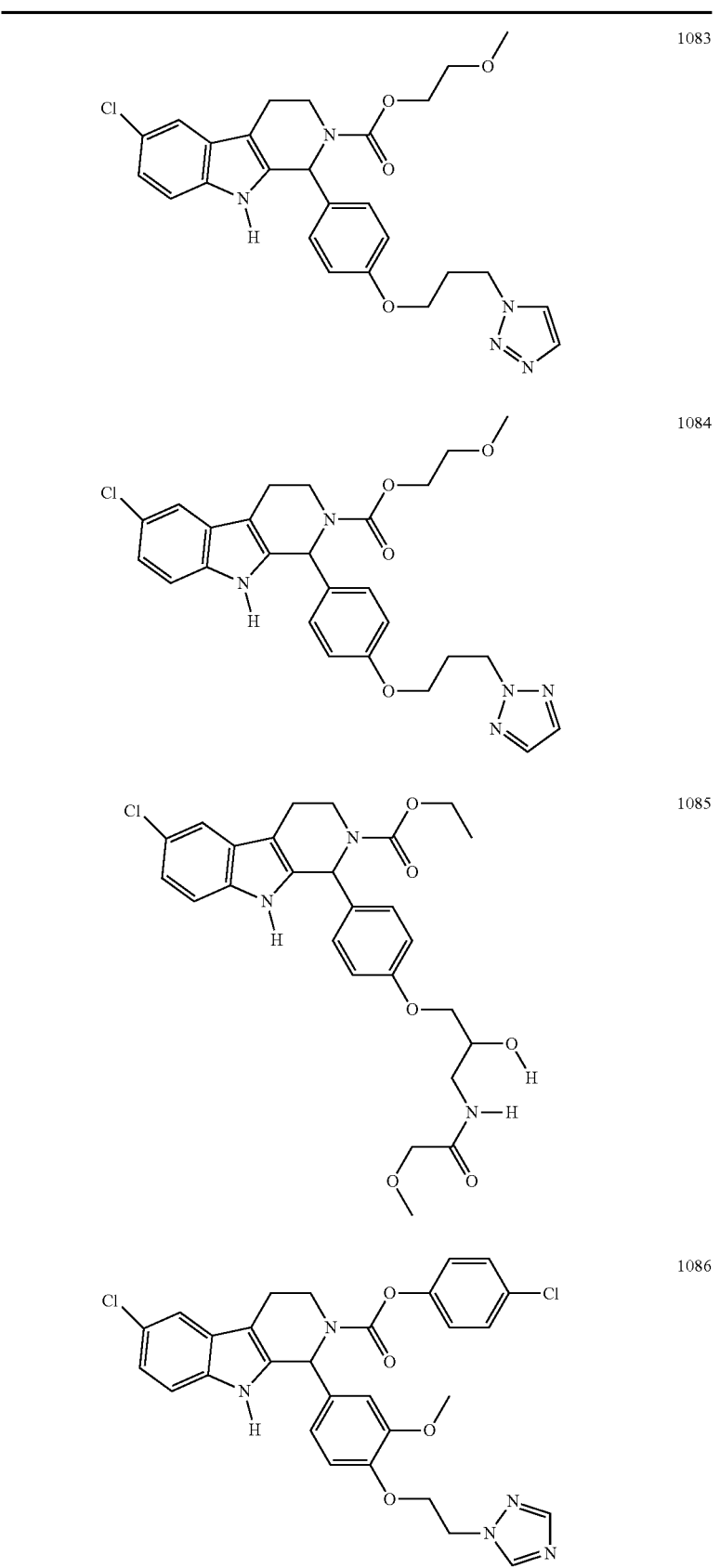

TABLE 1-continued
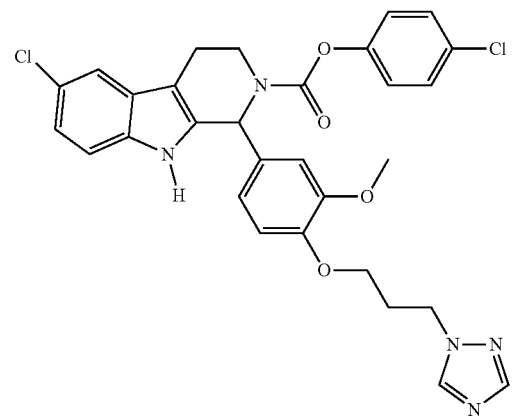 [SMILES: COc1cc(C2c3[nH]c4ccc(Cl)cc4c3CCN2C(=O)Oc2ccc(Cl)cc2)ccc1OCCCn1cncn1]
1087
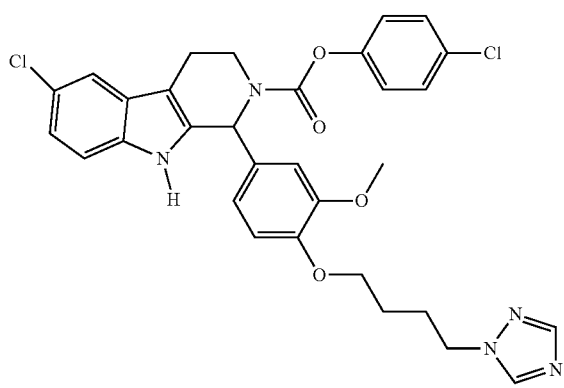 [SMILES: COc1cc(C2c3[nH]c4ccc(Cl)cc4c3CCN2C(=O)Oc2ccc(Cl)cc2)ccc1OCCCCn1cncn1]
1088
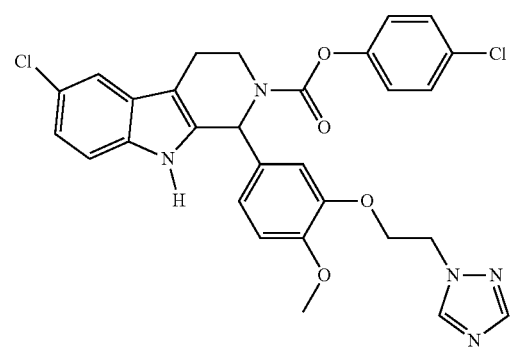 [SMILES: COc1ccc(C2c3[nH]c4ccc(Cl)cc4c3CCN2C(=O)Oc2ccc(Cl)cc2)cc1OCCn1cncn1]
1089
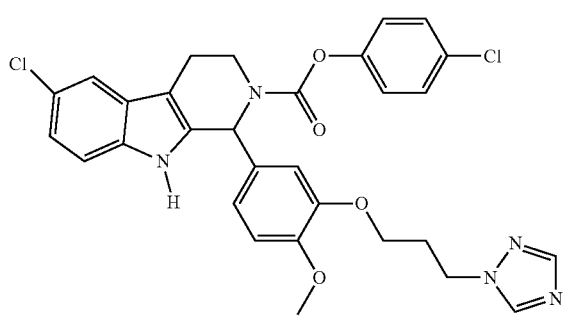 [SMILES: COc1ccc(C2c3[nH]c4ccc(Cl)cc4c3CCN2C(=O)Oc2ccc(Cl)cc2)cc1OCCCn1cncn1]
1090

TABLE 1-continued
| | |
|---|---|
| 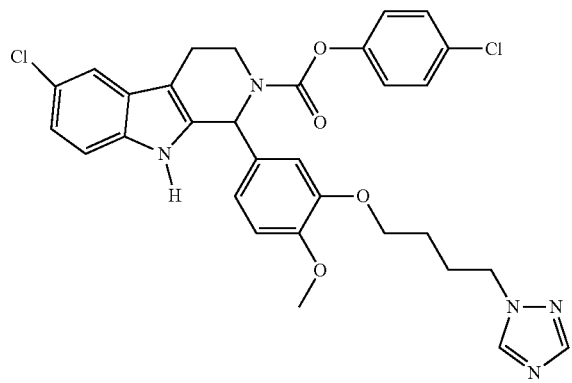 [SMILES: COc1ccc(C2c3[nH]c4ccc(Cl)cc4c3CCN2C(=O)Oc2ccc(Cl)cc2)cc1OCCCCn1cncn1] | 1091 |
| 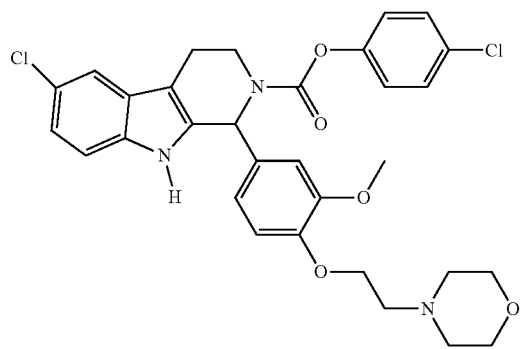 [SMILES: COc1cc(C2c3[nH]c4ccc(Cl)cc4c3CCN2C(=O)Oc2ccc(Cl)cc2)ccc1OCCN1CCOCC1] | 1092 |
| 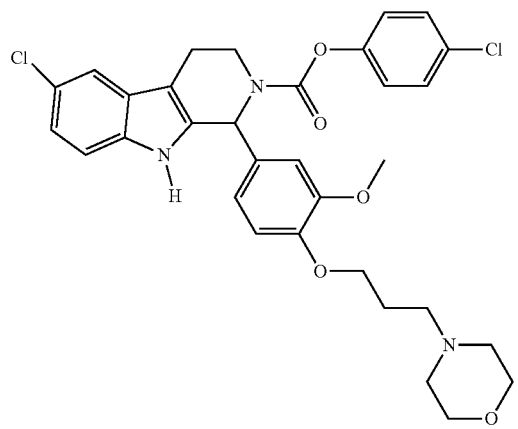 [SMILES: COc1cc(C2c3[nH]c4ccc(Cl)cc4c3CCN2C(=O)Oc2ccc(Cl)cc2)ccc1OCCCN1CCOCC1] | 1093 |
| 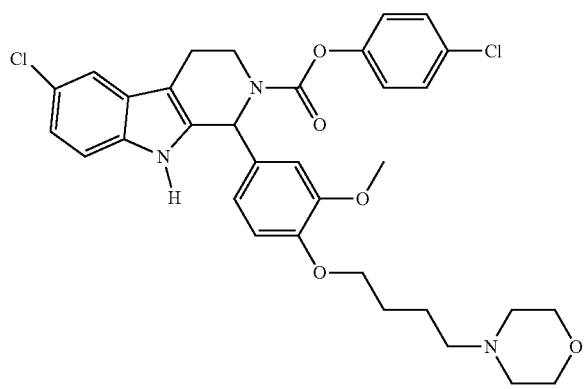 [SMILES: COc1cc(C2c3[nH]c4ccc(Cl)cc4c3CCN2C(=O)Oc2ccc(Cl)cc2)ccc1OCCCCN1CCOCC1] | 1094 |

TABLE 1-continued
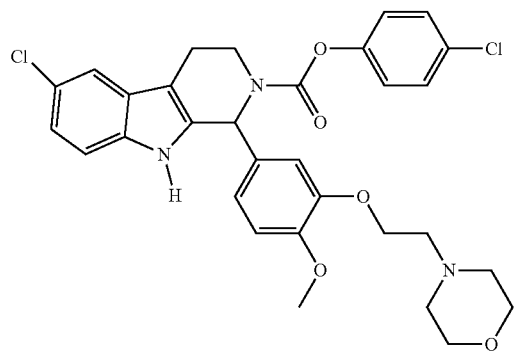 [SMILES: COc1ccc(C2c3[nH]c4ccc(Cl)cc4c3CCN2C(=O)Oc2ccc(Cl)cc2)cc1OCCN1CCOCC1]
1095
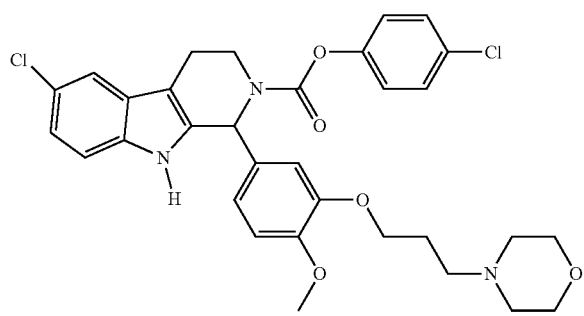 [SMILES: COc1ccc(C2c3[nH]c4ccc(Cl)cc4c3CCN2C(=O)Oc2ccc(Cl)cc2)cc1OCCCN1CCOCC1]
1096
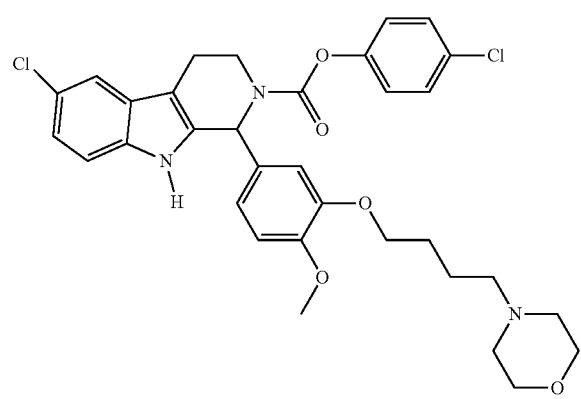 [SMILES: COc1ccc(C2c3[nH]c4ccc(Cl)cc4c3CCN2C(=O)Oc2ccc(Cl)cc2)cc1OCCCCN1CCOCC1]
1097
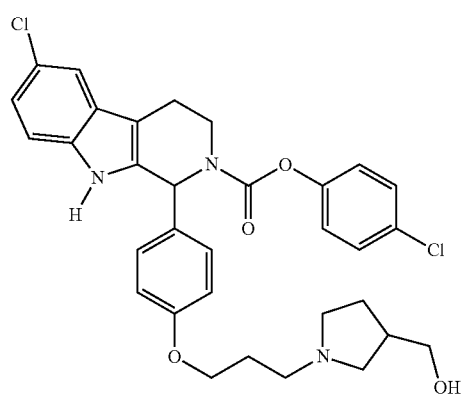 [SMILES: O=C(Oc1ccc(Cl)cc1)N1CCc2c([nH]c3ccc(Cl)cc23)C1c1ccc(OCCCN2CCC(CO)C2)cc1]
1098

TABLE 1-continued
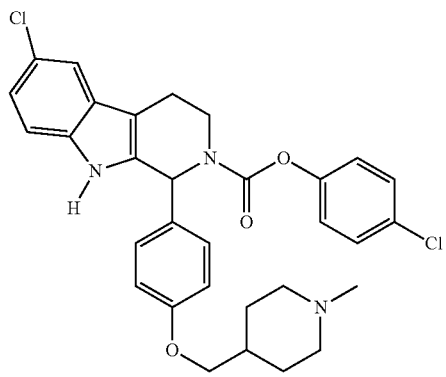 [SMILES: CN1CCC(COc2ccc(C3c4[nH]c5ccc(Cl)cc5c4CCN3C(=O)Oc3ccc(Cl)cc3)cc2)CC1]
1099
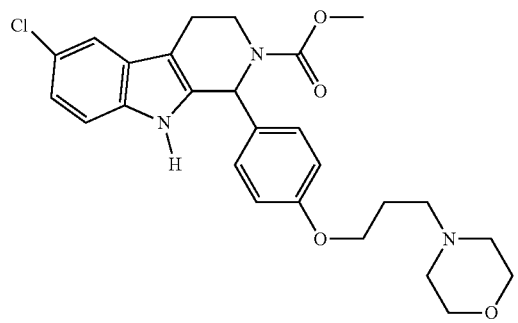 [SMILES: COC(=O)N1CCc2c([nH]c3ccc(Cl)cc23)C1c1ccc(OCCCN2CCOCC2)cc1]
1100
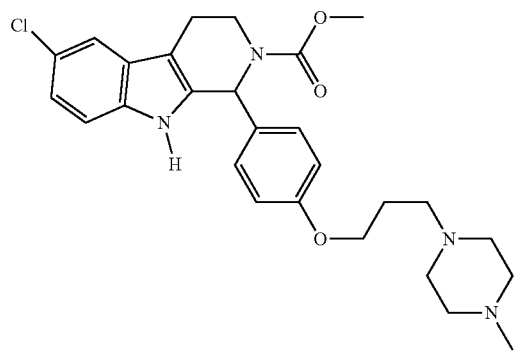 [SMILES: COC(=O)N1CCc2c([nH]c3ccc(Cl)cc23)C1c1ccc(OCCCN2CCN(C)CC2)cc1]
1101
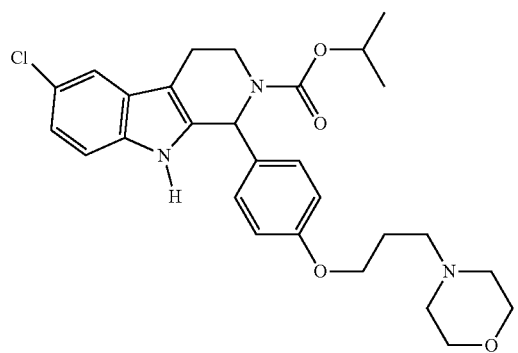 [SMILES: CC(C)OC(=O)N1CCc2c([nH]c3ccc(Cl)cc23)C1c1ccc(OCCCN2CCOCC2)cc1]
1102

TABLE 1-continued
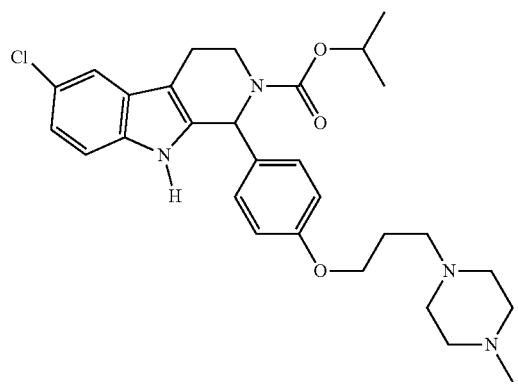 [SMILES: CC(C)OC(=O)N1CCc2c([nH]c3ccc(Cl)cc23)C1c1ccc(OCCCN2CCN(C)CC2)cc1]
1103
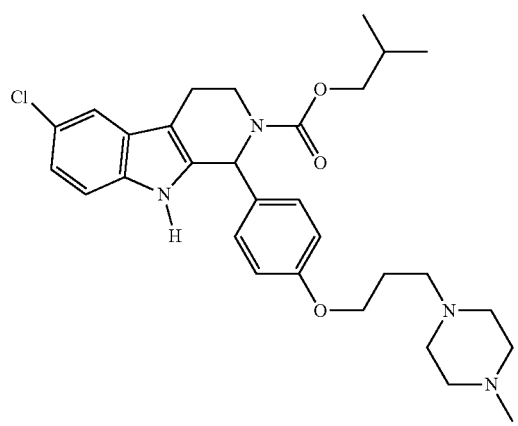 [SMILES: CC(C)COC(=O)N1CCc2c([nH]c3ccc(Cl)cc23)C1c1ccc(OCCCN2CCN(C)CC2)cc1]
1104
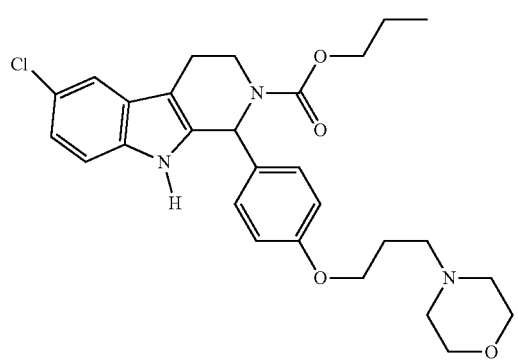 [SMILES: CCCOC(=O)N1CCc2c([nH]c3ccc(Cl)cc23)C1c1ccc(OCCCN2CCOCC2)cc1]
1105
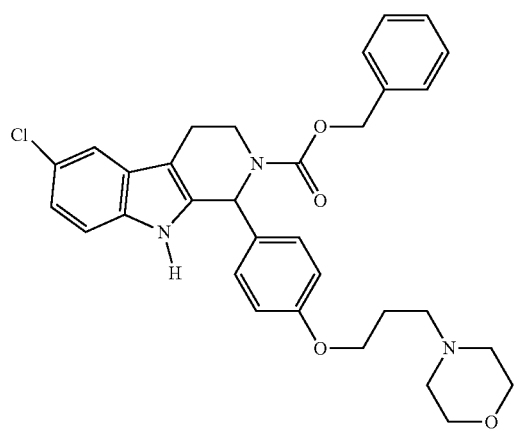 [SMILES: O=C(OCc1ccccc1)N1CCc2c([nH]c3ccc(Cl)cc23)C1c1ccc(OCCCN2CCOCC2)cc1]
1106

TABLE 1-continued
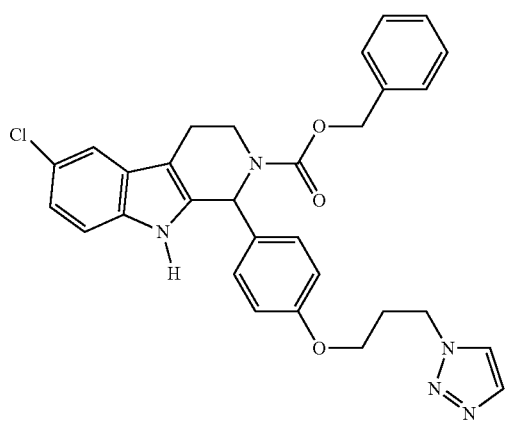 [SMILES: O=C(OCc1ccccc1)N1CCc2c([nH]c3ccc(Cl)cc23)C1c1ccc(OCCCn2ccnn2)cc1]
1107
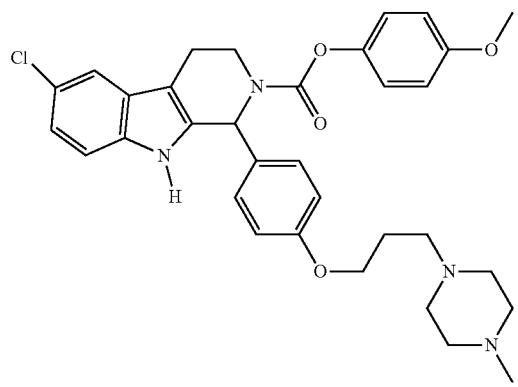 [SMILES: COc1ccc(OC(=O)N2CCc3c([nH]c4ccc(Cl)cc34)C2c2ccc(OCCCN3CCN(C)CC3)cc2)cc1]
1108
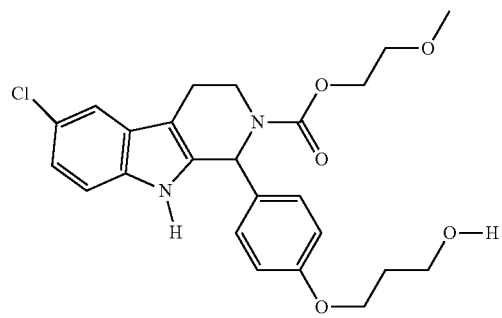 [SMILES: COCCOC(=O)N1CCc2c([nH]c3ccc(Cl)cc23)C1c1ccc(OCCCO)cc1]
1109
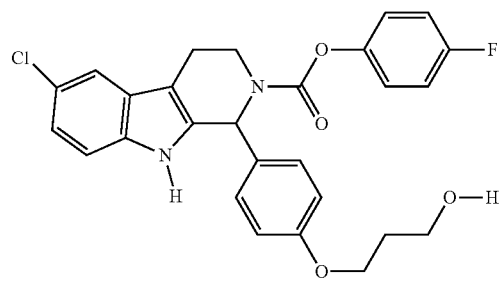 [SMILES: O=C(Oc1ccc(F)cc1)N1CCc2c([nH]c3ccc(Cl)cc23)C1c1ccc(OCCCO)cc1]
1110

TABLE 1-continued
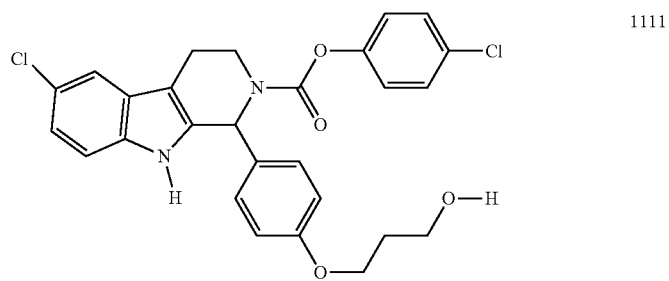
1111
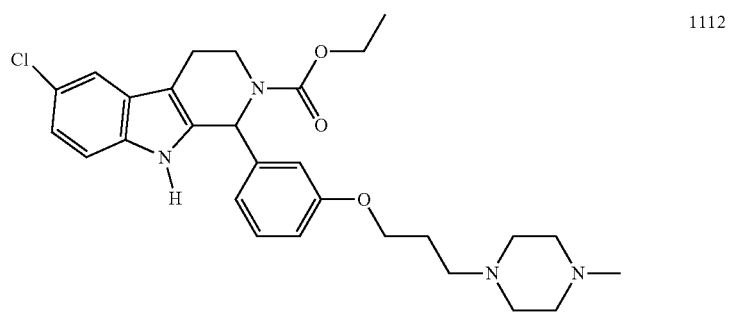
1112
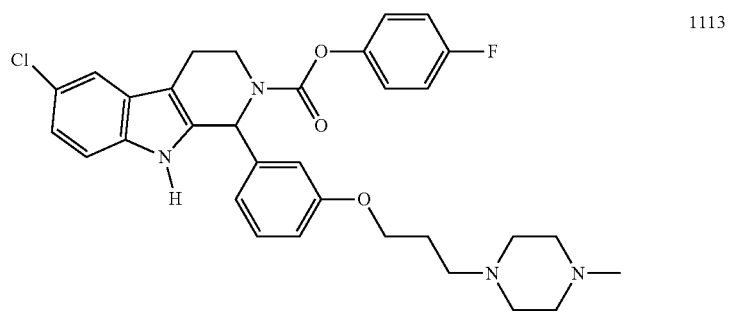
1113
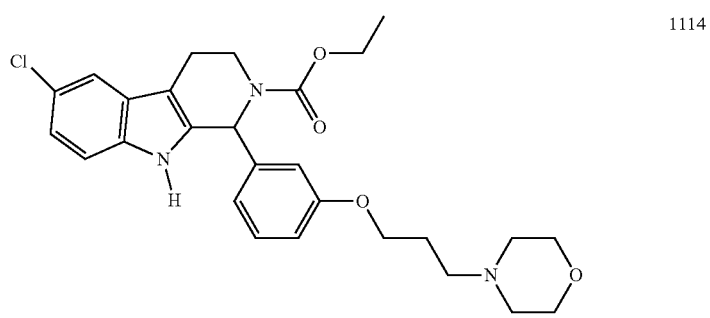
1114
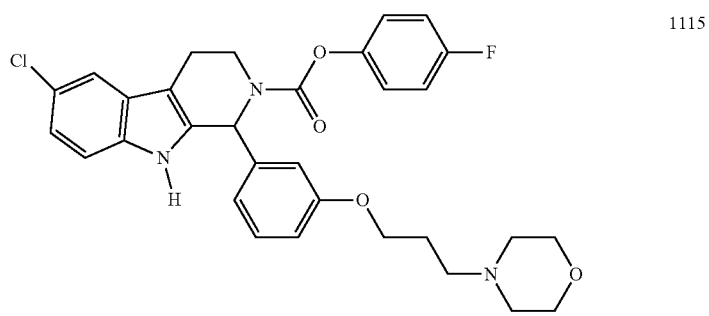
1115

TABLE 1-continued
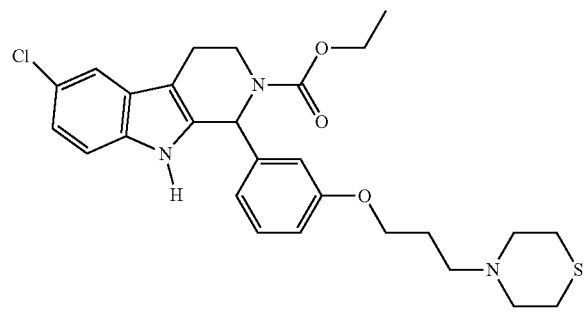 [SMILES: CCOC(=O)N1CCc2c([nH]c3ccc(Cl)cc23)C1c1cccc(OCCCN2CCOCC2)c1]
1116
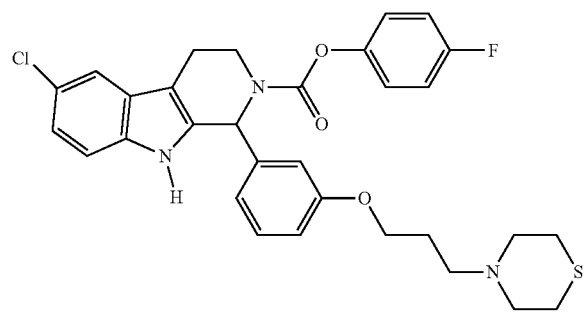 [SMILES: O=C(Oc1ccc(F)cc1)N1CCc2c([nH]c3ccc(Cl)cc23)C1c1cccc(OCCCN2CCOCC2)c1]
1117
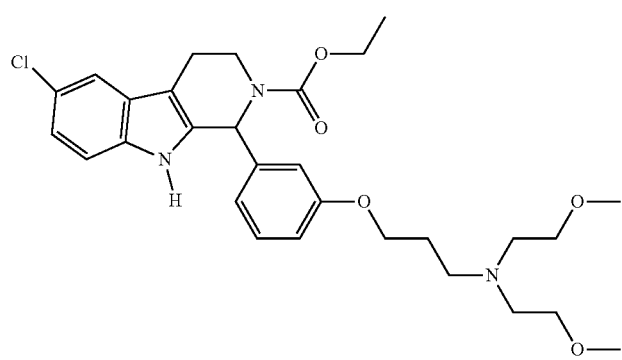 [SMILES: CCOC(=O)N1CCc2c([nH]c3ccc(Cl)cc23)C1c1cccc(OCCCN(CCOC)CCOC)c1]
1118
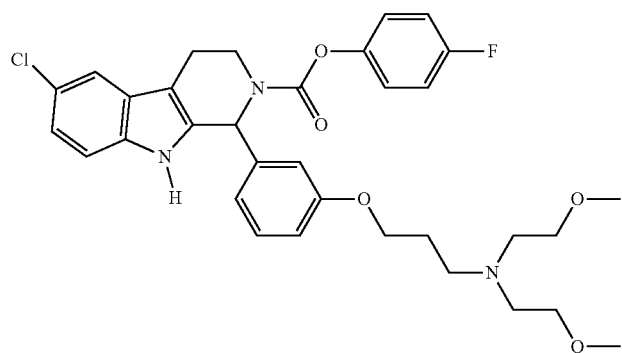 [SMILES: COCCN(CCCOc1cccc(C2c3[nH]c4ccc(Cl)cc4c3CCN2C(=O)Oc2ccc(F)cc2)c1)CCOC]
1119

TABLE 1-continued
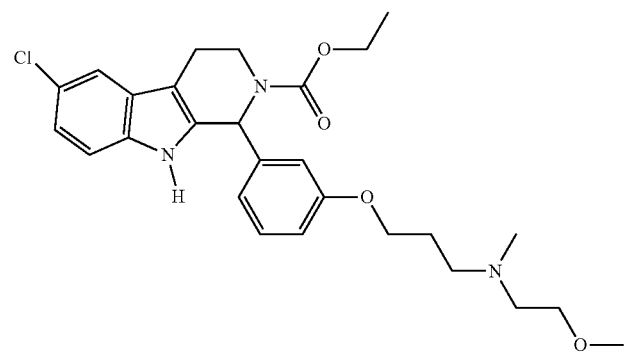 [SMILES: CCOC(=O)N1CCc2c([nH]c3ccc(Cl)cc23)C1c1cccc(OCCCN(C)CCOC)c1]
1120
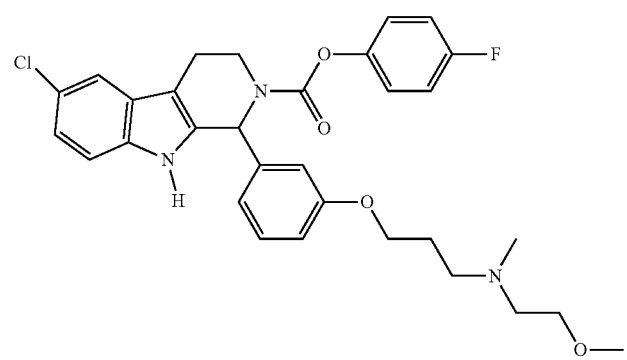 [SMILES: COCCN(C)CCCOc1cccc(C2c3[nH]c4ccc(Cl)cc4c3CCN2C(=O)Oc2ccc(F)cc2)c1]
1121
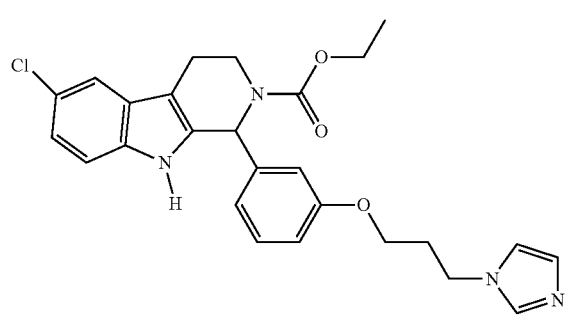 [SMILES: CCOC(=O)N1CCc2c([nH]c3ccc(Cl)cc23)C1c1cccc(OCCCn2ccnc2)c1]
1122
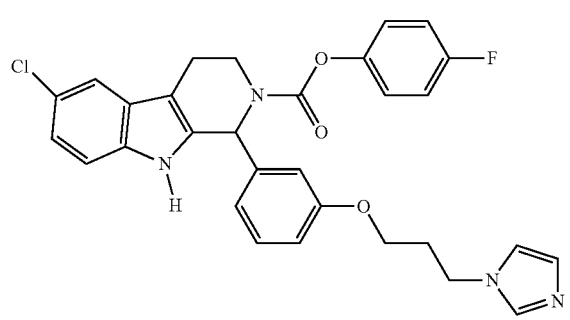 [SMILES: O=C(Oc1ccc(F)cc1)N1CCc2c([nH]c3ccc(Cl)cc23)C1c1cccc(OCCCn2ccnc2)c1]
1123
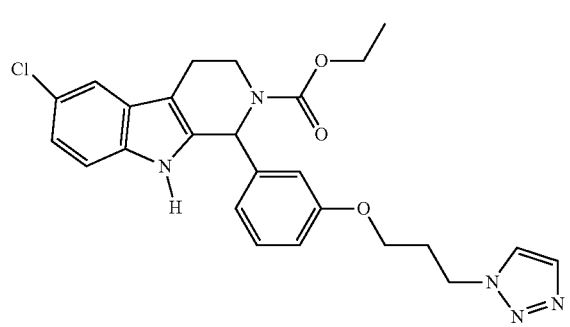 [SMILES: CCOC(=O)N1CCc2c([nH]c3ccc(Cl)cc23)C1c1cccc(OCCCn2ccnn2)c1]
1124

TABLE 1-continued
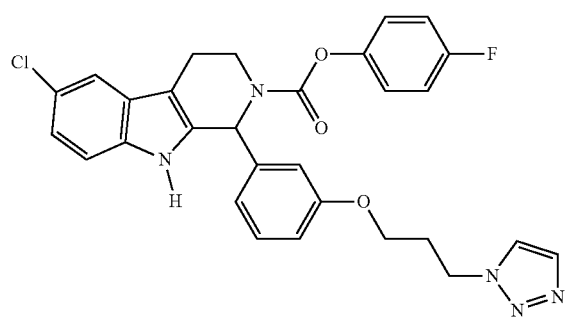 [SMILES: O=C(Oc1ccc(F)cc1)N1CCc2c([nH]c3ccc(Cl)cc23)C1c1cccc(OCCCn2ccnn2)c1]
1125
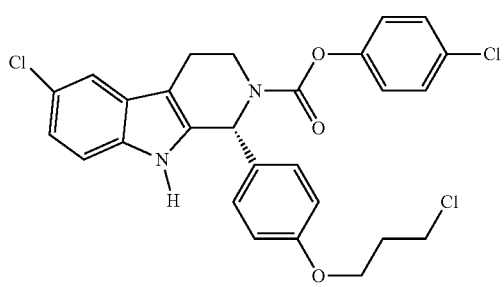 [SMILES: O=C(Oc1ccc(Cl)cc1)N1CCc2c([nH]c3ccc(Cl)cc23)[C@H]1c1ccc(OCCCCl)cc1]
1126
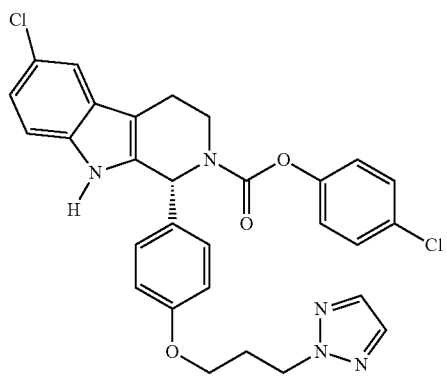
1127
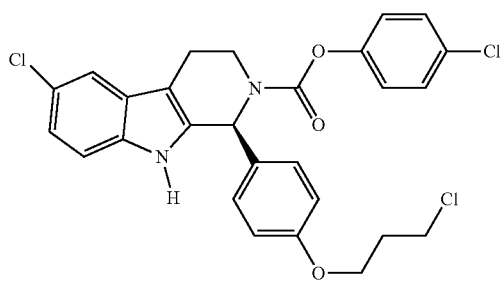 [SMILES: O=C(Oc1ccc(Cl)cc1)N1CCc2c([nH]c3ccc(Cl)cc23)[C@@H]1c1ccc(OCCCCl)cc1]
1128
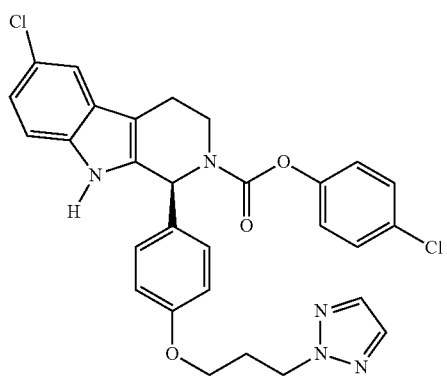 [SMILES: O=C(Oc1ccc(Cl)cc1)N1CCc2c([nH]c3ccc(Cl)cc23)[C@@H]1c1ccc(OCCCn2nccn2)cc1]
1129

TABLE 1-continued
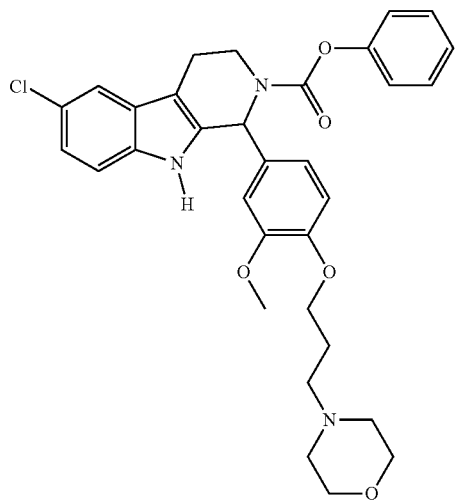 [SMILES: COc1cc(C2c3[nH]c4ccc(Cl)cc4c3CCN2C(=O)Oc2ccccc2)ccc1OCCCN1CCOCC1]
1130
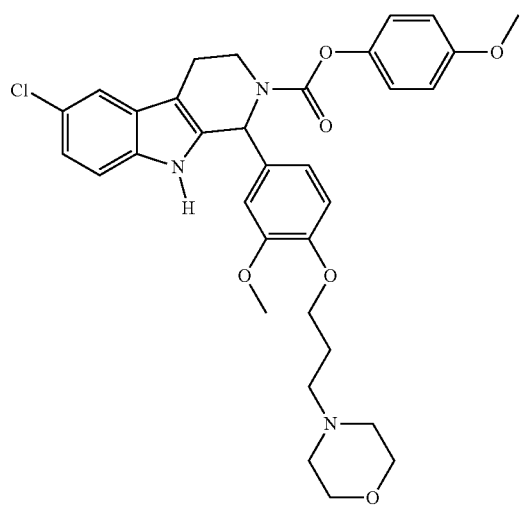 [SMILES: COc1ccc(OC(=O)N2CCc3c([nH]c4ccc(Cl)cc34)C2c2ccc(OCCCN3CCOCC3)c(OC)c2)cc1]
1131
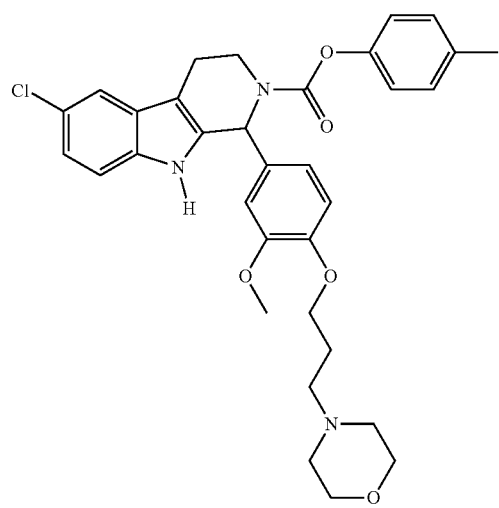 [SMILES: COc1cc(C2c3[nH]c4ccc(Cl)cc4c3CCN2C(=O)Oc2ccc(C)cc2)ccc1OCCCN1CCOCC1]
1132

TABLE 1-continued
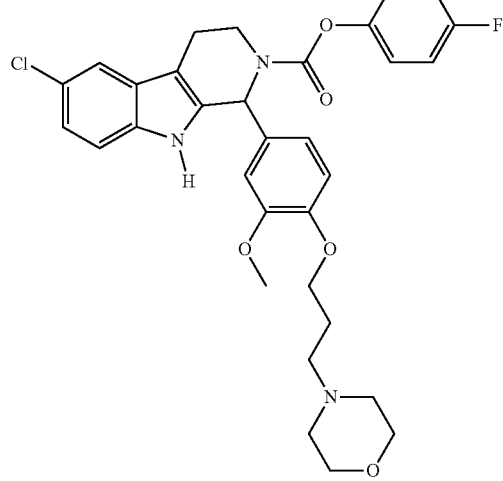
1133
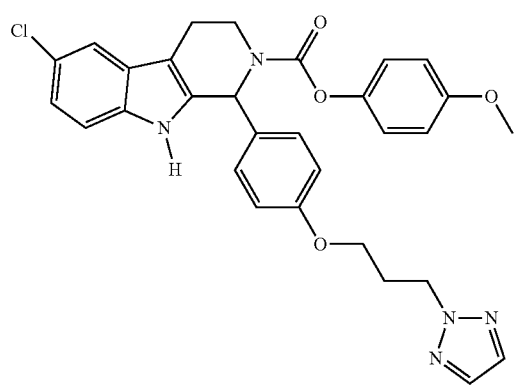 [SMILES: COc1ccc(OC(=O)N2CCc3c([nH]c4ccc(Cl)cc34)C2c2ccc(OCCCn3nccn3)cc2)cc1]
1134
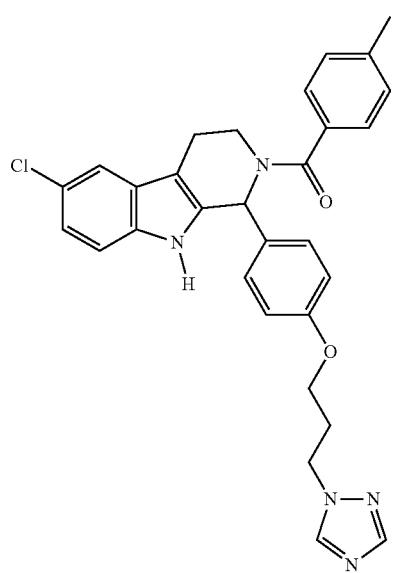 [SMILES: Cc1ccc(C(=O)N2CCc3c([nH]c4ccc(Cl)cc34)C2c2ccc(OCCCn3cncn3)cc2)cc1]
1135

TABLE 1-continued
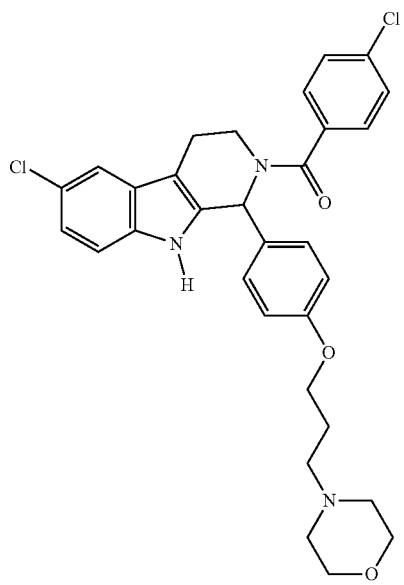 [SMILES: O=C(c1ccc(Cl)cc1)N1CCc2c([nH]c3ccc(Cl)cc23)C1c1ccc(OCCCN2CCOCC2)cc1]
1136
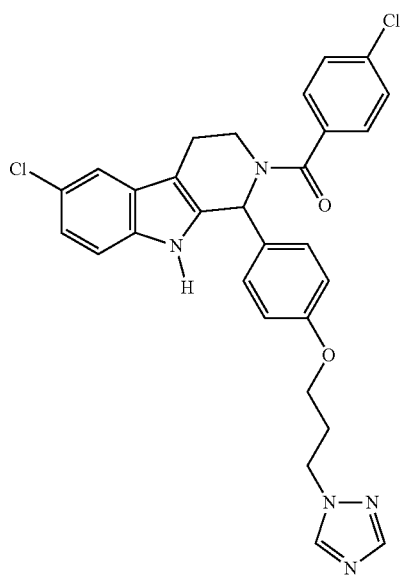 [SMILES: O=C(c1ccc(Cl)cc1)N1CCc2c([nH]c3ccc(Cl)cc23)C1c1ccc(OCCCn2cncn2)cc1]
1137

TABLE 1-continued
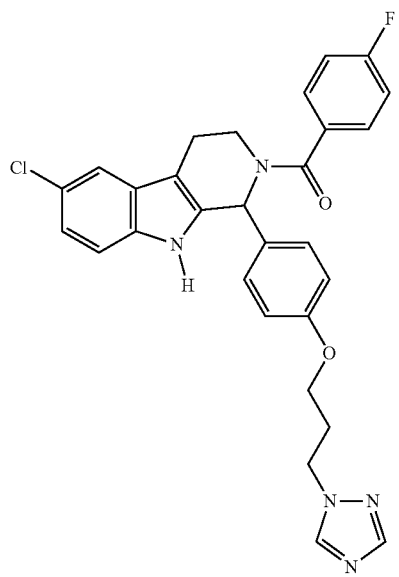 [SMILES: O=C(c1ccc(F)cc1)N1CCc2c([nH]c3ccc(Cl)cc23)C1c1ccc(OCCCn2cncn2)cc1]
1138
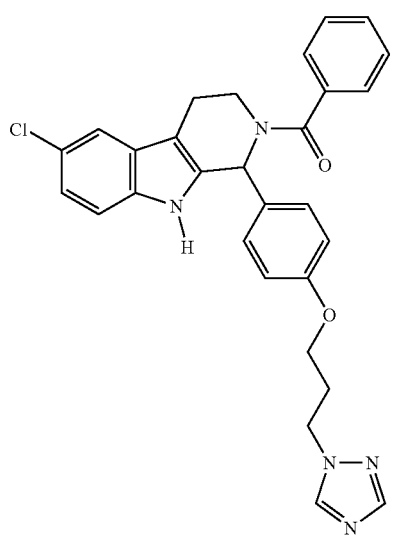 [SMILES: O=C(c1ccccc1)N1CCc2c([nH]c3ccc(Cl)cc23)C1c1ccc(OCCCn2cncn2)cc1]
1139
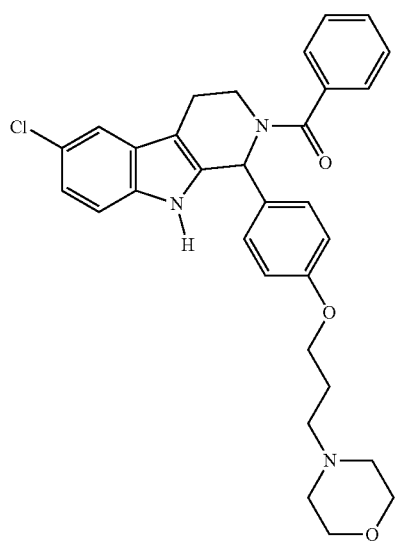 [SMILES: O=C(c1ccccc1)N1CCc2c([nH]c3ccc(Cl)cc23)C1c1ccc(OCCCN2CCOCC2)cc1]
1140

TABLE 1-continued
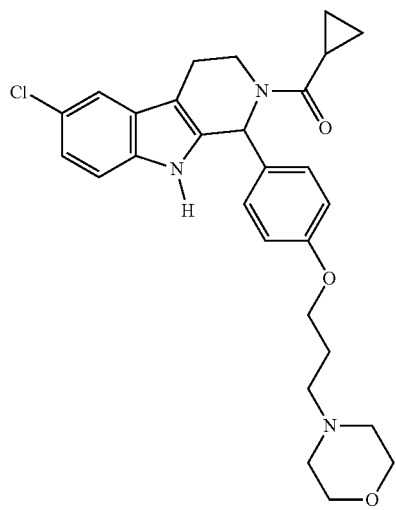 [SMILES: O=C(C1CC1)N1CCc2c([nH]c3ccc(Cl)cc23)C1c1ccc(OCCCN2CCOCC2)cc1]
1141
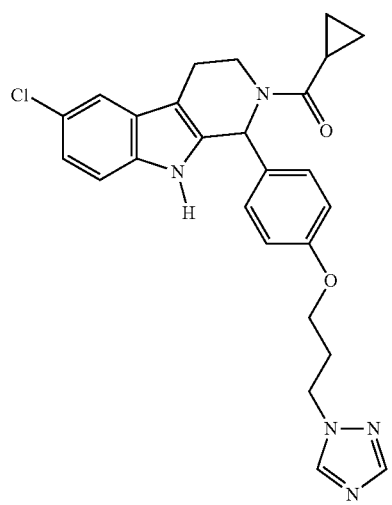 [SMILES: O=C(C1CC1)N1CCc2c([nH]c3ccc(Cl)cc23)C1c1ccc(OCCCn2cncn2)cc1]
1142
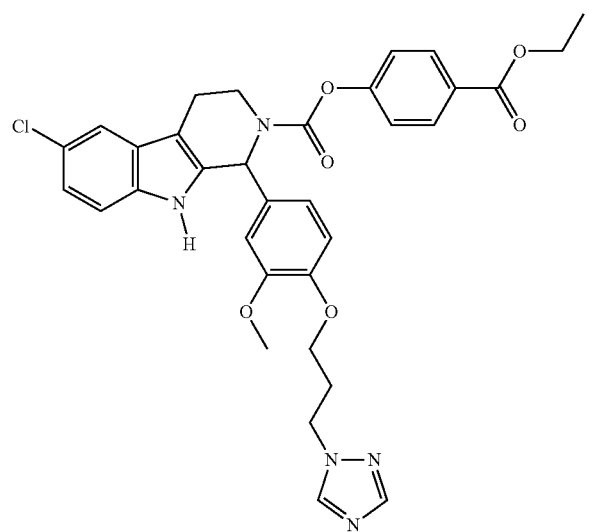 [SMILES: CCOC(=O)c1ccc(OC(=O)N2CCc3c([nH]c4ccc(Cl)cc34)C2c2ccc(OCCCn3cncn3)c(OC)c2)cc1]
1143

TABLE 1-continued
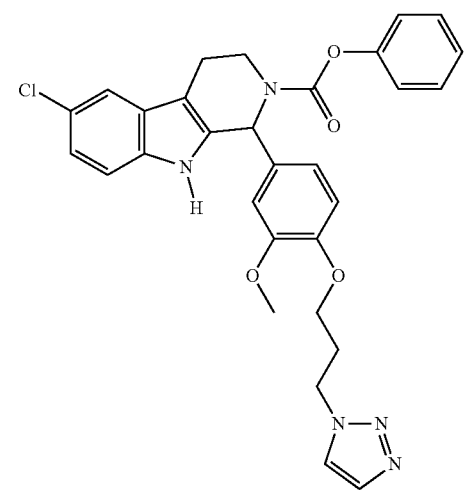 [SMILES: COc1cc(C2c3[nH]c4ccc(Cl)cc4c3CCN2C(=O)Oc2ccccc2)ccc1OCCCn1ccnn1]
1144
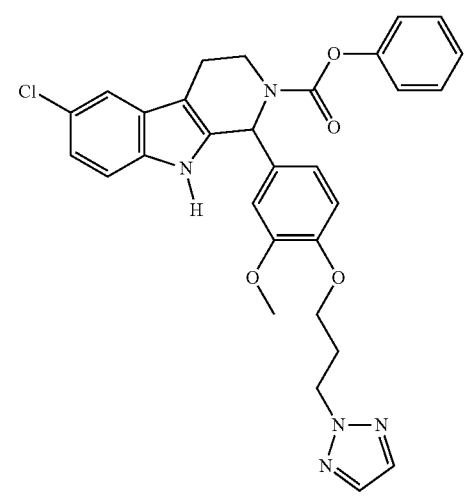 [SMILES: COc1cc(C2c3[nH]c4ccc(Cl)cc4c3CCN2C(=O)Oc2ccccc2)ccc1OCCCn1nccn1]
1145
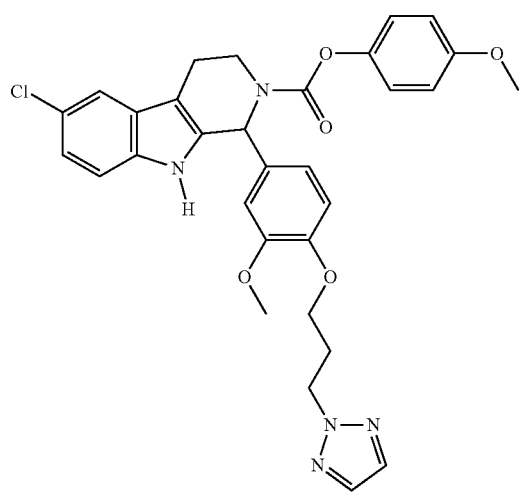 [SMILES: COc1ccc(OC(=O)N2CCc3c([nH]c4ccc(Cl)cc34)C2c2ccc(OCCCn3nccn3)c(OC)c2)cc1]
1146

TABLE 1-continued
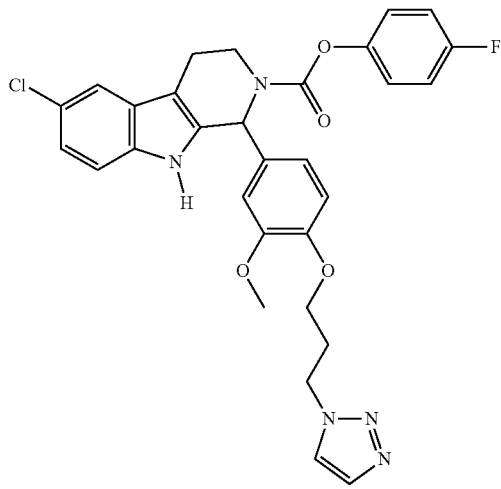 [SMILES: COc1cc(C2c3[nH]c4ccc(Cl)cc4c3CCN2C(=O)Oc2ccc(F)cc2)ccc1OCCCn1ccnn1]
1147
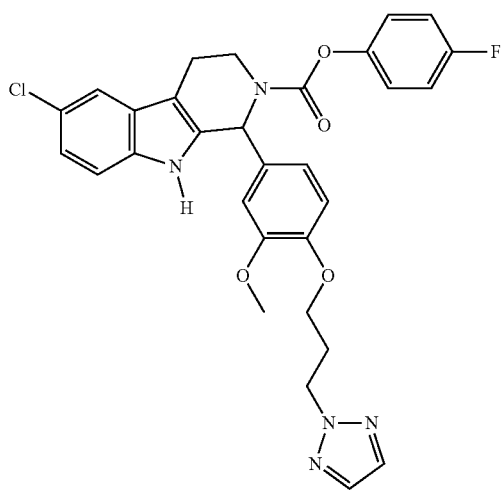 [SMILES: COc1cc(C2c3[nH]c4ccc(Cl)cc4c3CCN2C(=O)Oc2ccc(F)cc2)ccc1OCCCn1nccn1]
1148
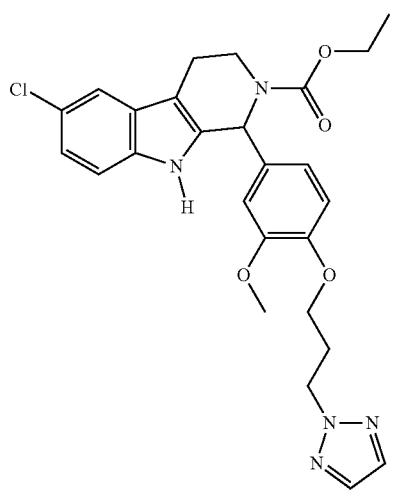 [SMILES: CCOC(=O)N1CCc2c([nH]c3ccc(Cl)cc23)C1c1ccc(OCCCn2nccn2)c(OC)c1]
1149

TABLE 1-continued
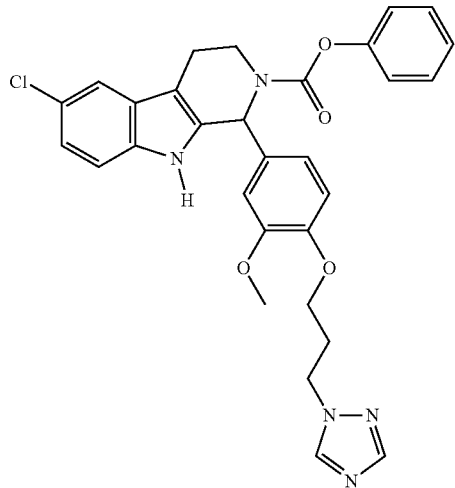 [SMILES: COc1cc(C2c3[nH]c4ccc(Cl)cc4c3CCN2C(=O)Oc2ccccc2)ccc1OCCCn1cncn1]
1150
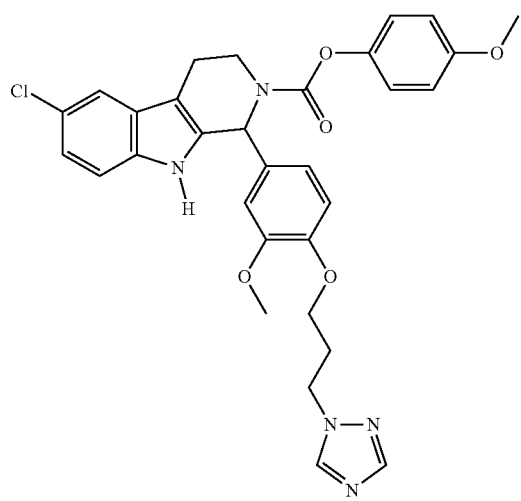 [SMILES: COc1ccc(OC(=O)N2CCc3c([nH]c4ccc(Cl)cc34)C2c2ccc(OCCCn3cncn3)c(OC)c2)cc1]
1151
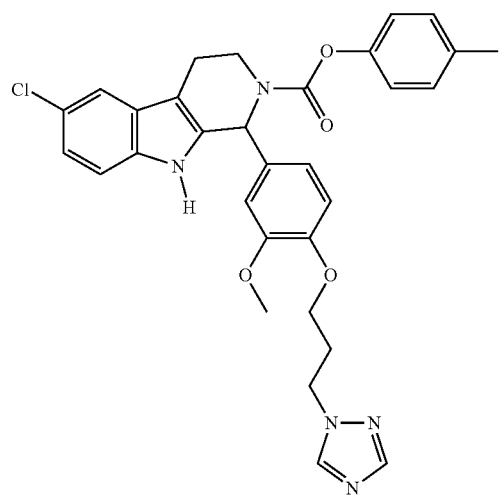 [SMILES: COc1cc(C2c3[nH]c4ccc(Cl)cc4c3CCN2C(=O)Oc2ccc(C)cc2)ccc1OCCCn1cncn1]
1152

TABLE 1-continued
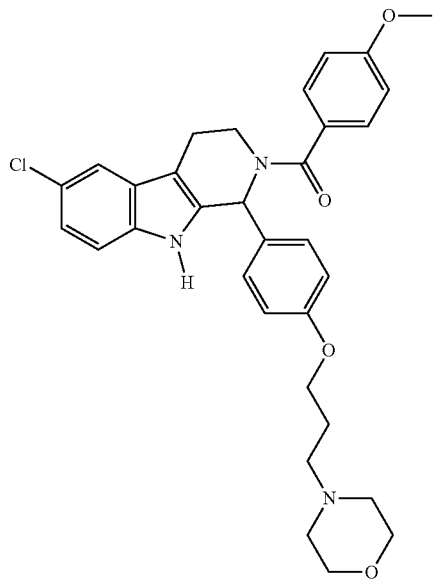 [SMILES: COc1ccc(C(=O)N2CCc3c([nH]c4ccc(Cl)cc34)C2c2ccc(OCCCN3CCOCC3)cc2)cc1]
1153
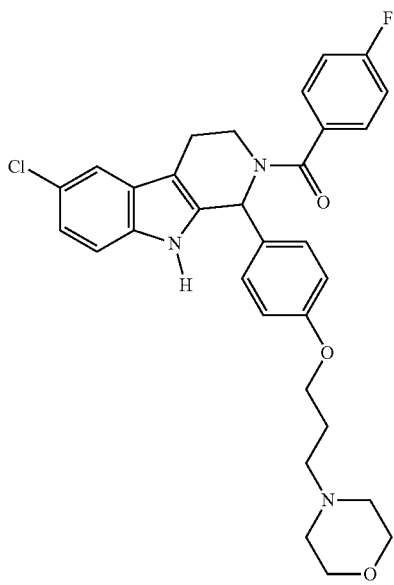 [SMILES: O=C(c1ccc(F)cc1)N1CCc2c([nH]c3ccc(Cl)cc23)C1c1ccc(OCCCN2CCOCC2)cc1]
1154
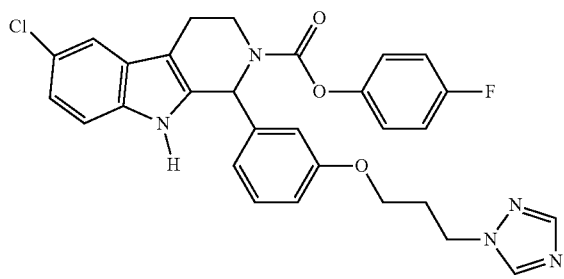 [SMILES: O=C(Oc1ccc(F)cc1)N1CCc2c([nH]c3ccc(Cl)cc23)C1c1cccc(OCCCn2cncn2)c1]
1155

TABLE 1-continued
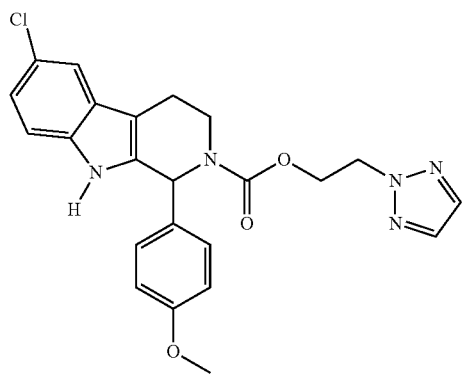 [SMILES: COc1ccc(C2c3[nH]c4ccc(Cl)cc4c3CCN2C(=O)OCCn2nccn2)cc1]
1156
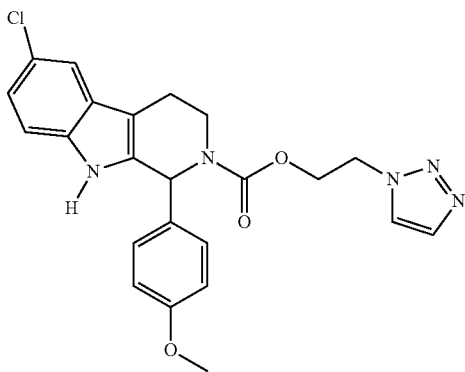 [SMILES: COc1ccc(C2c3[nH]c4ccc(Cl)cc4c3CCN2C(=O)OCCn2ccnn2)cc1]
1157
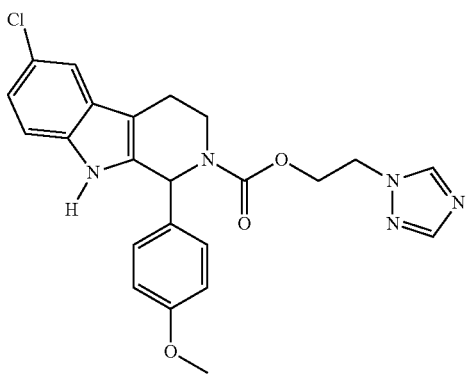 [SMILES: COc1ccc(C2c3[nH]c4ccc(Cl)cc4c3CCN2C(=O)OCCn2cncn2)cc1]
1158
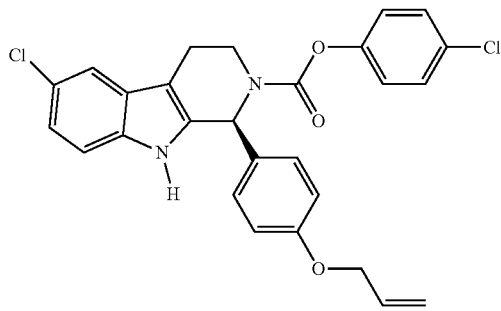 [SMILES: C=CCOc1ccc([C@H]2c3[nH]c4ccc(Cl)cc4c3CCN2C(=O)Oc2ccc(Cl)cc2)cc1]
1159

TABLE 1-continued
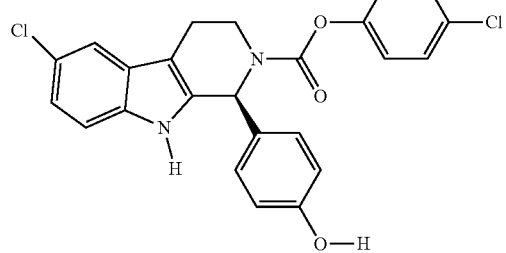
1160
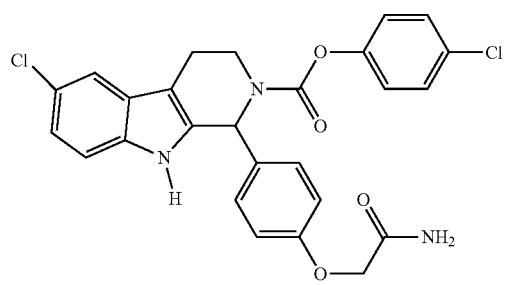 [SMILES: NC(=O)COc1ccc(C2c3[nH]c4ccc(Cl)cc4c3CCN2C(=O)Oc2ccc(Cl)cc2)cc1]
1161
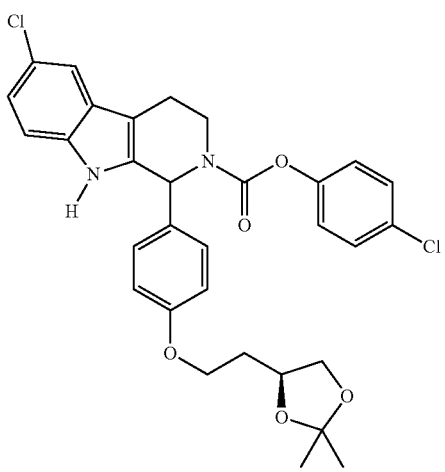 [SMILES: CC1(C)OC[C@H](CCOc2ccc(C3c4[nH]c5ccc(Cl)cc5c4CCN3C(=O)Oc3ccc(Cl)cc3)cc2)O1]
1162
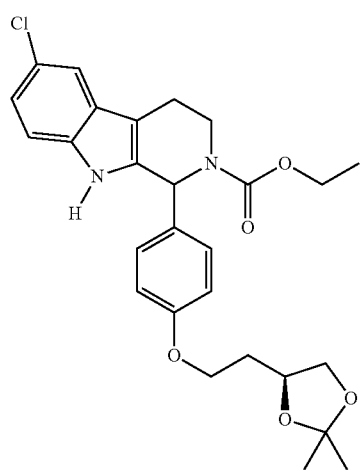 [SMILES: CCOC(=O)N1CCc2c([nH]c3ccc(Cl)cc23)C1c1ccc(OCC[C@H]2COC(C)(C)O2)cc1]
1163

TABLE 1-continued
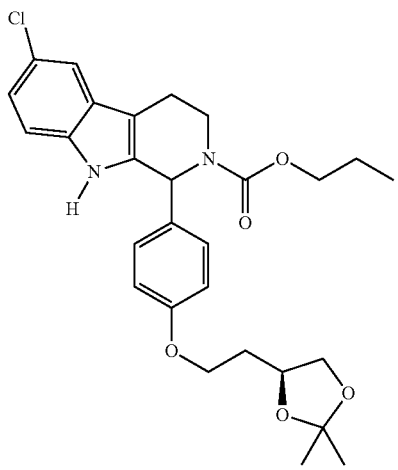 [SMILES: CCCOC(=O)N1CCc2c([nH]c3ccc(Cl)cc23)C1c1ccc(OCC[C@H]2COC(C)(C)O2)cc1]
1164
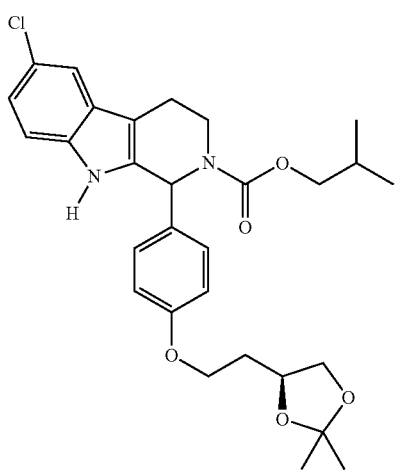 [SMILES: CC(C)COC(=O)N1CCc2c([nH]c3ccc(Cl)cc23)C1c1ccc(OCC[C@H]2COC(C)(C)O2)cc1]
1165
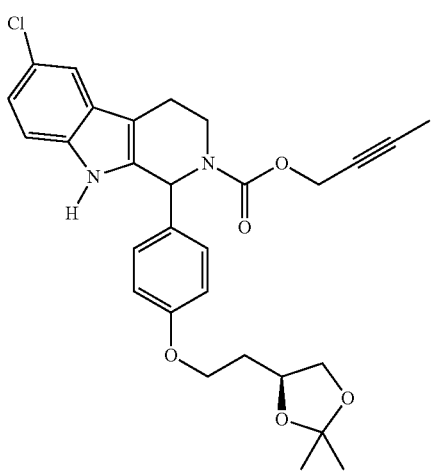 [SMILES: CC#CCOC(=O)N1CCc2c([nH]c3ccc(Cl)cc23)C1c1ccc(OCC[C@H]2COC(C)(C)O2)cc1]
1166

TABLE 1-continued
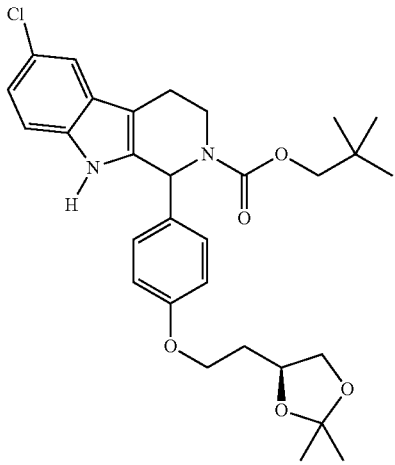 [SMILES: CC(C)(C)COC(=O)N1CCc2c([nH]c3ccc(Cl)cc23)C1c1ccc(OCC[C@H]2COC(C)(C)O2)cc1]
1167
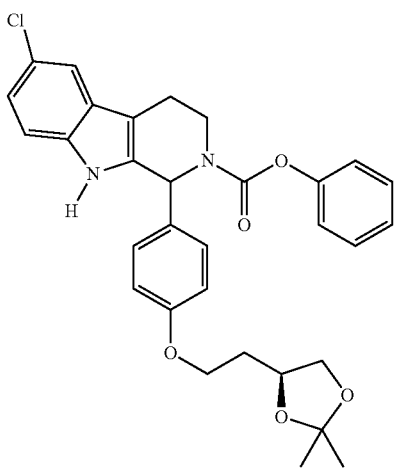 [SMILES: CC1(C)OC[C@H](CCOc2ccc(C3c4[nH]c5ccc(Cl)cc5c4CCN3C(=O)Oc3ccccc3)cc2)O1]
1168
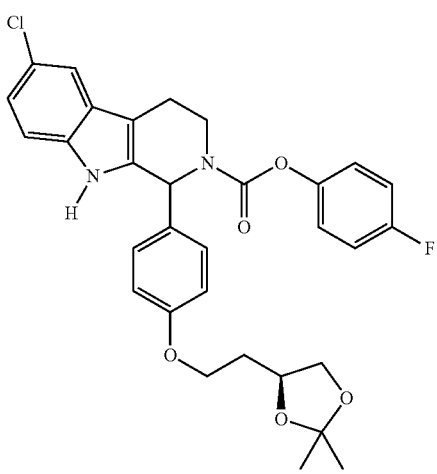 [SMILES: CC1(C)OC[C@H](CCOc2ccc(C3c4[nH]c5ccc(Cl)cc5c4CCN3C(=O)Oc3ccc(F)cc3)cc2)O1]
1169

TABLE 1-continued
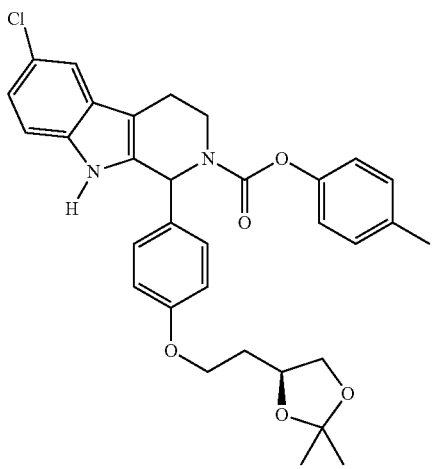 [SMILES: Cc1ccc(OC(=O)N2CCc3c([nH]c4ccc(Cl)cc34)C2c2ccc(OCC[C@H]3COC(C)(C)O3)cc2)cc1]
1170
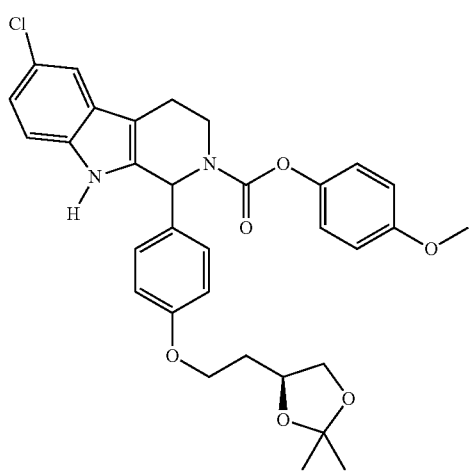 [SMILES: COc1ccc(OC(=O)N2CCc3c([nH]c4ccc(Cl)cc34)C2c2ccc(OCC[C@H]3COC(C)(C)O3)cc2)cc1]
1171
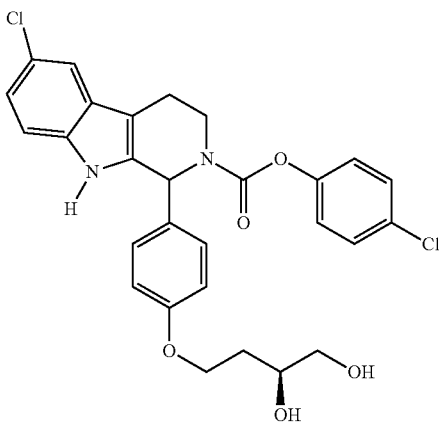 [SMILES: O=C(Oc1ccc(Cl)cc1)N1CCc2c([nH]c3ccc(Cl)cc23)C1c1ccc(OCC[C@H](O)CO)cc1]
1172

TABLE 1-continued
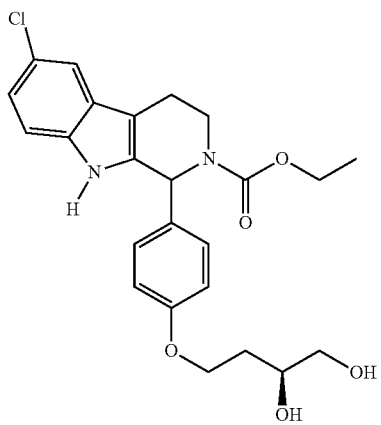 [SMILES: CCOC(=O)N1CCc2c([nH]c3ccc(Cl)cc23)C1c1ccc(OCC[C@H](O)CO)cc1]
1173
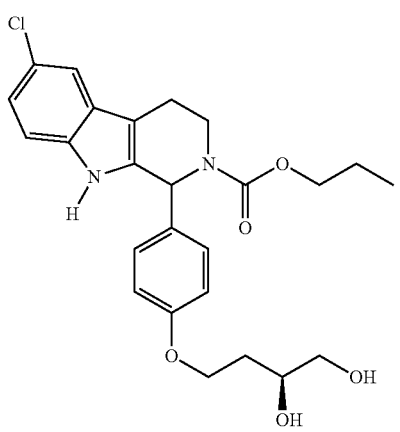 [SMILES: CCCOC(=O)N1CCc2c([nH]c3ccc(Cl)cc23)C1c1ccc(OCC[C@H](O)CO)cc1]
1174
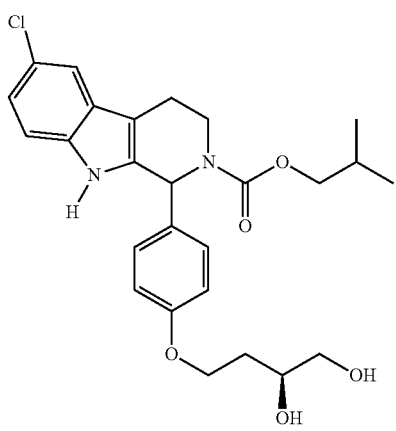 [SMILES: CC(C)COC(=O)N1CCc2c([nH]c3ccc(Cl)cc23)C1c1ccc(OCC[C@H](O)CO)cc1]
1175

TABLE 1-continued
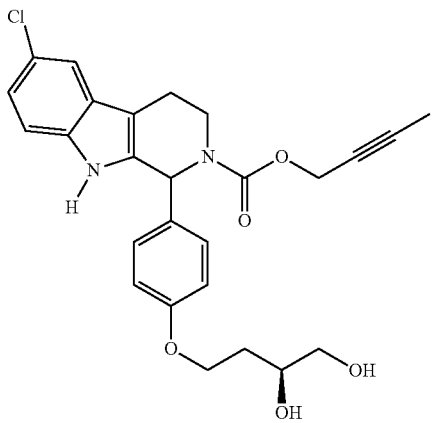 [SMILES: CC#CCOC(=O)N1CCc2c([nH]c3ccc(Cl)cc23)C1c1ccc(OCC[C@H](O)CO)cc1]
1176
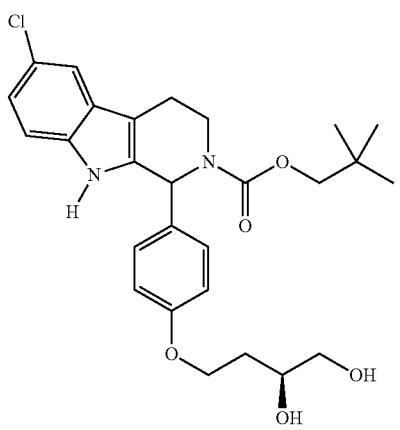 [SMILES: CC(C)(C)COC(=O)N1CCc2c([nH]c3ccc(Cl)cc23)C1c1ccc(OCC[C@H](O)CO)cc1]
1177
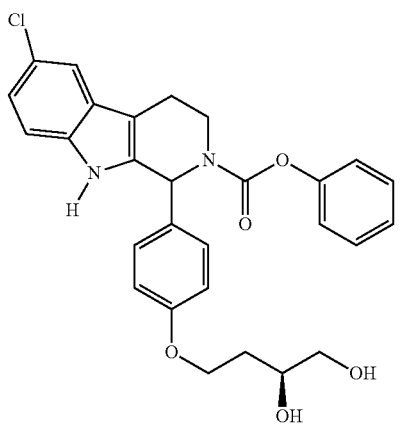 [SMILES: O=C(Oc1ccccc1)N1CCc2c([nH]c3ccc(Cl)cc23)C1c1ccc(OCC[C@H](O)CO)cc1]
1178

TABLE 1-continued
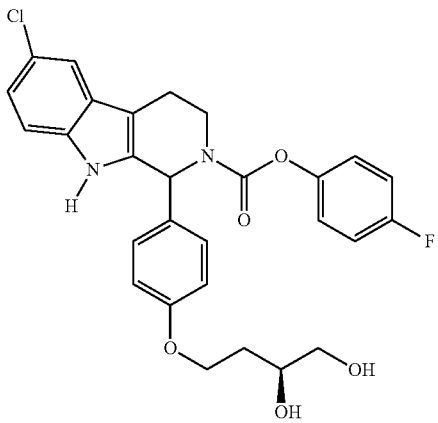 [SMILES: O=C(Oc1ccc(F)cc1)N1CCc2c([nH]c3ccc(Cl)cc23)C1c1ccc(OCC[C@H](O)CO)cc1]
1179
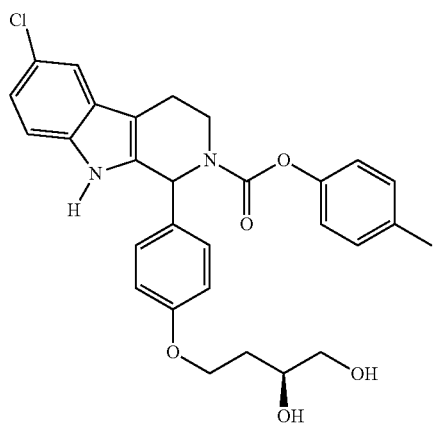 [SMILES: Cc1ccc(OC(=O)N2CCc3c([nH]c4ccc(Cl)cc34)C2c2ccc(OCC[C@H](O)CO)cc2)cc1]
1180
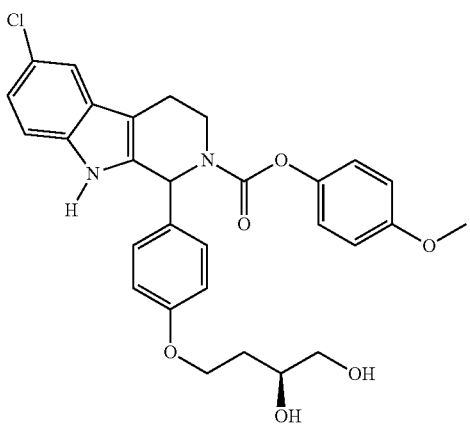 [SMILES: COc1ccc(OC(=O)N2CCc3c([nH]c4ccc(Cl)cc34)C2c2ccc(OCC[C@H](O)CO)cc2)cc1]
1181
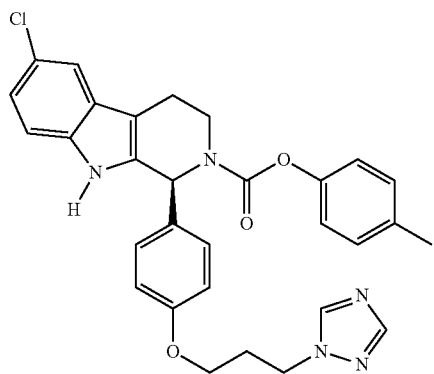 [SMILES: Cc1ccc(OC(=O)N2CCc3c([nH]c4ccc(Cl)cc34)[C@@H]2c2ccc(OCCCn3cncn3)cc2)cc1]
1182

TABLE 1-continued
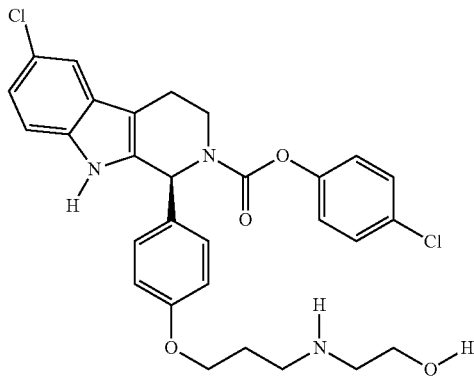 [SMILES: O=C(Oc1ccc(Cl)cc1)N1CCc2c([nH]c3ccc(Cl)cc23)[C@@H]1c1ccc(OCCCNCCO)cc1]
1183
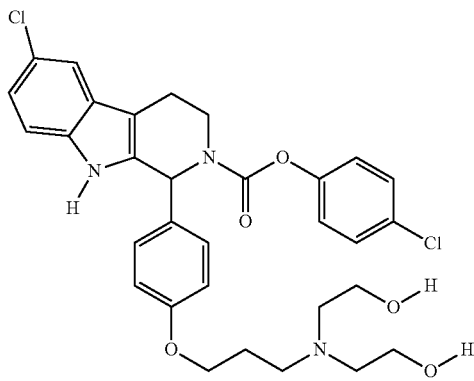 [SMILES: O=C(Oc1ccc(Cl)cc1)N1CCc2c([nH]c3ccc(Cl)cc23)C1c1ccc(OCCCN(CCO)CCO)cc1]
1184
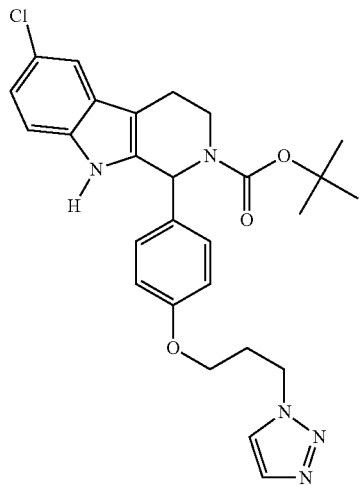 [SMILES: CC(C)(C)OC(=O)N1CCc2c([nH]c3ccc(Cl)cc23)C1c1ccc(OCCCn2ccnn2)cc1]
1185

TABLE 1-continued
| | |
|---|---|
| 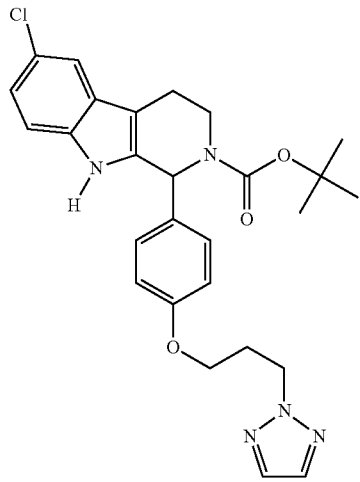 [SMILES: CC(C)(C)OC(=O)N1CCc2c([nH]c3ccc(Cl)cc23)C1c1ccc(OCCCn2nccn2)cc1] | 1186 |
| 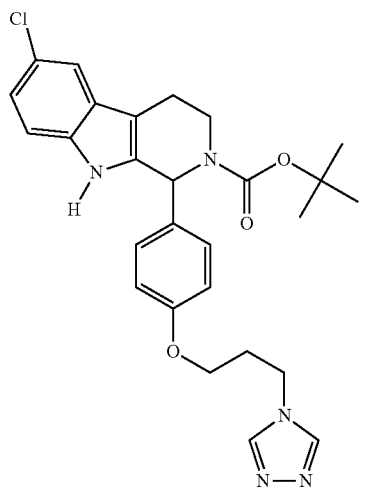 [SMILES: CC(C)(C)OC(=O)N1CCc2c([nH]c3ccc(Cl)cc23)C1c1ccc(OCCCn2cnnc2)cc1] | 1187 |
| 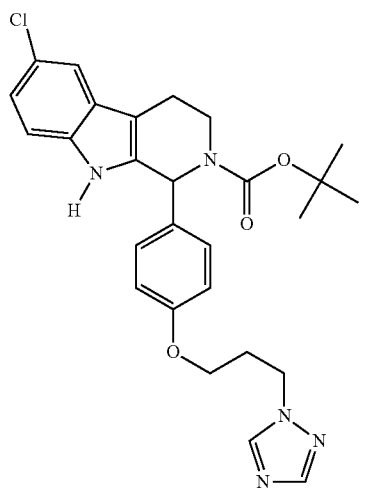 [SMILES: CC(C)(C)OC(=O)N1CCc2c([nH]c3ccc(Cl)cc23)C1c1ccc(OCCCn2cncn2)cc1] | 1188 |

TABLE 1-continued
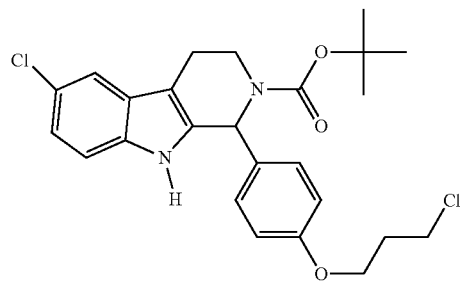 [SMILES: CC(C)(C)OC(=O)N1CCc2c([nH]c3ccc(Cl)cc23)C1c1ccc(OCCCCl)cc1]
1189
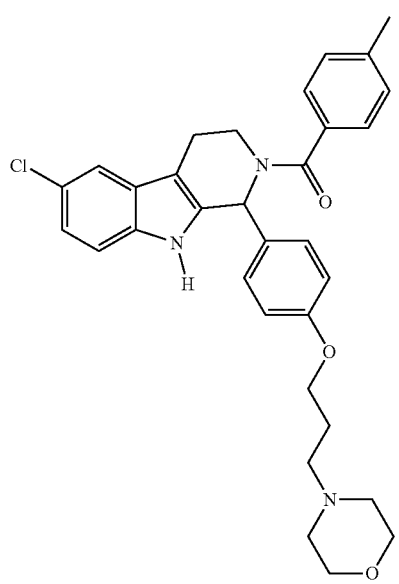 [SMILES: Cc1ccc(C(=O)N2CCc3c([nH]c4ccc(Cl)cc34)C2c2ccc(OCCCN3CCOCC3)cc2)cc1]
1190
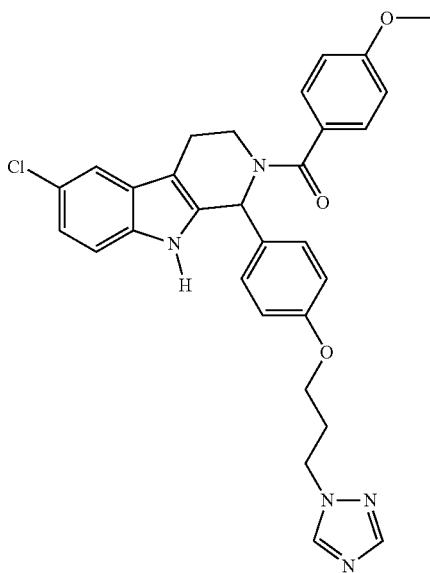 [SMILES: COc1ccc(C(=O)N2CCc3c([nH]c4ccc(Cl)cc34)C2c2ccc(OCCCn3cncn3)cc2)cc1]
1191

TABLE 1-continued
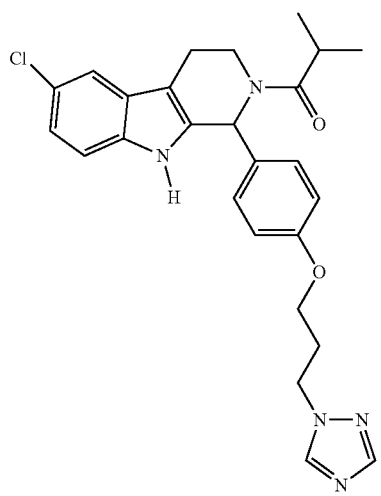 [SMILES: CC(C)C(=O)N1CCc2c([nH]c3ccc(Cl)cc23)C1c1ccc(OCCCn2cncn2)cc1]
1192
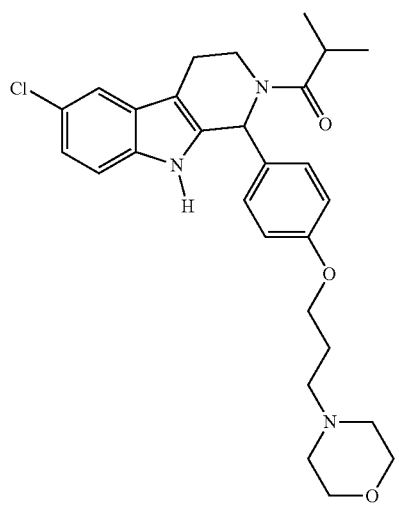 [SMILES: CC(C)C(=O)N1CCc2c([nH]c3ccc(Cl)cc23)C1c1ccc(OCCCN2CCOCC2)cc1]
1193
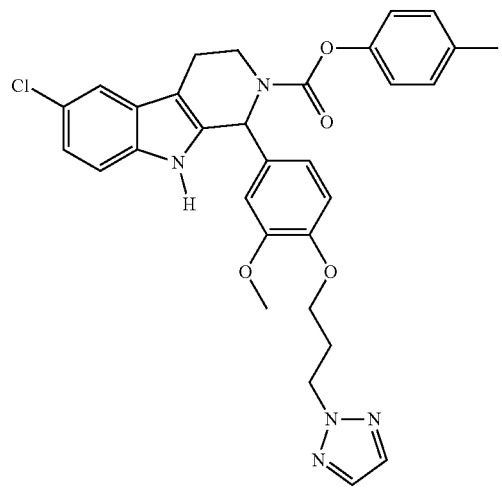 [SMILES: COc1cc(C2c3[nH]c4ccc(Cl)cc4c3CCN2C(=O)Oc2ccc(C)cc2)ccc1OCCCn1nccn1]
1194

TABLE 1-continued
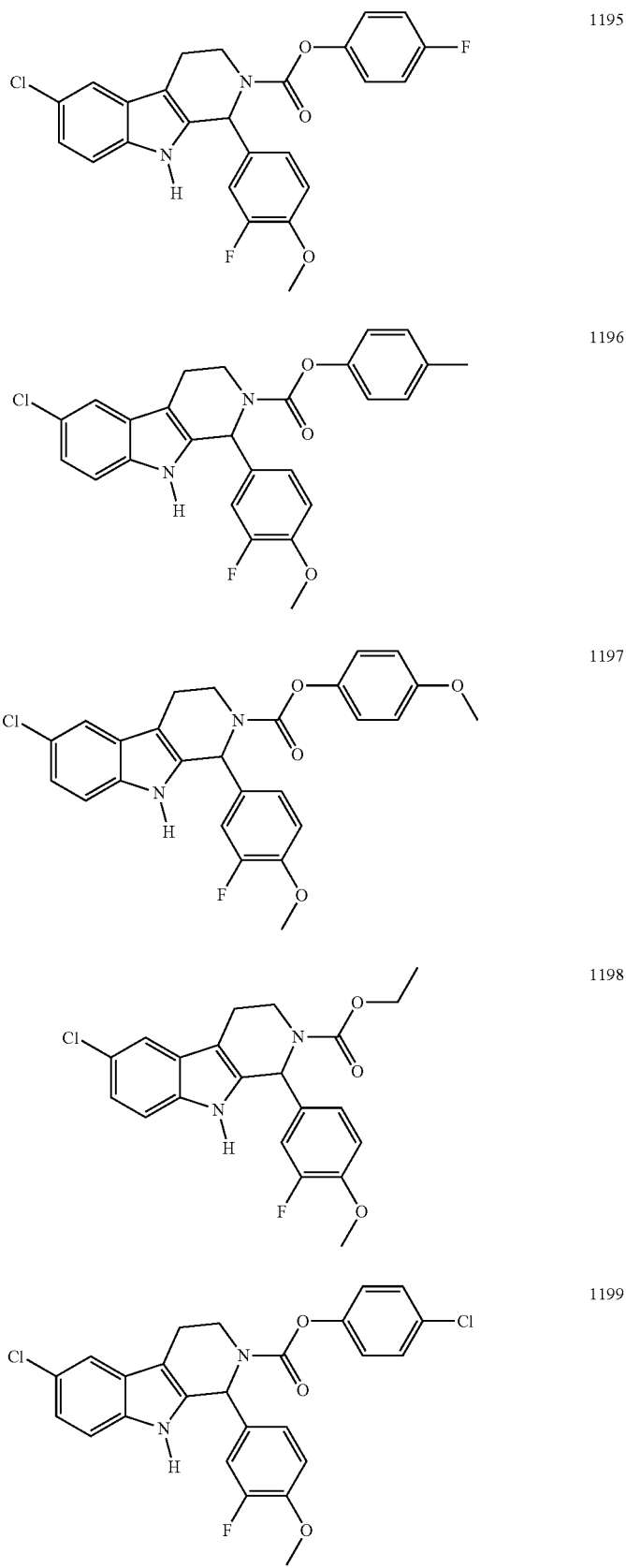

TABLE 1-continued
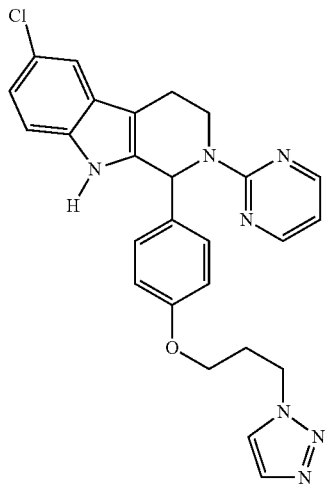 [SMILES: Clc1ccc2[nH]c3c(c2c1)CCN(c1ncccn1)C3c1ccc(OCCCn2ccnn2)cc1]
1200
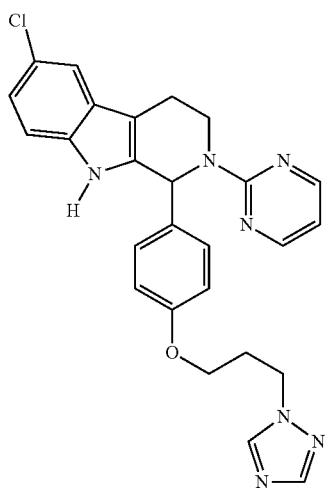 [SMILES: Clc1ccc2[nH]c3c(c2c1)CCN(c1ncccn1)C3c1ccc(OCCCn2cncn2)cc1]
1201
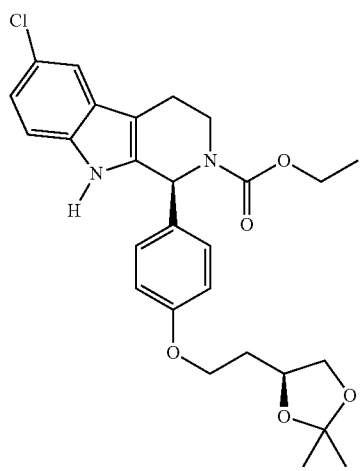 [SMILES: CCOC(=O)N1CCc2c([nH]c3ccc(Cl)cc23)[C@@H]1c1ccc(OCC[C@H]2COC(C)(C)O2)cc1]
1202

TABLE 1-continued
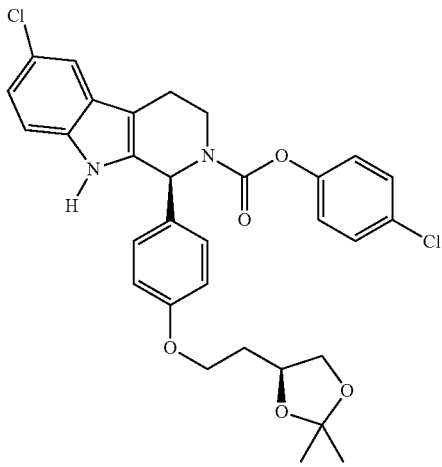 [SMILES: CC1(C)OC[C@H](CCOc2ccc([C@H]3c4[nH]c5ccc(Cl)cc5c4CCN3C(=O)Oc3ccc(Cl)cc3)cc2)O1]
1203
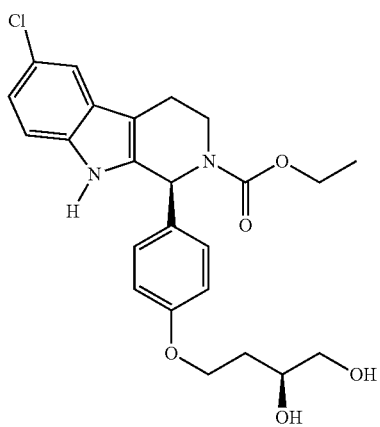 [SMILES: CCOC(=O)N1CCc2c([nH]c3ccc(Cl)cc23)[C@@H]1c1ccc(OCC[C@H](O)CO)cc1]
1204
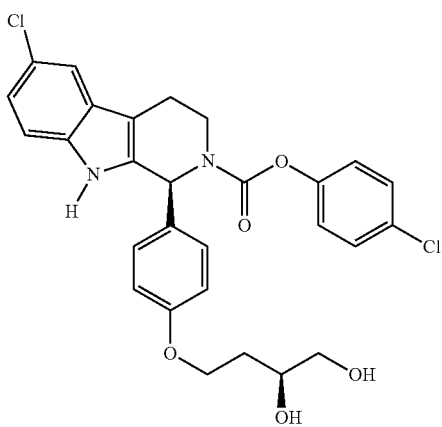 [SMILES: O=C(Oc1ccc(Cl)cc1)N1CCc2c([nH]c3ccc(Cl)cc23)[C@@H]1c1ccc(OCC[C@H](O)CO)cc1]
1205

TABLE 1-continued
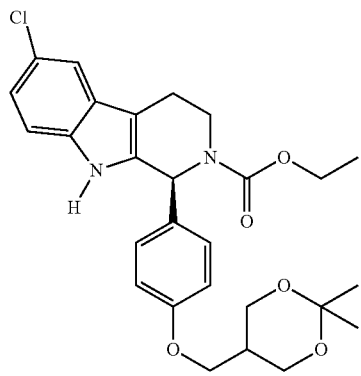 [SMILES: CCOC(=O)N1CCc2c([nH]c3ccc(Cl)cc23)[C@@H]1c1ccc(OCC2COC(C)(C)OC2)cc1]
1206
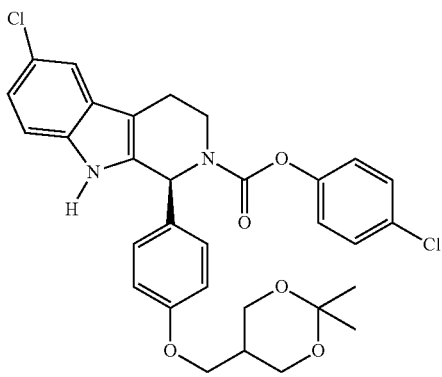 [SMILES: CC1(C)OCC(COc2ccc([C@H]3c4[nH]c5ccc(Cl)cc5c4CCN3C(=O)Oc3ccc(Cl)cc3)cc2)CO1]
1207
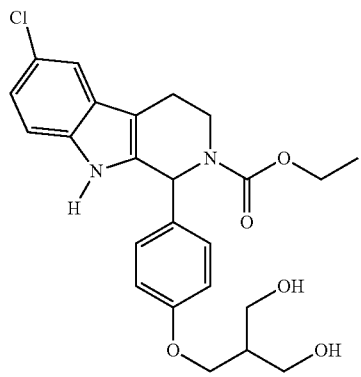 [SMILES: CCOC(=O)N1CCc2c([nH]c3ccc(Cl)cc23)C1c1ccc(OCC(CO)CO)cc1]
1208
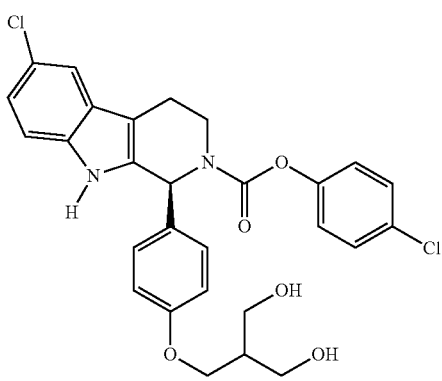 [SMILES: O=C(Oc1ccc(Cl)cc1)N1CCc2c([nH]c3ccc(Cl)cc23)[C@@H]1c1ccc(OCC(CO)CO)cc1]
1209

TABLE 1-continued
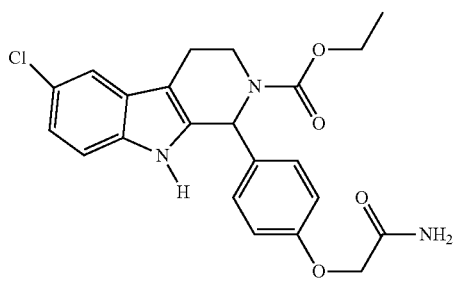 [SMILES: CCOC(=O)N1CCc2c([nH]c3ccc(Cl)cc23)C1c1ccc(OCC(N)=O)cc1]
1210
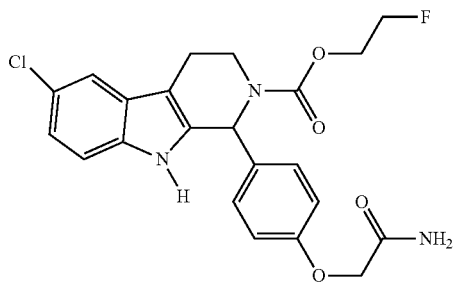 [SMILES: NC(=O)COc1ccc(C2c3[nH]c4ccc(Cl)cc4c3CCN2C(=O)OCCF)cc1]
1211
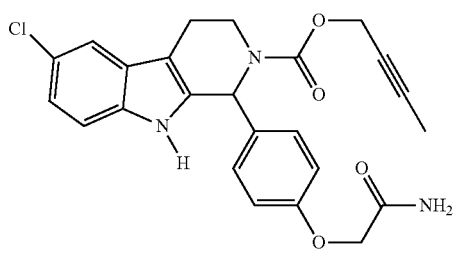 [SMILES: CC#CCOC(=O)N1CCc2c([nH]c3ccc(Cl)cc23)C1c1ccc(OCC(N)=O)cc1]
1212
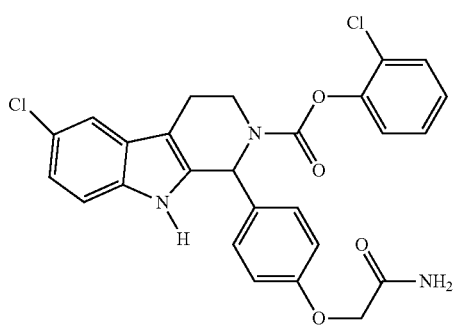 [SMILES: NC(=O)COc1ccc(C2c3[nH]c4ccc(Cl)cc4c3CCN2C(=O)Oc2ccccc2Cl)cc1]
1213
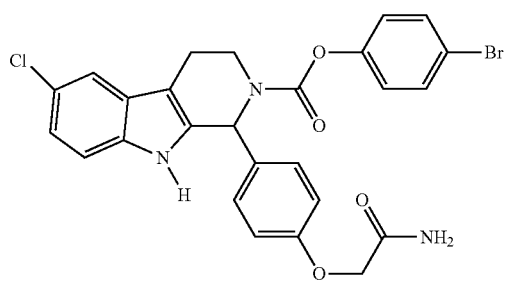 [SMILES: NC(=O)COc1ccc(C2c3[nH]c4ccc(Cl)cc4c3CCN2C(=O)Oc2ccc(Br)cc2)cc1]
1214

TABLE 1-continued
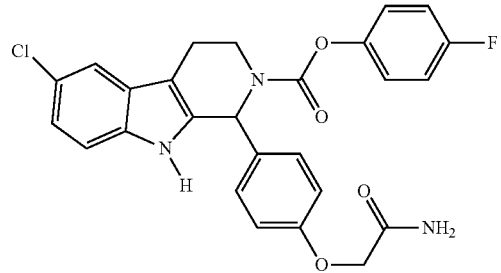 [SMILES: NC(=O)COc1ccc(C2c3[nH]c4ccc(Cl)cc4c3CCN2C(=O)Oc2ccc(F)cc2)cc1]
1215
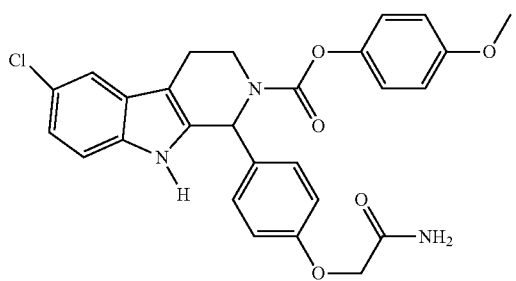 [SMILES: COc1ccc(OC(=O)N2CCc3c([nH]c4ccc(Cl)cc34)C2c2ccc(OCC(N)=O)cc2)cc1]
1216
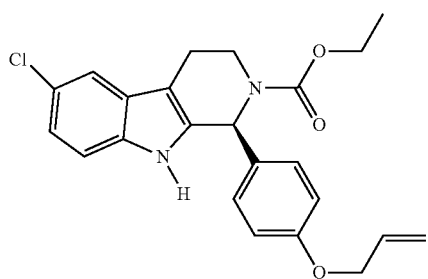 [SMILES: C=CCOc1ccc([C@H]2c3[nH]c4ccc(Cl)cc4c3CCN2C(=O)OCC)cc1]
1217
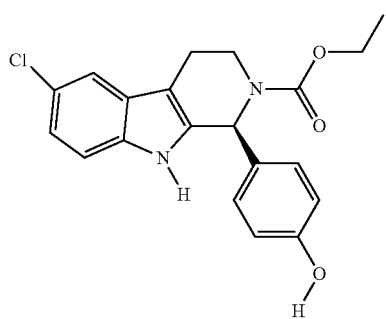 [SMILES: CCOC(=O)N1CCc2c([nH]c3ccc(Cl)cc23)[C@@H]1c1ccc(O)cc1]
1218
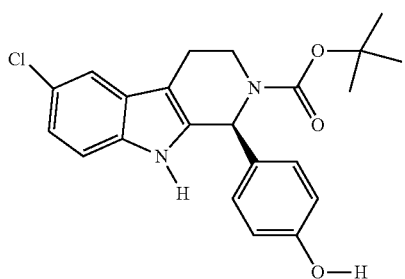 [SMILES: CC(C)(C)OC(=O)N1CCc2c([nH]c3ccc(Cl)cc23)[C@@H]1c1ccc(O)cc1]
1219

TABLE 1-continued
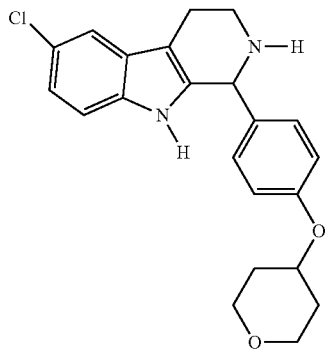 [SMILES: Clc1ccc2[nH]c3c(c2c1)CCNC3c1ccc(OC2CCOCC2)cc1]
1220
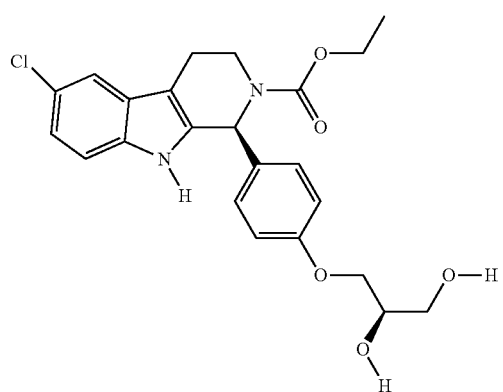 [SMILES: CCOC(=O)N1CCc2c([nH]c3ccc(Cl)cc23)[C@@H]1c1ccc(OC[C@H](O)CO)cc1]
1221
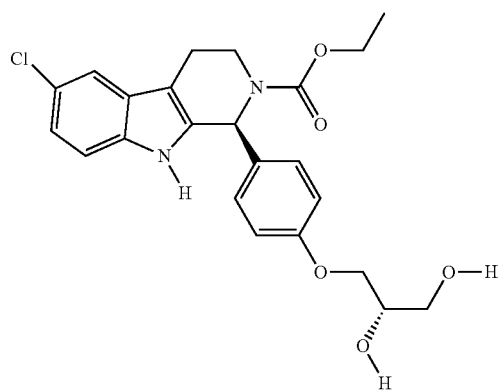 [SMILES: CCOC(=O)N1CCc2c([nH]c3ccc(Cl)cc23)[C@@H]1c1ccc(OC[C@@H](O)CO)cc1]
1222
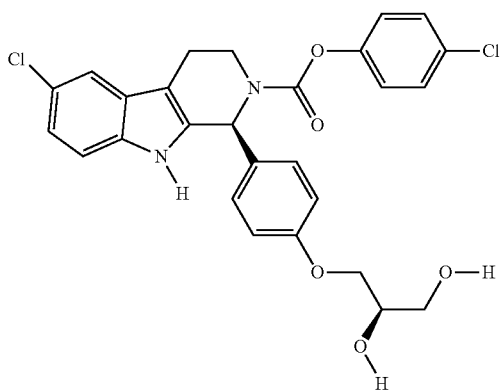 [SMILES: O=C(Oc1ccc(Cl)cc1)N1CCc2c([nH]c3ccc(Cl)cc23)[C@@H]1c1ccc(OC[C@H](O)CO)cc1]
1223

TABLE 1-continued
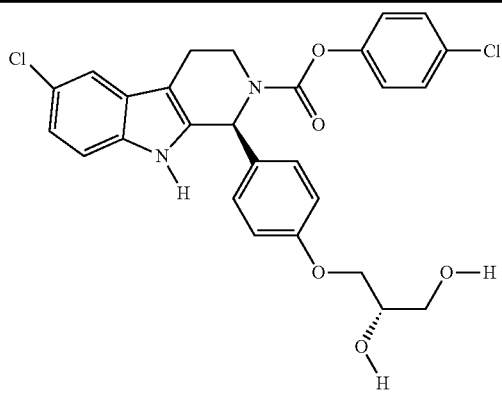
1224
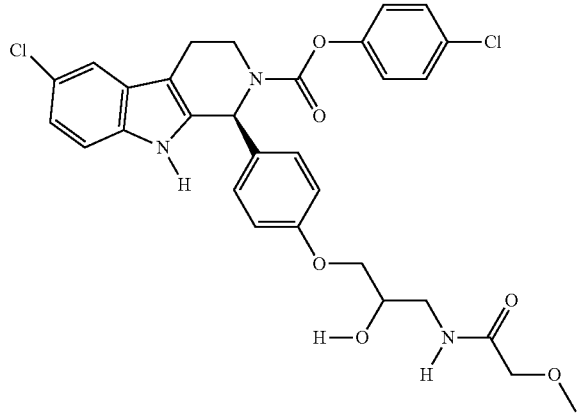 [SMILES: COCC(=O)NCC(O)COc1ccc([C@H]2c3[nH]c4ccc(Cl)cc4c3CCN2C(=O)Oc2ccc(Cl)cc2)cc1]
1225
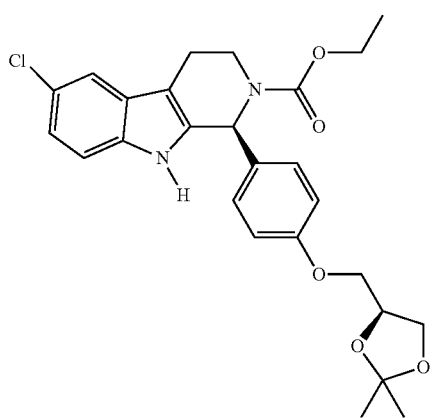 [SMILES: CCOC(=O)N1CCc2c([nH]c3ccc(Cl)cc23)[C@@H]1c1ccc(OC[C@H]2COC(C)(C)O2)cc1]
1226
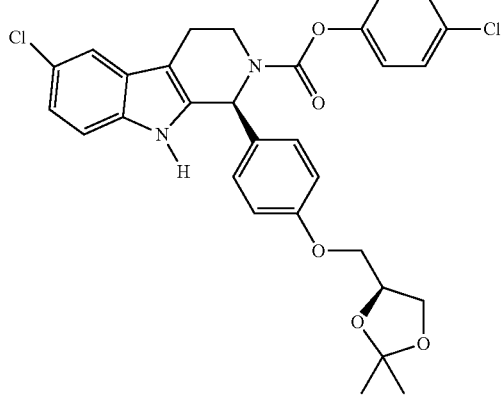
1227

TABLE 1-continued
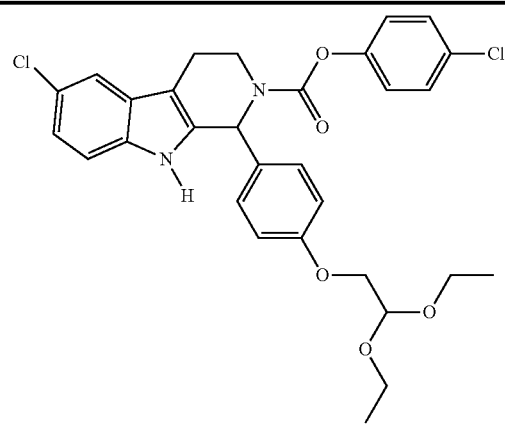
1228
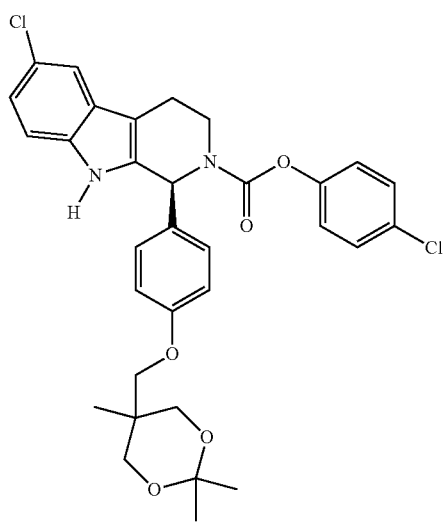 [SMILES: CC1(COc2ccc([C@H]3c4[nH]c5ccc(Cl)cc5c4CCN3C(=O)Oc3ccc(Cl)cc3)cc2)COC(C)(C)OC1]
1229
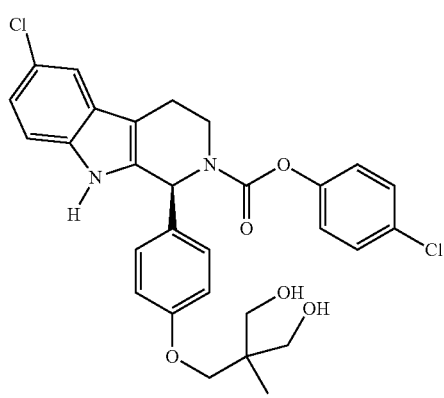 [SMILES: CC(CO)(CO)COc1ccc([C@H]2c3[nH]c4ccc(Cl)cc4c3CCN2C(=O)Oc2ccc(Cl)cc2)cc1]
1230
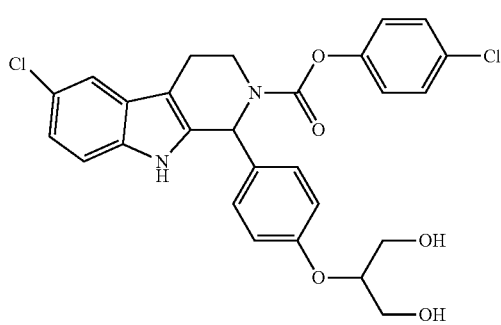 [SMILES: O=C(Oc1ccc(Cl)cc1)N1CCc2c([nH]c3ccc(Cl)cc23)C1c1ccc(OC(CO)CO)cc1]
1231

TABLE 1-continued
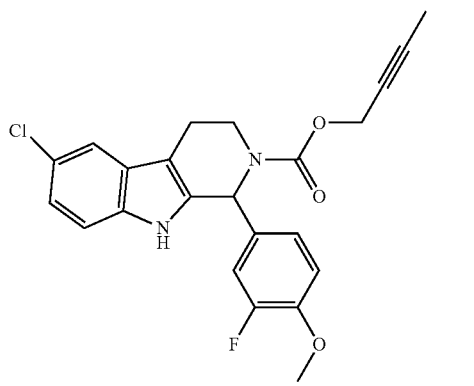 [SMILES: CC#CCOC(=O)N1CCc2c([nH]c3ccc(Cl)cc23)C1c1ccc(OC)c(F)c1]
1232
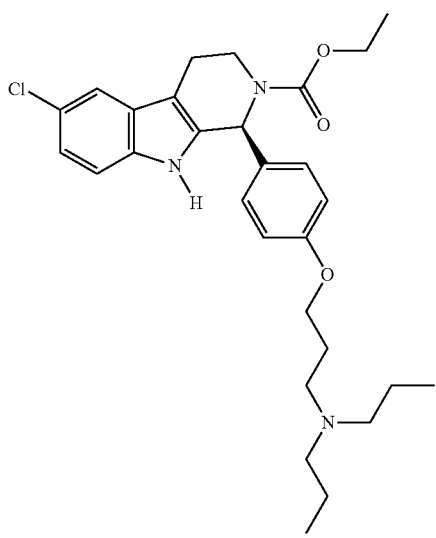 [SMILES: CCCN(CCC)CCCOc1ccc([C@H]2c3[nH]c4ccc(Cl)cc4c3CCN2C(=O)OCC)cc1]
1233
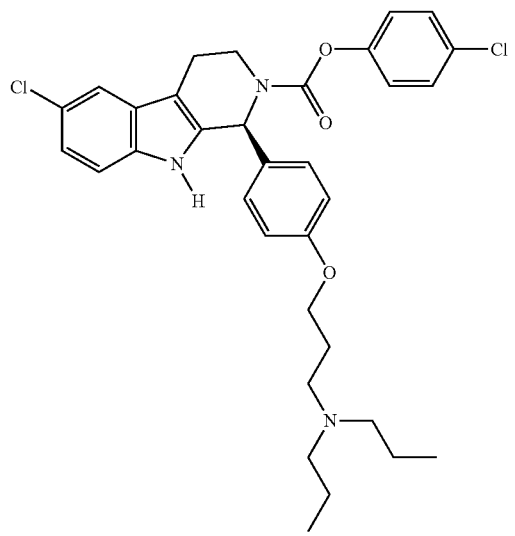 [SMILES: CCCN(CCC)CCCOc1ccc([C@H]2c3[nH]c4ccc(Cl)cc4c3CCN2C(=O)Oc2ccc(Cl)cc2)cc1]
1234

TABLE 1-continued
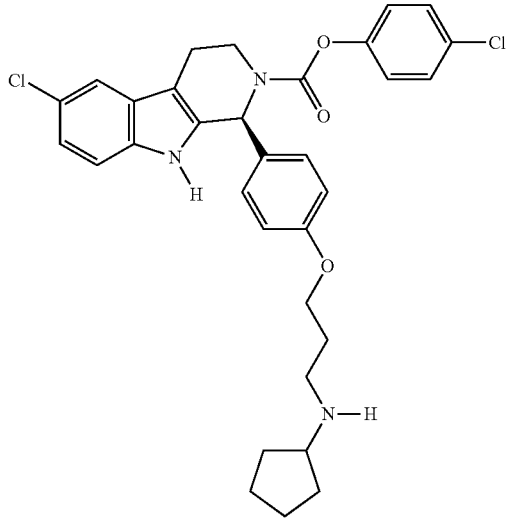 [SMILES: O=C(Oc1ccc(Cl)cc1)N1CCc2c([nH]c3ccc(Cl)cc23)[C@@H]1c1ccc(OCCCNC2CCCC2)cc1]
1235
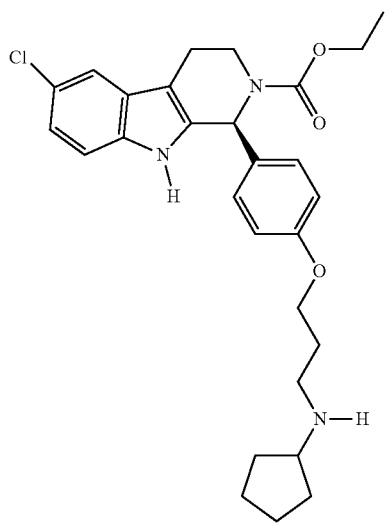 [SMILES: CCOC(=O)N1CCc2c([nH]c3ccc(Cl)cc23)[C@@H]1c1ccc(OCCCNC2CCCC2)cc1]
1236
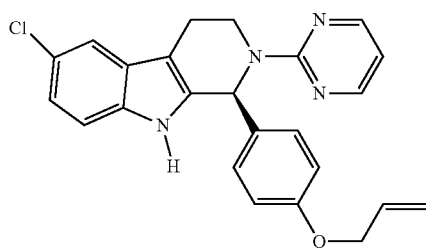 [SMILES: C=CCOc1ccc([C@H]2c3[nH]c4ccc(Cl)cc4c3CCN2c2ncccn2)cc1]
1237
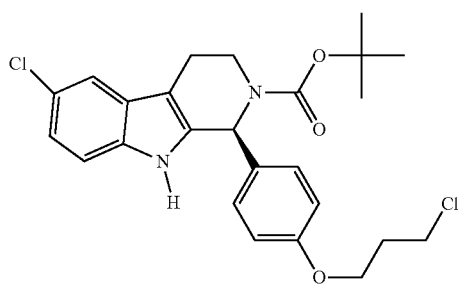 [SMILES: CC(C)(C)OC(=O)N1CCc2c([nH]c3ccc(Cl)cc23)[C@@H]1c1ccc(OCCCCl)cc1]
1238

TABLE 1-continued
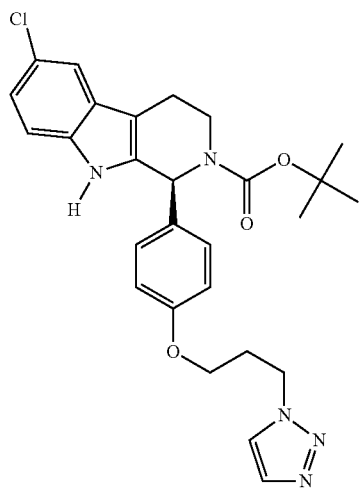 [SMILES: CC(C)(C)OC(=O)N1CCc2c([nH]c3ccc(Cl)cc23)[C@@H]1c1ccc(OCCCn2ccnn2)cc1]
1239
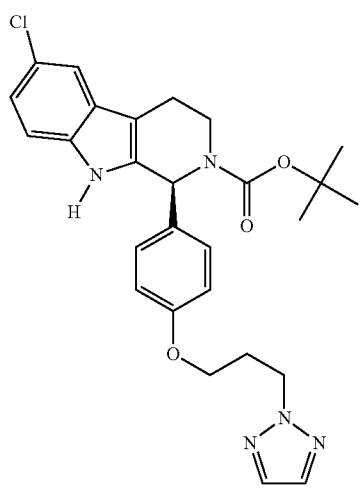 [SMILES: CC(C)(C)OC(=O)N1CCc2c([nH]c3ccc(Cl)cc23)[C@@H]1c1ccc(OCCCn2nccn2)cc1]
1240
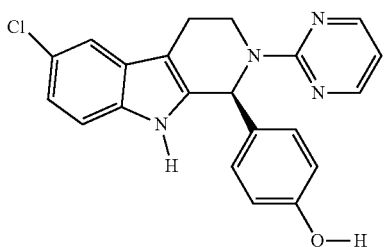 [SMILES: Oc1ccc([C@H]2c3[nH]c4ccc(Cl)cc4c3CCN2c2ncccn2)cc1]
1241
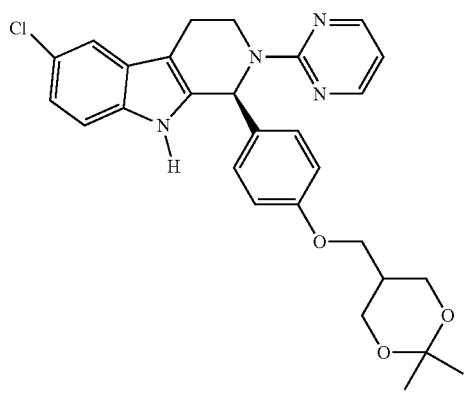 [SMILES: CC1(C)OCC(COc2ccc([C@H]3c4[nH]c5ccc(Cl)cc5c4CCN3c3ncccn3)cc2)CO1]
1242

TABLE 1-continued
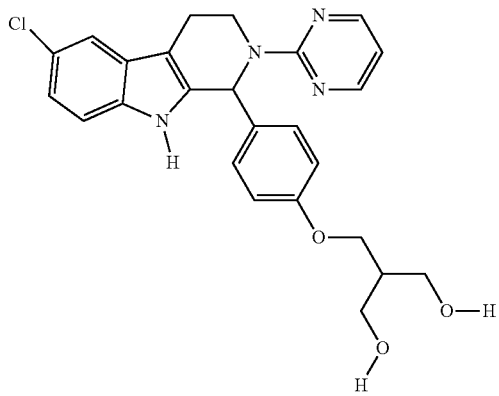 [SMILES: OCC(CO)COc1ccc(C2c3[nH]c4ccc(Cl)cc4c3CCN2c2ncccn2)cc1]
1243
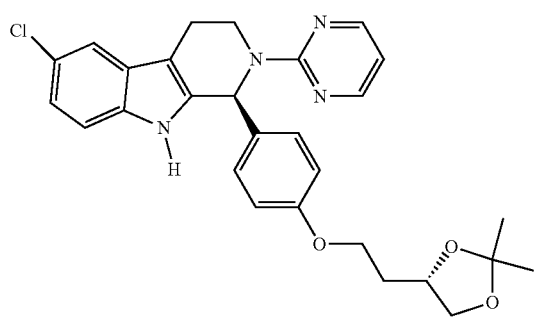 [SMILES: CC1(C)OC[C@H](CCOc2ccc([C@H]3c4[nH]c5ccc(Cl)cc5c4CCN3c3ncccn3)cc2)O1]
1244
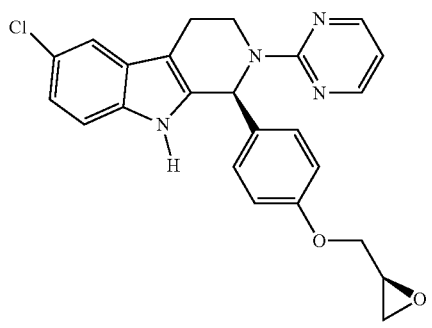 [SMILES: Clc1ccc2[nH]c3c(c2c1)CCN(c1ncccn1)[C@H]3c1ccc(OC[C@@H]2CO2)cc1]
1245
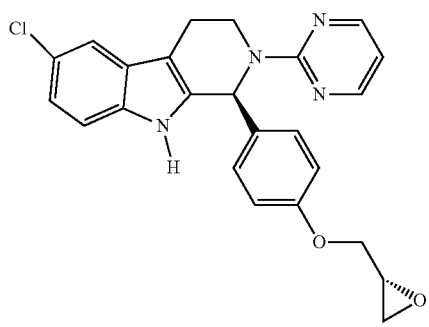 [SMILES: Clc1ccc2[nH]c3c(c2c1)CCN(c1ncccn1)[C@H]3c1ccc(OC[C@H]2CO2)cc1]
1246
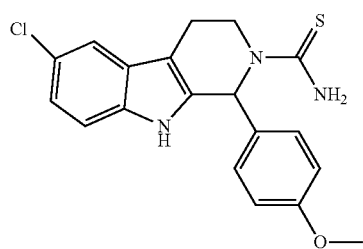 [SMILES: COc1ccc(C2c3[nH]c4ccc(Cl)cc4c3CCN2C(N)=S)cc1]
1247

TABLE 1-continued
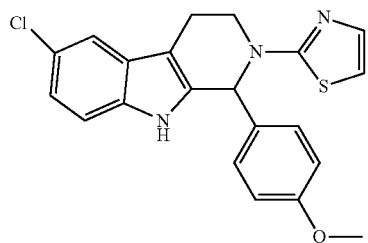 [SMILES: COc1ccc(C2c3[nH]c4ccc(Cl)cc4c3CCN2c2nccs2)cc1]
1248
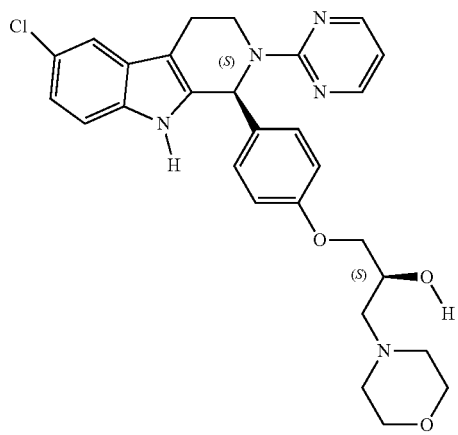
1249
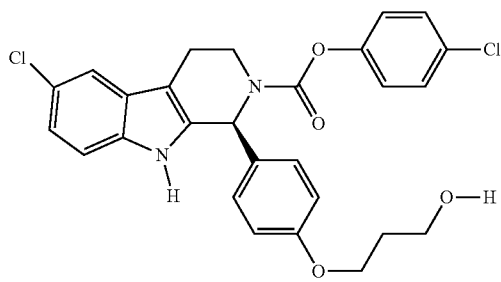 [SMILES: O=C(Oc1ccc(Cl)cc1)N1CCc2c([nH]c3ccc(Cl)cc23)[C@@H]1c1ccc(OCCCO)cc1]
1250
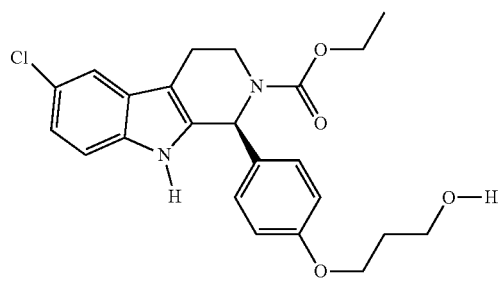 [SMILES: CCOC(=O)N1CCc2c([nH]c3ccc(Cl)cc23)[C@@H]1c1ccc(OCCCO)cc1]
1251
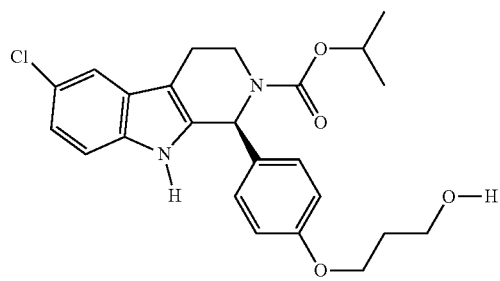 [SMILES: CC(C)OC(=O)N1CCc2c([nH]c3ccc(Cl)cc23)[C@@H]1c1ccc(OCCCO)cc1]
1252

TABLE 1-continued
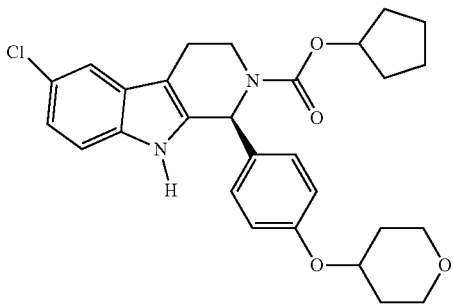 [SMILES: O=C(OC1CCCC1)N1CCc2c([nH]c3ccc(Cl)cc23)[C@@H]1c1ccc(OC2CCOCC2)cc1]
1253
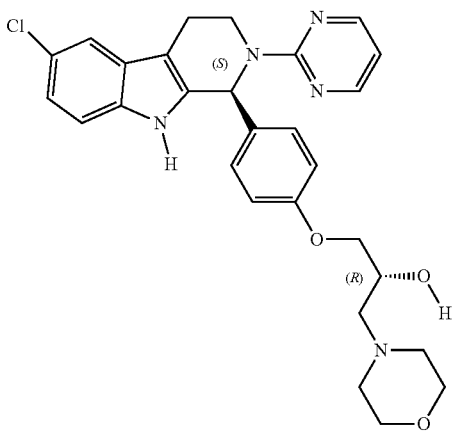
1254
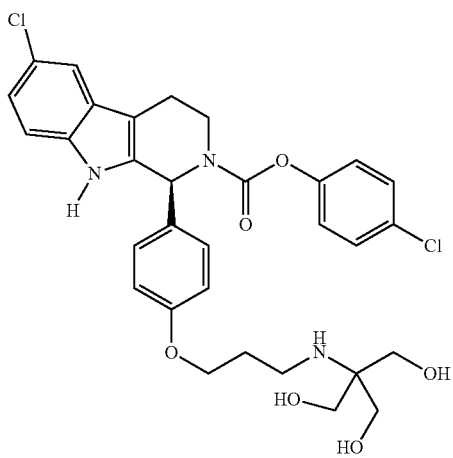 [SMILES: O=C(Oc1ccc(Cl)cc1)N1CCc2c([nH]c3ccc(Cl)cc23)[C@@H]1c1ccc(OCCCNC(CO)(CO)CO)cc1]
1255
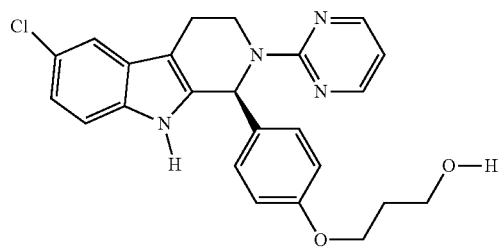 [SMILES: OCCCOc1ccc([C@H]2c3[nH]c4ccc(Cl)cc4c3CCN2c2ncccn2)cc1]
1256

TABLE 1-continued
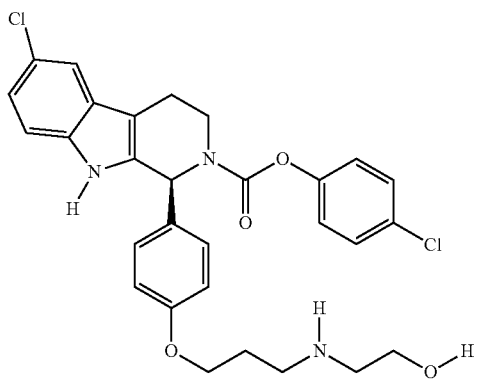 [SMILES: O=C(Oc1ccc(Cl)cc1)N1CCc2c([nH]c3ccc(Cl)cc23)[C@@H]1c1ccc(OCCCNCCO)cc1]
1257
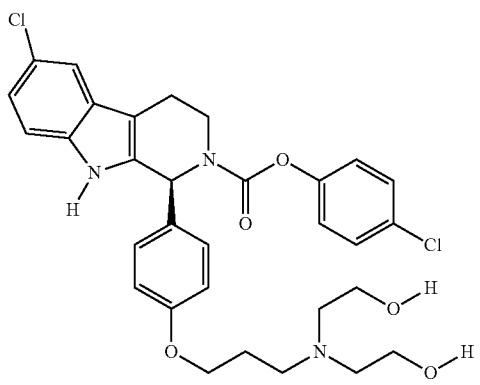 [SMILES: O=C(Oc1ccc(Cl)cc1)N1CCc2c([nH]c3ccc(Cl)cc23)[C@@H]1c1ccc(OCCCN(CCO)CCO)cc1]
1258
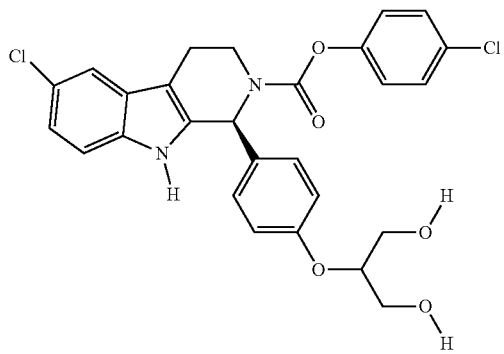 [SMILES: O=C(Oc1ccc(Cl)cc1)N1CCc2c([nH]c3ccc(Cl)cc23)[C@@H]1c1ccc(OC(CO)CO)cc1]
1259
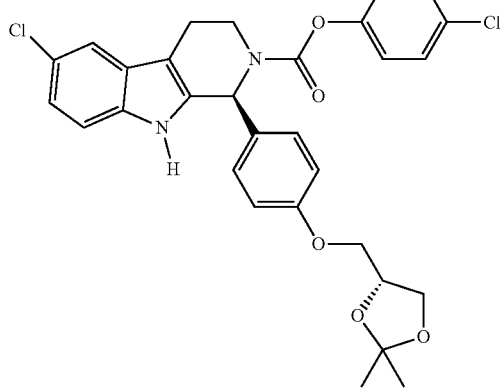
1260

TABLE 1-continued
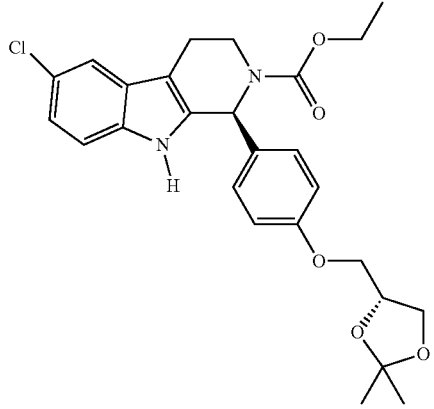 [SMILES: CCOC(=O)N1CCc2c([nH]c3ccc(Cl)cc23)[C@@H]1c1ccc(OC[C@@H]2COC(C)(C)O2)cc1]
1261
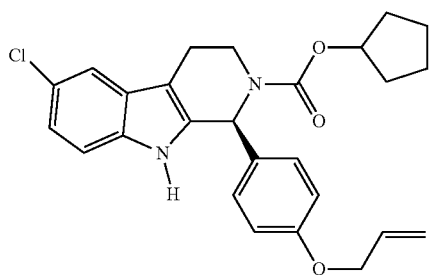 [SMILES: C=CCOc1ccc([C@H]2c3[nH]c4ccc(Cl)cc4c3CCN2C(=O)OC2CCCC2)cc1]
1262
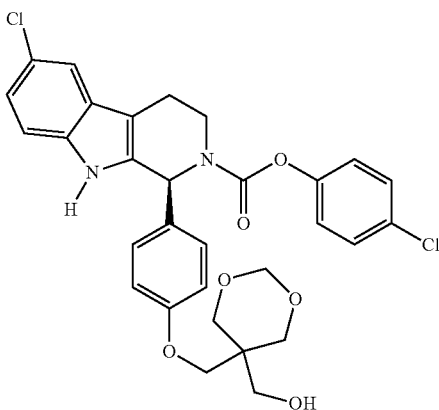 [SMILES: O=C(Oc1ccc(Cl)cc1)N1CCc2c([nH]c3ccc(Cl)cc23)[C@@H]1c1ccc(OCC2(CO)COCOC2)cc1]
1263
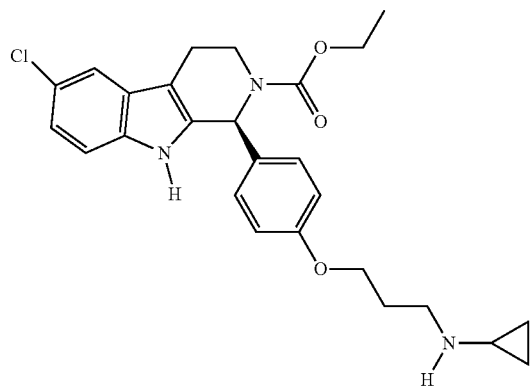 [SMILES: CCOC(=O)N1CCc2c([nH]c3ccc(Cl)cc23)[C@@H]1c1ccc(OCCCNC2CC2)cc1]
1264

TABLE 1-continued
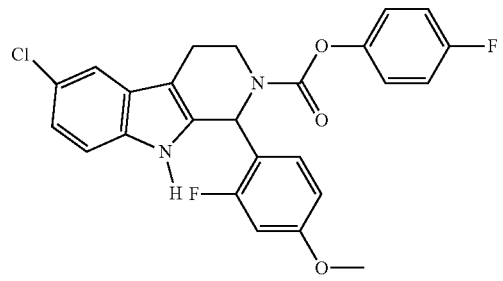 [SMILES: COc1ccc(C2c3[nH]c4ccc(Cl)cc4c3CCN2C(=O)Oc2ccc(F)cc2)c(F)c1]
1265
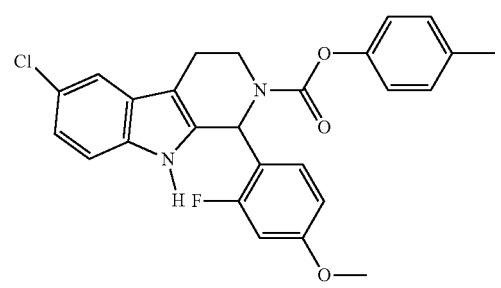 [SMILES: COc1ccc(C2c3[nH]c4ccc(Cl)cc4c3CCN2C(=O)Oc2ccc(C)cc2)c(F)c1]
1266
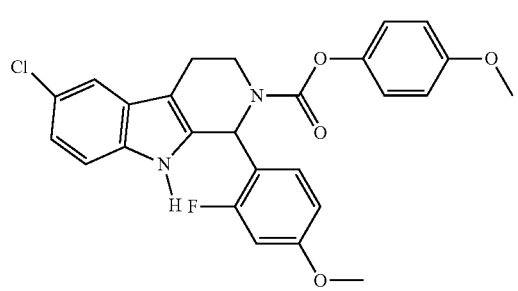 [SMILES: COc1ccc(OC(=O)N2CCc3c([nH]c4ccc(Cl)cc34)C2c2ccc(OC)cc2F)cc1]
1267
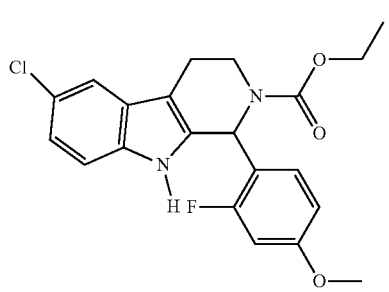 [SMILES: CCOC(=O)N1CCc2c([nH]c3ccc(Cl)cc23)C1c1ccc(OC)cc1F]
1268
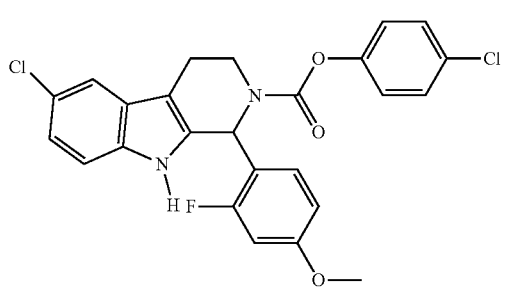 [SMILES: COc1ccc(C2c3[nH]c4ccc(Cl)cc4c3CCN2C(=O)Oc2ccc(Cl)cc2)c(F)c1]
1269

TABLE 1-continued
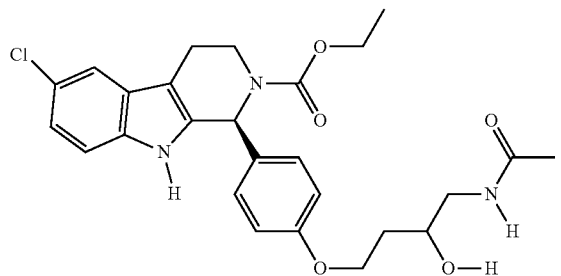 [SMILES: CCOC(=O)N1CCc2c([nH]c3ccc(Cl)cc23)[C@@H]1c1ccc(OCCC(O)CNC(C)=O)cc1] 1270
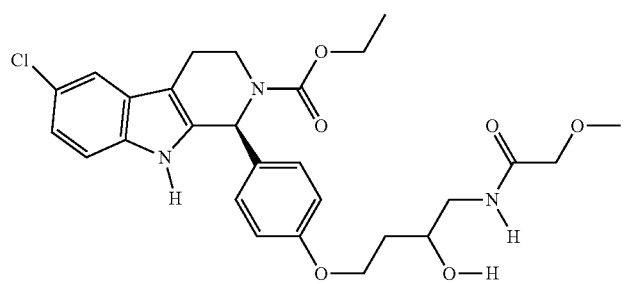 [SMILES: CCOC(=O)N1CCc2c([nH]c3ccc(Cl)cc23)[C@@H]1c1ccc(OCCC(O)CNC(=O)COC)cc1] 1271
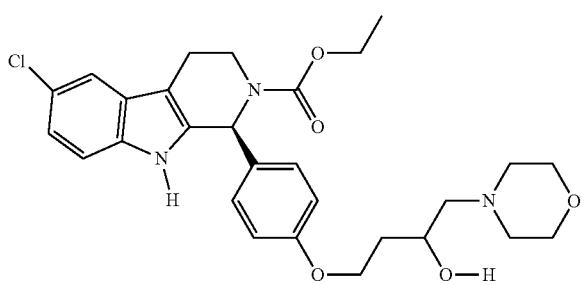 [SMILES: CCOC(=O)N1CCc2c([nH]c3ccc(Cl)cc23)[C@@H]1c1ccc(OCCC(O)CN2CCOCC2)cc1] 1272
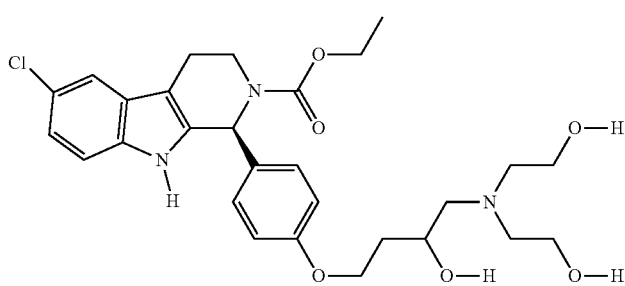 [SMILES: CCOC(=O)N1CCc2c([nH]c3ccc(Cl)cc23)[C@@H]1c1ccc(OCCC(O)CN(CCO)CCO)cc1] 1273
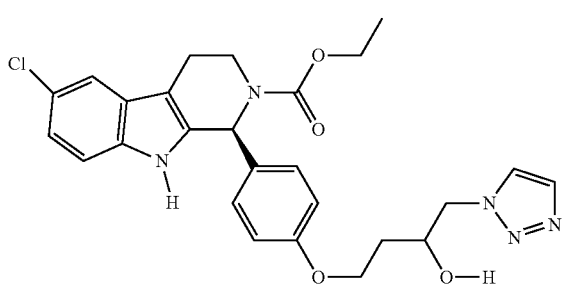 [SMILES: CCOC(=O)N1CCc2c([nH]c3ccc(Cl)cc23)[C@@H]1c1ccc(OCCC(O)Cn2ccnn2)cc1] 1274

TABLE 1-continued
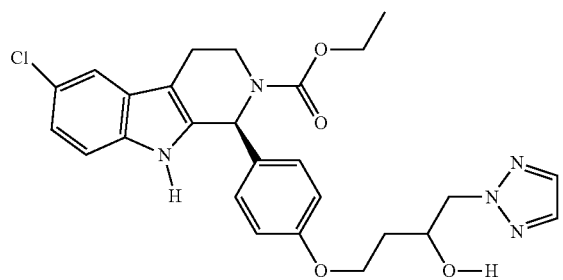 [SMILES: CCOC(=O)N1CCc2c([nH]c3ccc(Cl)cc23)[C@@H]1c1ccc(OCCC(O)Cn2nccn2)cc1]
1275
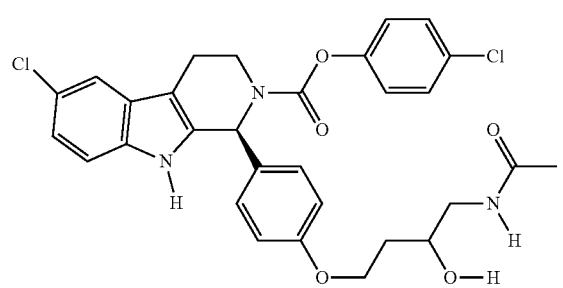 [SMILES: CC(=O)NCC(O)CCOc1ccc([C@H]2c3[nH]c4ccc(Cl)cc4c3CCN2C(=O)Oc2ccc(Cl)cc2)cc1]
1276
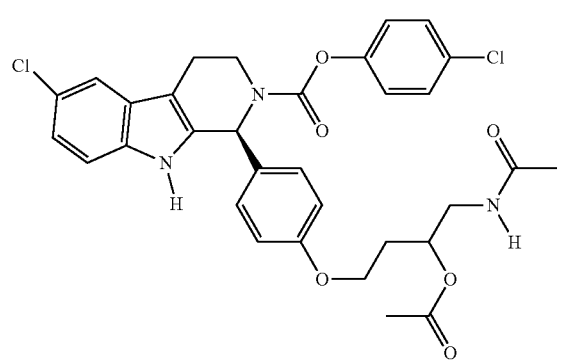 [SMILES: CC(=O)NCC(CCOc1ccc([C@H]2c3[nH]c4ccc(Cl)cc4c3CCN2C(=O)Oc2ccc(Cl)cc2)cc1)OC(C)=O]
1277
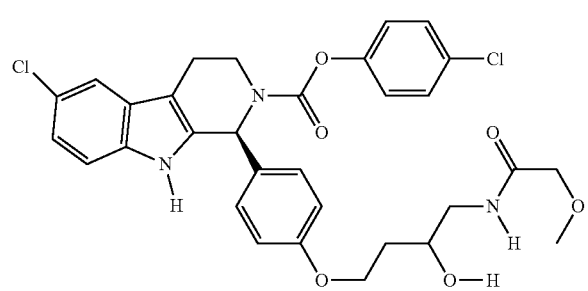 [SMILES: COCC(=O)NCC(O)CCOc1ccc([C@H]2c3[nH]c4ccc(Cl)cc4c3CCN2C(=O)Oc2ccc(Cl)cc2)cc1]
1278
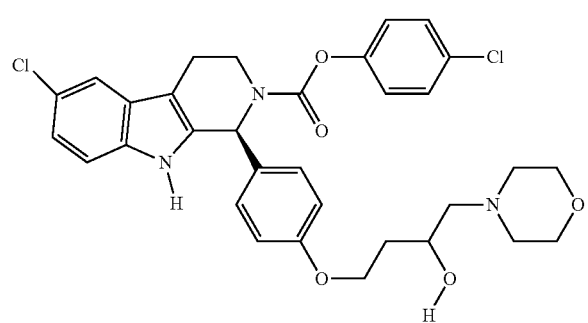
1279

TABLE 1-continued
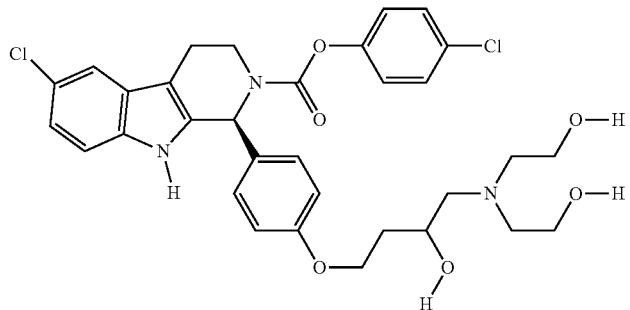 [SMILES: O=C(Oc1ccc(Cl)cc1)N1CCc2c([nH]c3ccc(Cl)cc23)[C@@H]1c1ccc(OCCC(O)CN(CCO)CCO)cc1]
1280
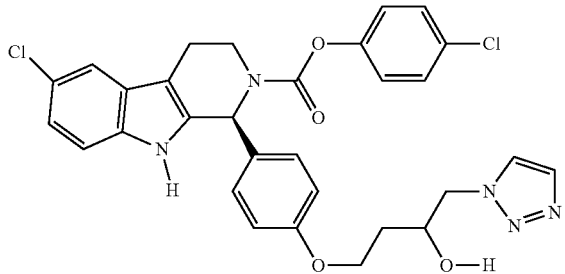 [SMILES: O=C(Oc1ccc(Cl)cc1)N1CCc2c([nH]c3ccc(Cl)cc23)[C@@H]1c1ccc(OCCC(O)Cn2ccnn2)cc1]
1281
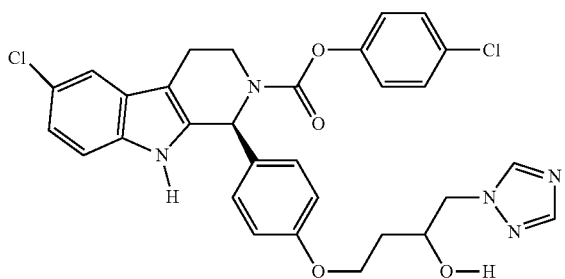 [SMILES: O=C(Oc1ccc(Cl)cc1)N1CCc2c([nH]c3ccc(Cl)cc23)[C@@H]1c1ccc(OCCC(O)Cn2cncn2)cc1]
1282
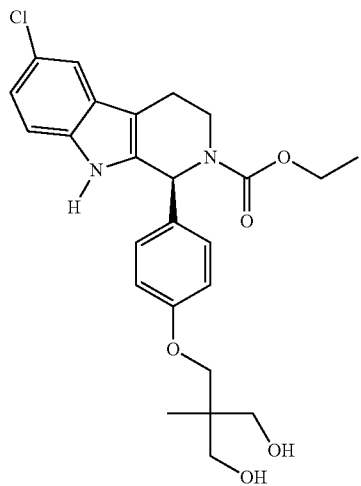 [SMILES: CCOC(=O)N1CCc2c([nH]c3ccc(Cl)cc23)[C@@H]1c1ccc(OCC(C)(CO)CO)cc1]
1283

TABLE 1-continued
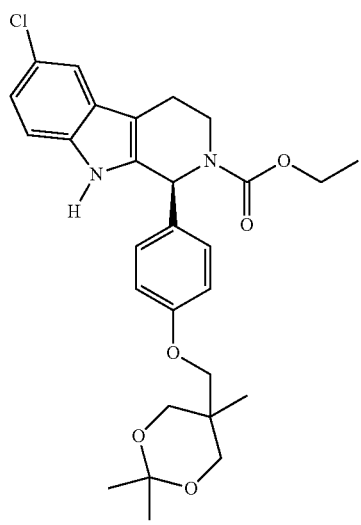 [SMILES: CCOC(=O)N1CCc2c([nH]c3ccc(Cl)cc23)[C@@H]1c1ccc(OCC2(C)COC(C)(C)OC2)cc1]
1284
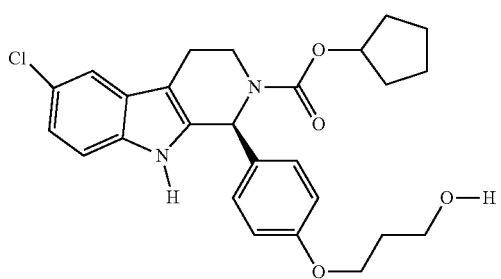 [SMILES: O=C(OC1CCCC1)N1CCc2c([nH]c3ccc(Cl)cc23)[C@@H]1c1ccc(OCCCO)cc1]
1285
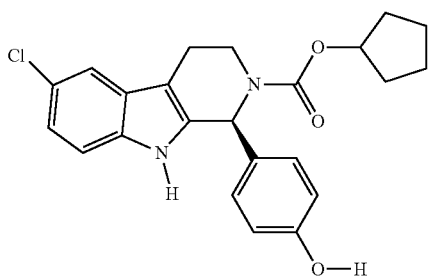
1286
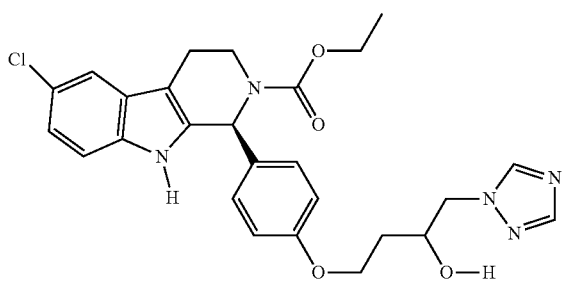 [SMILES: CCOC(=O)N1CCc2c([nH]c3ccc(Cl)cc23)[C@@H]1c1ccc(OCCC(O)Cn2cncn2)cc1]
1287

TABLE 1-continued
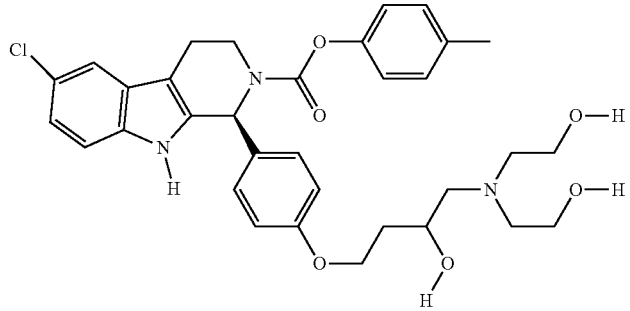
1288
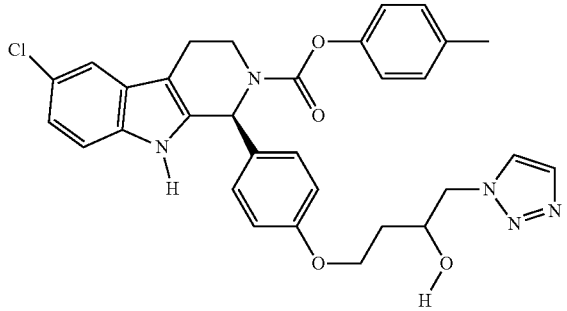 [SMILES: Cc1ccc(OC(=O)N2CCc3c([nH]c4ccc(Cl)cc34)[C@@H]2c2ccc(OCCC(O)Cn3ccnn3)cc2)cc1]
1289
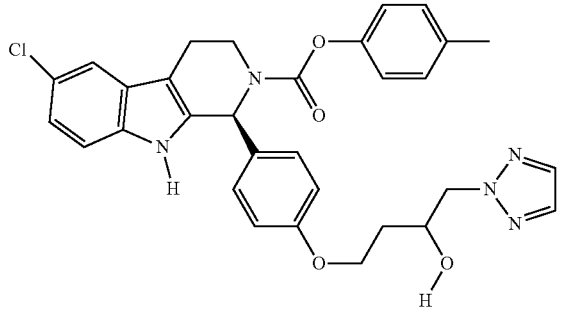 [SMILES: Cc1ccc(OC(=O)N2CCc3c([nH]c4ccc(Cl)cc34)[C@@H]2c2ccc(OCCC(O)Cn3nccn3)cc2)cc1]
1290
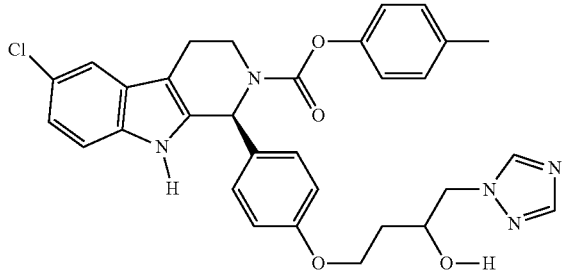 [SMILES: Cc1ccc(OC(=O)N2CCc3c([nH]c4ccc(Cl)cc34)[C@@H]2c2ccc(OCCC(O)Cn3cncn3)cc2)cc1]
1291
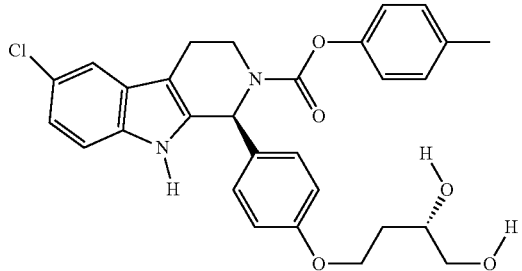 [SMILES: Cc1ccc(OC(=O)N2CCc3c([nH]c4ccc(Cl)cc34)[C@@H]2c2ccc(OCC[C@H](O)CO)cc2)cc1]
1292

TABLE 1-continued
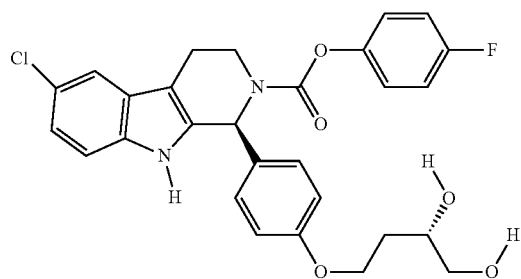 [SMILES: O=C(Oc1ccc(F)cc1)N1CCc2c([nH]c3ccc(Cl)cc23)[C@@H]1c1ccc(OCC[C@H](O)CO)cc1]
1293
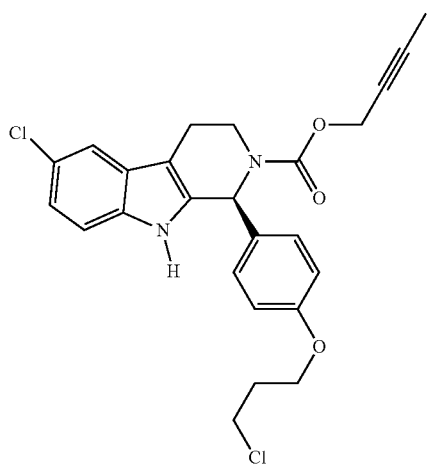 [SMILES: CC#CCOC(=O)N1CCc2c([nH]c3ccc(Cl)cc23)[C@@H]1c1ccc(OCCCCl)cc1]
1294
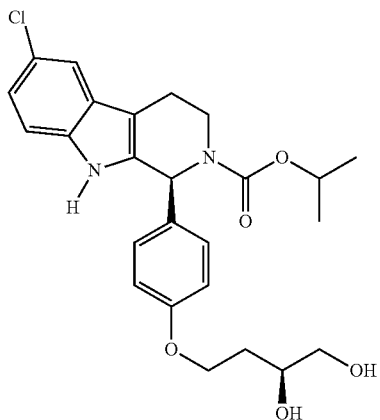 [SMILES: CC(C)OC(=O)N1CCc2c([nH]c3ccc(Cl)cc23)[C@@H]1c1ccc(OCC[C@H](O)CO)cc1]
1295
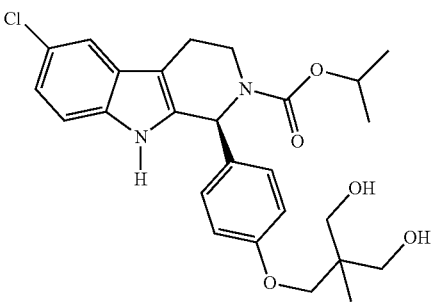 [SMILES: CC(C)OC(=O)N1CCc2c([nH]c3ccc(Cl)cc23)[C@@H]1c1ccc(OCC(C)(CO)CO)cc1]
1296

TABLE 1-continued
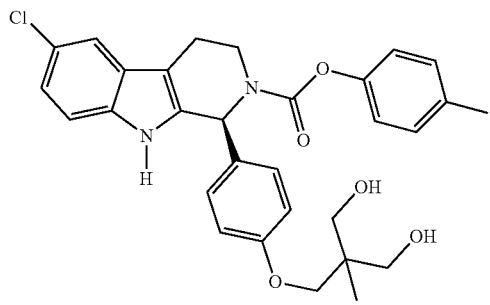 [SMILES: Cc1ccc(OC(=O)N2CCc3c([nH]c4ccc(Cl)cc34)[C@@H]2c2ccc(OCC(C)(CO)CO)cc2)cc1]
1297
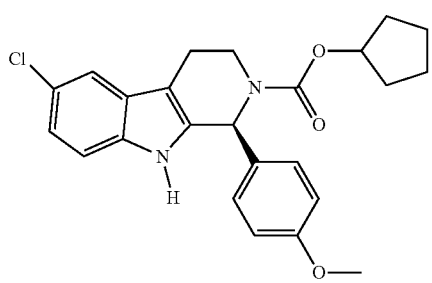 [SMILES: COc1ccc([C@H]2c3[nH]c4ccc(Cl)cc4c3CCN2C(=O)OC2CCCC2)cc1]
1298
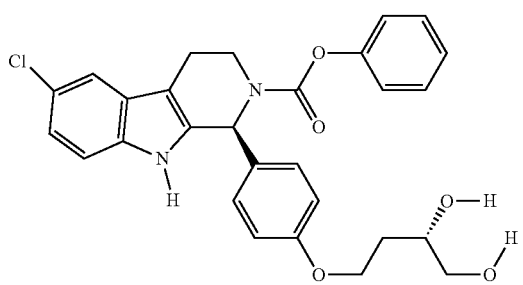 [SMILES: O=C(Oc1ccccc1)N1CCc2c([nH]c3ccc(Cl)cc23)[C@@H]1c1ccc(OCC[C@H](O)CO)cc1]
1299
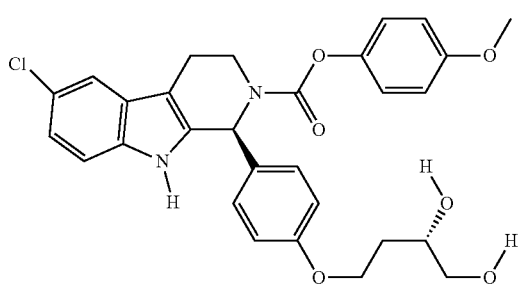 [SMILES: COc1ccc(OC(=O)N2CCc3c([nH]c4ccc(Cl)cc34)[C@@H]2c2ccc(OCC[C@H](O)CO)cc2)cc1]
1300
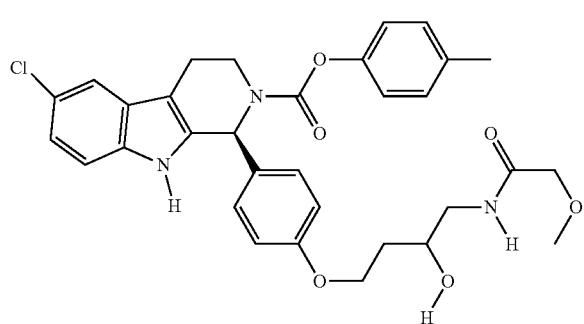 [SMILES: COCC(=O)NCC(O)CCOc1ccc([C@H]2c3[nH]c4ccc(Cl)cc4c3CCN2C(=O)Oc2ccc(C)cc2)cc1]
1301

TABLE 1-continued
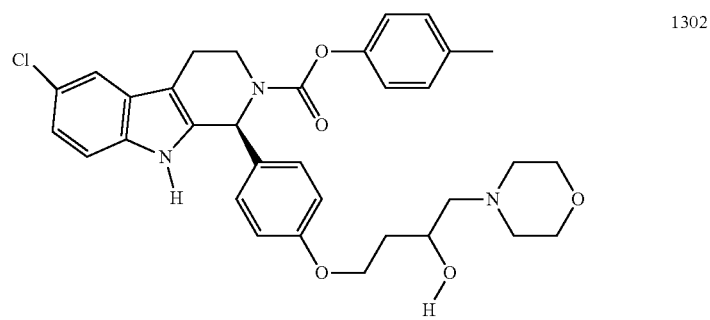
1302
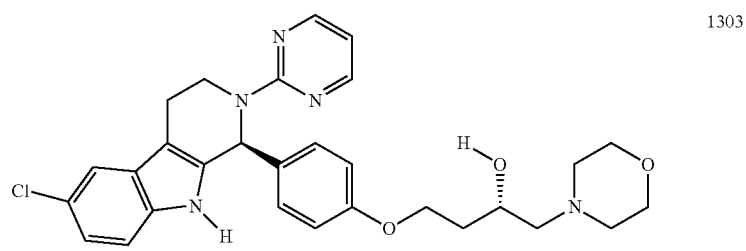
1303
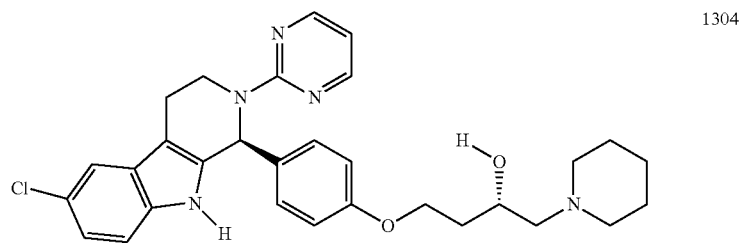
1304
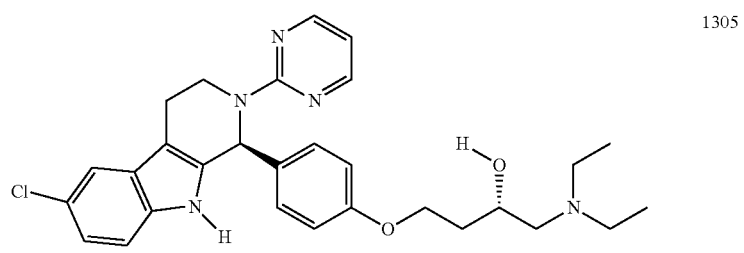
1305
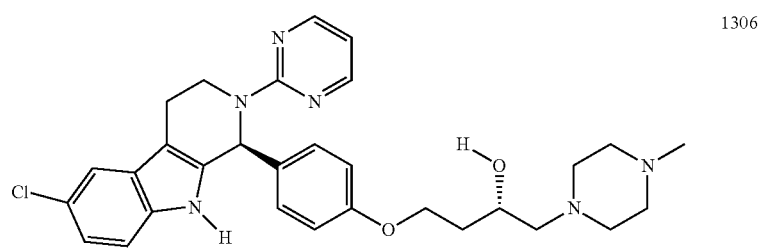
1306

TABLE 1-continued
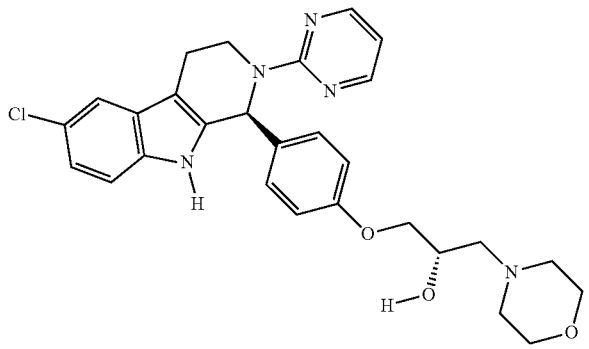 [SMILES: O[C@H](COc1ccc([C@H]2c3[nH]c4ccc(Cl)cc4c3CCN2c2ncccn2)cc1)CN1CCOCC1]
1307
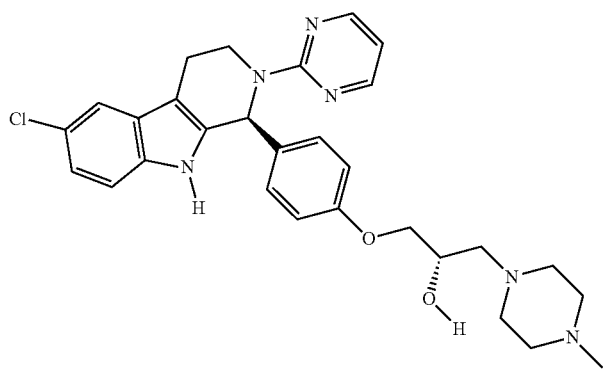 [SMILES: CN1CCN(C[C@H](O)COc2ccc([C@H]3c4[nH]c5ccc(Cl)cc5c4CCN3c3ncccn3)cc2)CC1]
1308
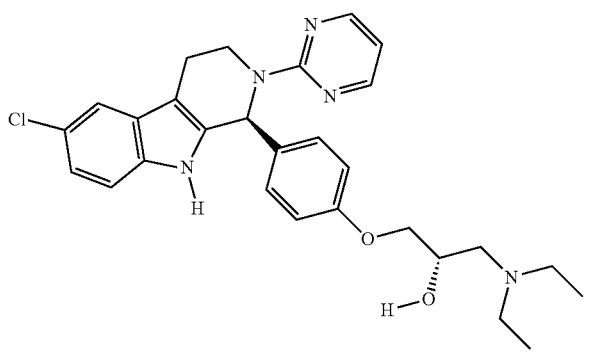 [SMILES: CCN(CC)C[C@H](O)COc1ccc([C@H]2c3[nH]c4ccc(Cl)cc4c3CCN2c2ncccn2)cc1]
1309
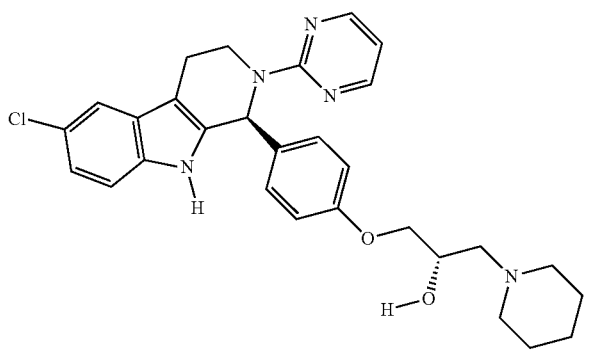 [SMILES: O[C@H](COc1ccc([C@H]2c3[nH]c4ccc(Cl)cc4c3CCN2c2ncccn2)cc1)CN1CCCCC1]
1310

TABLE 1-continued
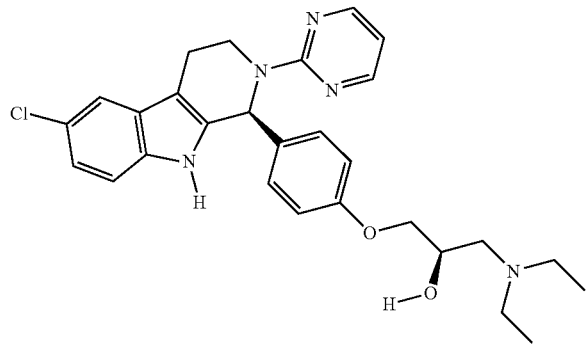 [SMILES: CCN(CC)C[C@@H](O)COc1ccc([C@H]2c3[nH]c4ccc(Cl)cc4c3CCN2c2ncccn2)cc1]
1311
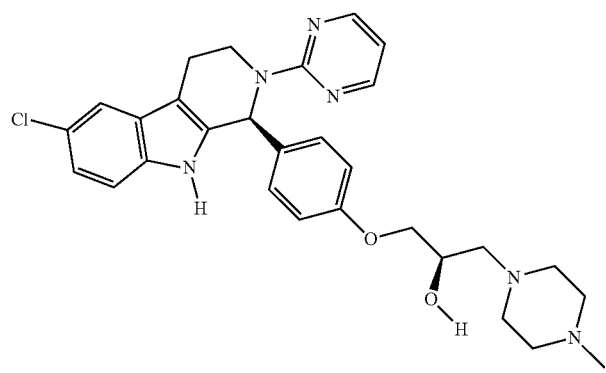 [SMILES: CN1CCN(C[C@@H](O)COc2ccc([C@H]3c4[nH]c5ccc(Cl)cc5c4CCN3c3ncccn3)cc2)CC1]
1312
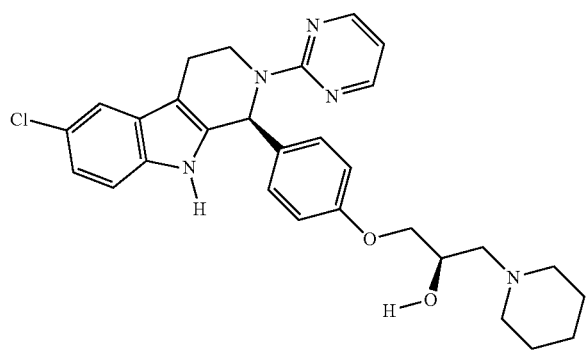 [SMILES: O[C@@H](COc1ccc([C@H]2c3[nH]c4ccc(Cl)cc4c3CCN2c2ncccn2)cc1)CN1CCCCC1]
1313
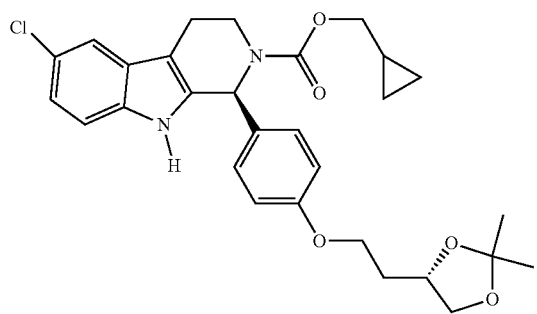 [SMILES: CC1(C)OC[C@H](CCOc2ccc([C@H]3c4[nH]c5ccc(Cl)cc5c4CCN3C(=O)OCC3CC3)cc2)O1]
1314

TABLE 1-continued
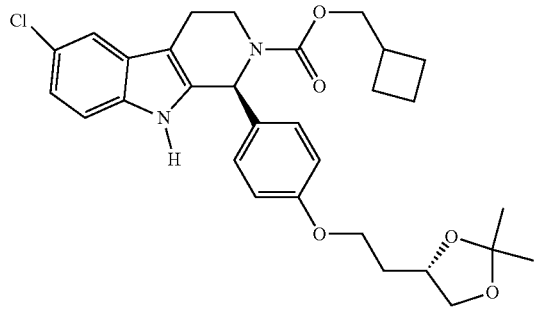 [SMILES: CC1(C)OC[C@H](CCOc2ccc([C@H]3c4[nH]c5ccc(Cl)cc5c4CCN3C(=O)OCC3CCC3)cc2)O1]
1315
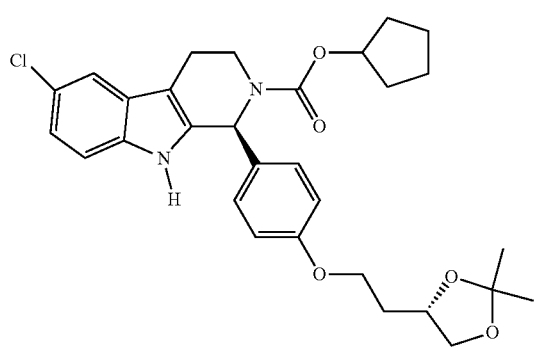 [SMILES: CC1(C)OC[C@H](CCOc2ccc([C@H]3c4[nH]c5ccc(Cl)cc5c4CCN3C(=O)OC3CCCC3)cc2)O1]
1316
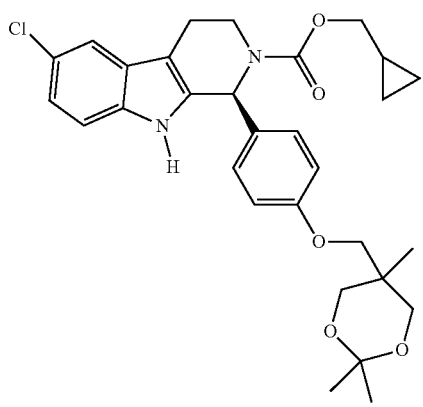 [SMILES: CC1(COc2ccc([C@H]3c4[nH]c5ccc(Cl)cc5c4CCN3C(=O)OCC3CC3)cc2)COC(C)(C)OC1]
1317
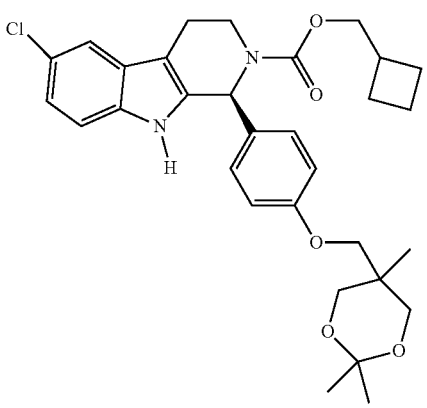 [SMILES: CC1(COc2ccc([C@H]3c4[nH]c5ccc(Cl)cc5c4CCN3C(=O)OCC3CCC3)cc2)COC(C)(C)OC1]
1318

TABLE 1-continued
| | |
|---|---|
| 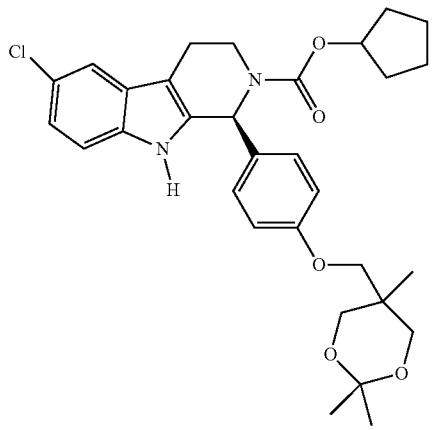 [SMILES: CC1(COc2ccc([C@H]3c4[nH]c5ccc(Cl)cc5c4CCN3C(=O)OC3CCCC3)cc2)COC(C)(C)OC1] | 1319 |
| 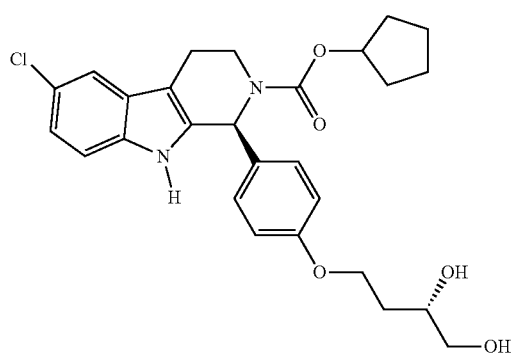 [SMILES: O=C(OC1CCCC1)N1CCc2c([nH]c3ccc(Cl)cc23)[C@@H]1c1ccc(OCC[C@H](O)CO)cc1] | 1320 |
| 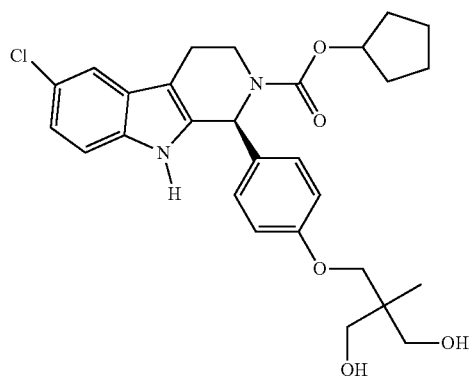 [SMILES: CC(CO)(CO)COc1ccc([C@H]2c3[nH]c4ccc(Cl)cc4c3CCN2C(=O)OC2CCCC2)cc1] | 1321 |
| 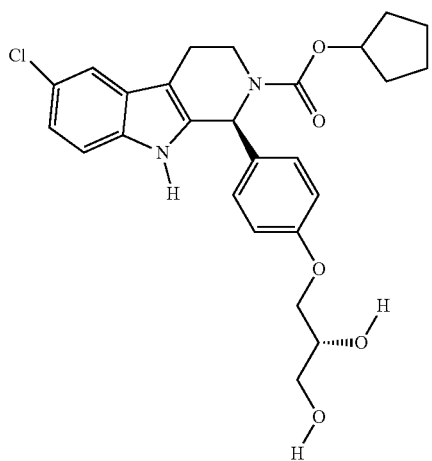 [SMILES: O=C(OC1CCCC1)N1CCc2c([nH]c3ccc(Cl)cc23)[C@@H]1c1ccc(OC[C@H](O)CO)cc1] | 1322 |

TABLE 1-continued
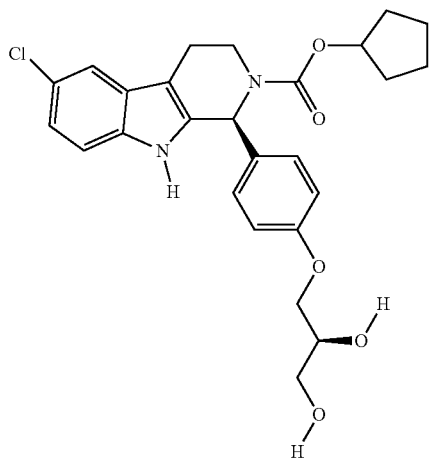 [SMILES: O=C(OC1CCCC1)N1CCc2c([nH]c3ccc(Cl)cc23)[C@@H]1c1ccc(OC[C@@H](O)CO)cc1]
1323
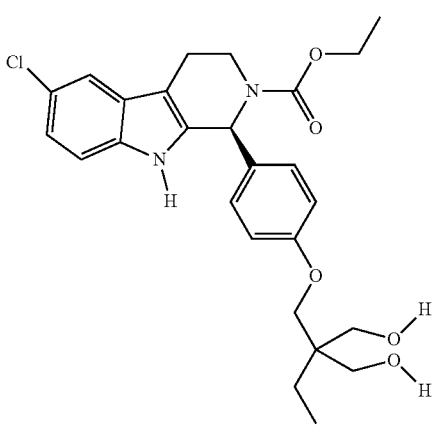 [SMILES: CCOC(=O)N1CCc2c([nH]c3ccc(Cl)cc23)[C@@H]1c1ccc(OCC(CC)(CO)CO)cc1]
1324
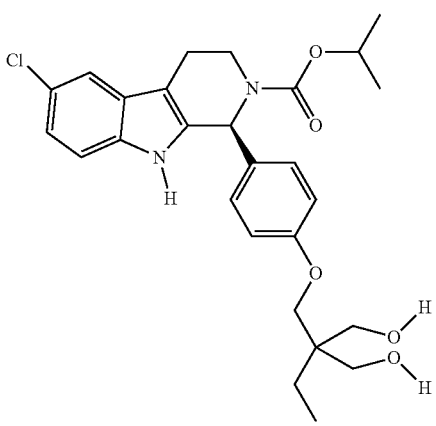 [SMILES: CCC(CO)(CO)COc1ccc([C@H]2c3[nH]c4ccc(Cl)cc4c3CCN2C(=O)OC(C)C)cc1]
1325

TABLE 1-continued
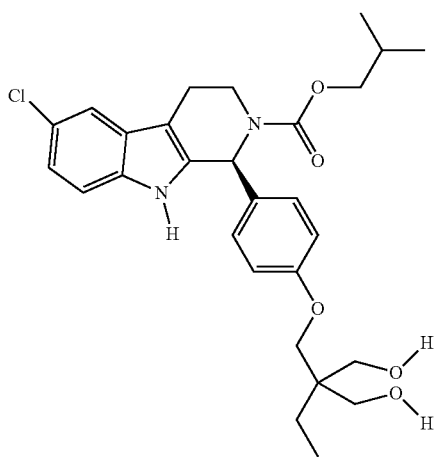 [SMILES: CCC(CO)(CO)COc1ccc([C@H]2c3[nH]c4ccc(Cl)cc4c3CCN2C(=O)OCC(C)C)cc1]
1326
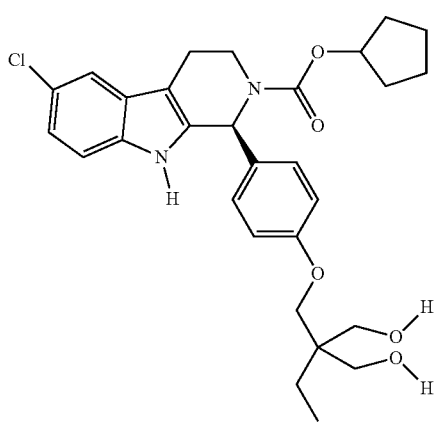 [SMILES: CCC(CO)(CO)COc1ccc([C@H]2c3[nH]c4ccc(Cl)cc4c3CCN2C(=O)OC2CCCC2)cc1]
1327
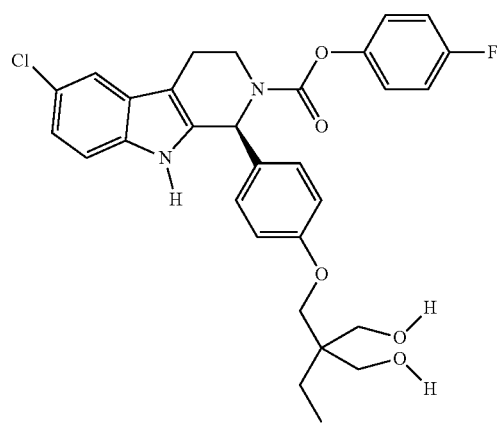 [SMILES: CCC(CO)(CO)COc1ccc([C@H]2c3[nH]c4ccc(Cl)cc4c3CCN2C(=O)Oc2ccc(F)cc2)cc1]
1328

TABLE 1-continued
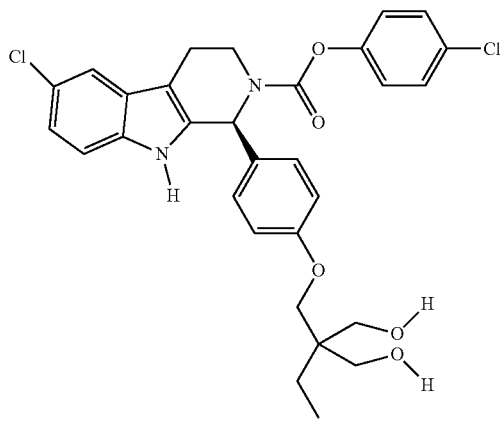 [SMILES: CCC(CO)(CO)COc1ccc([C@H]2c3[nH]c4ccc(Cl)cc4c3CCN2C(=O)Oc2ccc(Cl)cc2)cc1]
1329
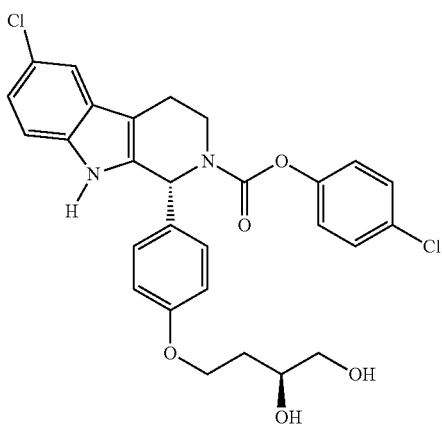 [SMILES: O=C(Oc1ccc(Cl)cc1)N1CCc2c([nH]c3ccc(Cl)cc23)[C@H]1c1ccc(OCC[C@H](O)CO)cc1]
1330
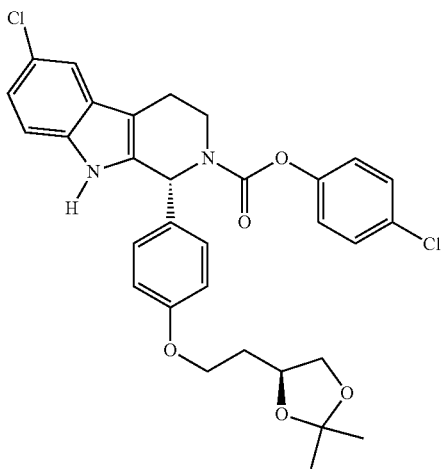 [SMILES: CC1(C)OC[C@H](CCOc2ccc([C@@H]3c4[nH]c5ccc(Cl)cc5c4CCN3C(=O)Oc3ccc(Cl)cc3)cc2)O1]
1331

TABLE 1-continued
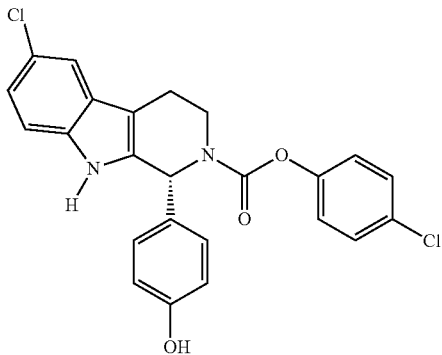 [SMILES: O=C(Oc1ccc(Cl)cc1)N1CCc2c([nH]c3ccc(Cl)cc23)[C@H]1c1ccc(O)cc1]
1332
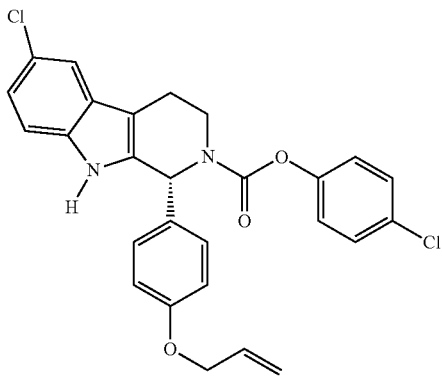 [SMILES: C=CCOc1ccc([C@@H]2c3[nH]c4ccc(Cl)cc4c3CCN2C(=O)Oc2ccc(Cl)cc2)cc1]
1333
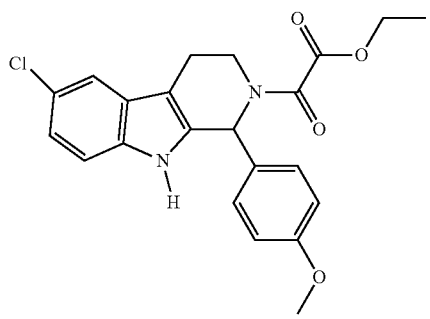 [SMILES: CCOC(=O)C(=O)N1CCc2c([nH]c3ccc(Cl)cc23)C1c1ccc(OC)cc1]
1334
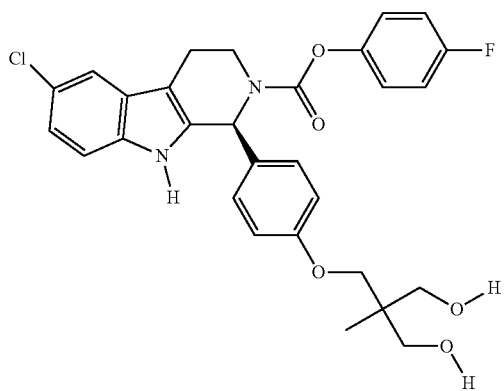 [SMILES: CC(CO)(CO)COc1ccc([C@H]2c3[nH]c4ccc(Cl)cc4c3CCN2C(=O)Oc2ccc(F)cc2)cc1]
1335

TABLE 1-continued
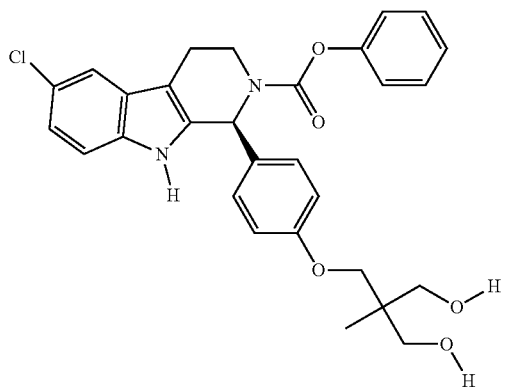 [SMILES: CC(CO)(CO)COc1ccc([C@H]2c3[nH]c4ccc(Cl)cc4c3CCN2C(=O)Oc2ccccc2)cc1]
1336
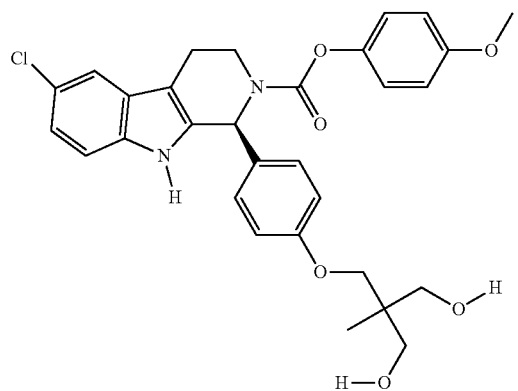 [SMILES: COc1ccc(OC(=O)N2CCc3c([nH]c4ccc(Cl)cc34)[C@@H]2c2ccc(OCC(C)(CO)CO)cc2)cc1]
1337
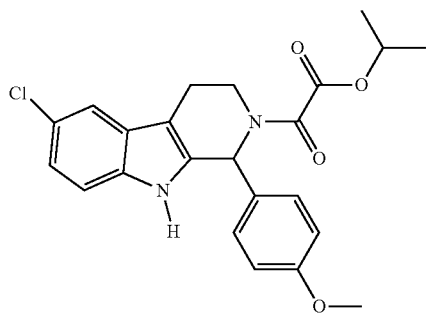 [SMILES: COc1ccc(C2c3[nH]c4ccc(Cl)cc4c3CCN2C(=O)C(=O)OC(C)C)cc1]
1338
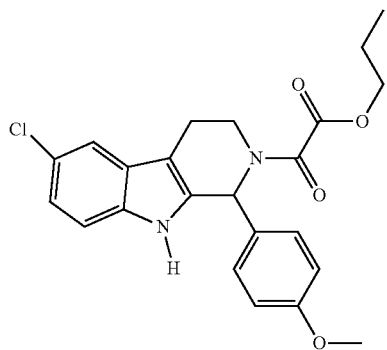 [SMILES: CCCOC(=O)C(=O)N1CCc2c([nH]c3ccc(Cl)cc23)C1c1ccc(OC)cc1]
1339

TABLE 1-continued
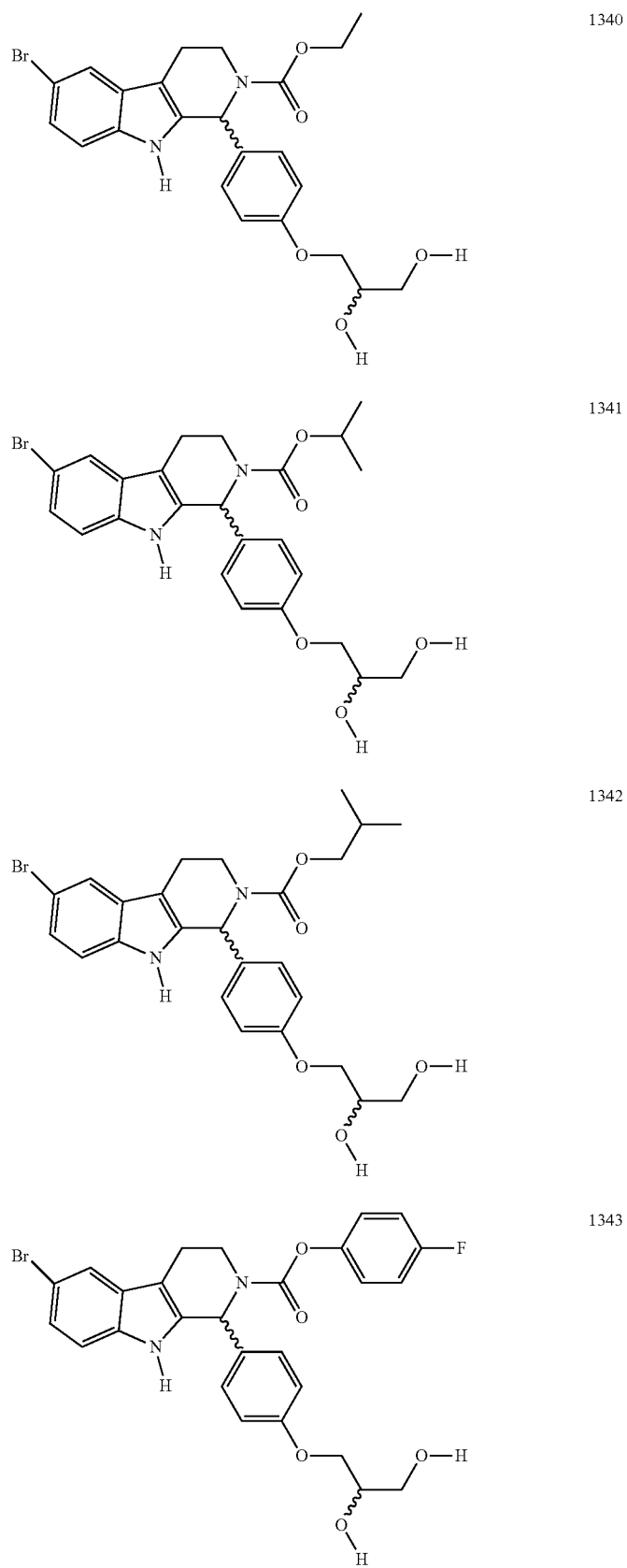

TABLE 1-continued
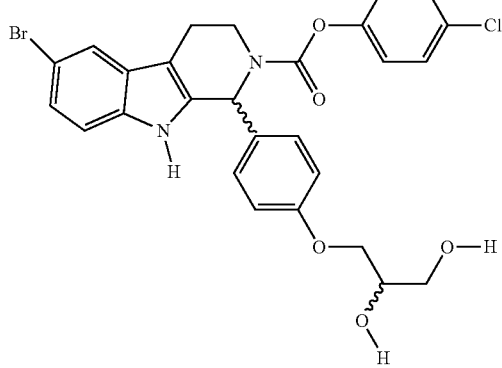
1344
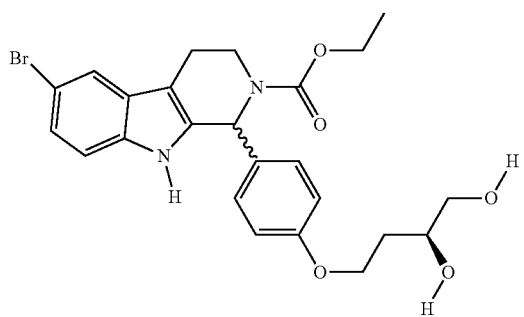 [SMILES: CCOC(=O)N1CCc2c([nH]c3ccc(Br)cc23)C1c1ccc(OCC[C@H](O)CO)cc1]
1345
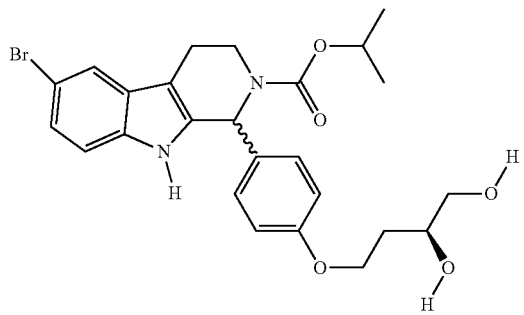 [SMILES: CC(C)OC(=O)N1CCc2c([nH]c3ccc(Br)cc23)C1c1ccc(OCC[C@H](O)CO)cc1]
1346
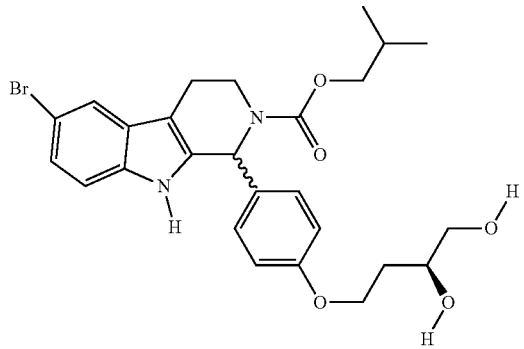 [SMILES: CC(C)COC(=O)N1CCc2c([nH]c3ccc(Br)cc23)C1c1ccc(OCC[C@H](O)CO)cc1]
1347

TABLE 1-continued
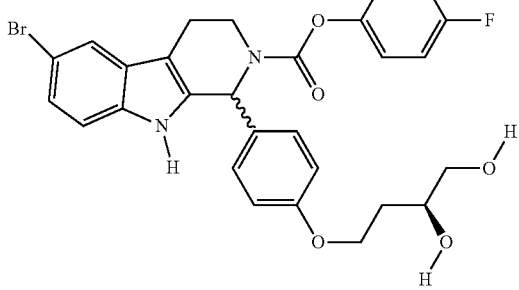
1348
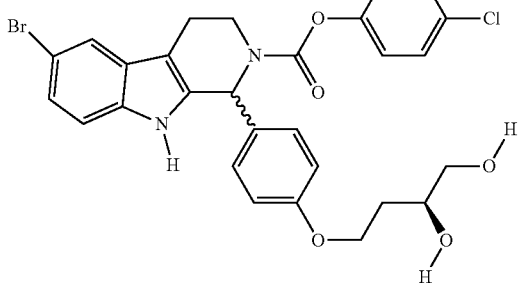
1349
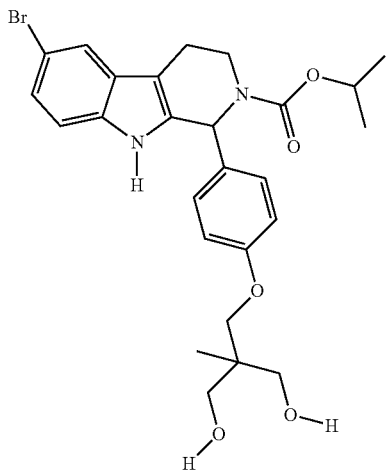 [SMILES: CC(C)OC(=O)N1CCc2c([nH]c3ccc(Br)cc23)C1c1ccc(OCC(C)(CO)CO)cc1]
1350
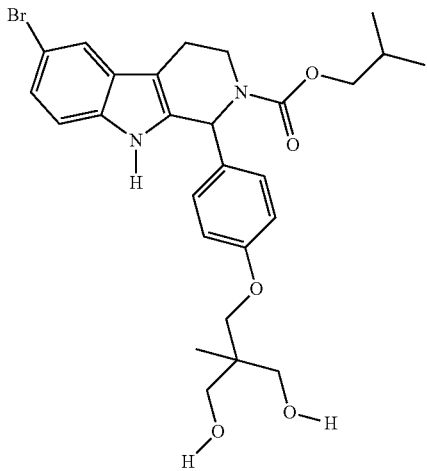 [SMILES: CC(C)COC(=O)N1CCc2c([nH]c3ccc(Br)cc23)C1c1ccc(OCC(C)(CO)CO)cc1]
1351

TABLE 1-continued
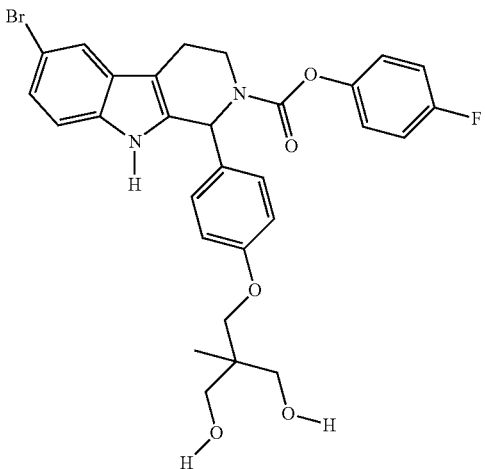 [SMILES: CC(CO)(CO)COc1ccc(C2c3[nH]c4ccc(Br)cc4c3CCN2C(=O)Oc2ccc(F)cc2)cc1]
1352
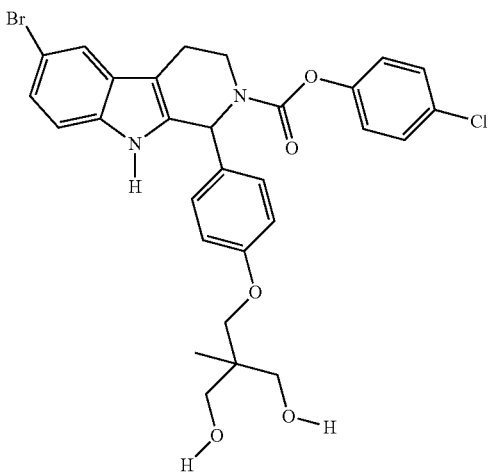 [SMILES: CC(CO)(CO)COc1ccc(C2c3[nH]c4ccc(Br)cc4c3CCN2C(=O)Oc2ccc(Cl)cc2)cc1]
1353
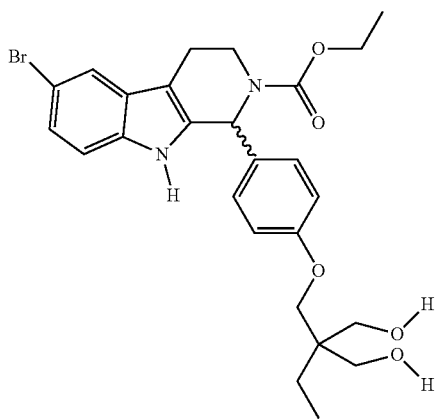 [SMILES: CCOC(=O)N1CCc2c([nH]c3ccc(Br)cc23)C1c1ccc(OCC(CC)(CO)CO)cc1]
1354

TABLE 1-continued
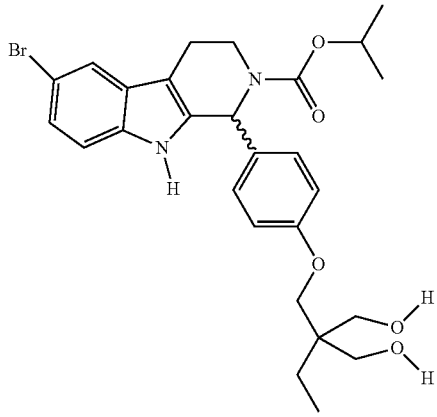 [SMILES: CCC(CO)(CO)COc1ccc(C2c3[nH]c4ccc(Br)cc4c3CCN2C(=O)OC(C)C)cc1]
1355
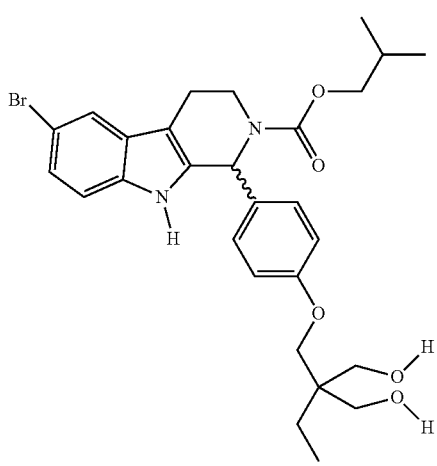 [SMILES: CCC(CO)(CO)COc1ccc(C2c3[nH]c4ccc(Br)cc4c3CCN2C(=O)OCC(C)C)cc1]
1356
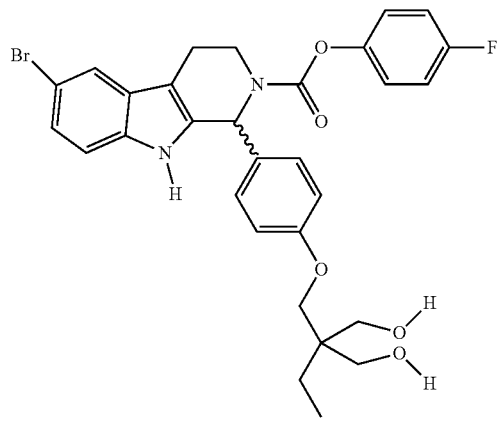 [SMILES: CCC(CO)(CO)COc1ccc(C2c3[nH]c4ccc(Br)cc4c3CCN2C(=O)Oc2ccc(F)cc2)cc1]
1357

TABLE 1-continued
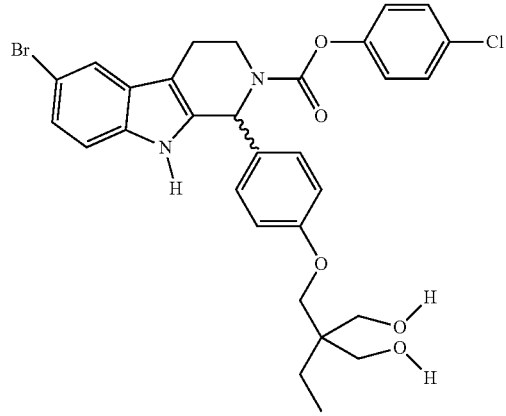 [SMILES: CCC(CO)(CO)COc1ccc(C2c3[nH]c4ccc(Br)cc4c3CCN2C(=O)Oc2ccc(Cl)cc2)cc1]
1358
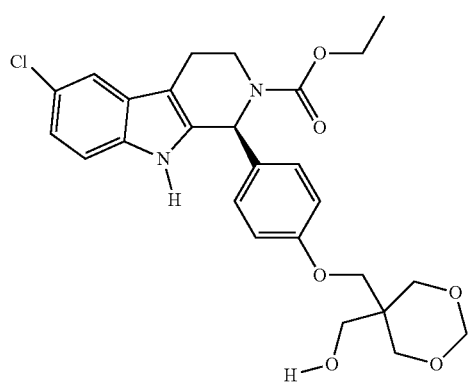 [SMILES: CCOC(=O)N1CCc2c([nH]c3ccc(Cl)cc23)[C@@H]1c1ccc(OCC2(CO)COCOC2)cc1]
1359
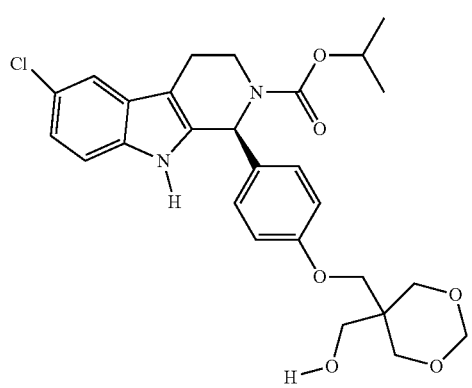 [SMILES: CC(C)OC(=O)N1CCc2c([nH]c3ccc(Cl)cc23)[C@@H]1c1ccc(OCC2(CO)COCOC2)cc1]
1360
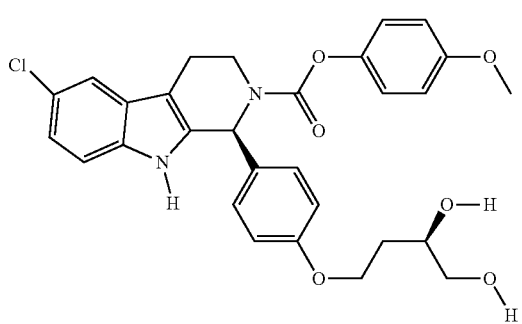 [SMILES: COc1ccc(OC(=O)N2CCc3c([nH]c4ccc(Cl)cc34)[C@@H]2c2ccc(OCC[C@@H](O)CO)cc2)cc1]
1361

TABLE 1-continued
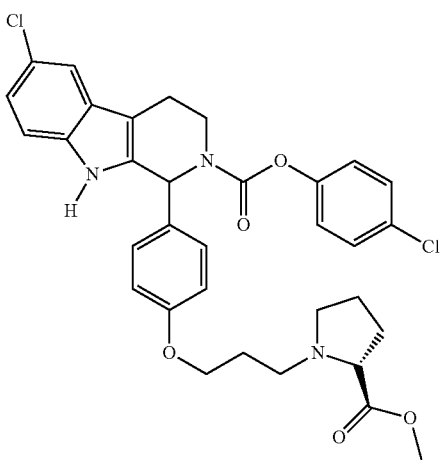
1362
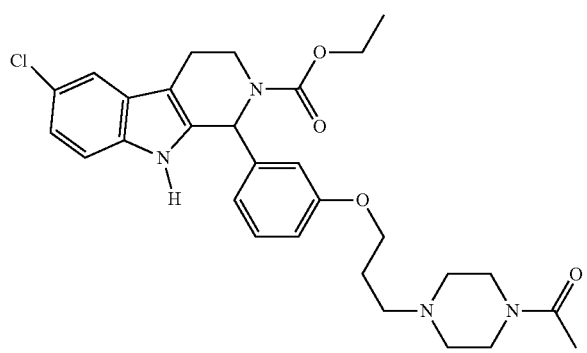 [SMILES: CCOC(=O)N1CCc2c([nH]c3ccc(Cl)cc23)C1c1cccc(OCCCN2CCN(C(C)=O)CC2)c1]
1363
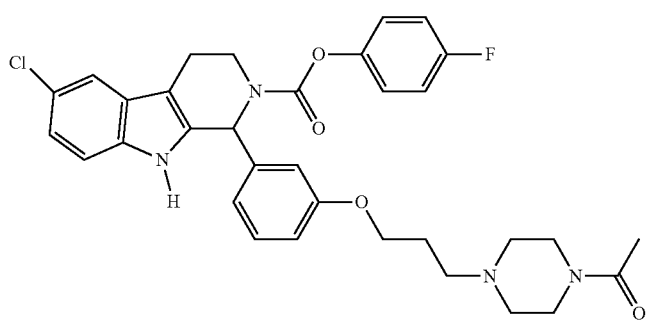 [SMILES: CC(=O)N1CCN(CCCOc2cccc(C3c4[nH]c5ccc(Cl)cc5c4CCN3C(=O)Oc3ccc(F)cc3)c2)CC1]
1364
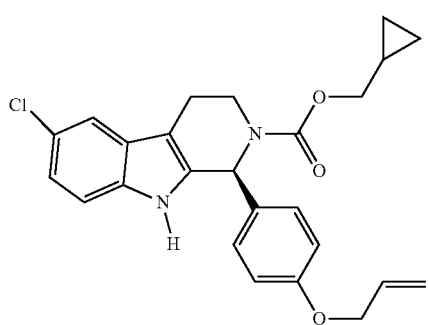 [SMILES: C=CCOc1ccc([C@H]2c3[nH]c4ccc(Cl)cc4c3CCN2C(=O)OCC2CC2)cc1]
1365

TABLE 1-continued
1366
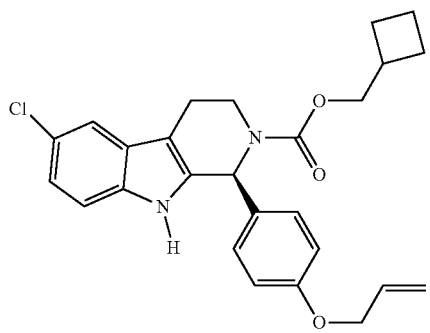 [SMILES: C=CCOc1ccc([C@H]2c3[nH]c4ccc(Cl)cc4c3CCN2C(=O)OCC2CCC2)cc1]
1367
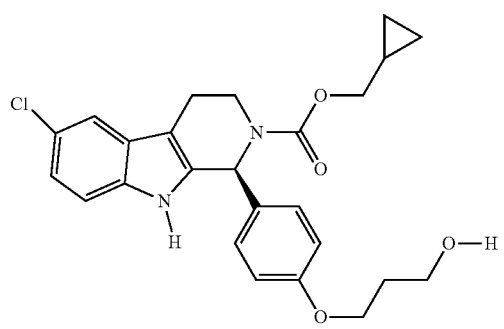 [SMILES: O=C(OCC1CC1)N1CCc2c([nH]c3ccc(Cl)cc23)[C@@H]1c1ccc(OCCCO)cc1]
1368
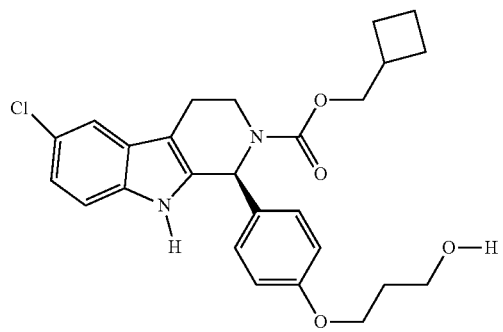 [SMILES: O=C(OCC1CCC1)N1CCc2c([nH]c3ccc(Cl)cc23)[C@@H]1c1ccc(OCCCO)cc1]
1369
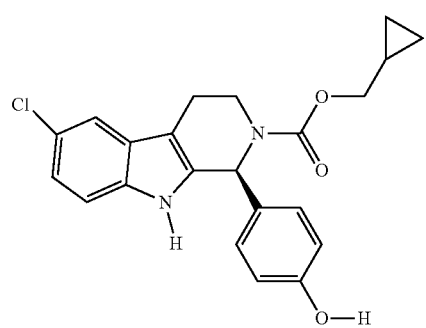
1370
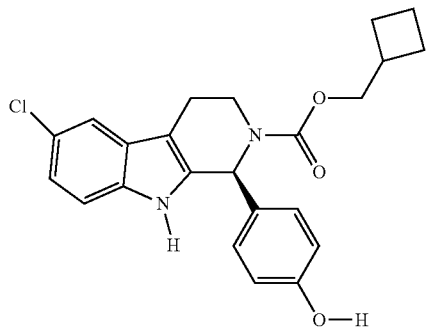 [SMILES: O=C(OCC1CCC1)N1CCc2c([nH]c3ccc(Cl)cc23)[C@@H]1c1ccc(O)cc1]

TABLE 1-continued
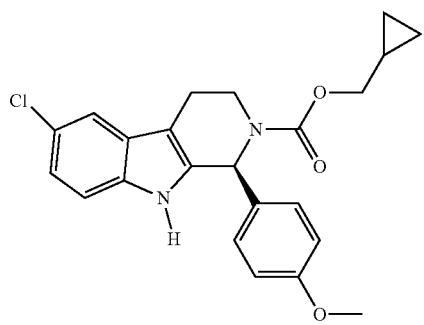 [SMILES: COc1ccc([C@H]2c3[nH]c4ccc(Cl)cc4c3CCN2C(=O)OCC2CC2)cc1]
1371
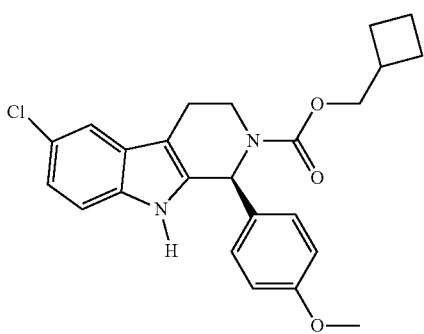 [SMILES: COc1ccc([C@H]2c3[nH]c4ccc(Cl)cc4c3CCN2C(=O)OCC2CCC2)cc1]
1372
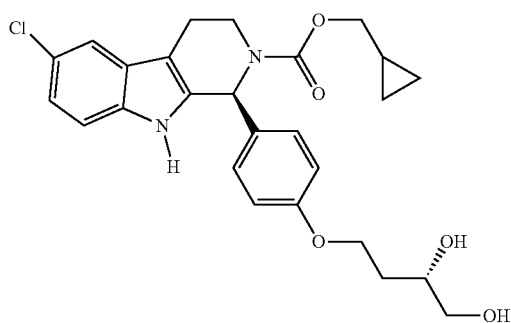 [SMILES: O=C(OCC1CC1)N1CCc2c([nH]c3ccc(Cl)cc23)[C@@H]1c1ccc(OCC[C@H](O)CO)cc1]
1373
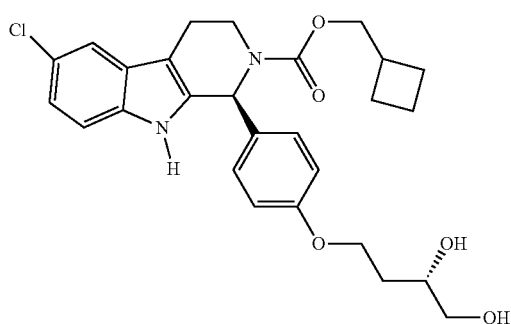 [SMILES: O=C(OCC1CCC1)N1CCc2c([nH]c3ccc(Cl)cc23)[C@@H]1c1ccc(OCC[C@H](O)CO)cc1]
1374

TABLE 1-continued
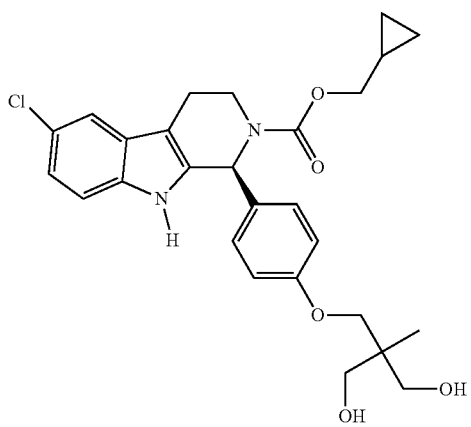 [SMILES: CC(CO)(CO)COc1ccc([C@H]2c3[nH]c4ccc(Cl)cc4c3CCN2C(=O)OCC2CC2)cc1]
1375
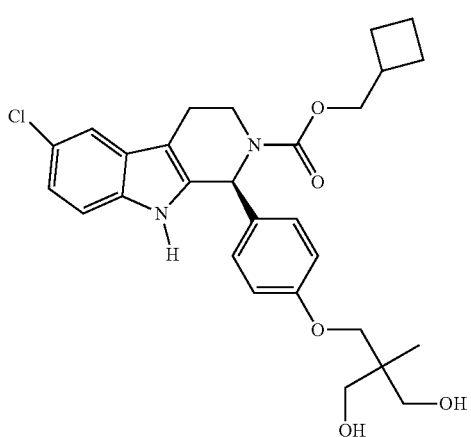 [SMILES: CC(CO)(CO)COc1ccc([C@H]2c3[nH]c4ccc(Cl)cc4c3CCN2C(=O)OCC2CCC2)cc1]
1376
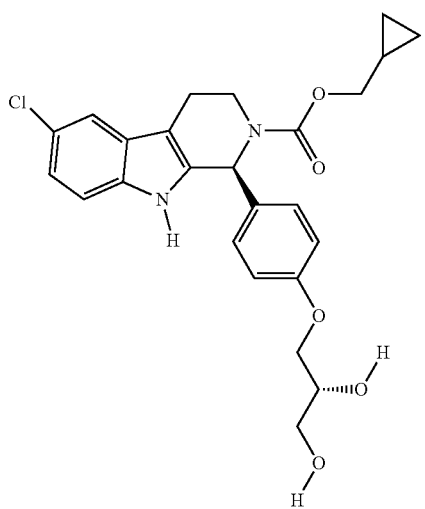 [SMILES: O=C(OCC1CC1)N1CCc2c([nH]c3ccc(Cl)cc23)[C@@H]1c1ccc(OC[C@H](O)CO)cc1]
1377

TABLE 1-continued
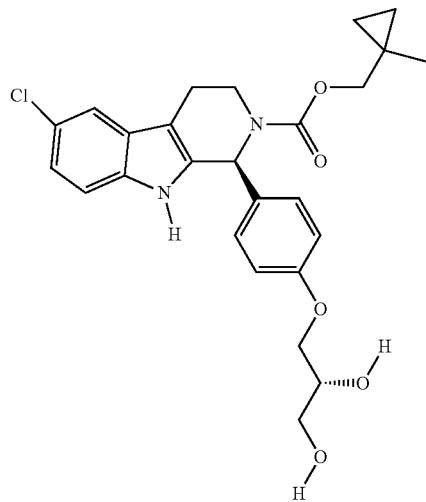 [SMILES: CC1(COC(=O)N2CCc3c([nH]c4ccc(Cl)cc34)[C@@H]2c2ccc(OC[C@H](O)CO)cc2)CC1]
1378
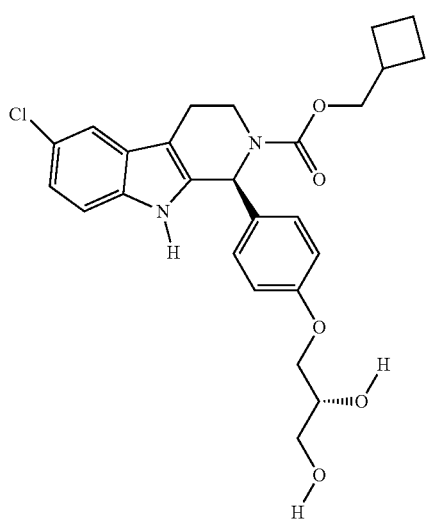 [SMILES: O=C(OCC1CCC1)N1CCc2c([nH]c3ccc(Cl)cc23)[C@@H]1c1ccc(OC[C@H](O)CO)cc1]
1379
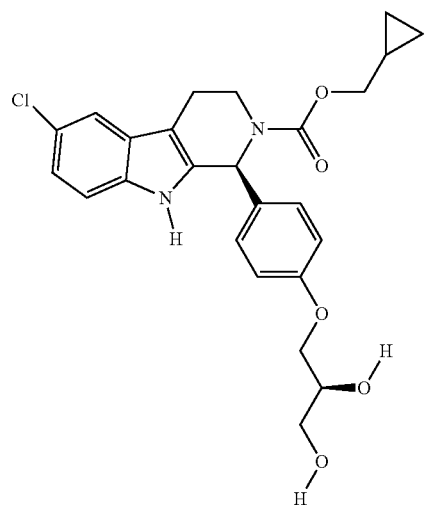 [SMILES: O=C(OCC1CC1)N1CCc2c([nH]c3ccc(Cl)cc23)[C@@H]1c1ccc(OC[C@@H](O)CO)cc1]
1380

TABLE 1-continued
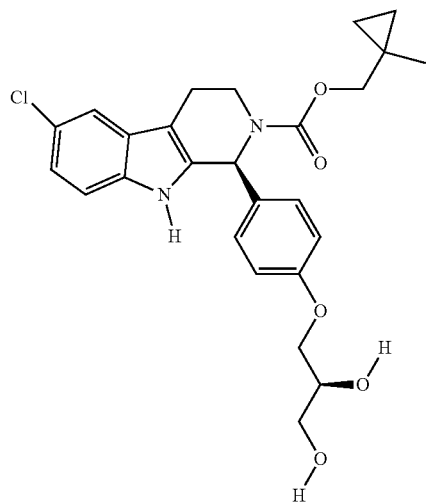 [SMILES: CC1(COC(=O)N2CCc3c([nH]c4ccc(Cl)cc34)[C@@H]2c2ccc(OC[C@@H](O)CO)cc2)CC1]
1381
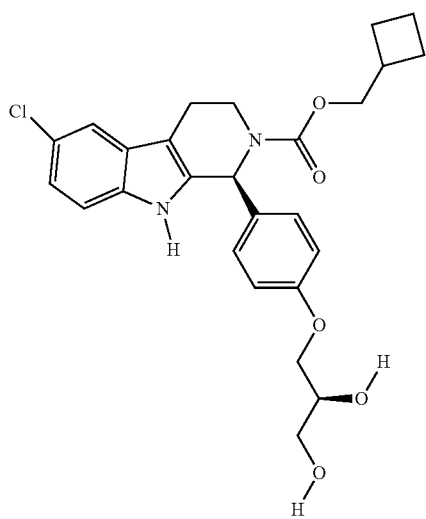 [SMILES: O=C(OCC1CCC1)N1CCc2c([nH]c3ccc(Cl)cc23)[C@@H]1c1ccc(OC[C@@H](O)CO)cc1]
1382
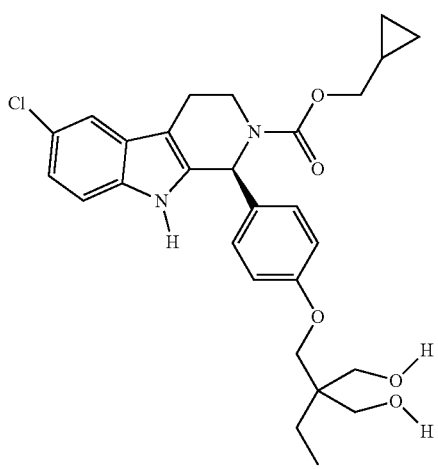 [SMILES: CCC(CO)(CO)COc1ccc([C@H]2c3[nH]c4ccc(Cl)cc4c3CCN2C(=O)OCC2CC2)cc1]
1383

TABLE 1-continued
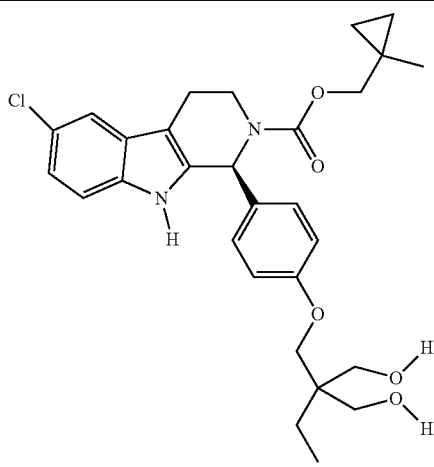
1384
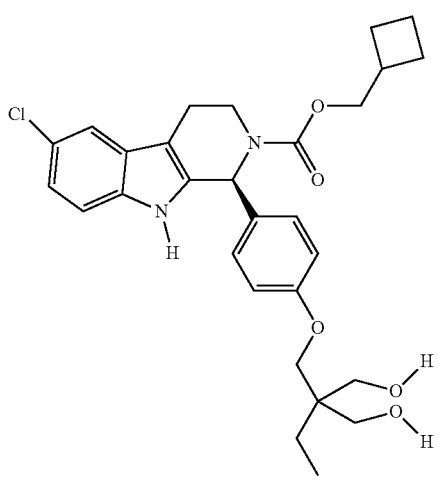 [SMILES: CCC(CO)(CO)COc1ccc([C@H]2c3[nH]c4ccc(Cl)cc4c3CCN2C(=O)OCC2CCC2)cc1]
1385
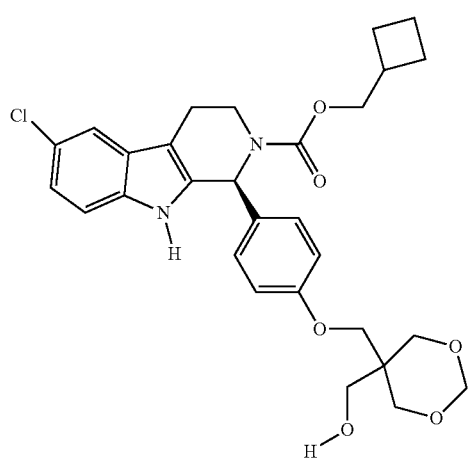 [SMILES: O=C(OCC1CCC1)N1CCc2c([nH]c3ccc(Cl)cc23)[C@@H]1c1ccc(OCC2(CO)COCOC2)cc1]
1386

TABLE 1-continued
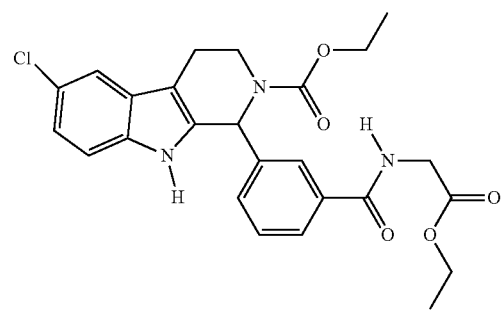 [SMILES: CCOC(=O)CNC(=O)c1cccc(C2c3[nH]c4ccc(Cl)cc4c3CCN2C(=O)OCC)c1]
1387
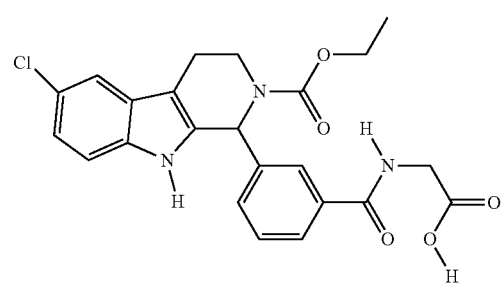 [SMILES: CCOC(=O)N1CCc2c([nH]c3ccc(Cl)cc23)C1c1cccc(C(=O)NCC(=O)O)c1]
1388
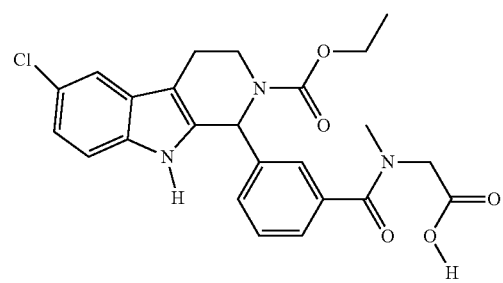 [SMILES: CCOC(=O)N1CCc2c([nH]c3ccc(Cl)cc23)C1c1cccc(C(=O)N(C)CC(=O)O)c1]
1389
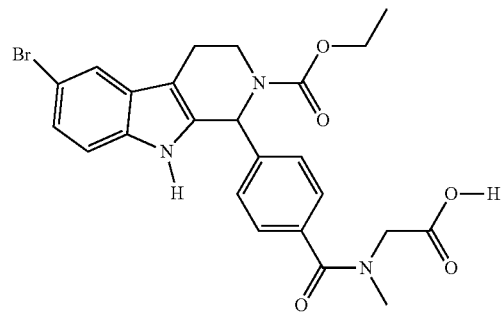 [SMILES: CCOC(=O)N1CCc2c([nH]c3ccc(Br)cc23)C1c1ccc(C(=O)N(C)CC(=O)O)cc1]
1390
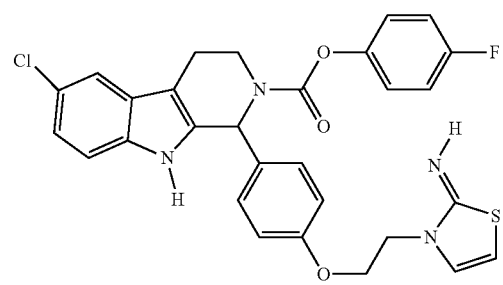
1391

TABLE 1-continued
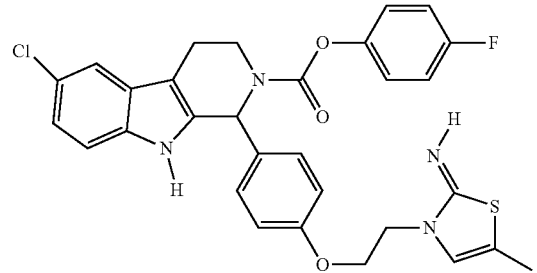 [SMILES: [H]/N=c1\sc(C)cn1CCOc1ccc(C2c3[nH]c4ccc(Cl)cc4c3CCN2C(=O)Oc2ccc(F)cc2)cc1]
1392
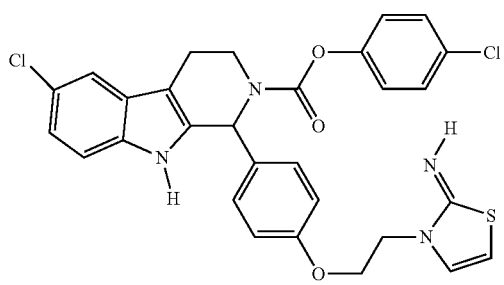 [SMILES: [H]/N=c1\sccn1CCOc1ccc(C2c3[nH]c4ccc(Cl)cc4c3CCN2C(=O)Oc2ccc(Cl)cc2)cc1]
1393
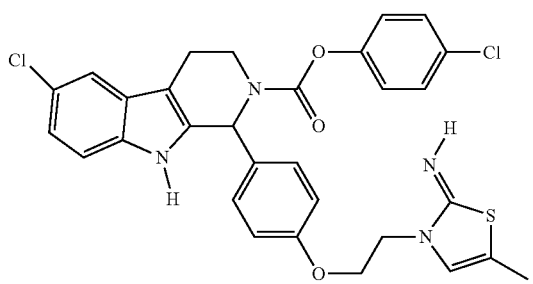 [SMILES: [H]/N=c1\sc(C)cn1CCOc1ccc(C2c3[nH]c4ccc(Cl)cc4c3CCN2C(=O)Oc2ccc(Cl)cc2)cc1]
1394
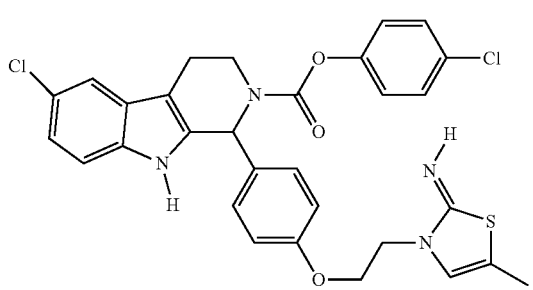 [SMILES: [H]/N=c1\sc(C)cn1CCOc1ccc(C2c3[nH]c4ccc(Cl)cc4c3CCN2C(=O)Oc2ccc(Cl)cc2)cc1]
1395
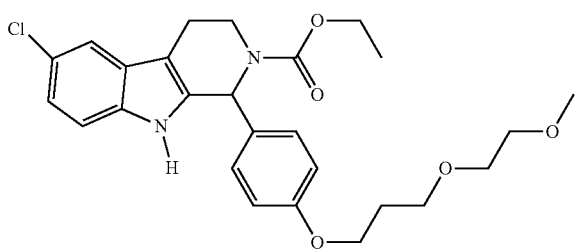 [SMILES: CCOC(=O)N1CCc2c([nH]c3ccc(Cl)cc23)C1c1ccc(OCCCOCCOC)cc1]
1396

TABLE 1-continued
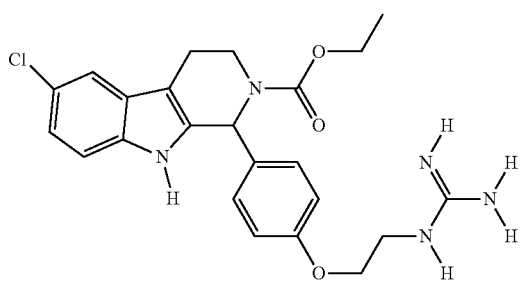 [SMILES: [H]/N=C(\N)NCCOc1ccc(C2c3[nH]c4ccc(Cl)cc4c3CCN2C(=O)OCC)cc1]
1397
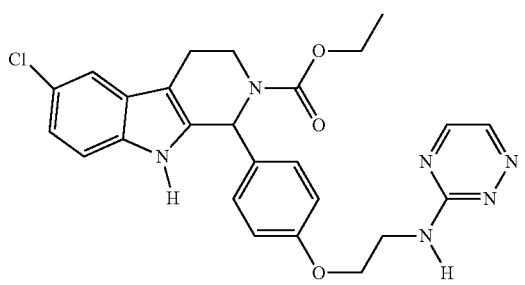 [SMILES: CCOC(=O)N1CCc2c([nH]c3ccc(Cl)cc23)C1c1ccc(OCCNc2nccnn2)cc1]
1398
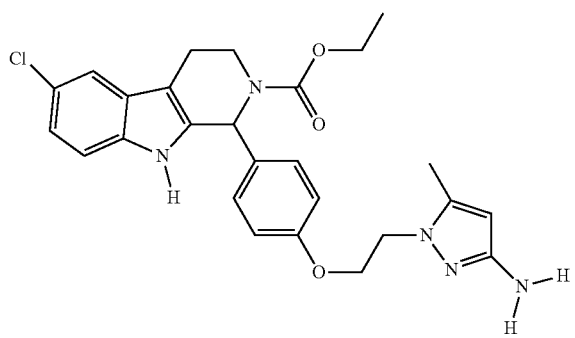 [SMILES: CCOC(=O)N1CCc2c([nH]c3ccc(Cl)cc23)C1c1ccc(OCCn2nc(N)cc2C)cc1]
1399
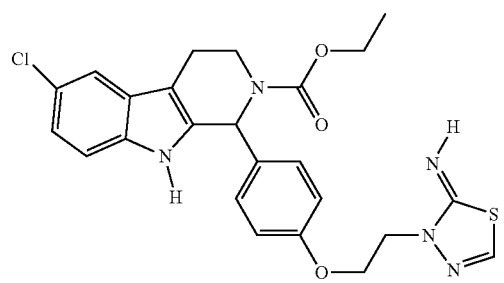 [SMILES: [H]/N=c1\scnn1CCOc1ccc(C2c3[nH]c4ccc(Cl)cc4c3CCN2C(=O)OCC)cc1]
1400
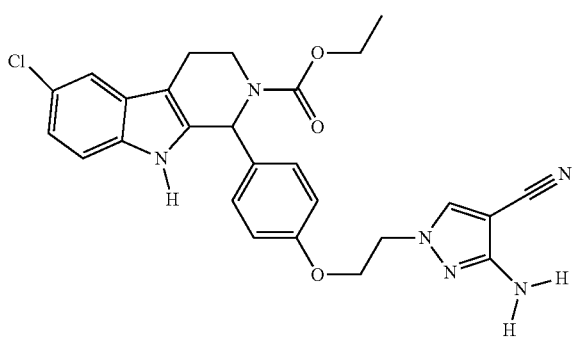 [SMILES: CCOC(=O)N1CCc2c([nH]c3ccc(Cl)cc23)C1c1ccc(OCCn2cc(C#N)c(N)n2)cc1]
1401

TABLE 1-continued
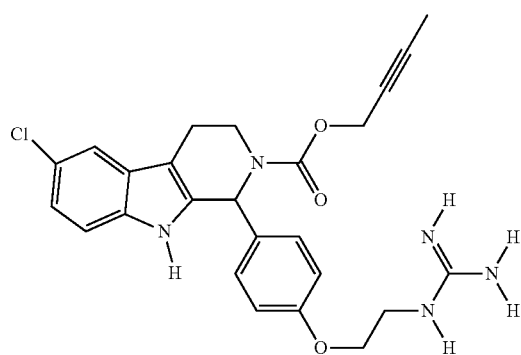 [SMILES: [H]/N=C(\N)NCCOc1ccc(C2c3[nH]c4ccc(Cl)cc4c3CCN2C(=O)OCC#CC)cc1]
1402
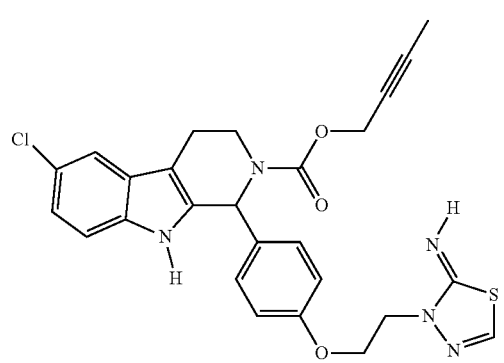 [SMILES: [H]/N=c1\scnn1CCOc1ccc(C2c3[nH]c4ccc(Cl)cc4c3CCN2C(=O)OCC#CC)cc1]
1403
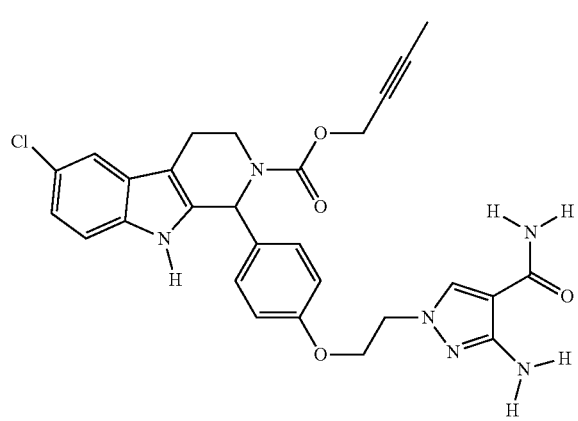 [SMILES: CC#CCOC(=O)N1CCc2c([nH]c3ccc(Cl)cc23)C1c1ccc(OCCn2cc(C(N)=O)c(N)n2)cc1]
1404
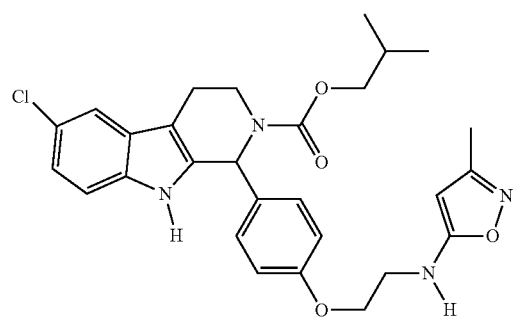 [SMILES: Cc1cc(NCCOc2ccc(C3c4[nH]c5ccc(Cl)cc5c4CCN3C(=O)OCC(C)C)cc2)on1]
1405

TABLE 1-continued
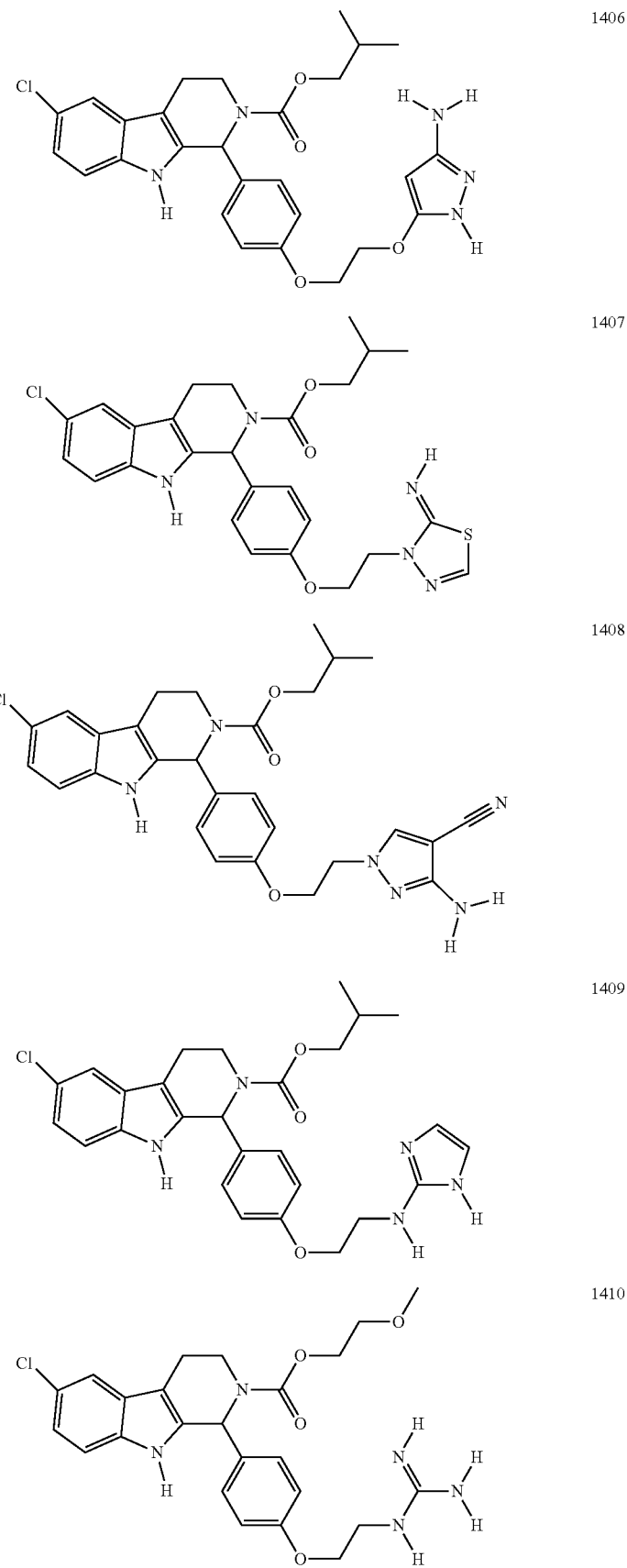
1406
1407
1408
1409
1410

TABLE 1-continued
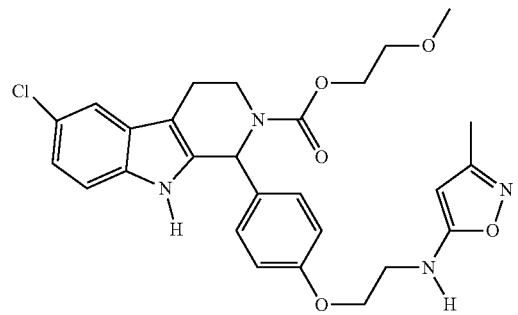 [SMILES: COCCOC(=O)N1CCc2c([nH]c3ccc(Cl)cc23)C1c1ccc(OCCNc2cc(C)no2)cc1]
1411
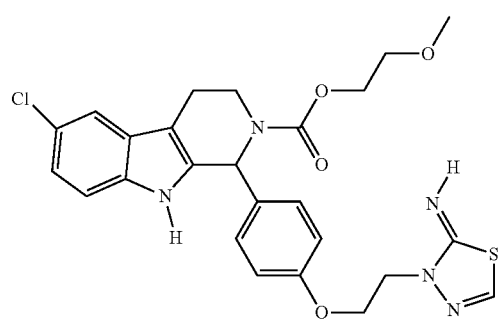 [SMILES: [H]/N=c1\scnn1CCOc1ccc(C2c3[nH]c4ccc(Cl)cc4c3CCN2C(=O)OCCOC)cc1]
1412
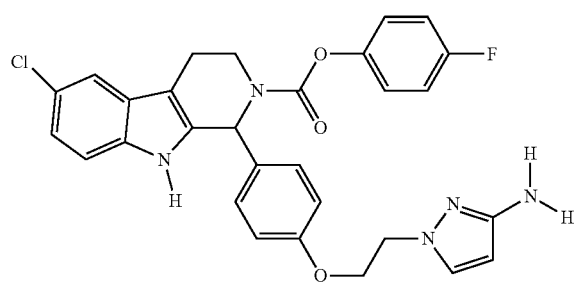
1413
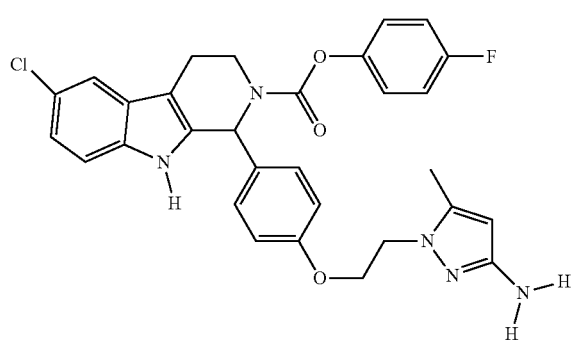
1414
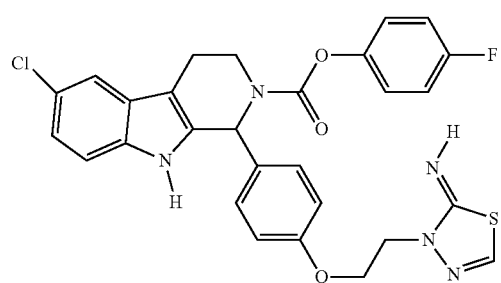
1415

TABLE 1-continued
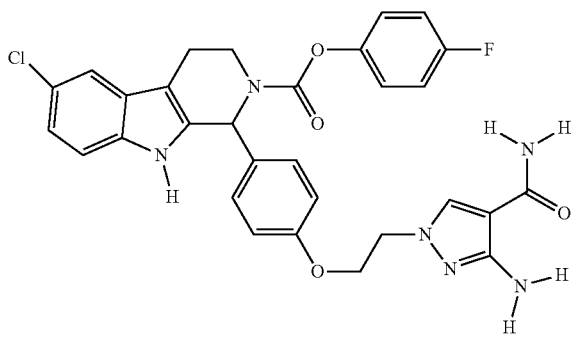
1416
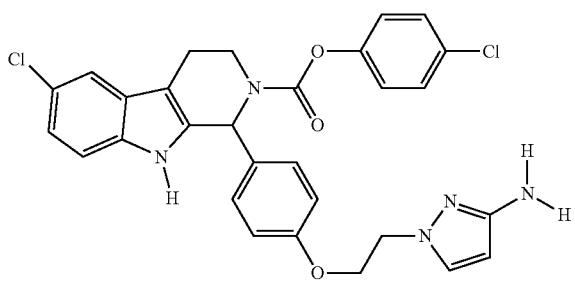 [SMILES: Nc1ccn(CCOc2ccc(C3c4[nH]c5ccc(Cl)cc5c4CCN3C(=O)Oc3ccc(F)cc3)cc2)n1]
1417
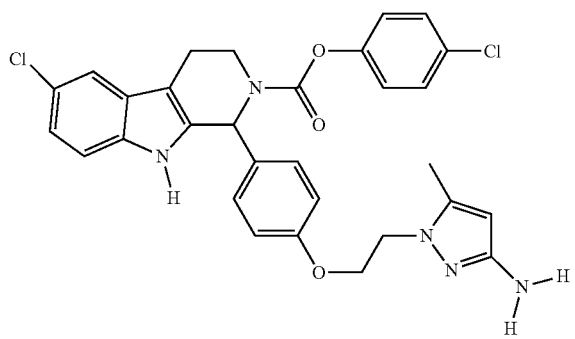 [SMILES: Cc1cc(N)nn1CCOc1ccc(C2c3[nH]c4ccc(Cl)cc4c3CCN2C(=O)Oc2ccc(F)cc2)cc1]
1418
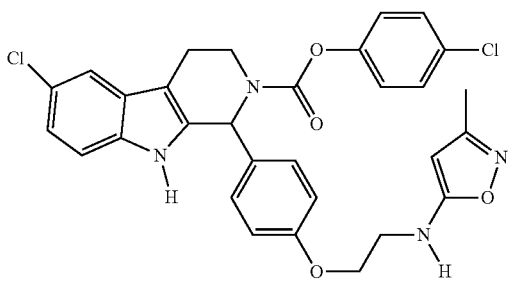 [SMILES: Cc1cc(NCCOc2ccc(C3c4[nH]c5ccc(Cl)cc5c4CCN3C(=O)Oc3ccc(Cl)cc3)cc2)on1]
1419
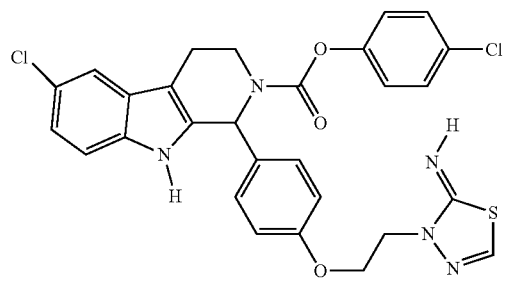 [SMILES: [H]/N=c1\scnn1CCOc1ccc(C2c3[nH]c4ccc(Cl)cc4c3CCN2C(=O)Oc2ccc(Cl)cc2)cc1]
1420

TABLE 1-continued
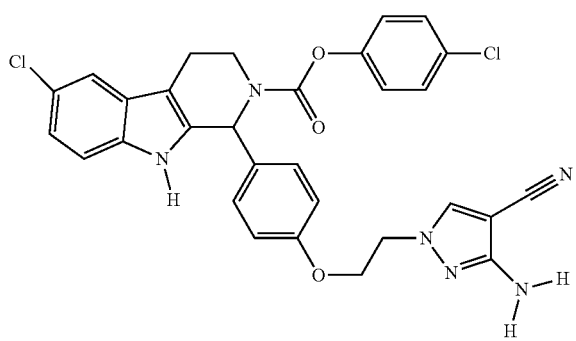 [SMILES: N#Cc1cn(CCOc2ccc(C3c4[nH]c5ccc(Cl)cc5c4CCN3C(=O)Oc3ccc(Cl)cc3)cc2)nc1N]
1421
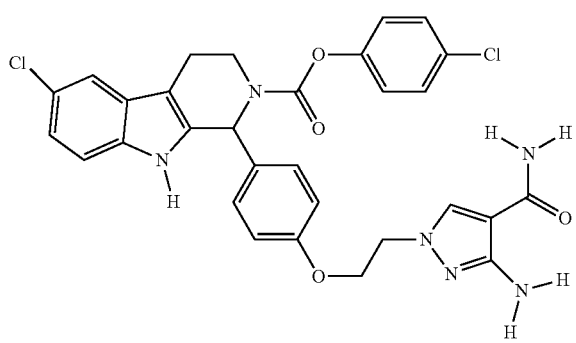 [SMILES: NC(=O)c1cn(CCOc2ccc(C3c4[nH]c5ccc(Cl)cc5c4CCN3C(=O)Oc3ccc(Cl)cc3)cc2)nc1N]
1422
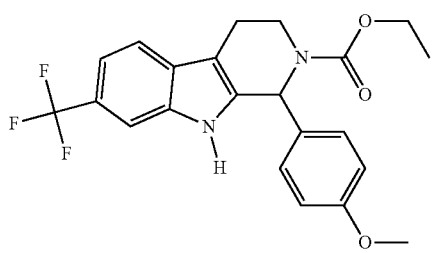 [SMILES: CCOC(=O)N1CCc2c([nH]c3cc(C(F)(F)F)ccc23)C1c1ccc(OC)cc1]
1423
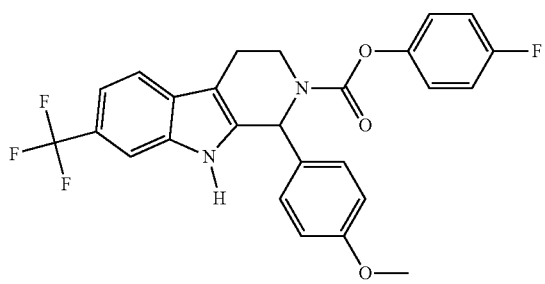 [SMILES: COc1ccc(C2c3[nH]c4cc(C(F)(F)F)ccc4c3CCN2C(=O)Oc2ccc(F)cc2)cc1]
1424
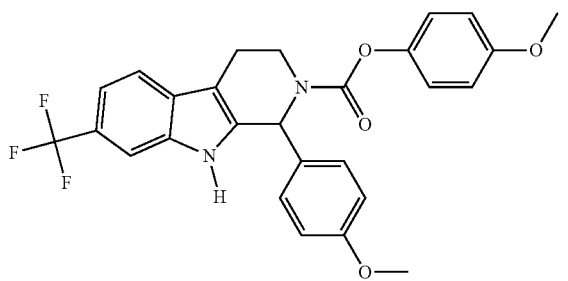 [SMILES: COc1ccc(OC(=O)N2CCc3c([nH]c4cc(C(F)(F)F)ccc34)C2c2ccc(OC)cc2)cc1]
1425

TABLE 1-continued
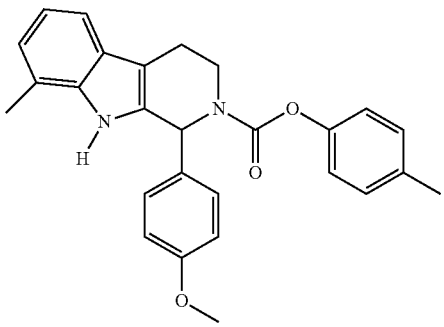
1426
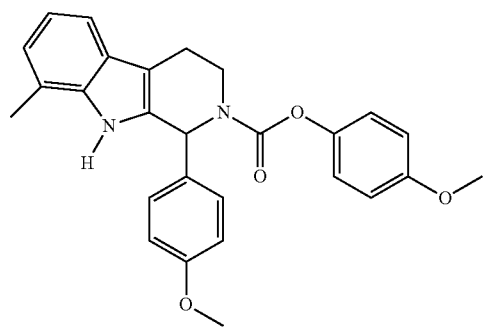
1427
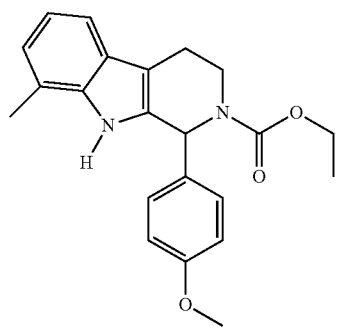 [SMILES: CCOC(=O)N1CCc2c([nH]c3c(C)cccc23)C1c1ccc(OC)cc1]
1428
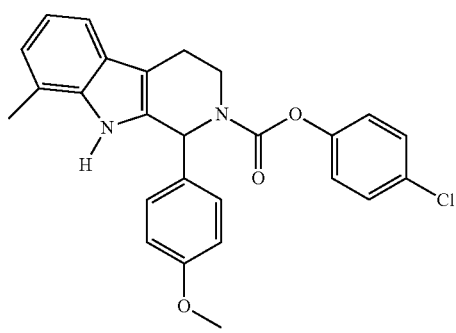 [SMILES: COc1ccc(C2c3[nH]c4c(C)cccc4c3CCN2C(=O)Oc2ccc(Cl)cc2)cc1]
1429
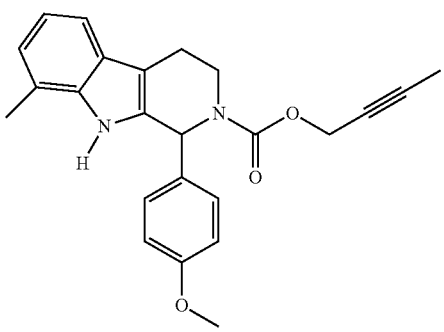 [SMILES: CC#CCOC(=O)N1CCc2c([nH]c3c(C)cccc23)C1c1ccc(OC)cc1]
1430

TABLE 1-continued
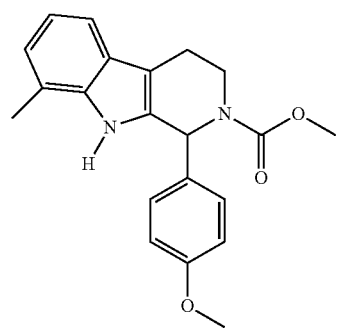
1431
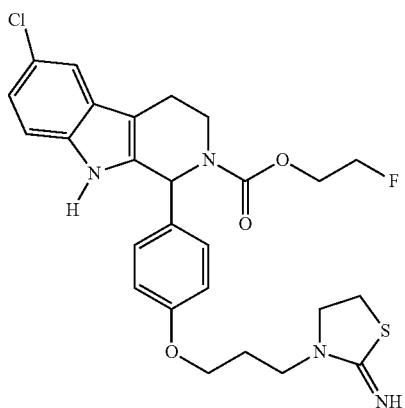 [SMILES: N=C1SCCN1CCCOc1ccc(C2c3[nH]c4ccc(Cl)cc4c3CCN2C(=O)OCCF)cc1]
1432
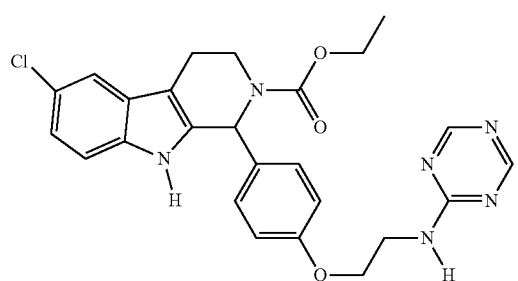 [SMILES: CCOC(=O)N1CCc2c([nH]c3ccc(Cl)cc23)C1c1ccc(OCCNc2ncncn2)cc1]
1433
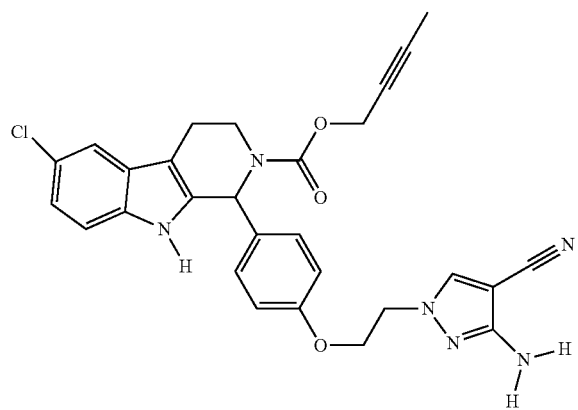 [SMILES: CC#CCOC(=O)N1CCc2c([nH]c3ccc(Cl)cc23)C1c1ccc(OCCn2cc(C#N)c(N)n2)cc1]
1434

TABLE 1-continued
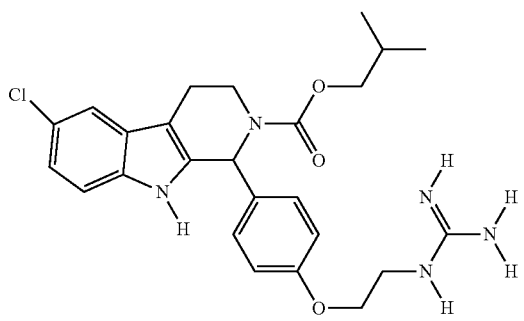 [SMILES: [H]/N=C(\N)NCCOc1ccc(C2c3[nH]c4ccc(Cl)cc4c3CCN2C(=O)OCC(C)C)cc1]
1435
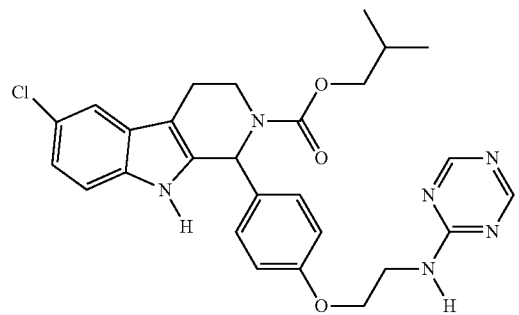 [SMILES: CC(C)COC(=O)N1CCc2c([nH]c3ccc(Cl)cc23)C1c1ccc(OCCNc2ncncn2)cc1]
1436
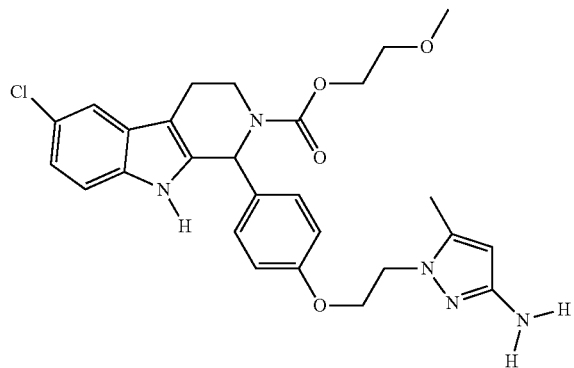 [SMILES: COCCOC(=O)N1CCc2c([nH]c3ccc(Cl)cc23)C1c1ccc(OCCn2nc(N)cc2C)cc1]
1437
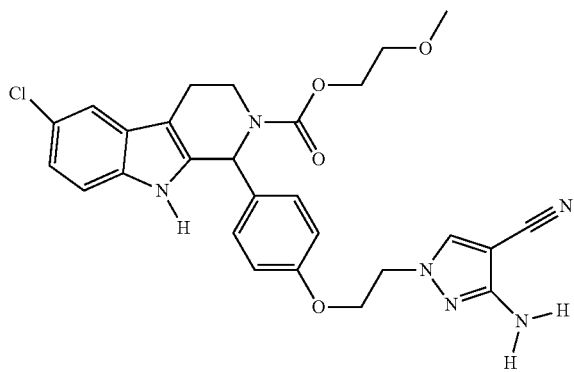 [SMILES: COCCOC(=O)N1CCc2c([nH]c3ccc(Cl)cc23)C1c1ccc(OCCn2cc(C#N)c(N)n2)cc1]
1438

TABLE 1-continued
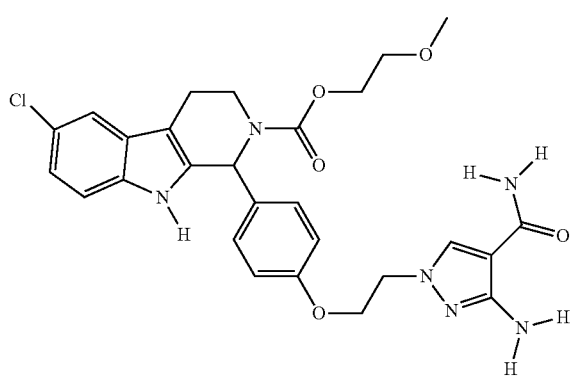 [SMILES: COCCOC(=O)N1CCc2c([nH]c3ccc(Cl)cc23)C1c1ccc(OCCn2cc(C(N)=O)c(N)n2)cc1]
1439
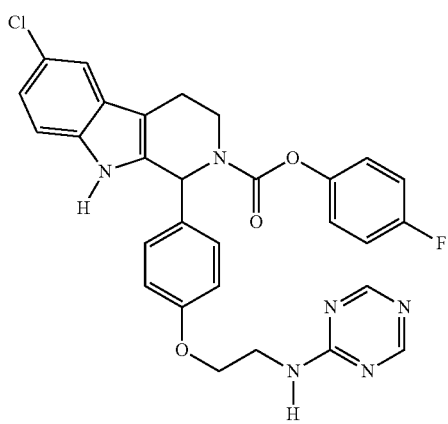 [SMILES: O=C(Oc1ccc(F)cc1)N1CCc2c([nH]c3ccc(Cl)cc23)C1c1ccc(OCCNc2ncncn2)cc1]
1440
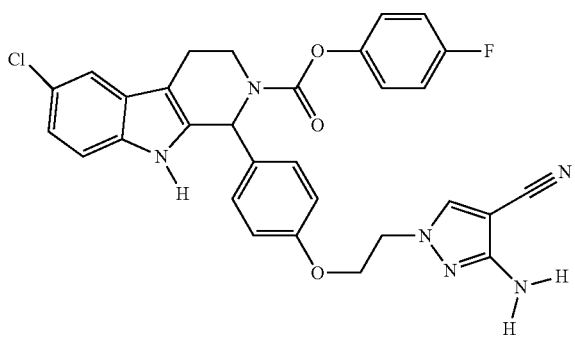 [SMILES: N#Cc1cn(CCOc2ccc(C3c4[nH]c5ccc(Cl)cc5c4CCN3C(=O)Oc3ccc(F)cc3)cc2)nc1N]
1441
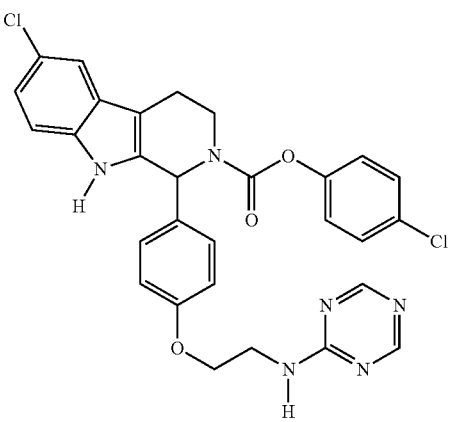 [SMILES: O=C(Oc1ccc(Cl)cc1)N1CCc2c([nH]c3ccc(Cl)cc23)C1c1ccc(OCCNc2ncncn2)cc1]
1442

TABLE 1-continued
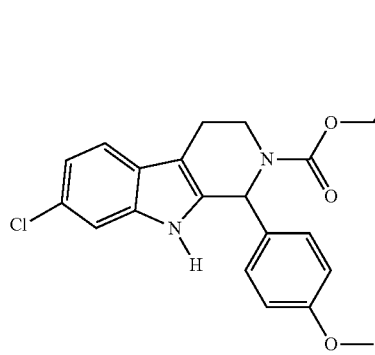
1443
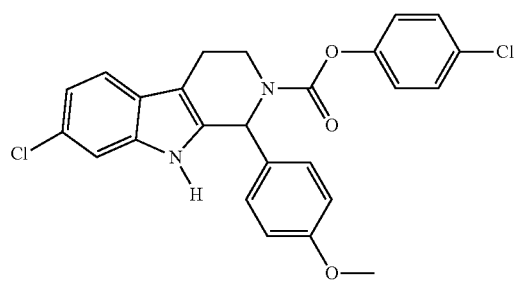 [SMILES: COc1ccc(C2c3[nH]c4cc(Cl)ccc4c3CCN2C(=O)Oc2ccc(Cl)cc2)cc1]
1444
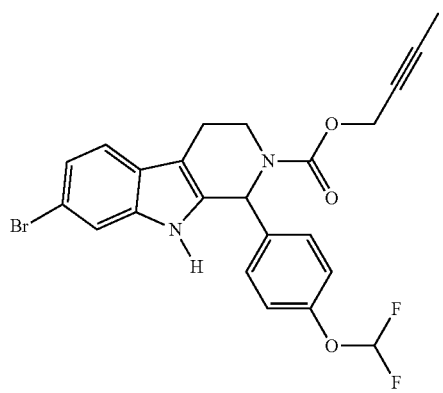 [SMILES: CC#CCOC(=O)N1CCc2c([nH]c3cc(Br)ccc23)C1c1ccc(OC(F)F)cc1]
1445
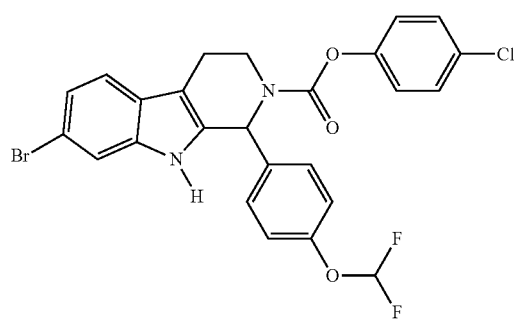 [SMILES: O=C(Oc1ccc(Cl)cc1)N1CCc2c([nH]c3cc(Br)ccc23)C1c1ccc(OC(F)F)cc1]
1446

TABLE 1-continued
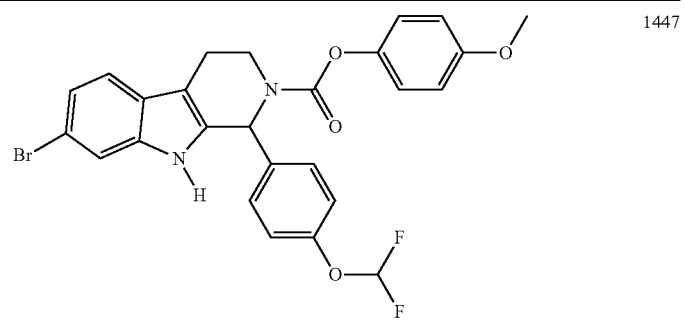
1447
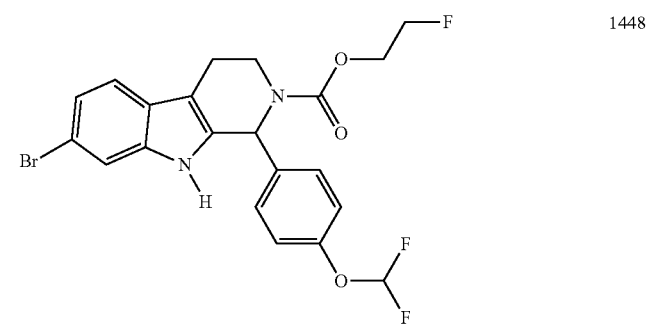
1448
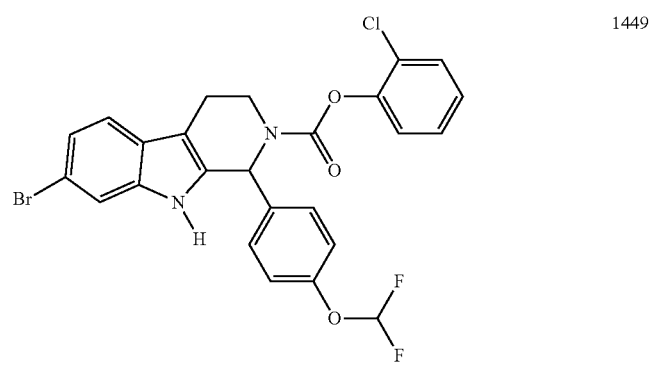
1449
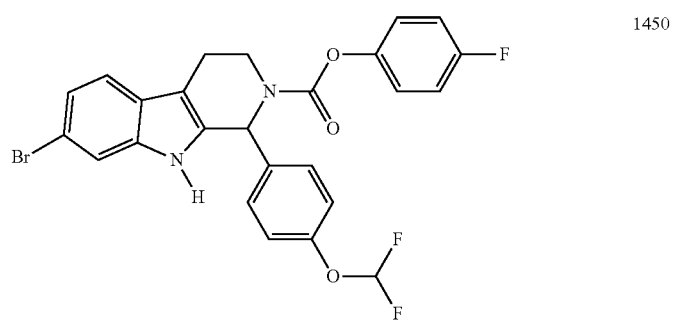
1450
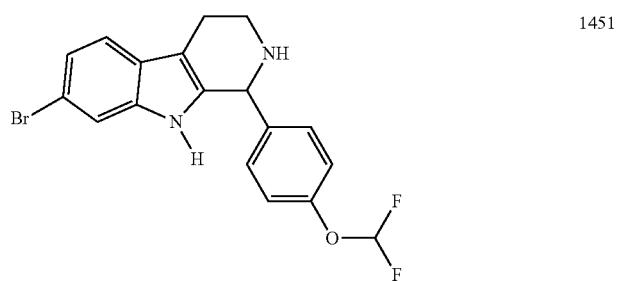
1451

TABLE 1-continued
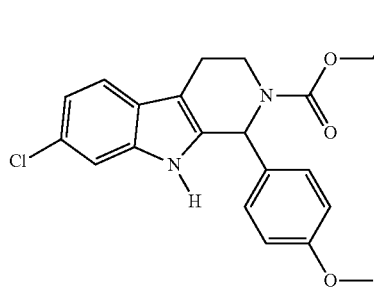 1452
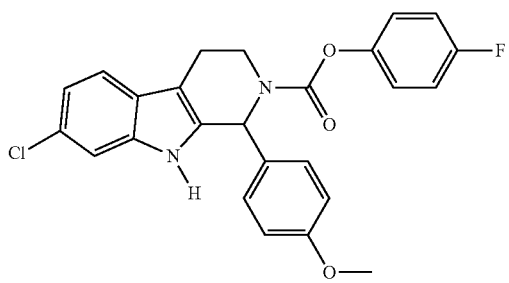 [SMILES: COc1ccc(C2c3[nH]c4cc(Cl)ccc4c3CCN2C(=O)Oc2ccc(F)cc2)cc1] 1453
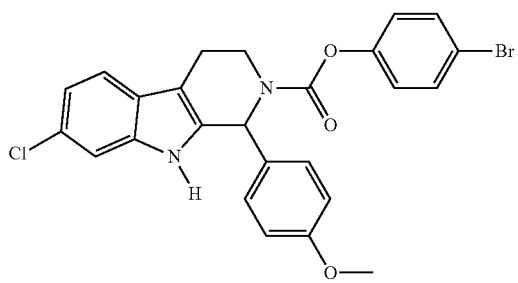 [SMILES: COc1ccc(C2c3[nH]c4cc(Cl)ccc4c3CCN2C(=O)Oc2ccc(Br)cc2)cc1] 1454
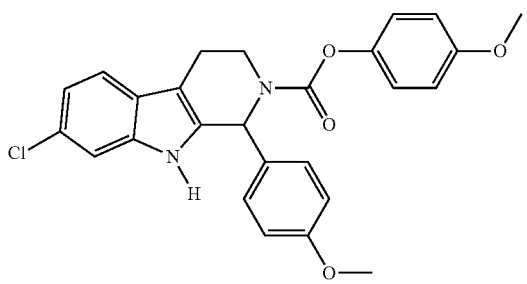 [SMILES: COc1ccc(OC(=O)N2CCc3c([nH]c4cc(Cl)ccc34)C2c2ccc(OC)cc2)cc1] 1455
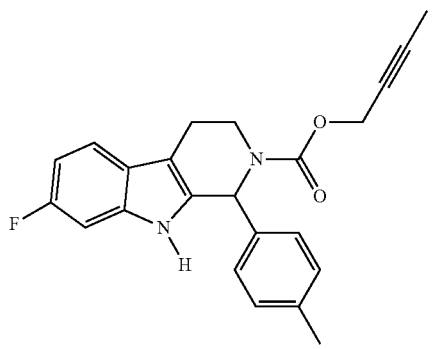 [SMILES: CC#CCOC(=O)N1CCc2c([nH]c3cc(F)ccc23)C1c1ccc(C)cc1] 1456

TABLE 1-continued
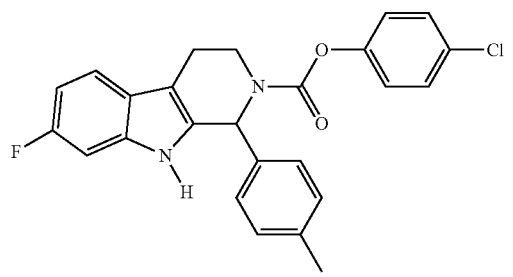 [SMILES: Cc1ccc(C2c3[nH]c4cc(F)ccc4c3CCN2C(=O)Oc2ccc(Cl)cc2)cc1]
1457
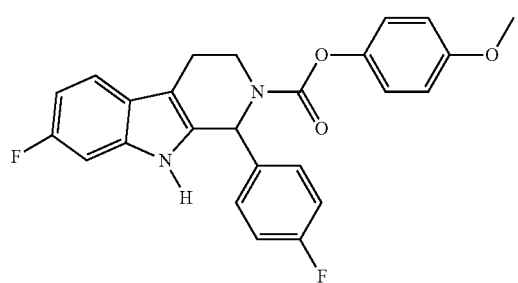 [SMILES: COc1ccc(OC(=O)N2CCc3c([nH]c4cc(F)ccc34)C2c2ccc(F)cc2)cc1]
1458
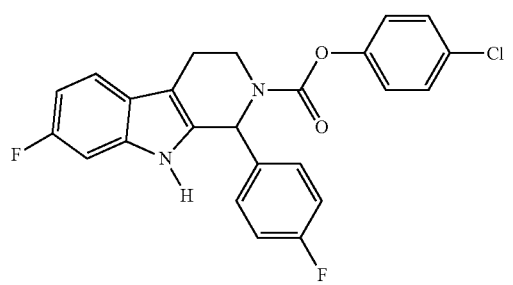 [SMILES: O=C(Oc1ccc(Cl)cc1)N1CCc2c([nH]c3cc(F)ccc23)C1c1ccc(F)cc1]
1459
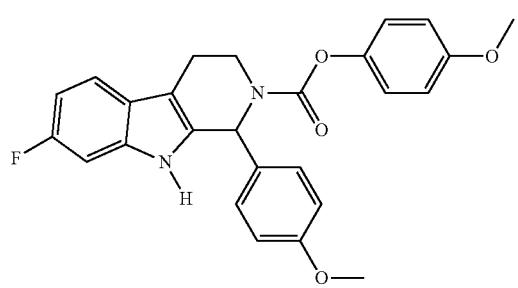
1460
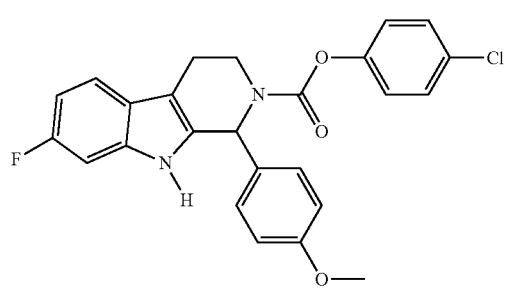 [SMILES: COc1ccc(C2c3[nH]c4cc(F)ccc4c3CCN2C(=O)Oc2ccc(Cl)cc2)cc1]
1461

TABLE 1-continued
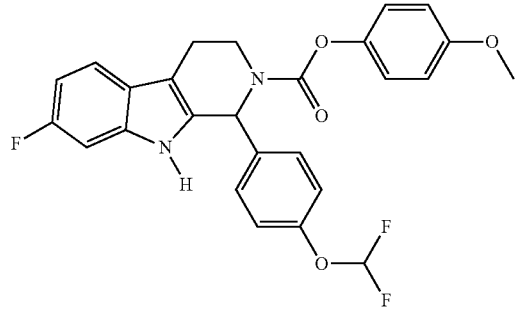 [SMILES: COc1ccc(OC(=O)N2CCc3c([nH]c4cc(F)ccc34)C2c2ccc(OC(F)F)cc2)cc1]
1462
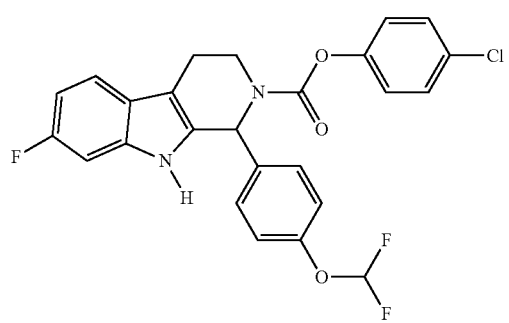 [SMILES: O=C(Oc1ccc(Cl)cc1)N1CCc2c([nH]c3cc(F)ccc23)C1c1ccc(OC(F)F)cc1]
1463
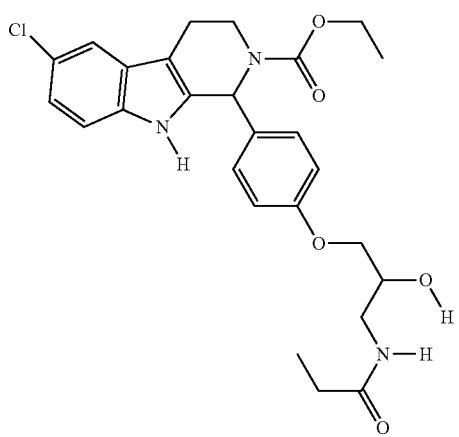 [SMILES: CCOC(=O)N1CCc2c([nH]c3ccc(Cl)cc23)C1c1ccc(OCC(O)CNC(=O)CC)cc1]
1464
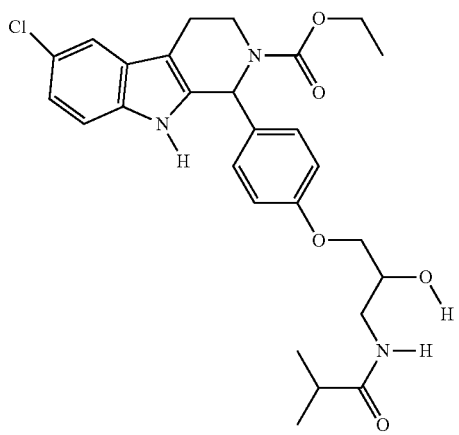 [SMILES: CCOC(=O)N1CCc2c([nH]c3ccc(Cl)cc23)C1c1ccc(OCC(O)CNC(=O)C(C)C)cc1]
1465

TABLE 1-continued
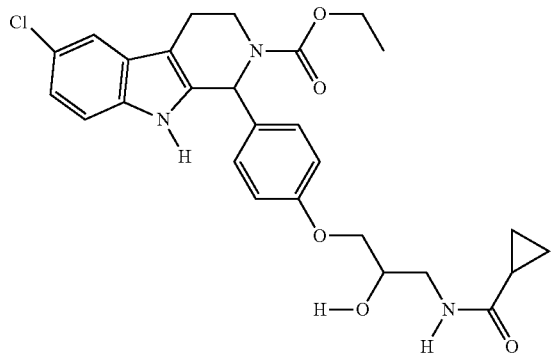 [SMILES: CCOC(=O)N1CCc2c([nH]c3ccc(Cl)cc23)C1c1ccc(OCC(O)CNC(=O)C2CC2)cc1]
1466
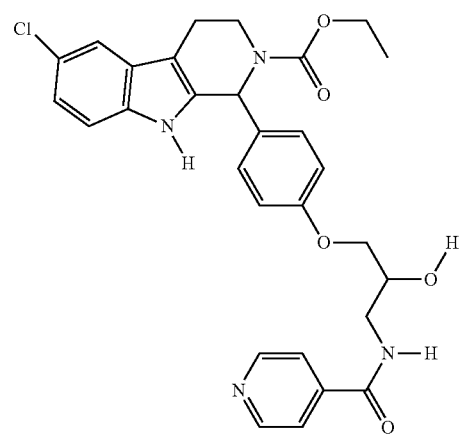 [SMILES: CCOC(=O)N1CCc2c([nH]c3ccc(Cl)cc23)C1c1ccc(OCC(O)CNC(=O)c2ccncc2)cc1]
1467
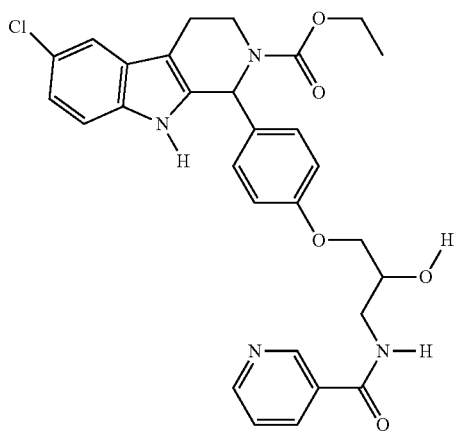 [SMILES: CCOC(=O)N1CCc2c([nH]c3ccc(Cl)cc23)C1c1ccc(OCC(O)CNC(=O)c2cccnc2)cc1]
1468
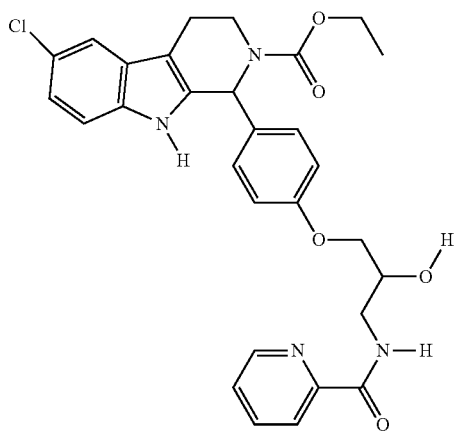 [SMILES: CCOC(=O)N1CCc2c([nH]c3ccc(Cl)cc23)C1c1ccc(OCC(O)CNC(=O)c2ccccn2)cc1]
1469

TABLE 1-continued
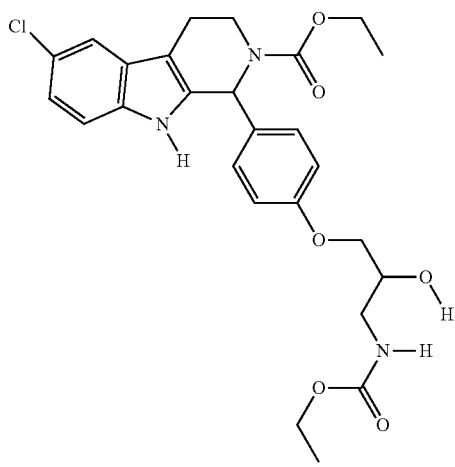 [SMILES: CCOC(=O)NCC(O)COc1ccc(C2c3[nH]c4ccc(Cl)cc4c3CCN2C(=O)OCC)cc1]
1470
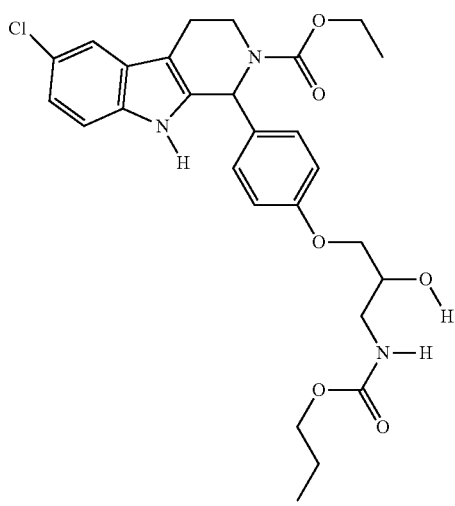 [SMILES: CCCOC(=O)NCC(O)COc1ccc(C2c3[nH]c4ccc(Cl)cc4c3CCN2C(=O)OCC)cc1]
1471
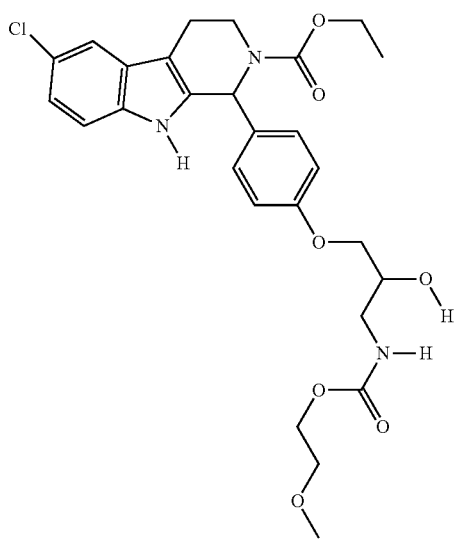 [SMILES: CCOC(=O)N1CCc2c([nH]c3ccc(Cl)cc23)C1c1ccc(OCC(O)CNC(=O)OCCOC)cc1]
1472

TABLE 1-continued
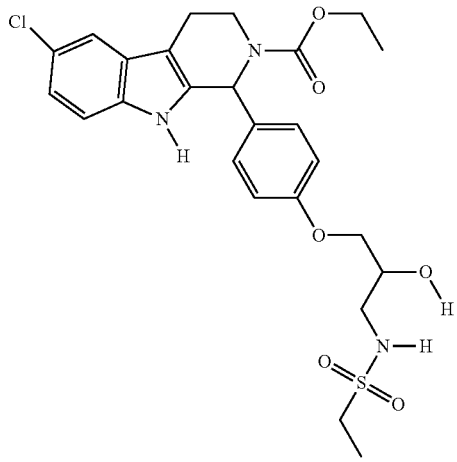 [SMILES: CCOC(=O)N1CCc2c([nH]c3ccc(Cl)cc23)C1c1ccc(OCC(O)CNS(=O)(=O)CC)cc1]
1473
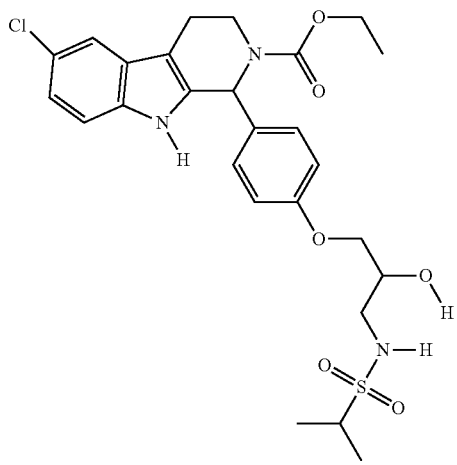 [SMILES: CCOC(=O)N1CCc2c([nH]c3ccc(Cl)cc23)C1c1ccc(OCC(O)CNS(=O)(=O)C(C)C)cc1]
1474
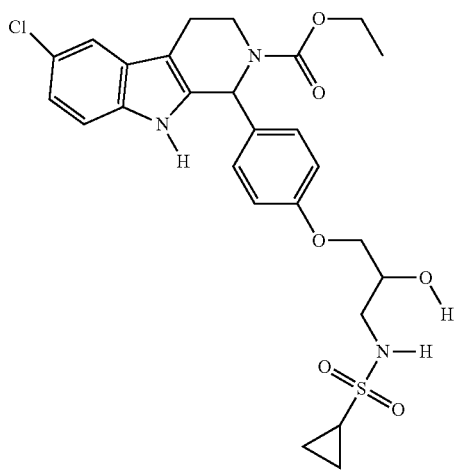 [SMILES: CCOC(=O)N1CCc2c([nH]c3ccc(Cl)cc23)C1c1ccc(OCC(O)CNS(=O)(=O)C2CC2)cc1]
1475

TABLE 1-continued
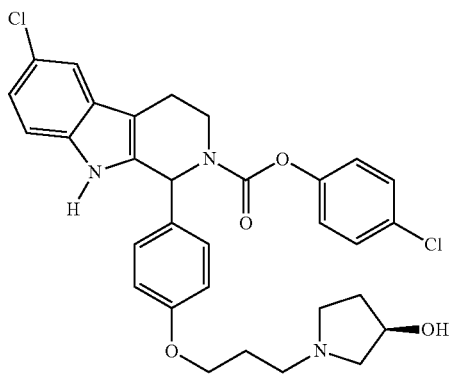 [SMILES: O=C(Oc1ccc(Cl)cc1)N1CCc2c([nH]c3ccc(Cl)cc23)C1c1ccc(OCCCN2CC[C@@H](O)C2)cc1]
1476
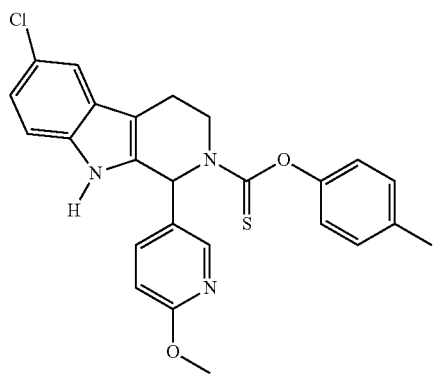 [SMILES: COc1ccc(C2c3[nH]c4ccc(Cl)cc4c3CCN2C(=S)Oc2ccc(C)cc2)cn1]
1477
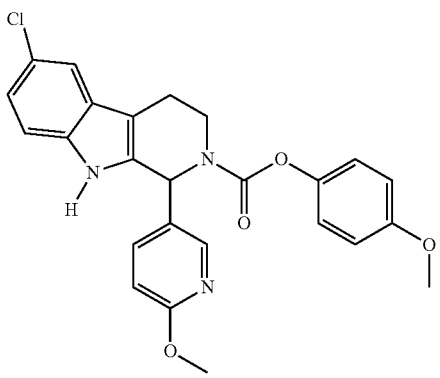 [SMILES: COc1ccc(OC(=O)N2CCc3c([nH]c4ccc(Cl)cc34)C2c2ccc(OC)nc2)cc1]
1478
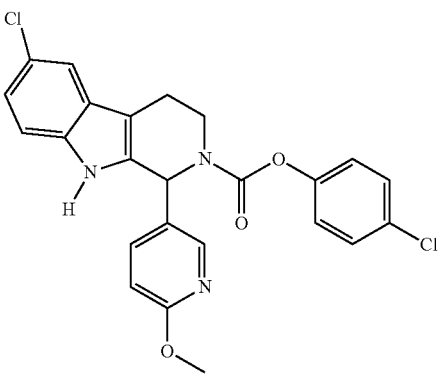 [SMILES: COc1ccc(C2c3[nH]c4ccc(Cl)cc4c3CCN2C(=O)Oc2ccc(Cl)cc2)cn1]
1479

TABLE 1-continued
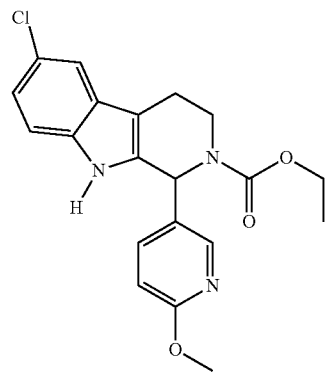 [SMILES: CCOC(=O)N1CCc2c([nH]c3ccc(Cl)cc23)C1c1ccc(OC)nc1]
1480
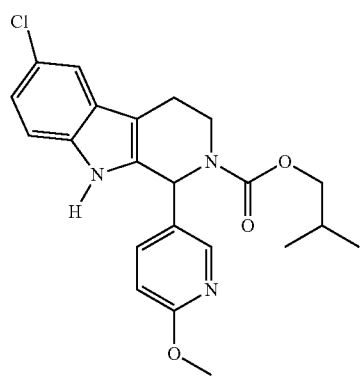 [SMILES: COc1ccc(C2c3[nH]c4ccc(Cl)cc4c3CCN2C(=O)OCC(C)C)cn1]
1481
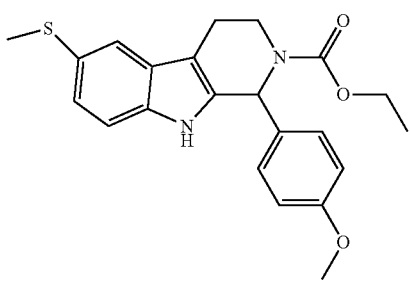 [SMILES: CCOC(=O)N1CCc2c([nH]c3ccc(SC)cc23)C1c1ccc(OC)cc1]
1482
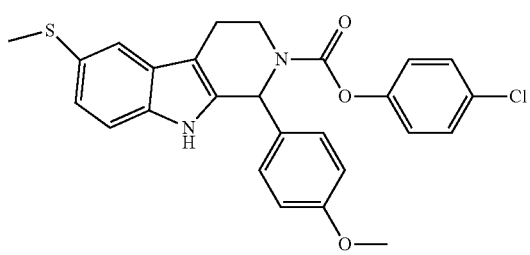 [SMILES: COc1ccc(C2c3[nH]c4ccc(SC)cc4c3CCN2C(=O)Oc2ccc(Cl)cc2)cc1]
1483
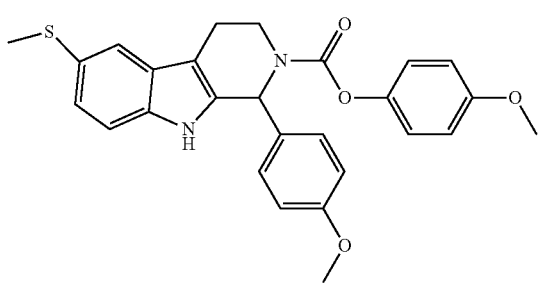
1484

TABLE 1-continued
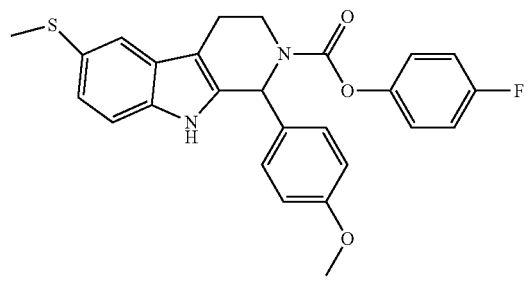
1485
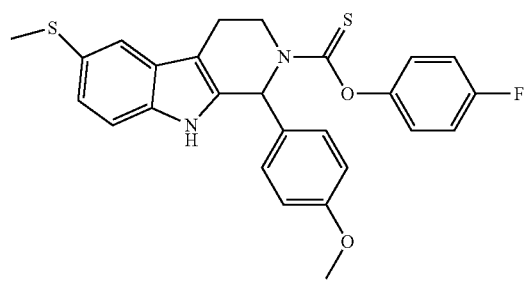 [SMILES: COc1ccc(C2c3[nH]c4ccc(SC)cc4c3CCN2C(=O)Oc2ccc(F)cc2)cc1]
1486
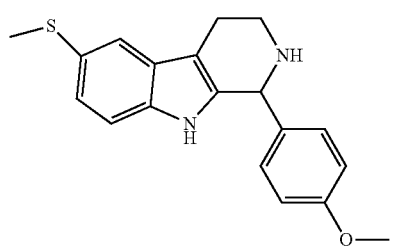
1487
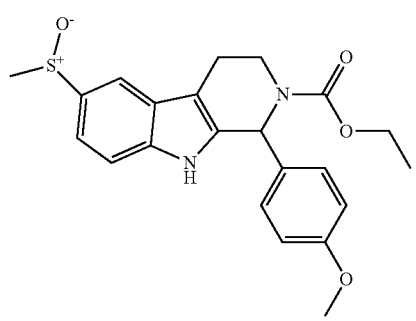 [SMILES: CCOC(=O)N1CCc2c([nH]c3ccc([S+](C)[O-])cc23)C1c1ccc(OC)cc1]
1488
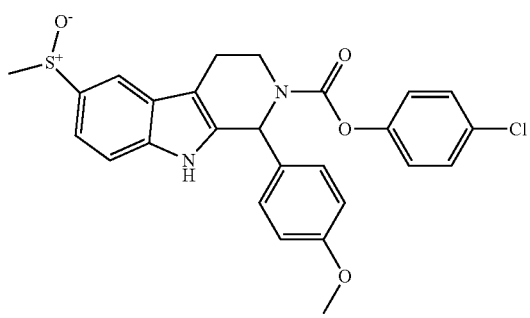 [SMILES: COc1ccc(C2c3[nH]c4ccc([S+](C)[O-])cc4c3CCN2C(=O)Oc2ccc(Cl)cc2)cc1]
1489

TABLE 1-continued
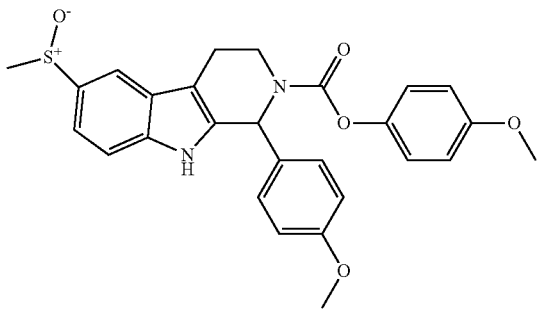 1490
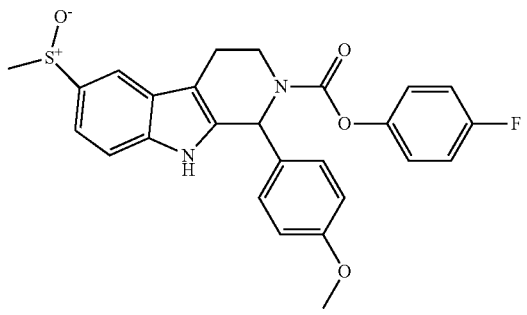 [SMILES: COc1ccc(C2c3[nH]c4ccc([S+](C)[O-])cc4c3CCN2C(=O)Oc2ccc(F)cc2)cc1] 1491
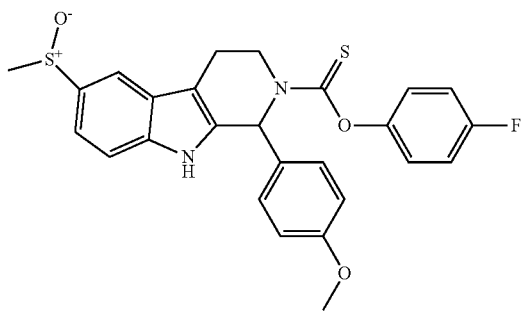 [SMILES: COc1ccc(C2c3[nH]c4ccc([S+](C)[O-])cc4c3CCN2C(=S)Oc2ccc(F)cc2)cc1] 1492
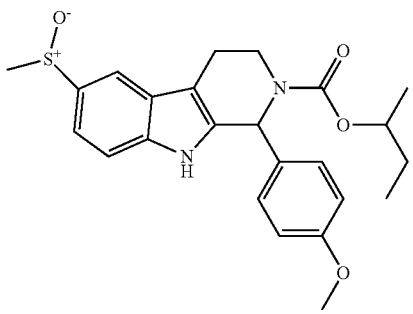 [SMILES: CCC(C)OC(=O)N1CCc2c([nH]c3ccc([S+](C)[O-])cc23)C1c1ccc(OC)cc1] 1493
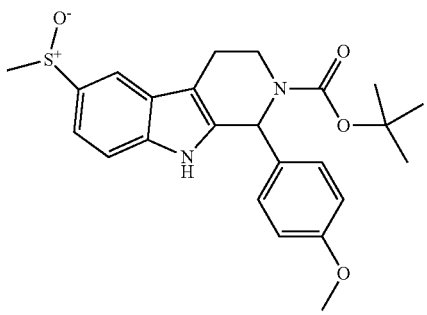 [SMILES: COc1ccc(C2c3[nH]c4ccc([S+](C)[O-])cc4c3CCN2C(=O)OC(C)(C)C)cc1] 1494

TABLE 1-continued
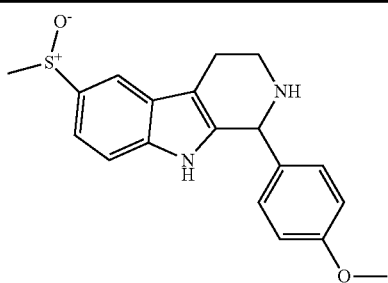
1495
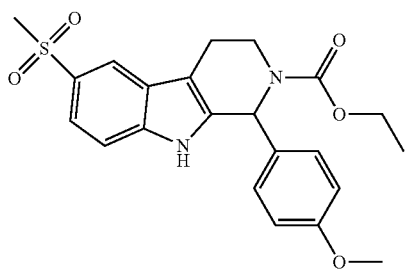 [SMILES: CCOC(=O)N1CCc2c([nH]c3ccc(S(C)(=O)=O)cc23)C1c1ccc(OC)cc1]
1496
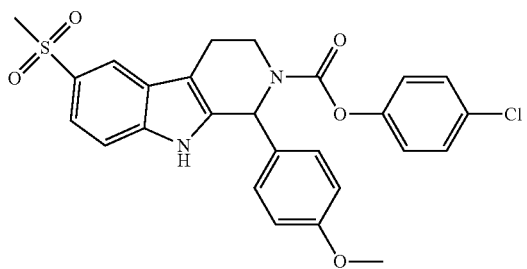 [SMILES: COc1ccc(C2c3[nH]c4ccc(S(C)(=O)=O)cc4c3CCN2C(=O)Oc2ccc(Cl)cc2)cc1]
1497
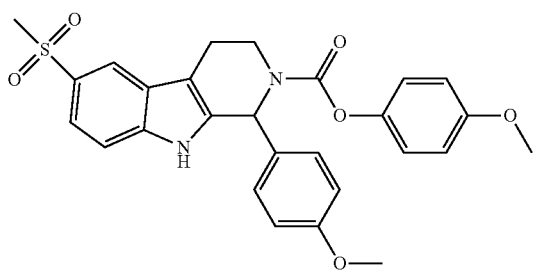
1498
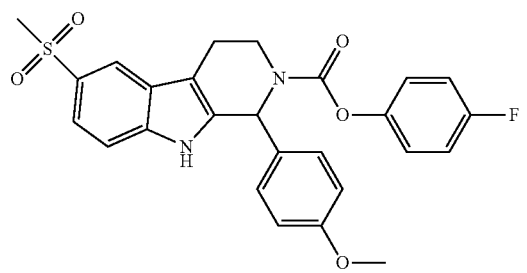 [SMILES: COc1ccc(C2c3[nH]c4ccc(S(C)(=O)=O)cc4c3CCN2C(=O)Oc2ccc(F)cc2)cc1]
1499
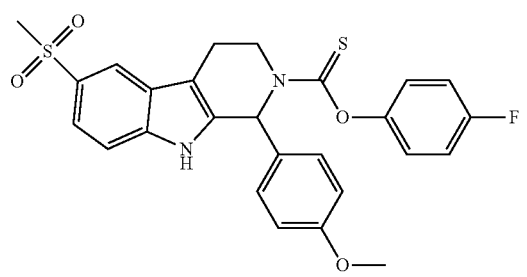 [SMILES: COc1ccc(C2c3[nH]c4ccc(S(C)(=O)=O)cc4c3CCN2C(=S)Oc2ccc(F)cc2)cc1]
1500

TABLE 1-continued
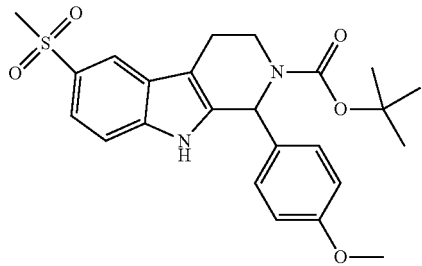 [SMILES: COc1ccc(C2c3[nH]c4ccc(S(C)(=O)=O)cc4c3CCN2C(=O)OC(C)(C)C)cc1]
1502
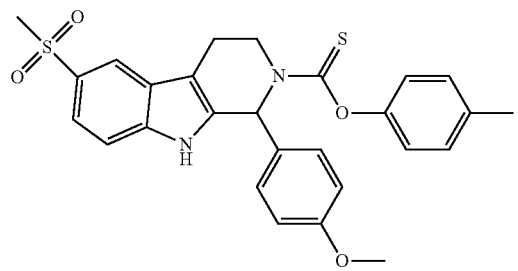
1503
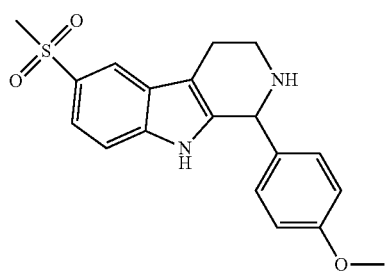
1504
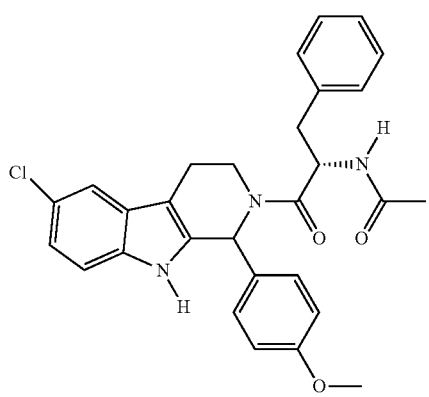 [SMILES: COc1ccc(C2c3[nH]c4ccc(Cl)cc4c3CCN2C(=O)[C@H](Cc2ccccc2)NC(C)=O)cc1]
1505

TABLE 1-continued
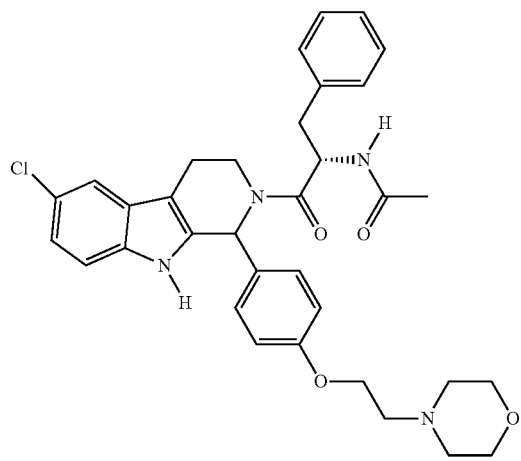 [SMILES: CC(=O)N[C@@H](Cc1ccccc1)C(=O)N1CCc2c([nH]c3ccc(Cl)cc23)C1c1ccc(OCCN2CCOCC2)cc1]
1506
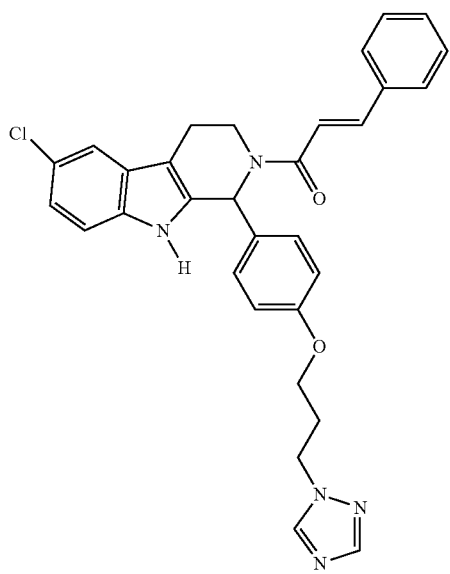 [SMILES: O=C(/C=C/c1ccccc1)N1CCc2c([nH]c3ccc(Cl)cc23)C1c1ccc(OCCCn2cncn2)cc1]
1508
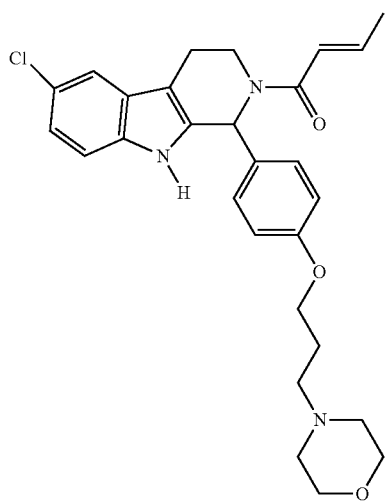 [SMILES: C/C=C/C(=O)N1CCc2c([nH]c3ccc(Cl)cc23)C1c1ccc(OCCCN2CCOCC2)cc1]
1509

TABLE 1-continued
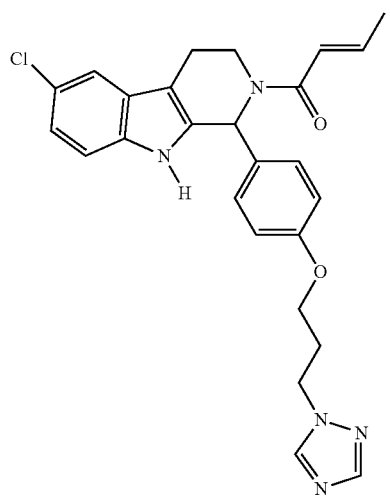 [SMILES: C/C=C/C(=O)N1CCc2c([nH]c3ccc(Cl)cc23)C1c1ccc(OCCCn2cncn2)cc1]
1510
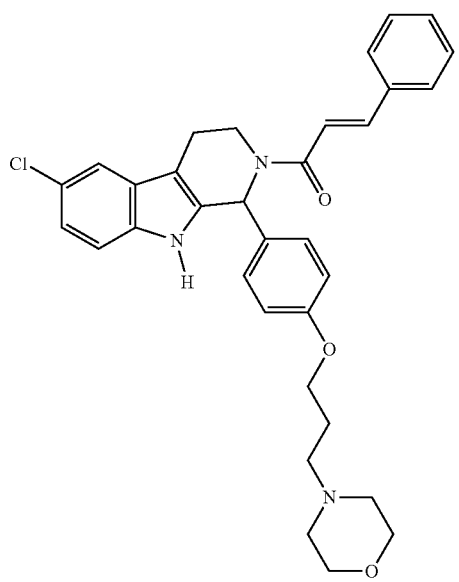 [SMILES: O=C(/C=C/c1ccccc1)N1CCc2c([nH]c3ccc(Cl)cc23)C1c1ccc(OCCCN2CCOCC2)cc1]
1511
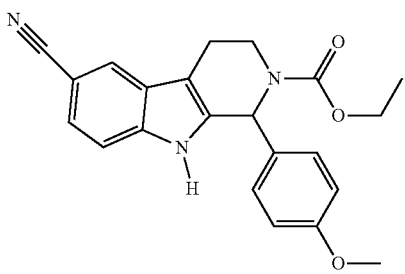 [SMILES: CCOC(=O)N1CCc2c([nH]c3ccc(C#N)cc23)C1c1ccc(OC)cc1]
1512
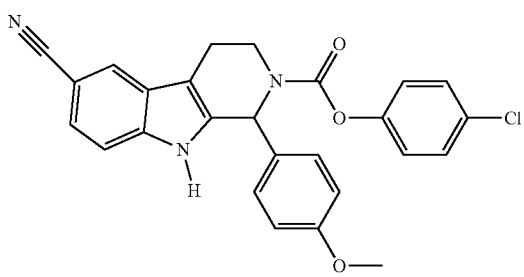 [SMILES: COc1ccc(C2c3[nH]c4ccc(C#N)cc4c3CCN2C(=O)Oc2ccc(Cl)cc2)cc1]
1513

TABLE 1-continued
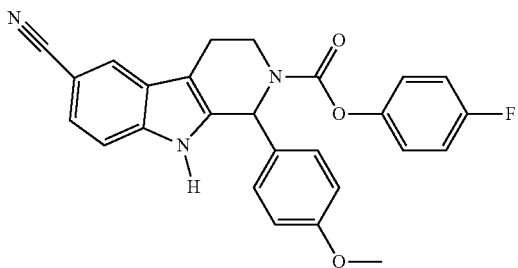 [SMILES: COc1ccc(C2c3[nH]c4ccc(C#N)cc4c3CCN2C(=O)Oc2ccc(F)cc2)cc1] 1514
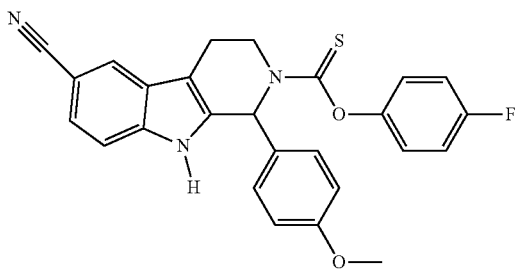 [SMILES: COc1ccc(C2c3[nH]c4ccc(C#N)cc4c3CCN2C(=S)Oc2ccc(F)cc2)cc1] 1515
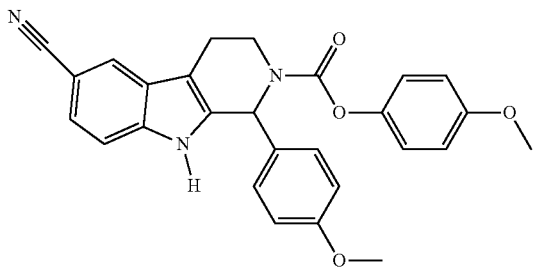 [SMILES: COc1ccc(OC(=O)N2CCc3c([nH]c4ccc(C#N)cc34)C2c2ccc(OC)cc2)cc1] 1516
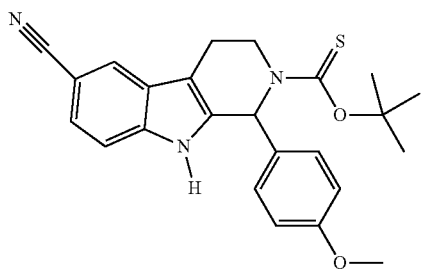 [SMILES: COc1ccc(C2c3[nH]c4ccc(C#N)cc4c3CCN2C(=S)OC(C)(C)C)cc1] 1517
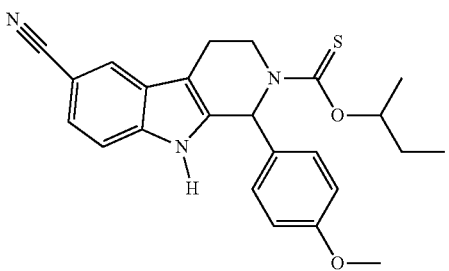 [SMILES: CCC(C)OC(=S)N1CCc2c([nH]c3ccc(C#N)cc23)C1c1ccc(OC)cc1] 1518
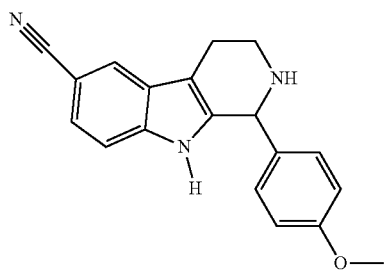 [SMILES: COc1ccc(C2NCCc3c2[nH]c2ccc(C#N)cc32)cc1] 1519

TABLE 1-continued
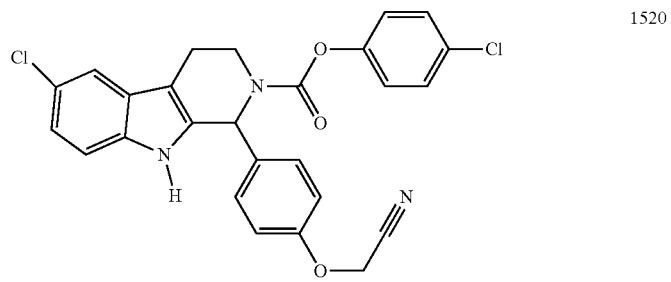 1520
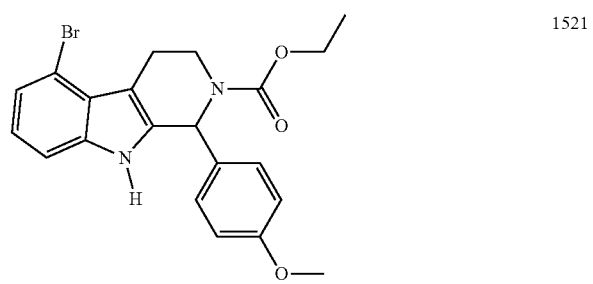 1521
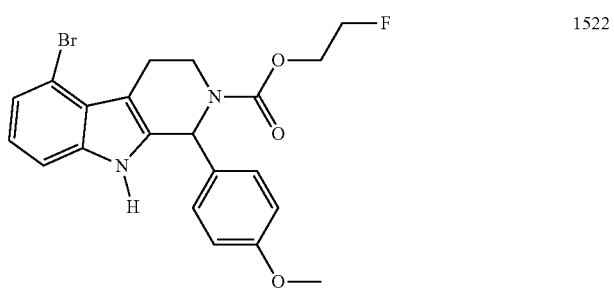 1522
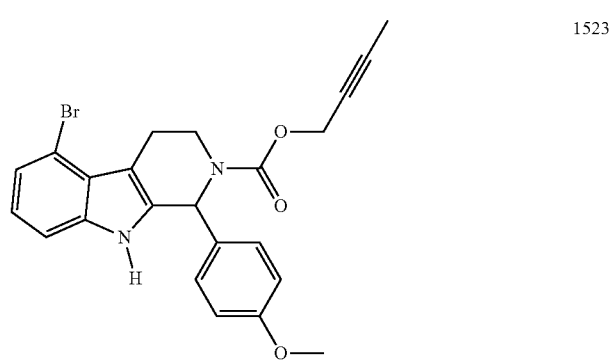 1523
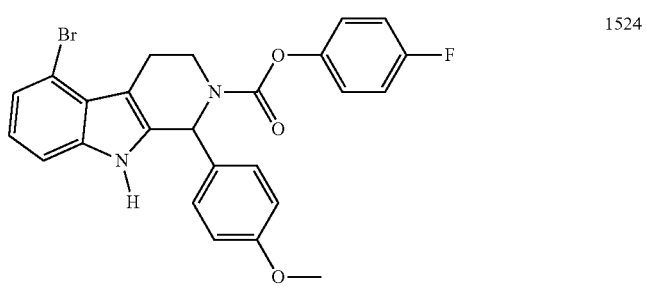 1524

TABLE 1-continued
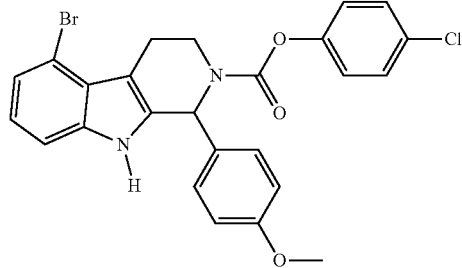 [SMILES: COc1ccc(C2c3[nH]c4cccc(Br)c4c3CCN2C(=O)Oc2ccc(Cl)cc2)cc1]
1525
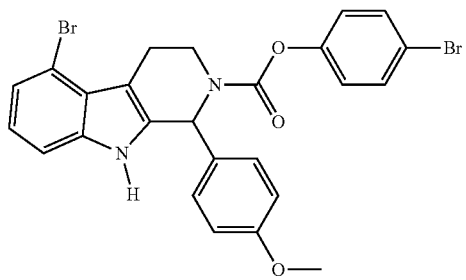 [SMILES: COc1ccc(C2c3[nH]c4cccc(Br)c4c3CCN2C(=O)Oc2ccc(Br)cc2)cc1]
1526
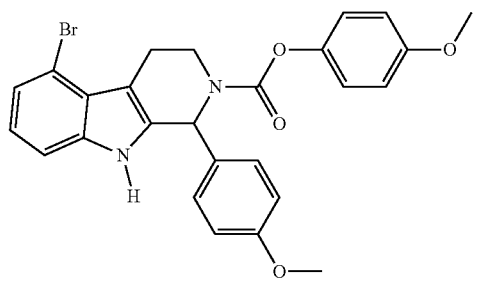 [SMILES: COc1ccc(OC(=O)N2CCc3c([nH]c4cccc(Br)c34)C2c2ccc(OC)cc2)cc1]
1527
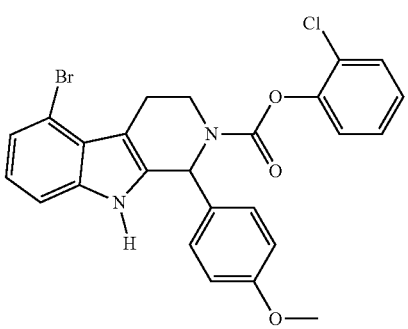 [SMILES: COc1ccc(C2c3[nH]c4cccc(Br)c4c3CCN2C(=O)Oc2ccccc2Cl)cc1]
1528
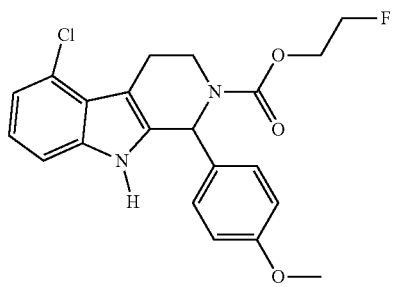 [SMILES: COc1ccc(C2c3[nH]c4cccc(Cl)c4c3CCN2C(=O)OCCF)cc1]
1529

TABLE 1-continued
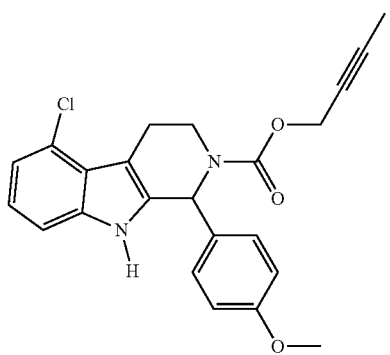 [SMILES: CC#CCOC(=O)N1CCc2c([nH]c3cccc(Cl)c23)C1c1ccc(OC)cc1]
1530
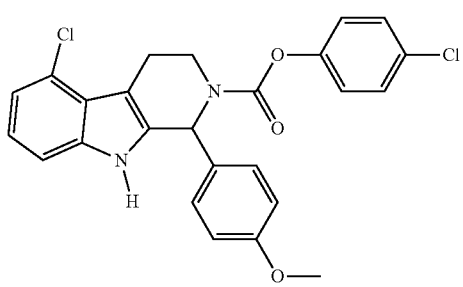 [SMILES: COc1ccc(C2c3[nH]c4cccc(Cl)c4c3CCN2C(=O)Oc2ccc(Cl)cc2)cc1]
1531
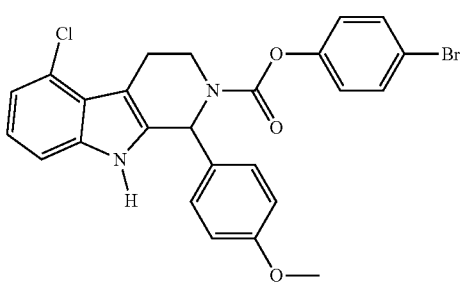 [SMILES: COc1ccc(C2c3[nH]c4cccc(Cl)c4c3CCN2C(=O)Oc2ccc(Br)cc2)cc1]
1532
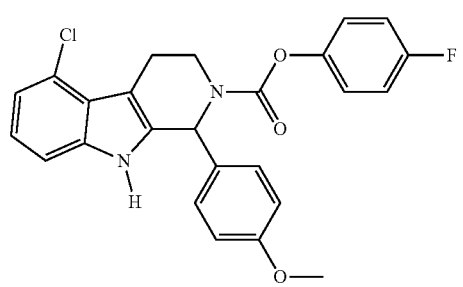 [SMILES: COc1ccc(C2c3[nH]c4cccc(Cl)c4c3CCN2C(=O)Oc2ccc(F)cc2)cc1]
1533
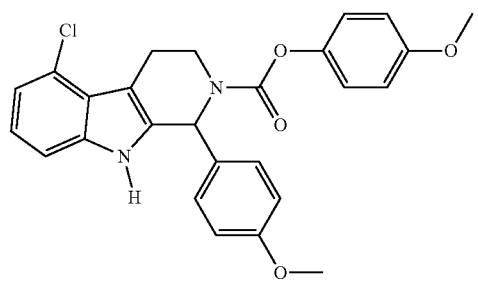 [SMILES: COc1ccc(OC(=O)N2CCc3c([nH]c4cccc(Cl)c34)C2c2ccc(OC)cc2)cc1]
1534

TABLE 1-continued
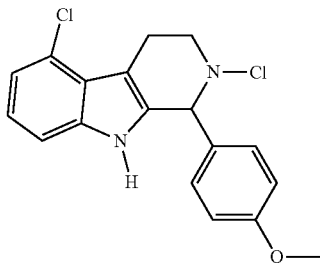 [SMILES: COc1ccc(C2c3[nH]c4cccc(Cl)c4c3CCN2Cl)cc1]
1535
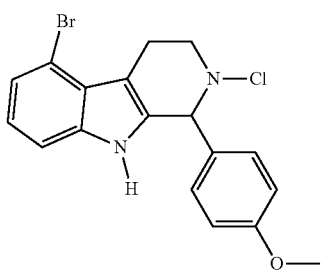 [SMILES: COc1ccc(C2c3[nH]c4cccc(Br)c4c3CCN2Cl)cc1]
1536
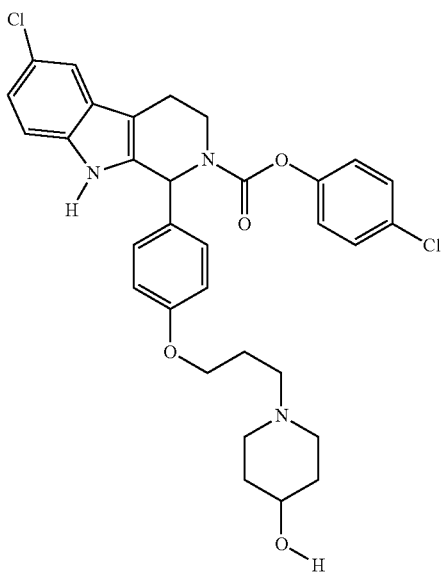 [SMILES: O=C(Oc1ccc(Cl)cc1)N1CCc2c([nH]c3ccc(Cl)cc23)C1c1ccc(OCCCN2CCC(O)CC2)cc1]
1537
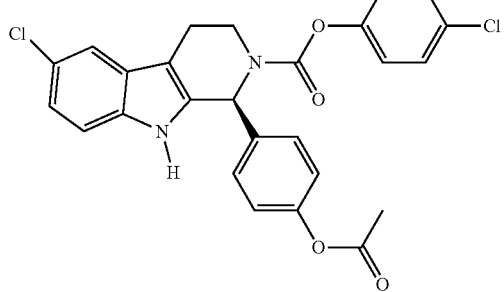
1538

TABLE 1-continued
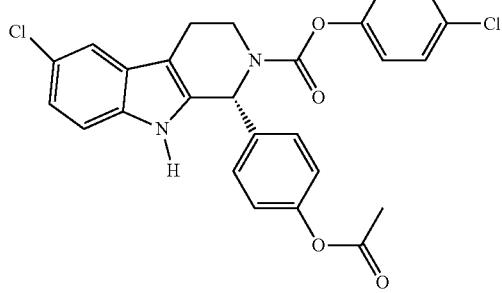
1539
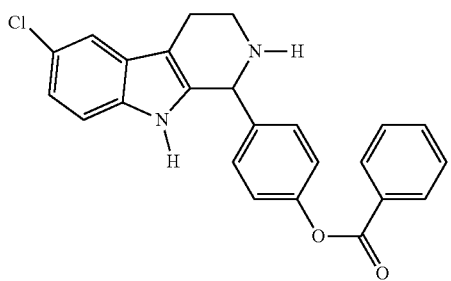 [SMILES: O=C(Oc1ccc(C2NCCc3c2[nH]c2ccc(Cl)cc32)cc1)c1ccccc1]
1540
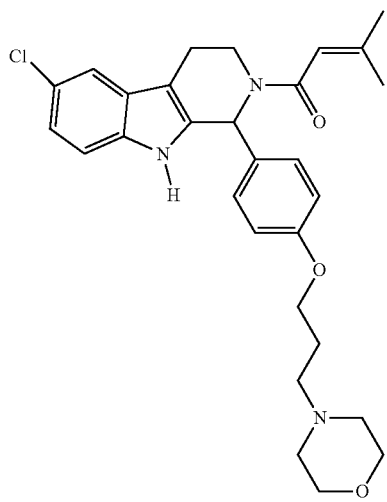 [SMILES: CC(C)=CC(=O)N1CCc2c([nH]c3ccc(Cl)cc23)C1c1ccc(OCCCN2CCOCC2)cc1]
1541
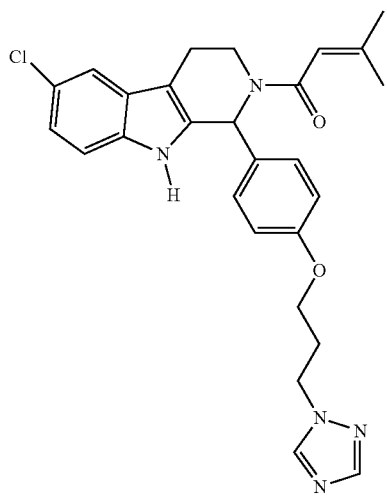 [SMILES: CC(C)=CC(=O)N1CCc2c([nH]c3ccc(Cl)cc23)C1c1ccc(OCCCn2cncn2)cc1]
1542

TABLE 1-continued
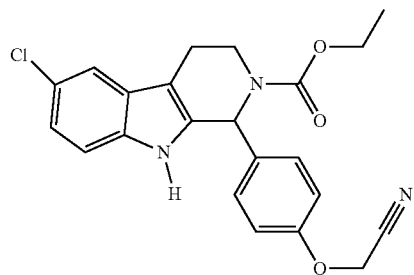 [SMILES: CCOC(=O)N1CCc2c([nH]c3ccc(Cl)cc23)C1c1ccc(OCC#N)cc1]
1543
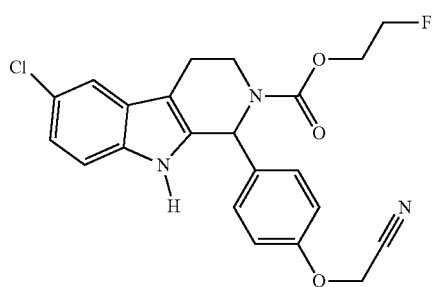 [SMILES: N#CCOc1ccc(C2c3[nH]c4ccc(Cl)cc4c3CCN2C(=O)OCCF)cc1]
1544
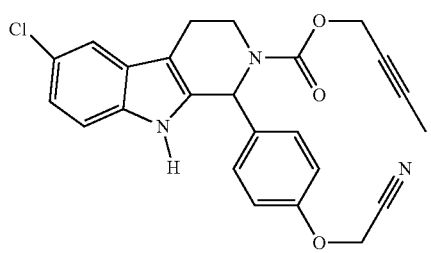 [SMILES: CC#CCOC(=O)N1CCc2c([nH]c3ccc(Cl)cc23)C1c1ccc(OCC#N)cc1]
1545
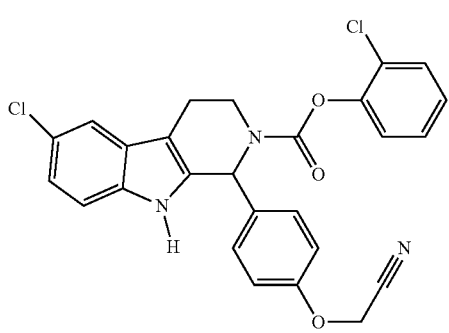 [SMILES: N#CCOc1ccc(C2c3[nH]c4ccc(Cl)cc4c3CCN2C(=O)Oc2ccccc2Cl)cc1]
1546
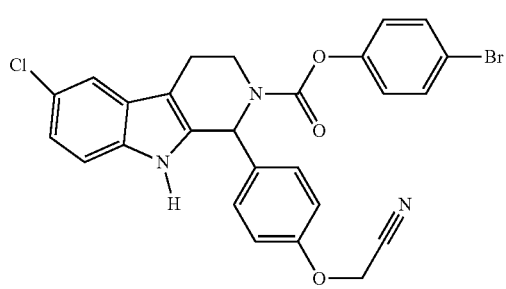 [SMILES: N#CCOc1ccc(C2c3[nH]c4ccc(Cl)cc4c3CCN2C(=O)Oc2ccc(Br)cc2)cc1]
1547

TABLE 1-continued
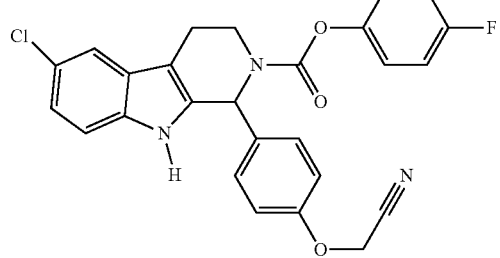
1548
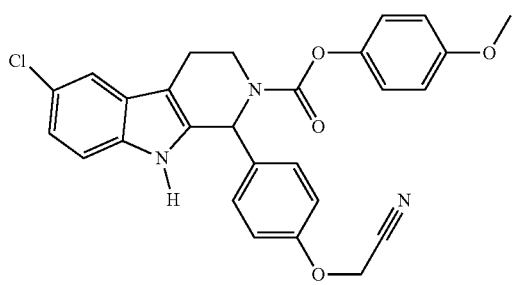 [SMILES: COc1ccc(OC(=O)N2CCc3c([nH]c4ccc(Cl)cc34)C2c2ccc(OCC#N)cc2)cc1]
1549
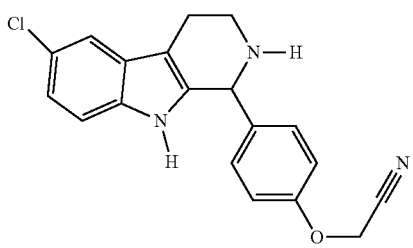 [SMILES: N#CCOc1ccc(C2NCCc3c2[nH]c2ccc(Cl)cc32)cc1]
1550
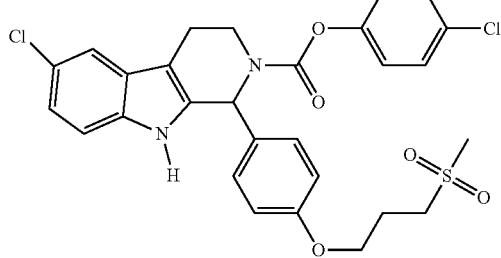
1551
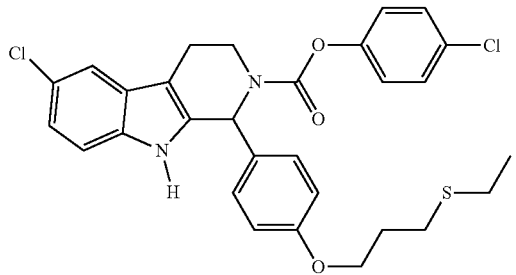
1552

TABLE 1-continued
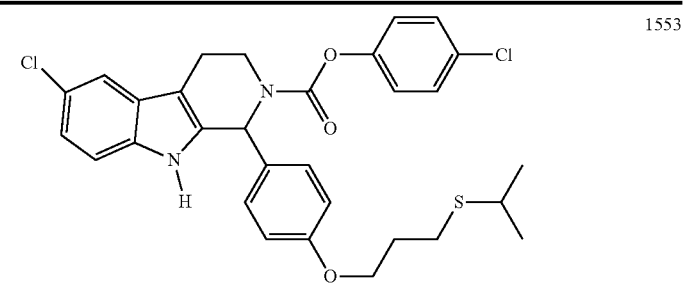
1553
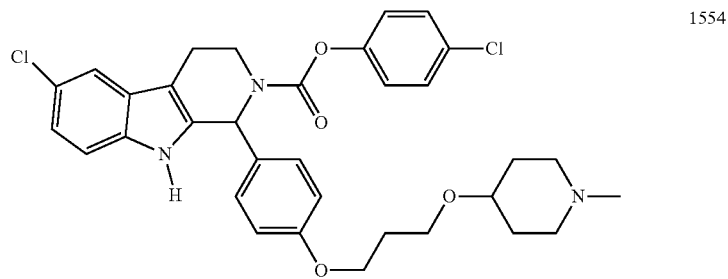
1554
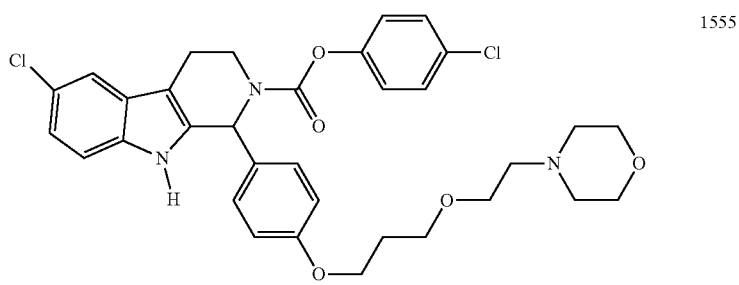
1555
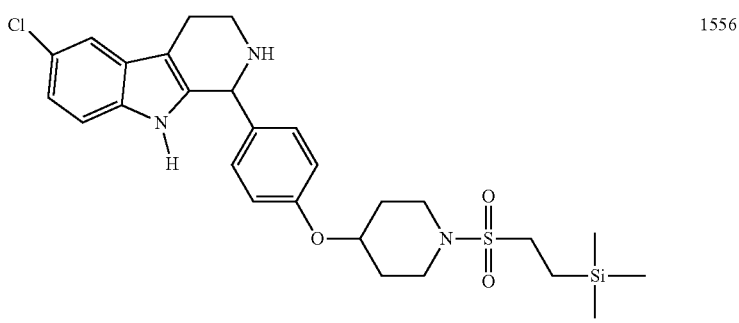
1556
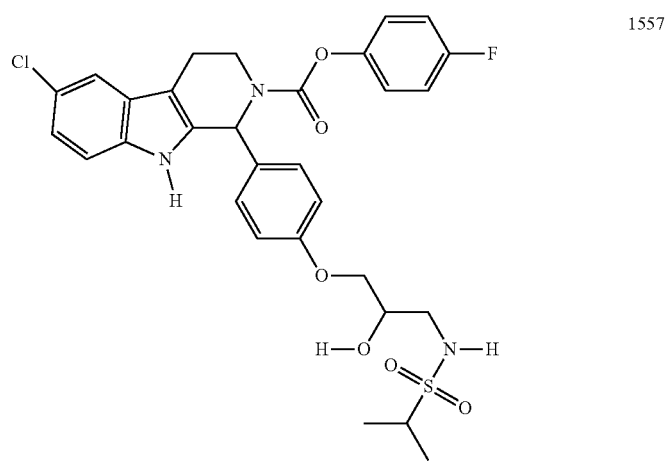
1557

TABLE 1-continued
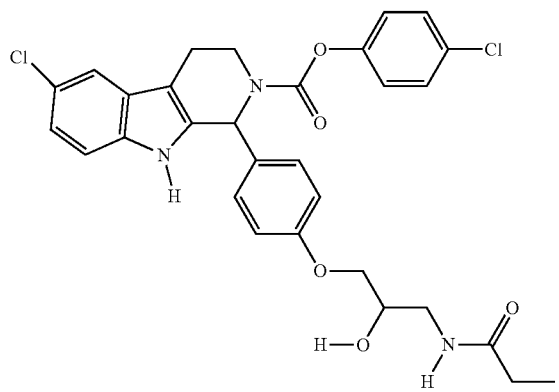 [SMILES: CCC(=O)NCC(O)COc1ccc(C2c3[nH]c4ccc(Cl)cc4c3CCN2C(=O)Oc2ccc(Cl)cc2)cc1]
1558
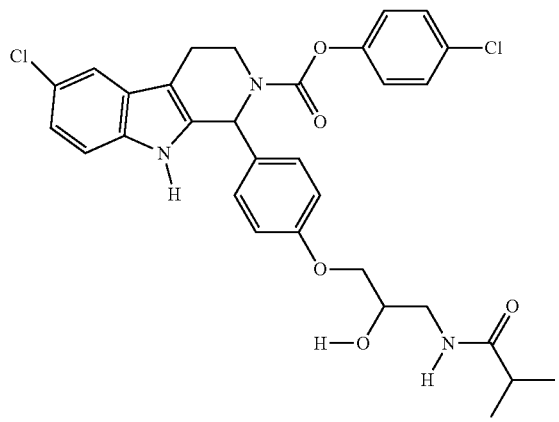 [SMILES: CC(C)C(=O)NCC(O)COc1ccc(C2c3[nH]c4ccc(Cl)cc4c3CCN2C(=O)Oc2ccc(Cl)cc2)cc1]
1559
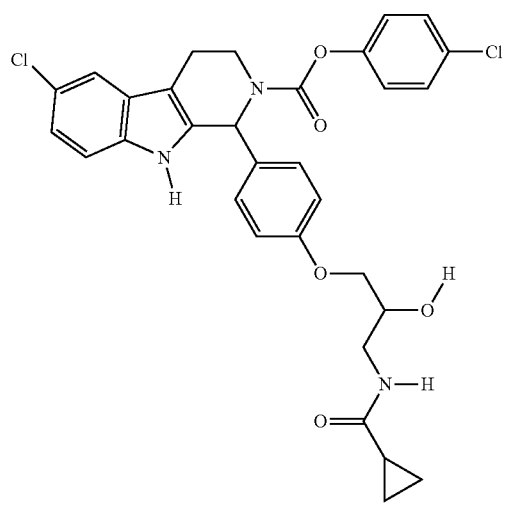 [SMILES: O=C(NCC(O)COc1ccc(C2c3[nH]c4ccc(Cl)cc4c3CCN2C(=O)Oc2ccc(Cl)cc2)cc1)C1CC1]
1560

TABLE 1-continued
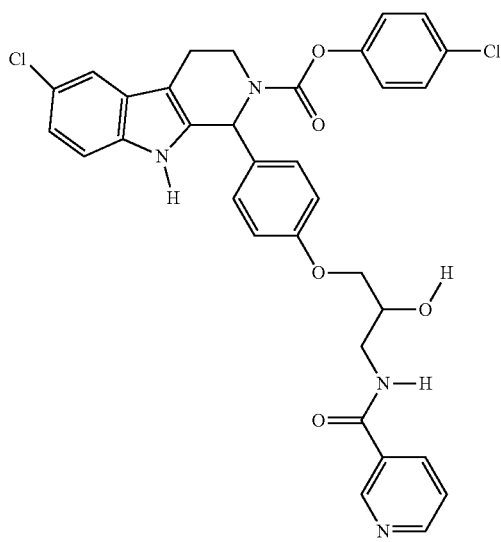 [SMILES: O=C(NCC(O)COc1ccc(C2c3[nH]c4ccc(Cl)cc4c3CCN2C(=O)Oc2ccc(Cl)cc2)cc1)c1cccnc1]
1561
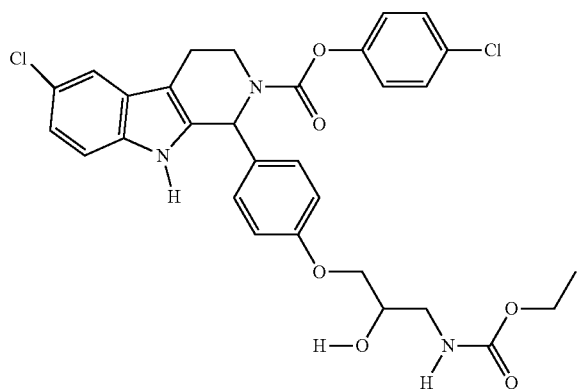 [SMILES: CCOC(=O)NCC(O)COc1ccc(C2c3[nH]c4ccc(Cl)cc4c3CCN2C(=O)Oc2ccc(Cl)cc2)cc1]
1562
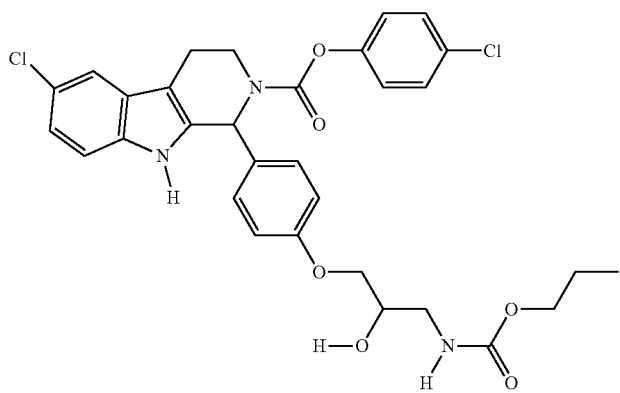 [SMILES: CCCOC(=O)NCC(O)COc1ccc(C2c3[nH]c4ccc(Cl)cc4c3CCN2C(=O)Oc2ccc(Cl)cc2)cc1]
1563

TABLE 1-continued
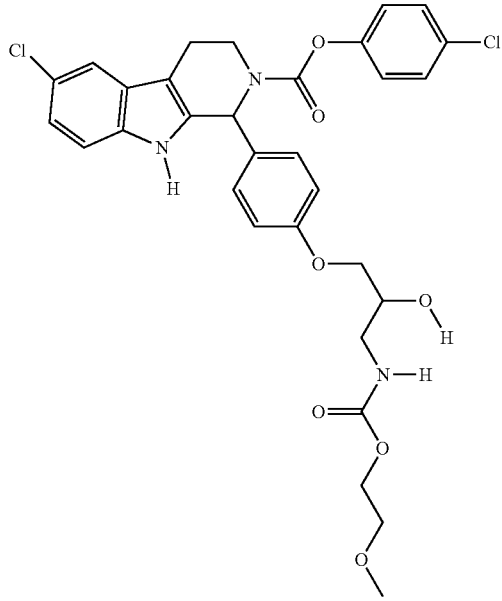 [SMILES: COCCOC(=O)NCC(O)COc1ccc(C2c3[nH]c4ccc(Cl)cc4c3CCN2C(=O)Oc2ccc(Cl)cc2)cc1]
1564
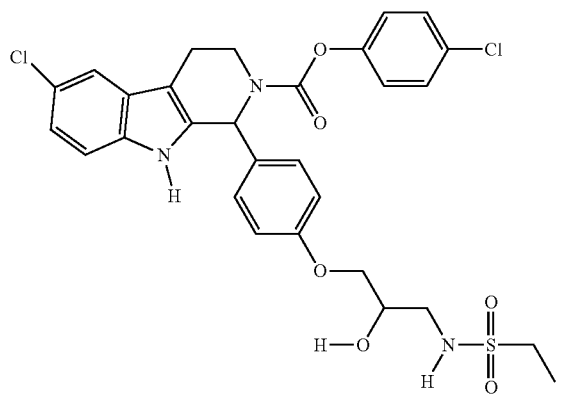 [SMILES: CCS(=O)(=O)NCC(O)COc1ccc(C2c3[nH]c4ccc(Cl)cc4c3CCN2C(=O)Oc2ccc(Cl)cc2)cc1]
1565
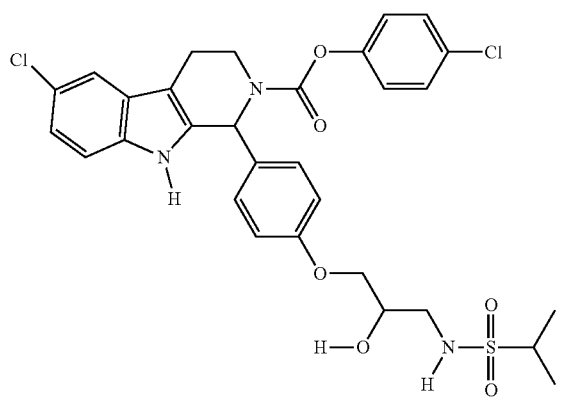 [SMILES: CC(C)S(=O)(=O)NCC(O)COc1ccc(C2c3[nH]c4ccc(Cl)cc4c3CCN2C(=O)Oc2ccc(Cl)cc2)cc1]
1566

TABLE 1-continued
| | |
|---|---|
| 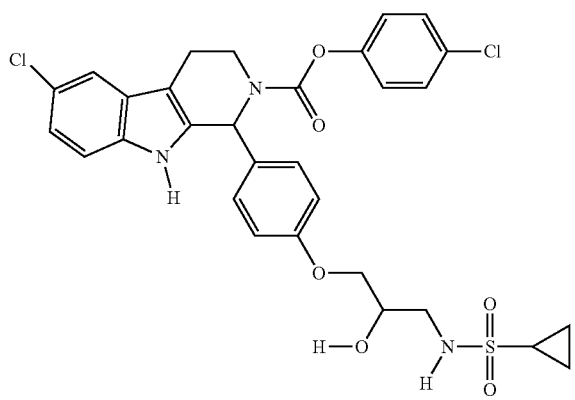 [SMILES: O=C(Oc1ccc(Cl)cc1)N1CCc2c([nH]c3ccc(Cl)cc23)C1c1ccc(OCC(O)CNS(=O)(=O)C2CC2)cc1] | 1567 |
| 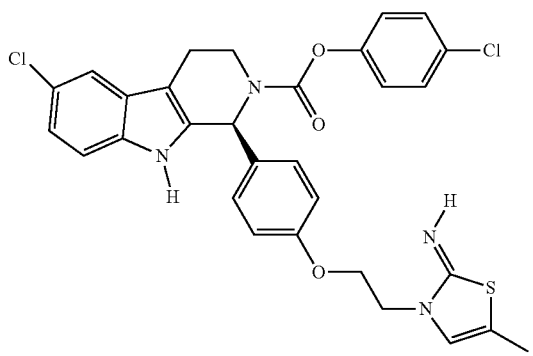 [SMILES: [H]/N=c1\sc(C)cn1CCOc1ccc([C@H]2c3[nH]c4ccc(Cl)cc4c3CCN2C(=O)Oc2ccc(Cl)cc2)cc1] | 1568 |
| 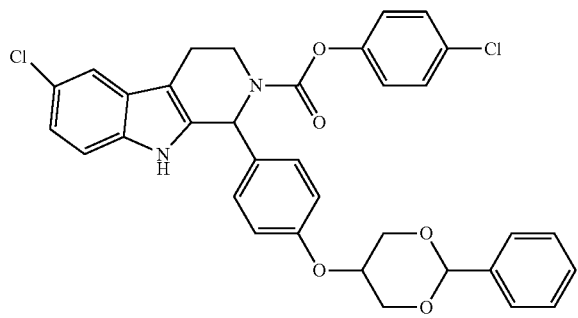 [SMILES: O=C(Oc1ccc(Cl)cc1)N1CCc2c([nH]c3ccc(Cl)cc23)C1c1ccc(OC2COC(c3ccccc3)OC2)cc1] | 1569 |
| 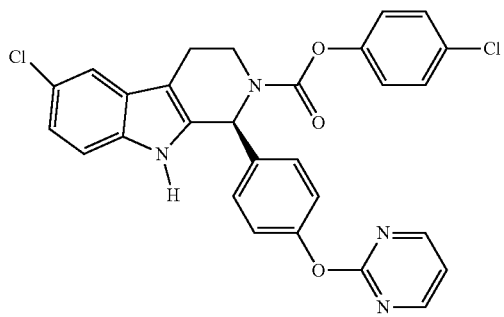 [SMILES: O=C(Oc1ccc(Cl)cc1)N1CCc2c([nH]c3ccc(Cl)cc23)[C@@H]1c1ccc(Oc2ncccn2)cc1] | 1570 |

TABLE 1-continued
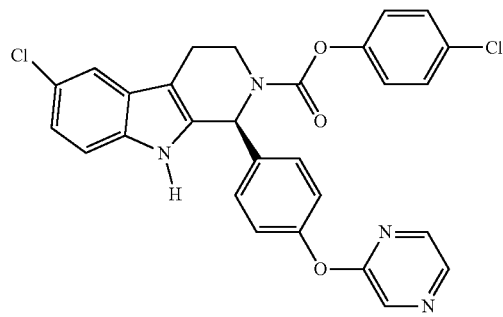 [SMILES: O=C(Oc1ccc(Cl)cc1)N1CCc2c([nH]c3ccc(Cl)cc23)[C@@H]1c1ccc(Oc2cnccn2)cc1]
1571
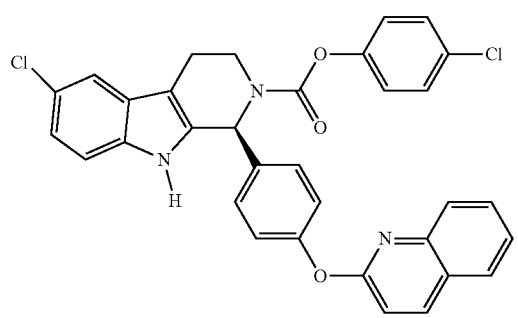 [SMILES: O=C(Oc1ccc(Cl)cc1)N1CCc2c([nH]c3ccc(Cl)cc23)[C@@H]1c1ccc(Oc2ccc3ccccc3n2)cc1]
1572
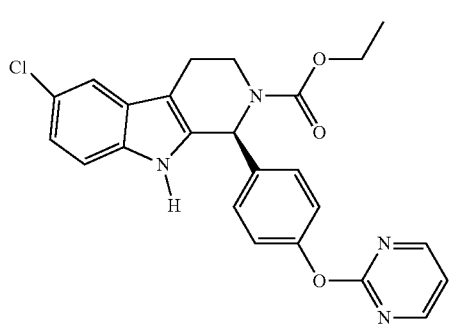 [SMILES: CCOC(=O)N1CCc2c([nH]c3ccc(Cl)cc23)[C@@H]1c1ccc(Oc2ncccn2)cc1]
1573
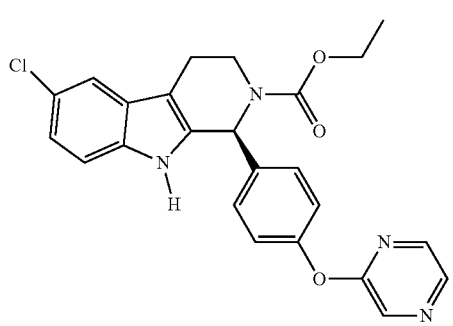 [SMILES: CCOC(=O)N1CCc2c([nH]c3ccc(Cl)cc23)[C@@H]1c1ccc(Oc2cnccn2)cc1]
1574
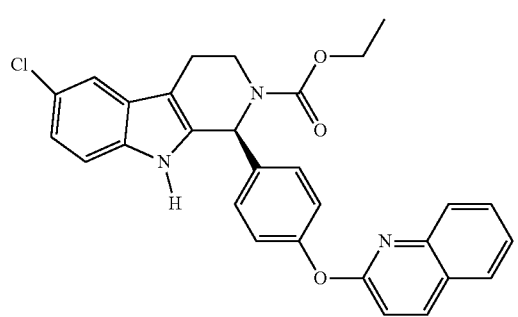 [SMILES: CCOC(=O)N1CCc2c([nH]c3ccc(Cl)cc23)[C@@H]1c1ccc(Oc2ccc3ccccc3n2)cc1]
1575

TABLE 1-continued
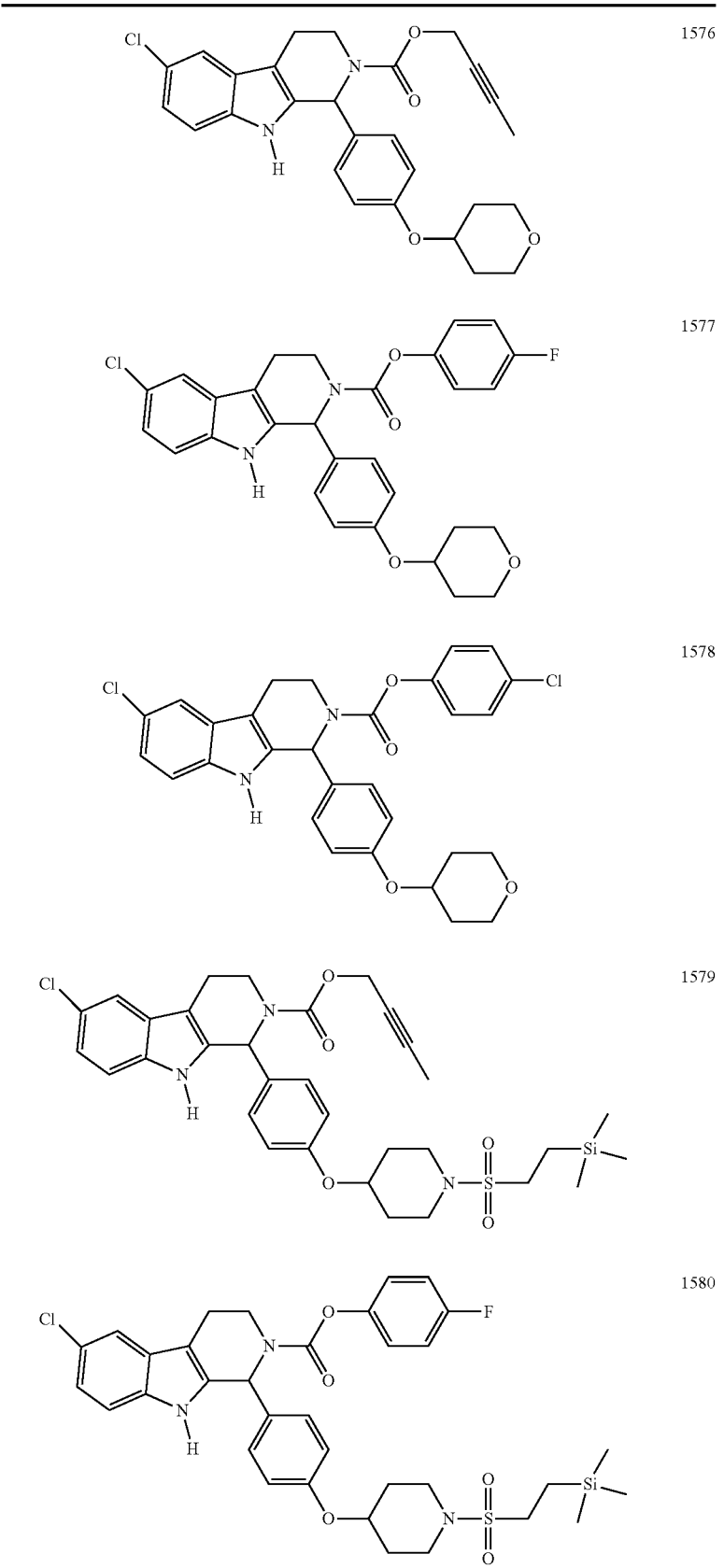

TABLE 1-continued
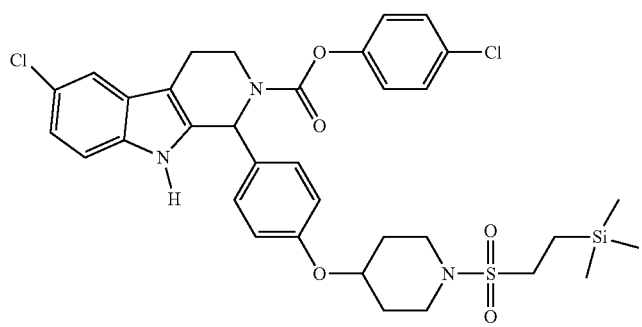 [SMILES: C[Si](C)(C)CCS(=O)(=O)N1CCC(Oc2ccc(C3c4[nH]c5ccc(Cl)cc5c4CCN3C(=O)Oc3ccc(Cl)cc3)cc2)CC1] 1581
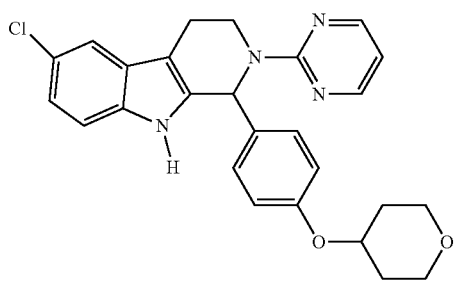 [SMILES: Clc1ccc2[nH]c3c(c2c1)CCN(c1ncccn1)C3c1ccc(OC2CCOCC2)cc1] 1582
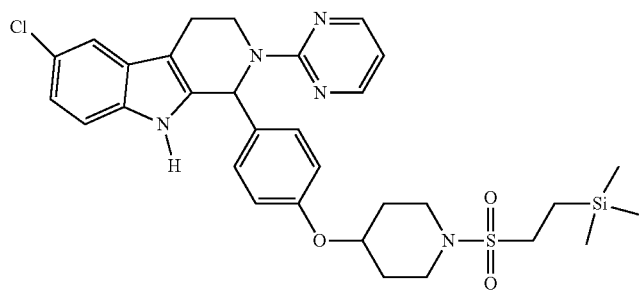 [SMILES: C[Si](C)(C)CCS(=O)(=O)N1CCC(Oc2ccc(C3c4[nH]c5ccc(Cl)cc5c4CCN3c3ncccn3)cc2)CC1] 1583
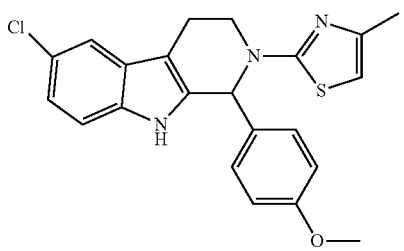 [SMILES: COc1ccc(C2c3[nH]c4ccc(Cl)cc4c3CCN2c2nc(C)cs2)cc1] 1584
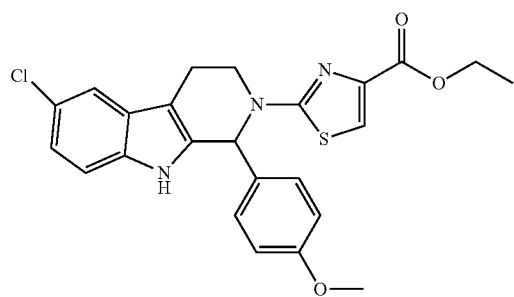 [SMILES: CCOC(=O)c1csc(N2CCc3c([nH]c4ccc(Cl)cc34)C2c2ccc(OC)cc2)n1] 1585

TABLE 1-continued
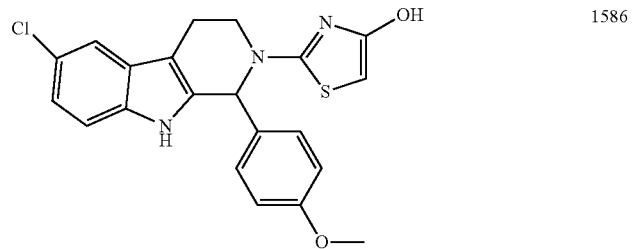 1586
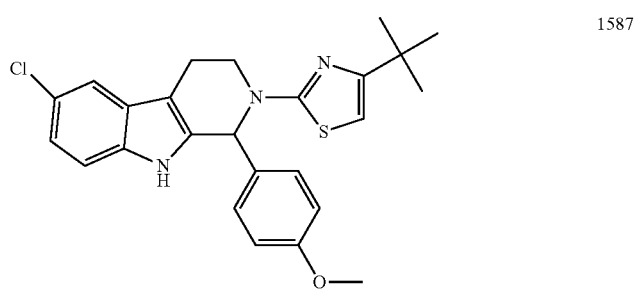 1587
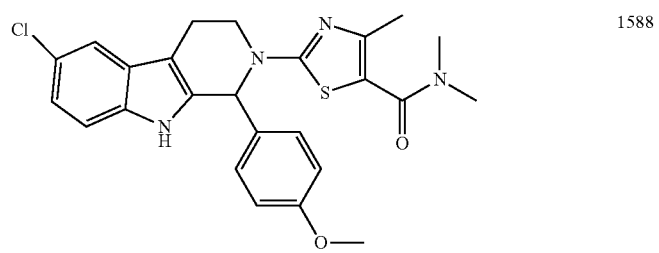 1588
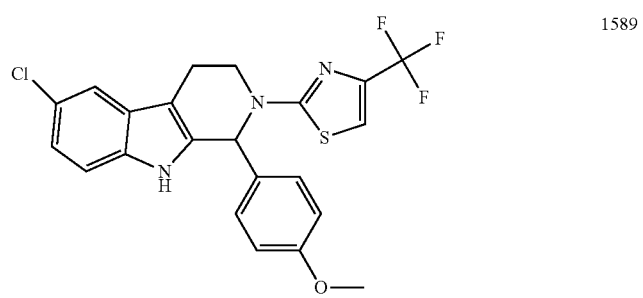 1589
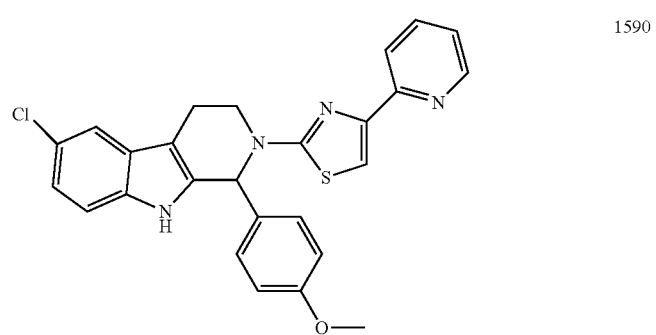 1590

TABLE 1-continued
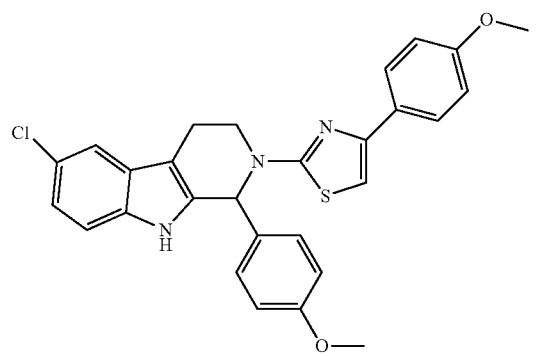 [SMILES: COc1ccc(-c2csc(N3CCc4c([nH]c5ccc(Cl)cc45)C3c3ccc(OC)cc3)n2)cc1]
1591
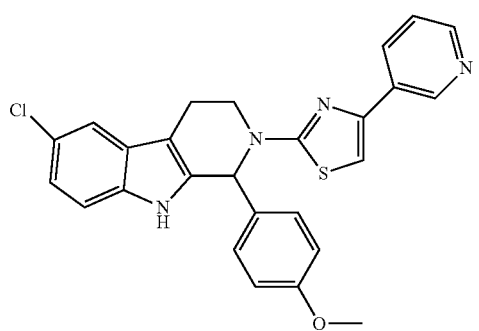 [SMILES: COc1ccc(C2c3[nH]c4ccc(Cl)cc4c3CCN2c2nc(-c3cccnc3)cs2)cc1]
1592
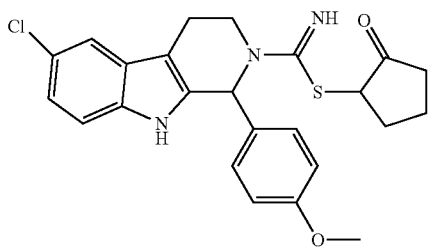 [SMILES: COc1ccc(C2c3[nH]c4ccc(Cl)cc4c3CCN2C(=N)SC2CCCC2=O)cc1]
1593
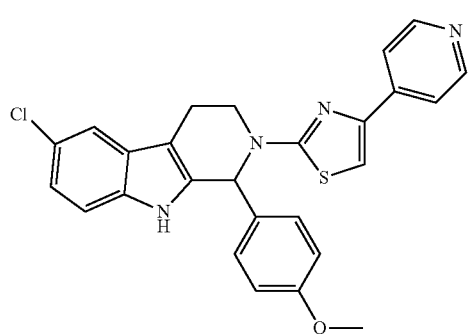 [SMILES: COc1ccc(C2c3[nH]c4ccc(Cl)cc4c3CCN2c2nc(-c3ccncc3)cs2)cc1]
1594
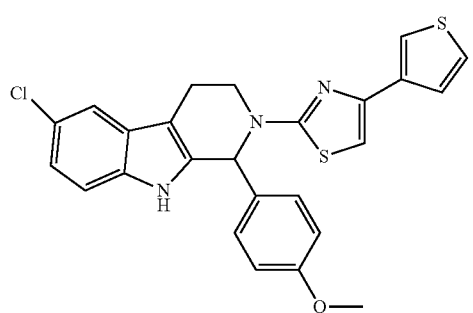 [SMILES: COc1ccc(C2c3[nH]c4ccc(Cl)cc4c3CCN2c2nc(-c3ccsc3)cs2)cc1]
1595

| | |
|---|---|
| 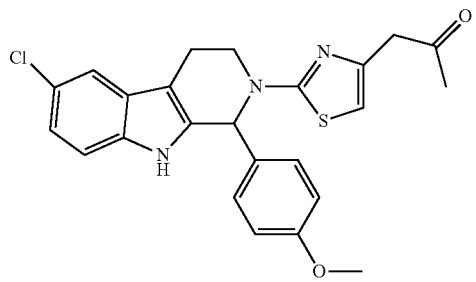 [SMILES: COc1ccc(C2c3[nH]c4ccc(Cl)cc4c3CCN2c2nc(CC(C)=O)cs2)cc1] | 1596 |
| 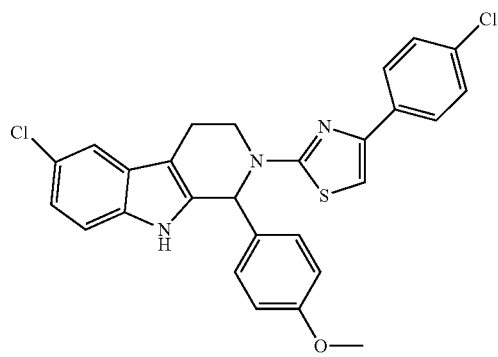 [SMILES: COc1ccc(C2c3[nH]c4ccc(Cl)cc4c3CCN2c2nc(-c3ccc(Cl)cc3)cs2)cc1] | 1597 |
| 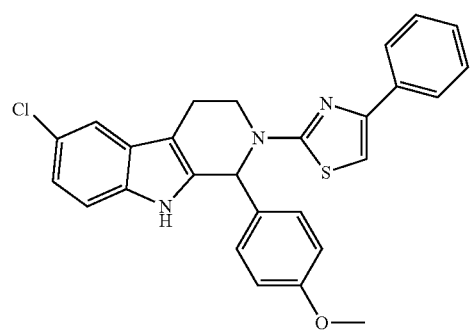 [SMILES: COc1ccc(C2c3[nH]c4ccc(Cl)cc4c3CCN2c2nc(-c3ccccc3)cs2)cc1] | 1598 |
| 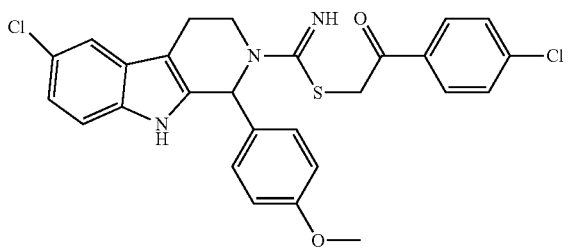 [SMILES: COc1ccc(C2c3[nH]c4ccc(Cl)cc4c3CCN2C(=N)SCC(=O)c2ccc(Cl)cc2)cc1] | 1599 |
| 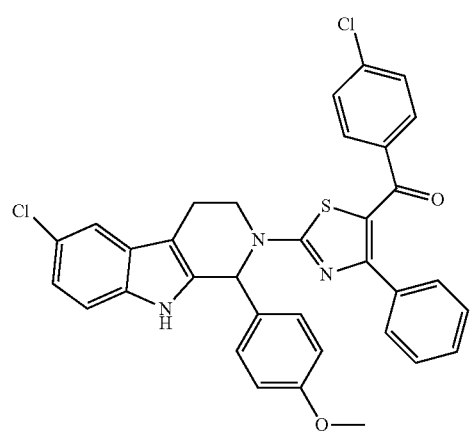 [SMILES: COc1ccc(C2c3[nH]c4ccc(Cl)cc4c3CCN2c2nc(-c3ccccc3)c(C(=O)c3ccc(Cl)cc3)s2)cc1] | 1600 |

TABLE 1-continued
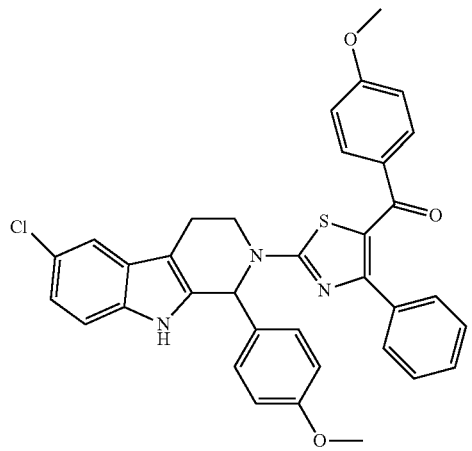 [SMILES: COc1ccc(C(=O)c2sc(N3CCc4c([nH]c5ccc(Cl)cc45)C3c3ccc(OC)cc3)nc2-c2ccccc2)cc1]
1601
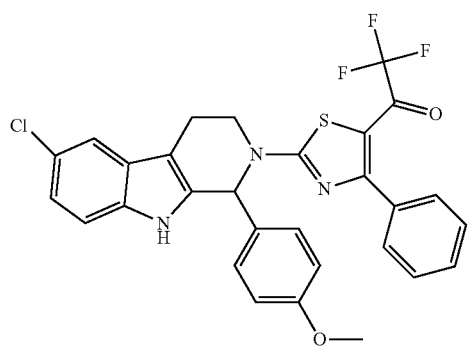 [SMILES: COc1ccc(C2c3[nH]c4ccc(Cl)cc4c3CCN2c2nc(-c3ccccc3)c(C(=O)C(F)(F)F)s2)cc1]
1602
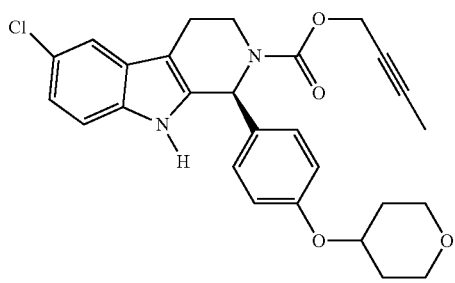 [SMILES: CC#CCOC(=O)N1CCc2c([nH]c3ccc(Cl)cc23)[C@@H]1c1ccc(OC2CCOCC2)cc1]
1603
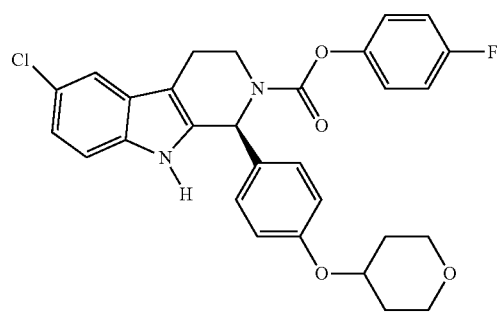 [SMILES: O=C(Oc1ccc(F)cc1)N1CCc2c([nH]c3ccc(Cl)cc23)[C@@H]1c1ccc(OC2CCOCC2)cc1]
1604

TABLE 1-continued
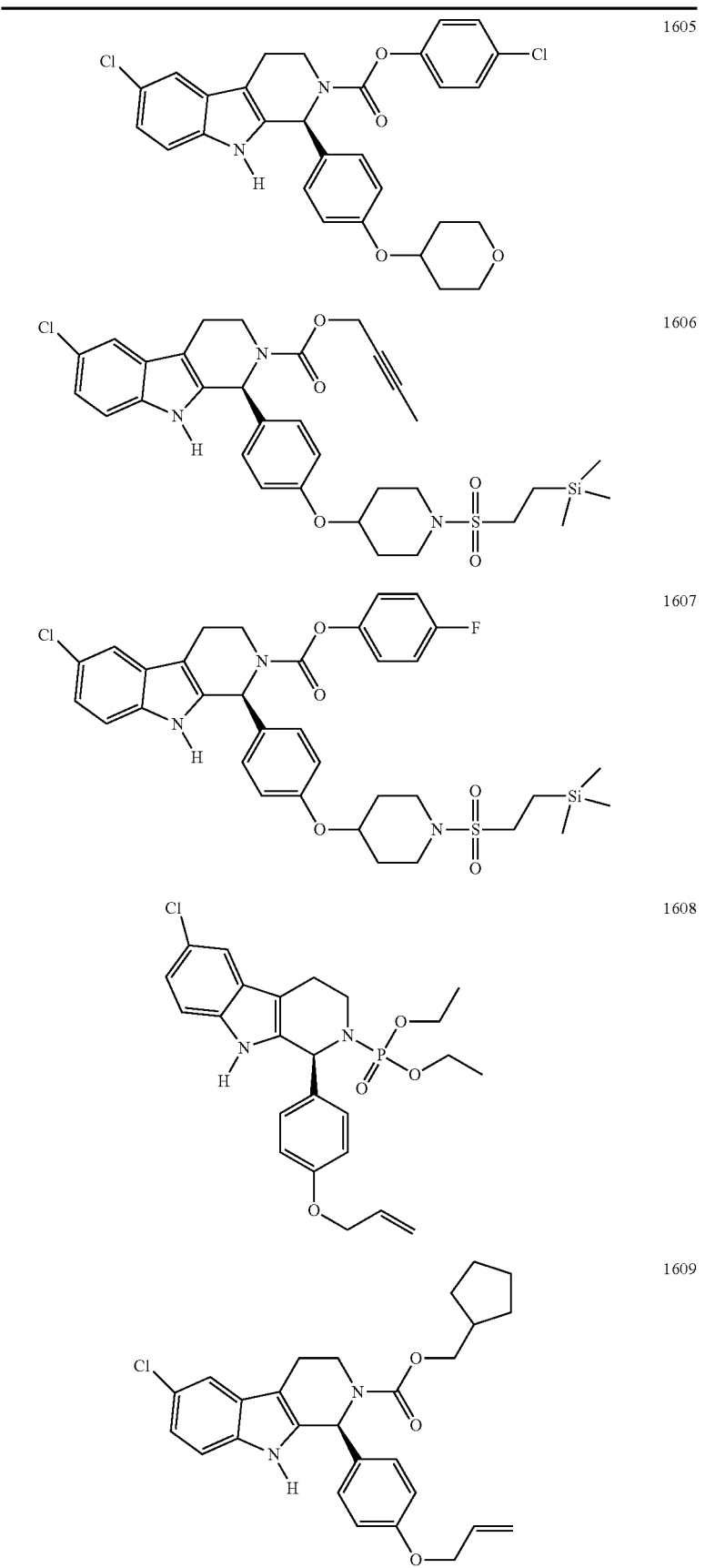

TABLE 1-continued
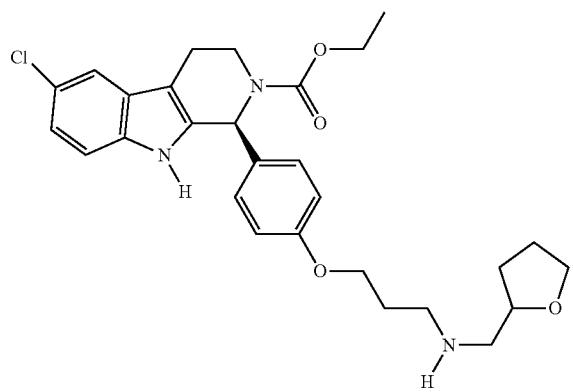 [SMILES: CCOC(=O)N1CCc2c([nH]c3ccc(Cl)cc23)[C@@H]1c1ccc(OCCCNCC2CCCO2)cc1]
1610
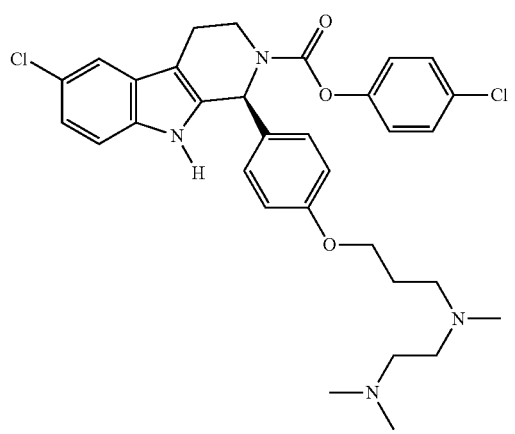 [SMILES: CN(C)CCN(C)CCCOc1ccc([C@H]2c3[nH]c4ccc(Cl)cc4c3CCN2C(=O)Oc2ccc(Cl)cc2)cc1]
1611
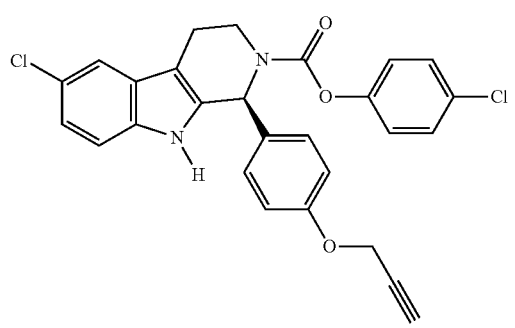 [SMILES: C#CCOc1ccc([C@H]2c3[nH]c4ccc(Cl)cc4c3CCN2C(=O)Oc2ccc(Cl)cc2)cc1]
1612
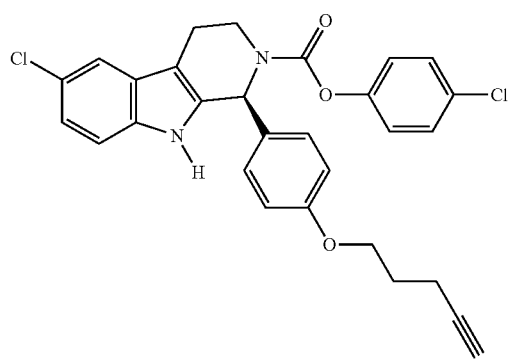 [SMILES: C#CCCCOc1ccc([C@H]2c3[nH]c4ccc(Cl)cc4c3CCN2C(=O)Oc2ccc(Cl)cc2)cc1]
1613

TABLE 1-continued
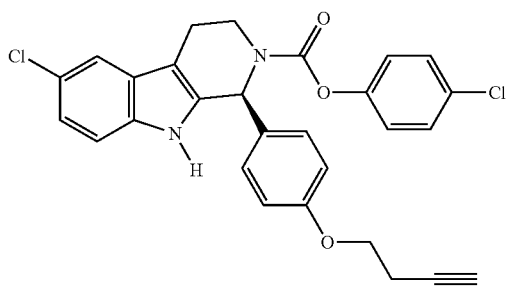 [SMILES: C#CCCOc1ccc([C@H]2c3[nH]c4ccc(Cl)cc4c3CCN2C(=O)Oc2ccc(Cl)cc2)cc1]
1614
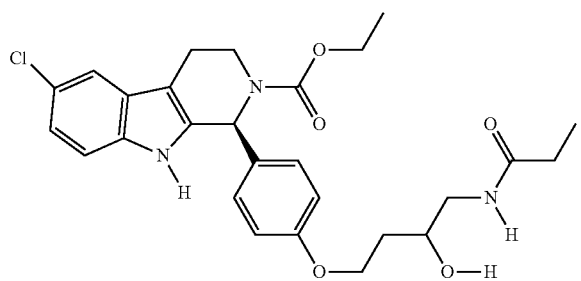 [SMILES: CCOC(=O)N1CCc2c([nH]c3ccc(Cl)cc23)[C@@H]1c1ccc(OCCC(O)CNC(=O)CC)cc1]
1615
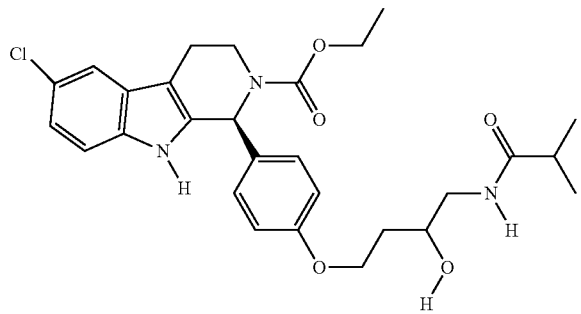 [SMILES: CCOC(=O)N1CCc2c([nH]c3ccc(Cl)cc23)[C@@H]1c1ccc(OCCC(O)CNC(=O)C(C)C)cc1]
1616
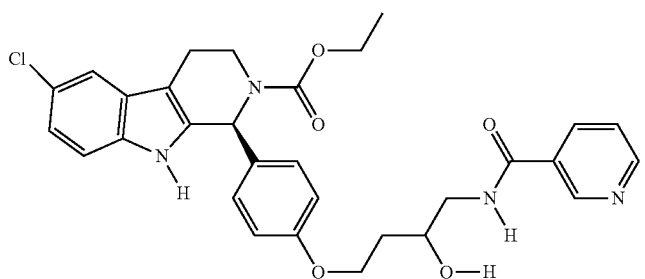 [SMILES: CCOC(=O)N1CCc2c([nH]c3ccc(Cl)cc23)[C@@H]1c1ccc(OCCC(O)CNC(=O)c2cccnc2)cc1]
1617
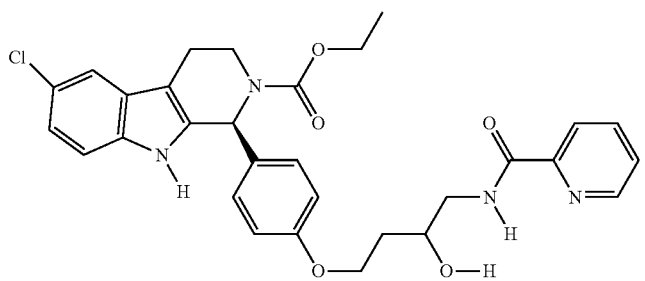 [SMILES: CCOC(=O)N1CCc2c([nH]c3ccc(Cl)cc23)[C@@H]1c1ccc(OCCC(O)CNC(=O)c2ccccn2)cc1]
1618

TABLE 1-continued
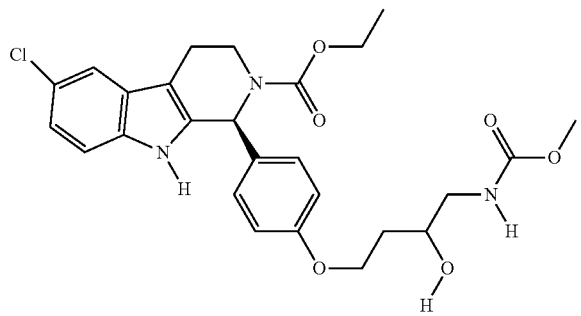 [SMILES: CCOC(=O)N1CCc2c([nH]c3ccc(Cl)cc23)[C@@H]1c1ccc(OCCC(O)CNC(=O)OC)cc1]
1619
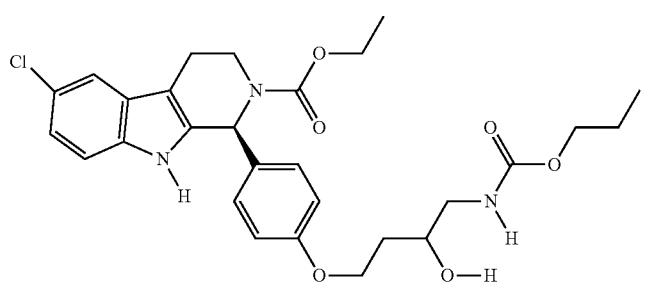 [SMILES: CCCOC(=O)NCC(O)CCOc1ccc([C@H]2c3[nH]c4ccc(Cl)cc4c3CCN2C(=O)OCC)cc1]
1620
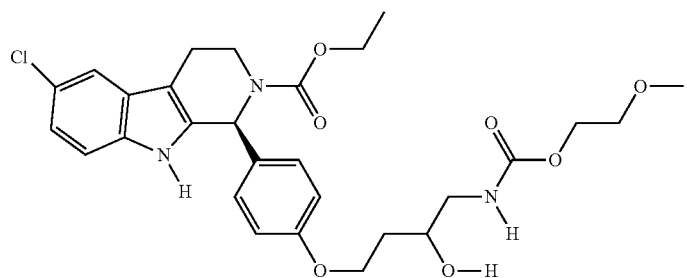 [SMILES: CCOC(=O)N1CCc2c([nH]c3ccc(Cl)cc23)[C@@H]1c1ccc(OCCC(O)CNC(=O)OCCOC)cc1]
1621
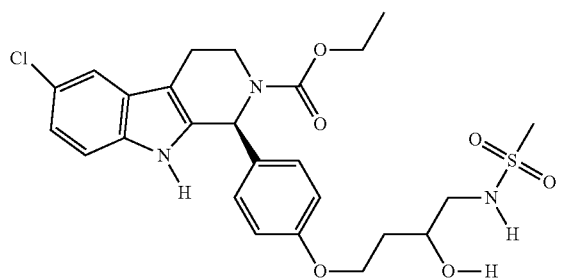 [SMILES: CCOC(=O)N1CCc2c([nH]c3ccc(Cl)cc23)[C@@H]1c1ccc(OCCC(O)CNS(C)(=O)=O)cc1]
1622
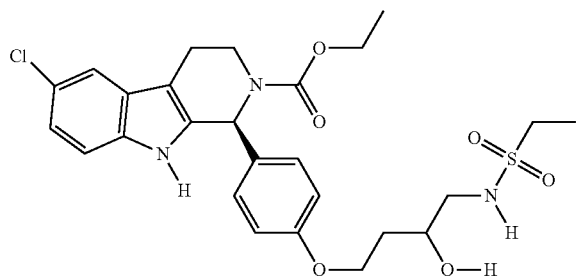 [SMILES: CCOC(=O)N1CCc2c([nH]c3ccc(Cl)cc23)[C@@H]1c1ccc(OCCC(O)CNS(=O)(=O)CC)cc1]
1623

TABLE 1-continued
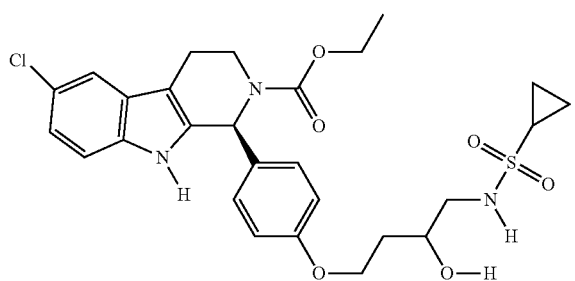 [SMILES: CCOC(=O)N1CCc2c([nH]c3ccc(Cl)cc23)[C@@H]1c1ccc(OCCC(O)CNS(=O)(=O)C2CC2)cc1]
1624
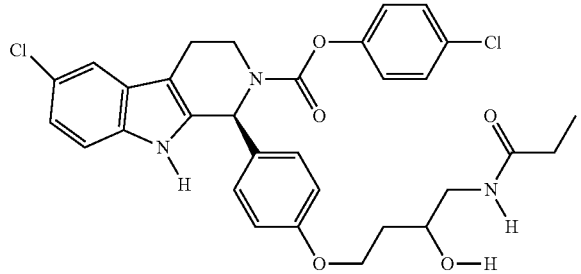
1625
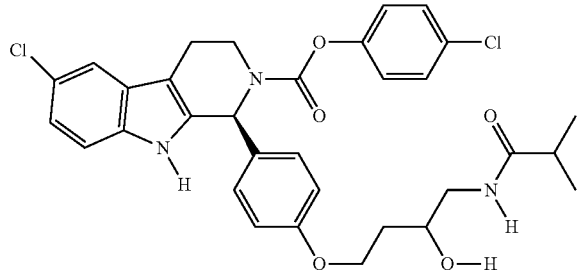
1626
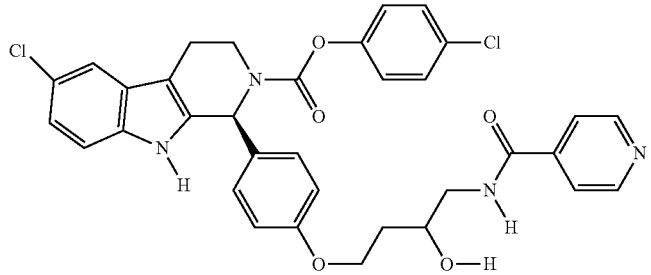 [SMILES: O=C(NCC(O)CCOc1ccc([C@H]2c3[nH]c4ccc(Cl)cc4c3CCN2C(=O)Oc2ccc(Cl)cc2)cc1)c1ccncc1]
1627
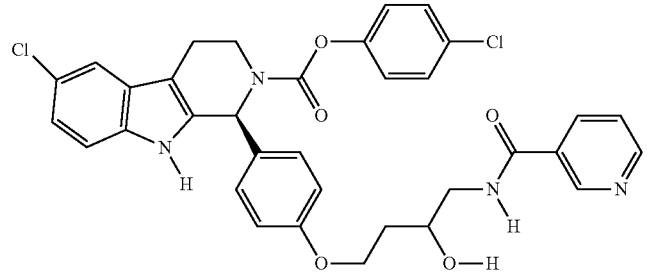 [SMILES: O=C(NCC(O)CCOc1ccc([C@H]2c3[nH]c4ccc(Cl)cc4c3CCN2C(=O)Oc2ccc(Cl)cc2)cc1)c1cccnc1]
1628

TABLE 1-continued
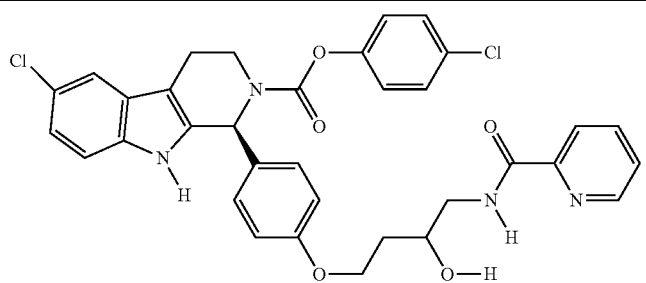
1629
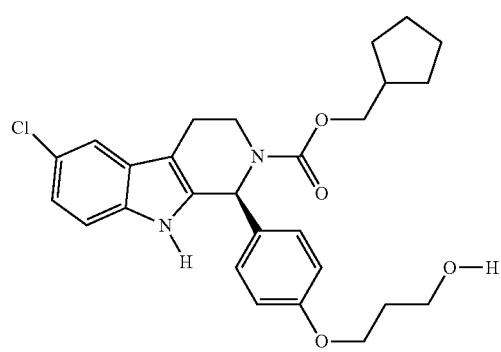 [SMILES: O=C(OCC1CCCC1)N1CCc2c([nH]c3ccc(Cl)cc23)[C@@H]1c1ccc(OCCCO)cc1]
1630
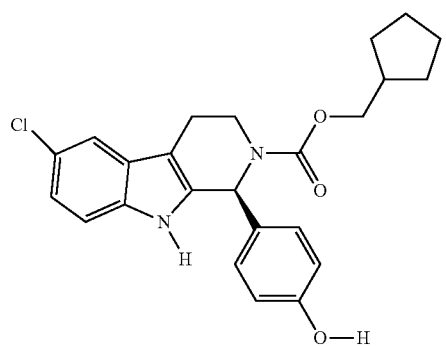 [SMILES: O=C(OCC1CCCC1)N1CCc2c([nH]c3ccc(Cl)cc23)[C@@H]1c1ccc(O)cc1]
1631
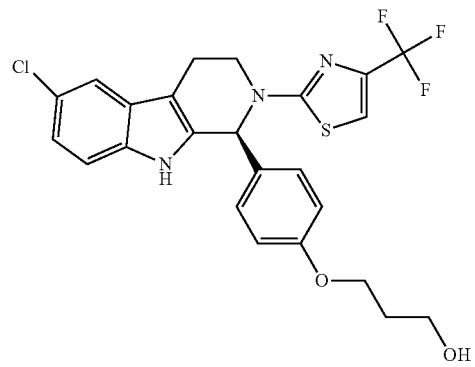 [SMILES: OCCCOc1ccc([C@H]2c3[nH]c4ccc(Cl)cc4c3CCN2c2nc(C(F)(F)F)cs2)cc1]
1632

TABLE 1-continued
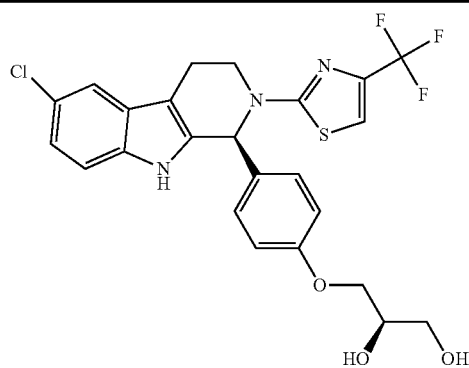
1633
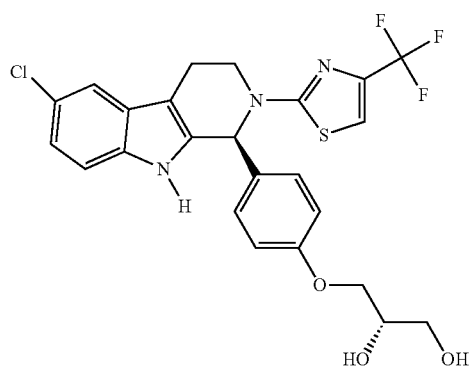 [SMILES: OC[C@H](O)COc1ccc([C@H]2c3[nH]c4ccc(Cl)cc4c3CCN2c2nc(C(F)(F)F)cs2)cc1]
1634
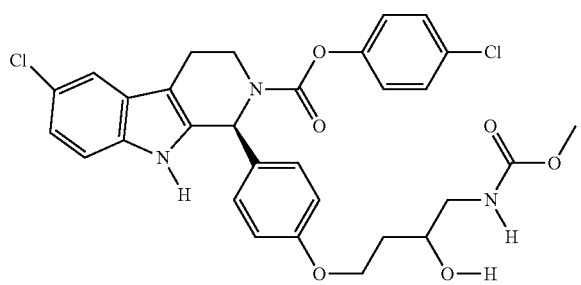 [SMILES: COC(=O)NCC(O)CCOc1ccc([C@H]2c3[nH]c4ccc(Cl)cc4c3CCN2C(=O)Oc2ccc(Cl)cc2)cc1]
1635
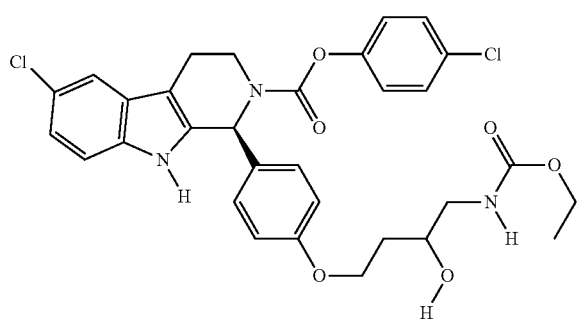 [SMILES: CCOC(=O)NCC(O)CCOc1ccc([C@H]2c3[nH]c4ccc(Cl)cc4c3CCN2C(=O)Oc2ccc(Cl)cc2)cc1]
1636
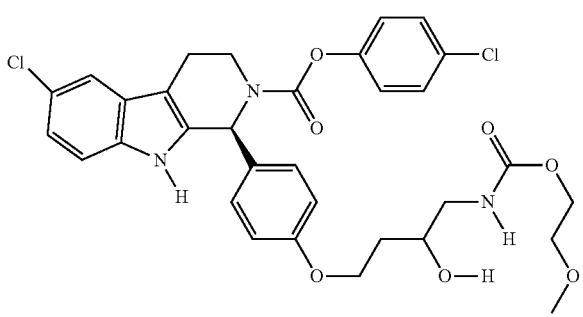 [SMILES: COCCOC(=O)NCC(O)CCOc1ccc([C@H]2c3[nH]c4ccc(Cl)cc4c3CCN2C(=O)Oc2ccc(Cl)cc2)cc1]
1637

TABLE 1-continued
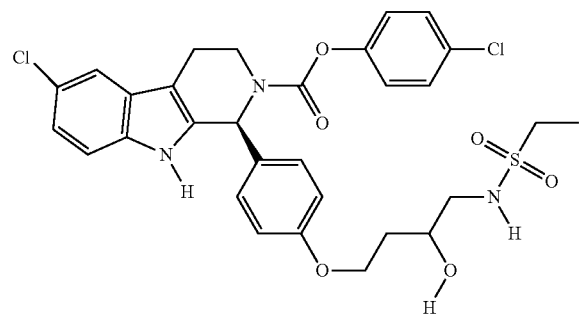 [SMILES: CCS(=O)(=O)NCC(O)CCOc1ccc([C@H]2c3[nH]c4ccc(Cl)cc4c3CCN2C(=O)Oc2ccc(Cl)cc2)cc1]
1638
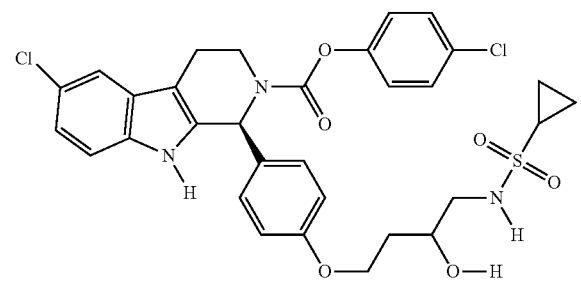 [SMILES: O=C(Oc1ccc(Cl)cc1)N1CCc2c([nH]c3ccc(Cl)cc23)[C@@H]1c1ccc(OCCC(O)CNS(=O)(=O)C2CC2)cc1]
1639
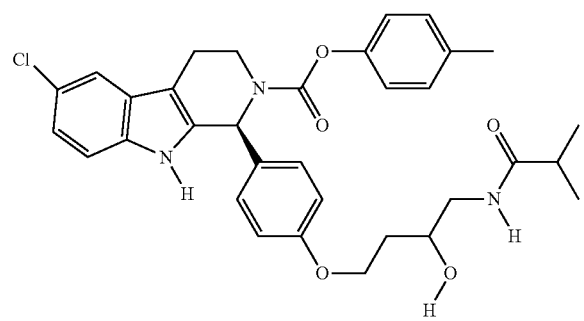 [SMILES: Cc1ccc(OC(=O)N2CCc3c([nH]c4ccc(Cl)cc34)[C@@H]2c2ccc(OCCC(O)CNC(=O)C(C)C)cc2)cc1]
1640
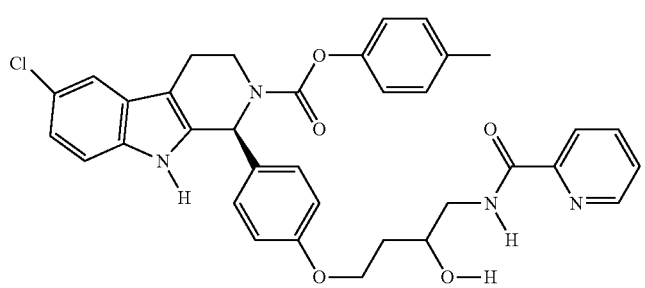 [SMILES: Cc1ccc(OC(=O)N2CCc3c([nH]c4ccc(Cl)cc34)[C@@H]2c2ccc(OCCC(O)CNC(=O)c3ccccn3)cc2)cc1]
1641
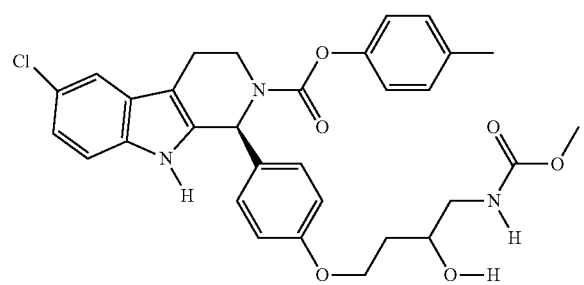 [SMILES: COC(=O)NCC(O)CCOc1ccc([C@H]2c3[nH]c4ccc(Cl)cc4c3CCN2C(=O)Oc2ccc(C)cc2)cc1]
1642

TABLE 1-continued
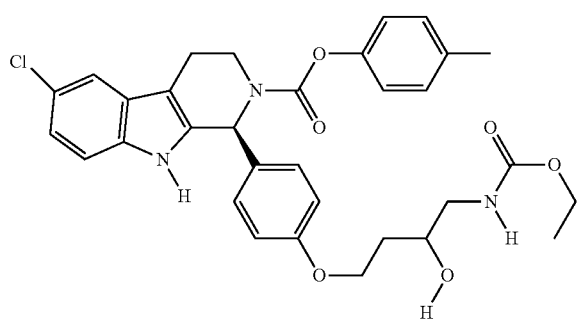 [SMILES: CCOC(=O)NCC(O)CCOc1ccc([C@H]2c3[nH]c4ccc(Cl)cc4c3CCN2C(=O)Oc2ccc(C)cc2)cc1]
1643
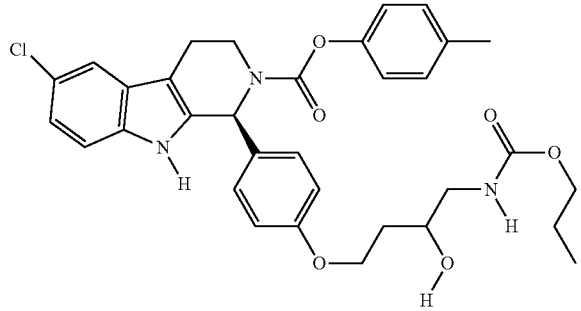 [SMILES: CCCOC(=O)NCC(O)CCOc1ccc([C@H]2c3[nH]c4ccc(Cl)cc4c3CCN2C(=O)Oc2ccc(C)cc2)cc1]
1644
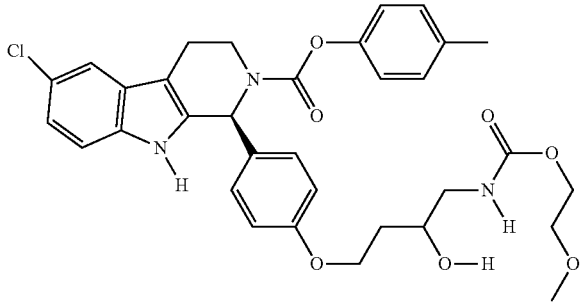 [SMILES: COCCOC(=O)NCC(O)CCOc1ccc([C@H]2c3[nH]c4ccc(Cl)cc4c3CCN2C(=O)Oc2ccc(C)cc2)cc1]
1645
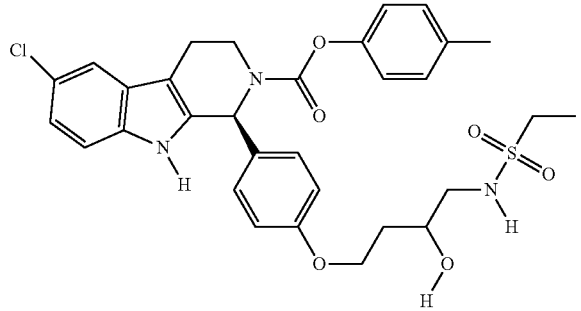 [SMILES: CCS(=O)(=O)NCC(O)CCOc1ccc([C@H]2c3[nH]c4ccc(Cl)cc4c3CCN2C(=O)Oc2ccc(C)cc2)cc1]
1646
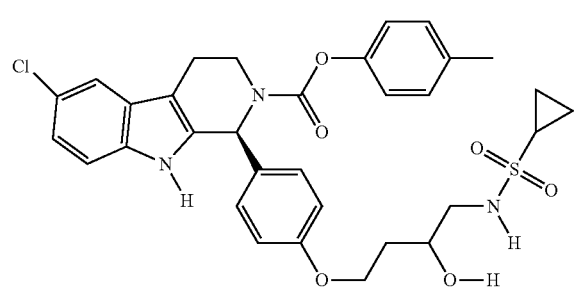
1647

TABLE 1-continued
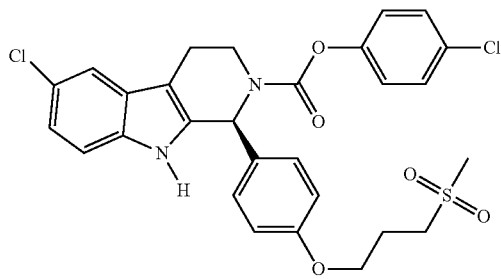 [SMILES: CS(=O)(=O)CCCOc1ccc([C@H]2c3[nH]c4ccc(Cl)cc4c3CCN2C(=O)Oc2ccc(Cl)cc2)cc1]
1648
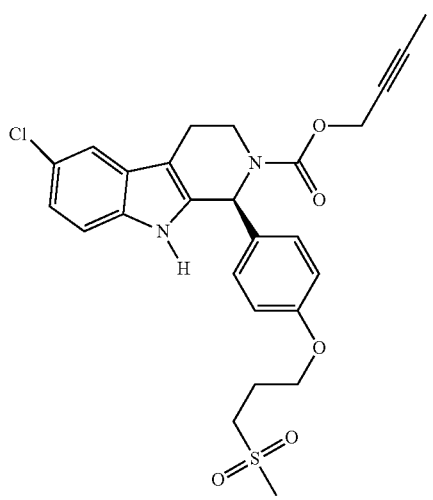 [SMILES: CC#CCOC(=O)N1CCc2c([nH]c3ccc(Cl)cc23)[C@@H]1c1ccc(OCCCS(C)(=O)=O)cc1]
1649
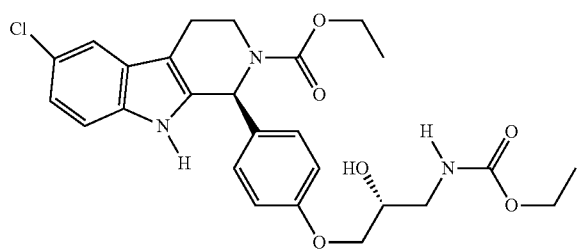 [SMILES: CCOC(=O)NC[C@@H](O)COc1ccc([C@H]2c3[nH]c4ccc(Cl)cc4c3CCN2C(=O)OCC)cc1]
1650
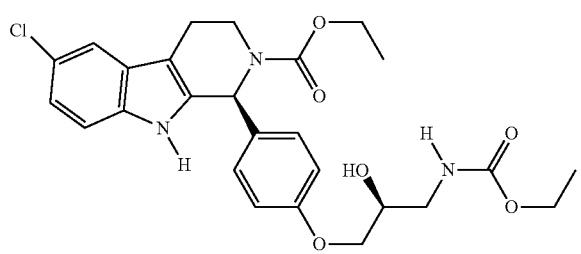 [SMILES: CCOC(=O)NC[C@H](O)COc1ccc([C@H]2c3[nH]c4ccc(Cl)cc4c3CCN2C(=O)OCC)cc1]
1651

TABLE 1-continued
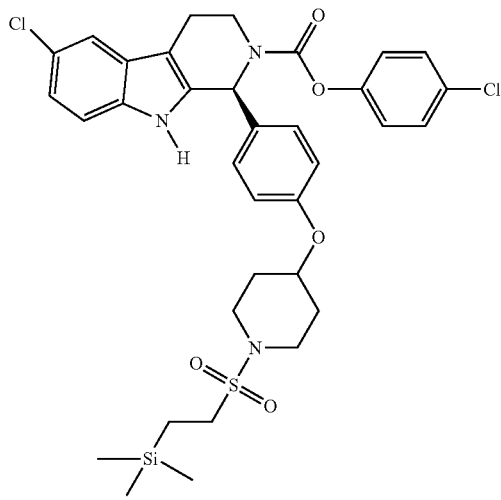 [SMILES: C[Si](C)(C)CCS(=O)(=O)N1CCC(Oc2ccc([C@H]3c4[nH]c5ccc(Cl)cc5c4CCN3C(=O)Oc3ccc(Cl)cc3)cc2)CC1]
1652
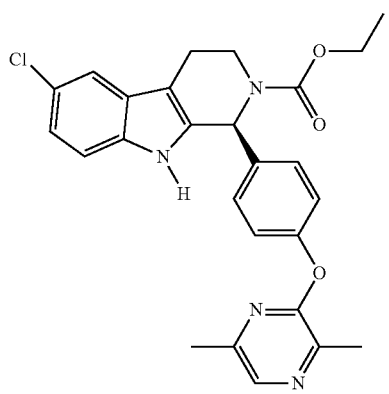 [SMILES: CCOC(=O)N1CCc2c([nH]c3ccc(Cl)cc23)[C@@H]1c1ccc(Oc2nc(C)cnc2C)cc1]
1653
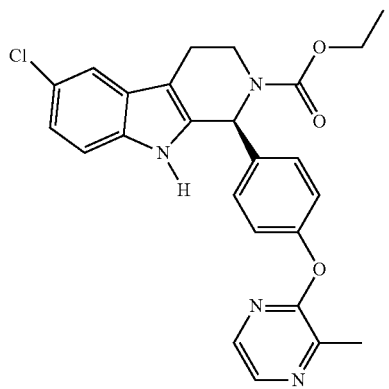 [SMILES: CCOC(=O)N1CCc2c([nH]c3ccc(Cl)cc23)[C@@H]1c1ccc(Oc2nccnc2C)cc1]
1654

TABLE 1-continued
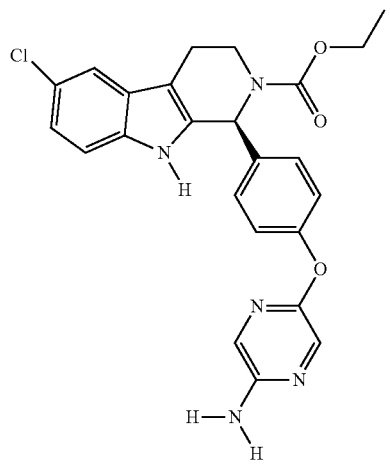 [SMILES: CCOC(=O)N1CCc2c([nH]c3ccc(Cl)cc23)[C@@H]1c1ccc(Oc2cnc(N)cn2)cc1]
1655
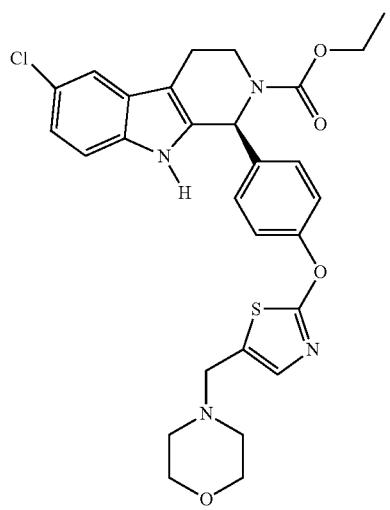 [SMILES: CCOC(=O)N1CCc2c([nH]c3ccc(Cl)cc23)[C@@H]1c1ccc(Oc2ncc(CN3CCOCC3)s2)cc1]
1656
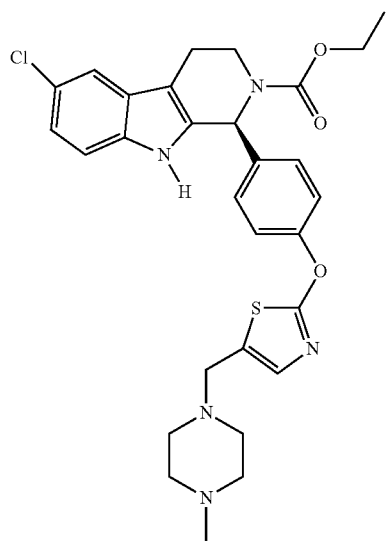 [SMILES: CCOC(=O)N1CCc2c([nH]c3ccc(Cl)cc23)[C@@H]1c1ccc(Oc2ncc(CN3CCN(C)CC3)s2)cc1]
1657

TABLE 1-continued
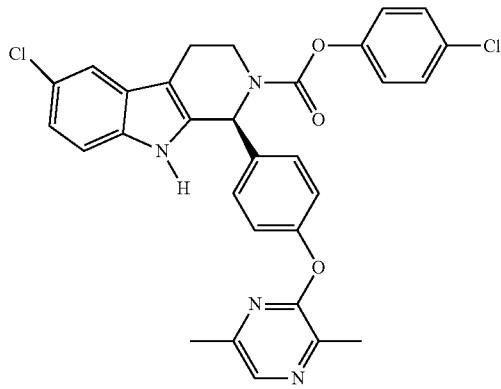 [SMILES: Cc1cnc(C)c(Oc2ccc([C@H]3c4[nH]c5ccc(Cl)cc5c4CCN3C(=O)Oc3ccc(Cl)cc3)cc2)n1]
1658
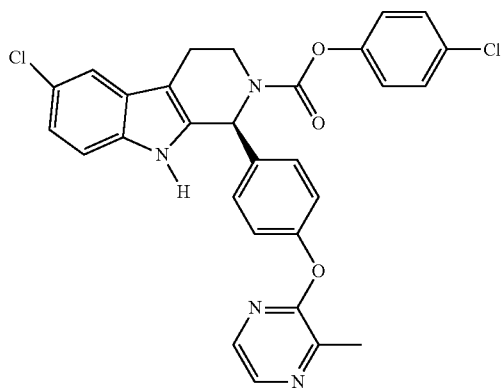 [SMILES: Cc1nccnc1Oc1ccc([C@H]2c3[nH]c4ccc(Cl)cc4c3CCN2C(=O)Oc2ccc(Cl)cc2)cc1]
1659
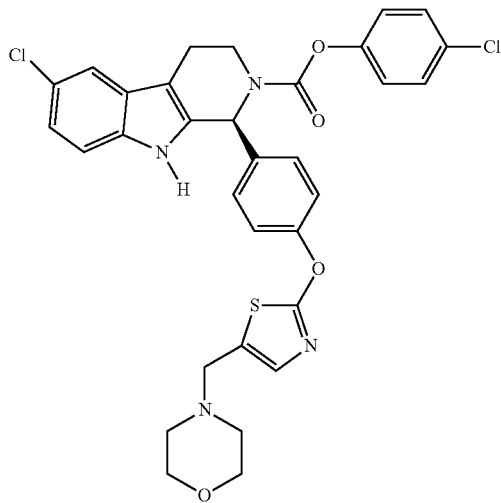 [SMILES: O=C(Oc1ccc(Cl)cc1)N1CCc2c([nH]c3ccc(Cl)cc23)[C@@H]1c1ccc(Oc2ncc(CN3CCOCC3)s2)cc1]
1660

TABLE 1-continued
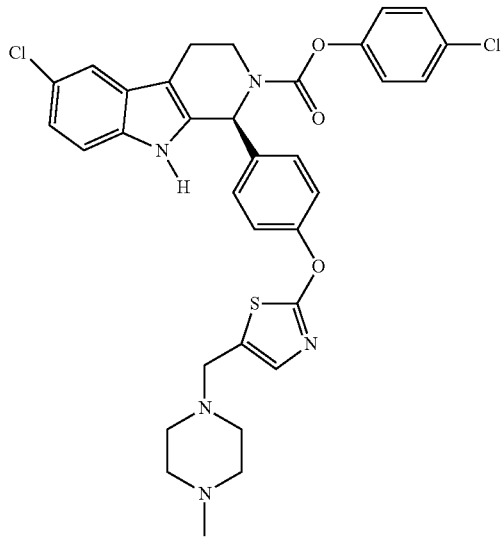 [SMILES: CN1CCN(Cc2cnc(Oc3ccc([C@H]4c5[nH]c6ccc(Cl)cc6c5CCN4C(=O)Oc4ccc(Cl)cc4)cc3)s2)CC1]
1661
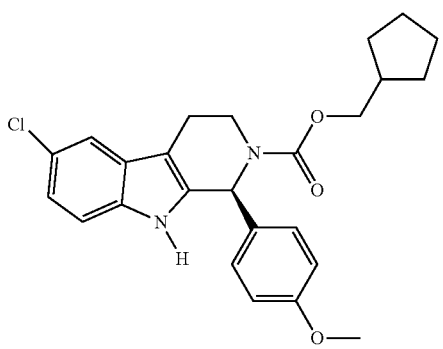
1662
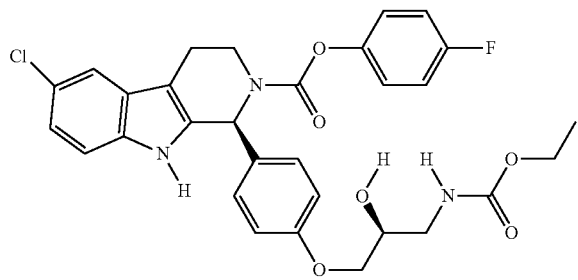 [SMILES: CCOC(=O)NC[C@H](O)COc1ccc([C@H]2c3[nH]c4ccc(Cl)cc4c3CCN2C(=O)Oc2ccc(F)cc2)cc1]
1663
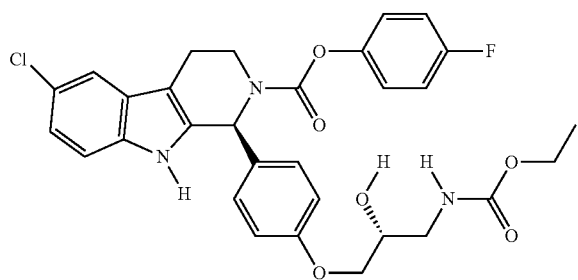 [SMILES: CCOC(=O)NC[C@@H](O)COc1ccc([C@H]2c3[nH]c4ccc(Cl)cc4c3CCN2C(=O)Oc2ccc(F)cc2)cc1]
1664

TABLE 1-continued
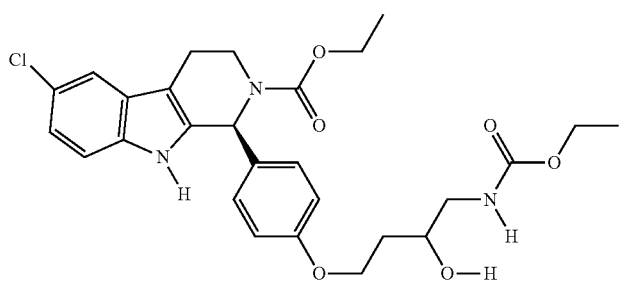 [SMILES: CCOC(=O)NCC(O)CCOc1ccc([C@H]2c3[nH]c4ccc(Cl)cc4c3CCN2C(=O)OCC)cc1]
1665
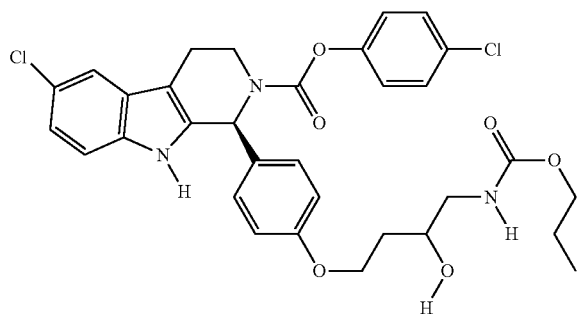
1666
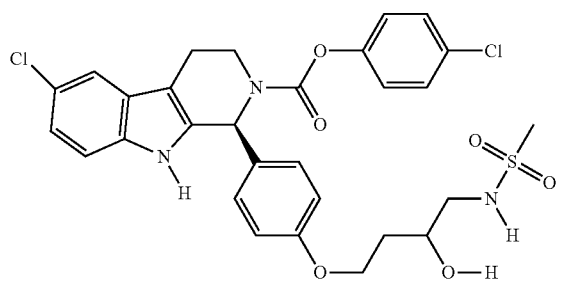 [SMILES: CS(=O)(=O)NCC(O)CCOc1ccc([C@H]2c3[nH]c4ccc(Cl)cc4c3CCN2C(=O)Oc2ccc(Cl)cc2)cc1]
1667
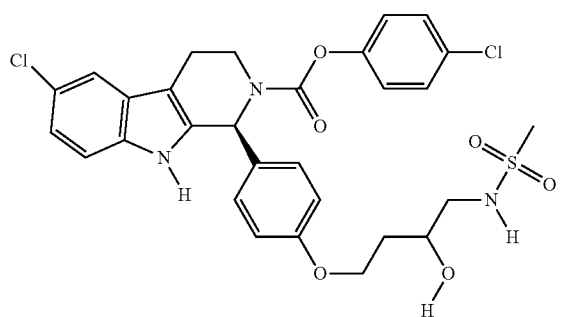 [SMILES: CS(=O)(=O)NCC(O)CCOc1ccc([C@H]2c3[nH]c4ccc(Cl)cc4c3CCN2C(=O)Oc2ccc(Cl)cc2)cc1]
1668
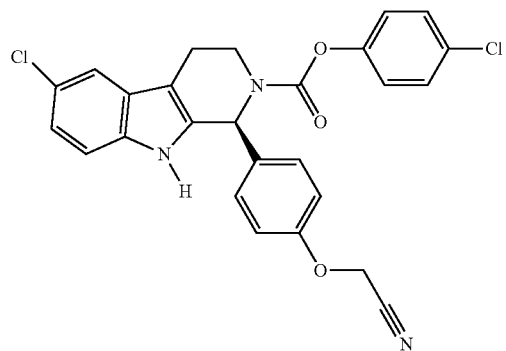 [SMILES: N#CCOc1ccc([C@H]2c3[nH]c4ccc(Cl)cc4c3CCN2C(=O)Oc2ccc(Cl)cc2)cc1]
1669

TABLE 1-continued
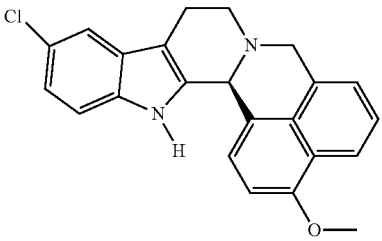
1670
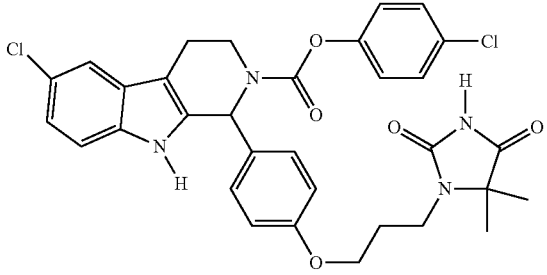 [SMILES: CC1(C)C(=O)NC(=O)N1CCCOc1ccc(C2c3[nH]c4ccc(Cl)cc4c3CCN2C(=O)Oc2ccc(Cl)cc2)cc1]
1671
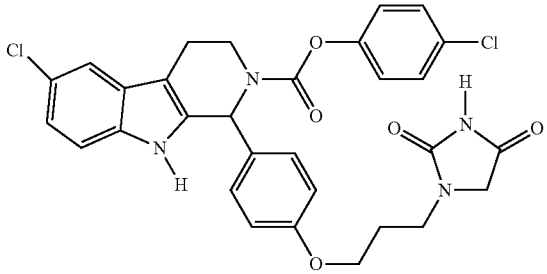 [SMILES: O=C1CN(CCCOc2ccc(C3c4[nH]c5ccc(Cl)cc5c4CCN3C(=O)Oc3ccc(Cl)cc3)cc2)C(=O)N1]
1672
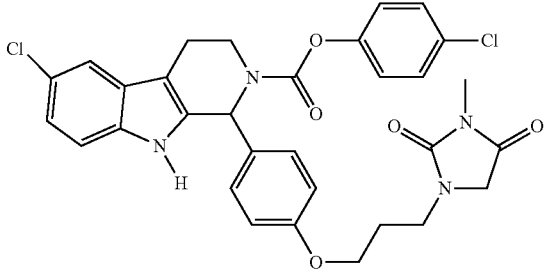 [SMILES: CN1C(=O)CN(CCCOc2ccc(C3c4[nH]c5ccc(Cl)cc5c4CCN3C(=O)Oc3ccc(Cl)cc3)cc2)C1=O]
1673
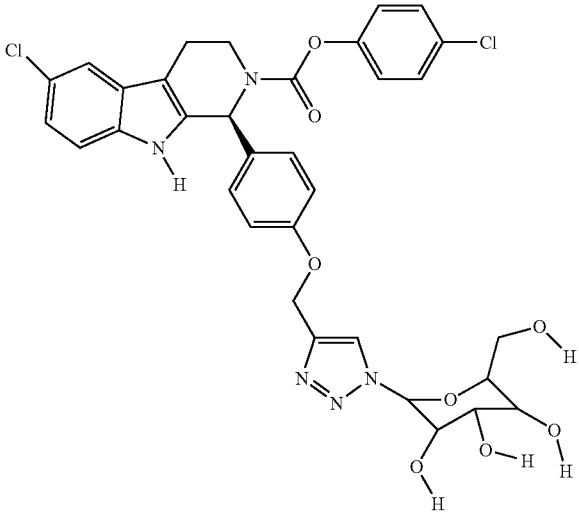 [SMILES: O=C(Oc1ccc(Cl)cc1)N1CCc2c([nH]c3ccc(Cl)cc23)[C@@H]1c1ccc(OCc2cn(C3OC(CO)C(O)C(O)C3O)nn2)cc1]
1674

TABLE 1-continued
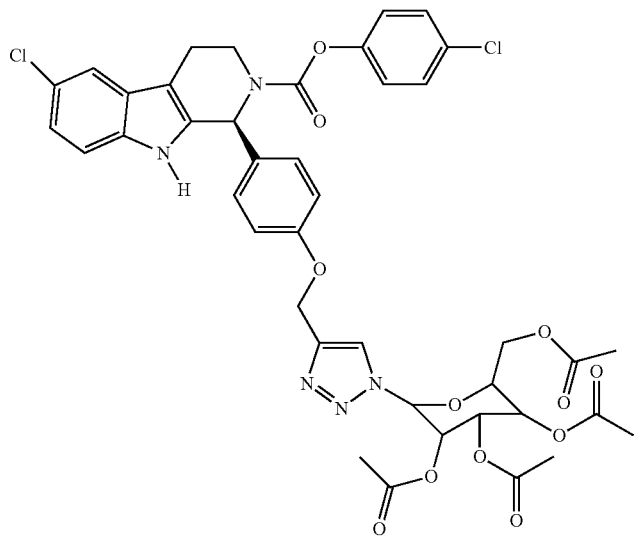 [SMILES: CC(=O)OCC1OC(n2cc(COc3ccc([C@H]4c5[nH]c6ccc(Cl)cc6c5CCN4C(=O)Oc4ccc(Cl)cc4)cc3)nn2)C(OC(C)=O)C(OC(C)=O)C1OC(C)=O]
1675
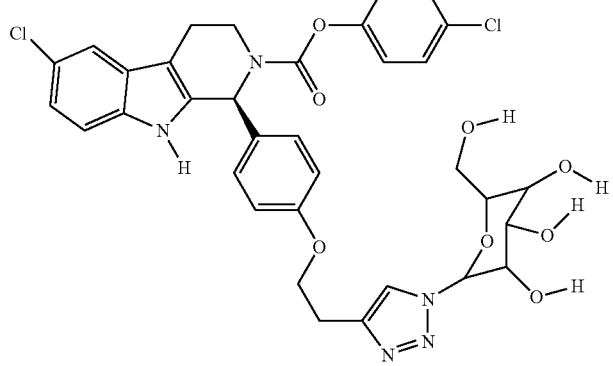
1676
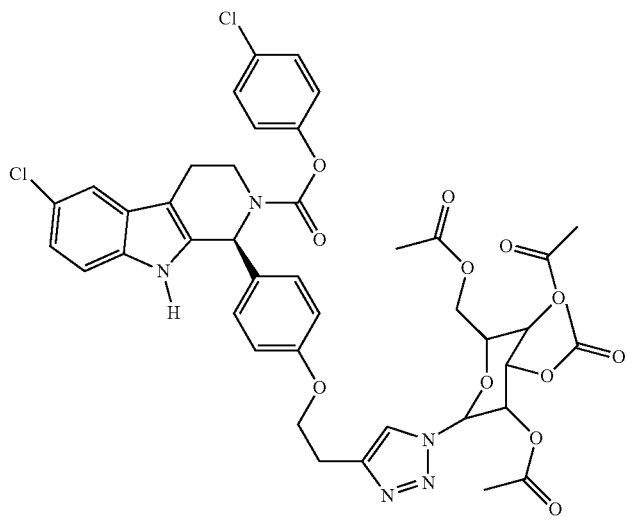 [SMILES: CC(=O)OCC1OC(n2cc(CCOc3ccc([C@H]4c5[nH]c6ccc(Cl)cc6c5CCN4C(=O)Oc4ccc(Cl)cc4)cc3)nn2)C(OC(C)=O)C(OC(C)=O)C1OC(C)=O]
1677

1678
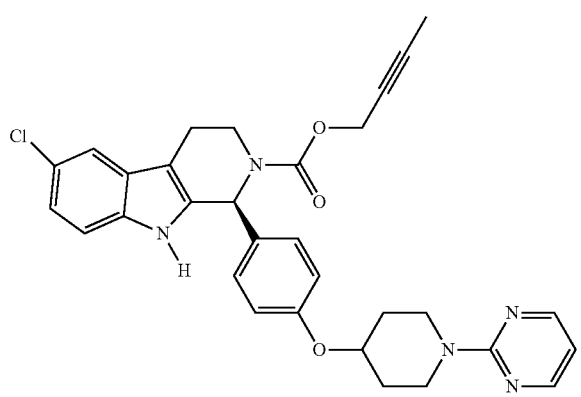 [SMILES: CC#CCOC(=O)N1CCc2c([nH]c3ccc(Cl)cc23)[C@@H]1c1ccc(OC2CCN(c3ncccn3)CC2)cc1]
1679
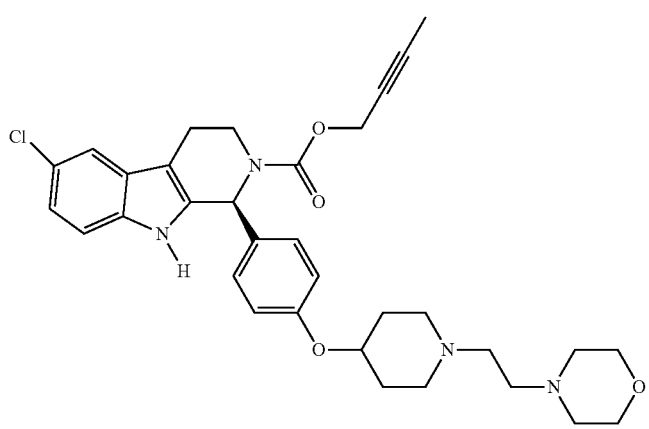 [SMILES: CC#CCOC(=O)N1CCc2c([nH]c3ccc(Cl)cc23)[C@@H]1c1ccc(OC2CCN(CCN3CCOCC3)CC2)cc1]
1680
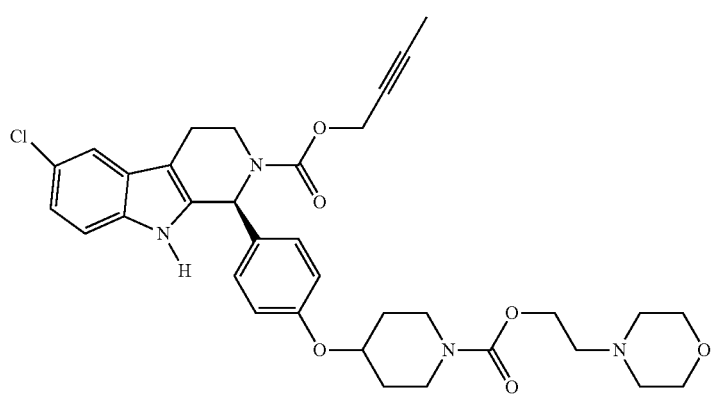 [SMILES: CC#CCOC(=O)N1CCc2c([nH]c3ccc(Cl)cc23)[C@@H]1c1ccc(OC2CCN(C(=O)OCCN3CCOCC3)CC2)cc1]
1681
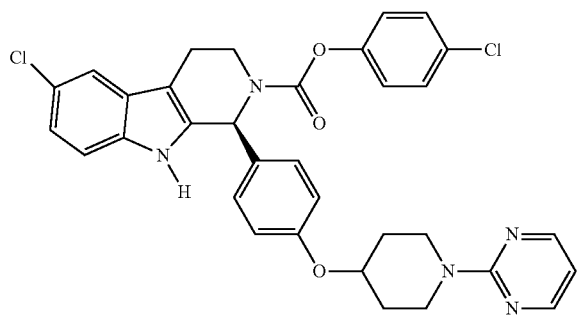 [SMILES: O=C(Oc1ccc(Cl)cc1)N1CCc2c([nH]c3ccc(Cl)cc23)[C@@H]1c1ccc(OC2CCN(c3ncccn3)CC2)cc1]

TABLE 1-continued
| | |
|---|---|
| 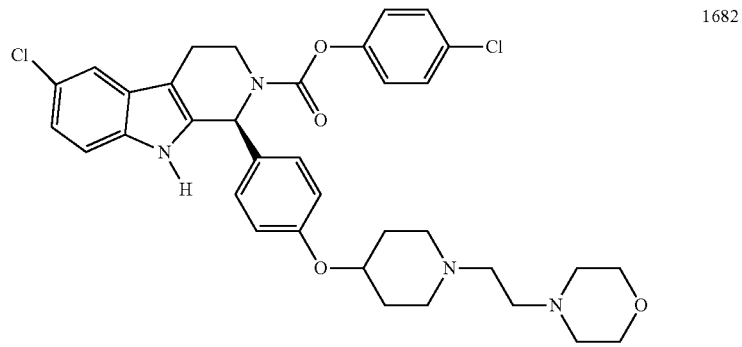 | 1682 |
| 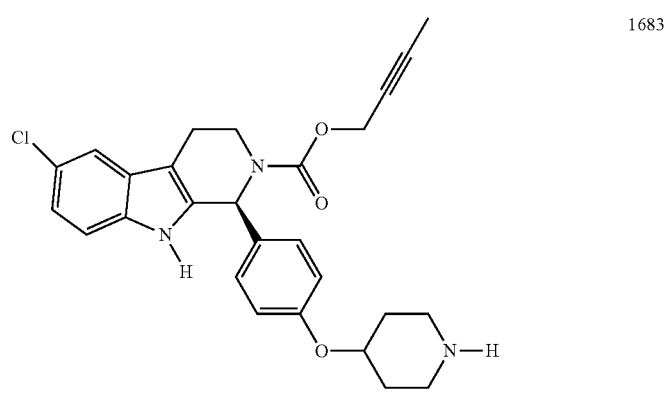 | 1683 |
| 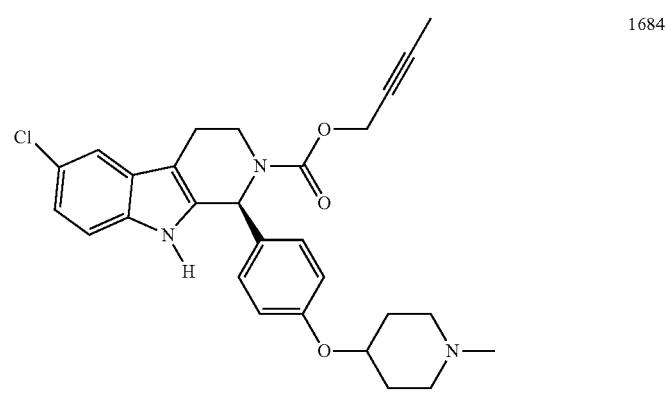 | 1684 |
| 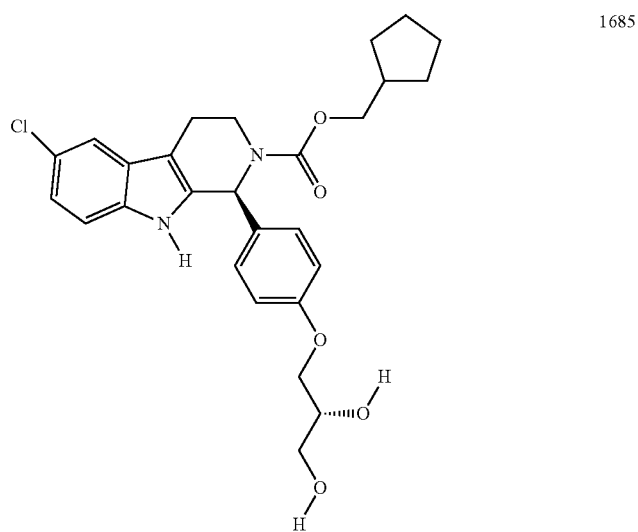 | 1685 |

TABLE 1-continued
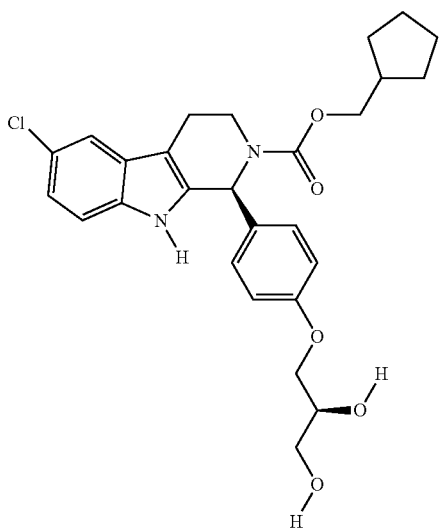 [SMILES: O=C(OCC1CCCC1)N1CCc2c([nH]c3ccc(Cl)cc23)[C@@H]1c1ccc(OC[C@@H](O)CO)cc1]
1686
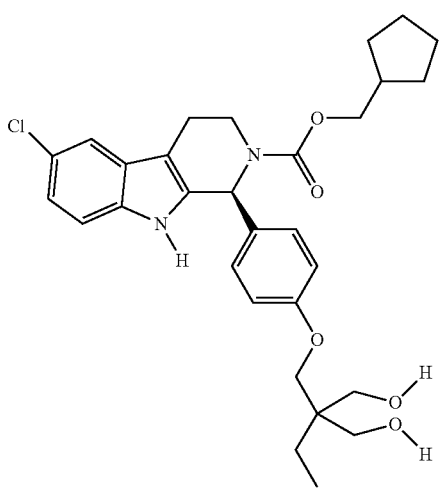 [SMILES: CCC(CO)(CO)COc1ccc([C@H]2c3[nH]c4ccc(Cl)cc4c3CCN2C(=O)OCC2CCCC2)cc1]
1687
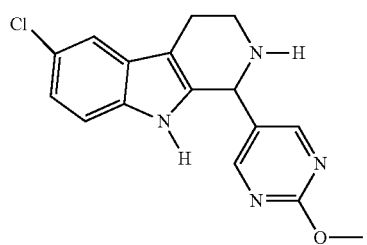 [SMILES: COc1ncc(C2NCCc3c2[nH]c2ccc(Cl)cc32)cn1]
1688
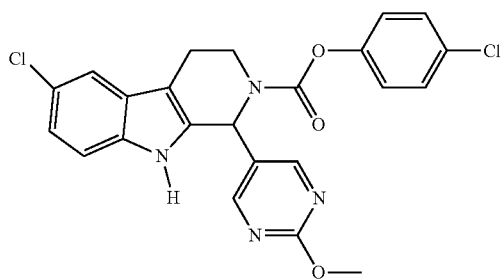 [SMILES: COc1ncc(C2c3[nH]c4ccc(Cl)cc4c3CCN2C(=O)Oc2ccc(Cl)cc2)cn1]
1689

TABLE 1-continued
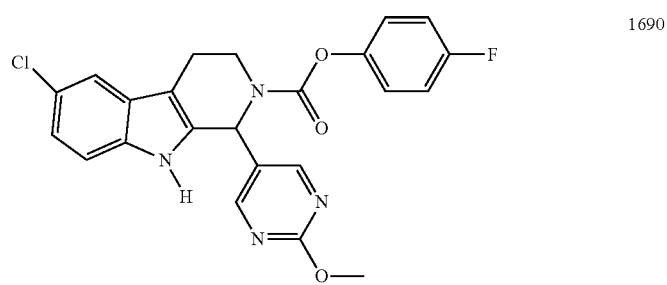
1690
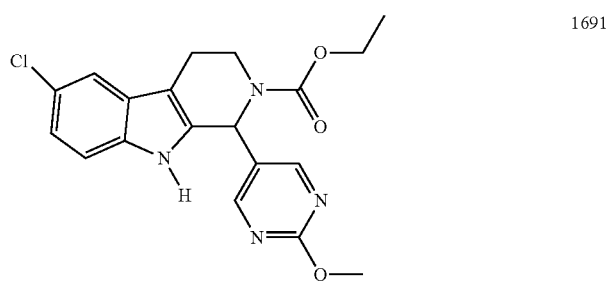
1691
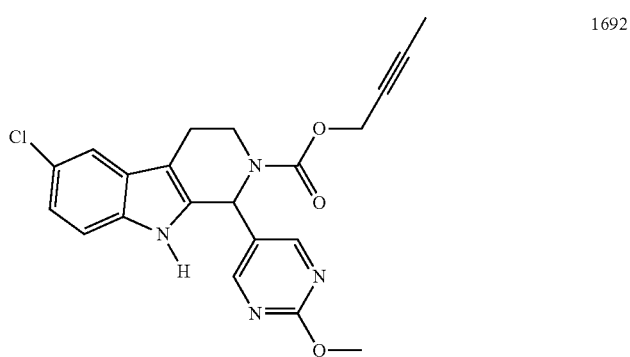
1692
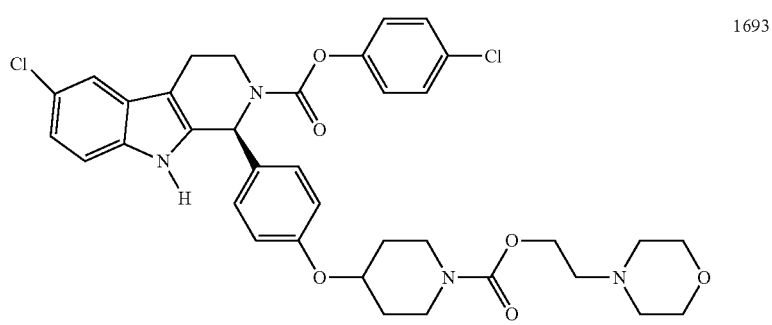
1693
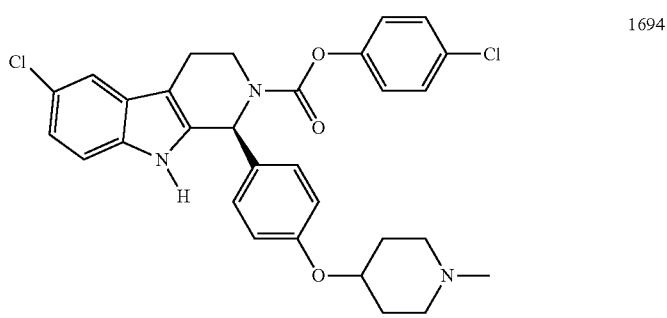
1694

TABLE 1-continued
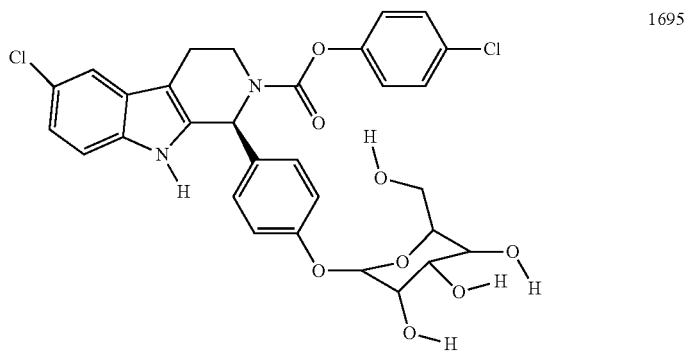
1695
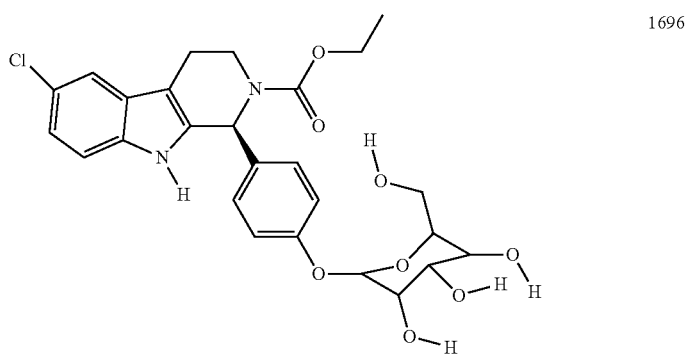
1696
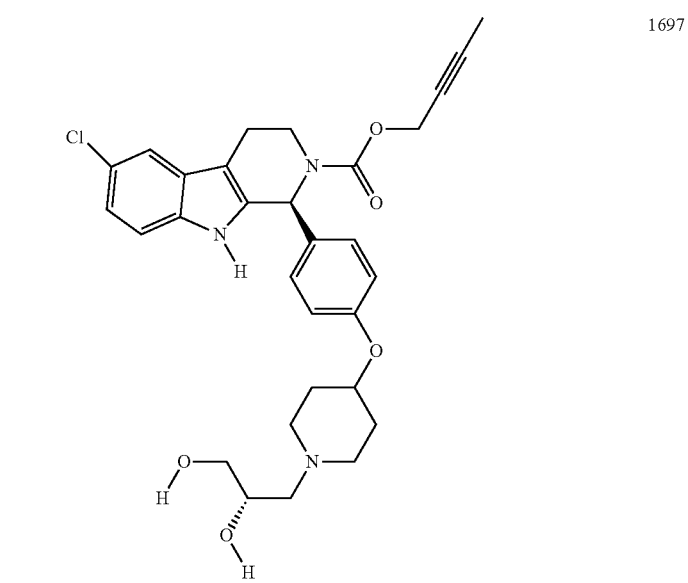
1697
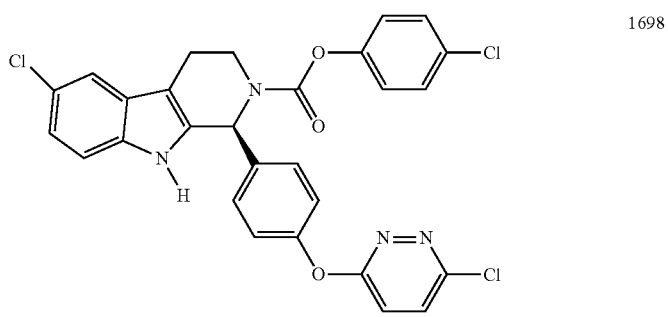
1698

TABLE 1-continued
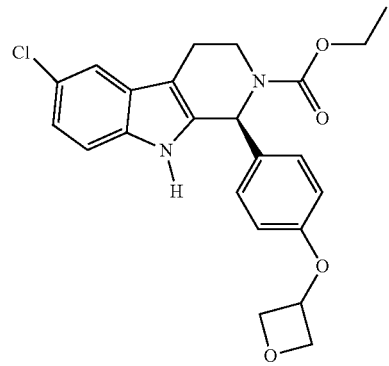 [SMILES: CCOC(=O)N1CCc2c([nH]c3ccc(Cl)cc23)[C@@H]1c1ccc(OC2COC2)cc1]
1699
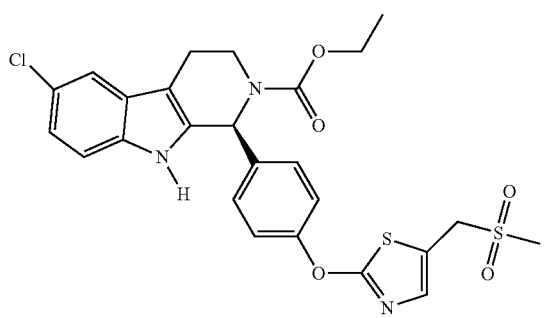 [SMILES: CCOC(=O)N1CCc2c([nH]c3ccc(Cl)cc23)[C@@H]1c1ccc(Oc2ncc(CS(C)(=O)=O)s2)cc1]
1700
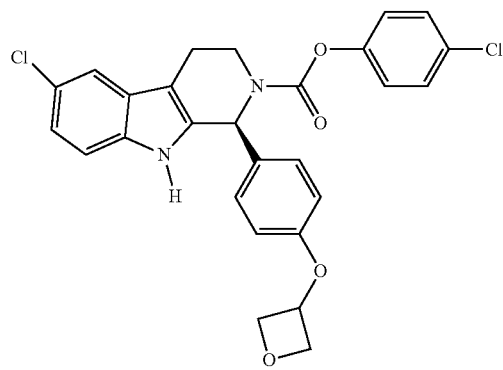 [SMILES: O=C(Oc1ccc(Cl)cc1)N1CCc2c([nH]c3ccc(Cl)cc23)[C@@H]1c1ccc(OC2COC2)cc1]
1701
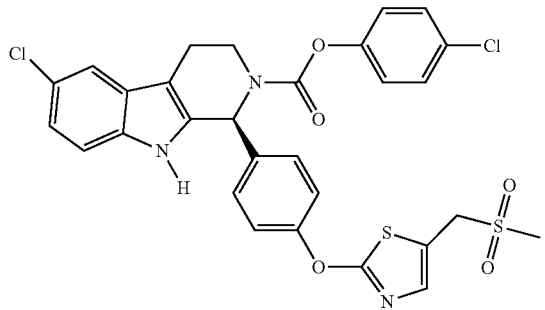 [SMILES: CS(=O)(=O)Cc1cnc(Oc2ccc([C@H]3c4[nH]c5ccc(Cl)cc5c4CCN3C(=O)Oc3ccc(Cl)cc3)cc2)s1]
1702

TABLE 1-continued
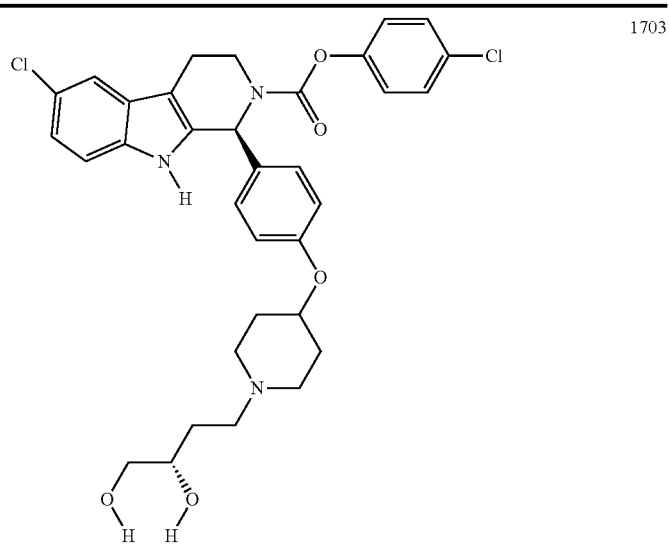
1703
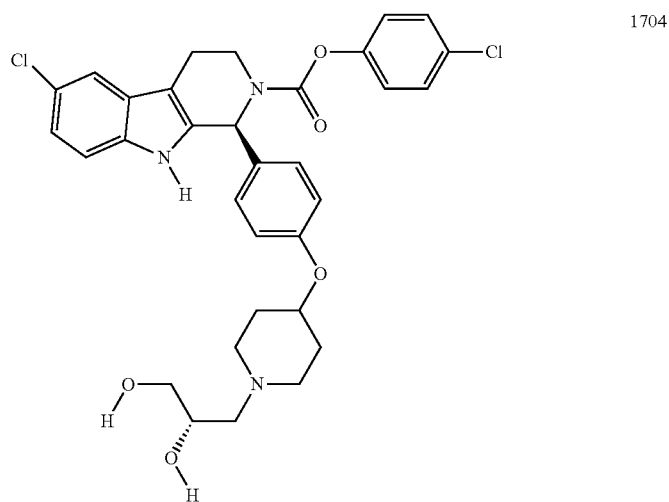
1704
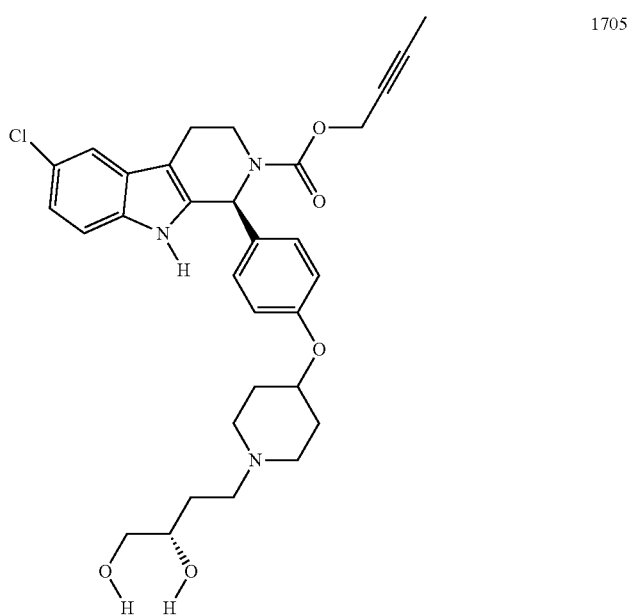
1705

TABLE 1-continued
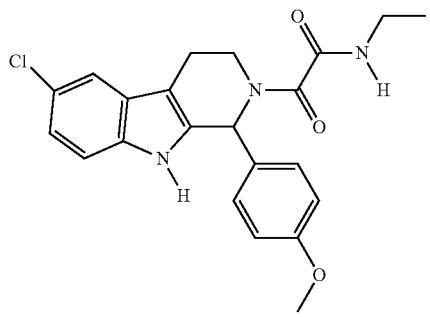 [SMILES: CCNC(=O)C(=O)N1CCc2c([nH]c3ccc(Cl)cc23)C1c1ccc(OC)cc1]
1706
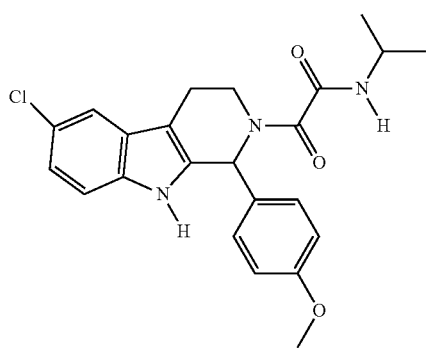 [SMILES: COc1ccc(C2c3[nH]c4ccc(Cl)cc4c3CCN2C(=O)C(=O)NC(C)C)cc1]
1707
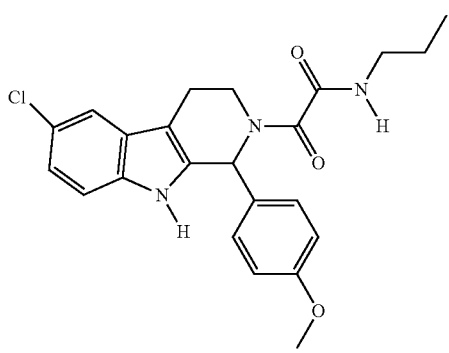 [SMILES: CCCNC(=O)C(=O)N1CCc2c([nH]c3ccc(Cl)cc23)C1c1ccc(OC)cc1]
1708
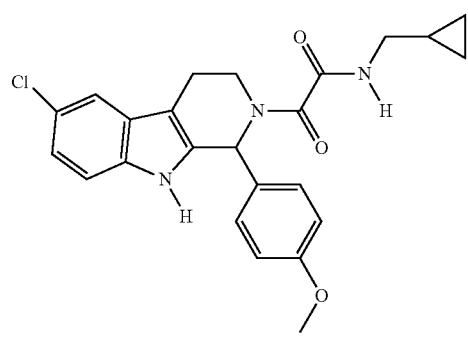 [SMILES: COc1ccc(C2c3[nH]c4ccc(Cl)cc4c3CCN2C(=O)C(=O)NCC2CC2)cc1]
1709

TABLE 1-continued
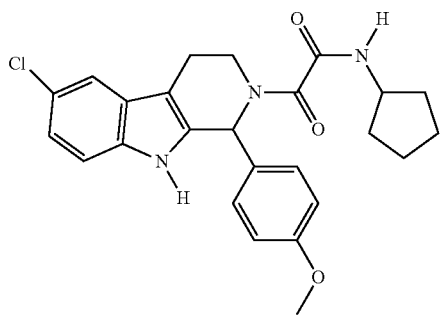 [SMILES: COc1ccc(C2c3[nH]c4ccc(Cl)cc4c3CCN2C(=O)C(=O)NC2CCCC2)cc1]
1710
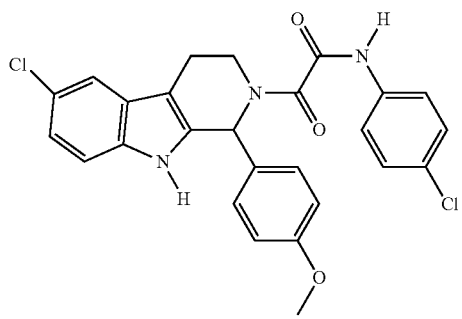 [SMILES: COc1ccc(C2c3[nH]c4ccc(Cl)cc4c3CCN2C(=O)C(=O)Nc2ccc(Cl)cc2)cc1]
1711
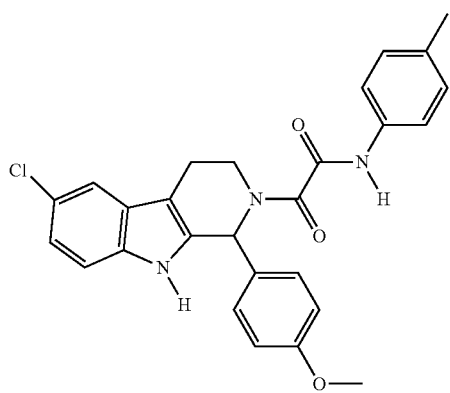 [SMILES: COc1ccc(C2c3[nH]c4ccc(Cl)cc4c3CCN2C(=O)C(=O)Nc2ccc(C)cc2)cc1]
1712
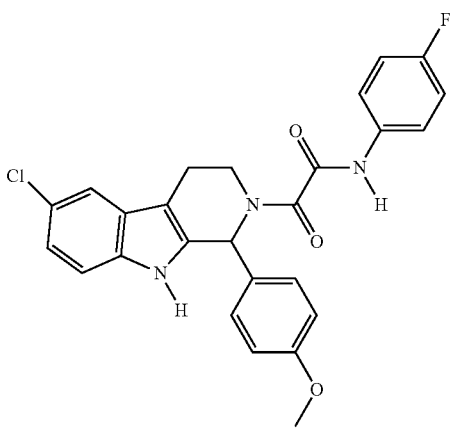 [SMILES: COc1ccc(C2c3[nH]c4ccc(Cl)cc4c3CCN2C(=O)C(=O)Nc2ccc(F)cc2)cc1]
1713

TABLE 1-continued
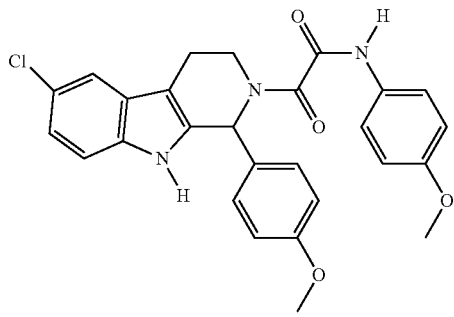 [SMILES: COc1ccc(NC(=O)C(=O)N2CCc3c([nH]c4ccc(Cl)cc34)C2c2ccc(OC)cc2)cc1]
1714
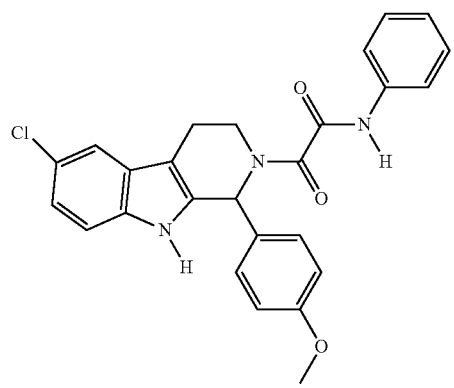 [SMILES: COc1ccc(C2c3[nH]c4ccc(Cl)cc4c3CCN2C(=O)C(=O)Nc2ccccc2)cc1]
1715
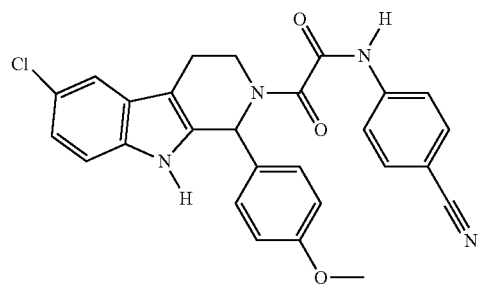 [SMILES: COc1ccc(C2c3[nH]c4ccc(Cl)cc4c3CCN2C(=O)C(=O)Nc2ccc(C#N)cc2)cc1]
1716
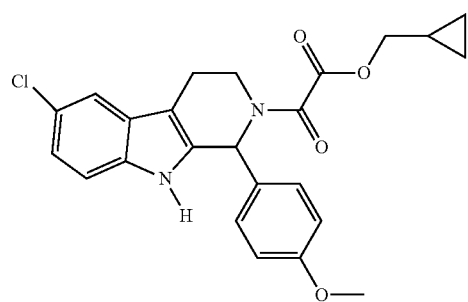 [SMILES: COc1ccc(C2c3[nH]c4ccc(Cl)cc4c3CCN2C(=O)C(=O)OCC2CC2)cc1]
1717
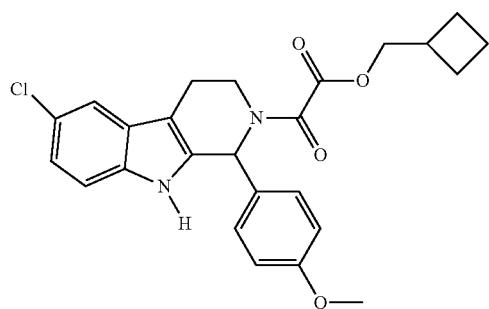 [SMILES: COc1ccc(C2c3[nH]c4ccc(Cl)cc4c3CCN2C(=O)C(=O)OCC2CCC2)cc1]
1718

TABLE 1-continued
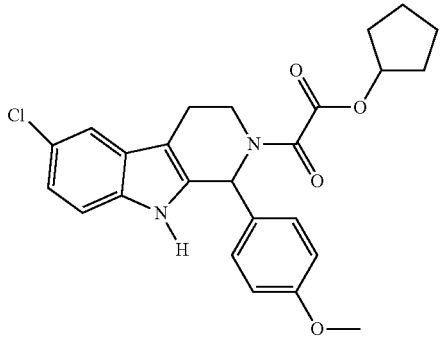 [SMILES: COc1ccc(C2c3[nH]c4ccc(Cl)cc4c3CCN2C(=O)C(=O)OC2CCCC2)cc1]
1719
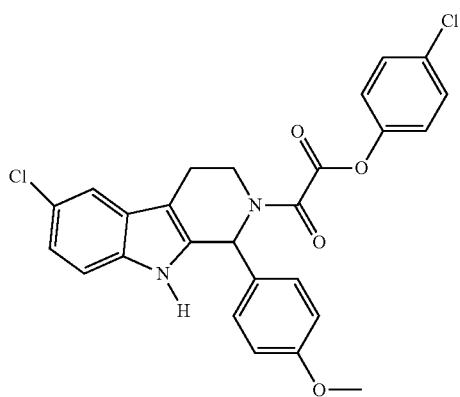 [SMILES: COc1ccc(C2c3[nH]c4ccc(Cl)cc4c3CCN2C(=O)C(=O)Oc2ccc(Cl)cc2)cc1]
1720
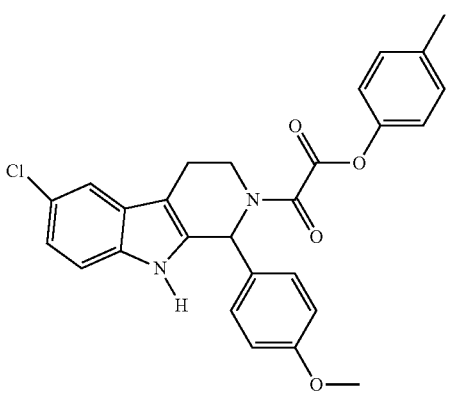 [SMILES: COc1ccc(C2c3[nH]c4ccc(Cl)cc4c3CCN2C(=O)C(=O)Oc2ccc(C)cc2)cc1]
1721
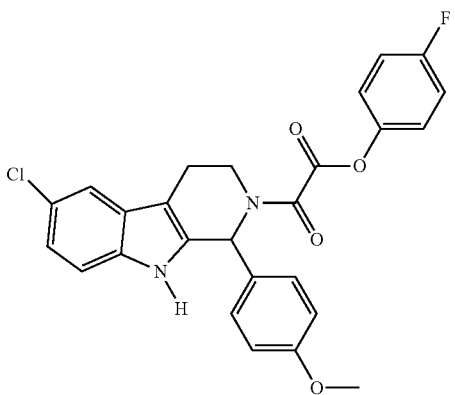 [SMILES: COc1ccc(C2c3[nH]c4ccc(Cl)cc4c3CCN2C(=O)C(=O)Oc2ccc(F)cc2)cc1]
1722

TABLE 1-continued
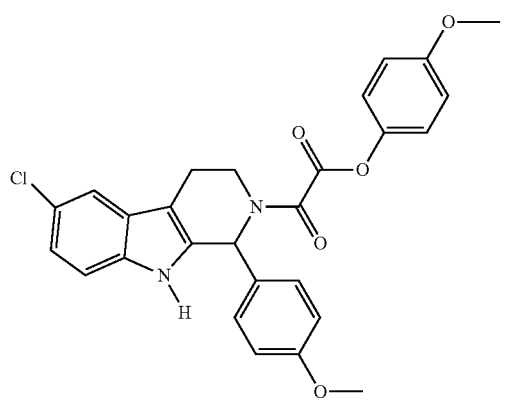 [SMILES: COc1ccc(OC(=O)C(=O)N2CCc3c([nH]c4ccc(Cl)cc34)C2c2ccc(OC)cc2)cc1]
1723
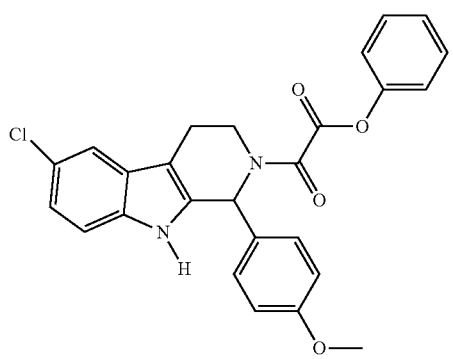 [SMILES: COc1ccc(C2c3[nH]c4ccc(Cl)cc4c3CCN2C(=O)C(=O)Oc2ccccc2)cc1]
1724
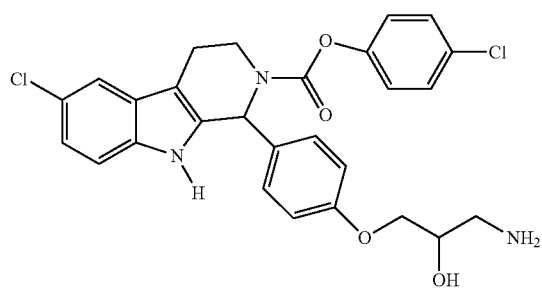 [SMILES: NCC(O)COc1ccc(C2c3[nH]c4ccc(Cl)cc4c3CCN2C(=O)Oc2ccc(Cl)cc2)cc1]
1725
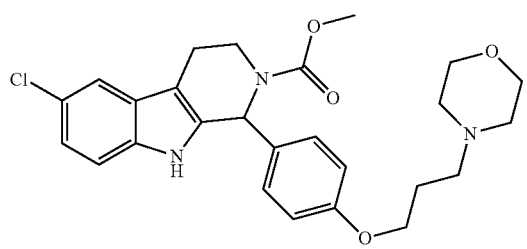 [SMILES: COC(=O)N1CCc2c([nH]c3ccc(Cl)cc23)C1c1ccc(OCCCN2CCOCC2)cc1]
1726
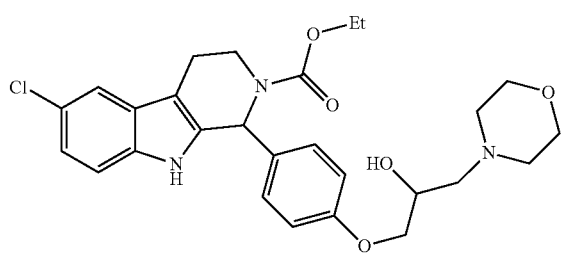 [SMILES: CCOC(=O)N1CCc2c([nH]c3ccc(Cl)cc23)C1c1ccc(OCC(O)CN2CCOCC2)cc1]
1727

TABLE 1-continued
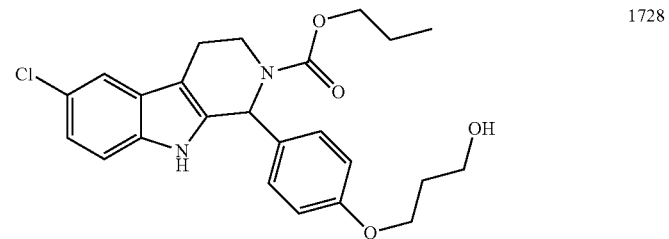
1728
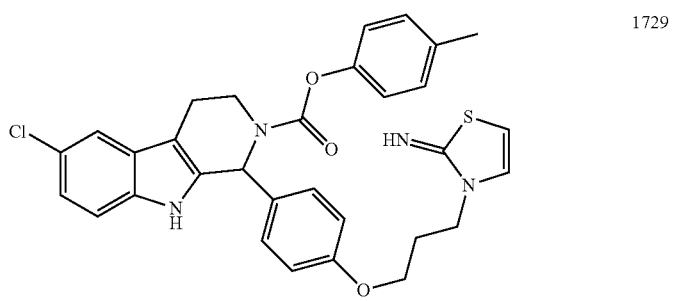
1729
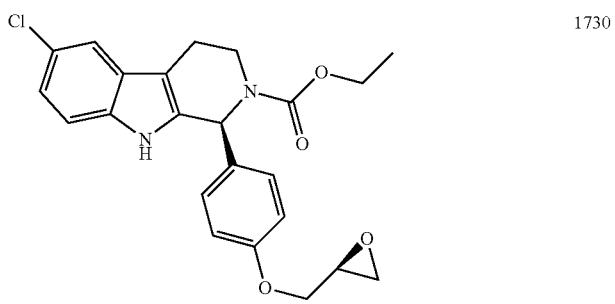
1730
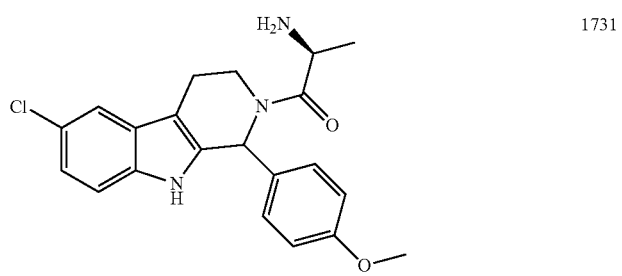
1731
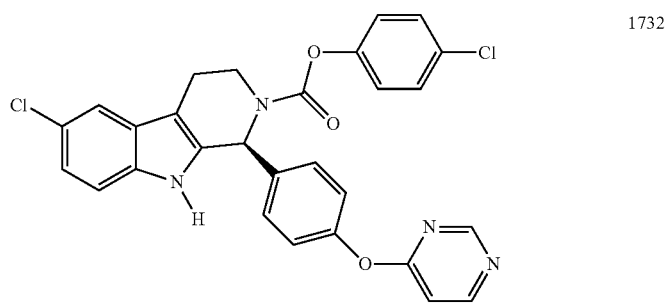
1732

TABLE 1-continued

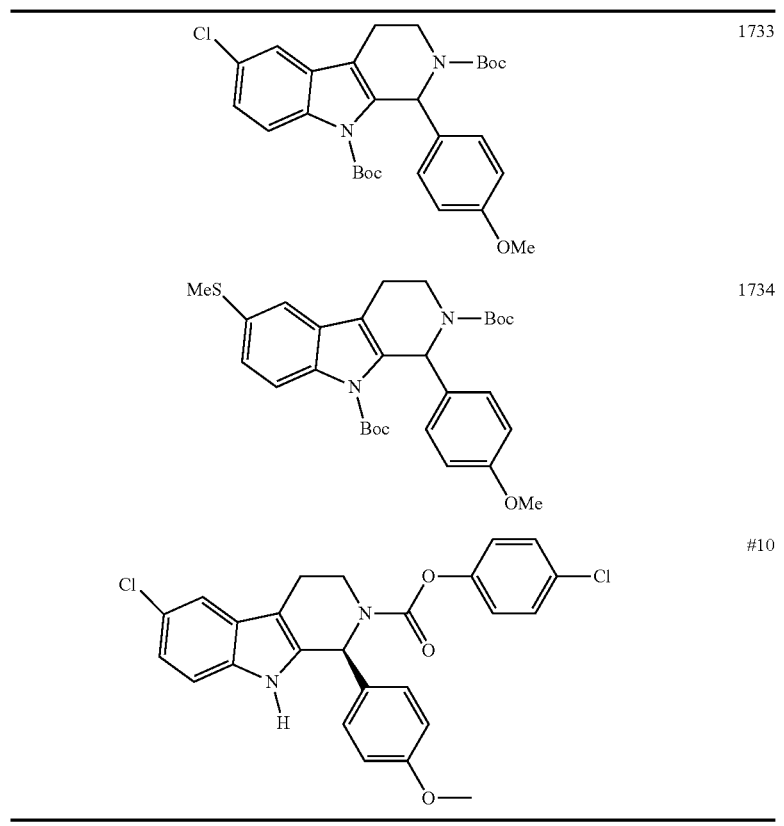

1733

1734

10

Compounds can be prepared by those skilled in the art using known methods, including those set forth in International Publication Nos. WO2005/089764, WO2006/113703, WO2008/127715, WO2008/127714, and as disclosed in copending U.S. Provisional Patent Application Ser. No. 61/181,652, filed May 27, 2009, entitled "Processes for the Preparation of Substituted Tetrahydro Beta-Carbolines," each of which is incorporated by reference herein in its entirety, as well as the procedures set forth below in Section 6.

5.2 Pharmaceutical Properties and Formulations 5.2.1 Activity

Without being bound by any theory, Compounds described herein inhibit the translation of pathologically expressed human VEGF mRNA and, thus, inhibit the pathologic production of human VEGF protein. In particular, the Compounds act specifically through a mechanism dependent on the 5' untranslated region (UTR) of the human VEGF mRNA to inhibit the pathologic production of human VEGF protein. The activity of the Compounds tested is post-transcriptional since quantitative real-time polymerase chain reaction (PCR) assessments of mRNA have shown that the Compounds do not alter the levels of human VEGF mRNA.

For the antiviral activity of the Compounds, without being bound by any particular theory, several lines of evidence appear to indicate that the precise molecular target of the Compounds is a host cell target rather than a direct viral target (see Section 10, et. seq., infra). For example, (1) broad spectrum activity against viruses from diverse and not closely related taxa; (2) the failure to select for a resistant HCV replicon despite long-term exposure at inhibitory concentrations of a Compound in cell culture; and (3) the lack of anti-PV activity in an HT-1080 cell line which is resistant to the cell cycle delay induced by a Compound.

5.2.1.1 Inhibition of Pathological VEGF Production

Compounds are described that reduce or inhibit pathological production of human VEGF (also known as VEGF-A and vascular permeability factor (VPF)). Exemplary Compounds have been shown to reduce or inhibit tumor production of VEGF as measured in cell culture and/or preclinical tumor models. Furthermore, the Compounds tested do not affect physiological plasma VEGF levels in healthy humans.

By way of background, the human VEGF-A gene encodes a number of different products (isoforms) due to alternative splicing. The VEGF-A isoforms include $VEGF_{121}$, $VEGF_{165}$, $VEGF_{189}$ and $VEGF_{206}$ having 121, 165, 189 and 206 amino acids, respectively. $VEGF_{165}$ and $VEGF_{121}$ isoforms are soluble, whereas $VEGF_{189}$ and $VEGF_{206}$ isoforms are sequestered within the extracellular matrix. The activity of the Compounds tested was assessed by measuring the concentrations of soluble VEGF in cell culture systems. In preclinical tumor models, the activity of the Compounds tested was assessed by measuring the concentrations of soluble VEGF. The data indicate that the Compounds tested inhibit the production of soluble forms of tumor derived VEGF.

In particular, a Compound provided herein has been shown to selectively inhibit stress (e.g., hypoxia) induced production of soluble human VEGF isoforms in cell culture without affecting soluble human VEGF production under normoxic conditions (see Section 8.1 et seq.). Thus, the Compound was shown to preferentially inhibit pathological production of soluble human VEGF isoforms resulting from hypoxia while sparing homeostatic production of soluble isoforms in unperturbed cells. Accordingly, in specific embodiments, a Compound selectively inhibits or reduces the pathological production of a soluble human VEGF isoform over inhibiting or reducing physiological or homeostatic production of a soluble human VEGF isoform.

In a specific embodiment, a Compound selectively inhibits or reduces the pathological production of a matrix-bound human VEGF isoform over inhibiting or reducing physiological production of a matrix-bound human VEGF isoform. In another specific embodiment, a Compound selectively inhibits or reduces the pathological production of one or more soluble human VEGF isoforms and one or more matrix-bound VEGF isoforms.

5.2.1.2 Inhibition of Pathological Angiogenesis and Tumor Growth

Compounds are described that reduce or inhibit tumor growth. A Compound provided herein has been shown to have a profound effect on the architecture of the tumor vasculature in animal models with pre-established human tumors. The Compound reduced the total volume and diameter of blood vessels formed compared to vehicle treated subjects. See Section 8.2. A Compound showed inhibition of tumor growth in the model. A dose-response effect of the Compound that correlated with decreases in tumor and plasma VEGF concentrations was observed when tumor size was assessed. See Section 8.1.3. Thus, in one embodiment, the concentration of soluble human VEGF in human plasma is used to assess and monitor the pharmacodynamic effect of a Compound provided herein. In a specific embodiment, the concentration of either $VEGF_{121}$, $VEGF_{165}$, or both in human plasma are used to assess and monitor the pharmacodynamic effect of a Compound provided herein.

5.2.1.3 Prolongation of Early $G_1$/Early S-Phase Cell Cycle Delay

Provided herein are Compounds that provoke a prolongation of early $G_1$/early S-Phase cell cycle delay.

In addition to its effects on pathological VEGF production, a Compound provided herein provokes a late $G_1$/early S-Phase cell cycle delay, i.e., between the late resting or pre-DNA synthesis phase, and the early DNA synthesis phase in those tumor cell lines in which VEGF generation is decreased by the Compound. See Section 8.3. Further characterization indicates that this effect is concentration dependent, occurring at low nanomolar $EC_{50}$ values similar to those associated with reducing pathological VEGF production. The cell cycle delay and inhibition of pathological VEGF protein production occur in concert, linking these phenotypes in inflammation, pathological angiogenesis and tumor growth. Inhibition of pathological VEGF production in these same tumor cells with small interfering RNA (siRNA) does not induce a cell cycle defect (data not shown). Conversely, mimosine, a DNA synthesis inhibitor that halts cell cycle progression at the $G_1$/S interface, does not reduce VEGF production (data not shown). In vivo, a Compound provided herein demonstrated in a HT1080 xenograft model that the Compound delays cycling through S-phase; this effect is distinct from that with bevacizumab, which has no effect on tumor cell cycling. Thus, these experiments indicate that the effects of the Compound on the tumor cell cycle occur in parallel with its actions on pathological VEGF production in tumors.

5.2.1.4 Inhibition of Viral Replication and the Production of viral RNA or DNA or Viral Protein Provided herein are Compounds that dose-dependently inhibit viral replication or the production of viral RNA or DNA or viral protein in a diverse panel of viruses. See Section 10.

In viral cell lines in which viral RNA or DNA or viral protein production is decreased by a Compound, further characterization indicates that inhibition of viral replication and production of viral RNA or DNA or viral protein is concentration dependent. Without being bound by any particular theory, the Compound appears to inhibit viral replication and production of viral RNA or DNA or viral protein by interfering with the biological processes of the host cell to inhibit or prevent the formation of a viral replication complex in a cell or in the endoplasmic reticulum. The interference of the Compound with the biological processes of the host cell is supported by data that includes: (1) broad spectrum activity against viruses from diverse and not closely related taxa; (2) the failure to select a resistant viral replicon despite long-term exposure at inhibitory concentrations of a Compound in cell culture; and (3) the lack of antiviral activity in a cell line which is resistant to the cell cycle delay induced by the Compound. Thus, these experiments indicate that the effects of the Compound on the host cell processes occur in parallel with the effects on viral replication and production of viral RNA or DNA or viral protein.

5.3 Formulations

The Compounds provided herein can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the Compound provided herein in the pharmaceutical composition may be at a level that will exercise the desired effect. Effective amounts contemplated are further discussed in Section 5.6 infra.

In any given case, the amount of the Compound provided herein administered will depend on such factors as the solubility of the active component, the formulation used and the route of administration.

The Compound provided herein can be formulated for any route of administration. In a specific embodiment the Compound provided herein is formulated for intradermal, intramuscular, intraperitoneal, percutaneous, intravenous, subcutaneous, intranasal, epidural, sublingual, intracerebral, intravaginal, transdermal, rectal, or mucosal administration, for inhalation, or topical administration to to the ears, nose, eyes, or skin. The mode of administration is left to the discretion of the health-care practitioner, and can depend in-part upon the site of the medical condition.

In one embodiment, the Compound provided herein is administered orally using a capsule dosage form composition, wherein the capsule contains the Compound provided herein without an additional carrier, excipient or vehicle.

In another embodiment, provided herein are compositions comprising an effective amount of a Compound provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing a Compound provided herein with a suitable carrier or diluent and filling the proper amount of the mixture in capsules.

5.4 Methods of Use

Presented herein are methods for inhibiting or reducing pathological production of human VEGF. In a specific embodiment, a method for inhibiting or reducing pathological production of human VEGF, comprises contacting a Compound or a composition thereof with a cell or cell line that pathologically produces human VEGF or are induced to pathologically produce human VEGF. The cell or cell line may be a cancer cell that pathologically produces human VEGF. Alternatively, or in addition, the cell or cell line may be induced to pathologically produce human VEGF by, e.g., exposure to stress such as hypoxia. Non-limiting examples of cell lines include HeLa, HT1080, HCT116, HEK293, NCI H460, U-87MG, ASPC-1, PL-45, HPAF-2, PC-3, MDA-MB-231, MDA-MB-468, A431, SNU-1, AGS, Kato III, A549, Calu-6, A375, SY5Y, SKOV3, Capan-1, sNF96.2, TIVE-L1, TIVE-L2, and LNCaP cells. In another embodiment, a method for inhibiting or reducing pathological production of human VEGF in a subject, comprises administering to a subject a Compound or a composition thereof. In certain embodiments, the subject has a condition associated with the pathological production of human VEGF. In specific embodiments, the subject is diagnosed with cancer or a non-neoplastic condition associated with pathological production of human VEGF.

In specific embodiments, the methods for inhibiting or reducing the pathological production of human VEGF provided herein inhibit or decrease pathological production of human VEGF by at least about 5%, 10%, 15%, 20%, 25%, 30%, 35%, 40%, 45%, 50%, 55%, 60%, 65%, 80%, 85%, 90%, 95%, or 100% relative to pathological production of human VEGF prior to administration of a Compound, as assessed by methods well known in the art. In particular embodiments, the methods for inhibiting or reducing the pathological production of human VEGF provided herein inhibit or decrease pathological production of human VEGF in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 40% to 100%, relative to pathological production of human VEGF prior to administration of a Compound or any range in between, as assessed by methods well known in the art.

Methods for inhibiting or reducing pathological angiogenesis or vascularization are also presented herein. In a specific embodiment, a method for inhibiting or reducing pathological angiogeneis or vascularization in a subject, comprises administering to a subject a Compound or a composition thereof. In certain embodiments, the subject has a condition associated with the pathological angiogenesis or vascularization. In specific embodiments, the subject is diagnosed with cancer or a non-neoplastic condition associated with pathological production of human VEGF.

In specific embodiments, the methods inhibiting or reducing pathological angiogenesis or vascularization provided herein inhibit or reduce angiogenesis or vascularization, by at least about 5%, 10%, 15%, 20%, 25%, 30%, 35%, 40%, 45%, 50%, 55%, 60%, 65%, 80%, 85%, 90%, 95%, or 100%, relative to angiogenesis or vascularization prior to administration of a Compound, as assessed by methods well known in the art, e.g., MRI scan, CT scan, PET scan. In particular embodiments, the methods for inhibiting or reducing pathological angiogenesis or vascularization provided herein inhibit or reduce angiogenesis or vascularization in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 40% to 100%, relative to angiogenesis or vascularization prior to administration of a Compound or any range in between, as assessed by methods well known in the art, e.g., MRI scan, CT scan, PET scan.

Presented herein are methods for treating a viral infection by inhibiting or reducing viral replication or the production of viral RNA or DNA or viral protein. In a specific embodiment, a method for inhibiting or reducing viral replication or the production of viral RNA or DNA or viral protein comprises contacting a Compound or a composition thereof with a cell or cell line that produces a virus or viral RNA or DNA or viral protein or may be induced to produce the virus or viral RNA or DNA or viral protein. The cell or cell line may be a virus-infected cell that constitutively produces a virus or viral RNA or DNA or viral protein. Alternatively, or in addition, the cell or cell line may be induced to produce a virus or viral RNA or DNA or viral protein by, e.g., exposure to an active virus. Non-limiting examples of viral cell lines include HeLa, Vero, Vero E6, MDCK, MT-2 and the like. In another embodiment, a method for treating a viral infection by inhibiting or reducing viral replication or the production of viral RNA or DNA or viral protein in a subject, comprises administering to a subject a Compound or a composition thereof. In certain embodiments, the subject has a viral infection or a condition associated with viral replication or the production of viral RNA or DNA or viral protein. In specific embodiments, the subject is diagnosed with a viral infection associated with viral replication or the production of viral RNA or DNA or viral protein.

In specific embodiments, the methods for treating a viral infection by inhibiting or reducing viral replication or the production of viral RNA or DNA or viral protein provided herein inhibit or decrease viral replication or the production of viral RNA or DNA or viral protein by at least about 5%, 10%, 15%, 20%, 25%, 30%, 35%, 40%, 45%, 50%, 55%, 60%, 65%, 80%, 85%, 90%, 95%, or 100% relative to viral replication or the production of viral RNA or DNA or viral protein prior to administration of a Compound, as assessed by methods well known in the art. In particular embodiments, the methods for inhibiting or reducing viral replication or the production of viral RNA or DNA or viral protein provided herein inhibit or decrease viral replication or the production of viral RNA or DNA or viral protein in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 40% to 100%, relative to viral replication or the production of viral RNA or DNA or viral protein prior to administration of a Compound or any range in between, as assessed by methods well known in the art.

Methods for treating cancer, non-neoplastic conditions and viral infections are also presented herein. In one aspect, the methods for treating cancer or a non-neoplastic condition or a viral infection involve the administration of a Compound, as a single agent therapy, to a patient in need thereof. In a specific embodiment, presented herein is a method for treating cancer or a non-neoplastic condition or a viral infection, comprising administering to a patient in need thereof an effective amount of a Compound, as a single agent. In another embodiment, presented herein is a method for treating cancer or a non-neoplastic condition or a viral infection, comprising administering to a patient in need thereof a pharmaceutical composition comprising a Compound, as the single active ingredient, and a pharmaceutically acceptable carrier, excipient or vehicle.

In another aspect, the methods for treating cancer or a non-neoplastic condition or a viral infection involve the administration of a Compound in combination with another therapy (e.g., one or more additional therapies that do not comprise a Compound, or that comprise a different Compound) to a patient in need thereof. Such methods may involve administering a Compound prior to, concurrent with, or subsequent to administration of the additional therapy. In certain embodiments, such methods have an additive or synergistic effect. In a specific embodiment, presented herein is a method for treating cancer or a non-neoplastic condition, comprising administering to a patient in need thereof an effective amount of a Compound and an effective amount of another therapy.

In specific embodiments, any cancer or non-neoplastic condition that is associated with pathological production of VEGF or a viral infection associated with viral replication or the production of viral RNA or DNA or viral protein can be treated in accordance with the methods provided herein.

In another specific embodiment, the cancer treated in accordance with the methods provided herein is a solid tumor cancer. Solid tumor cancers include, but are not limited to, sarcomas, carcinomas, and lymphomas. In specific embodiments, cancers that can be treated in accordance with the methods described include, but are not limited to, cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

Specific examples of cancers that can be treated in accordance with the methods provided herein include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers; KRAS-mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In certain embodiments cancers that can be treated in accordance with the methods provided herein include, the following: pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, and multiple myeloma.

In certain embodiments, cancers and conditions associated therewith that are treated in accordance with the methods provided herein are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer an astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor. In specific embodiments, the cancer treated in accordance with the methods provided herein is an acoustic neuroma, an anaplastic astrocytoma, a glioblastoma multiforme, or a meningioma. In other specific embodiments, the cancer treated in accordance with the methods provided herein is a brain stem glioma, a craniopharyngioma, an ependymoma, a juvenile pilocytic astrocytoma, a medulloblastoma, an optic nerve glioma, primitive neuroectodermal tumor, or a rhabdoid tumor.

Specific examples of non-neoplastic conditions that can be treated in accordance with the methods described herein include cystic fibrosis, muscular dystrophy, polycystic autosomal-dominant kidney disease, cancer-induced cachexia, benign prostatic hyperplasia, rheumatoid arthritis, psoriasis, atherosclerosis, obesity, retinopathies (including diabetic retinopathy and retinopathy of prematurity), retrolental fibroplasia, neovascular glaucoma, age-related macular degeneration, exudative macular degeneration, thyroid hyperplasias (including Grave's disease), corneal and other tissue transplantation, epidemic keratoconjunctivitis, Vitamin A deficiency, contact lens overwear, atopic keratitis, superior limbic keratitis, and pterygium keratitis sicca, viral infections, inflammation associated with viral infections, chronic inflammation, lung inflammation, nephrotic syndrome, preeclampsia, ascites, pericardial effusion (such as that associated with pericarditis), pleural effusion, Sjogren's syndrome, acne rosacea, phylectenulosis, syphilis, lipid degeneration, chemical burns, bacterial ulcers, fungal ulcers, Herpes simplex infection, Herpes zoster infections, protozoan infections, Mooren's ulcer, Terrien's marginal degeneration, marginal keratolysis, systemic lupus, polyarteritis, trauma, Wegener's sarcoidosis, Paget's disease, scleritis, Stevens-Johnson's disease, pemphigoid, radial keratotomy, Eales' disease, Behcet's disease, sickle cell anemia, pseudoxanthoma elasticum, Stargardt's disease, pars planitis, chronic retinal detachment, vein occlusion, artery occlusion, carotid obstructive disease, chronic uveitis/vitritis, ocular histoplasmosis, Mycobacteria infections, Lyme's disease, Best's disease, myopia, optic pits, hyperviscosity syndromes, toxoplasmosis, sarcoidosis, trauma, post-laser complications, diseases associated with rubeosis (neovascularization of the iris and of the angle), and diseases caused by the abnormal proliferation of fibrovascular or fibrous tissue, including all forms of prolific vitreoretinopathy.

In another embodiment, viral infections that can be treated in accordance with the methods described herein include those associated with (+) strand RNA or (−) strand RNA viruses belonging to the families Bunyaviridae, Coronaviridae, Filoviridae, Flaviviridae, Paramyxoviridae, Picornaviridae, Orthomyxoviridae or Rhabdoviridae. Other embodiments include viral infections associated with double-stranded RNA viruses belonging to the family Reoviridae or viruses belonging to the families Retroviridae or Hepadnaviridae. Another embodiment includes viral infections by DNA viruses belonging to the families Adenoviridae, Herpesviridae, Papillomaviridae or Papovaviridae.

Certain examples of viral infections that can be treated in accordance with the methods described herein include viral infections, including but not limited to, those associated with viruses belonging to Flaviviridae (such as West Nile virus (WNV), hepatitis C virus (HCV), yellow fever virus (YFV) and dengue virus (DENV)), Paramyxoviridae (such as parainfluenza virus and respiratory syncytial virus (RSV)), Picornaviridae (such as poliovirus (PV), hepatitis A virus (HAV), coxsackievirus and rhinovirus), Coronaviridae (such as severe acute respiratory syndrome coronavirus (SARS-CoV)), Orthomyxoviridae (such as influenza virus), or Filoviridae (such as Ebola and Marburg viruses). In one embodiment, the term refers to viral infections by members of the family Retroviridae (such as human immunodeficiency virus (HIV) and human T cell leukemia viruses (HTLV)), Hepadnaviridae (such as hepatitis B virus (HBV)). In another embodiment, the term refers to viral infections by DNA viruses (such as herpes simplex virus (HSV), Kaposi's sarcoma-associated herpesvirus, adenovirus, vaccinia virus or human papilloma virus (HPV)).

In one embodiment, the viral infection is by West Nile virus, hepatitis C virus, yellow fever virus, dengue virus, respiratory syncytial virus, poliovirus, severe acute respiratory syndrome coronavirus, influenza virus, parainfluenza virus, human immunodeficiency virus, human T cell leukemia viruses, herpes simplex virus or vaccinia virus. In another embodiment, the viral infection is by West Nile virus, hepatitis C virus, dengue virus, respiratory syncytial virus, poliovirus, influenza virus, parainfluenza virus or human immunodeficiency virus. In another embodiment, the viral infection is by a known or unknown genotype of the hepatitis C virus. In another embodiment, the genotype of the hepatitis C virus is the hepatitis C virus genotype 1a, the hepatitis C virus genotype 1b or the hepatitis C virus genotype 2a.

In certain embodiments examples of non-neoplastic conditions associated with pathological production of VEGF that can be treated with the methods described herein include diabetic retiopathy, exudative macular degeneration, rheumatoid arthritis, psoriasis, artheriosclerosis, chronic inflammation, obesity, and polycystic autosomal-dominant kidney disease.

The concentration of VEGF or other angiogenic or inflammatory mediators (e.g., P1GF, VEGF-C, VEGF-D, VEGFR-1, VEGFR-2, IL-6 and/or IL-8) in a biological specimen (e.g., plasma, serum, cerebral spinal fluid, urine, or any other biofluids) may be used to monitor the efficacy of a course of treatment for cancer or a non-neoplastic condition involving the administration of a compound that inhibits or reduces the pathological production of human VEGF, such as a Compound described herein or a compound described in U.S. Publication No. 2005-0272759 (having corresponding International Application Publication No. WO2005/089764), U.S. Publication No. 2005-0282849 (having corresponding International Application Publication No. WO2006/113703), U.S. Publication No. 2007-0254878 (having corresponding International Application Publication No. WO2008/127715), International Application Publication No. WO2008/127714, U.S. Provisional Application Ser. No. 60/181,649, filed May 27, 2009, entitled "Methods for Treating Prostate Cancer;" U.S. Provisional Application Ser. No. 60/181,651, filed May 27, 2009, entitled "Methods for Treating Kaposi's Sarcoma;" U.S. Provisional Application Ser. No. 60/181,650, filed May 27, 2009, entitled "Methods for Treating Neurofibromatosis;" U.S. Provisional Application Ser. No. 60/181,654, filed May 27, 2009, entitled "Methods for Treating Brain Cancer;" or U.S. Provisional Application Ser. No. 60/253,086, filed Oct. 20, 2009, entitled "Methods for Treating Breast Cancer," each of which is incorporated herein by reference in its entirety. The dosage, frequency and/or length of administration of a Compound or a pharmaceutical composition thereof to a patient may also be modified as a result of the concentration of VEGF or other angiogenic or inflammatory mediators. Alternatively, the changes in these monitoring the concentration of VEGF or other angiogenic or inflammatory mediators might indicate that the course of treatment involving the administration of the Compound or pharmaceutical composition thereof is effective in treating the cancer or a non-neoplastic condition.

In certain embodiments, the concentration of VEGF or other angiogenic or inflammatory mediators in biological specimens (e.g., plasma, serum, cerebral spinal fluid, urine, or any other biofluids) of a patient is monitored before, during and/or after a course of treatment for cancer involving the administration of a Compound or a pharmaceutical composition thereof to the patient. In certain embodiments, the tumoral blood flow or metabolism, or peritumoral inflammation or edema in a patient is monitored before, during and/or after a course of treatment for cancer involving the administration of a Compound or a pharmaceutical composition. The dosage, frequency and/or length of administration of a Compound or a pharmaceutical composition thereof to a patient might be modified as a result of the concentration of VEGF or other angiogenic or inflammatory mediators, or of tumoral blood flow or metabolism, or peritumoral inflammation or edema as assessed by imaging techniques. Alternatively, the changes in these monitoring parameters (e.g., concentration of VEGF or other angiogenic or inflammatory mediators, or of tumoral blood flow or metabolism, or peritumoral inflammation or edema) might indicate that the course of treatment involving the administration of the Compound or pharmaceutical composition thereof is effective in treating the cancer.

In a specific embodiment, presented herein is a method for treating cancer, comprising: (a) administering to a patient in need thereof one or more doses of a Compound or a pharmaceutical composition thereof; and (b) monitoring the concentration of VEGF or other angiogenic, or inflammatory mediators (e.g., detected in biological specimens such as plasma, serum, cerebral spinal fluid, urine, or any other biofluids), or monitoring tumoral blood flow or metabolism, or peritumoral inflammation or edema, before and/or after step (a). In specific embodiments, step (b) comprises monitoring the concentration of one or more inflammatory mediators including, but not limited to, cytokines and interleukins such as IL-6 and IL-8. In particular embodiments, step (b) comprises monitoring the concentration of VEGF-A, VEGF-R, P1GF, VEGF-C, and/or VEGF-D. In certain embodiments, the monitoring step (b) is carried out before and/or after a certain number of doses (e.g., 1, 2, 4, 6, 8, 10, 12, 14, 15, or 29 doses, or more doses; 2 to 4, 2 to 8, 2 to 20 or 2 to 30 doses) or a certain time period (e.g., 1, 2, 3, 4, 5, 6, or 7 days; or 1, 2, 3, 4, 5, 10, 15, 20, 30, 40, 45, 48, or 50 weeks) of administering the Compound. In certain embodiments, one or more of these monitoring parameters are detected prior to administration of the Compound or pharmaceutical composition thereof. In specific embodiments, a decrease in the concentration of VEGF or other angiogenic or inflammatory mediators or a change in tumoral blood flow or metabolism, or peritumor edema following administration of the Compound or pharmaceutical composition thereof indicates that the course of treatment is effective for treating the cancer. In some embodiments, a change in the concentration of VEGF or other angiogenic or inflammatory mediators or a change in tumoral blood flow or metabolism, or peritumoral inflammation or edema following administration of the Compound or pharmaceutical composition thereof may indicate that the dosage, frequency and/or length of administration of the Compound or a pharmaceutical composition thereof may be adjusted (e.g., increased, reduced or maintained). In specific embodiments, the cancer is a solid tumor.

In certain embodiments, the concentration of VEGF or other angiogenic or inflammatory mediators in biological specimens (e.g., plasma, serum, cerebral spinal fluid, urine, or any other biofluids) of a patient is monitored before, during and/or after a course of treatment for a non-neoplastic condition involving the administration of a Compound or a pharmaceutical composition thereof to the patient. The dosage, frequency and/or length of administration of a Compound or a pharmaceutical composition thereof to a patient might be modified as a result of the concentration of VEGF or other angiogenic or inflammatory mediators. Alternatively, the changes in these monitoring parameters (e.g., concentration of VEGF or other angiogenic or inflammatory mediators) might indicate that the course of treatment involving the administration of the Compound or pharmaceutical composition thereof is effective in treating the non-neoplastic condition.

In a specific embodiment, presented herein is a method for treating a non-neoplastic condition, comprising: (a) administering to a patient in need thereof one or more doses of a Compound or a pharmaceutical composition thereof; and (b) monitoring the concentration of VEGF or other angiogenic, or inflammatory mediators (e.g., detected in biological specimens such as plasma, serum, cerebral spinal fluid, urine, or any other biofluids) before and/or after step (a). In specific embodiments, step (b) comprises monitoring the concentration of one or more inflammatory mediators including, but not limited to, cytokines and interleukins such as IL-6 and IL-8. In particular embodiments, step (b) comprises monitoring the concentration of VEGF-A, VEGF-R, P1GF, VEGF-C, and/or VEGF-D. In certain embodiments, the monitoring step (b) is carried out before and/or after a certain number of doses (e.g., 1, 2, 4, 6, 8, 10, 12, 14, 15, or 20 doses, or more doses; 2 to 4, 2 to 8, 2 to 20 or 2 to 30 doses) or a certain time period (e.g., 1, 2, 3, 4, 5, 6, or 7 days; or 1, 2, 3, 4, 5, 10, 15, 20, 30, 40, 45, 48, or 50 weeks) of administering the Compound. In certain embodiments, one or more of these monitoring parameters are detected prior to administration of the Compound or pharmaceutical composition thereof. In specific embodiments, a decrease in the concentration of VEGF or other angiogenic or inflammatory mediators following administration of the Compound or pharmaceutical composition thereof indicates that the course of treatment is effective for treating the non-neoplastic condition. In some embodiments, a change in the concentration of VEGF or other angiogenic or inflammatory mediators following administration of the Compound or pharmaceutical composition thereof may indicate that the dosage, frequency and/or length of administration of the Compound or a pharmaceutical composition thereof may be adjusted (e.g., increased, reduced or maintained).

The concentration of VEGF or other angiogenic or inflammatory mediators or a change in tumor blood flow or metabolism, or peritumoral inflammation or edema of a patient may be detected by any technique known to one of skill in the art. In certain embodiments, the method for detecting the concentration of VEGF or other angiogenic or inflammatory mediators of a patient involves obtaining a biological sample (e.g., tissue or fluid sample) from the patient and detecting the concentration of VEGF or other angiogenic or inflammatory mediators in the biological sample (e.g., from plasma, serum, cerebral spinal fluid, urine, or any other biofluids), that has been subjected to certain types of treatment (e.g., centrifugation), and detection by use of immunological techniques, such as ELISA. In a specific embodiment, an ELISA described herein, e.g., in the working examples in Section 8.1.1. et seq. may be used to detect the concentration of VEGF or other angiogenic or inflammatory mediators, in a biological sample (e.g., from plasma, serum, cerebral spinal fluid, urine, or any other biofluids) that has been subjected to certain types of treatment (e.g., centrifugation). Other techniques known in the art that may be used to detect the concentration of VEGF or other angiogenic or inflammatory mediators, in a biological sample, include multiplex or proteomic assays. In a specific embodiment, a CT scan, an MRI scan, or a PET scan may be used to detect the tumor blood flow or metabolism, or peritumoral inflammation or edema.

In specific embodiments, the methods for treating cancer or a non-neoplastic condition provided herein alleviate or manage one, two or more symptoms associated with the cancer or the non-neoplastic condition. Alleviating or managing one, two or more symptoms of cancer or a non-neoplastic condition may be used as a clinical endpoint for efficacy of a Compound for treating the cancer or non-neoplastic condition. In some embodiments, the methods for treating cancer or a non-neoplastic condition provided herein reduce the duration and/or severity of one or more symptoms associated with the cancer or the non-neoplastic condition. In some embodiments, the methods for treating cancer or a non-neoplastic condition provided herein inhibit the onset, progression and/or recurrence of one or more symptoms associated with the cancer or the non-neoplastic condition. In some embodiments, the methods for treating cancer or a non-neoplastic condition provided herein reduce the number of symptoms associated with the cancer or the non-neoplastic condition. In a specific embodiment, the cancer is a solid tumor cancer.

The methods for treating cancer or a non-neoplastic condition provided herein inhibit or reduce pathological production of human VEGF. In specific embodiments, the methods for treating cancer or a non-neoplastic condition provided herein selectively inhibit pathologic production of human VEGF (e.g., by the tumor), but do not disturb the physiological activity of human VEGF protein. Preferably, the methods for treating cancer or a non-neoplastic condition provided herein do not significantly inhibit or reduce physiological or homeostatic production of human VEGF. For example, blood pressure, protein levels in urine, and bleeding are maintained within normal ranges in treated subjects. In a specific embodiment, the treatment does not result in adverse events as defined in Cancer Therapy Evaluation Program, Common Terminology Criteria for Adverse Events, Version 3.0, DCTD, NCI, NIH, DHHS Mar. 31, 2003 (http://cstep.cancer.gov), publish date Aug. 9, 2006, which is incorporated by reference herein in its entirety. In other embodiments, the methods for treating brain tumors provided herein do not result in adverse events of grade 2 or greater as defined in the Cancer Therapy Evaluation Program, Common Terminology Criteria for Adverse Events, Version 3.0, supra.

In specific embodiments, the methods for treating cancer or a non-neoplastic condition provided herein inhibit or decrease pathological production of VEGF by at least about 5%, 10%, 15%, 20%, 25%, 30%, 35%, 40%, 45%, 50%, 55%, 60%, 65%, 80%, 85%, 90%, 95%, or 100% relative to the pathological production of VEGF observed prior to the administration of a Compound as assessed by methods well known in the art. In particular embodiments, the methods for treating cancer or a non-neoplastic condition provided herein inhibit or decrease pathological production of VEGF in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the pathological production of VEGF observed prior to administration of a compound, as assessed by methods well known in the art.

In specific aspects, the methods for treating cancer or a non-neoplastic condition provided herein decrease the concentration of VEGF or other angiogenic or inflammatory mediators (e.g., cytokines or interleukins, such as IL-6) of a subject as assessed by methods well known in the art, e.g., ELISA. In particular embodiments, the methods for treating cancer or a non-neoplastic condition provided herein decrease the concentration of VEGF or other angiogenic or inflammatory mediators (e.g., cytokines or interleukins, such as IL-6) in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the respective concentration prior to administration of a Compound, as assessed by methods well known in the art, e.g., ELISA.

In specific aspects, the methods for treating cancer or a non-neoplastic condition provided herein decrease the concentrations of P1GF, VEGF-C, VEGF-D, VEGFR-1, VEGFR-2, IL-6 and/or IL-8 in the blood of a subject as assessed by methods well known in the art, e.g., ELISA. In specific embodiments, the methods for treating cancer or a non-neoplastic condition provided herein decrease the concentrations of P1GF, VEGF-C, VEGF-D, VEGFR-1, VEGFR-2, IL-6 and/or IL-8 in the blood of a subject by at least about 5%, 10%, 15%, 20%, 25%, 30%, 35%, 40%, 45%, 50%, 55%, 60%, 65%, 80%, 85%, 90%, 95%, or 100%, relative to the respective concentration observed prior to administration of a Compound as assessed by methods well known in the art, e.g., ELISA. In particular embodiments, the methods for treating cancer or a non-neoplastic condition provided herein decrease the concentrations of P1GF, VEGF-C, VEGF-D, VEGFR-1, VEGFR-2, IL-6 and/or IL-8 in the blood of a subject in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the respective concentration observed prior to administration of a Compound, as assessed by methods well known in the art, e.g., ELISA.

In certain embodiments, the methods for treating cancer or a non-neoplastic condition provided herein inhibit or reduce pathological angiogenesis or vascularization. In specific embodiments, the methods for treating cancer or a non-neoplastic condition provided herein inhibit or reduce pathological angiogenesis or vascularization, by at least about 5%, 10%, 15%, 20%, 25%, 30%, 35%, 40%, 45%, 50%, 55%, 60%, 65%, 80%, 85%, 90%, 95%, or 100%, relative to angiogenesis or vascularization observed prior to administration of a Compound as assessed by methods well known in the art, e.g., MRI scan, CT scan, PET scan. In particular embodiments, the methods for treating cancer or a non-neoplastic condition provided herein inhibit or reduce pathological angiogenesis or vascularization, in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to angiogenesis or vascularization observed prior to administration of a Compound as assessed by methods well known in the art, e.g., MRI scan, CT scan, PET scan.

In specific embodiments, the methods for treating cancer or a neoplastic condition provided herein inhibit or reduce inflammation, by at least about 5%, 10%, 15%, 20%, 25%, 30%, 35%, 40%, 45%, 50%, 55%, 60%, 65%, 80%, 85%, 90%, 95%, or 100%, relative to inflammation observed prior to administration of a Compound, or any percentage in between, as assessed by methods well known in the art, e.g., CT scan, MRI scan, or PET scan. In particular embodiments, the methods for treating cancer or a neoplastic condition provided herein inhibit or reduce inflammation, in the range of about 5% to 15%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to inflammation observed prior to administration of a Compound, or any percentage in between, as assessed by methods well known in the art, e.g., CT scan, MRI scan, or PET scan.

In specific embodiments, the methods for treating cancer or a non-neoplastic condition provided herein inhibit or reduce edema such as tumor-related edema, by at least about 5%, 10%, 15%, 20%, 25%, 30%, 35%, 40%, 45%, 50%, 55%, 60%, 65%, 80%, 85%, 90%, 95%, or 100%, relative to the edema observed prior to administration of a Compound, or any percentage in between, as assessed by methods well known in the art, e.g., CT scan, MRI scan, or PET scan. In particular embodiments, the methods for treating NF provided herein inhibit or reduce edema such as tumor-related, in the range of about 5% to 15%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the edema observed prior to administration of a Compound, or any percentage in between, as assessed by methods well known in the art, e.g., CT scan, MRI scan, or PET scan.

In certain embodiments, the methods for treating cancer or a non-neoplastic condition provided herein prolong or delay the G1/S or late G1/S phase of the cell cycle (i.e., the period between the late resting or pre-DNA synthesis phase, and the early DNA synthesis phase).

In some embodiments, the methods for treating cancer or a non-neoplastic condition provided herein reduce, ameliorate, or alleviate the severity of the cancer or the non-neoplastic condition and/or one or more symptoms thereof. In other embodiments, the methods for treating cancer or a non-neoplastic condition provided herein reduce hospitalization (e.g., the frequency or duration of hospitalization) of a subject diagnosed with the cancer or the non-neoplastic condition. In some embodiments, the methods for treating cancer or a non-neoplastic condition provided herein reduce hospitalization length of a subject diagnosed with the cancer or the non-neoplastic condition. In certain embodiments, the methods provided herein increase the survival of a subject diagnosed with cancer or a non-neoplastic condition. In specific embodiments, the methods provided herein increase the survival of a subject diagnosed with cancer or a non-neoplastic condition by about 6 months or more, about 7 months or more, about 8 months or more, about 9 months or more, or about 12 months or more. In particular embodiments, the methods for treating cancer or a non-neoplastic condition provided herein inhibit or reduce the progression of the cancer or the non-neoplastic condition, or one or more symptoms associated therewith. In specific embodiments, the methods for treating cancer or a non-neoplastic condition provided herein enhance or improve the therapeutic effect of another therapy (e.g., an anti-cancer agent, radiation, drug therapy, such as chemotherapy, anti-androgen therapy, or surgery). In certain embodiments, the methods for treating cancer or a non-neoplastic condition provided herein involve the use of a Compound as an adjuvant therapy. In certain embodiments, the methods for treating cancer provided herein improve the ease in removal of tumors (e.g., enhance resectability of the tumors) by reducing vascularization prior to surgery. In particular embodiments, the methods for treating cancer provided herein reduce vascularization after surgery, for example, reduce vascularization of the remaining tumor mass not removed by surgery. In some embodiments, the methods for treating cancer provided herein prevent recurrence of a tumor or one or more symptoms associated with cancer, e.g., recurrence of vascularization and/or tumor growth. In certain embodiments, the methods for treating a non-neoplastic condition provided herein prevent the recurrence of the non-neoplastic condition or one or more symptoms thereof.

In particular embodiments, the methods for treating cancer or a non-neoplastic condition provided herein reduce the mortality of subjects diagnosed with the cancer or the non-neoplastic condition. In certain embodiments, the methods for treating cancer or a non-neoplastic condition provided herein increase the number of patients in remission or decrease the hospitalization rate. In other embodiments, the methods for treating cancer or a non-neoplastic condition provided herein prevent the development, onset or progression of one or more symptoms associated with the cancer or a non-neoplastic condition. In particular embodiments, the methods for treating cancer or a non-neoplastic condition provided herein increase symptom-free survival of cancer patients or the non-neoplastic condition patients. In some embodiments, the methods for treating cancer or a non-neoplastic condition provided herein do not cure the cancer or non-neoplastic condition in patients, but prevent the progression or worsening of the disease. In some embodiments, the methods for treating cancer or a non-neoplastic condition provided herein improve the patient's quality of life.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of a Compound as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of a Compound as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of a Compound as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of a Compound, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of a Compound, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of a Compound, as assessed by methods well known in the art, e.g., PET scan.

In specific embodiments, the methods for treating cancer provided herein decrease the number of circulating tumor cells (CTCs) in the blood of the subject as assessed by methods known in the art, such as CellSearch immunomagnetic-capture (see, e.g., Danila D C, Heller G, Gignac G A, Gonzalez-Espinoza R, Anand A, Tanaka E, Lilja H, Schwartz L, Larson S, Fleisher M, Scher H I. Circulating tumor cell number and prognosis in progressive castration-resistant prostate cancer. Clin Cancer Res. 2007 Dec. 1; 13(23):7053-8; Shaffer D R, Leversha M A, Danila D C, Lin O, Gonzalez-Espinoza R, Gu B, Anand A, Smith K, Maslak P, Doyle G V, Terstappen L W, Lilja H, Heller G, Fleisher M, Scher H I. Circulating tumor cell analysis in patients with progressive castration-resistant prostate cancer. Clin Cancer Res. 2007 Apr. 1; 13(7): 2023-9). In specific embodiments, the methods for treating cancer provided herein decrease the number of CTCs in the blood of a subject by at least about 5%, 10%, 15%, 20%, 25%, 30%, 35%, 40%, 45%, 50%, 55%, 60%, 65%, 80%, 85%, 90%, 95%, 99%, or 100%, relative to the number of CTCs observed prior to administration of a Compound, as assessed by methods well known in the art. In particular embodiments, the methods for treating cancer provided herein decrease the number of CTCs in the blood of a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the number of CTCs in the blood observed prior to the administration of a Compound, as assessed by methods well known in the art, such as CellSearch immunomagnetic-capture.

In specific embodiments, the methods for treating cancer or a non-neoplastic condition provided herein inhibit or reduce inflammation, by at least about 5%, 10%, 15%, 20%, 25%, 30%, 35%, 40%, 45%, 50%, 55%, 60%, 65%, 80%, 85%, 90%, 95%, 99%, or 100%, or any percentage in between, relative to inflammation observed prior to administration of a Compound as assessed by methods well known in the art. In particular embodiments, the methods for treating cancer or a non-neoplastic condition provided herein inhibit or reduce inflammation, in the range of about 5% to 15%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to inflammation observed prior to administration of a Compound, as assessed by methods well known in the art.

In certain embodiments, the methods for treating cancer provided herein increase the cancer-free survival rate of patients diagnosed with the cancer. In some embodiments, the methods for treating cancer provided herein increase relapse-free survival. In certain embodiments, the methods for treating cancer provided herein increase the number of patients in remission. In other embodiments, the methods for treating cancer provided herein increase the length of remission in patients.

In specific embodiments, the methods for treating cancer or a non-neoplastic condition provided herein minimize the severity and/or frequency of one or more side effects observed with current anti-angiogenesis therapies. In certain embodiments, the methods for treating cancer or a non-neoplastic condition provided herein do not cause one or more side effects observed with current anti-angiogenesis therapies. Such side effects include, but are not limited to, bleeding, arterial and venous thrombosis, hypertension, delayed wound healing, proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, and heart failure.

In certain embodiments, treatment of cancer with a Compound described herein or a compound described in U.S. Publication Nos. 2005-0272759 (having corresponding International Application Publication No. WO2005/089764), U.S. Publication No. 2005-0282849 (having corresponding International Application Publication No. WO2006/113703), or U.S. Publication No. 2007-0254878 (having corresponding International Application Publication No. WO2008/127715); or U.S. Provisional Application Ser. No. 60/181,649, filed May 27, 2009 entitled "Methods for Treating Prostate Cancer;" or U.S. Provisional Application Ser. No. 60/181,651, filed May 27, 2009, entitled "Methods for Treating Kaposi's Sarcoma;" or U.S. Provisional Application Ser. No. 60/181,650, filed May 27, 2009, entitled "Methods for Treating Neurofibromatosis;" U.S. Provisional Application Ser. No. 60/181,654, filed May 27, 2009, entitled "Methods for Treating Brain Cancer;" or U.S. Provisional Application Ser. No. 60/253,086, filed Oct. 20, 2009, entitled "Methods for Treating Breast Cancer" (each of which is incorporated herein by reference in its entirety) inhibits or reduces tumor-induced cachexia. In specific embodiments, when the treatment of cancer comprises the administration of a Compound described herein or a compound described in U.S. Publication Nos. 2005-0272759 (having corresponding International Application Publication No. WO2005/089764), U.S. Publication No. 2005-0282849 (having corresponding International Application Publication No. WO2006/113703), or U.S. Publication No. 2007-0254878 (having corresponding International Application Publication No. WO2008/127715), or U.S. Provisional Application Ser. No. 60/181,649, filed May 27, 2009 entitled "Methods for Treating Prostate Cancer;" or U.S. Provisional Application Ser. No. 60/181,651, filed May 27, 2009, entitled "Methods for Treating Kaposi's Sarcoma;" or U.S. Provisional Application Ser. No. 60/181,650, filed May 27, 2009, entitled "Methods for Treating Neurofibromatosis;" U.S. Provisional Application Ser. No. 60/181,654, filed May 27, 2009, entitled "Methods for Treating Brain Cancer;" or U.S. Provisional Application Ser. No. 60/253, 086, filed Oct. 20, 2009, entitled "Methods for Treating Breast Cancer," (each of which is incorporated herein by reference in its entirety) in combination with one or more additional therapies, cachexia induced by the one or more additional therapies is reduced due to administration of a Compound.

The concentration of viral RNA or DNA or viral protein in a biological specimen (e.g., plasma, serum, urine, or any other biofluids or tissues) may be used to monitor the efficacy of a course of treatment for viral infection involving the administration of a compound that inhibits or reduces viral replication or the production of viral RNA or DNA or viral protein, such as a Compound described herein or a compound described in U.S. Publication No. 2005-0272759 (having corresponding International Application Publication No. WO2005/089764), U.S. Publication No. 2005-0282849 (having corresponding International Application Publication No. WO2006/113703), U.S. Publication No. 2007-0254878 (having corresponding International Application Publication No. WO2008/127715) or International Application Publication No. WO2008/127714, each of which is incorporated herein by reference in its entirety. The dosage, frequency and/or length of administration of a Compound or a pharmaceutical composition thereof to a patient may also be modified as a result of the concentration of viral RNA or DNA or viral protein. Alternatively, the changes in the concentration of viral RNA or DNA or viral protein might indicate that the course of treatment involving the administration of the Compound or pharmaceutical composition thereof is effective in treating the viral infection.

In certain embodiments, the concentration of viral RNA or DNA or viral protein in biological specimens (e.g., plasma, serum, urine, or any other biofluids or tissues) of a patient is monitored before, during and/or after a course of treatment for viral infection involving the administration of a Compound or a pharmaceutical composition thereof to the patient. In certain embodiments, the viral titer in a patient is monitored before, during and/or after a course of treatment for viral infection involving the administration of a Compound or a pharmaceutical composition thereof. The dosage, frequency and/or length of administration of a Compound or a pharmaceutical composition thereof to a patient might be modified as a result of the concentration of viral RNA or DNA or viral protein as assessed by standard techniques. Alternatively, the changes in the concentration of viral RNA or DNA or viral protein might indicate that the course of treatment involving the administration of the Compound or pharmaceutical composition thereof is effective in treating the viral infection.

In a specific embodiment, presented herein is a method for treating a viral infection, comprising: (a) administering to a patient in need thereof one or more doses of a Compound or a pharmaceutical composition thereof and (b) monitoring the concentration of viral RNA or DNA or viral protein (e.g., detected in biological specimens such as plasma, serum, urine, or any other biofluids or tissues) before and/or after step (a). In specific embodiments, step (b) comprises monitoring the patient's viral titer. In certain embodiments, the monitoring step (b) is carried out before and/or after a certain number of doses (e.g., 1, 2, 4, 6, 8, 10, 12, 14, 15, 30 or more doses, or more doses; 2 to 4, 2 to 8, 2 to 20 or 2 to 30 or more doses) or a certain time period (e.g., 1, 2, 3, 4, 5, 6, or 7 days; or 1, 2, 3, 4, 5, 10, 15, 20, 30, 40, 45, 48, or 50 weeks) of administering the Compound. In certain embodiments, one or more of these monitoring parameters are detected prior to administration of the Compound or pharmaceutical composition thereof. In specific embodiments, a decrease in the concentration of viral RNA or DNA or viral protein following administration of the Compound or pharmaceutical composition thereof indicates that the course of treatment is effective for treating the viral infection. In some embodiments, a change in the concentration of viral RNA or DNA or viral protein following administration of the Compound or pharmaceutical composition thereof may indicate that the dosage, frequency and/or length of administration of the Compound or a pharmaceutical composition thereof may be adjusted (e.g., increased, reduced or maintained).

The concentration of viral RNA or DNA or viral protein in a patient may be detected by any technique known to one of skill in the art. In certain embodiments, the method for detecting the concentration of viral RNA or DNA or viral protein in a patient involves obtaining a biological sample (e.g., tissue or fluid sample) from the patient and detecting the concentration of viral RNA or DNA or viral protein in the biological sample (e.g., from plasma, serum, urine, or any other biofluids or tissues), that has been subjected to certain types of treatment (e.g., centrifugation), and detection by use of standard molecular techniques known to a person of ordinary skill in the art, such as by polymerase chain reaction (PCR) or ELISA. In a specific embodiment, an ELISA described herein, e.g., in the working examples in Section 8.1.1. et seq. may be used to detect the concentration of viral protein. In another specific embodiment, PCR may be used to detect the concentration of viral RNA or DNA in a biological sample (e.g., from plasma, serum, urine, or any other biofluids or tissues) that has been subjected to certain types of treatment (e.g., centrifugation). Other techniques known in the art that may be used to detect the concentration of viral RNA or DNA in a biological sample, including nucleic acid hybridization or a combination of PCR and nucleic acid hybridization assays.

In specific embodiments, the methods for treating a viral infection provided herein alleviate or manage one, two or more symptoms associated with the viral infection. Alleviating or managing one, two or more symptoms of viral infection may be used as a clinical endpoint for efficacy of a Compound for treating the viral infection. In some embodiments, the methods for treating a viral infection provided herein reduce the duration and/or severity of one or more symptoms associated with the viral infection. In some embodiments, the methods for treating viral infection provided herein inhibit the onset, progression and/or recurrence of one or more symptoms associated with the viral infection. In some embodiments, the methods for treating the viral infection provided herein reduce the number of symptoms associated with the viral infection.

The methods for treating a viral infection provided herein inhibit or reduce viral replication or the production of viral RNA or DNA or viral protein. In specific embodiments, the methods for treating the viral infection provided herein selectively inhibit the production of viral RNA or DNA or viral protein. In a specific embodiment, the treatment does not result in an adverse event as defined in according to government safety standards or regulations.

In specific embodiments, the methods for treating a viral infection provided herein inhibit or decrease viral replication or the production of viral RNA or DNA or viral protein by at least about 5%, 10%, 15%, 20%, 25%, 30%, 35%, 40%, 45%, 50%, 55%, 60%, 65%, 80%, 85%, 90%, 95%, or 100% relative to viral replication or the production of viral RNA or DNA or viral protein observed prior to the administration of a Compound as assessed by methods well known in the art, e.g., PCR or ELISA. In particular embodiments, the methods for treating the viral infection provided herein inhibit or decrease viral replication or the production of viral RNA or DNA or viral protein in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to viral replication or the production of viral RNA or DNA or viral protein observed prior to administration of a compound, as assessed by methods well known in the art, e.g., PCR or ELISA.

In some embodiments, the methods for treating a viral infection provided herein reduce, ameliorate, or alleviate the severity of the viral infection and/or one or more symptoms thereof. In other embodiments, the methods for treating viral infection provided herein reduce hospitalization (e.g., the frequency or duration of hospitalization) of a subject diagnosed with the viral infection. In some embodiments, the methods for treating a viral infection provided herein reduce hospitalization length of a subject diagnosed with the viral infection. In certain embodiments, the methods provided herein increase the survival of a subject diagnosed with the viral infection. In specific embodiments, the methods provided herein increase the survival of a subject diagnosed with a viral infection by about 6 months or more, about 7 months or more, about 8 months or more, about 9 months or more, or about 12 months or more. In particular embodiments, the methods for treating a viral infection provided herein inhibit or reduce the progression of the viral infection, or one or more symptoms associated therewith. In specific embodiments, the methods for treating viral infection provided herein enhance or improve the therapeutic effect of another therapy (e.g., an antiviral agent, drug therapy, such as interferon, or transplant surgery). In certain embodiments, the methods for treating viral infection provided herein involve the use of a Compound as an adjuvant therapy. In some embodiments, the methods for treating viral infection provided herein prevent recurrence of the viral infection or one or more symptoms associated with the viral infection.

In particular embodiments, the methods for treating viral infection provided herein reduce the mortality of subjects diagnosed with the viral infection. In certain embodiments, the methods for treating a viral infection provided herein increase the number of patients in remission or decrease the hospitalization rate. In other embodiments, the methods for treating viral infection provided herein prevent the development, onset or progression of one or more symptoms associated with the viral infection. In particular embodiments, the methods for treating the viral infection provided herein increase symptom-free survival of the infected patients. In some embodiments, the methods for treating the viral infection provided herein do not cure the viral infection in patients, but prevent the progression or worsening of the disease. In some embodiments, the methods for treating viral infection provided herein improve the patient's quality of life.

In particular embodiments, the methods for treating viral infection provided herein inhibit, reduce, diminish, arrest, or stabilize the production of viral RNA or DNA or viral protein associated with the virus. In certain embodiments, the methods for treating viral infection provided herein reduce viral RNA or DNA or viral protein production in a subject by at least about 5%, 10%, 15%, 20%, 25%, 30%, 35%, 40%, 45%, 50%, 55%, 60%, 65%, 80%, 85%, 90%, 95%, 99%, or 100%, relative to viral RNA or DNA or viral protein production prior to administration of a Compound as assessed by methods well known in the art, e.g., PCR or ELISA. In particular embodiments, the methods for treating viral infection provided herein reduce the viral titer in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the viral titer in a subject prior to administration of a Compound as assessed by methods well known in the art, e.g., PCR or ELISA.

In specific embodiments, the methods for treating viral infection provided herein decrease the number of circulating viral proteins (CVPs) in the blood of the subject as assessed by methods known in the art. In specific embodiments, the methods for treating viral infection provided herein decrease the number of CVPs in the blood of a subject by at least about 5%, 10%, 15%, 20%, 25%, 30%, 35%, 40%, 45%, 50%, 55%, 60%, 65%, 80%, 85%, 90%, 95%, 99%, or 100%, relative to the number of CVPs observed prior to administration of a Compound, as assessed by methods well known in the art.

In certain embodiments, the methods for treating viral infection provided herein increase the viral-free survival rate of patients diagnosed with the viral infection. In some embodiments, the methods for treating viral infection provided herein increase relapse-free survival. In certain embodiments, the methods for treating viral infection provided herein increase the number of patients in remission. In other embodiments, the methods for treating viral infection provided herein increase the length of remission in patients.

In specific embodiments, the methods for treating viral infection provided herein minimize the severity and/or frequency of one or more side effects observed with current antiviral therapies. In certain embodiments, the methods for treating viral infection provided herein do not cause one or more side effects observed with current antiviral therapies.

5.5 Patient Population

In some embodiments, a subject treated for cancer or a non-neoplastic condition or a viral infection in accordance with the methods provided herein is a human who has or is diagnosed with cancer or a non-neoplastic condition or a viral infection. In other embodiments, a subject treated for cancer or a non-neoplastic condition or a viral infection in accordance with the methods provided herein is a human predisposed or susceptible to cancer or a non-neoplastic condition or a viral infection. In some embodiments, a subject treated for cancer or a non-neoplastic condition or a viral infection in accordance with the methods provided herein is a human at risk of developing cancer or a non-neoplastic condition or a viral infection.

In one embodiment, a subject treated for cancer or a non-neoplastic condition or a viral infection in accordance with the methods provided herein is a human infant. In another embodiment, a subject treated for cancer or a non-neoplastic condition or a viral infection in accordance with the methods provided herein is a human toddler. In another embodiment, a subject treated for cancer or a non-neoplastic condition or a viral infection in accordance with the methods provided herein is a human child. In another embodiment, a subject treated for cancer or a non-neoplastic condition or a viral infection in accordance with the methods provided herein is a human adult. In another embodiment, a subject treated for cancer or a non-neoplastic condition or a viral infection in accordance with the methods provided herein is a middle-aged human. In another embodiment, a subject treated for cancer or a non-neoplastic condition or a viral infection in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer or a non-neoplastic condition or a viral infection in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer or a non-neoplastic condition or a viral infection in accordance with the methods provided herein is a human that is 18 years old or older. In a particular embodiment, a subject treated for cancer or a non-neoplastic condition or a viral infection in accordance with the methods provided herein is a human child that is between the age of 1 year old to 18 years old. In a certain embodiment, a subject treated for cancer or a non-neoplastic condition or a viral infection in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In particular embodiments, a subject treated for cancer or a non-neoplastic condition or a viral infection in accordance with the methods provided herein is a human that is in an immunocompromised state or immunosuppressed state. In certain embodiments, a subject treated for cancer or a non-neoplastic condition or a viral infection in accordance with the methods provided herein is a human receiving or recovering from immunosuppressive therapy. In certain embodiments, a subject treated for cancer or a non-neoplastic condition or a viral infection in accordance with the methods provided herein is a human that has or is at risk of getting cancer (e.g., metastatic cancer), AIDS, or a bacterial infection. In certain embodiments, a subject treated for cancer or a non-neoplastic condition or a viral infection in accordance with the methods provided herein is a human who is, will or has undergone surgery, drug therapy, such as chemotherapy, hormonal therapy and/or radiation therapy.

In specific embodiments, a subject treated for cancer or a non-neoplastic condition in accordance with the methods provided herein is suffering from a condition, e.g., stroke or cardiovascular conditions that may require VEGF therapy, wherein the administration of anti-angiogenic therapies other than a Compound may be contraindicated. For example, in certain embodiments, a subject treated for cancer or a non-neoplastic condition in accordance with the methods provided herein has suffered from a stroke or is suffering from a cardiovascular condition. In some embodiments, a subject treated for cancer or a non-neoplastic condition in accordance with the methods provided herein is a human experiencing circulatory problems. In certain embodiments, a subject treated for cancer or a non-neoplastic condition in accordance with the methods provided herein is a human with diabetic polyneuropathy or diabetic neuropathy. In some embodiments, a subject treated for cancer or a non-neoplastic condition in accordance with the methods provided herein is a human receiving VEGF protein therapy. In other embodiments, a subject treated for cancer or a non-neoplastic condition in accordance with the methods provided herein is not a human receiving VEGF protein therapy.

In some embodiments, a subject treated for cancer or a non-neoplastic condition or a viral infection in accordance with the methods provided herein is administered a Compound or a pharmaceutical composition thereof, or a combination therapy before any adverse effects or intolerance to therapies other than the Compound develops. In some embodiments, a subject treated for cancer or a non-neoplastic condition or a viral infection in accordance with the methods provided herein is a refractory patient. In a certain embodiment, a refractory patient is a patient refractory to a standard therapy (e.g., surgery, radiation, anti-androgen therapy and/or drug therapy such as chemotherapy or antiviral therapy). In certain embodiments, a patient with cancer or a non-neoplastic condition or a viral infection is refractory to a therapy when the cancer or the non-neoplastic condition or the viral infection has not significantly been eradicated and/or the one or more symptoms have not been significantly alleviated. The determination of whether a patient is refractory can be made either in vivo or in vitro by any method known in the art for assaying the effectiveness of a treatment of cancer or a non-neoplastic condition or a viral infection, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer or a non-neoplastic condition or a viral infection in accordance with the methods provided herein is a human that has proven refractory to therapies other than treatment with a Compound, but is no longer on these therapies. In certain embodiments, a subject treated for cancer or a non-neoplastic condition or a viral infection in accordance with the methods provided herein is a human already receiving one or more conventional anti-cancer therapies, such as surgery, drug therapy such as chemotherapy, antiviral therapy, anti-androgen therapy or radiation. Among these patients are refractory patients, patients who are too young for conventional therapies, and patients with recurring tumors or viral infection despite treatment with existing therapies.

In some embodiments, a subject treated for cancer or a non-neoplastic condition or a viral infection in accordance with the methods provided herein is a human susceptible to adverse reactions to conventional therapies. In some embodiments, a subject treated for cancer or a non-neoplastic condition or a viral infection in accordance with the methods provided herein is a human that has not received a therapy, e.g., drug therapy such as chemotherapy, surgery, antiviral therapy, anti-androgen therapy or radiation therapy, prior to the administration of a Compound or a pharmaceutical composition thereof. In other embodiments, a subject treated for cancer or a non-neoplastic condition or a viral infection in accordance with the methods provided herein is a human that has received a therapy prior to administration of a Compound. In some embodiments, a subject treated for cancer or a non-neoplastic condition or a viral infection in accordance with the methods provided herein is a human that has experienced adverse side effects to the prior therapy or the prior therapy was discontinued due to unacceptable levels of toxicity to the human.

In some embodiments, a subject treated for cancer or a non-neoplastic condition in accordance with the methods provided herein has had no prior exposure to another anti-angiogenic therapy (e.g., an anti-VEGF monoclonal antibody, an anti-VEGFR monoclonal antibody, a tyrosine kinase inhibitor, or other angiogenesis pathway modulator). In particular embodiments, a subject treated for cancer or a non-neoplastic condition in accordance with the methods provided herein does not have uncontrolled hypertension, major bleeding, HIV infection or recent acute cardiovascular event. In some embodiments, a subject treated for cancer or a non-neoplastic condition in accordance with the methods provided herein has myocardial infarction, unstable angina, coronary/peripheral artery bypass graft, congestive heart failure, cerebrovascular accident, transient ischemic attack, an arterial thromboembolic event, or pulmonary embolism.

In some embodiments, a subject treated for cancer or a non-neoplastic condition or a viral infection in accordance with the methods provided herein is not, has not and/or will not receive a drug that is primarily metabolized by CYP2D6. In particular embodiments, a subject treated for cancer or a non-neoplastic condition or a viral infection in accordance with the methods provided herein has not and will not received a drug that is primarily metabolized by CYP2D6 1, 2, 3 or 4 weeks before receiving a Compound or a pharmaceutical composition thereof and 1, 2, 3 or 4 weeks after receiving the Compound or pharmaceutical composition. Examples of such drugs include, without limitation, some antidepressants (e.g., tricyclic antidepressants and selective serotonin uptake inhibitors), some antipsychotics, some beta-adrenergic receptor blockers, certain antiviral agents and certain anti-arrhythmics. In specific embodiments, a subject treated for cancer or a non-neoplastic condition in accordance with the methods provided herein is not, has not and/or will not receive tamoxifen. In particular embodiments, a subject treated for cancer or a non-neoplastic condition in accordance with the methods provided herein has not and will not received tamoxifen 1, 2, 3 or 4 weeks before receiving a Compound or a pharmaceutical composition thereof and 1, 2, 3 or 4 weeks after receiving the Compound or pharmaceutical composition. In specific embodiments, a subject treated for cancer or a non-neoplastic condition in accordance with the methods provided herein has received tamoxifen, e.g., for 1, 2, 3 or 4 weeks before receiving a Compound or a pharmaceutical composition thereof.

5.6 Dosage and Administration

In accordance with the methods for treating cancer or a non-neoplastic condition or a viral infection provided herein, a Compound or a pharmaceutical composition thereof can be administered to a subject in need thereof by a variety of routes in amounts which result in a beneficial or therapeutic effect. A Compound or pharmaceutical composition thereof may be orally administered to a subject in need thereof in accordance with the methods for treating cancer or a non-neoplastic condition or a viral infection provided herein. The oral administration of a Compound or a pharmaceutical composition thereof may facilitate subjects in need of such treatment complying with a regimen for taking the Compound or pharmaceutical composition. Thus, in a specific embodiment, a Compound or pharmaceutical composition thereof is administered orally to a subject in need thereof.

A Compound provided herein can be administered orally, with or without food or water.

Other routes of administration include, but are not limited to, intravenous, intradermal, intrathecal, intramuscular, subcutaneous, intranasal, inhalation, transdermal, topical, transmucosal, intracranial, intratumoral, epidural and intra-synovial. In one embodiment, a Compound or a pharmaceutical composition thereof is administered systemically (e.g., parenterally) to a subject in need thereof. In another embodiment, a Compound or a pharmaceutical composition thereof is administered locally (e.g., intratumorally) to a subject in need thereof. In one embodiment, a Compound or a pharmaceutical composition thereof is administered via a route that permits the Compound to cross the blood-brain barrier (e.g., orally).

Evaluation has indicated that Compound #10 penetrates the blood-brain barrier. Table 6 provides brain tissue plasma concentration ratios determined by whole-body autoradiography at specified times after a single oral administration of $^{14}C$-Compound #10 to rats (50 mg/kg).

TABLE 6

Blood-Brain Barrier Penetration

| Tissue | 6 Hours | | 12 Hours | | 24 Hours | | 48 Hours | | 72 Hours | |
|---|---|---|---|---|---|---|---|---|---|---|
| | M | F | M | F | M | F | M | F | M | F |
| Cerebellum | 1.55 | 1.23 | 1.85 | 2.85 | 1.74 | 1.59 | 1.21 | 1.17 | NA | 2.04 |
| Cerebrum | 1.52 | 1.22 | 1.75 | 2.79 | 1.89 | 1.57 | 1.35 | 1.68 | NA | 1.56 |
| Medulla | 1.60 | 1.42 | 1.98 | 3.82 | 1.83 | 1.69 | 1.20 | 2.01 | NA | 1.88 |
| Olfactory lobe | 1.42 | 1.38 | 1.35 | 2.45 | 1.23 | 1.13 | 0.967 | NA | NA | 3.33 |
| Pituitary gland | 4.06 | 4.27 | 3.22 | 5.48 | 2.72 | 2.33 | 0.890 | 3.68 | NA | 1.58 |
| Spinal cord | 1.14 | 0.898 | 1.24 | 1.92 | 1.75 | 1.60 | 1.43 | 1.60 | 1.84 | 2.75 |

In accordance with the methods for treating cancer or a non-neoplastic condition or a viral infection provided herein that involve administration of a Compound in combination with one or more additional therapies, the Compound and one or more additional therapies may be administered by the same route or a different route of administration.

The dosage and frequency of administration of a Compound or a pharmaceutical composition thereof is administered to a subject in need thereof in accordance with the methods for treating cancer or a non-neoplastic condition or a viral infection provided herein will be efficacious while minimizing any side effects. The exact dosage and frequency of administration of a Compound or a pharmaceutical composition thereof can be determined by a practitioner, in light of factors related to the subject that requires treatment. Factors which may be taken into account include the severity of the disease state, general health of the subject, age, weight, and gender of the subject, diet, time and frequency of administration, drug combination(s), reaction sensitivities, and tolerance/response to therapy. The dosage and frequency of administration of a Compound or a pharmaceutical composition thereof may be adjusted over time to provide sufficient levels of the Compound or to maintain the desired effect.

In certain embodiments, a Compound or pharmaceutical composition thereof is administered to a subject in accordance with the methods for treating cancer or a non-neoplastic condition or a viral infection presented herein once a day, twice a day, three times a day, or four times a day. In some embodiments, a Compound or pharmaceutical composition thereof is administered to a subject in accordance with the methods for treating cancer or a non-neoplastic condition or a viral infection presented herein once, twice, three times, or four times every other day (i.e., on alternate days), once, twice, three times, or four times every two days, once every three days, once, twice, three times, or four times every four days, once, twice, three times, or four times every 5 days, once, twice, three times, or four times a week, once, twice, three times, or four times every two weeks, once, twice, three times, or four times every three weeks, once, twice, three times, or four times every four weeks, once, twice, three times, or four times every 5 weeks, once, twice, three times, or four times every 6 weeks, once, twice, three times, or four times every 7 weeks, or once, twice, three times, or four times every 8 weeks. In particular embodiments, a Compound or pharmaceutical composition thereof is administered to a subject in accordance with the methods for treating cancer or a non-neoplastic condition or a viral infection presented herein in cycles, wherein the Compound or pharmaceutical composition is administered for a period of time, followed by a period of rest (i.e., the Compound or pharmaceutical composition is not administered for a period of time).

In certain embodiments, a Compound or a pharmaceutical composition thereof is administered to a subject in need thereof in accordance with the methods for treating cancer provided herein at a dosage and a frequency of administration that achieves one or more of the following: (i) decreases the production and/or concentration of VEGF or other angiogenic or inflammatory mediators or a change in tumor blood flow or metabolism, or peritumoral inflammation or edema of a subject with cancer or a non-neoplastic condition or an animal model with a pre-established human tumor; (ii) decreases the concentration of one, two, three or more, or all of the following of a subject with cancer or an animal model with a pre-established human tumor: VEGF-C, VEGF-D, P1GF, VEGFR-1, VEGFR-2, IL-6 and/or IL-8; (iii) reduces or ameliorates the severity of the cancer and/or one or more symptoms associated therewith in a subject with the cancer; (iv) reduces the number symptoms and/or the duration of one or more symptoms associated with the cancer in a subject with the cancer; (v) prevents the onset, progression or recurrence of one or more symptoms associated with the cancer in a subject with the cancer or an animal model with a pre-established human tumor; (vi) reduces the size of the tumor in a subject with the cancer or in an animal model with a pre-established human tumor; (vii) reduces angiogenesis associated with cancer in a subject or an animal model with a pre-established human tumor; and/or (vii) enhances or improves the therapeutic effect of another therapy in a subject with the cancer or an animal model with a pre-established human tumor.

In certain embodiments, a Compound or a pharmaceutical composition thereof is administered to a subject in need thereof in accordance with the methods for treating cancer provided herein at a dosage and a frequency of administration that results in one or more of the following: (i) a decrease in the number of circulating tumor cells (CTCs) in the blood of a subject with cancer or an animal model with a pre-established human tumor; (iii) survival of patients with cancer for about 6 months or more, about 7 months or more, about 8 months or more, about 9 months or more, or about 12 months or more; (iv) regression of a tumor associated with cancer and/or inhibition of the progression of a tumor associated with the cancer in a subject with cancer or an animal model with a pre-established human tumor; (v) reduction in the growth of a tumor or neoplasm associated with the cancer and/or decrease in the tumor size (e.g., volume or diameter) of tumors associated with the cancer in a subject with cancer or an animal model with a pre-established human tumor; (vi) the size of a tumor associated with cancer is maintained and/or the tumor does not increase or increases by less than the increase of a similar tumor in a subject with cancer or an animal model with a pre-established human tumor after administration of a standard therapy as measured by conventional methods available to one of skill in the art, such as digital rectal exam, ultrasound (e.g., transrectal ultrasound), CT Scan, PET scan, DCE-MRI, and MRI; (vii) reduction in the formation of a tumor associated with the cancer in a subject with the cancer or an animal model with a pre-established human tumor; (viii) the eradication, removal, or control of primary, regional and/or metastatic tumors associated with the cancer in a subject with the cancer or an animal model with a pre-established human tumor; (ix) a decrease in the number or size of metastases associated with the cancer in a subject with the cancer or an animal model with a pre-established human tumor; (x) a reduction or inhibition of the recurrence of a tumor; (xi) a reduction in edema or inflammation associated with a tumor; (xii) an inhibition or reduction in tumor vascularization; (xiii) a reduction of pathologic angiogenesis; and/or (x) reduction in the growth of a pre-established tumor or neoplasm and/or decrease in the tumor size (e.g., volume or diameter) of a pre-established tumor in a subject with the cancer or an animal model with a pre-established human tumor.

In certain embodiments, a Compound or a pharmaceutical composition thereof is administered to a subject in need thereof in accordance with the methods for treating a non-neoplastic condition provided herein at a dosage and a frequency of administration that achieves one or more of the following: (i) decreases the production or concentration of VEGF or other angiogenic or inflammatory mediators; (ii) decreases the concentration of one, two, three or more, or all of the following of a subject with a non-neoplastic condition or an animal model: VEGF-C, VEGF-D, P1GF, VEGFR-1, VEGFR-2, IL-6 and/or IL-8; (iii) reduces or ameliorates the severity of the non-neoplastic condition and/or one or more symptoms associated therewith in a subject with the non-neoplastic condition; (iv) reduces the number symptoms and/or the duration of one or more symptoms associated with the non-neoplastic condition in a subject with the non-neoplastic condition; (v) prevents the onset, progression or recurrence of one or more symptoms associated with the non-neoplastic condition in a subject with the non-neoplastic condition; (vi) reduces inflammation associated with the non-neoplastic condition; (vii) reduces pathologic angiogenesis associated with the non-neoplastic condition in a subject or an animal model; and/or (viii) enhances or improves the therapeutic effect of another therapy in a subject with the non-neoplastic condition or an animal model.

In certain embodiments, a Compound or a pharmaceutical composition thereof is administered to a subject in need thereof in accordance with the methods for treating a viral infection provided herein at a dosage and a frequency of administration that achieves one or more of the following: (i) decreases the production or concentration of viral RNA or DNA or viral protein; (ii) decreases the viral titer of a subject or an animal model with a viral infection; (iii) reduces or ameliorates the severity of the viral infection and/or one or more symptoms associated therewith in a subject with the viral infection; (iv) reduces the number symptoms and/or the duration of one or more symptoms associated with the viral infection in a subject with the viral infection; (v) prevents the onset, progression or recurrence of one or more symptoms associated with the viral infection in a subject with the viral infection; (vi) inhibits or reduces viral replication or the production or concentration of viral RNA or DNA or viral protein associated with the viral infection in a subject or an animal model; and/or (vii) enhances or improves the therapeutic efficacy of another antiviral therapy in a subject with the viral infection or an animal model.

In one aspect, a method for treating cancer or a non-neoplastic condition or a viral infection presented herein involves the administration of a unit dosage of a Compound or a pharmaceutical composition thereof. The dosage may be administered as often as determined effective (e.g., once, twice or three times per day, every other day, once or twice per week, biweekly or monthly). In certain embodiments, a method for treating cancer or a non-neoplastic condition or a viral infection presented herein involves the administration to a subject in need thereof of a unit dose of a Compound or a pharmaceutical composition thereof that ranges from about 0.001 milligram (mg) to about 1500 mg, from about 0.001 mg per kg to about 1400 mg per kg, from about 0.001 mg per kg to about 1300 mg per kg, from about 0.001 mg per kg to about 1200 mg per kg, from about 0.001 mg per kg to about 1100 mg per kg, from about 0.001 mg per kg to about 1000 mg per kg, from about 0.01 mg to about 1500 mg, from about 0.01 mg per kg to about 1000 mg per kg, from about 0.1 mg per kg to about 1500 mg per kg, from about 0.1 mg per kg to about 1000 mg per kg, from about 0.1 mg per kg to about 500 mg per kg, from about 0.05 mg to about 1000 mg, from about 0.1 mg per kg to about 100 mg per kg, from about 1 mg per kg to about 100 mg per kg, from about 10 mg to about 500 mg, from about 100 mg to about 500 mg, from about 150 mg to about 500 mg, from about 150 mg to about 1000 mg, from about 250 mg to about 1000 mg, from about 300 mg to about 1000 mg, or from about 500 mg to about 1000 mg, or any range in between. In specific embodiments, oral doses for use in the methods provided herein are from about 0.01 mg to about 300 mg per kg body weight, from about 0.1 mg to about 75 mg per kg body weight, or from about 0.5 mg to 5 mg per kg body weight. In some embodiments, a method for treating cancer or a non-neoplastic condition or a viral infection presented herein involves the administration to a subject in need thereof of a unit dose of a Compound or a pharmaceutical composition thereof of about 15 mg, 16, mg, 17 mg, 18 mg, 19 mg, 20 mg, 21, mg, 22 mg, 23 mg, 24 mg, 25 mg, 26 mg, 27 mg, 28 mg, 29 mg, 30 mg or 40 mg. In certain embodiments, a method for treating cancer or a non-neoplastic condition or a viral infection presented herein involves the administration to a subject in need thereof of a unit dose of a Compound or a pharmaceutical composition thereof of about 50 mg, 60 mg, 70 mg, 80 mg, 90 mg, 100 mg, 110 mg, 120 mg, 125 mg, 130 mg, 140 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1100 mg, 1200 mg, 1300 mg, 1400 mg or 1500 mg.

In some embodiments, a method for treating cancer or a non-neoplastic condition or a viral infection presented herein involves the administration to a subject in need thereof of a unit dose of a Compound or a pharmaceutical composition thereof of at least about 0.1 mg, 1 mg, 5 mg, 10 mg, 20 mg, 30 mg, 40 mg, 50 mg, 60 mg, 70 mg, 80 mg, 90 mg, 100 mg, 110 mg, 120 mg, 125 mg, 130 mg, 140 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1100 mg, 1200 mg, 1300 mg, 1400 mg, 1500 mg or more. In certain embodiments, a method for treating cancer or a non-neoplastic condition or a viral infection presented herein involves the administration to a subject in need thereof of a unit dose of a Compound or a pharmaceutical composition thereof of less than about 35 mg, less than about 40 mg, less than about 45 mg, less than about 50 mg, less than about 60 mg, less than about 70 mg, or less than about 80 mg.

In specific embodiments, a method for treating cancer or a non-neoplastic condition or a viral infection presented herein involves the administration to a subject in need thereof of a unit dose of a Compound or a pharmaceutical composition thereof of from about 20 mg to about 500 mg, from about 40 mg to about 500 mg, from about 40 mg to about 200 mg, from about 40 mg to about 150 mg, from about 75 mg to about 500 mg, from about 75 mg to about 450 mg, from about 75 mg to about 400 mg, from about 75 mg to about 350 mg, from about 75 mg to about 300 mg, from about 75 mg to about 250 mg, from about 75 mg to about 200 mg, from about 100 mg to about 200 mg, or any range in between. In other specific embodiments, a method for treating cancer or a non-neoplastic condition or a viral infection presented herein involves the administration to a subject in need thereof of a unit dose of a Compound or a pharmaceutical composition thereof of about 20 mg, 35 mg, 40 mg, 50 mg, 60 mg, 75 mg, 100 mg, 125 mg, 150 mg, 175 mg, 200 mg, 225 mg, 250 mg or 300 mg. In some embodiments, a method for treating cancer or a non-neoplastic condition or a viral infection presented herein involves the administration to a subject in need thereof of a unit dose of a Compound or a pharmaceutical composition thereof of about 350 mg, 400 mg, 500 mg, 600 mg, 700 mg, 800 mg, 900 mg, or 1000 mg. In some embodiments, a unit dose of a Compound or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

In certain embodiments, a method for treating cancer or a non-neoplastic condition or a viral infection presented herein involves the oral administration to a subject in need thereof of a unit dose of a Compound or a pharmaceutical composition thereof ranges from about 0.001 mg per kg to about 1500 mg per kg per day, from about 0.001 mg per kg to about 1400 mg per kg per day, from about 0.001 mg per kg to about 1300 mg per kg per day, from about 0.001 mg per kg to about 1200 mg per kg per day, from about 0.001 mg per kg to about 1100 mg per kg per day, from about 0.001 mg per kg to about 1000 mg per kg per day, 0.001 mg/kg to about 500 mg/kg, from about 0.01 mg per kg to about 1500 mg per kg per day, from about 0.01 mg per kg to about 1000 mg per kg per day, from about 0.1 mg per kg to about 1500 mg per kg per day, from about 0.1 mg per kg to about 1000 mg per kg per day, from about 0.1 mg per kg to about 500 mg per kg per day, from about 0.1 mg per kg to about 100 mg per kg per day, or from about 1 mg per kg to about 100 mg per kg per day. In a specific embodiment, a unit dose of a Compound or a pharmaceutical composition thereof ranges from about 0.01 mg to about 300 mg per kg body weight per day, from about 0.1 mg to about 75 mg per kg body weight per day, or from about 0.5 mg to 5 mg per kg body weight per day. In another specific embodiment, a unit dose of a Compound or a pharmaceutical composition thereof ranges from about 20 mg to about 1000 mg per day. In some embodiments, a method for treating cancer or a non-neoplastic condition or a viral infection presented herein involves the oral administration to a subject in need thereof of a unit dose of a Compound or a pharmaceutical composition thereof that ranges from about 80 mg to about 800 mg per day, from about 100 mg to about 800 mg per day, from about 80 mg to about 600 mg per day, from about 80 mg to about 400 mg per day, from about 80 mg to about 200 mg per day, from about 200 mg to about 300 mg per day, from about 200 mg to about 400 mg per day, from about 200 mg to about 800 mg per day, or any range in between.

In certain embodiments, a unit dose of a Compound that may be used in the methods provided herein include doses of about 0.1 mg/kg/day, 0.2 mg/kg/day, 0.3 mg/kg/day, 0.4 mg/kg/day, 0.5 mg/kg/day, 0.6 mg/kg/day, 0.7 mg/kg/day, 0.8 mg/kg/day, 0.9 mg/kg/day, 1 mg/kg/day, 1.5 mg/kg/day, 2 mg/kg/day, 2.5 mg/kg/day, 2.75 mg/kg/day, 3 mg/kg/day, 4 mg/kg/day, 5 mg/kg/day, 6 mg/kg/day, 6.5 mg/kg/day, 6.75 mg/kg/day, 7 mg/kg/day, 7.5 mg/kg/day, 8 mg/kg/day, 8.5 mg/kg/day, 9 mg/kg/day, 10 mg/kg/day, 11 mg/kg/day, 12 mg/kg/day, 13 mg/kg/day, 14 mg/kg/day or 15 mg/kg/day. In accordance with these embodiments, the dosage may be administered once, twice or three times per day, every other day, or once or twice per week and the dosage may be administered orally.

In a specific embodiment, a method for treating cancer or a non-neoplastic condition or a viral infection presented herein involves the oral administration of a unit dose of about 20 mg of a Compound or a pharmaceutical composition thereof once, twice or three times per day. In another specific embodiment, a method for treating cancer or a non-neoplastic condition or a viral infection presented herein involves the oral administration to a subject in need thereof of a unit dose of about 40 mg of a Compound or a pharmaceutical composition thereof once, twice or three times per day. In another specific embodiment, a method for treating cancer or a non-neoplastic condition or a viral infection presented herein involves the oral administration of a unit dose of about 60 mg of a compound or a pharmaceutical composition thereof once, twice or three times per day. In another specific embodiment, a method for treating cancer or a non-neoplastic condition or a viral infection presented herein involves the oral administration to a subject in need thereof of a unit dose of about 80 mg of a Compound or a pharmaceutical composition thereof once, twice or three times per day. In specific embodiments, a method for treating cancer or a non-neoplastic condition or a viral infection presented herein involves the oral administration to a subject in need thereof of a unit dose of from about 100 mg to about 250 mg, from about 150 mg to about 250 mg, from about 175 mg to about 250 mg, from about 200 mg to about 250 mg, or from about 200 mg to about 225 mg of a Compound or a pharmaceutical composition thereof once, twice or three times per day.

In some embodiments, a method for treating cancer or a non-neoplastic condition or a viral infection presented herein involves the administration of a dosage of a Compound or a pharmaceutical composition thereof that is expressed as mg per meter squared ($mg/m^2$). The $mg/m^2$ for a Compound may be determined, for example, by multiplying a conversion factor for an animal by an animal dose in mg per kilogram (mg/kg) to obtain the dose in $mg/m^2$ for human dose equivalent. For regulatory submissions the FDA may recommend the following conversion factors: Mouse=3, Hamster=4.1, Rat=6, Guinea Pig=7.7. (based on Freireich et al., Cancer Chemother. Rep. 50(4):219-244 (1966)). The height and weight of a human may be used to calculate a human body surface area applying Boyd's Formula of Body Surface Area.

In specific embodiments, a method for treating cancer or a non-neoplastic condition or a viral infection presented herein involves the administration to a subject in need thereof of an amount of a Compound or a pharmaceutical composition thereof in the range of from about 0.1 mg/m$^2$ to about 1000 mg/m$^2$, or any range in between.

Other non-limiting exemplary doses of a Compound or a pharmaceutical composition that may be used in the methods for treating cancer or a non-neoplastic condition or a viral infection provided herein include mg amounts per kg of subject or sample weight. In certain embodiments, a method for treating cancer or a non-neoplastic condition or a viral infection presented herein involves the administration to a subject in need thereof of a dosage of a Compound or a pharmaceutical composition thereof that ranges from about from about 0.001 mg/kg to about 1500 mg/kg per day, from about 0.001 mg/kg to about 1400 mg/kg per day, from about 0.001 mg/kg to about 1300 mg/kg per day, from about 0.001 mg/kg to about 1200 mg/kg per day, from about 0.001 mg/kg to about 1100 mg/kg per day, from about 0.001 mg/kg to about 1000 mg/kg per day, 0.001 mg/kg to about 500 mg/kg, from about 0.01 mg/kg to about 1500 mg/kg per day, from about 0.01 mg/kg to about 1000 mg/kg per day, from about 0.01 mg/kg to about 500 mg/kg, from about 0.1 mg/kg to about 1500 mg/kg per day, from about 0.1 mg/kg to about 1000 mg/kg per day, from about 0.1 mg/kg to about 500 mg/kg, from about 0.1 mg/kg to about 100 mg/kg per day, from about 1 mg/kg to about 500 mg/kg, from about 1 mg/kg to about 100 mg/kg per day, from about 10 mg/kg to about 500 mg/kg, from about 100 mg to about 500 mg/kg, from about 150 mg/kg to about 500 mg/kg, from about 250 mg/kg to about 500 mg/kg, or from about 300 mg/kg to about 500 mg/kg. In some embodiments, a method for treating cancer or a non-neoplastic condition or a viral infection presented herein involves the administration to a subject in need thereof of a dosage of a Compound or a pharmaceutical composition thereof that ranges from about 0.001 mg/kg to about 100 mg/kg, from about 0.001 mg/kg to about 50 mg/kg, from about 0.001 mg/kg to about 25 mg/kg, from about 0.001 mg/kg to about 10 mg/kg, from about 0.001 mg/kg to about 5 mg/kg; from about 0.001 mg/kg to about 1 mg/kg; or from about 0.001 mg/kg to about 0.01 mg/kg. In certain embodiments, a dosage of a Compound or a pharmaceutical composition thereof that may be used in the methods provided herein include doses of about 0.1 mg/kg/day, 0.2 mg/kg/day, 0.3 mg/kg/day, 0.4 mg/kg/day, 0.5 mg/kg/day, 0.6 mg/kg/day, 0.7 mg/kg/day, 0.8 mg/kg/day, 0.9 mg/kg/day, 1 mg/kg/day, 1.5 mg/kg/day, 2 mg/kg/day, 2.5 mg/kg/day, 2.75 mg/kg/day, 3 mg/kg/day, 4 mg/kg/day, 5 mg/kg/day, 6 mg/kg/day, 6.5 mg/kg/day, 6.75 mg/kg/day, 7 mg/kg/day, 7.5 mg/kg/day, 8 mg/kg/day, 8.5 mg/kg/day, 9 mg/kg/day, 10 mg/kg/day, 11 mg/kg/day, 12 mg/kg/day, 13 mg/kg/day, 14 mg/kg/day or 15 mg/kg/day. In accordance with these embodiments, the dosage may be administered once, twice or three times per day, every other day, or once or twice per week and the dosage may be administered orally.

In certain embodiments, a method for treating cancer or a non-neoplastic condition or a viral infection presented herein involves the administration to a subject in need thereof of a dosage of a Compound or a pharmaceutical composition thereof that ranges from about 0.01 mg/kg to about 100 mg/kg, from about 0.01 mg/kg to about 50 mg/kg, from about 0.01 mg/kg to about 25 mg/kg, from about 0.01 mg/kg to about 10 mg/kg, from about 0.01 mg/kg to about 5 mg/kg, from about 0.01 mg to about 1 mg/kg, or from about 0.01 mg/kg to about 0.1 mg/kg. In some embodiments, a method for treating cancer or a non-neoplastic condition or a viral infection presented herein involves the administration to a subject in need thereof of a dosage of a Compound or a pharmaceutical composition thereof that ranges from about 0.1 mg/kg to about 100 mg/kg, from about 0.1 mg/kg to about 50 mg/kg, from about 0.1 mg/kg to about 25 mg/kg, from about 0.1 mg/kg to about 10 mg/kg, from about 0.1 mg/kg to about 5 mg/kg; from about 0.1 mg/kg to about 4 mg/kg; from about 0.1 mg/kg to about 3 mg/kg; from about 0.1 mg/kg to about 2 mg/kg; from about 0.1 mg to about 1.5 mg/kg, from about 0.1 mg to about 1.2 mg/kg, from about 0.1 mg to about 1 mg/kg, or from about 0.5 mg/kg to about 1.5 mg/kg. In accordance with these embodiments, the dosage may be administered once, twice or three times per day, every other day, or once or twice per week and the dosage may be administered orally.

In specific embodiments, a method for treating cancer or a non-neoplastic condition or a viral infection presented herein involves the oral administration to a subject in need thereof of a dosage of a Compound or a pharmaceutical composition thereof of from about 0.1 mg/kg to about 5 mg/kg, from about 0.1 mg/kg to about 4 mg/kg, from about 0.1 mg/kg to about 3 mg/kg, from about 0.1 mg/kg to about 2 mg/kg, from about 0.5 mg/kg to about 2 mg/kg, or from about 1 mg/kg to about 1.5 mg/kg is administered once, twice or three times per day. In certain embodiments, a method for treating cancer or a non-neoplastic condition or a viral infection presented herein involves the oral administration to a subject in need thereof of a dosage of a Compound or a pharmaceutical composition thereof of about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg or about 1 mg/kg once, twice or three times per day. In certain specific embodiments, a method for treating cancer or a non-neoplastic condition or a viral infection presented herein involves the oral administration to a subject in need thereof of a dosage of a Compound or a pharmaceutical composition thereof of about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg or about 2 mg/kg once, twice or three times per day.

In specific aspects, a method for treating cancer or a non-neoplastic condition or a viral infection presented herein involves the administration to a subject in need thereof of a Compound or a pharmaceutical composition thereof at a dosage that achieves a target plasma concentration of the Compound in a subject with the cancer or the non-neoplastic condition or a viral infection or an animal model (e.g., an animal model with a pre-established human tumor or a viral infection). In a particular embodiment, a method for treating cancer or a non-neoplastic condition or a viral infection presented herein involves the administration to a subject in need thereof of a Compound or a pharmaceutical composition thereof at a dosage that achieves a plasma concentration of the Compound ranging from approximately 0.001 µg/mL to approximately 100 mg/mL, approximately 0.01 µg/mL to approximately 100 mg/mL, approximately 0.01 µg/mL to approximately 10 mg/mL, approximately 0.1 µg/mL to approximately 10 mg/mL, approximately 0.1 µg/mL to approximately 500 µg/mL, approximately 0.1 µg/mL to approximately 200 µg/mL, approximately 0.1 µg/mL to approximately 100 µg/mL, or approximately 0.1 µg/mL to approximately 75 µg/mL in a subject with the cancer or the non-neoplastic condition or the viral infection or an animal model (e.g., an animal model with a pre-established human tumor or viral infection). In specific embodiments, a method for treating cancer or a non-neoplastic condition or a viral infection presented herein involves the administration to a subject in need thereof of a Compound or a pharmaceutical composition thereof at a dosage that achieves a plasma concentration of the Compound ranging from approximately 0.1 to approximately 50 µg/mL, approximately 0.1 µg/mL to approximately 25 µg/mL, approximately 0.1 µg/mL to approximately 20 µg/mL or approximately 5 µg/mL to approximately 10 µg/mL in a subject with the cancer or the non-neoplastic condition or the viral infection or an animal model (e.g., an animal model with a pre-established human tumor or viral infection). To achieve such plasma concentrations, a Compound or a pharmaceutical composition thereof may be administered at doses that vary from 0.001 µg to 100,000 mg, depending upon the route of administration. In certain embodiments, subsequent doses of a Compound may be adjusted accordingly based on the plasma concentrations of the Compound achieved with initial doses of the Compound or pharmaceutical composition thereof administered to the subject.

In specific aspects, a method for treating cancer or a non-neoplastic condition presented herein involves the administration to a subject in need thereof of a Compound or a pharmaceutical composition thereof at a dosage that achieves a target plasma concentration of VEGF-A, P1GF, VEGF-C, VEGF-D, IL-6, IL-8, VEGFR1 and/or VEGFR2 in a subject with the cancer or the non-neoplastic condition or an animal model (e.g., an animal model with a pre-established human tumor). In a particular embodiment, a method for treating cancer or a non-neoplastic condition presented herein involves the administration to a subject in need thereof of a Compound or a pharmaceutical composition thereof at a dosage that achieves a plasma concentration of VEGF-A, P1GF, VEGF-C, VEGF-D, IL-6, IL-8, VEGFR1 and/or VEGFR2 ranging from approximately 0.1 pg/mL to approximately 100 mg/mL, approximately 0.1 pg/mL to approximately 1 mg/mL, approximately 0.1 pg/mL to approximately 500 µg/mL, approximately 0.1 pg/mL to approximately 500 µg/mL, approximately 0.1 pg/mL to approximately 100 µg/mL, or approximately 4 pg/mL to approximately 10 µg/mL in a subject with cancer or a non-neoplastic condition or an animal model (e.g., an animal model with a pre-established human tumor). To achieve such plasma concentrations, a Compound or a pharmaceutical composition thereof may be administered at doses that vary from 0.1 pg to 100,000 mg, depending upon the route of administration. In certain embodiments, subsequent doses of a Compound or a pharmaceutical composition thereof may be adjusted accordingly based on the plasma concentrations of VEGF-A, P1GF, VEGF-C, VEGF-D, IL-6, IL-8, VEGFR1 or VEGFR2 achieved with initial doses of the Compound or pharmaceutical composition thereof administered to the subject.

In particular embodiments, a method for treating cancer or a non-neoplastic condition or a viral infection presented herein involves the administration to a subject in need thereof of a Compound or a pharmaceutical composition thereof at a dosage that achieves the desired tissue to plasma concentration ratios of the Compound as determined, e.g., by any imaging techniques known in the art such as whole-body autoradiography, in a subject with the cancer or the non-neoplastic condition or the viral infection or an animal model (such as an animal model with a pre-established human tumor or a viral infection).

In some embodiments, a method for treating cancer or a non-neoplastic condition or a viral infection presented herein involves the administration to a subject in need thereof of one or more doses of an effective amount of a Compound or a pharmaceutical composition, wherein the effective amount may or may not be the same for each dose. In particular embodiments, a first dose of a Compound or pharmaceutical composition thereof is administered to a subject in need thereof for a first period of time, and subsequently, a second dose of a Compound is administered to the subject for a second period of time. The first dose may be more than the second dose, or the first dose may be less than the second dose. A third dose of a Compound also may be administered to a subject in need thereof for a third period of time.

In some embodiments, the dosage amounts described herein refer to total amounts administered; that is, if more than one Compound is administered, then, in some embodiments, the dosages correspond to the total amount administered. In a specific embodiment, oral compositions contain about 5% to about 95% of a Compound by weight.

The length of time that a subject in need thereof is administered a Compound or a pharmaceutical composition in accordance with the methods for treating cancer or a non-neoplastic condition or a viral infection presented herein will be the time period that is determined to be efficacious. In certain embodiments, a method for treating cancer or a non-neoplastic condition or a viral infection presented herein involves the administration of a Compound or a pharmaceutical composition thereof for a period of time until the severity and/or number of one or more symptoms associated with the cancer or the non-neoplastic condition or the viral infection decrease.

In some embodiments, a method for treating cancer or a non-neoplastic condition or a viral infection presented herein involves the administration of a Compound or a pharmaceutical composition thereof for up to 48 weeks. In other embodiments, a method for treating cancer or a non-neoplastic condition or a viral infection presented herein involves the administration of a Compound or a pharmaceutical composition thereof for up to 4 weeks, 8 weeks, 12 weeks, 16 weeks, 20 weeks, 24 weeks, 26 weeks (0.5 year), 52 weeks (1 year), 78 weeks (1.5 years), 104 weeks (2 years), or 130 weeks (2.5 years) or more. In certain embodiments, a method for treating cancer or a non-neoplastic condition or a viral infection presented herein involves the administration of a Compound or a pharmaceutical composition thereof for an indefinite period of time. In some embodiments, a method for treating cancer or a non-neoplastic condition or a viral infection presented herein involves the administration of a Compound or a pharmaceutical composition thereof for a period of time followed by a period of rest (i.e., a period wherein the Compound is not administered) before the administration of the Compound or pharmaceutical composition thereof is resumed. In specific embodiments, a method for treating cancer or a non-neoplastic condition or a viral infection presented herein involves the administration of a Compound or pharmaceutical composition thereof in cycles, e.g., 1 week cycles, 2 week cycles, 3 week cycles, 4 week cycles, 5 week cycles, 6 week cycles, 8 week cycles, 9 week cycles, 10 week cycles, 11 week cycles, or 12 week cycles. In such cycles, the Compound or a pharmaceutical composition thereof may be administered once, twice, three times, or four times daily. In particular embodiments, a method for treating a prostate condition presented herein involves the administration of a Compound or a pharmaceutical composition thereof twice daily in 4 week cycles.

In specific embodiments, the period of time of administration of a Compound or pharmaceutical composition thereof may be dictated by one or more monitoring parameters, e.g., concentration of VEGF or other angiogenic or inflammatory mediators (e.g., cytokines or interleukins such as IL-6 or IL-8); tumor size, blood flow, or metabolism; peritumoral inflammation or edema. In particular embodiments, the period of time of administration of a Compound or pharmaceutical composition thereof may be adjusted based on one or more monitoring parameters, e.g., concentration of VEGF or other angiogenic or inflammatory mediators (e.g., cytokines or interleukins such as IL-6 or IL-8); tumor size, blood flow, or metabolism; and/or peritumoral inflammation or edema.

In certain embodiments, in accordance with the methods for treating cancer or a non-neoplastic condition or a viral infection presented herein, a Compound or a pharmaceutical composition thereof is administered to a subject in need thereof prior to, concurrently with, or after a meal (e.g., breakfast, lunch, or dinner). In specific embodiments, in accordance with the methods for treating cancer or a non-neoplastic condition or a viral infection presented herein, a Compound or a pharmaceutical composition thereof is administered to a subject in need thereof in the morning (e.g., between 5 am and 12 pm). In certain embodiments, in accordance with the methods for treating cancer or a non-neoplastic condition or a viral infection presented herein, a Compound or a pharmaceutical composition thereof is administered to a subject in need thereof at noon (i.e., 12 pm). In particular embodiments, in accordance with the methods for treating cancer or a non-neoplastic condition or a viral infection presented herein, a Compound or a pharmaceutical composition thereof is administered to a subject in need thereof in the afternoon (e.g., between 12 pm and 5 pm), evening (e.g., between 5 pm and bedtime), and/or before bedtime.

In specific embodiments, a dose of a Compound or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly.

5.7 Combination Therapy

Presented herein are combination therapies for the treatment of cancer or a non-neoplastic condition or a viral infection which involve the administration of a Compound in combination with one or more additional therapies to a subject in need thereof. In a specific embodiment, presented herein are combination therapies for the treatment of cancer or a non-neoplastic condition or a viral infection which involve the administration of an effective amount of a Compound in combination with an effective amount of another therapy to a subject in need thereof.

As used herein, the term "in combination," refers, in the context of the administration of a Compound, to the administration of a Compound prior to, concurrently with, or subsequent to the administration of one or more additional therapies (e.g., agents, surgery, or radiation) for use in treating cancer or a non-neoplastic condition or a viral infection. The use of the term "in combination" does not restrict the order in which one or more Compounds and one or more additional therapies are administered to a subject. In specific embodiments, the interval of time between the administration of a Compound and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, a Compound and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering a Compound daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, a Compound and one or more additional therapies are cyclically administered to a subject. Cycling therapy involves the administration of the Compound for a period of time, followed by the administration of one or more additional therapies for a period of time, and repeating this sequential administration. In certain embodiments, cycling therapy may also include a period of rest where the Compound or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer or a non-neoplastic condition or a viral infection provided herein comprise administering a Compound as a single agent for a period of time prior to administering the Compound in combination with an additional therapy. In certain embodiments, the methods for treating cancer or a non-neoplastic condition or a viral infection provided herein comprise administering an additional therapy alone for a period of time prior to administering a Compound in combination with the additional therapy.

In some embodiments, the administration of a Compound and one or more additional therapies in accordance with the methods presented herein have an additive effect relative the administration of the Compound or said one or more additional therapies alone. In some embodiments, the administration of a Compound and one or more additional therapies in accordance with the methods presented herein have a synergistic effect relative to the administration of the Compound or said one or more additional therapies alone.

As used herein, the term "synergistic," refers to the effect of the administration of a Compound in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of a Compound or an additional therapy and/or less frequent administration of a Compound or an additional therapy to a subject. In certain embodiments, the ability to utilize lower dosages of a Compound or of an additional therapy and/or to administer a Compound or said additional therapy less frequently reduces the toxicity associated with the administration of a Compound or of said additional therapy, respectively, to a subject without reducing the efficacy of a Compound or of said additional therapy, respectively, in the treatment of cancer or a non-neoplastic condition or a viral infection. In some embodiments, a synergistic effect results in improved efficacy of a Compound and each of said additional therapies in treating cancer or a non-neoplastic condition or a viral infection. In some embodiments, a synergistic effect of a combination of a Compound and one or more additional therapies avoids or reduces adverse or unwanted side effects associated with the use of any single therapy.

The combination of a Compound and one or more additional therapies can be administered to a subject in the same pharmaceutical composition. Alternatively, a Compound and one or more additional therapies can be administered concurrently to a subject in separate pharmaceutical compositions. A Compound and one or more additional therapies can be administered sequentially to a subject in separate pharmaceutical compositions. A Compound and one or more additional therapies may also be administered to a subject by the same or different routes of administration.

The combination therapies provided herein involve administering to a subject to in need thereof a Compound in combination with conventional, or known, therapies for treating cancer or a non-neoplastic condition or a viral infection. Other therapies for cancer or a non-neoplastic condition or a viral infection or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with cancer or a non-neoplastic condition or a viral infection or a condition associated therewith.

Specific examples of anti-cancer agents that may be used in combination with a Compound for treating cancer or a non-neoplastic condition include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with a Compound for treating cancer or a non-neoplastic condition include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with a Compound for treating cancer include microtubule disassembly blocker, antimetabolite, topisomerase inhibitor, and DNA crosslinker or damaging agent. Chemotherapeutic agents that are microtubule dissembly blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of anti-angiogenic agents that may be used in combination with a Compound for treating cancer or a non-neoplastic condition include VEGF antagonists, receptor antagonists, integrin antagonists (e.g., vitaxin, cilengitide, and S247), and VTAs/VDAs (e.g., fosbretabulin). VEGF antagonists include, but are not to, anti-VEGF antibodies (e.g., bevacizumab (branded/marketed as AVASTIN®) and ranibizumab (branded/marketed as LUCENTIS)), VEGF traps (e.g., aflibercept), VEGF antisense or siRNA or miRNA, and aptamers (e.g., pegaptanib (branded/marketed as MACUGEN®)). Anti-angiogenic agents that are receptor antagonists include, but are not limited to, antibodies (e.g., ramucirumab) and kinase inhibitors (e.g., sunitinib, sorafenib, cediranib, panzopanib, vandetanib, axitinib, and AG-013958) such as tyrosine kinase inhibitors. Other non-limiting examples of anti-angiogenic agents include ATN-224, anecortave acetate (branded/marketed as RETAANE®), microtubule depolymerization inhibitor such as combretastatin A4 prodrug, and protein or protein fragment such as collagen 18 (endostatin).

Non-limiting examples of other therapies that may be administered to a subject in combination with a Compound for treating cancer or a non-neoplastic condition include:
 (1) a statin such as lovostatin (e.g., branded/marketed as MEVACOR®);
 (2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as) AFINITOR®), and deforolimus;
 (3) a farnesyltransferase inhibitor agent such as tipifarnib (e.g., branded/marketed as ZARNESTRA®);
 (4) an antifibrotic agent such as pirfenidone;
 (5) a pegylated interferon such as PEG-interferon alfa-2b;
 (6) a CNS stimulant such as methylphenidate (branded/marketed as RITALIN®);

(7) a HER-2 antagonist such as anti-HER-2 antibody (e.g., trastuzumab) and kinase inhibitor (e.g., lapatinib);
(8) an IGF-1 antagonist such as an anti-IGF-1 antibody (e.g., AVE1642 and IMC-A11) or an IGF-1 kinase inhibitor;
(9) EGFR/HER-1 antagonist such as an anti-EGFR antibody (e.g., cetuximab, panitumamab) or EGFR kinase inhibitor (e.g., erlotinib (e.g., branded/marketed as TARCEVA®), gefitinib);
(10) SRC antagonist such as bosutinib;
(11) cyclin dependent kinase (CDK) inhibitor such as seliciclib;
(12) Janus kinase 2 inhibitor such as lestaurtinib;
(13) proteasome inhibitor such as bortezomib;
(14) phosphodiesterase inhibitor such as anagrelide;
(15) inosine monophosphate dehydrogenase inhibitor such as tiazofurine;
(16) lipoxygenase inhibitor such as masoprocol;
(17) endothelin antagonist;
(18) retinoid receptor antagonist such as tretinoin or alitretinoin;
(19) immune modulator such as lenalidomide, pomalidomide, or thalidomide (e.g., branded/marketed as THALIDOMID®);
(20) kinase (e.g., tyrosine kinase) inhibitor such as imatinib (e.g., branded/marketed as GLEEVEC®), dasatinib, erlotinib, nilotinib, gefitinib, sorafenib, sunitinib (e.g., branded/marketed as SUTENT®), lapatinib, AEE788, or TG100801;
(21) non-steroidal anti-inflammatory agent such as celecoxib (branded/marketed as CELEBREX®);
(22) human granulocyte colony-stimulating factor (G-CSF) such as filgrastim (branded/marketed as NEUPOGEN®);
(23) folinic acid or leucovorin calcium;
(24) integrin antagonist such as an integrin α5β1-antagonist (e.g., JSM6427);
(25) nuclear factor kappa beta (NFκβ) antagonist such as OT-551, which is also an anti-oxidant;
(26) hedgehog inhibitor such as CUR61414, cyclopamine, GDC-0449, or anti-hedgehog antibody;
(27) histone deacetylase (HDAC) inhibitor such as SAHA (also known as vorinostat (branded/marketed as ZOLINZA®)), PCI-24781, SB939, CHR-3996, CRA-024781, ITF2357, JNJ-26481585, or PCI-24781;
(28) retinoid such as isotretinoin (e.g., branded/marketed as ACCUTANE®);
(29) hepatocyte growth factor/scatter factor (HGF/SF) antagonist such as HGF/SF monoclonal antibody (e.g., AMG 102);
(30) synthetic chemical such as antineoplaston;
(31) anti-diabetic such as rosiglitazone maleate (e.g., branded/marketed as AVANDIA®);
(32) antimalarial and amebicidal drug such as chloroquine (e.g., branded/marketed as ARALEN®);
(33) synthetic bradykinin such as RMP-7;
(34) platelet-derived growth factor receptor inhibitor such as SU-101;
(35) receptor tyrosine kinase inhibitors of Flk-1/KDR/VEGFR2, FGFR1 and PDGFR beta such as SU5416 and SU6668;
(36) anti-inflammatory agent such as sulfasalazine (e.g., branded/marketed as AZULFIDINE®); and
(37) TGF-beta antisense therapy.

Non-limiting examples of other therapies that may be administered to a subject in combination with a Compound for treating cancer or a non-neoplastic condition include: a synthetic nonapeptide analog of naturally occurring gonadotropin releasing hormone such as leuprolide acetate (branded/marketed as LUPRON®); a nonsteroidal, anti-androgen such as flutamide (branded/marketed as EULEXIN®) or nilutamide (branded/marketed as NILANDRON®); a non-steroidal androgen receptor inhibitor such as bicalutamide (branded/marketed as CASODEX®); steroid hormone such as progesterone; anti-fungal agent such as Ketoconazole (branded/marketed as NIZORAL®); glucocorticoid such as prednisone; estramustine phosphate sodium (branded/marketed as EMCYT®); and bisphosphonate such as pamidronate, alendronate, and risedronate.

Other specific examples of therapies that may be used in combination with a Compound for treating cancer or a non-neoplastic condition include, but are not limited to, antibodies that specifically bind to a tumor specific antigen or tumor associated antigen, e.g., anti-EGFR/HER-1 antibodies.

Additional specific examples of therapies that may be used in combination with a Compound for treating cancer or a non-neoplastic condition include, but are not limited to, agents associated with cancer immunotherapy, e.g., cytokines, interleukins, and cancer vaccines.

Specific examples of agents alleviating side-effects associated with cancer or a non-neoplastic condition that can be used as therapies in combination with a Compound, include, but are not limited to: antiemetics, e.g., Ondansetron hydrochloride (branded/marketed as ZOFRAN®), Granisetron hydrochloride (branded/marketed as KYTRIL®), Lorazepam (branded/marketed as ATIVAN®) and Dexamethasone (branded/marketed as DECADRON®).

In certain embodiments, combination therapies provided herein for treating cancer or a non-neoplastic condition comprise administering a Compound in combination with one or more agents used to treat and/or manage a side effect, such as, bleeding (usually transient, low-grade epistaxis), arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, or heart failure.

In certain embodiments, a Compound is not used in combination with a drug that is primarily metabolized by CYP2D6 (such as an antidepressant (e.g., a atricyclic antidepressant, a selective serotonin reuptake inhibitor, and the like), an antipsychotic, a beta-adrenergic receptor blocker, or certain types of anti-arrhythmics) to treat cancer or a non-neoplastic condition.

Non-limiting examples of other therapies that may be used in combination with a Compound for treating a viral infection include a HCV protease inhibitor such as a NS2 protease inhibitor, a NS3 protease inhibitor, a peptide or dipeptide NS3 protease inhibitor or a NS4a protease cofactor inhibitor; a nucleoside or non-nucleoside HCV NS5b polymerase inhibitor; one or more agents such as a NS4b inhibitor, NS5a inhibitor, IRES inhibitor (such as a steroid, a ribozyme, miRNA, siRNA or an antisense RNA), p7 inhibitor, entry inhibitor, fusion inhibitor, helicase inhibitor, ribavirin, a ribavirin analogue, ribavirin and at least one or more of a non-pegylated interferon or a pegylated interferon, a TLR agonist, cyclophilin inhibitor, caspase or pancaspase inhibitor, immunomodulator, immunomodulator/antiinflammatory, antiinflammatory, antiinflammatory/antifibrotic, broad spectrum immune stimulator, antifibrotic, antioxidant, hemopurifier, IMPDH inhibitor, glycosidase inhibitor, glucosidase inhibitor, HCV therapeutic vaccine, A3 adenosine receptor (AR)

agonist, polypeptide eglin c analog inhibitor, human pancreatic secretory trypsin and minibody repertoire inhibitor or a monoclonal antibody and fragment thereof; or, one or more different agents such as a HIV inhibitor, HBV inhibitor, RNA inhibitor, RNAi, anti-phospholipid therapy, protein therapeutic, interferon replacement agent, botanical or non-specific pharmaceutical.

A specific non-limiting example of other therapies that may be used in combination with a Compound for treating a viral infection include the NS3 HCV protease inhibitor BI 201335 (Boehringer Ingelheim Pharma), boceprevir (also referred to as SCH-503034, Schering-Plough Corporation), ciluprevir (also referred to as BILN-2061, Boehringer Ingelheim Pharma), IDX136 (Idenix Pharmaceuticals, Inc.), IDX316 (Idenix Pharmaceuticals, Inc.), ITMN-191 (also referred to as R-7227, InterMune/Roche Pharmaceuticals), MK-7009 (Merck), PHX1766 (Phenomix), SCH-6 (Schering-Plough Corporation), SCH-900518 (also referred to as SCH-518, Schering-Plough Corporation), telaprevir (also referred to as VX 950, Vertex Pharmaceuticals, Inc.), TMC435350 (also referred to as TMC435, Medivir/Tibotec), VBY-376 and VBY-106 (Virobay), VP50406 (ViroPharma, Inc.), VX-500 (Vertex Pharmaceuticals, Inc.), VX 550 (Vertex Pharmaceuticals, Inc.) or VX-813 (Vertex Pharmaceuticals, Inc.).

Another specific non-limiting example of other therapies that may be used in combination with a Compound for treating a viral infection include the HCV NS4a protease cofactor inhibitor or HCV NS4a protease cofactor inhibitor ACH-806 (also referred to as GS-9132, Achillion/Gilead) or ACH-1095 (also known as GS-9525, Gilead/Achillion.

Another specific non-limiting example of other therapies that may be used in combination with a Compound for treating a viral infection include the nucleoside or non-nucleoside NS5b polymerase inhibitor A-837093 (Abbott Laboratories), A-848837 (Abbott Laboratories), ABT-333 (Abbott Laboratories), AG-021541 (Pfizer Pharmaceuticals), ANA598 (Anadys Pharmaceuticals, Inc.), BILN-1941 (Boehringer Ingelheim Pharma), GL-59728 (Genelabs), GL-60667 (Genelabs), GS-9190 (Gilead), GSK-625433 (GlaxoSmithKline), HCV-796 (Wyeth/Viropharma, Inc.), HCV-896 (ViroPharma, Inc.), IDX102 (Idenix Pharmaceuticals, Inc.), IDX184 (Idenix Pharmaceuticals, Inc.), IDX375 (Idenix Pharmaceuticals, Inc.), JDK-003 (Akros Pharmaceuticals), MK-0608 (Merck), MK-3281 (Merck), NM107 (active moiety of valopicitabine, Idenix/Novartis), PF-00868554 (also referred to as PF-868554 or PF-868,554, Pfizer Pharmaceuticals), PSI-6130 (Pharmasset), PSI-7851 (Pharmasset), R1626 (a prodrug of R1479, Roche Pharmaceuticals), R7128 (a prodrug of PSI-6130, Pharmasset/Roche Pharmaceuticals), valopicitabine (also referred to as NM-283, Idenix/Novartis), VBY-708 (Virobay), VCH-222 (Virochem), VCH-759 (Virochem), VCH-916 (Virochem) or XTL-2125 (also referred to as BC2125, XTL Biopharmaceuticals, Ltd.).

Another specific non-limiting example of other therapies that may be used in combination with a Compound for treating a viral infection include the NS4b inhibitor anguizole (Genelabs/GSK/Viropharma, Inc.), clemizole (Stanford University) or Compound A (BMS).

Another specific non-limiting example of other therapies that may be used in combination with a Compound for treating a viral infection include the N55a inhibitor A-689 (also referred to as AZD7295, Arrow Therapeutics, Ltd./AstraZeneca), A-831 (also referred to as AZD2836, Arrow Therapeutics, Ltd./AstraZeneca), BMS-790052 (Bristol-Myers Squibb).

Another specific non-limiting example of other therapies that may be used in combination with a Compound for treating a viral infection include the IRES inhibitor steroid mifepristone (also referred to as VGX-410C, VGX Pharmaceuticals), an antisense oligonucleotide ISIS-14803 (Isis Pharmaceuticals), a ribozyme such as HEPTAZYME®, (a synthetic ribozyme, Ribozyme Pharmaceuticals, Inc.), a RNAi such as TT033 (Benitec/Tacere Bio/Pfizer) or SIRNA-034 (Sirna Therapeutics), a miRNA such as SPC3649 (LNA-antimiR™-122 brand, Santaris Pharma) or an anti-miR-122 miRNA (Regulus Therapeutics) or siRNA.

Another specific non-limiting example of other therapies that may be used in combination with a Compound for treating a viral infection include the p7 inhibitor BIT225 (Biotron Limited), the viral entry inhibitor ITX5061 (iTherX Pharmaceuticals, Inc.), PRO206 (Progenics), an SP-30 entry inhibitor (Samaritan Pharmaceuticals) or a broad spectrum entry inhibitor such as REP 9AC (an amphipathic DNA polymer, REPLICor, Inc.).

Another specific non-limiting example of other therapies that may be used in combination with a Compound for treating a viral infection include ribavirin (VIRAZOLE® and VILONA® brands, ICN Pharmaceuticals), ribavirin for oral administration (REBETOL® brand, Schering-Plough Corporation), ribavirin tablets (COPEGUS® brand, Roche Pharmaceuticals), ribavirin capsules (RIBASPHERE® brand, Three Rivers Pharmaceuticals, LLC), Another specific non-limiting example of other therapies that may be used in combination with a Compound for treating a viral infection include the ribavirin analogue levovirin (L-isomer of ribavirin, Valeant Pharmaceuticals), R1518 (a prodrug of levovirin, also referred to as levovirin valinate, Roche Pharmaceuticals) or taribavirin (an oral prodrug of ribavirin, also referred to as viramidine, Valeant Pharmaceuticals).

Another specific non-limiting example of other therapies that may be used in combination with a Compound for treating a viral infection include the non-pegylated interferon (optionally administered with ribavirin) interferon alfa-2a (ROFERON®-A brand, Roche Pharmaceuticals), interferon alfa-2b (INTRON® A brand, Schering-Plough Corporation), interferon alfa-2c (BEROFOR® brand, Boehringer Ingelheim), interferon-alpha variant GEA007.1 (GenOdyssee SA), interferon-alpha for low dose oral administration (Amarillo Biosciences, Inc./CytoPharm, Inc.), interferon-alpha for oral administration (BELEROFON® brand, Nautilus Biotech), long-acting interferon-alpha (LOCTERON® brand, also referred to as BLX-883, Biolex Therapeutics/OctoPlus), long-acting albuminfusion interferon alfa-2b (ALBUFERON® brand, also referred to as albinterferon alfa-2b, Human Genome Sciences), purified multi-subtype human leukocyte interferon-alpha (MULTIFERON® brand, Swedish Orphan International), interferon beta-1a (REBIF® brand, Merck Serono), interferon omega (also referred to as leukocycle (II) interferon, Intarcia Therapeutics), interferon omega (VIRBAGEN OMEGA® brand, Virbac), interferon omega (OMEGA INTERFERON® brand, Biomedicines), consensus interferon (INFERGEN® brand, also referred to as interferon alfacon-1, Three Rivers Pharma), medusa interferon (MEDUSA INTERFERON® brand, Flamel Technologies).

Another specific non-limiting example of other therapies that may be used in combination with a Compound for treating a viral infection include the pegylated interferon (optionally adiministered with ribavirin) Peginterferon alfa-2a (PEGASYS® brand, Roche Pharmaceuticals), Peginterferon alfa-2b (PEGINTRON® brand, Schering-Plough Corporation), Peginterferon alfacon-1 (pegylated form of interferon alfacon-1, also referred to as PEG-Alfacon, InterMune), Peg-Interferon Lambda IL-29 (Zymogenetics/Bristol-Myers Squibb).

Another specific non-limiting example of other therapies that may be used in combination with a Compound for treating a viral infection include the TLR agonist ANA773 (Anadys Pharmaceuticals, Inc.), a TLR-7 agonist selected from isatoribine (also referred to as ANA245, Anadys Pharmaceuticals, Inc.), ANA-971 (a prodrug of TLR-7 agonist isatoribine, Anadys Pharmaceuticals, Inc.), ANA975 (a prodrug of TLR-7 agonist isatoribine, Anadys Pharmaceuticals, Inc.), a TLR9 agonist selected from IMO-2125 (Idera Pharmaceuticals), a TLR9 agonist (Actilon brand, Coley), a cyclophilin B inhibitor selected from Debio 025 (Debiopharm Group) or SCY-635 (Scynexis) or a cyclosporin A analog selected from NIM811 (Novartis), a pancaspase inhibitor selected from PF-03491390 (also referred to as IDN-6556, Pfizer Pharmaceuticals), an interleukin-7 immunomodulator selected from CYT107 (Cytheris SA), NOV-205 (Novelos Therapeutics), oglufanide disodium (Implicit Bioscience) or thymosin alpha 1 (also referred to as thymalfasin, ZADAXIN® brand, SciClone Pharmaceuticals), a immunomodulator/antiinflammatory selected from NOV205 (Novelos Therapeutics, Inc.), an antiinflammatory selected from CTS-1027, a matrix metalloproteinase selected from a (MMP) inhibitor (Conatus) or CF102, an A3AR agonist (Can-Fite BioPharma, Ltd.), an antiinflammatory/antifibrotic selected from mitoquinone (MitoQ® brand, Antipodean Pharmaceuticals) or PYN17 (Phynova), a broad spectrum immune stimulator selected from SCV-07 (SciClone), an immune regulator selected from ECH18 (Enzo BioChem/ Therapeutics), an antifibrotic selected from JKB-122 (Jenken Biosciences), a tumor necrosis factor inhibitor antifibrotic selected from ENBREL® brand (Wyeth), a phospholipid antifibrotic for oral administration selected from IP-501 (Indevus Pharmaceuticals), a hemopurifier (Aethlon Medical), an IMPDH inhibitor selected from merimepodib (also referred to as VX-497, Vertex Pharmaceuticals, Inc.), a glucosidase inhibitor selected from celgosivir, an alpha-glucosidase I inhibitor selected from MX-3253 (Migenix), a HCV therapeutic vaccine selected from a DNA vaccine (ChronVac-C® brand, Inovio/Tripep AB), a MVA virus vaccine carrying and expressing HCV non-structural proteins (NS3, NS4 and NS5b) selected from TG4040 (Transgene) or (Inovio/Tripep AB), an antiviral vaccine selected from GNI-103 (GENimmune), a virosome-based combination vaccine of synthetic HCV peptide antigens (Pevion Biotect), an E1 vaccine (Innogenetics), a HCV E1/E2/MF59 vaccine (Chiron/Novartis), a vaccine selected from CSL123 (Chiron/CSL), a targeted molecular immunogen vaccine selected from GI-5005 (GlobeImmune), a vaccine having a combination of five synthetic peptides selected from IC-41 (Intercell AG/Novartis), an antiviral vaccine (AMANTADINE® brand, Endo Labs), a monoclonal antibody selected from 170® (also referred to as HCV-AB$^{XTL}$68 or HCV-AB, Biochem Therapeutics/OSI Pharmaceuticals), an immune globulin polyclonal antibody selected from intravenous human immune globulin (CI-VACIR® brand, NABI), a humanized Y-90 labeled antibody (Immunomedics, Inc.) an anti-PD1 antibody selected from MDX-1106 (also referred to as ONO-4538, Medarex, Inc./ Ono Pharmaceutical), an anti-CD20 monoclonal antibody (RITUXIMAB® brand, Genentech), a monoclonal antibody selected from XTL-6865 or XTL-002 (XTL Biopharmaceuticals, Ltd.), a HIV fusion inhibitor selected from enfuvirtide (FUZEON® brand, Trimeris/Roche Pharmaceuticals), an anti-phospholipid therapy selected from bavituximab (formerly TARVACIN® brand, Peregrine Pharmaceuticals, Inc.), a protein therapeutic or interferon replacement agent selected from oligoadenylate synthetase stimulant CB-183,872 (Cubist Pharmaceuticals, also referred to as IB657 from Illumigen Biosciences), a botanical selected from an antiviral botanical extract PYN18 (Phynova) or a non-specific pharmaceutical selected from the cholesterol-lowering agent fluvastatin (Oklahoma University Health Sciences Center), atorvastatin (Okayama University, Japan), lovastatin (Okayama University, Japan) or simvastatin (Okayama University, Japan), a thiazolide analog selected from nitazoxanide (ALINIA™ brand, Romark Pharmaceuticals), photo-sensitized methylene blue (SUVUS® brand, Bioenvision), a synthetic phytochemical selected from KPE02003002 (Kemin Pharma) or KPE00001133 (Kemin Pharma), an antiviral agent selected from CB5300 (Canopus BioPharma, Inc.) or a tyrosine phosphatase inhibitor selected from sodium stibogluconate (LE-NOCTA™ brand, VioQuest Pharmaceuticals).

Another specific non-limiting example of other therapies that may be used in combination with a Compound for treating a viral infection include the non-specific pharmaceutical histamine dihydrochloride (CEPLENE® and MAXAM-INE® brands, Maxim Pharmaceuticals), an immunosuppressive agent selected from mycophenolate mofetil (Roche Pharmaceuticals), mycophenolic acid (Roche Pharmaceuticals), or α1-antichymotrypsin.

5.8 Kits

Provided herein is a pharmaceutical pack or kit comprising one or more containers filled with a Compound or pharmaceutical composition thereof. Additionally, one or more other therapies useful for the treatment of cancer or a non-neoplastic condition, or other relevant agents can also be included in the pharmaceutical pack or kit. Also provided herein is a pharmaceutical pack or kit comprising one or more containers filled with one or more of the ingredients of the pharmaceutical compositions described herein. Optionally associated with such kits can be a notice in the form prescribed by a governmental agency regulating the manufacture, use or sale of pharmaceuticals or biological products, which notice reflects approval by the agency of manufacture, use or sale for human administration.

6. GENERAL SYNTHETIC METHODS

Compounds provided herein can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3rd Edition, John Wiley & Sons, 1999. The protecting groups may be removed at a convenient subsequent stage using methods known in the art.

6.1
Scheme I:
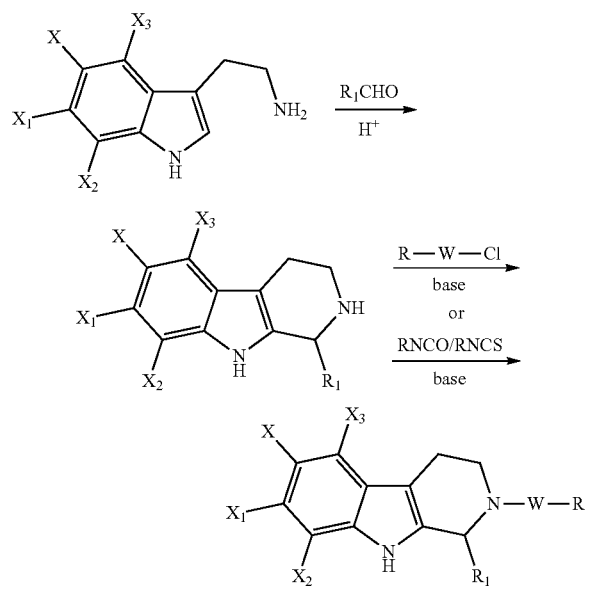
6.2
Scheme II:
6.3
Scheme III:
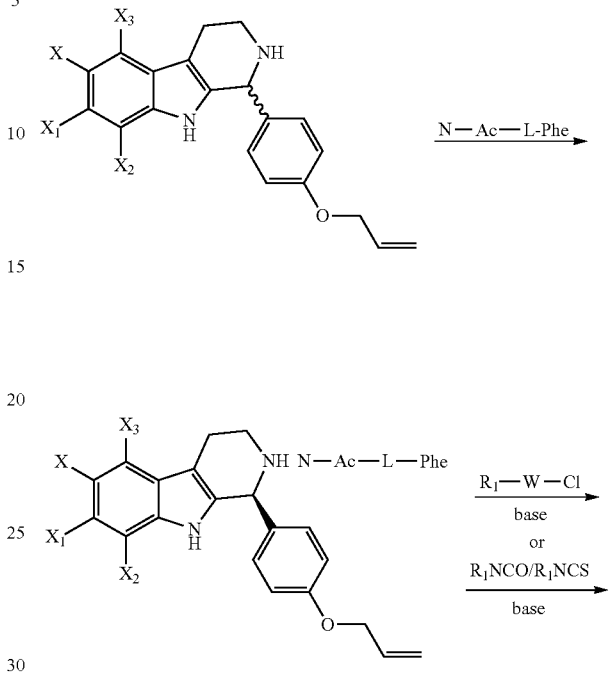
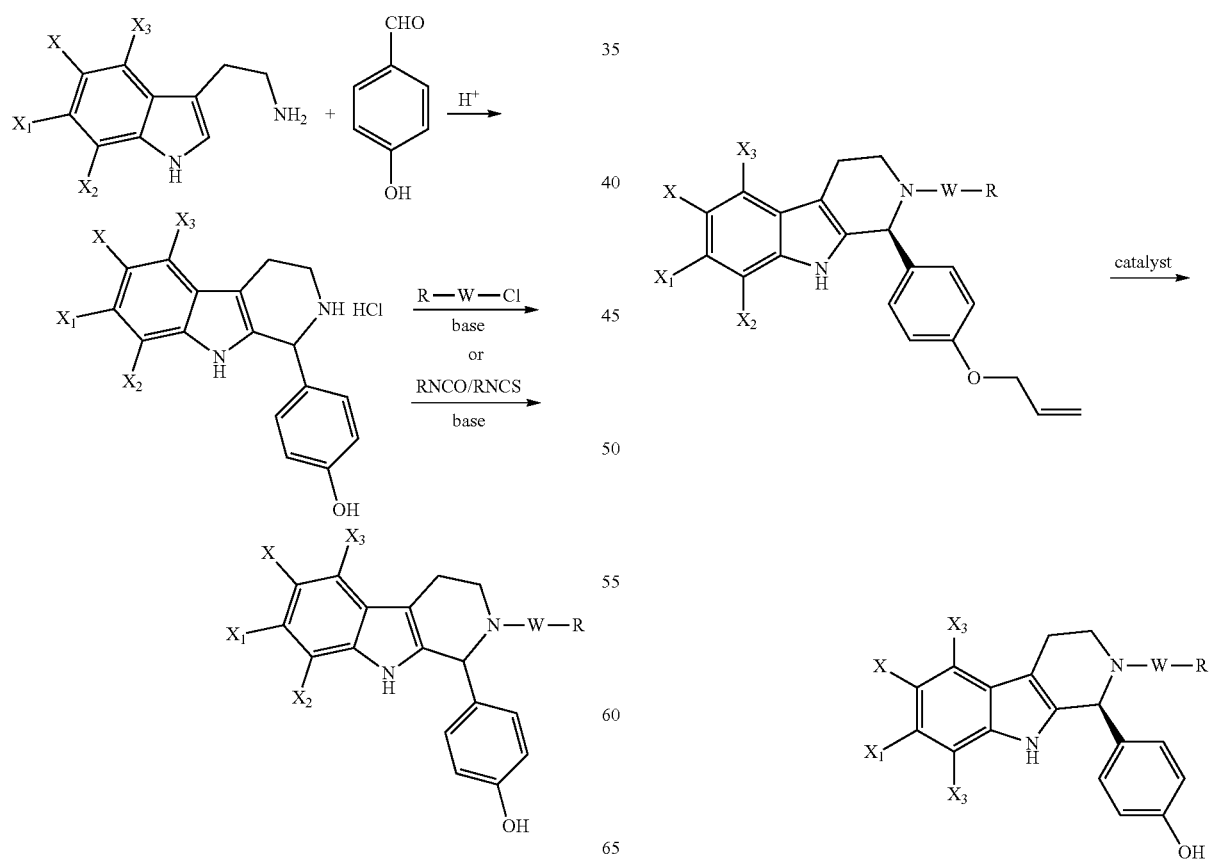
W=bond, C=O, CO₂, COS, CON, SO₂, SO₂N, PO₃R'₂

Scheme IV:
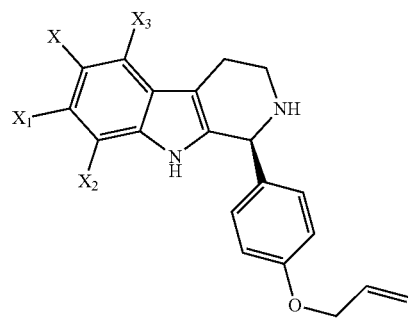
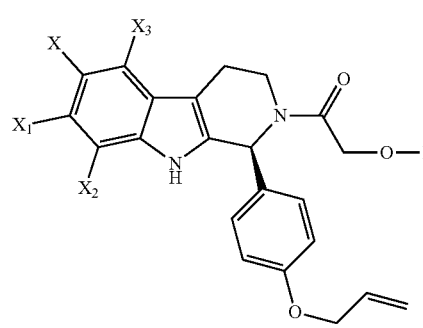
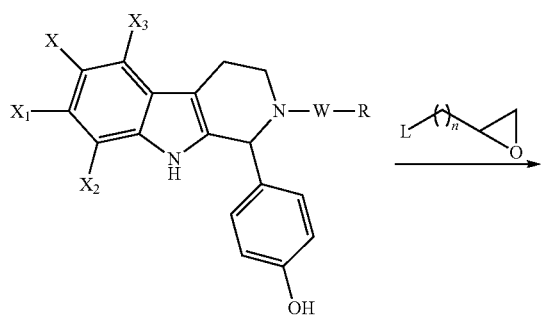
Scheme V:
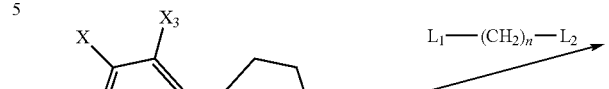
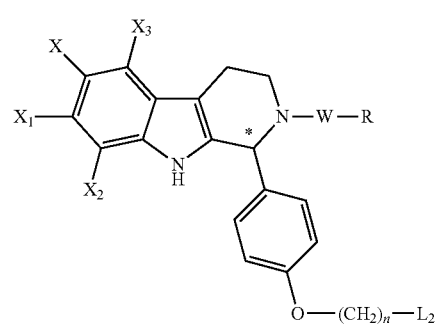
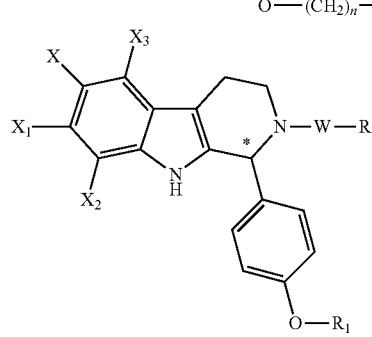
L, L₁, L₂: leaving groups.
The chiral center can be racemic or R or S
Scheme VI:
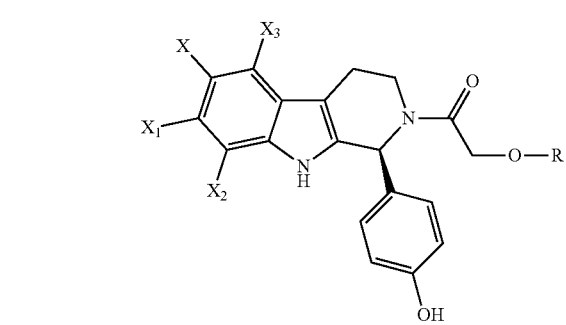

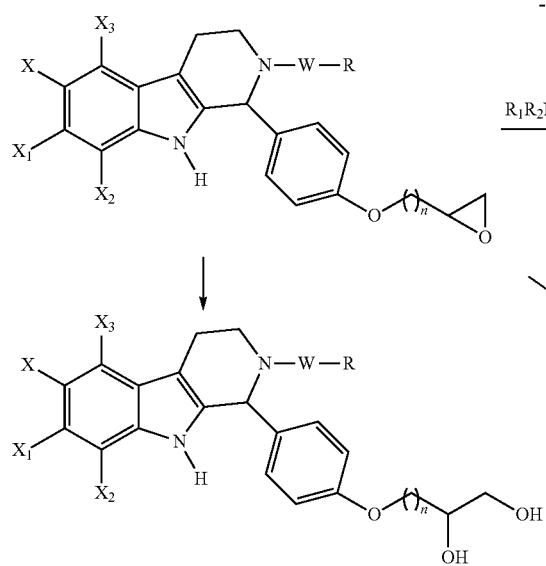
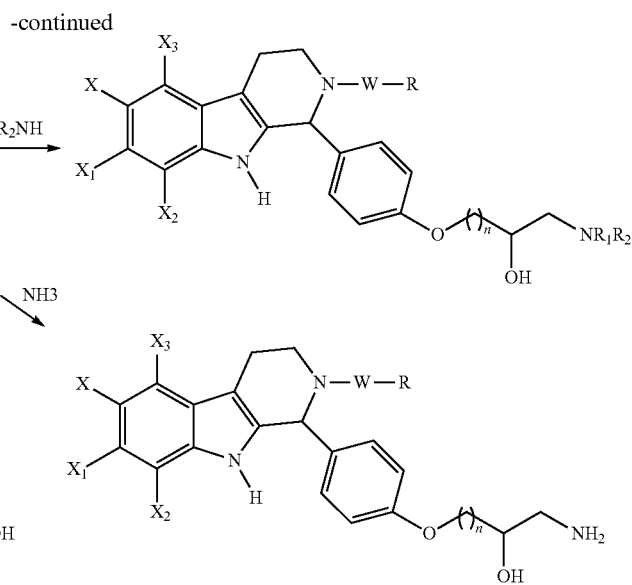
6.7
Scheme VII:
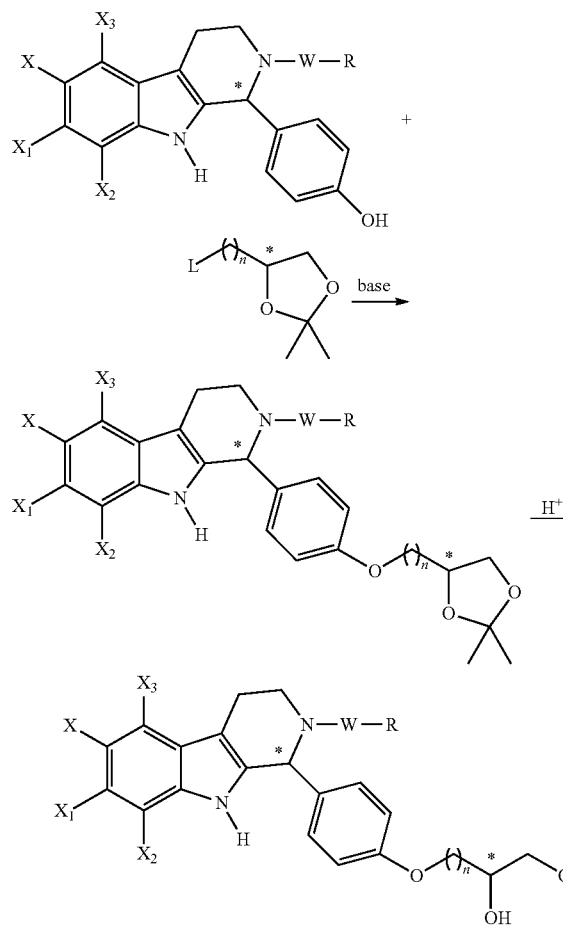
6.8
Scheme VIII:
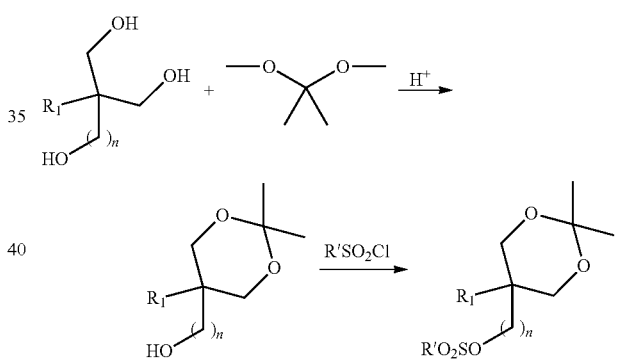
6.9
Scheme IX:
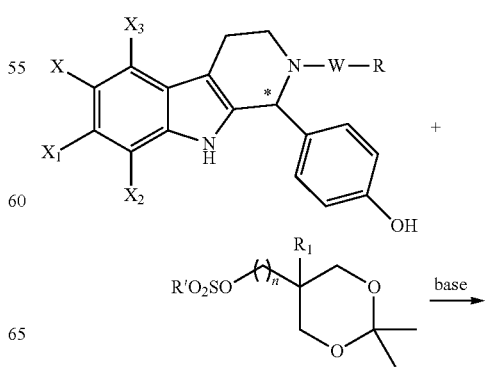

431
-continued
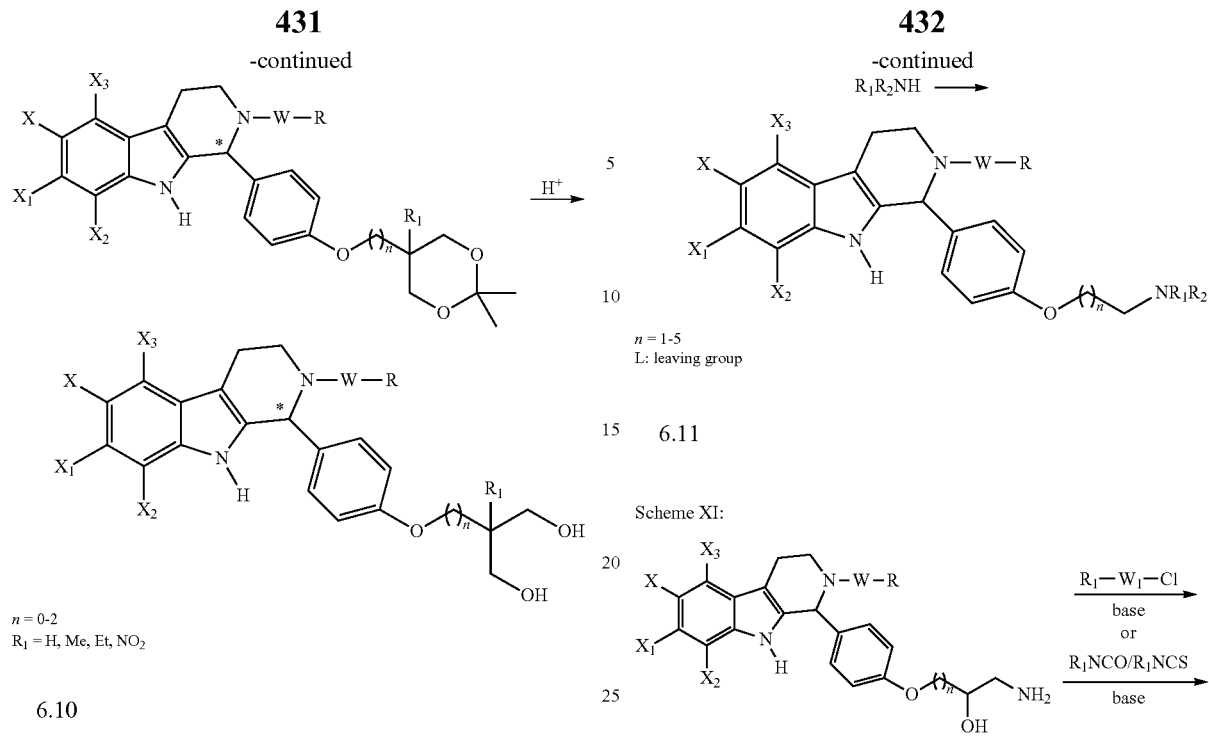
$n = 0-2$
$R_1 = H, Me, Et, NO_2$
6.10
Scheme X:
432
-continued
$R_1R_2NH \longrightarrow$
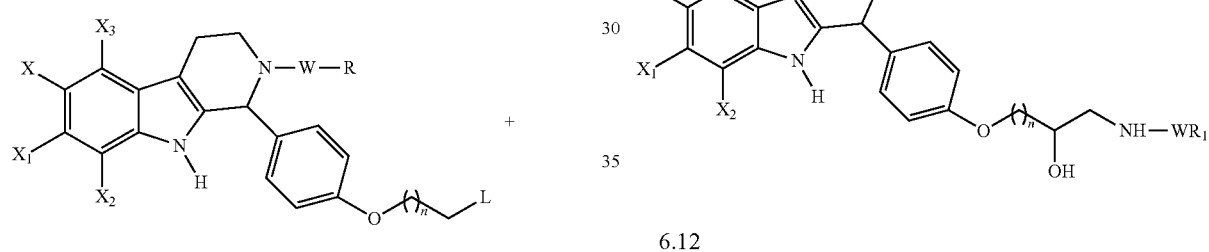
$n = 1-5$
L: leaving group
6.11
Scheme XI:
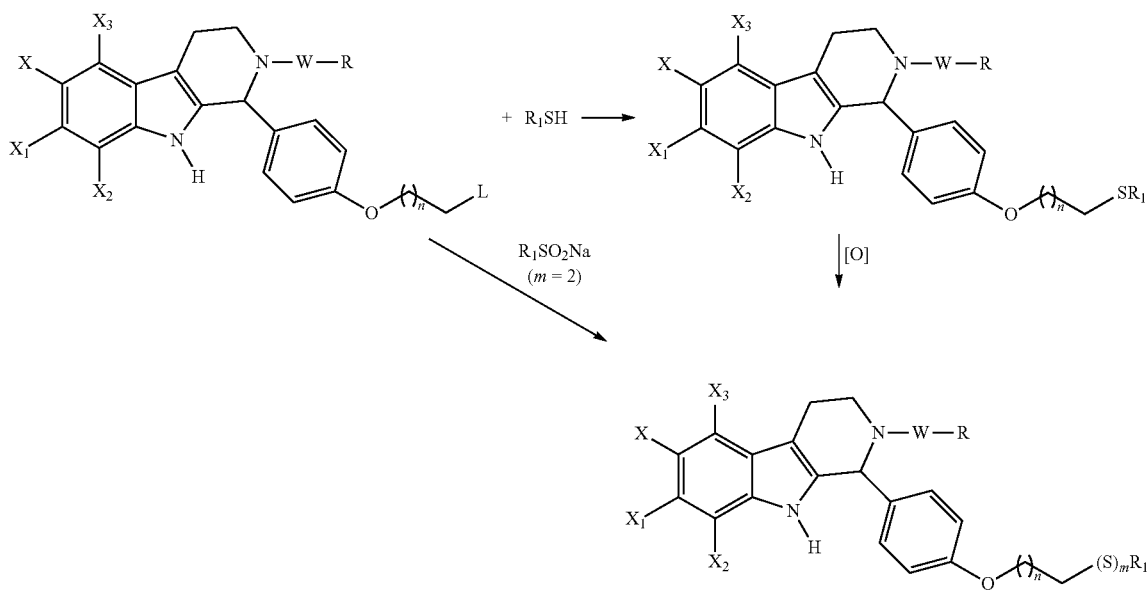
6.12
Scheme XII:
$n = 1-5$
L: leaving group 6.13
Scheme XIII:
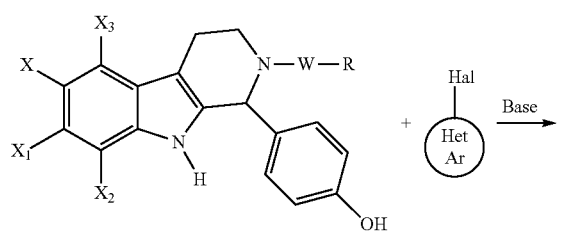
6.14
Scheme XIV:
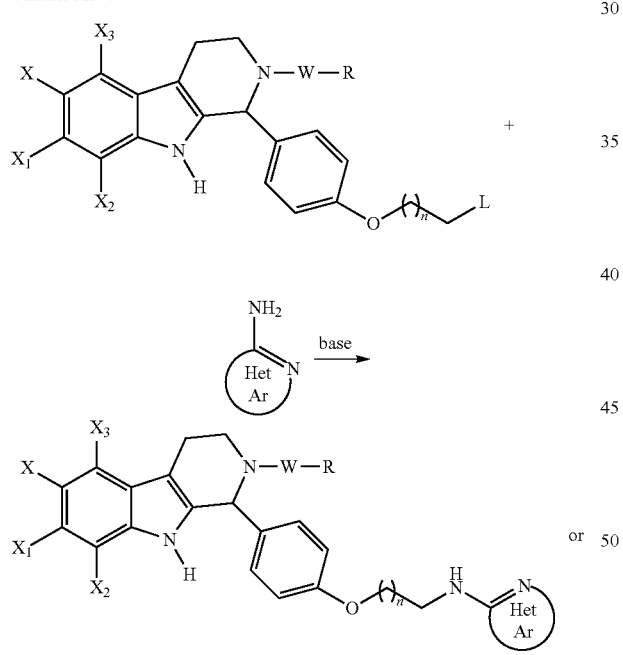
n = 1-5
L: leaving group
6.15
Scheme XV:
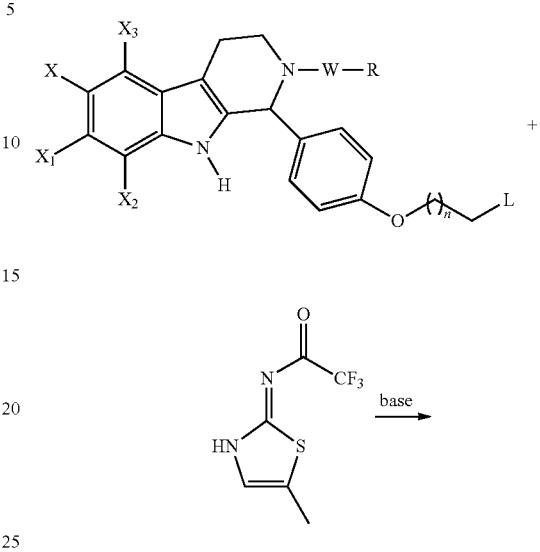
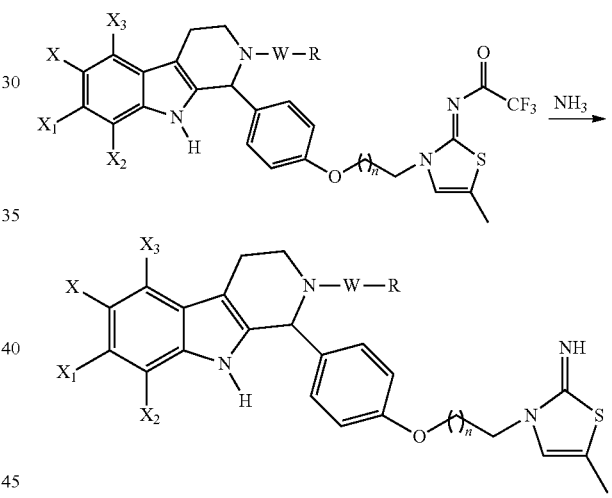
n = 1-5
L: leaving group
6.16
Scheme XVI:
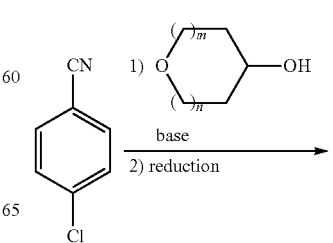

435
-continued
436
-continued
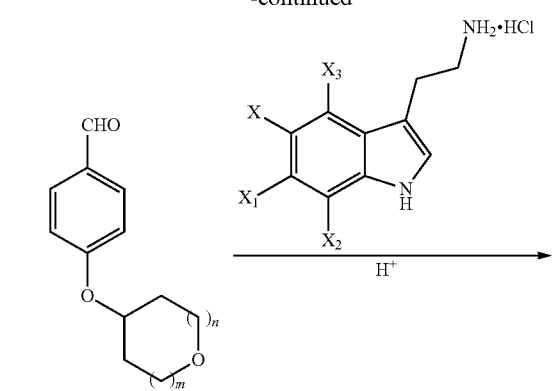
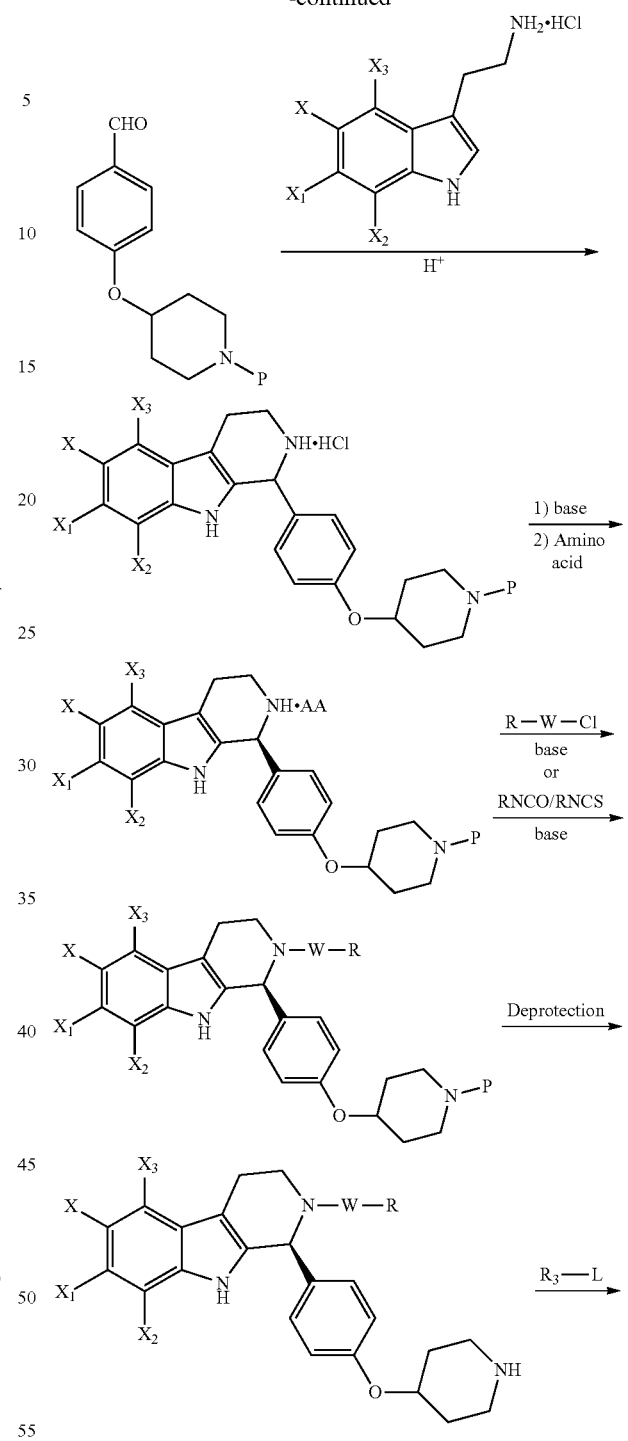
6.17
Scheme XVII:
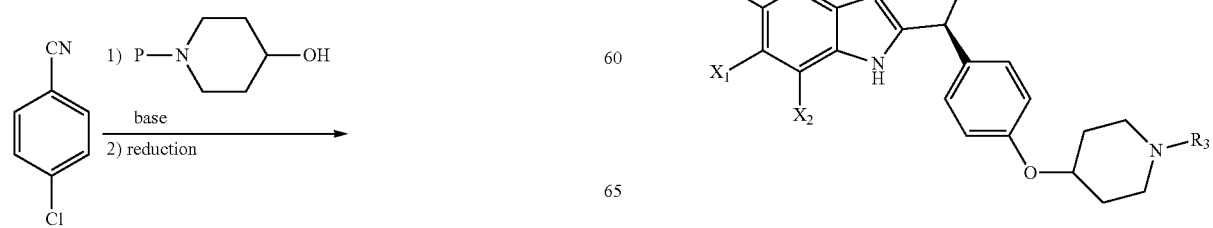

6.18
Scheme XVIII:
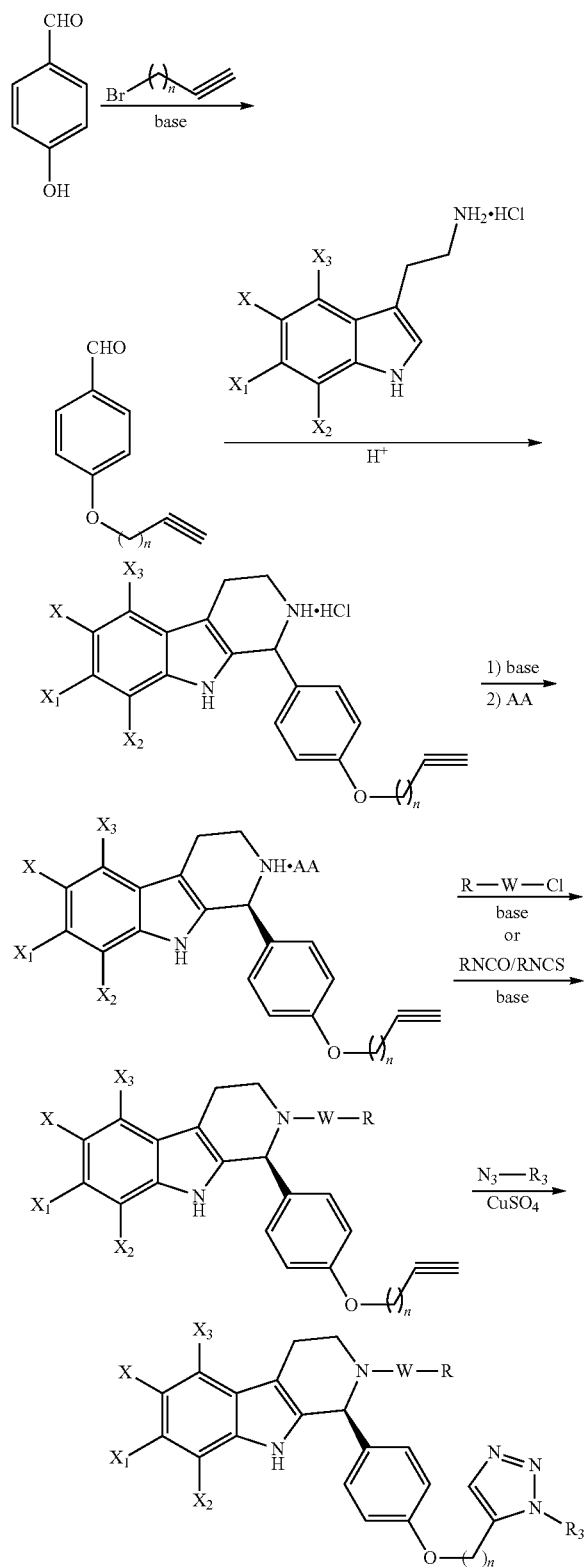
$n = 1-3$
6.19
Scheme XIX:
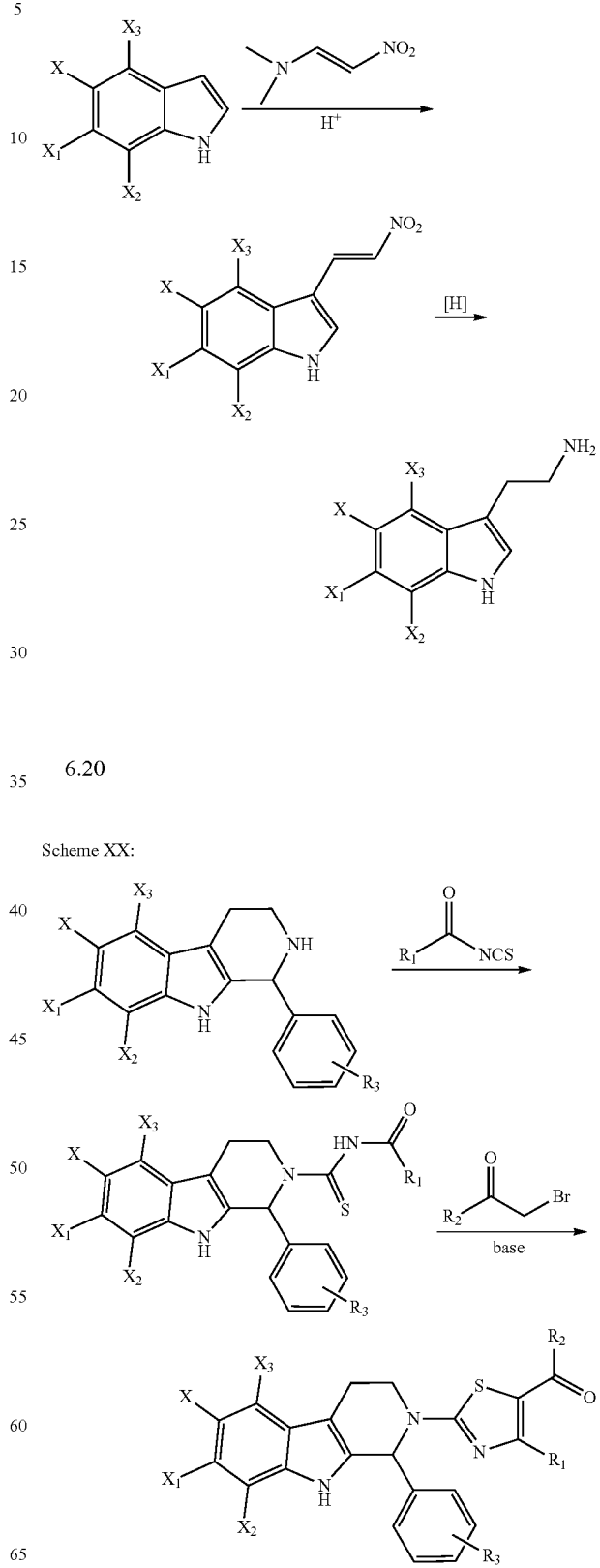
6.20
Scheme XX:

6.21

Scheme XXI:

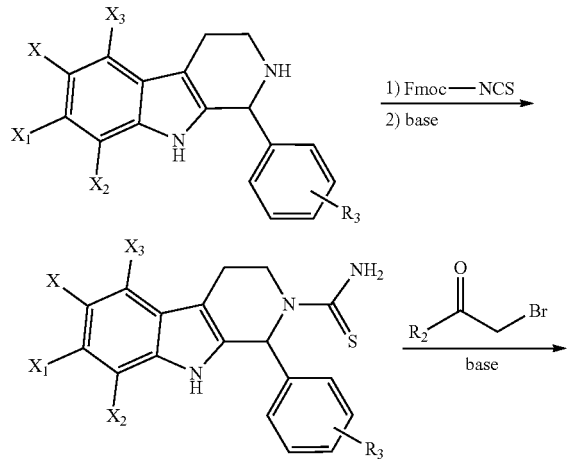

6.22

Scheme XXII:

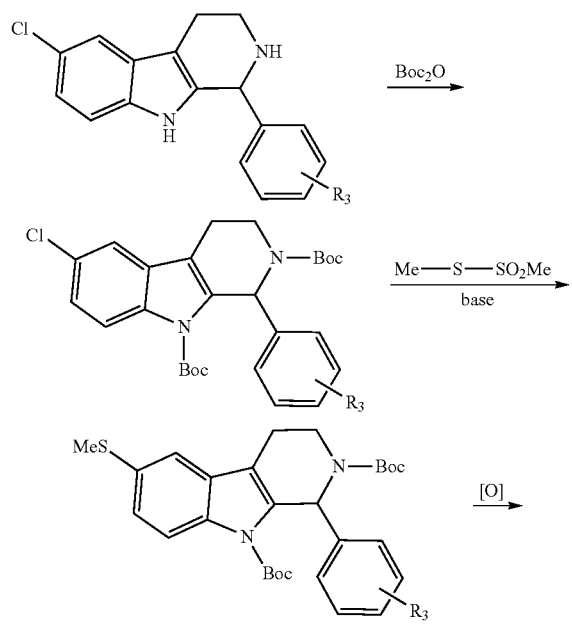

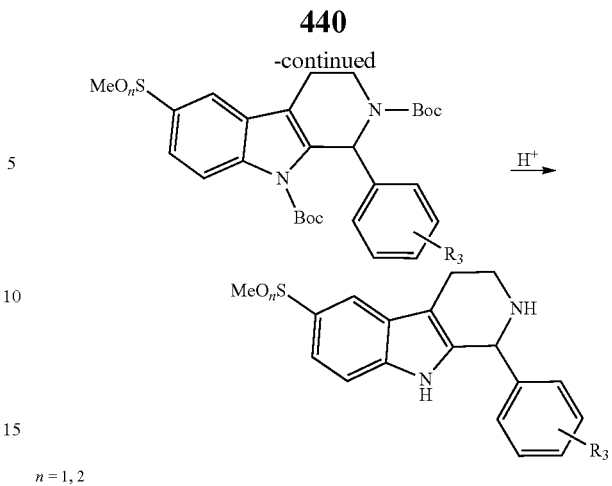

$n = 1, 2$

6.23

Scheme XXIII:

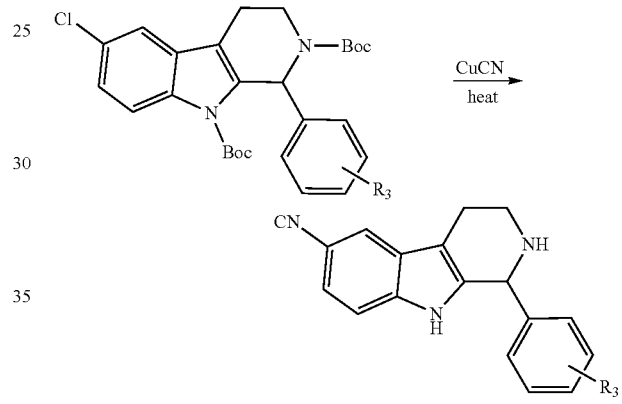

6.24 Synthetic Routes

Where the processes for the preparation of the Compounds provided herein give rise to mixtures of stereoisomers, these isomers may be separated by conventional techniques such as preparative chromatography. The Compounds provided herein may be prepared in racemic form, or individual enantiomers may be prepared either by enantiospecific synthesis or by resolution. The Compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The Compounds may also be resolved by formation of diastereomeric esters or amides, followed by chromatographic separation and removal of the chiral auxiliary. Alternatively, the Compounds may be resolved using a chiral HPLC column.

The terms used in describing the invention are commonly used and known to those skilled in the art. Some reagents are referred to as a chemical formula. Other reagents are referred to as abbreviations known to persons skilled in the art.

Specific Compounds provided herein may be prepared as per the following examples offered by way of illustration and not by way of limitation. No attempt has been made to optimize the yields obtained in any of the reactions. One skilled in the art would know how to increase such yields through

Example I

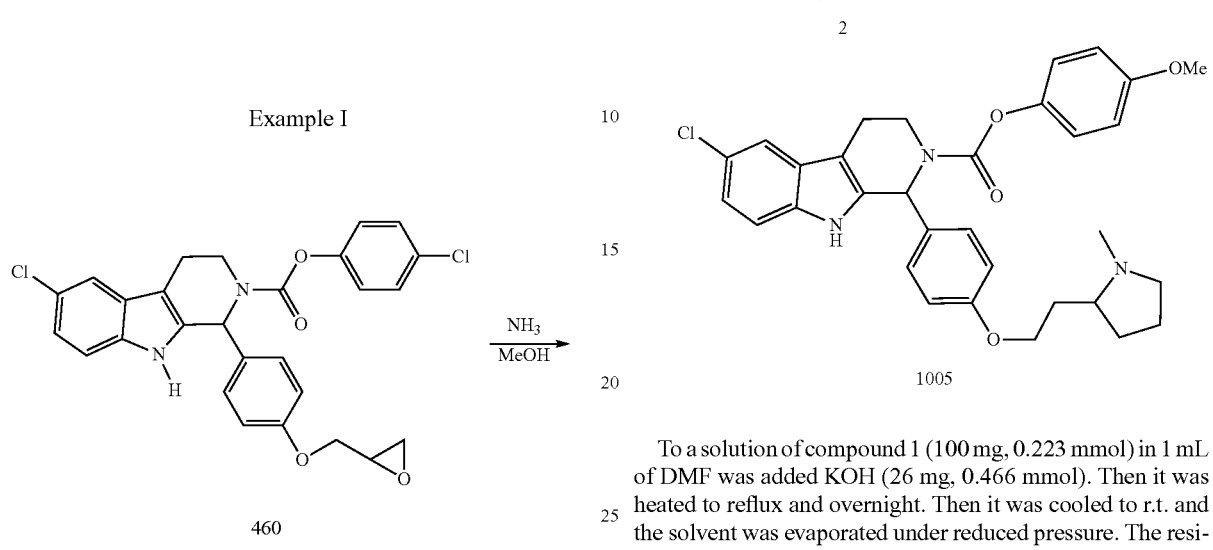

To epoxide Compound 460 (prepared as described in U.S. Publication No. 2005-0272759) (0.76 g, 1.5 mmol) was added to a solution of ammonia in MeOH (7 M, excess) and stirred at rt overnight. The mixture was concentrated in-Vacuo and chromatographed (15% MeOH and 0.5% i-Pr$_2$NH in DCM) to give 0.693 g (88%) of the amino alcohol B (1725) as a white solid.

Example II

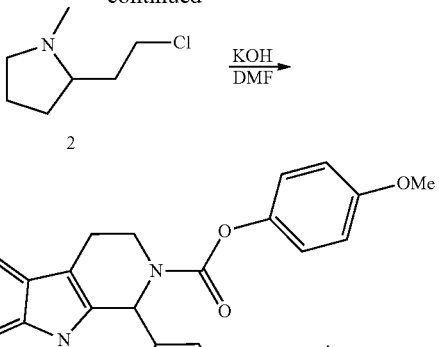

To a solution of compound 1 (100 mg, 0.223 mmol) in 1 mL of DMF was added KOH (26 mg, 0.466 mmol). Then it was heated to reflux and overnight. Then it was cooled to r.t. and the solvent was evaporated under reduced pressure. The residue was dissolved with EA (5 mL), washed with water (3×5 mL), brine, dried over Na$_2$SO$_4$ and evaporated under reduced pressure. The residue was purified by preparative HPLC to give 34 mg of compound 1005. Yield: 26%.

Example III

To a solution of compound 1 (3.7 g, 0.01 mol) in 30 mL of DMF was added K$_2$CO$_3$ (4.14 g, 0.03 mol) and ClCH$_2$COOMe (1.62 g, 0.015 mol). The mixture was heated to 80° C. After 4 h, it was cooled to r.t. The solvent was evaporated under reduced pressure and the residue was dissolved with EA (20 mL). The organic layer was washed with water (3×20 mL), brine, dried over Na$_2$SO$_4$ and evaporated under reduced pressure. The crude solid was dissolved with 20 mL of THF. Then LiOH (4N, 20 mL) was added to it. The mixture was stirred overnight. The solvent was evaporated under reduced pressure. The residue was purified by flash column chromatography to yield 2.2 g compound 2. Yield: 51%

To a solution of compound 2 (100 mg, 0.233 mmol) in 1 mL of DMF was added compound 3 (67 mg, 0.466 mmol), HOBT (71 mg, 0.466 mmol), EDCI (89 mg, 0.466 mmol), NMM (116 mg, 1.16 mmol). The mixture was stirred at r.t. for 16 h. Then the solvent was evaporated under reduced pressure and the residue was purified by preparative HPLC to yield 42 mg of compound 1003. Yield: 32%

Example IV

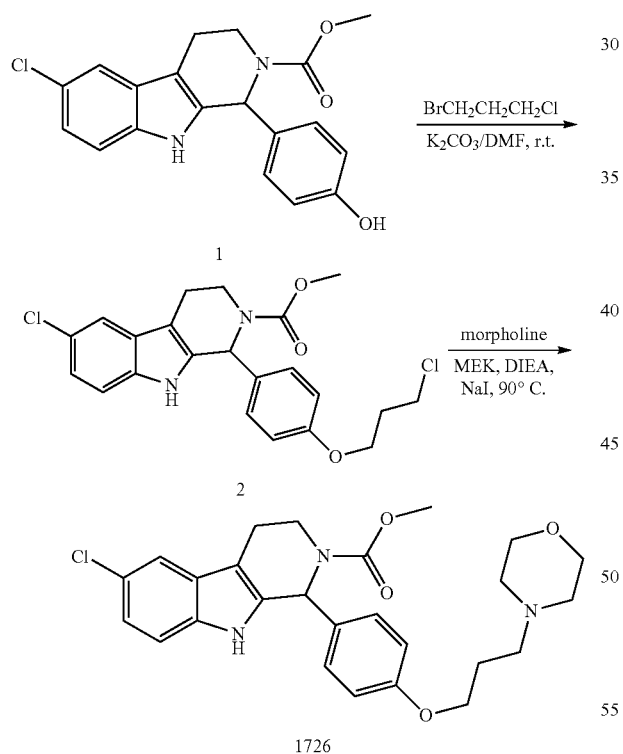

To a solution of compound 1 (1 g, 2.8 mmol) in 10 mL of DMF was added K$_2$CO$_3$ (1.16 g, 8.4 mmol) and BrCH$_2$CH$_2$CH$_2$Cl (0.66 g, 4.2 mmol). Then it was stirred at r.t. overnight. Then it was evaporated under reduced pressure and the residue was dissolved with EA (15 mL). The organic layer was washed with water (3×15 mL), brine, dried over Na$_2$SO$_4$ and evaporated under reduced pressure. The residue was purified by preparative HPLC.

To a solution of compound 2 (100 mg, 0.23 mmol) in 1 mL of MEK was added DIEA (59 mg, 0.46 mmol), NaI (34 mg, 0.23 mmol), morpholine (40 mg, 0.46 mmol). Then it was heated to 90° C. overnight. The mixture was cooled to r.t. and evaporated under reduced pressure and the residue was dissolved with EA (5 mL). The organic layer was washed with water (3×5 mL), brine, dried over Na$_2$SO$_4$ and evaporated under reduced pressure. The residue was purified by preparative HPLC.

Example V

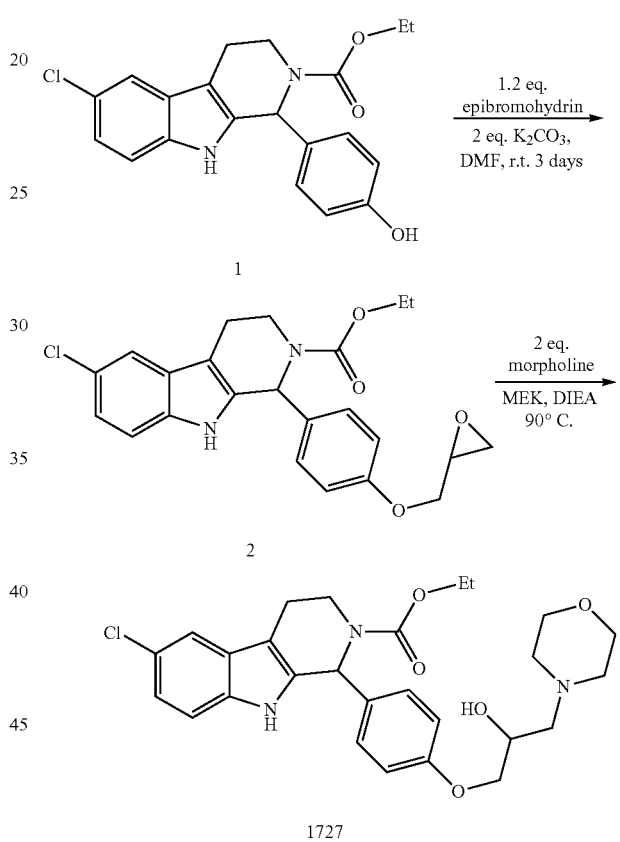

To a solution of compound 1 (3 g, 8 mmol) in 15 mL of DMF was added K$_2$CO$_3$ (2.3 g, 16 mmol) and epobromohydrin (1.3 g, 9.6 mmol). After the addition, it was stirred at r.t. for 3 days. Then it was quenched with water, washed with brine, dried over Na$_2$SO$_4$ and evaporated under reduced pressure. The residue was purified by flash column chromatography to give 1.7 g compound 2. Yield: 49%

To a solution of compound 2 (100 mg, 0.23 mmol) in 1 mL of methylethylketone was added diisopropylethylamine (59 mg, 0.46 mmol) and morpholine (40 mg, 0.46 mmol). After the addition, it was heated to 90° C. overnight. Then it was cooled to r.t., quenched with water, washed with water, brine, dried over Na$_2$SO$_4$, and evaporated under reduced pressure. The residue was purified by flash column chromatography to give 53 mg of compound 1727. Yield: 45%.

Example VI

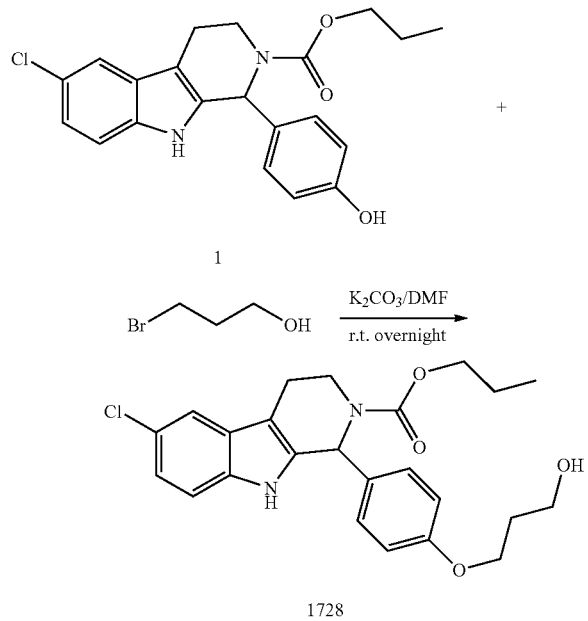

To a solution of 1 (81 mg, 0.21 mmol) in 1 mL of DMF was added K$_2$CO$_3$ (89 mg, 0.63 mmol) and 2 (35 mg, 0.25 mmol). Then it was stirred at r.t. overnight. The solvent was evaporated under reduced pressure and the residue was dissolved with ethyl acetate (5 mL) and washed with water (5 mL×3). The organic layer was washed with brine, dried over Na$_2$SO$_4$ and evaporated under reduced pressure. Then the crude solid was purified by preparative HPLC to give 41 mg of compound 1728. Yield: 44%

Example VII

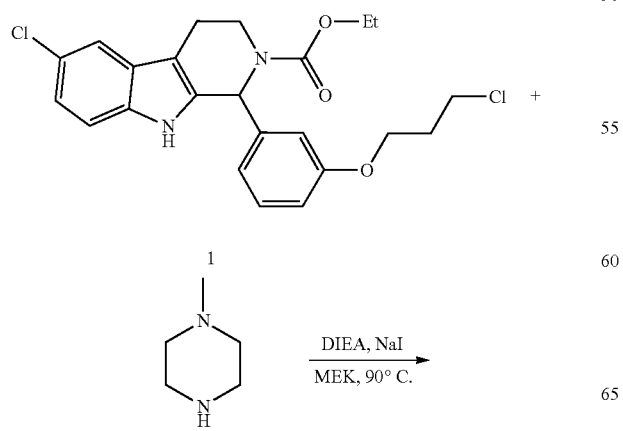

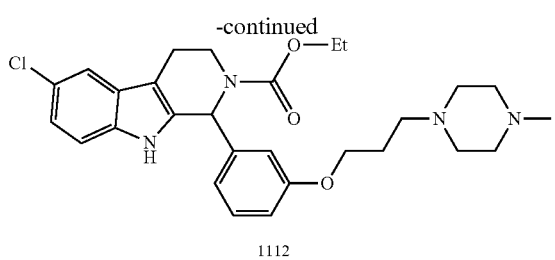

To a solution of compound 1 (100 mg, 0.22 mmol) in 1 mL of MEK was added DIEA (57 mg, 0.44 mmol), NaI (10 mg) and compound 2 (44 mg, 0.44 mmol). Then it was heated to 90° C. and stirred overnight. After cooled to r.t., the solvent was removed under reduced pressure. The residue was treated with EA and water. The organic layer was washed with brine, dried over Na$_2$SO$_4$ and evaporated under reduced pressure. The crude product was purified by flash column chromatography to give 45 mg compound 1112. Yield: 40%

Example VIII

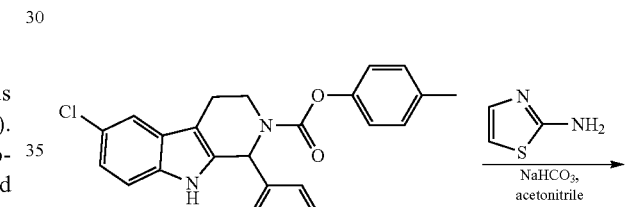

To a solution of compound 1 (150 mg, 0.29 mmol) in 2 mL of acetonitrile was added NaHCO$_3$ (73 mg, 0.87 mmol) and 2-amino-thiazole (29 mg, 0.29 mmol). The mixture was heated to reflux for 2 days. Then it was evaporated under reduced pressure and dissolved in EA. The organic layer was washed with water and brine, dried, evaporated under reduced pressure and purified by preparative HPLC to give 21 mg of compound 1729. Yield: 12%

Example IX
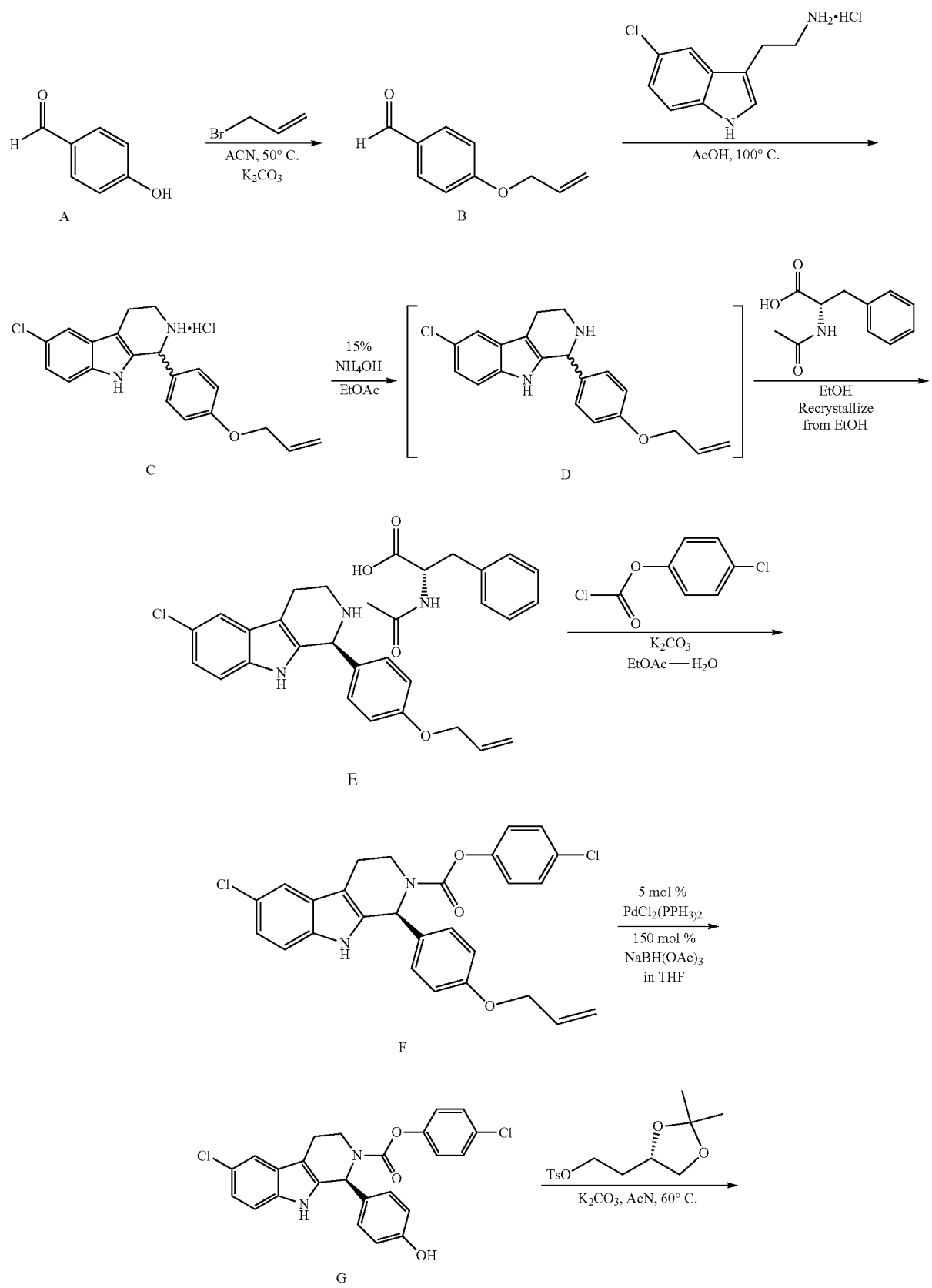

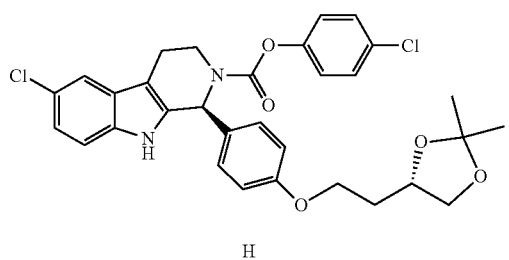 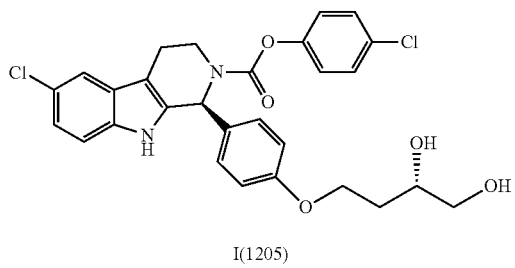

H    I(1205)

Compound 1205 may be prepared by reacting allyl bromide (79.2 g, 656 mmol) and 4-hydroxybenzaldehyde A (40.0 g, 328 mmol) in the presence of potassium carbonate (90.6 g, 656 mmol) in acetonitrile (400 mL). The reaction is stirred at ambient temperature under an atmosphere of nitrogen for 4 hours. The reaction is filtered, washed with acetonitrile (200 mL), and concentrated in-vacuo. The residue is chromatographed on silica gel using a gradient of ethyl acetate from 10% to 30% in hexanes to give 50.0 g of aldehyde B as a colorless oil. LC/MS [M+H$^+$] 163.2 (100), 2.85 min; $^1$H NMR (300 MHz, DMSO-d$_6$) δ ppm 4.67 (d, J=5.03 Hz, 2H) 5.33 (dd, J=23.98, 1.51 Hz, 2H) 6.03 (dt, J=22.39, 5.07 Hz, 1H) 7.12 (d, J=8.72 Hz, 2H) 7.85 (d, J=8.38 Hz, 2H) 9.86 (s, 1H).

Aldehyde B (50.0 g, 308 mmol) is dissolved in 1.5 L of glacial acetic acid and heated to 100° C. To this solution is added 5-chlorotryptamine HCl (59.4 g, 257 mmol) in small portions. The reaction is stirred for 48 hours under nitrogen then cooled to ambient temperature. The solids are filtered, washed with glacial acetic acid (2×200 mL), and dried in a stream of nitrogen for 48 hours to produce the Pictet-Spengler intermediate C (73.3 g, 76%). LC/MS: 2.02 min, M−H=337 (100); $^1$H-NMR (300 MHz, d$_6$-DMSO): δ 11.10 (S, 1H), 10.36 (br-s, 2H), 7.60 (d, J=2.0 Hz, 1H), 7.32 (m, 3H), 7.11 (dd, J=8.6 & 2.0 Hz, 1H), 7.04 (d, J=8.7 Hz, 2H), 6.04 (m, 1H), 5.87 (s, 1H), 5.40 (dd, J=17.3 & 1.7 Hz, 1H), 5.27 (dd, J=10.5 & 1.4 Hz, 1H), 4.61 (br-d, J=5.2 Hz, 2H), 3.38 (m, 2H), 3.06 (m, 2H).

The Pictet-Spengler intermediate C (50.0 g, 133 mmol) is suspended in ethyl acetate (2 L) and 15% aqueous ammonium hydroxide (1 L) and stirred vigorously for 1 hour. The organic layer is separated, washed with brine (500 mL), dried over anhydrous sodium sulfate, and concentrated in vacuo to give the free base D as a pale yellow oil. The pale yellow oil is used for the next stage without further purification.

To the above-described preparation of D, is added absolute ethanol (2 L) and L-N-acetyl-phenylalanine (16.6 g, 79.9 mmol). The mixture is stirred at ambient temperature overnight. The white precipitate (93% ee) is filtered and recrystallized from refluxing absolute ethanol. Upon cooling to ambient temperature, the solid is filtered, washed with ethanol (100 mL), and dried in a stream of nitrogen to give the chiral salt E (28.8 g, 32.7%). Chiral High-Performance Liquid Chromatography (HPLC) indicates the presence of the desired (S) enantiomer at 16.2 minutes, and the absence of the undesired (R) at 19.4 minutes; LC/MS indicates a peak of compound at 2.02 minutes with a parent ion of M−H=337 (100).

To a suspension of E (20.0 g, 36.6 mmol) in EtOAc (150 mL) and water (50 mL) at room temperature is added K$_2$CO$_3$ (12.63 g, 91.5 mmol). After all the solid is dissolved, 4-chlorophenyl chloroformate is introduced by dropwise addition over 5 min at 0° C. The mixture is stirred at room temperature for 5.5 h. The two layers are separated. The organic layer is washed with 10% K$_2$CO$_3$ and brine, dried over Na$_2$SO$_4$, and concentrated under reduced pressure to give 18.50 g of crude compound F as a yellowish foam. The crude product is used without further purification in the subsequent reaction.

To a N$_2$ degassed solution of crude compound F (about 36.6 mmol) in 360 mL of Acros HPLC grade tetrahydrofuran (THF), 0.98 g (1.396 mmol, 3.8%) of 99.9% pure Aldrich grade PdCl$_2$(PPh$_3$)$_2$ is added. The resulting yellow suspension is stirred for 3-5 minutes, followed by the addition of 12.02 g (56.7 mmol, 1.55 eq) of solid 95% pure Aldrich grade NaBH(OAc)$_3$ in one portion. The mixture, which turns black after about an hour, is stirred at room temperature overnight. The black mixture is concentrated under reduced pressure at room temperature. The residue is taken into EtOAc and washed with saturated aqueous NaHCO$_3$, saturated aqueous NH$_4$Cl and brine (saturated aqueous NaCl). The organics are dried over MgSO$_4$, concentrated to about 30 mL, and filtered through a short silica plug, which is eluted with 30% of EtOAc in hexanes. The combined filtrate is concentrated to a thick oil, treated with a minimal amount of dichloromethane (about 15 mL), and stirred at room temperature overnight. An off-white colored solid precipitates out. That solid is filtered, washed with dichloromethane:hexanes::1:2, and dried under vacuum to give compound G as an off-white solid (14.64 g, 88.5%). The filtrate is concentrated and purified by chromatography on silica gel using 30% of EtOAc in hexanes to give 1.33 g of G. Overall yield of G from E: 15.97 g, 96.5%.

A suspension of compound G (36.26 g, 80.0 mmol) and K$_2$CO$_3$ (11.04 g, 160.0 mmol) in MeCN (300 mL) at 80° C. is dropped into a solution of (S)-2-(2,2-dimethyl-1,3-dioxolan-4-yl)ethyl 4-methylbenzenesulfonate (26.4 g, 88.0 mmol) in MeCN (60 mL) over 4-5 h. The mixture is heated at 80° C. for 15 h with stirring. The mixture is then concentrated under vacuum, taken into EtOAc, and washed with three portions of water. The organics are dried over Na$_2$SO$_4$, concentrated under vacuum, and purified by chromatography on approximately 400 g of silica gel using 30% EtOAc in hexanes as the eluent. The process provides compound H as a white solid (46.0 g, 98.6%). Chemical purity: >99.5%, LC/MS (Electrospray) indicates a parent ion of 579.61; Chiral LC: 20.07 min, >99% ee. $^1$H-NMR (300 MHz, CDCl$_3$); 7.98 (s, 1H), 7.53 (s, 1H), 7.33 (d, J=8.7 Hz, 2H), 7.25 (d, J=9.3 Hz, 2H), 7.15 (s, 2H), 7.05 (d, J=9.0 Hz, 2H), 6.83 (d, J=7.2, 2 H). 6.46 (s 1H), 4.45 (dd, J=13.5, 4.2 Hz, 1H), 4.28 (m, J=6.3 Hz, 1H), 4.06 (m, 3H), 3.63 (dd, J=9.0, 7.2 Hz, 1H), 3.32 (m, 1H), 3.00 (m, 1H), 2.85 (dd, J=15.3, 3.3 Hz, 1H), 2.03 (q, J=5.1 Hz, 2H), 1.41 (s, 3H), 1.35 (s, 3H).

To a solution of compound H (21.0 g, 36.1 mmol) in MeCN (150 mL) is added 0.1 M H$_2$SO$_4$ (18.0 mL, 1.80 mmol) over 5 minutes. The solution is stirred at room temperature for 15 hours, at which time LC/MS shows no starting material. Solid K$_2$CO$_3$ (2.48 g, 18 mmol) is added and the mixture is concentrated under vacuum. The residue is taken into EtOAc and washed with three portions of water. The organics are concentrated and purified by chromatography on 200 g of silica gel employing 30% EtOAc in hexanes as a first eluent, and 100% EtOAc as a second eluent. Chromatography gives 17.97 g (92%) of Compound 1205 as a white solid. m.p.: 110-130° C.; Solubility in water: about 1 μg/mL; ClogP 5.4; MW: 541.42; Chemical purity: >99.5%; LC/MS (electrospray) 539.29; Chiral LC: 19.96 min, >99% e.e.; $^1$H-NMR (300 MHz, CDCl$_3$): 8.20 (s, 1H), 7.52 (s, 1H), 7.33 (d, J=9.0 Hz, 2H), 7.21 (d, J=7.8 Hz, 2H), 1.72 (S, 2H), 7.05 (d, J=8.7, 2 H), 6.82 (d, J=7.2 Hz, 2H), 6.43 (s, 1H), 4.44 (dd, J=14.1, 3.9 Hz, 1H), 4.10 (m, 2H), 3.97 (m, 1H), 3.69 (d, J=9.6, 1H), 3.51 (dd, J=11.1, 7.2 Hz, 1H), 3.30 (m, 1H), 2.99 (m, 1H), 2.84 (dd, J=15.6, 3.6 Hz, 1H), 2.16 (s, 1H), 1.90 (q, J=5.7 Hz, 2H).

Example X

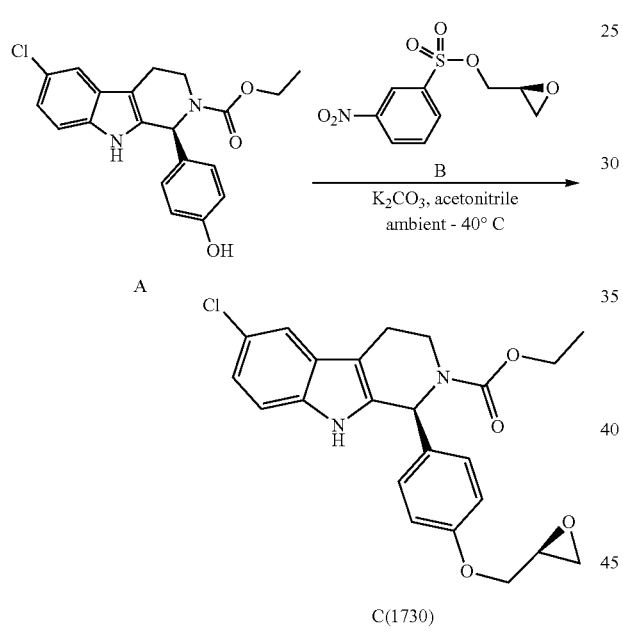

Phenol A (1.85 g, 5.00 mmol), potassium carbonate (1.52 g, 11.0 mol), and nosyl glycidol B (1.56 g, 6.00 mmol) were combined in acetonitrile (50 mL) at room temperature and stirred at 40° C. for 48 hours. The reaction was cooled to ambient temperature and filtered. The solids were washed with acetonitrile (50 mL). The washings were combined with the original mother liquor and concentrated in-vacuo. The residue was chromatographed on silica gel using a gradient (0-30%) of ethyl acetate in methylene chloride to give 1.72 g of C (1730) as a white foam. LCMS [M+H$^+$] 427.2 (100), 3.86 min; Chiral HPLC (OD-H) 40.52 min; $^1$H NMR (300 MHz, DMSO-d$_6$) δ ppm 1.21 (br. s., 3H) 2.67 (dd, J=5.03, 2.68 Hz, 1H) 2.75 (d, J=4.02 Hz, 2H) 2.81 (dd, J=5.03, 4.36 Hz, 1H) 2.92-3.09 (m, 1H) 3.24-3.31 (m, 1H) 3.78 (dd, J=11.40, 6.71 Hz, 1H) 4.05-4.18 (m, 3H) 4.28 (dd, J=11.40, 2.68 Hz, 1H) 6.31 (br. s., 1H) 6.93 (d, J=8.72 Hz, 2H) 7.05 (dd, J=8.72, 2.01 Hz, 1H) 7.11 (d, J=8.38 Hz, 2H) 7.28 (d, J=8.72 Hz, 1H) 7.49 (d, J=2.01 Hz, 1H) 11.11 (br. s., 1H).

Example XI

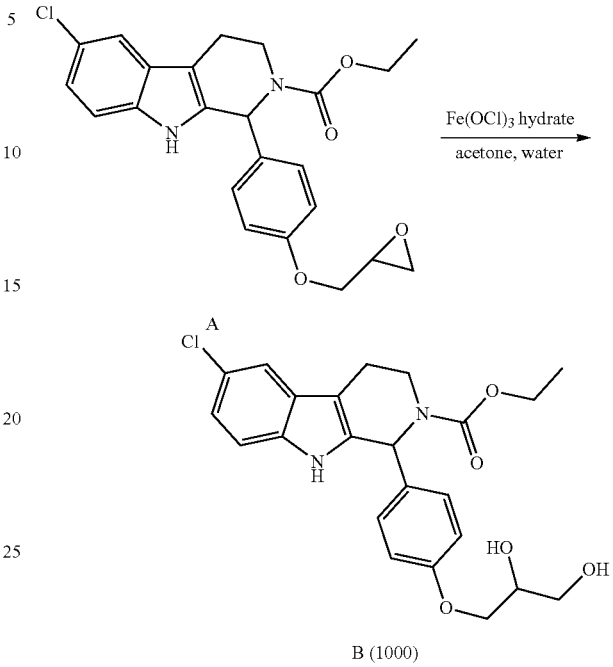

To epoxide A (2.10 g, 4.92 mmol) dissolved in acetone (50 mL) was added ferric perchlorate hydrate (350 mg, 0.982 mmol) dissolved in water (10 mL). Additional acetone was added until the solution was no longer cloudy. The reaction was stirred at ambient temperature for 20 hours then at 30° C. for an additional 18 hours. Water (50 mL) was added to the cooled reaction mixture. The reaction was subsequently washed with methylene chloride (3×100 mL) and the organics were concentrated in-vacuo. The residue was chromatographed on silica gel using ethyl acetate (100%) to give 1.47 g of 1000 as a white foam. LCMS [M+H$^+$] 445.0 (100), 3.12 min; $^1$H NMR (300 MHz, DMSO-d$_6$) δ ppm 1.22 (br. s., 3H) 2.60-2.86 (m, 2H) 2.91-3.13 (m, 1H) 3.41 (t, J=5.56 Hz, 2H) 3.67-3.86 (m, 2H) 3.95 (dd, J=9.54, 4.13 Hz, 1H) 4.05-4.24 (m, 3H) 4.56-4.72 (m, 1H) 4.92 (d, J=5.09 Hz, 1H) 6.31 (br. s., 1H) 6.90 (d, J=8.58 Hz, 2H) 7.05 (dd, J=8.58, 1.91 Hz, 1H) 7.10 (d, J=8.58 Hz, 2H) 7.28 (d, J=8.58 Hz, 1H) 7.50 (d, J=1.91 Hz, 1H) 11.11 (br. s., 1H).

Example XII

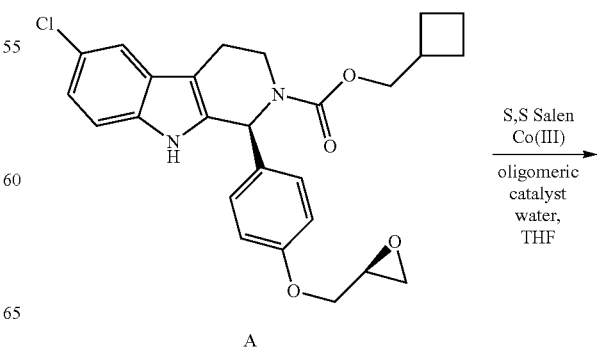

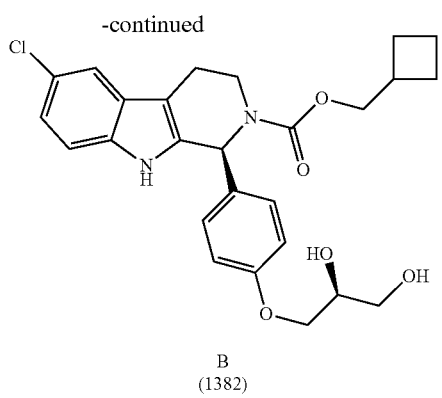

B
(1382)

Epoxide A (280 mg, 0.600 mmol) was dissolved in tetrahydrofuran (6 mL) and cooled to 0° C. After adding the chiral (S,S) oligomeric Salen cobalt (III) catalyst (12.0 mg, 0.015 mmol—provided by Prof. Eric Jacobson, Harvard U.) and water (12 μl, 0.66 mmol), the reaction was stirred while warming to ambient temperature until all epoxide was consumed. The solvent was removed under a stream of nitrogen and the brown residue was purified by preparative HPLC without any buffer to give chiral diol 1382. LCMS [M+H$^+$] 485.4 (100), 3.45 min; Chiral HPLC (OD-H) 28.56 min; $^1$H NMR (300 MHz, DMSO-d$_6$) δ ppm 1.64-1.91 (m, 4H) 1.99 (br. s., 2H) 2.59 (br. s., 1H) 2.67-2.86 (m, 2H) 2.92-3.15 (m, 1H) 3.40 (br. s., 2H) 3.74 (br. s., 1H) 3.77-3.87 (m, 1H) 3.90-4.04 (m, 2H) 4.10 (br. s., 2H) 4.65 (br. s., 1H) 4.93 (br. s., 1H) 6.27 (br. s., 1H) 6.90 (d, J=8.58 Hz, 2H) 7.05 (dd, J=8.58, 1.98 Hz, 1H) 7.09 (d, J=8.58 Hz, 2H) 7.28 (d, J=8.58 Hz, 1H) 7.49 (d, J=1.98 Hz, 1H) 11.11 (br. s., 1H).

Example XIII

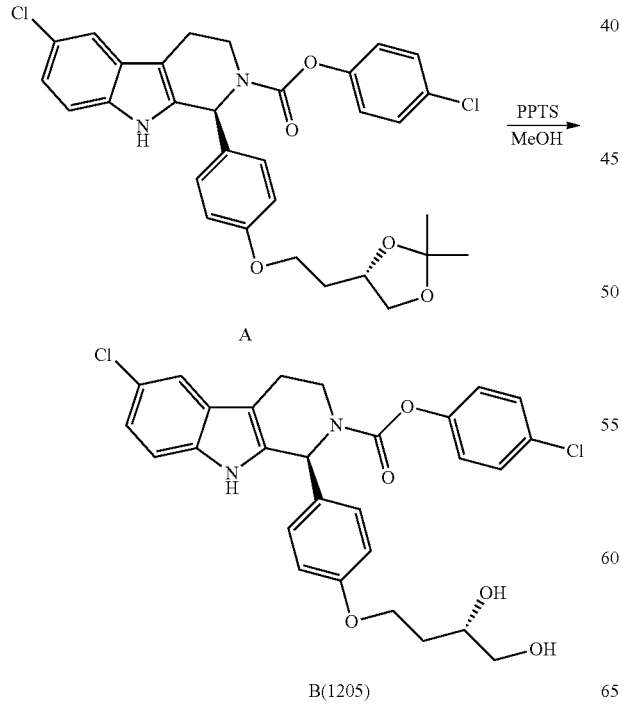

To a solution of A (16.3 g, 28.0 mmol) in MeOH (100 mL) was added PPTS (3.53 g, 14 mmol, 20%). The mixture was stirred at room temperature for 15 h. LC-MS showed about 24% starting material. Another 50% of PPTS was added and the solution was stirred at room temperature for 8 h. LC-MS showed no change. The mixture was concentrated under vacuum at room temperature. The residue was taken into EtOAc, washed by water and brine. The organics were concentrated and purified by chromatography to give 11.45 g (75.6%) of G as a white solid and 3.37 g of SM A. The recovered A and 1.46 g of PPTS were dissolved in MeOH (20 mL). The solution was stirred at room temperature for 15 h. LC-MS showed about 23% SM 9. The same work-up gave 2.4 g of B (1205) and 0.58 g of SM A. Total yield of B (1205): 13.85 g, 91.4%. Chemical purity: >99.5%, LC-MS (ES$^-$) 539.29; Chiral LC: 19.96 min, >99% ee. $^1$H-NMR (300 MHz, CDCl$_3$): δ 8.20 (s, 1H), 7.52 (s, 1H), 7.33 (d, J=9.0 Hz, 2H), 7.21 (d, J=7.8 Hz, 2H), 1.72 (S, 2H), 7.05 (d, J=8.7, 2 H), 6.82 (d, J=7.2 Hz, 2H), 6.43 (s, 1H), 4.44 (dd, J=14.1, 3.9 Hz, 1H), 4.10 (m, 2H), 3.97 (m, 1H), 3.69 (d, J=9.6, 1H), 3.51 (dd, J=11.1, 7.2 Hz, 1H), 3.30 (m, 1H), 2.99 (m, 1H), 2.84 (dd, J=15.6, 3.6 Hz, 1H), 2.16 (s, 1H), 1.90 (q, J=5.7 Hz, 2H).

Example XIV

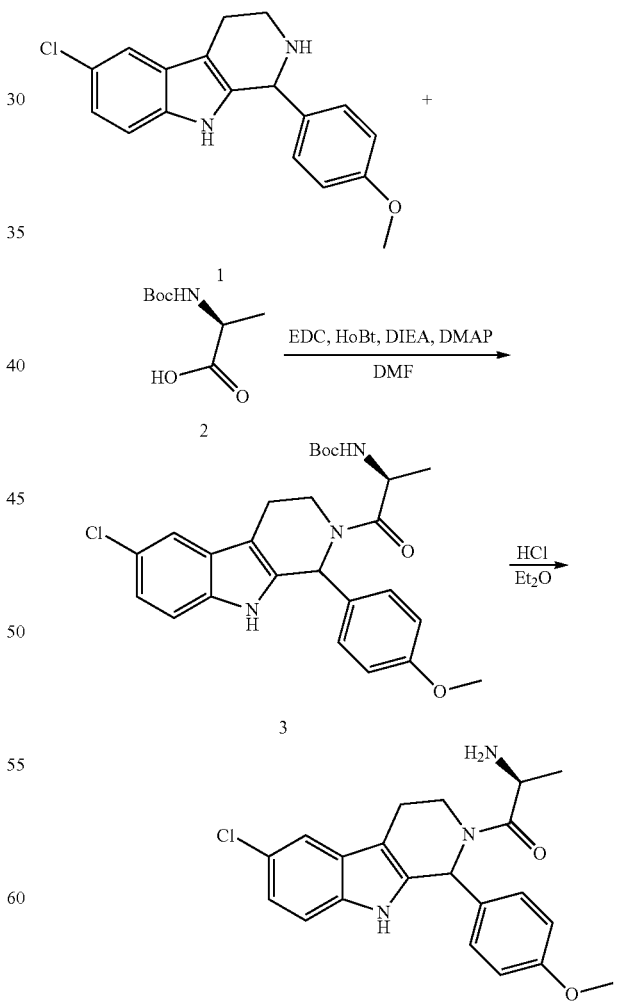

1731

To a solution of compound 1 (350 mg, 1.12 mmol) in 3 mL of DMF was added compound 2 (254 mg, 1.34 mmol) and EDC (215 mg, 1.12 mmol), HOBT (151 mg, 1.12 mmol), NMM (226 mg, 2.24 mmol). This reaction mixture was stirred at r.t. for 5 h. Then it was treated with water and EA. The organic layer was separated, washed with brine, dried over $Na_2SO_4$ and evaporated under reduced pressure. The residue was purified by flash column chromatography to give 340 mg of compound 3. Yield 63%

To a solution of compound 3 (240 mg, 0.5 mmol) in 2 mL of ether was added 1 M HCl. The mixture was stirred at r.t. for 6 h. Then the solvent was removed under reduced pressure. The residue was dissolved with EA (5 mL), washed with water (5 mL×2), brine, dried over $Na_2SO_4$ and evaporated under reduced pressure. The crude product was purified by flash column chromatography to give 80 mg of compound 1731. Yield 42%

Example XV

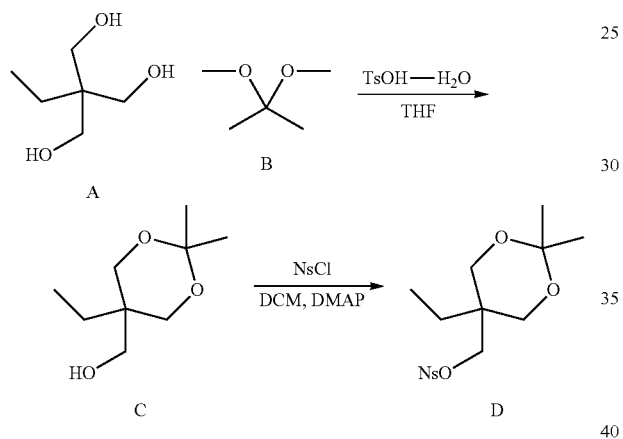

Triol A (22.3 g, 166 mmol), acetal B (26.0 g, 250 mmol), and p-toluene sulfonic acid (1.58 g, 8.32 mol) were combined in THF (1 L) and stirred at ambient temperature until all starting material was consumed (6.5 hr). The reaction was monitored by TLC (1:1 hexanes:EtOAc, stained with $KMnO_4$. Triethyl amine (15 mL) was added to raise the pH the reaction and the solvent was removed in-vacuo. The residue was passed through a plug of silica gel, eluting with 1:1 hexanes in EtOAc to produce C as a colorless oil (24.4 g). $^1$H NMR (300 MHz, DMSO-$d_6$) δ ppm 0.74 (t, J=7.71 Hz, 3H) 1.19-1.29 (m, 2H) 1.24-1.32 (m, 6H) 3.25-3.62 (m, 6H) 4.48 (t, J=5.20 Hz, 1H).

Protected triol C (24.4 g, 138 mmol), triethyl amine (28 g, 275 mmol), and dimethylaminopyridine (DMAP, 1.7 g, 13.8 mmol) were combined in DCM (1 L) and cooled to 0° C. under nitrogen. 3-Nitrophenyl sulfonyl chloride (NsCl, 37 g, 165 mmol) was dissolved in DCM (500 mL) and added dropwise to the cooled reaction. The reaction was stirred while warming to ambient temperature for 20 hours. The reaction was washed with water (500 mL), concentrated ammonium chloride (500 mL), brine (500 mL), dried over anhydrous sodium sulfate, and concentrated in-vacuo. The residue was passed through a plug of silica gel eluting with 1:1 hexanes: EtOAc to give D (50 g). LCMS [M+H$^+$] 360.2 (100), 3.23 min.

Example XVI

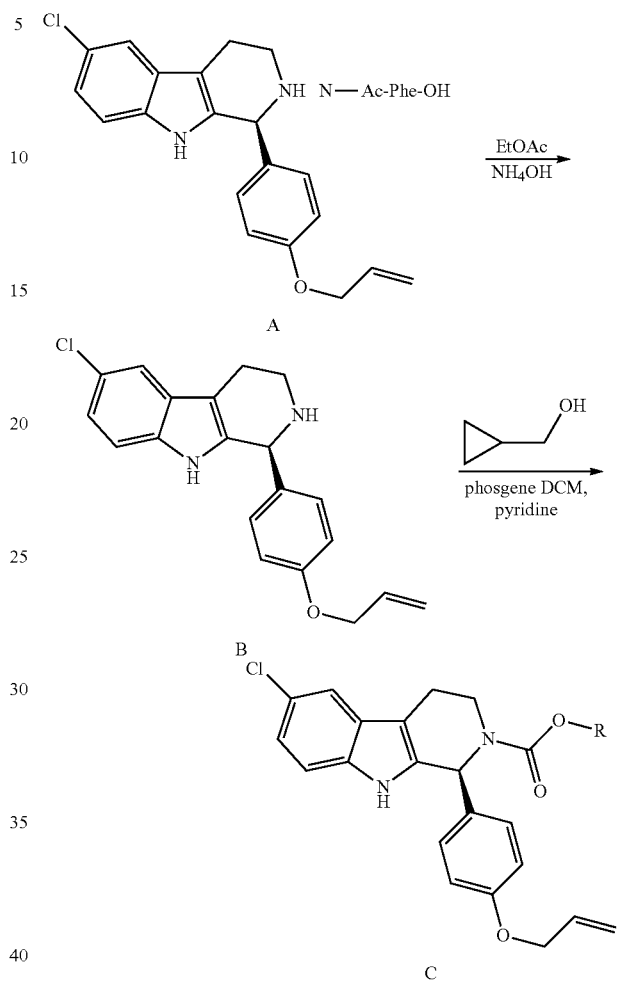

In a sealed vessel, phosgene (20% in toluene, 5.5 mL, 11.0 mmol) was added to cyclopropanemethanol (793 mg, 11.0 mmol) dissolved in DCM (5 mL) at −40° C. Pyridine (937 mg, 11.0 mmol) was added dropwise and the reaction was stirred at −40° C. for 1 hour. (Caution: this reaction generates a dramatic increase in pressure if the temperature starts to rise because the chloroformate appears to be volatile. It is very important to keep the temperature under control. Venting results in very little carbamate formation). Diastereomeric salt A (3.0 g, 5.5 mmol), dissolved in EtOAc (100 mL), was washed with about 15% aqueous ammonium hydroxide solution (2×100 mL) and brine (100 mL), dried over anhydrous sodium sulfate, and concentrated in-vacuo. The free base B was dissolved in DCM (10 mL) and pyridine (1 mL) and added to the chilled chloroformate solution. The reaction was warmed slowly to ambient temperature over 5 hours. The reaction was poured into saturated sodium bicarbonate solution (100 mL) and the layers were separated. The aqueous layer was washed with DCM (2×20 mL) and the combined organics were dried over anhydrous sodium sulfate. The residue was purified on silica gel with a gradient of EtOAc in hexanes (10-50%) to produce carbamate C as a white foam (4.11 g). LCMS [M+H⁺] 437.0 (100), 4.15 min; Chiral HPLC (OD-H) 12.70 min; ¹H NMR (300 MHz, DMSO-$d_6$) δ ppm 0.28 (br. s., 2H) 0.51 (br. s., 2H) 1.13 (br. s., 1H) 2.67-2.84 (m, 2H) 2.93-3.10 (m, 1H) 3.82-4.02 (m, 2H) 4.17 (br. s., 1H) 4.47-4.56 (m, 2H) 5.16-5.27 (m, 1H) 5.29-5.42 (m, 1H) 5.90-6.09 (m, 1H) 6.31 (br. s., 1H) 6.91 (d, J=8.72 Hz, 2H) 7.05 (dd, J=8.55, 2.18 Hz, 2H) 7.12 (d, J=7.38 Hz, 2H) 7.28 (d, J=8.38 Hz, 1H) 7.50 (d, J=2.01 Hz, 1H) 11.11 (br. s., 1H).

Example XVII

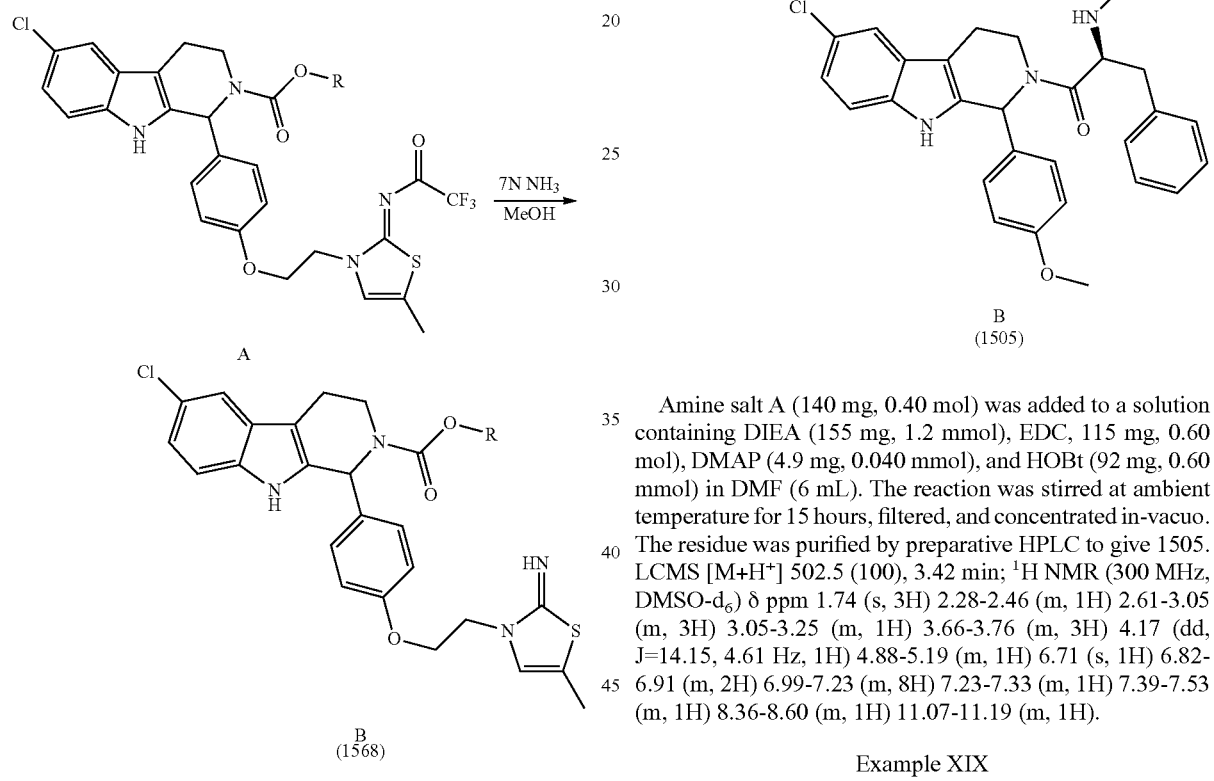

Compound A (0.91 g, 1.3 mmol) was stirred in a solution of ammonia in methanol (7N, 30 mL) for 72 hours at ambient temperatue. The solvent was removed and the residue was dissolved in ether (100 mL) and washed with water (3×25 mL) and brine (20 mL) and dried over anhydrous sodium sulfate to provide 1568 (707 mg). LCMS [M+H⁺] 593.2 (100), 2.43 min; Chiral HPLC (OD-H) 31.63 min; ¹H NMR (300 MHz, DMSO-$d_6$) δ ppm 1.94 (d, J=1.32 Hz, 3H) 2.86 (br. s., 2H) 3.10-3.27 (m, 1H) 3.89 (t, J=5.61 Hz, 2H) 4.12 (t, J=5.44 Hz, 2H) 4.31 (d, J=14.52 Hz, 1H) 6.38 (br. s., 1H) 6.47 (d, J=1.32 Hz, 1H) 6.96 (d, J=8.25 Hz, 2H) 7.07 (dd, J=8.58, 1.98 Hz, 1H) 7.11-7.25 (m, 4H) 7.30 (d, J=8.91 Hz, 1H) 7.44 (d, J=8.58 Hz, 2H) 7.54 (d, J=2.31 Hz, 1H) 8.63 (d, J=83.14 Hz, 1H) 11.06-11.21 (m, 1H).

Example XVIII

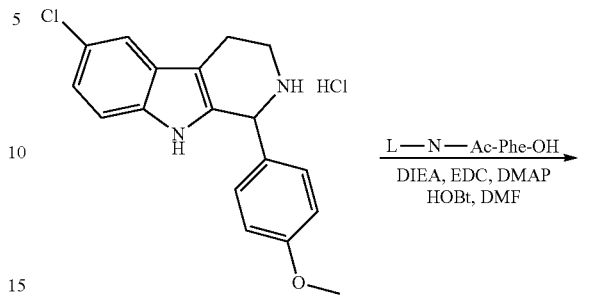

Amine salt A (140 mg, 0.40 mol) was added to a solution containing DIEA (155 mg, 1.2 mmol), EDC, 115 mg, 0.60 mol), DMAP (4.9 mg, 0.040 mmol), and HOBt (92 mg, 0.60 mmol) in DMF (6 mL). The reaction was stirred at ambient temperature for 15 hours, filtered, and concentrated in-vacuo. The residue was purified by preparative HPLC to give 1505. LCMS [M+H⁺] 502.5 (100), 3.42 min; ¹H NMR (300 MHz, DMSO-$d_6$) δ ppm 1.74 (s, 3H) 2.28-2.46 (m, 1H) 2.61-3.05 (m, 3H) 3.05-3.25 (m, 1H) 3.66-3.76 (m, 3H) 4.17 (dd, J=14.15, 4.61 Hz, 1H) 4.88-5.19 (m, 1H) 6.71 (s, 1H) 6.82-6.91 (m, 2H) 6.99-7.23 (m, 8H) 7.23-7.33 (m, 1H) 7.39-7.53 (m, 1H) 8.36-8.60 (m, 1H) 11.07-11.19 (m, 1H).

Example XIX

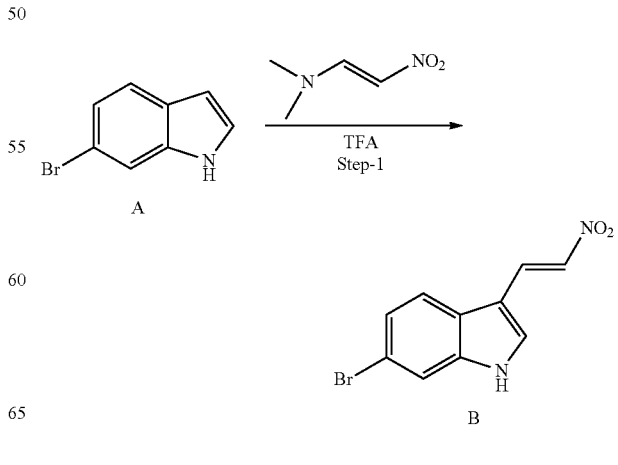

Step 1: A suspension of reaction material A (4.0 g, 20.40 mmol) and 1-(dimethylamino)-2-nitroethylene (2.04 g, 17.57 mmol) in 20 mL of TFA was stirred for 45 min. The reaction mixture was poured into saturated aqueous NaHCO3 solution (250 mL) and extracted repeatedly with EtOAc (4×75 mL). The combined organic layers are dried and evaporated under vacuum. The red-orange solid is triturated with CH$_2$Cl$_2$/THF (3×100 mL), and filtered to give 3.10 g (66%) indole product B. The crude mother liquor was chromatographed over an Isco 120 g column (eluted with DCM to 50% EtOAc/DCM to afford 1.7 g of solid which after trituration with Et2O afforded 1.0 g (21%) of additional indole product B: LCMS [MH+] 265, 267, Rt=3.13; $^1$H NMR (300 MHz, DMSO-d6) 7.32 (dd, J=8.7, 1.2 Hz, 1H), 7.70 (d, J=1.2 Hz, 1H), 7.94 (d, J=8.7 Hz, 1H), 8.01 (d, J=13.5 Hz, 1H), 8.24 (s, 1H), 8.37 (d, J=13.8 Hz, 1H), 12.28 (s, 1H).

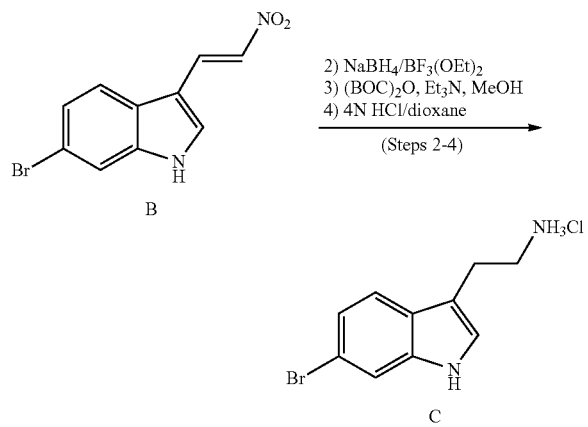

Step-2: A solution of sodium borohydride (2.03 g, 60 mmol) in THF (150 mL) cooled to 0° C. was treated with a solution of BF$_3$.(OEt)$_2$ (8.5 mL, 66 mmol) for about 15 minutes and then warmed to rt and stirred 15 min more. To this mixture was added dropwise a solution of 3 g (11.25 mmol) of indole product B in THF (30 mL), and the mixture heated to reflux for 2 h. The reaction was cooled to room temperature for about 1 hour, cooled to 0° C. and the solution adjusted to pH 3 using 1N aqueous HCl. The mixture was extracted with Et$_2$O (3×75 mL) and the aqueous solution made basic using 6N aqueous NaOH to liberate the amine. The aqueous layer was saturated with solid NaCl was extracted with Et$_2$O (10× 100 mL). The combined organic layers are dried evaporated under vacuum and used in the next step without further purification.

Step-3: The crude was dissolved 4.80 g (22 mmol) of (BOC)$_2$O and 3.1 mL (22 mmol) of Et$_3$N in 30 mL of MeOH. The mixture was stirred 1 h, concentrated and the residue purified over a 120 g Isco column (eluted with hexanes to 80% EtOAc/hexanes) to afford 1.95 g of pure N—BOC precursor to C (51%-2 steps) which was taken directly into the next reaction: LCMS [MH$^+$−1] 293, 295, Rt=3.30; $^1$H NMR (300 MHz, (CD$_3$)$_2$CO-d$^6$) δ 1.40 (s, 9H), 2.88-2.94 (m, 1H), 3.32-3.39 (m, 1H), 6.01 (s, 1H), 7.15 (dd, J=8.4, 1.8 Hz, 1H), 7.21 (d, J=2.1 Hz, 1H), 7.54 (d, J=8.4 Hz, 1H), 7.58 (d, J=1.8 Hz, 1H), 10.17 (s, 1H).

Step-4: To 1.86 g (5.50 mmol) of the N—BOC precursor of C dissolved in 12 mL of DCM was added 8 mL (32 mmol) of 4N HCl in dioxanes, The mixture was stirred 2 h, concentrated to around 1 mL of solvent remaining, added dropwise to 65 mL of 30% hexanes/Et$_2$O added to form a precipitate which was filtered and dried overnite (50° C., 5 torr) to afford 1.36 g (90%) of 6-bromotryptamine hydrochloride C as a white solid: LCMS [MH$^+$] 239, 241, Rt=1.60; $^1$H NMR (300 MHz, DMSO-d$^6$) δ 2.99 (m, 4H), 7.12 (dd, J=8.4, 2.1 Hz, 1H), 7.26 (d, J=2.1 Hz, 1H), 7.51 (d, J=8.4 Hz, 1H), 7.54 (d, J=1.5 Hz, 1H), 7.95 (s, 3H), 11.14 (s, 1H).

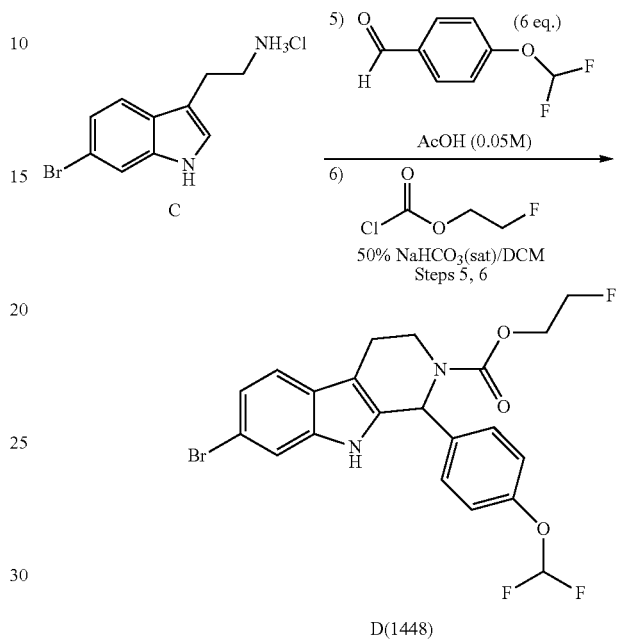

Step-5: 4-Difluoromethoxybenzaldehyde (1.16 g, 6.66 mmol) is dissolved in 22 mL of acetic acid at room temperature. The reaction mixture is then heated to 90° C.; six 52 mg portions (309 mg total, 1.11 mmol) of indole C is added in equal time intervals over 1 h, and the mixture heated to reflux overnite. The mixture was cooled to room temperature and put in the refrigerator for 1 day. The resulting solid was filtered, washed with AcOH (2×5 mL) followed by hexanes (2×5 mL) and dried under vacuum (1 torr, 70° C.) to afford 190 mg (40%) of the intermediate Pictet-Spengler product, 7-Bromo-1-(4-difluoromethoxyphenyl)-2,3,4,9-tetrahydro-1H-β-carboline hydrochloride. The resultant mother liquor was concentrated under vacuum. The residue is triturated with 20% DCM/hexanes (removes excess aldehyde) to yield a powdery brown solid. This solid was taken up in 8 mL of CH$_3$CN, filtered, washed with 20% DCM/hexanes (2×5 mL) and dried as before to afford an additional 130 mg (27%) of the intermediate Pictet-Spengler product, 7-Bromo-1-(4-difluoromethoxyphenyl)-2,3,4,9-tetrahydro-1H-β-carboline hydrochloride: LCMS [MH$^+$] 393, 395, Rt=2.05.

Step-6: To 45 mg (0.105 mmol) of the intermediate Pictet-Spengler product in 6 mL of 50% saturated aqueous NaHCO$_3$/DCM, was added 16 mg (0.126 mmol) of 2-fluoroethyl chloroformate. The mixture was stirred 20 min, the DCM layer separated, concentrated and the crude product purified by preparative HPLC to afford 32.2 mg (64%) of carbamate D(1448): LCMS [MH$^+$] 483, 485, Rt=3.72; $^1$H NMR (300 MHz, (CD$_3$)$_2$CO-d$^6$) δ 2.86-2.88 (m, 3H), 3.14-3.23 (m, 1H), 4.34-4.36 (m, 1H), 4.43-4.46 (m, 1H), 4.62 (bm, 1H), 4.77 (bm, 1H), 6.50 (bm, 1H), 6.87 (t, J=74.7 Hz, 1H), 7.14-7.21 (m, 3H), 7.37 (bd, J=8.4 Hz, 2H), 7.49 (d, J=8.4 Hz, 1H), 7.55 (d, J=1.2 Hz, 1H), 10.21 (s, 1H).

Example XX

Preparation of Compounds 1612 and 1674

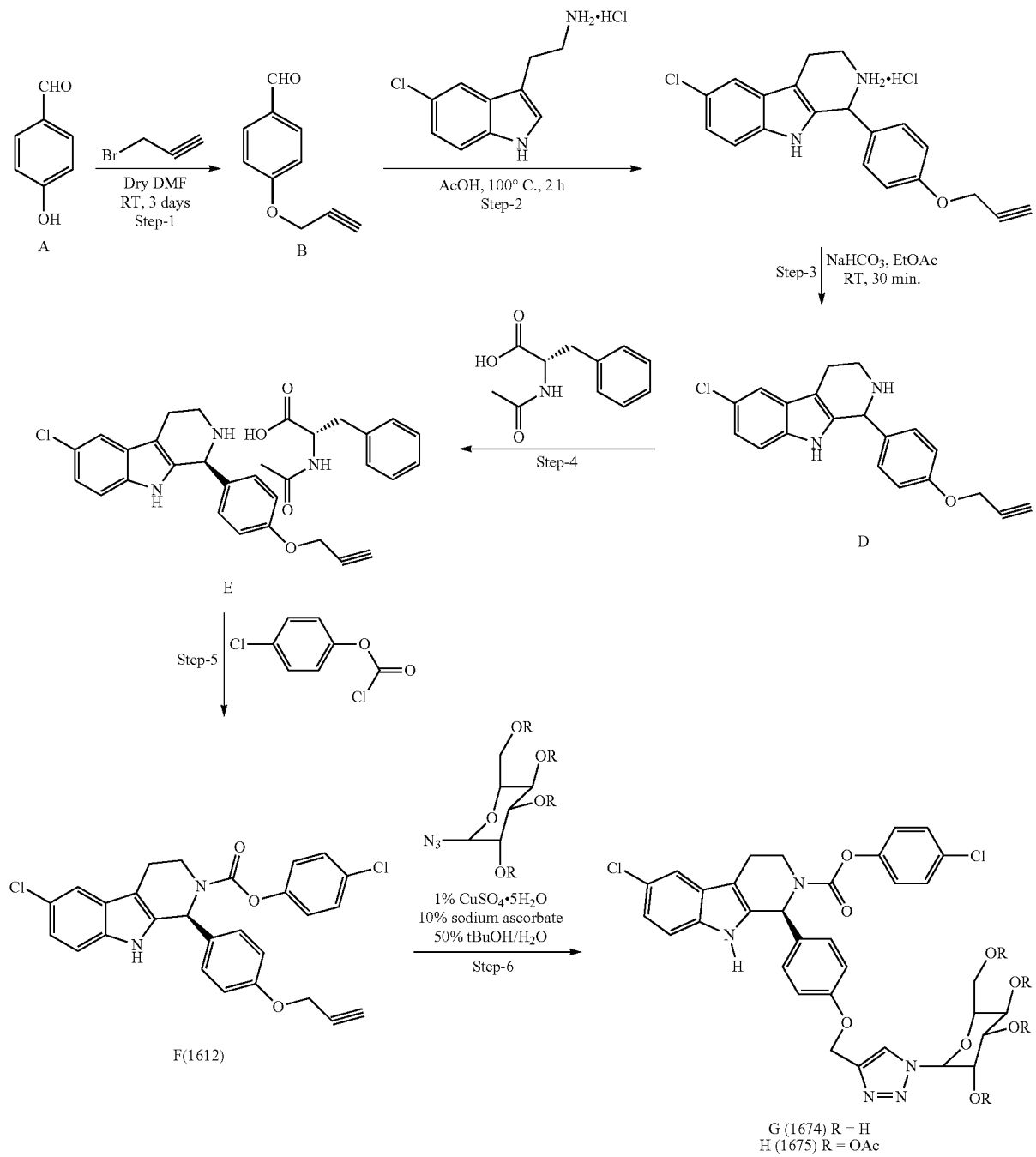

Step-1: To the stirred solution of 4-hydroxy benzaldehyde (compound A, 15 g, 0.122 mol) in dry DMF (120 mL) was added $K_2CO_3$ (25.4 g, 0.18 mol), KI (0.04 g, 0.002 mol) and propargyl bromide (21.91 g, 0.18 mol) at rt under inert atmosphere. After stirring at rt for 3 days, it was diluted with water (600 mL). It was then extracted with EtOAc (3×200 mL). The combined organic layer was washed with water (3×150 mL), brine (150 mL), dried over anhydrous $Na_2SO_4$ and concentrated under vacuum. The crude product was purified by passing through silica gel column using 5-20% EtOAc in Pet. Ether as an eluent to get step-1 product (O-propargyl benzaldehyde, Compound B) as a light brown solid. (19.3 g, 98%): $R_f$=0.7 (PE:EA, 7:3); MS [MH$^+$] 161 (M, 160 Calcd. for $C_{10}H_8O_2$); $^1$H NMR (300 MHz, $CDCl_3$) δ 2.57 (t, J=3 Hz, 1H), 4.77 (d, J=3 Hz, 2H), 7.08 (d, J=9 Hz, 2H), 7.86 (d, J=9 Hz, 2H), 9.9 (s, 1H).

Step-2: To a stirred suspension of 5-Chlorotryptamine.HCl salt (15 g, 0.064 mol) in glacial AcOH (500 mL) was added Step-1 product, O-propargyl benzaldehyde (10.75 g, 0.073 mol of compound B). The reaction mixture was heated to 100° C. for 8 hours. The reaction mixture was allowed to come to rt and stirred overnite. The precipitated white solid was filtered under suction. The residue was washed with glacial AcOH (200 mL), DCM (200 mL) and dried to get step-2 product, compound C, as a white solid (17 g, 77%): MS [MH$^+$] 337 (M, 336 Calcd. for $C_{20}H_{17}ClN_2O.HCl$); $^1$H NMR (400 MHz, DMSO-$d_6$) δ 2.96-3.00 (m, 1H), 3.06-3.13 (m, 1H), 3.39-3.44 (m, 2H), 3.58 (s, 1H), 4.83 (s, 2H), 5.8 (s, 1H), 7.06-7.11 (m, 3H), 7.27-7.58 (m, 3H), 7.59 (s, 1H), 9.42 (bs, 1H), 10.2 (bs, 1H), 11.09 (s, 1H).

Step-3: To a stirred solution of Step-2 HCl salt (4.5 g of compound C) in EtOAc (90 mL) was added aq. 10% aqueous NaHCO$_3$ solution (45 mL). The reaction mixture was vigorously stirred at rt for 30 minutes. The clear biphasic mixture was separated. The organic layer was washed with water (50 mL), brine (50 mL), dried over anhydrous Na$_2$SO$_4$ and concentrated under vacuum to get gummy product. This was washed with hexane to afford the step-3 product, compound D, (4.0 g, 98%): $R_f$=0.3 (PE:EA, 6:4); MS [MH$^+$] 337 (M, 336 Calcd. for $C_{20}H_{17}ClN_2O$); $^1$H NMR (400 MHz, DMSO-$d_6$) δ 2.51-2.70 (m, 2H), 2.91 (m, 1H), 3.04-3.07 (m, 1H), 3.30 (s, 1H), 3.56 (t, J=2 Hz, 1H), 4.77 (d, J=2 Hz, 2H), 5.03 (s, 1H, CH), 6.94-7.00 (m, 3H), 7.18-7.22 (m, 3H), 7.43 (s, 1H), 10.61 (s, 1H).

Step-4: To a stirred solution of Step-3 product (3.9 g, 0.011 mol of compound D) in abs. EtOH (80 mL) was added N-acetyl-L-phenylalanine (1.44 g, 0.0069 mol) and refluxed for 2 hours. The reaction mixture was allowed to cool to RT and stand for 20 hours. The separated solid was filtered and dried (2.8 g). It was further crystallized in 1:1 mixture of IPA and MeOH (100 mL) to get final compound E as a white solid (1.71 g, 26%). For the purpose of chiral HPLC and $^1$H-NMR a small amount of salt was suspended in EtOAc and treated with 5% NH$_4$OH solution. The layers were separated and organic layer was concentrated and checked for chiral purity (99% ee): MS [MH$^+$] 337 (M, 336 Calcd. for $C_{20}H_{17}ClN_2O$): $^1$H NMR (400 MHz, DMSO-$d_6$) δ 2.63 (m$_c$, 2H), 2.90 (m$_c$, 1H), 3.01 (m$_c$, 1H), 3.54 (s, 1H), 4.76 (s, 2H), 5.01 (s, 1H), 6.92-6.98 (m, 3H), 7.16-7.20 (m, 3H), 7.41 (s, 1H), 10.59 (s, 1H).

Step-5 Compound F (1612): To a stirred suspension of chiral salt from Step-4 (375 mg, 0.69 mmol of compound E) in EtOAc (8 mL) and water (8 mL) was cooled to 0-5° C. was added K$_2$CO$_3$ (285 mg, 2.06 mmol). The mixture was stirred for 10 min and 4-chlorophenyl chloroformate (197 mg, 1.03 mmol) was added while maintaining the reaction mixture at 0-5° C. The mixture was then warmed to rt, stirred for 3 hours, and the organic layer and aqueous layers partitioned. The aqueous layer was extracted with additional EtOAc (20 mL). The combined organic layers were washed with water (10 mL), brine (10 mL), dried over anhydrous Na$_2$SO$_4$ and evaporated in vacuum. The crude product was purified by silica gel column using 5-20% EtOAc in hexane as an eluent to afford step-5 product (320 mg, 94% of compound F) as a pale yellow solid. The % ee was checked by chiral HPLC (99% ee): $R_f$=0.4 (PE:EA, 5:5); MS [M$^+$] 491 (M, 491.365 Calcd. for $C_{27}H_{20}Cl_2N_2O_3$); $^1$H NMR (400 MHz, DMSO-$d_6$) δ 3.21 (m$_c$, 2H, CH$_2$), 3.28 (m$_c$, 2H), 3.60 (s, 1H), 4.30 (bs, 1H), 4.78 (s, 2H), 6.40 (bs, 1H), 6.98 (m, 2H), 7.31-7.08 (m, 6H), 7.45 (d, 2H), 8.3 (s, 1H), 11.17 (bs, 1H).

Step-6 Compound G (1674): To a stirred suspension of β-carboline carbamate from Step-5 (100 mg, 0.20 mmol of compound F) in 50% tBuOH/H$_2$O (1.2 mL) and 54 mg (0.26 mmol) of 1-azido-1-deoxy-β-D-galactopyranoside (R═H), was added a solution of sodium ascorbate in water (40 μL, 0.03 mmol of a solution of 594 mg sodium ascorbate in 3 mL of water), followed by a solution of CuSO$_4$.5H$_2$O in water (15 μL, 0.003 mmol of a solution of 75 mg of CuSO$_4$.5H$_2$O in 1 mL of water. The mixture was heated to 46° C. for 10 min, THF added to aid solubility (400 μL), an additional portion of CuSO$_4$.5H$_2$O in water (15 μL, 0.003 mmol of a solution of 75 mg of CuSO$_4$.5H$_2$O in 1 mL of water) added, and the mixture was then heated to 75° C. and stirred 2 days. The mixture was evaporated under vacuum and purified by HPLC to afford the step-6 product (R═H, 59 mg, 42% of compound G): LCMS [MH$^+$] 696, Rt=3.33; $^1$H NMR (300 MHz, (CD$_3$OD) δ 2.80-3.04 (m, 2H), 3.30-3.40 (m, 2H), 3.66-3.76 (m, 3H), 3.81 (q, J=6.3 Hz, 1H), 3.97 (d, J=3.0 Hz, 1H), 4.13 (t, J=9.3 Hz, 1H), 4.30-4.50 (m, 1H), 5.19 (s, 2H), 5.57 (d, J=9.3 Hz, 1H), 6.44-6.56 (bm, 1H), 6.96-7.04 (bm, 2H), 7.06 (dd, J=8.7, 1.9 Hz, 1H), 7.13 (d, J=8.7 Hj, 1H), 7.24 (bd, J=8.4 Hz, 2H), 7.38 (bd, J=8.7 Hz, 1H), 7.49 (d, J=2.1 Hz, 1H), 8.30 (s, 1H).

Step-6 Compound H (1675): Following an identical procedure to that used in preparing compound G, but using 99 mg (0.26 mmol) of 1-azido-1-deoxy-β-D-galactopyranoside tetraacetate (R═OAc) instead of 54 mg (0.26 mmol) of 1-azido-1-deoxy-β-D-galactopyranoside (R═H), afforded 54 mg (31%) of the step 6 (R═OAc) product, compound H: LCMS [MH$^+$] 864, Rt=3.88; $^1$H NMR (300 MHz, (CD$_3$)$_2$CO) δ 1.80 (s, 3H), 1.95 (s, 3H), 1.97 (s, 3H), 2.19 (s, 3H), 2.90-3.05 (m, 1H), 3.30-3.42 (m, 2H), 4.12 (dd, J=11.4, 7.2 Hz, 1H), 4.23 (dd, J=11.4, 5.8 Hz, 1H), 4.36-4.52 (bm, 1H), 4.62 (t, J=6.3 Hz, 1H), 5.22 (s, 2H), 5.45 (dd, J=10.2, 3.3 Hz, 1H), 5.56 (dm, J=2.4 Hz, 1H), 5.72 (t, J=9.7 Hz, 1H), 6.23 (d, J=9.0 Hz, 1H), 6.50-6.60 (bm, 1H), 7.05 (bd, J=8.1 Hz, 2H), 7.12 (dd, J=8.7, 2.1 Hz, 1H), 7.23 (d, J=8.9 Hz, 2H), 7.24-7.28 (m, 1H), 7.37 (bd, J=8.4 Hz, 2H), 7.42 (d, J=8.9 Hz, 2H), 7.56 (d, J=1.5 Hz, 1H), 8.30 (s, 1H). 10.22 (s, 1H).

Example XXI

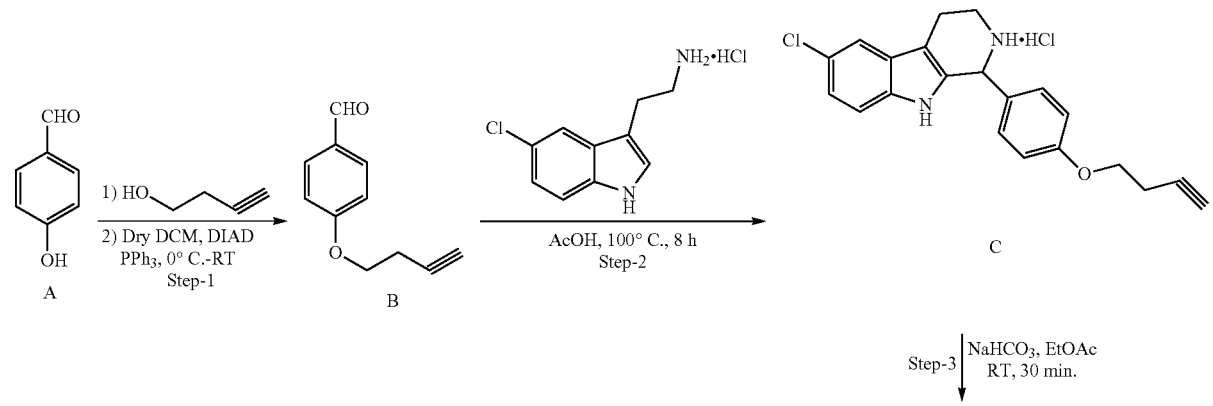

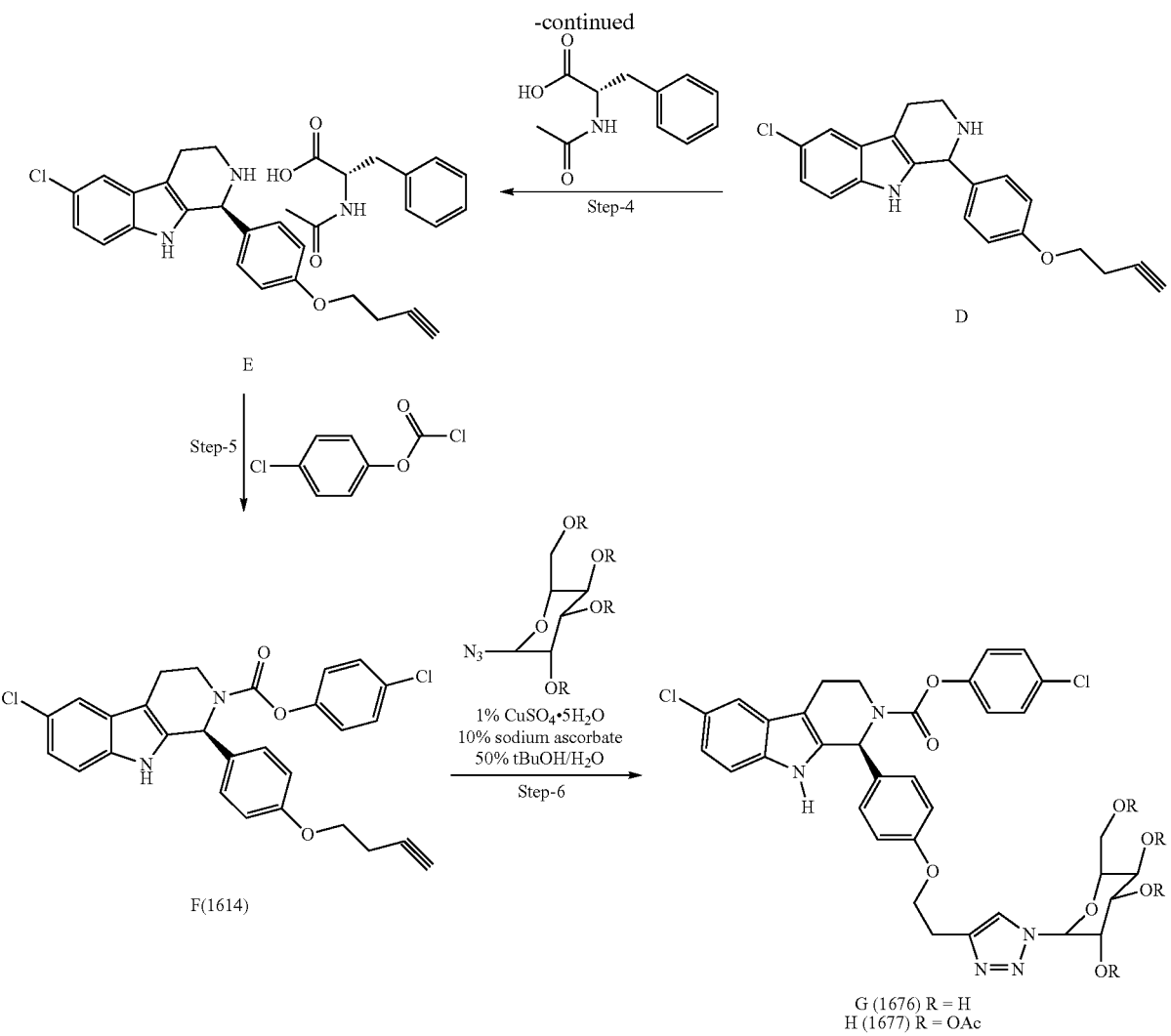

G (1676) R = H
H (1677) R = OAc

Step-1: To a stirred solution of DIAD (24.2 g, 0.12 mol) in dry DCM (70 mL) was added triphenylphosphine (22.45 g, 0.0859 mol) and 3-butyn-1-ol (6.36 g, 0.0859 mol) in a dropwise manner at 0-5° C. in a dark. The reaction flask was covered with aluminium foil to avoid the exposure to the light. After stirring for 30 minutes, 4-hydroxy benzaldehyde (7 g, 0.057 mol, compound A) dissolved in dry DCM (30 mL) was added in dropwise manner. The stirring was continued for 4 hours at 0-5° C. The temperature was slowly raised to rt and stirring was continued for 24 hours. After completion of the reaction, it was evaporated under vacuum. The crude product was purified by silica gel column using gradient from 5% to 20% EtOAc in Pet. Ether as an eluent to afford pale yellow solid of step-1 product, compound B (5.6 g, 56%): $R_f$=0.6 (Pe:EA, 6:4); MS [M$^+$] 174 (M, 174 Calcd. for $C_{11}H_{10}O_2$); $^1$H NMR (400 MHz, CDCl$_3$) δ 2.08 (s, 1H), 2.74 (m, 2H), 4.20 (t, J=7.2 Hz, 2H), 7.04 (d, J=8.8 Hz, 2H), 7.86 (d, J=8.8 Hz, 2H), 9.91 (s, 1H, CHO).

Step-2: To a stirred suspension of 5-Chlorotryptamine.HCl salt (15 g, 0.064 mol) in glacial AcOH (500 mL) was added Step-1 product (14 g, 0.08 mol of compound B). The reaction mixture was heated to 100° C. for 8 hours. The reaction mixture was allowed to come to rt and stirred overnite. The precipitated white solid was filtered under suction. The residue was washed with glacial AcOH (200 mL), DCM (200 mL) and dried to get step-2 product, compound C, as a white solid (16 g, 63%): MS 351 [MH$^+$] (M, 350.84 Calcd. for $C_{21}H_{19}ClN_2O$.HCl); $^1$H NMR (400 MHz, DMSO-d$_6$) δ 2.63 (m, 2H), 2.88 (s, 1H), 3.1 (m, 2H), 3.38 (m, 2H), 4.08 (t, J=8.0 Hz, 2H), 5.87 (s, 1H), 7.03-7.11 (m, 3H), 7.29 (m$_c$, 3H), 7.59 (s, 1H), 9.38 (bs, 1H), 10.15 (bs, 1H), 11.06 (s, 1H).

Step-3: To a stirred solution of Step-2 HCl salt (2.0 g of compound C) in EtOAc (40 mL) was added 10% aqueous NaHCO$_3$ solution (20 mL). The reaction mixture was vigorously stirred at rt for 30 minutes. The clear biphasic mixture was separated. The organic layer was washed with water (20 mL), brine (20 mL), dried over anhydrous Na$_2$SO$_4$ and concentrated under vacuum to get a gummy product. This was washed with hexane to get step-3 product, compound D, as a white powder (1.71 g, 95%). This was found to be pure enough for the next step. $R_f$=0.3 (PE/EA, 6:4); MS 351 [MH$^+$] (M, 350.84 calcd. for $C_{21}H_{19}ClN_2O$); $^1$H NMR (400 MHz, DMSO-d$_6$) δ 2.48-2.70 (m, 4H), 2.68 (m, 2H), 2.87 (m, 1H), 4.02 (t, J=6.4 Hz, 2H), 5.00 (s, 1H), 6.88-6.98 (m, 3H), 7.14-7.40 (m, 3H), 7.41 (s, 1H), 10.56 (s, 1H).

Step-4: To a stirred solution of step-3 product (26 g, 0.074 mol of compound D) in abs. EtOH (1000 mL) was added N-acetyl-L-phenylalanine (9.24 g, 0.044 mol). The mixture was refluxed for 2 hours, cooled to rt and left to stand for 20 hours. The separated solid was filtered and dried to get a white powder (19.5 g, 46% of compound E). For the purpose of chiral HPLC and $^1$H NMR, small amount of salt was suspended in EtOAc and treated with 5% NH$_4$OH solution. The layers were separated and organic layer was concentrated and checked for chiral purity using chiral LC (% ee=98): MS 351 [MH$^+$] (M, 350.84 Calcd. for C$_{21}$H$_{19}$ClN$_2$O); $^1$H NMR (400 MHz, DMSO-d$_6$) δ 2.50-2.63 (m, 4H), 3.00 (m$_c$, 2H), 3.04 (m$_c$, 1H), 4.04 (t, J=6.4 Hz, 2H), 5.02 (s, 1H), 6.90-7.00 (m, 3H), 7.20 (m, 3H), 7.43 (s, 1H), 10.58 (s, 1H).

Step-5 Compound F (1614): To a stirred suspension of chiral salt (1 g, 0.0017 mol of compound E) in EtOAc (15 mL) and water (15 mL) cooled to 0-5° C., was added K$_2$CO$_3$ (0.742 g, 0.00537 mol). The mixture was stirred for 10 minutes, 4-chlorophenylchloroformate (0.573 g, 0.00268 mol) added, and the mixture stirred at rt for 3 hours. The organic and aqueous layers were partitioned and the aqueous layer back extracted with more EtOAc (25 mL). The combined organic layers were washed with water (15 mL), brine (15 mL), dried over anhydrous Na$_2$SO$_4$ and evaporated in vacuum. The crude product was purified by silica gel column using 5-20% EtOAc in hexane to get compound F as a pale yellow solid (860 mg, 95%): R$_f$=0.4 (PE/EA, 5:5); MS 505 [MH$^+$] (M, 505.391 Calcd. for C$_{28}$H$_{22}$Cl$_2$N$_2$O$_3$); $^1$H NMR (400 MHz, DMSO-d$_6$) δ 2.61 (m, 2H), 2.87 (m, 3H), 3.20 (m, 1H), 4.03 (t, J=6.4 Hz, 2H), 4.3 (m, 1H), 6.4 (bs, 1H), 6.95 (m, 2H), 7.31-6.98 (m, 6H), 7.45 (m, 2H), 7.54 (s, 1H), 11.17 (bs, 1H).

Step-6 Compound G (1676): Following an identical procedure to that used in preparing compound K, but using compound F (105 mg, 0.207 mmol) as the alkyne and 54 mg (0.26 mmol) of 1-azido-1-deoxy-β-D-galactopyranoside (R═H) as the azide, afforded 96 mg (65%) of the step 6 (R═OAc) product, compound G: LCMS [MH$^+$] 710, Rt=3.33

Step-6 Compound H (1677): Following an identical procedure to that used in preparing compound K, but using compound F (105 mg, 0.207 mmol) as the alkyne and 99 mg (0.26 mmol) of 1-azido-1-deoxy-β-D-galactopyranoside tetraacetate (R═OAc) as the azide, afforded 103 mg (58%) of the step 6 (R═OAc) product, compound H: LCMS [MH$^+$] 878, Rt=3.88.

Example XXII

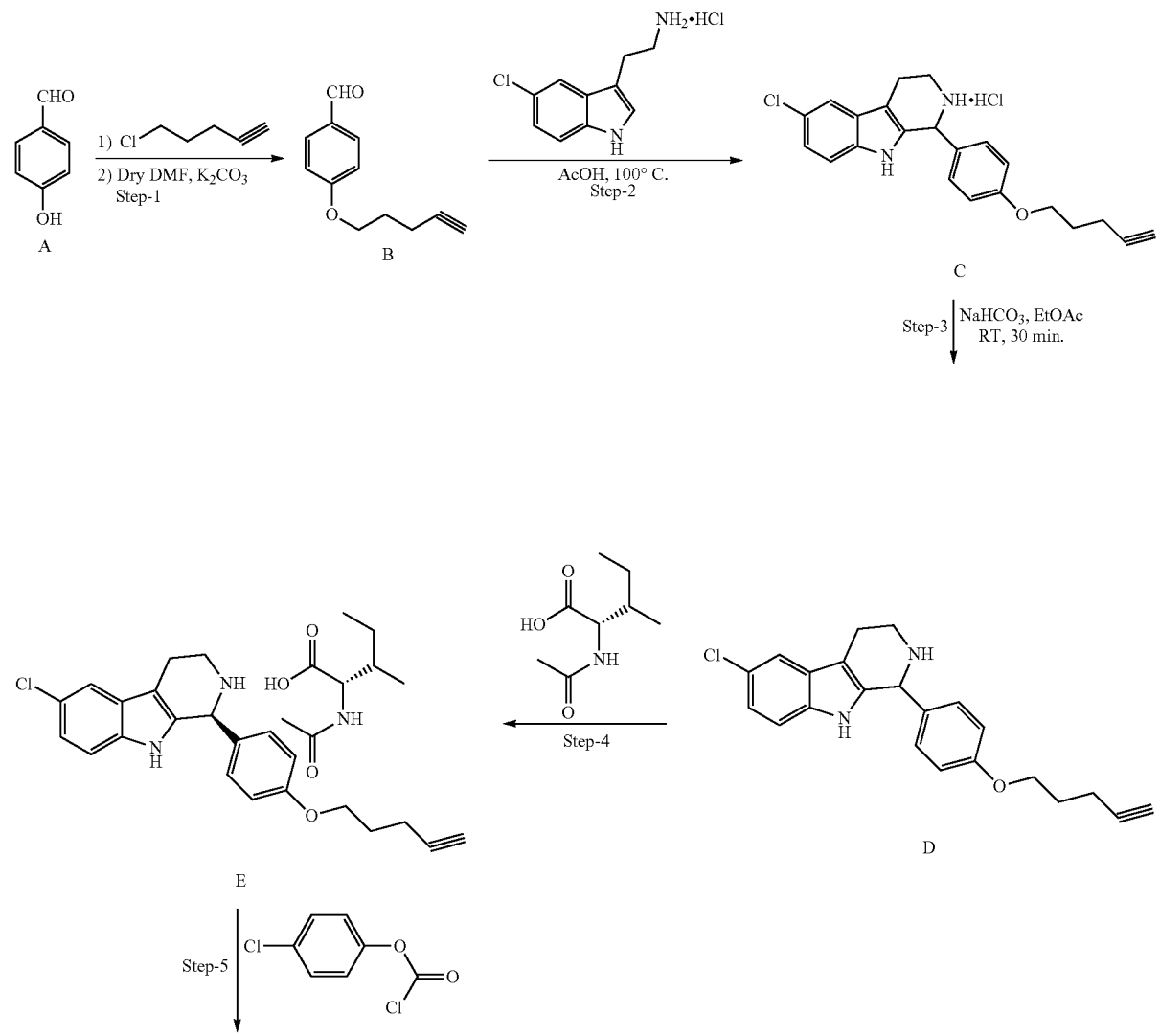

-continued

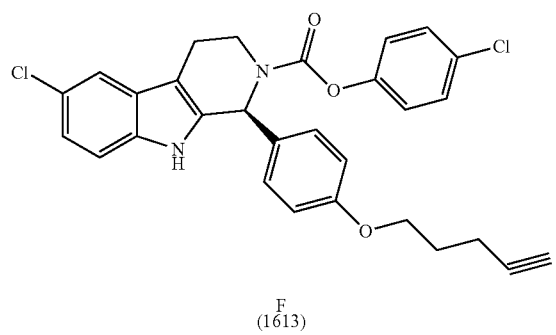

F
(1613)

Step-1: To a stirred solution of 4-hydroxybenzaldehyde (12 g, 0.098 mol, compound A) in dry DMF (93 mL) was added $K_2CO_3$ (20.28 g, 0.14 mol), KI (0.32 g, 0.0019 mol), and 5-Chloro-1-pentyne (12.1 g, 0.11 mol) at rt. The mixture was stirred for 3 days, diluted with water (550 mL), and extracted with EtOAc (3×200 mL). The combined organic layers were washed with water (3×100 mL), brine (100 mL), dried over anhydrous $Na_2SO_4$ and concentrated. The crude product was purified through silica gel column using a gradient from 5 to 25% EtOAc in Pet. Ether as an eluent to obtain step-1 product, compound B, as a pale yellow solid (18 g, 97%): LCMS 189 [MH⁺] (M, 188.22 Calcd. for $C_{12}H_{12}O_2$); ¹H NMR (400 MHz, CDCl₃) δ 1.60 (s, 1H), 2.00-2.09 (m, 2H), 2.43-2.47 (m, 2H), 4.18 (t, J=6.4 Hz, 2H), 7.03 (d, J=8.8 Hz, 2H), 7.85 (d, J=8.4 Hz, 2H), 9.9 (s, 1H, CHO).

Step-2: To a stirred suspension of 5-Chlorotryptamine.HCl salt (10 g, 0.043 mol) in glacial AcOH (430 mL) was added Step-1 product (9.36 g, 0.048 mol of compound B). The reaction mixture was heated to 100° C. for 8 hours. The reaction mixture was allowed to come to rt and stirred overnite. The precipitated white solid was filtered under suction. The residue was washed with glacial AcOH (100 mL), MDC (150 mL) and dried to get step-2 product, compound C, as a white solid (10 g, 58%): MS 365 [MH⁺] (M, 401.344, Calcd. for $C_{22}H_{21}ClN_2O.HCl$); ¹H NMR (400 MHz, DMSO-d₆) δ 1.9 (t, J=5.6 Hz, 2H), 2.33 (m, 2H), 2.84 (s, 1H), 3.1 (m, 2H), 3.39 (m, 2H), 4.08 (t, J=6 Hz, 2H), 5.89 (s, 1H), 7.04-7.13 (m, 3H), 7.29-7.32 (m, 3H), 7.61 (s, 1H), 9.4 (brs, 1H), 10.1 (bs, 1H), 11.08 (s, 1H).

Step-3: To a stirred solution of Step-2 HCl salt (7.5 g of compound C) in EtOAc (150 mL) was added 10% aqueous $NaHCO_3$ solution (75 mL). The reaction mixture was vigorously stirred at RT for 30 minutes. The clear biphasic mixture was separated. The organic layer was washed with water (75 mL), brine (75 mL), dried over anhydrous $Na_2SO_4$ and concentrated under vacuum to get gummy product. This was washed with hexane to get step-3 product, compound D, as a white powder (6.7 g, 98%). This was found pure enough for the next step: $R_f$=0.3 (PE:EA, 6:4); MS 365 (M⁺) (M, 365 Calcd. for $C_{22}H_{21}ClN_2O$); ¹H NMR (400 MHz, DMSO-d₆) δ 1.88 (m, 2H), 2.32 (m, 2H), 2.65 (m, 2H), 2.86 (s, 1H), 2.82 (m, 1H), 3.04 (m, 1H), 4.02 (t, J=6 Hz, 2H), 5.02 (s, 1H), 6.90 (d, J=8.8 Hz, 2H), 6.98 (s, 1H), 7.16-7.42 (m, 3H), 7.43 (s, 1H), 10.57 (s, 1H).

Step-4: To a stirred solution of step-3 product (6.6 g, 0.018 mol of compound D) in abs. EtOH (150 mL) was added N-acetyl-L-isoleucine (1.87 g, 0.01 mol) and refluxed for 2 hours. The reaction mixture was allowed to cool to rt and stand for 20 hours. The solid separated was filtered and dried to get white powder. This was further crystallized in ethanol (125 mL) to get step-4 salt, compound E, as off-white solid (2.4 g, 24%). For the purpose of chiral HPLC and ¹H NMR, small amount of salt was suspended in EtOAc and treated with 5% $NH_4OH$ solution. The layers were separated and organic layer was concentrated and checked for chiral purity by chiral LC (100% ee): MS 365 (M⁺) (M, 538 Calcd. for $C_{30}H_{36}ClN_3O_4$); ¹H NMR (400 MHz, DMSO-d₆) δ 1.86 (m, 2H), 2.30 (m, 2H), 2.62 (m, 2H), 2.8 (s, 1H), 2.88 (m, 1H), 3.02 (m, 1H), 4.00 (t, J=6.0 Hz, 2H), 5.00 (s, 1H), 6.88 (d, J=8.4 Hz, 2H), 6.97 (d, J=8.0 Hz, 1H), 7.14-7.20 (m, 3H), 7.41 (s, 1H), 10.55 (s, 1H).

Step-5: To a stirred suspension of chiral salt (0.15 g, 000278 mol of compound E) in EtOAc (4 mL) and water (4 mL) cooled to 0-5° C., was added $K_2CO_3$ (0.0115 g, 0.000836 mol). The mixture was stirred for 10 minutes and 4-chlorophenyl chloroformate (0.0796 g, 0.0004176 mol) was added. The mixture was stirred at rt for 3 hour, the organic and aqueous layers partitioned and the aqueous layer back extracted with EtOAc (10 mL). The combined organic layers were washed with water (5 mL), brine (5 mL), dried over anhydrous $Na_2SO_4$ and evaporated in vacuum. The crude product was purified by silica gel column using 5-20% EtOAc in Pet. Ether to get pale yellow colored step-5 product (110 mg, 76% of compound F (1613)). $R_f$=0.4 (PE:EA, 5:5): MS 519 (M⁺) (M, 519.418 Calcd. for $C_{29}H_{24}Cl_2N_2O_3$), ¹H NMR (400 MHz, DMSO-d₆) δ 1.86 (m, 2H), 2.29 (m, 2H), 2.8 (s, 1H), 2.9 (m, 2H), 3.2 (m, 1H), 4.01 (t, J=6.0 Hz, 2H), 4.30 (m, 1H), 6.4 (s, 1H), 6.94 (m, 2H), 7.07 (m, 1H), 7.22-7.2 (m, 4H), 7.3 (d, J=8.8 Hz, 1H), 7.45 (m_e, 2H), 7.54 (s, 1H), 11.16 (bs, 1H).

Example XXIII

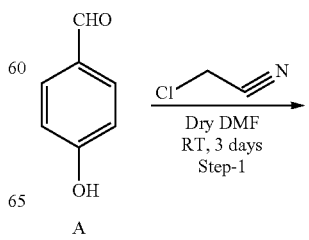

A

-continued

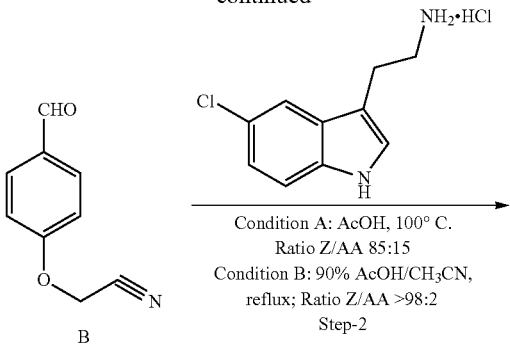

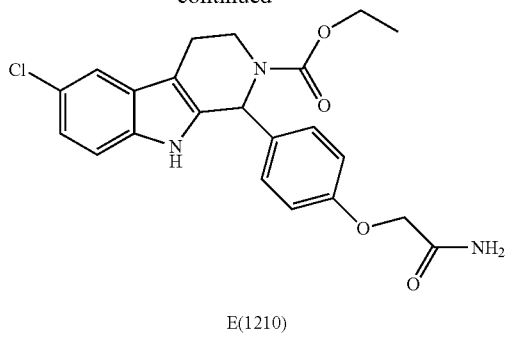

E(1210)

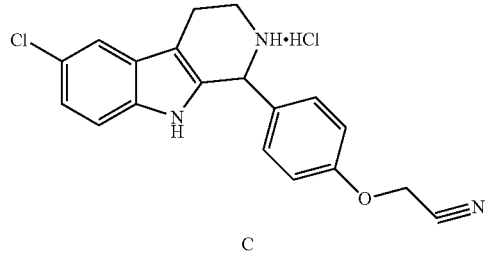

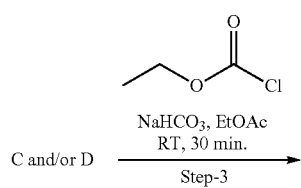

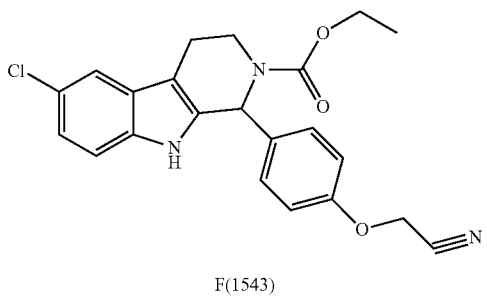

F(1543)

and

Step-1: To the stirred solution of 4-hydroxybenzaldehyde (compound A, 3 g, 0.0246 mol) in dry DMF (24 mL) was added $K_2CO_3$ (6.80 g, 0.49 mol), and chloroacetonitrile (1.9 mL, 0.030 mol) at rt under inert atmosphere. After stirring at rt for 3 days, it was diluted with water (50 mL). It was then extracted with 75% $Et_2O$ in hexanes (4×75 mL). The combined organic layer was washed with water (2×40 mL), brine (50 mL), dried over anhydrous $MgSO_4$ and concentrated under vacuum. The crude product was purified by passing through silica gel column using 0-20% EtOAc in hexanes as an eluent to get step-1 product, Compound B. (2.60 g, 66%): LC Rt=2.38.

Step-2: To a stirred suspension of 5-Chlorotryptamine.HCl salt (5.7 g, 0.0245 mol) in glacial AcOH (245 mL) was added Step-1 product, (4.57 g, 0.0284 mol of compound B). The reaction mixture was heated to 115° C. overnite. The reaction mixture was allowed to come to rt and the precipitated white solid was filtered under suction. The residue was washed with 50% glacial AcOH/$Et_2O$ (50 mL), DCM (50 mL) and dried to get a mixture of step-2 products, compound C and compound D (about 85:15 ratio), as a beige solid (6.88 g, 75%): Mixture LCMS [$MH^+$] 338, 356, Rt=1.77.

Alternative Step-2: Following the above procedure exactly, except that 90% $CH_3CN$/AcOH was used in place of AcOH, gave a >98:2 mixture of C: D.

Step-3 Compounds F and E (1543 and 1210): To a stirred suspension of the products from Step-4 (100 mg, 0.27 mmol of compound C/D, 85:15 mixture) in 50% DCM/saturated aqueous $NaHCO_3$ was added ethyl chloroformate (31 µL, 0.32 mmol) and the mixture stirred for 30 min. The organic layer and aqueous layers were partitioned. The aqueous layer was extracted with additional DCM (20 mL). The combined organic layers were washed with water (10 mL), brine (10 mL), dried over anhydrous $MgSO_4$ and evaporated in vacuum. The crude product was purified by preparative HPLC to afford step-3 products (60 mg, 54% of compound F and 8 mg (7%) of compound E): Data for F (1543): LCMS [$MH^+$] 410, Rt=3.53; $^1H$ NMR (300 MHz, $(CD_3)_2CO$-$d^6$) δ 1.28 (t, J=6.5 Hz, 3H), 2.84-2.86 (m, 2H), 3.11-3.18 (m, 1H), 4.17 (q, J=6.9 Hz, 1H), 4.30 (bs, 1H), 5.10 (s, 2H), 6.47 (bs, 1H), 7.04-7.12 (m, 3H), 7.29-7.37 (m, 3H), 7.53 (d, J=1.8 Hz, 1H), 10.19 (bs, 1H). Data for E (1210): LCMS [$MH^+$] 428, Rt=3.12; $^1H$ NMR (300 MHz, $(CD_3)_2CO$-$d^6$) δ 1.27 (t, J=6.4 Hz, 3H), 2.78-2.86 (m, 2H), 3.11-3.17 (m, 1H), 4.17 (q, J=6.9 Hz, 1H), 4.30 (bs, 1H), 4.44 (s, 2H), 6.45 (bs, 1H), 6.71 (bs, 1H), 6.96 (dm, J=8.7 Hz, 2H), 7.09 (dd, J=2.4 Hz, 1H), 7.18 (m, 1H), 7.24 (d, J=8.7 Hz, 2H), 7.35 (d, J=8.4 Hz, 1H), 7.52 (d, J=2.1 Hz, 1H), 10.19 (bs, 1H).

Example XXIV

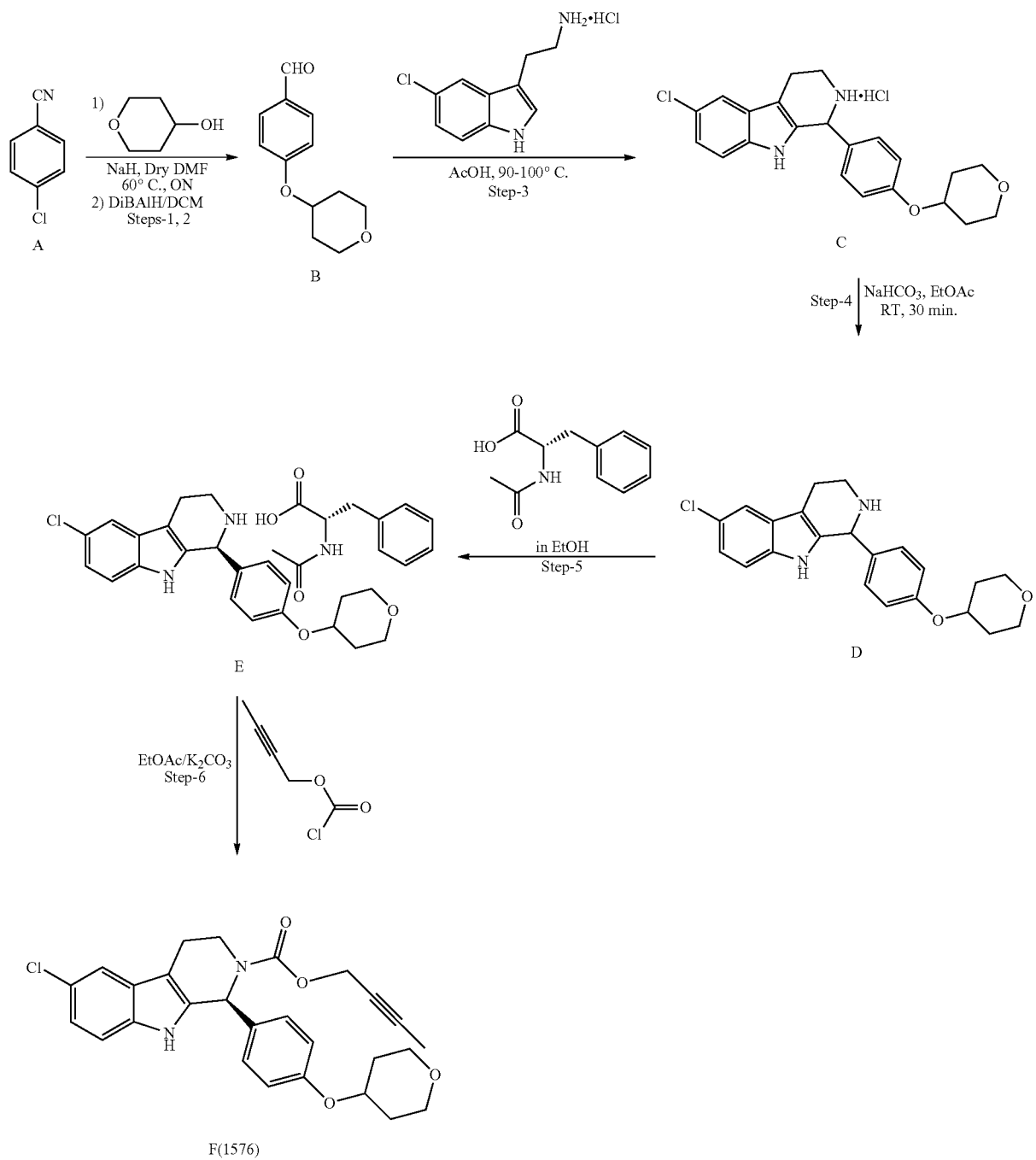

Step-1: To a stirred solution of 4-hydroxytetrahydropyran (3.80 g, 0.0373 mol) in dry DMF (50 mL) was added 95% NaH solid (1.12 g, 0.0466 mol) in small portions over 5-10 min. After the evolution of gas had subsided, 4-chlorobenzonitrile (5.18 g, 0.038 mol) was added in one portion, and the mixture heated to 60° C. overnite. The mixture was diluted with tBuOH (about 5 mL) and neutralized to pH 7 using glacial AcOH. The DMF was concentrated in vacuo, and the crude product chromatographed over a 120 g Isco column using 30% DCM/hexanes to DCM as an eluent to get step-1 product, 4-(tetrahydropyran-4-yloxy)benzonitrile), as a white solid. (5.7 g, 76%): LC Rt=2.72; $^1$H NMR (300 MHz, $(CD_3)_2CO\text{-}d^6$) δ 1.63-1.75 (m, 2H), 2.02-2.10 (m, 2H), 3.55 (ddd, J=11.8, 9.1, 3.3 Hz, 2H), 3.90 (dt, J=12.0, 4.5 Hz, 2H), 4.76 (septet, J=4.5 Hz, 1H), 7.16 (d, J=9 Hz, 2H), 7.69 (d, J=9 Hz, 2H).

Step-2: To the stirred solution of 4-(tetrahydropyran-4-yloxy)benzonitrile (7.50 g, 0.0369 mol) in dry DCM (90 mL) was added 1M DIBALH in DCM (46.50 mL, 0.0465 mol) and the mixture stirred 30 min at 0° C. The reaction mixture was cooled to −20° C., and EtOAc (7 mL) was added slowly dropwise. The mixture was stirred 15 min, a solution of saturated aqueous Rochelle's salt added (85 mL), the mixture warmed to 0° C. and stirred 1 h. The mixture was extracted with DCM (100 mL). The combined organic layers were washed twice with saturated aqueous NaHCO$_3$ (2×30 mL), dried (MgSO$_4$) and concentrated in vacuo. The crude product was chromatographed over a 80 g Isco column using 70% DCM/hexanes to DCM to 40% EtOAc/DCM as an eluent to get the step-2 product, compound B, as a white solid. (6.80 g, 90%): LCMS [MH$^+$] 207, Rt 2.58; $^1$H NMR (300 MHz, CDCl$_3$) δ 1.80 (tt, J=12.9, 3.9 Hz, 2H), 1.99-2.07 (m, 2H), 3.58 (ddd, J=11.6, 6.7, 3.3 Hz, 2H), 3.96 (ddd, J=11.2, 6.5, 4.0 Hz, 2H), 4.61 (septet, J=4.0 Hz, 1H), 6.98 (d, J=8.8 Hz, 2H), 7.80 (d, J=8.8 Hz, 2H), 9.95 (s, 1H).

Step-3 Compound C (1220): To a stirred suspension of the Step-2 product (6.80 g, 0.033 mol of compound B) in glacial AcOH (380 mL) heated to 90° C. was added 5-Chlorotryptamine.HCl salt (6.80 g, 0.0294 mol) in four portions added 30 min apart. The reaction mixture was heated to reflux overnite. The reaction mixture was allowed to come to rt and put in the refrigerator overnite. The precipitated white solid was filtered under suction. The solid residue was washed with 40% glacial AcOH/Et$_2$O (100 mL), Et$_2$O (100 mL) and dried under vacuum to get step-3 product, compound C, as a white solid (10.37 g, 84%). The mother liquor was concentrated to one-third volume, put in the fridge overnite and the same wash cycle and drying of the solid residue utilized to provide an additional 450 mg (4%) of compound C: LCMS [MH$^+$] 383, Rt 1.85, 193 (salt/nonsalt form); $^1$H NMR (300 MHz, DMSO-d$_6$) δ 1.50-1.62 (m, 2H), 1.92-1.98 (m, 2H), 2.93-3.12 (m, 2H), 3.32-3.51 (m, 4H), 3.83 (dt, J=11.7, 4.2 Hz, 2H), 4.61 (septet, 1H), 5.86 (s, 1H), 7.04-7.11 (m, 3H), 7.26-7.30 (m, 3H), 7.59 (d, J=1.8 Hz, 1H), 9.50 (bs, 1H), 10.17 (bs, 1H), 11.07 (s, 1H).

Step-4: To a stirred solution of Step-3 HCl salt (10.56 g, 0.0252 mol of compound C) in EtOAc (300 mL) was added saturated aqueous NaHCO$_3$ solution (150 mL). The reaction mixture was vigorously stirred at rt for 30 minutes. The clear biphasic mixture was separated. The organic layer was washed with water (50 mL), brine (50 mL), dried over anhydrous MgSO$_4$ and concentrated under vacuum to get a foam. This was washed with hexane to afford the step-4 product, compound D, (9.64 g, 100%): This material was taken directly into the next reaction without further purification.

Step-5: To a stirred solution of Step-4 product (9.64 g, 25.18 mmol of compound D) in abs. EtOH (930 mL) was added N-acetyl-L-phenylalanine (3.39 g, 0.0164 mol) and refluxed until dissolution occurred. The reaction mixture was allowed to cool to RT and stand for 48 hours. The separated solid was filtered and dried (6.80 g, 46% recovery, 95% ee by chiral LC of free base form). It was further crystallized in abs. EtOH (500 mL) to get the step-5 product, compound E as a white solid (6.60 g, 44% recovery, >98.5% ee by chiral LC of free base form). This salt was taken directly into the next reaction without further purification. Data for E: Chiral HPLC ODH-280-40 column (rt 47.29 min).

Step-6 Compound F (1576): To a stirred suspension of chiral salt from Step-5 (84 mg, 0.14 mmol of compound E) in EtOAc (4 mL) and saturated aqueous K$_2$CO$_3$ (2 mL) was added 2-butynylchloroformate (24 μL, 0.21 mmol) and the mixture stirred for 2.5 hours. The organic layer and aqueous layers were partitioned. The aqueous layer was extracted with additional EtOAc (20 mL). The combined organic layers were washed with water (10 mL), brine (10 mL), dried over anhydrous Na$_2$SO$_4$ and evaporated in vacuum. The crude product was purified by preparative LC to afford the step-6 product (52.5 mg, 94% of compound F) as a white solid. LCMS [MH$^+$] 479, Rt 3.78; $^1$H NMR (300 MHz, (CD$_3$)$_2$CO) δ 1.58-1.69 (m, 2H), 1.82 (s, 3H), 1.96-2.05 (m, 2H), 2.80-2.94 (m, 3H), 3.10-3.25 (m, 1H), 3.50 (ddd, J=11.8, 9.0, 2.9 Hz, 2H), 3.96 (dt, J=11.7, 4.5 Hz, 2H), 4.28 (m$_c$, 1H), 4.56 (septet, J=4.0 Hz, 1H), 4.74 (s, 2H), 6.45 (m$_c$, 1H), 6.93 (d, J=8.7 Hz, 2H), 7.11 (dd, J=8.7, 1.8 Hz, 1H), 7.20 (dm, J=8.4 Hz, 2H), 7.36 (d, J=8.7 Hz, 1H), 7.52 (d, J=1.8 Hz, 2H), 10.19 (s, 1H).

Example XXV

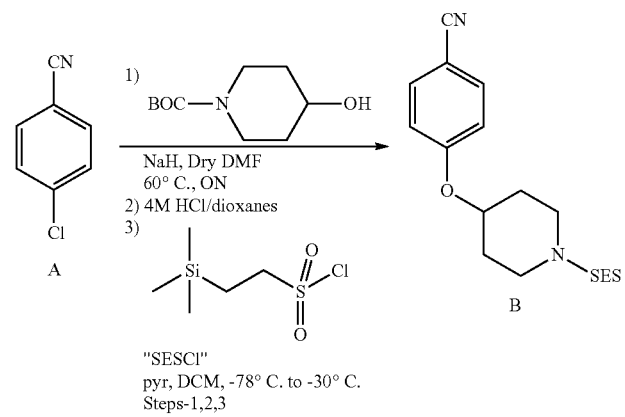
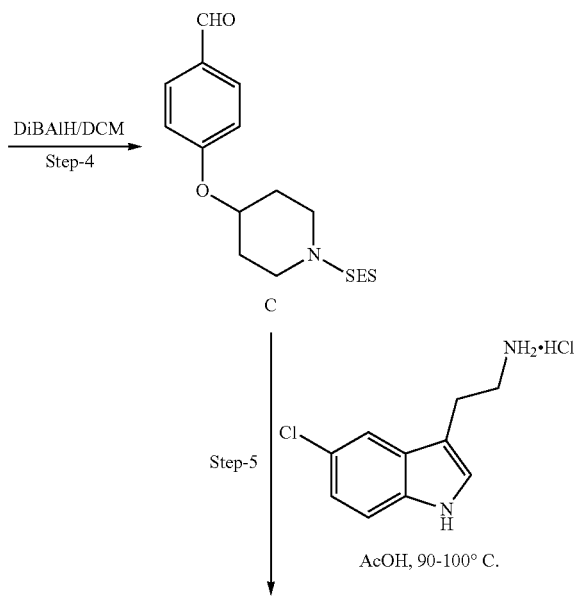

-continued

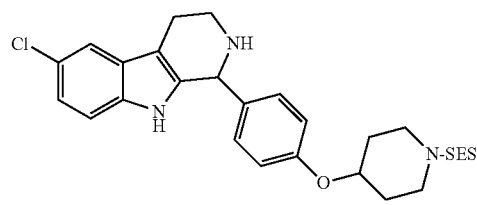

E

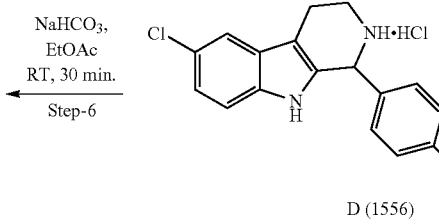

D (1556)

Step-6  NaHCO₃, EtOAc RT, 30 min.

Step-7  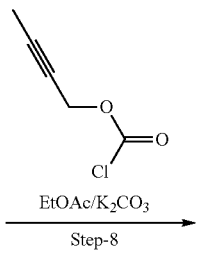 in EtOH

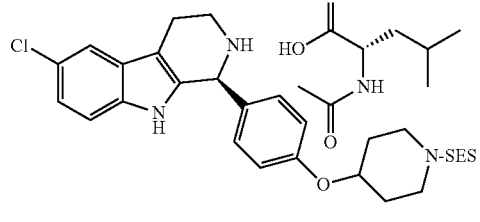

F

EtOAc/K₂CO₃
Step-8

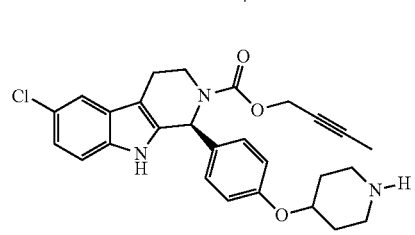

G(1606)

Step 9 | CsF, DMA, 73° C.

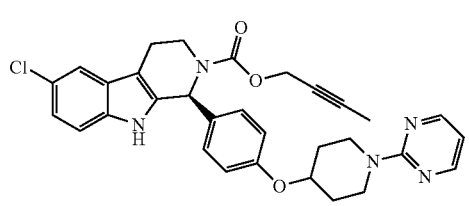

I(1678)

K₂CO₃/DMA/45° C.
Step-10

H(1683)

Step-1: To a stirred solution of N—BOC 4-hydroxypiperidine (7.50 g, 0.0373 mol) in dry DMF (50 mL) was added 95% NaH solid (1.12 g, 0.047 mol) in small portions over 5-10 min. After the evolution of gas had subsided, 4-chlorobenzonitrile (5.18 g, 0.0376 mol) was added in one portion, and the mixture heated to 60° C. overnite. The mixture was diluted with tBuOH (about 5 mL) and neutralized to pH 7 using glacial AcOH. The DMF was concentrated in vacuo, and the crude product chromatographed over a 120 g Isco column using 20% DCM/hexanes to DCM as an eluent to get step-1 product, 4-(4-cyanophenoxy)piperidine-1-carboxylic acid tert-butyl ester, as a white solid (10.33 g, 92%): LC Rt=3.40; ¹H NMR (300 MHz, CDCl₃) δ 1.46 (s, 9H), 1.74-1.80 (m, 2H), 1.89-1.97 (m, 2H), 3.40 (ddd, J=10.3, 7.6, 4.0 Hz, 2H), 3.68 (ddd, J=10.3, 8.7, 4.0 Hz, 2H), 4.55 (septet, J=3.6 Hz, 1H), 6.94 (d, J=9.0 Hz, 2H), 7.58 (d, J=9.0 Hz, 2H).

Step-2: To a stirred solution of 100 mL (400 mmol) of 4N HCl in dioxanes was added the step-1 product, 4-(4-cyanophenoxy)piperidine-1-carboxylic acid tert-butyl ester, (12.60 g, 0.0417 mol) and the mixture stirred 2 h, and 150 mL of 67% Et₂O/hexanes added. The resulting slurry was filtered and dried under vacuum (1 torr, 60° C.) to afford the step-2 product, 4-(piperidin-4-yloxy)benzonitrile hydrochloride, as a white solid (9.10 g, 91%): LCMS [MH⁺]203, Rt 1.23.

Step-3: To a stirred solution of 9.84 g (0.049 mol) of 2-trimethylsilanylethanesulfonyl chloride (SESCl) in DCM (100 mL) cooled to −78° C., was added the step-2 product, 4-(piperidin-4-yloxy)benzonitrile hydrochloride, (9.00 g, 0.038 mol). The mixture was stirred 30 min, warmed to −30° C., and stirred 3 h. To this mixture was added 20 mL of 1N NaOH solution added, and the DCM and aqueous layers partitioned. The aqueous layer was back extracted with DCM (50 mL) and the combined organic layers washed with brine (50 mL), saturated aqueous NaHCO₃ (2×30 mL), dried (MgSO₄) and concentrated in vacuo. The crude product was repeatedly crystallized from the minimum amount of DCM in hexanes to get the step-3 product, 4-[1-(2-trimethylsilanylethanesulfonyl)piperidin-4-yloxy]benzonitrile, compound B, as a white solid. (12.95 g, 94%): LCMS [MH+] 367, Rt 3.53; ¹H NMR (300 MHz, (CD₃)₂CO-d⁶) δ 0.80 (s, 9H), 0.97-1.02 (m, 2H), 1.79-1.88 (m, 2H), 2.04-2.15 (m, 2H), 3.28-3.36 (m, 2H), 3.52-3.60 (m, 2H), 4.79 (septet, J=3.9 Hz, 1H), 7.16 (d, J=9.0 Hz, 2H), 7.70 (d, J=9.0 Hz, 2H).

Step-4: To the stirred solution of the step-3 product, 4-[1 (2-trimethylsilanylethanesulfonyl)piperidin-4-yloxy]benzonitrile (12.30 g, 0.0336 mol of compound B) in dry DCM (83 mL) was added 1M DIBALH in DCM (44 mL, 0.044 mol) and the mixture stirred 30 min at 0° C. The reaction mixture was cooled to −20° C., and EtOAc (7 mL) was added slowly dropwise. The mixture was stirred 15 min, a solution of saturated aqueous Rochelle's salt added (85 mL), the mixture warmed to 0° C. and stirred 1 h. The mixture was extracted with DCM (100 mL). The combined organic layers were washed twice with saturated aqueous NaHCO₃ (2×30 mL), dried (MgSO₄) and concentrated in vacuo. The crude product was chromatographed over a 80 g Isco column using 70% DCM/hexanes to DCM to 40% EtOAc/DCM as an eluent to get the step-4 product, compound C, as a white solid. (12.4 g, 99%): LCMS [MH+] 370, Rt 3.45; ¹H NMR (300 MHz, (CD₃)₂CO-d⁶) δ 0.80 (s, 9H), 0.97-1.04 (m, 2H), 1.80-1.96 (m, 2H), 2.06-2.164 (m, 2H), 2.96-3.02 (m, 2H), 3.29-3.37 (m, 2H), 3.53-3.61 (m, 2H), 4.80 (septet, J=3.9 Hz, 1H), 7.17 (d, J=8.8 Hz, 2H), 7.88 (d, J=8.8 Hz, 2H), 9.90 (s, 1H).

Step-5 Compound D (1556): To a stirred suspension of the Step-4 product (12.40 g, 0.034 mol of compound C) in glacial AcOH (380 mL) heated to 90° C. was added 5-Chlorotryptamine.HCl salt (6.75 g, 0.029 mol) in four portions added 30 min apart. The reaction mixture was heated to reflux overnite. The reaction mixture was allowed to come to rt and put in the refrigerator overnite. The precipitated white solid was filtered under suction. The solid residue was washed with 40% glacial AcOH/Et₂O (100 mL), Et₂O (100 mL) and dried under vacuum to get step-5 product, compound D, as a white solid (7.76 g, 45%). The mother liquor was concentrated to one-third volume, put in the fridge overnite and the same wash cycle and drying of the solid residue utilized to provide additional compound D (2.28 g, 13.3%). Repetition of this cycle one more time gave additional compound D (0.67 g, 2.5%, only 90% pure by LC/MS): LCMS [MH+] 546, Rt 2.33.

Step-6: To a stirred solution of Step-5 HCl salt (10.3 g, 17.67 mmol of compound D) in EtOAc (300 mL) was added saturated aqueous NaHCO₃ solution (150 mL). The reaction mixture was vigorously stirred at rt for 30 minutes. The clear biphasic mixture was separated. The organic layer was washed with water (50 mL), brine (50 mL), dried over anhydrous MgSO₄ and concentrated under vacuum to get a foam. This was washed with hexane to afford the step-6 product, compound E, (9.65 g, 100%): This material was taken directly into the next reaction without further purification.

Step-7: To a stirred solution of Step-6 product (9.65 g, 0.0177 mol of compound E) in abs. EtOH (200 mL) was added N-acetyl-L-leucine (1.99 g, 0.0115 mol) and refluxed until dissolution occurred. The reaction mixture was allowed to cool to rt and stand for 48 hours. The separated solid was filtered and dried (5.30 g, 40% recovery, 72% ee by chiral LC of free base form). It was further crystallized in abs. EtOH (150 mL) to get the step-7 product, compound F, as a white solid (3.86 g, 29% recovery, 99% ee by chiral LC of free base form). This salt was taken directly into the next reaction without further purification. Data for F: Chiral HPLC ODH-280-40 column (rt 19.01 min).

Step-8 Compound G (1606): To a stirred suspension of chiral salt from Step-7 (1200 mg, 1.69 mmol of compound F) in EtOAc (40 mL) and H₂O (20 mL) containing K₂CO₃ (820 mg, 5.93 mmol), was added 2-butynyl chloroformate (231 µL, 2.033 mmol). The mixture was stirred for 2.5 hours, and the organic layer and aqueous layers were partitioned. The aqueous layer was extracted with additional EtOAc (2×70 mL). The combined organic layers were washed with water (10 mL), brine (10 mL), dried over anhydrous MgSO₄ and evaporated under vacuum. The crude residue was chromatographed over a 120 g Isco column using 10% to 40% EtOAc/hexanes as an eluent, to get the step-8 product, compound G, as a white solid (1.08 g, 99%): LCMS [MH+] 642, Rt 4.17; ¹H NMR (300 MHz, (CD₃)₂CO) δ 0.069 (s, 9H), 0.96-1.02 (m, 2H), 1.70-1.85 (m, 2H), 1.82 (s, 3H), 1.98-2.08 (m, 2H), 2.85 (dd, J=7.8, 3.0 Hz, 2H), 2.94-3.00 (m, 2H), 3.12-3.23 (m, 1H), 3.24-3.32 (m, 2H), 3.45 (s, 1H), 3.48-3.56 (m, 2H), 4.18-4.40 (m_e, 1H), 4.59 (septet, J=3.9 Hz, 1H), 4.74 (s, 2H), 6.46 (m_e, 1H), 6.94 (d, J=8.8 Hz, 2H), 7.10 (dd, J=8.7, 2.1 Hz, 1H), 7.21 (dm, J=8.1 Hz, 2H), 7.36 (d, J=8.7 Hz, 1H), 7.53 (d, J=1.8 Hz, 2H), 10.17 (s, 1H).

Step-9, 10 Compounds H and I (1683 and 1678): A stirred suspension of the product from Step-8 (80 mg, 0.12 mmol of compound G) and anhydrous CsF (85 mg, 0.56 mmol), in DMA (0.6 mL) was heated to 73° C. for 20 h. The mixture was cooled to rt, the anion neutralized with glacial AcOH (1 equiv.), and the slurry filtered through a 5µ frit washing with 1 mL of DMA to afford crude compound H. Data for H: LCMS [MH+] 6478, Rt 2.23.

To this solution was added 2-bromopyrimidine (40 mg, 0.248 mmol) and the mixture was heated to 45° C. overnite. The mixture was cooled to rt, filtered through a 5µ frit and the crude product was purified by preparative HPLC to afford the step-10 product (55 mg, 80% over 2-steps) of compound I: LCMS [MH+] 556, Rt 4.00; ¹H NMR (300 MHz, (CD₃)₂CO) δ 1.63-1.75 (m, 2H), 1.82 (s, 3H), 1.97-2.06 (m, 2H), 2.86 (dd, J=8.1, 3.0 Hz, 2H), 3.20 (m_c, 2H), 3.60-3.69 (m, 2H), 4.12-4.34 (m, 2H), 4.70 (septet, J=4.2 Hz, 1H), 4.74 (s, 2H), 6.46 (m_c, 1H), 6.59 (t, J=4.8 Hz, 1H), 6.98 (d, J=8.7 Hz, 2H), 7.10 (dd, J=8.4, 2.1 Hz, 1H), 7.22 (dm, J=8.4 Hz, 2H), 7.36 (d, J=8.4 Hz, 1H), 7.53 (d, J=2.1 Hz, 2H), 8.36 (d, J=4.8 Hz, 2H), 10.19 (s, 1H).

Example XXVI

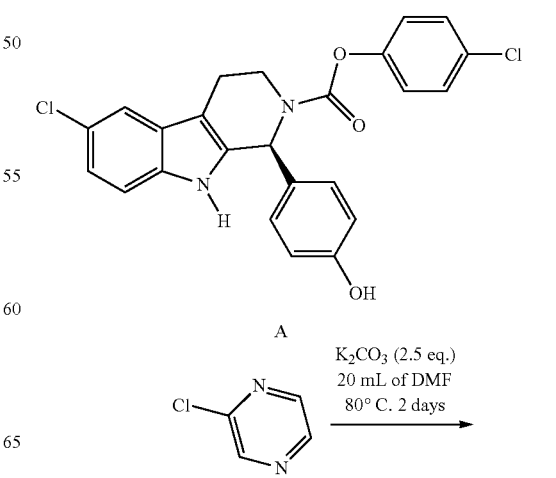

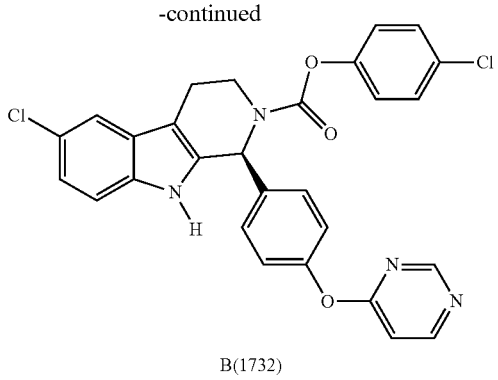

B(1732)

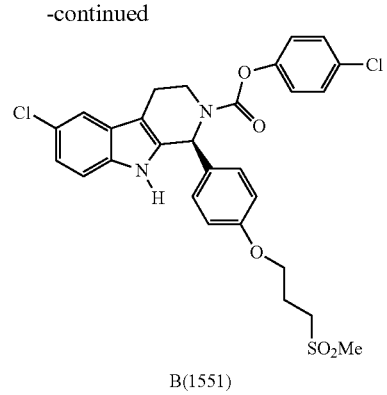

B(1551)

To a suspension of 2.0 g (4.40 mmol) of phenol A and 1.4 g (9.90 mmol) of K$_2$CO$_3$ in 20 mL of DMF was added 505 mg (4.40 mmol) of 2-chloropyrazine, and the mixture heated 24 h at 80° C. showing incomplete conversion of A by LC/MS. An additional portion of 253 mg (2.20 mmol) of 2-chloropyrazine was added and the reaction heated for an additional 1.5 days then cooled to room temperature. The slurry was diluted with an equal volume of ether, filtered to remove the carbonate salts, and then concentrated in vacuo to afford a brownish crude residue. This residue was absorbed onto 25 g of silica gel and carefully chromatographed over an Isco 80 g column (eluted with 10% to 40% EtOAc/Hexanes) to afford 1100 mg (48%, 90% ee) of the product of step-3, compound B (1732) as a colorless foam: LCMS [MH$^+$] 531, Rt 4.02; Chiral HPLC ODH-280-40 column (rt 21.077 min); $^1$H NMR (300 MHz, (CD$_3$)$_2$CO) δ 2.91-3.10 (m, 2H), 3.33-3.44 (m, 1H), 4.38-4.58 (m, 1H), 6.58-6.70 (bm, 1H), 7.13 (dd, J=8.4, 1.8 Hz, 1H), 7.40-7.58 (m, 4H), 7.37-7.60 (m, 5H), 7.58 (dm, J=2.4, 1H), 8.15 (dd, J=2.7, 1.2 Hz, 1H), 8.33 (d, J=2.7 Hz, 1H), 8.46 (d, J=1.2 Hz, 1H), 10.32 (s, 1H).

To a solution of compound A (1.50 g, 2.83 mmol) in Acetone (20 mL) and DMF (1 mL) at 0° C. was added KI (2.27 g, 13.7 mmol). The mixture was heated to 55° C. overnite to obtain a 60:40 mixture of alkyl iodide/alkyl chloride. The mixture concentrated under vacuum, diluted with 10 mL of DMF and 1.75 g (17.1 mmol) of NaSO$_2$Me. The mixture was heated to 45° C. overnite for 18 h, then heated to 100° C. for 10 min to complete the reaction. The reaction mixture was cooled to rt, diluted with EtOAc (100 mL) and water (30 mL). The two layers were separated. The organic layer was washed with water (30 mL) brine (30 mL), dried over MgSO$_4$, concentrated and chromatographed over an Isco 80 g column (eluted with 15% to 40% EtOAc/Hexanes) to afford 1.36 g (84%, >99% ee) of the product of step-2, compound B(1551): LCMS [M$^+$−1] 571, Rt 3.80; Chiral HPLC ODH-280-40 column (rt 75.53 min); $^1$H NMR (300 MHz, CD$_3$)$_2$CO) δ 2.22-2.32 (m, 2H), 2.90-3.10 (m, 5H), 3.26-3.31 (m, 3H), 4.17 (t, J=6.3 Hz, 2H), 4.43 (m$_c$, 1H), 6.52 (bm, 1H), 6.95 (d, J=9.0 Hz, 2H), 7.11 (dd, J=9.0, 2.4 Hz, 1H), 7.40-7.58 (m, 4H), 7.37 (d, J=8.4 Hz, 1H), 7.42 (dm, J=9.3 Hz, 2H), 7.56 (d, J=2.2 Hz, 1H), 10.22 (s, 1H).

Example XVIII

Example XXVII

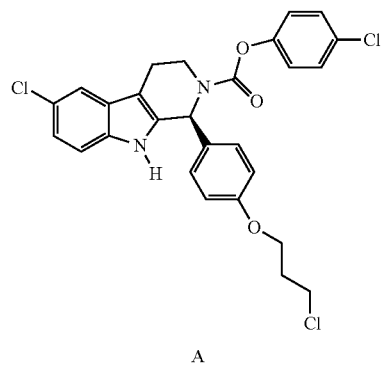

A

1) KI/Acetone/DMF/Δ
2) NaSO$_2$Me/DMF/Δ
(Steps 1-2)

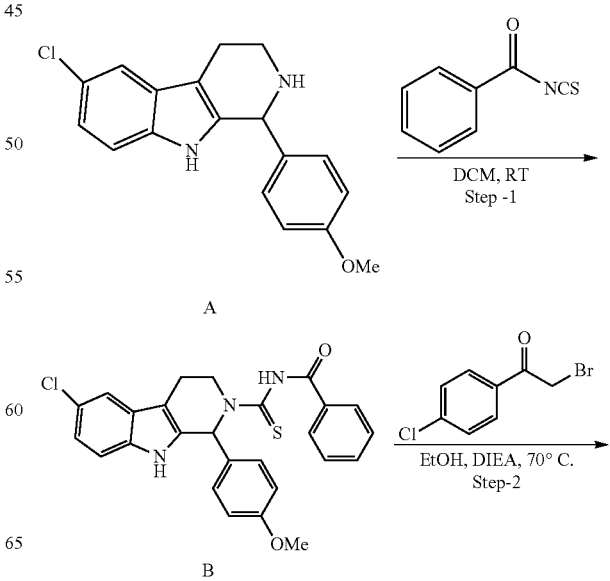

-continued

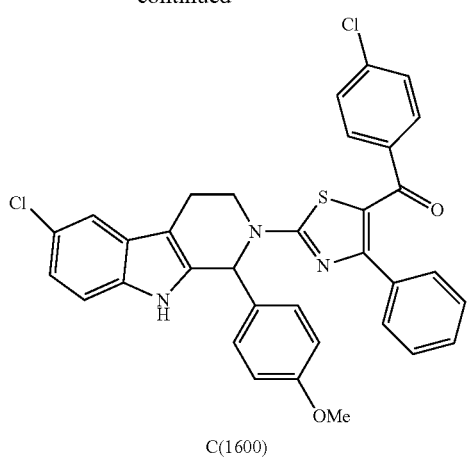

C(1600)

Step 1: Dissolve A (1.00 g, 3.22 mmol) in 10 mL of dichloromethane with stirring. Add benzoylisothiocyanate (577 mg, 3.54 mmol) in one aliquot. Heat the reaction to 70° C. overnight. The reaction was complete after 16 hours. The reaction mixture was concentrated and washed repeatedly with hexane until a fine yellow powder remained. The acylthiourea product B was pure by LC/MS. LCMS [M+H$^+$] 476.05, Rt=3.27 minutes.

Step-2: The acylthiourea B (100 mg, 0.210 mmol) was dissolved in 2 mL of EtOH. 2-Bromo-4-Chloroacetophenone (59 mg, 0.252 mmol) and DIEA (52 uL, 0.315 mmol) were added. The reaction was warmed to 70° C. for 1 hour at which time is was complete by LC/MS. The reactions were concentrated, dissolved in EtOAc and purified on SiO$_2$ with 1:4 EtOAc/Hexanes. The product C (1660) was pure by LC/MS. LC/MS [M+H$^+$] 610.17, Rt=4.02 minutes.

Example XXIX

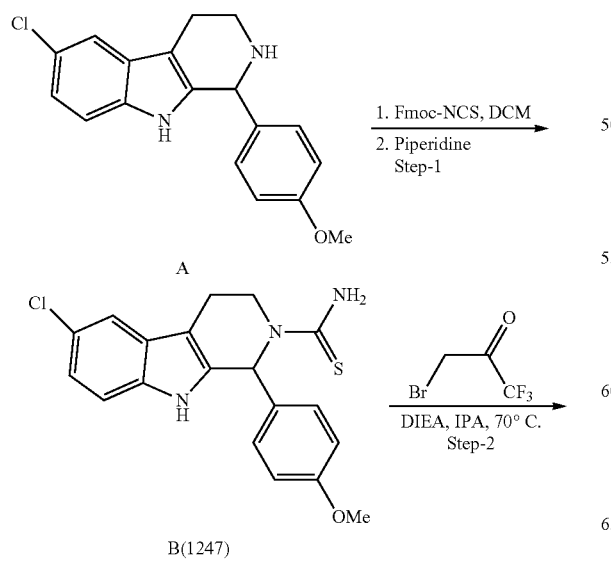

-continued

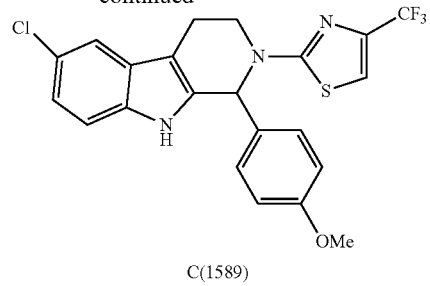

C(1589)

Step 1: Dissolve A (5 g, mmol) in 15 mL of dichloromethane. Add Fmoc-NCS in one portion with stirring. The reaction becomes very warm and is complete after 30 minutes. Add 5 mL of piperidine to the reaction. After 15 hours, the reaction mixture has become a white solid and is complete after three hours. The reaction is poured into 10 mL of saturated Na$_2$CO$_3$. The aqueous layer is extracted four times with dichloromethane. The organic layers are combined, dried over MgSO$_4$, filtered, and concentrated. The resulting brown semi-solid is recrystallized from EtOH and hexanes. Product B(1247) is pure by LC/MS. LC/MS [M+H$^+$] 372.1 Rt=3.23 minutes.

Step-2: Thiourea B (26.6 mg, 0.071 mmol) was dissolved in 1 mL of isopropyl alcohol. 3-Bromo-trifluoroacetone (17.2 mg, 0.09 mmol) and DIEA (27.9 mg, 0.216 mmol) were added to the reaction with stirring. The reactions were warmed to 70° C. for 2 hours. The reaction was complete at this time. The reaction was concentrated, dissolved in DMF, and purified by reverse-phased HPLC. The trifluoromethyl aminothiazole product C(1589) was pure by LC/MS. LC/MS [M+H$^+$] 464.08, Rt=4.13 minutes.

Example XXX

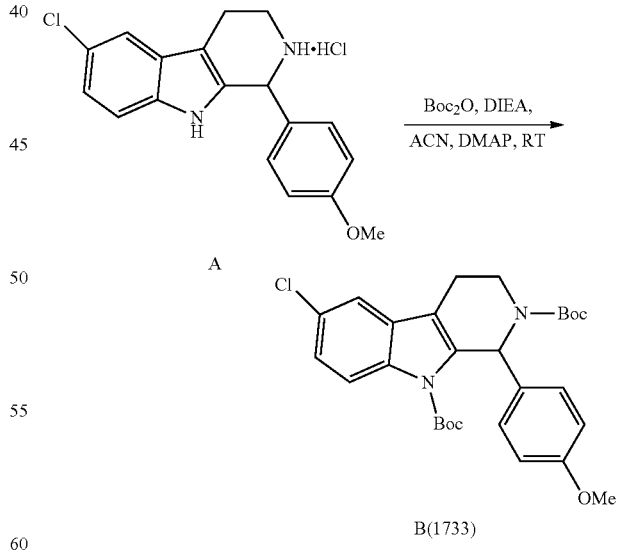

Dissolve A (1.00 g, 2.19 mmol) in acetonitrile with stirring. Add Boc$_2$O (1.05 g, 4.81 mmol), DIEA (0.70 mL, 0.55 mmol), and DMAP (26.7 mg, 0.219 mmol). The reaction stirred overnight and was complete after 12 hours. The reaction was concentrated in situ. The residue was dissolved in dichloromethane and purified on a silica gel plug. The pure Di-Boc product B was obtained in 98% yield. LC/MS [M+H⁺] 515.2, Rt=4.9 minutes.

Example XXXI

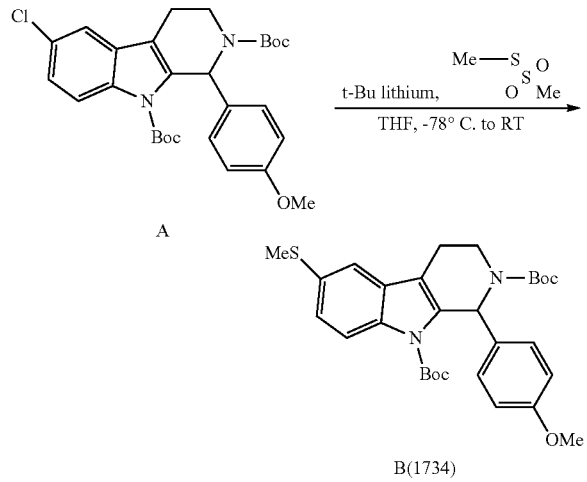

Dissolve Di-Boc A (200 mg, 0.359 mmol) in 10 mL THF under an $N_2$ atmosphere. Cool to −78° C. in a dry ice bath. Add t-butyl lithium drop wise and stir the reaction for 20 minutes at −78° C. Methyl methanethiolsulfonate (136 mg, 1.08 mmol) was dissolved in 4 mL of THF and added to the reaction drop wise through an addition funnel over 5 minutes. Remove the ice bath and allow the reaction to warm to room temperature. Add 10 mL of saturated $NH_4Cl$ drop wise to quench the reaction. The organic layer was extracted with EtOAc (4×10 mL). The organic extracts were combined, dried with $MgSO_4$, filtered, and concentrated in situ. The residue was purified on a $SiO_2$ column with 4:1 hexanes/EtOAc. The methylsulfide product B was pure by LC/MS. LC/MS [M+H⁺] 525.6, Rt=3.22.

Example XXXII

Methylsulfide A (500 mg, 0.871 mmol) was dissolved in 20 mL of dichloromethane and cooled to 0° C. with stirring. MCPBA (215 mg, 0.871 mmol) was dissolved in dichloromethane and added drop wise the methylsulfide C solution over a 15-minute period. The reaction was allowed to warm to room temperature overnight. The reaction was concentrated in situ. The residue was dissolved in 40% EtOAc/60% hexanes and purified on a $SiO_2$ column. The sulfoxide B was pure by LC/MS. LC/MS [M+H⁺] 540.0, Rt=3.38 minutes.

Example XXXIII

Methylsulfide A (718 mg, 1.25 mmol) was dissolved in 20 mL of dichloromethane and cooled to 0° C. with stirring. MCPBA (453.3 mg, 2.62 mmol) was dissolved in 10 mL dichloromethane and added drop wise to the methylsulfide A solution over a 15-minute period. The reaction was allowed to warm to room temperature over a 2-hour period and to stir at room temperature for an additional 4 hours at which time the reaction was complete. The reaction was concentrated in situ. The residue was dissolved in 40% EtOAc/60% hexanes and purified on a $SiO_2$ column. The sulfone B (1482) was pure by LC/MS. LC/MS [M+H⁺] 557.12, Rt=3.90 minutes.

Example XXXIV

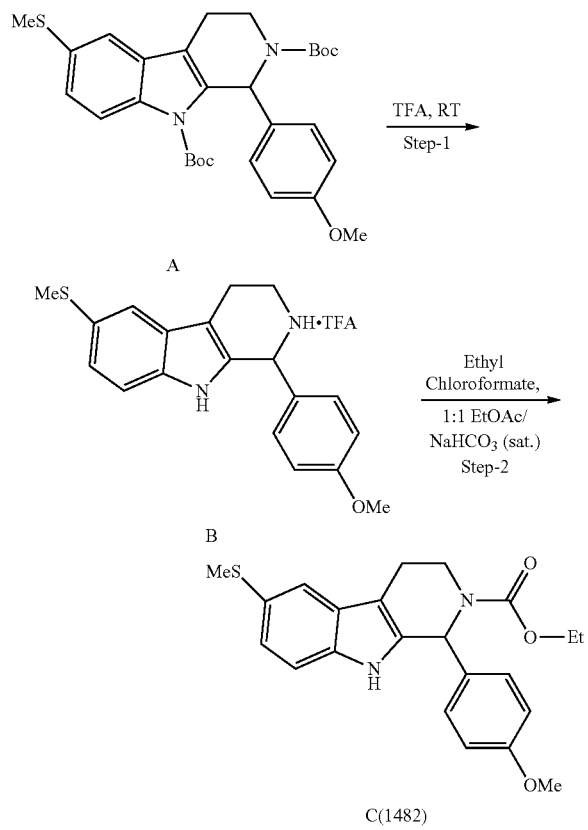

A

B

C(1482)

Step-1: The methylsulfide A (250 mg, 0.477 mmol) was dissolved in 5 mL of TFA. The reaction was stirred overnight under an $N_2$ atmosphere. The deprotection was complete by LC/MS and was then concentrated in situ to give B in quantitative yield. LC/MS [M+H$^+$] 324.94, Rt=2.48 minutes.

Step-2: All of the TFA salt of B from the previous step was dissolved in 10 mL EtOAc. 2 mL of this solution (0.095 mmol) was aliquoted into a 20 mL scintillation vial. Saturated NaHCO$_3$ (2 mL) was added to this scintillation vial with stirring. Ethyl chloroformate (13.5 mg, 0.124 mmol) was added with stirring to the reaction. The acylation was complete after 2 hours. The organic layer was removed, dried in situ, and dissolved in 1 mL of DMF. The product was purified with reverse phase chromatography. Pure ethyl carbamate C (1482) was obtained in 30% yield (11 mg, 0.028 mmol). LC/MS [M+H$^+$] 397.28, Rt=3.37 minutes.

Example XXXV

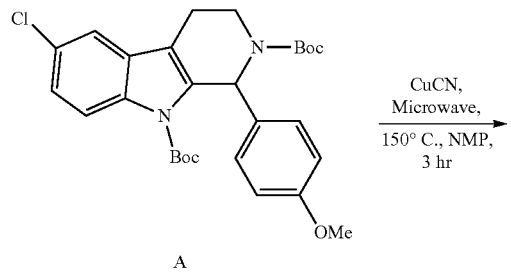

A

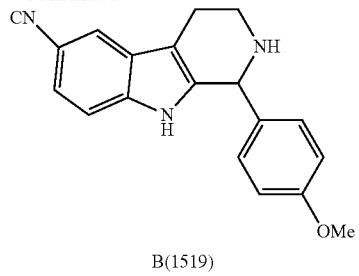

B(1519)

Di-Boc A (55.6 mg, 0.10 mmol) was dissolved in 2 mL of NMP. CuCN (19 mg, 0.20 mmol) and BHT (22 mg, 0.1 mmol) were added to the reaction vessel with stirring. The heterogeneous suspension was degassed by five cycles of a vacuum purge and back filled with $N_2$. The reaction was microwaved at 150° C. for three hours. The reaction was poured into 4 mL of saturated NaHCO$_3$ and extracted with EtOAc (4×4 mL). The organic extracts were combined, dried with MgSO$_4$, filtered, and concentrated. The residue was dissolved in 2 mL of DMF and purified by reverse phase chromatography. Both Boc groups were removed during the microwave heating process. Pure product B (1519) was obtained. LC/MS [M+H$^+$] 304.19, Rt=2.16 minutes.

Example XXXVI

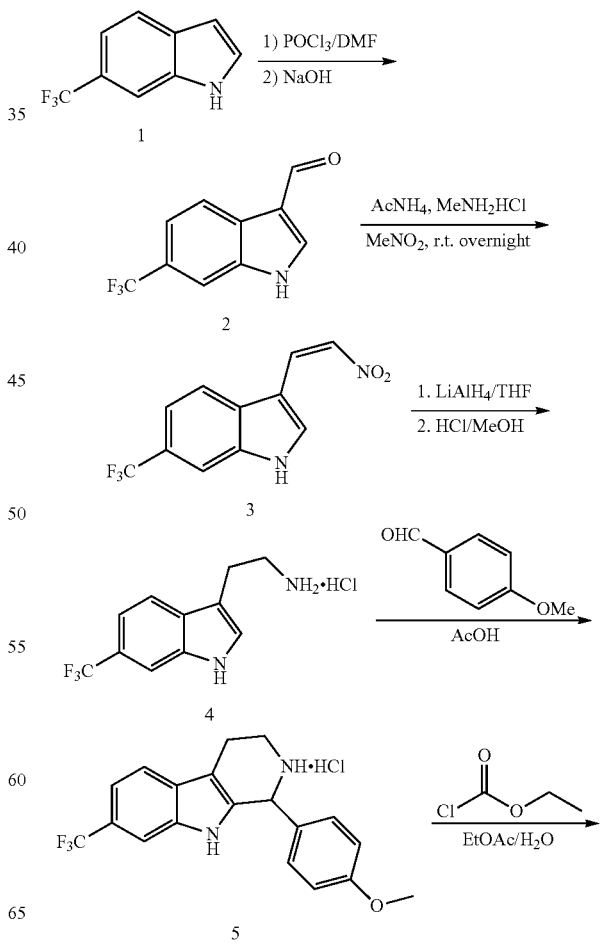

-continued

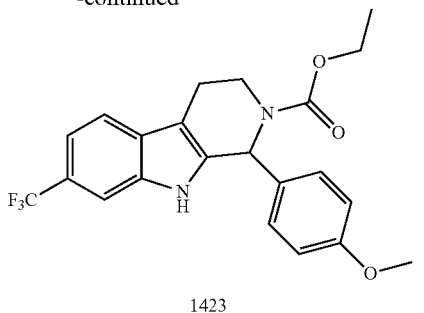

1423

POCl3 (3.6 g, 23.3 mmol) was added to anhydrous DMF (3 mL) at 0° C. and stirred for 15 min at r.t. Then the mixture was added dropwise to a solution of compound 1 (3.6 g, 19.5 mmol) in 10 ml, of anhydrous DMF at 0° C. and stirred at r.t. for 2 h. The mixture was poured into 50 mL of 40% aq.NaOH at 0° C., followed by 100 mL of water. The precipitate was filtered and washed with water, dried to give 3 g of compound 2. Yield: 72%

To a solution of compound 2 (3 g, 14.1 mmol) in 10 mL of $CH_3NO_2$ was added $AcNH_4$ (1.08 g, 14.1 mmol), $CH_3NH_2HCl$ (0.95 g, 14.1 mmol). The mixture was stirred at r.t. overnight. After filtration, 3 g of compound 3 was collected. Yield: 83%

To a suspension of LAH (1.8 g, 47.4 mmol) in 50 mL of anhydrous THF was added compound 3 (3 g, 11.7 mmol) portionwise at 0° C. After the addition, it was allowed to be warmed to r.t. and stirred overnight. Then it was quenched with 1.8 mL of aq. NaOH (15%). The mixture was filtered through Celite, and washed with THF. The filtrate was removed under reduced pressure. The residue was dissolved with HCl/MeOH to give 1.2 g of compound 4 as precipitate. Yield: 40%

To a solution of compound 4 (1.2 g, 4.7 mmol) in 15 mL of AcOH was added 4-methoxybenzaldehyde (0.76 g, 5.6 mmol) and heated to 80° C. stirring overnight. Then it was cooled to r.t., 1.3 g product 5 was collected after filtered and washed with DCM. Yield: 72%

To a solution of compound 5 (191 mg, 0.5 mmol) in 10 mL of $EA/H_2O$ (1:1) was added $NaHCO_3$ (92 mg, 1.1 mmol) and ethyl chloroformate (60 mg, 0.55 mmol). The mixture was stirred overnight. Then the organic layer was separated, washed with brine, dried over $Na_2SO_4$ and evaporated under reduced pressure. The residue was purified by flash column chromatography to give 170 mg of compound 1423. Yield: 81%

Example XXXVII

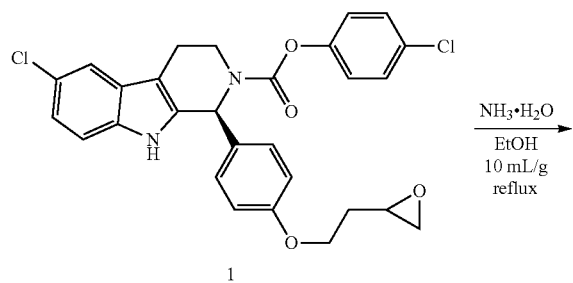

-continued

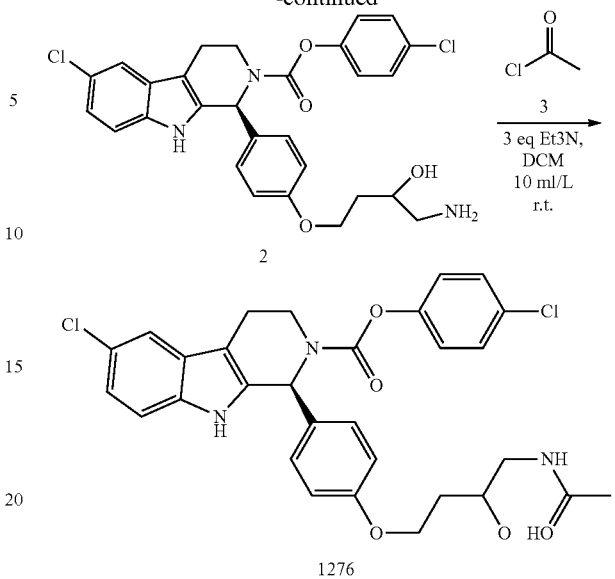

1276

To a solution of compound 1 (4 g, 7.7 mmol) in 40 mL of EtOH was added 10 mL of $NH_3.H_2O$. The mixture was heated to 80° C. overnight. The solvent was evaporated under reduced pressure and the residue was dissolved with EA (40 mL). The organic layer was washed with water (3×40 mL), brine, dried over $Na_2SO_4$ and evaporated under reduced pressure. The residue was purified by flash column chromatography to yield 2.2 g of compound 2. Yield: 54%

To a solution of compound 2 (100 mg, 0.19 mmol) in 1 mL of DCM was added compound 3 (17 mg, 0.22 mmol) and $Et_3N$ (57 mg, 0.57 mmol) at 0° C. The mixture was stirred at r.t. for 16 h. Then the solvent was evaporated under reduced pressure and the residue was dissolved with EA (10 mL). The organic layer was washed with water (3×10 mL), brine, dried over $Na_2SO_4$ and evaporated under reduced pressure. The residue was purified by preparative TLC to yield 26 mg of compound 1276. Yield: 24%

Example XXXVIII

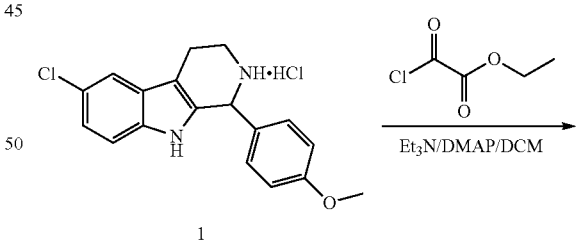

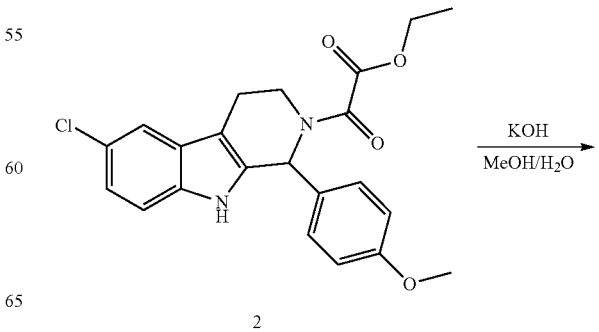

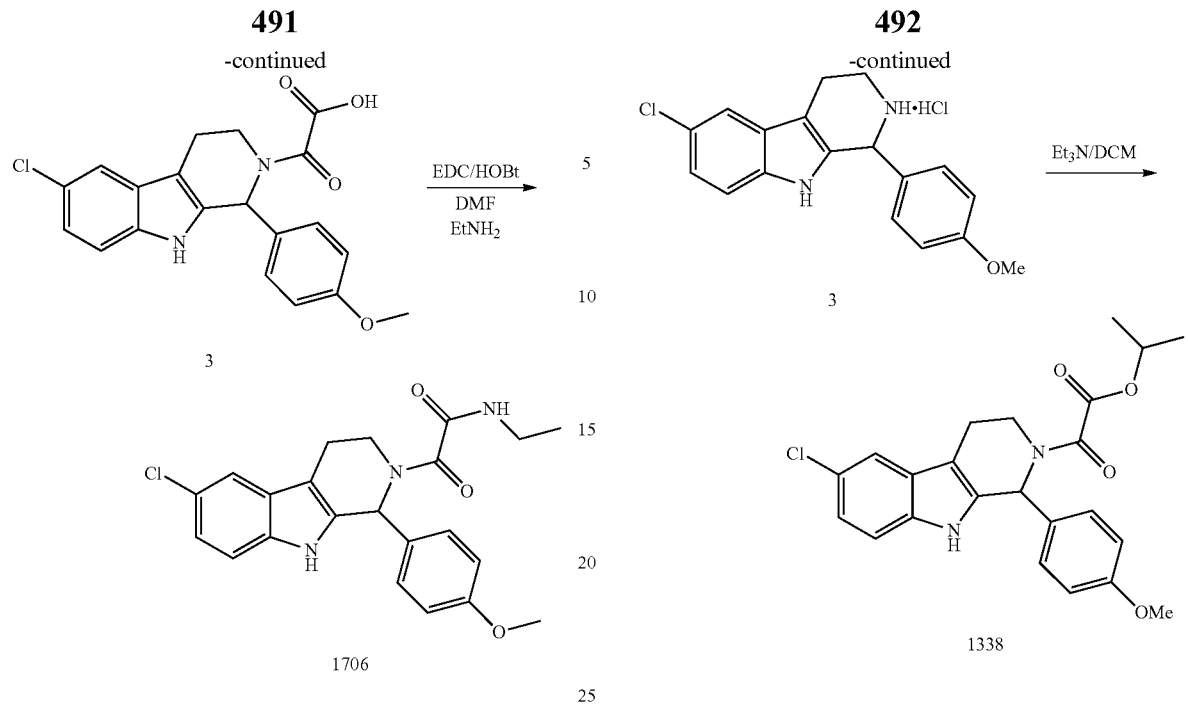

To a solution of compound 1 (10 g, 28.6 mmol) in 100 mL of DCM was added Et$_3$N (8.7 g, 85.8 mmol) and DMAP (0.3 g, 2.86 mmol) and ethoxy oxalyl chloride (4.7 g, 34.3 mmol). Then it was stirred at r.t. overnight. The solvent was removed under reduced pressure and the residue was dissolved with EA, washed with water and brine, dried over Na$_2$SO$_4$ and evaporated under reduced pressure to give 11 g of compound 2. Yield: 93%

To a solution of compound 2 (11 g, 26.6 mmol) in 100 mL of MeOH was added aq. KOH (2 M, 40 mL). It was stirred for 5 h. Then MeOH was removed under reduced pressure and 1M HCl was added to it until it became acidic. EA was added to it and separated, washed with brine, dried over Na$_2$SO$_4$ and evaporated under reduced pressure to give 9.3 g of compound 3. Yield: 93%

To a solution of compound 3 (100 mg, 0.26 mmol) in 2 mL of DMF was added ethanamine (23 mg, 0.52 mmol), EDC (50 mg, 0.26 mmol), HOBT (35 mg, 0.26 mmol), NMM (0.168 mL) and it was stirred for 16 h at r.t. Then it was quenched by water (5 mL) and extracted with ethyl acetate (2×5 mL), and the organic layer was washed with brine, dried over Na$_2$SO$_4$ and evaporated under reduced pressure. The residue was purified by flash column chromatography on silica gel using EtOAc/petro ether (1:5) as eluent to give 47 mg of compound 1706. Yield: 44%

Example XXXIX

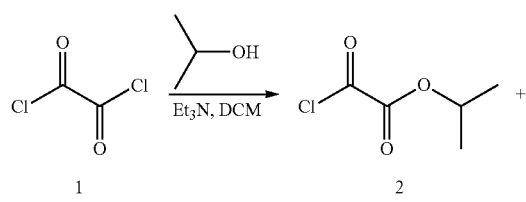

To a solution of i-PrOH (108 mg, 1.8 mmol) in 3 mL of DCM was added Et$_3$N (364 mg, 3.6 mmol) and compound 1 (343 mg, 2.7 mmol). After stirred overnight, the solvent was removed under reduced pressure and the residue was dissolved with EA, washed with water and brine, dried over Na$_2$SO$_4$, evaporated under reduced pressure. Then it was purified by flash column chromatography to give 200 mg of compound 2. Yield: 74%

To a solution of compound 3 (200 mg, 0.58 mmol) in 4 mL of DCM was added Et$_3$N (232 mg, 2.3 mmol) and compound 2 (130 mg, 0.86 mmol). After stirred overnight, the solvent was removed under reduced pressure and the residue was dissolved with EA, washed with water and brine, dried over Na$_2$SO$_4$, evaporated under reduced pressure. Then it was purified by flash column chromatography to give 151 mg of compound 1338. Yield: 61%

Using the procedures shown in the preceding Examples and as described in U.S. Publication No. 2005-0272759 (having corresponding International Application Publication No. WO2005/089764), U.S. Publication No. 2005-0282849 (having corresponding International Application Publication No. WO2006/113703), or U.S. Publication No. 2007-0254878 (having corresponding International Application Publication No. WO2008/127715); and International Application Publication No. WO2008/127714, each of which is incorporated by reference herein in its entirety, additional Compounds presented herein may be prepared including the following, wherein Cpd represents Compound, MS represents mass spec (M+1, unless otherwise indicated) RT represents HPLC retention time (minutes), the RT value of 10-80 and 30-60 represent eluent gradient during the HPLC run and EC$_{50}$ represents the 50% Effective Concentration value for activity in the Hela cell line tested (μM):

The EC$_{50}$ for a series of Compounds is provided in Table 2.

TABLE 2

| Cpd | MS | NMR | RT | EC$_{50}$ |
|---|---|---|---|---|
| 999 | 493.3 | | 4.43 | ***** |
| 1000 | 445.5 | $^1$H NMR (300 MHz, DMSO-d$_6$) δ ppm 1.22 (br. s., 3 H) 2.60-2.86 (m, 2 H) 2.91-3.13 (m, 1 H) 3.41 (t, J = 5.56 Hz, 2 H) 3.67-3.86 (m, 2 H) 3.95 (dd, J = 9.54, 4.13 Hz, 1 H) 4.05-4.24 (m, 3 H) 4.56-4.72 (m, 1 H) 4.92 (d, J = 5.09 Hz, 1 H) 6.31 (br. s., 1 H) 6.90 (d, J = 8.58 Hz, 2 H) 7.05 (dd, J = 8.58, 1.91 Hz, 1 H) 7.10 (d, J = 8.58 Hz, 2 H) 7.28 (d, J = 8.58 Hz, 1 H) 7.50 (d, J = 1.91 Hz, 1 H) 11.11 (br. s., 1 H) | 3.23 | **** |
| 1001 | 575.5 | | 2.98 | **** |
| 1002 | 468.40 | | 2.38 | *** |
| 1003 | 555.1 (cal.554.2) | $^1$H NMR (DMSO, 300 MHz) δ11.09 (b, 1H), 7.47 (s, 1H), 7.25 (d, J = 8.4 Hz, 1H), 7.08-7.01 (m, 3H), 6.84 (d, J = 8.4 Hz, 2H), 6.28 (b, 1H), 4.75 (s, 2H), 4.07 (b, 3H), 3.40-3.37 (m, 6H), 3.20 (b, 4H), 3.18 (s, 3H), 2.99 (b, 1H), 2.73 (b, 1H), 2.32 (b, 3H), 1.20 (b, 3H) | 10-80 3.86 | **** |
| 1004 | 541.2 (cal.540.2) | $^1$H NMR (DMSO, 300 MHz) δ11.09 (b, 1H), 7.92 (t, J = 5.1 Hz, 1H), 7.48 (s, 1H), 7.24 (d, J = 8.4 Hz, 1H), 7.11-7.01 (m, 3H), 6.90 (d, J = 8.4 Hz, 2H), 6.28 (b, 1H), 4.42 (s, 2H), 4.17-4.09 (b, 3H), 3.48-3.43 (m, 4H), 3.28-3.15 (m, 2H), 2.99-2.94 (m, 1H), 2.73-2.69 (m, 1H), 2.32-2.20 (m, 7H), 1.20 (b, 3H) | 10-80 3.82 | **** |
| 1005 | 560.3 (cal.559.2) | $^1$H NMR (CD$_3$OD, 300 MHz) δ7.48 (d, J = 1.8 Hz, 1H), 7.24-7.21 (m, 3H), 7.07-6.90 (m 7H), 6.53-6.46 (m, 1H), 4.77 (b, 1H), 4.42 (b, 1H), 4.15 (b, 1H), 3.77 (s, 3H), 3.52-3.49 (m, 2H), 3.29-3.19 (m, 1H), 2.95-2.83 (m, 5H), 2.42 (b, 2H), 2.17-2.03 (m, 5H) | 10-80 4.55 | ** |
| 1006 | 482.2 (cal.481.2) | $^1$H NMR (CD$_3$OD, 300 MHz) δ7.43 (s, 1H), 7.19-7.18 (m, 3H),), 7.04-7.01 (d, J = 8.7 Hz, 1H), 6.91-6.88 (d, J = 7.8 Hz, 2H), 6.39 (b, 1H), 4.73 (b, 1H), 4.19-4.11 (m, 3H), 3.61-3.50 (m, 2H), 3.21-3.13 (m, 3H), 2.93-2.89 (m, 3H), 2.81-2.78 (m, 2H), 2.40-1.79 (m, 6H), 1.28 (b, 3H) | 10-80 4.11 | *** |
| 1007 | 468.1 (cal.467.2) | $^1$H NMR (CDCl$_3$, 300 MHz) δ7.83-7.78 (m, 1H), 7.50 (s, 1H), 7.24-7.18 (m, 2H), 7.12 (dd, J = 8.7 Hz and 1.8 Hz, 1H), 6.81-6.77 (m, 2H), 6.43-6.40 (m, 1H), 4.72-4.60 (m, 1H), 4.41-4.12 (m, 2H), 4.00-3.91 (m, 1H), 3.77-3.62 (m, 3H), 2.91-2.72 (m, 5H), 2.52-2.47 (m, 1H), 2.27-2.65 (m, 2H), 2.07-1.98 (m, 2H) | 10-80 3.90 | *** |
| 1008 | 548.2 (cal.547.2) | $^1$H NMR (CD$_3$OD, 300 MHz) δ7.49 (s, 1H), 7.24-7.21 (m, 3H), 7.14-6.96 (m 7H), 6.53-6.46 (m, 1H), 4.76 (b, 1H), 4.41 (b, 1H), 4.12 (b, 1H), 3.77 (s, 3H), 3.57-3.48 (m, 2H), 2.96-2.84 (m, 5H), 2.42 (b, 2H), 2.17-1.82 (m, 5H) | 10-80 4.79 | *** |
| 1009 | 468.1 (cal.467.2) | $^1$H NMR (CDCl$_3$, 300 MHz) δ7.83-7.78 (m, 1H), 7.50 (s, 1H), 7.24-7.18 (m, 2H), 7.12 (dd, J = 8.7 Hz and 1.8 Hz, 1H), 6.81-6.77 (m, 2H), 6.43-6.40 (m, 1H), 4.72-4.60 (m, 1H), 4.41-4.12 (m, 2H), 4.00-3.91 (m, 1H), 3.77-3.62 (m, 3H), 2.91-2.72 (m, 5H), 2.52-2.47 (m, 1H), 2.27-2.65 (m, 2H), 2.07-1.98 (m, 2H) | 10-80 3.90 | *** |
| 1010 | 468.2 (cal.467.2) | $^1$H NMR (CD$_3$OD, 400 MHz) δ7.45 (s, 1H), 7.26-7.20 (m, 3H), 7.06-6.98 (m, 3H), 6.40 (b, 1H), 4.25 (m, 2H), 3.79 (s, 3H), 3.61-3.40 (m, 4H), 3.19-3.14 (m, 1H), 2.95-2.65 (m, 5H), 2.00-1.93 (m, 6H) | 10-80 4.59 | *** |
| 1011 | 560.2 (cal.559.2) | $^1$H NMR (CD$_3$OD, 400 MHz) δ7.51 (d, J = 2.0 Hz, 1H), 7.35-7.28 (m, 3H), 7.15-7.01-7.18 (m, 5H), 6.93 (d, J = 8.8 Hz, 2H), 4.83-4.76 (m, 1H), 4.52-4.27 (m, 1H), 3.79 (s, 3H), 3.72-3.41 (m, 4H), 3.05-2.84 (m, 5H), 2.19-1.67 (m, 6H) | 10-80 5.54 | *** |
| 1012 | 497.8 (cal.497.2) | $^1$H NMR (DMSO, 300 MHz) δ11.09 (b, 1H), 7.48 (s, 1H), 7.24 (d, J = 8.4 Hz, 1H), 7.08-7.01 (m, 3H), 6.85 (d, J = 8.4 Hz, 2H), 6.28 (b, 1H), 4.77 (s, 2H), 4.17-4.09 (m, 3H), 3.54 (b, 4H), 3.39 (b, 4H), 3.0 (b, 2H), 2.69-2.68 (m, 1H), 1.20 (b, 3H) | 10-80 4.63 | *** |
| 1013 | 472.0 (cal.471.2) | $^1$H NMR (CD$_3$OD, 300 MHz) δ7.45 (s, 1H), 7.23-7.20 (m, 3H), 7.04 (dd, J = 8.7 Hz and 2.1 Hz, 1H), 6.96 (d, J = 8.7 Hz, 2H), 6.40 (b, 1H), 4.49 (s, 2H), 4.25-4.22 (m, 3H), 3.63-3.59 (m, 2H), 3.40-3.36 (m, 2H), 3.15 (b, 1H), 2.80 (b, 2H), 1.30 (b, 3H) | 10-80 5.05 | **** |
| 1014 | 541.2 (cal.540.2) | $^1$H NMR (CD$_3$OD, 300 MHz) δ7.45 (s, 1H), 7.23-7.19 (m, 3H), 7.04 (dd, J = 8.7 Hz and 2.1 Hz, 1H), 6.93 (d, J = 8.7 Hz, 2H), 6.39 (b, 1H), 4.87 (s, 2H), 4.20-4.19 (m, 3H), 3.90-3.85 (m, 2H), 3.55 (b, 3H), 3.15 (m, 5H), 2.80 (b, 3H), 1.30 (b, 3H) | 10-80 4.41 | *** |
| 1015 | 486.0 (cal.485.2) | $^1$H NMR (CD$_3$OD, 300 MHz) δ7.45 (s, 1H), 7.23-7.20 (m, 3H), 7.03 (dd, J = 8.7 Hz and 2.1 Hz, 1H), 6.93 (d, J = 8.7 Hz, 2H), 6.39 (b, 1H), 4.49 (s, 2H), 4.25-4.22 (m, 3H), 3.46-3.41 (m, 4H), 3.33 (b, 3H), 3.15 (b, 1H), 2.80 (b, 2H), 1.31 (b, 3H) | 10-80 5.48 | *** |
| 1016 | 560.51 (ES−) | | 4.23 | * |
| 1017 | 544.39 (ES−) | | 4.08 | ***** |
| 1018 | 467.14 | | 3.28 | **** |
| 1019 | 467.23 | | 3.20 | **** |
| 1020 | 453.27 (ES−) | | 3.15 | **** |
| 1021 | 621.2 (cal.620.2) | $^1$H NMR (DMSO, 400 MHz), δ 7.51 (d, J = 2.4 Hz, 1H), 7.30-7.24 (m, 3H), 7.16-7.13 (m, 3H), 7.08 (dd, J = 8.8 Hz and 2.1 Hz, 2H), 6.98 (b, 2H), 6.51 (b, 1H), 4.45 (b, 1H), 3.62-3.53 (m, 6H), 3.35 (s, 3H), 3.11-2.80 (m, 3H), 2.64-2.53 (m, 5H) | 10-80 4.35 | *** |
| 1022 | 607.2 (cal.606.2) | $^1$H NMR (CD$_3$OD, 300 MHz) δ7.49 (s, 1H), 7.25-7.20 (m, 3H), 7.14-7.05 (m, 5H), 6.99 (b, 2H), 6.50 (b, 1H), 4.52 (s, 2H), 4.62-4.58 (m, 4H), 3.42-3.37 (m, 2H), 2.80 (b, 3H), 2.49-2.43 (m, 6H) | 10-80 5.05 | *** |
| 1023 | M + 23:586.1 (cal.563.2) | $^1$H NMR (CD$_3$OD, 300 MHz) δ7.49 (s, 1H), 7.25-7.22 (m, 3H), 7.14-7.05 (m, 5H), 6.99 (b, 2H), 6.50 (b, 1H), 4.81 (s, 2H), 4.42 (m, 2H), 3.67-3.56 (m, 8H), 2.60 (b, 3H)) | 10-80 5.93 | **** |

TABLE 2-continued

| Cpd | MS | NMR | RT | EC$_{50}$ |
|---|---|---|---|---|
| 1024 | 591.2 (cal.590.2) | $^1$H NMR (CD$_3$OD, 300 MHz) δ7.49 (s, 1H), 7.25-7.22 (m, 3H), 7.13-7.05 (m, 5H), 6.96 (b, 2H), 6.50 (b, 1H), 4.81 (s, 2H), 4.42 (b, 2H), 3.59 (b, 4H), 2.90 (b, 3H), 2.46-2.44 (m, 5H), 1.10 (b, 3H) | 10-80 5.01 | *** |
| 1025 | 633.2 (cal.632.2) | $^1$H NMR (CD$_3$OD, 300 MHz) δ7.49 (d, J = 1.8 Hz, 1H), 7.26-7.23 (m, 3H), 7.09-7.02 (m, 3H), 6.97-6.91 (m, 4H), 6.50 (b, 1H), 4.81 (s, 2H), 4.42 (b, 2H), 3.79 (s, 3H), 3.63-3.52 (m, 6H), 3.35 (s, 3H), 2.90 (b, 3H), 2.61-2.51 (m, 6H) | 10-80 4.29 | *** |
| 1026 | 619.2 (cal.618.2) | $^1$H NMR (CD$_3$OD, 300 MHz) δ7.49 (d, J = 2.1 Hz, 1H), 7.28-7.22 (m, 3H), 7.08-7.02 (m, 5H), 6.93-6.90 (m, 2H), 6.47 (b, 1H), 4.52 (s, 2H), 4.41 (b, 2H), 3.78 (s, 3H), 3.60 (t, J = 4.8 Hz, 4H), 3.40 (t, J = 6.3 Hz, 3H), 2.90 (b, 3H), 2.61-2.51 (m, 6H) | 10-80 4.24 | **** |
| 1027 | M − 1:574.1 (cal.575.2) | $^1$H NMR (DMSO, 300 MHz) δ11.15 (b, 1H), 7.51 (s, 1H), 7.27 (d, J = 8.7 Hz, 1H), 7.13 (b, 2H), 7.06-7.02 (m, 3H), 6.90-6.88 (m, 4H), 6.40 (b, 1H), 4.79 (s, 2H), 4.27 (b, 2H), 3.71 (s, 3H), 3.61-3.40 (m, 5H), 3.29 (s, 1H), 3.13 (b, 1H), 2.95-2.69 (m, 4H), | 10-80 5.03 | *** |
| 1028 | 603.2 (cal.602.2) | $^1$H NMR (CD$_3$OD, 300 MHz) δ7.48 (d, J = 1.8 Hz, 1H), 7.08-7.01 (m, 3H), 6.93-6.90 (m, 4H), 6.47 (b, 1H), 4.81 (s, 2H), 4.40 (b, 2H), 3.78 (s, 3H), 3.60-3.56 (m, 4H), 2.89 (b, 2H), 2.50-2.41 (m, 6H), 1.10 (t, J = 7.2 Hz, 3H) | 10-80 4.23 | *** |
| 1029 | 660.2 (cal.659.3) | $^1$H NMR (CD$_3$OD, 300 MHz) δ7.48 (s, 1H), 7.24-7.22 (m, 3H), 6.93-6.90 (m, 4H), 6.46 (b, 1H), 4.80 (s, 2H), 4.40 (b, 2H), 3.78 (s, 3H), 3.58 (b, 4H), 2.89 (b, 2H), 2.49-2.33 (m, 8H), 2.24-2.21 (m, 6H), 1.70-1.68 (m, 2H) | 10-80 3.87 | * |
| 1030 | 576.2 (cal.575.2) | $^1$H NMR (DMSO, 300 MHz) δ11.08 (b, 1H), 7.48 (s, 1H), 7.26-6.87 (m, 10H), 6.33 (b, 1H), 4.23 (b, 1H), 3.92 (b, 2H), 3.68 (s, 3H), 3.29 (b, 4H), 3.11 (b, 1H), 2.66 (b, 2H), 2.32-2.27 (m, 6H), 1.78 (b, 2H) | 10-80 5.29 | **** |
| 1031 | 558.0 (cal.557.2) | $^1$H NMR (DMSO, 300 MHz) δ11.30 (b, 1H), 8.13 (s, 1H), 7.71 (s, 1H), 7.53 (s, 1H), 7.42-6.81 (m, 10H), 6.42-6.39 (m, 1H), 4.53-4.29 (m, 3H), 3.92 (s, 2H), 3.73 (s, 3H), 3.22-3.18 (m, 1H), 2.92-2.82 (m, 2H), 2.62 (s, 2H) | 30-90 4.69 | ***** |
| 1032 | 443.4 | | 3.55 | **** |
| 1033 | 456.8 | $^1$H NMR (300 MHz, DMSO-d$_6$) δ ppm 1.21 (t, J = 6.36 Hz, 3 H) 2.67-2.82 (m, 2 H) 2.90-3.08 (m, 1 H) 3.78-3.93 (m, 4 H) 3.93-3.98 (m, 2 H) 4.10 (q, J = 6.78 Hz, 3 H) 5.15 (t, J = 3.97 Hz, 1 H) 6.30 (br. s., 1 H) 6.92 (d, J = 8.90 Hz, 2 H) 7.05 (dd, J = 8.58, 1.91 Hz, 1 H) 7.10 (d, J = 8.58 Hz, 2 H) 7.27 (d, J = 8.58 Hz, 1 H) 7.49 (d, J = 1.91 Hz, 1 H) 11.10 (br. s., 1 H) | 3.75 | **** |
| 1034 | 471.4 | | 3.83 | ***** |
| 1035 | 485.4 | | 3.98 | ***** |
| 1036 | 471.4 | | 3.82 | ***** |
| 1037 | 485.5 | | 3.95 | ***** |
| 1038 | 499.4 | | 4.07 | ***** |
| 1039 | 475.4 | | 3.52 | ***** |
| 1040 | 491.3 | | 3.68 | **** |
| 1041 | 503.5 (M − H) | | 3.75 | **** |
| 1042 | 487.4 | | 3.47 | **** |
| 1043 | 455.42 | | 3.75 | ***** |
| 1044 | 469.4 | | 3.73 | ***** |
| 1045 | 483.3 | | 3.83 | ***** |
| 1046 | 469.4 | | 3.75 | **** |
| 1047 | 481.4 | | 3.73 | ***** |
| 1048 | 467.4 | | 3.58 | ***** |
| 1049 | 481.4 | | 3.63 | ***** |
| 1050 | 505.33 | | 3.85 | ***** |
| 1051 | 523.4 | | 3.88 | ***** |
| 1052 | 539.3 | | 3.97 | **** |
| 1053 | 537.5 | $^1$H NMR (300 MHz, DMSO-d$_6$) δ ppm 2.87 (br. s., 2 H) 3.19 (br. s., 1 H) 3.79-4.00 (m, 6 H) 4.28 (br. s., 1 H) 5.16 (t, J = 3.97 Hz, 1 H) 6.41 (br. s., 1 H) 6.96 (d, J = 7.95 Hz, 2 H) 7.07 (dd, J = 8.58, 1.91 Hz, 1 H) 7.10-7.24 (m, 4 H) 7.30 (d, J = 8.58 Hz, 1 H) 7.44 (d, J = 8.58 Hz, 2 H) 7.54 (d, J = 2.23 Hz, 1 H) 11.14 (br. s., 1 H) | 4.00 | ***** |
| 1054 | 583.4 | | 4.07 | ***** |
| 1055 | 535.4 | | 3.82 | **** |
| 1056 | 519.4 | | 3.92 | ***** |
| 1057 | 553.4 | | 4.05 | ***** |
| 1058 | 507.0 (cal.506.2) | $^1$H NMR (CD$_4$O, 300 MHz) δ7.48 (d, J = 1.8 Hz, 1H), 7.25-7.22 (m, 3H), 7.07-7.02 (m, 3H), 6.93-6.90 (m, 4H), 6.52-6.46 (m, 1H), 4.43-4.39 (m, 1H), 4.06 (t, J = 6.0 Hz, 2H), 3.78 (s, 3H), 3.72 (t, J = 6.3 Hz, 2H), 3.05-2.85 (m, 3H), 2.00-1.94 (m, 2H) | 10-80 5.88 | ***** |
| 1059 | 491.0 (cal.490.2) | $^1$H NMR (DMSO, 300 MHz) δ11.12-11.08 (m, 1H), 7.50 (s, 1H), 7.36-7.26 (m, 6H), 7.06-7.04 (m, 3H), 6.86-6.84 (m, 2H), 6.35-6.34 (m, 1H), 5.17-5.10 (m, 2H), 4.20-4.17 (m, 1H), 3.98 (t, J = 6.3 Hz, 2H), 3.51 (t, J = 6.3 Hz, 2H), 3.07-3.02 (m, 1H), 2.76-2.71 (m, 2H), 1.83-1.79 (m, 2H) | 10-80 5.61 | ***** |
| 1060 | 441.0 (cal.440.2) | $^1$H NMR (DMSO, 300 MHz) δ11.12-11.09 (m, 1H), 7.50 (s, 1H), 7.28 (d, J = 8.4 Hz, 1H), 7.10-7.04 (m, 3H), 6.89 (d, J = 7.5 Hz, 2H), 6.34-6.27 (m, 1H), 5.99-5.91 (m, 1H), | 10-80 5.18 | ***** |

TABLE 2-continued

| Cpd | MS | NMR | RT | EC$_{50}$ |
|---|---|---|---|---|
| | | 5.31-5.15 (m, 2H), 4.60-4.58 (m, 1H), 4.19-4.14 (m, 1H), 4.00-3.96 (m, 2H), 3.51-3.48 (m, 2H), 3.08-3.02 (m, 1H), 2.78-2.71 (m, 2H), 1.83-1.79 (m, 2H) | | |
| 1061 | 457.1 (cal.456.2) | $^1$H NMR (DMSO, 300 MHz) δ11.09 (s, 1H), 7.48 (d, J = 2.1 Hz, 1H), 7.26 (d, J = 8.4 Hz, 1H), 7.08-7.01 (m, 3H), 6.87 (d, J = 8.7 Hz, 2H), 6.30 (s, 1H), 4.13-4.10 (m, 1H), 3.96 (t, J = 6.6 Hz, 2H), 3.87-3.71 (m, 2H), 3.49 (t, J = 6.3 Hz, 2H), 3.08-2.97 (m, 1H), 2.74-2.69 (m, 2H), 1.92-1.89 (m, 1H), 1.83-1.77 (m, 2H), 0.87 (d, J = 6.6 Hz, 6H) | 30-90 4.28 | ***** |
| 1062 | 477.1 (cal.476.2) | $^1$H NMR (CD$_4$O, 300 MHz) δ7.49 (d, J = 1.8 Hz, 1H), 7.39 (t, J = 7.8 Hz, 1H), 7.25-7.22 (m, 4H), 7.13 (d, J = 7.8 Hz, 2H), 7.06 (dd, J = 8.7 Hz and 1.5 Hz, 1H), 6.91 (d, J = 8.7 Hz, 2H), 6.54-6.48 (m, 1H), 4.45-4.39 (m, 1H), 4.06 (t, J = 6.0 Hz, 2H), 3.72 (t, J = 6.0 Hz, 2H), 3.05-2.88 (m, 3H), 2.00-1.94 (m, 2H) | 10-80 5.53 | ***** |
| 1063 | M + 23:560.1 (cal.537.2) | $^1$H NMR (CD$_3$OD, 300 MHz) δ7.81 (dd, J = 6.3 Hz and 3.0 Hz, 2H), 7.49 (d, J = 1.8 Hz, 1H), 7.35 (dd, J = 6.3 Hz and 3.0 Hz, 1H), 7.25-7.23 (m, 1H), 7.14-6.98 (m, 6H), 6.48 (b, 1H), 4.52 (s, 2H), 4.40 (b, 2H), 3.62 (t, J = 5.7 Hz, 2H), 3.39 (t, J = 5.7 Hz, 2H), 2.90 (b, 2H) | 10-80 5.47 | **** |
| 1064 | 607.1 (cal.606.2) | $^1$H NMR (CD$_3$OD, 300 MHz) δ7.49 (d, J = 2.1 Hz, 1H), 7.25-7.22 (m, 4H), 7.13-7.05 (m, 4H), 6.96 (b, 2H), 6.50 (b, 1H), 4.80 (s, 2H), 4.42 (b, 2H), 3.69-3.53 (m, 5H), 3.34 (s, 2H), 2.90 (b, 3H), 2.55-2.51 (m, 5H) | 10-80 4.84 | **** |
| 1066 | 562.55 | | 3.63 | ***** |
| 1067 | 562.1 (cal: 561.2) | $^1$H NMR (DMSO, 300 MHz) δ 11.18 (b, 1H), 8.04 (s, 1H), 7.68 (s, 1H), 7.52 (s, 1H), 7.30-7.01 (m, 9H), 6.93-6.92 (m, 2H), 6.35 (b, 1H), 5.53 (s, 1H), 4.60-4.45 (m, 2H), 4.40-4.20 (m, 2H), 3.88 (b, 2H), 3.22 (b, 1H), 2.85 (b, 2H) | 10-80 5.33 | **** |
| 1068 | 562.1 (cal: 561.2) | $^1$H NMR (DMSO, 300 MHz) δ 11.18 (b, 1H), 7.81 (s, 3H), 7.74 (s, 2H), 7.52 (s, 1H), 7.30-7.01 (m, 6H), 6.93-6.90 (m, 2H), 6.35 (b, 1H), 5.43 (s, 1H), 4.54-4.50 (m, 2H), 4.28 (b, 2H), 3.90 (b, 2H), 2.85 (b, 2H) | 10-80 5.70 | |
| 1069 | 562.27 | | 3.9 | ***** |
| 1070 | 596.24 | | 2.40 | ***** |
| 1071 | 598.21 | | 2.48 | ***** |
| 1072 | 523.3 (cal.522.4) | $^1$H NMR (DMSO, 400 MHz) δ11.12-11.07 (m, 1H), 7.51 (s, 1H), 7.26 (d, J = 8.4 Hz, 1H), 7.13-7.03 (m, 3H), 6.87 (d, J = 8.8 Hz, 2H), 6.31-6.24 (m, 1H), 5.97-5.90 (m, 1H), 5.33-5.16 (m, 2H), 4.59-4.53 (m, 2H), 4.15-4.14 (m, 1H), 4.01-3.94 (m, 2H), 3.03-2.97 (m, 1H), 2.75-2.68 (m, 2H), 2.66-2.65 (m, 1H), 2.42-2.27 (m, 8H), 2.13 (s, 3H), 1.83-1.78 (m, 2H) | 10-80 2.67 | ***** |
| 1073 | 496.1 (cal: 495.2) | $^1$H NMR (CDCl$_3$, 300 MHz) δ 7.90 (b, 1H), 7.70 (s, 2H), 7.50 (s, 1H), 7.23-7.10 (m, 4H), 6.81 (d, J = 8.4 Hz, 2H), 6.42 (b, 1H), 4.69 (d, J = 12.9 Hz, 1H), 3.60-4.54 (m, 1H), 4.48 (b, 1H), 4.38-4.12 (m, 3H), 3.99-3.84 (m, 2H), 3.17-3.08 (m, 1H), 2.92-2.74 (m, 2H), 1.39-1.18 (m, 3H). | 10-80 5.16 | ***** |
| 1074 | 443.1 (cal.442.2) | $^1$H NMR (DMSO, 300 MHz) δ11.09 (s, 1H), 7.47 (d, J = 1.8 Hz, 1H), 7.25 (d, J = 8.7 Hz, 1H), 7.08-7.02 (m, 3H), 6.87 (d, J = 8.7 Hz, 2H), 6.31-6.20 (m, 1H), 4.83-4.79 (m, 1H), 4.17-4.10 (m, 1H), 3.96 (t, J = 6.3 Hz, 2H), 3.49 (t, J = 6.3 Hz, 2H), 3.05-2.96 (m, 1H), 2.70-2.69 (m, 2H), 1.81-1.77 (m, 2H), 1.19 (d, J = 6.0 Hz, 6H) | 10-80 5.29 | ***** |
| 1075 | 546.3 (cal.545.2) | $^1$H NMR (DMSO, 300 MHz) δ11.19 (b, 1H), 7.52 (d, J = 1.8 Hz, 1H), 7.37 (t, J = 7.8 Hz, 2H), 7.29 (d, J = 8.7 Hz, 1H), 7.21 (t, J = 7.5 Hz, 2H), 7.14-7.11 (m, 3H), 7.05 (dd, J = 8.7 Hz and 2.1 Hz, 1H), 6.91 (d, J = 7.8 Hz, 2H), 6.43-6.38 (m, 1H), 4.30-4.29 (m, 1H), 3.96 (t, J = 6.3 Hz, 2H), 3.52 (t, J = 4.8 Hz, 4H), 3.24-3.16 (m, 1H), 2.86-2.85 (m, 2H), 2.47-2.24 (m, 6H), 1.84-1.79 (m, 2H) | 10-80 4.55 | **** |
| 1076 | 559.3 (cal.558.2) | $^1$H NMR (DMSO, 400 MHz) δ11.15 (b, 1H), 7.52 (d, J = 1.8 Hz, 1H), 7.37 (t, J = 8.1 Hz, 2H), 7.28 (d, J = 8.4 Hz, 1H), 7.21 (t, J = 7.5 Hz, 2H), 7.15-7.12 (m, 3H), 7.06 (dd, J = 8.4 Hz and 2.1 Hz, 2H), 6.90 (d, J = 8.1 Hz, 2H), 6.43-6.37 (m, 1H), 4.32-4.21 (m, 1H), 3.95 (t, J = 6.3 Hz, 2H), 3.18-3.11 (m, 1H), 2.89-2.81 (m, 2H), 2.41-2.27 (m, 10H), 2.09 (s, 3H), 1.83-1.78 (m, 2H) | 10-80 4.08 | *** |
| 1077 | 528.1 (cal.527.2) | $^1$H NMR (DMSO, 300 MHz) δ11.15 (b, 1H), 8.12 (s, 1H), 7.69 (s, 1H), 7.52 (d, J = 2.1 Hz, 1H), 7.37 (t, J = 7.8 Hz, 2H), 7.29 (d, J = 8.7 Hz, 1H), 7.21 (t, J = 7.2 Hz, 2H), 7.14-7.11 (m, 3H), 7.06 (dd, J = 8.4 Hz and 2.1 Hz, 2H), 6.91 (d, J = 8.1 Hz, 2H), 6.43-6.37 (m, 1H), 4.51 (t, J = 6.9 Hz, 2H), 4.28-4.26 (m, 1H), 3.91 (t, J = 6.0 Hz, 2H), 3.22-3.11 (m, 1H), 2.86-2.82 (m, 2H), 2.24-2.22 (m, 2H) | 10-80 5.51 | **** |
| 1078 | 528.1 (cal.527.2) | $^1$H NMR (DMSO, 300 MHz) δ11.19 (b, 1H), 7.74 (s, 2H), 7.52 (d, J = 1.5 Hz, 1H), 7.37 (t, J = 7.8 Hz, 2H), 7.28 (d, J = 8.4 Hz, 1H), 7.21 (t, J = 7.2 Hz, 2H), 7.14-7.11 (m, 3H), 7.05 (dd, J = 8.4 Hz and 1.8 Hz, 2H), 6.90 (d, J = 8.1 Hz, 2H), 6.42-6.37 (m, 1H), 4.55 (t, J = 6.9 Hz, 2H), 4.32-4.27 (m, 1H), 3.92 (t, J = 6.0 Hz, 2H), 3.18-3.15 (m, 1H), 2.91-2.83 (m, 2H), 2.27-2.23 (m, 2H) | 30-90 4.74 | **** |
| 1079 | 510.2 (cal.509.2) | $^1$H NMR (DMSO, 300 MHz) δ11.11 (b, 1H), 7.48 (d, J = 1.8 Hz, 1H), 7.26 (d, J = 8.4 Hz, 1H), 7.08 (J, J = 8.7 Hz, 2H), 7.03 (dd, J = 8.7 Hz and 2.1 Hz, 1H), 6.87 (d, J = 8.7 Hz, 2H), 6.31 (s, 1H), 6.01-5.92 (m, 1H), 5.31-5.12 (m, 2H), 4.58 (s, 2H), 4.21-4.12 (m, 1H), 3.94 (t, J = 6.3 Hz, 2H), 3.52 (t, J = 7.5 Hz, 4H), 3.09-3.00 (m, 1H), 2.75-2.69 (m, 2H), 2.37-2.30 (m, 6H), 1.83-1.78 (m, 2H) | 10-80 4.10 | ***** |

TABLE 2-continued

| Cpd | MS | NMR | RT | EC$_{50}$ |
|---|---|---|---|---|
| 1080 | 492.1 (cal.492.2) | $^1$H NMR (DMSO, 300 MHz) δ11.09 (b, 1H), 8.11 (d, J = 0.6 Hz, 1H), 7.68 (d, J = 0.6 Hz, 1H), 7.48 (d, J = 2.1 Hz, 1H), 7.26 (d, J = 8.4 Hz, 1H), 7.08 (J, J = 8.7 Hz, 2H), 7.03 (dd, J = 8.7 Hz and 1.8 Hz, 1H), 6.87 (d, J = 8.7 Hz, 2H), 6.30 (s, 1H), 5.95-5.90 (m, 1H), 5.30-5.15 (m, 2H), 4.60 (s, 2H), 4.50 (t, J = 6.9 Hz, 2H), 4.18-4.11 (m, 1H), 3.89 (t, J = 6.0 Hz, 2H), 3.08-3.00 (m, 1H), 2.79-2.71 (m, 2H), 2.24-2.23 (m, 2H) | 10-80 5.28 | ***** |
| 1081 | 492.1 (cal.491.2) | $^1$H NMR (DMSO, 300 MHz) δ11.10 (b, 1H), 8.74 (s, 2H), 7.48 (d, J = 1.8 Hz, 1H), 7.26 (d, J = 8.7 Hz, 1H), 7.08 (J, J = 8.7 Hz, 2H), 7.05 (dd, J = 8.7 Hz and 2.1 Hz, 1H), 6.86 (d, J = 8.7 Hz, 2H), 6.30 (s, 1H), 5.98-5.90 (m, 1H), 5.32-5.18 (m, 2H), 4.58 (s, 2H), 4.54 (t, J = 6.9 Hz, 2H), 4.18-4.11 (m, 1H), 3.89 (t, J = 6.0 Hz, 2H), 3.08-2.98 (m, 1H), 2.78-2.72 (m, 2H), 2.26-2.22 (m, 2H) | 10-80 4.39 | ***** |
| 1082 | 510.2 (cal.509.2) | $^1$H NMR (DMSO, 300 MHz) δ11.10 (b, 1H), 7.48 (d, J = 1.8 Hz, 1H), 7.26 (d, J = 8.7 Hz, 1H), 7.05-7.04 (m, 3H), 6.86 (d, J = 8.7 Hz, 2H), 6.31-6.26 (m, 1H), 4.22-4.15 (m, 3H), 3.93 (t, J = 6.6 Hz, 2H), 3.51 (t, J = 4.8 Hz, 6H), 3.28 (s, 3H), 3.04-2.98 (m, 1H), 2.77-2.74 (m, 2H), 2.41-2.36 (m, 6H), 1.83-1.75 (m, 2H) | 10-80 3.73 | **** |
| 1083 | 510.2 (cal.509.2) | $^1$H NMR (DMSO, 300 MHz) δ11.11 (b, 1H), 8.12 (s, 1H), 7.68 (s, 1H), 7.48 (d, J = 2.1 Hz, 1H), 7.26 (d, J = 8.7 Hz, 1H), 7.08-7.01 (m, 3H), 6.86 (d, J = 8.7 Hz, 2H), 6.32-6.25 (m, 1H), 4.50 (t, J = 7.2 Hz, 2H), 4.30-4.06 (m, 3H), 3.89 (t, J = 6.0 Hz, 2H), 3.68-3.50 (m, 5H), 3.03-3.01 (m, 2H), 2.79-2.73 (m, 1H), 2.37-2.24 (m, 2H) | 30-90 4.21 | **** |
| 1084 | 510.2 (cal.509.2) | $^1$H NMR (DMSO, 300 MHz) δ11.11 (b, 1H), 7.74 (s, 2H), 7.52 (s, 1H), 7.26 (d, J = 8.7 Hz, 1H), 7.09-7.01 (m, 3H), 6.85 (d, J = 8.4 Hz, 2H), 6.28-6.24 (m, 1H), 4.54 (t, J = 6.9 Hz, 2H), 4.29-4.09 (m, 4H), 3.90 (t, J = 6.0 Hz, 2H), 3.60-3.53 (m, 2H), 3.24-3.16 (m, 2H), 3.13-3.09 (m, 1H), 3.02-2.94 (m, 1H), 2.76-2.69 (m, 1H), 2.24-2.20 (m, 2H) | 30-90 4.67 | **** |
| 1085 | 516.1 (cal: 515.2) | $^1$H NMR (CDCl$_3$, 300 MHz) δ 7.77 (b, 1H), 7.50 (d, J = 1.5 Hz, 1H), 7.23-7.10 (m, 4H), 6.99 (b, 1H), 6.82 (d, J = 8.4 Hz, 2H), 6.40 (b, 1H), 4.45-4.05 (m, 4H), 3.96-3.87 (m, 4H), 3.70-3.60 (m, 1H), 3.50-3.38 (m, 4H), 3.20-3.08 (m, 1H), 2.96-2.71 (m, 2H), 1.30 (t, J = 6.6 Hz, 3H). | 10-80 5.07 | ***** |
| 1086 | 577.9 | | 3.73 | **** |
| 1087 | 591.9 | | 3.78 | **** |
| 1088 | 605.9 | | 3.87 | **** |
| 1089 | 577.9 | | 3.75 | ** |
| 1090 | 591.9 | | 3.80 | ** |
| 1091 | 605.9 | | 3.85 | ** |
| 1092 | 595.9 | | 2.45 | **** |
| 1093 | 610.0 | | 2.47 | **** |
| 1094 | 624.0 | | 2.48 | **** |
| 1095 | 596.0 | | 2.47 | ** |
| 1096 | 610.0 | | 2.47 | ** |
| 1097 | 624.0 | | 2.50 | *** |
| 1098 | 594.57 | | 2.47 | **** |
| 1099 | 564.52 | | 2.45 | **** |
| 1100 | 484.3 (cal.483.2) | $^1$H NMR (CD3CN, 300 MHz) δ9.08 (b, 1H), 7.51 (d, J = 1.8 Hz, 1H), 7.28 (d, J = 8.7 Hz, 1H), 7.17 (d, J = 8.7 Hz, 2H), 7.09 (dd, J = 8.4 Hz and 1.8 Hz, 1H), 6.86 (d, J = 8.7 Hz, 2H), 6.41 (s, 1H), 4.28-4.21 (m, 1H), 4.00 (t, J = 6.9 Hz, 2H), 3.70 (s, 3H), 3.59 (t, J = 4.8 Hz, 2H), 3.17-3.12 (m, 1H), 2.81-2.75 (m, 2H), 2.43 (t, J = 7.2 Hz, 2H), 2.38-2.32 (m, 4H), 1.90-1.87 (m, 2H) | 10-80 3.77 | **** |
| 1101 | 497.3 (cal.496.2) | $^1$H NMR (CD3CN, 300 MHz) δ9.07 (b, 1H), 7.51 (d, J = 1.5 Hz, 1H), 7.28 (d, J = 8.4 Hz, 1H), 7.17 (d, J = 8.7 Hz, 2H), 7.08 (dd, J = 8.7 Hz and 2.1 Hz, 1H), 6.85 (d, J = 8.4 Hz, 2H), 6.34 (s, 1H), 4.23-4.20 (m, 1H), 3.98 (t, J = 6.3 Hz, 2H), 3.70 (s, 3H), 3.15-3.11 (m, 1H), 2.81-2.76 (m, 2H), 2.44-2.35 (m, 8H), 2.17 (s, 3H), 1.86-1.81 (m, 2H) | 10-80 3.52 | *** |
| 1102 | 512.2 (cal.511.2) | $^1$H NMR (CD$_3$CN, 400 MHz) δ9.11 (s, 1H), 7.51 (d, J = 2.1 Hz, 1H), 7.27 (d, J = 8.7 Hz, 1H), 7.17 (d, J = 8.7 Hz, 2H), 7.08 (dd, J = 8.7 Hz and 2.1 Hz, 1H), 6.86 (dd, J = 8.7 Hz and 2.1 Hz, 1H), 6.36 (s, 1H), 4.95-4.87 (m, 1H), 4.32-4.25 (m, 1H), 4.00 (t, J = 6.0 Hz, 2H), 3.59 (t, J = 4.8 Hz, 3H), 3.18-3.06 (m, 1H), 2.83-2.73 (m, 2H), 2.45-2.35 (m, 6H), 1.90-1.82 (m, 2H), 1.25 (d, J = 6.0 Hz, 6H) | 10-80 4.28 | ***** |
| 1103 | 525.3 (cal.524.3) | $^1$H NMR (DMSO, 300 MHz) δ11.10 (b, 1H), 7.46 (d, J = 1.8 Hz, 1H), 7.25 (d, J = 8.4 Hz, 1H), 7.08-7.00 (m, 3H), 6.86 (d, J = 8.7 Hz, 2H), 6.28-6.22 (m, 1H), 4.84-4.80 (m, 1H), 4.15-4.09 (m, 1H), 3.92 (t, J = 6.3 Hz, 2H), 3.05-2.96 (m, 1H), 2.72-2.69 (m, 2H), 2.38-2.20 (m, 10H), 2.11 (s, 3H), 1.81-1.76 (m, 2H), 1.19 (d, J = 5.4 Hz, 6H) | 30-90 2.41 | **** |
| 1104 | 539.3 (cal.538.3) | $^1$H NMR (CD3CN, 300 MHz) δ9.13 (b, 1H), 7.51 (d, J = 1.8 Hz, 1H), 7.28 (d, J = 8.4 Hz, 1H), 7.16 (d, J = 8.7 Hz, 2H), 7.08 (dd, J = 8.4 Hz and 2.1 Hz, 1H), 6.84 (d, J = 8.4 Hz, 2H), 6.35 (s, 1H), 4.30-4.25 (m, 1H), 3.97 (t, J = 6.3 Hz, 2H), 3.91-3.86 (m, 4H), 3.19-3.08 (m, 1H), 2.80-2.77 (m, 2H), 2.43-2.33 (m, 10H), 2.15 (s, 3H), 1.93-1.82 (m, 2H), 0.93 (d, J = 6.9 Hz, 6H) | 10-80 3.94 | **** |
| 1105 | 512.2 (cal.511.2) | $^1$H NMR (CD3CN, 300 MHz) δ9.10 (b, 1H), 7.51 (s 1H), 7.28 (d, J = 8.7 Hz, 1H), 7.18 (d, J = 8.7 Hz, 2H), 7.08 (dd, J = 8.7 Hz and 1.8 Hz, 1H), 6.86 (d, J = 8.4 Hz, 2H), 6.38 (s, 1H), 4.30-4.24 (m, 1H), | 10-80 4.32 | ***** |

TABLE 2-continued

| Cpd | MS | NMR | RT | EC$_{50}$ |
|---|---|---|---|---|
| | | 4.07-3.98 (m, 4H), 3.59 (t, J = 4.8 Hz, 4H), 3.19-3.09 (m, 1H), 2.80-2.77 (m, 2H), 2.46-2.38 (m, 6H), 1.88-1.65 (m, 2H), 0.94 (t, J = 4.5 Hz, 3H) | | |
| 1106 | 560.3 (cal.559.2) | $^1$H NMR (DMSO, 300 MHz) δ11.10 (b, 1H), 7.47 (d, J = 2.1 Hz, 1H), 7.35-7.31 (m, 5H), 7.25 (d, J = 8.4 Hz, 1H), 7.06-7.01 (m, 3H), 6.84 (d, J = 7.2 Hz, 2H), 6.32 (s, 1H), 5.14-5.07 (m, 2H), 4.21-4.12 (m, 1H), 3.93 (t, J = 6.0 Hz, 2H), 3.51 (t, J = 4.8 Hz, 4H), 3.08-3.00 (m, 1H), 2.74-2.68 (m, 2H), 2.49-2.35 (m, 6H), 2.04-1.82 (m, 2H) | 10-80 4.62 | ***** |
| 1107 | 542.2 (cal.541.2) | $^1$H NMR (DMSO, 300 MHz) δ11.09 (b, 1H), 8.11 (d, J = 0.6 Hz, 1H), 7.68 (d, J = 0.6 Hz, 1H), 7.47 (d, J = 1.8 Hz, 1H), 7.35-7.29 (m, 5H), 7.25 (d, J = 8.7 Hz, 1H), 7.08-7.01 (m, 3H), 6.84 (d, J = 8.1 Hz, 2H), 6.31 (s, 1H), 5.19-5.08 (m, 2H), 4.50 (t, J = 6.9 Hz, 2H), 4.19-4.16 (m, 1H), 3.89 (t, J = 6.0 Hz, 2H), 3.07-3.00 (m, 1H), 2.79-2.71 (m, 2H), 2.26-2.22 (m, 2H) | 10-80 5.82 | ***** |
| 1108 | 589.4 (cal.588.3) | $^1$H NMR (CD3CN, 300 MHz) δ9.14 (b, 1H), 7.55 (d, J = 1.8 Hz, 1H), 7.30 (d, J = 8.7 Hz, 1H), 7.24-7.20 (m, 1H), 7.11 (dd, J = 8.7 Hz and 2.1 Hz, 1H), 7.04-7.00 (m, 2H), 6.93-6.87 (m, 3H), 6.47 (s, 1H), 4.38 4.36 (m, 1H), 4.00 (t, J = 6.3 Hz, 2H), 3.78 (s, 3H), 3.27-3.24 (m, 1H), 2.89-2.84 (m, 2H), 2.42 (t, J = 7.2 Hz, 2H), 2.37-2.22 (m, 8H), 2.16 (s, 3H), 1.93-1.87 (m, 2H) | 10-80 3.97 | **** |
| 1109 | 459.1 (cal.458.2) | $^1$H NMR (DMSO, 300 MHz) δ11.09 (s, 1H), 7.48 (d, J = 2.1 Hz, 1H), 7.25 (d, J = 8.4 Hz, 1H), 7.07-7.01 (m, 3H), 6.86 (d, J = 8.7 Hz, 2H), 6.32-6.28 (m, 1H), 4.25-4.13 (m, 1H), 3.96 (t, J = 6.6 Hz, 2H), 3.51-3.47 (m, 4H), 3.30 (s, 3H), 3.05-2.96 (m, 1H), 2.73-2.68 (m, 2H), 1.81-1.77 (m, 2H) | 10-80 4.55 | ***** |
| 1110 | M − 1:493.1 (cal.494.1) | $^1$H NMR (DMSO, 300 MHz) δ11.16 (b, 1H), 7.52 (s, 1H), 7.27 (d, J = 8.4 Hz, 1H), 7.23-7.17 (m, 6H), 7.04 (dd, J = 8.4 Hz and 2.1 Hz, 1H), 6.90 (d, J = 7.8 Hz, 2H), 6.43-6.35 (m, 1H), 4.30-4.28 (m, 1H), 3.98 (t, J = 6.3 Hz, 2H), 3.51 (t, J = 6.3 Hz, 2H), 3.17-3.12 (m, 1H), 2.83-2.69 (m, 2H), 1.84-1.76 (m, 2H) | 10-80 5.48 | ***** |
| 1111 | 509.1 (cal.510.1) | $^1$H NMR (CD$_4$CN 300 MHz) δ 9.12 (s, 1H), 7.56 (d, J = 1.8 Hz, 1H), 7.38 (dd, J = 6.6 Hz and 2.1 Hz 2H), 7.31-7.24 (m, 3H), 7.16-7.09 (m, 3H), 6.91 (d, J = 8.7 Hz, 2H), 6.47 (b, 1H), 4.38 (b, 1H), 4.05 (t, J = 6.3 Hz, 2H), 3.65 (t, J = 6.3 Hz, 2H), 3.30 (b, 1H), 2.90 (b, 2H), 1.86 (b, 2H) | 30-90 4.84 | ***** |
| 1112 | 511.3 (cal.510.2) | $^1$H NMR (CD3CN, 300 MHz) δ9.14 (b, 1H), 7.52 (d, J = 2.1 Hz, 1H), 7.30 (d, J = 8.7 Hz, 1H), 7.26 (d, J = 8.1 Hz, 1H), 7.09 (dd, J = 8.7 Hz and 2.1 Hz, 1H), 6.87-6.84 (m, 2H), 6.78 (d, J = 2.1 Hz, 1H), 6.37 (s, 1H), 4.31-4.25 (m, 1H), 4.19-4.11 (m, 2H), 3.98-3.93 (m, 2H), 3.17-3.11 (m, 1H), 2.82-2.78 (m, 2H), 2.49-2.39 (m, 8H), 2.18-2.15 (m, 5H), 1.89-1.81 (m, 2H), 1.26 (t, J = 7.2 Hz, 3H) | 10-80 3.54 | * |
| 1113 | 577.4 (cal.576.2) | $^1$H NMR (CDCl3, 300 MHz) δ8.26-8.02 (m, 1H), 7.53 (s, 1H), 7.25-7.05 (m, 5H), 6.97-6.86 (m, 4H), 6.47 (s, 1H), 4.56-4.48 (m, 1H), 3.93-3.91 (m, 2H), 3.40-3.30 (m, 1H), 3.07-2.90 (m, 2H), 2.50-2.47 (m, 8H), 2.30-2.18 (m, 5H), 1.92-1.90 (m, 2H) | 10-80 34.06 | ** |
| 1114 | 498.3 (cal.497.2) | $^1$H NMR (CD3CN, 300 MHz) δ9.12 (b, 1H), 7.52 (d, J = 2.1 Hz, 1H), 7.29 (d, J = 8.7 Hz, 1H), 7.23 (d, J = 7.2 Hz, 1H), 7.09 (dd, J = 8.7 Hz and 2.1 Hz, 1H), 6.88-6.83 (m, 2H), 6.79 (d, J = 1.8 Hz, 1H), 6.39 (s, 1H), 4.32-4.29 (m, 1H), 4.18-4.13 (m, 2H), 3.99-3.95 (m, 2H), 3.58 (t, J = 4.8 Hz, 2H), 3.20-3.10 (m, 1H), 2.80-2.78 (m, 2H), 2.43-2.33 (m, 6H), 1.90-1.83 (m, 2H), 1.26 (t, J = 7.2 Hz, 3H) | 10-80 4.10 | **** |
| 1115 | 564.3 (cal.563.2) | $^1$H NMR (CD3CN, 300 MHz) δ9.17 (b, 1H), 7.56 (d, J = 1.8 Hz, 1H), 7.33-7.26 (m, 2H), 7.13-7.10 (m, 5H), 6.91-6.84 (m, 3H), 6.47 (s, 1H), 4.42-4.39 (m, 1H), 4.00-3.95 (m, 2H), 3.57 (t, J = 4.8 Hz, 2H), 3.37-3.27 (m, 1H), 2.90-2.85 (m, 2H), 2.42-2.34 (m, 6H), 1.88-1.80 (m, 2H) | 10-80 4.61 | **** |
| 1116 | 514.3 (cal.513.2) | $^1$H NMR (CD3CN, 300 MHz) δ9.14 (b, 1H), 7.52 (d, J = 2.1 Hz, 1H), 7.29 (d, J = 8.7 Hz, 1H), 7.23 (d, J = 8.1 Hz, 1H), 7.09 (dd, J = 8.7 Hz and 2.1 Hz, 1H), 6.86-6.83 (m, 2H), 6.78 (d, J = 2.1 Hz, 1H), 6.38 (s, 1H), 4.33-4.28 (m, 1H), 4.20-4.14 (m, 2H), 3.95-3.92 (m, 2H), 3.20-3.11 (m, 1H), 2.80-2.78 (m, 2H), 2.63-2.57 (m, 2H), 2.43 (t, J = 7.2 Hz, 2H), 1.86-1.81 (m, 2H), 1.26 (t, J = 7.2 Hz, 3H) | 10-80 4.25 | **** |
| 1117 | 580.3 (cal.579.2) | $^1$H NMR (CD3CN, 300 MHz) δ9.20 (b, 1H), 7.56 (d, J = 2.4 Hz, 1H), 7.33-7.29 (m, 2H), 7.14-7.11 (m, 5H), 6.90-6.84 (m, 3H), 6.47 (s, 1H), 4.43-4.40 (m, 1H), 3.99-3.94 (m, 2H), 3.38-3.27 (m, 1H), 3.02-2.87 (m, 2H), 2.65-2.60 (m, 8H), 2.47 (t, J = 7.2 Hz, 2H), 1.88-1.81 (m, 2H) | 10-80 4.79 | **** |
| 1118 | 544.3 (cal.543.2) | $^1$H NMR (CD3CN, 300 MHz) δ9.21 (b, 1H), 7.51 (s, 1H), 7.29 (d, J = 8.7 Hz, 1H), 7.08 (d, J = 7.5 Hz, 1H), 7.08 (dd, J = 8.7 Hz and 1.8 Hz, 1H), 6.85 (d, J = 7.8 Hz, 2H), 6.78 (s, 1H), 6.38 (s, 1H), 4.32-4.27 (m, 1H), 4.15-4.13 (m, 2H), 4.02-3.99 (m, 2H), 3.40 (t, J = 6.0 Hz, 4H), 3.21-3.11 (m, 5H), 2.82-2.63 (m, 7H), 1.83-1.70 (m, 4H), 1.25 (t, J = 6.9 Hz, 3H) | 10-80 4.34 | ** |
| 1119 | 610.3 (cal.609.2.2) | $^1$H NMR (CD3CN, 300 MHz) δ9.19 (b, 1H), 7.56 (d, J = 1.8 Hz, 1H), 7.33-7.29 (m, 2H), 7.14-7.10 (m, 5H), 6.91-6.85 (m, 3H), 6.48 (s, 1H), 4.42-4.39 (m, 1H), 3.96 (t, J = 6.3 Hz, 2H), 3.33 (t, J = 6.0 Hz, 4H), 3.30-3.28 (m, 2H), 3.18 (s, 6H), 2.99-2.88 (m, 2H), 2.60 (t, J = 6.0 Hz, 6H), 1.83-1.79 (m, 2H) | 10-80 4.85 | *** |
| 1120 | 500.3 (cal.499.2) | $^1$H NMR (CD3CN, 300 MHz) δ9.13 (b, 1H), 7.52 (d, J = 2.1 Hz, 1H), 7.29 (d, J = 8.7 Hz, 1H), 7.23 (d, J = 8.1 Hz, 1H), 7.09 (dd, J = 8.7 Hz and 2.1 Hz, 1H), 6.87-6.84 (m, 2H), 6.78 (s, 1H), 6.39 (s, 1H), 4.32-4.28 (m, 1H), 4.18-4.12 (m, 2H), 3.97-3.93 (m, 2H), 3.37 (t, J = 6.0 Hz, 2H), 3.20 (s, 3H), 3.18-3.10 (m, 1H), 2.82-2.74 (m, 2H), 2.50-2.44 (m, 4H), 2.18 (s, 3H), 1.87-1.78 (m, 2H), 1.26 (t, J = 6.9 Hz, 3H) | 10-80 4.19 | ** |

TABLE 2-continued

| Cpd | MS | NMR | RT | EC$_{50}$ |
|---|---|---|---|---|
| 1121 | 566.3 (cal.465.2) | $^1$H NMR (CD3CN, 300 MHz) δ9.21 (b, 1H), 7.56 (d, J = 1.5 Hz, 1H), 7.33-7.26 (m, 2H), 7.13-7.11 (m, 5H), 6.90-6.85 (m, 3H), 6.48 (s, 1H), 4.47-4.45 (m, 1H), 4.00-3.97 (m, 2H), 3.41-3.37 (m, 2H), 3.20 (s, 3H), 2.91-2.90 (m, 1H), 2.53-2.51 (m, 4H), 2.22 (s, 3H), 1.85-1.79 (m, 4H) | 10-80 4.74 | * |
| 1122 | 479.2 (cal.478.2) | $^1$H NMR (CD3CN, 300 MHz) δ9.29 (b, 1H), 7.52 (s, 1H), 7.38 (s, 1H), 7.32-7.22 (m, 2H), 7.09 (dd, J = 8.7 Hz and 2.1 Hz, 1H), 7.00 (s, 1H), 6.88-6.85 (m, 3H), 6.77 (s, 1H), 6.34 (s, 1H), 4.32-4.28 (m, 1H), 4.15-4.09 (m, 4H), 3.89-3.85 (m, 2H), 3.19-3.12 (m, 1H), 2.81-2.79 (m, 2H), 1.72-1.69 (m, 2H), 1.25 (t, J = 7.2 Hz, 3H) | 10-80 4.18 | * |
| 1123 | 545.2 (cal.544.2) | $^1$H NMR (CD3CN, 300 MHz) δ 9.34 (b, 1H), 7.55 (d, J = 2.1 Hz, 1H), 7.50 (s, 1H), 7.32 (d, J = 8.7 Hz), 7.26 (d, J = 7.5 Hz, 1H), 7.12-7.09 (m, 5H), 7.02 (s, 1H), 6.91-6.84 (m, 4H), 6.45 (s, 1H), 4.42-4.40 (m, 1H), 4.13 (t, J = 6.6 Hz, 2H), 3.88-3.82 (m, 2H), 3.36-3.30 (m, 1H), 2.92-2.85 (m, 2H), 1.86-1.84 (m, 2H) | 10-80 4.65 | *** |
| 1124 | 480.1 (cal.479.2) | $^1$H NMR (CD3CN, 300 MHz) δ 9.13 (b, 1H), 7.73 (s, 1H), 7.59 (s, 1H), 7.52 (d, J = 1.8 Hz, 1H), 7.30 (d, J = 8.7 Hz, 1H), 7.24 (d, J = 8.7 Hz, 1H), 7.10 (dd, J = 8.7 Hz and 2.1 Hz, 1H), 6.88-6.84 (m, 3H), 6.77 (d, J = 1.8 Hz, 1H), 6.37 (s, 1H), 4.53 (t, J = 6.9 Hz, 2H), 4.33-4.27 (m, 1H), 4.16-4.13 (m, 2H), 3.92-3.90 (m, 2H), 3.19-3.11 (m, 1H), 2.81-2.78 (m, 2H), 2.30-2.26 (m, 2H), 1.25 (t, J = 7.2 Hz, 3H) | 10-80 5.30 | ** |
| 1125 | 546.1 (cal.545.2) | $^1$H NMR (CD3CN, 300 MHz) δ 9.22 (b, 1H), 7.73 (s, 1H), 7.59 (s, 1H), 7.56 (d, J = 2.1 Hz, 1H), 7.34-7.27 (m, 2H), 7.14-7.10 (m, 5H), 6.89-6.83 (m, 3H), 6.48 (s, 1H), 4.53 (t, J = 6.9 Hz, 2H), 4.43-4.40 (m, 1H), 3.95-3.90 (m, 2H), 3.37-3.29 (m, 1H), 2.94-2.89 (m, 2H), 2.30-2.24 (m, 2H) | 10-80 5.84 | ** |
| 1126 | 530.8 | $^1$H NMR (CDCl3, 300 MHz), δ 7.89 (d, 1H), 7.54 (s, 1H), 7.33 (d, 2H), 7.34 (d, 2H), 7.27 (d, 2H), 7.18 (m, 2H), 7.05 (d, 2H), 6.90 (d, 2H), 6.47 (s, 1H), 4.44 (d, 1H), 4.10 (t, 2H), 3.74 (t, 2H), 3.00-2.83 (m, 2H), 2.23 (m, 2H) | 4.3 | ** |
| 1127 | 562.24 | | 4.20 | *** |
| 1128 | 530.8 | | 4.32 | ***** |
| 1129 | 562.26 | $^1$H NMR (CDCl3, 300 MHz), δ 7.89 (d, 1H), 7.59 (s, 1H), 7.53 (s, 1H), 7.34 (d, 2H), 7.26 (d, 2H), 7.20 (m, 1H), 7.06 (d, 2H), 6.82 (d, 2H), 6.46 (s, 1H), 4.66 (t, 2H), 4.36 (dd, 1H), 3.97 (t, 2H), 3.32 (m, 1H), 3.00 (m, 1H), 2.85 (m, 2H), 2.43 (m, 2H) | 4.13 | ***** |
| 1130 | C$_{32}$H$_{34}$ClN$_3$O$_5$, (576.3) | $^1$H NMR (DMSO-d6, 400 MHz), 11.18 (brs, 1H, Ar—NH); 7.57 (s, 1H, Ar—H); 7.34 (d, 1H, Ar—H); 7.25 (s, 1H, Ar—H); 7.18 (d, 2H, 2Ar—H); 7.11-7.08 (dd, 1H, Ar—H); 6.96 (d, 2H, 2Ar—H); 6.65 (brs, 1H, Ar—H); 6.35 (brs, 1H, CH); 4.35 (s, 1H, CH); 3.98 (t, 2H, CH2); 3.70 (s, 3H, —OCH3); 3.56 (t, 4H, 2CH2); 2.90 (brs, 2H, CH2); 3.39 (t, 6H, 3CH2); 1.86 (m, 2H, CH2) | 4.668 | **** |
| 1131 | C$_{33}$H$_{36}$ClN$_3$O$_6$, (606.0) | | 4.646 | **** |
| 1132 | C$_{33}$H$_{36}$ClN$_3$O$_5$, (590.5) | $^1$H NMR (CD3OD; 400 MHz); 7.51 (d, 1H, Ar—H); 7.27 (d, 1H, Ar—H); 7.22 (d, 2H, 2Ar—H); 7.10-7.07 (dd, 1H, Ar—H); 7.02-6.99 (dd, 3H, 3Ar—H); 6.90 (brs, 1H, Ar—H); 6.75 (brs, 1H, Ar—H); 6.5 (brs, 1H, CH); 4.40 (brs, 1H, CH); 4.07 (t, 2H, CH2); 3.74 (brs, 7H, 2CH2 and —OCH3); 3.4 (s, 1H, CH); 3.1 (s, 1H, CH); 2.8 (s, 1H, CH); 2.73-2.65 (m, 5H, 2CH2 and CH); 2.35 (s, 3H, CH3); 2.27 (t, 1H, CH); 2.04 (d, 2H, CH2); | 4.826 | **** |
| 1133 | C$_{32}$H$_{33}$ClFN$_3$O$_5$, (594.0) | | 4.662 | ***** |
| 1134 | 558.1 | $^1$H NMR (300 MHz, DMSO-d$_6$) δ ppm 2.18-2.36 (m, 2 H) 2.86 (br. s., 2 H) 3.09-3.26 (m, 1 H) 3.73 (s, 3 H) 3.94 (t, J = 6.04 Hz, 2 H) 4.30 (br. s., 1 H) 4.57 (t, J = 6.84 Hz, 2 H) 6.38 (br. s., 1 H) 6.91 (d, J = 8.90 Hz, 4 H) 7.01-7.10 (m, 3 H) 7.15 (br. s., 2 H) 7.30 (d, J = 8.58 Hz, 1 H) 7.54 (d, J = 2.23 Hz, 1 H) 7.84 (br. s., 2 H) 11.15 (br. s., 1 H) | 3.68 | |
| 1135 | C$_{30}$H$_{28}$ClN$_5$O$_2$, (526.2) | | 4.701 | **** |
| 1136 | C$_{31}$H$_{31}$Cl$_2$N$_3$O$_3$, (564.0) | | 4.747 | *** |
| 1137 | C$_{27}$H$_{25}$Cl$_2$N$_5$O$_2$, (546.0) | | 4.857 | **** |
| 1138 | C$_{29}$H$_{25}$ClFN$_5$O$_2$, (530.0) | | 4.471 | **** |
| 1139 | C$_{29}$H$_{26}$ClN$_5$O$_2$, (512.0) | | 4.433 | **** |
| 1140 | C$_{31}$H$_{32}$ClN$_3$O$_3$, (530.0) | | 4.29 | *** |
| 1141 | C$_{28}$H$_{32}$ClN$_3$O$_3$, (494.0) | | 3.900 | *** |
| 1142 | C$_{26}$H$_{26}$ClN$_5$O$_2$, (476) | $^1$H NMR (CD3OD, 400 MHz), 8.4 (s, 1H, Ar—H); 7.9 (s, 1H, Ar—H); 7.4 (d, 1H, Ar—H); 7.35 (d, 1H, Ar—H); 7.25 (d, 1H, Ar—H); 7.07 (d, 1H, Ar—H); 6.87-6.85 (t, 3H, 2Ar—H and CH); 4.45 (m, 2H, CH2); 3.9 (t, 2H, CH2); 3.32 (brs, 1H, CH); 3.3 (brs, 2H, CH2); 2.33 (t, 2H, CH2); 2.32 (brs, H, CH); 1.1 (brs, H, CH); 0.89 (d, 3H, CH3); | 3.888 | **** |
| 1143 | C$_{26}$H$_{28}$ClN$_5$O$_4$, (510) | | 4.300 | **** |
| 1144 | C$_{30}$H$_{28}$ClN$_5$O$_4$, (558.5) | | 4.711 | *** |

TABLE 2-continued

| Cpd | MS | NMR | RT | EC$_{50}$ |
|---|---|---|---|---|
| 1145 | C$_{30}$H$_{28}$ClN$_5$O$_4$, (558.5) | | 5.05 | **** |
| 1146 | C$_{31}$H$_{30}$ClN$_5$O$_5$, (588.5) | | 5.006 | **** |
| 1147 | C$_{30}$H$_{27}$ClFN$_5$O$_4$, (576) | | 4.734 | **** |
| 1148 | C$_{30}$H$_{27}$ClFN$_5$O$_4$, (576) | | 5.063 | **** |
| 149 | C$_{28}$H$_{28}$ClN$_5$O$_4$, (510.5) | | 4.787 | **** |
| 1150 | C$_{30}$H$_{28}$ClN$_5$O$_4$, (558.5) | | 4.664 | **** |
| 1151 | C$_{31}$H$_{30}$ClN$_5$O$_5$, (588.5) | | 4.616 | *** |
| 1152 | C$_{31}$H$_{30}$ClN$_5$O$_4$, (572.5) | | 4.891 | **** |
| 1153 | C$_{32}$H$_{34}$ClN$_3$O$_4$, (560.5) | | 4.232 | *** |
| 1154 | C$_{31}$H$_{31}$ClFN$_3$O$_3$, (548) | | 4.397 | *** |
| 1155 | 546.3 (cal.545.2) | $^1$H NMR (CD3CN, 300 MHz) δ9.28 (b, 1H), 8.10 (s, 1H), 7.81 (s, 1H), 7.55 (d, J = 1.8 Hz, 1H), 7.32-7.25 (m, 2H), 7.12-7.10 (m, 5H), 6.87-6.84 (m, 3H), 6.46 (s, 1H), 4.42-4.38 (m, 1H), 4.30 (t, J = 6.9 Hz, 2H), 3.93-3.26 (m, 2H), 3.31-3.26 (m, 1H), 2.88-2.76 (m, 2H), 2.27-2.23 (m, 2H) | 10-80 5.54 | *** |
| 1156 | 453.12 | | 3.55 | **** |
| 1157 | 453.17 | | 3.27 | ** |
| 1158 | 453.14 | | 3.17 | * |
| 1159 | 493 | $^1$H NMR (300 MHz, (CD$_3$)$_2$CO, slight broadening due to rotomers) δ 1.27 (t, J = 6.9 Hz, 3H), 2.90-3.10 (m, 2H), 3.28-3.42 (m, 2H), 4.43 (bm, 1H), 4.52-4.60 (m, 2H), 5.20-5.28 (m, 1H), 5.34-5.45 (m, 1H), 6.00-6.13 (m, 1H), 6.52 (bm, 1H), 6.90-7.00 (bd, J = 8.8 Hz, 2H), 7.08-7.14 (m,, 1H), 7.20-7.44 (m, 7H), 7.56 (m$_c$, 1H), 10.22 (s, 1H). | 4.22 | ***** |
| 1160 | 453 | $^1$H NMR (300 MHz, (CD$_3$)$_2$CO, slight broadening due to rotomers) δ 2.90-3.00 (m, 1H), 3.30-3.40 (m, 2H), 3.28-3.42 (m, 2H), 4.42 (bm, 1H), 6.50 (bm, 1H), 6.90 (d, J = 8.4 Hz, 2H), 7.09-7.24 (m, 5H), 7.26-7.41 (m, 3H), 7.56 (d$_c$, J = 2.4 Hz, 1H), 8.48 (s, 1H), 10.20 (s, 1H). | 3.73 | ***** |
| 1161 | 492 | | 3.65 | ***** |
| 1162 | 579.17 (ES−) | | 4.28 | ***** |
| 1163 | 497.23 (ES−) | | 3.93 | ***** |
| 1164 | 513.28 | | 4.12 | ***** |
| 1165 | 527.27 | | 4.28 | ***** |
| 1166 | 523.09 | | 3.88 | ***** |
| 1167 | 541.33 | | 4.43 | ***** |
| 1168 | 547.27 | | 4.18 | ***** |
| 1169 | 565.24 | | 4.17 | ***** |
| 1170 | 561.28 | | 4.37 | ***** |
| 1171 | 577.28 | | 4.13 | ***** |
| 1172 | 539.20 (ES−) | | 3.58 | ***** |
| 1173 | 459.18 | | 3.10 | ***** |
| 1174 | 473.18 | | 3.28 | **** |
| 1175 | 487.24 | | 3.45 | **** |
| 1176 | 500.21 | | 3.20 | ***** |
| 1177 | 501.23 | | 3.58 | ***** |
| 1178 | 507.19 | | 3.37 | ***** |
| 1179 | 525.25 | | 3.38 | ***** |
| 1180 | 521.23 | | 3.52 | ***** |
| 1181 | 537.20 | | 3.35 | ***** |
| 1182 | 542.27 | | 3.70 | ***** |
| 1183 | 556.26 | | 2.45 | ***** |
| 1184 | 600.38 | | 2.43 | ***** |
| 1185 | 508.26 | | 3.77 | ***** |
| 1186 | 508.26 | | 4.03 | ***** |
| 1187 | 508.32 | | 3.42 | ***** |
| 1188 | 508.26 | | 3.42 | ***** |
| 1189 | 475.2 | $^1$H NMR (CDCl3, 300 MHz), δ 7.85 (br, 1H), 7.50 (d, 1H), 7.26-7.10 (m, 4H), 6.82 (d, 2H), 6.39 (br, 1H), 4.25 (br, 1H), 4.09 (t, 2H), 3.73 (t, 2H), 3.09 (m, 1H), 2.85 (m, 2H), 2.22 (m, 2H), 1.50 (s, 9H) | 4.23 | ***** |
| 1190 | C$_{32}$H$_{34}$ClN$_3$O$_3$, (544.1) | | 4.562 | *** |
| 1191 | C$_{30}$H$_{28}$ClN$_5$O$_3$, (542.5) | | 4.385 | *** |
| 1192 | C$_{26}$H$_{28}$ClN$_3$O$_3$, (478) | | 4.248 | **** |
| 1193 | | | 4.082 | *** |
| 1194 | | | 5.237 | ***** |
| 1195 | | | 5.192 | **** |
| 1196 | | | 5.373 | **** |
| 1197 | | | 5.156 | **** |

TABLE 2-continued

| Cpd | MS | NMR | RT | EC$_{50}$ |
|---|---|---|---|---|
| 1198 | | | 4.952 | **** |
| 1199 | | | 5.407 | **** |
| 1200 | | | 3.63 | ***** |
| 1201 | | | 3.55 | ***** |
| 1202 | | | 3.95 | ***** |
| 1203 | | $^1$H NMR δ 7.98 (s, 1 H), 7.53 (s, 1 H), 7.33 (d, J = 8.7 Hz, 2 H), 7.25 (d, J = 9.3 Hz, 2 H), 7.15 (s, 2 H), 7.05 (d, J = 9.0 Hz, 2 H), 6.83 (d, J = 7.2 Hz, 2 H). 6.46 (s 1 H) 4.45 (dd, J = 13.5, 4.2 Hz, 1 H), 4.28 (m, J = 6.3 Hz, 1 H), 4.06 (m, 3 H), 3.63 (dd, J = 9.0, 7.2 Hz, 1 H), 3.32 (m, 1 H), 3.00 (m, 1 H), 2.85 (dd, J = 15.3, 3.3 Hz, 1 H), 2.03 (q, J = 5.1 Hz, 2 H), 1.41 (s, 3 H), 1.35 (s, 3 H) | 4.40 | ***** |
| 1204 | | | 3.13 | |
| 1205 | 539.29 (ES−) | $^1$H-NMR (300 MHz, CDCl$_3$): 8.20 (s, 1H), 7.52 (s, 1H), 7.33 (d, J = 9.0 Hz, 2H), 7.21 (d, J = 7.8 Hz, 2 H), 1.72 (S, 2 H), 7.05 (d, J = 8.7 Hz, 2 H), 6.82 (d, J = 7.2 Hz, 2 H), 6.43 (s, 1 H), 4.44 (dd, J = 14.1, 3.9 Hz, 1 H), 4.10 (m, 2 H), 3.97 (m, 1 H), 3.69 (d, J = 9.6, 1 H), 3.51 (dd, J = 11.1, 7.2 Hz, 1 H), 3.30 (m, 1 H), 2.99 (m, 1 H), 2.84 (dd, J = 15.6, 3.6 Hz, 1 H), 2.16 (s, 1 H), 1.90 (q, J = 5.7 Hz, 2 H) | 3.58 | ***** |
| 1206 | 499.28 | | 3.97 | ***** |
| 1207 | 581.24 | | 4.35 | ***** |
| 1208 | 459.18 | | 3.12 | **** |
| 1209 | 539.26 (ES−) | | 3.67 | ***** |
| 1210 | 428 | $^1$H NMR (300 MHz, (CD$_3$)$_2$CO-d$^6$) δ 1.27 (t, J = 6.4 Hz, 3H), 2.78-2.86 (m, 2H), 3.11-3.17 (m, 1H), 4.17 (q, J = 6.9 Hz, 1H), 4.30 (bs, 1H), 4.44 (s, 2H), 6.45 (bs, 1H), 6.71 (bs, 1H), 6.96 (dm, J = 8.7 Hz, 2H), 7.09 (dd, J = 2.4 Hz, 1H), 7.18 (m, 1H), 7.24 (d, J = 8.7 Hz, 2H), 7.35 (d, J = 8.4 Hz, 1H), 7.52 (d, J = 2.1 Hz, 1H), 10.19 (bs, 1H). | 3.12 | **** |
| 1211 | 446 | | 2.98 | **** |
| 1212 | 452 | | 3.20 | **** |
| 1213 | 510 | | 3.45 | *** |
| 1214 | 554, 556 | | 3.60 | **** |
| 1215 | 494 | | 3.37 | **** |
| 1216 | 506 | | 3.37 | **** |
| 1217 | 411 | $^1$H NMR (300 MHz, (CD$_3$)$_2$CO) δ 1.27 (t, J = 6.9 Hz, 3H), 2.82-2.85 (m, 2H), 3.15 (dt, J = 14, 7.8 Hz, 2H), 4.16 (q, J = 6.9 Hz, 2H), 4.23-4.40 (m, 1H), 4.55-4.57 (m, 2H), 5.21-5.26 (m, 1H), 5.36-5.43 (m, 1H), 5.99-6.12 (m, 1H), 6.44 (bm, 1H), 6.91 (d, J = 8.8 Hz, 2H), 7.09 (dd, J = 8.4, 2.4 Hz, 1H), 7.19 (d, J = 8.8 Hz, 2H), 7.34 (d, J = 8.4 Hz, 1H), 7.52 (d, J = 1.9 Hz, 1H), 10.16 (s, 1H). | 3.93 | ***** |
| 1218 | 371 | $^1$H NMR (300 MHz, (CD$_3$)$_2$CO) δ 1.27 (t, J = 6.9 Hz, 3H), 2.81-2.87 (m, 2H), 3.11-3.21 (m, 2H), 4.16 (q, J = 6.9 Hz, 2H), 4.20-4.40 (m, 1H), 6.41 (bm, 1H), 6.78 (dm, J = 8.8 Hz, 2H), 7.07-7.12 (m, 3H), 7.34 (d, J = 8.7 Hz, 2H), 7.52 (d, J = 1.9 Hz, 1H), 8.41 (s, 1H), 10.13 (s, 1H). | 3.32 | **** |
| 1219 | 399 | $^1$H NMR (300 MHz, (CD$_3$)$_2$CO) δ 1.42 (s, 9H), 2.77-2.85 (m, 2H), 3.06-3.156 (m, 1H), 4.25 (bm, 1H), 6.38 (bm, 1H), 6.79 (d, J = 8.8 Hz, 2H), 7.06-7.10 (m, 1H), 7.34 (d, J = 8.4 Hz, 1H), 7.51 (d, J = 1.9 Hz, 1H), 8.40 (s, 1H), 10.11 (s, 1H). | 3.65 | *** |
| 1220 | 383 | $^1$H NMR (300 MHz, DMSO-d$_6$) δ 1.50-1.62 (m, 2H), 1.92-1.98 (m, 2H), 2.93-3.12 (m, 2H), 3.32-3.51 (m, 4H), 3.83 (dt, J = 11.7, 4.2 Hz, 2H), 4.61 (septet, 1H), 5.86 (s, 1H), 7.04-7.11 (m, 3H), 7.26-7.30 (m, 3H), 7.59 (d, J = 1.8 Hz, 1H), 9.50 (bs, 1H), 10.17 (bs, 1H,), 11.07 (s, 1H). | 1.93 | *** |
| 1221 | 3.13 | $^1$H NMR (300 MHz, DMSO-d$_6$) ppm 1.22 (br. s., 3 H) 2.65-2.84 (m, 2 H) 2.93-3.10 (m, 1 H) 3.40 (t, J = 5.53 Hz, 2 H) 3.68-3.86 (m, 2 H) 3.94 (dd, J = 9.39, 3.69 Hz, 1 H) 4.02-4.26 (m, 3 H) 4.64 (t, J = 5.53 Hz, 1 H) 4.92 (d, J = 4.70 Hz, 1 H) 6.30 (br. s., 1 H) 6.90 (d, J = 8.72 Hz, 2 H) 7.00-7.17 (m, 3 H) 7.28 (d, J = 8.72 Hz, 1 H) 7.49 (d, J = 1.68 Hz, 1 H) 11.10 (br. S., 1 H) | 445.2 | ***** |
| 1222 | 3.13 | $^1$H NMR (300 MHz, DMSO-d$_6$) ppm 1.22 (d, J = 2.68 Hz, 3 H) 2.62-2.85 (m, 2 H) 2.89-3.10 (m, 1 H) 3.40 (t, J = 5.53 Hz, 2 H) 3.67-3.86 (m, 2 H) 3.88-4.00 (m, 1 H) 4.01-4.28 (m, 3 H) 4.64 (t, J = 5.53 Hz, 1 H) 4.92 (d, J = 5.03 Hz, 1 H) 6.31 (br. s., 1 H) 6.90 (d, J = 8.72 Hz, 2 H) 7.01-7.16 (m, 3 H) 7.28 (d, J = 8.38 Hz, 1 H) 7.49 (d, J = 1.68 Hz, 1 H) 11.10 (br. s., 1 H) | 445.2 | ***** |
| 1223 | 527.2 | $^1$H NMR (300 MHz, DMSO-d$_6$) ppm 2.87 (br. s., 2 H) 3.10-3.26 (m, 1 H) 3.41 (t, J = 5.53 Hz, 2 H) 3.68-3.89 (m, 2 H) 3.91-4.03 (m, 1 H) 4.17-4.40 (m, 1 H) 4.65 (t, J = 5.70 Hz, 1 H) 4.93 (d, J = 5.03 Hz, 1 H) 6.31-6.54 (m, 1 H) 6.93 (d, J = 8.05 Hz, 2 H) 7.07 (dd, J = 8.55, 1.84 Hz, 1 H) 7.10-7.26 (m, 4 H) 7.30 (d, J = 8.72 Hz, 1 H) 7.44 (d, J = 8.72 Hz, 2 H) 7.54 (d, J = 1.68 Hz, 1 H) 11.02-11.24 (m, 1 H) | 3.52 | ***** |
| 1224 | 527.0 | | 3.53 | ***** |
| 1225 | 597.9 (cal: 597.1) | $^1$H NMR (CD$_3$CN, 300 MHz) δ 9.19 (b, 1H), 7.54 (d, J = 1.8 Hz, 1H), 7.37 (d, J = 9.0 Hz, 2H), 7.30-7.27 (m, 3H), 7.13-7.05 (m, 4H), 6.90 (d, J = 8.7 Hz, 2H), 6.46 (b, 1H), 4.39 (b, 1H), 3.98-3.86 (m, 3H), 3.81 (s, 2H), 3.46-3.42 (m, 1H), 3.35 (s, 3H), 3.33-3.26 (m, 2H), 2.88-2.82 (m, 2H). | 30-90 4.69 | **** |

TABLE 2-continued

| Cpd | MS | NMR | RT | EC$_{50}$ |
|---|---|---|---|---|
| 1226 | 485.3 | | 3.83 | ***** |
| 1227 | 565.2 (M − H) | | 4.18 | ***** |
| 1228 | 567.2 (M − H) | $^1$H NMR (300 MHz, DMSO-d$_6$) δ ppm 1.11 (t, J = 6.93 Hz, 6 H) 2.87 (br. s., 2 H) 3.10-3.27 (m, 1 H) 3.45-3.73 (m, 4 H) 3.92 (d, J = 5.28 Hz, 2 H) 4.18-4.40 (m, 1 H) 4.78 (t, J = 5.28 Hz, 1 H) 6.32-6.50 (m, 1 H) 6.96 (d, J = 8.25 Hz, 2 H) 7.07 (dd, J = 8.58, 1.98 Hz, 1 H) 7.14 (d, J = 7.92 Hz, 1 H) 7.17-7.25 (m, 3 H) 7.30 (d, J = 8.58 Hz, 1 H) 7.44 (d, J = 8.91 Hz, 2 H) 7.54 (d, J = 1.98 Hz, 1 H) 11.05-11.22 (m, 1 H) | 4.37 | ***** |
| 1229 | 595.39 | | 4.47 | ***** |
| 1230 | 555.24 | | 3.73 | ***** |
| 1231 | 528 | | 3.48 | **** |
| 1232 | C$_{23}$H$_{20}$ClFN$_2$O$_3$, (427.5) | | 5.221 | *** |
| 1233 | C$_{29}$H$_{38}$ClN$_3$O$_3$, (512.5) | | 5.107, Chiral 8.111 | **** |
| 1234 | C$_{33}$H$_{37}$Cl$_2$N$_3$O$_3$, (594.00) | | 5.135, Chiral 9.655 | ***** |
| 1235 | C$_{32}$H$_{33}$Cl$_2$N$_3$O$_3$, (578.0) | | 4.785 | **** |
| 1236 | C$_{28}$H$_{34}$ClN$_3$O$_3$, (497.0) | | 10.832, Chiral 10.954 | **** |
| 1237 | 417.23 | (CDCl3, 300 MHz), δ 8.34 (d, 2H), 7.80 (s, 1H), 7.51 (d, 1H), 7.32 (d, 2H), 7.20 (d, 1H), 7.10 (d, 1H), 6.84 (dd, 2H), 6.50 (t, 1H), 6.02 (m, 1H), 5.42-5.24 (m, 2H), 4.96 (dd, 1H), 4.50 (d, 2H), 3.35-3.25 (m, 1H), 2.98-2.91 (m, 1H), 2.82-2.76 (dd, 1H) | 4.07 | ***** |
| 1238 | 475.17 | | 4.27 | ***** |
| 1239 | 508.26 | | 3.7 | ***** |
| 1240 | 508.23 | | 3.98 | ***** |
| 1241 | 377.23 | | 3.43 | **** |
| 1242 | 505.25 | | 4.05 | ***** |
| 1243 | 465.21 | | 3.22 | **** |
| 1244 | 505.25 | | 4.03 | ***** |
| 1245 | 433.2 | | 3.75 | **** |
| 1246 | 433.2 | | 3.73 | **** |
| 1247 | 372.14 | | 3.23 | ** |
| 1249 | 520.3 | $^1$H NMR (CDCl3, 300 MHz), δ 8.34 (d, 2H), 7.88 (s, 1H), 7.51 (d, 1H), 7.32 (d, 2H), 7.20 (d, 2H), 7.10 (d, 1H), 6.83 (d, 2H), 6.50 (t, 1H), 4.96 (dd, 1H), 4.07 (m, 1H), 3.94 (d, 2H), 3.72 (m, 4H), 3.29 (m, 1H), 2.96 (m, 2H), 2.80 (dd, 1H), 2.69-2.41 (m, 6H) | 2.15 | ***** |
| 1250 | 511.07 | | 3.93 | ***** |
| 1251 | 429.06 | | 3.48 | ***** |
| 1252 | 443.31 | | 3.57 | ***** |
| 1253 | 495 | | 4.10 | ***** |
| 1254 | 520.36 | $^1$H NMR (CDCl3, 300 MHz), δ 8.34 (d, 2H), 7.88 (s, 1H), 7.51 (d, 1H), 7.32 (d, 2H), 7.20 (d, 2H), 7.10 (d, 1H), 6.83 (d, 2H), 6.50 (t, 1H), 4.96 (dd, 1H), 4.07 (m, 1H), 3.94 (d, 2H), 3.72 (m, 4H), 3.29 (m, 1H), 2.96 (m, 2H), 2.80 (dd, 1H), 2.69-2.41 (m, 6H) | 2.18 | ***** |
| 1255 | 614.35 | | 2.35 | *** |
| 1256 | 435.21 | | 3.52 | ***** |
| 1257 | 554.26 | | 2.42 | **** |
| 1258 | 600.14 | | 2.43 | ***** |
| 1259 | 527.2 | | 3.50 | **** |
| 1260 | 565.2 (M − H) | | 4.18 | ***** |
| 1261 | 485.3 | | 3.85 | ***** |
| 1262 | 451.21 | $^1$H NMR (CDCl3, 300 MHz), δ 8.10 (br, 1H), 7.50 (d, 1H), 7.19-7.09 (m, 4H), 6.84 (d, 2H), 6.37 (br, 1H), 6.02 (m, 1H), 5.42-5.24 (m, 2H), 5.17 (m, 1H), 4.49 (d, 2H), 4.24 (br, 1H), 3.12 (m, 1H), 2.91-2.72 (m, 2H), 1.76 (m, 8H) | 4.35 | ***** |
| 1263 | 583.00 | | 3.85 | ***** |
| 1264 | C$_{26}$H$_{30}$ClN$_3$O$_3$, (468.0) | $^1$HNMR, CD3OD, 400 MHz, 7.47 (d, 1H, 1Ar—H); 7.25-7.18 (dd, 3H, 3Ar—H); 7.07-7.05 (dd, 1H, 1Ar—H); 6.90 (d, 2H, 2Ar—H); 6.42 (brs, 1H, CH); 4.30 (brm, 3H, 1CH$_2$ and 1CH); 4.00 (t, 2H, CH$_2$); 3.30 (brm, 1H, CH); 2.86 (t, 5H, CH$_3$ and CH$_2$); 2.20 (brm, 1H, CH); 1.98 (t, 2H, CH$_2$); 1.,33 (d, 2H, CH$_2$); 0.50 (t, 2H, CH$_2$); 0.38 (t, 2H, CH$_2$); | 4.584 | **** |
| 1265 | C$_{25}$H$_{19}$ClF$_2$N$_2$O$_2$, (469.0) | | 5.478 | **** |
| 1266 | C$_{26}$H$_{22}$ClFN$_2$O$_3$, (465.0) | $^1$HNMR, DMSO-D$_6$ 400 MHz, 11.09 (brs, 1H, Ar—N—H); 7.54 (d, 1H, 1Ar—H); 7.30 (dd, 1H, 1 Ar—H); 7.17-7.08 (dd, 2H, 2 Ar—H); 7.06 (dd, 1H, 1Ar—H); 6.97-6.75 (brm, 4H, 4Ar—H); 6.73-6.70 (brm, 2H, 1Ar—H and 1CH); 4.29-4.26 (brm, 1H, CH); 3.75 (s, 3H, O—CH$_3$); 3.22-3.1`9 (m, 1H, CH); 2.85 (m, 2H, CH$_2$); 2.27 (s, 3H, Ar—CH$_3$); | 5.667 | ***** |

TABLE 2-continued

| Cpd | MS | NMR | RT | EC$_{50}$ |
|---|---|---|---|---|
| 1267 | C$_{26}$H$_{22}$ClFN$_2$O$_4$ (481.0) | | 5.426 | **** |
| 1268 | C$_{21}$H$_{20}$ClFN$_2$O$_3$, (403) | | 5.224 | ***** |
| 1269 | C$_{25}$H$_{19}$Cl$_2$N$_2$FO$_3$, (485.0) | | 5.723 | ***** |
| 1270 | M + 23:522.1 (cal.499.2) | $^1$H NMR (DMSO, 300 MHz), δ11.13 (b, 1H), 7.91 (s, 1H), 7.48 (s, 1H), 7.27 (d, J = 8.4 Hz, 1H), 7.10-7.03 (m, 3H), 6.88 (d, J = 8.7 Hz, 2H), 6.29 (s, 1H), 4.86 (d, J = 5.4 Hz, 1H), 4.20-4.05 (m, 3H), 4.00 (t, J = 6.3 Hz, 2H), 3.69-3.62 (m, 1H), 3.10-2.94 (m, 3H), 2.74-2.69 (m, 2H), 1.84-1.75 (m, 4), 1.64-1.55 (m, 1H), 1.22-1.20 (m, 3H). | 30-90 3.69 | **** |
| 1271 | M + 23:552.1 (cal.529.2) | $^1$H NMR (DMSO, 300 MHz), δ11.15 (b, 1H), 7.67 (s, 1H), 7.48 (s 1H), 7.27 (d, J = 8.1 Hz, 1H), 7.10-7.02 (m, 3H), 6.87 (d, J = 8.4 Hz, 2H), 6.29 (s, 1H), 4.93 (d, J = 5.4 Hz, 1H), 4.10-4.00 (m, 5H), 3.78-3.76 (m, 2H), 3.64-3.62 (m, 1H), 3.26 (s, 3H), 3.19-3.11 (m, 3H), 3.09-2.99 (m, 2H), 2.86-2.73 (m, 2H), 1.90-1.73 (m, 1H), 1.69-1.59 (m, 1H), 1.22-1.20 (m, 3H). | 10-80 5.39 | **** |
| 1272 | 528.2 (cal.527.2) | $^1$H NMR (CD3CN, 300 MHz), δ9.21 (b, 1H), 7.50 (d, J = 1.8 Hz, 1H), 7.26 (d, J = 8.7 Hz, 1H), 7.14 (d, J = 8.7 Hz, 2H), 7.06 (dd, J = 8.7 Hz and 1.8 Hz, 1H), 6.83 (d, J = 8.7 Hz, 2H), 6.34 (s, 1H), 4.28-4.20 (m, 1H), 4.11 (q, J = 7.2 Hz, 2H), 4.09-4.02 (m, 2H), 3.86-3.81 (m, 1H), 3.59 (t, J = 4.8 Hz, 4H), 3.35-3.34 (m, 1H), 3.13-3.03 (m, 1H), 2.77-2.71 (m, 2H), 2.54-2.48 (m, 2H), 2.30-2.27 (m, 4H), 1.90-1.81 (m, 1H), 1.73-1.69 (m, 1H), 1.24 (t, J = 7.2 Hz, 3H). | 30-90 3.11 | ***** |
| 1273 | 546.1 (cal.545.2) | $^1$H NMR (DMSO, 300 MHz), δ11.18 (b, 1H), 7.48 (s, 1H), 7.28 (d, J = 8.4 Hz, 1H), 7.10-7.02 (m, 3H), 6.89 (d, J = 8.7 Hz, 2H), 6.29 (s, 1H), 4.52-4.51 (m, 1H), 4.44-4.42 (m, 2H), 4.11-4.09 (m, 3H), 4.02 (t, J = 6.6 Hz, 2H), 3.65-3.63 (m, 1H), 3.41-3.39 (m, 4H), 3.04-2.99 (m, 1H), 2.72-2.71 (m, 2H), 2.54-2.53 (m, 4H), 2.42-2.36 (m, 2H), 1.90-1.81 (m, 1H), 1.63-1.59 (m, 1H), 1.22-1.21 (m, 3H). | 30-90 2.98 | **** |
| 1274 | 510.1 (cal.509.2) | $^1$H NMR (DMSO, 300 MHz), δ11.16 (b, 1H), 8.04 (s, 1H), 7.68 (s, 1H), 7.48 (d, J = 1.8 Hz, 1H), 7.28 (d, J = 8.4 Hz, 1H), 7.11-7.03 (m, 3H), 6.89 (d, J = 8.7 Hz, 2H), 6.30 (s, 1H), 5.26 (d, J = 5.7 Hz, 1H), 4.50-4.44 (m, 1H), 4.34-4.30 (m, 1H), 4.15-4.00 (m, 6H), 3.05-2.98 (m, 1H), 2.77-2.74 (m, 2H), 2.65-5.50 (m, 2H), 1.85-1.80 (m, 1H), 1.66-1.60 (m, 1H), 1.21-1.15 (m, 3H). | 30-90 3.97 | ***** |
| 1275 | 510.1 (cal.509.2) | $^1$H NMR (CD3CN, 300 MHz), δ9.19 (b, 1H), 7.64 (d, J = 1.8 Hz, 2H), 7.51 (d, J = 1.8 Hz, 1H), 7.27 (d, J = 8.4 Hz, 1H), 7.17 (d, J = 8.4 Hz, 2H), 7.08 (dd, J = 8.4 Hz and 2.1 Hz, 1H), 6.85 (d, J = 8.7 Hz, 2H), 6.37 (s, 1H), 4.46-4.42 (m, 2H), 4.32-4.21 (m, 2H), 4.15-4.03 (m, 4H), 3.15-3.09 (m, 1H), 2.81-2.77 (m, 2H), 2.65-5.50 (m, 2H), 1.92-1.85 (m, 1H), 1.83-1.71 (m, 1H), 1.25 (t, J = 7.2 Hz, 3H). | 30-90 4.36 | ***** |
| 1276 | M + 23:604.2 (cal.581.1) | $^1$H NMR (CD3CN, 300 MHz), δ9.20 (b, 1H), 7.55 (d, J = 1.8 Hz, 1H), 7.39-7.36 (m, 2H), 7.30-7.22 (m, 3H), 7.15-7.09 (m, 3H), 6.89 (d, J = 8.7 Hz, 2H), 6.57 (b, 1H), 6.46 (s, 1H), 4.41-4.33 (m, 1H), 4.07 (t, J = 6.3 Hz, 2H), 3.81-3.76 (m, 1H), 3.56-3.49 (m, 1H), 3.30-3.21 (m, 2H), 3.13-3.07 (m, 1H), 2.99-2.81 (m, 2H), 1.84 (s, 3H), 1.76-1.69 (m, 2H). | 30-90 4.47 | ***** |
| 1277 | M + 23:646.2 (cal.623.2) | $^1$H NMR (CD3CN, 300 MHz), δ9.21 (b, 1H), 7.55 (d, J = 1.8 Hz, 1H), 7.40-7.37 (m, 2H), 7.31-7.22 (m, 3H), 7.15-7.09 (m, 3H), 6.87 (d, J = 8.7 Hz, 2H), 6.52 (b, 1H), 6.46 (s, 1H), 5.05-5.04 (m, 1H), 4.41-4.33 (m, 1H), 4.03-3.99 (m, 2H), 3.52-3.51 (m, 1H), 3.45-3.38 (m, 1H), 3.31-3.21 (m, 2H), 2.99-2.83 (m, 2H), 2.11-2.10 (m, 1H), 1.99 (s, 3H), 1.83 (s, 3H). | 30-90 4.83 | ***** |
| 1278 | M + 23:634.2 (cal.611.2) | $^1$H NMR (CD3CN, 400 MHz), δ9.20 (b, 1H), 7.55 (d, J = 2.0 Hz, 1H), 7.38 (d, J = 8.8 Hz, 2H), 7.31-7.23 (m, 3H), 7.14-7.10 (m, 3H), 7.03 (b, 1H), 6.90 (d, J = 8.0 Hz, 2H), 6.45 (s, 3H), 4.41-4.33 (m, 1H), 4.08 (t, J = 6.4 Hz, 2H), 3.83-3.80 (m, 3H), 3.51-3.49 (m, 1H), 3.37 (s, 3H), 3.32-3.24 (m, 2H), 3.13-3.07 (m, 1H), 2.99-2.81 (m, 2H), 1.90-1.82 (m, 1H), 1.76-1.69 (m, 1H). | 30-90 4.60 | ***** |
| 1279 | 610.2 (cal.609.2) | $^1$H NMR (CD3CN, 300 MHz), δ9.16 (b, 1H), 7.54 (d, J = 1.8 Hz, 1H), 7.39-7.36 (m, 2H), 7.30-7.21 (m, 3H), 7.14-7.08 (m, 3H), 6.89 (d, J = 8.4 Hz, 2H), 6.46 (s, 1H), 4.41-4.38 (m, 1H), 3.88-3.85 (m, 1H), 3.61 (t, J = 4.8 Hz, 4H), 3.30-3.28 (m, 2H), 2.98-2.82 (m, 2H), 2.59-2.51 (m, 2H), 2.38-2.29 (m, 4H), 1.90-1.81 (m, 1H), 1.73-1.69 (m, 1H). | 10-80 5.28 | ***** |
| 1280 | 628.2 (cal.627.2) | $^1$H NMR (CD3CN, 300 MHz), δ9.19 (b, 1H), 7.55 (d, J = 2.1 Hz, 1H), 7.39 (d, J = 8.7 Hz, 2H), 7.31-7.25 (m, 3H), 7.14-7.09 (m, 3H), 6.91 (d, J = 8.7 Hz, 2H), 6.47 (s, 1H), 4.41-4.39 (m, 1H), 4.10 (t, J = 6.0 Hz, 2H), 3.81-3.76 (m, 7H), 3.57-3.48 (m, 3H), 3.33-3.27 (m, 2H), 2.98-2.82 (m, 3H), 2.77-2.72 (m, 3H), 2.58-2.56 (m, 2H), 2.47-2.44 (m, 2H), 1.90-1.81 (m, 1H), 1.73-1.69 (m, 1H). | 10-80 5.22 | **** |
| 1281 | M + 23:614.1 (cal.591.1) | $^1$H NMR (CD3CN, 300 MHz), δ9.20 (b, 1H), 7.80 (d, J = 0.9 Hz, 1H), 7.63 (d, J = 0.9 Hz, 1H), 7.55 (d, J = 2.1 Hz, 1H), | 30-90 4.65 | ***** |

TABLE 2-continued

| Cpd | MS | NMR | RT | EC$_{50}$ |
|---|---|---|---|---|
| | | 7.39-7.36 (m, 2H), 7.31-7.23 (m, 3H), 7.13-7.08 (m, 3H), 6.90 (d, J = 8.7 Hz, 2H), 6.46 (s, 1H), 4.52-4.46 (m, 1H), 4.38-4.31 (m, 2H), 4.21-4.15 (m, 1H), 4.12-4.08 (m, 2H), 3.45-3.22 (m, 2H), 3.02-2.84 (m, 2H), 1.92-1.89 (m, 1H), 1.79-1.71 (m, 1H). | | |
| 1282 | 592.0 (cal.591.1) | $^1$H NMR (CD3CN, 300 MHz), δ 9.22 (b, 1H), 8.17 (s, 1H), 7.85 (s, 1H), 7.55 (d, J = 1.8 Hz, 1H), 7.38 (d, J = 8.7 Hz, 2H), 7.30-7.24 (m, 3H), 7.13-7.09 (m, 3H), 6.90 (d, J = 8.7 Hz, 2H), 6.46 (s, 1H), 4.42-4.40 (m, 1H), 4.27-4.24 (m, 1H), 4.15-4.08 (m, 4H), 3.45 (d, J = 4.8 Hz, 1H), 3.32-3.28 (m, 1H), 2.88-2.87 (m, 2H), 1.92-1.89 (m, 1H), 1.79-1.71 (m, 1H). | 10-80 5.90 | ***** |
| 1283 | 471.99 (ES−) | | 3.28 | ***** |
| 1284 | 513.28 | | 4.10 | ***** |
| 1285 | 469.22 | | 3.82 | ***** |
| 1286 | 411.24 | | 3.7 | *** |
| 1287 | 510.1 (cal.509.2) | $^1$H NMR (DMSO, 300 MHz), δ 11.09 (b, 1H), 8.40 (s, 1H), 7.95 (s, 1H), 7.49 (d, J = 2.1 Hz, 2H), 7.27 (d, J = 8.4 Hz, 1H), 7.10 (d, J = 8.7 Hz, 2H), 7.04 (dd, J = 8.4 Hz and 2.1 Hz, 1H), 6.89 (d, J = 8.7 Hz, 2H), 6.29 (s, 1H), 5.13 (d, J = 5.4 Hz, 1H), 4.24-4.01 (m, 8H), 3.05-2.97 (m, 1H), 2.76-2.69 (m, 2H), 1.90-1.81 (m, 1H), 1.71-1.63 (m, 1H), 1.21-1.18 (m, 3H). | 30-90 3.77 | **** |
| 1288 | 608.2 (cal.607.2) | $^1$H NMR (CD3CN, 300 MHz), δ 9.15 (b, 1H), 7.55 (d, J = 1.8 Hz, 1H), 7.31-7.15 (m, 5H), 7.10 (dd, J = 8.7 Hz and 2.1 Hz, 1H), 6.99 (d, J = 8.4 Hz, 2H), 6.91 (d, J = 8.7 Hz, 2H), 6.48 (s, 1H), 4.42-4.39 (m, 1H), 4.11 (t, J = 6.6 Hz, 2H), 3.82-3.73 (m, 1H), 3.60-3.45 (m, 5H), 3.35-2.80 (m, 5H), 2.74-2.42 (m, 7H), 2.33 (s, 3H), 1.71-1.69 (m, 1H). | 10-80 4.51 | **** |
| 1289 | M + 23:594.2 (cal.571.2) | $^1$H NMR (DMSO, 400 MHz), δ 11.13-11.10 (m, 1H), 8.02 (s, 1H), 7.68 (s, 1H), 7.52 (d, J = 1.6 Hz, 1H), 7.29 (d, J = 8.4 Hz, 1H), 7.17-7.15 (m, 4H), 7.06 (dd, J = 8.4 Hz and 2.0 Hz, 1H), 7.00 (d, J = 8.4 Hz, 2H), 6.93-6.91 (m, 2H), 6.42-6.37 (m, 1H), 5.20 (d, J = 5.6 Hz, 1H), 4.49-4.41 (m, 1H), 4.34-4.28 (m, 2H), 4.06-4.03 (m, 3H), 3.17-3.12 (m, 1H), 2.89-2.81 (m, 2H), 2.27 (s, 3H), 1.90-1.80 (m, 1H), 1.70-1.61 (m, 1H). | 30-90 4.80 | ***** |
| 1290 | M + 23:594.2 (cal.571.2) | $^1$H NMR (DMSO, 400 MHz), δ 11.17-11.10 (m, 1H), 7.74 (s, 2H), 7.52 (d, J = 2.0 Hz, 1H), 7.29 (d, J = 8.4 Hz, 1H), 7.17-7.15 (m, 4H), 7.06 (dd, J = 8.4 Hz and 2.0 Hz, 1H), 7.00 (d, J = 8.4 Hz, 2H), 6.91 (d, J = 7.6 Hz, 2H), 6.42-6.37 (m, 1H), 5.09 (d, J = 6.4 Hz, 1H), 4.39 (d, J = 6.4 Hz, 2H), 4.23-4.19 (m, 1H), 4.14-4.10 (m, 1H), 4.04 (t, J = 6.0 Hz, 2H), 3.19-3.11 (m, 1H), 2.89-2.81 (m, 2H), 2.27 (s, 3H), 1.90-1.80 (m, 1H), 1.70-1.61 (m, 1H). | 30-90 5.18 | ***** |
| 1291 | M + 23:594.2 (cal.571.2) | $^1$H NMR (DMSO, 400 MHz), δ 11.13-11.10 (m, 1H), 8.40 (s, 1H), 7.92 (s, 1H), 7.52 (d, J = 2.0 Hz, 1H), 7.29 (d, J = 8.4 Hz, 1H), 7.17-7.15 (m, 4H), 7.06 (dd, J = 8.4 Hz and 2.0 Hz, 1H), 7.00 (d, J = 8.0 Hz, 2H), 6.93-6.91 (m, 2H), 6.42-6.37 (m, 1H), 5.14 (d, J = 6.0 Hz, 1H), 4.30-4.27 (m, 1H), 4.23-4.19 (m, 1H), 4.14-4.10 (m, 1H), 4.09-4.06 (m, 2H), 4.03-4.01 (m, 1H), 3.17-3.12 (m, 1H), 2.89-2.81 (m, 2H), 2.27 (s, 3H), 1.90-1.80 (m, 1H), 1.70-1.61 (m, 1H). | 30-90 4.88 | **** |
| 1292 | M − 1:519.2 (cal.520.2) | $^1$H NMR (DMSO, 300 MHz), δ 11.15 (b, 1H), 7.53 (d, J = 2.1 Hz, 1H), 7.30 (d, J = 8.7 Hz, 1H), 7.19-7.16 (m, 4H), 7.07 (dd, J = 8.7 Hz and 2.1 Hz, 1H), 7.02 (d, J = 8.4 Hz, 2H), 6.93 (d, J = 8.1 Hz, 2H), 6.41 (s, 1H), 4.36-4.25 (m, 1H), 4.04 (t, J = 6.3 Hz, 2H), 3.31-3.26 (m, 2H), 3.20-3.15 (m, 1H), 2.91-2.80 (m, 2H), 2.27 (s, 3H), 1.94-1.87 (m, 1H), 1.63-1.54 (m, 1H). | 10-80 5.53 | ***** |
| 1293 | M − 1:523.2 (cal.524.2) | $^1$H NMR (DMSO, 300 MHz), δ 11.15-11.13 (m, 1H), 7.53 (d, J = 1.8 Hz, 1H), 7.30 (d, J = 8.4 Hz, 1H), 7.21-7.19 (m, 6H), 7.07 (dd, J = 8.7 Hz and 2.1 Hz, 1H), 6.93 (d, J = 7.8 Hz, 2H), 6.41-6.37 (m, 1H), 4.35-4.26 (m, 1H), 4.04 (t, J = 6.3 Hz, 2H), 3.61-3.57 (m, 2H), 3.33-3.28 (m, 2H), 3.20-3.15 (m, 1H), 2.91-2.80 (m, 2H), 1.93-1.84 (m, 1H), 1.63-1.54 (m, 1H). | 10-80 5.34 | ***** |
| 1294 | 471 | | 3.98 | ***** |
| 1295 | 473.30 | | 3.27 | ***** |
| 1296 | 487.17 | | 3.42 | **** |
| 1297 | 535.31 | | 3.67 | **** |
| 1298 | 425.1 | | 4.02 | ***** |
| 1299 | M − 1:505.2 (cal.506.2) | $^1$H NMR (DMSO, 300 MHz), δ 11.15 (b, 1H), 7.54 (d, J = 2.1 Hz, 1H), 7.39 (t, J = 7.8 Hz, 2H), 7.30 (d, J = 8.7 Hz, 1H), 7.29-7.14 (m, 5H), 7.07 (dd, J = 8.7 Hz and 2.1 Hz, 1H), 6.93 (d, J = 8.4 Hz, 2H), 6.41 (s, 1H), 4.36-4.25 (m, 1H), 4.04 (t, J = 6.3 Hz, 2H), 3.62-3.58 (m, 1H), 3.36-3.23 (m, 3H), 2.91-2.88 (m, 2H), 1.94-1.87 (m, 1H), 1.63-1.54 (m, 1H). | 10-80 5.28 | ***** |
| 1300 | M − 1:535.2 (cal.536.2) | $^1$H NMR (DMSO, 300 MHz), δ 11.13 (b, 1H), 7.53 (d, J = 1.8 Hz, 1H), 7.30 (d, J = 8.7 Hz, 1H), 7.21-7.18 (m, 2H), 7.09-7.04 (m, 3H), 6.94-6.90 (m, 4H), 6.40 (s, 1H), 4.35-4.26 (m, 1H), 4.04 (t, J = 6.6 Hz, 2H), 3.73 (s, 3H), 3.62-3.59 (m, 1H), 3.32-3.21 (m, 2H), 3.19-3.11 (m, 1H), 2.89-2.82 (m, 2H), 1.93-1.84 (m, 1H), 1.63-1.54 (m, 1H). | 10-80 4.55 | ***** |
| 1301 | M + 23:614.2 (cal.591.2) | $^1$H NMR (CD3CN, 300 MHz), δ 9.19 (b, 1H), 7.55 (d, J = 1.5 Hz, 1H), 7.31-7.17 (m, 5H), 7.11 (dd, J = 8.4 Hz and 2.1 Hz, 1H), 6.99 (d, J = 8.4 Hz, 2H), 6.90 (d, J = 8.4 Hz, 2H), 6.47 (s, 1H), | 10-80 5.96 | **** |

TABLE 2-continued

| Cpd | MS | NMR | RT | EC$_{50}$ |
|---|---|---|---|---|
| | | 4.42-4.37 (m, 1H), 4.08 (s, 2H), 3.86-3.84 (m, 3H), 3.14-3.12 (m, 7H), 2.96-2.85 (m, 2H), 2.34-2.33 (m, 5H). | | |
| 1302 | 590.2 (cal.589.2) | $^1$H NMR (CD3CN, 300 MHz), δ9.10 (s, 1H), 7.49 (d, J = 1.8 Hz, 1H), 7.22-7.17 (m, 3H), 7.12 (d, J = 8.7 Hz, 2H), 7.04 (dd, J = 8.7 Hz and 1.8 Hz, 1H), 6.91 (d, J = 8.4 Hz, 2H), 6.84 (d, J = 8.7 Hz, 2H), 6.40 (s, 1H), 4.39-4.15 (m, 2H), 4.08-4.06 (m, 2H), 3.82-3.74 (m, 4H), 3.29-3.00 (m, 6H), 2.91-2.74 (m, 4H), 2.24-2.21 (m, 4H). | 10-80 5.37 | *** |
| 1303 | C$_{29}$H$_{32}$ClN$_5$O$_3$, (534.0) | | 9.233, Chiral 15.390 | ***** |
| 1304 | C$_{30}$H$_{34}$ClN$_5$O$_2$, (532) | | 4.755, Chiral 9.709 | ***** |
| 1305 | C$_{29}$H$_{34}$ClN$_5$O$_2$, (520.5) | | 4.703, Chiral, 8.511 | **** |
| 1306 | C$_{30}$H$_{35}$ClN$_6$O$_2$, (547) | | 4.080, Chiral, 10.043 | **** |
| 1307 | C$_{28}$H$_{30}$ClN$_5$O$_3$, (520.0) | | 4.230, Chiral, 33.131 | ***** |
| 1308 | C$_{29}$H$_{33}$ClN$_6$O$_2$, (533.0) | | 7.074, Chiral, 26.147 | ***** |
| 1309 | C$_{28}$H$_{32}$ClN$_5$O$_2$, (506.5) | | 4.541, Chiral, 18.909 | **** |
| 1310 | C$_{29}$H$_{32}$ClN$_5$O$_2$, (518.0) | | 4.595, Chiral, 19.672 | **** |
| 1311 | C$_{28}$H$_{32}$ClN$_5$O$_2$, (506.0) | | 4.559, Chiral, 18.552 | *** |
| 1312 | C$_{29}$H$_{33}$ClN$_6$O$_2$, (533.5) | | 7.068, Chiral, 27.053 | **** |
| 1313 | C$_{29}$H$_{32}$ClN$_5$O$_2$, (518.05) | | 4.573, Chiral, 27.244 | **** |
| 1314 | 525.07 | | 4.10 | ***** |
| 1315 | 537.37 (ES−) | | 4.37 | ***** |
| 1316 | 539.39 | | 4.30 | ***** |
| 1317 | 539.08 | | 4.23 | ***** |
| 1318 | 553.09 | | 4.60 | ***** |
| 1319 | 553.12 | | 4.52 | ***** |
| 1320 | 499.41 | | 3.45 | ***** |
| 1321 | 513.11 | | 3.63 | ***** |
| 1322 | 485.3 | | 3.37 | ***** |
| 1323 | 485.4 | | 3.38 | ***** |
| 1324 | 487.4 | $^1$H NMR (300 MHz, DMSO-d$_6$) δ ppm 0.79 (t, J = 7.59 Hz, 3 H) 1.21 (br. s., 3 H) 1.33 (q, J = 7.59 Hz, 2 H) 2.62-2.84 (m, 2 H) 2.92-3.13 (m, 1 H) 3.34 (br. s., 3 H) 3.72 (s, 2 H) 4.02-4.22 (m, 3 H) 4.38 (t, J = 5.11 Hz, 2 H) 6.31 (br. s., 1 H) 6.88 (d, J = 8.58 Hz, 2 H) 6.99-7.17 (m, 3 H) 7.27 (d, J = 8.58 Hz, 1 H) 7.49 (d, J = 1.98 Hz, 1 H) 11.09 (br. s., 1 H) | 3.42 | ***** |
| 1325 | 501.4 | | 3.55 | WLENNOX |
| 1326 | 515.4 | | 3.73 | ***** |
| 1327 | 527.4 | | 3.75 | ***** |
| 1328 | 553.4 | | 3.65 | ***** |
| 1329 | 569.3 | | 3.83 | ***** |
| 1330 | 539.28 (ES−) | | 3.60 | * |
| 1331 | 581.25 | | 4.50 | * |
| 1332 | 451.27 (ES−) | | 3.75 | * |
| 1333 | 499.40 | | 3.90 | * |
| 1334 | 412.9 (cal.412.2) | $^1$H NMR (DMSO, 300 MHz), δ 11.21-11.18 (m, 1H), 7.54 (d, J = 2.1 Hz, 1H), 7.30 (d, J = 8.7 Hz, 1H), 7.13-7.06 (m, 3H), 6.93 (dd, J = 8.7 Hz and 2.1 Hz, 2H), 6.62 (s, 1H), 4.35-4.28 (m, 2H), 3.72 (s, 3H), 3.62-3.60 (m, 1H), 3.48-3.38 (m, 1H), 2.90-2.80 (m, 2H), 1.29-1.24 (m, 3H). | 10-80 4.59 | *** |
| 1335 | M − 1:573.0 (cal.538.2) | $^1$H NMR (CD3CN, 300 MHz), δ 9.13 (b, 1H), 7.56 (d, J = 2.1 Hz, 1H), 7.31-7.24 (m, 3H), 7.14-7.09 (m, 5H), 6.92 (d, J = 8.4 Hz, 2H), 6.47 (s, 1H), 4.41-4.36 (m, 1H), 3.85 (s, 2H), 3.50 (d, J = 8.1 Hz, 4H), 3.33-3.28 (m, 1H), 2.91-2.84 (m, 4H), 0.91 (s, 3H). | 30-90 4.82 | **** |
| 1336 | M − 1:519.1 (cal.520.2) | $^1$H NMR (CDCl3, 400 MHz), δ 8.58-8.26 (m, 1H), 7.51 (s, 1H), 7.37 (t, J = 8.0 Hz, 2H), 7.23-7.20 (m, 3H), 7.11-7.02 (m, 4H), 6.82-6.80 (m, 2H), 6.39 (s, 1H), 4.46-4.41 (m, 1H), | 10-80 5.76 | **** |

TABLE 2-continued

| Cpd | MS | NMR | RT | EC$_{50}$ |
|---|---|---|---|---|
| | | 3.91-3.84 (m, 2H), 3.69-3.60 (m, 4H), 3.31-3.25 (m, 1H), 3.02-2.98 (m, 1H), 2.84-2.54 (m, 3H), 0.94 (s, 3H). | | |
| 1337 | M − 1:549.2 (cal.550.2) | $^1$H NMR (CD3CN, 300 MHz), δ 9.13 (b, 1H), 7.55 (d, J = 2.1 Hz, 1H), 7.31-7.23 (m, 3H), 7.11 (dd, J = 8.1 Hz and 2.1 Hz, 1H), 7.03-7.00 (m, 2H), 6.93-6.89 (m, 4H), 6.47 (s, 1H), 4.41-4.36 (m, 1H), 3.85 (s, 2H), 3.78 (s, 3H), 3.50 (d, J = 3.6 Hz, 4H), 3.31-3.28 (m, 1H), 2.91-2.84 (m, 4H), 0.91 (s, 3H). | 30-90 4.33 | **** |
| 1338 | 426.8 (cal.426.1) | $^1$H NMR (DMSO, 400 MHz), δ 11.21-11.18 (m, 1H), 7.55 (s, 1H), 7.30 (d, J = 8.4 Hz, 1H), 7.12-7.07 (m, 3H), 6.93 (d, J = 8.8 Hz, 2H), 6.61-5.90 (m, 1H), 3.72 (s, 3H), 3.62-3.60 (m, 1H), 3.45-3.38 (m, 1H), 2.90-2.80 (m, 2H), 1.30-1.24 (m, 6H). | 10-80 5.58 | **** |
| 1339 | 426.8 (cal.426.1) | $^1$H NMR (DMSO, 400 MHz), δ 11.21-11.10 (m, 1H), 7.55 (s, 1H), 7.31 (d, J = 8.8 Hz, 1H), 7.11 (d, J = 8.8 Hz, 2H), 7.08 (dd, J = 8.4 Hz and 1.6 Hz, 1H), 6.93 (d, J = 8.8 Hz, 2H), 6.62-5.92 (m, 1H), 4.25-4.21 (m, 2H), 3.72 (s, 3H), 3.65-3.63 (m, 1H), 2.92-2.76 (m, 2H), 1.69-1.64 (m, 2H), 0.90 (t, J = 7.6 Hz, 3H). | 10-80 5.63 | **** |
| 1340 | 489.5 | | 3.25 | **** |
| 1341 | 503.1 | | 3.38 | **** |
| 1342 | 517.1 | | 3.58 | ***** |
| 1343 | 555.1 | | 3.53 | ***** |
| 1344 | 571.0 | | 3.70 | ***** |
| 1345 | 503.0 | $^1$H NMR (300 MHz, DMSO-d$_6$) δ ppm 1.21 (br. s., 3 H) 1.46-1.67 (m, 1 H) 1.76-1.98 (m, 1 H) 2.60-2.85 (m, 2 H) 2.91-3.10 (m, 1 H) 3.18-3.44 (m, 3 H) 3.49-3.66 (m, 1 H) 4.02 (t, J = 6.54 Hz, 2 H) 4.05-4.25 (m, 3 H) 4.55 (br. s., 1 H) 6.30 (br. s., 1 H) 6.89 (d, J = 8.72 Hz, 2 H) 7.09 (d, J = 8.72 Hz, 2 H) 7.12-7.20 (m, 1 H) 7.24 (d, J = 8.72 Hz, 1 H) 7.63 (d, J = 1.68 Hz, 1 H) 11.11 (br. s., 1 H) | 3.32 | ***** |
| 1346 | 517.1 | | 3.45 | ***** |
| 1347 | 531.1 | | 3.65 | ***** |
| 1348 | 569.1 | | 3.60 | ***** |
| 1349 | 585.0 | | 3.77 | ***** |
| 1350 | 531.1 | | 3.62 | ***** |
| 1351 | 545.1 | | 3.80 | ***** |
| 1352 | 583.1 | | 3.72 | ***** |
| 1353 | 599.0 | | 3.88 | ***** |
| 1354 | 531.0 | | 3.62 | ***** |
| 1355 | 545.1 | | 3.77 | ***** |
| 1356 | 559.2 | | 3.87 | ***** |
| 1357 | 597.2 | | 3.77 | ***** |
| 1358 | 613.2 | | 3.93 | ***** |
| 1359 | M − 1:499.2 (cal.500.2) | $^1$H NMR (CD3CN, 300 MHz), δ 9.09 (b, 1H), 7.51 (d, J = 1.8 Hz, 1H), 7.28 (d, J = 8.7 Hz, 1H), 7.19 (d, J = 8.7 Hz, 2H), 7.08 (dd, J = 8.4 Hz and 1.8 Hz, 1H), 6.91 (d, J = 8.7 Hz, 2H), 6.36 (s, 1H), 4.78 (d, J = 6.0 Hz, 1H), 4.73 (d, J = 6.0 Hz, 1H), 4.29-4.21 (m, 1H), 4.19-4.11 (m, 2H), 3.98 (s, 2H), 3.84 (d, J = 11.4 Hz, 2H), 3.75 (d, J = 11.7 Hz, 2H), 3.56 (d, J = 5.4 Hz, 2H), 3.16-3.06 (m, 1H), 2.85 (t, J = 5.7 Hz, 1H), 2.78-2.76 (m, 2H), 1.26 (t, J = 6.9 Hz, 3H). | 10-80 4.37 | **** |
| 1360 | M − 1:513.2 (cal.514.2) | $^1$H NMR (CD3CN, 300 MHz), δ 9.09 (b, 1H), 7.51 (d, J = 1.8 Hz, 1H), 7.28 (d, J = 8.4 Hz, 1H), 7.19 (d, J = 8.7 Hz, 2H), 7.08 (dd, J = 8.7 Hz and 2.1 Hz, 1H), 6.91 (d, J = 8.7 Hz, 2H), 6.37 (s, 1H), 4.92-4.88 (m, 1H), 4.79 (d, J = 5.7 Hz, 1H), 4.73 (d, J = 6.0 Hz, 1H), 4.19-4.11 (m, 1H), 3.98 (s, 2H), 3.84 (d, J = 11.4 Hz, 2H), 3.75 (d, J = 10.8 Hz, 2H), 3.56 (d, J = 5.4 Hz, 2H), 3.13-3.06 (m, 1H), 2.85 (t, J = 5.7 Hz, 1H), 2.78-2.76 (m, 2H), 1.24 (d, J = 6.3 Hz, 6H). | 10-80 5.44 | **** |
| 1361 | M − 1:535.2 (cal.536.2) | $^1$H NMR (CD3CN, 400 MHz), δ 9.19 (b, 1H), 7.54 (d, J = 1.6 Hz, 1H), 7.28-7.22 (m, 3H), 7.10 (dd, J = 8.8 Hz and 2.0 Hz, 1H), 7.03-7.00 (m, 2H), 6.91-6.88 (m, 4H), 6.47 (s, 1H), 4.41-4.36 (m, 1H), 4.06 (t, J = 6.0 Hz, 2H), 3.77 (s, 3H), 3.76-3.75 (m, 1H), 3.51-3.46 (m, 1H), 3.41-3.32 (m, 1H), 3.28-3.22 (m, 1H), 3.11-3.02 (m, 1H), 2.91-2.84 (m, 3H), 1.90-1.81 (m, 1H), 1.74-1.69 (m, 1H). | 10-80 5.42 | **** |
| 1362 | 622.57 | | 2.53 | ***** |
| 1363 | 539.2 (cal.538.2) | $^1$H NMR (CD3CN, 300 MHz) δ9.13 (b, 1H), 7.52 (d, J = 1.8 Hz, 1H), 7.29 (d, J = 8.7 Hz, 1H), 7.24 (d, J = 8.1 Hz, 1H), 7.09 (dd, J = 8.7 Hz and 2.1 Hz, 1H), 6.88-6.83 (m, 2H), 6.79 (d, J = 2.1 Hz, 1H), 6.37 (s, 1H), 4.33-4.28 (m, 1H), 4.18-4.11 (m, 2H), 3.97 (t, J = 6.3 Hz, 2H), 3.44 (t, J = 5.1 Hz, 2H), 3.37 (t, J = 5.1 Hz, 2H), 3.19-3.12 (m, 1H), 2.82-2.78 (m, 2H), 2.42 (t, J = 7.2 Hz, 2H), 2.35 (t, J = 5.4 Hz, 2H), 2.30 (t, J = 5.1 Hz, 2H), 1.97 (s, 3H), 1.95-1.82 (m, 2H), 1.26 (t, J = 7.2 Hz, 3H) | 10-80 3.93 | *** |
| 1364 | 605.3 (cal.604.2) | $^1$H NMR (CD3CN, 300 MHz) δ9.17 (b, 1H), 7.56 (d, J = 2.1 Hz, 1H), 7.33-7.26 (m, 2H), 7.14-7.10 (m, 5H), 6.91-6.84 (m, 3H), 6.47 (s, 1H), 4.42-4.40 (m, 1H), 3.98 (t, J = 6.3 Hz, 2H), 3.50-3.27 (m, 5H), 2.89-2.89 (m, 2H), 2.45-2.30 (m, 6H), 1.97 (s, 3H), 1.90-1.87 (m, 2H) | 10-80 4.41 | *** |
| 1365 | 437.22 | | 3.95 | ***** |
| 1366 | 451.21 | | 4.42 | ***** |
| 1367 | 465.23 | | 3.63 | ***** |
| 1368 | 469.23 | | 3.87 | ***** |
| 1369 | 397.24 | | 3.6 | **** |

TABLE 2-continued

| Cpd | MS | NMR | RT | EC$_{50}$ |
|---|---|---|---|---|
| 1370 | 411.18 | | 3.73 | **** |
| 1371 | 411.27 | | 3.88 | **** |
| 1372 | 425.28 | | 4.10 | ***** |
| 1373 | 485.36 | | 3.30 | ***** |
| 1374 | 499.36 | | 3.53 | ***** |
| 1375 | 499.06 | | 3.45 | ***** |
| 1376 | 513.10 | | 3.82 | ***** |
| 1377 | 471.3 | | 3.23 | ***** |
| 1378 | 485.3 | | 3.38 | ***** |
| 1379 | 485.4 | | 3.45 | ***** |
| 1380 | 471.3 | | 3.22 | ***** |
| 1381 | 485.3 | | 3.38 | ***** |
| 1382 | 485.3 | $^1$H NMR (300 MHz, DMSO-d$_6$) δ ppm 1.64-1.91 (m, 4 H) 1.99 (br. s., 2 H) 2.59 (br. s., 1 H) 2.67-2.86 (m, 2 H) 2.92-3.15 (m, 1 H) 3.40 (br. s., 2 H) 3.74 (br. s., 1 H) 3.77-3.87 (m, 1 H) 3.90-4.04 (m, 2 H) 4.10 (br. s., 2 H) 4.65 (br. s., 1 H) 4.93 (br. s., 1 H) 6.27 (br. s., 1 H) 6.90 (d, J = 8.58 Hz, 2 H) 7.05 (dd, J = 8.58, 1.98 Hz, 1 H) 7.09 (d, J = 8.58 Hz, 2 H) 7.28 (d, J = 8.58 Hz, 1 H) 7.49 (d, J = 1.98 Hz, 1 H) 11.11 (br. s., 1 H) | 3.45 | ***** |
| 1383 | 513.4 | | 3.58 | ***** |
| 1384 | 527.4 | | 3.73 | ***** |
| 1385 | 527.4 | | 3.82 | ***** |
| 1386 | M − 1:539.2 (cal.540.2) | $^1$H NMR (CD3CN, 300 MHz), δ 9.09 (b, 1H), 7.51 (d, J = 2.1 Hz, 1H), 7.28 (d, J = 8.7 Hz, 1H), 7.18 (d, J = 8.7 Hz, 2H), 7.08 (dd, J = 8.7 Hz and 2.1 Hz, 1H), 6.91 (d, J = 8.4 Hz, 2H), 6.37 (s, 1H), 4.79 (d, J = 6.0 Hz, 1H), 4.73 (d, J = 6.0 Hz, 1H), 4.28-4.23 (m, 1H), 4.16-4.02 (m, 2H), 3.98 (s, 2H), 3.84 (d, J = 11.7 Hz, 2H), 3.75 (d, J = 11.7 Hz, 2H), 3.56 (d, J = 5.7 Hz, 2H), 3.18-3.09 (m, 1H), 2.89-2.74 (m, 3H), 2.65-2.60 (m, 1H), 2.10-2.01 (m, 2H), 1.89-1.75 (m, 4H). | 10-80 4.97 | **** |
| 1387 | 484.0 (cal.483.2) | $^1$H NMR (CD3OD, 400 MHz), δ 7.83 (d, J = 8.0 Hz, 2H), 7.47 (d, J = 1.6 Hz, 1H), 7.39 (d, J = 8.0 Hz, 2H), 7.24 (d, J = 8.4 Hz, 1H), 7.06 (dd, J = 8.4 Hz and 1.6 Hz, 1H), 6.49 (b, 1H), 4.25-4.17 (m, 5H), 4.08 (s, 2H), 3.17-3.09 (m, 1H), 2.90-2.78 (m, 2H), 1.32 (s, 3H), 1.27 (t, J = 7.2 Hz, 3H). | 30-90 4.48 | *** |
| 1388 | 456.0 (cal.455.1) | $^1$H NMR (CD3OD, 300 MHz), δ 7.83 (d, J = 8.4 Hz, 2H), 7.46 (d, J = 1.8 Hz, 1H), 7.38 (d, J = 8.1 Hz, 2H), 7.24 (d, J = 8.4 Hz, 1H), 7.06 (dd, J = 8.4 Hz and 2.1 Hz, 1H), 6.49 (b, 1H), 4.35-4.19 (m, 3H), 4.07 (s, 2H), 3.19-3.11 (m, 1H), 2.91-2.76 (m, 2H), 1.31 (t, J = 6.9 Hz, 3H) | 10-80 5.49 | * |
| 1389 | 470.0 (cal.469.1) | $^1$H NMR (CD3OD, 300 MHz), δ 7.45 (d, J = 6.0 Hz, 2H), 7.40 (s, 1H), 7.36 (t, J = 5.1 Hz, 2H), 7.23 (d, J = 8.7 Hz, 1H), 7.05 (dd, J = 8.7 Hz and 1.5 Hz, 1H), 6.42 (b, 1H), 4.35-4.21 (m, 4H), 4.00 (s, 1H), 3.18-3.1 (m, 1H), 3.02 (s, 3H), 2.85-2.80 (m, 2H), 1.31 (s, 3H) | 10-80 5.57 | * |
| 1390 | 513.9 | $^1$H NMR (CD3OD, 300 MHz), δ 7.62 (s, 1H), 7.45 (d, J = 8.4 Hz, 1H), 7.38 (d, J = 8.4 Hz, 1H), 7.35 (s, 2H), 7.19 (s, 2H), 6.47 (b, 1H), 4.37-4.20 (m, 5H), 3.21-3.02 (m, 4H), 2.91-2.88 (s, 2H), 1.30 (s, 3H) | 5.66 | * |
| 1391 | 563.4 | 1H NMR (300 MHz, Acetone) ppm 2.95 (d, J = 5.09 Hz, 2 H) 3.24-3.43 (m, 1 H) 3.82 (t, J = 4.77 Hz, 2 H) 4.29 (t, J = 5.25 Hz, 2 H) 4.44 (br. s., 1 H) 6.53 (br. s., 1 H) 6.86 (d, J = 4.13 Hz, 1 H) 6.98 (d, J = 8.58 Hz, 2 H) 7.08-7.43 (m, 9 H) 7.56 (d, J = 1.91 Hz, 1 H) 10.21 (br. s., 1 H) | 2.93 | ***** |
| 1392 | 577.4 | | 2.82 | ***** |
| 1393 | 579.4 | | 3.08 | ***** |
| 1394 | 593.3 | | 2.95 | ***** |
| 1396 | 486.9 (cal.486.2) | $^1$H NMR (CD3OD, 300 MHz) δ7.48 (s, 1H), 7.32 (d, J = 8.1 Hz, 1H), 7.15-7.12 (m, 3H), 691-6.88 (m, 2H), 6.68 (s, 1H), 4.27-4.20 (m, 3H), 4.09-4.01 (m, 3H), 3.77-3.70 (m, 3H), 3.49-3.37 (m, 2H), 2.85-2.76 (m, 2H), 1.98-1.93 (m, 2H), 1.43-1.29 (m, 3H) | 10-80 5.13 | * |
| 1397 | 456.2 | | 2.33 | *** |
| 1398 | 493.3 | | 3.47 | *** |
| 1399 | 494.4 | | 2.63 | ***** |
| 1400 | 498.4 | | 3.40 | ***** |
| 1401 | 505.4 | | 3.52 | **** |
| 1402 | 480.4 | | 2.38 | ** |
| 1403 | 522.3 | | 3.48 | ***** |
| 1404 | 547.5 | | 3.22 | *** |
| 1405 | 523.4 | | 4.00 | *** |
| 1406 | 524.4 | | 3.10 | *** |
| 1407 | 526.4 | | 3.72 | ***** |
| 1408 | 533.4 | | 3.78 | ***** |
| 1409 | 508.6 | | 2.53 | ** |
| 1410 | 486.4 | | 2.25 | * |
| 1411 | 525.4 | | 3.52 | ** |
| 1412 | 528.4 | | 3.20 | **** |
| 1413 | 546.4 | | 3.23 | ***** |
| 1414 | 560.4 | | 2.83 | ***** |
| 1415 | 564.4 | | 3.65 | ***** |
| 1416 | 589.5 | | 3.40 | *** |
| 1417 | 562.4 | | 3.42 | ***** |
| 1418 | 576.4 | | 2.95 | **** |

TABLE 2-continued

| Cpd | MS | NMR | RT | EC$_{50}$ |
|---|---|---|---|---|
| 1419 | 577.4 | | 4.05 | **** |
| 1420 | 580.3 | | 3.83 | ***** |
| 1421 | 587.4 | | 3.88 | ***** |
| 1422 | 605.4 | | 3.55 | **** |
| 1423 | M − 1:417.2 (cal.418.2) | $^1$H NMR (DMSO, 400 MHz) δ11.37 (b, 1H), 7.64 (d, J = 8.4 Hz, 1H), 7.59 (s, 1H), 7.27 (d, J = 8.4 Hz, 1H), 7.11 (d, J = 8.4 Hz, 2H), 6.89 (d, J = 8.4 Hz, 2H), 6.38-6.34 (m, 1H), 4.12-4.09 (m, 3H), 3.70 (s, 3H), 3.06-3.00 (m, 1H), 2.84-2.75 (m, 2H), 1.20-1.13 (m, 3H) | 10-80 4.90 | * |
| 1424 | M − 1:483.2 (cal.484.1) | $^1$H NMR (DMSO, 400 MHz) δ11.42-11.35 (m, 1H), 7.69 (d, J = 8.0 Hz, 1H), 7.62 (s, 1H), 7.30 (d, J = 8.8 Hz, 1H), 7.21-7.16 (m, 6H), 6.94-6.93 (m, 2H), 6.52-6.41 (m, 1H), 3.72 (s, 3H), 3.29-3.19 (m, 1H), 3.00-2.84 (m, 2H) | 30-90 5.39 | * |
| 1425 | M − 1:495.2 (cal.496.2) | $^1$H NMR (DMSO, 400 MHz) δ11.43-11.36 (m, 1H), 7.69 (d, J = 8.0 Hz, 1H), 7.62 (s, 1H), 7.30 (d, J = 8.0 Hz, 1H), 7.26-7.15 (m, 2H), 7.05 (d, J = 8.8 Hz, 2H), 6.92-6.90 (m, 2H), 6.52-6.43 (m, 1H), 4.32-4.30 (m, 1H), 3.72 (s, 3H), 3.22-3.19 (m, 1H), 3.00-2.91 (m, 2H) | 30-90 5.33 | * |
| 1426 | | | | * |
| 1427 | 443.45 | | 3.98 | * |
| 1428 | 365.42 | | 3.82 | * |
| 1429 | 445.36 (ES−) | | 4.18 | * |
| 1430 | 389.46 | | 3.83 | * |
| 1431 | 351.41 | | 3.67 | * |
| 1432 | 531.31 | | 2.48 | **** |
| 1433 | 492.9 | | 3.37 | ***** |
| 1434 | 528.9 | | 3.53 | ***** |
| 1435 | 483.8 | | 2.40 | ** |
| 1436 | 521.0 | | 3.73 | ***** |
| 1437 | 523.9 | | 2.43 | **** |
| 1438 | 534.9 | | 3.30 | *** |
| 1439 | 552.9 | | 2.90 | ** |
| 1440 | 558.9 | | 3.65 | ***** |
| 1441 | 571.5 | | 3.75 | **** |
| 1442 | 574.9 | | 3.85 | ***** |
| 1443 | 409 | | 3.80 | ** |
| 1444 | 465 (M − H) | | 4.07 | *** |
| 1445 | 489 | | 3.88 | *** |
| 1446 | 547 | | 4.12 | *** |
| 1447 | 543 | | 3.97 | *** |
| 1448 | 483-485 | 1H NMR (300 MHz, (CD3)2CO-d6) δ 2.86-2.88 (m, 3H), 3.14-3.23 (m, 1H), 4.34-4.36 (m, 1H), 4.43-4.46 (m, 1H), 4.62 (bm, 1H), 4.77 (bm, 1H), 6.50 (bm, 1H), 6.87 (t, J = 74.7 Hz, 1H), 7.14-7.21 (m, 3H), 7.37 (bd, J = 8.4 Hz, 2H), 7.49 (d, J = 8.4 Hz, 1H), 7.55 (d, J = 1.2 Hz, 1H), 10.21 (s, 1H). | 3.72 | ** |
| 1449 | 549 | | 4.05 | ** |
| 1450 | 531 | | 3.98 | *** |
| 1451 | 395-397 | | 2.05 | |
| 1452 | 403 | | 3.62 | |
| 1453 | 451 | | 3.97 | |
| 1454 | 513 | | 4.23 | |
| 1455 | 463 | | 3.95 | * |
| 1456 | 377 | | 3.78 | * |
| 1457 | 435 | | 4.12 | ** |
| 1458 | 435 | | 3.82 | * |
| 1459 | 439 | | 3.98 | * |
| 1460 | 447 | | 3.78 | * |
| 1461 | 451 | | 3.97 | ** |
| 1462 | 483 | | 3.80 | ** |
| 1463 | 487 | | 3.98 | *** |
| 1464 | 500.1 (cal: 499.2) | $^1$H NMR (CDCl3, 300 MHz) δ 7.87 (b, 1H), 7.50 (d, J = 1.8 Hz, 1H), 7.23-7.10 (m, 4H), 6.82 (d, J = 8.7 Hz, 2H), 6.42 (b, 1H), 5.94 (t, J = 3.3 Hz, 1H), 4.40-4.13 (m, 3H), 4.11-4.02 (m, 1H), 3.90 (d, J = 5.4 Hz, 2H), 3.65-3.55 (m, 1H), 3.42-3.33 (m, 1H), 3.20-3.07 (m, 1H), 2.92-2.70 (m, 2H), 2.25 (q, J = 7.5 Hz, 2H), 1.30 (t, J = 6.9 Hz, 3H), 1.16 (t, J = 7.5 Hz, 3H). | 10-80 5.09 | **** |
| 1465 | 514.1 (cal: 513.2) | $^1$H NMR (CDCl3, 300 MHz) δ 7.89 (b, 1H), 7.50 (d, J = 1.5 Hz, 1H), 7.23-7.10 (m, 4H), 6.82 (d, J = 8.4 Hz, 2H), 6.40 (b, 1H), 5.98 (b, 1H), 4.47-4.18 (m, 3H), 4.13-4.02 (m, 1H), 3.90 (d, J = 4.8 Hz, 2H), 3.65-3.55 (m, 1H), 3.45-3.33 (m, 1H), 3.19-3.04 (m, 1H), 2.92-2.70 (m, 2H), 2.45-2.34 (m, 1H), 1.27 (t, J = 3.9 Hz, 3H), 1.18 (d, J = 6.3 Hz, 6H). | 10-80 5.24 | **** |
| 1466 | 512.1 (cal: 511.2) | $^1$H NMR (CDCl3, 300 MHz) δ 7.85 (b, 1H), 7.50 (d, J = 1.2 Hz, 1H), 7.23-7.10 (m, 4H), 6.82 (d, J = 8.4 Hz, 2H), 6.40 (b, 1H), 6.12 (b, 1H), 4.45-4.15 (m, 3H), 4.13-4.05 (m, 1H), 3.90 (d, J = 5.4 Hz, 2H), 3.67-3.60 (m, 1H), 3.47-3.35 (m, 1H), 3.19-3.06 (m, 1H), 2.94-2.70 (m, 2H), 1.45-1.28 (m, 4H), 1.00-0.93 (m, 2H), 0.80-0.76 (m, 2H). | 10-80 5.19 | **** |

TABLE 2-continued

| Cpd | MS | NMR | RT | EC$_{50}$ |
|---|---|---|---|---|
| 1467 | 549.1 (cal: 548.2) | $^1$H NMR (DMSO, 300 MHz) δ 11.06 (b, 1H), 8.73-8.63 (m, 3H), 7.68 (b, 2H), 7.44 (s, 1H), 7.22 (d, J = 8.4 Hz, 1H), 7.11-6.93 (m, 3H), 6.90-6.76 (m, 2H), 6.25 (b, 1H), 5.21 (s, 1H), 4.20-3.78 (m, 6H), 3.50-3.40 (m, 2H), 2.95 (b, 1H), 2.69 (b, 2H), 1.16 (b, 3H). | 10-80 4.61 | ***** |
| 1468 | 549.1 (cal: 548.2) | $^1$H NMR (DMSO, 300 MHz) δ 11.05 (b, 1H), 8.96 (s, 1H), 8.71-8.62 (m, 2H), 8.13 (d, J = 7.2 Hz, 1H), 7.46-7.42 (m, 2H), 7.24 (d, J = 8.4 Hz, 1H), 7.08-7.01 (m, 3H), 6.87 (d, J = 5.4 Hz, 2H), 6.28 (b, 1H), 5.21 (d, J = 4.8 Hz, 1H), 4.08-3.83 (m, 6H), 3.50-3.40 (m, 1H), 3.05-2.90 (m, 1H), 2.78-2.59 (m, 2H), 1.27-1.13 (m, 3H). | 10-80 4.65 | ***** |
| 1469 | 549.1 (cal: 548.2) | $^1$H NMR (CDCl3, 300 MHz) δ 8.55 (d, J = 4.2 Hz, 1H), 8.49 (t, J = 3.9 Hz, 1H), 8.18 (d, J = 7.8 Hz, 1H), 7.87 (t, J = 6.0 Hz, 1H), 7.79 (b, 1H), 7.50-7.45 (m, 2H), 7.23-7.11 (m, 4H), 6.85 (d, J = 8.1 Hz, 2H), 6.41 (b, 1H), 4.44-4.12 (m, 4H), 3.99 (d, J = 5.4 Hz, 2H), 3.98-3.82 (m, 1H), 3.70-3.59 (m, 1H), 3.21-3.09 (m, 1H), 2.94-2.72 (m, 2H), 1.28 (t, J = 7.2 Hz, 3H). | 10-80 5.42 | ***** |
| 1470 | 516.1 (cal: 515.2) | $^1$H NMR (CDCl3, 300 MHz) δ 7.86 (b, 1H), 7.50 (s, 1H), 7.22-7.10 (m, 4H), 6.82 (d, J = 8.4 Hz, 2H), 6.41 (b, 1H), 5.09 (b, 1H), 4.40-4.05 (m, 6H), 3.95-3.90 (m, 2H), 3.47-3.34 (m, 1H), 3.39-3.28 (m, 1H), 3.20-3.05 (m, 1H), 2.96-2.75 (m, 2H), 1.26-1.78 (m, 6H). | 10-80 5.39 | ***** |
| 1471 | 530.1 (cal: 529.2) | $^1$H NMR (CDCl3, 300 MHz) δ 8.15 (b, 1H), 7.49 (s, 1H), 7.20-7.10 (m, 4H), 6.78 (d, J = 8.1 Hz, 2H), 6.39 (b, 1H), 5.13 (b, 1H), 4.43-4.13 (m, 3H), 4.03-3.99 (m, 3H), 3.90 (b, 2H), 3.52-3.43 (m, 1H), 3.38-3.23 (m, 1H), 3.19-3.04 (m, 1H), 2.95-2.69 (m, 2H), 1.66-1.59 (m, 2H), 1.27 (t, J = 6.0 Hz, 3H), 0.92 (t, J = 7.5 Hz, 3H). | 10-80 5.24 | ***** |
| 1472 | 546.1 (cal: 545.2) | $^1$H NMR (CDCl3, 300 MHz) δ 7.85 (b, 1H), 7.50 (d, J = 1.5 Hz, 1H), 7.23-7.10 (m, 4H), 6.82 (d, J = 8.7 Hz, 2H), 6.42 (b, 1H), 5.22 (b, 1H), 4.46-4.11 (m, 6H), 3.99-3.87 (m, 2H), 3.60-3.46 (m, 3H), 3.39 (s, 3H), 3.37-3.31 (m, 1H), 3.20-3.06 (m, 1H), 2.93-2.72 (m, 2H), 1.30 (t, J = 6.3 Hz, 3H). | 10-80 5.20 | ***** |
| 1473 | 536.1 (cal: 535.2) | $^1$H NMR (CDCl3, 300 MHz) δ 7.85 (b, 1H), 7.50 (s, 1H), 7.23-7.18 (m, 3H), 7.12 (dd, J = 8.4 Hz and 1.8 Hz, 1H), 6.83 (d, J = 8.4 Hz, 2H), 6.42 (b, 1H), 4.70 (t, J = 6 Hz, 1H), 4.21-4.07 (m, 4H), 3.99 (s, 2H), 3.45-3.37 (m, 1H), 3.31-3.23 (m, 1H), 3.18-3.05 (m, 3H), 2.92-2.85 (m, 1H), 2.79-2.74 (m, 1H), 1.38 (t, J = 7.5 Hz, 3H), 1.30 (t, J = 6.3 Hz, 3H). | 10-80 5.23 | ***** |
| 1474 | 550.1 (cal: 549.2) | $^1$H NMR (CDCl3, 300 MHz) δ 8.89 (b, 1H), 7.46 (s, 1H), 7.19-7.05 (m, 4H), 6.73 (d, J = 7.8 Hz, 2H), 6.35 (b, 1H), 5.17 (b, 1H), 4.20-4.10 (m, 5H), 3.65-3.35 (m, 3H), 3.10-3.02 (m, 2H), 2.84-2.68 (m, 3H), 1.37-1.25 (m, 6H), 1.18-1.16 (m, 3H). | 10-80 4.89 | **** |
| 1475 | 548.1 (cal: 547.2) | $^1$H NMR (CDCl3, 300 MHz) δ 7.83 (b, 1H), 7.50 (s, 1H), 7.23-7.18 (m, 3H), 7.12 (dd, J = 8.4 Hz and 1.5 Hz, 1H), 8.43 (d, J = 8.1 Hz, 2H), 6.41 (b, 1H), 4.73 (s, 1H), 4.25-4.15 (m, 4H), 4.00-3.99 (m, 2H), 3.45-3.43 (m, 1H), 3.34-3.30 (m, 1H), 3.18-3.08 (m, 1H), 2.92-2.74 (m, 2H), 2.45 (b, 1H), 1.32-1.28 (m, 3H), 1.19-1.18 (m, 2H), 1.02-1.00 (m, 2H). | 10-80 5.31 | ***** |
| 1476 | 580.56 | | 2.43 | *** |
| 1477 | 464.14 | | 4.25 | **** |
| 1478 | 464.14 | | 3.88 | *** |
| 1479 | 468.09 | | 4.10 | **** |
| 1480 | 387.92 | | 3.70 | **** |
| 1481 | 414.37 | | 4.05 | **** |
| 1482 | 397.28 | | 3.37 | *** |
| 1483 | 478.70 | | 3.90 | **** |
| 1484 | 474.69 | | 3.62 | *** |
| 1485 | 464.82 | | 3.55 | *** |
| 1486 | 478.00 | | 3.73 | **** |
| 1487 | 324.94 | | 2.48 | * |
| 1488 | 413.21 | | 2.43 | * |
| 1489 | 495.15 | | 3.03 | * |
| 1490 | 491.20 | | 2.73 | * |
| 1491 | 479.00 | | 2.08 | * |
| 1492 | 479.00 | | 2.92 | *** |
| 1493 | 441.04 | | 2.07 | * |
| 1494 | 441.05 | | 2.00 | * |
| 1495 | 341.29 | | 1.47 | * |
| 1496 | 429.05 | | 2.05 | * |
| 1497 | 511.01 | | 2.78 | * |
| 1498 | 507.06 | | 2.42 | * |
| 1499 | 495.01 | | 2.52 | * |
| 1500 | 511.01 | | 2.80 | * |
| 1502 | 457.04 | | 2.50 | * |
| 1503 | 507.26 | | 2.55 | * |
| 1504 | 357.02 | | 2.42 | * |
| 1505 | 502.4 | | 3.43 | * |
| 1506 | 601.6 | | 2.18 | * |
| 1508 | C$_{31}$H$_{28}$ClN$_5$O$_2$, (538.5) | | 4.070 | **** |

TABLE 2-continued

| Cpd | MS | NMR | RT | EC$_{50}$ |
|---|---|---|---|---|
| 1509 | C$_{28}$H$_{32}$ClN$_3$O$_3$, (494.5) | | 3.903 | *** |
| 1510 | C$_{26}$H$_{26}$ClN$_5$O$_2$, (476.5) | | 4.067 | **** |
| 1511 | C$_{33}$H$_{34}$ClN$_3$O$_4$, (556.5) | | 4.539 | **** |
| 1512 | 376.35 | | 2.27 | ** |
| 1513 | 458.14 | | 2.87 | *** |
| 1514 | 442.30 | | 2.62 | *** |
| 1515 | 458.23 | | 2.83 | *** |
| 1516 | 454.30 | | 2.53 | ** |
| 1517 | 404.36 | | 2.67 | ** |
| 1518 | 404.36 | | 2.73 | *** |
| 1519 | 304.19 | | 1.73 | * |
| 1520 | 492 | | 3.87 | ***** |
| 1521 | 429, 431 | 1H NMR (300 MHz, (CD3)2CO) δ 1.28 (t, J = 6.9 Hz, 3H), 3.00-3.20 (m, 2H), 3.16-3.23 (m, 2H), 3.25-3.40 (m, 1H), 3.78 (s, 3H), 4.16 (q, J = 6.9 Hz, 2H), 4.13-4.33 (m, 1H), 6.41 (bm, 1H), 6.89 (dm, J = 8.7 Hz, 1H), 6.99 (t, J = 8.6 Hz, 2H), 7.17-7.25 (m, 3H), 7.35 (dd, J = 8.6, 2.1 Hz, 1H), 7.53 (d, J = 1.8 Hz, 1H), 8.60 (J = 4.8 Hz, 2H), 10.28 (s, 1H). | 3.87 | ** |
| 1522 | 447, 449 | | 3.65 | ** |
| 1523 | 453, 455 | | 3.87 | *** |
| 1524 | 495, 497 | | 4.02 | *** |
| 1525 | 511, 513 | | 4.25 | *** |
| 1526 | 555, 557 | | 4.33 | *** |
| 1527 | 507, 509 | | 3.98 | ** |
| 1528 | 511, 513 | | 4.18 | * |
| 1529 | 403 | | 3.60 | ** |
| 1530 | 409 | 1H NMR (300 MHz, (CD3)2CO)δ 1.82 (s, 3H), 2.96-3.31 (m, 3H), 3.78 (s, 3H), 4.25 (mc, 1H), 4.74 (s, 2H), 6.44 (mc, 1H), 6.90 (dm, J = 9.0 Hz, 2H), 7.00-7.09 (m,, 2H), 7.23 (bm, J = 9.0 Hz, 1H), 7.31 (dd, J = 7.2, 1.5 Hz, 1.5 Hz, 1H), 10.28 (s, 1H). | 3.82 | *** |
| 1531 | 467 | | 4.18 | *** |
| 1532 | 511, 513 | | 4.25 | *** |
| 1533 | 451 | | 3.97 | *** |
| 1534 | 463 | | 3.95 | ** |
| 1535 | 357 | | 1.83 | * |
| 1536 | 313 | | 1.80 | * |
| 1537 | 594.23 | | 2.40 | ***** |
| 1538 | 495.2 | | 3.95 | ***** |
| 1539 | 495.08 | | 3.95 | *** |
| 1540 | 403.21 | | 2.12 | **** |
| 1541 | C$_{29}$H$_{34}$ClN$_3$O$_4$, (508.5) | | 4.127 | **** |
| 1542 | C$_{27}$H$_{28}$ClN$_5$O$_2$, (490.5) | | 4.282 | ***** |
| 1543 | 410 | 1H NMR (300 MHz, (CD3)2CO-d6) δ 1.28 (t, J = 6.5 Hz, 3H), 2.84-2.86 (m, 2H), 3.11-3.18 (m, 1H), 4.17 (q, J = 6.9 Hz, 1H), 4.30 (bs, 1H), 5.10 (s, 2H), 6.47 (bs, 1H), 7.04-7.12 (m, 3H), 7.29-7.37 (m, 3H), 7.53 (d, J = 1.8 Hz, 1H), 10.19 (bs, 1H). | 3.53 | ***** |
| 1544 | 428 | | 3.42 | **** |
| 1545 | 446 | | 2.98 | ***** |
| 1546 | 492 | | 3.85 | *** |
| 1547 | 534, 536 | | 3.93 | ***** |
| 1548 | 474 | | 3.75 | **** |
| 1549 | 488 | | 3.77 | **** |
| 1550 | 338 | | 1.77 | ** |
| 1551 | (573, 571) (M ++ 1, M +− 1) | 1H NMR (300 MHz, CD3)2CO δ 2.22-2.32 (m, 2H), 2.90-3.10 (m, 5H), 3.26-3.31 (m, 3H), 4.17 (t, J = 6.3 Hz, 2H), 4.43 (mc, 1H), 6.52 (bm, 1H), 6.95 (d, J = 9.0 Hz, 2H), 7.11 (dd, J = 9.0, 2.4 Hz, 1H), 7.40-7.58 (m, 4H), 7.37 (d, J = 8.4 Hz, 1H), 7.42 (dm, J = 9.3 Hz, 2H), 7.56 (d, J = 2.2 Hz, 1H), 10.22 (s, 1H). | 3.83 | ***** |
| 1552 | 555 | | 4.68 | ***** |
| 1553 | 569 | | 4.88 | ***** |
| 1554 | 608 | | 2.40 | * |
| 1555 | 624 | | 3.80 | ***** |
| 1556 | 546 | | 2.33 | *** |
| 1557 | M − 1:614.2 (cal: 615.2) | $^1$H NMR (CD3CN, 300 MHz) δ 9.17 (s, 1H), 7.54 (d, J = 2.1 Hz, 1H), 7.32-7.21 (m, 3H), 7.14-7.10 (m, 5H), 6.92 (d, J = 8.4 Hz, 2H), 6.45 (b, 1H), 5.28 (b, 1H), 4.39 (b, 1H), 4.00-3.90 (m, 3H), 3.33-3.10 (m, 4H), 3.02-2.82 (m, 3H), 1.27 (q, J = 6.9 Hz, 6H). | 30-90 4.52 | ** |
| 1558 | M + 23:604.2 (cal: 581.2) | $^1$H NMR (CD3CN, 300 MHz) δ 9.25 (s, 1H), 7.53 (d, J = 1.8 Hz, 1H), 7.36 (d, J = 8.7 Hz, 2H), 7.29-7.23 (m, 3H), 7.12-7.07 (m, 3H), 6.87 (d, J = 8.1 Hz, 2H), 6.59 (b, 1H), 6.45 (b, 1H), 4.35 (b, 1H), 3.90-3.85 (m, 3H), 3.42-3.19 (m, 3H), 2.87-2.82 (m, 2H), 2.14 (q, J = 7.8 Hz, 2H), 1.03 (t, J = 7.5 Hz, 3H). | 30-90 4.57 | **** |

TABLE 2-continued

| Cpd | MS | NMR | RT | EC$_{50}$ |
|---|---|---|---|---|
| 1559 | 596.1 (cal: 595.2) | $^1$H NMR (CD3CN, 300 MHz) δ 9.21 (b, 1H), 7.54 (s, 1H), 7.37 (d, J = 8.7 Hz, 2H), 7.30-7.23 (m, 3H), 7.12-7.08 (m, 3H), 6.89 (d, J = 8.1 Hz, 2H), 6.58 (b, 1H), 6.46 (b, 1H), 4.38 (b, 1H), 3.90-3.86 (m, 3H), 3.38-3.34 (m, 1H), 3.29-3.22 (m, 2H), 2.88-2.84 (m, 3H), 2.38-2.32 (m, 1H), 1.04 (d, J = 6.9 Hz, 6H). | 30-90 4.88 | **** |
| 1560 | M + 23:616.2 (cal: 593.2) | $^1$H NMR (CD3CN, 300 MHz) δ 9.29 (b, 1H), 7.53 (s, 1H), 7.35 (d, J = 9.0 Hz, 2H), 7.28-7.21 (m, 3H), 7.11-7.07 (m, 3H), 6.88-6.85 (m, 2H), 6.44 (b, 1H), 4.34 (s, 1H), 3.90-3.85 (m, 3H), 3.44-3.36 (m, 1H), 3.28-3.19 (m, 2H), 2.87-2.81 (m, 3H), 1.52-1.44 (m, 1H), 0.75-0.67 (m, 4H). | 30-90 4.82 | **** |
| 1561 | 631.1 (cal: 630.1) | $^1$H NMR (CD3CN, 300 MHz) δ 9.23 (b, 1H), 8.92 (s, 1H), 8.67 (d, J = 3.3 Hz, 1H), 8.10 (d, J = 7.8 Hz, 1H), 7.55 (s, 1H), 7.43-7.36 (m, 3H), 7.30-7.23 (m, 3H), 7.13-7.08 (m, 3H), 7.91 (d, J = 8.4 Hz, 2H), 6.46 (s, 1H), 4.38 (b, 1H), 4.10-4.05 (m, 1H), 4.00-3.96 (m, 2H), 3.65-3.45 (m, 2H), 3.33-3.22 (m, 1H), 2.88-2.84 (m, 3H). | 30-90 4.15 | **** |
| 1562 | M − 1:596.0 (cal: 597.1) | $^1$H NMR (CDCl3, 300 MHz) δ 8.16-7.95 (m, 1H), 7.52 (s, 1H), 7.32 (d, J = 8.1 Hz, 2H), 7.26-7.22 (m, 2H), 7.14 (s, 2H), 7.04 (d, J = 8.7 Hz, 2H), 6.82 (d, J = 8.1 Hz, 2H), 6.46 (s, 1H), 5.13 (b, 1H), 4.45-4.42 (m, 1H), 4.15-4.08 (m, 3H), 3.92-3.90 (m, 2H), 3.51-3.46 (m, 1H), 3.33-3.19 (m, 3H), 3.03-2.82 (m, 2H), 1.24 (t, J = 6.6 Hz, 3H). | 30-90 4.98 | **** |
| 1563 | M − 1:610.0 (cal: 611.2) | $^1$H NMR (CD3CN, 300 MHz) δ 9.12 (b, 1H), 7.55 (s, 1H), 7.37 (d, J = 8.4 Hz, 2H), 7.30-7.23 (m, 3H), 7.13-7.08 (m, 3H), 6.92-6.89 (d, J = 8.1 Hz, 2H), 6.46 (b, 1H), 5.61 (b, 1H), 4.40-4.32 (m, 1H), 3.95-3.91 (m, 5H), 3.32-3.14 (m, 3H), 2.97-2.82 (m, 2H), 1.56 (q, J = 6.9 Hz, 2H), 0.89 (t, J = 7.5 Hz, 3H). | 30-90 5.25 | **** |
| 1564 | M + 23:650.2 (cal: 627.2) | $^1$H NMR (CD3CN, 300 MHz) δ 9.16 (b, 1H), 7.54 (s, 1H), 7.37 (d, J = 8.7 Hz, 2H), 7.30-7.27 (m, 3H), 7.13-7.08 (m, 3H), 6.90 (d, J = 8.4 Hz, 2H), 6.46 (b, 1H), 5.68 (b, 1H), 4.39 (b, 1H), 4.10 (t, J = 4.5 Hz, 2H), 3.94-3.87 (m, 3H), 3.50-3.47 (m, 3H), 3.22-3.15 (m, 6H), 2.88-2.83 (m, 3H). | 30-90 4.83 | ***** |
| 1565 | M − 1:616.1 (cal: 617.1) | $^1$H NMR (CD3CN, 300 MHz) δ 9.16 (b, 1H), 7.55 (d, J = 1.5 Hz, 1H), 7.38 (d, J = 8.7 Hz, 2H), 7.31-7.28 (m, 3H), 7.13-7.09 (m, 3H), 6.92 (d, J = 8.4 Hz, 2H), 6.47 (b, 1H), 5.35 (b, 1H), 4.36 (b, 1H), 3.98-3.92 (m, 3H), 3.33-3.12 (m, 3H), 3.02 (q, J = 7.5 Hz, 2H), 2.88-2.84 (m, 3H), 1.11 (t, J = 7.2 Hz, 3H). | 30-90 4.83 | **** |
| 1566 | M − 1:630.1 (cal: 631.1) | $^1$H NMR (CD3CN, 300 Hz) δ 9.15 (b, 1H), 7.55 (d, J = 1.8 Hz, 1H), 7.38 (d, J = 9.0 Hz, 2H), 7.31-7.28 (m, 3H), 7.14-7.09 (m, 3H), 6.92 (d, J = 8.7 Hz, 2H), 6.48 (b, 1H), 5.28 (b, 1H), 4.40 (b, 1H), 3.98-3.91 (m, 3H), 3.28-3.18 (m, 4H), 3.01-2.88 (m, 3H), 1.27 (d, J = 6.9 Hz, 6H). | 30-90 4.85 | *** |
| 1567 | M + 23:652.1 (cal: 629.1) | $^1$H NMR (CD3CN, 300 MHz) δ 9.17 (b, 1H), 7.55 (s, J = 1.8 Hz, 1H), 7.37 (d, J = 9.0 Hz, 2H), 7.30-7.27 (m, 3H), 7.13-7.08 (m, 3H), 6.91 (d, J = 8.7 Hz, 2H), 6.46 (b, 1H), 5.38 (b, 1H), 4.35 (b, 1H), 3.99-3.92 (m, 3H), 3.33-3.15 (m, 3H), 2.88-2.83 (m, 2H), 2.51-2.43 (m, 1H), 0.98-0.93 (m, 4H). | 30-90 4.93 | *** |
| 1568 | 593.2 | 1H NMR (300 MHz, DMSO-d6) δ ppm 1.94 (d, J = 1.32 Hz, 3 H) 2.86 (br. s., 2 H) 3.10-3.27 (m, 1 H) 3.89 (t, J = 5.61 Hz, 2 H) 4.12 (t, J = 5.44 Hz, 2 H) 4.31 (d, J = 14.52 Hz, 1 H) 6.38 (br. s., 1 H) 6.47 (d, J = 1.32 Hz, 1 H) 6.96 (d, J = 8.25 Hz, 2 H) 7.07 (dd, J = 8.58, 1.98 Hz, 1 H) 7.11-7.25 (m, 4 H) 7.30 (d, J = 8.91 Hz, 1 H) 7.44 (d, J = 8.58 Hz, 2 H) 7.54 (d, J = 2.31 Hz, 1 H) 8.63 (d, J = 83.14 Hz, 1 H) 11.06-11.21 (m, 1 H) | 2.43 | **** |
| 1569 | 615 | | 4.52 | ***** |
| 1570 | 531 | | 3.90 | ***** |
| 1571 | 531 | 1H NMR (300 MHz, CD3)2CO) δ 2.91-3.10 (m, 2H), 3.33-3.44 (m, 1H), 4.38-4.58 (m, 1H), 6.58-6.70 (bm, 1H), 7.13 (dd, J = 8.4, 1.8 Hz, 1H), 7.40-7.58 (m, 4H), 7.37-7.60 (m, 5H), 7.58 (dm, J = 2.4, 1H), 8.15 (dd, J = 2.7, 1.2 Hz, 1H), 8.33 (d, J = 2.7 Hz, 1H), 8.46 (d, J = 1.2 Hz, 1H), 10.32 (s, 1H). | 4.00 | ***** |
| 1572 | 580 | | 4.53 | ***** |
| 1573 | 449 | 1H NMR (300 MHz, (CD3)2CO) δ 1.29 (t, J = 6.7 Hz, 3H), 2.85-2.89 (m, 1H), 3.16-3.23 (m, 2H), 3.38 (mcc, 1H), 4.17 (q, J = 6.9 Hz, 2H), 4.20-4.40 (m, 1H), 6.54 (bm, 1H), 7.10 (dd, J = 8.7, 2.1 Hz, 1H), 7.16 (dm, J = 8.7 Hz, 2H), 7.21 (t, J = 4.8 Hz, 1H), 7.33-7.39 (m, 3H), 7.53 (d, J = 1.8 Hz, 1H), 8.60 (J = 4.8 Hz, 2H), 10.28 (s, 1H). | 3.53 | ***** |
| 1574 | 449 | 1H NMR (300 MHz, (CD3)2CO) δ 1.28 (t, J = 6.9 Hz, 3H), 2.85-2.88 (m, 1H), 3.15-3.25 (m, 2H), 3.60 (mc, 1H), 4.16 (q, J = 6.9 Hz, 2H), 4.20-4.40 (m, 1H), 6.54 (bm, 1H), 7.10 (dd, J = 8.8, 1.9 Hz, 1H), 7.18 (dm, J = 8.8 Hz, 2H), 7.36-7.38 (m, 3H), 7.53 (d, J = 1.9 Hz, 1H), 8.13 (dd, J = 2.6, 1.5 Hz, 1H), 8.31 (d, J = 2.6 Hz, 1H), 8.44 (d, J = 1.4 Hz, 1H), 10.13 (s, 1H). | 3.67 | ***** |
| 1575 | 498 | | 4.15 | ***** |
| 1576 | 479 | 1H NMR (300 MHz, (CD3)2CO) δ 1.58-1.69 (m, 2H), 1.82 (s, 3H), 1.96-2.05 (m, 2H), 2.80-2.94 (m, 3H), 3.10-3.25 (m, 1H), 3.50 (ddd, J = 11.8, 9.0, 2.9 Hz, 2H), 3.96 (dt, J = 11.7, 4.5 Hz, 2H), 4.28 (mc, 1H), 4.56 (septet, J = 4.0 Hz, 1H), 4.74 (s, 2H), 6.45 (mc, 1H), 6.93 (d, J = 8.7 Hz, 2H), 7.11 (dd, J = 8.7, 1.8 Hz, | 3.78 | ***** |

TABLE 2-continued

| Cpd | MS | NMR | RT | EC$_{50}$ |
|---|---|---|---|---|
| | | 1H), 7.20 (dm, J = 8.4 Hz, 2H), 7.36 (d, J = 8.7 Hz, 1H), 7.52 (d, J = 1.8 Hz, 2H), 10.19 (s, 1H). | | |
| 1577 | 521 | | 3.93 | ***** |
| 1578 | 537 | | 4.12 | ***** |
| 1579 | 642 | 1H NMR (300 MHz, (CD3)2CO) δ 0.069 (s, 9H), 0.96-1.02 (m, 2H), 1.70-1.85 (m, 2H), 1.82 (s, 3H), 1.98-2.08 (m, 2H), 2.85 (dd, J = 7.8, 3.0 Hz, 2H), 2.94-3.00 (m, 2H), 3.12-3.23 (m, 1H), 3.24-3.32 (m, 2H), 3.45 (s, 1H), 3.48-3.56 (m, 2H), 4.18-4.40 (mc, 1H), 4.59 (septet, J = 3.9 Hz, 1H), 4.74 (s, 2H), 6.46 (mc, 1H), 6.94 (d, J = 8.8 Hz, 2H), 7.10 (dd, J = 8.7, 2.1 Hz, 1H), 7.21 (dm, J = 8.1 Hz, 2H), 7.36 (d, J = 8.7 Hz, 1H), 7.53 (d, J = 1.8 Hz, 2H), 10.17 (s, 1H). | 4.18 | ***** |
| 1580 | 684 | | 4.32 | ***** |
| 1581 | 700 | | 4.60 | ***** |
| 1582 | 461 | | 3.92 | ***** |
| 1583 | 624 | | 438 | ***** |
| 1584 | 410.17 | | 3.57 | ***** |
| 1585 | 468.16 | | 3.93 | ***** |
| 1586 | 412.18 | | 3.07 | *** |
| 1587 | 452.22 | | 4.80 | ***** |
| 1588 | 481.21 | | 3.40 | *** |
| 1589 | 464.08 | | 4.13 | ***** |
| 1590 | 473.24 | | 2.62 | **** |
| 1591 | 502.23 | | 4.13 | ***** |
| 1592 | 473.24 | | 2.55 | *** |
| 1593 | 454.23 | | 0.88 | *** |
| 1594 | 473.16 | | 1.62 | *** |
| 1595 | 478.19 | | 4.08 | **** |
| 1596 | 452.16 | | 3.37 | **** |
| 1597 | 506.12 | | 4.47 | ***** |
| 1598 | 472.23 | | 4.22 | ***** |
| 1600 | 610.17 | | 4.02 | ***** |
| 1601 | 606.32 | | 3.62 | ***** |
| 1603 | 479 | 1H NMR (300 MHz, (CD3)2CO) δ 1.58-1.69 (m, 2H), 1.82 (s, 3H), 1.96-2.05 (m, 2H), 2.80-2.94 (m, 3H), 3.10-3.25 (m, 1H), 3.50 (ddd, J = 11.8, 9.0, 2.9 Hz, 2H), 3.96 (dt, J = 11.7, 4.5 Hz, 2H), 4.28 (mc, 1H), 4.56 (septet, J = 4.0 Hz, 1H), 4.74 (s, 2H), 6.45 (mc, 1H), 6.93 (d, J = 8.7 Hz, 2H), 7.11 (dd, J = 8.7, 1.8 Hz, 1H), 7.20 (dm, J = 8.4 Hz, 2H), 7.36 (d, J = 8.7 Hz, 1H), 7.52 (d, J = 1.8 Hz, 2H), 10.19 (s, 1H). | 3.78 | ***** |
| 1604 | 521 | | 3.95 | ***** |
| 1605 | 537 | | 4.13 | ***** |
| 1606 | 642 | 1H NMR (300 MHz, (CD3)2CO) δ 0.069 (s, 9H), 0.96-1.02 (m, 2H), 1.70-1.85 (m, 2H), 1.82 (s, 3H), 1.98-2.08 (m, 2H), 2.85 (dd, J = 7.8, 3.0 Hz, 2H), 2.94-3.00 (m, 2H), 3.12-3.23 (m, 1H), 3.24-3.32 (m, 2H), 3.45 (s, 1H), 3.48-3.56 (m, 2H), 4.18-4.40 (mc, 1H), 4.59 (septet, J = 3.9 Hz, 1H), 4.74 (s, 2H), 6.46 (mc, 1H), 6.94 (d, J = 8.8 Hz, 2H), 7.10 (dd, J = 8.7, 2.1 Hz, 1H), 7.21 (dm, J = 8.1 Hz, 2H), 7.36 (d, J = 8.7 Hz, 1H), 7.53 (d, J = 1.8 Hz, 2H), 10.17 (s, 1H). | 4.17 | ***** |
| 1607 | 684 | | 4.30 | ***** |
| 1608 | 475.25 | | 3.75 | * |
| 1609 | 465.25 | | 4.67 | ***** |
| 1610 | $C_{28}H_{34}ClN_3O_4$, (M + 1, 512) | | 10.208, Chiral 13.9 and 15.057 | *** |
| 1611 | $C_{32}H_{30}Cl_2N_4O_3$, (595.2) | | 24.453, Chiral, 14.878 | ***** |
| 1612 | $C_{27}H_{20}Cl_2N_2O_3$, (491.365) | 1H NMR (DMSO-d6, 400 MHz) δ = 11.17 (brs, 1H, NH), 8.3 (s, 1H, Ar—H), 7.45 (d, 2H, 2Ar—H), 7.31-7.08 (m, 6H, 6Ar—H), 6.98 (m, 2H, 2Ar—H), 6.4 (brs, 1H, CH), 4.78 (s, 2H, CH2), 4.3 (brs, 1H, CH), 3.6 (s, 1H, ≡CH), 3.28 (m, 1H, CH), 3.21 (m, 2H, CH2). | 5.676, Chiral, 17.302 | ***** |
| 1613 | $C_{29}H_{24}Cl_2N_2O_3$, (519.5) | 1H NMR (DMSO-d6, 400 MHz) δ = 11.16 (brs, 1H, NH), 7.54 (s, 1H, Ar—H), 7.45 (d, 2H, 2Ar—H), 7.3 (d, 1H, J = 8.8 Hz, Ar—H), 7.22-7.2 (m, 4H, 4Ar—H), 7.07 (m, 1H, Ar—H), 6.94 (m, 2H, 2Ar—H), 6.4 (s, 1H, CH), 4.3 (m, 1H, CH), 4.01 (t, 2H, J = 6 Hz, CH2), 3.2 (m, 1H, CH), 2.9 (m, 2H, CH2), 2.8 (s, 1H, ≡CH), 2.29 (m, 2H, CH2), 1.86 (m, 2H, CH2). | 5.932, Chiral, 15.625 | ***** |
| 1614 | $C_{28}H_{22}Cl_2N_2O_3$, (505.5) | 1H NMR (DMSO-d6, 400 MHz) δ = 11.17 (brs, 1H, NH), 7.54 (s, 1H, Ar—H), 7.45 (d, 2H, 2Ar—H), 7.31-6.98 (m, 6H, 6Ar—H), 6.95 (m, 2H, 2Ar—H), 6.4 (brs, 1H, CH), 4.3 (m, 1H, CH), 4.03 (t, 2H, J = 6.4 Hz, CH2), 3.2 (m, 1H, CH), 2.87 (m, 3H, CH and ≡CH), 2.61 (m, 2H, CH2). | 5.775, Chiral, 26.04 | ***** |
| 1615 | M + 23:536.2 (cal.513.2) | $^1$H NMR (DMSO, 300 MHz), δ11.13 (b, 1H), 7.86 (s, 1H), 7.48 (s, 1H), 7.28 (d, J = 8.7 Hz, 1H), 7.10-7.03 (m, 3H), 6.88 (d, J = 8.4 Hz, 2H), 6.29 (s, 1H), 4.90 (d, J = 2.1 Hz, 1H), 4.15-4.09 (m, 3H), | 30-90 3.91 | **** |

TABLE 2-continued

| Cpd | MS | NMR | RT | EC$_{50}$ |
|---|---|---|---|---|
| | | 4.00 (t, J = 6.3 Hz, 1H), 3.67-3.61 (m, 1H), 3.11-2.98 (m, 3H), 2.74-2.69 (m, 2H), 2.06 (q, J = 7.5 Hz, 2H), 1.86-1.78 (m, 1H), 1.66-1.57 (m, 1H), 1.22-1.20 (m, 3H), 0.95 (t, J = 7.5 Hz, 3H). | | |
| 1616 | M + 23:550.2 (cal.527.2) | $^1$H NMR (DMSO, 300 MHz), δ11.15 (b, 1H), 7.86 (s, 1H), 7.47 (d, J = 8.1 Hz, 1H), 7.30-7.27 (m, 1H), 7.07-7.01 (m, 3H), 6.86-6.83 (m, 2H), 6.28 (s, 1H), 4.93-4.92 (m, 1H), 4.09-4.00 (m, 5H), 3.69-3.63 (m, 1H), 3.11-2.98 (m, 3H), 2.81-2.69 (m, 3H), 1.90-1.73 (m, 1H), 1.69-1.59 (m, 1H), 1.22-1.20 (m, 3H), 0.96-0.91 (m, 3H). | 10-80 5.58 | **** |
| 1617 | 563.1 (cal.562.2) | $^1$H NMR (DMSO, 300 MHz), δ11.09 (b, 1H), 8.99 (s, 1H), 8.76-8.68 (m, 2H), 8.19 (d, J = 8.1 Hz, 1H), 7.50-7.48 (m, 2H), 7.27 (d, J = 8.4 Hz, 1H), 7.09-7.03 (m, 3H), 6.89 (d, J = 8.7 Hz, 2H), 6.29 (s, 1H), 5.00-4.99 (m, 1H), 4.19-4.01 (m, 5H), 3.85-3.80 (m, 1H), 3.06-3.00 (m, 1H), 2.77-2.70 (m, 3H), 1.94-1.82 (m, 1H), 1.71-1.62 (m, 1H), 1.24-1.21 (m, 3H). | 30-90 3.27 | **** |
| 1618 | 563.1 (cal.562.2) | $^1$H NMR (DMSO, 300 MHz), δ11.13 (s, 1H), 8.66-8.61 (m, 2H), 8.03-7.94 (m, 2H), 7.57 (t, J = 5.4 Hz, 1H), 7.48 (s, 1H), 7.27 (d, J = 8.4 Hz, 1H), 7.09-7.03 (m, 3H), 6.88 (d, J = 8.4 Hz, 2H), 6.29 (s, 1H), 5.06 (d, J = 5.4 Hz, 1H), 4.16-4.04 (m, 5H), 3.83-3.82 (m, 1H), 3.01-2.95 (m, 1H), 2.80-2.69 (m, 3H), 1.91-1.79 (m, 1H), 1.78-1.62 (m, 1H), 1.22-1.20 (m, 3H). | 30-90 4.30 | ***** |
| 1619 | M + 23:538.1 (cal.515.2) | $^1$H NMR (DMSO, 300 MHz), δ11.18 (b, 1H), 7.48 (s, 1H), 7.27 (d, J = 8.7 Hz, 1H), 7.10-7.02 (m, 4H), 6.87 (d, J = 8.7 Hz, 2H), 6.30 (s, 1H), 4.85 (d, J = 5.4 Hz, 1H), 4.11-4.08 (m, 2H), 4.00 (t, J = 6.3 Hz, 2H), 3.64-3.60 (m, 1H), 3.48 (s, 3H), 3.09-2.92 (m, 3H), 2.80-2.62 (m, 2H), 1.79-1.74 (m, 1H), 1.62-1.54 (m, 1H), 1.22-1.20 (m, 3H). | 30-90 4.07 | ***** |
| 1620 | 544.1 (cal.543.2) | $^1$H NMR (DMSO, 300 MHz), δ11.09 (b, 1H), 7.48 (d, J = 1.5 Hz, 1H), 7.27 (d, J = 8.7 Hz, 1H), 7.10-6.98 (m, 4H), 6.87 (d, J = 8.7 Hz, 2H), 6.29 (s, 1H), 4.75 (d, J = 5.4 Hz, 1H), 4.20-4.06 (m, 3H), 4.02 (t, J = 6.3 Hz, 2H), 3.87 (t, J = 6.6 Hz, 2H), 3.63-3.61 (m, 1H), 3.10-2.94 (m, 3H), 2.78-2.67 (m, 2H), 1.89-1.73 (m, 1H), 1.62-1.45 (m, 3H), 1.23 (t, J = 7.2 Hz, 3H) 0.82 (t, J = 6.6 Hz, 3H). | 30-90 4.56 | ***** |
| 1621 | 560.1 (cal.559.2) | $^1$H NMR (DMSO, 300 MHz), δ11.18 (b, 1H), 7.48 (s, 1H), 7.28 (d, J = 8.4 Hz, 1H), 7.15-7.03 (m, 4H), 6.88 (d, J = 8.4 Hz, 2H), 6.29 (s, 1H), 4.82 (d, J = 5.4 Hz, 1H), 4.20-4.00 (m, 7H), 3.62-3.61 (m 1H), 3.44 (t, J = 4.8 Hz, 2H), 3.21 (s, 3H), 3.08-2.93 (m, 3H), 2.82-2.64 (m, 2H), 1.90-1.73 (m, 1H) 1.62-1.49 (m, 1H) 1.22-1.20 (m, 3H). | 30-90 4.07 | ***** |
| 1622 | M + 23:558.0 (cal.535.2) | $^1$H NMR (CD3CN, 300 MHz), δ9.11 (b, 1H), 7.51 (d, J = 1.8 Hz, 1H), 7.28 (d, J = 8.7 Hz, 1H), 7.18 (d, J = 8.7 Hz, 2H), 7.08 (dd, J = 8.7 Hz and 2.1 Hz, 1H), 6.88 (d, J = 8.7 Hz, 2H), 6.36 (s, 1H), 5.32 (b, 1H), 4.28-4.26 (m, 1H), 4.20-4.13 (m, 2H), 4.10-4.05 (m, 2H), 3.89-3.87 (m, 1H), 3.21 (s, 3H), 3.22-3.00 (m, 4H), 2.90 (s, 3H), 2.81-2.77 (m, 2H) 1.89-1.71 (m, 2H), 1.26 (t, J = 7.2 Hz, 3H). | 10-80 3.69 | ***** |
| 1623 | M + 23:572.1 (cal.549.2) | $^1$H NMR (DMSO, 300 MHz), δ11.11 (b, 1H), 7.49 (s, 1H), 7.27 (d, J = 8.1 Hz, 1H), 7.11-6.97 (m, 4H), 6.89 (d, J = 8.1 Hz, 2H), 6.29 (s, 1H), 4.88 (d, J = 5.4 Hz, 1H), 4.13-4.00 (m, 5H), 3.66-3.64 (m, 1H), 3.00 (q, J = 7.2 Hz, 2H), 2.91 (t, J = 6.0 Hz, 2H), 2.66-2.64 (m, 3H), 1.94-1.88 (m, 1H) 1.68-1.60 (m, 1H) 1.21-1.13 (m, 6H). | 10-80 4.80 | ***** |
| 1624 | M + 23:584.1 (cal.561.2) | $^1$H NMR (DMSO, 300 MHz), δ11.16 (b, 1H), 7.52 (s, 1H), 7.37-7.36 (m 1H), 7.11-7.07 (m, 4H), 6.30 (s, 1H), 4.96 (b, 1H), 4.20-3.99 (m, 5H), 3.71-3.69 (m, 1H), 3.00-2.99 (m, 3H), 2.73-2.70 (m, 3H), 1.94-1.88 (m, 1H) 1.68-1.60 (m, 1H) 1.21-1.13 (m, 3H), .090-0.88 (m, 3H). | 10-80 4.88 | ***** |
| 1625 | M + 23:618.2 (cal.595.2) | $^1$H NMR (CD3CN, 300 MHz), δ9.25 (b, 1H), 7.54 (d, J = 2.1 Hz, 1H), 7.38-7.34 (m, 2H), 7.30-7.21 (m, 3H), 7.14-7.09 (m, 3H), 6.87 (d, J = 8.7 Hz, 2H), 6.55 (b, 1H), 6.45 (s, 1H), 4.41-4.33 (m, 1H), 4.05 (t, J = 6.3 Hz, 2H), 3.81-3.76 (m, 1H), 3.63-3.52 (m, 1H), 3.32-3.21 (m, 2H), 3.13-3.07 (m, 1H), 2.99-2.81 (m, 2H), 2.14 (q, J = 7.5 Hz, 2H), 1.90-1.82 (m, 1H), 1.76-1.69 (m, 1H), 1.04 (t, J = 7.8 Hz, 3H). | 30-90 4.61 | ***** |
| 1626 | M + 23:632.2 (cal.609.2) | $^1$H NMR (CD3CN, 400 MHz), δ9.26 (b, 1H), 7.55 (d, J = 2.0 Hz, 1H), 7.38 (d, J = 8.8 Hz, 2H), 7.31-7.23 (m, 3H), 7.13-7.09 (m, 3H), 6.89 (d, J = 8.4 Hz, 2H), 6.71 (b, 1H), 6.45 (s, 1H), 4.41-4.33 (m, 1H), 4.07 (t, J = 6.4 Hz, 2H), 3.81-3.76 (m, 1H), 3.51 (s, 1H), 3.31-3.24 (m, 2H), 3.13-3.07 (m, 1H), 2.99-2.81 (m, 2H), 2.41-2.40 (m, 1H), 1.90-1.82 (m, 1H), 1.76-1.69 (m, 1H), 1.05 (d, J = 7.8 Hz, 6H). | 30-90 4.76 | ***** |
| 1627 | M + 23:667.2 (cal.644.2) | $^1$H NMR (CD3CN, 400 MHz), δ9.18 (b, 1H), 8.69 (d, J = 6.0 Hz, 2H), 7.66 (d, J = 6.0 Hz, 2H), 7.56 (s, 1H), 7.39 (d, J = 8.8 Hz, 2H), 7.31-7.24 (m, 3H), 7.14-7.10 (m, 3H), 6.91 (d, J = 8.0 Hz, 2H), 6.49 (s, 1H), 4.41-4.33 (m, 1H), 4.12 (t, J = 6.4 Hz, 2H), 3.94-3.92 (m, 1H), 3.54-3.48 (m, 2H), 3.37-3.24 (m, 2H), 3.01-2.81 (m, 2H), 1.88-1.76 (m, 2H). | 30-90 3.96 | ***** |
| 1628 | M + 23:667.1 (cal.644.2) | $^1$H NMR (CD3CN, 400 MHz), δ9.43-9.39 (m, 1H), 8.99-8.86 (m, 1H), 8.69-8.68 (m, 1H), 8.13-8.10 (m, 1H), 7.56 (d, J = 2.0 Hz, 1H), 7.44-7.38 (m, 3H), 7.31-7.23 (m, 4H), 7.14-7.10 (m, 3H), 6.93-6.90 (m, 2H), 6.47 (s, 1H), 4.41-4.33 (m, 1H), 4.15-4.12 (m, 2H), 3.96-3.92 (m, 1H), 3.54-3.48 (m, 2H), 3.41-3.23 (m, 2H), 3.01-2.81 (m, 2H), 1.90-1.76 (m, 2H). | 30-90 4.03 | ***** |

TABLE 2-continued

| Cpd | MS | NMR | RT | EC$_{50}$ |
|---|---|---|---|---|
| 1629 | M + 23:667.1 (cal.644.2) | $^1$H NMR (CD3CN, 400 MHz), δ9.23 (b, 1H), 8.59 (d, J = 4.8 Hz, 1H), 8.40 (s, 1H), 8.10-8.08 (m, 1H), 7.94-7.92 (m, 1H), 7.55 (d, J = 2.0 Hz, 1H), 7.39 (d, J = 8.8 Hz, 2H), 7.31-7.23 (m, 3H), 7.14-7.10 (m, 3H), 6.92 (d, J = 8.4 Hz, 2H), 6.47 (s, 1H), 4.41-4.33 (m, 1H), 4.11 (t, J = 6.4 Hz, 2H), 3.96-3.92 (m, 1H), 3.54-3.50 (m, 1H), 3.41-3.32 (m, 1H), 3.30-3.27 (m, 1H), 1.90-1.76 (m, 2H). | 30-90 4.92 | ***** |
| 1630 | 483.22 | | 4.03 | ***** |
| 1631 | 425.18 | | 3.97 | *** |
| 1632 | 508 | | 3.88 | ***** |
| 1633 | 524 | | 3.62 | ***** |
| 1634 | 524 | | 3.62 | ***** |
| 1635 | M + 23:620.1 (cal.597.1) | $^1$H NMR (CD3CN, 300 MHz), δ9.14 (b, 1H), 7.55 (d, J = 2.1 Hz, 1H), 7.40-7.36 (m, 2H), 7.31-7.23 (m, 3H), 7.14-7.09 (m, 3H), 6.90 (d, J = 8.4 Hz, 2H), 6.47 (s, 1H), 5.65 (b, 1H), 4.10-4.05 (m, 2H), 3.85-3.74 (m, 1H), 3.58 (s, 3H), 3.32-3.16 (m, 3H), 3.07-3.00 (m, 1H), 2.96-2.84 (m, 2H), 1.90-1.81 (m, 1H), 1.78-1.71 (m, 1H). | 30-90 4.73 | ***** |
| 1636 | M + 23:634.1 (cal.611.2) | $^1$H NMR (CD3CN, 400 MHz), δ9.17 (b, 1H), 7.55 (d, J = 2.0 Hz, 1H), 7.39 (d, J = 8.8 Hz, 2H), 7.31-7.23 (m, 3H), 7.14-7.10 (m, 3H), 6.90 (d, J = 8.0 Hz, 2H), 6.47 (s, 1H), 5.60 (b, 1H), 4.41-4.35 (m, 1H), 4.10-4.00 (m, 4H), 3.82-3.76 (m, 1H), 3.32-3.16 (m, 3H), 3.07-3.00 (m, 1H), 2.96-2.84 (m, 2H), 1.90-1.81 (m, 1H), 1.76-1.69 (m, 1H), 1.18 (t, J = 7.2 Hz, 3H). | 30-90 4.92 | ***** |
| 1637 | M + 23:664.1 (cal.641.2) | $^1$H NMR (DMSO, 400 MHz), δ11.19-11.11 (m, 1H), 7.52 (d, J = 1.6 Hz, 1H), 7.43 (d, J = 8.4 Hz, 2H), 7.29 (d, J = 8.4 Hz, 1H), 7.20-7.12 (m, 5H), 7.04 (dd, J = 8.4 Hz and 2.0 Hz, 1H), 6.92-6.90 (m, 2H), 6.42-6.37 (m, 1H), 4.78 (d, J = 5.6 Hz, 1H), 4.31-4.20 (m, 1H), 4.01-4.00 (m, 4H), 3.64-3.61 (m, 1H), 3.46-3.43 (m, 2H), 3.22-3.19 (m, 5H), 2.96 (t, J = 6.0 Hz, 2H), 2.90-2.82 (m, 2H), 1.91-1.79 (m, 1H), 1.61-1.53 (m, 1H). | 30-90 5.03 | ***** |
| 1638 | M + 23:654.1 (cal.631.1) | $^1$H NMR (DMSO, 300 MHz), δ11.19-11.10 (m, 1H), 7.53 (d, J = 2.1 Hz, 1H), 7.44 (d, J = 8.7 Hz, 2H), 7.30 (d, J = 8.1 Hz, 1H), 7.22-7.19 (m, 3H), 7.07 (dd, J = 8.7 Hz and 2.4 Hz, 1H), 6.99 (t, J = 6.3 Hz, 1H), 6.93 (d, J = 9.0 Hz, 2H), 6.42-6.37 (m, 1H), 4.88 (d, J = 5.4 Hz, 1H), 4.33-4.22 (m, 1H), 4.04 (t, J = 6.6 Hz, 2H), 3.71-3.63 (m, 1H), 3.22-3.12 (m, 1H), 3.02-2.83 (m, 5H), 1.93-1.86 (m, 1H), 1.64-1.60 (m, 1H), 1.16 (t, J = 7.2 Hz, 3H). | 30-90 5.03 | ***** |
| 1639 | M + 23:666.1 (cal.643.1) | $^1$H NMR (DMSO, 300 MHz), δ11.19-11.12 (m, 1H), 7.53 (d, J = 1.8 Hz, 1H), 7.44 (d, J = 8.4 Hz, 2H), 7.30 (d, J = 8.1 Hz, 1H), 7.22-7.19 (m, 3H), 7.07 (dd, J = 8.7 Hz and 2.4 Hz, 1H), 7.00-6.96 (m, 1H), 6.93 (d, J = 9.0 Hz, 2H), 6.45-6.37 (m, 1H), 4.92-4.89 (m, 1H), 4.35-4.26 (m, 1H), 4.04 (t, J = 6.0 Hz, 2H), 3.71-3.63 (m, 1H), 3.22-3.12 (m, 1H), 3.00-2.91 (m, 2H), 2.91-2.82 (m, 2H), 1.97-1.89 (m, 1H), 1.69-1.62 (m, 1H), 0.90-0.88 (m, 4H). | 30-90 5.10 | ***** |
| 1640 | M + 23:612.2 (cal.589.2) | $^1$H NMR (DMSO, 400 MHz), δ 11.13-11.10 (m, 1H), 7.73 (s, 1H), 7.52 (d, J = 1.6 Hz, 1H), 7.29 (d, J = 8.4 Hz, 1H), 7.17-7.15 (m, 4H), 7.06 (dd, J = 8.4 Hz and 2.0 Hz, 1H), 7.00 (d, J = 8.4 Hz, 2H), 6.91-6.89 (m, 2H), 6.42-6.37 (m, 1H), 4.84 (d, J = 4.4 Hz, 1H), 4.30-4.27 (m, 1H), 4.02 (t, J = 6.4 Hz, 2H), 3.64-3.61 (m, 1H), 3.19-3.13 (m, 1H), 3.09-3.01 (m, 3H), 2.89-2.81 (m, 2H), 2.27 (s, 3H), 1.82-1.78 (m, 1H), 1.63-1.57 (m, 1H), 0.94 (d, J = 6.8 Hz, 6H). | 30-90 4.93 | ***** |
| 1641 | M + 23:647.2 (cal.624.2) | $^1$H NMR (DMSO, 400 MHz), δ 11.14-11.10 (m, 1H), 8.67-8.66 (m, 1H), 8.61 (d, J = 4.4 Hz, 1H), 8.00 (t, J = 8.0 Hz, 1H), 7.96 (dd, J = 7.6 Hz and 1.6 Hz, 1H), 7.58-7.56 (m, 1H), 7.52 (d, J = 2.0 Hz, 1H), 7.29 (d, J = 8.4 Hz, 1H), 7.17-7.10 (m, 3H), 7.06 (dd, J = 8.8 Hz and 2.0 Hz, 1H), 7.00 (d, J = 8.4 Hz, 2H), 6.91 (d, J = 8.0 Hz, 2H), 6.41-6.32 (m, 2H), 5.02 (d, J = 5.6 Hz, 1H), 4.32-4.22 (m, 1H), 4.04 (t, J = 6.4 Hz, 2H), 3.86-3.81 (m, 1H), 3.44-3.42 (m, 2H), 3.14-3.12 (m, 1H), 2.87-2.83 (m, 3H), 2.27 (s, 3H), 1.87-1.82 (m, 1H), 1.71-1.62 (m, 1H). | 30-90 5.13 | ***** |
| 1642 | M + 23:600.1 (cal.577.2) | $^1$H NMR (DMSO, 400 MHz), δ 11.17-11.10 (m, 1H), 7.52 (d, J = 2.0 Hz, 1H), 7.29 (d, J = 8.8 Hz, 1H), 7.17-7.01 (m, 6H), 7.00 (d, J = 8.4 Hz, 2H), 6.92-6.91 (m, 2H), 6.43-6.39 (m, 1H), 4.80 (d, J = 5.6 Hz, 1H), 4.32-4.22 (m, 1H), 4.01 (t, J = 6.0 Hz, 2H), 3.63-3.60 (m, 1H), 3.48 (s, 3H), 3.17-3.12 (m, 1H), 2.97 (t, J = 6.0 Hz, 2H), 2.87-2.83 (m, 2H), 2.27 (s, 3H), 1.84-1.79 (m, 1H), 1.61-1.58 (m, 1H). | 30-90 4.92 | ***** |
| 1643 | M + 23:614.2 (cal.591.2) | $^1$H NMR (DMSO, 400 MHz), δ 11.17-11.10 (m, 1H), 7.52 (d, J = 1.6 Hz, 1H), 7.29 (d, J = 8.4 Hz, 1H), 7.17-7.15 (m, 4H), 7.07-7.01 (m, 4H), 6.92-6.90 (m, 2H), 6.43-6.36 (m, 1H), 4.78 (d, J = 5.2 Hz, 1H), 4.35-4.20 (m, 1H), 4.01 (t, J = 6.4 Hz, 2H), 3.93 (q, J = 7.2 Hz, 2H), 3.63-3.60 (m, 1H), 3.17-3.12 (m, 1H), 2.96 (t, J = 6.0 Hz, 2H), 2.87-2.83 (m, 2H), 2.27 (s, 3H), 1.85-1.79 (m, 1H), 1.61-1.58 (m, 1H). | 30-90 5.12 | ***** |
| 1644 | M + 23:628.2 (cal.605.2) | $^1$H NMR (DMSO, 400 MHz), δ 11.17-11.10 (m, 1H), 7.52 (d, J = 1.6 Hz, 1H), 7.29 (d, J = 8.8 Hz, 1H), 7.17-7.15 (m, 4H), 7.07-6.99 (m, 4H), 6.92-6.90 (m, 2H), 6.43-6.36 (m, 1H), 4.79 (d, J = 5.2 Hz, 1H), 4.30-4.20 (m, 1H), 4.01 (t, J = 6.4 Hz, 2H), 3.84 (q, J = 7.2 Hz, 2H), 3.63-3.60 (m, 1H), 3.17-3.12 (m, 1H), 2.96 (t, | 30-90 5.35 | ***** |

TABLE 2-continued

| Cpd | MS | NMR | RT | EC$_{50}$ |
|---|---|---|---|---|
| 1645 | M + 23:644.2 (cal.621.2) | J = 6.0 Hz, 2H), 2.87-2.83 (m, 2H), 2.27 (s, 3H), 1.85-1.79 (m, 1H), 1.61-1.58 (m, 1H), 1.50 (q, J = 7.2 Hz, 2H), 0.83 (t, J = 7.2 Hz, 3H). $^1$H NMR (DMSO, 400 MHz), δ 11.17-11.10 (m, 1H), 7.52 (d, J = 1.6 Hz, 1H), 7.29 (d, J = 8.8 Hz, 1H), 7.17-7.15 (m, 4H), 7.06 (dd, J = 8.4 Hz and 2.0 Hz, 1H), 7.00 (d, J = 8.4 Hz, 2H), 6.92-6.90 (m, 2H), 6.43-6.36 (m, 1H), 4.80 (d, J = 5.2 Hz, 1H), 4.30-4.20 (m, 1H), 4.00 (s, 3H), 3.64-3.60 (m, 2H), 3.42-3.41 (m, 2H), 3.21 (s, 3H), 3.16-3.11 (m, 1H), 2.97 (t, J = 6.0 Hz, 2H), 2.87-2.83 (m, 2H), 2.27 (s, 3H), 1.85-1.79 (m, 1H), 1.61-1.58 (m, 1H). | 30-90 4.91 | ***** |
| 1646 | M + 23:634.2 (cal.611.2) | $^1$H NMR (DMSO, 400 MHz), δ 11.17-11.10 (m, 1H), 7.52 (s, 1H), 7.29 (d, J = 8.4 Hz, 1H), 7.17-7.15 (m, 4H), 7.06 (dd, J = 8.4 Hz and 2.0 Hz, 1H), 7.00 (d, J = 8.4 Hz, 2H), 6.93-6.91 (m, 2H), 6.43-6.36 (m, 1H), 4.89 (d, J = 5.6 Hz, 1H), 4.30-4.20 (m, 1H), 4.03 (t, J = 7.2, 2H), 3.67-3.62 (m, 1H), 3.57-3.56 (m, 1H), 3.16-3.11 (m, 1H), 2.95 (q, J = 7.2 Hz, 2H), 2.91 (t, J = 6.0 Hz, 2H), 2.87-2.81 (m, 2H), 2.27 (s, 3H), 1.90-1.82 (m, 1H), 1.66-1.61 (m, 1H), 1.15 (t, J = 7.2 Hz, 3H). | 30-90 4.88 | ***** |
| 1647 | M + 23:646.2 (cal.623.2) | $^1$H NMR (DMSO, 400 MHz), δ 11.17-11.10 (m, 1H), 7.52 (s, 1H), 7.29 (d, J = 8.4 Hz, 1H), 7.23-7.15 (m, 3H), 7.06 (d, J = 6.8 Hz, 2H), 7.00 (d, J = 8.4H, 2H), 6.92-6.90 (m, 2H), 6.43-6.36 (m, 1H), 4.95 (d, J = 5.2 Hz, 1H), 4.03-4.01 (m, 2H), 3.70-3.69 (m, 1H), 3.19-3.11 (m, 1H), 2.94-2.91 (m, 2H), 2.84-2.81 (m, 2H), 2.27 (s, 3H), 1.90-1.86 (m, 1H), 1.66-1.61 (m, 1H), 0.88-0.85 (m, 4H). | 30-90 4.99 | ***** |
| 1648 | 571 (M +− 1) | 1H NMR (300 MHz, CD3)2CO) δ 2.22-2.32 (m, 2H), 2.90-3.10 (m, 5H), 3.26-3.31 (m, 3H), 4.17 (t, J = 6.3 Hz, 2H), 4.43 (mc, 1H), 6.52 (bm, 1H), 6.95 (d, J = 9.0 Hz, 2H), 7.11 (dd, J = 9.0, 2.4 Hz, 1H), 7.40-7.58 (m, 4H), 7.37 (d, J = 8.4 Hz, 1H), 7.42 (dm, J = 9.3 Hz, 2H), 7.56 (d, J = 2.2 Hz, 1H), 10.22 (s, 1H). | 3.80 | ***** |
| 1649 | 515 | | 3.50 | ***** |
| 1650 | 516.28 | | 3.38 | ***** |
| 1651 | 516.31 | | 3.38 | ***** |
| 1652 | 700 | | 4.53 | ***** |
| 1653 | 477 | | 3.88 | ***** |
| 1654 | 463 | | 3.77 | ***** |
| 1655 | 464 | | 3.57 | *** |
| 1656 | 553 | 1H NMR (300 MHz, (CD3)2CO) δ 1.28 (t, J = 6.9 Hz, 3H), 2.85-2.88 (m, 1H), 3.09-3.22 (m, 2H), 3.33 (mcc, 4H), 3.94 (mc, 4H), 4.17 (q, J = 6.9 Hz, 2H), 4.20-4.40 (m, 1H), 4.58 (s, 2H), 6.54 (bm, 1H), 7.10 (dd, J = 8.4, 1.9 Hz, 1H), 7.30-7.44 (m, 6H), 7.54 (d, J = 1.9 Hz, 1H), 10.27 (s, 1H). | 2.40 | ***** |
| 1657 | 566 | | 2.27 | ***** |
| 1658 | 559 | | 4.25 | ***** |
| 1659 | 545 | | 4.12 | ***** |
| 1660 | 635 | | 2.80 | ***** |
| 1661 | 650 | | 2.47 | ***** |
| 1662 | 439.31 | | 4.3 | **** |
| 1663 | M − 1:580.0 (cal.581.2) | $^1$H NMR (DMSO, 300 MHz), δ 11.14 (b, 1H), 7.54 (s, 1H), 7.30 (d, J = 8.4 Hz, 1H), 7.21-7.19 (m, 6H), 7.06 (d, J = 9.0 Hz, 2H), 6.92 (d, J = 7.5 Hz, 2H), 6.38 (b, 1H), 5.10 (b, 1H), 4.29 (b, 1H), 4.05-3.80 (m, 5H), 3.16-2.87 (m, 5H), 1.12-1.04 (m, 3H) | 30-90 4.59 | ***** |
| 1664 | M − 1:579.9 (cal.581.2) | $^1$H NMR (DMSO, 300 MHz), δ 11.14 (b, 1H), 7.54 (s, 1H), 7.30 (d, J = 8.4 Hz, 1H), 7.21-7.19 (m, 6H), 7.06 (d, J = 9.0 Hz, 2H), 6.92 (d, J = 7.5 Hz, 2H), 6.38 (b, 1H), 5.10 (b, 1H), 4.29 (b, 1H), 4.05-3.80 (m, 5H), 3.16-2.87 (m, 5H), 1.12-1.04 (m, 3H) | 10-80 4.84 | ***** |
| 1665 | M + 23:552.2 (cal.529.2) | $^1$H NMR (CD3CN, 300 MHz), δ9.11 (b, 1H), 7.51 (d, J = 1.8 Hz, 1H), 7.28 (d, J = 8.7 Hz, 1H), 7.18 (d, J = 8.4 Hz, 2H), 7.08 (dd, J = 8.7 Hz and 2.1 Hz, 1H), 6.87 (d, J = 8.7 Hz, 2H), 6.36 (s, 1H), 5.59 (b, 1H), 4.28-4.26 (m, 1H), 4.19-4.11 (m, 2H), 4.09-3.99 (m, 4H), 3.84-3.79 (m, 1H), 3.22-3.02 (m, 4H), 2.79-2.77 (m, 2H), 1.83-1.81 (m, 1H), 1.73-1.64 (m, 1H), 1.26 (t, J = 6.4 Hz, 3H), 1.19 (t, J = 7.2 Hz, 3H). | 10-80 5.71 | **** |
| 1666 | M + 23:648.1 (cal.625.2) | $^1$H NMR (CD3CN, 400 MHz), δ9.20-9.18 (m, 1H), 7.56 (d, J = 2.0 Hz, 1H), 7.39 (d, J = 8.8 Hz, 2H), 7.31-7.24 (m, 3H), 7.15-7.10 (m, 3H), 6.92-6.89 (m, 2H), 6.47 (s, 1H), 5.61 (b, 1H), 4.41-4.35 (m, 1H), 4.08 (t, J = 6.4 Hz, 2H), 3.95 (t, J = 6.8 Hz, 2H), 3.82-3.76 (m, 1H), 3.32-3.18 (m, 3H), 3.07-3.00 (m, 1H), 2.96-2.84 (m, 2H), 1.90-1.84 (m, 1H), 1.76-1.69 (m, 1H), 1.61-1.56 (m, 2H), 0.93-0.90 (m, 3H). | 10-80 5.44 | ***** |
| 1667 | M + 23:640.1 (cal.617.1) | $^1$H NMR (CD3CN, 300 MHz), δ9.18 (b, 1H), 7.55 (s, 1H), 7.38 (d, J = 8.78 Hz, 2H), 7.28-7.23 (m, 3H), 7.14-7.09 (m, 3H), 6.91 (d, J = 8.4 Hz, 2H), 6.47 (s, 1H), 5.35 (b, 1H), 4.41-4.35 (m, 1H), 4.09 (t, J = 6.4 Hz, 2H), 3.88-3.82 (m, 1H), 3.35-3.22 (m, 1H), 3.17-3.11 (m, 1H), 3.07-2.81 (m, 6H), 1.81-1.70 (m, 2H). | 30-90 4.55 | ***** |
| 1668 | M + 23:620.1 (cal.597.2) | $^1$H NMR (DMSO, 400 MHz), δ 11.17-11.10 (m, 1H), 7.52 (d, J = 2.0 Hz, 1H), 7.29 (d, J = 8.4 Hz, 1H), 7.17-7.15 (m, 3H), 7.06 (dd, J = 8.4 Hz and 2.0 Hz, 1H), 7.00 (d, J = 8.4 Hz, 2H), 6.97-6.994 (m, 3H), 6.43-6.36 (m, 1H), 4.92 (d, J = 5.6 Hz, 1H), 4.30-4.20 (m, 1H), 4.04-4.00 (m, 2H), 3.67-3.62 (m, 1H), 3.16-3.11 (m, | 10-80 5.45 | **** |

TABLE 2-continued

| Cpd | MS | NMR | RT | EC$_{50}$ |
|---|---|---|---|---|
| | | 2H), 2.93-2.90 (m, 2H), 2.87 (s, 3H), 2.86-2.85 (m, 1H), 2.27 (s, 3H), 1.90-1.82 (m, 1H), 1.66-1.61 (m, 1H). | | |
| 1669 | C$_{26}$H$_{19}$Cl$_2$N$_3$O$_3$, (M+, 492.1) | | 13.380, Chiral, 22.133 | ***** |
| 1670 | 403.30 | | 2.33 | **** |
| 1671 | 623.3 | | 3.85 | ***** |
| 1672 | 593.34 | | 3.70 | ***** |
| 1673 | 605.18 | | 3.82 | ***** |
| 1674 | 696 | 1H NMR (300 MHz, (CD3OD) δ 2.80-3.04 (m, 2H), 3.30-3.40 (m, 2H), 3.66-3.76 (m, 3H), 3.81 (q, J = 6.3 Hz, 1H), 3.97 (d, J = 3.0 Hz, 1H), 4.13 (t, J = 9.3 Hz, 1H), 4.30-4.50 (m, 1H), 5.19 (s, 2H), 5.57 (d, J = 9.3 Hz, 1H), 6.44-6.56 (bm, 1H), 6.96-7.04 (bm, 2H), 7.06 (dd, J = 8.7, 1.9 Hz, 1H), 7.13 (d, J = 8.7 Hz, 1H), 7.24 (bd, J = 8.4 Hz, 2H), 7.38 (bd, J = 8.7 Hz, 1H), 7.49 (d, J = 2.1 Hz, 1H), 8.30 (s, 1H). | 3.33 | ** |
| 1675 | 864 | 1H NMR (300 MHz, (CD3)2CO) δ 1.80 (s, 3H), 1.95 (s, 3H), 1.97 (s, 3H), 2.19 (s, 3H), 2.90-3.05 (m, 1H), 3.30-3.42 (m, 2H), 4.12 (dd, J = 11.4, 7.2 Hz, 1H), 4.23 (dd, J = 11.4, 5.8 Hz, 1H), 4.36-4.52 (bm, 1H), 4.62 (t, J = 6.3 Hz, 1H), 5.22 (s, 2H), 5.45 (dd, J = 10.2, 3.3 Hz, 1H), 5.56 (dm, J = 2.4 Hz, 1H), 5.72 (t, J = 9.7 Hz, 1H), 6.23 (d, J = 9.0 Hz, 1H), 6.50-6.60 (bm, 1H), 7.05 (bd, J = 8.1 Hz, 2H), 7.12 (dd, J = 8.7, 2.1 Hz, 1H), 7.23 (d, J = 8.9 Hz, 2H), 7.24-7.28 (m, 1H), 7.37 (bd, J = 8.4 Hz, 2H), 7.42 (d, J = 8.9 Hz, 2H), 7.56 (d, J = 1.5 Hz, 1H), 8.30 (s, 1H). 10.22 (s, 1H). | 3.88 | *** |
| 1676 | 710 | | 3.33 | * |
| 1677 | 878 | | 3.90 | *** |
| 1678 | 556 | 1H NMR (300 MHz, (CD3)2CO) δ 1.63-1.75 (m, 2H), 1.82 (s, 3H), 1.97-2.06 (m, 2H), 2.86 (dd, J = 8.1, 3.0 Hz, 2H), 3.20 (mc, 2H), 3.60-3.69 (m, 2H), 4.12-4.34 (m, 2H), 4.70 (septet, J = 4.2 Hz, 1H), 4.74 (s, 2H), 6.46 (mc, 1H), 6.59 (t, J = 4.8 Hz, 1H), 6.98 (d, J = 8.7 Hz, 2H), 7.10 (dd, J = 8.4, 2.1 Hz, 1H), 7.22 (dm, J = 8.4 Hz, 2H), 7.36 (d, J = 8.4 Hz, 1H), 7.53 (d, J = 2.1 Hz, 2H), 8.36 (d, J = 4.8 Hz, 2H), 10.19 (s, 1H). | 4.00 | ***** |
| 1679 | 591 | | 2.15 | **** |
| 1680 | 635 | | 2.37 | ***** |
| 1681 | 614 | | 4.42 | ***** |
| 1682 | 649 | | 2.33 | ***** |
| 1683 | 478 | | 2.23 | **** |
| 1684 | 492 | | 2.18 | **** |
| 1685 | 499.4 | | 3.63 | ***** |
| 1686 | 499.4 | | 3.62 | ***** |
| 1687 | 541.2 | | 3.97 | ***** |
| 1688 | 315.28 | | 1.7 | * |
| 1689 | 469.22 | $^1$H NMR (DMSO, 300 MHz), δ 11.15 (s, br, 1H), 8.48 (d, 2H), 7.56 (d, 1H), 7.43 (dd, 2H), 7.33 (s, 1H), 7.20 (d, 2H), 7.07 (d, 1H), 6.39 (d, 1H), 4.37 (m, 1H), 3.90 (s, 3H), 3.33 (br, 1H), 2.89 (m, 2H) | 3.75 | **** |
| 1690 | 453.28 | | 3.57 | **** |
| 1691 | 387.27 | $^1$H NMR (DMSO, 300 MHz), δ 11.15 (s, br, 1H), 8.43 (s, 2H), 7.52 (d, J = 1.8 Hz, 1H), 7.32 (s, br, 1H), 7.06 (dd, J = 8.7 Hz and 2.1 Hz, 1H), 6.30 (s, 1H), 4.30-4.05 (m, 3H), 3.88 (s, 3H), 3.16 (br, 1H), 2.80 (m, 2H), 1.21 (t, 3H) | 3.3 | *** |
| 1692 | 411.28 | $^1$H NMR (DMSO, 300 MHz), δ 11.15 (s, br, 1H), 8.43 (s, 2H), 7.52 (d, J = 2.1 Hz, 1H), 7.35 (s, br, 1H), 7.06 (dd, J = 8.7 Hz and 1.8 Hz, 1H), 6.31 (s, 1H), 4.72 (s, 2H), 4.2 (br, 1H), 3.88 (s, 3H), 3.18 (br, 1H), 2.72-2.87 (m, 2H), 1.80 (s, 3H) | 3.37 | **** |
| 1693 | 693 | | 2.53 | ***** |
| 1694 | 550 | | 2.40 | ***** |
| 1695 | 615 | | 3.13 | ** |
| 1696 | 533 | | 2.72 | * |
| 1697 | 552 | | 2.17 | ***** |
| 1698 | 567.19 | | 4.02 | ***** |
| 1699 | 427 | | 3.52 | ***** |
| 1700 | 546 | | 3.45 | ***** |
| 1701 | 509 | | 3.87 | ***** |
| 1702 | 628 | | 3.80 | ***** |
| 1703 | 624 | | 2.35 | ** |
| 1704 | 610 | | 2.40 | **** |
| 1705 | 566 | | 2.22 | *** |
| 1706 | M + 23:434.0 (cal.411.1) | $^1$H NMR (DMSO, 400 MHz), δ 11.22-11.21 (m, 1H), 8.90-8.79 (m, 1H), 7.52 (d, J = 1.6 Hz, 1H), 7.30 (d, J = 8.8 Hz, 1H), 7.15-7.7.11 (m, 2H), 7.07 (dd, J = 8.8 Hz and 2.0 Hz, 1H), 6.92-6.89 (m, 2H), 6.63-6.60 (m, 1H), 3.85-3.81 (m, 1H), 3.72 (s, 3H), 3.43-3.39 (m, 1H), 3.22-3.13 (m, 2H), 2.84-2.79 (m, 2H), 1.07-1.02 (m, 3H). | 10-80 4.05 | *** |
| 1707 | M + 23:448.0 (cal.425.2) | $^1$H NMR (DMSO, 400 MHz), δ 11.22 (b, 1H), 8.81-8.67 (m, 1H), 7.52 (s, 1H), 7.30 (d, J = 8.4 Hz, 1H), 7.15-7.7.11 (m, 2H), 7.07 (d, J = 8.8 Hz, 1H), 6.91 (d, J = 8.4 Hz, 2H), 6.62-6.38 (m, | 10-80 4.25 | *** |

TABLE 2-continued

| Cpd | MS | NMR | RT | EC$_{50}$ |
|---|---|---|---|---|
| | | 1H), 3.85-3.81 (m, 1H), 3.72 (s, 3H), 3.43-3.39 (m, 1H), 2.90-2.79 (m, 2H), 1.14-1.02 (m, 6H). | | |
| 1708 | M + 23:448.0 (cal.425.2) | $^1$H NMR (DMSO, 300 MHz), δ 11.22 (b, 1H), 8.74-8.71 (m, 1H), 7.52 (s, 1H), 7.30 (d, J = 9.0 Hz, 1H), 7.14-7.05 (m, 3H), 6.91 (d, J = 9.0 Hz, 2H), 6.62-6.38 (m, 1H), 3.85-3.81 (m, 1H), 3.71 (s, 3H), 3.43-3.39 (m, 1H), 3.19-3.09 (m, 2H), 2.82-2.79 (m, 2H), 1.52-1.42 (m, 2H), 0.85 (t, J = 7.5 Hz, 3H). | 30-90 2.80 | ** |
| 1709 | M + 23:438.0 (cal.437.2) | $^1$H NMR (DMSO, 400 MHz), δ 11.32 (b, 1H), 9.01-8.89 (m, 1H), 7.52 (s, 1H), 7.31 (d, J = 8.4 Hz, 1H), 7.19-7.05 (m, 3H), 6.90 (d, J = 8.4 Hz, 2H), 6.65-6.45 (m, 1H), 3.85-3.82 (m, 1H), 3.71 (s, 3H), 3.43-3.39 (m, 1H), 3.11-3.07 (m, 2H), 2.82-2.76 (m, 1H), 1.05-0.95 (m, 1H), 0.42-0.40 (m, 2H), 0.19-0.18 (m, 2H) | 30-90 3.81 | *** |
| 1710 | 450.2 (cal.451.2) | $^1$H NMR (DMSO, 400 MHz), δ 11.20 (b, 1H), 8.90-8.76 (m, 1H), 7.53 (d, J = 1.6 Hz, 1H), 7.29 (d, J = 8.4 Hz, 1H), 7.14-7.11 (m, 2H), 7.07 (dd, J = 8.8 Hz and 2.0 Hz, 1H), 6.91 (d, J = 8.8 Hz, 2H), 6.62-6.32 (m, 1H), 4.10-4.02 (m, 1H), 3.72-3.71 (m, 4H), 3.27-3.20 (m, 1H), 2.90-2.76 (m, 2H), 1.89-1.79 (m, 2H), 1.64-1.62 (m, 2H), 1.52-1.48 (m, 4H). | 30-90 3.91 | *** |
| 1711 | M − 1:492.1 (cal.493.1) | $^1$H NMR (DMSO, 400 MHz), δ 11.22-11.11 (m, 1H), 11.10-11.01 (m, 1H), 7.72-7.67 (m, 2H), 7.54 (d, J = 2.0 Hz, 1H), 7.44-7.40 (m, 2H), 7.32-7.29 (m, 1H), 7.17 (d, J = 8.4 Hz, 2H), 7.08 (dd, J = 8.8 Hz and 2.0 Hz, 1H), 6.94 (d, J = 8.8 Hz, 2H), 6.69-6.37 (m, 1H), 3.90-3.88 (m, 1H), 3.73 (s, 3H), 3.27-3.20 (m, 1H), 2.96-2.80 (m, 3H). | 30-90 4.64 | **** |
| 1712 | M + 23:496.0 (cal.473.2) | $^1$H NMR (DMSO, 400 MHz), δ 11.32-11.18 (m, 1H), 10.91-10.82 (m, 1H), 7.60-7.58 (m, 3H), 7.37 (d, J = 8.8 Hz, 1H), 7.25-7.19 (m, 4H), 7.16 (dd, J = 8.0 Hz and 2.0 Hz, 1H), 7.00 (d, J = 8.8 Hz, 2H), 6.75-6.42 (m, 1H), 3.94-3.90 (m, 1H), 3.79 (s, 3H), 3.50-3.45 (m, 1H), 2.96-2.89 (m, 2H), 2.32 (s, 3H). | 10-80 5.05 | **** |
| 1713 | M − 1:476.1 (cal.477.1) | $^1$H NMR (DMSO, 400 MHz), δ 11.28-11.14 (m, 1H), 11.01-10.92 (m, 1H), 7.68-7.64 (m, 2H), 7.53 (s, 1H), 7.30 (d, J = 8.4 Hz, 1H), 7.20-7.15 (m, 4H), 7.07 (d, J = 8.4 Hz, 1H), 6.93 (d, J = 8.4 Hz, 2H), 6.69-6.37 (m, 1H), 3.90-3.87 (m, 1H), 3.72 (s, 3H), 3.43-3.40 (m, 1H), 2.91-2.80 (m, 2H). | 30-90 4.42 | *** |
| 1714 | M − 1:458.1 (cal.459.1) | $^1$H NMR (DMSO, 400 MHz), δ 11.28-11.14 (m, 1H), 10.92-10.86 (m, 1H), 7.65-7.63 (m, 2H), 7.53 (d, J = 2.0 Hz, 1H), 7.36-7.31 (m, 3H), 7.18 (d, J = 8.4 Hz, 2H), 7.14-7.07 (m, 1H), 6.94 (d, J = 8.8 Hz, 2H), 6.69-6.37 (m, 1H), 3.90-3.87 (m, 1H), 3.73 (s, 3H), 3.43-3.40 (m, 1H), 2.91-2.80 (m, 2H). | 10-80 4.83 | **** |
| 1715 | 412.9 (cal.412.1) | $^1$H NMR (DMSO, 300 MHz), δ 11.20-11.08 (m, 1H), 7.54 (d, J = 1.8 Hz, 1H), 7.30 (d, J = 8.7 Hz, 1H), 7.11 (d, J = 8.7 Hz, 2H), 7.07 (dd, J = 8.4 Hz and 1.8 Hz, 1H), 6.95-6.91 (m, 2H), 6.62-5.94 (m, 1H), 4.37-4.30 (m, 2H), 3.72 (s, 3H), 3.69-3.63 (m, 1H), 3.40-3.32 (m, 1H), 2.94-2.75 (m, 2H), 1.29-1.24 (m, 3H). | 10-80 4.59 | *** |
| 1716 | M − 1:483.1 (cal.484.1) | $^1$H NMR (DMSO, 400 MHz), δ 11.37-11.30 (m, 1H), 11.22-11.08 (m, 1H), 7.89-7.83 (m, 4H), 7.54 (s, 1H), 7.31 (d, J = 8.4 Hz, 1H), 7.17 (d, J = 8.4 Hz, 2H), 7.07 (d, J = 8.8 Hz, 1H), 6.94 (d, J = 8.8 Hz, 2H), 6.69-6.37 (m, 1H), 3.91-3.89 (m, 1H), 3.73 (s, 3H), 3.05-2.90 (m, 3H). | 30-90 4.41 | ** |
| 1717 | 438.8 (cal.438.1) | $^1$H NMR (DMSO, 300 MHz), δ 11.25-11.16 (m, 1H), 7.55 (s, 1H), 7.30 (d, J = 8.4 Hz, 1H), 7.13-7.07 (m, 3H), 6.93 (d, J = 8.7 Hz, 2H), 6.63-5.95 (m, 1H), 4.20-4.09 (m, 2H), 3.72 (s, 3H), 3.69-3.62 (m, 1H), 3.45-3.41 (m, 1H), 2.92-2.76 (m, 2H), 1.22-1.13 (m, 1H), 0.55-0.53 (m, 2H), 0.37-0.34 (m, 2H). | 10-80 5.66 | **** |
| 1718 | 452.8 (cal.452.1) | $^1$H NMR (CD3CN, 300 MHz), δ 9.19 (b, 1H), 7.53 (d, J = 2.1 Hz, 1H), 7.30 (d, J = 9.0 Hz, 1H), 7.20 (d, J = 8.7 Hz, 2H), 7.11 (dd, J = 8.7 Hz and 2.1 Hz, 1H), 6.90 (d, J = 8.7 Hz, 2H), 6.69-5.95 (m, 1H), 4.32-4.20 (m, 2H), 3.77 (s, 3H), 3.72-3.62 (m, 1H), 3.52-3.42 (m, 1H), 2.92-2.86 (m, 2H), 2.76-2.66 (m, 1H), 2.11-2.03 (m, 2H), 1.90-1.78 (m, 4H). | 30-90 4.65 | **** |
| 1719 | 452.8 (cal.452.1) | $^1$H NMR (DMSO, 300 MHz), δ 11.22-11.20 (m, 1H), 7.55 (d, J = 2.1 Hz, 1H), 7.30 (d, J = 8.7 Hz, 1H), 7.12-7.06 (m, 3H), 6.96-6.92 (m, 2H), 6.61-5.90 (m, 1H), 5.34-5.30 (m, 1H), 3.72 (s, 3H), 3.62-3.59 (m, 1H), 3.43-3.40 (m, 1H), 2.92-2.86 (m, 2H), 1.95-1.86 (m, 2H), 1.72-1.54 (m, 6H). | 10-80 5.90 | * |
| 1720 | 494.9 (cal.494.1) | $^1$H NMR (DMSO, 400 MHz), δ 11.22-11.09 (m, 1H), 7.57-7.54 (m, 3H), 7.39 (d, J = 8.8 Hz, 1H), 7.31 (d, J = 8.1 Hz, 1H), 7.15 (d, J = 8.8 Hz, 2H), 7.09 (dd, J = 8.8 Hz and 2.0 Hz, 1H), 6.95 (d, J = 8.4 Hz, 2H), 6.69-6.22 (m, 1H), 3.96-3.91 (m, 1H), 3.76 (s, 3H), 3.50-3.42 (m, 1H), 3.43-3.40 (m, 2H). | 30-90 4.82 | * |
| 1721 | 474.8 (cal.474.1) | $^1$H NMR (DMSO, 400 MHz), δ 11.22-11.09 (m, 1H), 7.55 (s, 1H), 7.31 (d, J = 8.0 Hz, 1H), 7.26 (d, J = 8.4 Hz, 2H), 7.18-7.13 (m, 4H), 7.08 (d, J = 8.4 Hz, 1H), 6.94 (d, J = 8.8 Hz, 2H), 6.69-6.15 (m, 1H), 3.88-3.85 (m, 1H), 3.72 (s, 3H), 3.50-3.42 (m, 1H), 2.99-2.89 (m, 2H), 2.30 (s, 3H). | 30-90 4.74 | * |
| 1722 | 478.8 (cal.478.1) | $^1$H NMR (DMSO, 300 MHz), δ 11.22-11.12 (m, 1H), 7.55 (d, J = 2.1 Hz, 1H), 7.39-7.30 (m, 5H), 7.15 (d, J = 8.7 Hz, 2H), 7.10-7.08 (m, 1H), 6.95 (d, J = 8.7 Hz, 2H), 6.69-6.21 (m, 1H), 3.95-3.85 (m, 1H), 3.72 (s, 3H), 3.50-3.42 (m, 1H), 2.99-2.89 (m, 2H). | 10-80 5.87 | * |

TABLE 2-continued

| Cpd | MS | NMR | RT | EC$_{50}$ |
|---|---|---|---|---|
| 1723 | M − 1:489.1 (cal.490.1) | $^1$H NMR (DMSO, 400 MHz), δ 11.28-11.15 (m, 1H), 7.55 (s, 1H), 7.32 (d, J = 8.4 Hz, 1H), 7.23 (d, J = 8.8 Hz, 2H), 7.14 (d, J = 8.4 Hz, 2H), 7.09 (dd, J = 8.4 Hz and 1.6 Hz, 1H), 6.99 (d, J = 8.8 Hz, 2H), 6.94 (d, J = 8.4 Hz, 2H), 6.69-6.17 (m, 1H), 3.90-3.85 (m, 1H), 3.89 (s, 3H), 3.74 (s, 3H), 3.50-3.42 (m, 1H), 2.99-2.89 (m, 2H). | 10-80 5.79 | * |
| 1724 | 460.8 (cal.460.1) | $^1$H NMR (DMSO, 400 MHz), δ 11.28-11.15 (m, 1H), 7.56 (s, 1H), 7.48 (t, J = 8.0 Hz, 2H), 7.37-7.26 (m, 4H), 7.16 (d, J = 8.4 Hz, 2H), 7.09 (dd, J = 8.8 Hz and 1.6 Hz, 1H), 6.95 (d, J = 8.4 Hz, 2H), 6.75-6.20 (m, 1H), 3.90-3.85 (m, 1H), 3.73 (s, 3H), 3.50-3.42 (m, 1H), 2.99-2.89 (m, 2H). | 10-80 5.80 | * |
| #10 | 467.15 | | 4.51 | ***** |

Wherein:
1 star, >1 μM (1000 nM)
2 stars, 0.2 to 1 μM (200 nM to 1000 nM)
3 stars, 0.04 μM to 0.2 μM (40 nM to 200 nM)
4 stars, 0.008 μM to 0.04 μM (8 nM to 40 nM)
5 stars, <0.008 μM (<8 nM)

The EC$_{50}$ data was obtained using the protocol set forth below in Section 8.1.1.

LC/MS for certain Compounds was performed on either a Waters 2795 or 2690 model separations module coupled with a Waters Micromass ZQ mass spectrometer using a Waters Xterra MS C$_{18}$ 4.6×50 mm reverse phase column (detection at 254 nM). The methods employed a gradient of acetonitrile (ACN) in water at 2 mL/min at ambient temperature as shown in Table 2a. The mobile phase was buffered with a 0.1 N formic acid.

The standard 6 minute method maintains a constant 85/5/10 ratio of water/ACN/1% aqueous formic acid from 0 minutes to 0.5 minutes. The method runs a linear gradient from 85/5/10 at 0.5 minutes to 0/90/10 at 3.5 minutes. The methods holds at 0/90/10 until 4.5 minutes then immediately drops back down to 85/5/10 and holds there until 6 minutes.

The non-polar 6 minute method maintains a constant 60/30/10 ratio of water/ACN/1% aqueous formic acid from 0 minutes to 0.5 minutes. The method runs a linear gradient from 60/30/10 at 0.5 minutes to 0/90/10 at 3.5 minutes. The methods holds at 0/90/10 until 4.5 minutes then immediately drops back down to 60/30/10 and holds there until 6 minutes.

The polar 6 minute method maintains a constant 90/0/10 ratio of water/ACN/1% aqueous formic acid from 0 minutes to 0.5 minutes. The method runs a linear gradient from 90/0/10 at 0.5 minutes to 20/70/10 at 3.5 minutes. The methods holds at 20/70/10 until 4.5 minutes then immediately drops back down to 90/0/10 and holds there until 6 minutes.

TABLE 2a

| Time | % Acetonitrile | % Water | % 1% Aq. Formic Acid | Gradient |
|---|---|---|---|---|
| Standard | | | | |
| 0.00 | 5 | 85 | 10 | |
| 0.50 | 5 | 85 | 10 | hold |
| 3.50 | 90 | 0 | 10 | linear hold |
| 4.50 | 5 | 85 | 10 | instant |
| 6.00 | 5 | 85 | 10 | hold |
| Non-Polar | | | | |
| 0.00 | 30 | 60 | 10 | |
| 0.50 | 30 | 60 | 10 | hold |
| 3.50 | 90 | 0 | 10 | linear hold |
| 4.50 | 30 | 60 | 10 | instant |
| 6.00 | 30 | 60 | 10 | hold |

TABLE 2a-continued

| Time | % Acetonitrile | % Water | % 1% Aq. Formic Acid | Gradient |
|---|---|---|---|---|
| Polar | | | | |
| 0.00 | 0 | 90 | 10 | |
| 0.50 | 0 | 90 | 10 | hold |
| 3.50 | 70 | 20 | 10 | linear hold |
| 4.50 | 0 | 90 | 10 | instant |
| 6.00 | 0 | 90 | 10 | hold |

LC/MS for Compounds 1611 and 1669 was performed using a C18-BDS 5 (250×4.6 mm) column with a 0.7 mL/min flow rate. The following solvent gradient was employed using 0.1% TFA/water as solvent A and acetonitrile as solvent B: 20% B for 0-20 minutes, 70% B for 20-30 minutes, 100% B for 30-40 minutes, 20% B for 40-50 minutes.

7. EXAMPLE

Formulation of Compound 1205

Compound 1205 is bioavailable in vivo when administered in an aqueous suspension. It is anticipated that Compound 1205 can be clinically administered via a solid-dosage form. For all the studies outlined herein, Compound 1205 was lyophilized prior to formulation to minimize batch-to-batch variations in particle-size.

The compound was dissolved in acetonitrile at a concentration of 15 mg/mL. An equal amount of water was added to bring the final concentration to 7.5 mg/mL in a 1:1 acetonitrile/water solution (v/v). The solution was frozen on the shelf of the freeze dryer for a minimum of 3 hours and then lyophilized. The resulting solid was determined to be amorphous by differential scanning calorimetry and polarized light microscopy. Suspensions were prepared by the addition of 0.5% HPMC with 1% Tween-80, followed by stirring and homogenization for 2 minutes.

8. EXAMPLE

Pharmacodynamics of Compound 1205

The examples that follow demonstrate that the Compounds tested can inhibit the production of tumor-generated human VEGF and delay tumor growth. Compounds tested have been shown to inhibit the pathological production of human VEGF by human tumor cells and/or human tumors in an animal model with pre-established human tumors.

8.1 Inhibition of Pathological Production of VEGF 8.1.1 Effect of Compounds on Hypoxia-Inducible Endogenous VEGF Expression The ability of the Compounds to modulate hypoxia-inducible endogenous VEGF expression may be analyzed as follows. VEGF protein levels may be monitored by an ELISA assay (R&D Systems). Briefly, HeLa cells may be cultured for 24-48 hours under hypoxic conditions (1% $O_2$, 5% $CO_2$, balanced with nitrogen) in the presence or absence of a Compound. The conditioned media may then be assayed by ELISA, and the concentration of VEGF calculated from the standard ELISA curve of each assay.

A dose-response analysis may be performed using the ELISA assay and conditions described above. The conditions for the dose-response ELISA are analogous to those described above. A series of, e.g., seven different concentrations may be analyzed. In parallel, a dose-response cytotoxicity assay may be performed using Cell Titer Glo (Promega) under the same conditions as the ELISA to ensure that the inhibition of VEGF expression was not due to the cytotoxicity. Dose-response curves may be plotted using percentage inhibition versus concentration of the Compound, and $EC_{50}$ and $CC_{50}$ values may be generated for each Compound with the maximal inhibition set as 100% and the minimal inhibition as 0%. In one embodiment, Compounds will have an $EC_{50}$ of less than 50, less than 10, less than 2, less than 0.5, or less than 0.01.

8.1.2 Compound 1205 Inhibit Pathological VEGF Production in Transformed Cells Grown under hypoxic Conditions This example demonstrates the selective inhibition of Compound 1205 on pathological human VEGF production in transformed HeLa cells grown under stressed conditions while sparing human VEGF production in HeLa cells grown under non-stressed conditions.

Experimental Design.

HeLa (human cervical carcinoma) cell cultures were established under normoxic conditions (21% oxygen). HeLa cells increase VEGF production 4- to 5-fold in response to hypoxia. In one experimental design, vehicle (0.5% DMSO) alone, or a range of concentrations of Compound #10, Compound 1205, or Compound 1330 was added to the culture medium and the cells were incubated for 48 hours. At the completion of treatment, the conditioned media were collected and the VEGF protein levels were assayed in an enzyme-linked immunosorbent assay (ELISA) with primary antibodies that recognize the soluble $VEGF_{121}$ and $VEGF_{165}$ isoforms (R & D Systems, Minneapolis, Minn., USA). To ensure that decreases in VEGF concentration were not due to cytotoxicity, cultures were assayed using a standard assay (CellTiter-Glo® Luminescent Cell Viability Assay; Promega, Madison, Wis., USA) that measures total cellular adenosine triphosphate (ATP) concentrations as an indicator of cell viability.

Results.

FIG. 1 shows the concentrations of VEGF in conditioned media across the dose range tested for Compound #10, Compound 1205 and Compound 1330. The data indicate that Compound #10 and Compound 1205 inhibit stress-induced VEGF production.

8.1.3 Compound 1205 Reduces Tumor and Pathological Plasma VEGF Concentrations In Vivo This example demonstrates that Compound 1205 reduces intratumoral and pathological plasma human VEGF concentrations in vivo.

Experimental Design.

Human HT1080 cells ($5 \times 10^6$ cells/mice) were implanted subcutaneously into male athymic nude mice. Human HT1080 cells constitutively produce human VEGF. Treatment with vehicle alone or Compound 1205 was initiated when the median tumor volume was approximately 311±88 $mm^3$. Table 3 and Table 4 provide the study design for assessing tumor and pathological plasma VEGF concentrations—each group in each study included eight (8) mice. When the tumors in vehicle-treated mice had reached the target size of about 1200 $mm^3$ for study #21 and about 1500 $mm^3$ for study #23, all mice in the study were sacrificed, and excised tumors were homogenized in buffer containing protease inhibitors. Both intra-tumor and plasma human VEGF levels were measured using an ELISA that recognizes human $VEGF_{121}$ and $VEGF_{165}$. Intra-tumor VEGF levels were normalized to the total tumor protein concentration and plasma VEGF levels were expressed in pg/mL. Because smaller tumors produce less VEGF per mg of tumor protein, intra-tumor VEGF levels were normalized to tumor size. Table 4 provides the study design for assessing tumor and plasma VEGF.

Results.

Treatment with Compound 1205 at 0.5 or 3 mg/kg for 14-days significantly reduced the levels of human VEGF measured in excised tumors (FIG. 2) and in plasma (FIG. 3) compared to levels measured in tumors and plasma from mice treated with vehicle. At the dose of 0.5 or 3 mg/kg QD, Compound 1205 inhibits both tumor and plasma VEGF levels by more than 95%. Even with the reduction in tumor size in the treated groups, the volume normalized intra-tumor VEGF levels were significantly reduced (FIG. 2; Table 3).

TABLE 3

Inhibition of Intra-Tumor and Plasma VEGF by Compound 1205

| | Study #21 | | | Study #23 | |
|---|---|---|---|---|---|
| | Vehicle | Compound 1205 | | Vehicle | Compound 1205 |
| 1) Dose (mg/kg) | 0 | 0.5 | 3 | 0 | 1 |
| 2) Regimen | QD | QD | QD | QD | QD |
| 3) Test-Compound duration (days) | 14 | 14 | 14 | 14 | 14 |
| 4) Mean difference in human tumor VEGF (%) at Day 14 (Compound 1205) or Day 18 (Compound #10) | NA | 95%** | 98%** | NA | 95** |

TABLE 3-continued

Inhibition of Intra-Tumor and Plasma VEGF by Compound 1205

| | Study #21 | | Study #23 | |
|---|---|---|---|---|
| | Vehicle | Compound 1205 | Vehicle | Compound 1205 |
| 5) Mean difference in human plasma VEGF (%) on Day 14 (Compound 1205) or on Day 18 (Compound #10) | NA | 97%** | 99% | NA | 100%** |

**$p < 0.05$ (ANOVA vs. vehicle).

8.2 Compound 1205 Inhibits Tumor Growth In Vivo

This example demonstrates that Compound 1205 inhibits tumor growth in nude mice bearing HT1080 xenografts.

Experimental Design.

HT1080 cells ($5 \times 10^6$ cells/mouse) were implanted subcutaneously in male athymic nude mice. When tumors had become established (i.e., the mean tumor size had reached $311 \pm 88$ mm$^3$), mice were divided into 5 groups and treatment was administered as shown in Tables 4 and 5. Compound 1330 is a relatively inactive (R,S) diastereomer of Compound 1205, which has (S,S) configuration. For comparison, Compound #10 was included in this study.

Results.

The results of the studies are described in Table 5 and FIG. 4. The data shown in FIG. 4 is for study #24a. The data indicate that Compound 1205 (S,S) inhibits tumor growth in an animal model with a pre-established human tumor. As shown in FIG. 4, treatment with Compound 1205 (S,S), but not with the (R,S) diastereomer Compound 1330, significantly delayed growth of HT1080 tumor cells in vivo. The growth of the tumors in mice treated with Compound 1330 overlapped with the growth of tumors in mice treated with 0.5% HPMC vehicle. See FIG. 4. This suggests that the relatively inactive (R,S) diastereomer (Compound 1330)

TABLE 4

Study Design for HT1080 Xenograft Studies Assessing In Vivo Efficacy of Compound 1205 and Compound #10.

| Test Compound | # of Animals (Male) | Dose (mg/kg) | Regimen | Dose Volume (mL/kg) | Dose Conc. (mg/mL) | Study # | Study Termination |
|---|---|---|---|---|---|---|---|
| Vehicle† | 8 | 0 | QD | 8 | 0 | 21 | All mice were taken off study when tumors in vehicle reached 1200 mm$^3$ |
| Compound 1205 | 8 | 0.5 | QD | 8 | 0.0625 | 21 | |
| Compound 1205 | 8 | 3 | QD | 8 | 0.375 | 21 | |
| Vehicle† | 8 | 0 | QD | 8 | 0 | 22 | (A) Vehicle-treated mice were taken off study when the average tumor size of the group wais 1500 mm$^3$. (B) Each treated mouse was taken off study when its tumor was 1500 mm$^3$ |
| Compound 1205 | 8 | 0.5 | QD | 8 | 0.0625 | 22 | |
| Compound 1205 | 8 | 3 | QD | 8 | 0.375 | 22 | |
| Vehicle† | 8 | 0 | QD | 8 | 0 | 23 | All mice were taken off study when tumors in vehicle reached 1500 mm$^3$ |
| Compound 1205 | 8 | 1 | QD | 8 | 0.125 | 23 | |
| Vehicle† | 8 | 0 | QD | 8 | 0 | 24a | A) Vehicle- and Compound 1330 -treated mice were taken off study when the average tumor size of the group wais 1500 mm$^3$. (B) Each treated mouse was taken off study when its tumor was 1500 mm$^3$ |
| Compound 1205 | 8 | 10 | QD | 8 | 1.25 | 24a | |
| Compound 1330 Φ | 8 | 10 | QD | 8 | 1.25 | 24a | |
| Vehicle† | 8 | 0 | QD | 8 | 0 | 24b | (A) Vehicle-treated mice were taken off study when the average tumor size of the group wais 1500 mm$^3$. (B) Each treated mouse was taken off study when its tumor was 1500 mm$^3$ |
| Compound 1205 | 8 | 0.3 | QD | 8 | 0.0375 | 24b | |

† Vehicle was 0.5% HPMC/1% Tween-80
‡ Vehicle was L21 (35% Labrasol, 35% Labrafac, and 30% Solutol).
Φ Inactive (R, S) diastereomer of Compound 1205
Abbreviations:
BID = twice per day,
QD = once per day does not appreciably isomerize to active Compound 1205 in vivo. Compound 1205 is active at doses as low as 0.3 mg/kg.

TABLE 5

Effect of Compound 1205 and Compound #10 on Growth of HT1080 Tumor Cells in vivo.

| | Compound 1205 | | | | | | Compound #10 | |
|---|---|---|---|---|---|---|---|---|
| Study Information | | | | | | | | |
| 1) Study #[C] | 24b | 22 | 21 | 23 | 22 | 21 | 24a | 24a |
| 2) Dose (mg/kg) | 0.3 | 0.5 | 0.5 | 1 | 3 | 3 | 10 | 10 |
| 3) Regimen | QD | QD | QD | QD | QD | QD | QD | QD |
| 4) Dose (mg/kg/week) | 2.1 | 3.5 | 3.5 | 7 | 21 | 21 | 70 | 70 |
| 5) Study design | Xeno | Xeno | PD | PD | Xeno | PD | Xeno | Xeno |
| 6) Number of days that test compound was administered | 16[A] | 28[A] | 14 | 14 | 32[A] | 14 | 30[A] | 27[A] |
| 7) Initial mean tumor size ($mm^3$) | 204 | 170 | 167 | 157 | 170 | 167 | 311 | 311 |
| 8) Day that vehicle-treated mice were taken off study | 15 | 11 | 14 | 14 | 11 | 14 | 11 | 11 |
| 9) Mean tumor size in vehicle-treated mice when taken off study | 1790 | 1390 | 1210 | 1500 | 1390 | 1210 | 1500 | 1500 |
| 10) Final mean terminal tumor size in treatment group ($mm^3$) | 1540 | 1750 | 580 | 710 | 1840 | 379 | 1400 | 1460 |
| Results | | | | | | | | |
| 11) Mean difference in tumor growth rate at the Day that the vehicle-treated tumors taken off study (%)[B] | 28% | 62%** | 61%** | 59%** | 75%** | 80%** | 76%** | 59%** |
| 12) Difference vs. vehicle in median number of days to reach 1000 $mm^3$ (Days) | 0.7 | 11 | NA | NA | 14** | NA | 14** | 8** |

[A]See Table 4 for additional study information.
[B]% Difference in the rat of growth in compound-treated vs. vehicle-treated
**$P < 0.05$ (ANOVA vs. vehicle)
[C]Average time on study.
NA not applicable. The time to progression could not be calculated for PD (pharmacodynamic) studies 8.3 Compound 1205 Provokes a Late $G_1$/Early S-Phase Cell Cycle Delay This example demonstrates that Compound 1205 provokes a cell cycle delay at the $G_1$/S-phase border.

Experimental Design.

During the in vitro evaluation of Compound 1205 effects on VEGF expression, an examination of its actions on tumor cell cycling was performed. HT1080 cells were incubated under normoxic conditions (21% oxygen) for 18 hours with vehicle (0.5% DMSO) alone, or with 10 nM of Compound 1205. After treatment, cells were trypsinized, and stained with propidium iodide (PI) dye to measure DNA content of individual cells by flow cytometry. Output comprised histograms showing relative DNA content in 10,000 cells.

Results.

As shown in FIG. 5, Compound 1205 induced a redistribution of the cycling characteristics of the cell population.

9. EXAMPLE

Selectivity of Compound 1205 for Human VEGF

This example demonstrates that Compound 1205 is selective for human VEGF.

Experimental Design.

After mouse tumors reached 1500 $mm^3$, mice were sacrificed and tissues were collected at the time of necropsy, homogenized, and analyzed. On average, mice treated with Compound 1205 at 0.5 mg/kg were on study for 28 days, and mice treated with Compound 1205 at 3 mg/kg were on study for 32 days.

Results.

As shown in FIG. 6, Compound 1205 did not significantly decrease murine kidney VEGF levels, indicating that Compound 1205 is likely to act in a species-selective manner.

10. EXAMPLE

Inhibition of Viral Replication

Viral Replication Assays

A person of ordinary skill in the art may test a Compound for antiviral activity using a variety of different approaches, with a representative number of selected examples as detailed below.

HCV Replicon Assay

The lack of validated and readily accessible cell-culture whole virus infection systems and small animal models permissive for HCV replication has limited the development of new anti-HCV agents. Self-replicating genomic and subgenomic HCV systems, termed HCV replicons, have been described and have been widely used to assess the efficacy of anti-HCV inhibitors (see Blight K J, et al., 2000, Efficient initiation of HCV RNA replication in cell culture. Science 290:1972-1974; Blight K J, et al., 2002, Highly permissive cell lines for subgenomic and genomic hepatitis C virus RNA replication. J Virol 76:13001-13014; Ikeda M, et al., 2002. Selectable subgenomic and genome-length dicistronic RNAs derived from an infectious molecular clone of the HCV-N strain of hepatitis C virus replicate efficiently in cultured Huh7 cells. J Virol 76:2997-3006; Lohmann V, et al., 1999, Replication of subgenomic hepatitis C virus RNAs in a hepatoma cell line. Science 285:110-113; Pietschmann T, et al., 2002, Persistent and transient replication of full-length hepatitis C virus genomes in cell culture. J Virol 76:4008-4021; and, Pietschmann T, et al., 2001, Characterization of cell lines carrying self-replicating hepatitis C virus RNAs. J Virol 75:1252-1264).

U.S. Pat. No. 6,630,343 describes a bicistronic HCV 1b replicon and 2a replicon for use in testing a Compound by quantitating replicon RNA (GenBank Accession No. AJ242654) reduction and/or the Fluc reporter signal. The amount of HCV replicon RNA is determined by quantitative reverse transcription polymerase chain reaction (qRT-PCR). In some cases, a Compound is tested against the HCV replicon in a spheroid culture. Replicon-containing cells may be cultured with a Compound for up to 3 days. Interferon (IFN) α is used as a positive control.

Standard cell culture assays employing hepatitis C virus (HCV) subgenomic replicons showed that the Compound had an average $IC_{50}$ of 0.036 μM against the genotype 1b replicon and an $IC_{50}$ of <0.003 μM against the genotype 2a replicon. Performing a replicon assay under three-dimensional culture conditions (spheroid culture) resulted in an $IC_{50}$ of 0.001 μM against the genotype 1b replicon and >310 fold selectivity index. Notably, the R-enantiomer of the Compound failed to exhibit significant antiviral activity in parallel experiments.

Attempts to generate resistant HCV replicons using standard virological techniques were unsuccessful despite exposure of replicon cells to the Compound under various conditions for up to four months. Classical antivirals acting directly on viral targets typically generate robustly resistant variants within 3-4 weeks using this technique.

Poliovirus (PV) Assay

Antiviral activity is tested against PV strain Mahoney (obtained from Dr. Eckard Wimmer, State University of New York at Stony Brook, Stony Brook, N.Y.) in HeLa S3 cells by determining the viral RNA reduction using qRT-PCR. HeLa S3 cells are seeded onto 96 well plates at a density of 5000 cells per well and incubated in DMEM supplemented with 10% FBS and 1% penicillin-streptomycin at 37° C. under 5% $CO_2$ for 24 hours and then treated with a Compound at a series of test concentrations for 18 hours. The cells are then infected with PV at a multiplicity of infection of 0.1 in DMEM without FBS for 30 minutes, followed by treatment with a Compound at a series of concentrations in DMEM with 1% FBS for 20 hours. After removing supernatant and washing the cells with PBS, RNA is prepared by adding 50 μL of Cells-to-cDNA Cell Lysis Buffer (Ambion, Catalog #8723) to each well and then heating at 75° C. for 10 minutes. The cell lysate is then treated with DNase I (DNA-free™ Ambion, Catalog #1906) at 37° C. for 20 minutes and then heated at 75° C. for 5 minutes to inactivate DNase. cDNA is prepared using iScript RT kit (Bio-Rad, Catalog #170-8897). The viral cDNA is determined by qRT-PCR using a pair of primers and a probe complementary to the viral internal ribosome entry site. The $IC_{50}$ shown in Table 7 is calculated based on percentage of viral RNA reduction under treatment of a Compound using Prism nonlinear fit sigmoidal dose-response variable slope (GraphPad Prism Software).

Additionally, in a 24-hour assay of infected HeLa cells when the Compound was added about 16 hours pre-infection, PV was inhibited with an average $IC_{50}$ of 0.0006 μM. Adding the Compound at the time of infection, though, resulted in a 65-fold decrease in activity. In HT-1080 cells, the Compound inhibited PV with an average $IC_{50}$ of 0.0004 μM. A variant HT-1080 cell line which displayed resistance to the cell cycle effects of the Compound was generated through serial passage; in these cells the Compound inhibited PV with an average $IC_{50}$ of 4.7 μM, a 10.000-fold difference in activity from that observed in non-resistant cells.

Other Viral Assays

Antiviral activity of a Compound against WNV is tested in Vero cells by protection of virus induced cytopathic effects (i.e. cytoprotection measured as cell viability, $IC_{50}$). The effect of a Compound on inhibition of virus induced cytopathic effects is determined using MTS (CellTiter) assay.

Antiviral activity against vaccinia virus is determined in Vero E6 cells by a plaque reduction assay. For a plaque reduction assay, inhibition of viral replication is determined as a reduction in virus-induced plaque formation assessed by microscopic inspection following staining of the culture with crystal violet.

Antiviral activity against HIV-1 is determined in a human cell line. The Compound prevented cytopathic effect 3 days post-infection with an $EC_{50}$ of 0.022 μM when normalized to cell number after treatment in the absence of infection. The activity against HIV may also be tested in human peripheral blood mononuclear cells in cell culture.

TABLE 7

| Activity of Compound #10 in Antiviral Assay Panel | | | | | | |
|---|---|---|---|---|---|---|
| Virus | | Cell line | Assay | $IC_{50}$ (μM) | $IC_{90}$ (μM) | $CC_{50}$ (μM) |
| Vaccinia | DNA | Vero E6 | Plaque | 0.040 | 0.080 | 0.083 |
| Adenovirus | DNA | HeLa | CPE protection | >1 | >1 | >1 |
| HSV-1 | DNA | Vero | CPE protection | >1 | >1 | >1 |
| Influenza A | (−) RNA | MDCK | CPE protection | >1 | >1 | >1 |
| Parainfluenza | (−) RNA | Vero | CPE protection | 0.029 | 0.044 | >1 |
| RSV | (−) RNA | Vero | CPE protection | 0.25 | >0.16 | >1 |
| Yellow Fever | (+) RNA | HeLa | CPE protection | >1 | >1 | >1 |
| Dengue 2 | (+) RNA | Vero E6 | CPE protection | >1 | >1 | 0.70 |
| WNV | (+) RNA | Vero | CPE protection | 0.067 | 0.28 | >1 |
| PV | (+) RNA | HeLa | qRT-PCR | 0.00057 | 0.0028 | >1 |
| HIV-1 | Retro | MT-2 | CPE protection | 0.022 | NA | 0.0041 |

Results.

As shown in Table 7, the Compound has inhibitory activity against a diverse panel of DNA viruses, RNA viruses and retroviruses in vitro. At the doses tested in the human or monkey cell lines tested, the Compound did not inhibit the two DNA viruses adenovirus and herpes simplex virus-1 (HSV-1). At the doses tested in the human or monkey cell lines tested, the Compound was inactive against the two RNA viruses dengue and yellow fever. However, the Compound displayed potent activity against the three RNA viruses parainfluenza virus, respiratory syncytial virus (RSV), and West Nile virus (WNV) in the cell lines tested. The Compound did not exhibit any selective inhibition of influenza virus when grown in the canine kidney cell line tested. The broad-spectrum activity of the Compound was demonstrated by its inhibition of both plus-strand (PV, HCV, WNV) and minus-strand (RSV, parainfluenza) RNA viruses. No antiviral activity was detected for the R-enantiomer of the Compound.

11. EXAMPLE

Effect Of Compound #10 in a 786-0 Renal Cancer Cell Line (VHL-Negative)

The in vivo activity of Compound #10 was assessed as a monotherapy and in combination with sunitinib (e.g., branded/marketed as SUTENT®) or rapamycin (e.g., branded/marketed as RAPAMUNE®) in a renal cell carcinoma (RCC) model (786-0 cells) in vivo. Both sunitinib and rapamycin are used clinically for treatment of renal cancer.

The 786-O cell line does not express the von Hippel-Lindau (VHL) protein (VHL-negative cell), therefore preventing its interaction with HIF-1α (hypoxia-inducible factor 1α), which accumulates and stimulates expression of growth factors, such as vascular endothelial growth factor (VEGF), that are responsible for the high vascularization of RCC (see Turcotte S, Desrosiers R R, Beliveau R. Hypoxia upregulates von Hippel-Lindau tumor-suppressor protein through RhoA-dependent activity in renal cell carcinoma. Am J Physiol Renal Physiol. First published 2003 Oct. 23; doi:10.1152/ajprenal.00254.2003; and, Zimmer M, Doucette D, Siddiqui N, Iliopoulos O. Inhibition of hypoxia-inducible factor is sufficient for growth suppression of VHL−/− tumors. Mol Cancer Res. 2004 2:89-95). Individuals with mutations in the VHL gene resulting in von Hippel-Lindau disease are at increased risk for developing clear cell carcinoma of the kidney, which is the most common histologic type of renal cancer. Biallelic VHL mutations (frequently involving point mutation of one allele and loss of the other) are common in sporadic renal cell carcinomas of the clear cell type (Kim W Y and Kaelin W G. The role of VHL gene mutation in human cancer. J Clin Oncol. In press 2004). Moreover, VHL inactivation due to DNA hypermethylation has been documented in some renal cell carcinomas that lack VHL mutation (Herman J G, Latif F, Weng Y, et al Silencing of the VHL tumor-suppressor gene by DNA methylation in renal carcinoma. Proc Natl Acad Sci USA 1994; 91:9700-4).

Sunitinib inhibits the kinase activities of VEGF receptors, platelet derived growth factor (PDGF) receptors, Flt3, and c-kit (CD117; see Mendel D B, Laird A D, Xin X, et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res. 2003; 9:327-37). SUTENT® is approved for treatment of RCC, having demonstrating clinical efficacy (Package insert for SUTENT®; http://www.pfizer.com/files/products/uspi_sutent.pdf). Previous studies have demonstrated that Compound #10 demonstrates favorable activities compared with sunitinib and an additive effect with sunitinib in a mouse lung cancer xenograft model. In the previous study, the dose utilized was 50 mg/kg. Here, a dose of 75 mg/kg was used.

The mTOR (mammalian target of rapamycin) inhibitors rapamycin and analogs are active in RCC in preclinical models and in the clinic (see Dasanu C A, Clark B A, Alexandrescu D T. mTOR-Blocking Agents in Advanced Renal Cancer: An Emerging Therapeutic Option. Expert opinion on investigational drugs 2009; 18(2):175-87; Package insert for rapamycin: http://www.huntingtonproject.org/Portals/0/rapamycin.pdf). The antitumor activity of agents that block the PI3-K/Akt/mTOR pathway may at least in part be attributable to the suppression of tumor angiogenesis as a result of suppression of VEGF production at the translational level. Although mTOR inhibitors block cap-dependent translation, the VEGF mRNA can be translated by a cap-independent mechanism, possibly involving the use of an internal ribosome entry site (IRES). Stressful conditions (e.g., rapamycin-treatment) may favor the use of this alternative pathway. An additive or synergistic combination between the two approaches (Compound #10 and an mTOR inhibitor) may produce an optimal blockade of VEGF via different pathways.

786-O cells were obtained from the American Type Culture Collection (ATCC) (Manassas, Va.) and cultured using methods provided by the ATCC.

Compound #10 was formulated in 30% Solutol HS15®, 35% Labrasol®, and 35% Labrafac® (L21) and stored at room temperature in ambient humidity and protected from light. Rapamycin was formulated in 0.4% ethanol (100%) stock, which was stored at −70° C. in aliquots and aliquot thawed daily for dilution. The stock of rapamycin was then diluted in 5% Tween-80, 5% PEG-400, 90% water. Sunitinib was formulated in 0.5% HPMC and 1% Tween-80.

TABLE 8

Dosing Solutions and Suspensions

| Test Compound | Dose (mg/kg) | Dosing Volume | Dose Concentration (mg/mL)[a] |
|---|---|---|---|
| Vehicle (L21) | 0 | 0.1 mL/mouse | 0 |
| Compound #10 | 10 | 0.1 mL/mouse | 2.8, 2.8, 3.0, 3.1 |
| Sunitinib | 75 | 0.2 mL/mouse | 10.5, 10.5, 11.25, 11.62, 11.62 |
| Rapamycin | 15 | 0.1 mL/mouse | 4.2 |

[a]Mice weighed an average of 28 g at the time dosing was initiated. The concentration of the dosing solution was adjusted as necessary so that a volume of 0.1 mL delivered the target dose. The dosing solutions were prepared five times.

Mice were inoculated with 786-O tumor cells ($5 \times 10^6$ cells/mouse) obtained from the ATCC(CRL-1932; Manassas, Va.). Tumor cells were mixed 1:1 with BD MATRIGEL™ (Becton, Dickinson and Company, San Jose, Calif.) prior to inoculation. Mice were inoculated using a 25-gauge needle in the right flank in a volume of 0.2 mL. A total of 100 mice were injected, of which 60 were used in the study.

Fourteen days after inoculation, the mice were randomized into six groups as outlined in Table 9. Animals were distributed into groups such that the average tumor size did not differ between groups. Groups were taken off study when the mean tumor volume in a group was 1300 mm³ or more. Vehicle-treatment started on Day 0 and continued through Day 57. Compound #10-treatment started on Day 0 and continued through Day 88.

TABLE 9

Group Designations

| Group | Compound #10 Treatment | Compound #10 Dose (mg/kg), Route, Regimen | Chemotherapy Treatment | Chemotherapy Dose (mg/kg), Route, Regimen | No of Mice |
|---|---|---|---|---|---|
| 1 | Vehicle | 0 | None | None | 10 |
| 2 | Compound #10 | 10, PO, QD | None | None | 10 |
| 3 | Vehicle | 0 | Sunitinib | 75 mg/kg PO, QD | 10 |
| 4 | Compound #10 | 10, PO, QD | Sunitinib | 75 mg/kg PO, QD | 10 |
| 5 | Vehicle | 0 | Rapamycin | 15 mg/kg PO, Days 0-4, 7-11, 65-67, 70-74, 77 and 78 | 10 |
| 6 | Compound #10 | 10, PO, QD | Rapamycin | 15 mg/kg PO, Days 0-4, 7-11, 65-67, 70-74, 77 and 78 | 10 |

Abbreviations: No = number, PO = oral dosing, QD = once per day.

Body Weight: The mice were weighed once per week.

Tumor Size: Tumors were measured twice per week using digital calipers. To calculate tumor volume, the following calculation was used, where L equals the longest dimension measurement and W equals the shortest dimension measurement:

$$\text{Tumor Volume} = \frac{L \times (W)^2}{2}$$

Clinical Observations: Each animal was observed twice daily for mortality and signs of pain or distress. Findings of overt toxicity were recorded as they were observed.

Plasma VEGF: Plasma was run in the Human VEGF ELISA, R&D Systems Cat#DY293B. Plasma was diluted at 1:1 with reagent diluent prior to quantification via ELISA.

Tumor Growth was calculated as:

[1−[(final tumor size minus initial tumor size in test compound treated–mice)/(final tumor size minus initial tumor size in vehicle-treated mice)]×100%

Values were calculated for individual mice and then averaged across the group.

Body Weight: The mice were weighed once per week. The percent change was calculated as:

[(Body weight on Day of study)−(initial body weight)/(initial body weight)]×100%

Values were calculated for individual mice and then averaged across the group.

The time to progression to reach a tumor volume 1000 mm$^3$ was calculated for each mouse. The median values were reported. For statistical analysis, if the tumor in a given mouse did not reach 1000 mm$^3$, the time on study was utilized (e.g., 119 days for mice in the sunitinib-treated group). Differences in tumor size, tumor growth, and body weight change between groups were analyzed by Two-way ANOVA (Bonferroni).

Results: Vehicle and Compound #10 Monotherapy: All mice treated with vehicle or with Compound #10 survived until sacrificed (at the time that the mean tumor size of the group reached about 1500 mm$^3$). Mouse 2-10 treated with Compound #10 (10 mg/kg) was cured, as defined by reduction of tumor size (<60 mm$^3$), such that the tumor was not measurable or appeared to be absent.

Results: Sunitinib Monotherapy: All mice treated with sunitinib survived until sacrificed (at the time that the mean tumor size of the group reached about 1500 mm$^3$). From Day 7 onward, all mice in Group 3 (sunitinib, 75 mg/kg) had yellow-tinged skin.

Results: Combination of Compound #10 and Sunitinib: From Day 7 onward, all mice in Group 4 (Compound #10 and sunitinib) had yellow-tinged skin. Mouse 4-3 and mouse 4-5 in Group 4 (Compound #10 and sunitinib) were sacrificed on Day 87.

Results: Rapamycin Monotherapy and Combination of Compound #10 and Rapamycin: All mice treated with rapamycin survived until sacrificed (at the time that the mean tumor size of the group reached about 1500 mm$^3$).

Results: Tumor Measurements: A total of 60/100 mice that were inoculated with 786-O cells developed tumors that were within the appropriate range at the start of this study. The tumor volume (mean±SD) for mice used in this study was 297±53 mm$^3$ at the initiation of treatment.

FIG. 9 and FIG. 11 show the effect of Compound #10 alone and in combination with sunitinib and rapamycin, respectively, on mean tumor size over the study time period. Tumors in vehicle-treated mice grew from a size (mean±SD) 297±57 mm$^3$ to 1442±322 mm$^3$ on Day 57. The median time to reach 1000 mm$^3$ or more was 50 days.

Tumors in Compound #10-treated mice (10 mg/kg QD, PO) grew from a size (mean±SD) of 296±62 mm$^3$ to 1569±671 mm$^3$ on Day 88. Tumors in Compound #10-treated mice were smaller than vehicle-treated mice. On Day 57, tumors in Compound #10-treated mice were 945±408 mm$^3$, or 34% smaller than the mean tumor size in vehicle-treated mice (p<0.05 ANOVA, multiple comparisons vs vehicle). The median time for tumors in Compound #10-treated mice to reach 1000 mm$^3$ was 71 days.

Tumors in sunitinib-treated mice (75 mg/kg QD, PO) grew from a size (mean±SD) of 297±24 mm$^3$ on Day 0 to 709±938 mm$^3$ on Day 119. By Day 119, 1 of the 10 mice in the treatment group had died. On Day 57, tumors in sunitinib-treated mice were 83% smaller than those in vehicle-treated mice. The median time for tumors in sunitinib-treated mice to reach 1000 mm$^3$ was 119 days (p<0.05, ANOVA—multiple comparisons vs vehicle control).

Tumors in rapamycin-treated mice grew from a size (mean±SD) of 296±64 mm$^3$ on Day 0 to 1715±393 mm$^3$ on Day 93. By Day 93, 1 of the 10 mice in the treatment group had died. On Day 57, tumors in rapamycin-treated mice were 49% smaller than those in vehicle-treated mice. The median time for tumors in rapamycin-treated mice to reach 1000 mm$^3$ was 87 days (p<0.05, ANOVA—multiple comparisons vs vehicle control).

The combination of Compound #10 and sunitinib was not more effective than sunitinib only, and unexpectedly, the combination of sunitinib and Compound #10 was less effective than sunitinib only. Tumor volume was significantly smaller in mice treated with sunitinib-only than that in mice treated with the combination of Compound #10 and sunitinib on Days 22 to 84. By Day 119, 2 of the 10 mice in the treatment group were sacrificed due to sickness on Day 87. The median time for tumors in mice treated with the combination of sunitinib and Compound #10-treated mice to reach 1000 mm$^3$ was 119 days.

The combination of Compound #10 and rapamycin was more effective than rapamycin only. Differences in tumor volume were significantly different on Day 57 to 88. The median time for tumors in mice treated with the combination of rapamycin and Compound #10 mice to reach 1000 mm$^3$ was 119 days.

Effect of Treatment on Body Weight: Mice were not randomized by body weight but by initial tumor size. Nevertheless, the mean initial body weights did not statistically differ between treatment groups. The effect of treatment was determined by normalizing the body weight over time to initial body weight (i.e., by determining the percent change from the initial body weight).

FIG. 10 and FIG. 12 show the effect of Compound #10 alone and in combination with sunitinib and rapamycin, respectively, on mean tumor size over the study time period.

Vehicle-treated mice did not lose weight from their initial body weight at any point over the course of the study.

Compound #10-treated mice did not lose weight from their initial body weight at any point over the course of the study. Body weights did not statistically differ between vehicle-treated and Compound #10-treated mice.

Sunitinib-treated mice transiently lost weight as measured at Day 14 (p<0.05, ANOVA—multiple comparisons vs vehicle control, and Compound #10). Mice then gained weight, with the weight gain from Day 0 reaching significance by Day 46 (p<0.05, ANOVA-multiple comparisons vs vehicle control, and Compound #10), and remaining significant through Day 119.

Rapamycin-treated mice transiently lost weight as measured at Day 7 and Day 14 (2.4% loss and 2.8% loss on Day 7 and 14, respectively; p<0.05, ANOVA-multiple comparisons vs vehicle control and vs Compound #10).

The mean body weight in mice treated with the combination of Compound #10 and sunitinib was greater than that of mice treated with sunitinib-only on Day 14 and Day 57 (p<0.05, ANOVA—multiple comparisons). Therefore, Compound #10 prevented the transient weight loss observed in sunitinib-treated mice.

The mean body weight in mice treated with the combination of Compound #10 and rapamycin did not weigh more than those treated with rapamycin-only. Therefore, the addition of Compound #10 did not prevent rapamycin-induced weight loss.

Discussion of Results

Treatment of mice with Compound #10 delayed the growth of 786-O renal cells in vivo. The median time to reach 1000 mm$^3$ was 50 days in vehicle-treated mice vs 71 days in Compound #10-treated mice. The median time to reach 1000 mm$^3$ in sunitinib-treated mice was 119 days. Compound #10 was not as effective as sunitinib at the dose of sunitinib used in this study (75 mg/kg). Sunitinib publications describe a typical dose of about 40 mg/kg (see, Bagi C M, Christensen J, Cohen D P, Roberts W G, Wilkie D, Swanson T, Tuthill T, Andresen C J. Sunitinib and PF-562,271 (FAK/Pyk2 inhibitor) effectively block growth and recovery of human hepatocellular carcinoma in a rat xenograft model. Cancer Biol Ther. 2009 May; 8(9):856-65; Hillman G G, Singh-Gupta V, Zhang H, Al-Bashir A K, Katkuri Y, Li M, Yunker C K, Patel A D, Abrams J, Haacke E M. Dynamic contrast-enhanced magnetic resonance imaging of vascular changes induced by sunitinib in papillary renal cell carcinoma xenograft tumors. Neoplasia. 2009 September; 11(9):910-20; and, Zhang L, Smith K M, Chong A L, Stempak D, Yeger H, Marrano P, Thorner P S, Irwin M S, Kaplan D R, Baruchel S. In vivo antitumor and antimetastatic activity of sunitinib in preclinical neuroblastoma mouse model. Neoplasia. 2009 May; 11(5):426-35). At the dose used in this study, the skin of the mice were yellow-tinged.

Rapamycin delayed the growth of 786-O renal tumor cells in vivo. Dosing of rapamycin was limited by weight loss. In addition, the combination of Compound #10 and rapamycin did not prevent weight loss.

The tumor did not induce weight loss, and there were no differences in the body weight gain in the vehicle-treated mice as in the monotherapy Compound #10-treated mice. While sunitinib-treated mice transiently lost weight then regained the weight mice treated with the combination of Compound #10 and sunitinib did not lose weight, indicating that Compound #10 prevented sunitinib-induced transient weight loss. Mice treated with the combination of Compound #10 and rapamycin lost weight, indicating that Compound #10 did not prevent rapamycin-induced weight loss in this cell line.

The combination of Compound #10 and sunitinib was not as effective as sunitinib alone, perhaps as a result of either a pharmacodynamic or pharmacokinetic drug-drug interaction.

12. EXAMPLE

Effect of Compound #10 in a CAKI-1 Renal Cancer Animal Model (VHL-Positive)

The in vivo activity of Compound #10 was assessed as a monotherapy and in combination with sunitinib (e.g., branded/marketed as SUTENT®) or rapamycin (e.g., branded/marketed as RAPAMUNE®) in a renal cell carcinoma (RCC) model (Caki-1 cells) in vivo. The Caki-1 cell line expresses the von Hippel-Lindau (VHL) protein which acts as a tumor suppressor by promoting the rapid degradation of HIF-1α (hypoxia-inducible factor 1α) under normoxia. Under hypoxic conditions, HIF-1α is stabilized and activated by the inability of VHL to act resulting in increased transcription of VEGF that is responsible for the high vascularization of RCC (see Turcotte et al, 2003, Zimmer et al, 2004).

Caki-1 cells were obtained from the American Type Culture Collection (ATCC) (Manassas, Va.) and cultured using methods provided by the ATCC.

Compound #10 was formulated in 30% Solutol HS15®, 35% Labrasol®, and 35% Labrafac® (L21) and stored at room temperature in ambient humidity and protected from light.

Rapamycin was formulated in 0.4% ethanol (100%) stock, which was stored at −70° C. in aliquots and aliquot thawed daily for dilution. The stock of rapamycin was then diluted in 5% Tween-80, 5% PEG-400, 90% water.

Sunitinib was formulated in 0.5% HPMC and 1% Tween-80.

TABLE 10

Dosing Solutions and Suspensions

| Test Compound | Dose (mg/kg) | Dosing Volume | Dose Concentration (mg/mL)[a] |
|---|---|---|---|
| Vehicle (L21) | 0 | 0.1 mL/mouse | 0 |
| Compound #10 | 10 | 0.1 mL/mouse | 3.0, 3.45, 3.23 |
| Sunitinib | 75 | 0.2 mL/mouse | 6.67, 6.90, 6.45 |
| Rapamycin | 15 | 0.1 mL/mouse | 4.35 |

[a]Mice weighed an average of 29 g at the time dosing was initiated. The concentration of the dosing solution was adjusted as necessary so that a volume of 0.1 mL delivered the target dose. The dosing solutions were prepared three times.

Mice were inoculated with Caki-1 tumor cells ($5 \times 10^6$ cells/mouse) obtained from the ATCC (Manassas, Va.). Tumor cells were mixed 1:1 with BD MATRIGEL™ (Becton, Dickinson and Company, San Jose, Calif.) prior to inoculation. Mice were inoculated using a 25-gauge needle in the right flank in a volume of 0.2 mL. A total of 100 mice were injected, of which 60 were used in the study.

Thirty days after inoculation, the mice were randomized into six groups as outlined in Table 11. Animals were distributed into groups such that the average tumor size did not differ between groups. Groups were taken off study when the mean tumor volume in a group was 1300 mm$^3$ or more. Vehicle-treatment started on Day 0 and continued through Day 35. Compound #10-treatment started on Day 0 and continued through Day 52.

TABLE 11

Group Designations

| Group | Compound #10 Treatment | Dose (mg/kg), Route, regimen | Chemotherapy Treatment | Dose (mg/kg), Route, regimen | Number of Mice |
|---|---|---|---|---|---|
| 1 | Vehicle | 0 | None | None | 10 |
| 2 | Compound #10 | 10, PO, QD | None | None | 10 |
| 3 | Vehicle | 0 | Sunitinib | 75 mg/kg PO, QD | 10 |
| 4 | Compound #10 | 10, PO, QD | Sunitinib | 75 mg/kg PO, QD | 10 |
| 5 | Vehicle | 0 | Rapamycin | 15 mg/kg PO, Days 0-4, 6-10, 51-53, 56-60, 63 and 64 | 10 |
| 6 | Compound #10 | 10, PO, QD | Rapamycin | 15 mg/kg PO, Days 0-4, 6-10, 51-53, 56-60, 63 and 64 | 10 |

Abbreviations: PO = oral dosing, QD = once per day.

Tumor Size: Tumors were measured twice per week using digital calipers. To calculate tumor volume, the following calculation was used, where L equals the longest dimension measurement and W equals the shortest dimension measurement:

$$\text{Tumor Volume} = \frac{L \times (W)^2}{2}$$

Clinical Observations: Each animal was observed twice daily for mortality and signs of pain or distress. Findings of overt toxicity were recorded as they were observed.

Plasma VEGF: Plasma was run in the Human VEGF Elisa, R&D Systems Cat#DY293B. Plasma was diluted at 1:1 with reagent diluent prior to quantification via ELISA.

Tumor Growth was calculated as:

[1−[(final tumor size minus initial tumor size in test compound treated−mice)/(final tumor size minus initial tumor size in vehicle-treated mice)]×100%

Values were calculated for individual mice and then averaged across the group.

Body Weight: The mice were weighed once per week. The percent change was calculated as:

[(Body weight on Day of study)−(initial body weight)/(initial body weight)]×100%

Values were calculated for individual mice and then averaged across the group.

The time to progression to reach a tumor volume 1500 mm3 was calculated for each mouse. The median values were reported. For statistical analysis, if the tumor in a given mouse did not reach 1500 mm3, the time on study was utilized (e.g., 50 days for mice in the Compound #10-treated group). Differences in tumor size, tumor growth, and body weight change between groups were analyzed by Student's t-test).

Results: Vehicle and Compound #10 treatment: All mice treated with vehicle or with Compound #10 survived until sacrificed (at the time that the mean tumor size of the group reached about 1500 mm$^3$).

Results: Sunitinib Monotherapy and Combination of Compound #10 and Sunitinib: From Day 8 onward, all mice in Group 3 (sunitinib, 75 mg/kg) and Group 4 (Compound #10 and sunitinib) had yellow-tinged skin. Mouse 3-4 (sunitinib, 75 mg/kg) was sacrificed on Day 4. Mouse 3-7 (sunitinib, 75 mg/kg) was found dead on Day 17. Mouse 3-3 (sunitinib, 75 mg/kg) was found dead on Day 95.

Results: Rapamycin Monotherapy: One mouse (5-10) was found dead on Day 14. Two mice (5-1 and 5-2) were found dead on Day 62. Three mice (5-3, 5-4, and 5-5) were found dead on Day 63.

Tumor Measurements: A total of 60/100 mice that were inoculated with Caki-1 cells developed tumors that were within the appropriate range at the start of this study. The mean±SD tumor volume for mice used in this study was 286±27 mm$^3$ at the initiation of treatment.

FIG. 13 and FIG. 15 show the effect of Compound #10 alone and in combination with sunitinib and rapamycin, respectively, on mean tumor size over the study time period. Tumors in vehicle-treated mice grew from a size (mean±SD) of 285±33 mm$^3$ to 1544±606 mm$^3$ on Day 35. The median time to reach 1000 mm$^3$ was 25 days.

Tumors in Compound #10-treated mice (10 mg/kg QD, PO) grew from a size (mean±SD) of 285±26 mm$^3$ to 1538±1070 mm$^3$ on Day 52. Tumors in Compound #10-treated mice were smaller than vehicle-treated mice. On Day 35, tumors in Compound #10-treated mice were 866±450 mm$^3$, or 44% smaller than the mean tumor size in vehicle-treated mice (p<0.05 ANOVA, multiple comparisons vs vehicle). The median time for tumors in Compound #10-treated mice to reach 1000 mm$^3$ was 39 days.

Tumors in sunitinib-treated mice (75 mg/kg QD, PO) grew from a size (mean±SD) of 285±25 mm$^3$ on Day 0 to 1494±1150 mm$^3$ on Day 98. On Day 35, tumors in sunitinib-treated mice were 66% smaller than those in vehicle-treated mice. The median time for tumors in sunitinib-treated mice to reach 1000 mm$^3$ was 66 days (p<0.05, ANOVA—multiple comparisons vs. vehicle control).

Tumors in rapamycin-treated mice grew from a size (mean±SD) of 286±24 mm$^3$ on Day 0 to 1689±1081 mm$^3$ on Day 63. By Day 65, 6 of the 10 mice in the treatment group had died, and the mice were taken off study. On Day 35, tumors in rapamycin-treated mice were 60% smaller than those in vehicle-treated mice. The median time for tumors in rapamycin-treated mice to reach 1000 mm$^3$ was 43 days.

The combination of Compound #10 and sunitinib was not more effective than sunitinib only, and unexpectedly, the combination of sunitinib and Compound #10 was less effective than sunitinib only. Tumor volume was significantly smaller in mice treated with sunitinib-only than that in mice treated with the combination of Compound #10 and sunitinib on Days 49 to 63, at which point the mice treated with the combination of Compound #10 and sunitinib were sacrificed. The median time for tumors in mice treated with the combination of sunitinib and Compound #10 mice to reach 1000 mm$^3$ was 43 days.

The combination of Compound #10 and rapamycin was not more effective than rapamycin only. Differences in tumor volume were not significantly different at any time point. The median time for tumors in mice treated with the combination of rapamycin and Compound #10 mice to reach 1000 mm$^3$ was 40 days.

Effect of Treatment on Body Weight: Mice were not randomized by body weight but by initial tumor size. Nevertheless, the mean initial body weights did not statistically differ between the two groups. The effect of treatment was determined by normalizing the body weight over time to initial body weight (i.e., by determining the percent change from the initial body weight).

FIG. 14 and FIG. 16 show the effect of Compound #10 alone and in combination with sunitinib and rapamycin, respectively, on mean tumor size over the study time period.

Vehicle-treated mice did not lose weight from their initial body weight at any point over the course of the study.

Compound #10-treated mice transiently lost weight as measured at Day 8 and Day 14 (2.2% loss from Day 0; p<0.05, Paired Student's test comparing Day 0 with Day 8 or Day 0 with Day 14). Mice then gained weight, with the weight gain from Day 0 reaching significance by Day 38 (Paired Student's test comparing Day 0 with Day 38), and remaining significant until these mice were sacrificed.

Sunitinib-treated mice transiently lost weight as measured at Day 14, although this difference did not reach statistical significance. Mice then gained weight, with the weight gain from Day 0 reaching significance by Day 38 (Paired Student's test comparing Day 0 with Day 38), and remaining significant through Day 63.

Rapamycin-treated mice transiently lost weight as measured at Day 8 and Day 14 (4.3% loss and 5.8% loss on Day 8 and 14, respectively; Paired Student's test comparing Day 0 with Day 8 or Day 0 with Day 14).

The body weights in mice treated with the combination of Compound #10 and Sunitinib did not differ from those in mice treated with sunitinib-only (Student's t-test).

The body weight in mice treated with the combination of Compound #10 and rapamycin weighed more on Days 8 and 14 than did those treated with rapamycin-only. Therefore, the addition of Compound #10 prevented rapamycin-induced weight loss.

Discussion of Results

Treatment of mice with Compound #10 delayed the growth of Caki-1 renal cells in vivo. The median time to reach 1500 mm$^3$ was 25 days in vehicle-treated mice vs 39 days in Compound #10-treated mice. The median time to reach 1000 mm$^3$ in sunitinib-treated mice was 66 days. Compound #10 was not as effective as sunitinib as the dose of sunitinib used in this model (75 mg/kg).

Rapamycin delayed the growth of Caki-1 renal tumor cells in vivo. Dosing of rapamycin was limited by weight loss. However, the combination of Compound #10 and rapamycin prevented weight loss.

The tumor did not induce weight loss, and there were no differences in the body weight gain in the vehicle-treated mice as in the monotherapy Compound #10-treated mice. While monotherapy rapamycin-treatment elicited weight loss, mice treated with the combination of Compound #10 and rapamycin did not lose weight, indicating that Compound #10 prevented rapamycin-induced weight loss in this cell line. Tumors in mice treated with rapamycin and with the combination of Compound #10 and rapamycin were of similar size, indicating that the effect on weight loss was independent of the effect on body weight.

The combination of Compound #10 and sunitinib was not as effective as sunitinib alone, perhaps as a result of either a pharmacodynamic or pharmacokinetic drug-drug interaction. The levels of sunitinib were lower in mice treated with the combination of Compound #10 and sunitinib when compared to mice treated with sunitinib alone. However, as the plasma was collected on different days (Day 63 vs. Day 98) and at different times (23 h post-dose vs. 30 h post-dose), the levels could not be directly compared to assess the potential for a drug-drug interaction.

13. EXAMPLE

Effect of Compound #10 as Monotherapy and in Combination with a PI3-K Inhibitor

FIG. 7A shows the effect of Compound #10 ("P") as monotherapy (at µM dose levels) and in combination with a PI3-K inhibitor ("B") on protein expression in a series of Western blot analyses of lysates of various cell lines treated with various concentrations a PI3-K inhibitor ("B") and various concentrations of Compound #10 ("P") in a 786-0 Renal Cancer Cell (RCC) line using techniques known to a person of ordinary skill in the art.

The Vinculin, c-Myc, Survivin, ornithine decarboxylase (ODC), Cyclin D and pS6 mRNA are cap-dependent mRNAs that are considered difficult to translate. The blots for each mRNA shown were translated via a cap-independent manner with mTOR inhibition (Akt has been inactivated).

FIG. 7A shows that the monotherapy treatment of c-Myc in the 786-0 cell line by the PI3-K inhibitor and Compound #10 at different dose levels was not completely effective in suppressing c-Myc expression. The combination at different dose levels, though, effectively suppressed c-Myc expression. Although the monotherapy treatment of the PI3-K inhibitor was relatively effective at suppressing ODC, survivin, cyclin D and pS6 expression, Compound #10 enhanced the ability of the PI3-K inhibitor "B" to suppress c-myc expression and VEGF production.

The ELISA data in FIG. 7B demonstrate the effect of Compound #10 as monotherapy and in combination with a PI3-K inhibitor on VEGF expression in a 786-0 Renal Cancer Cell (RCC) line using techniques familiar to a person of ordinary skill in the art. In general, the tumor cells were exposed to Compound #10, the PI3-K inhibitor and the combination for several hours. The media was then discarded and replaced with fresh agent-containing media. This was done to ensure that the ELISA did not measure VEGF produced before the agent was able to achieve an inhibitory intracellular concentration. This procedure enhances the apparent effectiveness of agents that suppress VEGF synthesis. Although the cells were not rinsed, the ELISA data in FIG. 7B show a significant dose-dependent additive effect of the PI3-K inhibitor and Compound #10 in combination to suppress VEGF production.

FIG. 8 shows the effect of various concentrations of Compound #10 as monotherapy (at different µM dose levels) on expression of various proteins in a series of Western blot analyses of lysates of a panel of RCC lines (786-0, 769-P and A498) using techniques known to a person of ordinary skill in the art. The results in FIG. 8 demonstrate that the effect on protein expression was dose-dependent and depended on the RCC line used.

14. EXAMPLE

Effect of Compound #10 as Monotherapy and in Combination with Cancer Therapeutic Agents for the Treatment of Cancer FIG. 17 shows the effect of Compound #10 monotherapy on target plasma concentrations, enabling target plasma trough levels between 550 and 1010 ng/mL to be achieved in patients having a variety of cancers.

Figure 1:
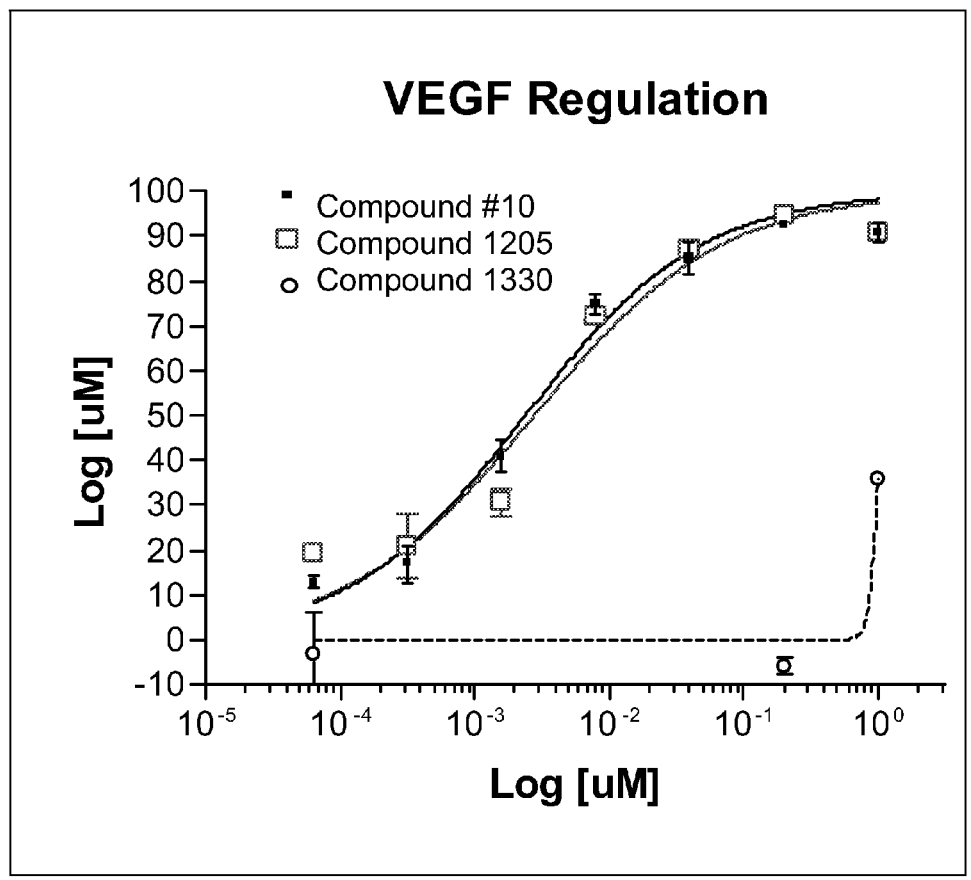
Figure 2:
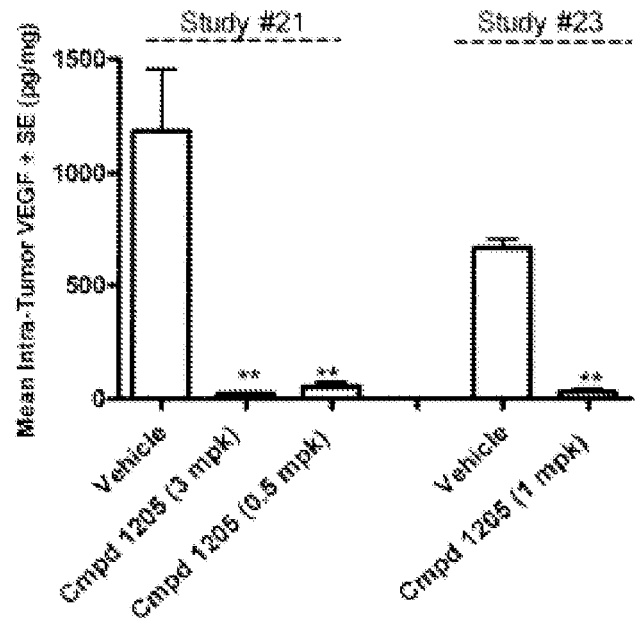
Figure 2:
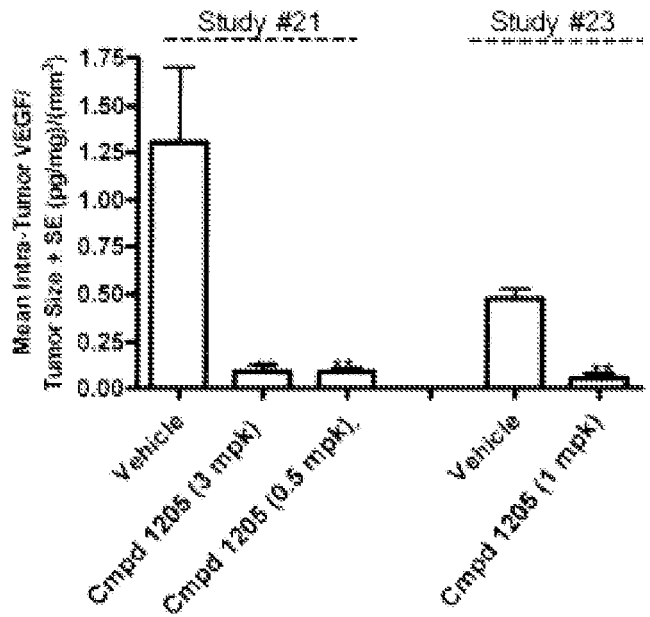
Figure 3:
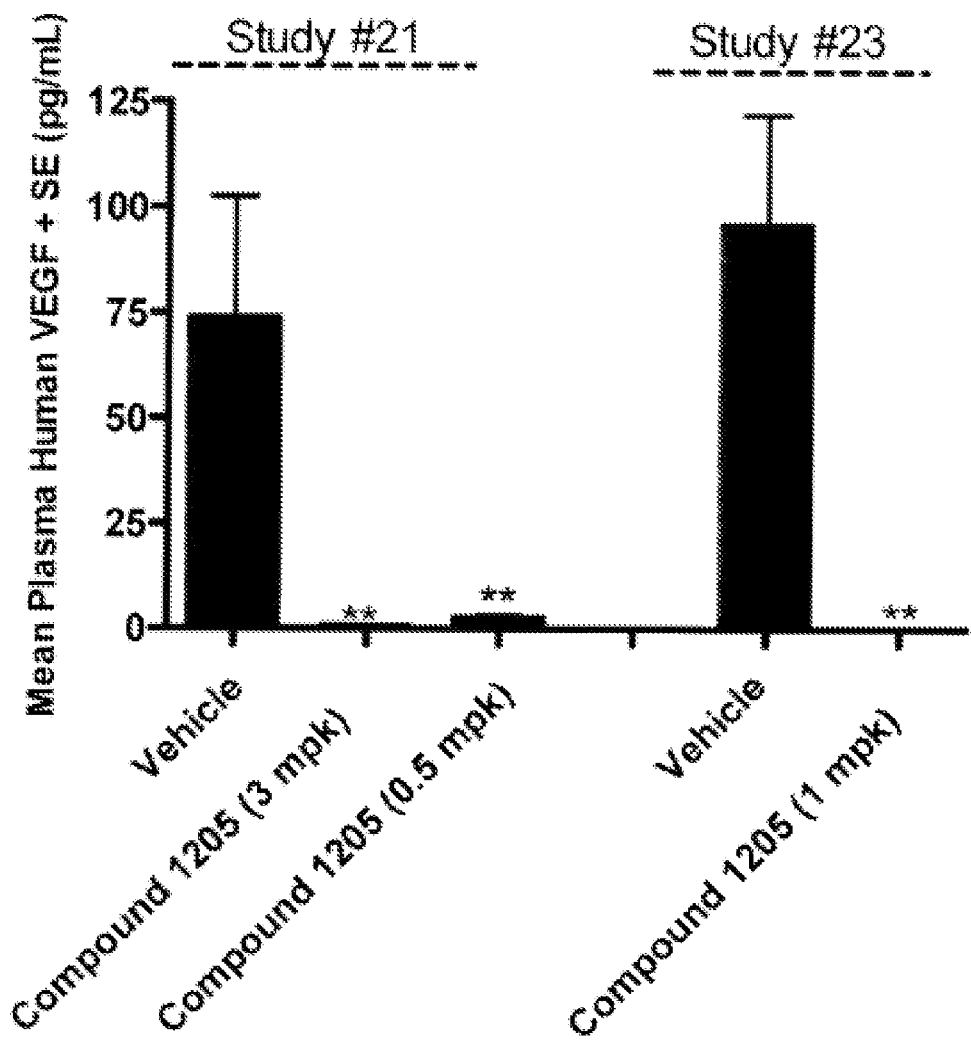
Figure 4:
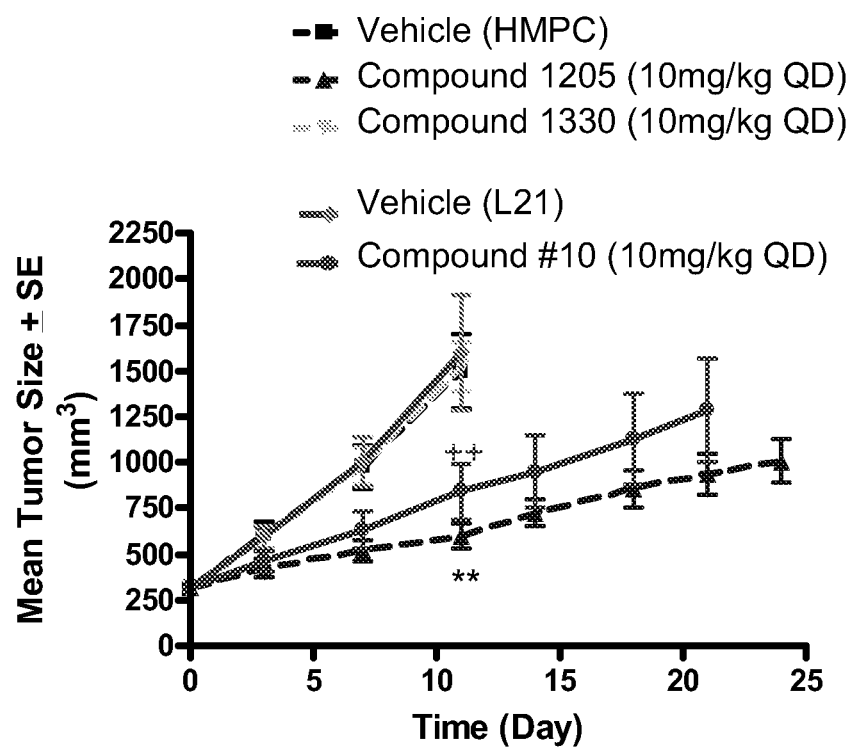
Figure 5:
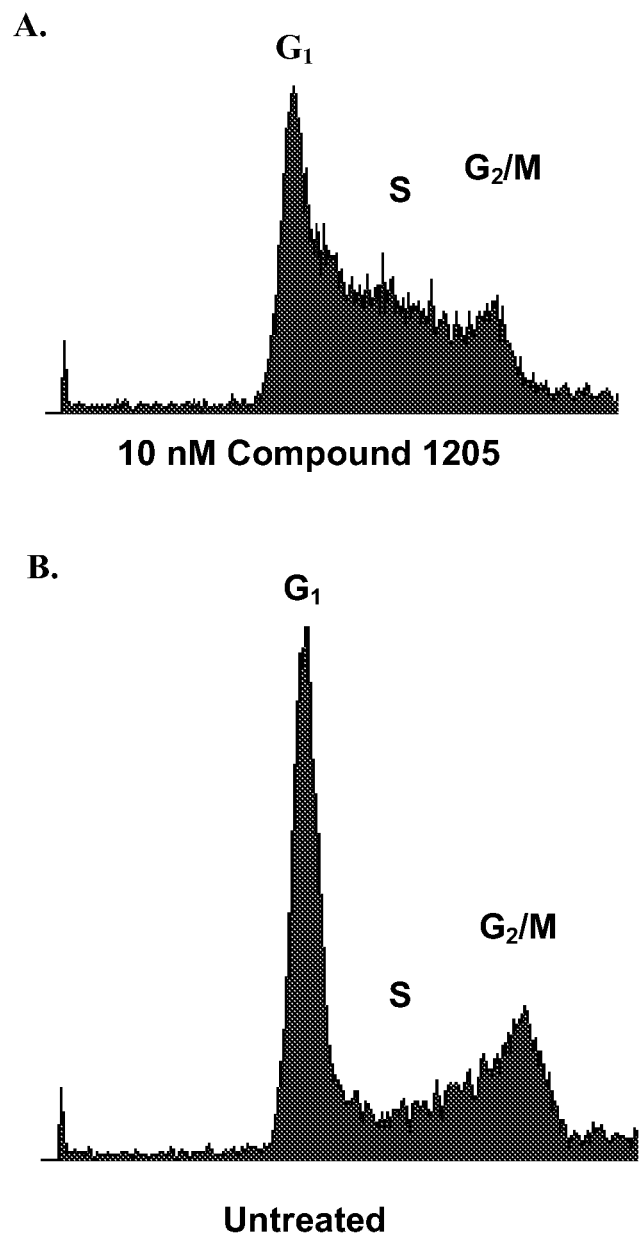
Figure 6:
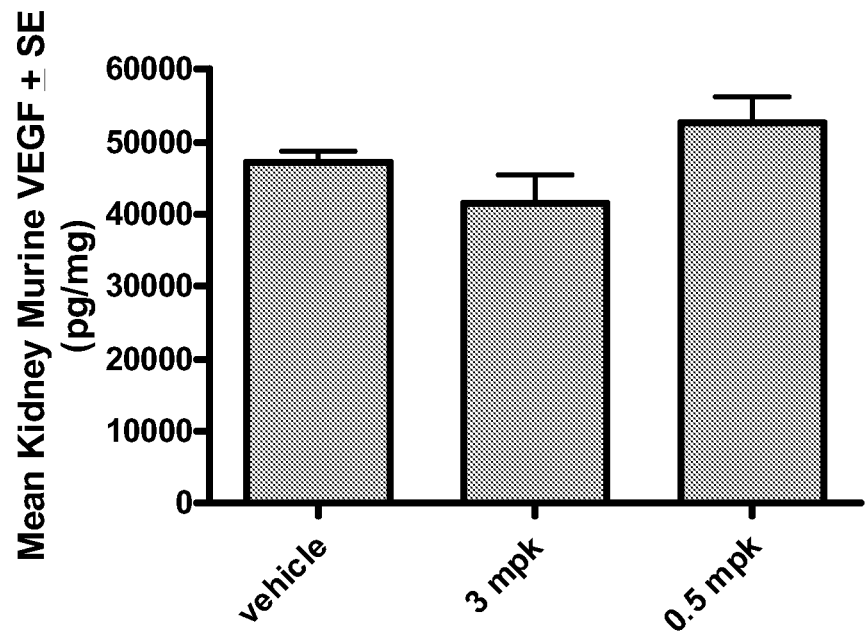
Figure 7:
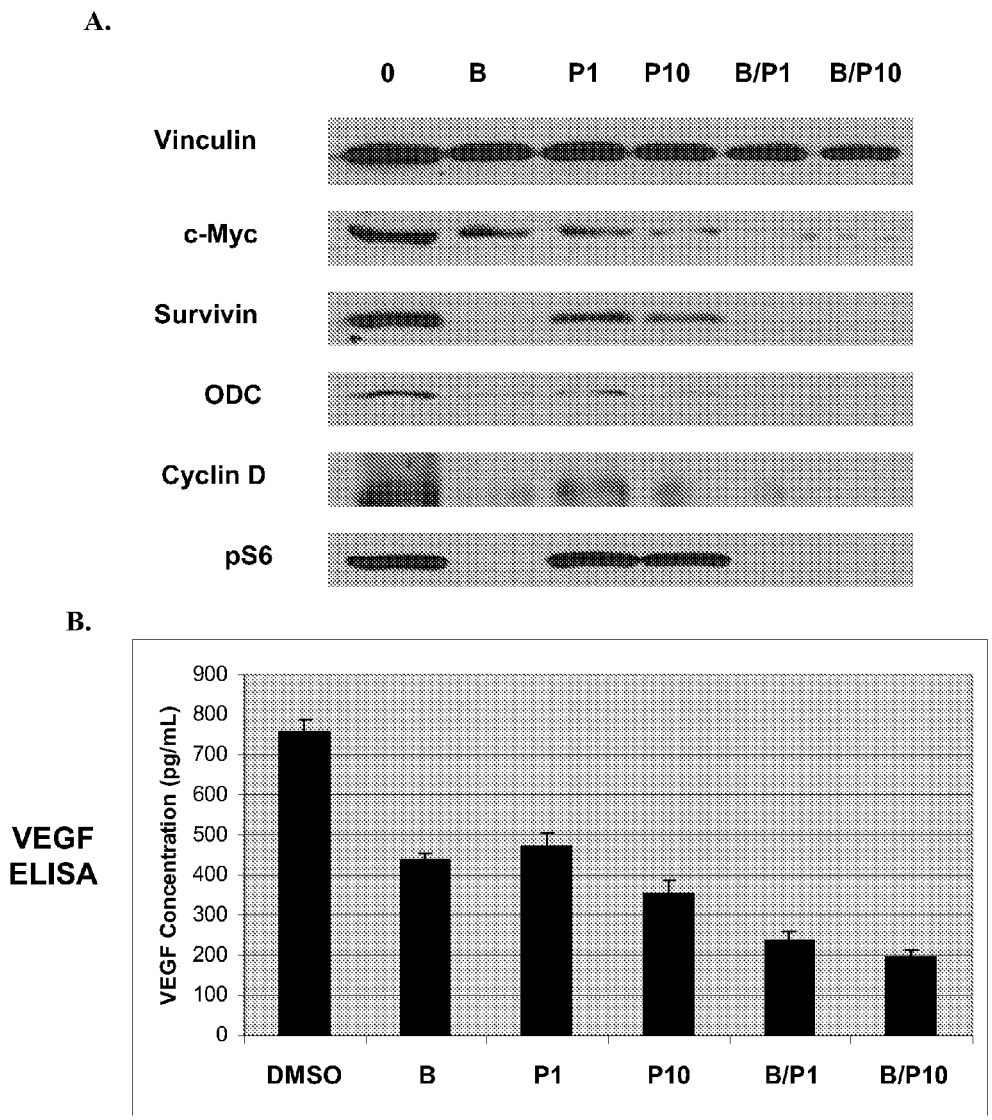
Figure 8:
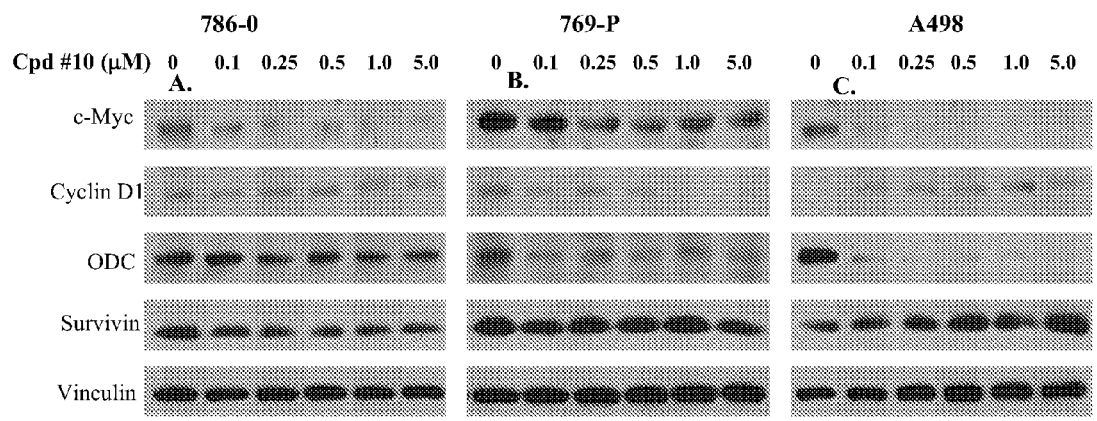
Figure 9:
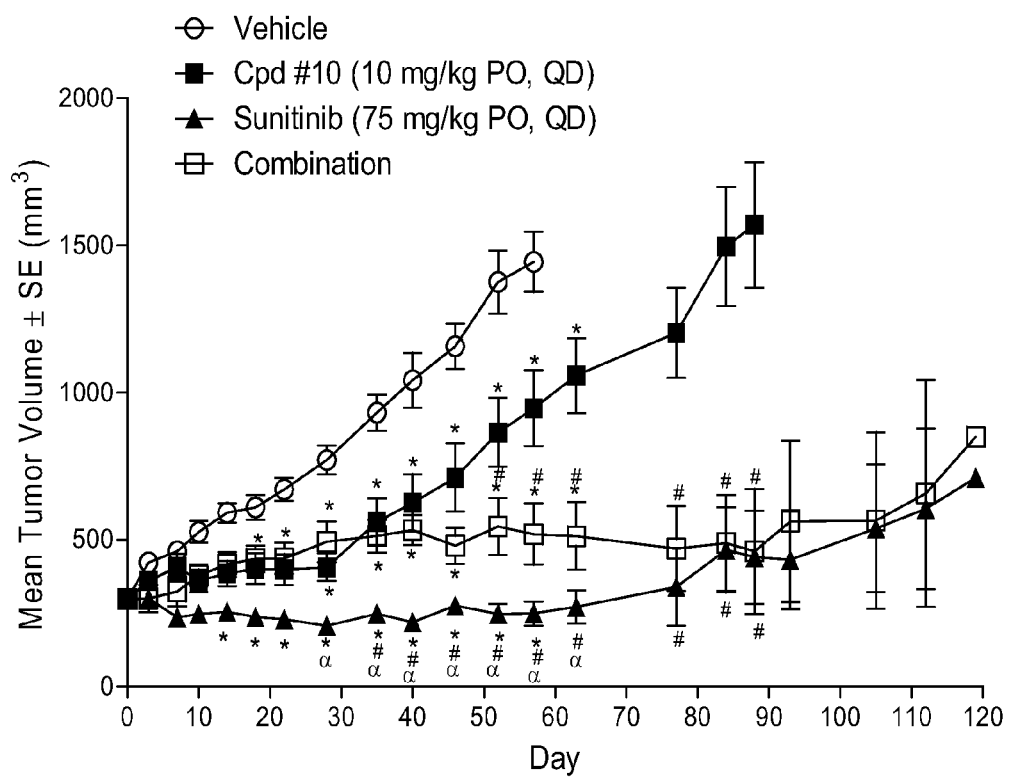
Figure 10:
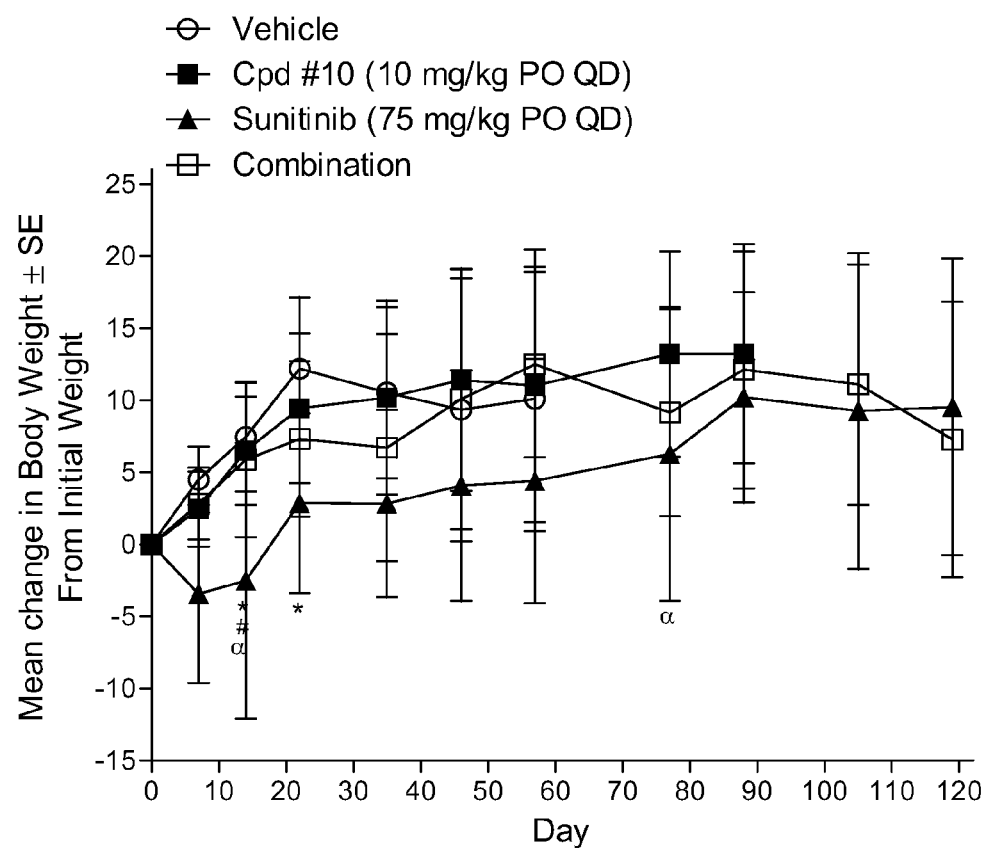
Figure 11:
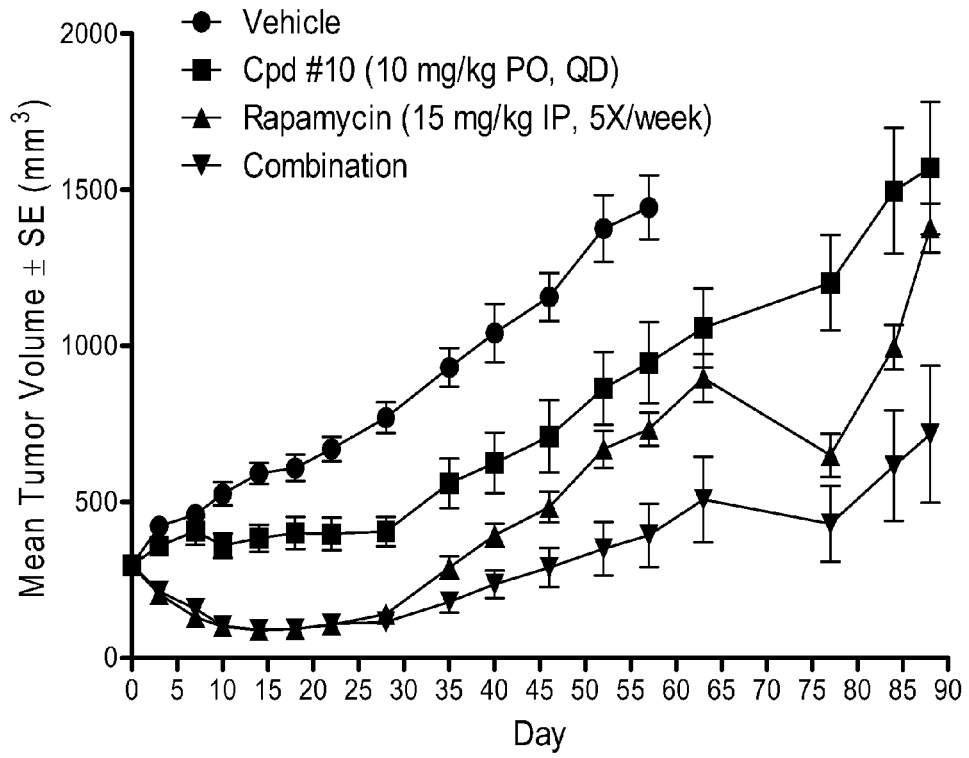
Figure 12:
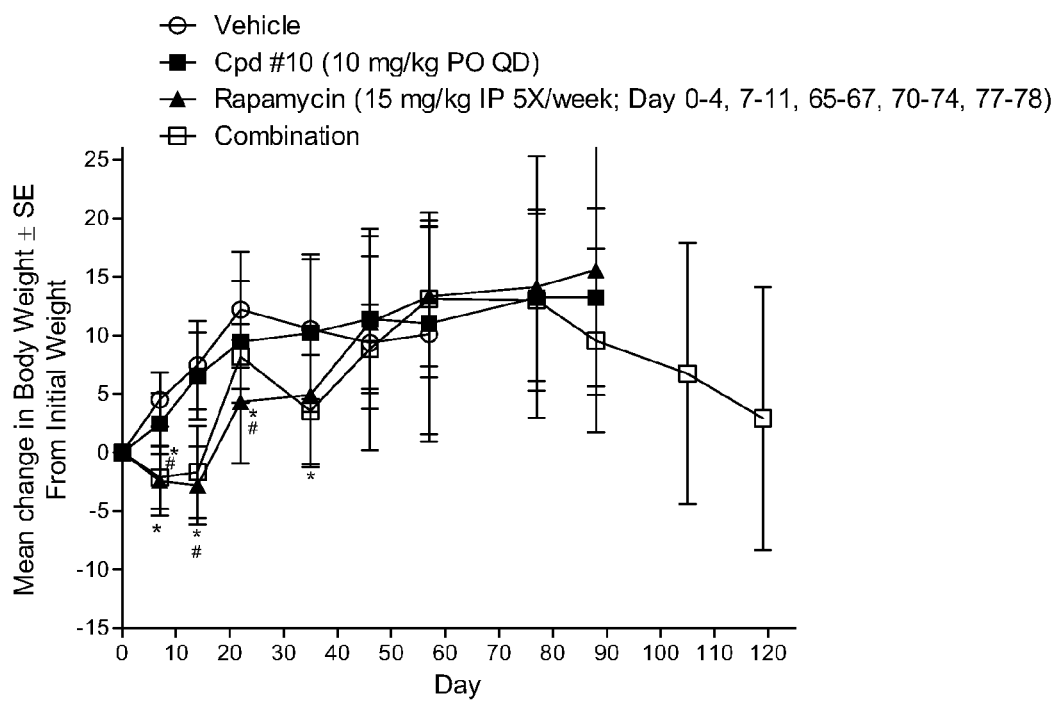
Figure 13:
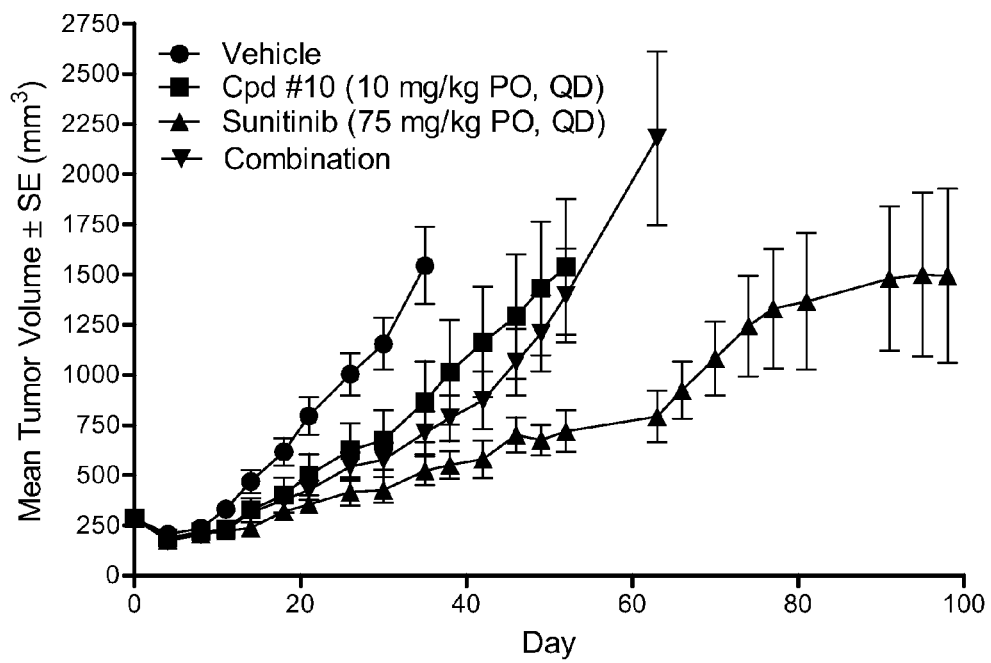
Figure 14:
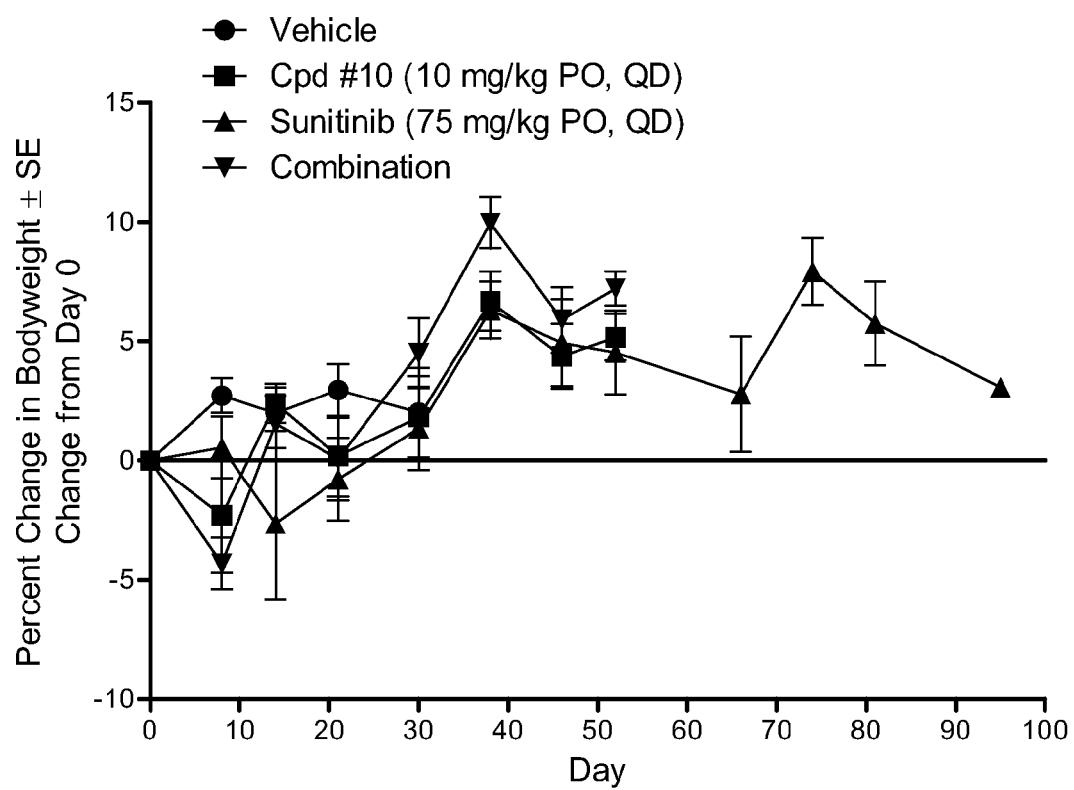
Figure 15:
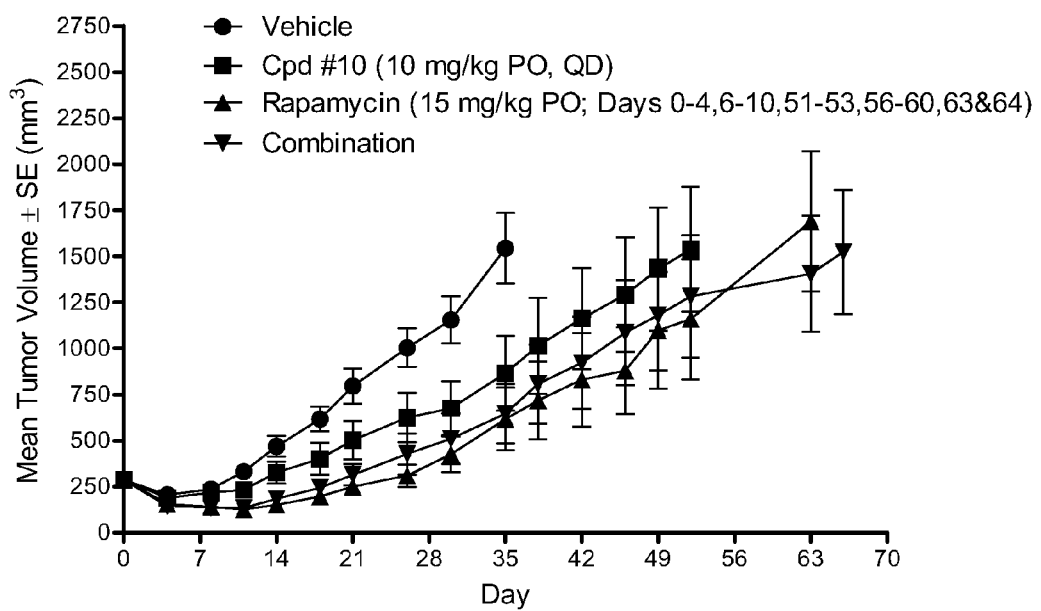
Figure 16:
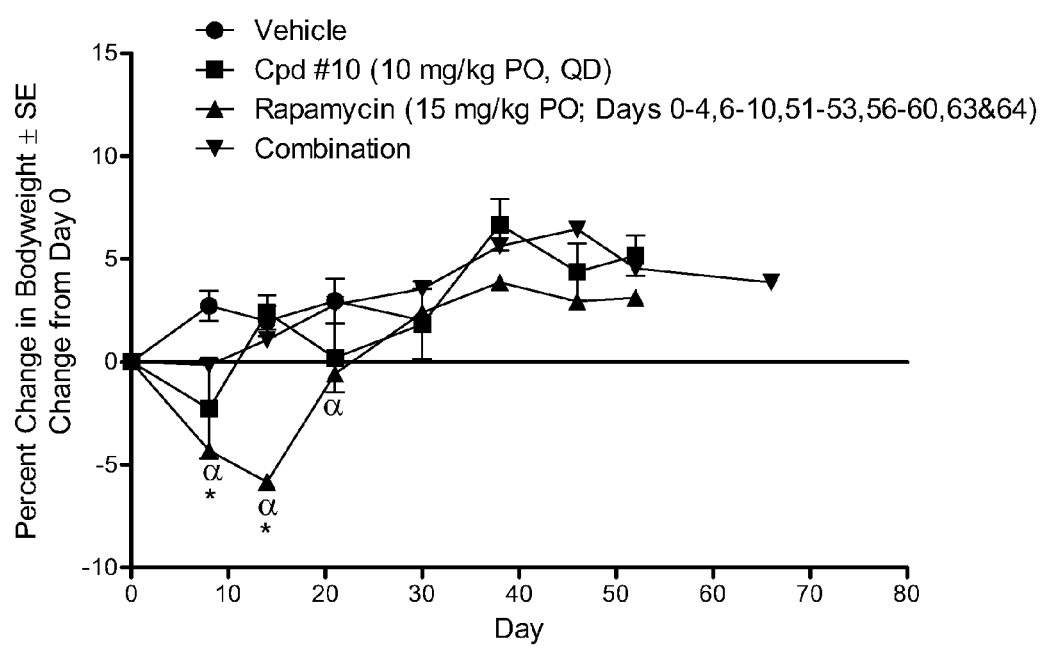
Figure 17:
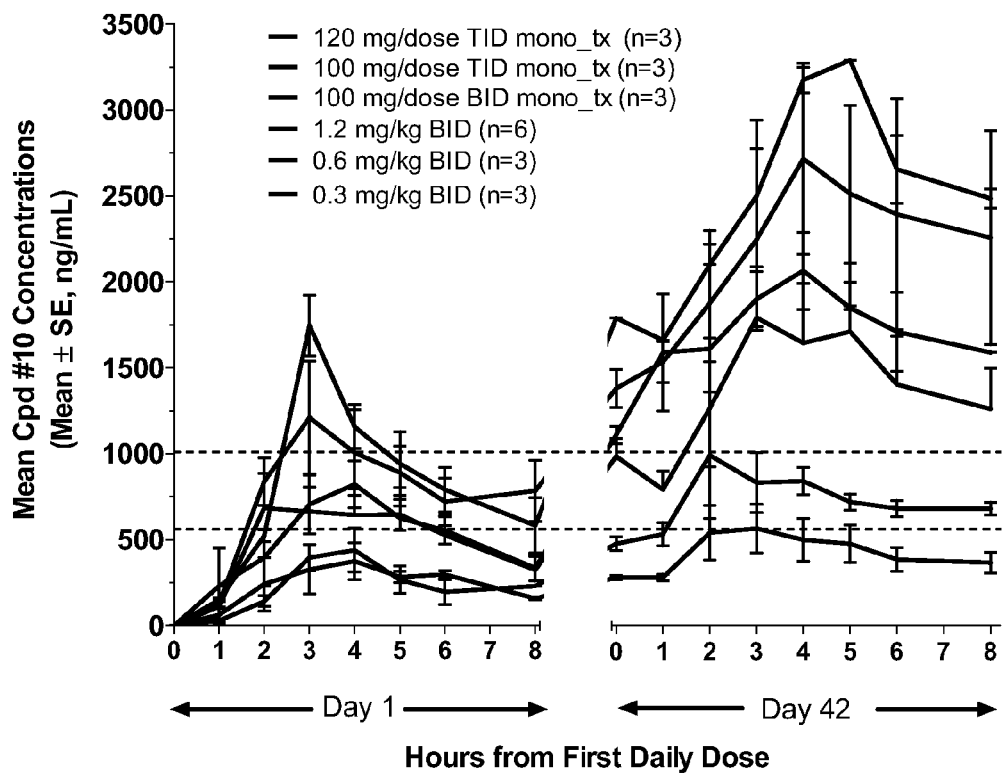
Figure 18:
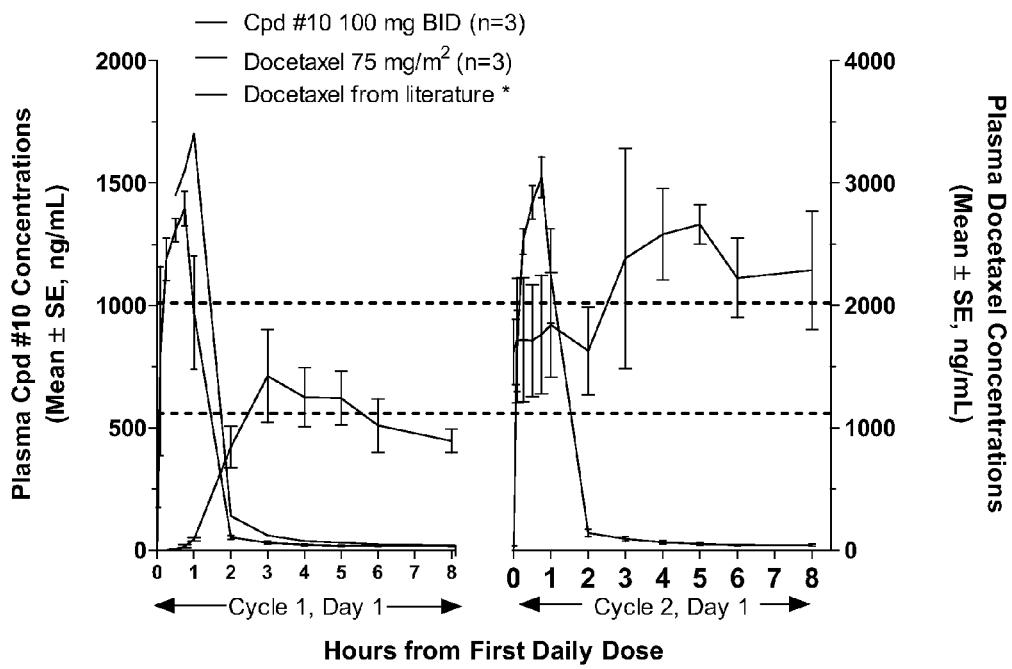
FIG. 18 shows the effect of Compound #10 monotherapy and combination therapy with docetaxel on target plasma concentrations, enabling target plasma trough levels between 550 and 1010 ng/mL to be achieved in patients having a variety of cancers.
Figure 19:
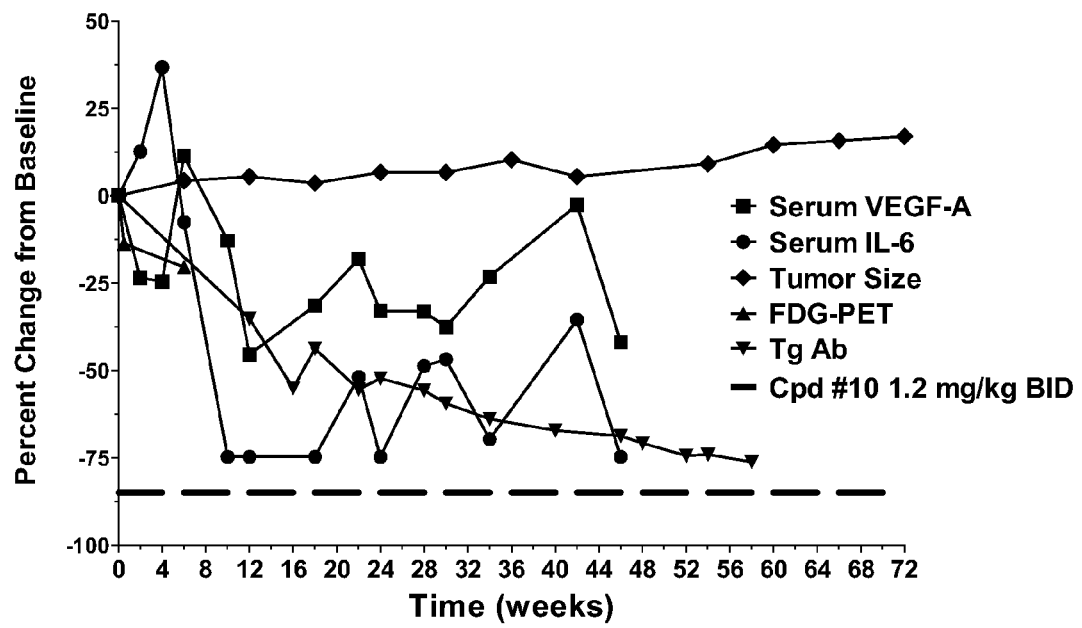
FIG. 19 shows the effect of Compound #10 monotherapy in a patient having thyroid cancer where, after three previous therapeutic modalities, the result of monotherapy treatment with Compound #10 has led to stabilization and reduction in a number of clinical parameters and tumor markers.
Figure 20:
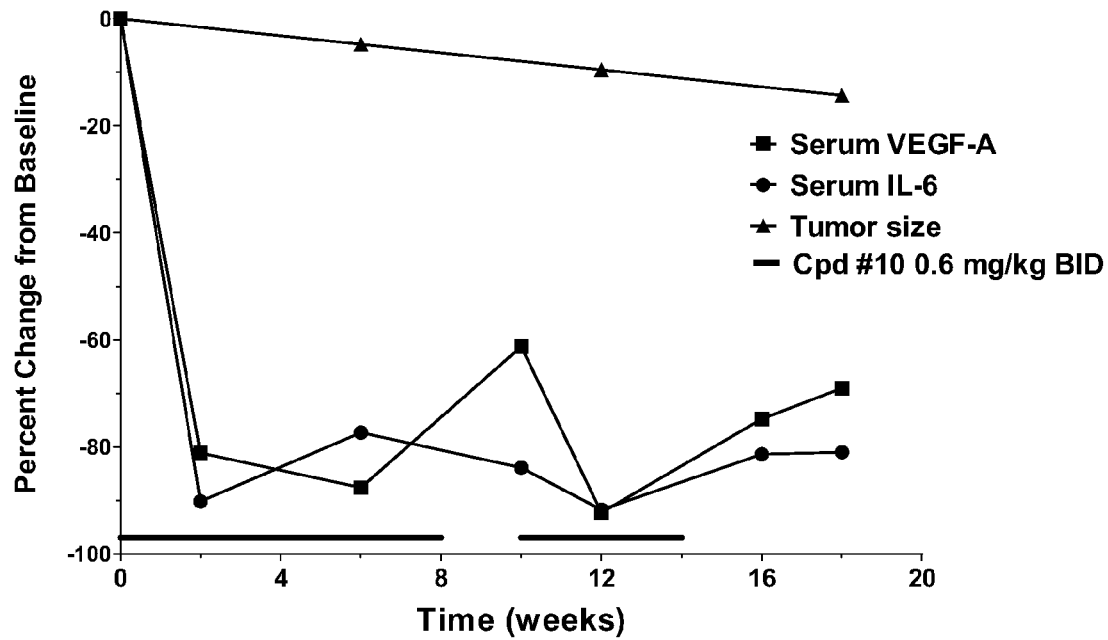
FIG. 20 shows the effect of Compound #10 monotherapy in a patient having melanoma where, after two previous therapeutic modalities, the result of monotherapy treatment with Compound #10 has led to stabilization and reduction in a number of clinical parameters and tumor markers.
Figure 21:
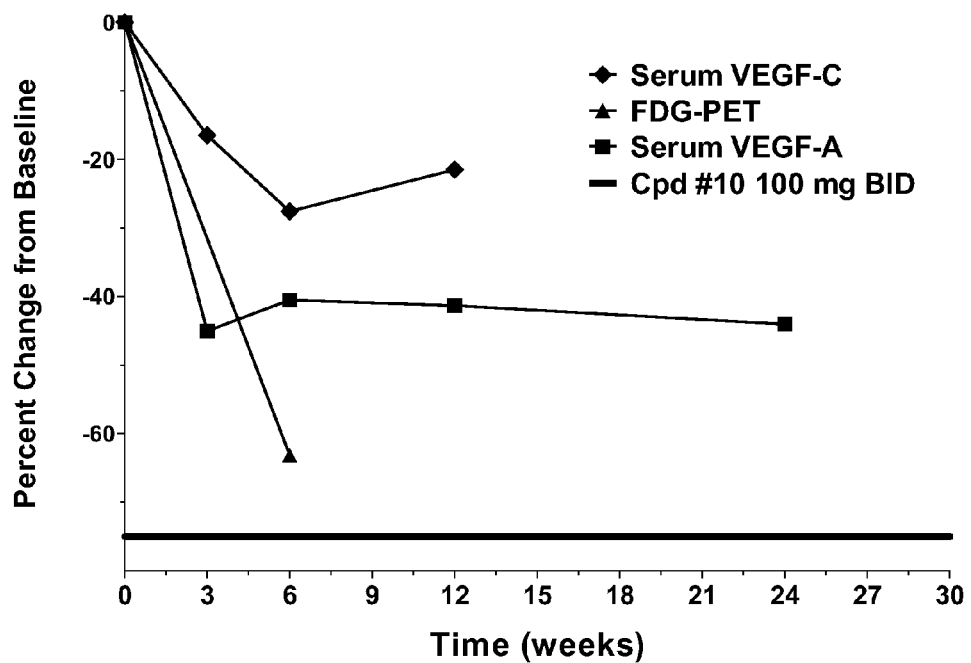
FIG. 21 shows the effect of Compound #10 monotherapy in a patient having chondrosarcoma where, after one previous therapeutic modalities, the result of monotherapy treatment with Compound #10 has led to stabilization and reduction in a number of clinical parameters and tumor markers.
Figure 22:
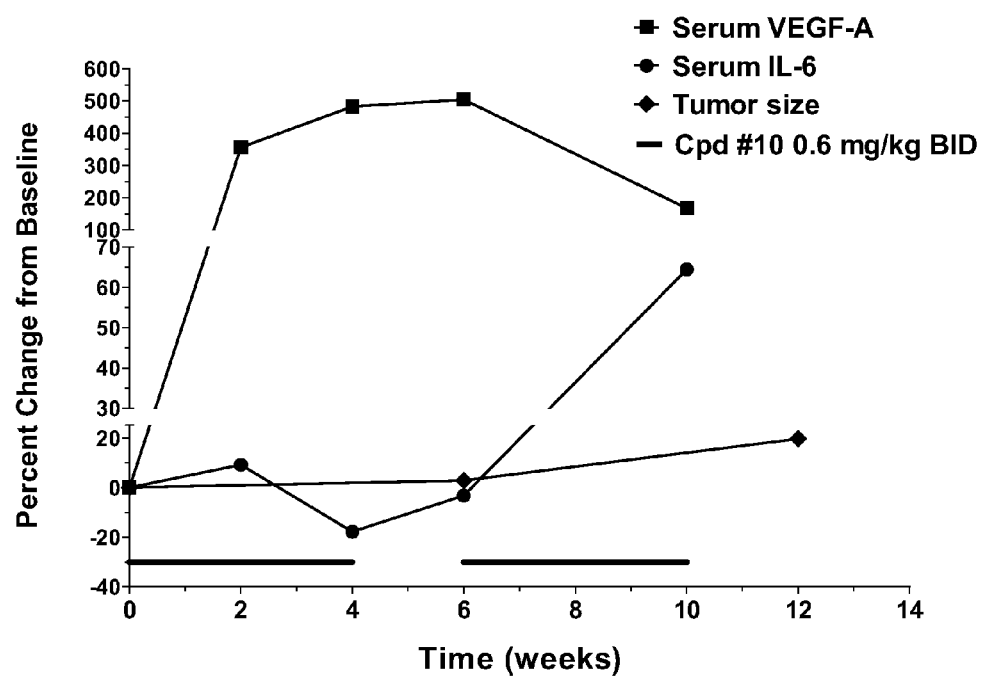
FIG. 22 shows the effect of Compound #10 monotherapy in a patient having cholangiocarcinoma where, after four previous therapeutic modalities, the result of monotherapy treatment with Compound #10 has led to stabilization for a tumor marker.
Figure 23:
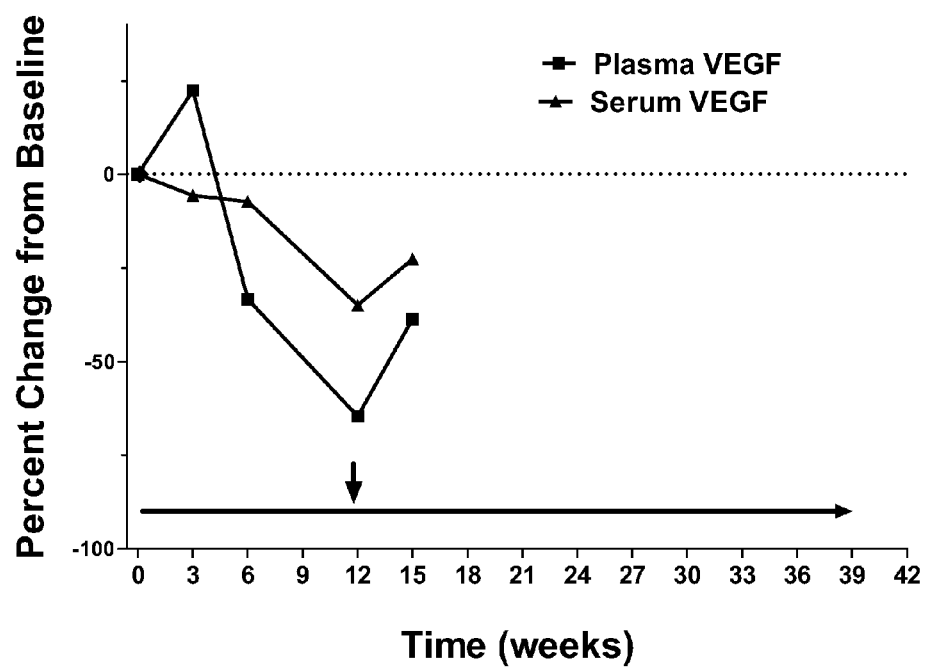

FIG. 23 shows the effect of Compound #10 monotherapy and combination therapy with docetaxel in a patient having head and neck cancer with metastasis to the lung where, after previous radiotherapy and no prior chemotherapy, the result of treatment with a combination of Compound #10 and docetaxel led to stabilization and reduction in a number of clinical parameters and tumor markers. The arrow symbol represents the timepoint at which docetaxel was reduced to 60 mg/m$^2$.

Figure 24:
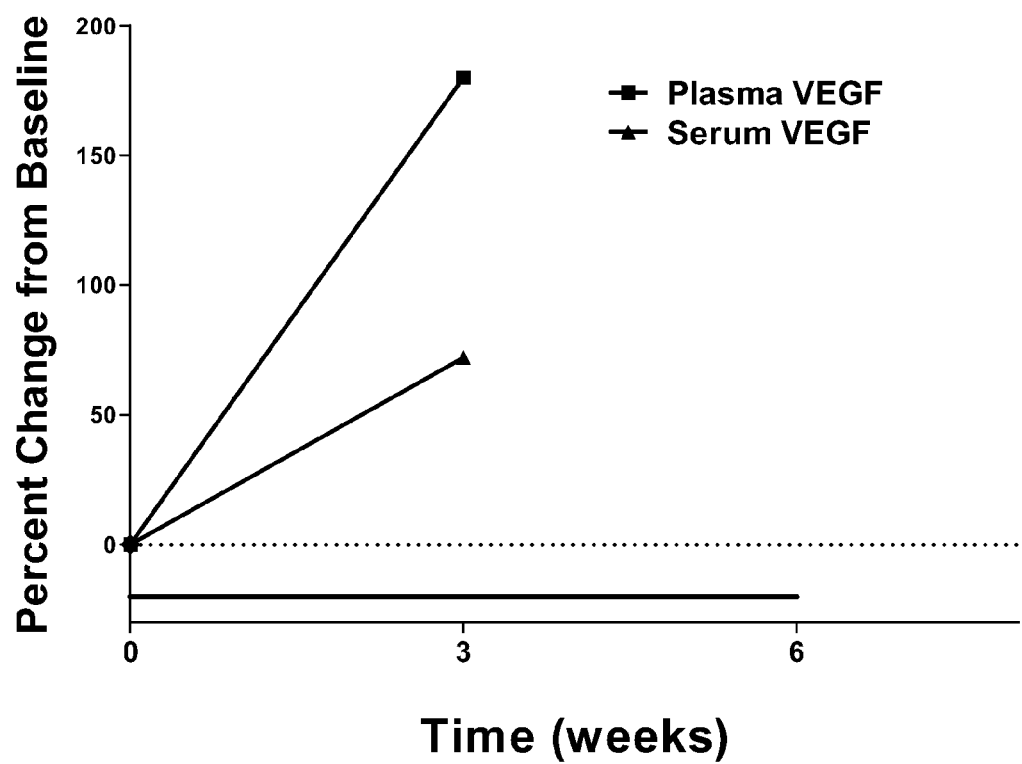

FIG. 24 shows the effect of Compound #10 monotherapy in a patient jejunal adenocarcinoma with metastasis to the lung where, after five previous therapeutic modalities for the metastasis, the result of monotherapy treatment with Compound #10 is presented.

Figure 25:
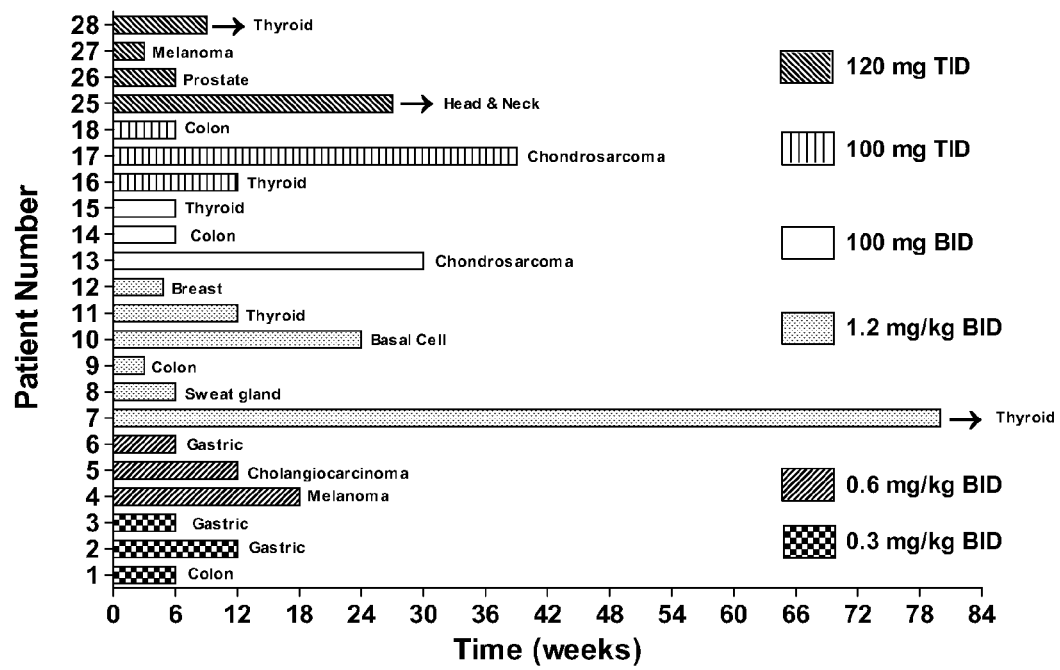

FIG. 25 shows the use Compound #10 monotherapy at various concentrations for treatment of various cancers.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A compound having the formula:

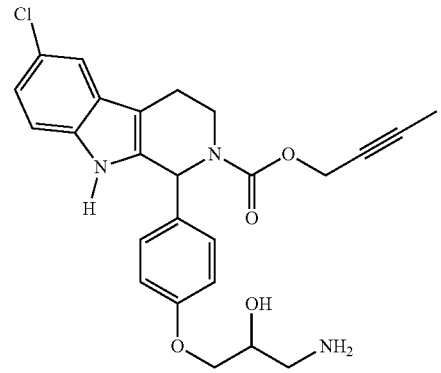

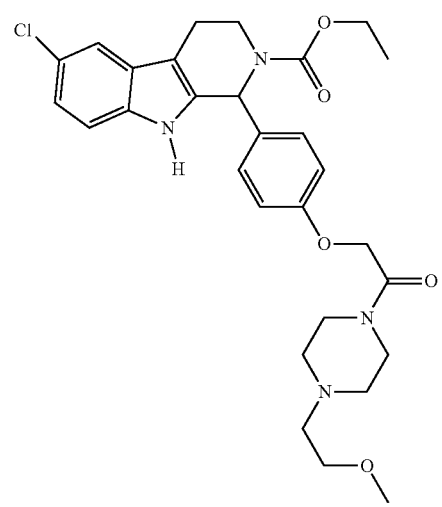

1004
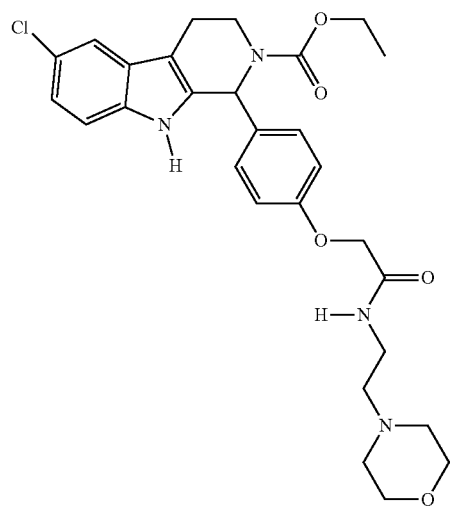
1005
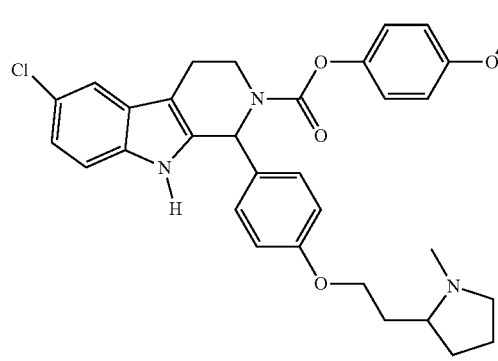
1006
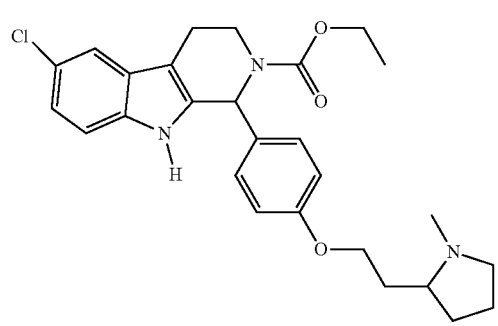
1007
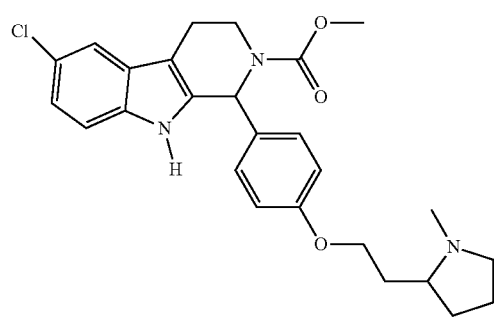
1008
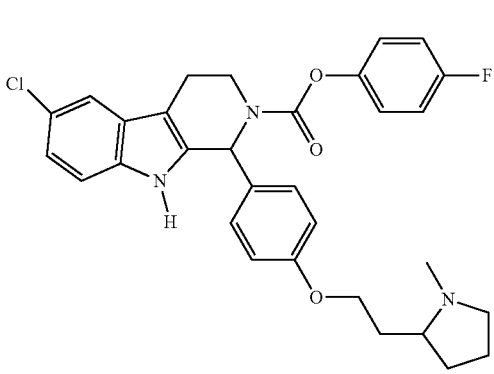
1009
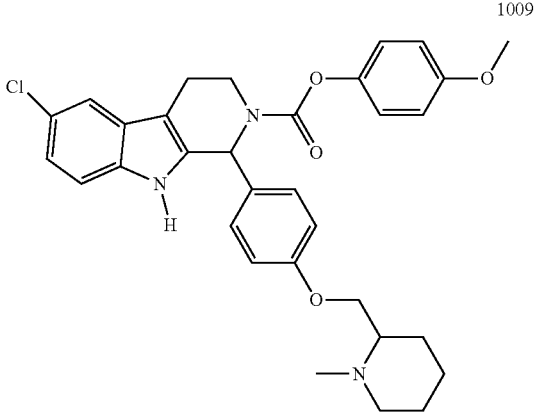
1010
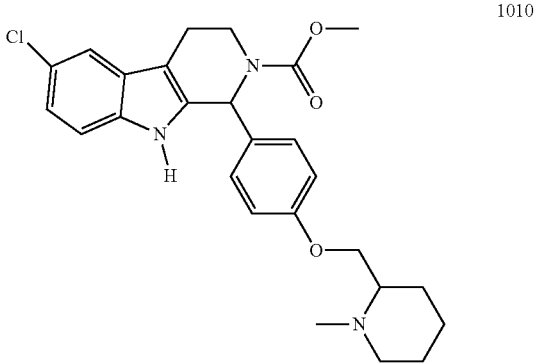
1011
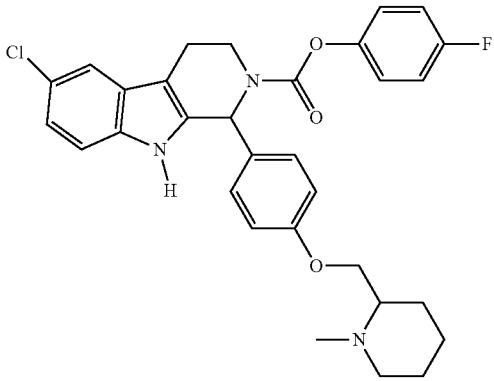

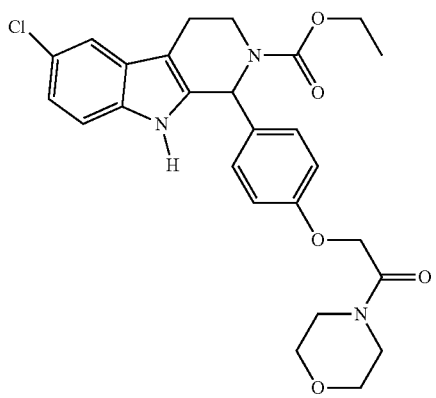
1012
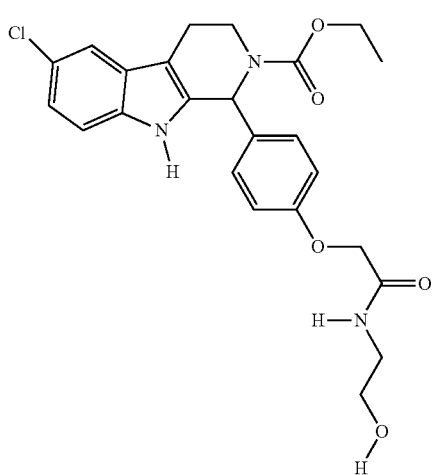
1013
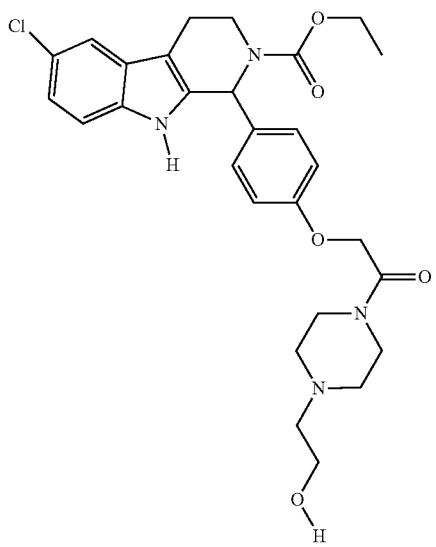
1014
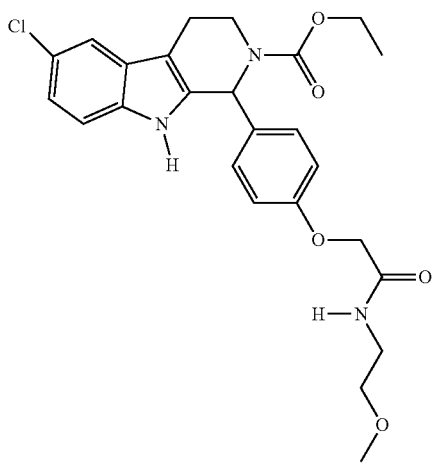
1015
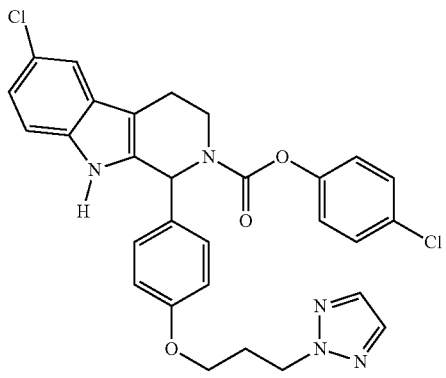
1016
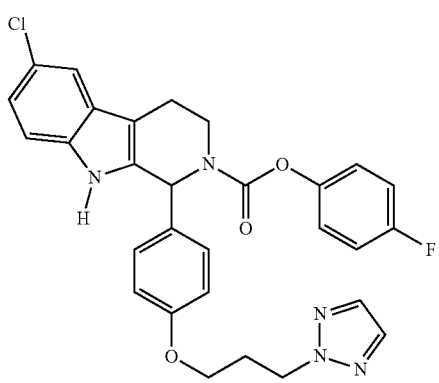
1017
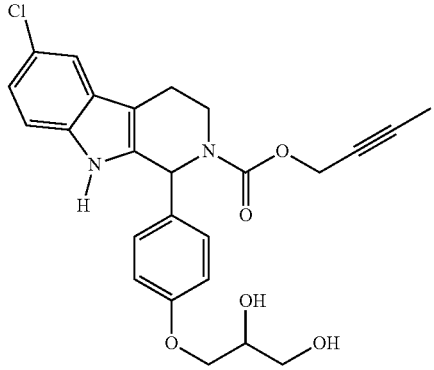
1018

567
-continued
1019
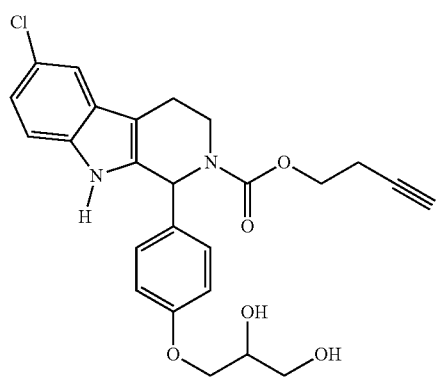
1020
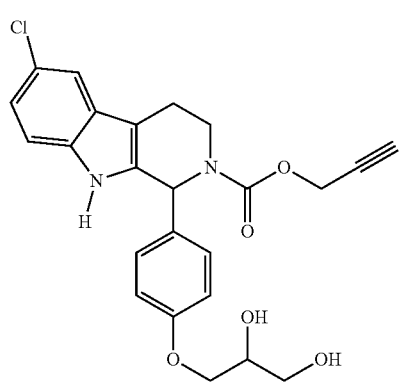
1021
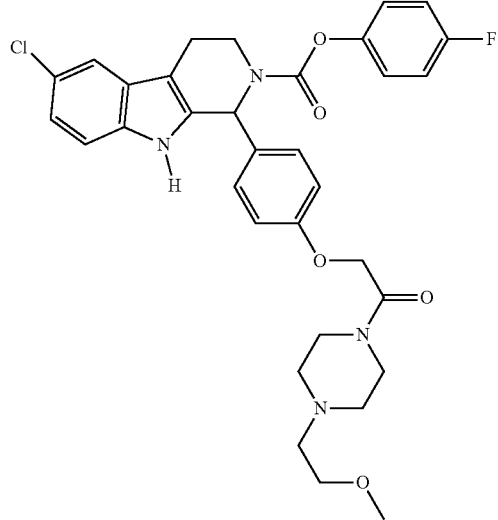
568
-continued
1022
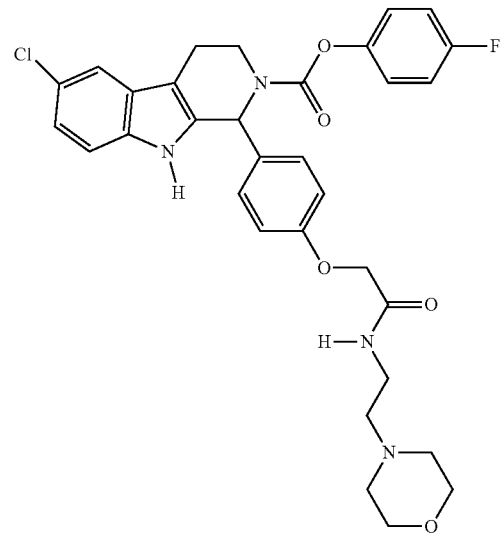
1023
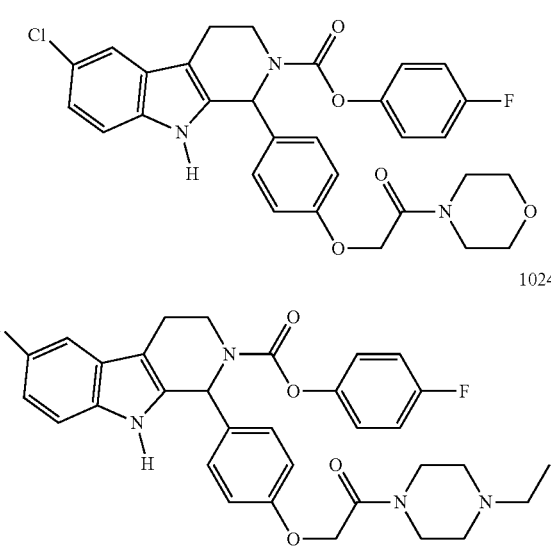
1024
1025
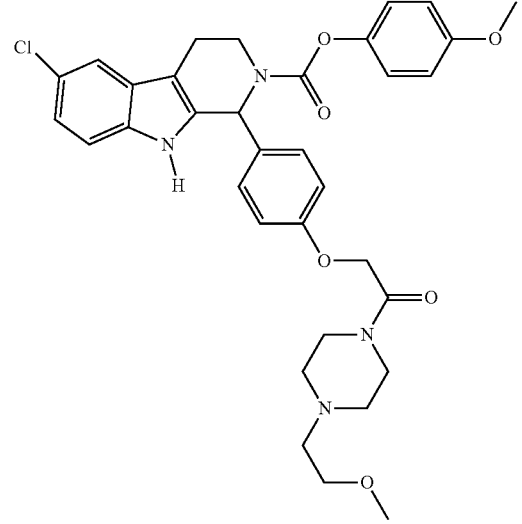

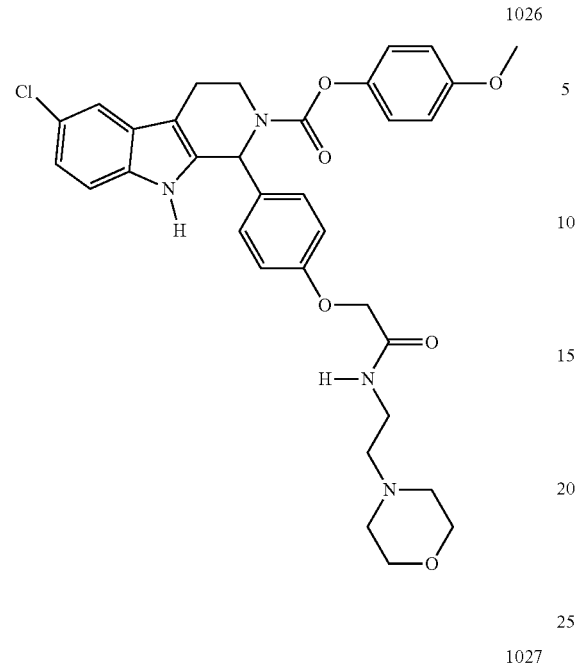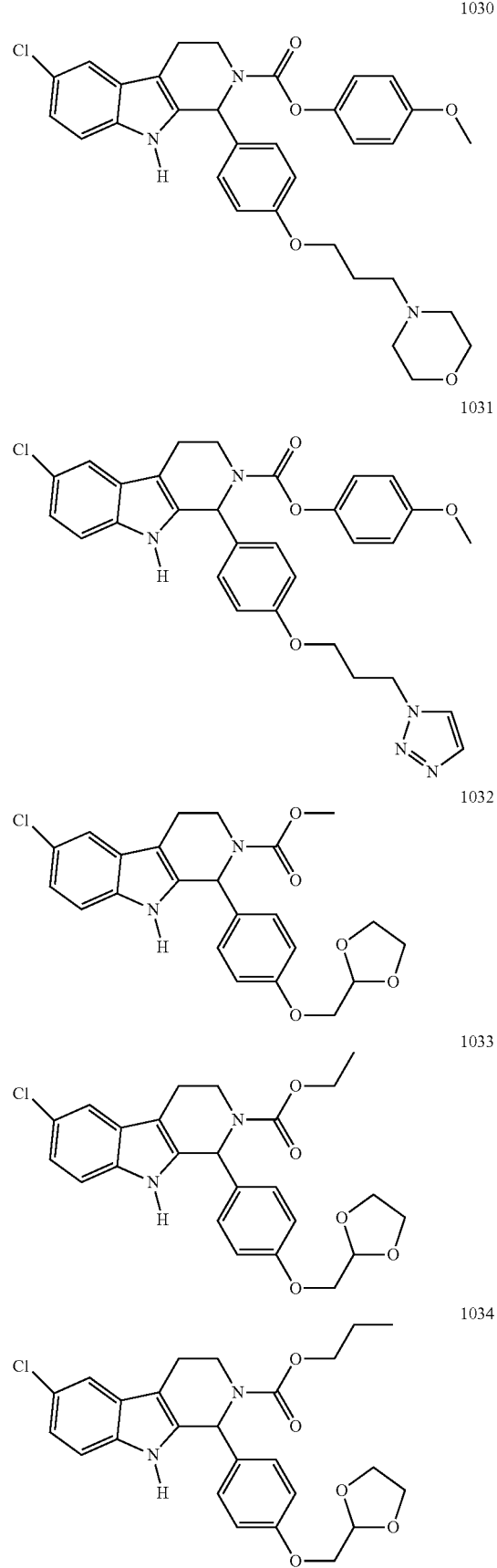

-continued
1035
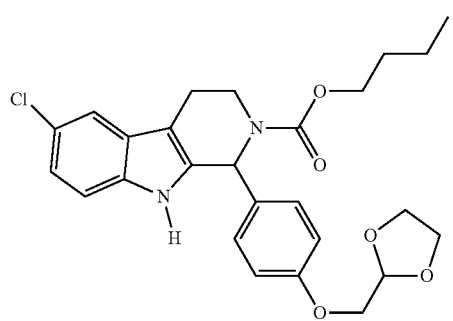
1036
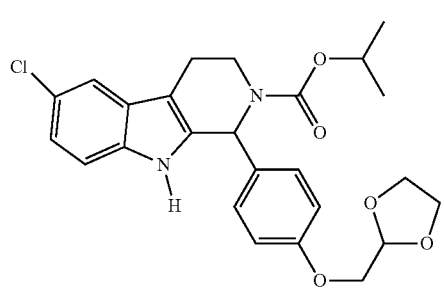
1037
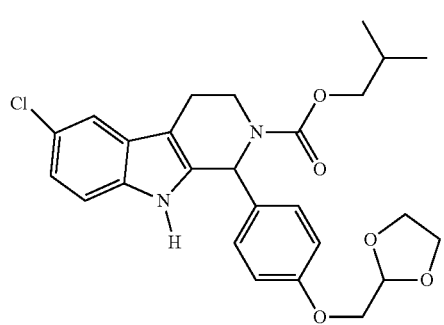
1038
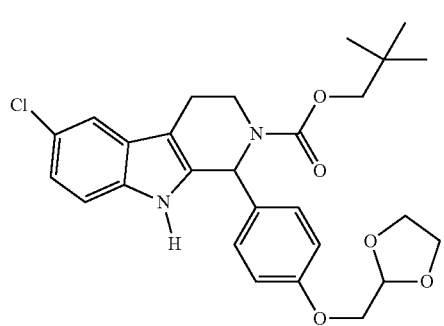
1039
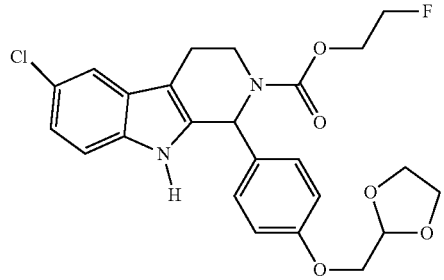
-continued
1040
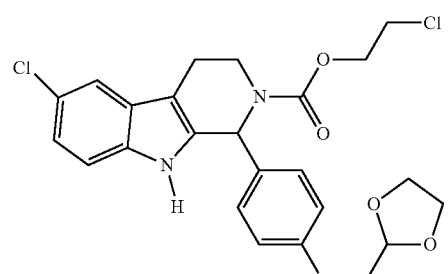
1041
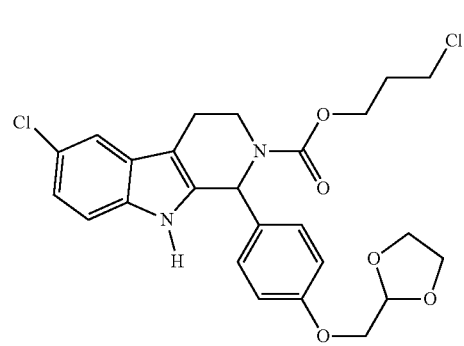
1042
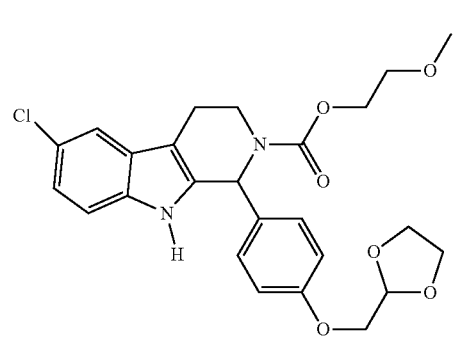
1043
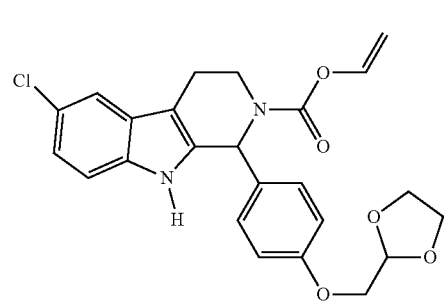
1044
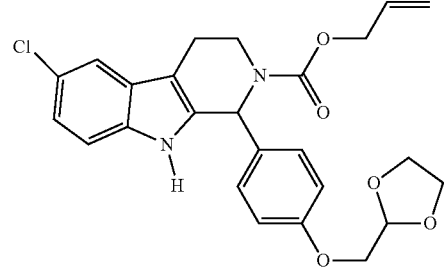

-continued
1045
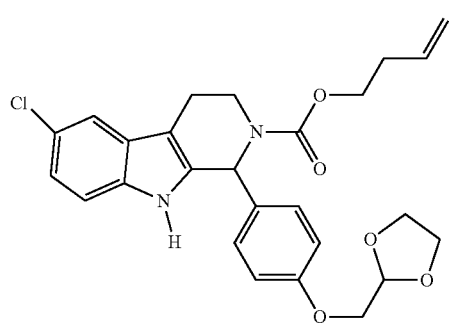
1046
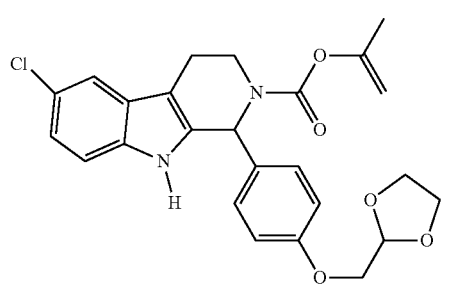
1047
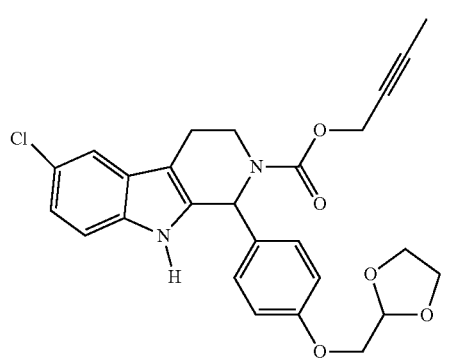
1048
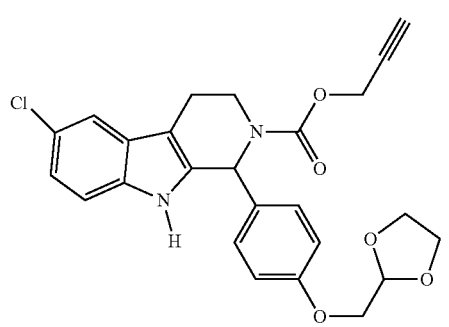
1049
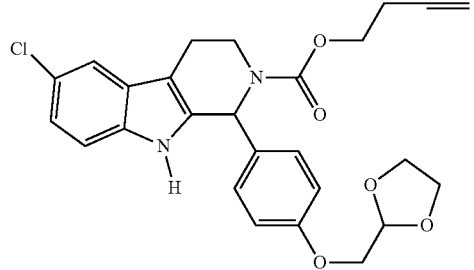
-continued
1050
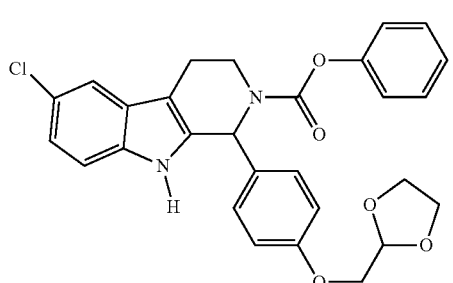
1051
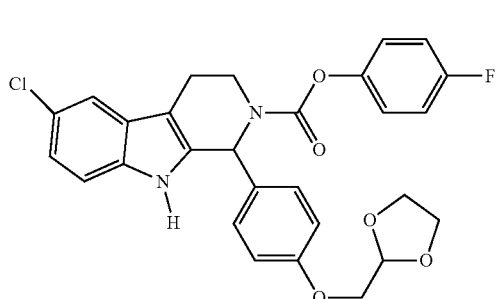
1052
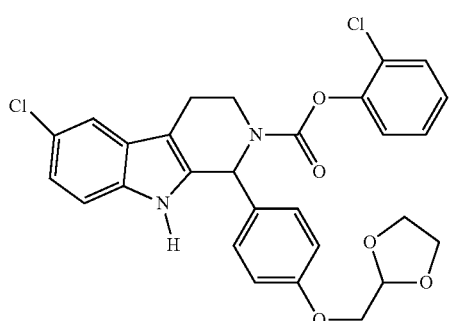
1053
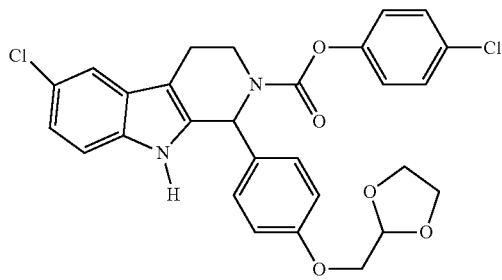
1054
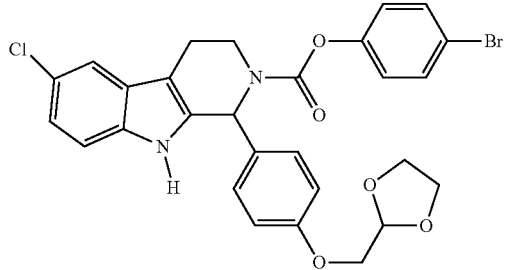

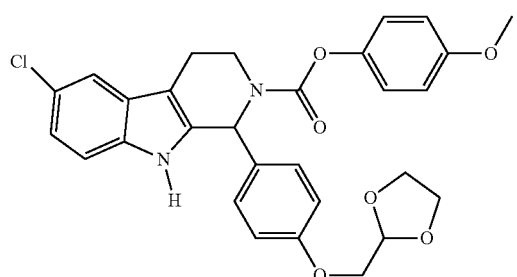
1055
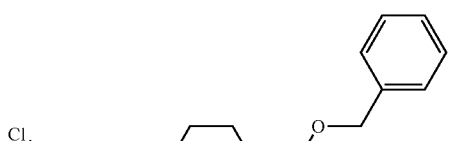
1059
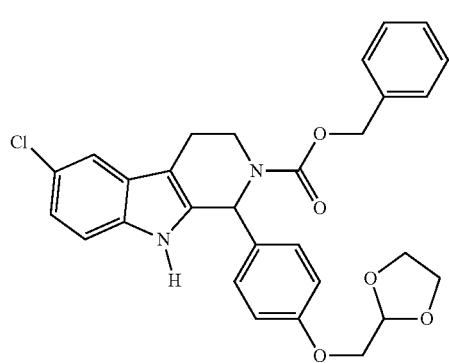
1056
1060
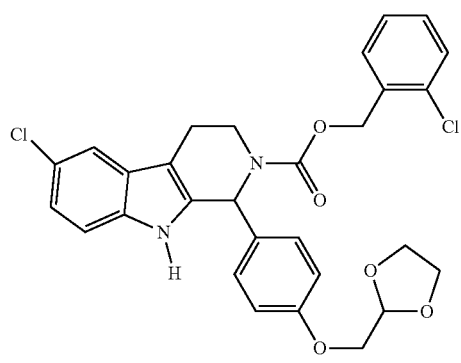
1057
1061
1058
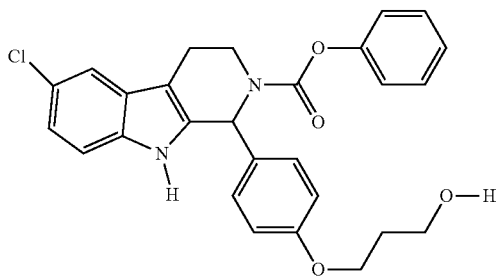
1062

1063
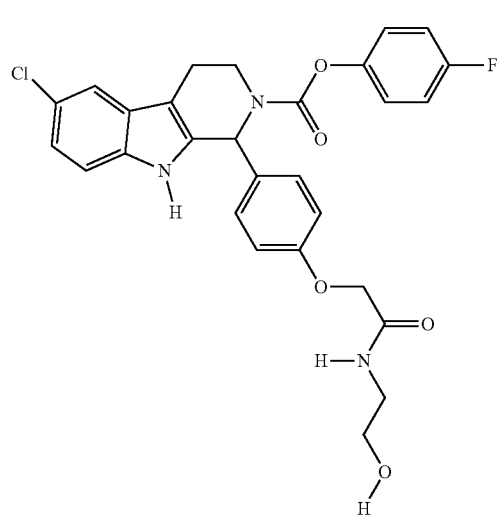
1064
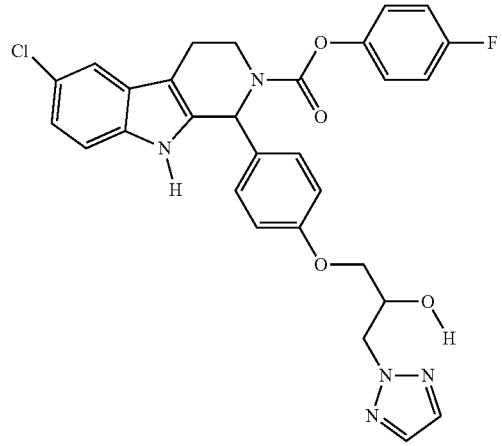
1067
1068
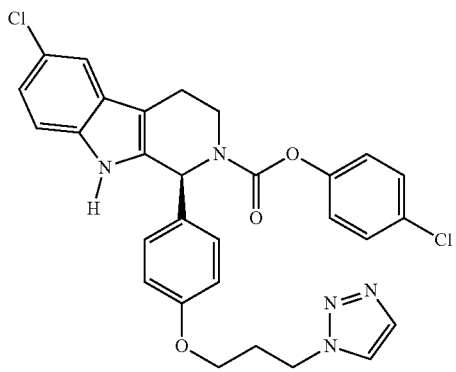
1069
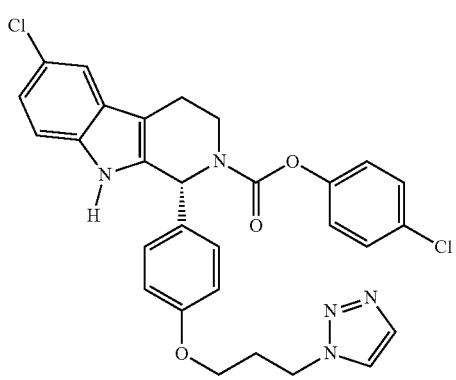
1070
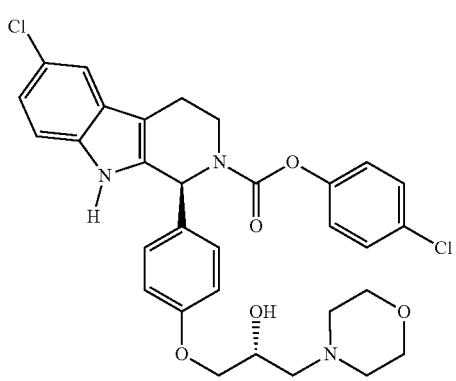
1071
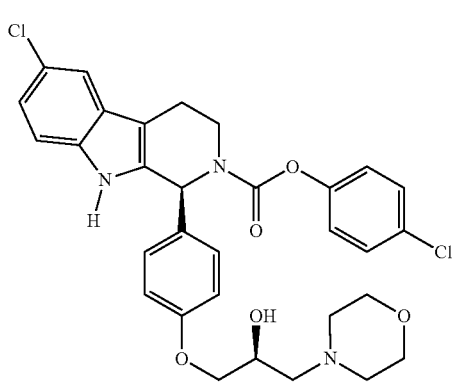

| 1072 | 1076 |
|---|---|
| 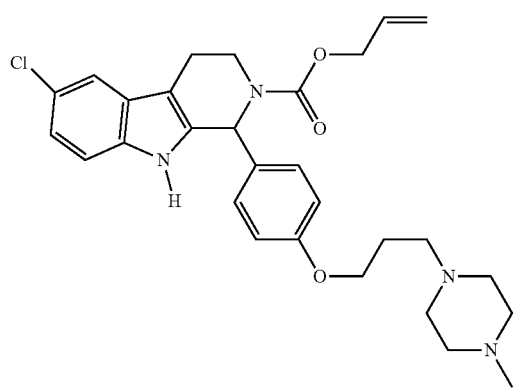 | 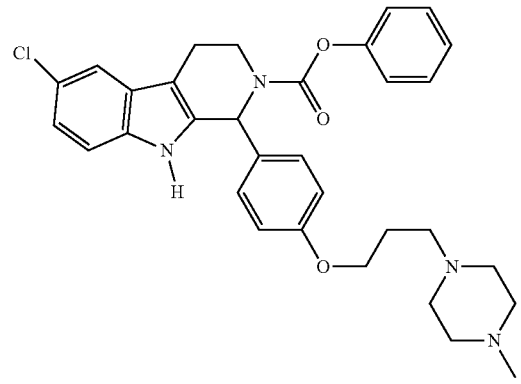 |
| 1073 | 1077 |
| 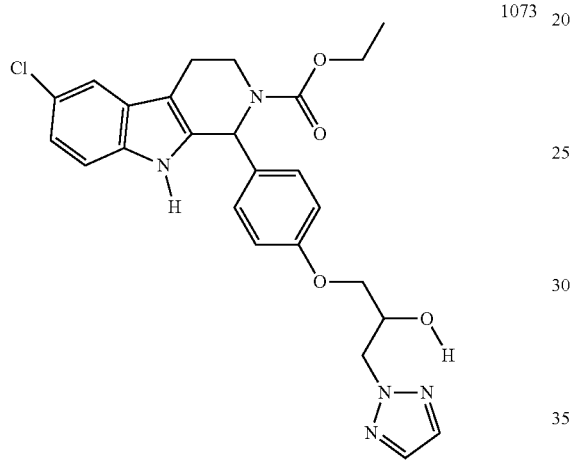 | 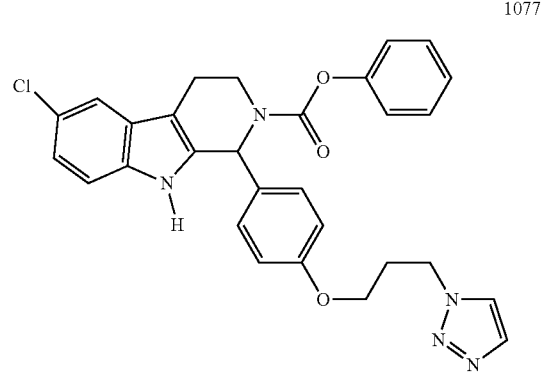 |
| 1074 | 1078 |
| 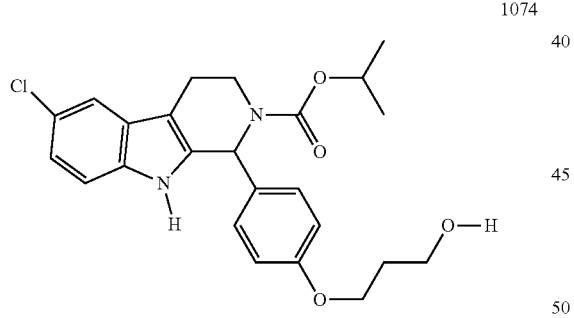 | 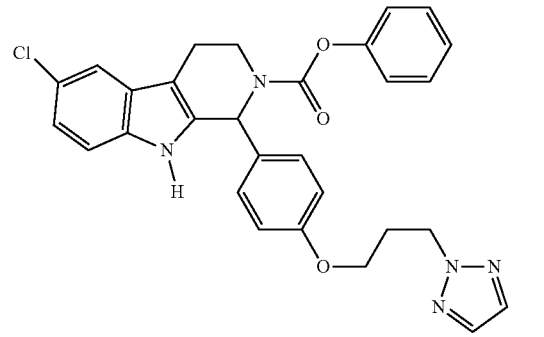 |
| 1075 | 1079 |
| 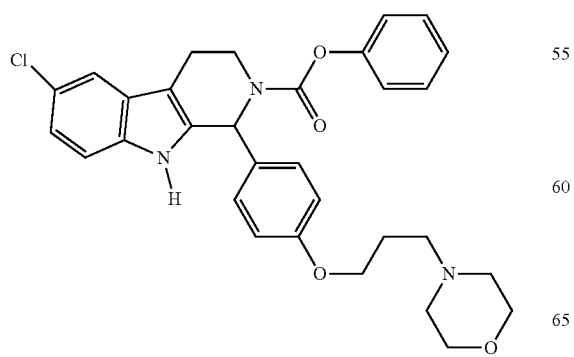 | 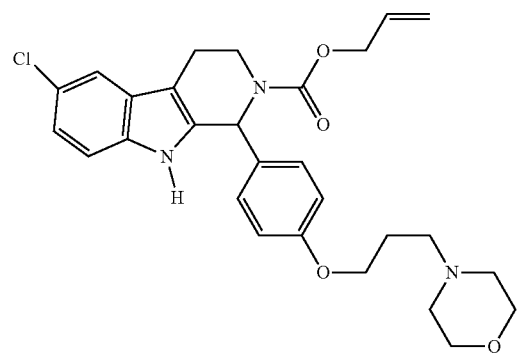 |

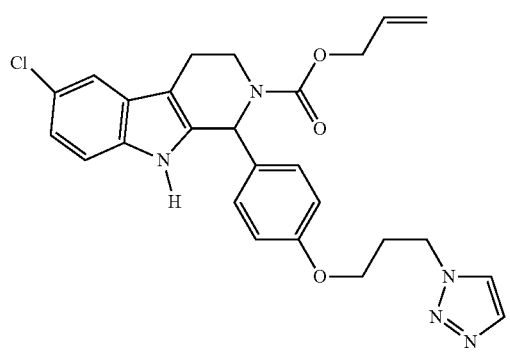
1080
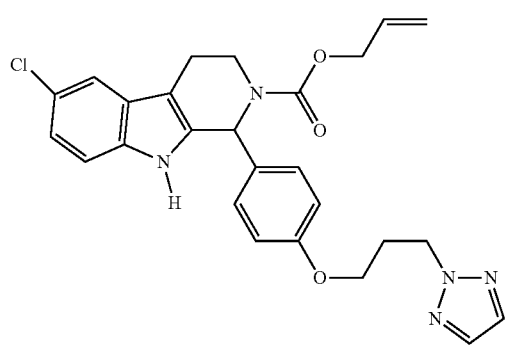
1081
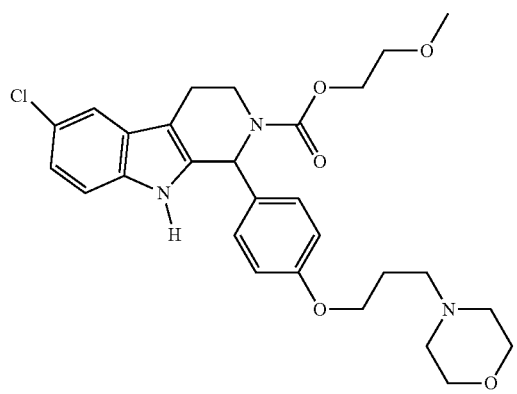
1082
1083
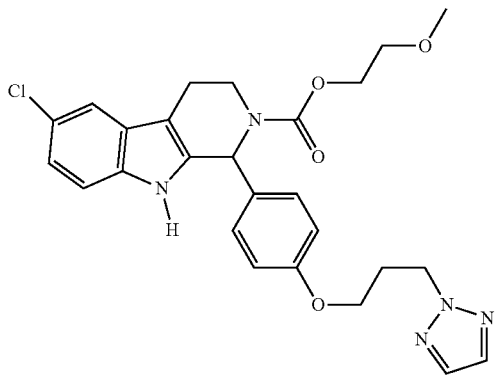
1084
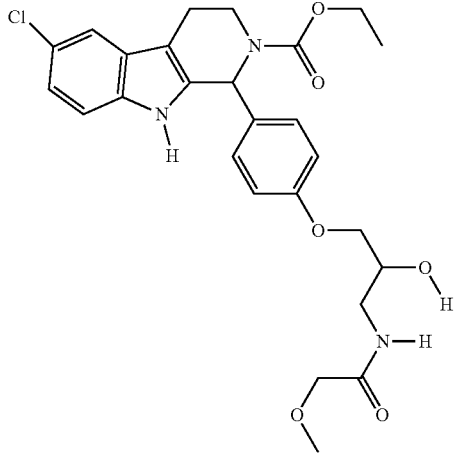
1085
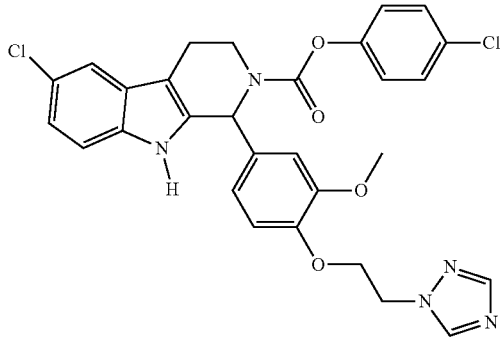
1086
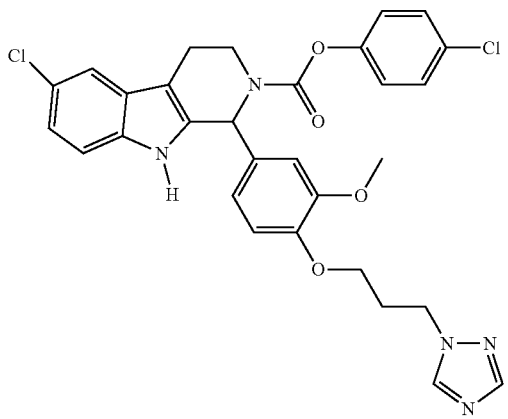
1087

1088
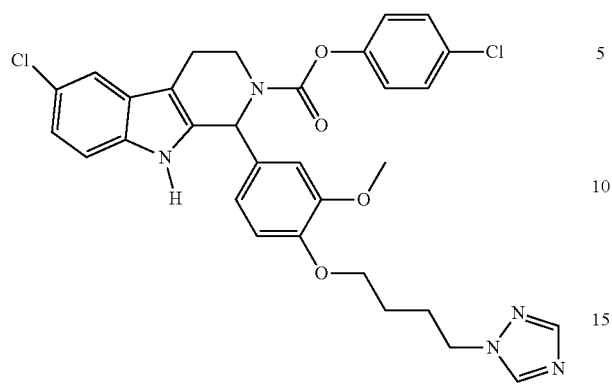
1089
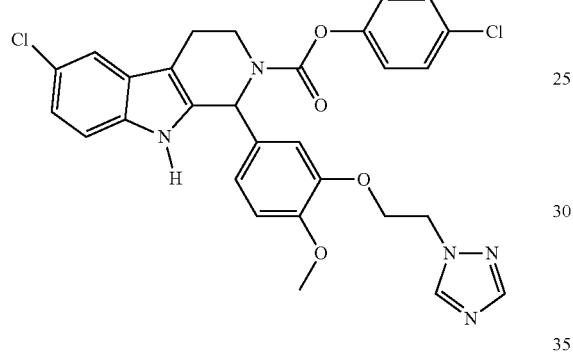
1090
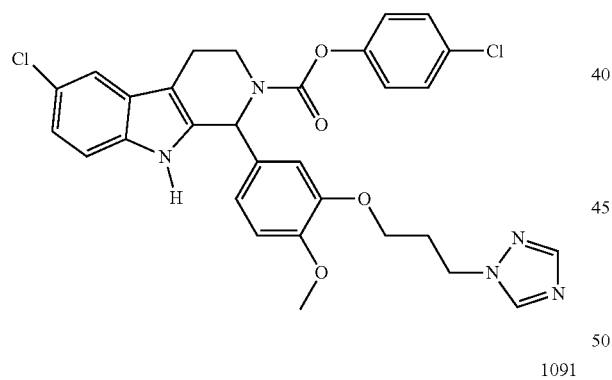
1091
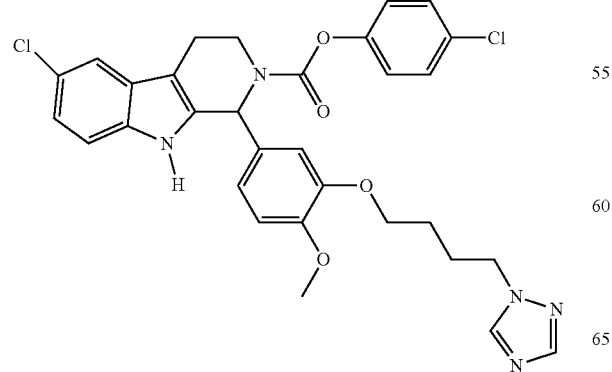
1092
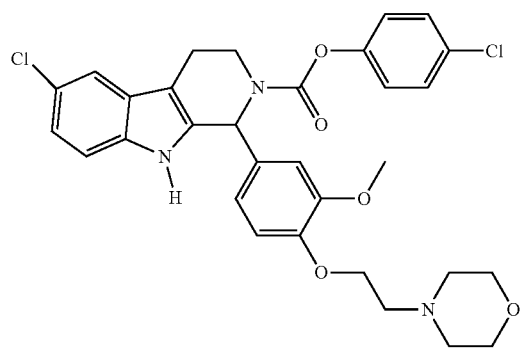
1093
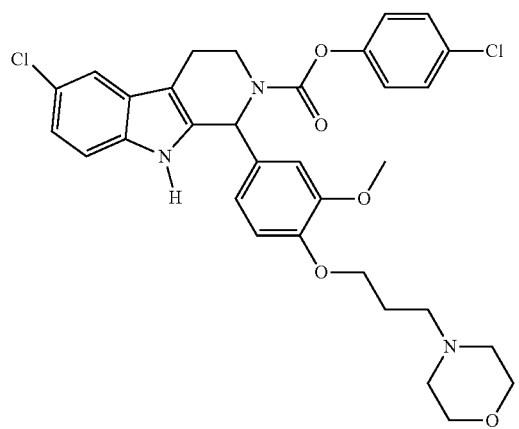
1094
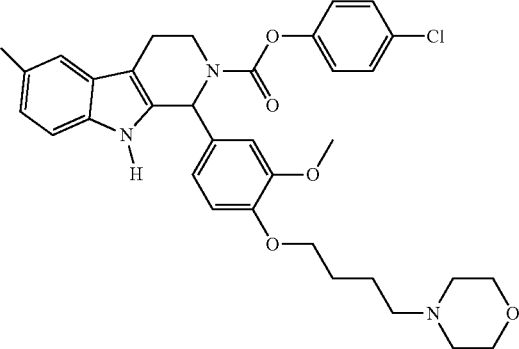
1095
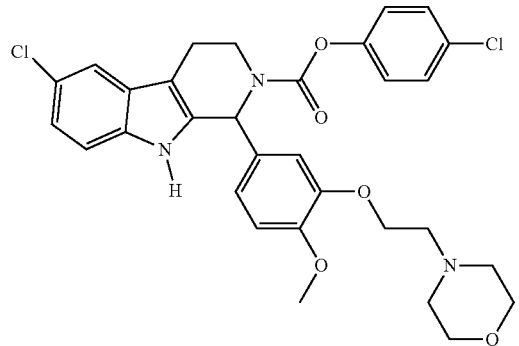

1096
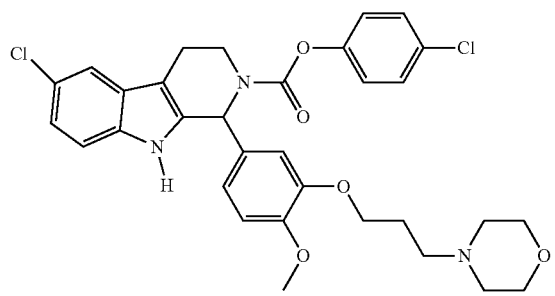
1097
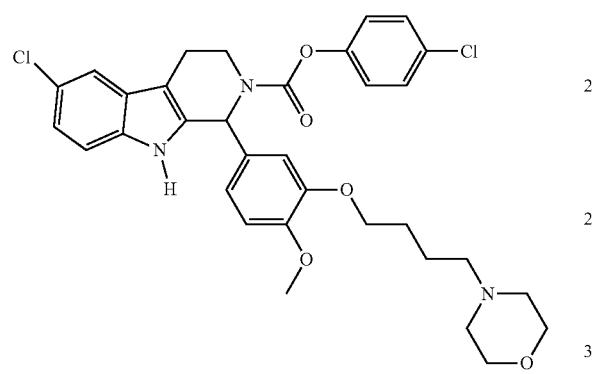
1098
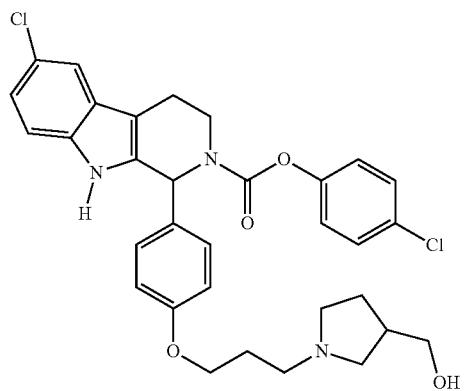
1099
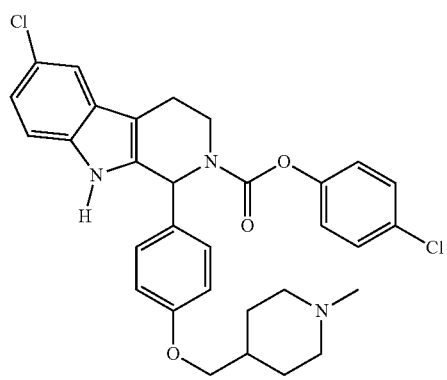
1100
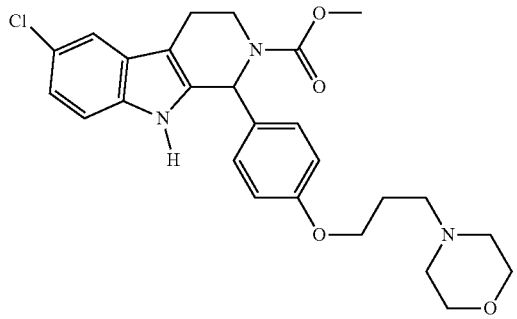
1101
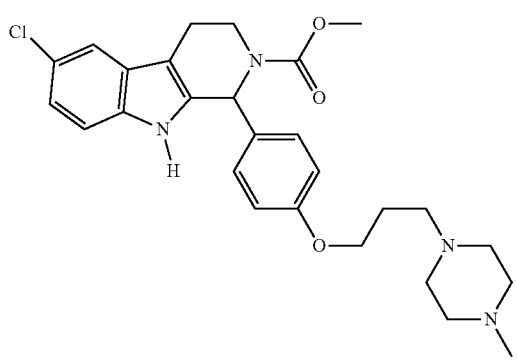
1102
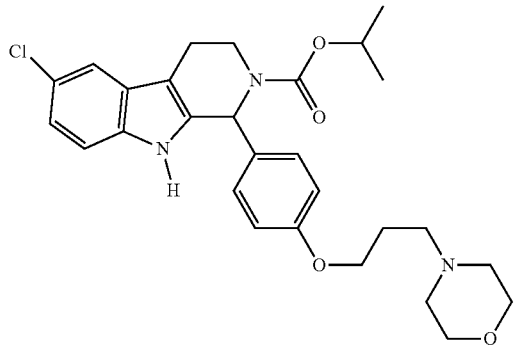
1103
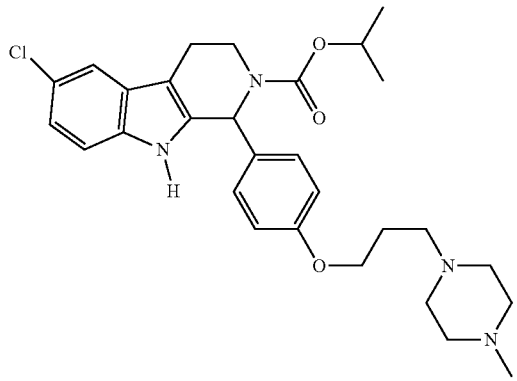

1104
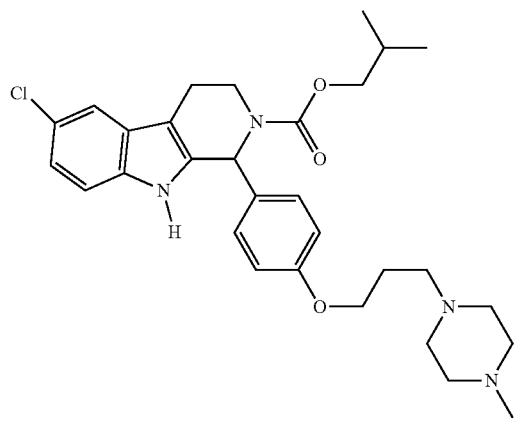
1105
1106
1107
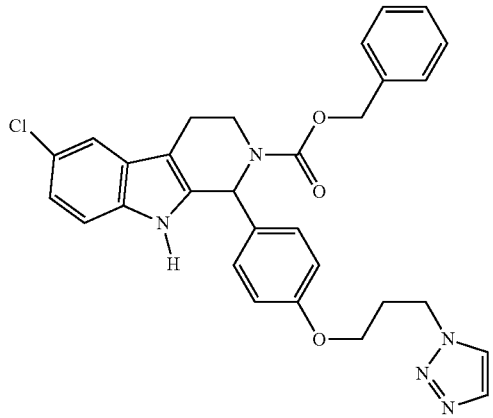
1108
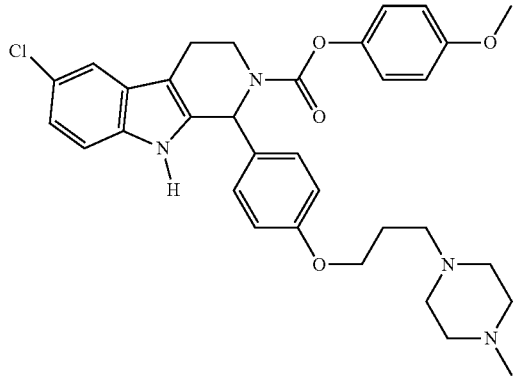
1109
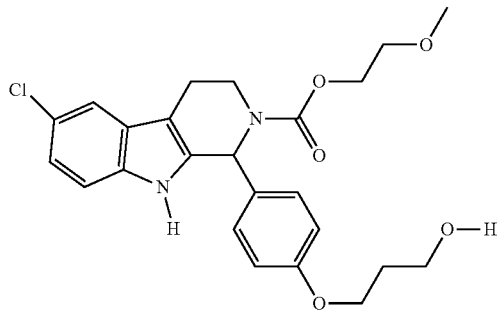
1110
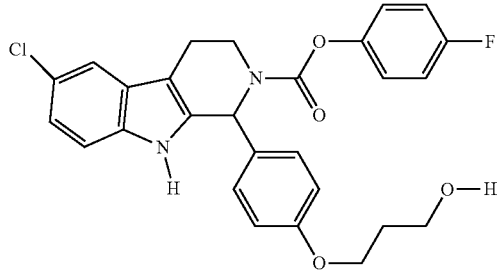

1111
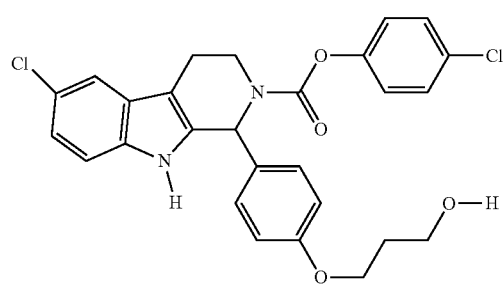
1112
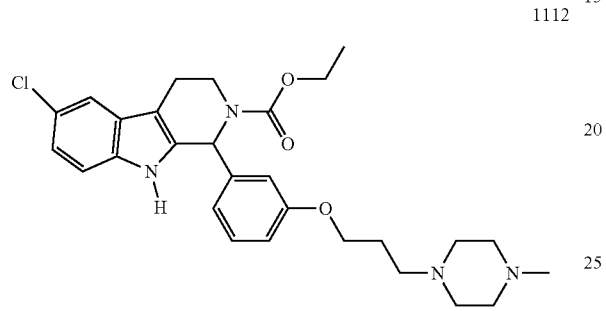
1113
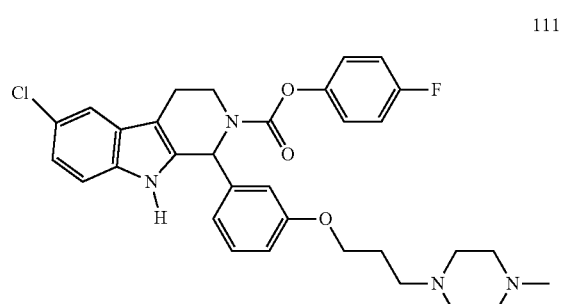
1114
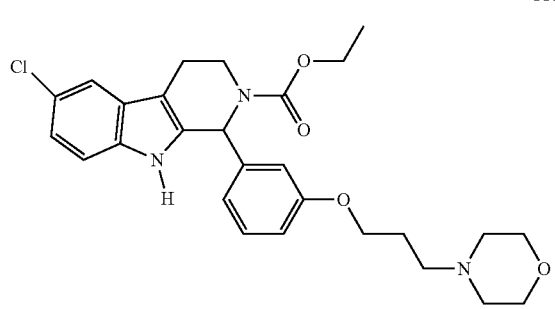
1115
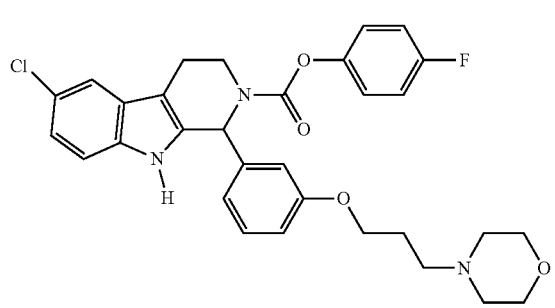
1116
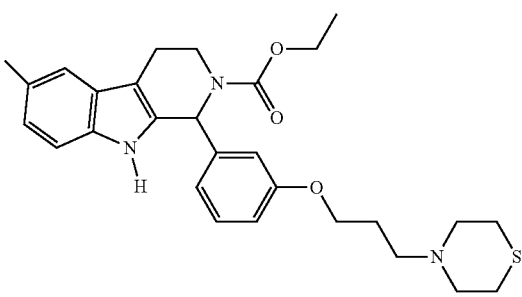
1117
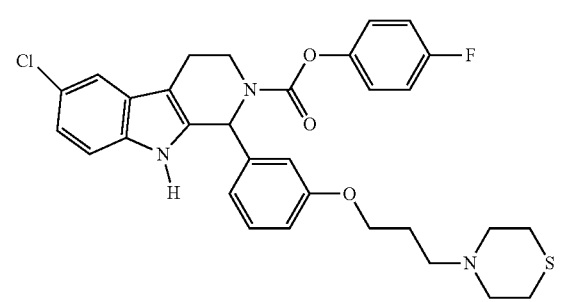
1118
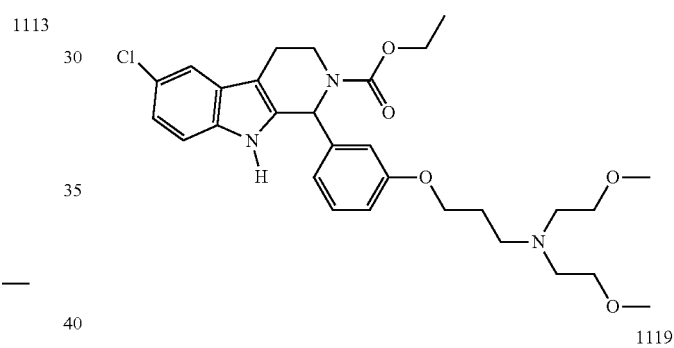
1119
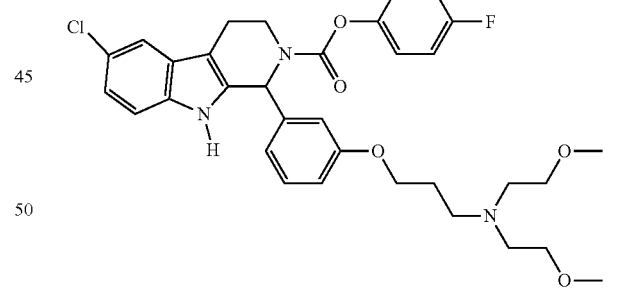
1120
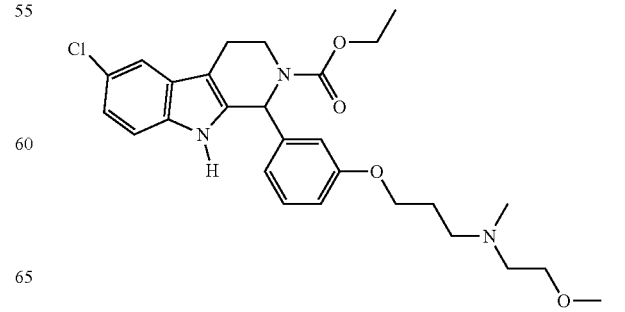

-continued
1121
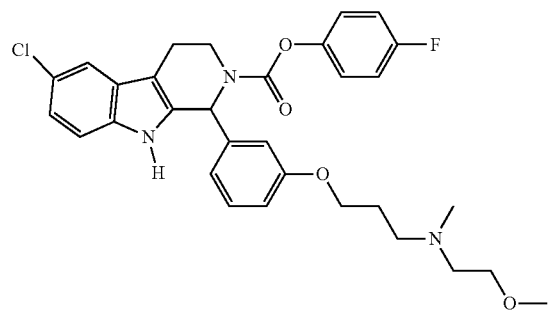
1122
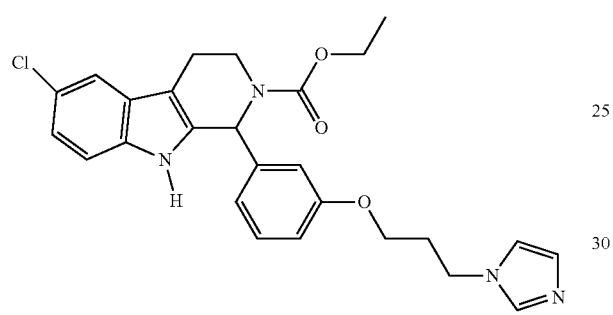
1123
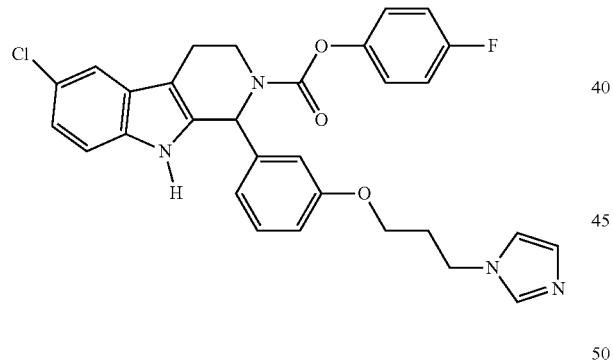
1124
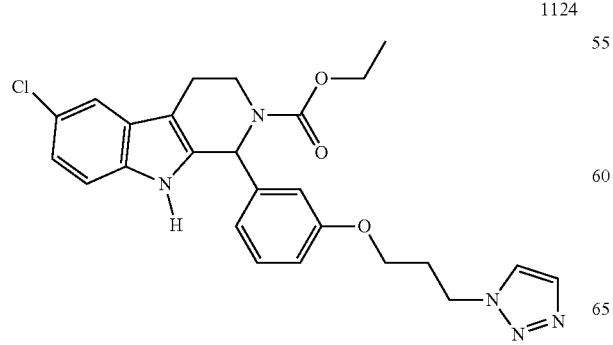
-continued
1125
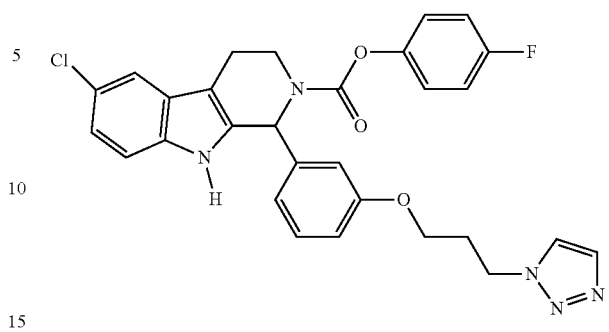
1126
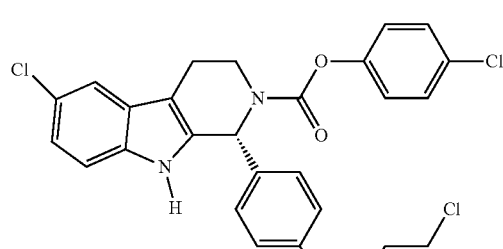
1127
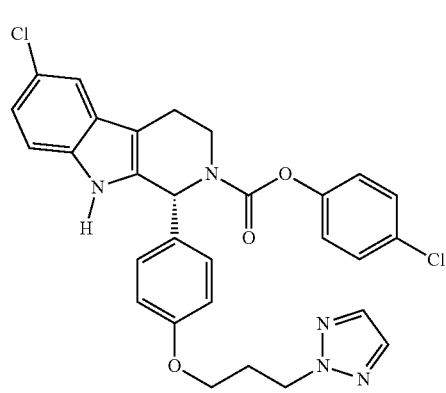
1128
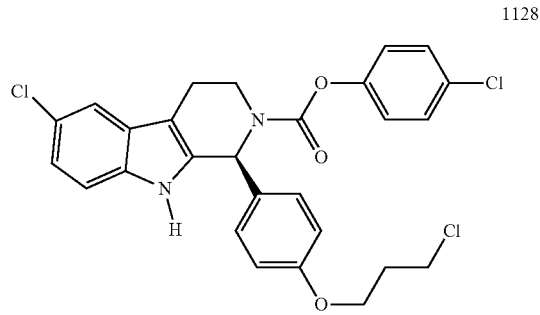

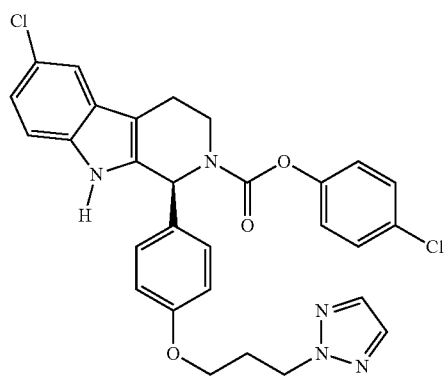
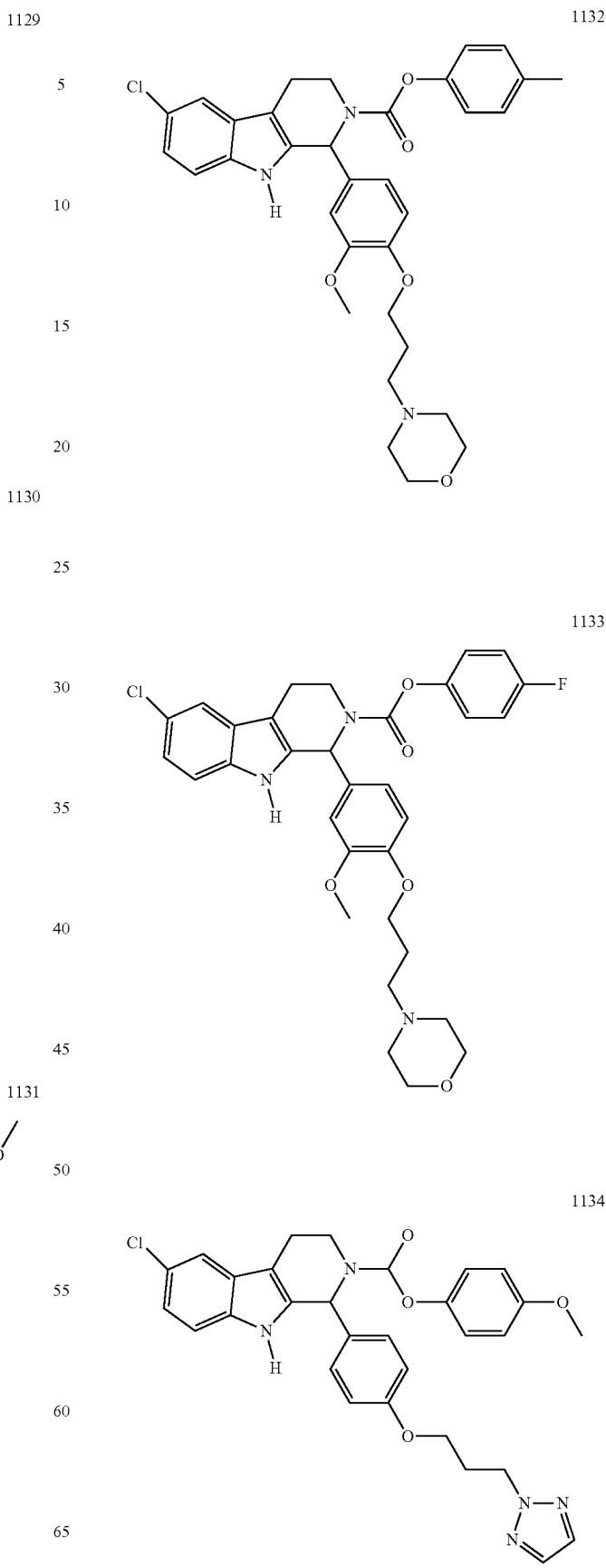

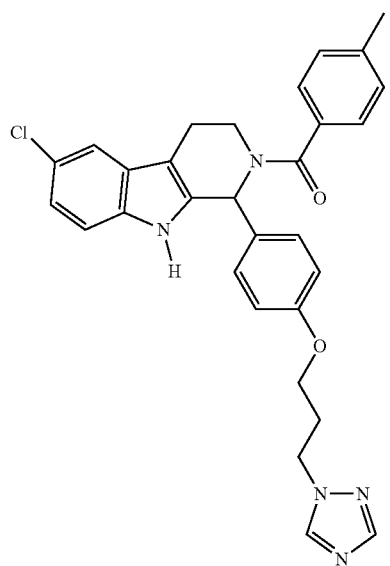
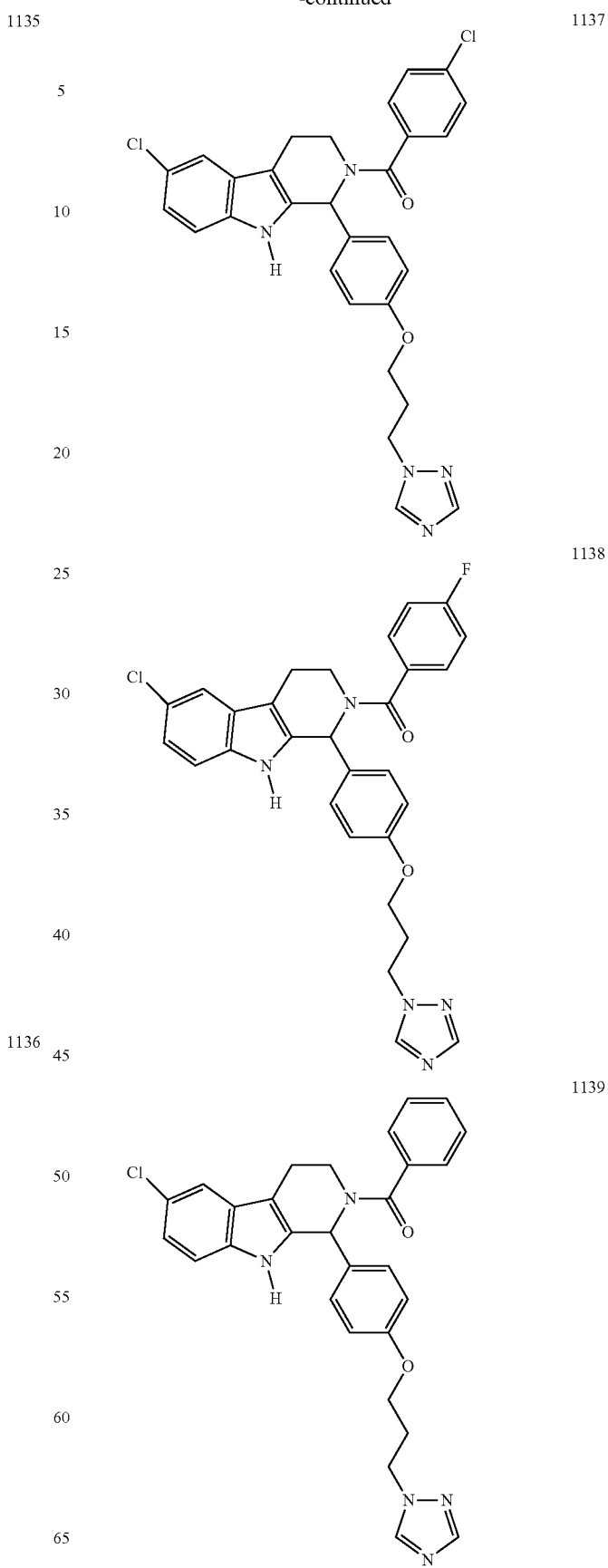

597
-continued
1140 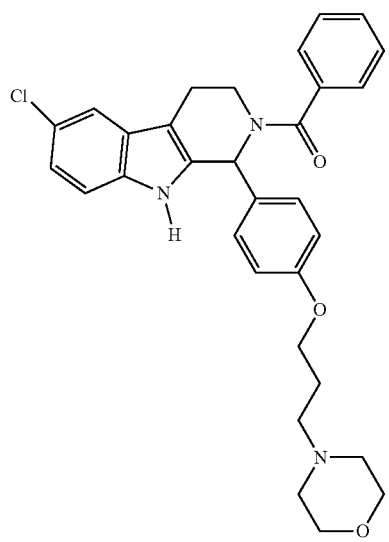
1141 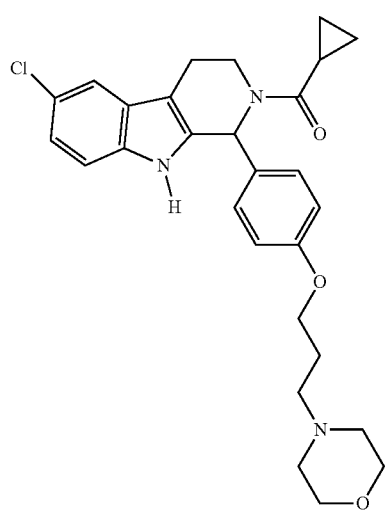
1142 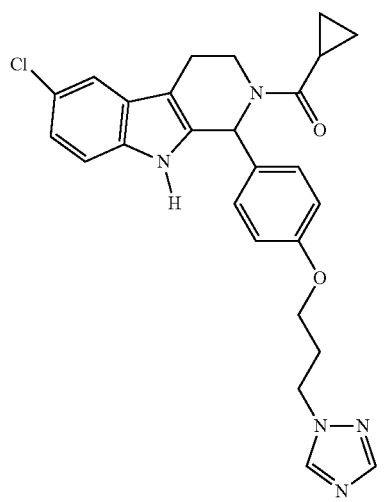
598
-continued
1143 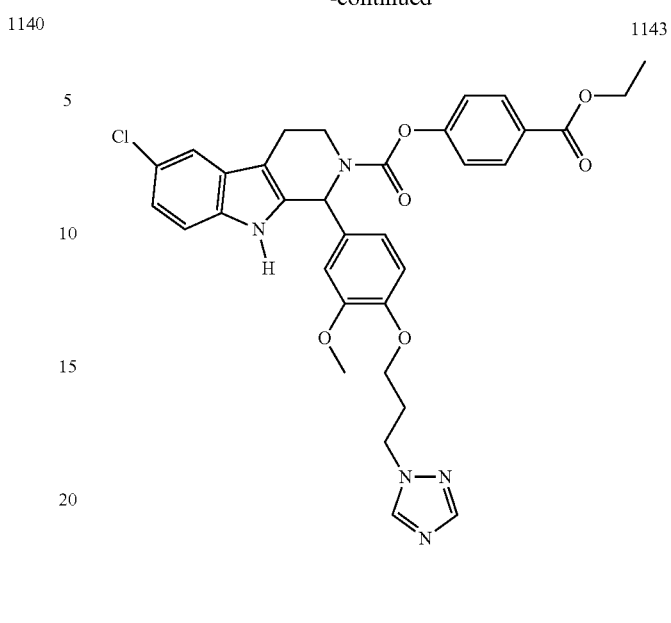
1144 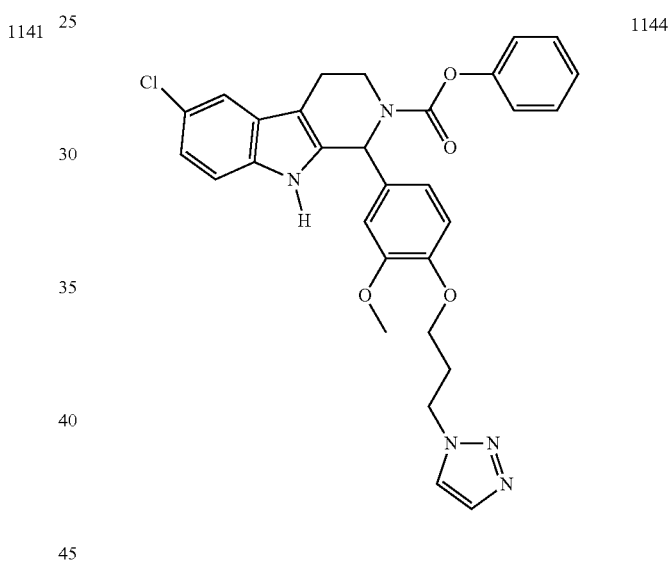
1145 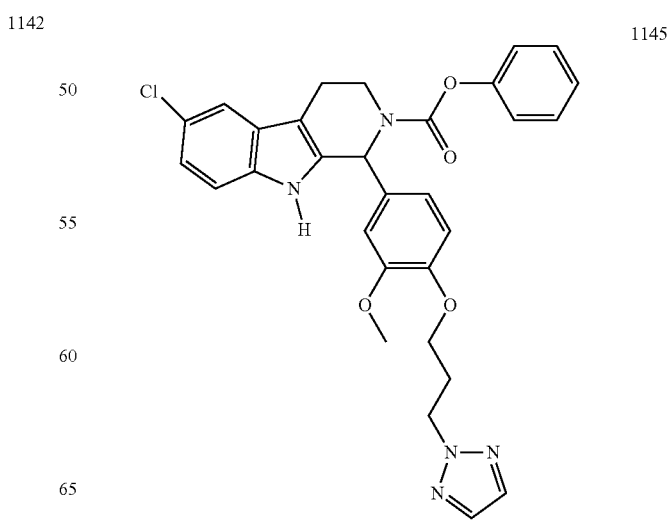

1146
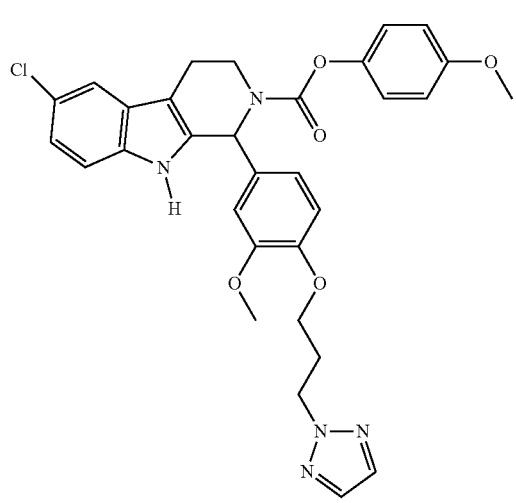
1147
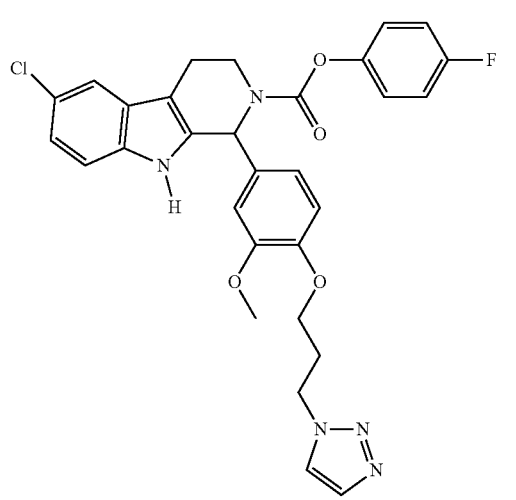
1148
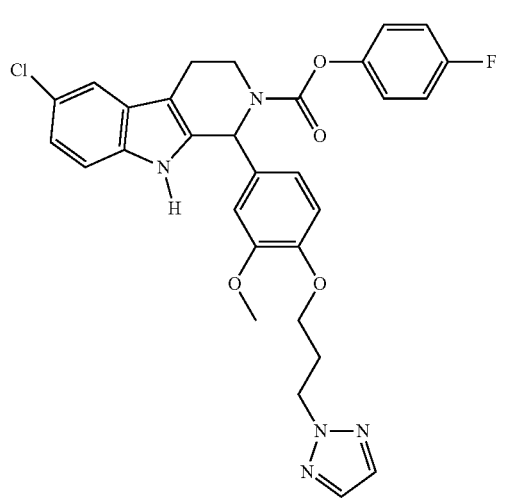
1149
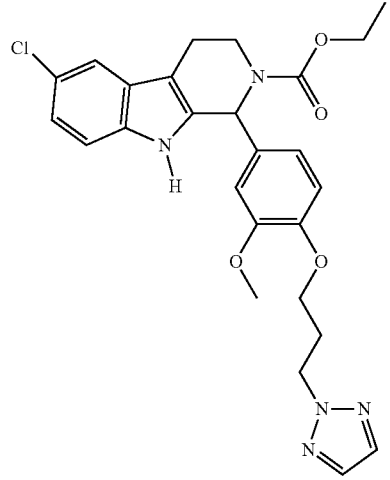
1150
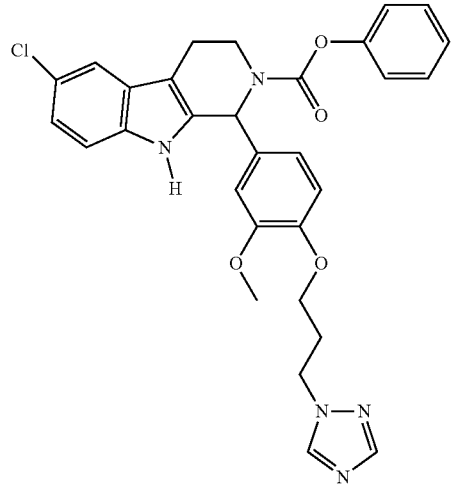
1151
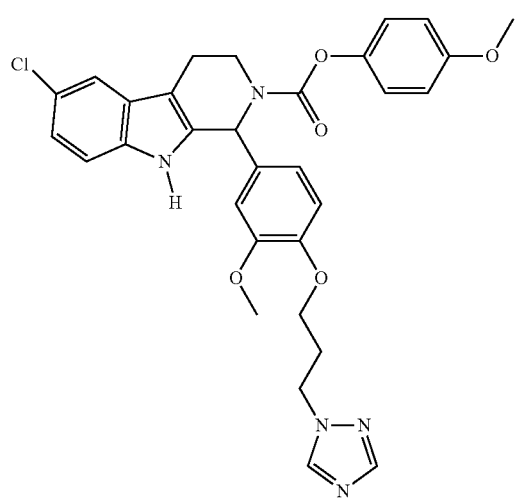

-continued
1152
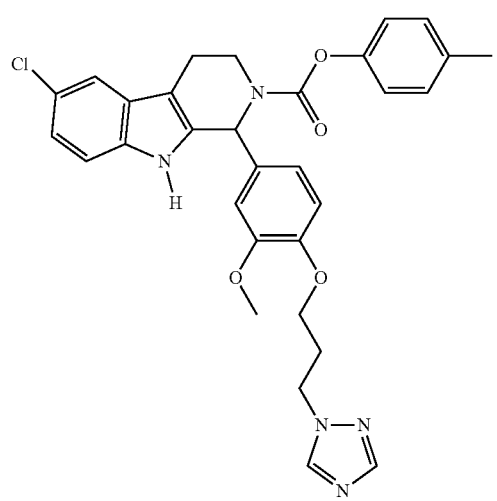
1153
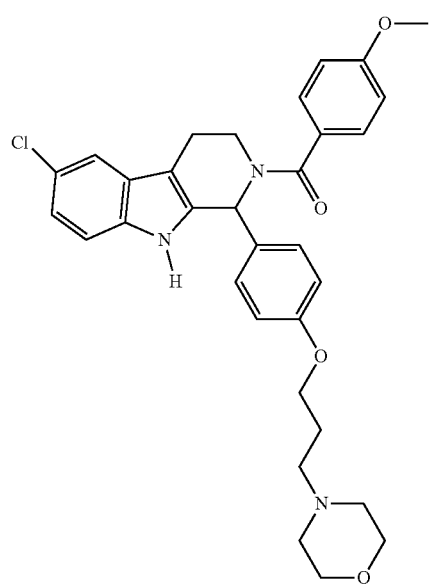
1154
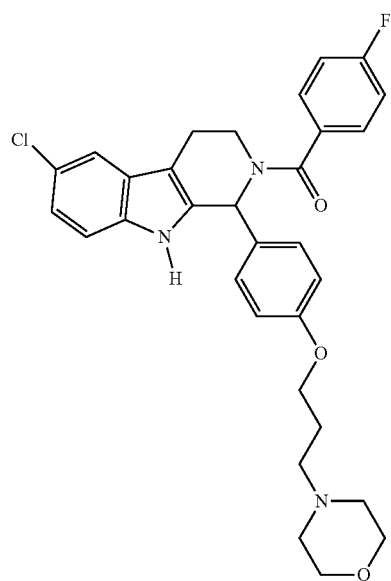
-continued
1155
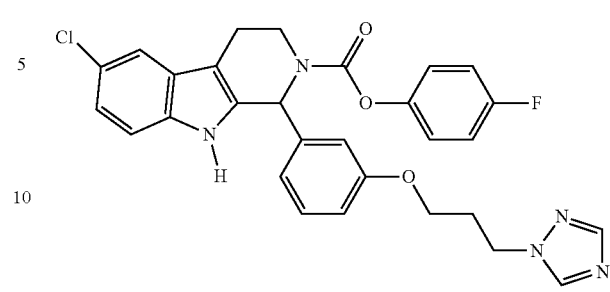
1156
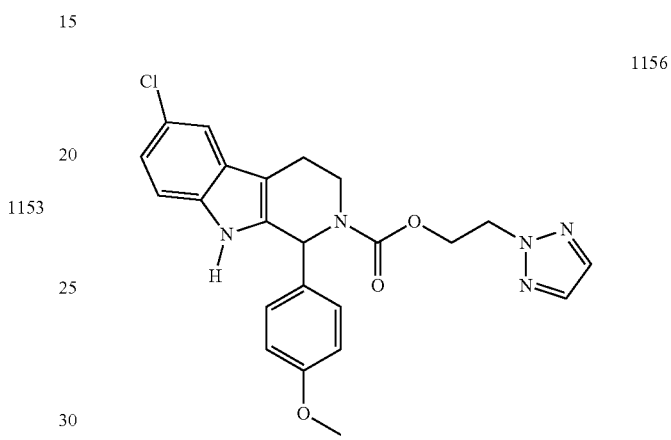
1157
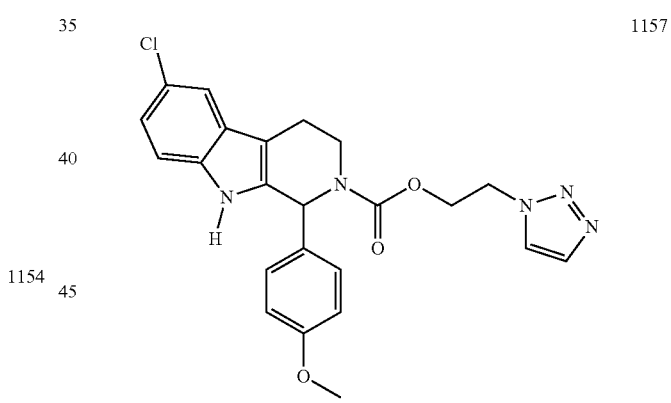
1158
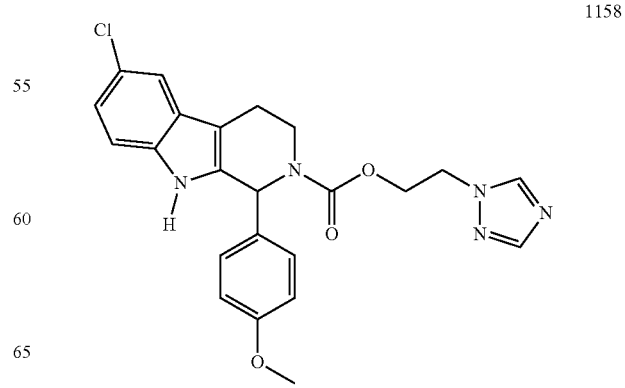

603
-continued
1160
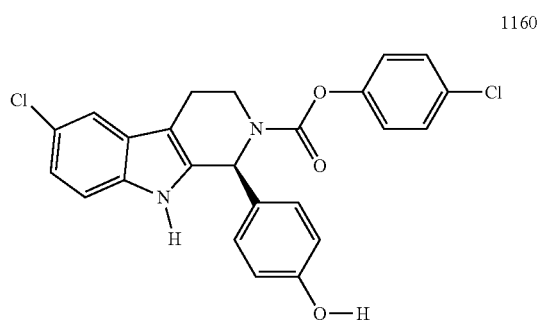
1161
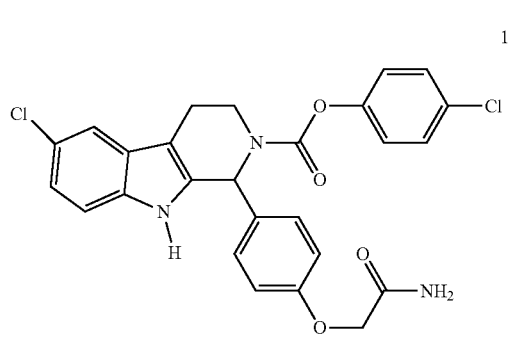
1162
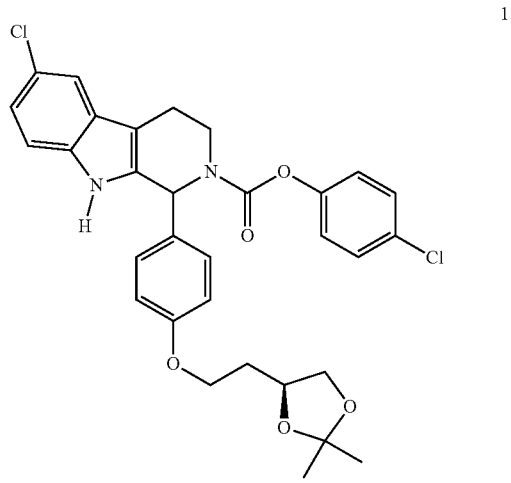
1163
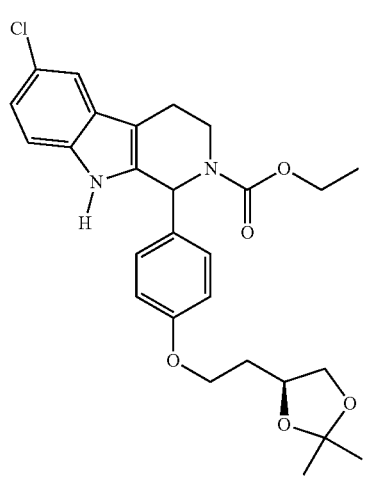
604
-continued
1164
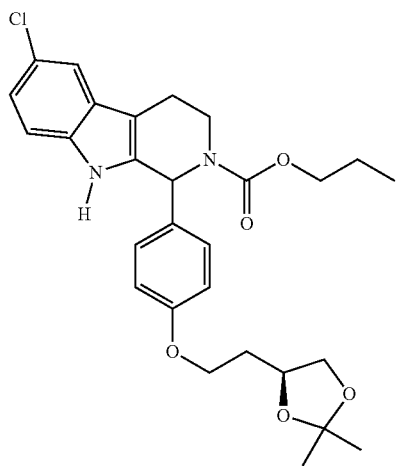
1165
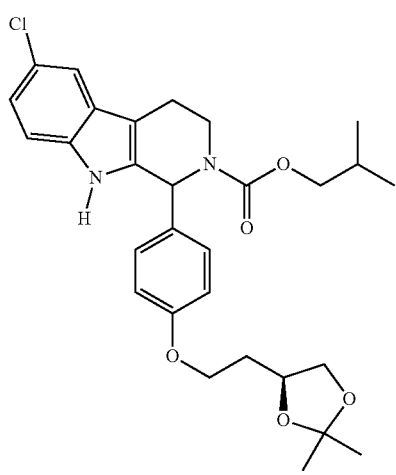
1166
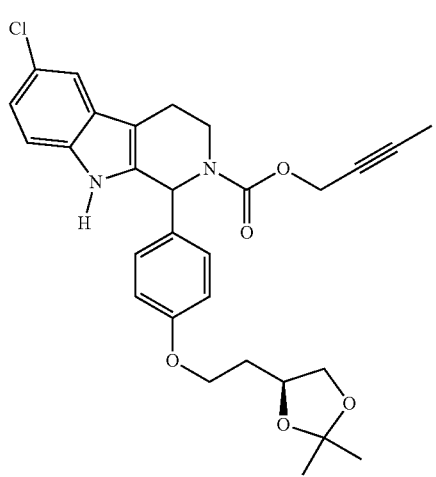

1167 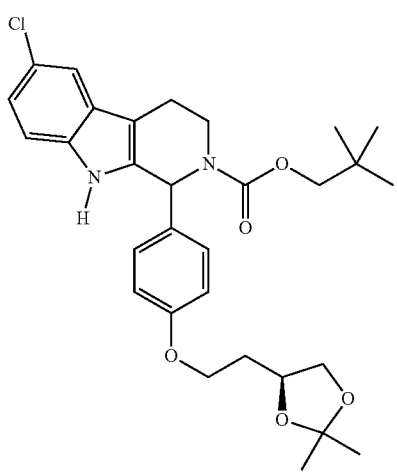
1170 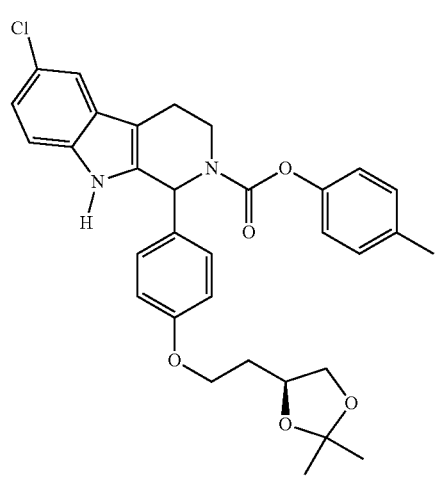
1168 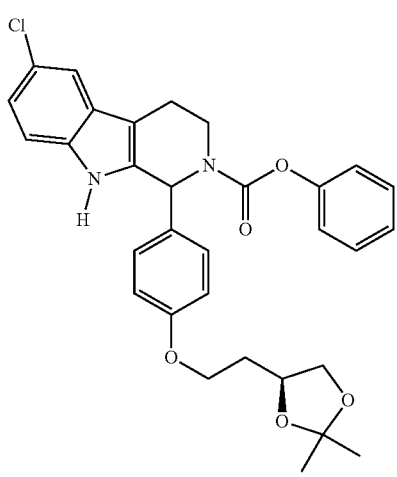
1171 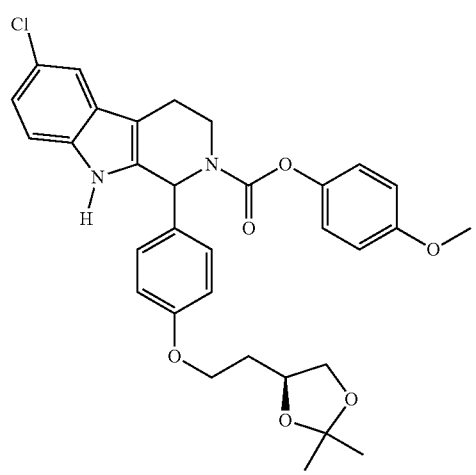
1169 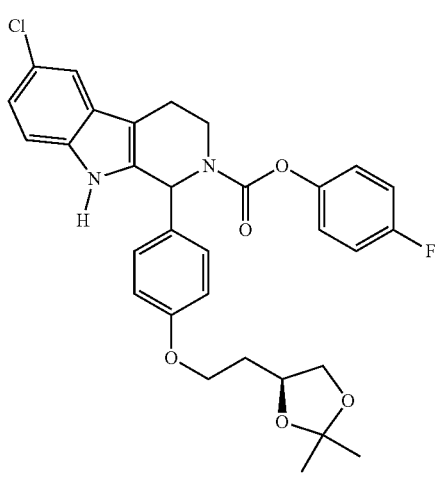
1172 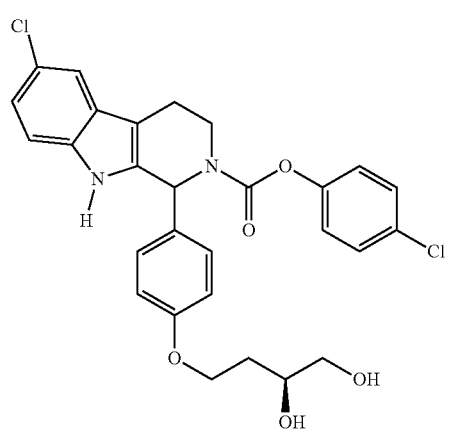

607
-continued
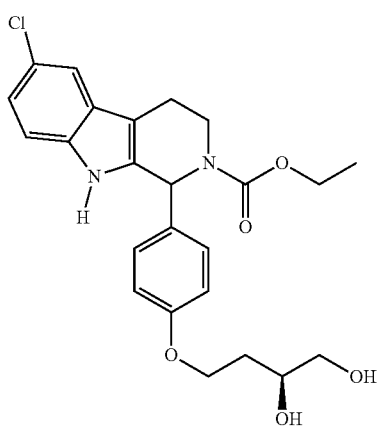
1173
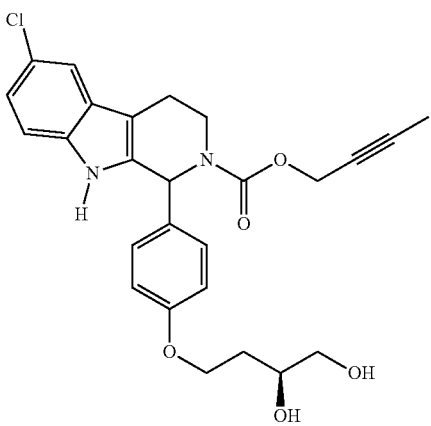
1176
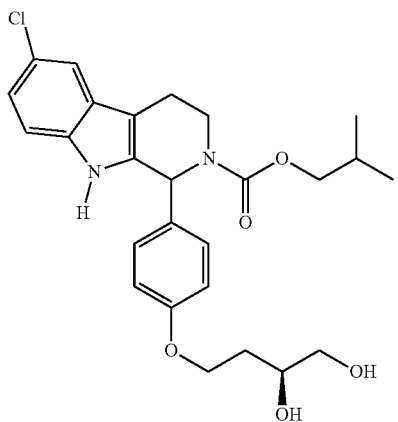
1174
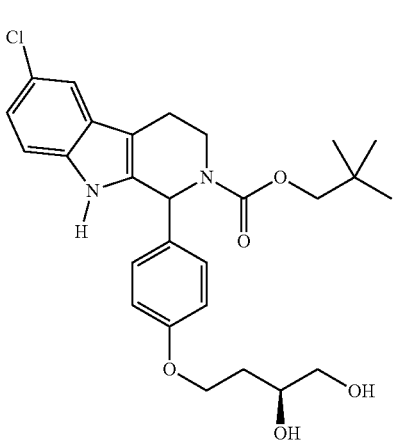
1177
608
-continued
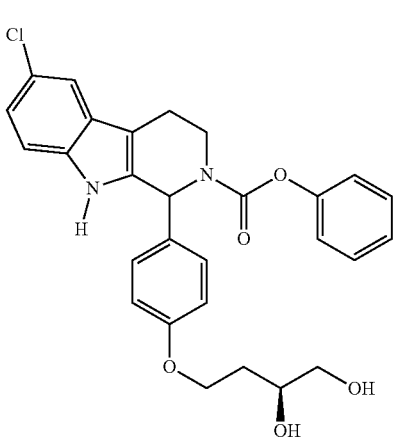
1175
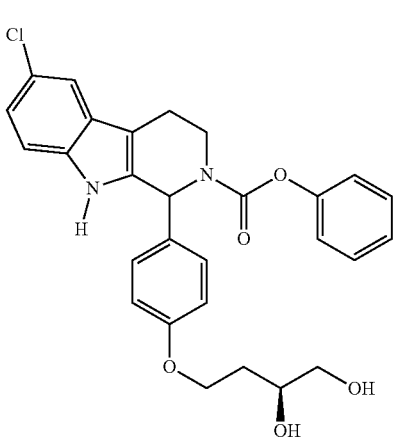
1178

609
-continued
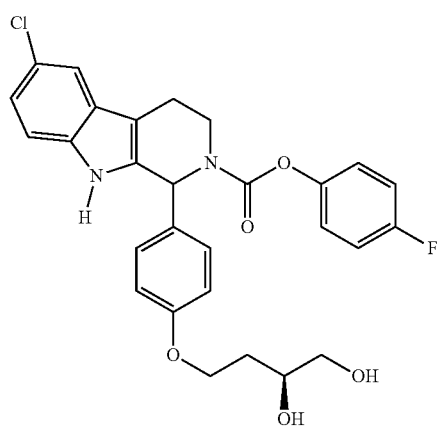
1179
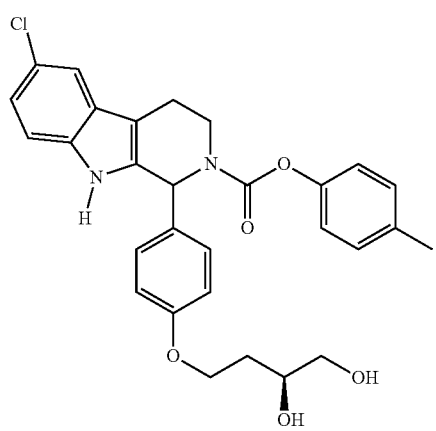
1180
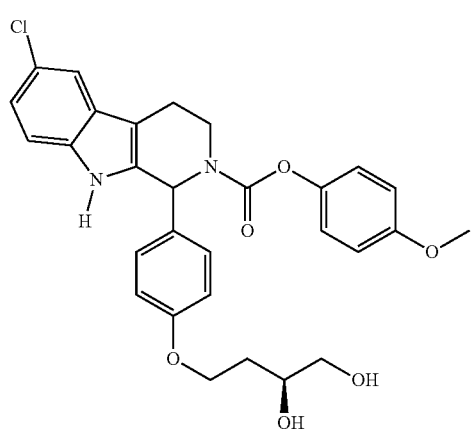
1181
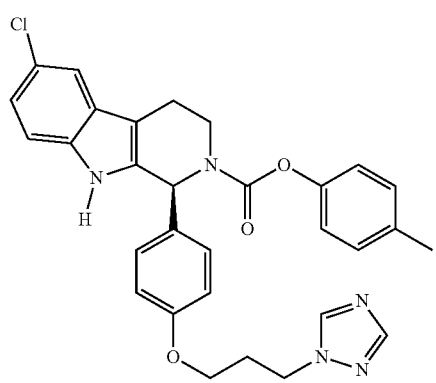
1182
610
-continued
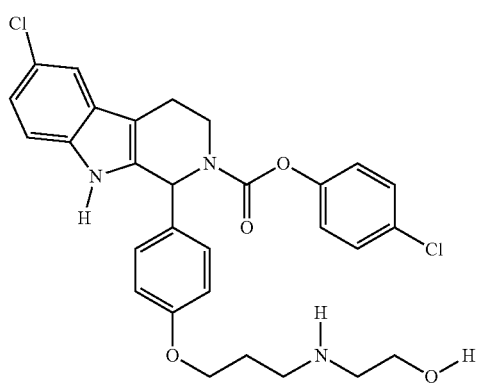
1183
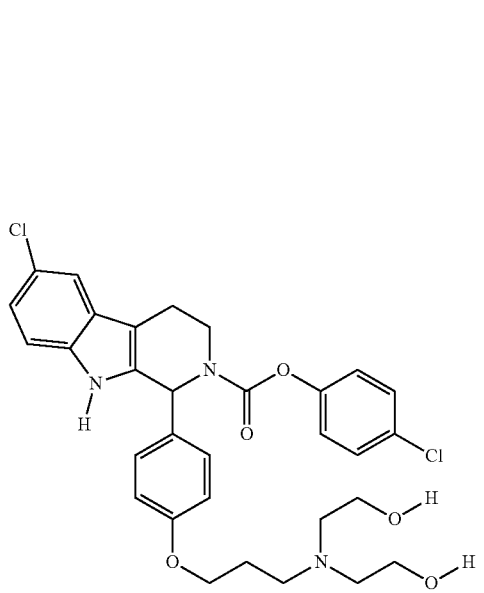
1184
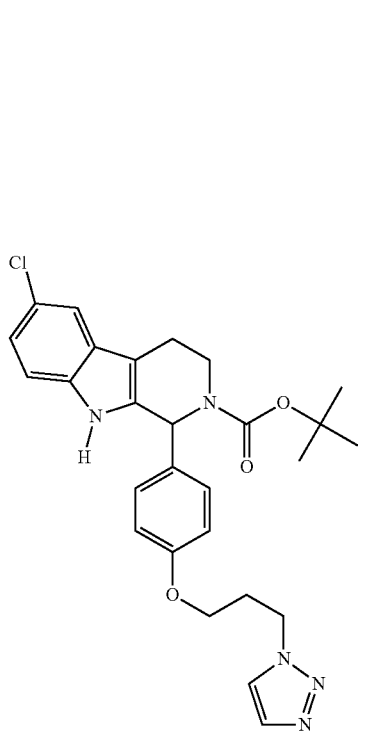
1185

611
-continued
1187
1188
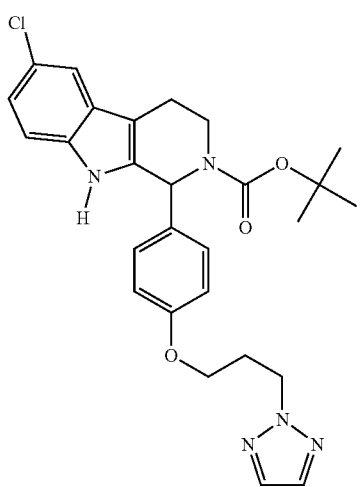
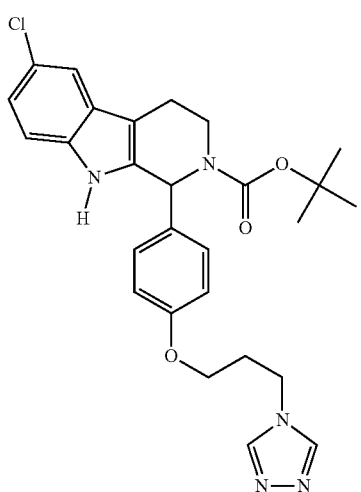
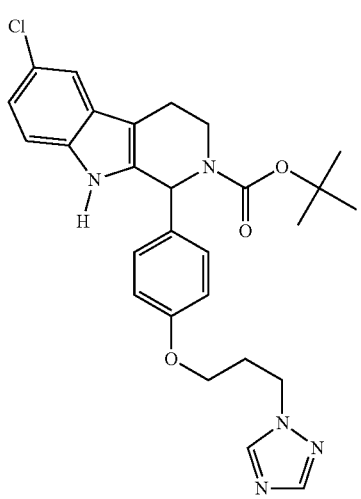
612
-continued
1186
1189
1190
1191
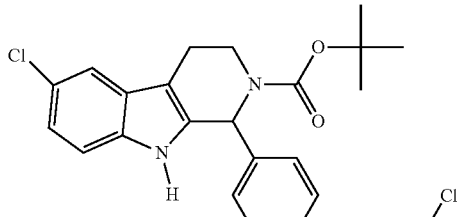
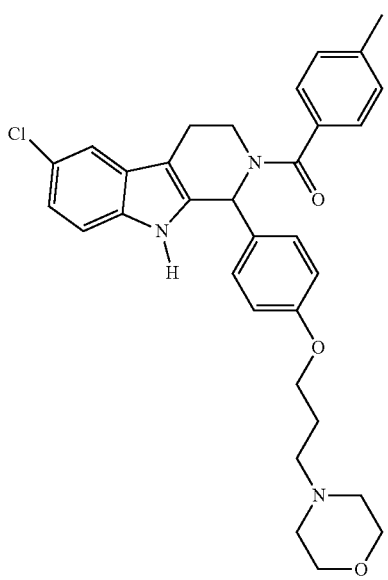
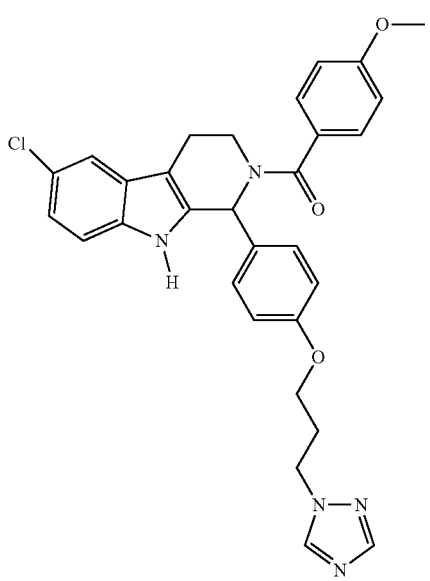

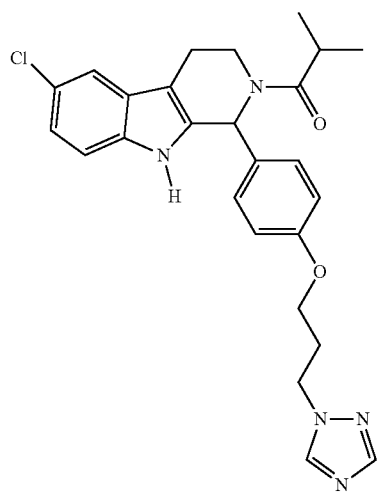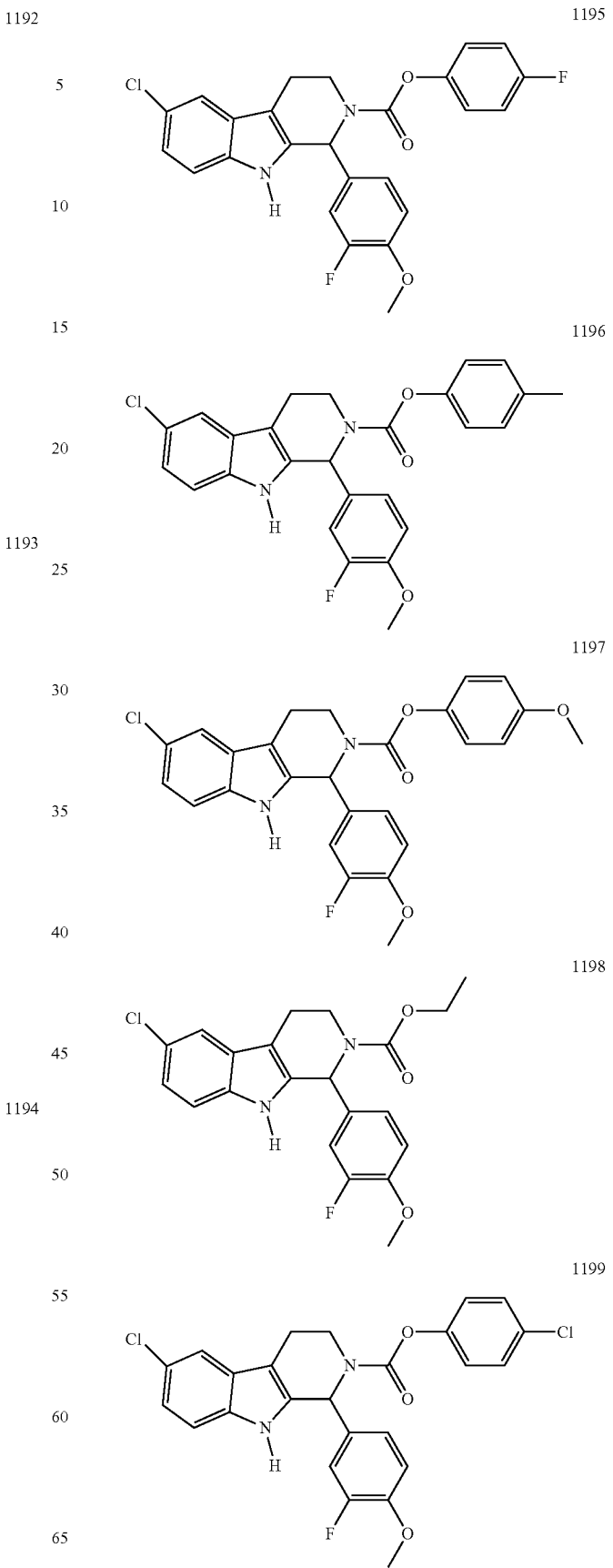

1200 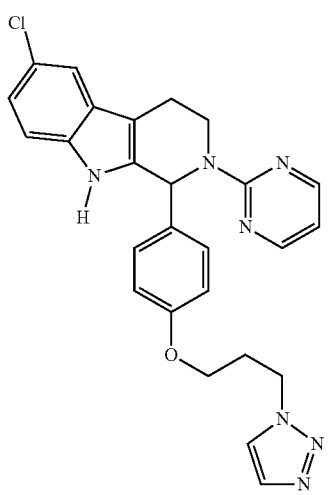
1201 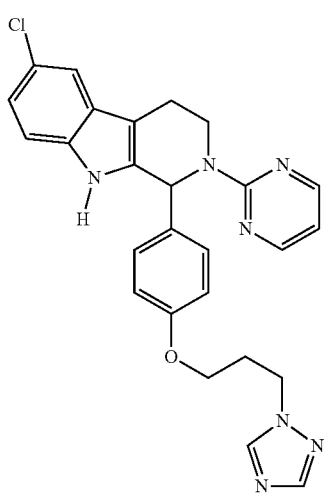
1202 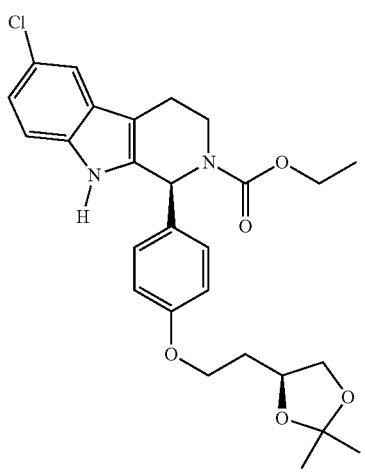
1203 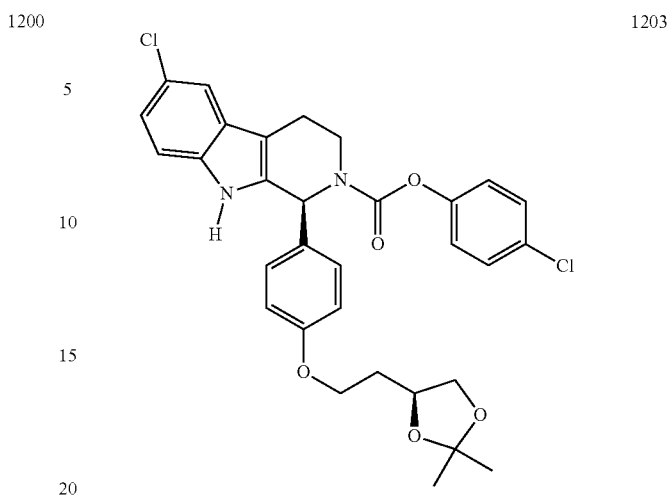
1204 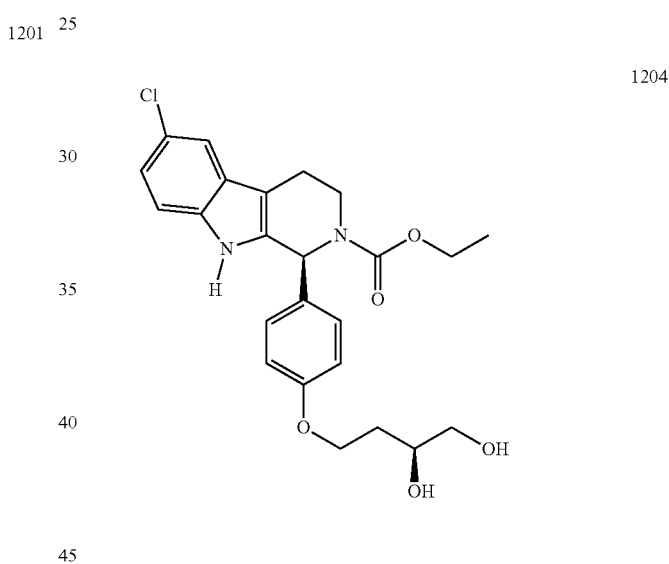
1205 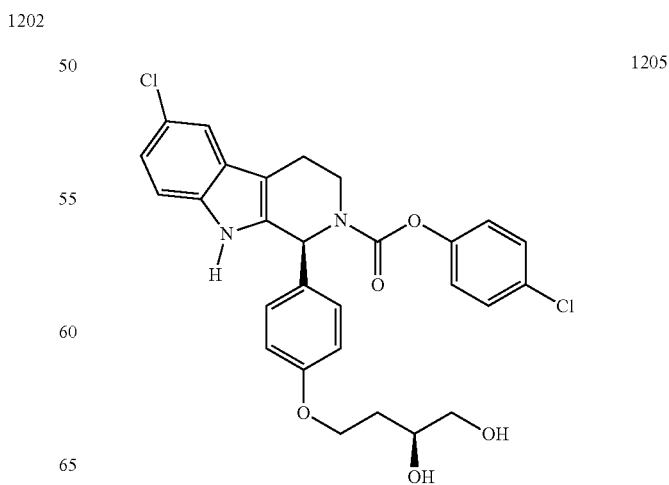

617
-continued
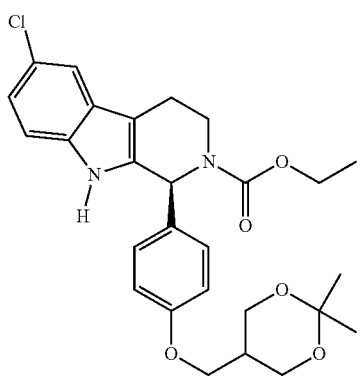
1206
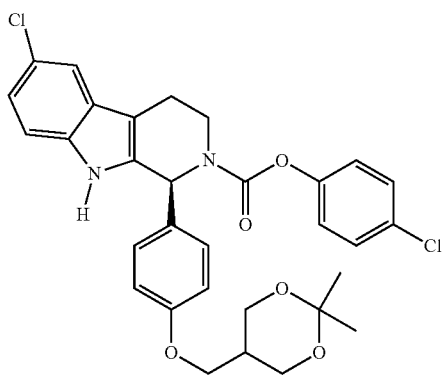
1207
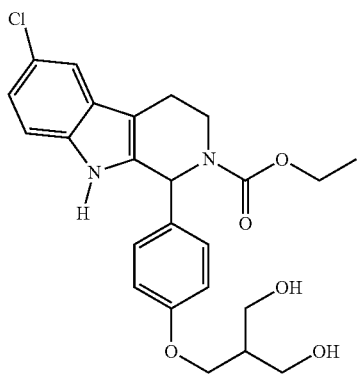
1208
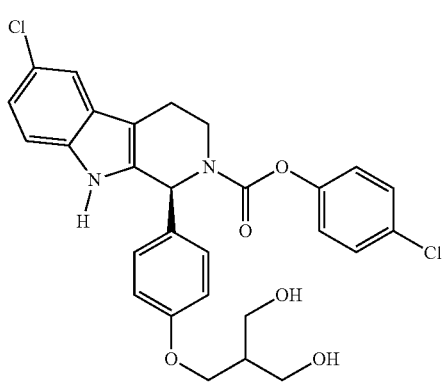
1209
618
-continued
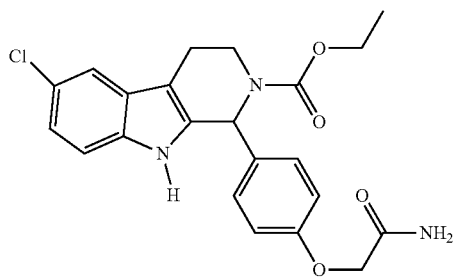
1210
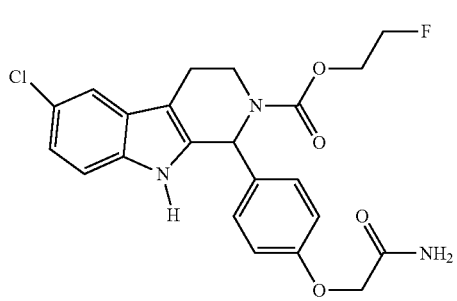
1211
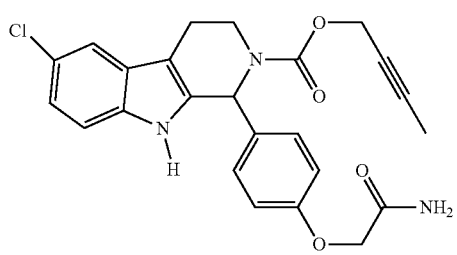
1212
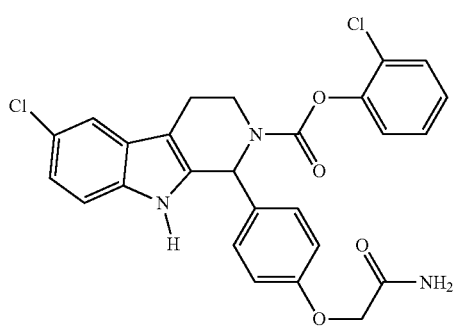
1213
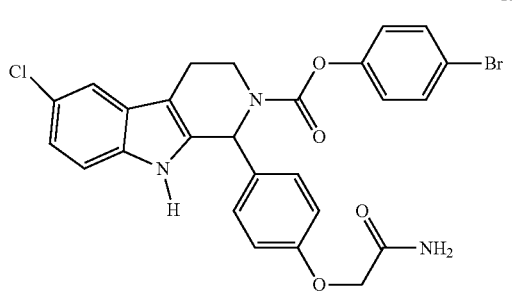
1214

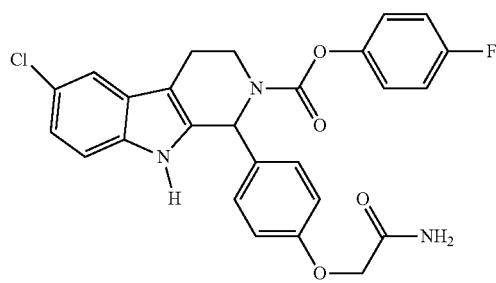
1215
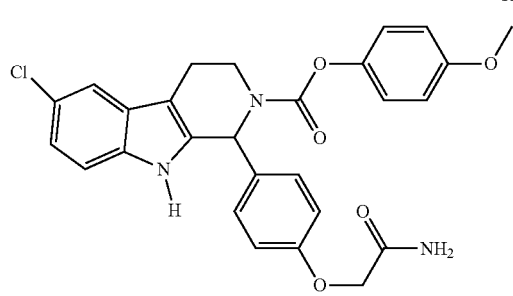
1216
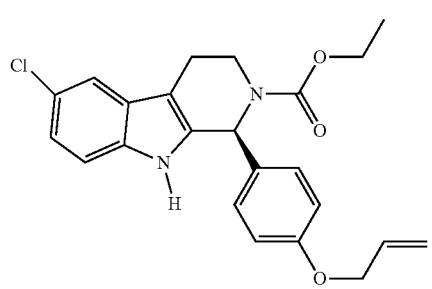
1217
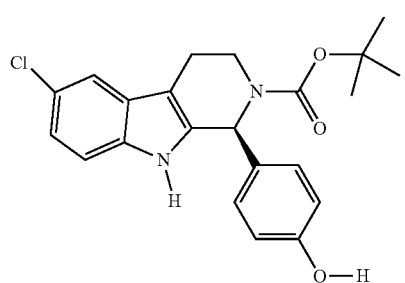
1219
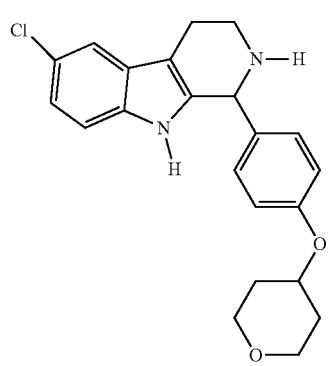
1220
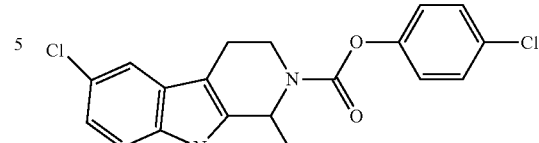
1225
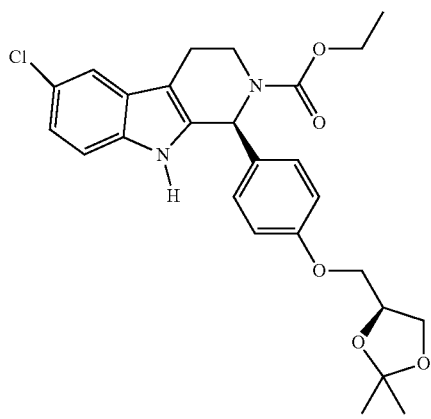
1226
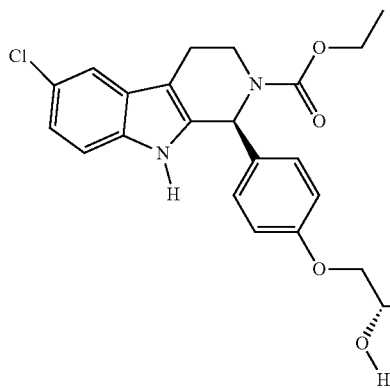
1222

1227
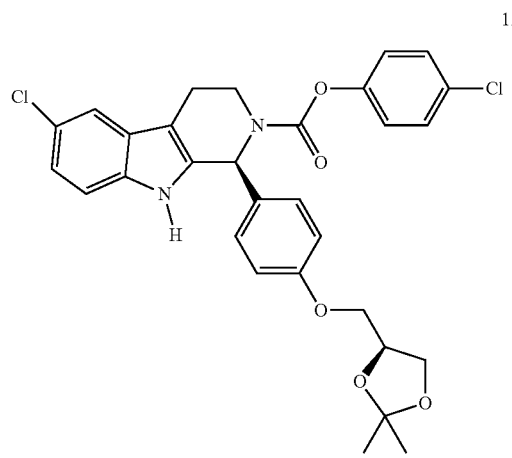
1228
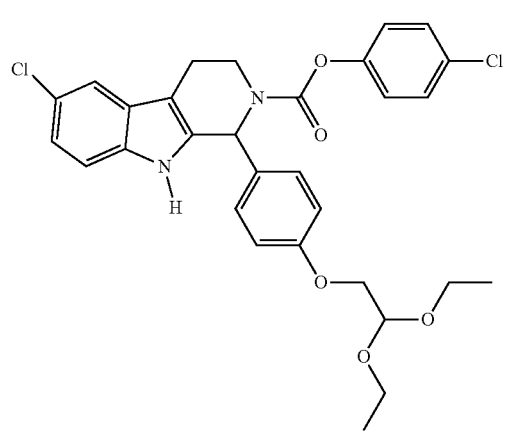
1229
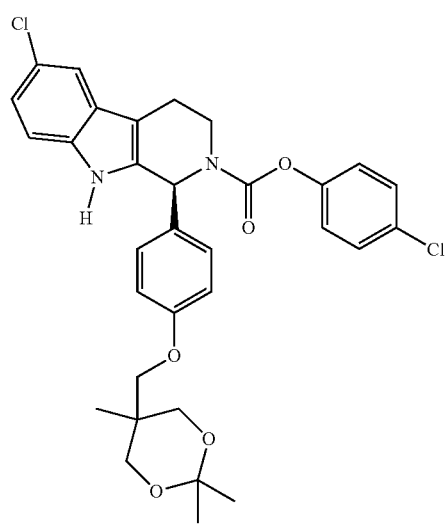
1230
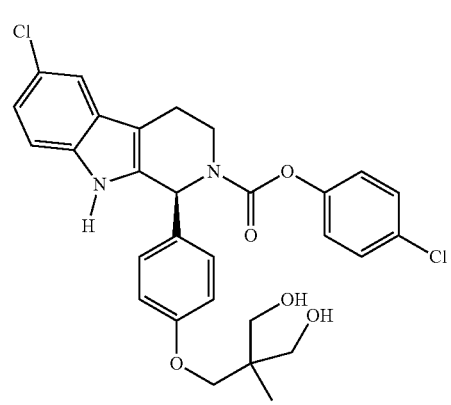
1231
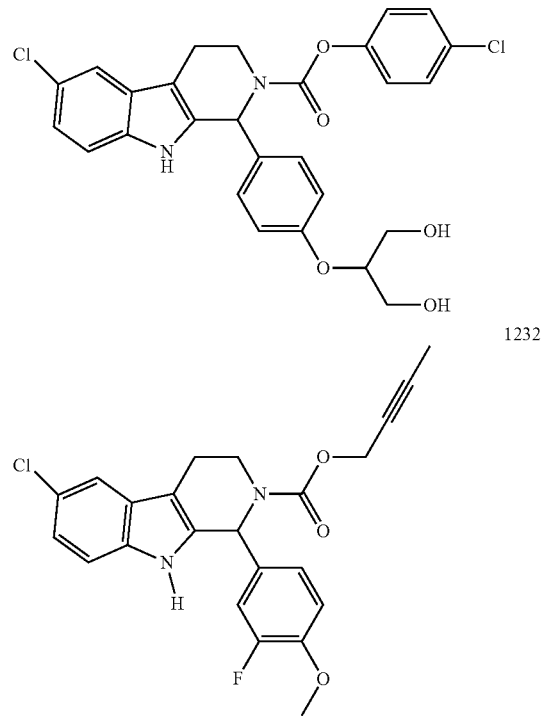
1232
1233
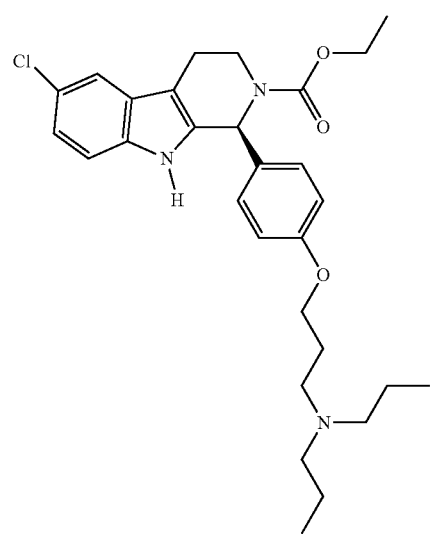

-continued
1234
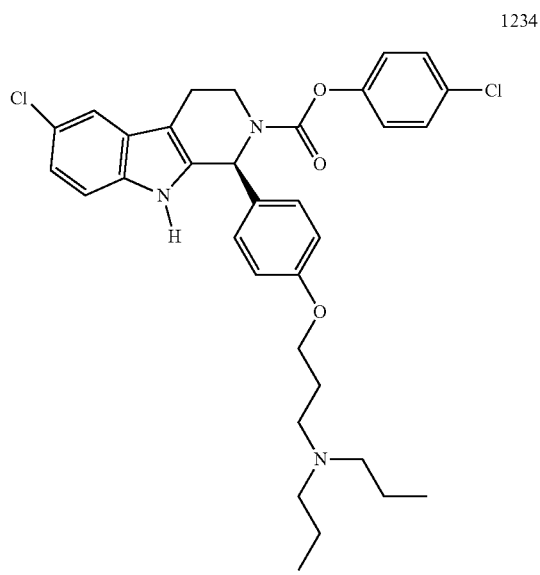
1235
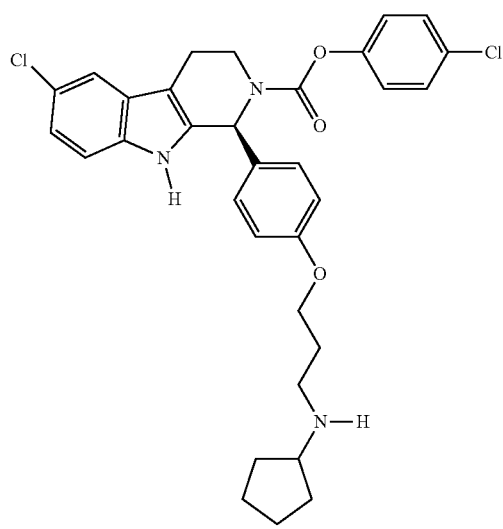
1236
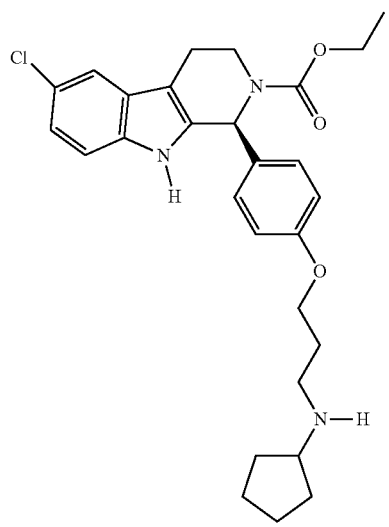
-continued
1237
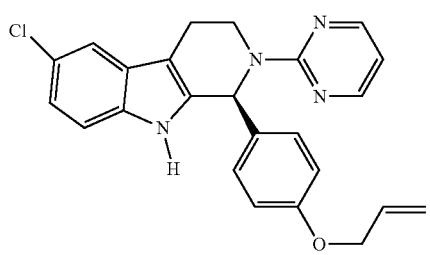
1238
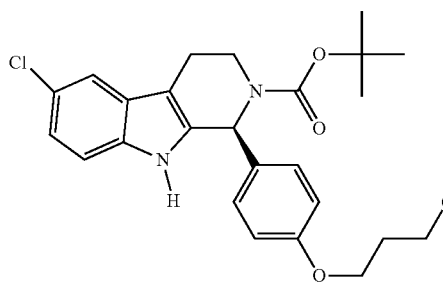
1239
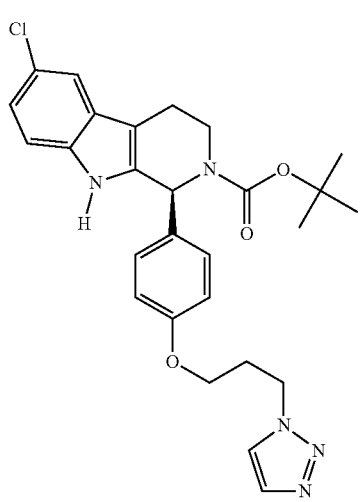
1240
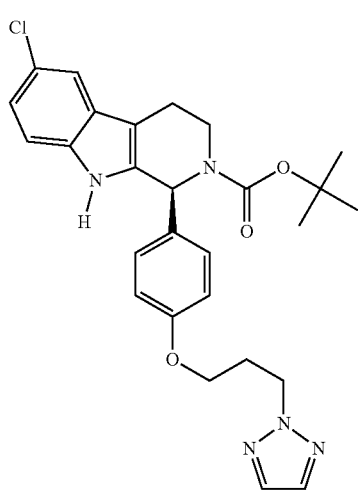

625
-continued
1241
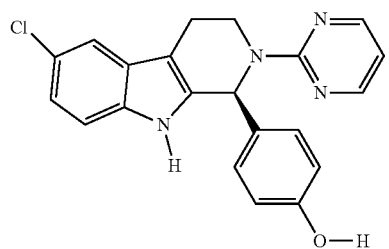
1242
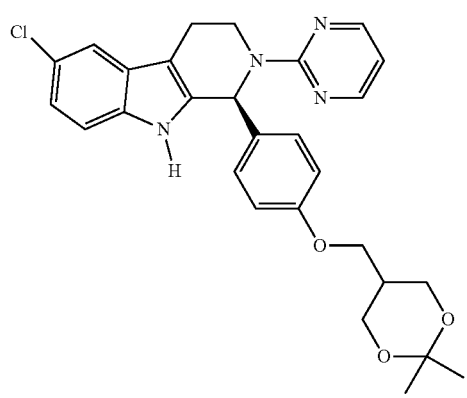
1243
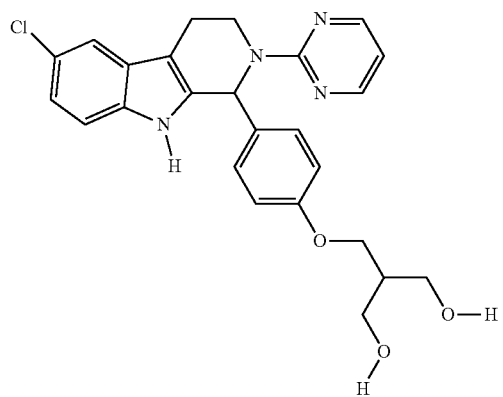
1244
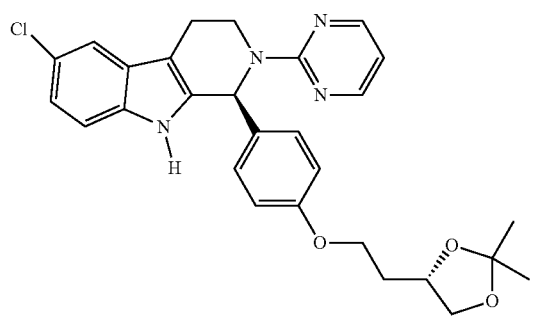
626
-continued
1245
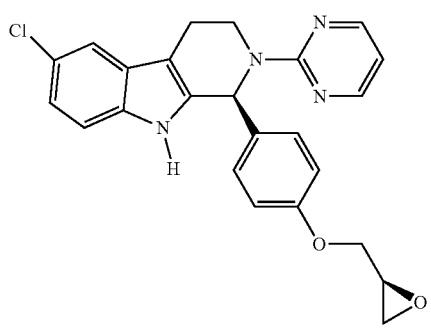
1246
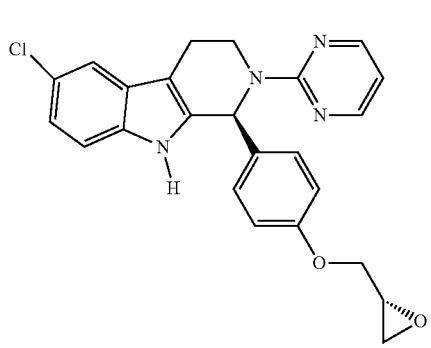
1247
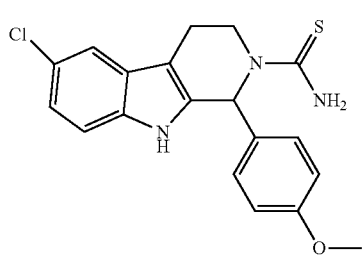
1248
1249
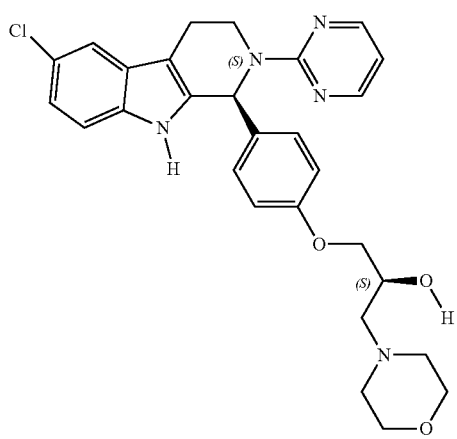

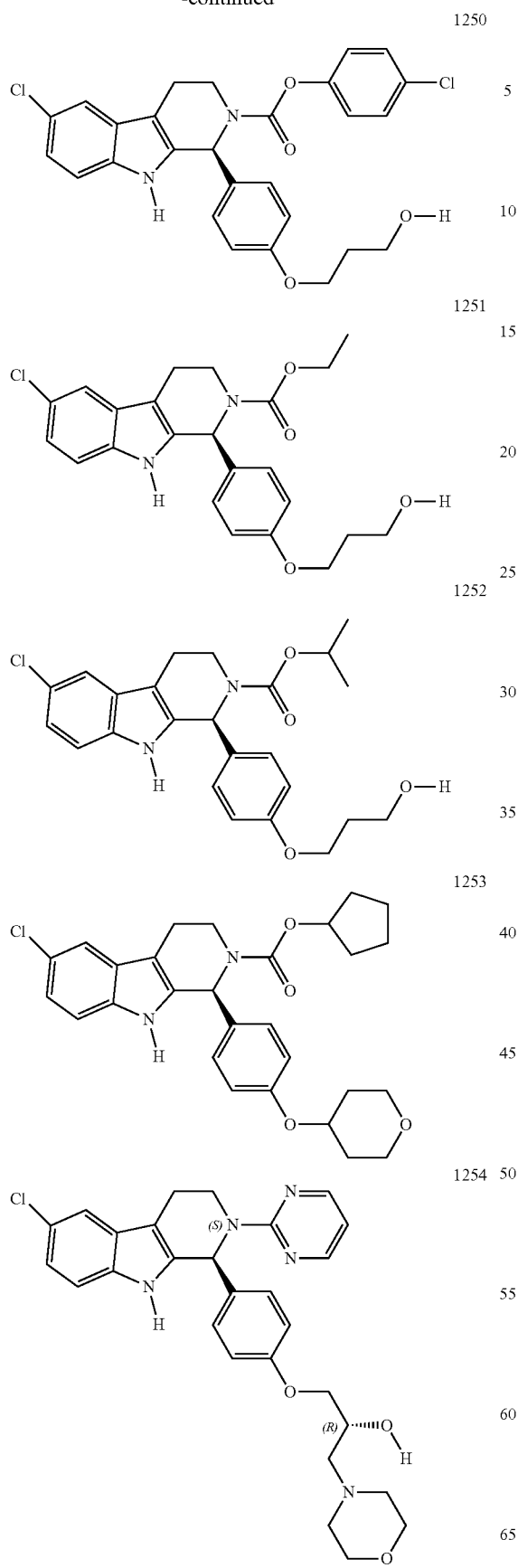
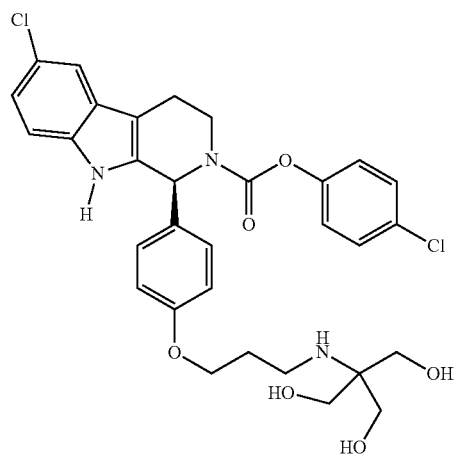
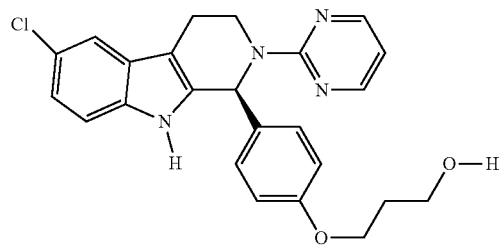
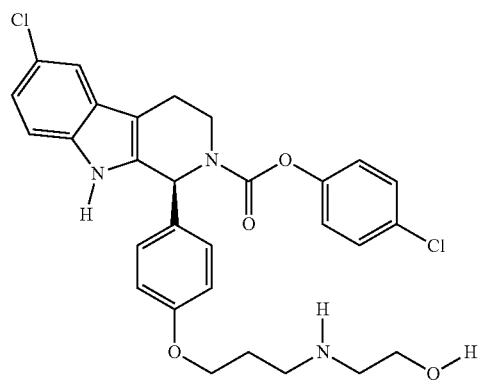
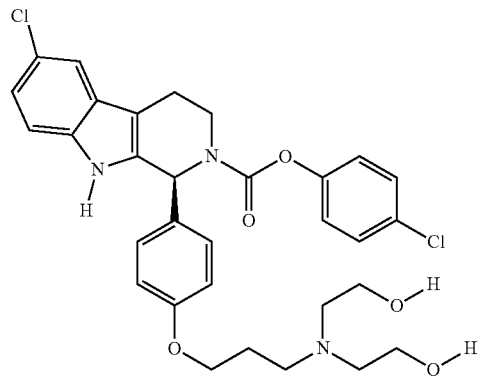

-continued
1259
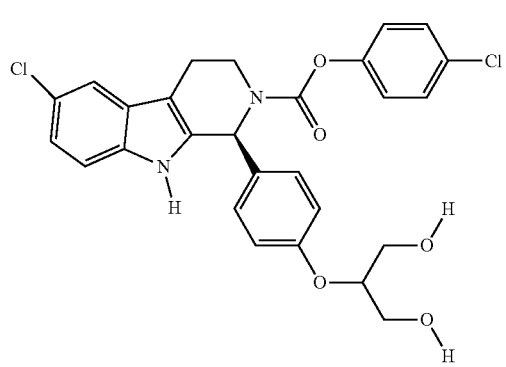
1260
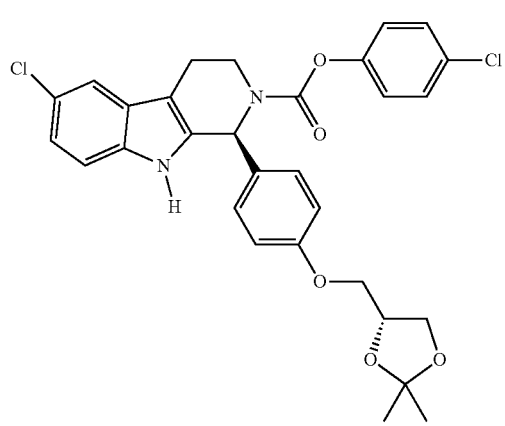
1261
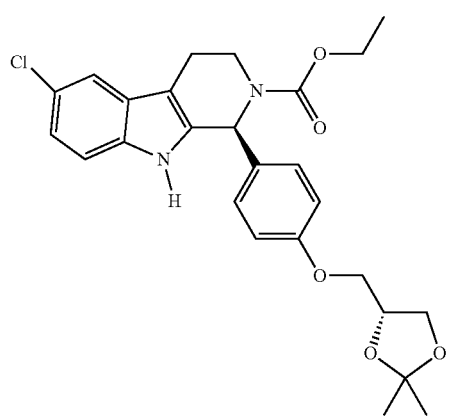
1262
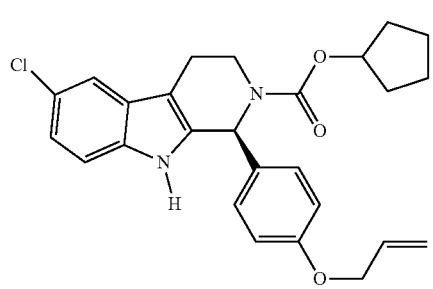
-continued
1263
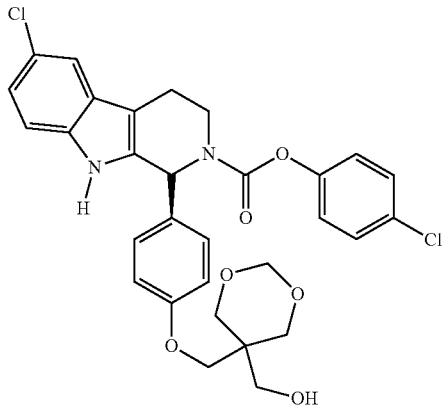
1264
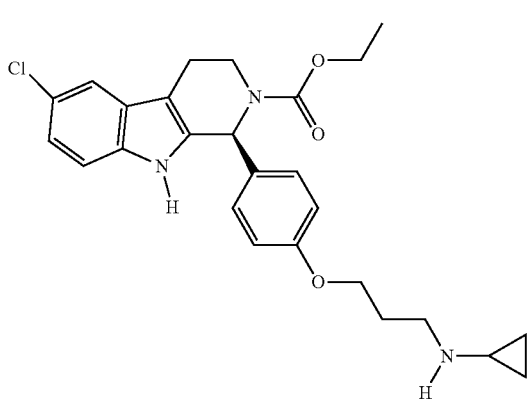
1265
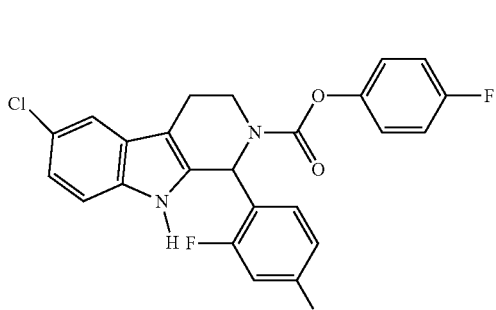
1266
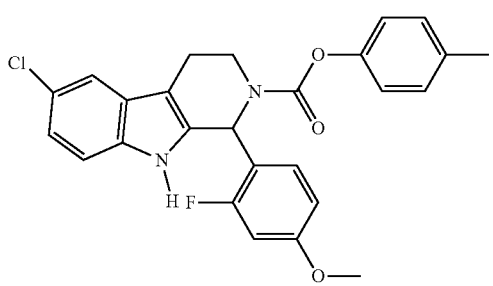

631
-continued
1267
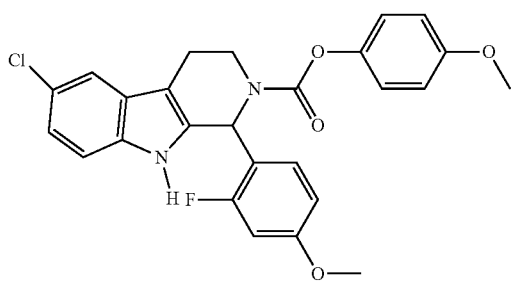
1268
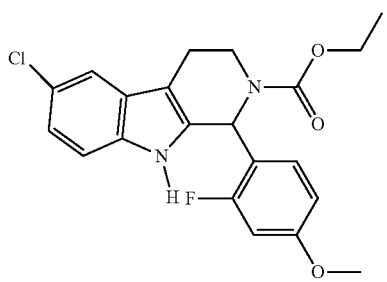
1269
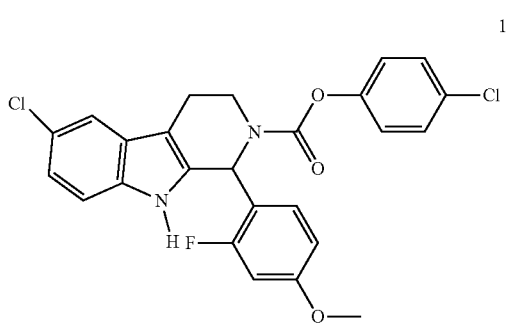
1270
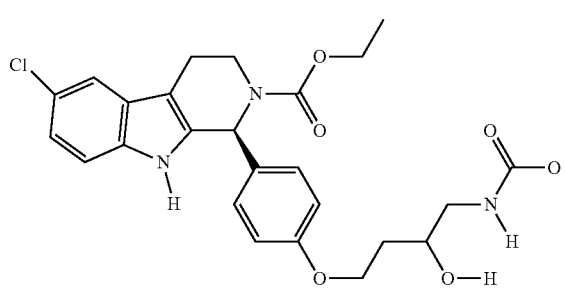
1271
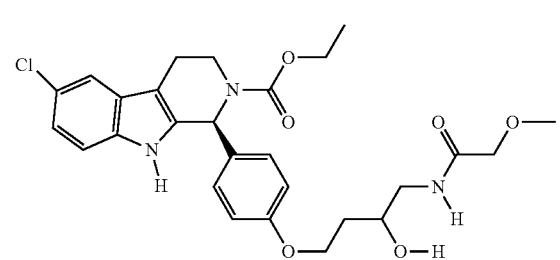
632
-continued
1272
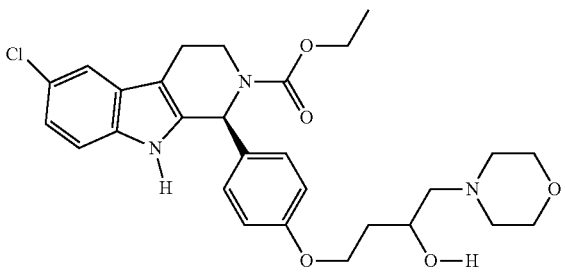
1273
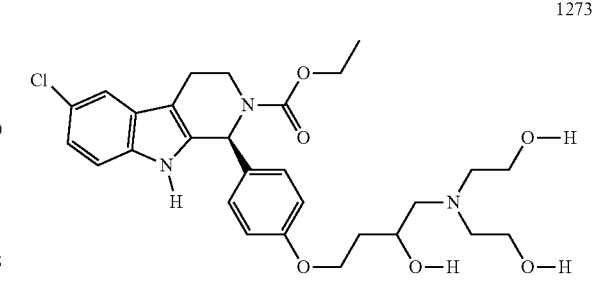
1274
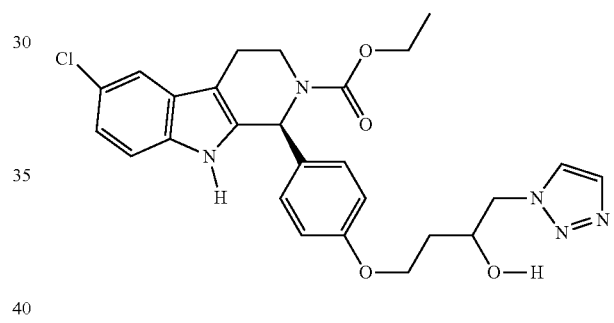
1275
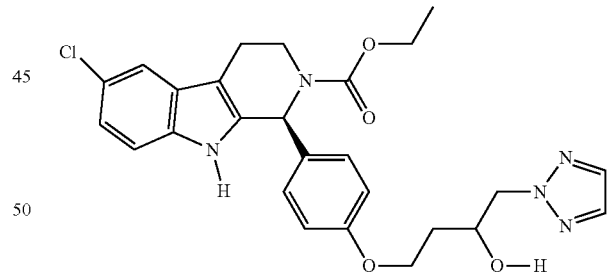
1276
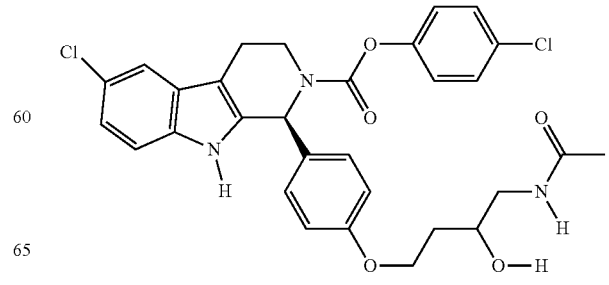

1277
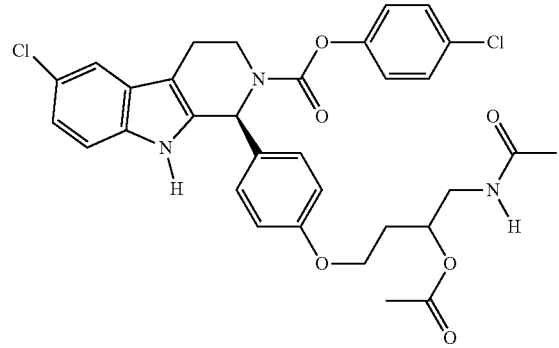
1278
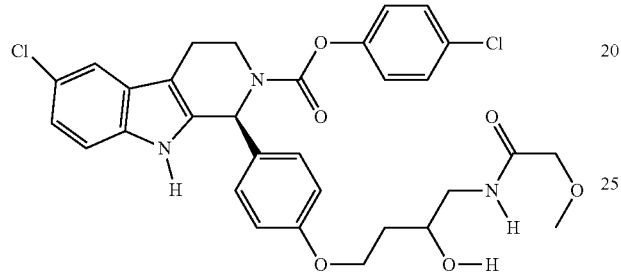
1279
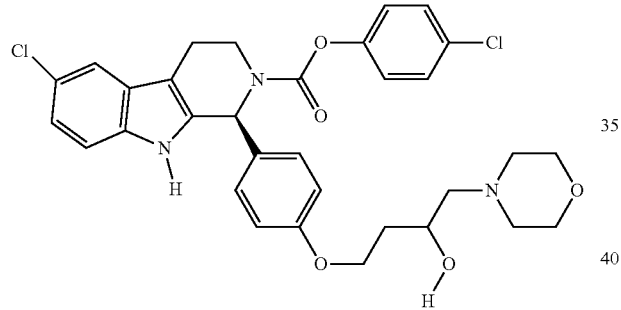
1280
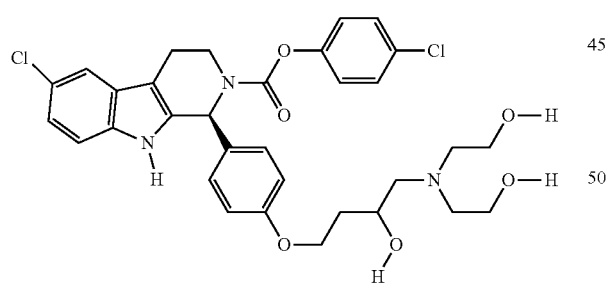
1281
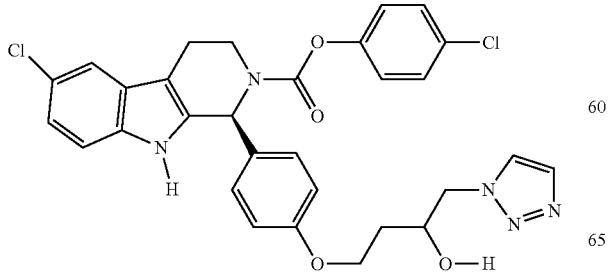
1282
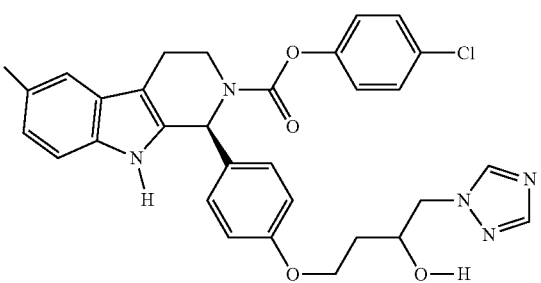
1283
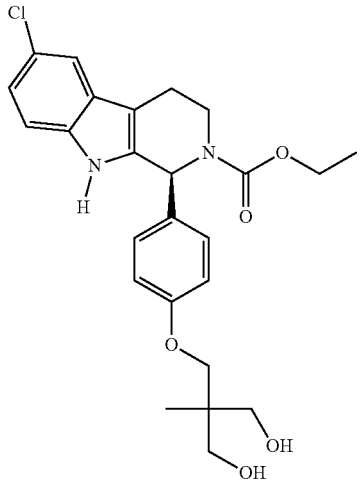
1284
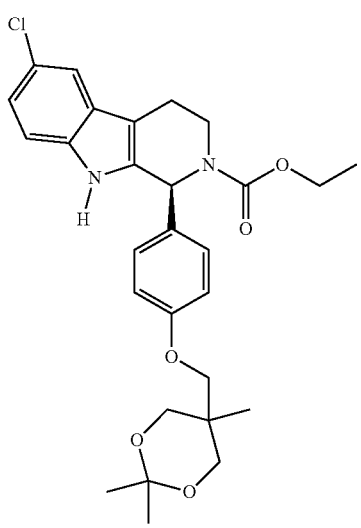
1285
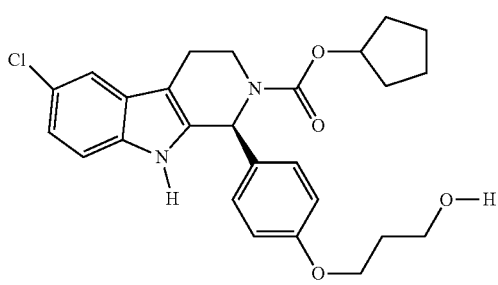

1286
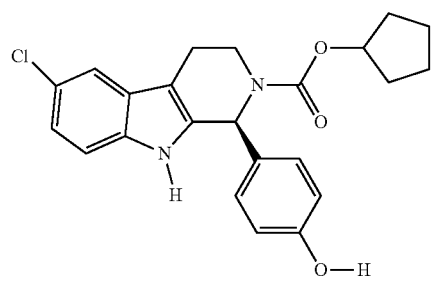
1287
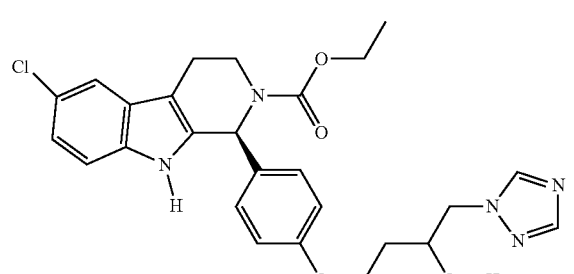
1288
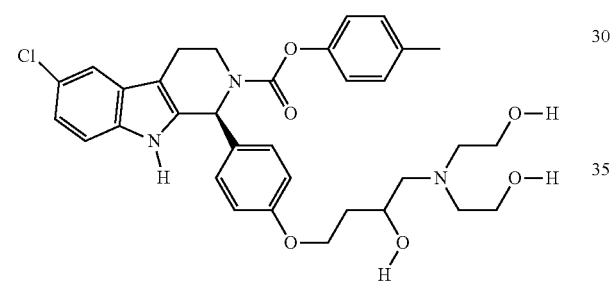
1289
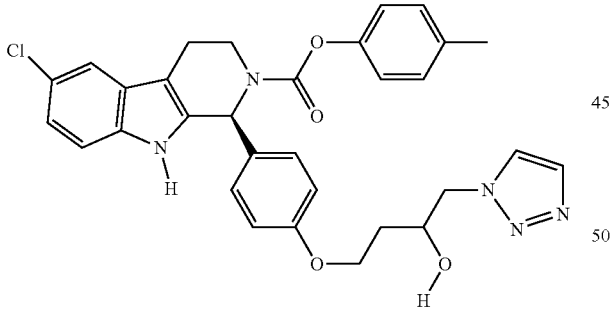
1290
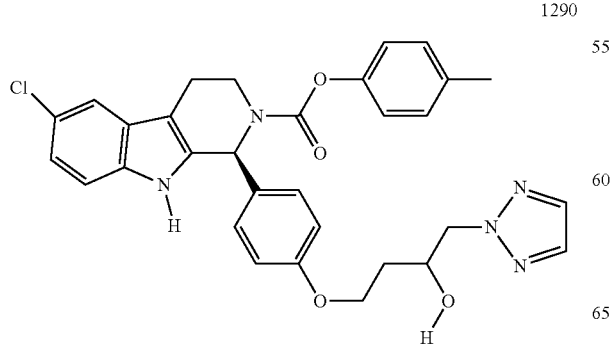
1291
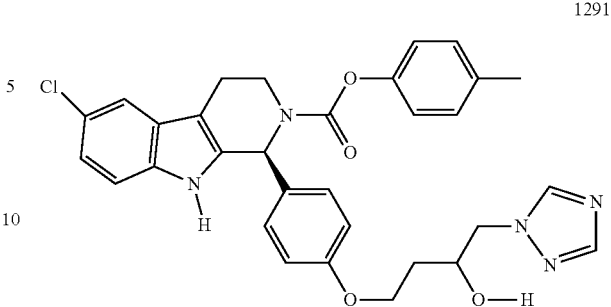
1292
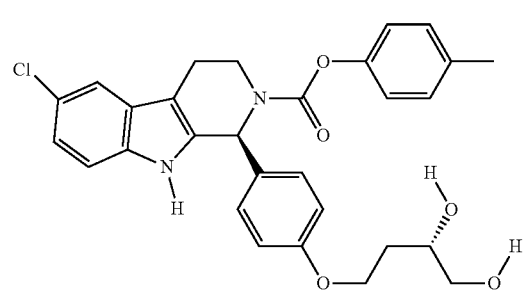
1293
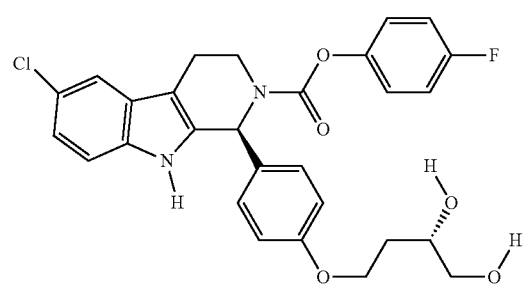
1294
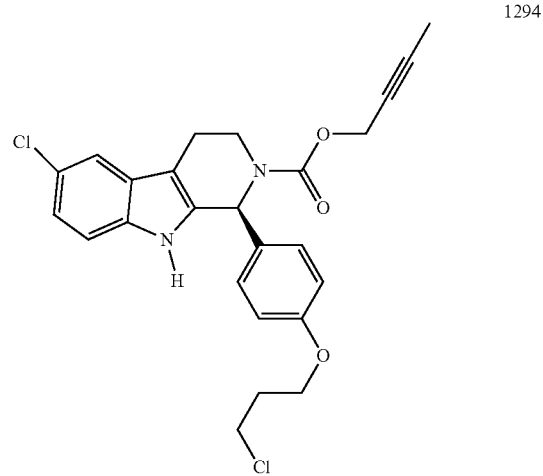

1295
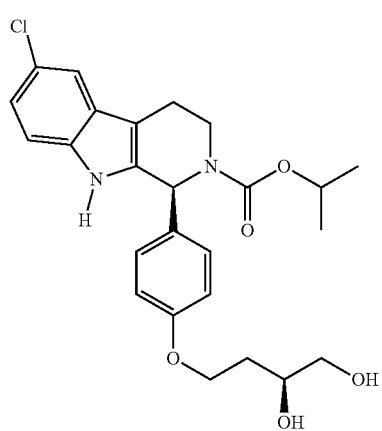
1296
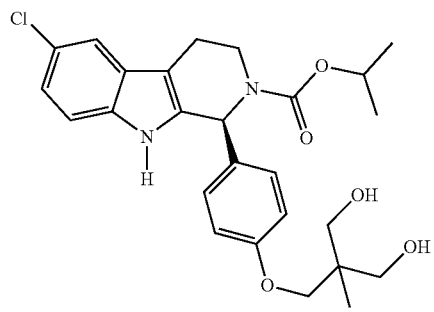
1297
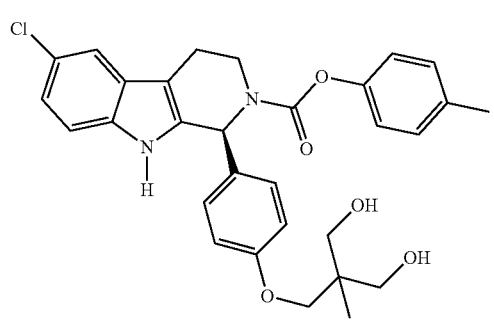
1298
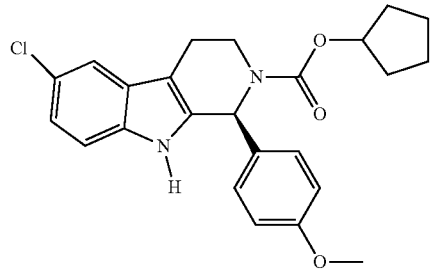
1299
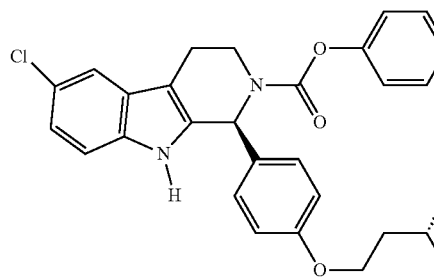
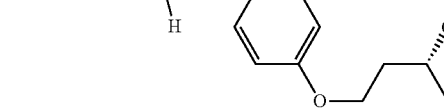
1300
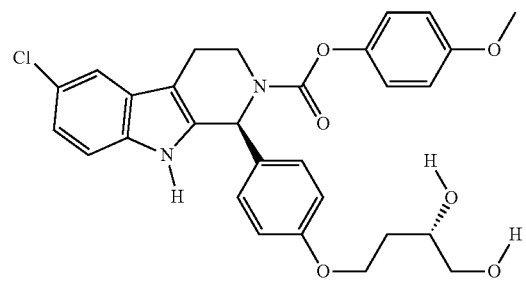
1301
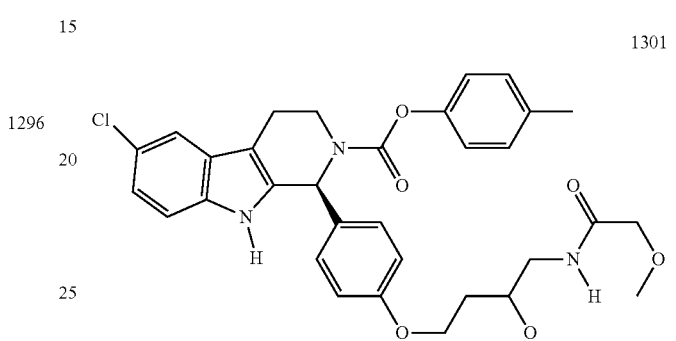
1302
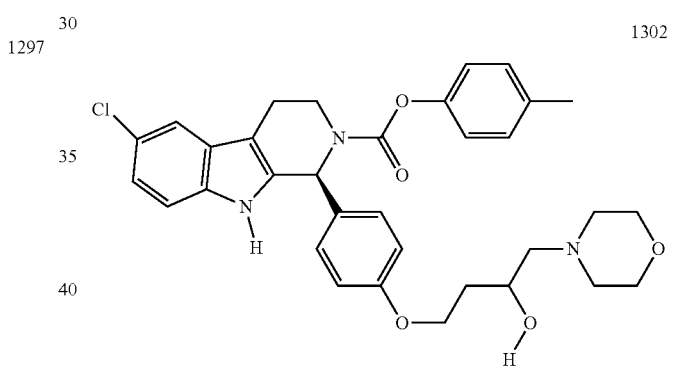
1303
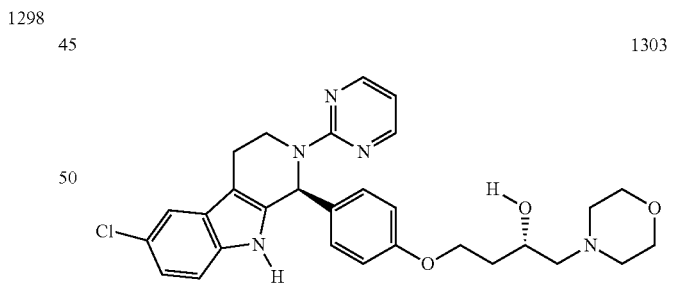
1304
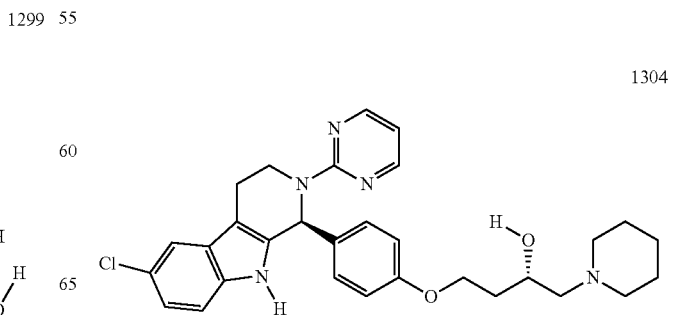

1305
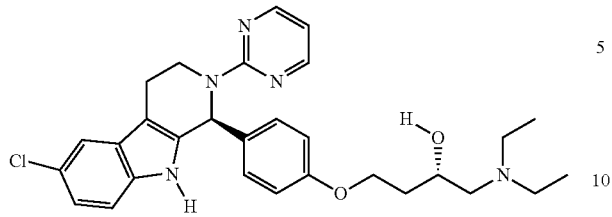
1306
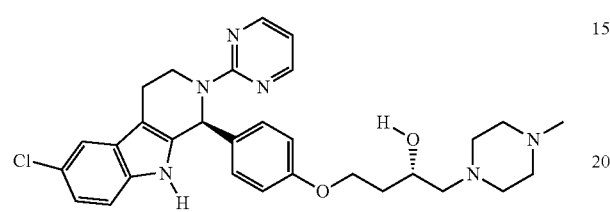
1307
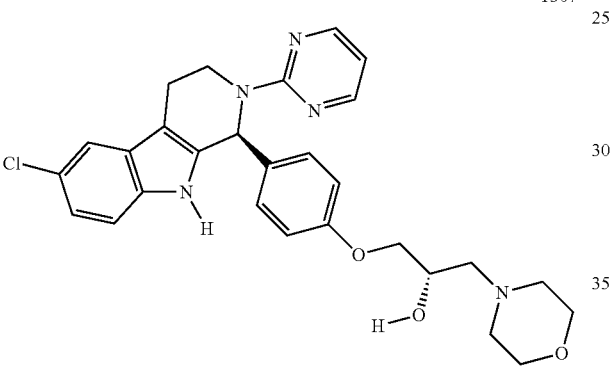
1308
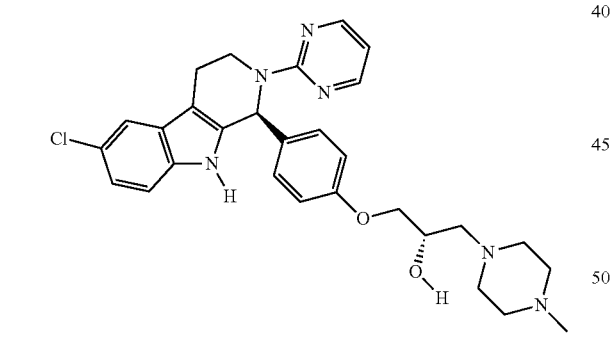
1309
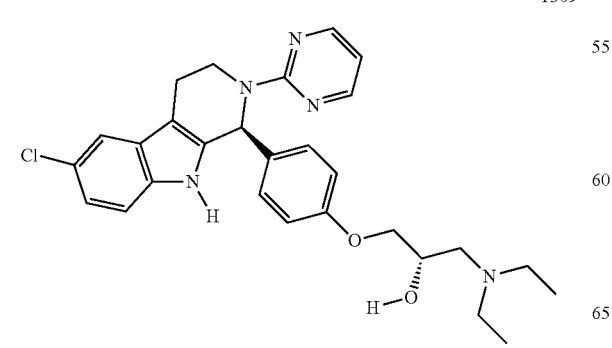
1310
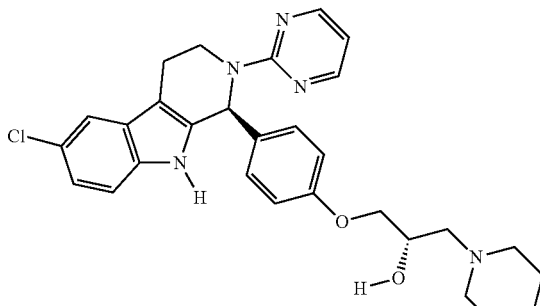
1311
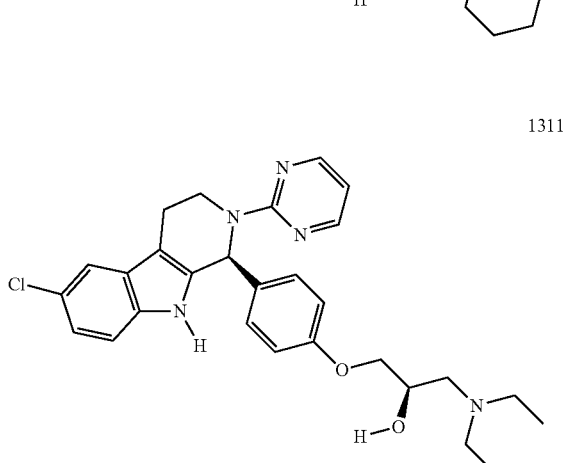
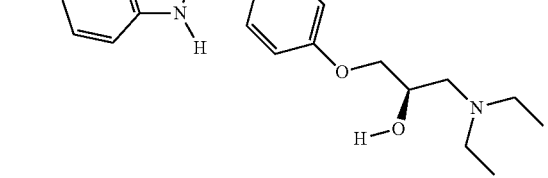
1312
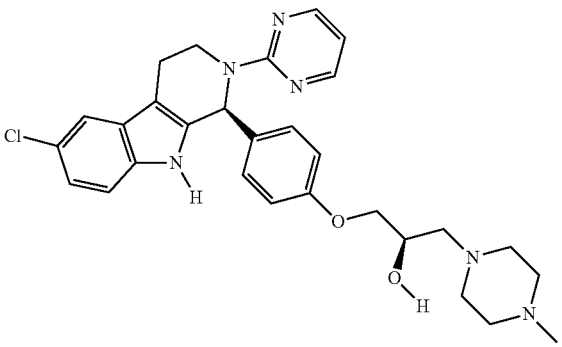
1313
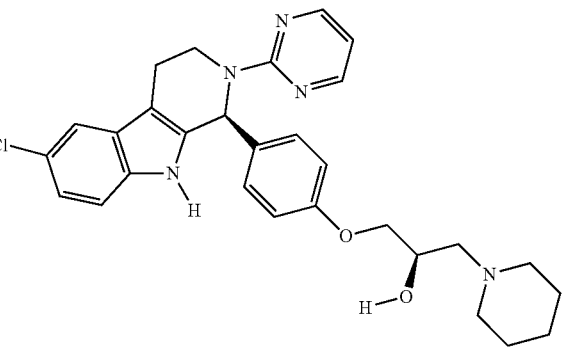

1314
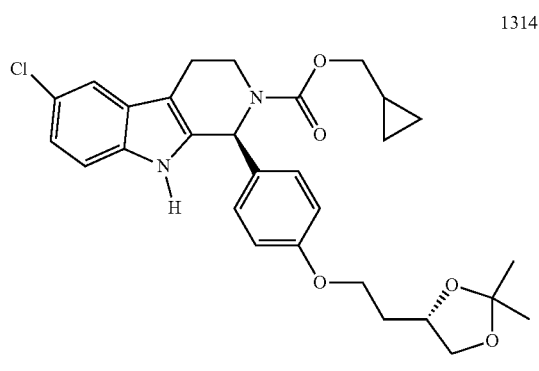
1315
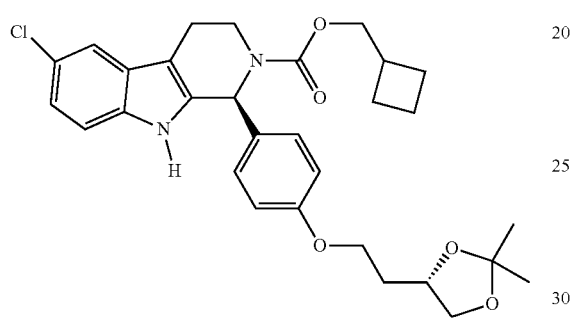
1316
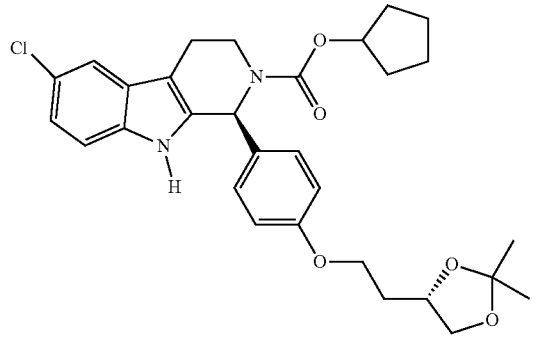
1317
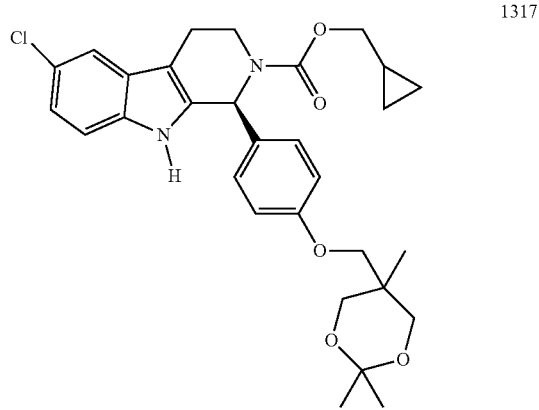
1318
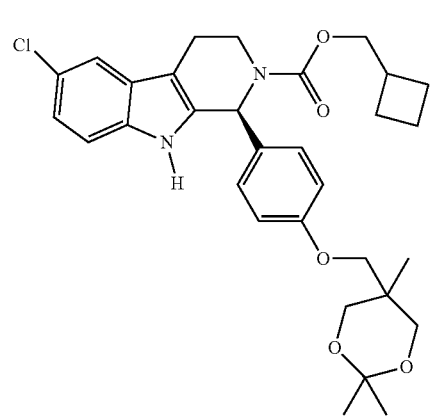
1319
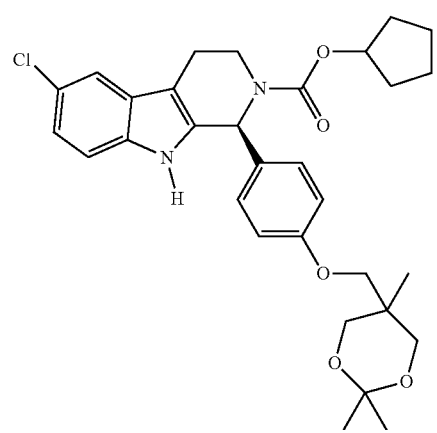
1320
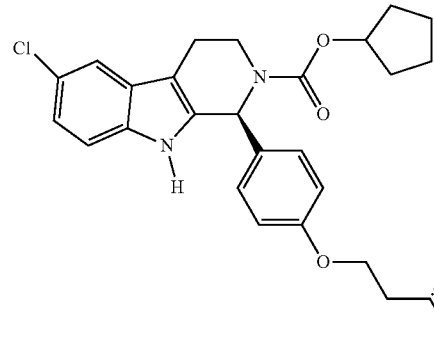
1321
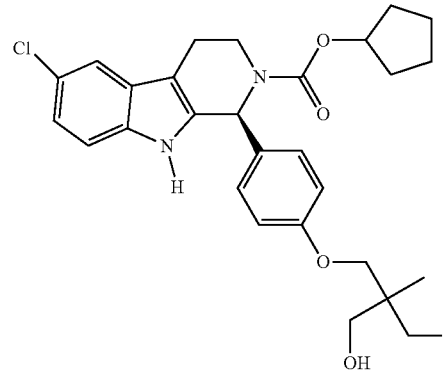

643
-continued
1322
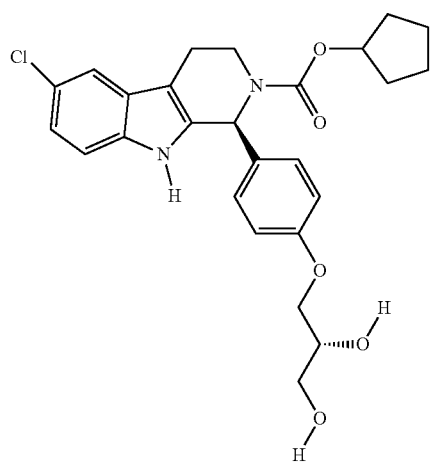
1323
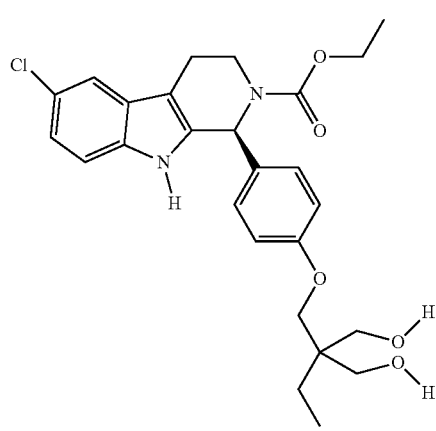
1324
644
-continued
1325
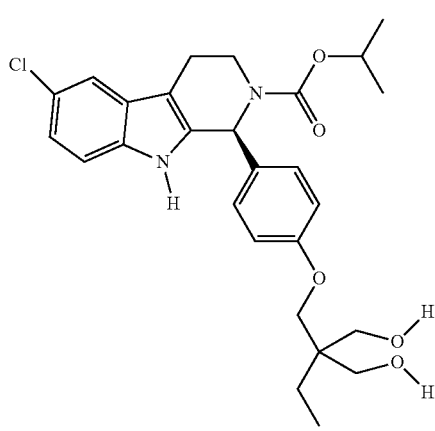
1326
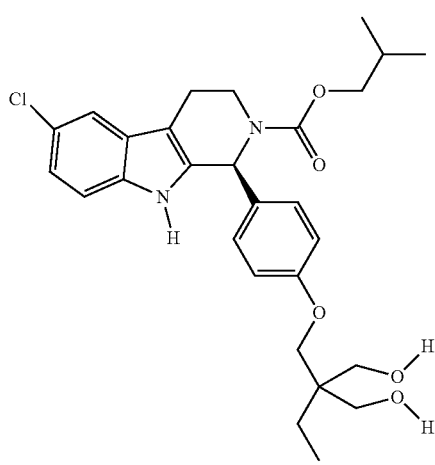
1327
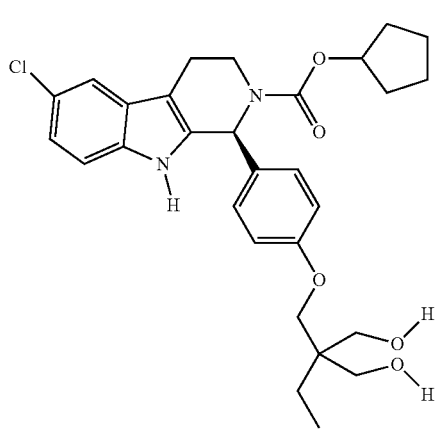

1328
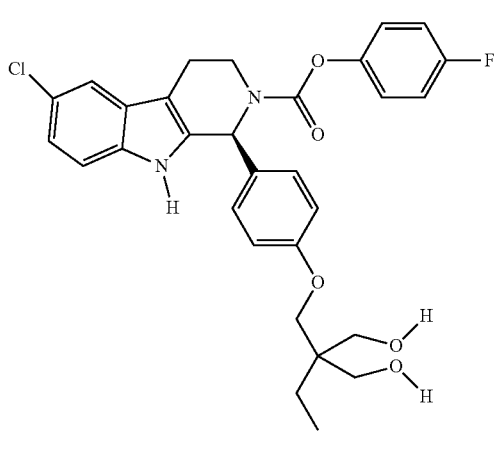
1329
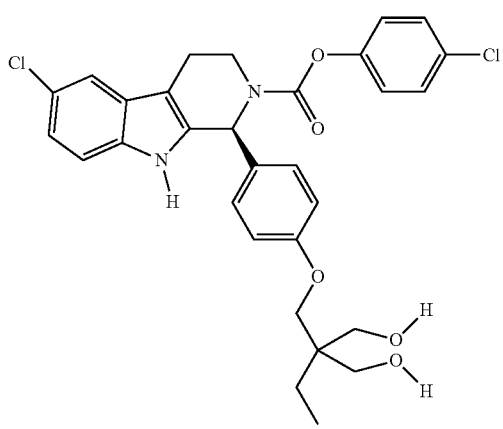
1330
1331
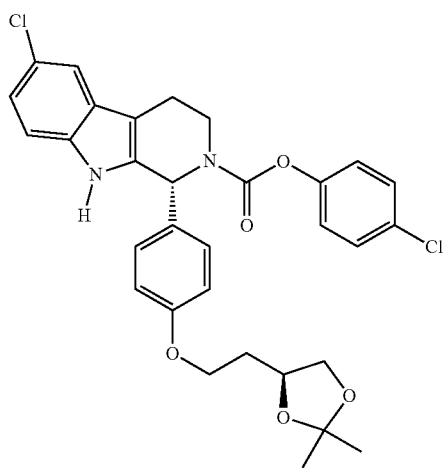
1332
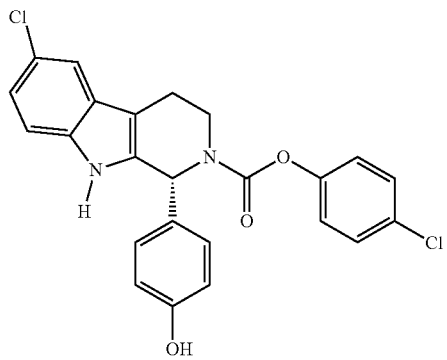
1333
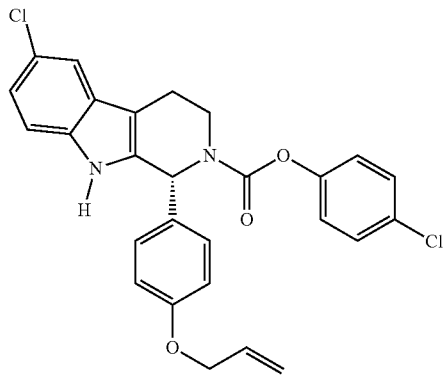
1334
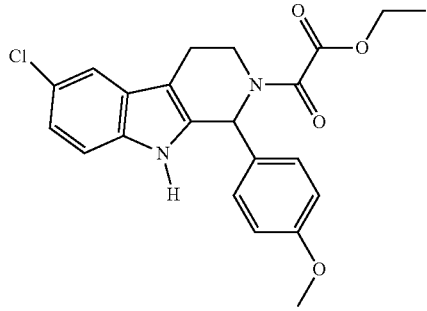

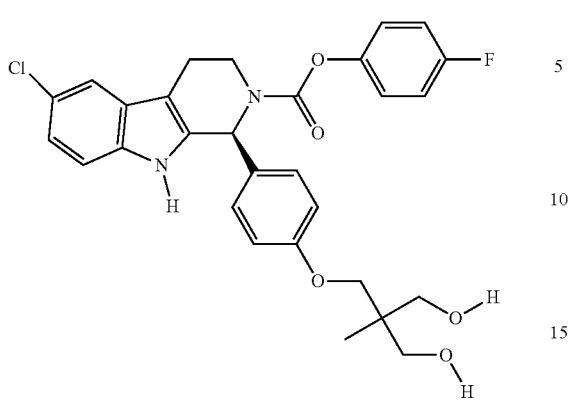
1335
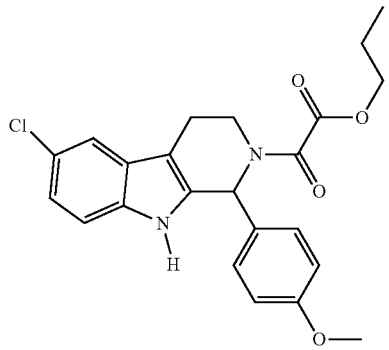
1339
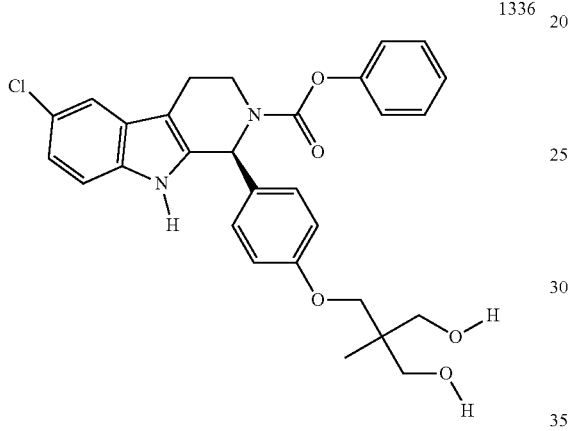
1336
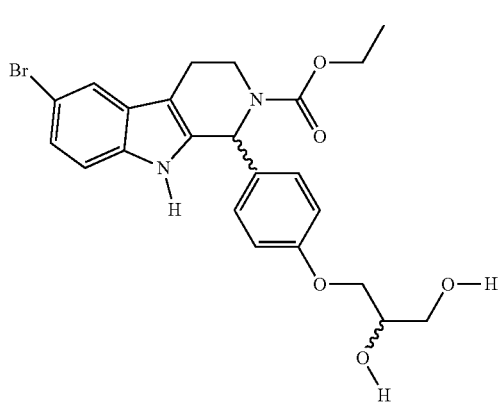
1340
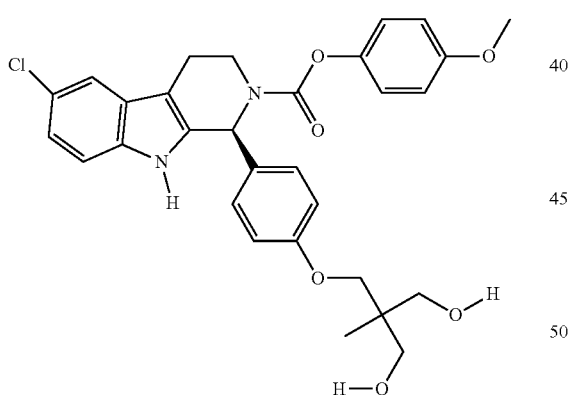
1337
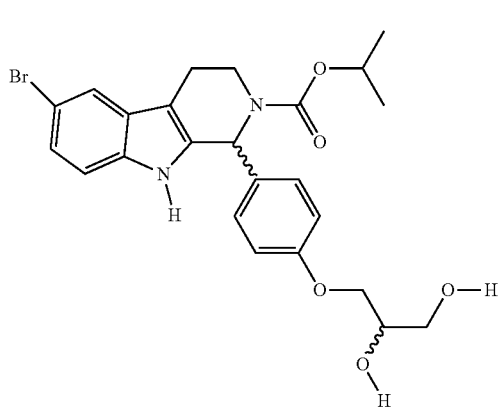
1341
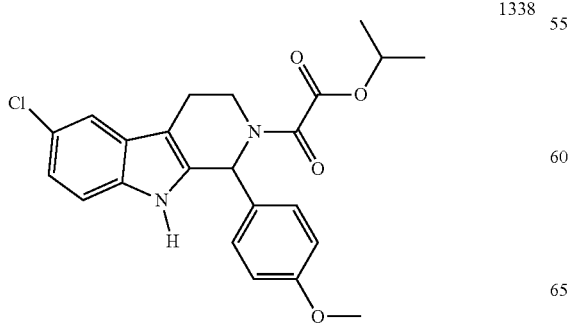
1338
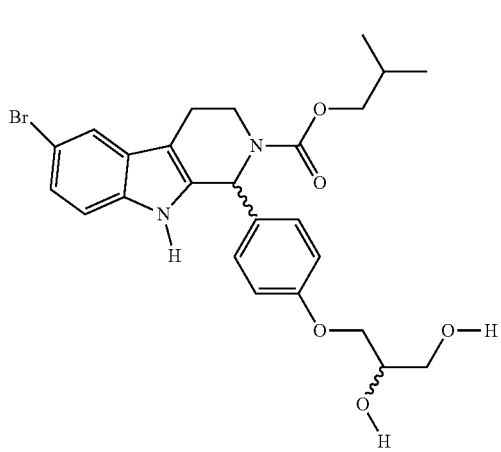
1342

649
-continued
1343
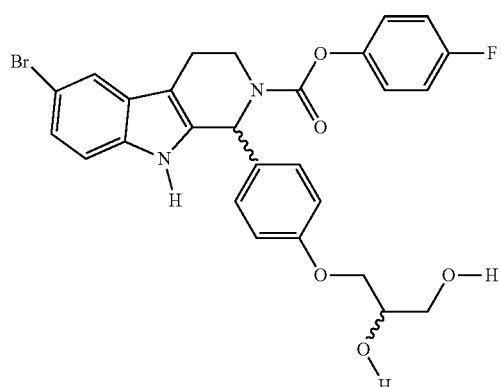
1344
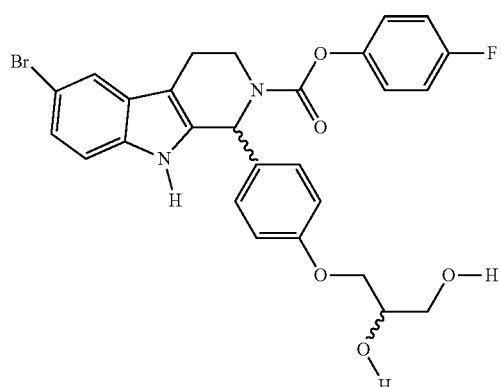
1345
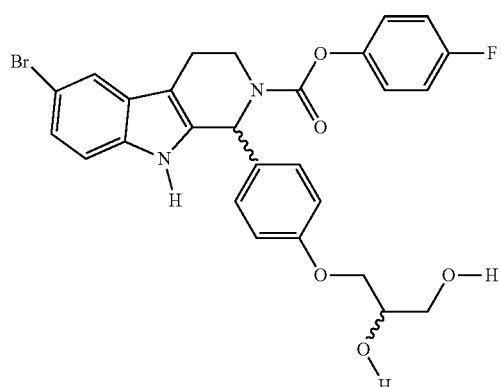
1346
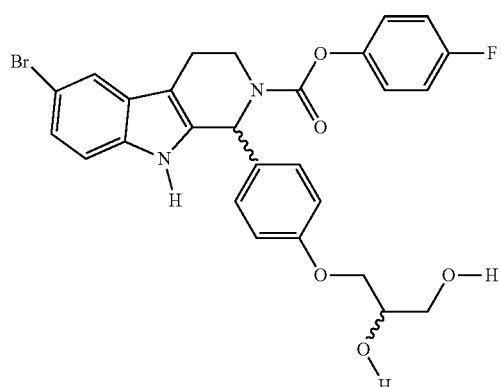
650
-continued
1347
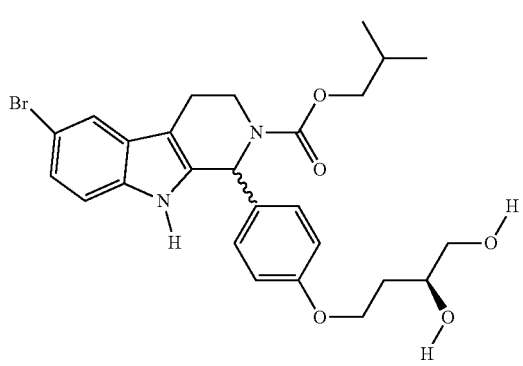
1348
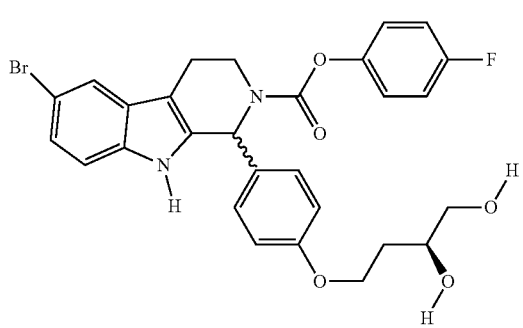
1349
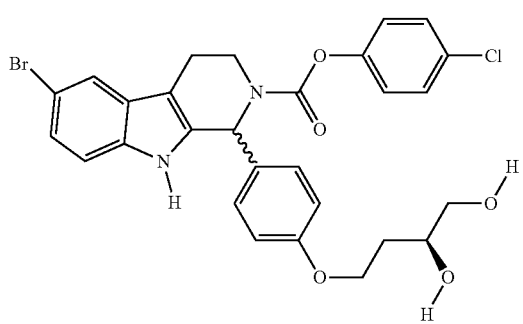
1350
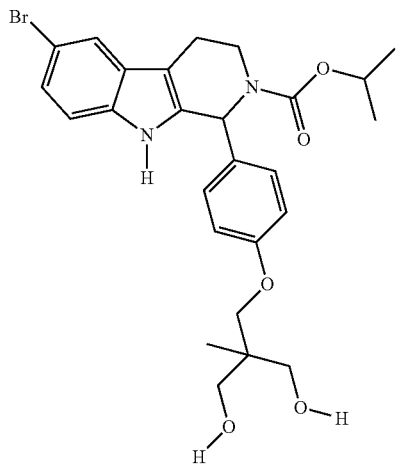

651
-continued
1351
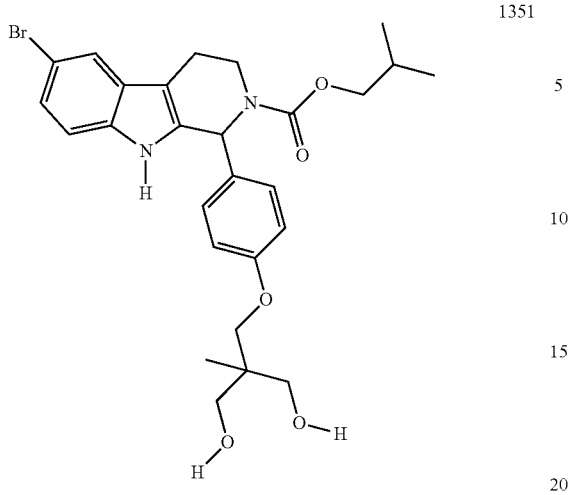
1352
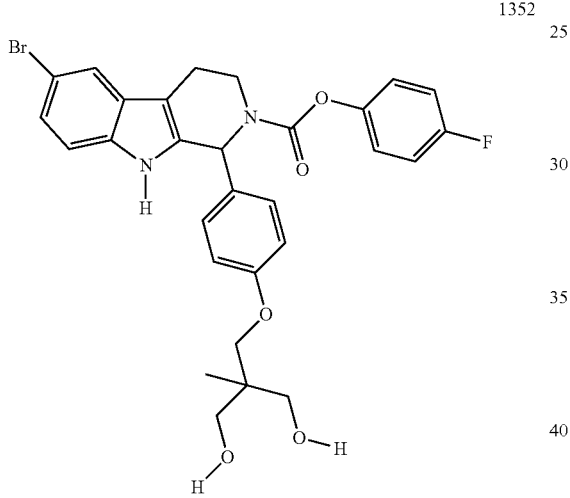
1353
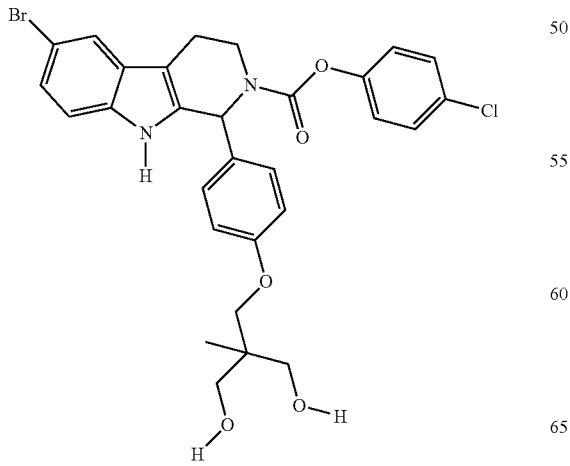
652
-continued
1354
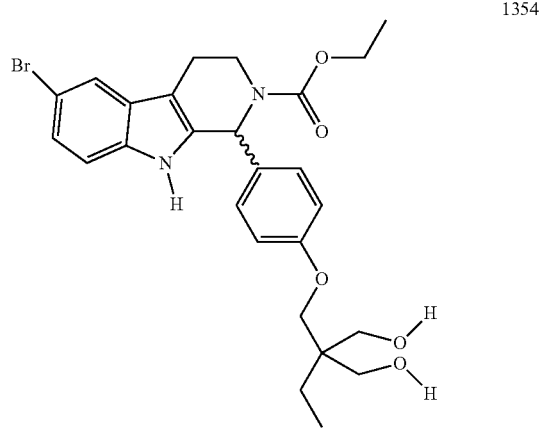
1355
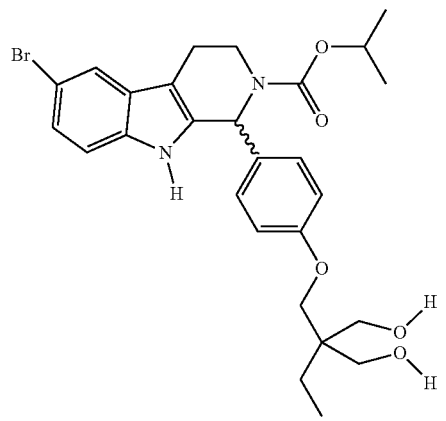
1356
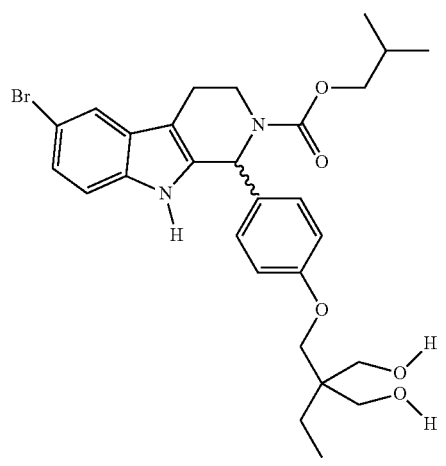

653
-continued
1357
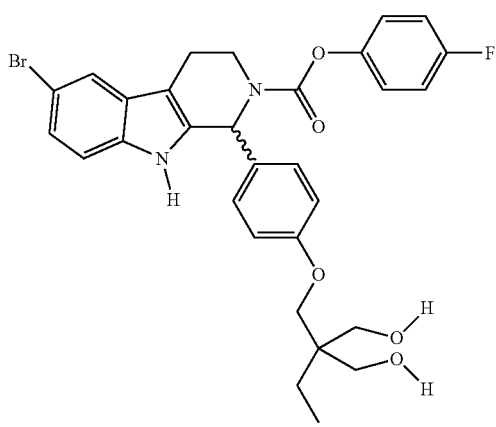
1358
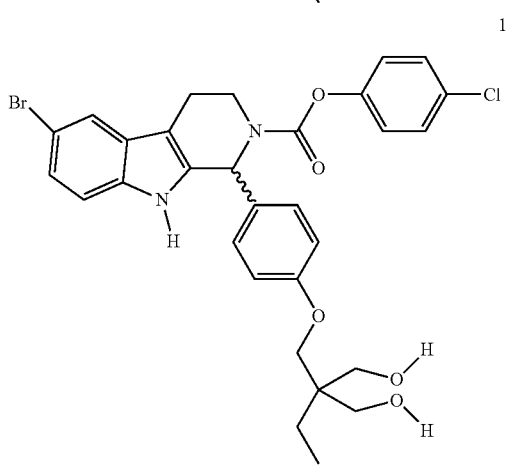
1359
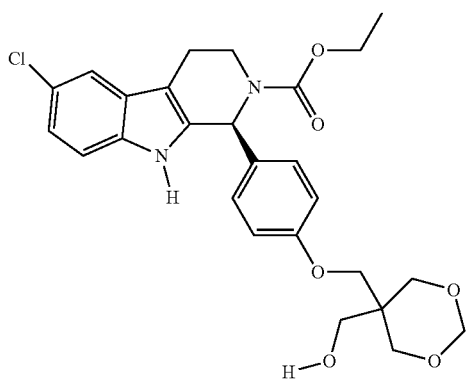
1360
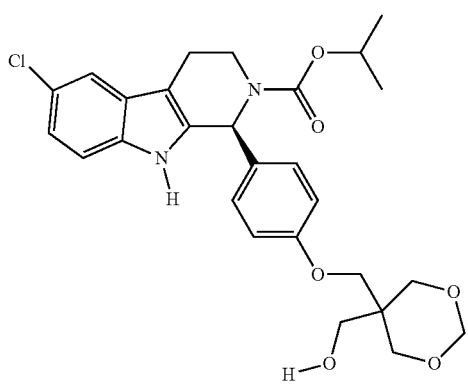
654
-continued
1361
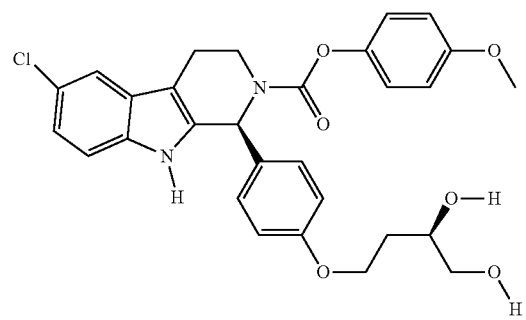
1362
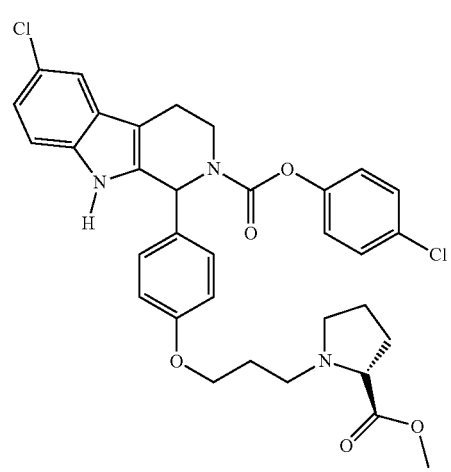
1363
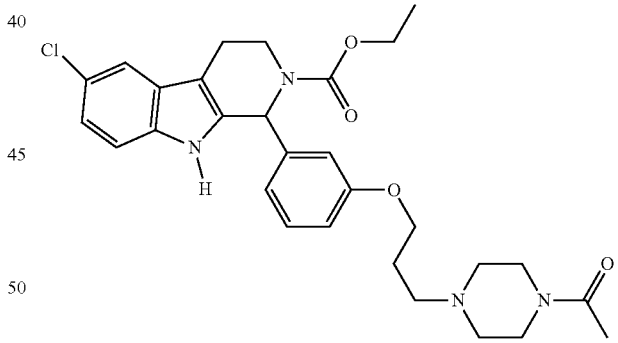
1364
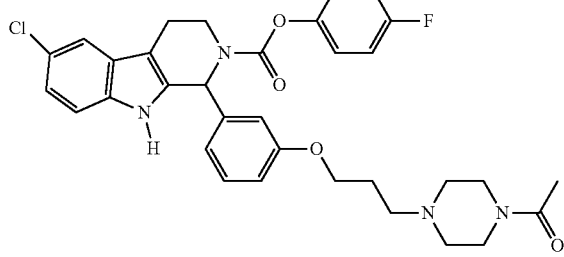

1365
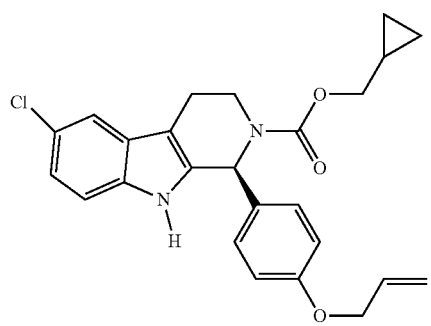
1366
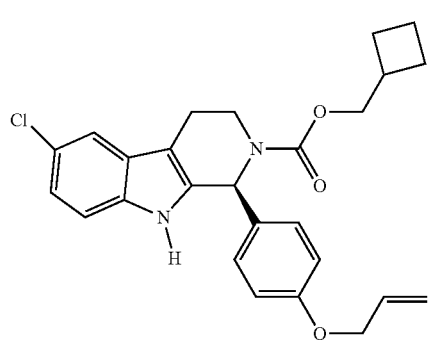
1367
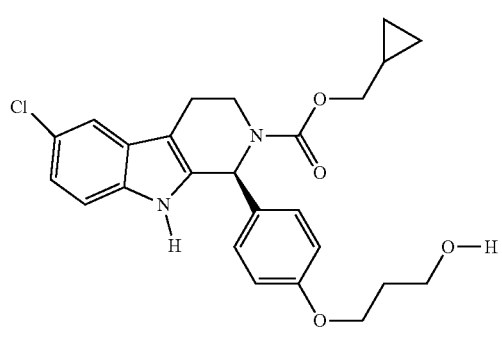
1368
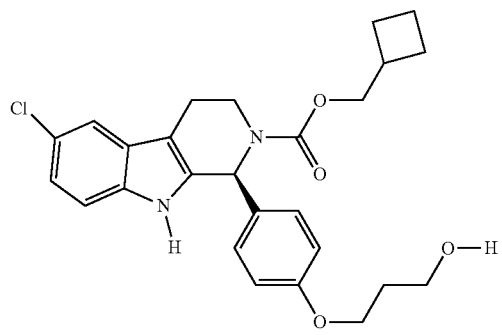
1369
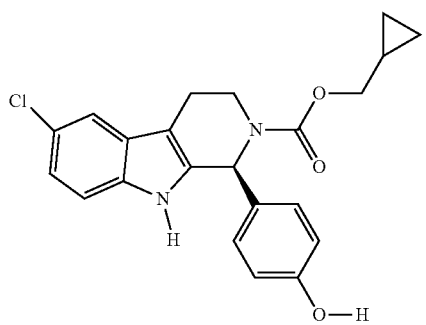
1370
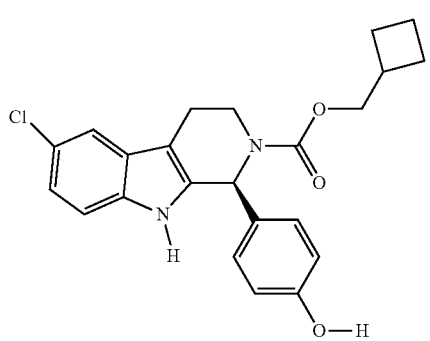
1371
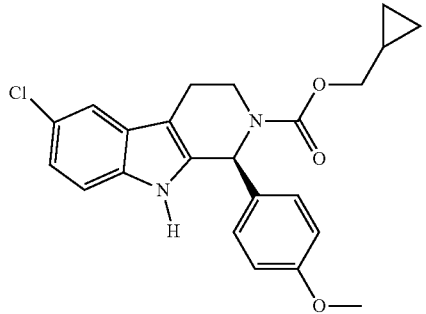
1372
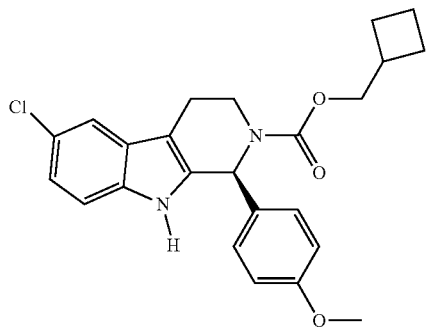

1373
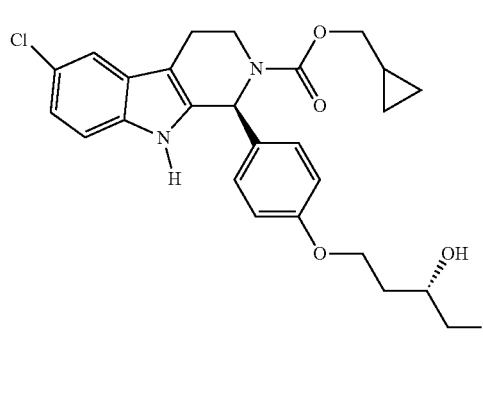
1374
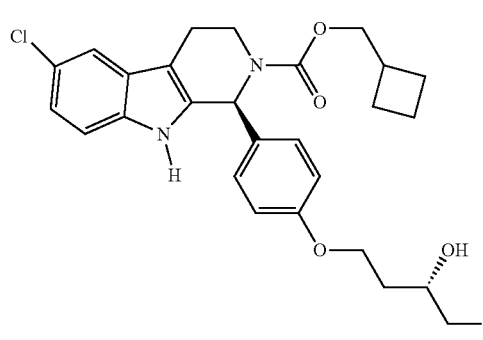
1375
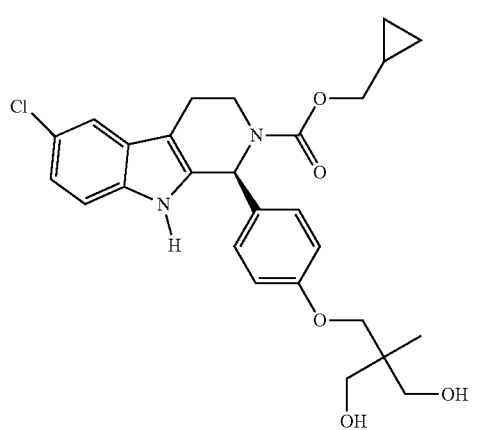
1376
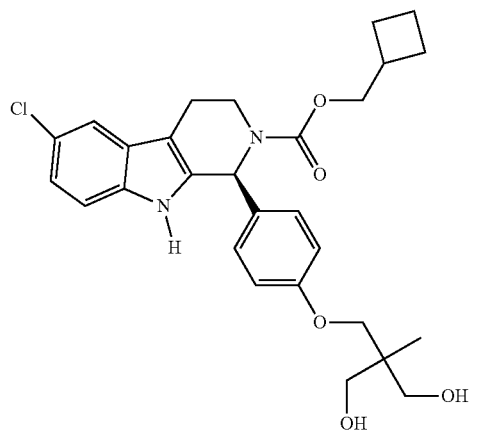
1377
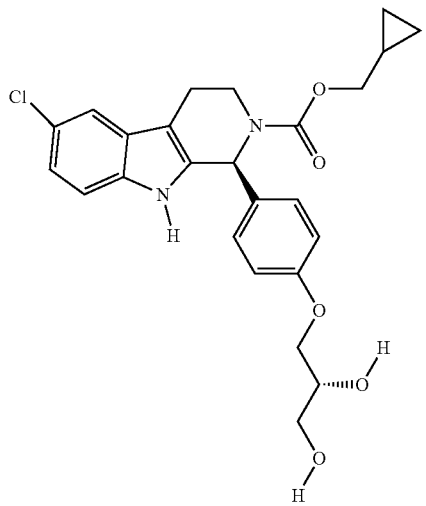
1378
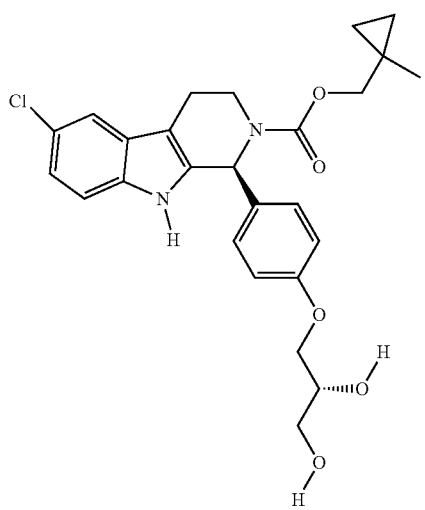
1379
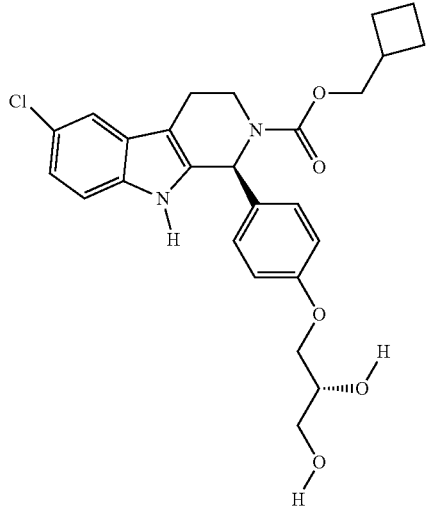

1380
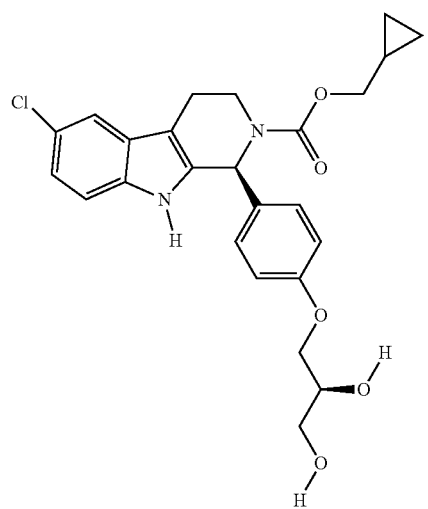
1381
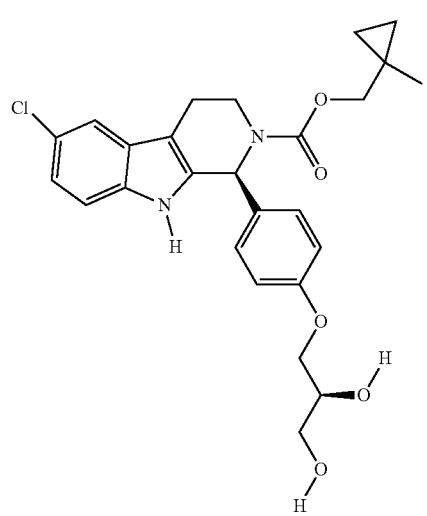
1382
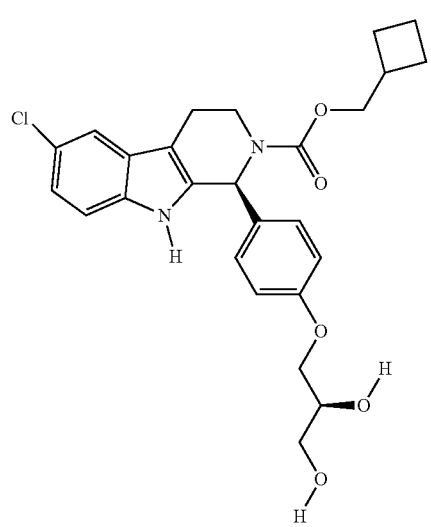
1383
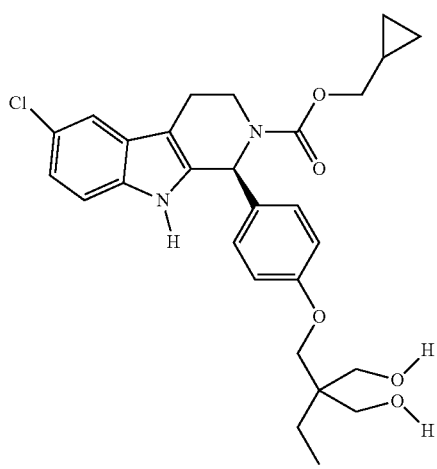
1384
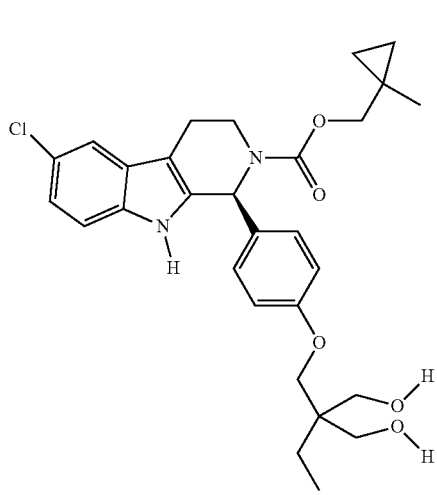
1385
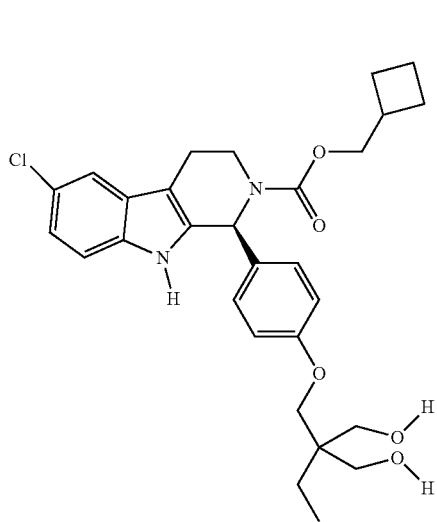

1386
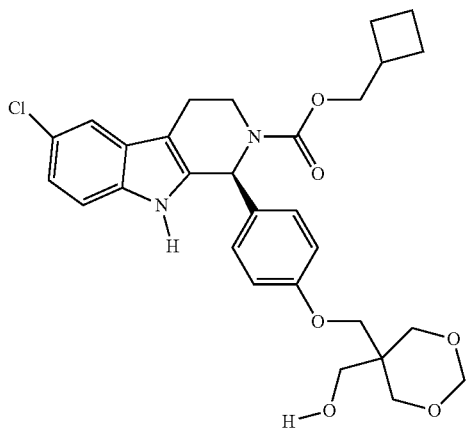
1387
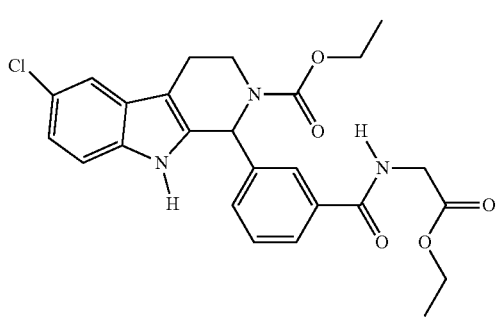
1388
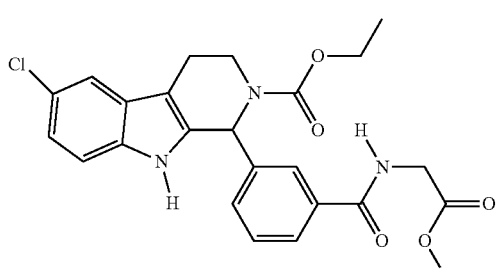
1389
1390
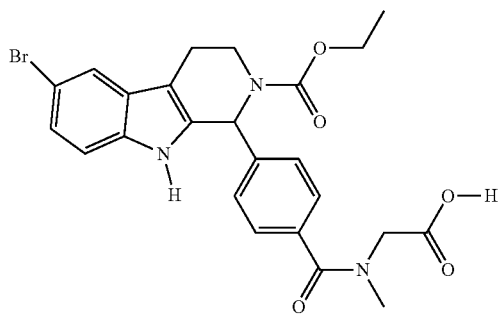
1391
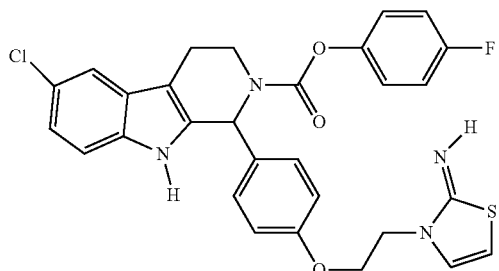
1392
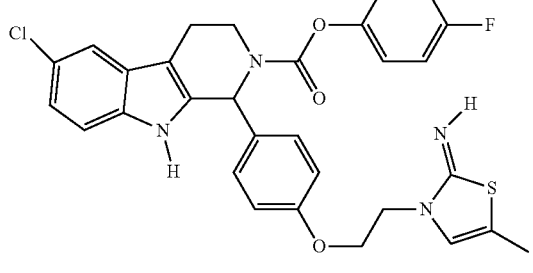
1393
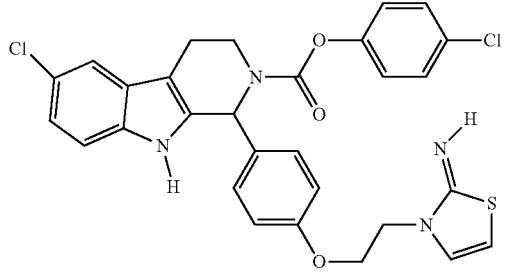
1394
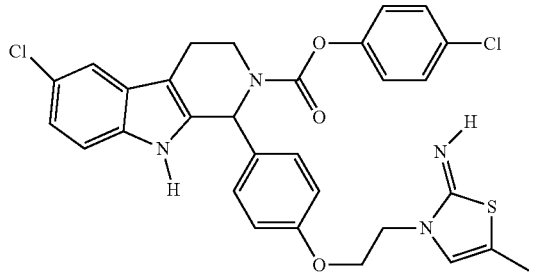

1395
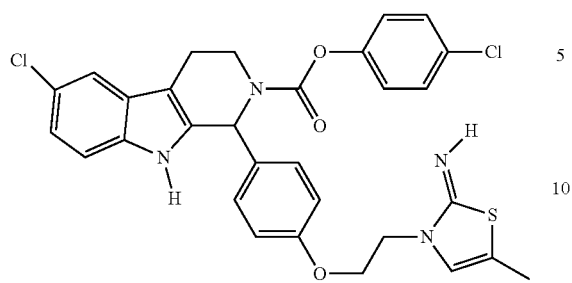
1396
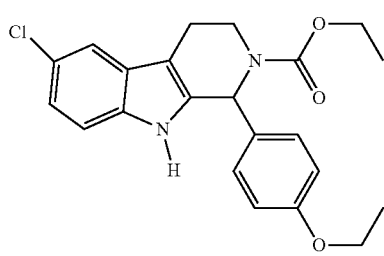
1397
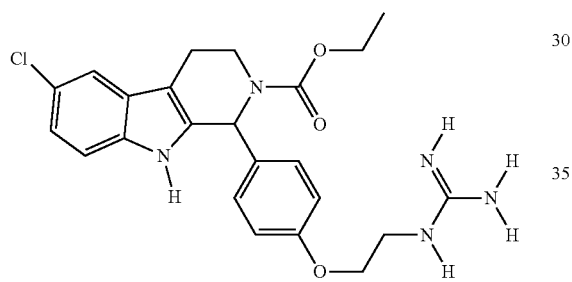
1398
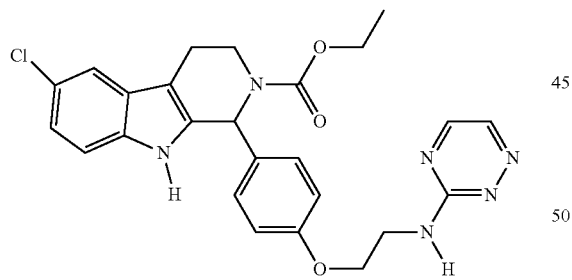
1399
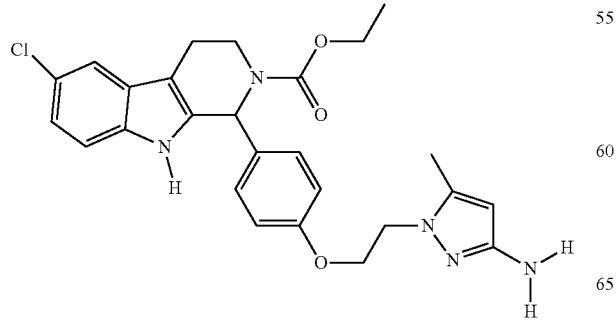
1400
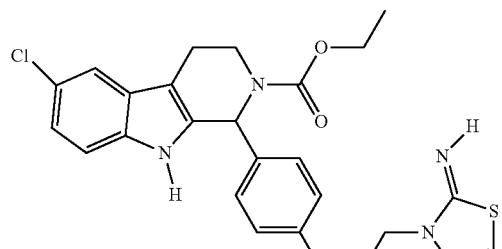
1401
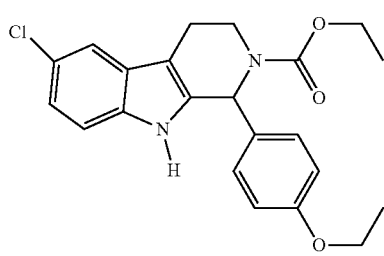
1402
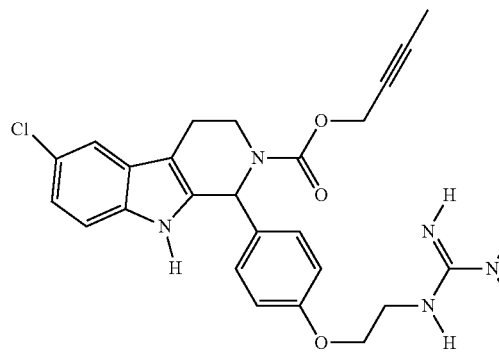
1403
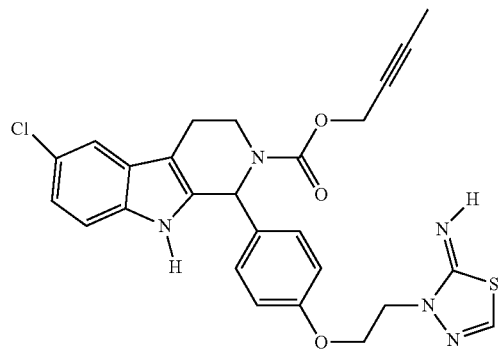

1404
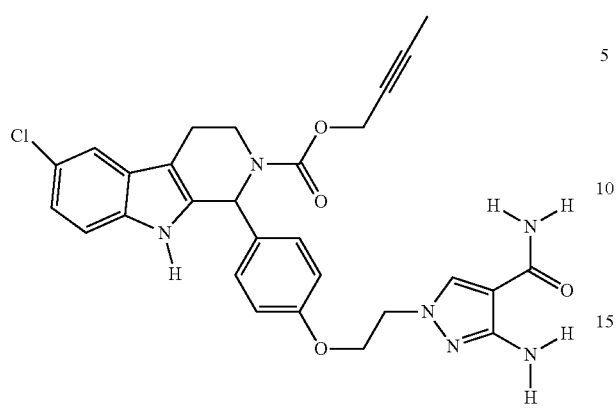
1405
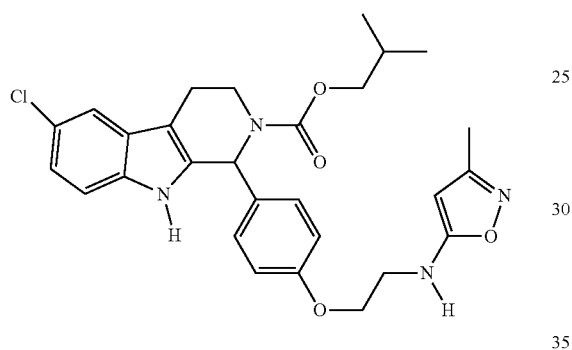
1406
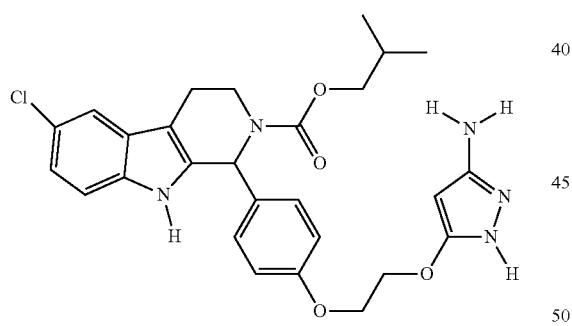
1407
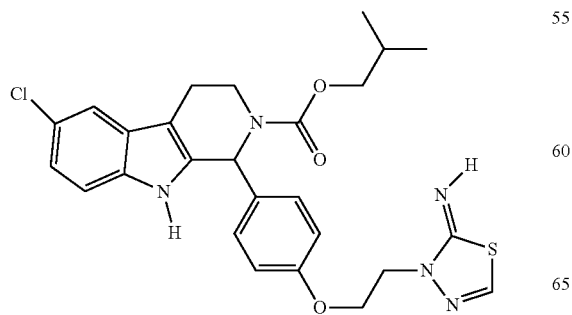
1408
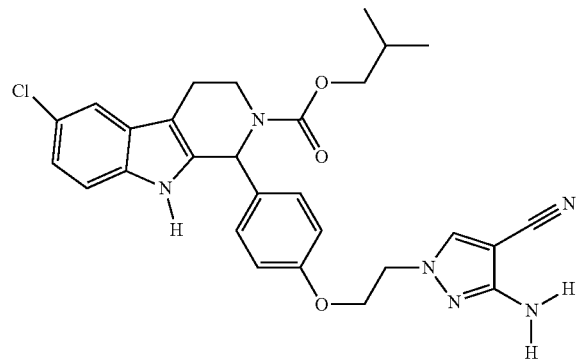
1409
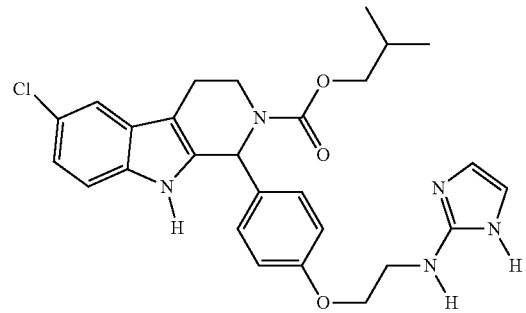
1410
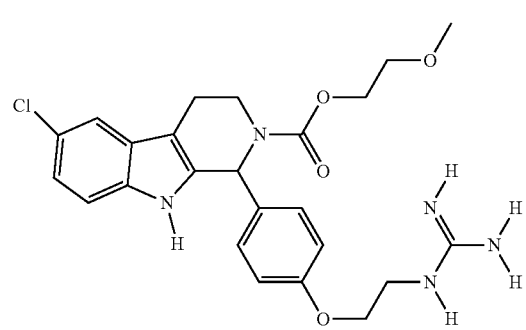
1411
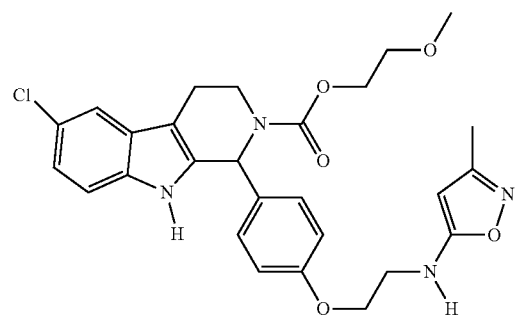

1412
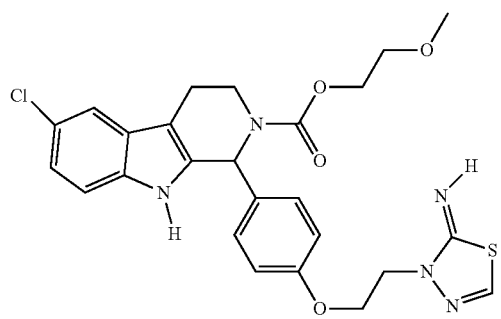
1413
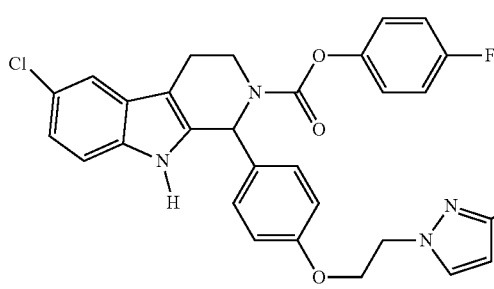
1414
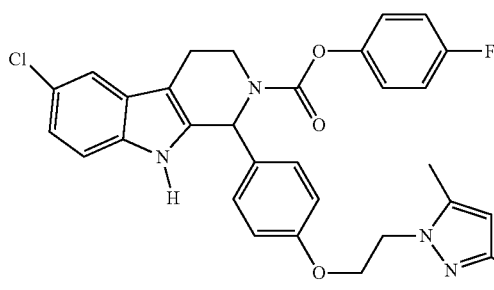
1415
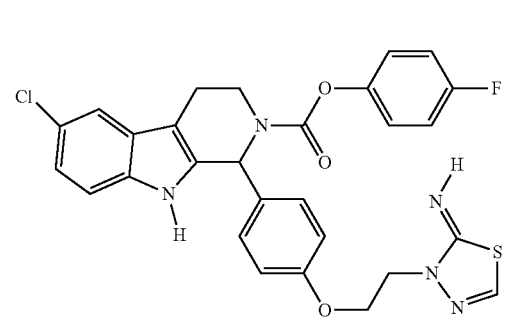
1416
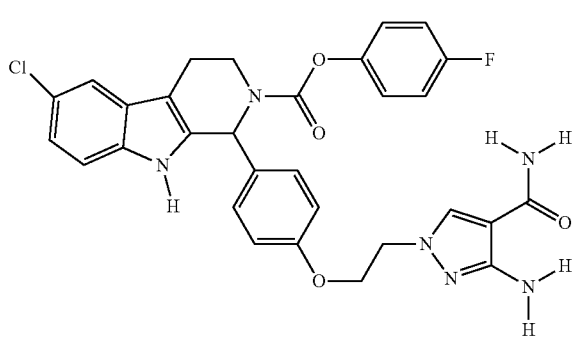
1417
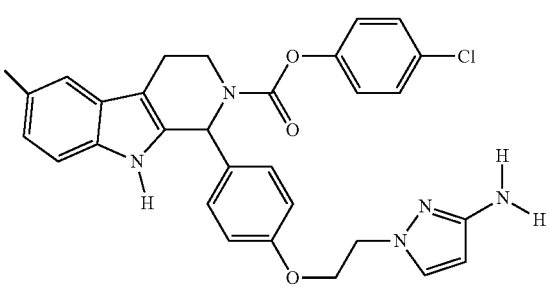
1418
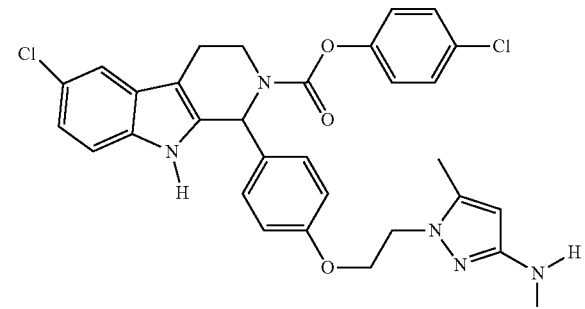
1419
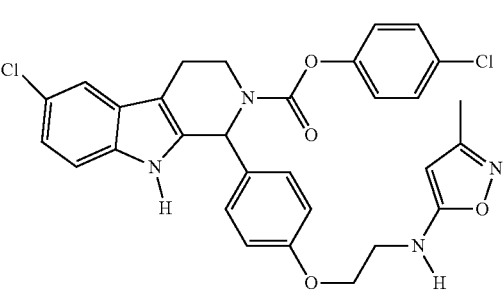
1420
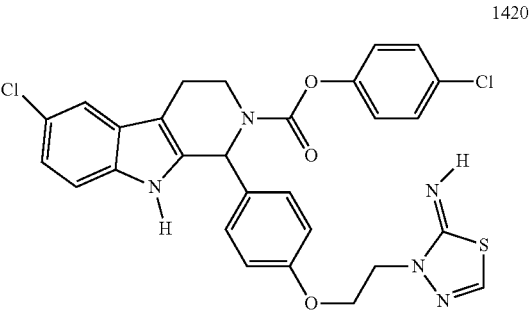
1421
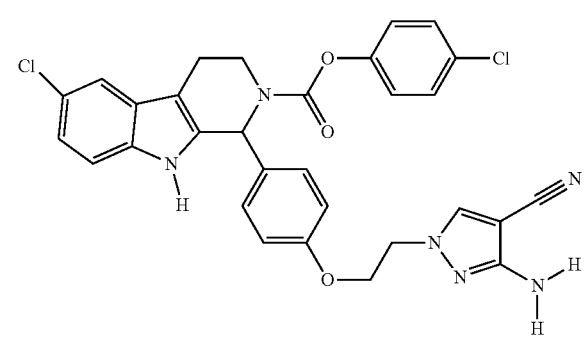

| 669 -continued | 670 -continued |
|---|---|
| 1422 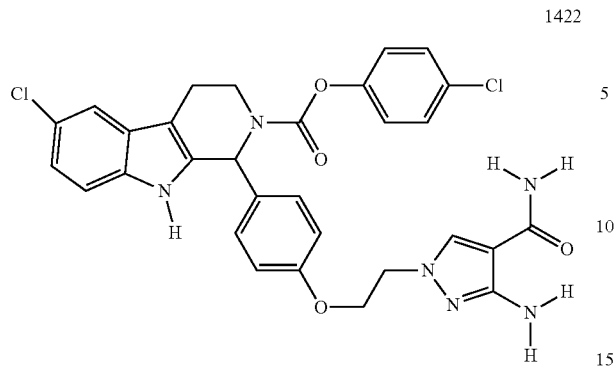 | 1427 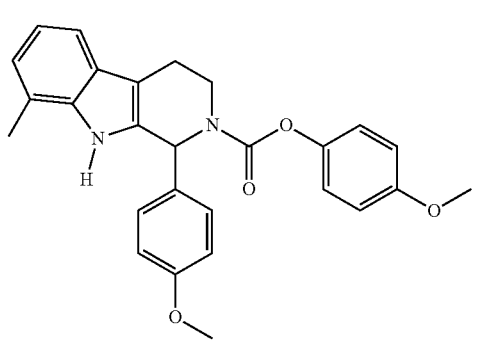 |
| 1423 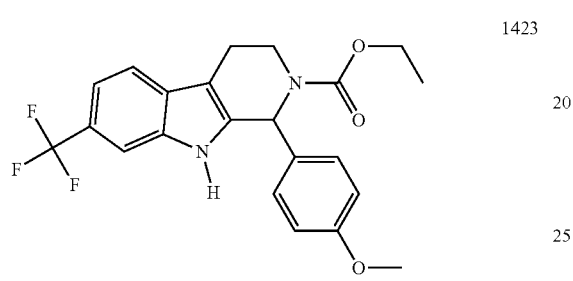 | 1428 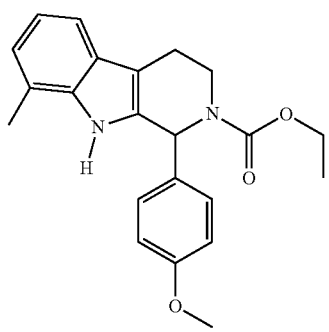 |
| 1424 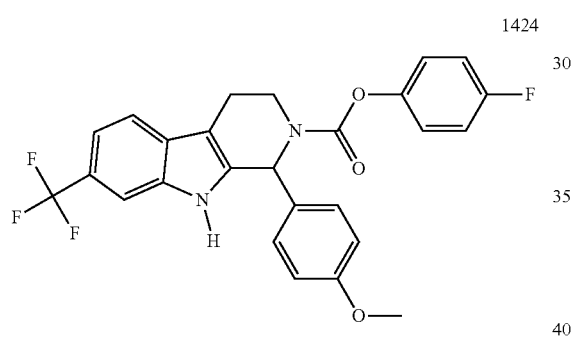 | 1429 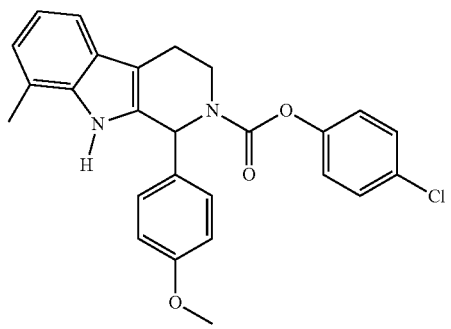 |
| 1425 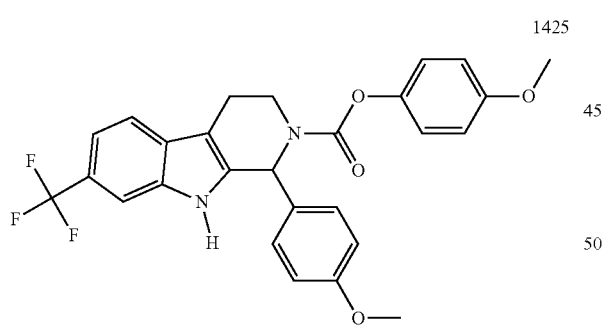 | 1430 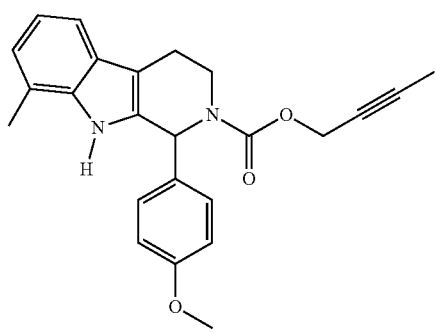 |
| 1426 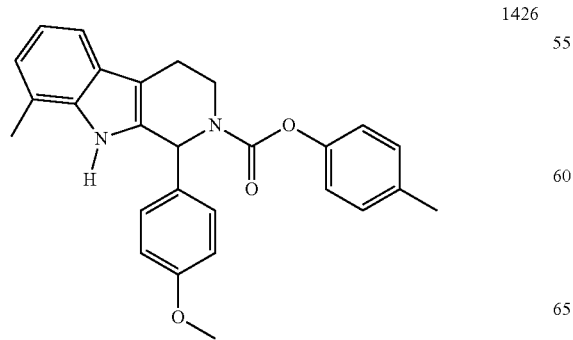 | 1431 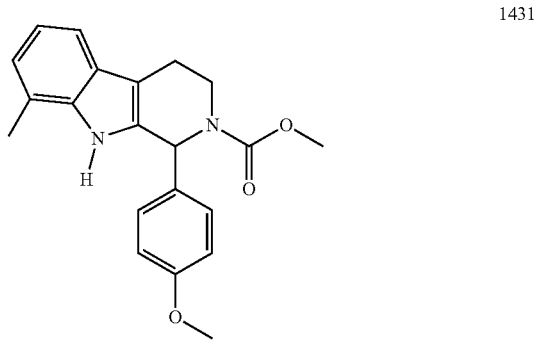 |

671
-continued
1432
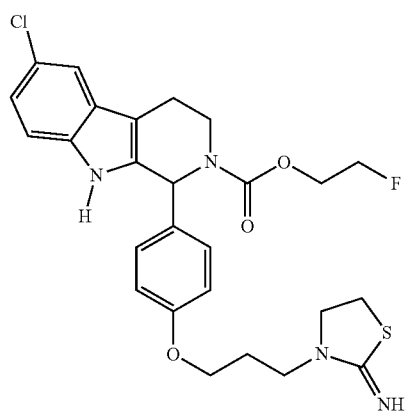
1433
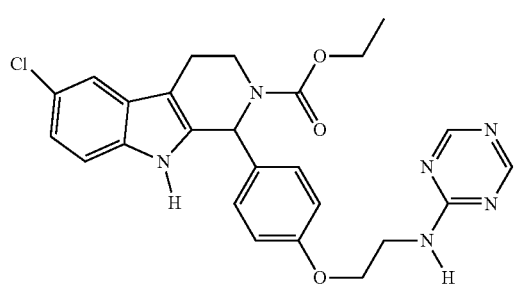
1434
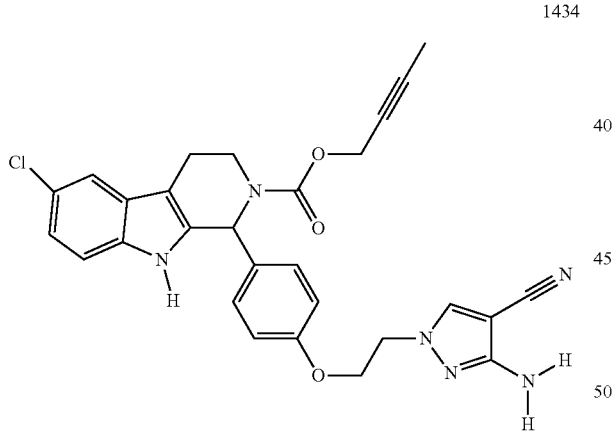
1435
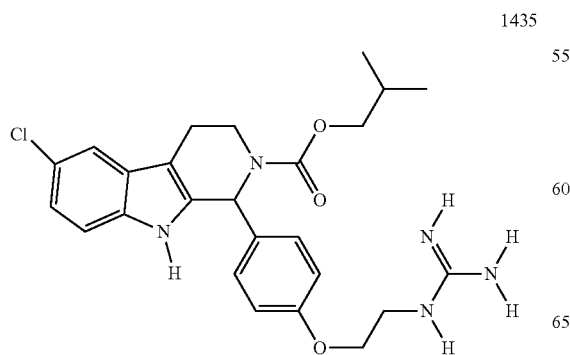
672
-continued
1436
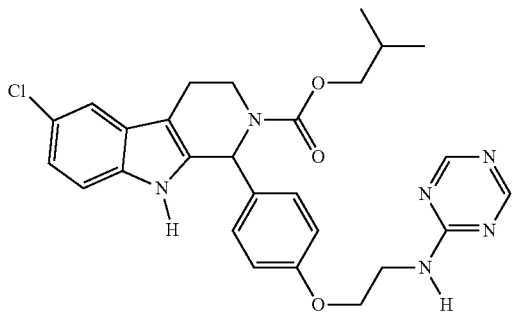
1437
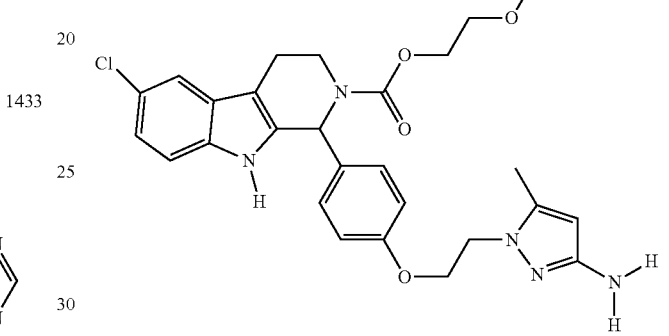
1438
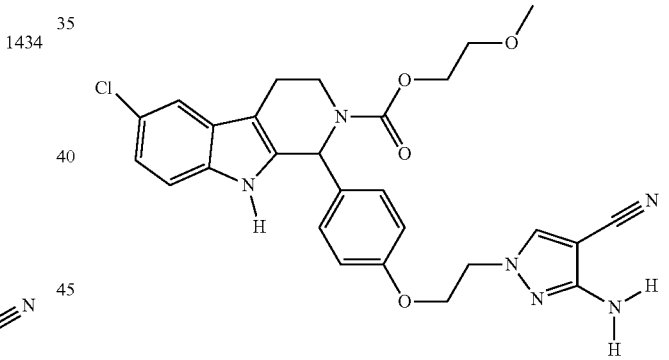
1439
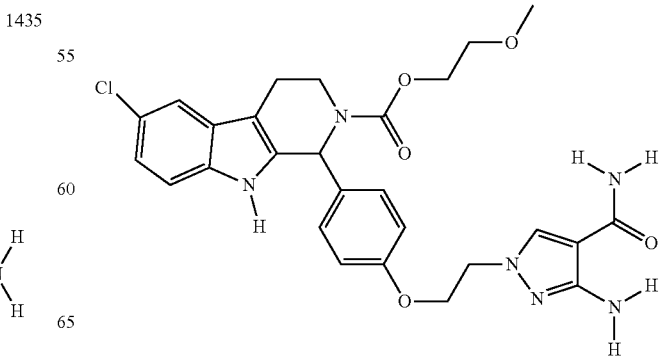

1440
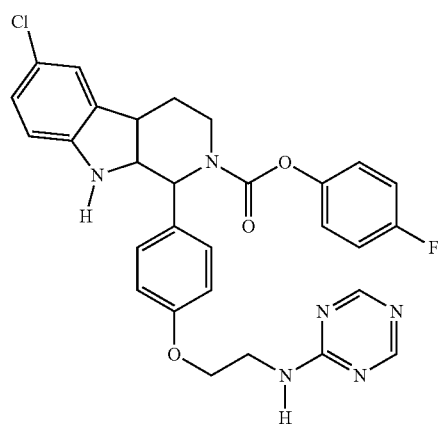
1441
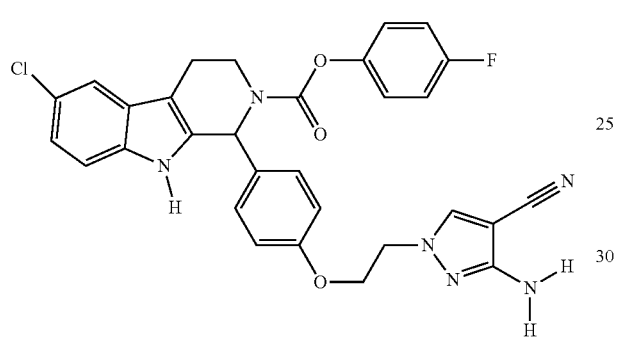
1442
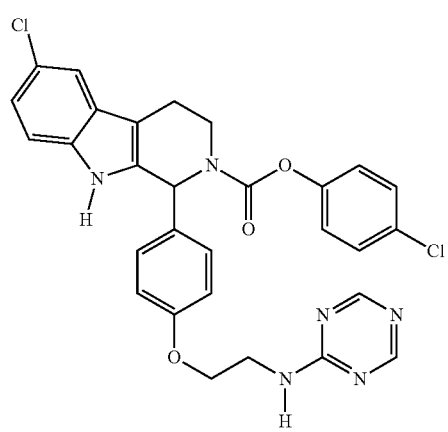
1443
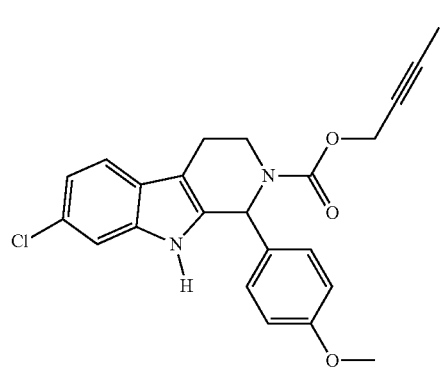
1444
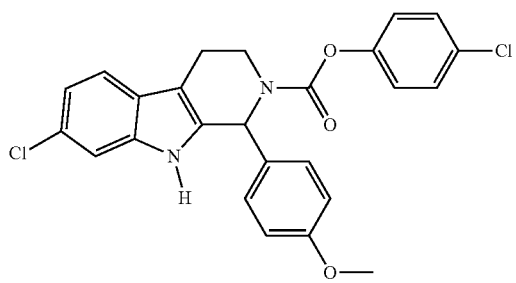
1445
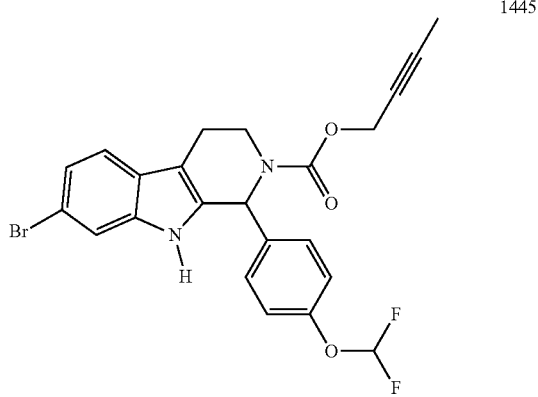
1446
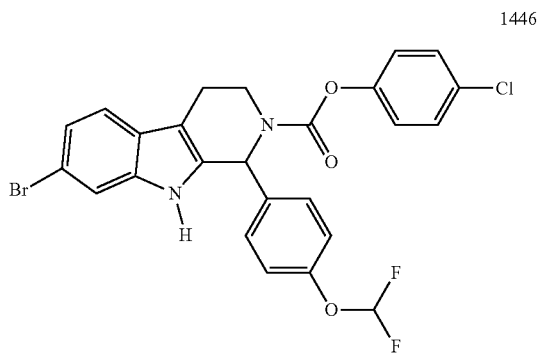
1447
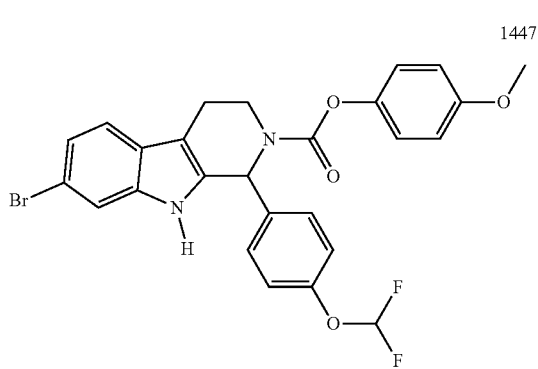

1448
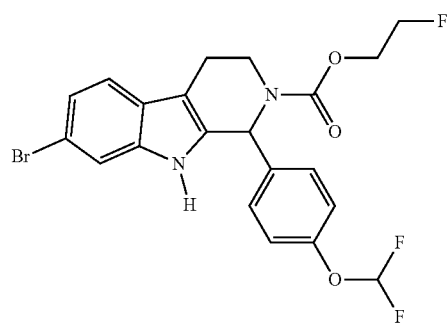
1449
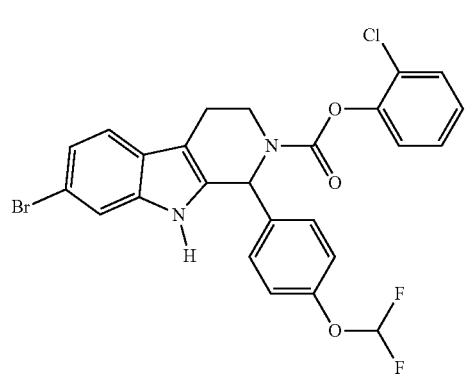
1450
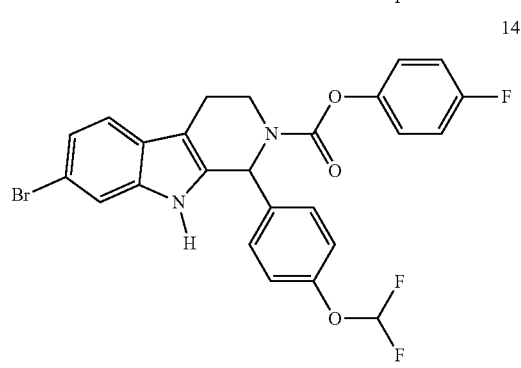
1451
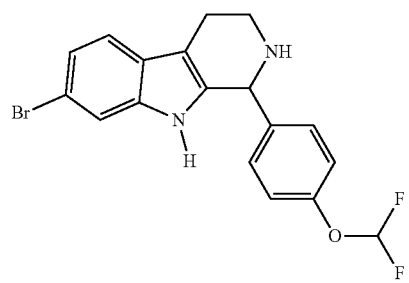
1452
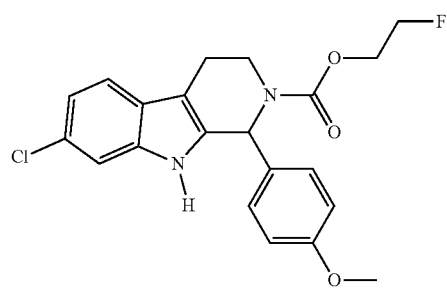
1453
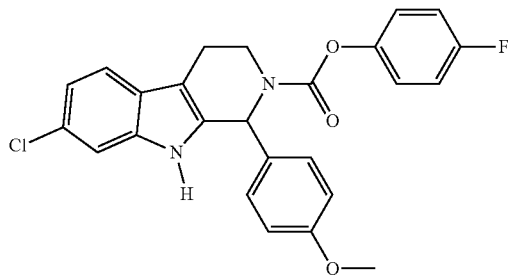
1454
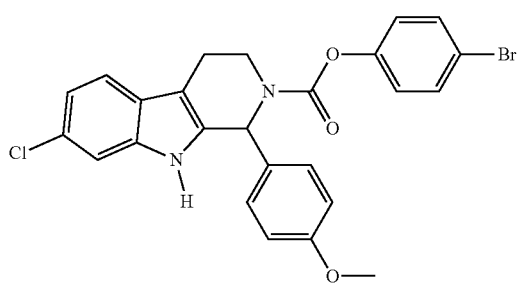
1455
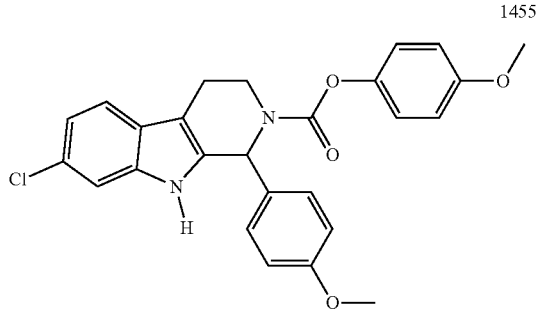
1456
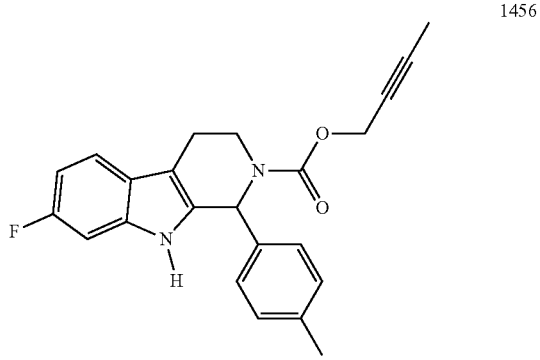
1457
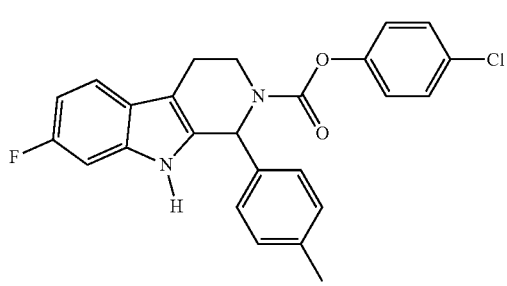

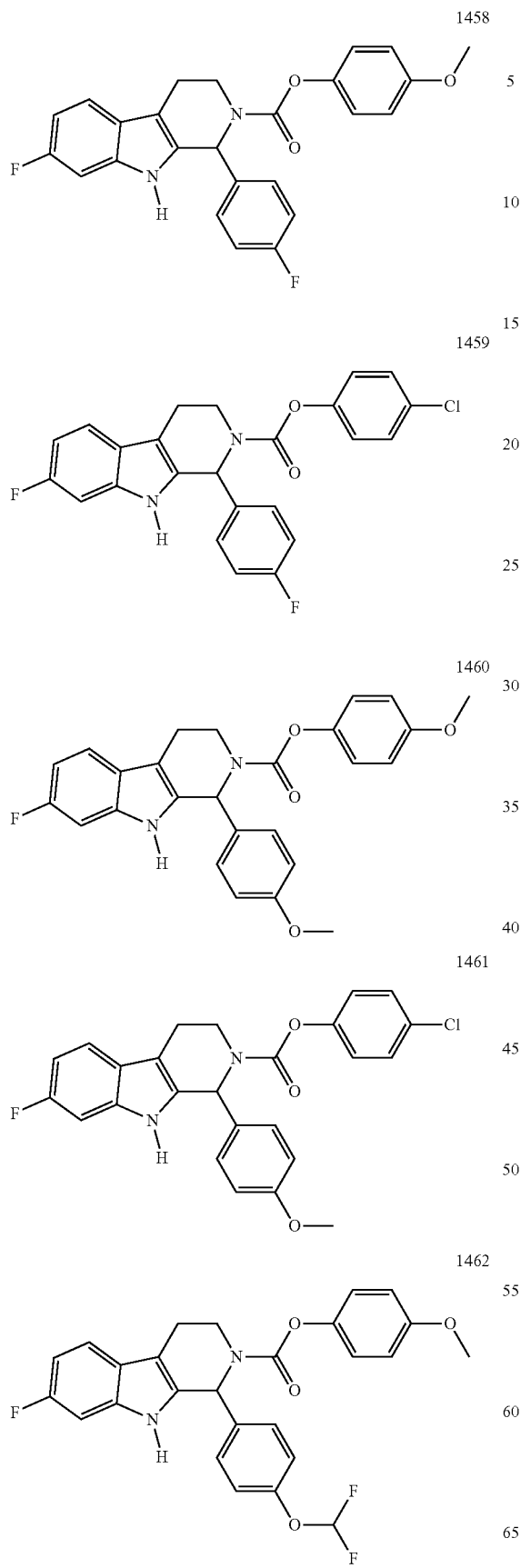
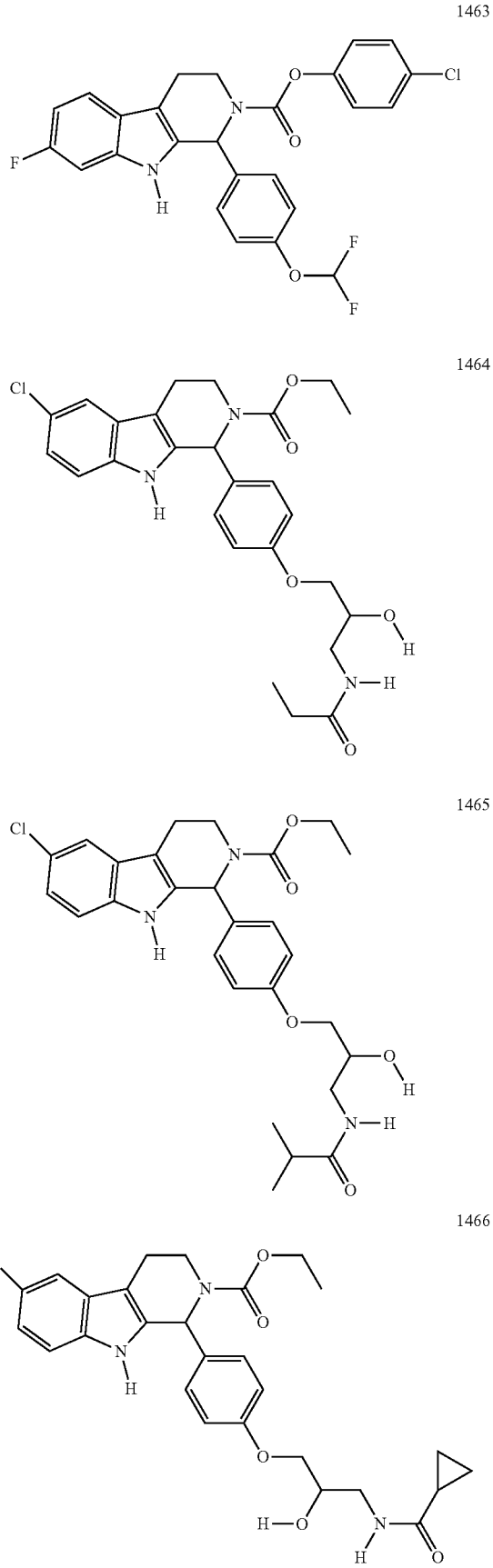

679
-continued
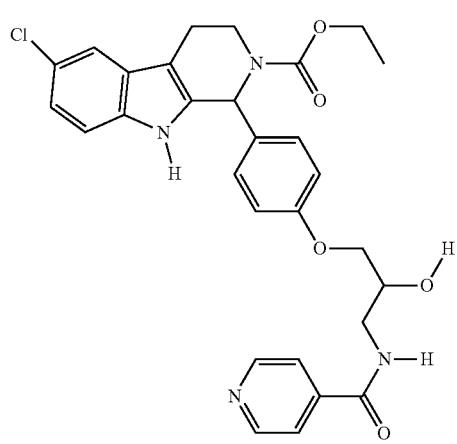
1467
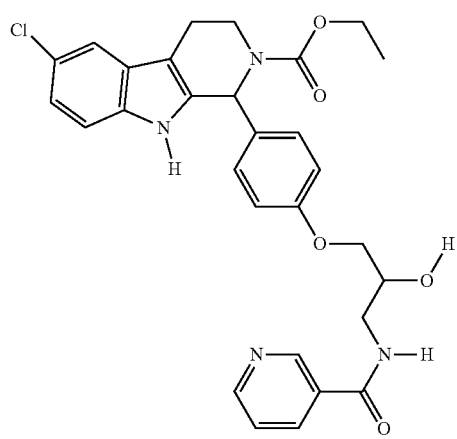
1468
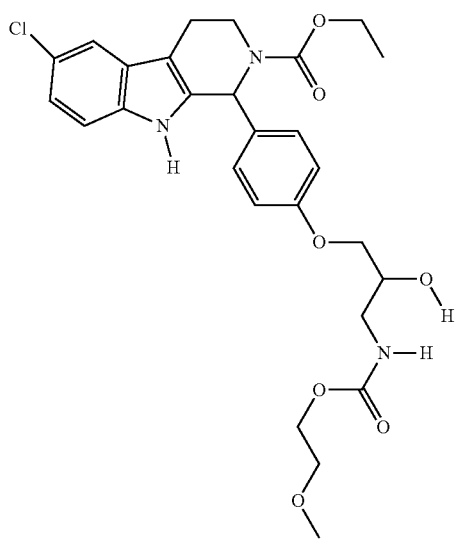
1469
680
-continued
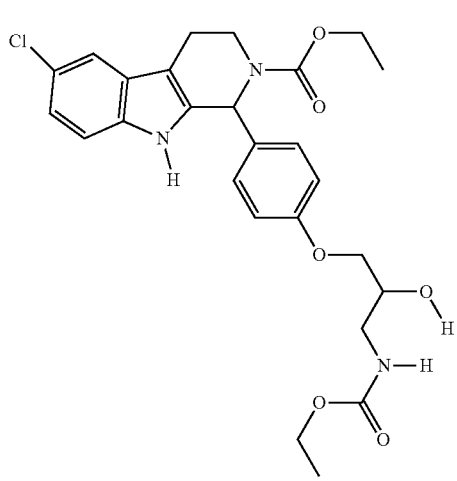
1470
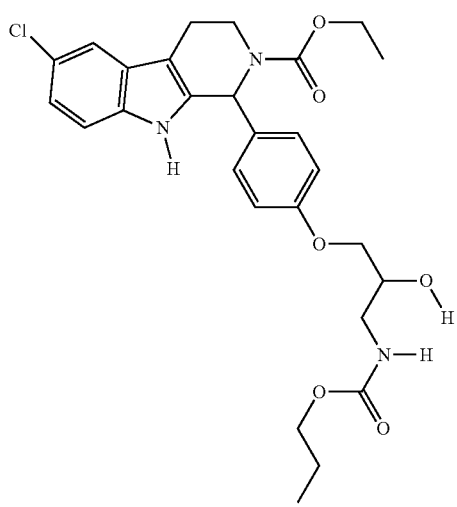
1471
1472

| 1473 | 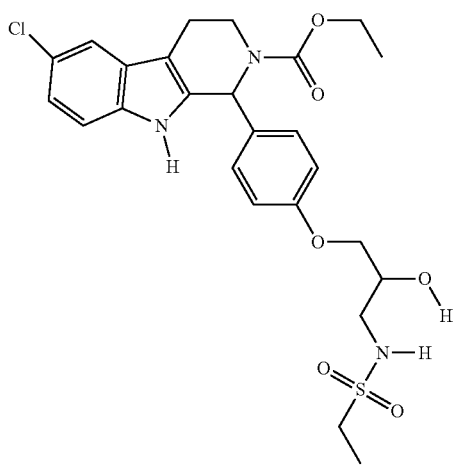 |
|---|---|
| 1474 | 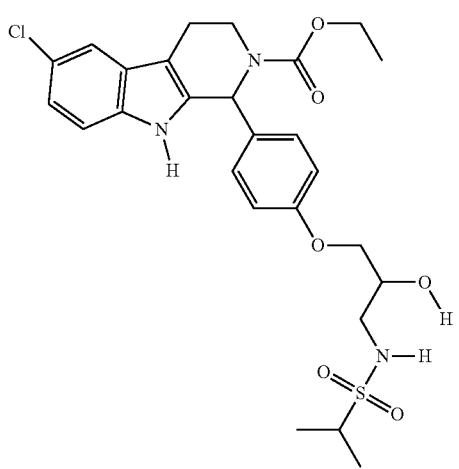 |
| 1475 | 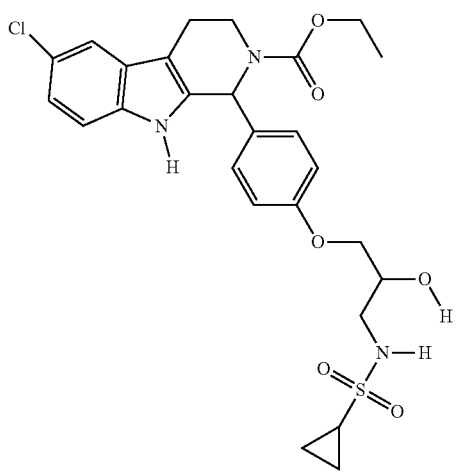 |
| 1476 | 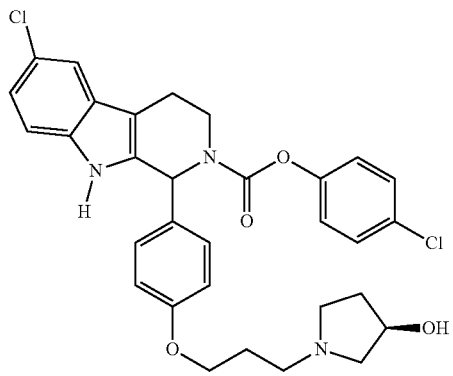 |
| 1477 | 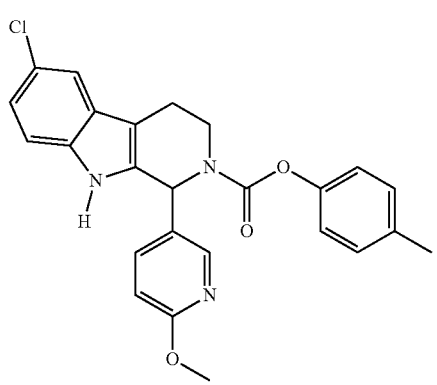 |
| 1478 | 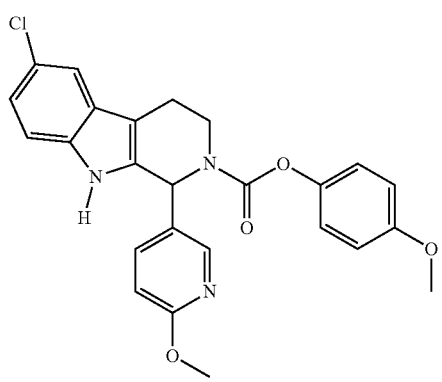 |
| 1479 | 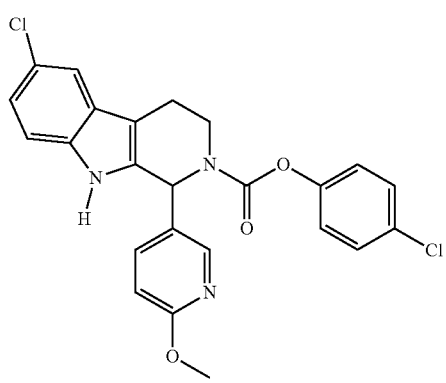 |

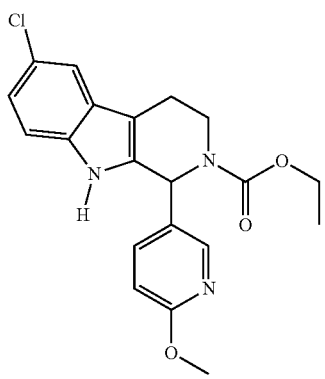
1480
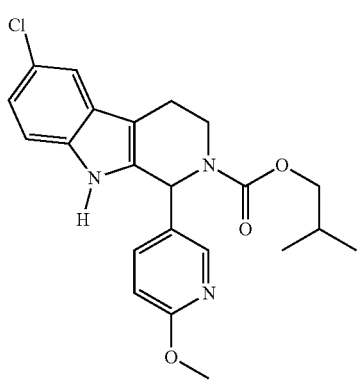
1481
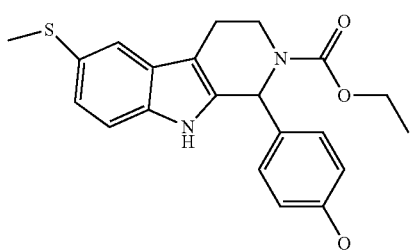
1482
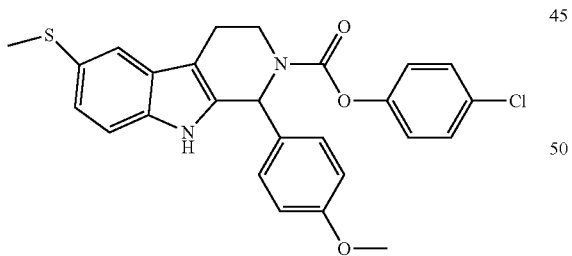
1483
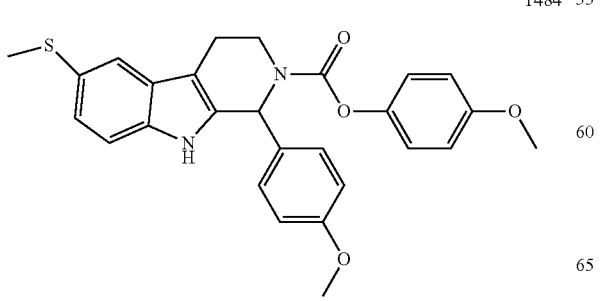
1484
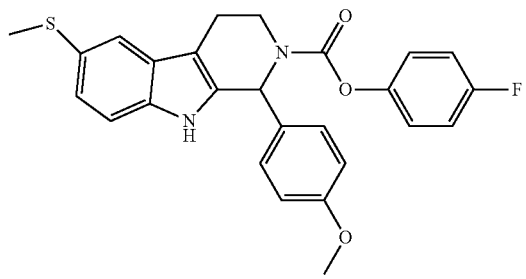
1485
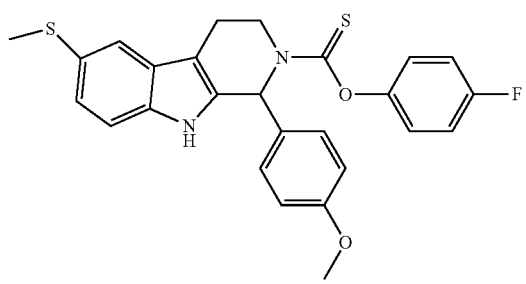
1486
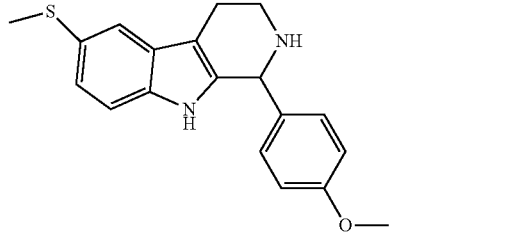
1487
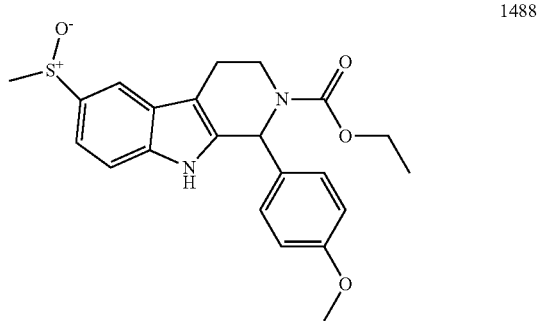
1488
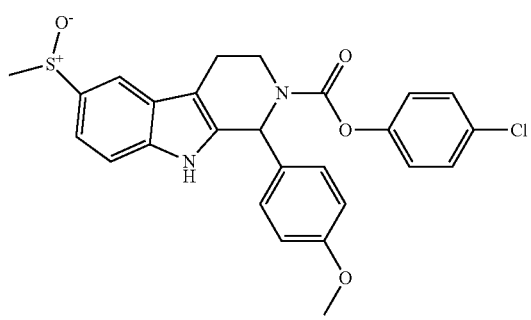
1489

| 1490 | 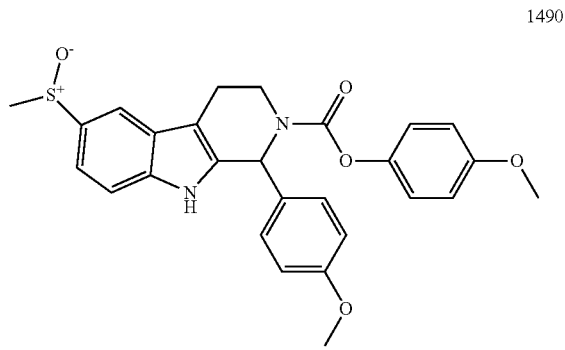 | 1495 | 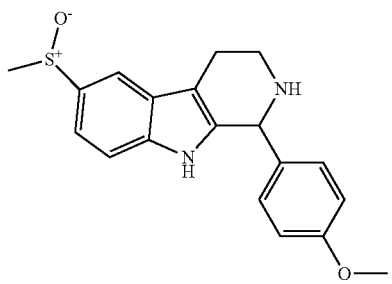 |
| 1491 | 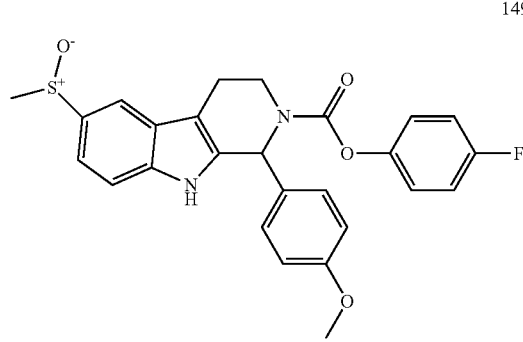 | 1496 | 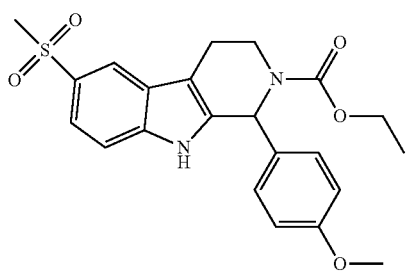 |
| 1492 | 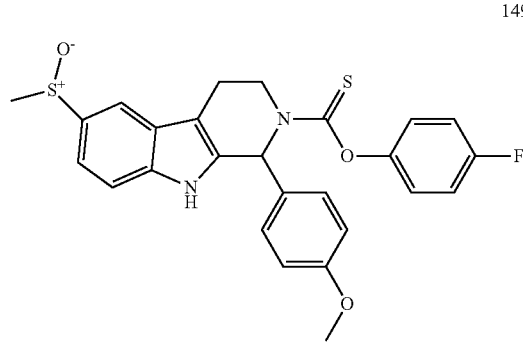 | 1497 | 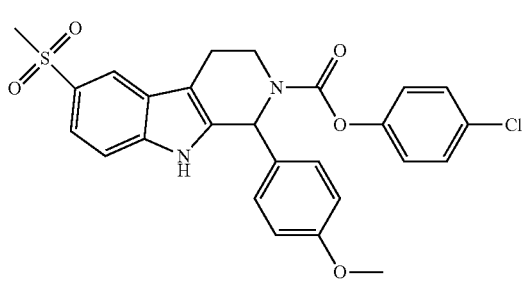 |
| 1493 | 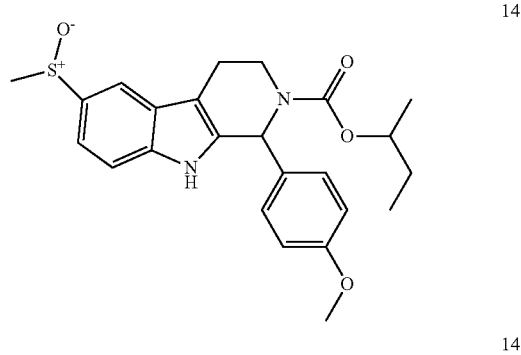 | 1498 | 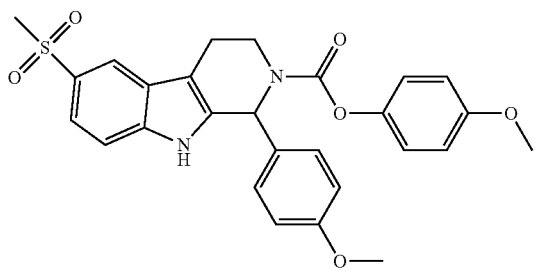 |
| 1494 | 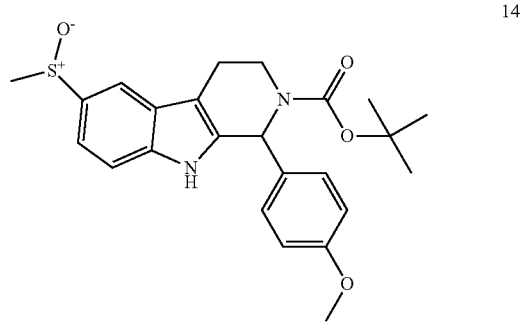 | 1499 | 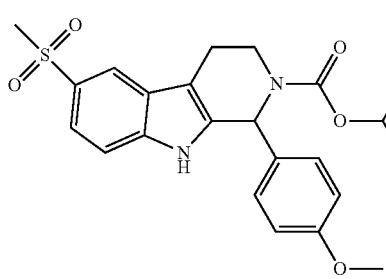 |

687
-continued
1500
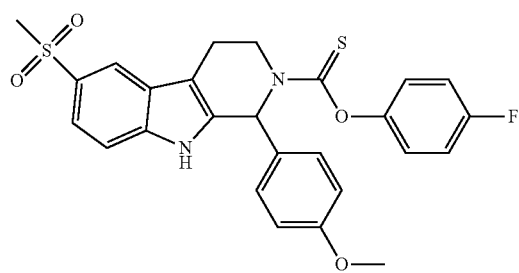
1502
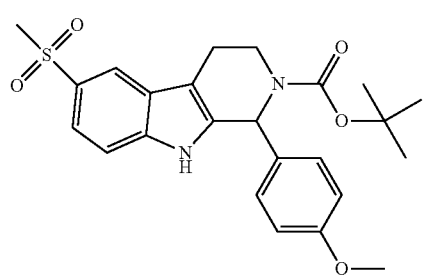
1503
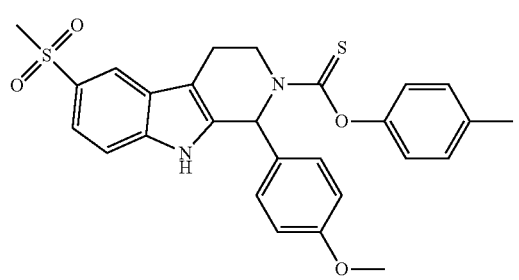
1504
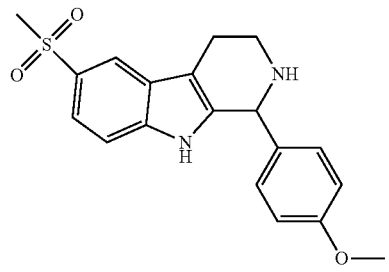
1505
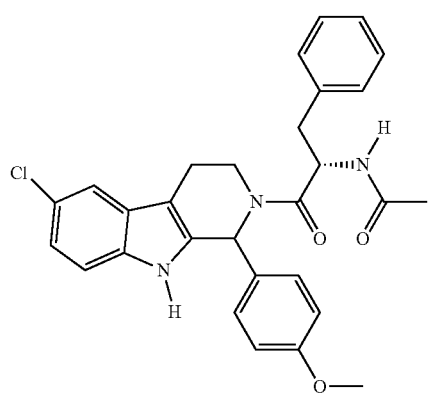
688
-continued
1506
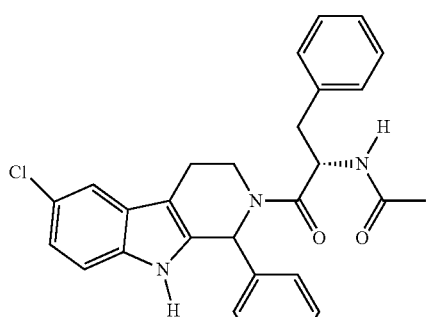
1508
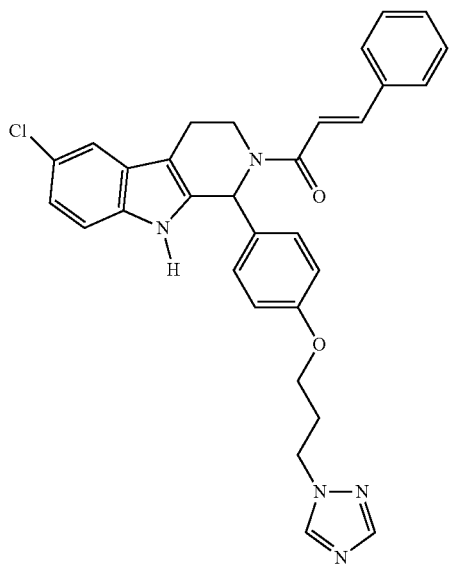
1509
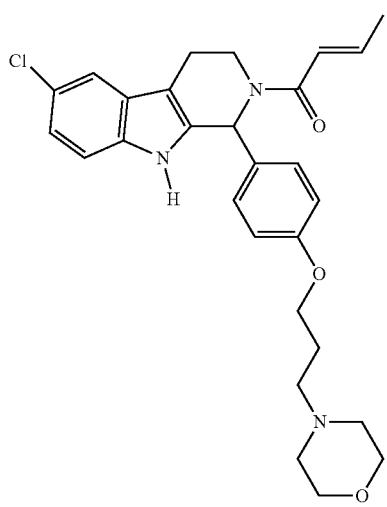

689
-continued
1510
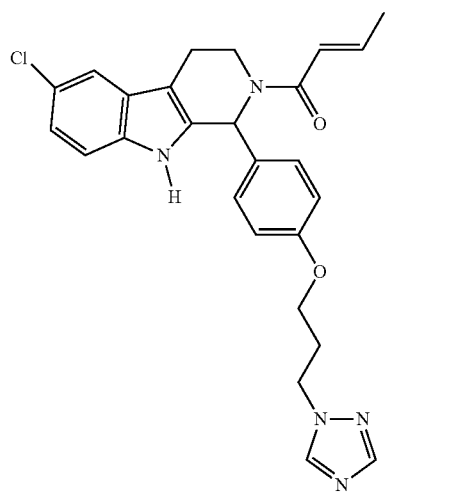
1511
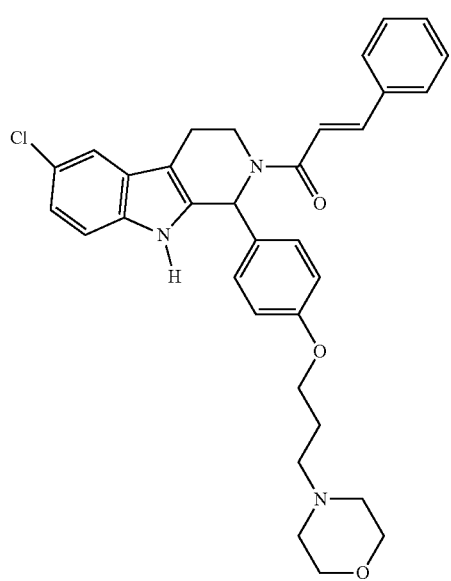
1512
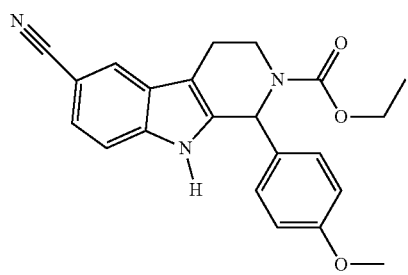
1513
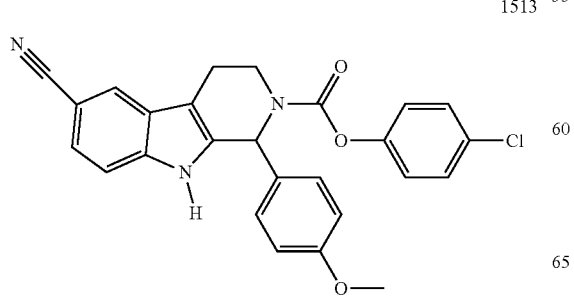
690
-continued
1514
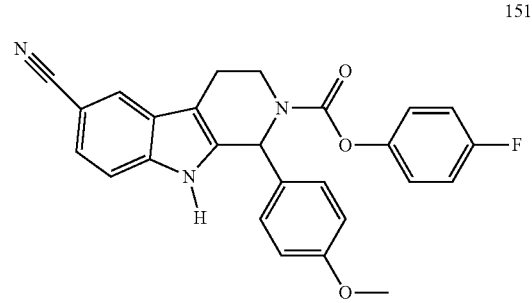
1515
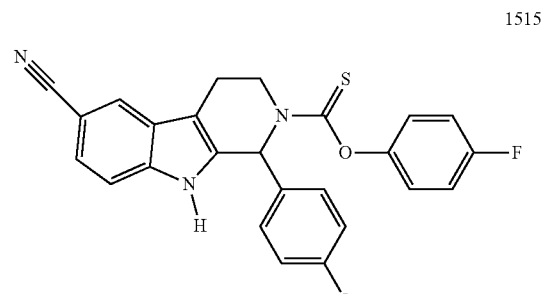
1516
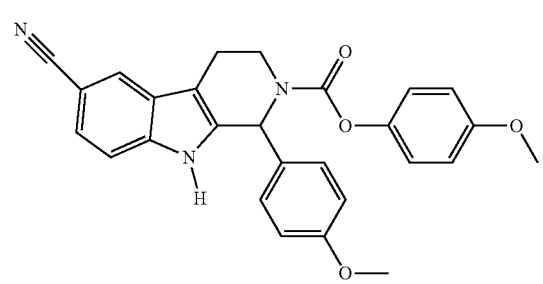
1517
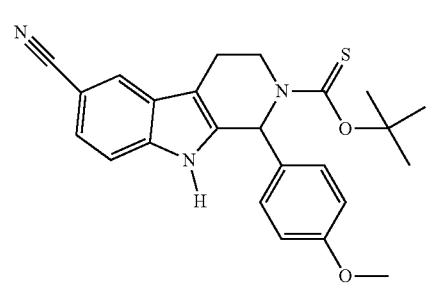
1518
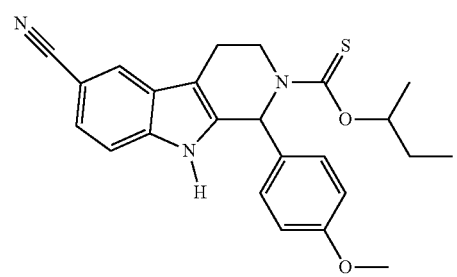

| 691 | 692 |
|---|---|
| -continued | -continued |
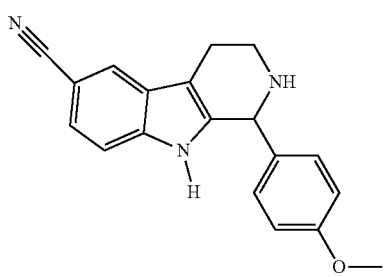
1519
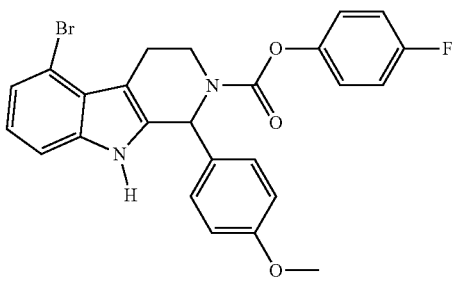
1524
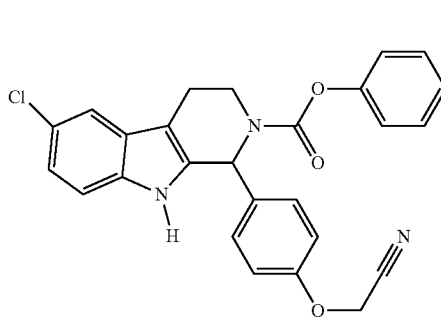
1520
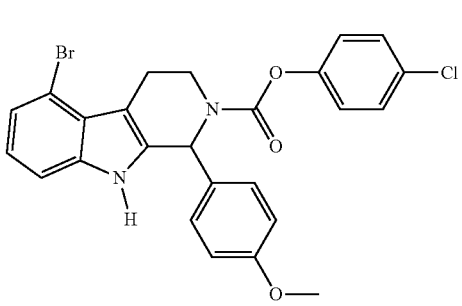
1525
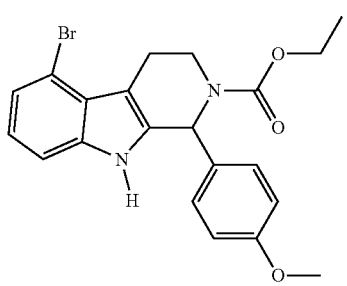
1521
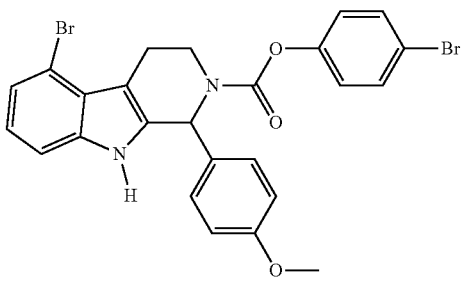
1526
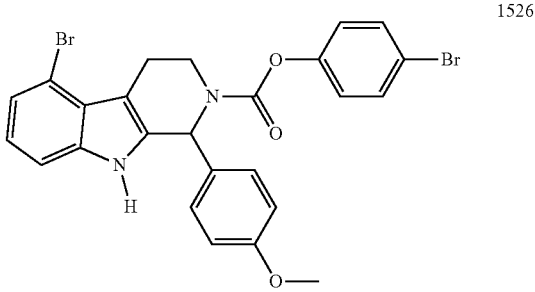
1522
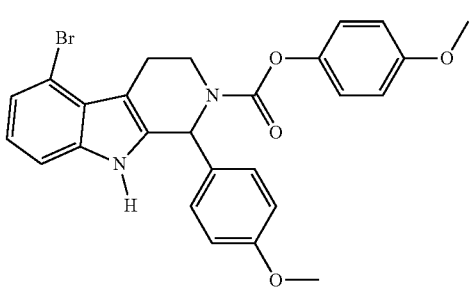
1527
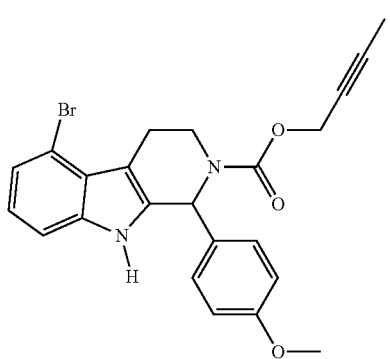
1523
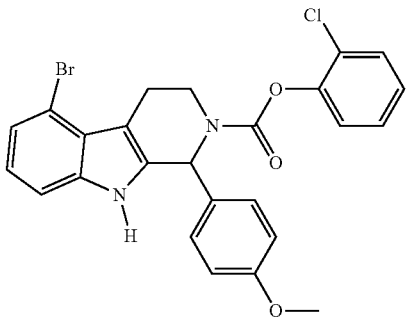
1528

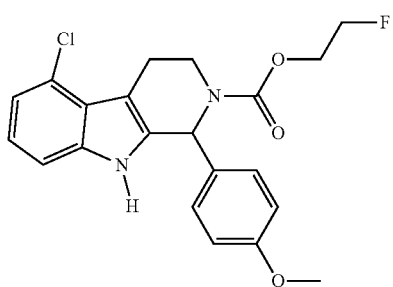
1529
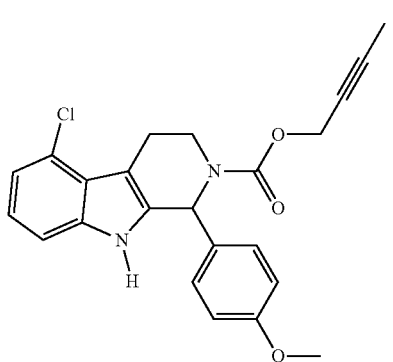
1530
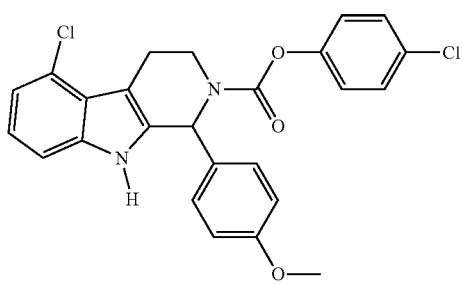
1531
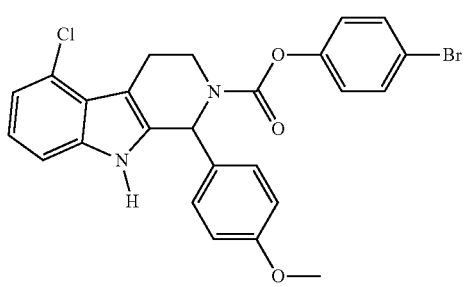
1532
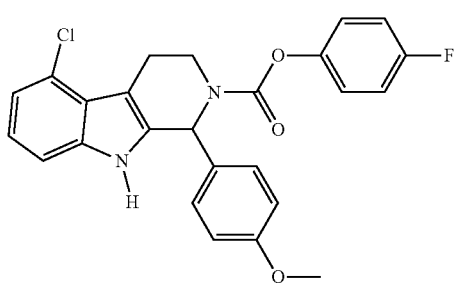
1533
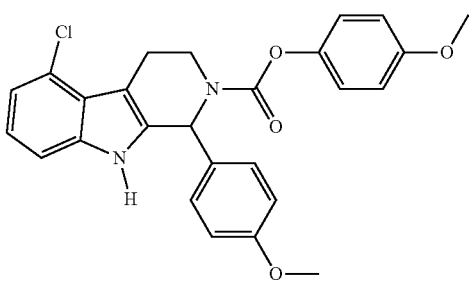
1534
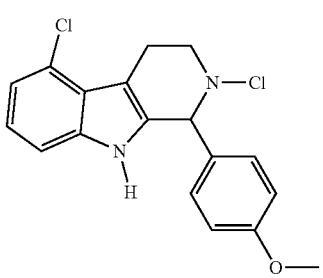
1535
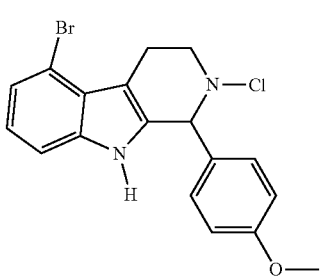
1536
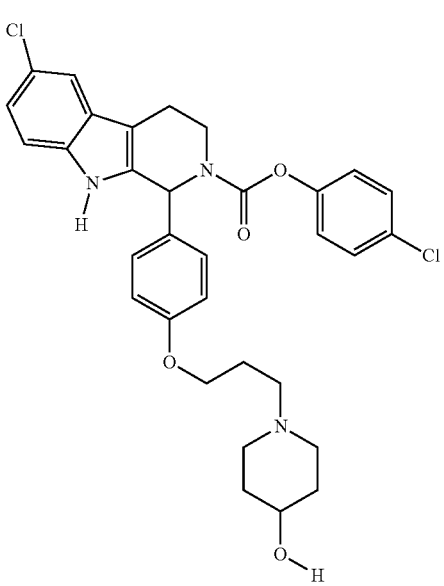
1537

1538 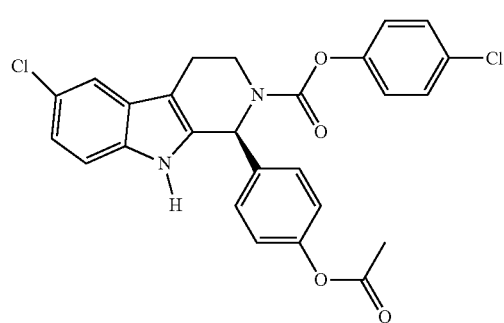
1539 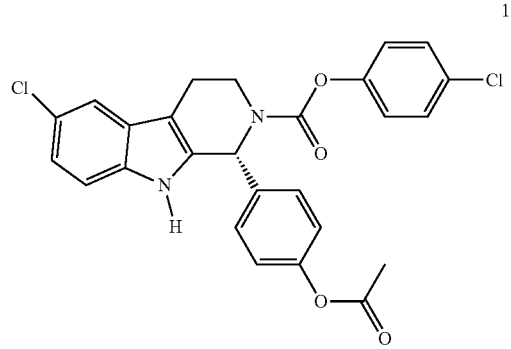
1540 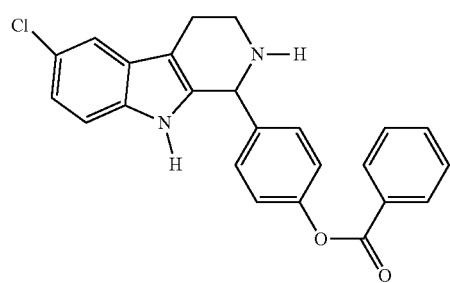
1541 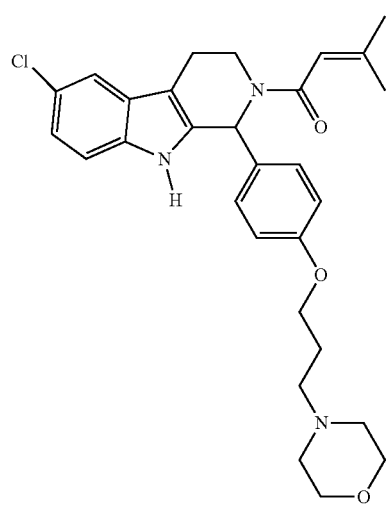
1542 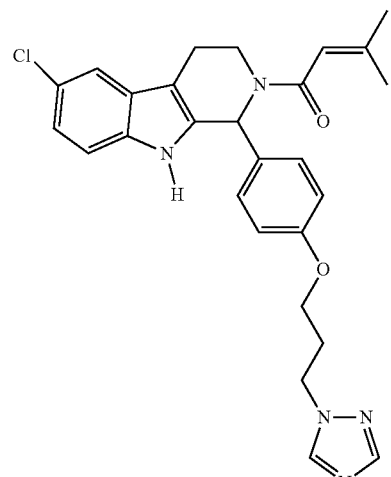
1543 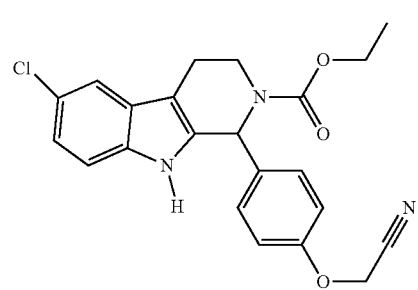
1544 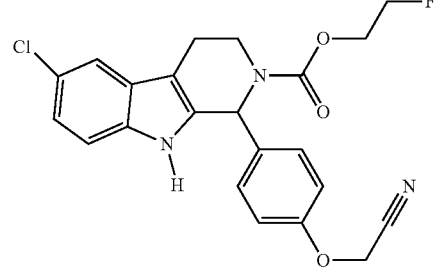
1545 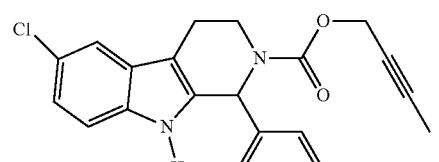
1546 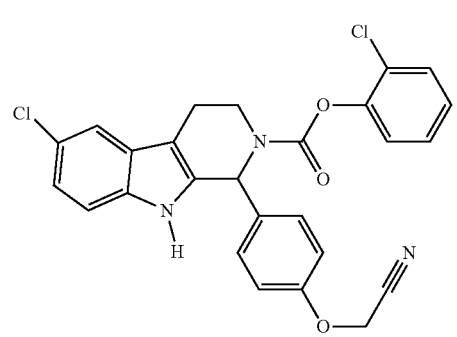

697
-continued
1547
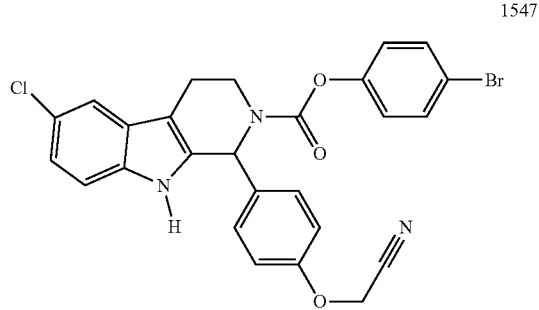
1548
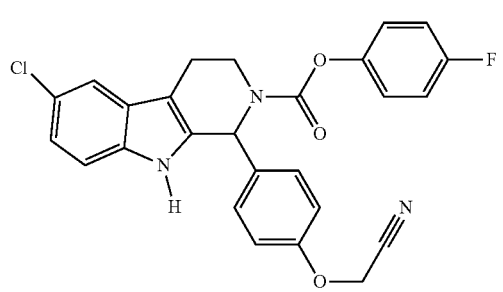
1549
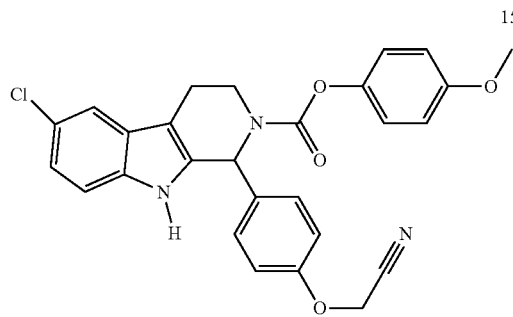
1550
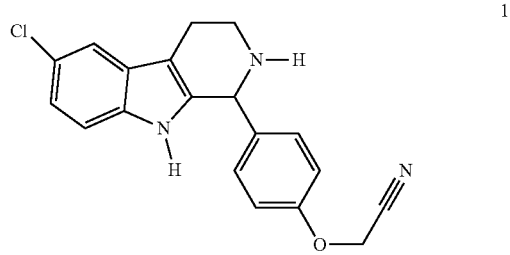
1551
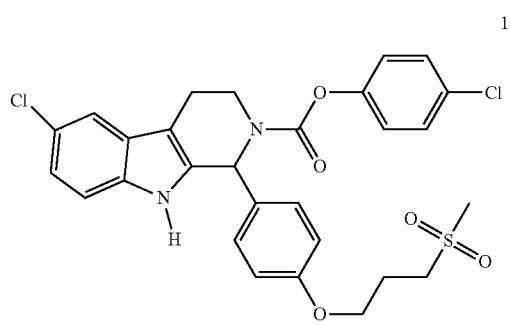
698
-continued
1552
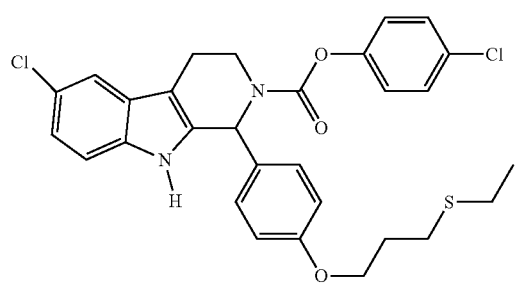
1553
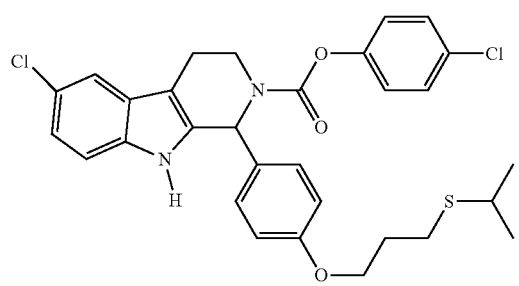
1554
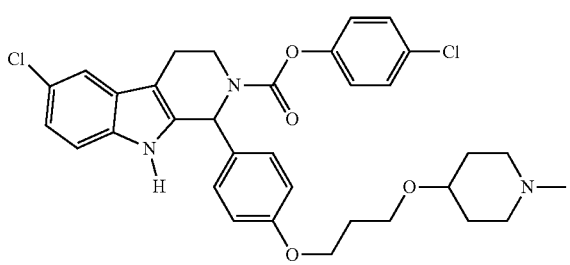
1555
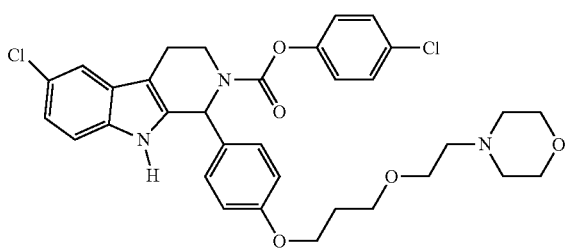
1556
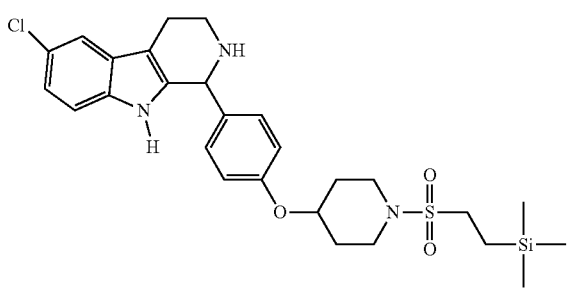

1557
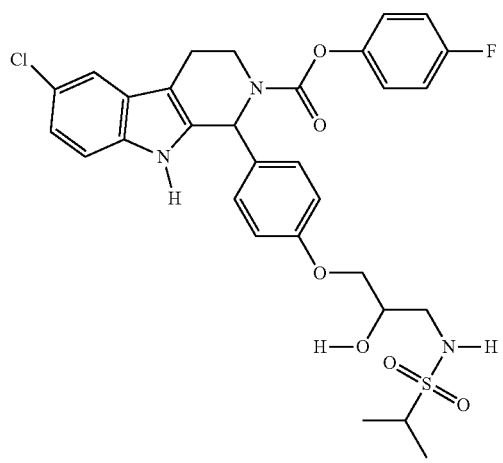
1558
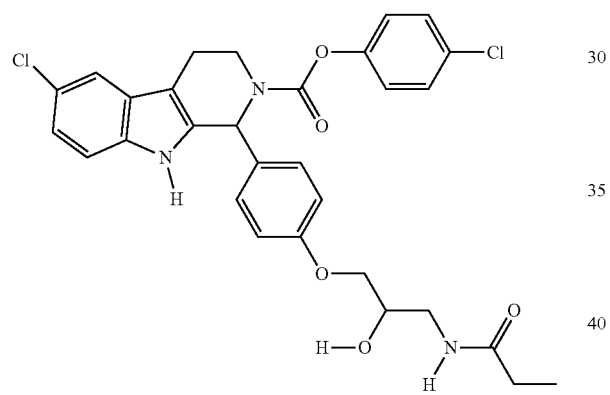
1559
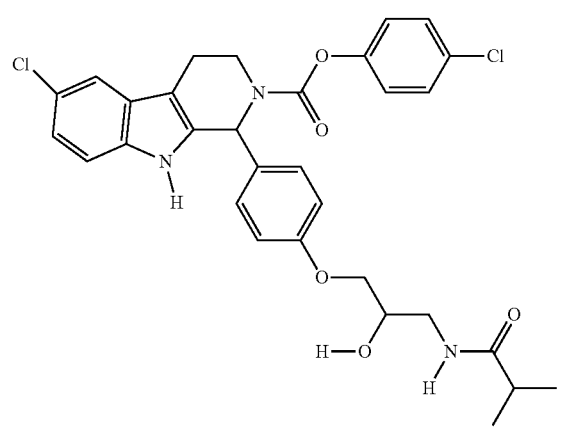
1560
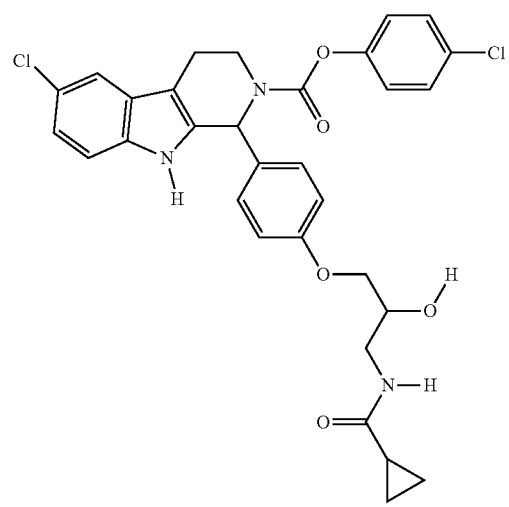
1561
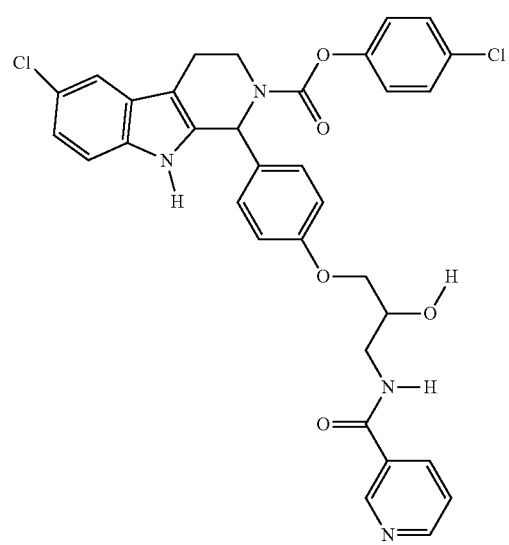
1562
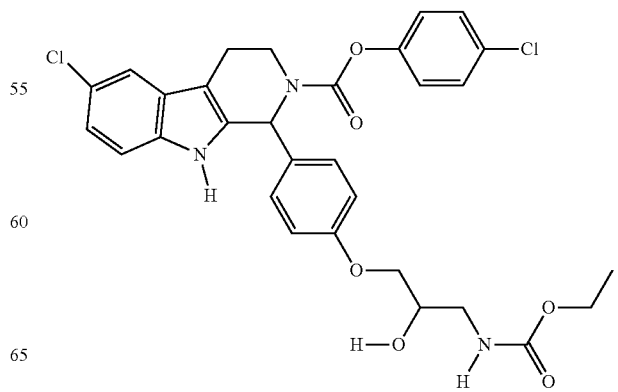

| 1563 | 1566 |
|---|---|
| 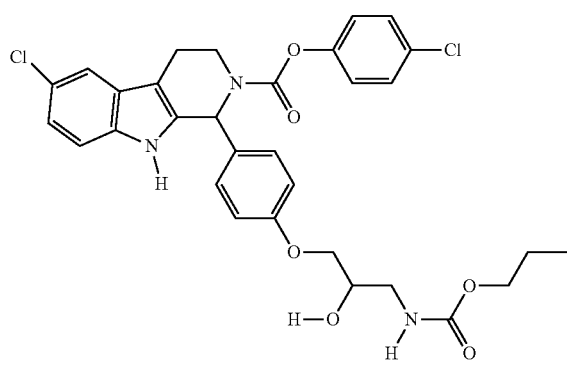 | 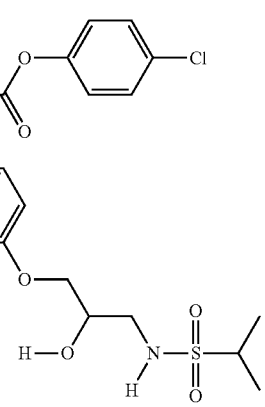 |
| 1564 | 1567 |
|---|---|
| 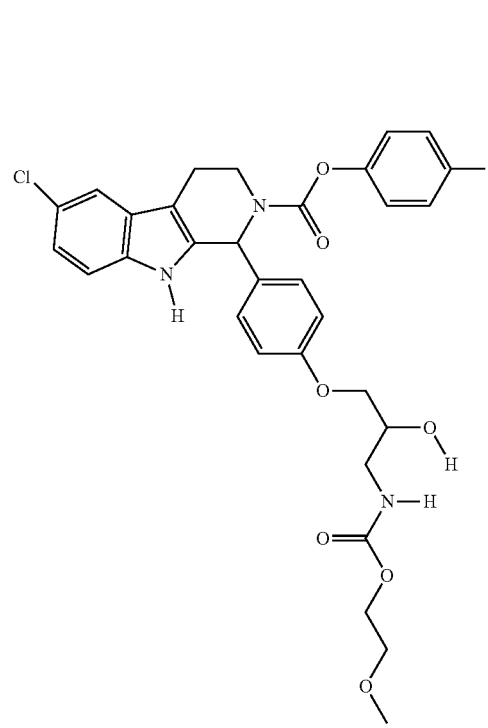 | 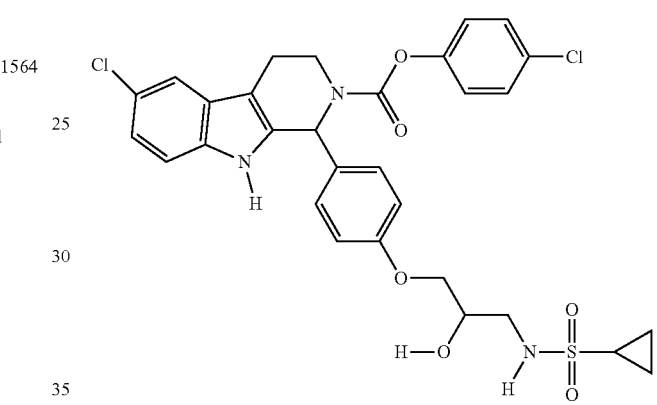 |
| | 1568 |
|---|---|
| | 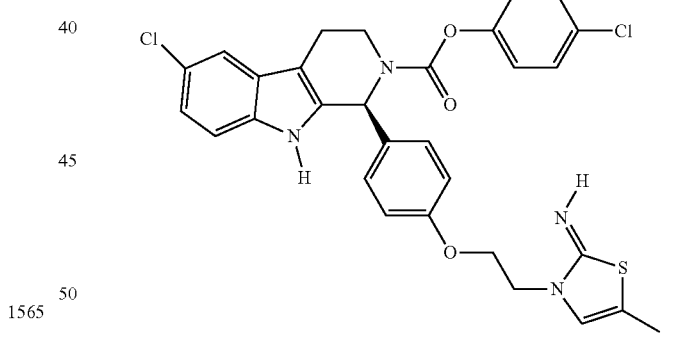 |
| 1565 | 1569 |
|---|---|
| 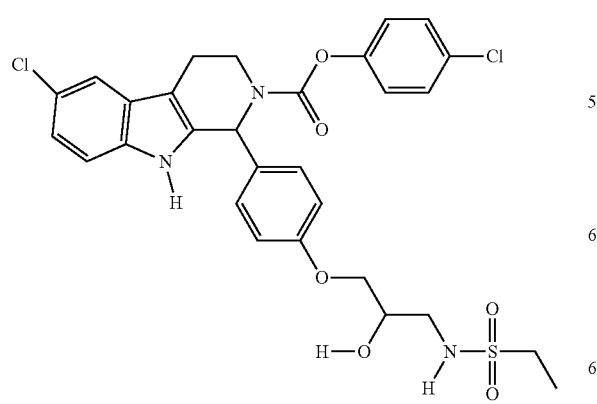 | 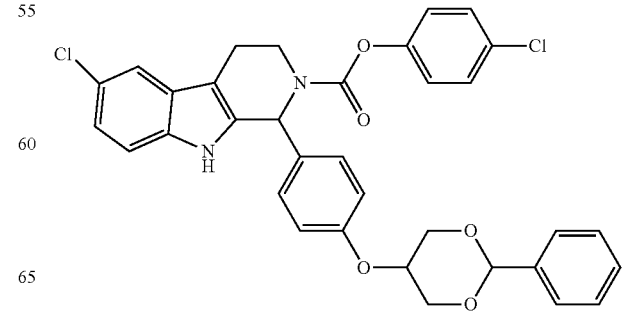 |

703
-continued
1570
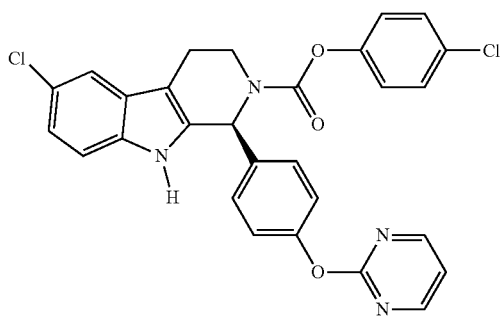
1571
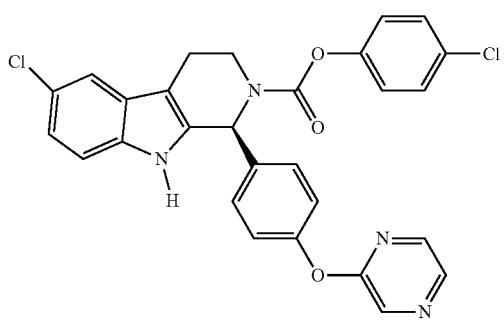
1572
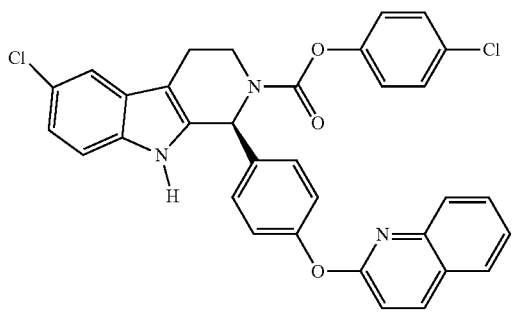
1573
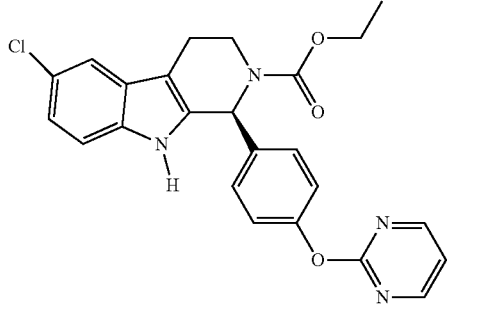
1574
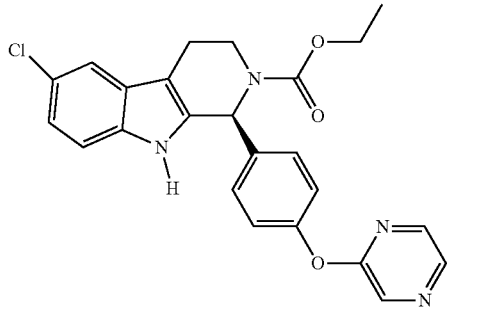
704
-continued
1575
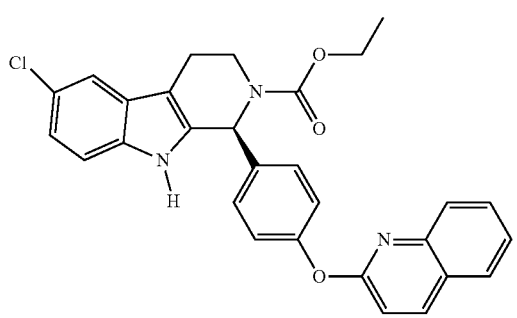
1576
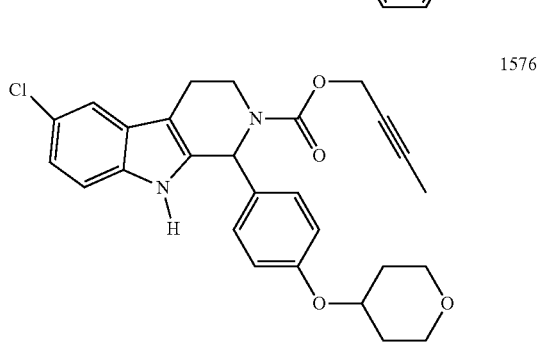
1577
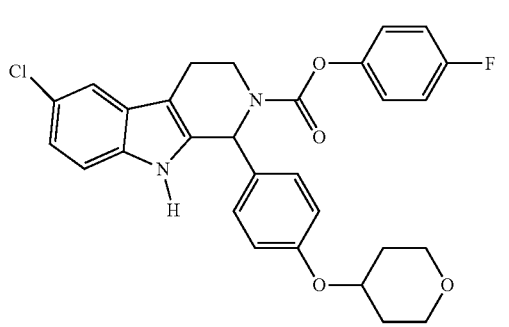
1578
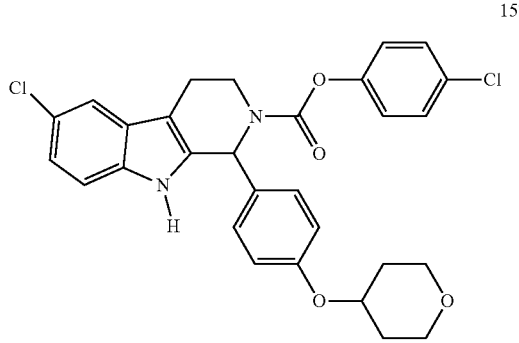
1579
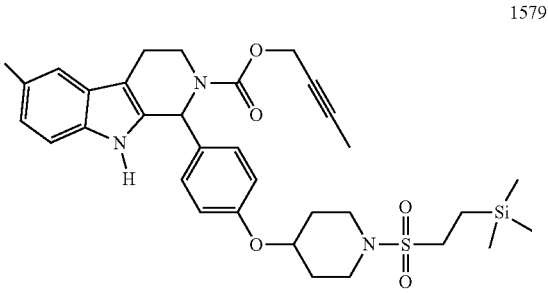

1580
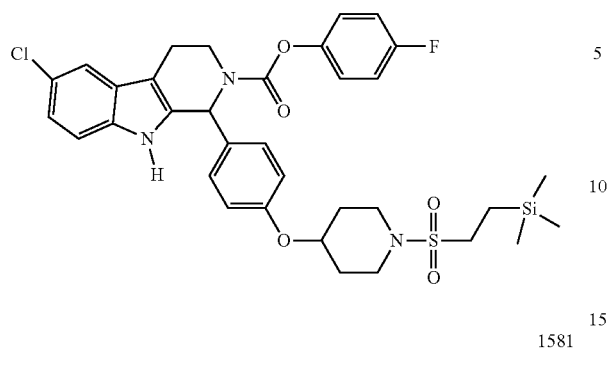
1581
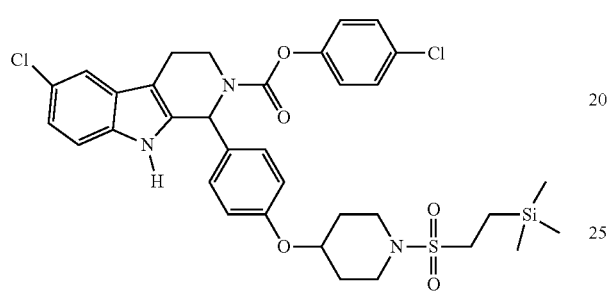
1582
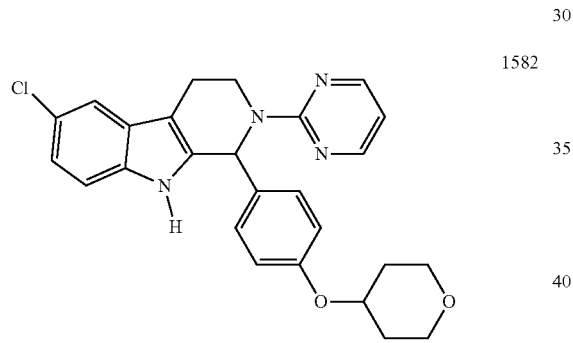
1583
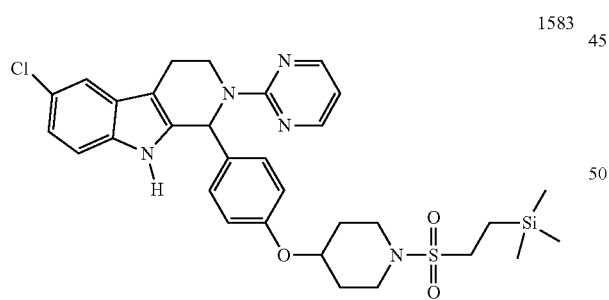
1584
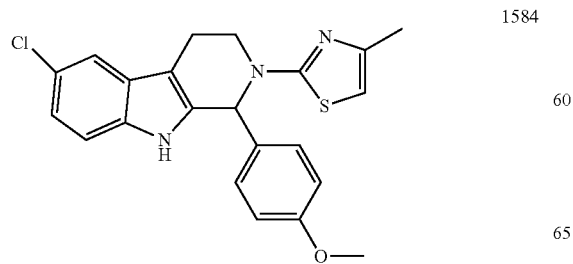
1585
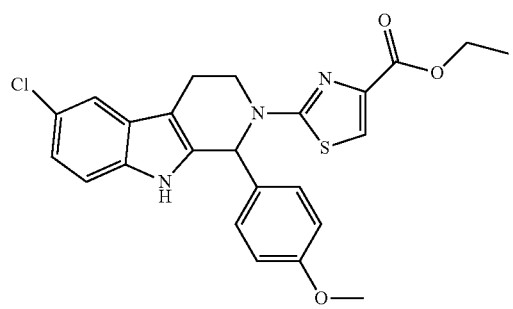
1586
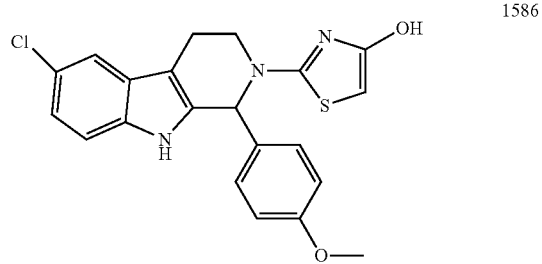
1587
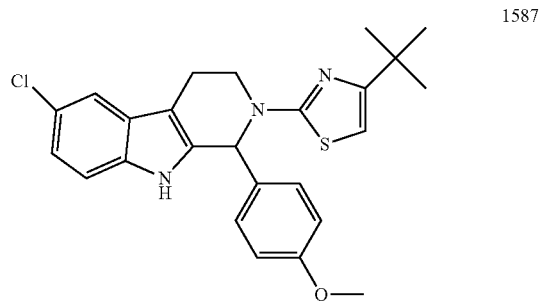
1588
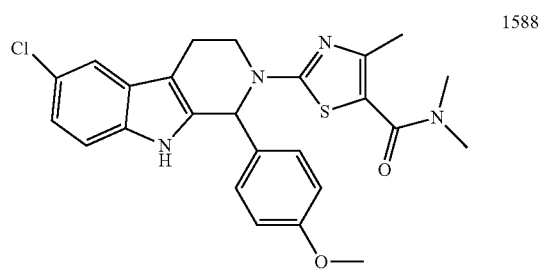
1589
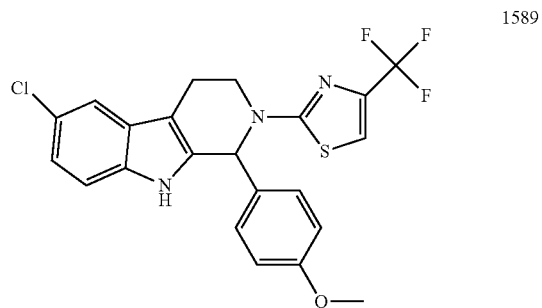

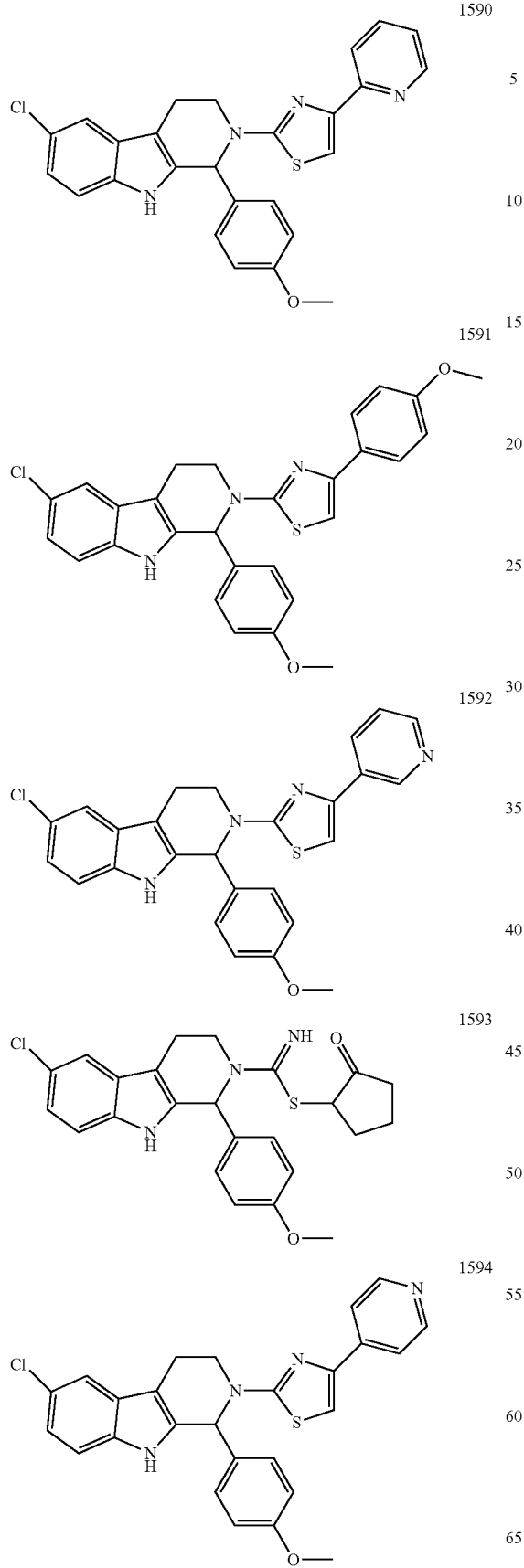
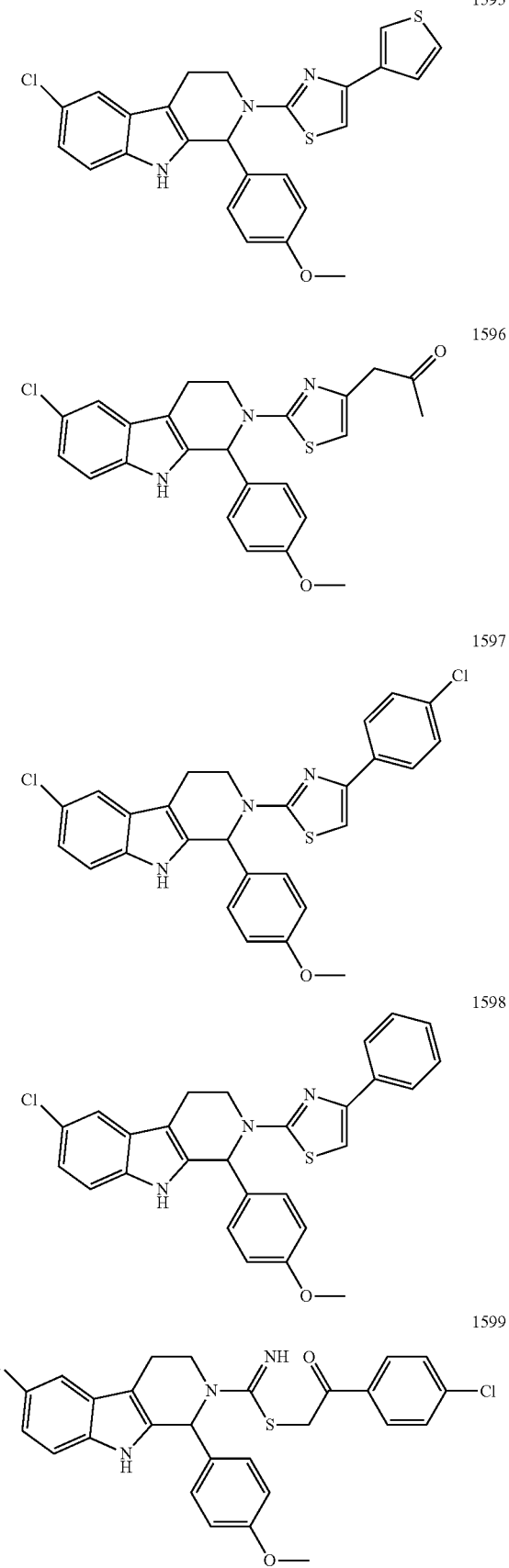

1600 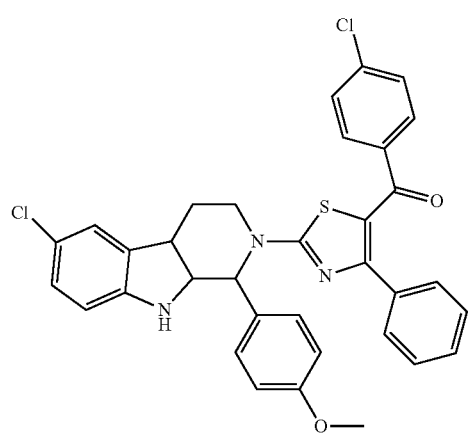
1601 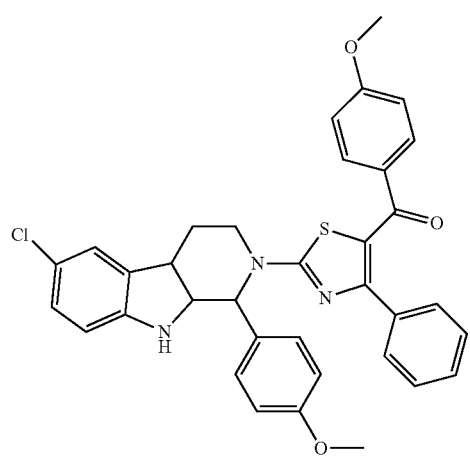
1602 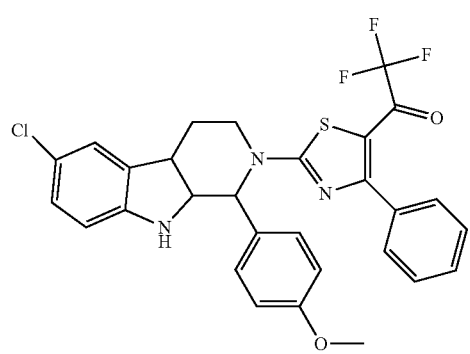
1603 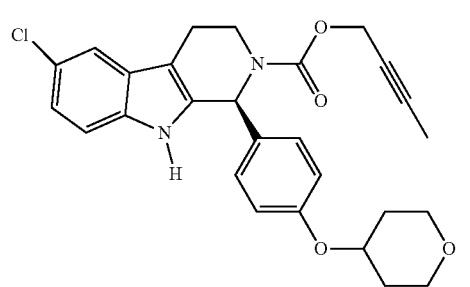
1604 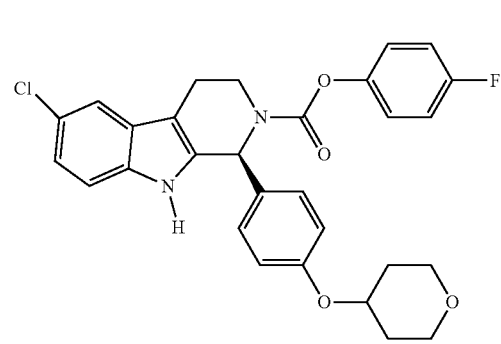
1605 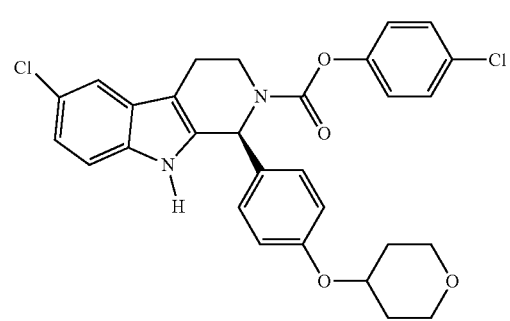
1606 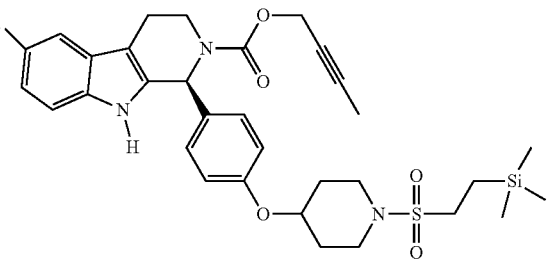
1607 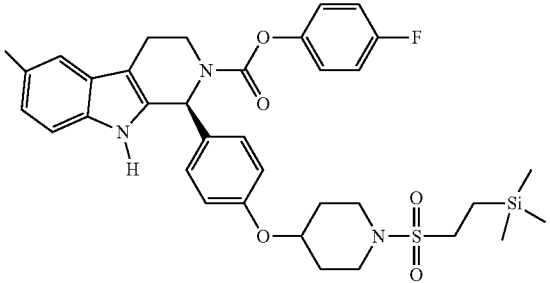
1608 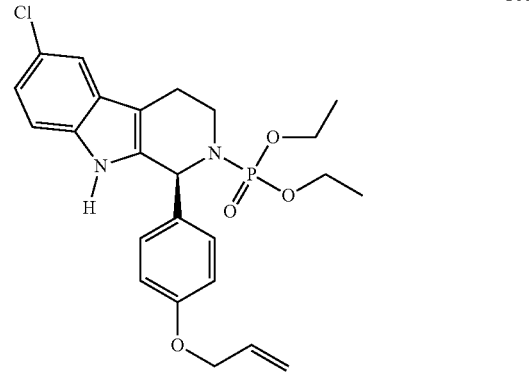

1609
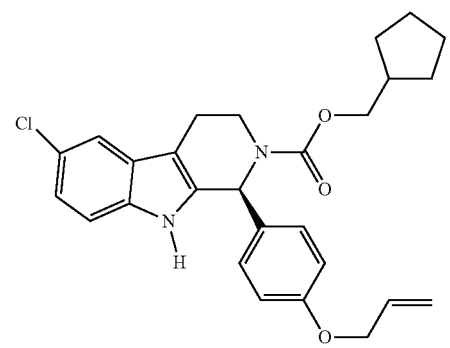
1610
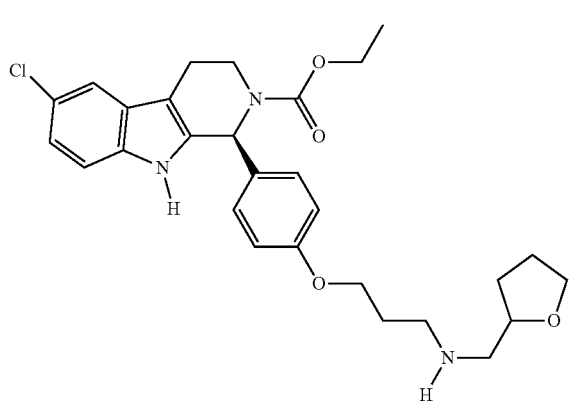
1611
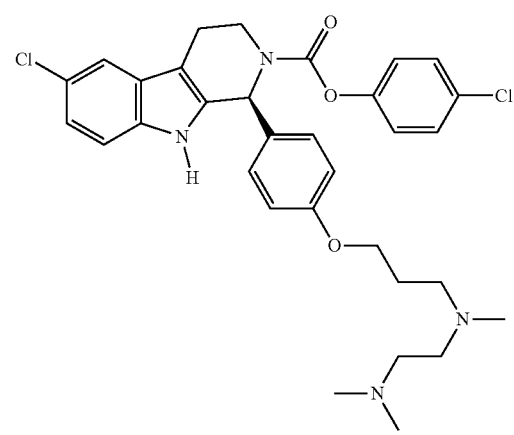
1612
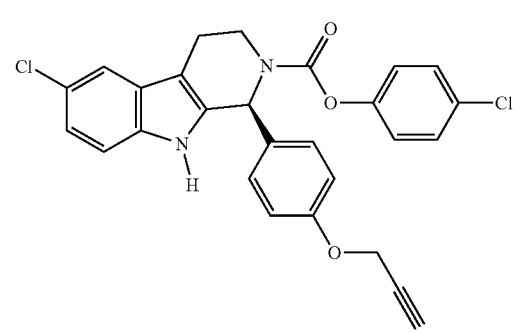
1613
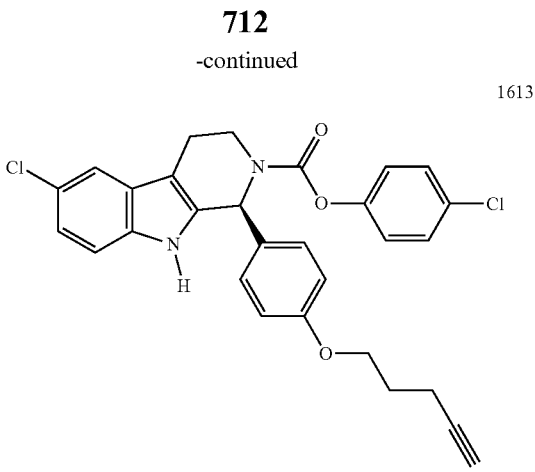
1614
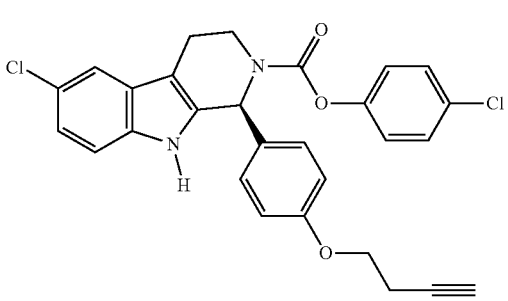
1615
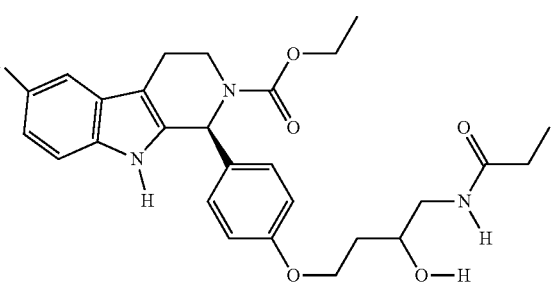
1616
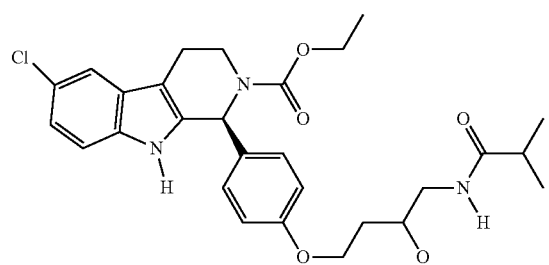
1617
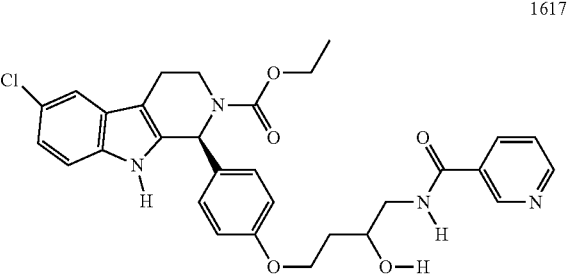

1618
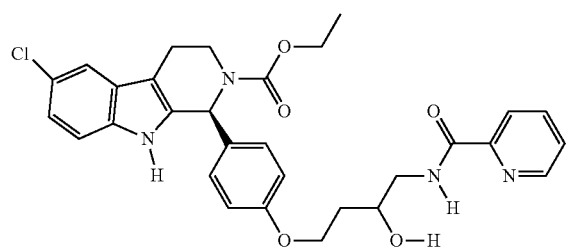
1619
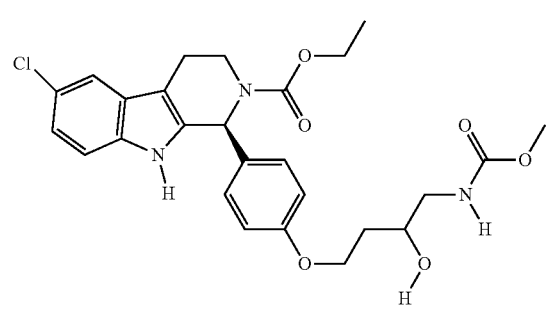
1620
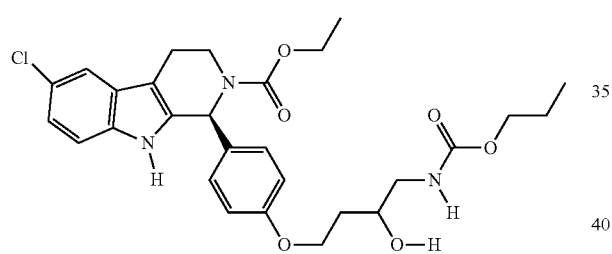
1621
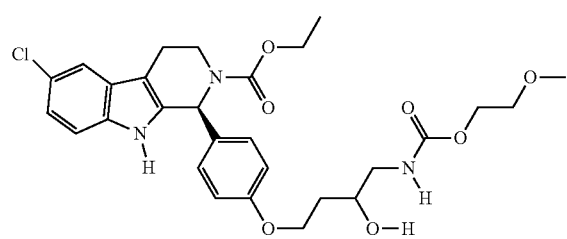
1622
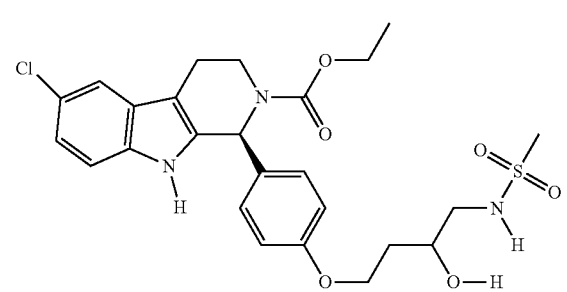
1623
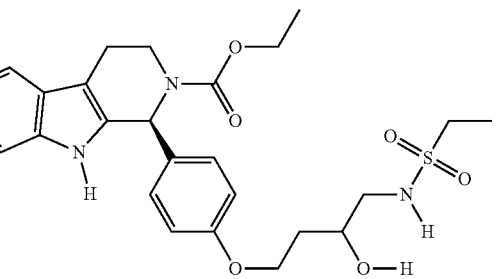
1624
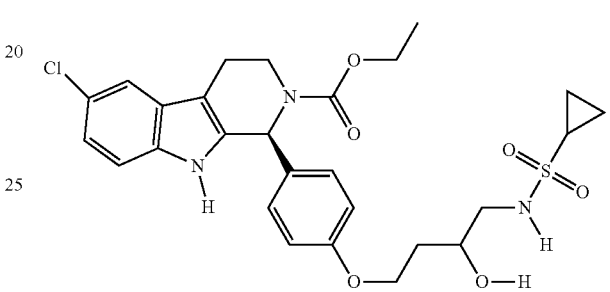
1625
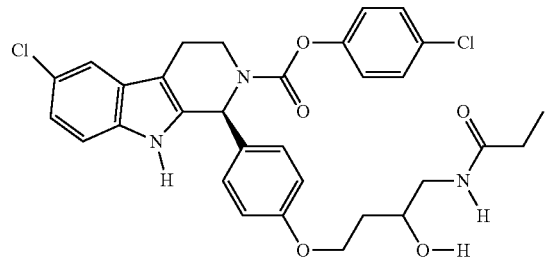
1626
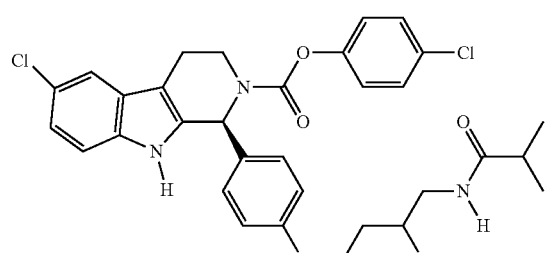
1627
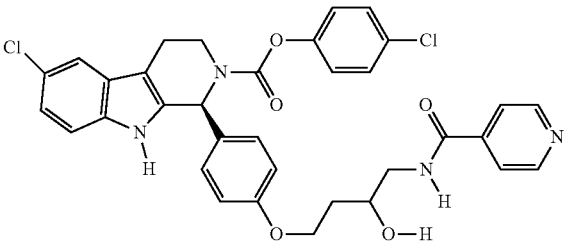

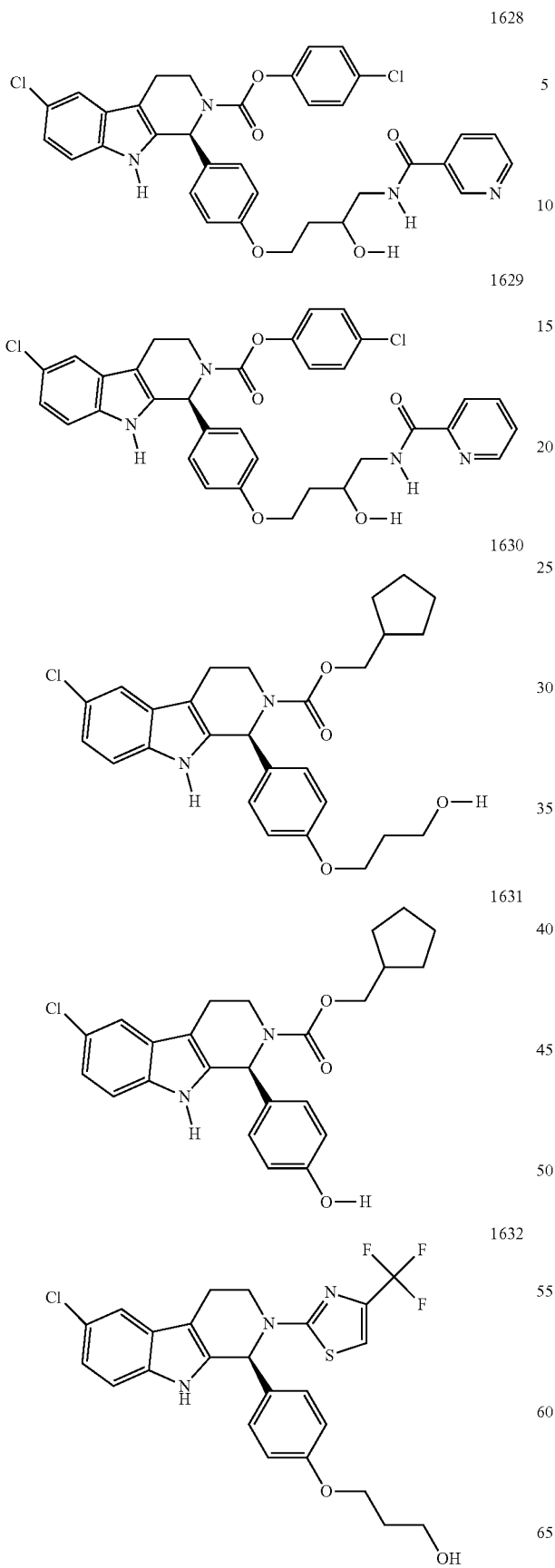
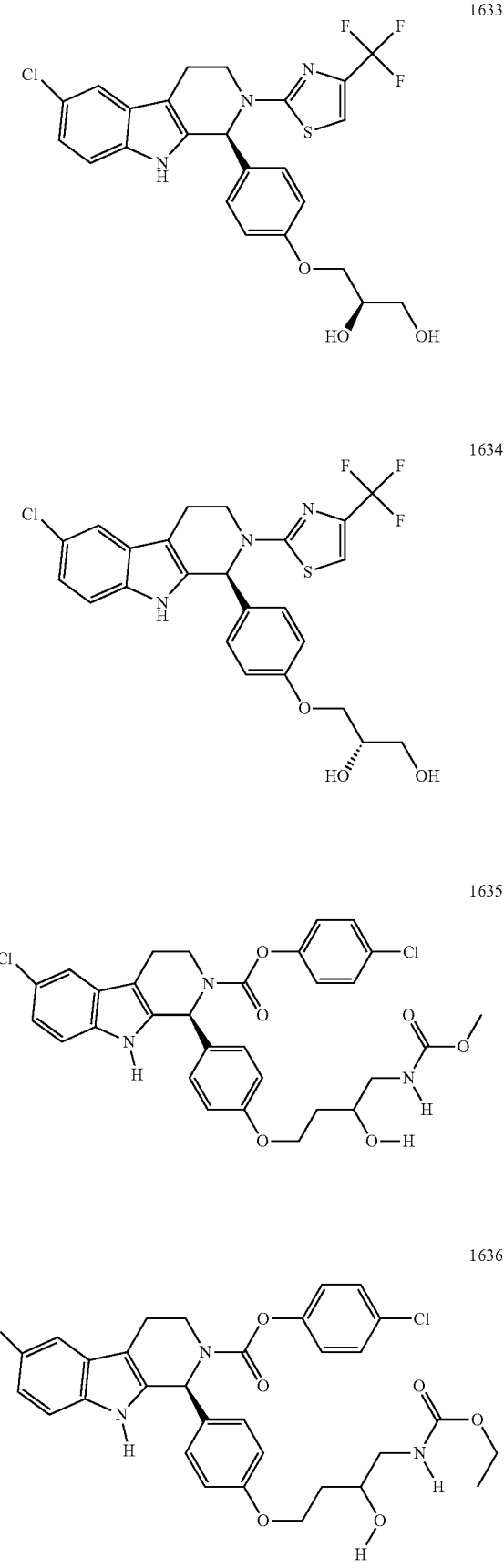

1637
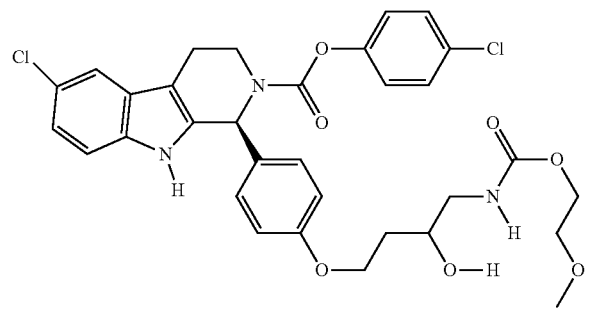
1638
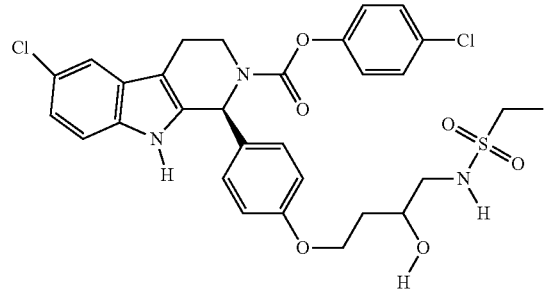
1639
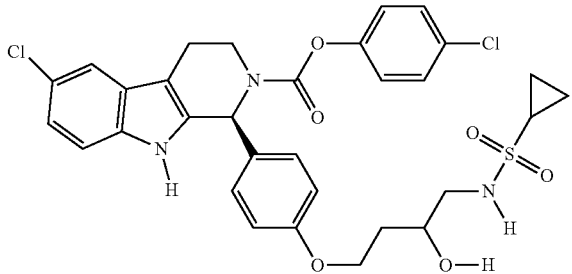
1640
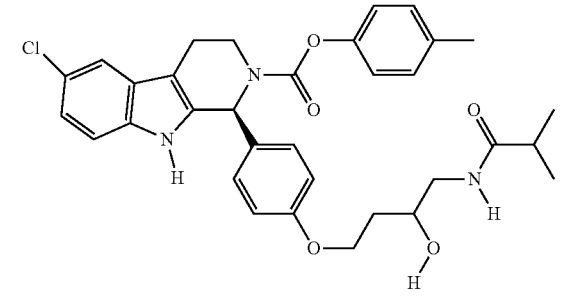
1641
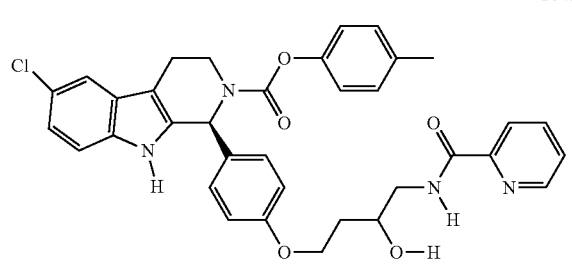
1642
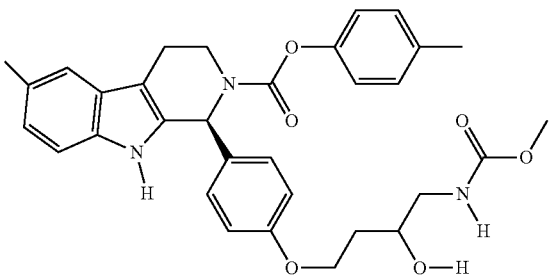
1643
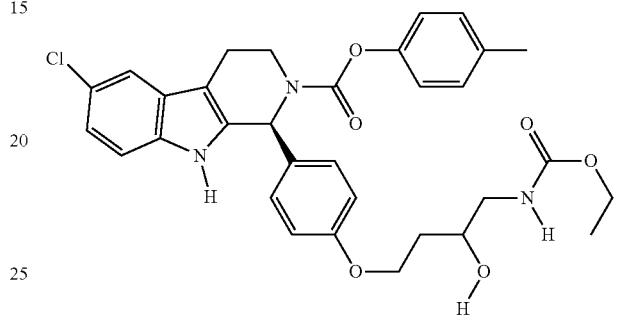
1644
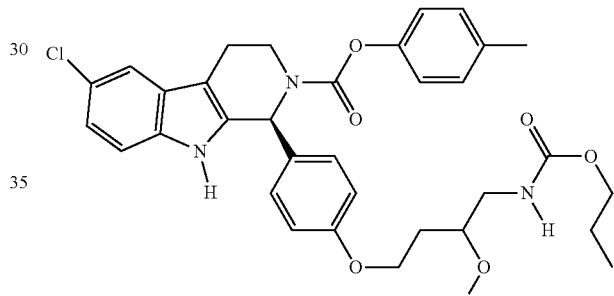
1645
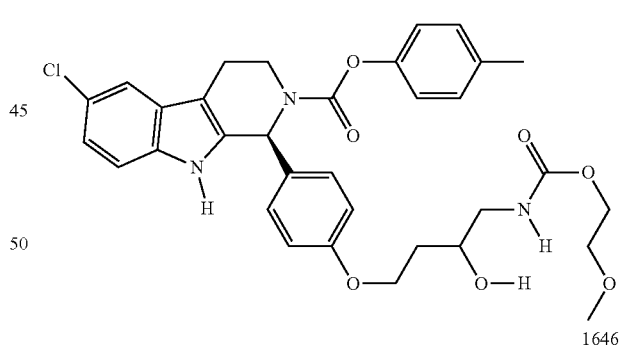
1646

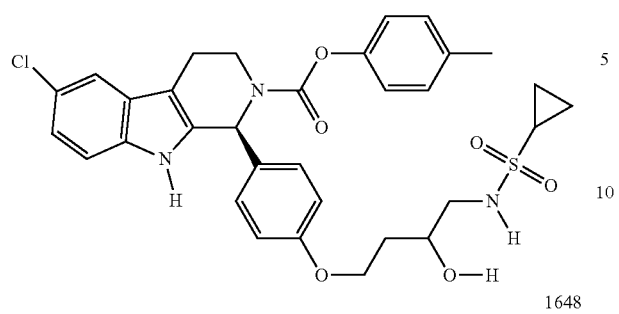
1647
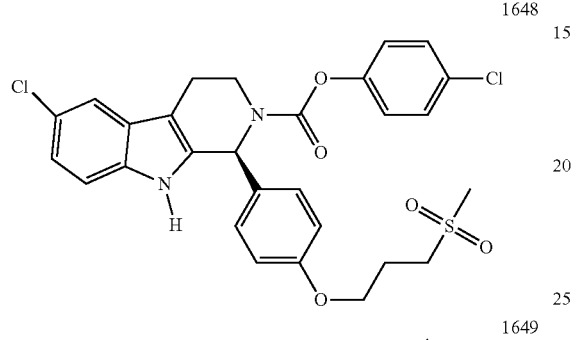
1648
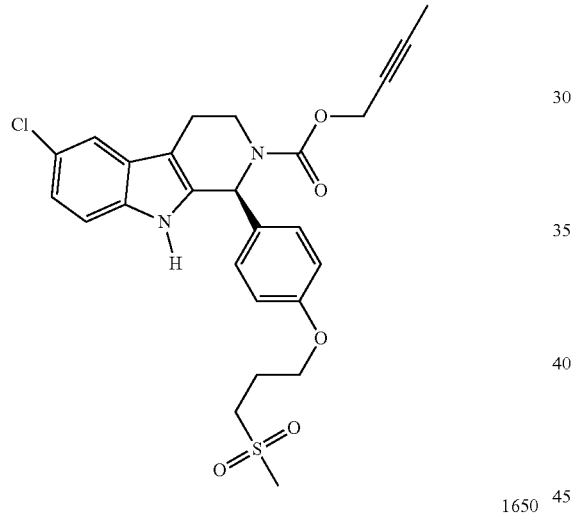
1649
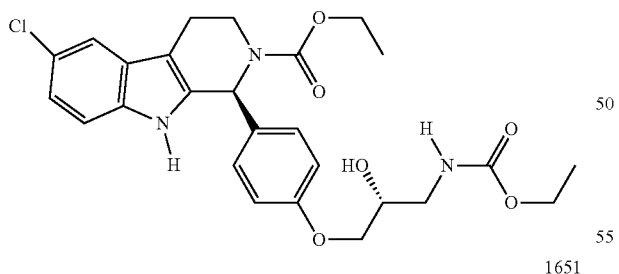
1650
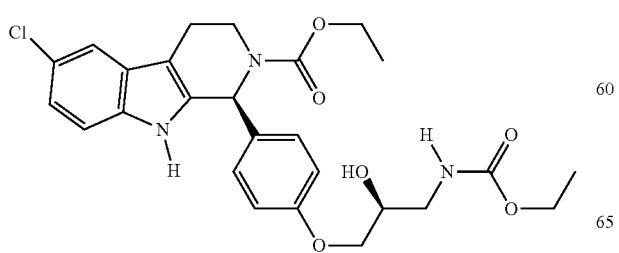
1651
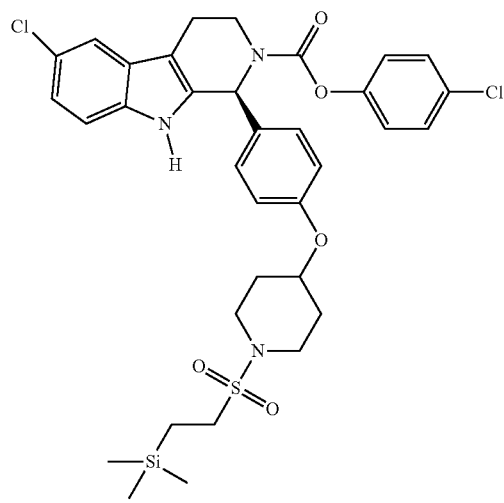
1652
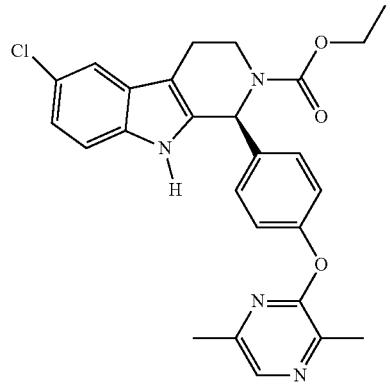
1653
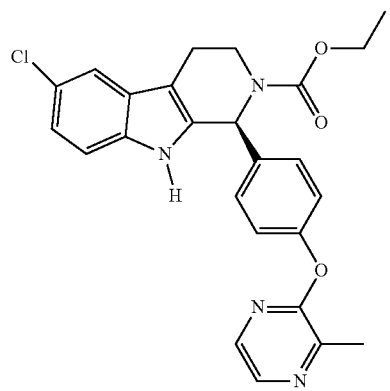
1654

| 721 | 722 |
|---|---|
| 1655 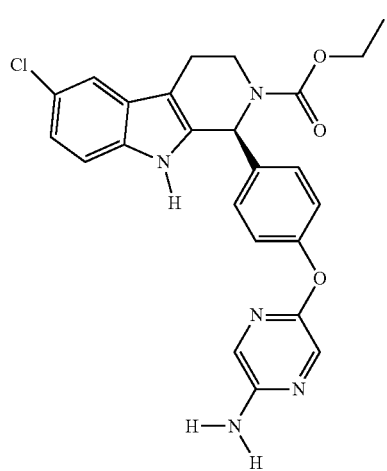 | 1658 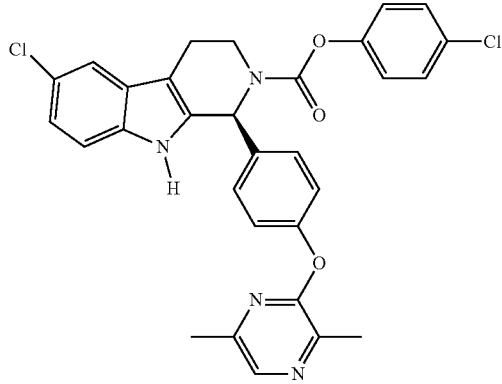 |
| 1656 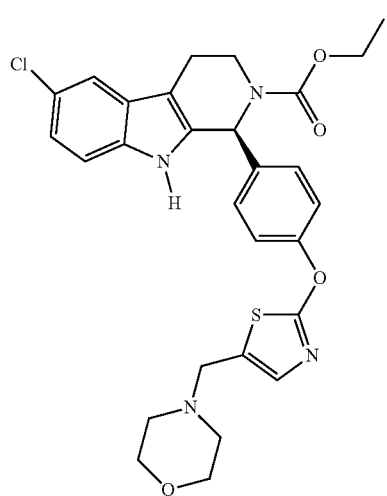 | 1659 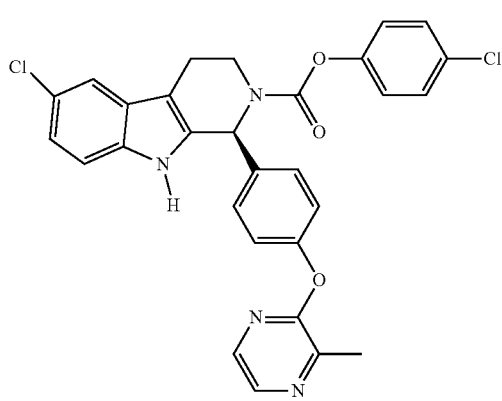 |
| 1657 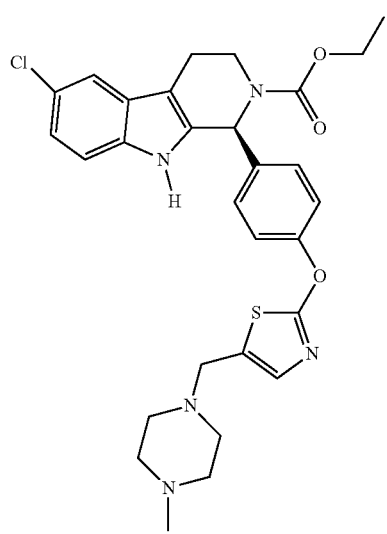 | 1660 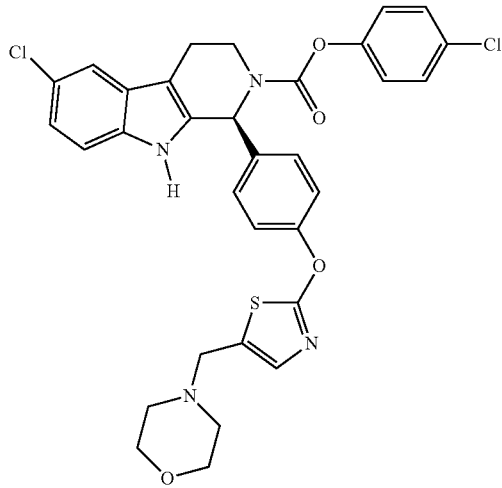 |

723
-continued
1661
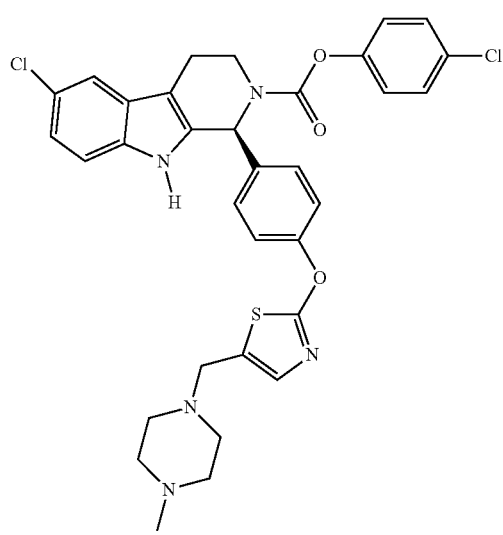
1662
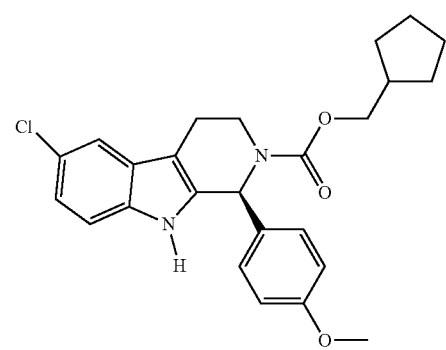
1663
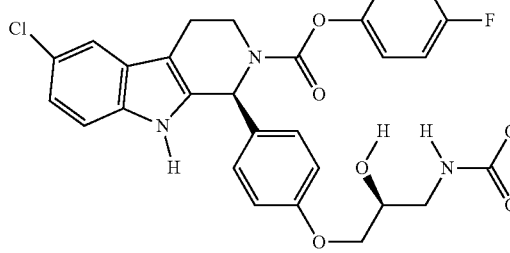
1664
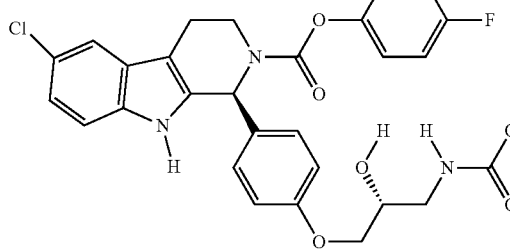
724
-continued
1665
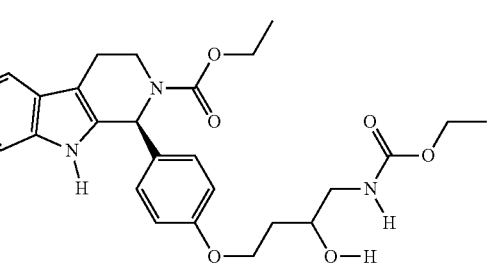
1666
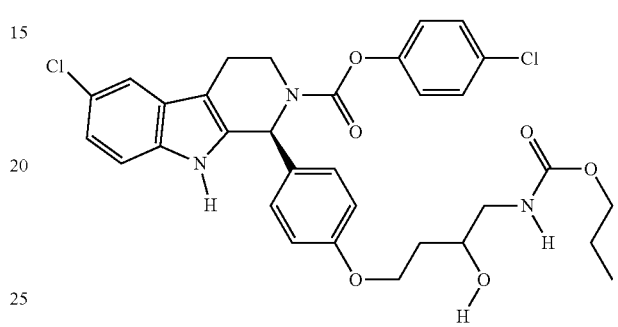
1667
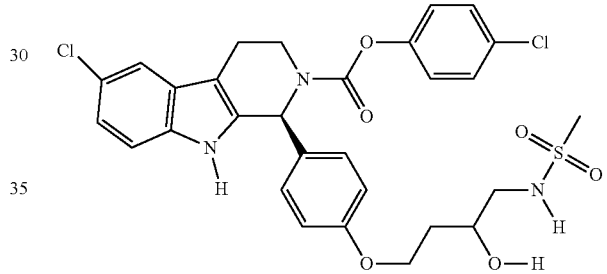
1668
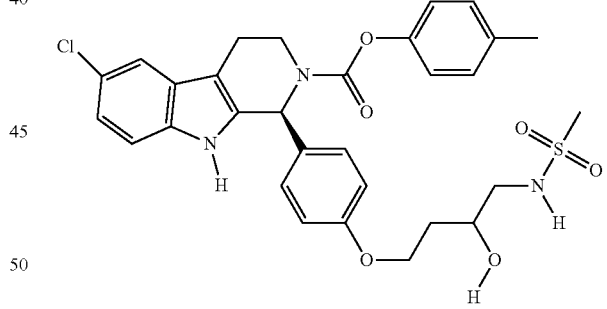
1669
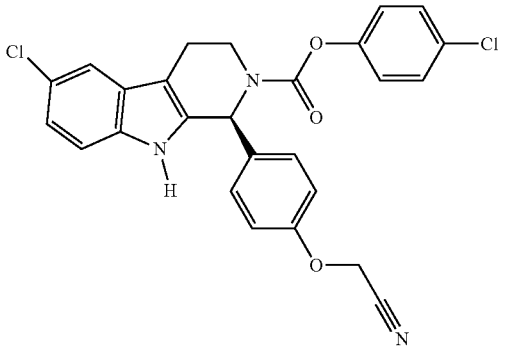

725
-continued
1670
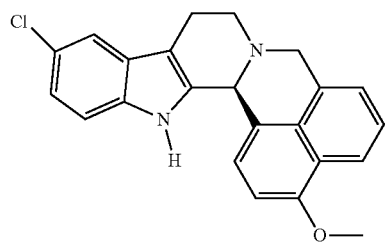
1671
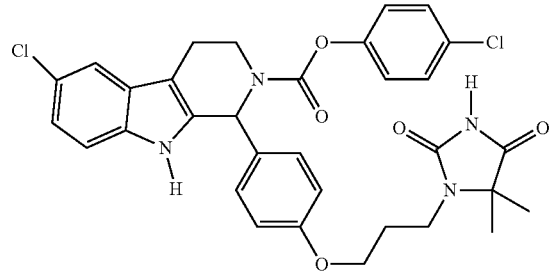
1672
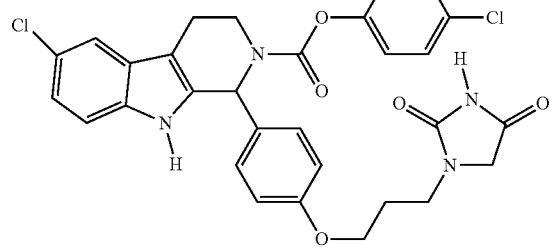
1673
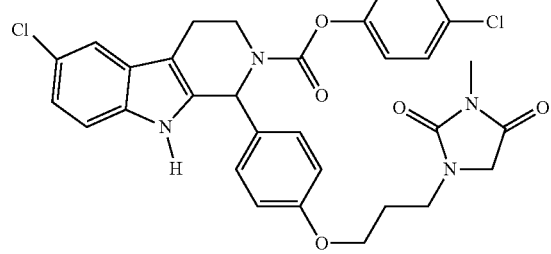
726
-continued
1674
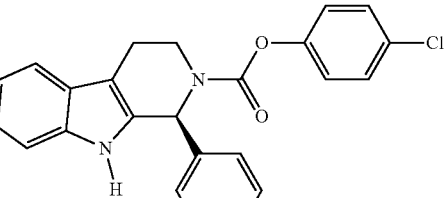
1675
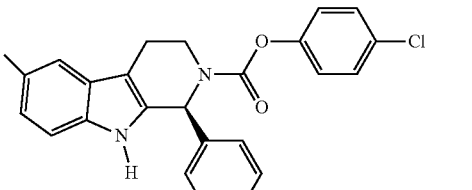
1676
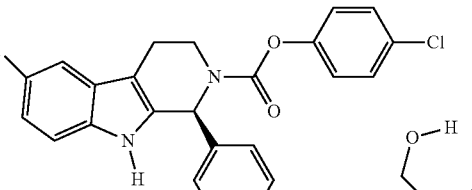

727
-continued
1677
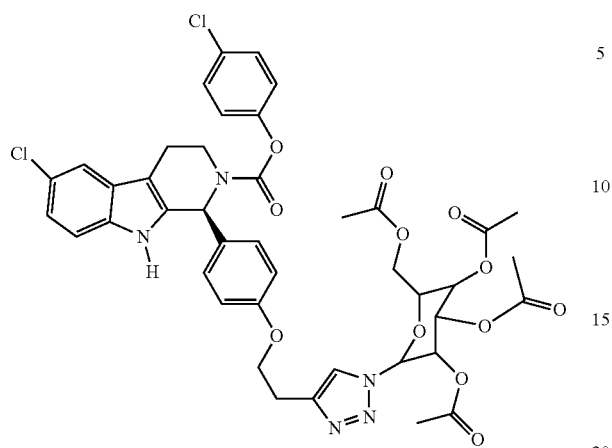
1678
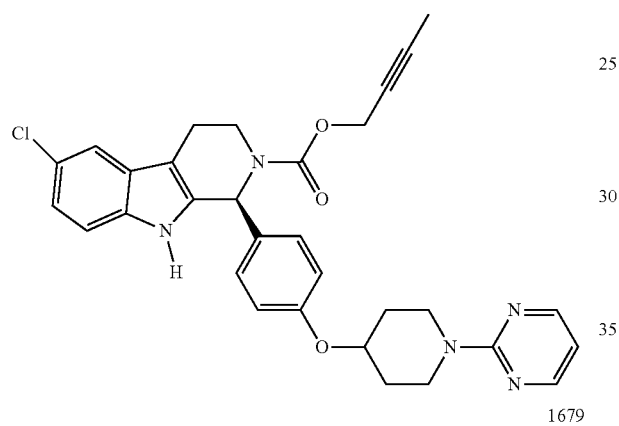
1679
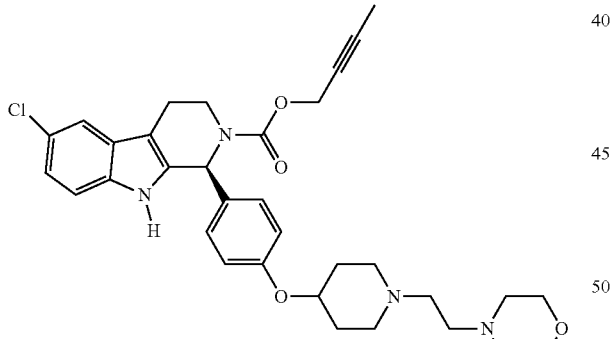
1680
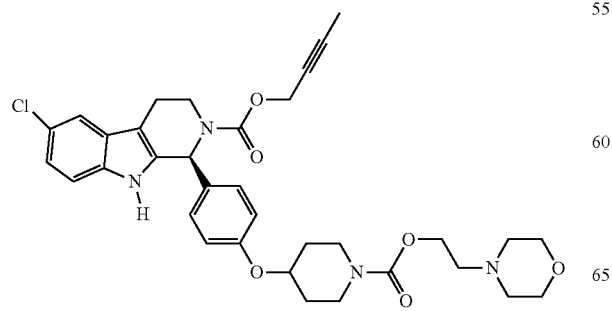
728
-continued
1681
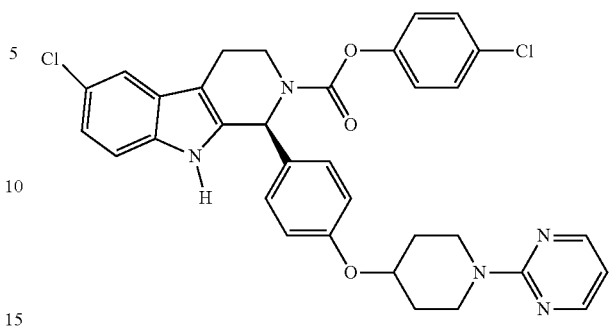
1682
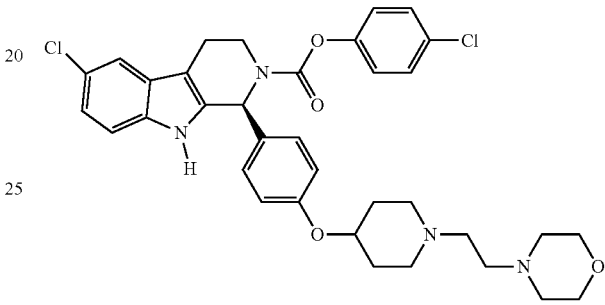
1683
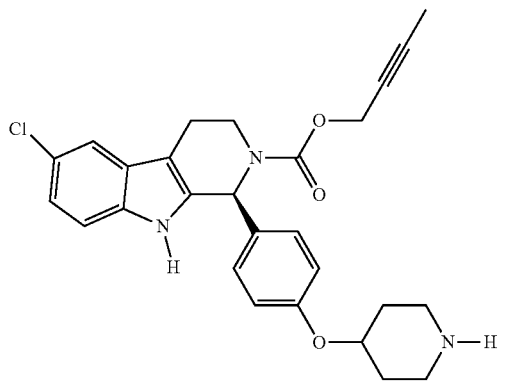
1684
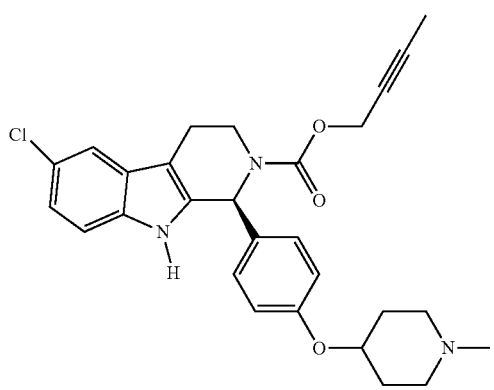

| 729 -continued | 730 -continued |
|---|---|
| 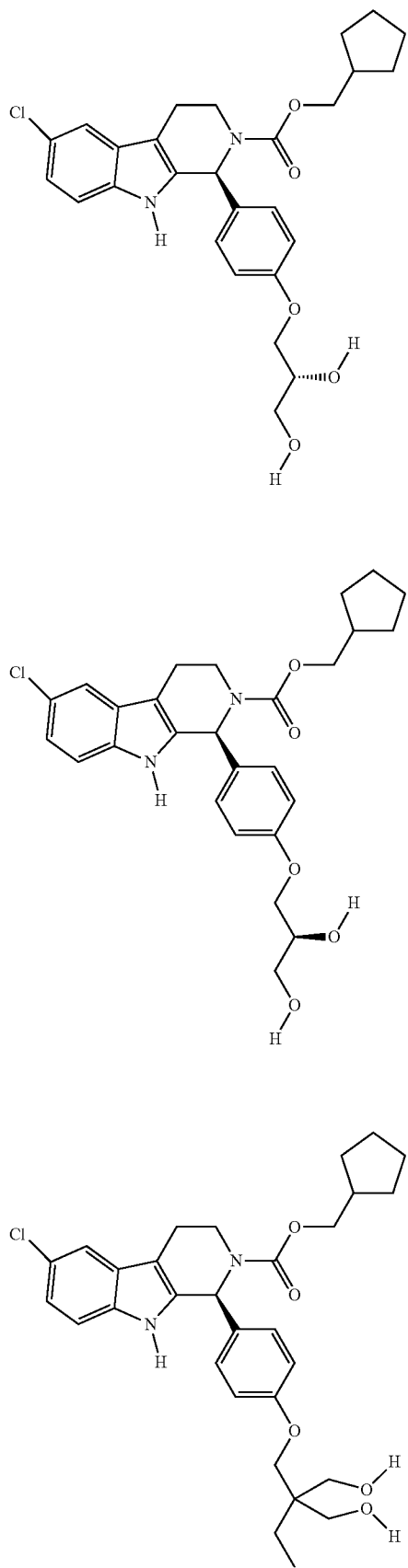 | 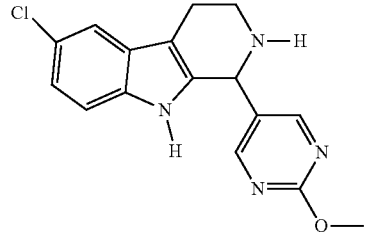 1688 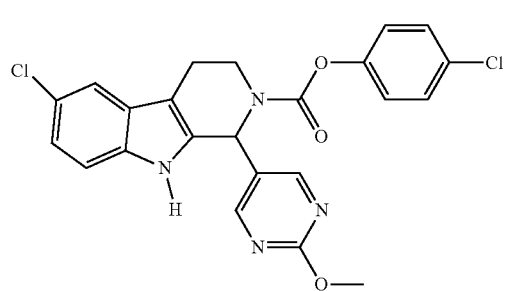 1689 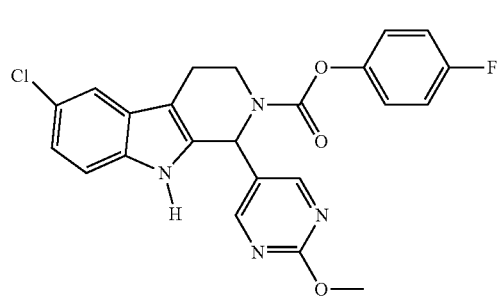 1690 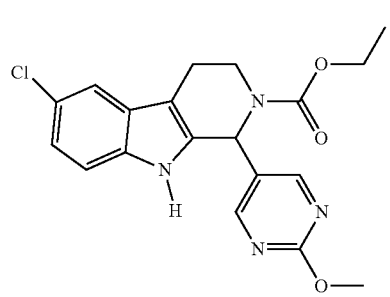 1691 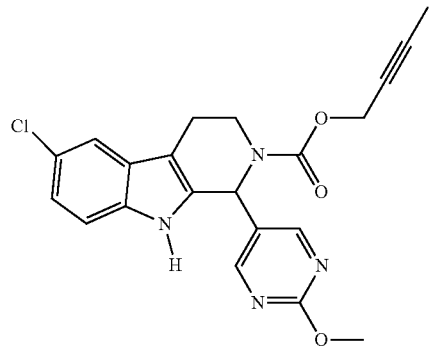 1692 |

731
-continued
1693
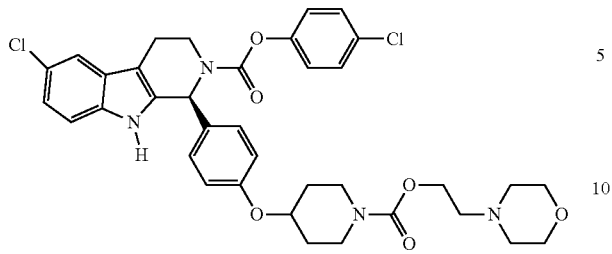
1694
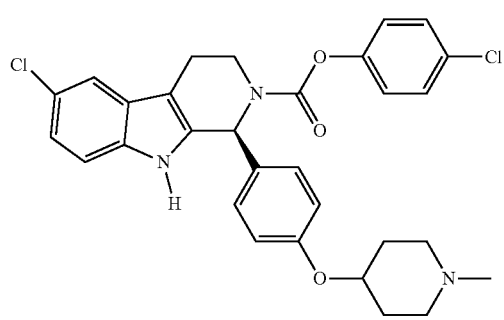
1695
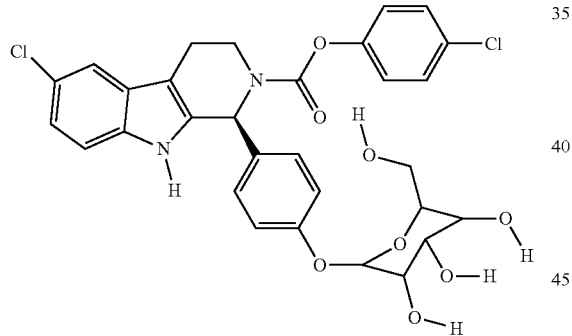
1696
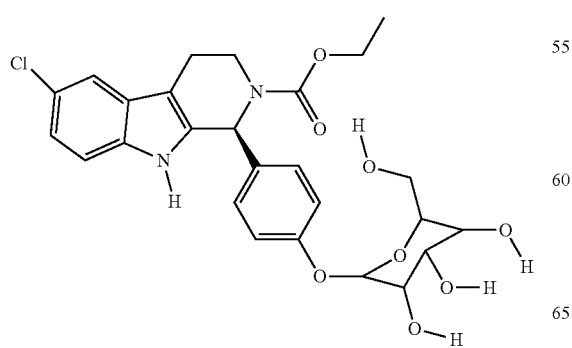
732
-continued
1697
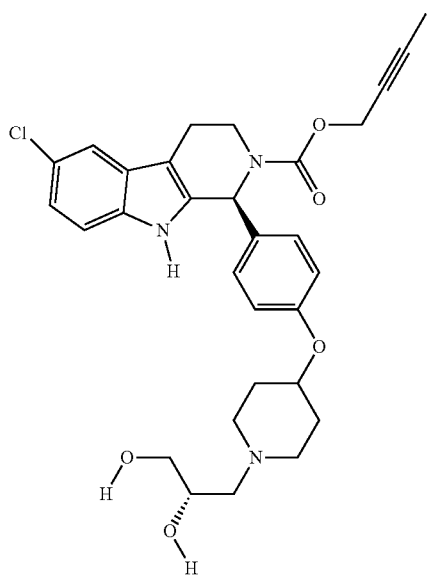
1698
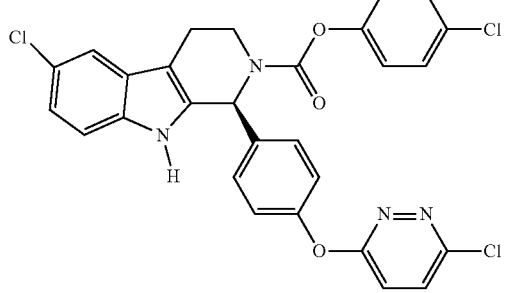
1699
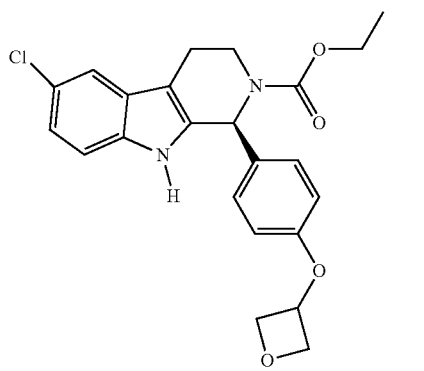
1700
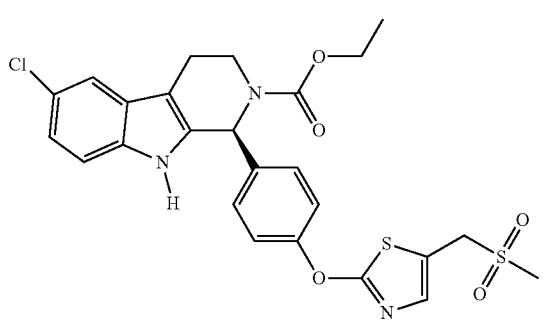

733
-continued
1701
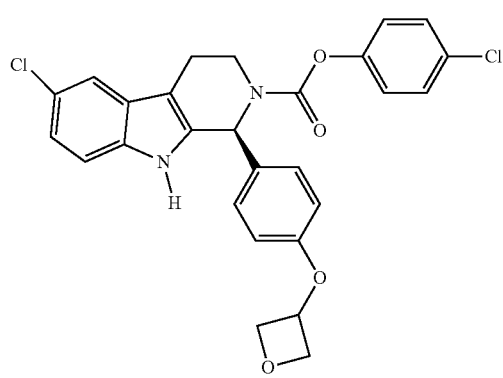
1702
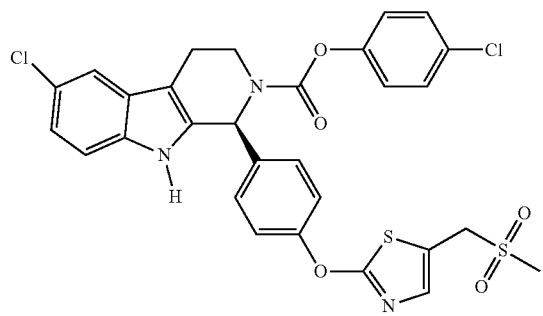
1703
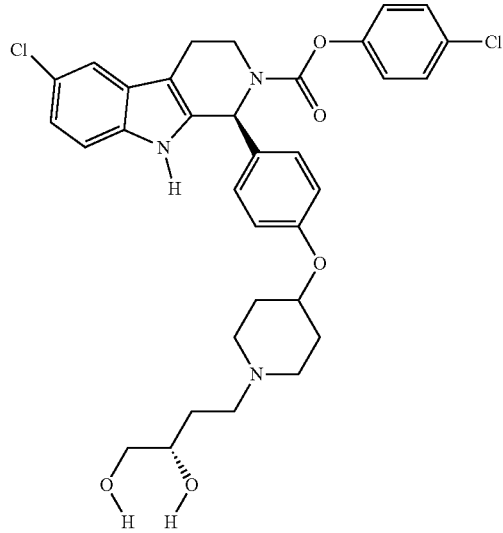
734
-continued
1704
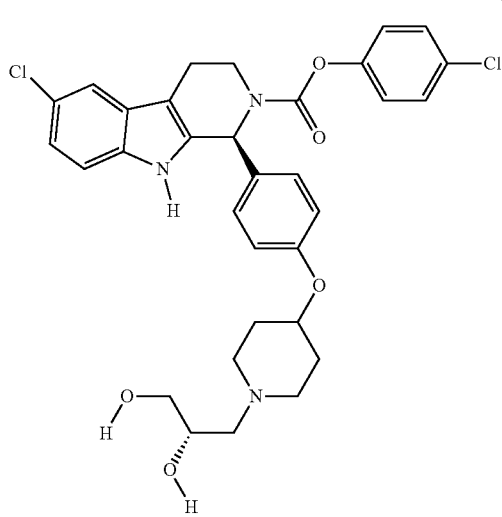
1705
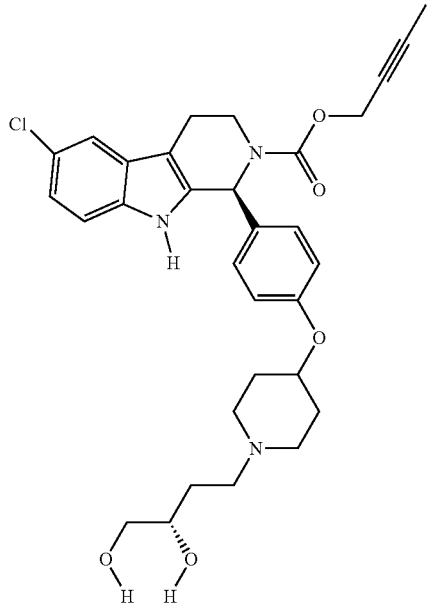
1706
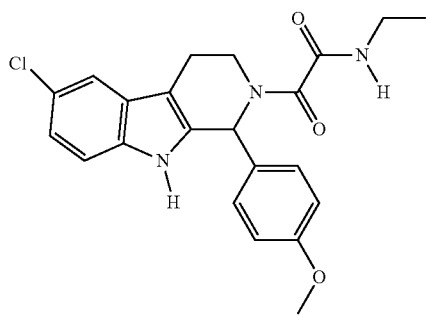

1707
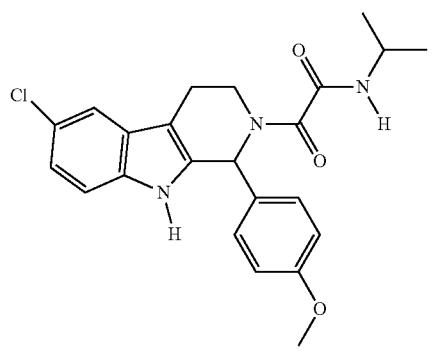
1708
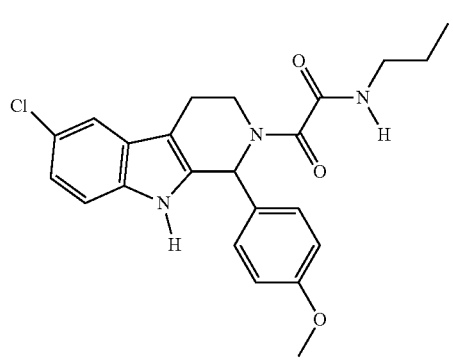
1709
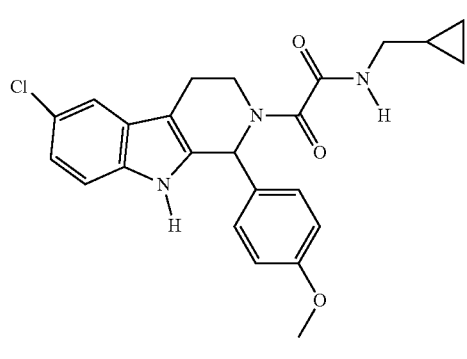
1710
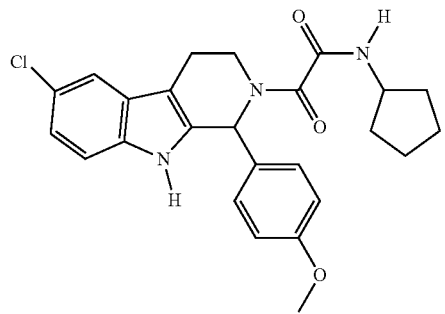
1711
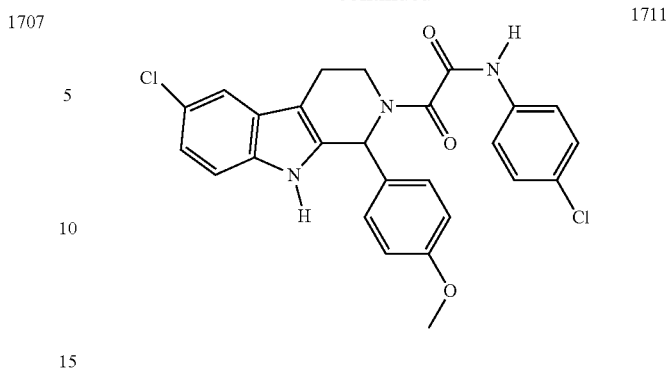
1712
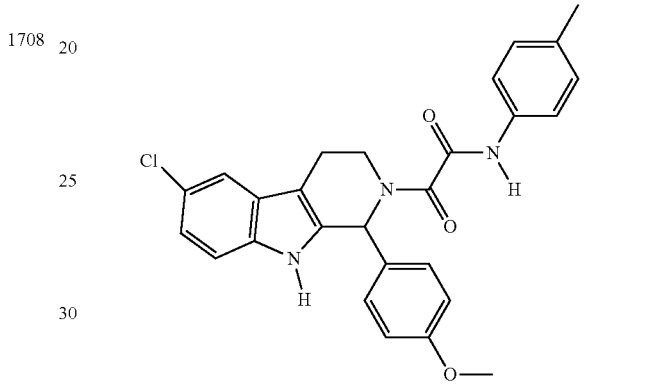
1713
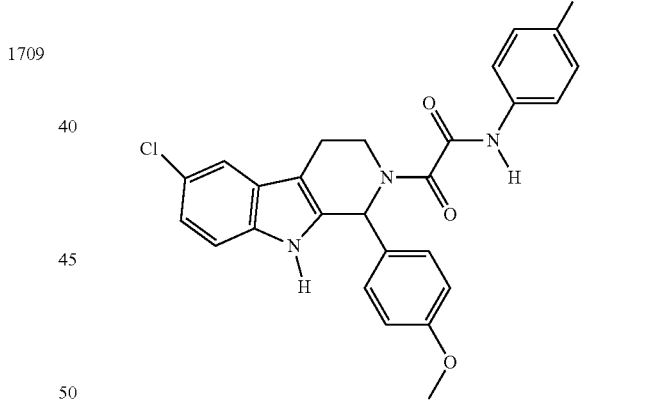
1714
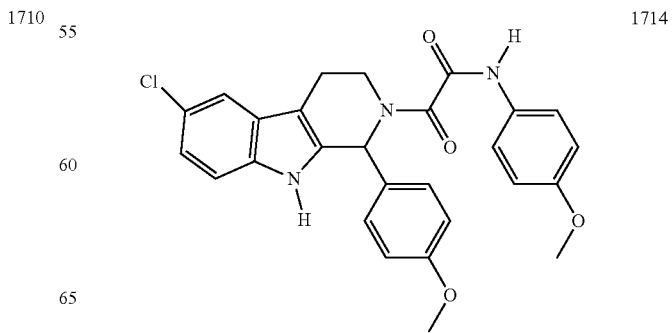

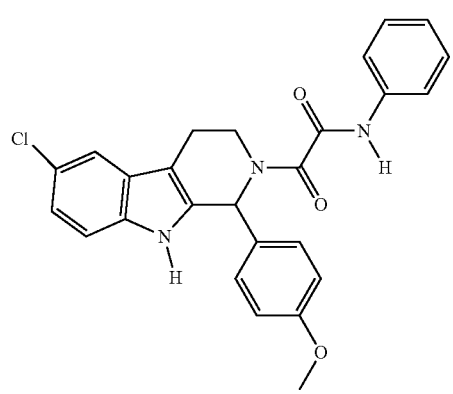
1715
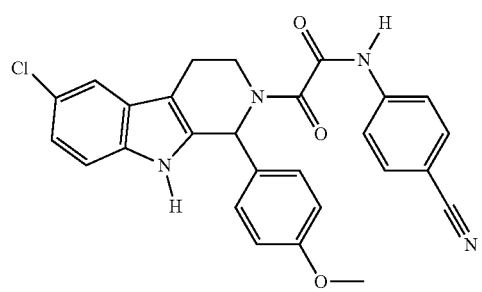
1716
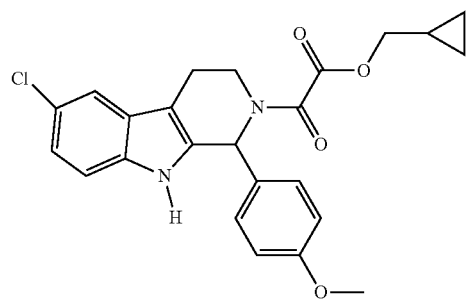
1717
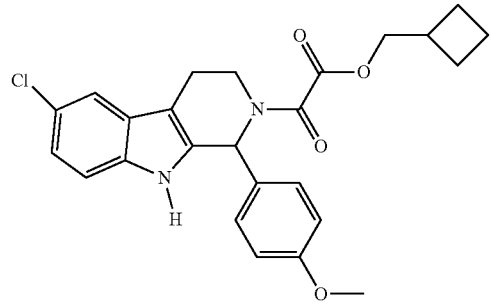
1718
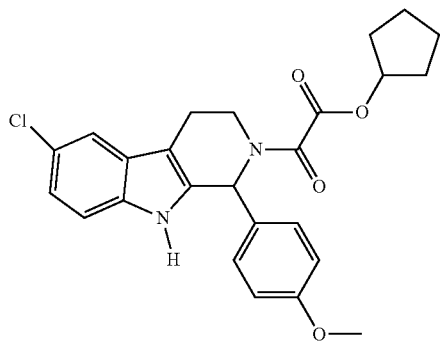
1719
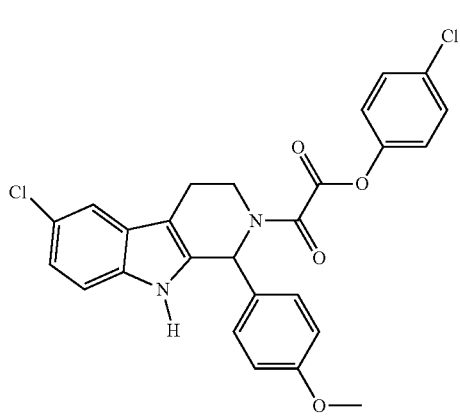
1720
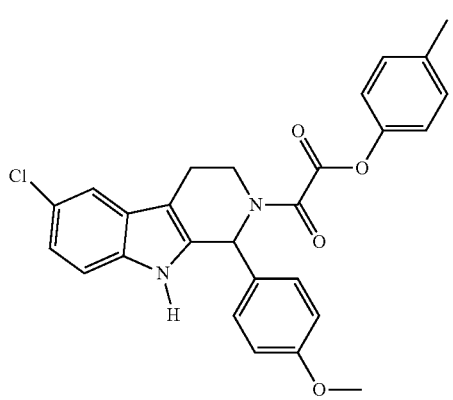
1721
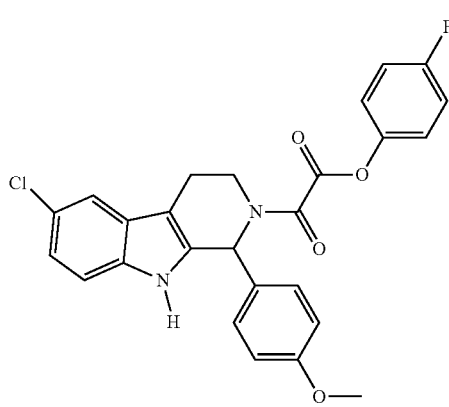
1722

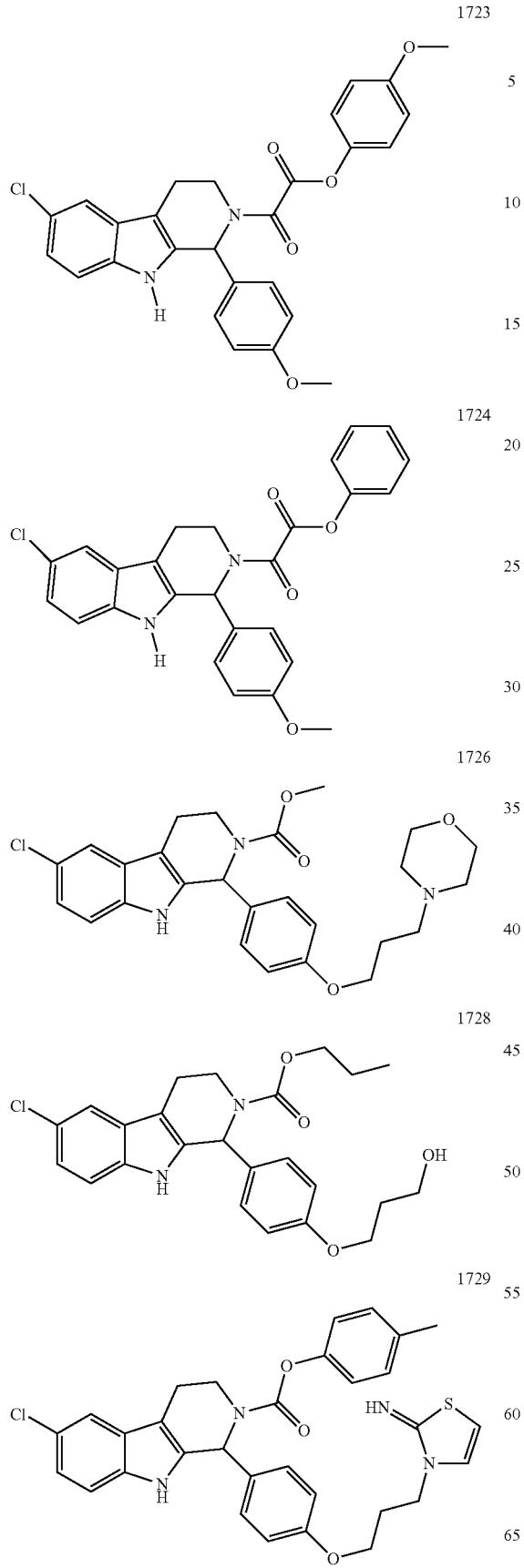
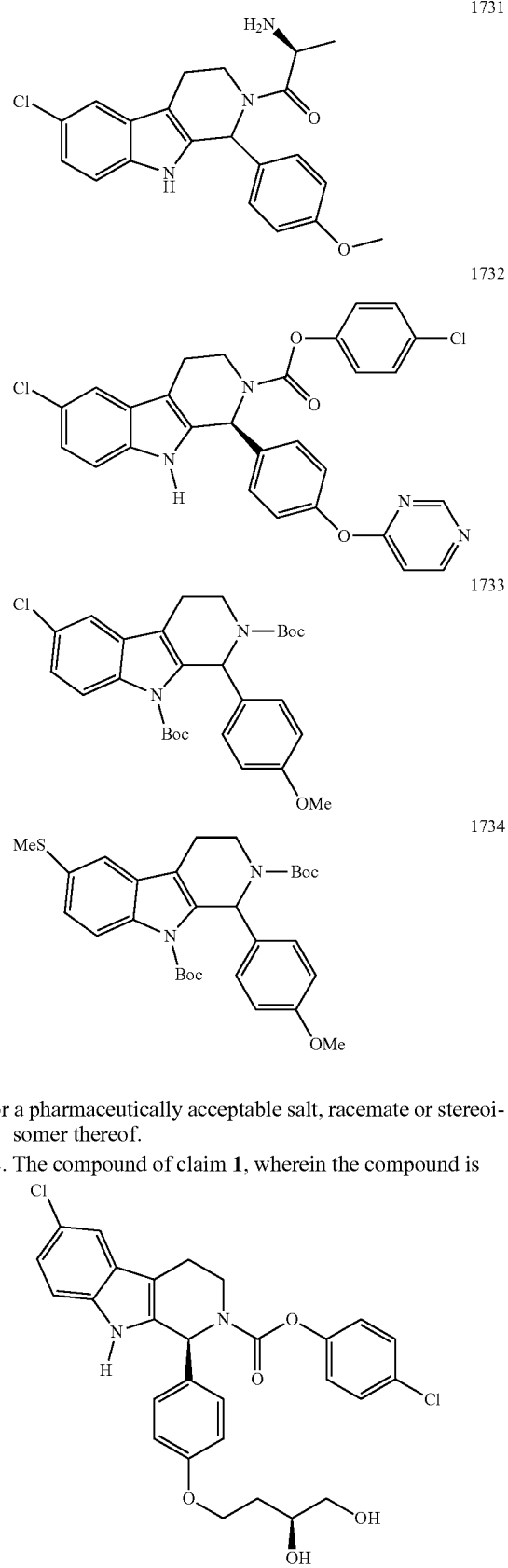
or a pharmaceutically acceptable salt, racemate or stereoisomer thereof.
2. The compound of claim 1, wherein the compound is
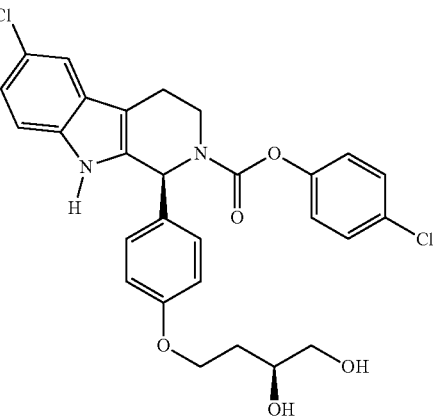
or a pharmaceutically acceptable salt thereof.

3. A pharmaceutical composition comprising a compound of claim 1 or 2.

4. A method for inhibiting or reducing the pathological production of human VEGF, comprising contacting an effective amount of a compound of claim 1 or 2 with a cell or a cell line that pathologically produces human VEGF or is induced to pathologically produce human VEGF.

5. The method of claim 4, wherein the cell is in a subject.

6. A method for treating a non-neoplastic condition associated with pathological production of VEGF in a human having the non-neoplastic condition, comprising administering to the human an effective amount of a compound of claim 1 or 2, wherein the non-neoplastic condition is a age-related macular degeneration, rheumatoid arthritis, psoriasis, obesity, atherosclerosis, diabetic retinopathy, retinopathy of prematurity, retrolental fibroplasia, neovascular glaucoma, exudative macular degeneration, thyroid hyperplasia, contact lens overwear, atopic keratitis, chronic inflammation, lung inflammation, nephrotic syndrome, preeclampsia, ascites, pericardial effusion, pleural effusion, acne rosacea, syphilis, fungal ulcer, Herpes Simplex Infection, protozoan infection, Mooren's ulcer, Terrien's marginal degeneration, systemic lupus, polyarteritis, Stevens-Johnson disease, pemphigoid, Eales' disease, Behcet's disease, sickle cell anemia, pseudoxanthoma elasticum, Stargardt's disease, chronic retinal detachment, vein occlusion, chronic uveitis, ocular histoplasmosis, Mycobacterial infection, Best's disease, myopia, toxoplasmosis, sarcoidosis, post-laser complication, disease associated with rubeosis, cystic fibrosis, polycystic autosomal-dominant kidney disease, or benign prostatic hyperplasia.

\* \* \* \* \*